US011091785B2

(12) United States Patent
McBrayer et al.

(10) Patent No.: US 11,091,785 B2
(45) Date of Patent: Aug. 17, 2021

(54) COMPOSITIONS FOR SACCHARIFICATION OF CELLULOSIC MATERIAL

(71) Applicant: Novozymes, Inc., Davis, CA (US)

(72) Inventors: Brett McBrayer, Davis, CA (US); Tarana Shaghasi, Davis, CA (US); Elena Vlasenko, Davis, CA (US)

(73) Assignee: Novoyzmes, Inc., Davis, CA (US)

( * ) Notice: Subject to any disclaimer, the term of this patent is extended or adjusted under 35 U.S.C. 154(b) by 0 days.

(21) Appl. No.: 16/840,012

(22) Filed: Apr. 3, 2020

(65) Prior Publication Data

US 2020/0354762 A1 Nov. 12, 2020

Related U.S. Application Data

(62) Division of application No. 16/115,930, filed on Aug. 29, 2018, now Pat. No. 10,648,009, which is a division of application No. 15/422,245, filed on Feb. 1, 2017, now Pat. No. 10,072,280, which is a division of application No. 14/885,555, filed on Oct. 16, 2015, now Pat. No. 9,587,262, which is a division of application No. 14/052,360, filed on Oct. 11, 2013, now Pat. No. 9,175,277, which is a division of application No. 12/940,952, filed on Nov. 5, 2010, now Pat. No. 8,580,536.

(60) Provisional application No. 61/259,014, filed on Nov. 6, 2009.

(51) Int. Cl.

| | |
|---|---|
| ***C12P 19/14*** | (2006.01) |
| ***C12N 1/22*** | (2006.01) |
| ***C12N 9/42*** | (2006.01) |
| ***C12P 19/02*** | (2006.01) |
| ***C12N 9/24*** | (2006.01) |
| ***C12P 19/12*** | (2006.01) |
| ***C12P 21/02*** | (2006.01) |

(52) U.S. Cl.

CPC ................ *C12P 19/14* (2013.01); *C12N 1/22* (2013.01); *C12N 9/2402* (2013.01); *C12N 9/248* (2013.01); *C12N 9/2437* (2013.01); *C12N 9/2445* (2013.01); *C12P 19/02* (2013.01); *C12P 19/12* (2013.01); *C12P 21/02* (2013.01); *C12Y 302/01* (2013.01); *C12Y 302/01004* (2013.01); *C12Y 302/01008* (2013.01); *C12Y 302/01021* (2013.01); *C12Y 302/01091* (2013.01); *C12P 2203/00* (2013.01); *C12Y 302/01037* (2013.01); *Y02P 20/52* (2015.11)

(58) Field of Classification Search

CPC .. C12N 9/2445; C12N 9/2402; C12N 9/2437; C12N 9/248; C12N 1/22; C12P 19/14; C12P 19/12; C12P 21/02; C12P 19/02; C12P 2203/00; Y02P 20/52; C12Y 302/01037; C12Y 302/01004; C12Y 302/01008; C12Y 302/01021; C12Y 302/01091; C12Y 302/01

See application file for complete search history.

(56) References Cited

U.S. PATENT DOCUMENTS

| | | | | |
|---|---|---|---|---|
| 7,244,605 | B2 * | 7/2007 | Harris ............ | C12Y 302/01021 435/183 |
| 7,271,244 | B2 | 9/2007 | Dotson et al. | |
| 7,960,160 | B2 | 6/2011 | Yaver et al. | |
| 8,148,103 | B2 | 4/2012 | Tang et al. | |
| 8,211,665 | B2 | 7/2012 | Tang et al. | |
| 8,541,651 | B2 | 9/2013 | Wogulis | |
| 8,580,536 | B2 | 11/2013 | McBrayer et al. | |
| 9,115,368 | B2 | 8/2015 | Abad et al. | |
| 9,175,277 | B2 * | 11/2015 | McBrayer ...... | C12Y 302/01021 |
| 2005/0210548 | A1 | 9/2005 | Yaver et al. | |
| 2009/0123979 | A1 | 5/2009 | Xu | |
| 2009/0130707 | A1 | 5/2009 | Xu | |

FOREIGN PATENT DOCUMENTS

| | | | |
|---|---|---|---|
| WO | 2003000941 | | 1/2003 |
| WO | 2007071818 | | 6/2007 |
| WO | 2008025165 | | 3/2008 |
| WO | 2008095033 | A2 | 8/2008 |
| WO | 2008140749 | A2 | 11/2008 |
| WO | 2008151079 | A2 | 12/2008 |
| WO | 2009018537 | A2 | 2/2009 |
| WO | 2009059175 | | 5/2009 |
| WO | 2009059234 | A2 | 5/2009 |
| WO | 2009085868 | A1 | 7/2009 |
| WO | 2009085935 | | 7/2009 |
| WO | 2009108941 | A2 | 9/2009 |

OTHER PUBLICATIONS

Pauly et al., A xyloglucan-specific endo-B-1.4-glucanase from Aspergillus aculeatus: expression cloning yeast, purification and characterization of the recombinant enzymes, Glycobiology, vol. 9, No. 1, pp. 93-100, 1999.

Zhou et al., Optimization of cellulose mixture for efficient hydrolysis of steam-exploded corn stover by statistically designed experiments, Bioresource Technology, 100, pp. 819-825, 2009.

Dashtban et al., Fungal Bioconversion of Lignocellulosic Residues; Opportunities & Perspectives, International Journal of Biological Sciences, pp. 578-595, 2009.

Rosgaard et al., Efficiency of New Fungal Cellulase Systems in Boosting Enzymatic Degradation of Barley Straw Lignocellulose, Biotechnol. Prog, 22, pp. 493-498, 2006.

(Continued)

*Primary Examiner* — Ganapathirama Raghu
(74) *Attorney, Agent, or Firm* — David Fazzolare

(57) ABSTRACT

The present invention relates to enzyme compositions for high temperature saccharification of cellulosic material and to uses thereof.

36 Claims, 42 Drawing Sheets

Specification includes a Sequence Listing.

(56) References Cited

OTHER PUBLICATIONS

Merino et al., Progress and Challenges in Enzyme Development for Biomass Utilization, Adv. Biochem Engin/Biotechnol, 108, pp. 95-120, 2007.
Viikari et al., Thermostable Enzymes in Lignocellulase Hydrolysis, Adv. Biochem Engin/Biotechnol, 108, pp. 121-145, 2007.
Wood et al., The mechanism of fungal cellulose action; Synergism between enzyme components of Penicillium binophilum cellulose in solubilizing hydrogen bond-ordered cellulose, Biochem, J., 260, pp. 37-43, 1989.
Zhang et al., Toward an Aggregated Understanding of Enzymatic Hydrolysis of Cellulose: Noncomplexed Cellulase Systems, Biotechnology and Bioengineering, vol. 88, No. 7, pp. 797-824, 2004.
Broun et al, 1998, Science 282, 1315-1317.
Chica et al, 2005, Curr Opi Biotechnol 16, 378-384.
Devos et al, 2000, Proteins Stru, Fun, and Gene 41, 98-107.
Sen et al, 2007, Appl Biochem Biotechnol 143, 212-223.
Whisstock et al, 2003, Q Rev Biophysics 36(3), 307-340.
Wishart et al, 1995, J Biol Chem 270(45), 26782-26785.
Witkowski et al, 1999, Biochem J 38, 11643-11650.
Nierman et al, NCBI Access No. XP_748511.
Hong et al, 2003—EMBL Access No. AAL88714.
Birren et al, 2008—NCBI Access No. XP_001217291.
Kawaguchi et al, 1996—Uniprot Access No. P48825.
WO 2001-047944 A2—Geneseq Access No. AAL33603.
Rasmussen et al, 2006, Biotechnol Bioeng 94(5), 869-876.
WO 2009-108941 A2—EBI Accession No. AXR38839.
WO 2009-108941 A2—EBI Accession No. AXR38993.
WO 2009-108941 A2—EBI Accession No. AXR38839, , Univ Cent Florida Res Found Inc., Jan. 21, 2010.
WO 2009-108941 A2—EBI Accession No. AXR38993, Univ Cent Florida Res Found Inc., Jan. 21, 2010.
WO 2001-047944 A2—Geneseq Access No. AAL33603, Curagen Corp., Jan. 24, 2002.
Nierman et al, NCBI Access No. XP_748511, Feb. 19, 2008.

* cited by examiner

SEQUENCE LISTING

```
<160> NUMBER OF SEQ ID NOS: 305

<210> SEQ ID NO 1
<211> LENGTH: 1590
<212> TYPE: DNA
<213> ORGANISM: Chaetomium thermophilum

<400> SEQUENCE: 1

atgatgtaca agaagttcgc cgctctcgcc gccctcgtgg ctggcgccgc cgcccagcag      60

gcttgctccc tcaccactga gacccacccc agactcactt ggaagcgctg cacctctggc     120

ggcaactgct cgaccgtgaa cggcgccgtc accatcgatg ccaactggcg ctggactcac     180

accgtttccg gctcgaccaa ctgctacacc ggcaacgagt gggatacctc catctgctct     240

gatggcaaga gctgcgccca gacctgctgc gtcgacggcg ctgactactc ttcgacctat     300

ggtatcacca ccagcggtga ctccctgaac ctcaagttcg tcaccaagca ccagtacggc     360

accaatgtcg gctctcgtgt ctacctgatg gagaacgaca ccaagtacca gatgttcgag     420

ctcctcggca acgagttcac cttcgatgtc gatgtctcta acctgggctg cggtctcaac     480

ggtgccctct acttcgtctc catggacgct gatggtggta tgagcaagta ctctggcaac     540

aaggctggcg ccaagtacgg gacggggtac tgtgatgctc agtgcccgcg cgaccttaag     600

ttcatcaacg gcgaggccaa cattgagaac tggacccctt cgaccaatga tgccaacgcc     660

ggtttcggcc gctatggcag ctgctgctct gagatggata tctgggaggc caacaacatg     720

gctactgcct tcactcctca cccttgcacc attatcggcc agagccgctg cgagggcaac     780

agctgcggtg gcacctacag ctctgagcgc tatgctggtg tttgcgatcc tgatggctgc     840

gacttcaacg cctaccgcca gggcgacaag accttctacg gcaagggcat gaccgtcgac     900

accaccaaga agatgaccgt cgtcacccag ttccacaaga actcggctgg cgtcctcagc     960

gagatcaagc gcttctacgt tcaggacggc aaggtcattg ccaacgccga gtccaagatc    1020

cccggcaacc ccggcaactc catcacccag gagtggtgcg atgcccagaa ggtcgccttc    1080
```

-continued

```
ggtgacatcg atgacttcaa ccgcaagggc ggtatggctc agatgagcaa ggccctcgaa   1140

ggccctatgg tcctggtcat gtccgtctgg gatgaccact acgccaacat gctctggctc   1200

gactcgacct accccatcga caaggccggc acccccggcg ccgagcgcgg tgcttgcccg   1260

accacctccg gtgtccctgc cgagattgag gcccaggtcc ccaacagcaa cgtcatcttc   1320

tccaacatcc gcttcggccc catcggctcg accgtccctg gcctcgacgg cagcactccc   1380

agcaacccga ccgccaccgt tgctcctccc acttctacca ccagcgtgag aagcagcact   1440

actcagattt ccaccccgac tagccagccc ggcggctgca ccacccagaa gtggggccag   1500

tgcggtggta tcggctacac cggctgcact aactgcgttg ctggcactac ctgcactgag   1560

ctcaacccct ggtacagcca gtgcctgtaa                                    1590
```

<210> SEQ ID NO 2
<211> LENGTH: 529
<212> TYPE: PRT
<213> ORGANISM: Chaetomium thermophilum

<400> SEQUENCE: 2

```
Met Met Tyr Lys Lys Phe Ala Ala Leu Ala Ala Leu Val Ala Gly Ala
1               5                   10                  15

Ala Ala Gln Gln Ala Cys Ser Leu Thr Thr Glu Thr His Pro Arg Leu
            20                  25                  30

Thr Trp Lys Arg Cys Thr Ser Gly Gly Asn Cys Ser Thr Val Asn Gly
        35                  40                  45

Ala Val Thr Ile Asp Ala Asn Trp Arg Trp Thr His Thr Val Ser Gly
    50                  55                  60

Ser Thr Asn Cys Tyr Thr Gly Asn Glu Trp Asp Thr Ser Ile Cys Ser
65                  70                  75                  80

Asp Gly Lys Ser Cys Ala Gln Thr Cys Cys Val Asp Gly Ala Asp Tyr
                85                  90                  95

Ser Ser Thr Tyr Gly Ile Thr Thr Ser Gly Asp Ser Leu Asn Leu Lys
            100                 105                 110

Phe Val Thr Lys His Gln Tyr Gly Thr Asn Val Gly Ser Arg Val Tyr
        115                 120                 125

Leu Met Glu Asn Asp Thr Lys Tyr Gln Met Phe Glu Leu Leu Gly Asn
    130                 135                 140

Glu Phe Thr Phe Asp Val Asp Val Ser Asn Leu Gly Cys Gly Leu Asn
145                 150                 155                 160

Gly Ala Leu Tyr Phe Val Ser Met Asp Ala Asp Gly Gly Met Ser Lys
                165                 170                 175

Tyr Ser Gly Asn Lys Ala Gly Ala Lys Tyr Gly Thr Gly Tyr Cys Asp
            180                 185                 190

Ala Gln Cys Pro Arg Asp Leu Lys Phe Ile Asn Gly Glu Ala Asn Ile
        195                 200                 205

Glu Asn Trp Thr Pro Ser Thr Asn Asp Ala Asn Ala Gly Phe Gly Arg
    210                 215                 220

Tyr Gly Ser Cys Cys Ser Glu Met Asp Ile Trp Glu Ala Asn Asn Met
225                 230                 235                 240

Ala Thr Ala Phe Thr Pro His Pro Cys Thr Ile Ile Gly Gln Ser Arg
                245                 250                 255

Cys Glu Gly Asn Ser Cys Gly Gly Thr Tyr Ser Ser Glu Arg Tyr Ala
            260                 265                 270

Gly Val Cys Asp Pro Asp Gly Cys Asp Phe Asn Ala Tyr Arg Gln Gly
```

-continued

```
        275                 280                 285

Asp Lys Thr Phe Tyr Gly Lys Gly Met Thr Val Asp Thr Thr Lys Lys
    290                 295                 300

Met Thr Val Val Thr Gln Phe His Lys Asn Ser Ala Gly Val Leu Ser
305                 310                 315                 320

Glu Ile Lys Arg Phe Tyr Val Gln Asp Gly Lys Val Ile Ala Asn Ala
                325                 330                 335

Glu Ser Lys Ile Pro Gly Asn Pro Gly Asn Ser Ile Thr Gln Glu Trp
            340                 345                 350

Cys Asp Ala Gln Lys Val Ala Phe Gly Asp Ile Asp Asp Phe Asn Arg
        355                 360                 365

Lys Gly Gly Met Ala Gln Met Ser Lys Ala Leu Glu Gly Pro Met Val
    370                 375                 380

Leu Val Met Ser Val Trp Asp Asp His Tyr Ala Asn Met Leu Trp Leu
385                 390                 395                 400

Asp Ser Thr Tyr Pro Ile Asp Lys Ala Gly Thr Pro Gly Ala Glu Arg
                405                 410                 415

Gly Ala Cys Pro Thr Thr Ser Gly Val Pro Ala Glu Ile Glu Ala Gln
            420                 425                 430

Val Pro Asn Ser Asn Val Ile Phe Ser Asn Ile Arg Phe Gly Pro Ile
        435                 440                 445

Gly Ser Thr Val Pro Gly Leu Asp Gly Ser Thr Pro Ser Asn Pro Thr
    450                 455                 460

Ala Thr Val Ala Pro Pro Thr Ser Thr Thr Ser Val Arg Ser Ser Thr
465                 470                 475                 480

Thr Gln Ile Ser Thr Pro Thr Ser Gln Pro Gly Gly Cys Thr Thr Gln
                485                 490                 495

Lys Trp Gly Gln Cys Gly Gly Ile Gly Tyr Thr Gly Cys Thr Asn Cys
            500                 505                 510

Val Ala Gly Thr Thr Cys Thr Glu Leu Asn Pro Trp Tyr Ser Gln Cys
        515                 520                 525

Leu


<210> SEQ ID NO 3
<211> LENGTH: 1353
<212> TYPE: DNA
<213> ORGANISM: Myceliophthora thermophila

<400> SEQUENCE: 3

atgaagcagt acctccagta cctcgcggcg accctgcccc tggtgggcct ggccacggcc      60

cagcaggcgg gtaacctgca gaccgagact caccccaggc tcacttggtc caagtgcacg     120

gccccgggat cctgccaaca ggtcaacggc gaggtcgtca tcgactccaa ctggcgctgg     180

gtgcacgacg agaacgcgca gaactgctac gacggcaacc agtggaccaa cgcttgcagc     240

tctgccaccg actgcgccga gaattgcgcg ctcgagggtg ccgactacca gggcacctat     300

ggcgcctcga ccagcggcaa tgccctgacg ctcaccttcg tcactaagca cgagtacggc     360

accaacattg gctcgcgcct ctacctcatg aacggcgcga acaagtacca gatgttcacc     420

ctcaagggca acgagctggc cttcgacgtc gacctctcgg ccgtcgagtg cggcctcaac     480

agcgccctct acttcgtggc catggaggag gatggcggtg tgtcgagcta cccgaccaac     540

acggccggtg ctaagttcgg cactgggtac tgcgacgccc aatgcgcacg cgacctcaag     600

ttcgtcggcg gcaagggcaa catcgagggc tggaagccgt ccaccaacga tgccaatgcc     660
```

```
ggtgtcggtc cttatggcgg gtgctgcgct gagatcgacg tctgggagtc gaacaagtat    720

gctttcgctt tcaccccgca cggttgcgag aaccctaaat accacgtctg cgagaccacc    780

aactgcggtg gcacctactc cgaggaccgc ttcgctggtg actgcgatgc caacggctgc    840

gactacaacc cctaccgcat gggcaaccag gacttctacg gtcccggctt gacggtcgat    900

accagcaaga agttcaccgt cgtcagccag ttcgaggaga acaagctcac ccagttcttc    960

gtccaggacg gcaagaagat tgagatcccc ggccccaagg tcgagggcat cgatgcggac   1020

agcgccgcta tcacccctga gctgtgcagt gccctgttca aggccttcga tgaccgtgac   1080

cgcttctcgg aggttggcgg cttcgatgcc atcaacacgg ccctcagcac tcccatggtc   1140

ctcgtcatgt ccatctggga tgatcactac gccaatatgc tctggctcga ctcgagctac   1200

ccccctgaga aggctggcca gcctggcggt gaccgtggcc cgtgtcctca ggactctggc   1260

gtcccggccg acgttgaggc tcagtaccct aatgccaagg tcatctggtc caacatccgc   1320

ttcggcccca tcggctcgac tgtcaacgtc taa                                1353


<210> SEQ ID NO 4
<211> LENGTH: 450
<212> TYPE: PRT
<213> ORGANISM: Myceliophthora thermophila

<400> SEQUENCE: 4

Met Lys Gln Tyr Leu Gln Tyr Leu Ala Ala Thr Leu Pro Leu Val Gly
1               5                   10                  15

Leu Ala Thr Ala Gln Gln Ala Gly Asn Leu Gln Thr Glu Thr His Pro
            20                  25                  30

Arg Leu Thr Trp Ser Lys Cys Thr Ala Pro Gly Ser Cys Gln Gln Val
        35                  40                  45

Asn Gly Glu Val Val Ile Asp Ser Asn Trp Arg Trp Val His Asp Glu
    50                  55                  60

Asn Ala Gln Asn Cys Tyr Asp Gly Asn Gln Trp Thr Asn Ala Cys Ser
65                  70                  75                  80

Ser Ala Thr Asp Cys Ala Glu Asn Cys Ala Leu Glu Gly Ala Asp Tyr
                85                  90                  95

Gln Gly Thr Tyr Gly Ala Ser Thr Ser Gly Asn Ala Leu Thr Leu Thr
            100                 105                 110

Phe Val Thr Lys His Glu Tyr Gly Thr Asn Ile Gly Ser Arg Leu Tyr
        115                 120                 125

Leu Met Asn Gly Ala Asn Lys Tyr Gln Met Phe Thr Leu Lys Gly Asn
    130                 135                 140

Glu Leu Ala Phe Asp Val Asp Leu Ser Ala Val Glu Cys Gly Leu Asn
145                 150                 155                 160

Ser Ala Leu Tyr Phe Val Ala Met Glu Glu Asp Gly Gly Val Ser Ser
                165                 170                 175

Tyr Pro Thr Asn Thr Ala Gly Ala Lys Phe Gly Thr Gly Tyr Cys Asp
            180                 185                 190

Ala Gln Cys Ala Arg Asp Leu Lys Phe Val Gly Gly Lys Gly Asn Ile
        195                 200                 205

Glu Gly Trp Lys Pro Ser Thr Asn Asp Ala Asn Ala Gly Val Gly Pro
    210                 215                 220

Tyr Gly Gly Cys Cys Ala Glu Ile Asp Val Trp Glu Ser Asn Lys Tyr
225                 230                 235                 240

Ala Phe Ala Phe Thr Pro His Gly Cys Glu Asn Pro Lys Tyr His Val
                245                 250                 255
```

-continued

```
Cys Glu Thr Thr Asn Cys Gly Gly Thr Tyr Ser Glu Asp Arg Phe Ala
            260                 265                 270

Gly Asp Cys Asp Ala Asn Gly Cys Asp Tyr Asn Pro Tyr Arg Met Gly
        275                 280                 285

Asn Gln Asp Phe Tyr Gly Pro Gly Leu Thr Val Asp Thr Ser Lys Lys
    290                 295                 300

Phe Thr Val Val Ser Gln Phe Glu Glu Asn Lys Leu Thr Gln Phe Phe
305                 310                 315                 320

Val Gln Asp Gly Lys Lys Ile Glu Ile Pro Gly Pro Lys Val Glu Gly
                325                 330                 335

Ile Asp Ala Asp Ser Ala Ala Ile Thr Pro Glu Leu Cys Ser Ala Leu
            340                 345                 350

Phe Lys Ala Phe Asp Asp Arg Asp Arg Phe Ser Glu Val Gly Gly Phe
        355                 360                 365

Asp Ala Ile Asn Thr Ala Leu Ser Thr Pro Met Val Leu Val Met Ser
    370                 375                 380

Ile Trp Asp Asp His Tyr Ala Asn Met Leu Trp Leu Asp Ser Ser Tyr
385                 390                 395                 400

Pro Pro Glu Lys Ala Gly Gln Pro Gly Gly Asp Arg Gly Pro Cys Pro
                405                 410                 415

Gln Asp Ser Gly Val Pro Ala Asp Val Glu Ala Gln Tyr Pro Asn Ala
            420                 425                 430

Lys Val Ile Trp Ser Asn Ile Arg Phe Gly Pro Ile Gly Ser Thr Val
        435                 440                 445

Asn Val
    450
```

<210> SEQ ID NO 5
<211> LENGTH: 1599
<212> TYPE: DNA
<213> ORGANISM: Aspergillus fumigatus

<400> SEQUENCE: 5

```
atgctggcct ccaccttctc ctaccgcatg tacaagaccg cgctcatcct ggccgccctt     60

ctgggctctg gccaggctca gcaggtcggt acttcccagg cggaagtgca tccgtccatg    120

acctggcaga gctgcacggc tggcggcagc tgcaccacca acaacggcaa ggtggtcatc    180

gacgcgaact ggcgttgggt gcacaaagtc ggcgactaca ccaactgcta caccggcaac    240

acctgggaca cgactatctg ccctgacgat gcgacctgcg catccaactg cgcccttgag    300

ggtgccaact acgaatccac ctatggtgtg accgccagcg gcaattccct ccgcctcaac    360

ttcgtcacca ccagccagca gaagaacatt ggctcgcgtc tgtacatgat gaaggacgac    420

tcgacctacg agatgtttaa gctgctgaac caggagttca ccttcgatgt cgatgtctcc    480

aacctcccct gcggtctcaa cggtgctctg tactttgtcg ccatggacgc cgacggtggc    540

atgtccaagt acccaaccaa caaggccggt gccaagtacg gtactggata ctgtgactcg    600

cagtgccctc gcgacctcaa gttcatcaac ggtcaggcca acgtcgaagg gtggcagccc    660

tcctccaacg atgccaatgc gggtaccggc aaccacgggt cctgctgcgc ggagatggat    720

atctgggagg ccaacagcat ctccacggcc ttcacccccc atccgtgcga cacgcccggc    780

caggtgatgt gcaccggtga tgcctgcggt ggcacctaca gctccgaccg ctacggcggc    840

acctgcgacc ccgacggatg tgatttcaac tccttccgcc agggcaacaa gaccttctac    900

ggccctggca tgaccgtcga caccaagagc aagtttaccg tcgtcaccca gttcatcacc    960
```

-continued

```
gacgacggca cctccagcgg caccctcaag gagatcaagc gcttctacgt gcagaacggc   1020

aaggtgatcc ccaactcgga gtcgacctgg accggcgtca gcggcaactc catcaccacc   1080

gagtactgca ccgcccagaa gagcctgttc caggaccaga acgtcttcga aaagcacggc   1140

ggcctcgagg gcatgggtgc tgccctcgcc cagggtatgg ttctcgtcat gtccctgtgg   1200

gatgatcact cggccaacat gctctggctc gacagcaact acccgaccac tgcctcttcc   1260

accactcccg gcgtcgcccg tggtacctgc gacatctcct ccggcgtccc tgcggatgtc   1320

gaggcgaacc accccgacgc ctacgtcgtc tactccaaca tcaaggtcgg ccccatcggc   1380

tcgaccttca acagcggtgg ctcgaacccc ggtggcggaa ccaccacgac aactaccacc   1440

cagcctacta ccaccacgac cacggctgga aaccctggcg gcaccggagt cgcacagcac   1500

tatggccagt gtggtggaat cggatggacc ggacccacaa cctgtgccag cccttatacc   1560

tgccagaagc tgaatgatta ttactctcag tgcctgtag                          1599
```

```
<210> SEQ ID NO 6
<211> LENGTH: 532
<212> TYPE: PRT
<213> ORGANISM: Aspergillus fumigatus

<400> SEQUENCE: 6

Met Leu Ala Ser Thr Phe Ser Tyr Arg Met Tyr Lys Thr Ala Leu Ile
1               5                   10                  15

Leu Ala Ala Leu Leu Gly Ser Gly Gln Ala Gln Gln Val Gly Thr Ser
            20                  25                  30

Gln Ala Glu Val His Pro Ser Met Thr Trp Gln Ser Cys Thr Ala Gly
        35                  40                  45

Gly Ser Cys Thr Thr Asn Asn Gly Lys Val Val Ile Asp Ala Asn Trp
    50                  55                  60

Arg Trp Val His Lys Val Gly Asp Tyr Thr Asn Cys Tyr Thr Gly Asn
65                  70                  75                  80

Thr Trp Asp Thr Thr Ile Cys Pro Asp Asp Ala Thr Cys Ala Ser Asn
                85                  90                  95

Cys Ala Leu Glu Gly Ala Asn Tyr Glu Ser Thr Tyr Gly Val Thr Ala
            100                 105                 110

Ser Gly Asn Ser Leu Arg Leu Asn Phe Val Thr Thr Ser Gln Gln Lys
        115                 120                 125

Asn Ile Gly Ser Arg Leu Tyr Met Met Lys Asp Asp Ser Thr Tyr Glu
    130                 135                 140

Met Phe Lys Leu Leu Asn Gln Glu Phe Thr Phe Asp Val Asp Val Ser
145                 150                 155                 160

Asn Leu Pro Cys Gly Leu Asn Gly Ala Leu Tyr Phe Val Ala Met Asp
                165                 170                 175

Ala Asp Gly Gly Met Ser Lys Tyr Pro Thr Asn Lys Ala Gly Ala Lys
            180                 185                 190

Tyr Gly Thr Gly Tyr Cys Asp Ser Gln Cys Pro Arg Asp Leu Lys Phe
        195                 200                 205

Ile Asn Gly Gln Ala Asn Val Glu Gly Trp Gln Pro Ser Ser Asn Asp
    210                 215                 220

Ala Asn Ala Gly Thr Gly Asn His Gly Ser Cys Cys Ala Glu Met Asp
225                 230                 235                 240

Ile Trp Glu Ala Asn Ser Ile Ser Thr Ala Phe Thr Pro His Pro Cys
                245                 250                 255
```

```
Asp Thr Pro Gly Gln Val Met Cys Thr Gly Asp Ala Cys Gly Gly Thr
            260                 265                 270

Tyr Ser Ser Asp Arg Tyr Gly Gly Thr Cys Asp Pro Asp Gly Cys Asp
        275                 280                 285

Phe Asn Ser Phe Arg Gln Gly Asn Lys Thr Phe Tyr Gly Pro Gly Met
    290                 295                 300

Thr Val Asp Thr Lys Ser Lys Phe Thr Val Val Thr Gln Phe Ile Thr
305                 310                 315                 320

Asp Asp Gly Thr Ser Ser Gly Thr Leu Lys Glu Ile Lys Arg Phe Tyr
                325                 330                 335

Val Gln Asn Gly Lys Val Ile Pro Asn Ser Glu Ser Thr Trp Thr Gly
            340                 345                 350

Val Ser Gly Asn Ser Ile Thr Thr Glu Tyr Cys Thr Ala Gln Lys Ser
        355                 360                 365

Leu Phe Gln Asp Gln Asn Val Phe Glu Lys His Gly Gly Leu Glu Gly
    370                 375                 380

Met Gly Ala Ala Leu Ala Gln Gly Met Val Leu Val Met Ser Leu Trp
385                 390                 395                 400

Asp Asp His Ser Ala Asn Met Leu Trp Leu Asp Ser Asn Tyr Pro Thr
                405                 410                 415

Thr Ala Ser Ser Thr Thr Pro Gly Val Ala Arg Gly Thr Cys Asp Ile
            420                 425                 430

Ser Ser Gly Val Pro Ala Asp Val Glu Ala Asn His Pro Asp Ala Tyr
        435                 440                 445

Val Val Tyr Ser Asn Ile Lys Val Gly Pro Ile Gly Ser Thr Phe Asn
    450                 455                 460

Ser Gly Gly Ser Asn Pro Gly Gly Gly Thr Thr Thr Thr Thr Thr Thr
465                 470                 475                 480

Gln Pro Thr Thr Thr Thr Thr Thr Ala Gly Asn Pro Gly Gly Thr Gly
                485                 490                 495

Val Ala Gln His Tyr Gly Gln Cys Gly Gly Ile Gly Trp Thr Gly Pro
            500                 505                 510

Thr Thr Cys Ala Ser Pro Tyr Thr Cys Gln Lys Leu Asn Asp Tyr Tyr
        515                 520                 525

Ser Gln Cys Leu
    530


<210> SEQ ID NO 7
<211> LENGTH: 1374
<212> TYPE: DNA
<213> ORGANISM: Thermoascus aurantiacus

<400> SEQUENCE: 7

atgtatcagc gcgctcttct cttctctttc ttcctctccg ccgcccgcgc gcagcaggcc     60

ggtaccctaa ccgcagagaa tcacccttcc ctgacctggc agcaatgctc cagcggcggt    120

agttgtacca cgcagaatgg aaaagtcgtt atcgatgcga actggcgttg ggtccatacc    180

acctctggat acaccaactg ctacacgggc aatacgtggg acaccagtat ctgtcccgac    240

gacgtgacct gcgctcagaa ttgtgccttg gatggagcgg attacagtgg cacctatggt    300

gttacgacca gtggcaacgc cctgagactg aactttgtca cccaaagctc agggaagaac    360

attggctcgc gcctgtacct gctgcaggac gacaccactt atcagatctt caagctgctg    420

ggtcaggagt ttaccttcga tgtcgacgtc tccaatctcc cttgcgggct gaacggcgcc    480

ctctactttg tggccatgga cgccgacggc ggattgtcca aataccctgg caacaaggca    540
```

-continued

```
ggcgctaagt atggcactgg ttactgcgac tctcagtgcc ctcgggatct caagttcatc    600

aacggtcagg ccaacgttga aggctggcag ccgtctgcca acgacccaaa tgccggcgtt    660

ggtaaccacg gttcctgctg cgctgagatg gatgtctggg aagccaacag catctctact    720

gcggtgacgc ctcacccatg cgacaccccc ggccagacca tgtgccaggg agacgactgt    780

ggtggaacct actcctccac tcgatatgct ggtacctgcg accctgatgg ctgcgacttc    840

aatccttacc gccagggcaa ccactcgttc tacggccccg ggaagatcgt cgacactagc    900

tccaaattca ccgtcgtcac ccagttcatc accgacgacg ggacccccctc cggcaccctg    960

acggagatca aacgcttcta cgtccagaac ggcaaggtga tcccccagtc ggagtcgacg   1020

atcagcggcg tcaccggcaa ctcaatcacc accgagtatt gcacggccca gaaggccgcc   1080

ttcggcgaca acaccggctt cttcacgcac ggcgggcttc agaagatcag tcaggctctg   1140

gctcagggca tggtcctcgt catgagcctg tgggacgatc acgccgccaa catgctctgg   1200

ctggacagca cctacccgac tgatgcggac ccggacaccc ctggcgtcgc gcgcggtacc   1260

tgccccacga cctccggcgt cccggccgac gttgagtcgc agaaccccaa ttcatatgtt   1320

atctactcca acatcaaggt cggacccatc aactcgacct tcaccgccaa ctaa         1374
```

```
<210> SEQ ID NO 8
<211> LENGTH: 420
<212> TYPE: PRT
<213> ORGANISM: Thermoascus aurantiacus

<400> SEQUENCE: 8

Met Tyr Gln Arg Ala Leu Leu Phe Ser Phe Phe Leu Ser Ala Ala Arg
1               5                   10                  15

Ala Gln Gln Ala Gly Thr Leu Thr Ala Glu Asn His Pro Ser Leu Thr
            20                  25                  30

Trp Gln Gln Cys Ser Ser Gly Gly Ser Cys Thr Thr Gln Asn Gly Lys
        35                  40                  45

Val Val Ile Asp Ala Asn Trp Arg Trp Val His Thr Thr Ser Gly Tyr
    50                  55                  60

Thr Asn Cys Tyr Thr Gly Asn Thr Trp Asp Thr Ser Ile Cys Pro Asp
65                  70                  75                  80

Asp Val Thr Cys Ala Gln Asn Cys Ala Leu Asp Gly Ala Asp Tyr Ser
                85                  90                  95

Gly Thr Tyr Gly Val Thr Thr Ser Gly Asn Ala Leu Arg Leu Asn Phe
            100                 105                 110

Val Thr Gln Ser Ser Gly Lys Asn Ile Gly Ser Arg Leu Tyr Leu Leu
        115                 120                 125

Gln Asp Asp Thr Thr Tyr Gln Ile Phe Lys Leu Leu Gly Gln Glu Phe
    130                 135                 140

Thr Phe Asp Val Asp Val Ser Asn Leu Pro Cys Gly Leu Asn Gly Ala
145                 150                 155                 160

Leu Tyr Phe Val Ala Met Asp Ala Asp Gly Gly Leu Ser Lys Tyr Pro
                165                 170                 175

Gly Asn Lys Ala Gly Ala Lys Tyr Gly Thr Gly Tyr Cys Asp Ser Gln
            180                 185                 190

Cys Pro Arg Asp Leu Lys Phe Ile Asn Gly Gln Ala Asn Val Glu Gly
        195                 200                 205

Trp Gln Pro Ser Ala Asn Asp Pro Asn Ala Gly Val Gly Asn His Gly
    210                 215                 220
```

```
Ser Cys Cys Ala Glu Met Asp Val Trp Glu Ala Asn Ser Ile Ser Thr
225                 230                 235                 240

Ala Val Thr Pro His Pro Cys Asp Thr Pro Gly Gln Thr Met Cys Gln
                245                 250                 255

Gly Asp Asp Cys Gly Gly Thr Tyr Ser Ser Thr Arg Tyr Ala Gly Thr
            260                 265                 270

Cys Asp Pro Asp Gly Cys Asp Phe Asn Pro Tyr Arg Gln Gly Asn His
        275                 280                 285

Ser Phe Tyr Gly Pro Gly Lys Ile Val Asp Thr Ser Ser Lys Phe Thr
    290                 295                 300

Val Val Thr Gln Phe Ile Thr Asp Asp Gly Thr Pro Ser Gly Thr Leu
305                 310                 315                 320

Thr Glu Ile Lys Arg Phe Tyr Val Gln Asn Gly Lys Val Ile Pro Gln
                325                 330                 335

Ser Glu Ser Thr Ile Ser Gly Val Thr Gly Asn Ser Ile Thr Thr Glu
            340                 345                 350

Tyr Cys Thr Ala Gln Lys Ala Ala Phe Gly Asp Asn Thr Gly Phe Phe
        355                 360                 365

Thr His Gly Gly Leu Gln Lys Ile Ser Gln Ala Leu Ala Gln Gly Met
    370                 375                 380

Val Leu Val Met Ser Leu Trp Asp Asp His Ala Ala Asn Met Leu Trp
385                 390                 395                 400

Leu Asp Ser Thr Tyr Pro Thr Asp Ala Asp Pro Asp Thr Pro Gly Val
                405                 410                 415

Ala Arg Gly Thr
            420
```

<210> SEQ ID NO 9
<211> LENGTH: 1802
<212> TYPE: DNA
<213> ORGANISM: Myceliophthora thermophila

<400> SEQUENCE: 9

```
atggccaaga agcttttcat caccgccgcg cttgcggctg ccgtgttggc ggcccccgtc      60

attgaggagc gccagaactg cggcgctgtg tggtaagaaa gcccggtccg agtctcccat     120

gattttctcg tcgagtaatg gcataagggc cacccccttcg actgaccgtg agaatcgatc    180

aaatccagga ctcaatgcgg cggtaacggg tggcaaggtc ccacatgctg cgcctcgggc     240

tcgacctgcg ttgcgcagaa cgagtggtac tctcagtgcc tgcccaacag ccaggtgacg     300

agttccacca ctccgtcgtc gacttccacc tcgcagcgca gcaccagcac ctccagcagc     360

accaccagga gcggcagctc ctcctcctcc tccaccacgc ccccgcccgt ctccagcccc     420

gtgaccagca ttcccggcgg tgcgacctcc acggcgagct actctggcaa ccccttctcg     480

ggcgtccggc tcttcgccaa cgactactac aggtccgagg tccacaatct cgccattcct     540

agcatgactg gtactctggc ggccaaggct tccgccgtcg ccgaagtccc tagcttccag     600

tggctcgacc ggaacgtcac catcgacacc ctgatggtcc agactctgtc ccaggtccgg     660

gctctcaata aggccggtgc caatcctccc tatgctggtg agttacatgg cgacttgcct     720

tctcgtcccc tacctttctt gacgggatcg gttacctgac ctggaggcaa aacaacaaca     780

gcccaactcg tcgtctacga cctccccgac cgtgactgtg ccgccgctgc gtccaacggc     840

gagttttcga ttgcaaacgg cggcgccgcc aactacagga gctacatcga cgctatccgc     900

aagcacatca ttgagtactc ggacatccgg atcatcctgg ttatcgagcc cgactcgatg     960
```

-continued

```
gccaacatgg tgaccaacat gaacgtggcc aagtgcagca acgccgcgtc gacgtaccac   1020

gagttgaccg tgtacgcgct caagcagctg aacctgccca acgtcgccat gtatctcgac   1080

gccggccacg ccggctggct cggctggccc gccaacatcc agcccgccgc cgagctgttt   1140

gccggcatct acaatgatgc cggcaagccg gctgccgtcc gcggcctggc cactaacgtc   1200

gccaactaca acgcctggag catcgcttcg gccccgtcgt acacgtcgcc taaccctaac   1260

tacgacgaga agcactacat cgaggccttc agcccgctct tgaactcggc cggcttcccc   1320

gcacgcttca ttgtcgacac tggccgcaac ggcaaacaac ctaccggtat gtttttttt   1380

cttttgtctc tgtccccccc ttttctcccc cttcagttgg cgtccacaag gtctcttagt   1440

cctgcttcat ctgtgaccaa cctccccccc cccggcaccg cccacaaccg tttgactcta   1500

tactcttggg aatgggcgcc gaaactgacc gttccacagg ccaacaacag tggggtgact   1560

ggtgcaatgt caagggcacc ggctttggcg tgcgcccgac ggccaacacg ggccacgagc   1620

tggtcgatgc ctttgtctgg gtcaagcccg gcggcgagtc cgacggcaca agcgacacca   1680

gcgccgcccg ctacgactac cactgcggcc tgtccgatgc cctgcagcct gcccccgagg   1740

ctggacagtg gttccaggcc tacttcgagc agctgctcac caacgccaac ccgcccttct   1800

aa                                                                  1802
```

<210> SEQ ID NO 10
<211> LENGTH: 481
<212> TYPE: PRT
<213> ORGANISM: Myceliophthora thermophila

<400> SEQUENCE: 10

```
Met Ala Lys Lys Leu Phe Ile Thr Ala Ala Leu Ala Ala Ala Val Leu
1               5                   10                  15

Ala Ala Pro Val Ile Glu Glu Arg Gln Asn Cys Gly Ala Val Trp Thr
            20                  25                  30

Gln Cys Gly Gly Asn Gly Trp Gln Gly Pro Thr Cys Cys Ala Ser Gly
        35                  40                  45

Ser Thr Cys Val Ala Gln Asn Glu Trp Tyr Ser Gln Cys Leu Pro Asn
    50                  55                  60

Ser Gln Val Thr Ser Ser Thr Thr Pro Ser Ser Thr Ser Thr Ser Gln
65                  70                  75                  80

Arg Ser Thr Ser Thr Ser Ser Ser Thr Thr Arg Ser Gly Ser Ser Ser
                85                  90                  95

Ser Ser Ser Thr Thr Pro Pro Pro Val Ser Ser Pro Val Thr Ser Ile
            100                 105                 110

Pro Gly Gly Ala Thr Ser Thr Ala Ser Tyr Ser Gly Asn Pro Phe Ser
        115                 120                 125

Gly Val Arg Leu Phe Ala Asn Asp Tyr Tyr Arg Ser Glu Val His Asn
    130                 135                 140

Leu Ala Ile Pro Ser Met Thr Gly Thr Leu Ala Ala Lys Ala Ser Ala
145                 150                 155                 160

Val Ala Glu Val Pro Ser Phe Gln Trp Leu Asp Arg Asn Val Thr Ile
                165                 170                 175

Asp Thr Leu Met Val Gln Thr Leu Ser Gln Val Arg Ala Leu Asn Lys
            180                 185                 190

Ala Gly Ala Asn Pro Pro Tyr Ala Ala Gln Leu Val Val Tyr Asp Leu
        195                 200                 205

Pro Asp Arg Asp Cys Ala Ala Ala Ala Ser Asn Gly Glu Phe Ser Ile
    210                 215                 220
```

Ala Asn Gly Gly Ala Ala Asn Tyr Arg Ser Tyr Ile Asp Ala Ile Arg
225 230 235 240

Lys His Ile Ile Glu Tyr Ser Asp Ile Arg Ile Ile Leu Val Ile Glu
245 250 255

Pro Asp Ser Met Ala Asn Met Val Thr Asn Met Asn Val Ala Lys Cys
260 265 270

Ser Asn Ala Ala Ser Thr Tyr His Glu Leu Thr Val Tyr Ala Leu Lys
275 280 285

Gln Leu Asn Leu Pro Asn Val Ala Met Tyr Leu Asp Ala Gly His Ala
290 295 300

Gly Trp Leu Gly Trp Pro Ala Asn Ile Gln Pro Ala Ala Glu Leu Phe
305 310 315 320

Ala Gly Ile Tyr Asn Asp Ala Gly Lys Pro Ala Ala Val Arg Gly Leu
325 330 335

Ala Thr Asn Val Ala Asn Tyr Asn Ala Trp Ser Ile Ala Ser Ala Pro
340 345 350

Ser Tyr Thr Ser Pro Asn Pro Asn Tyr Asp Glu Lys His Tyr Ile Glu
355 360 365

Ala Phe Ser Pro Leu Leu Asn Ser Ala Gly Phe Pro Ala Arg Phe Ile
370 375 380

Val Asp Thr Gly Arg Asn Gly Lys Gln Pro Thr Gly Gln Gln Gln Trp
385 390 395 400

Gly Asp Trp Cys Asn Val Lys Gly Thr Gly Phe Gly Val Arg Pro Thr
405 410 415

Ala Asn Thr Gly His Glu Leu Val Asp Ala Phe Val Trp Val Lys Pro
420 425 430

Gly Gly Glu Ser Asp Gly Thr Ser Asp Thr Ser Ala Ala Arg Tyr Asp
435 440 445

Tyr His Cys Gly Leu Ser Asp Ala Leu Gln Pro Ala Pro Glu Ala Gly
450 455 460

Gln Trp Phe Gln Ala Tyr Phe Glu Gln Leu Leu Thr Asn Ala Asn Pro
465 470 475 480

Pro

<210> SEQ ID NO 11
<211> LENGTH: 1812
<212> TYPE: DNA
<213> ORGANISM: Myceliophthora thermophila

<400> SEQUENCE: 11
atggccaaga agcttttcat caccgccgcc cttgcggctg ccgtgttggc ggcccccgtc 60
attgaggagc gccagaactg cggcgctgtg tggtaagaaa gcccggtctg agtttcccat 120
gactttctca tcgagtaatg gcataaggcc cacccccttcg actgactgtg agaatcgatc 180
aaatccagga ctcaatgcgg cggcaacggg tggcagggtc ccacatgctg cgcctcgggc 240
tcgacctgcg ttgcgcagaa cgagtggtac tctcagtgcc tgcccaacaa tcaggtgacg 300
agttccaaca ctccgtcgtc gacttccacc tcgcagcgca gcagcagcac ctccagcagc 360
agcaccagga gcggcagctc ctcctcctcc accaccacgc cccctcccgt ctccagcccc 420
gtgactagca ttcccggcgg tgcgaccacc acggcgagct actctggcaa ccccttctcg 480
ggcgtccggc tcttcgccaa cgactactac aggtccgagg tccacaatct cgccattcct 540
agcatgaccg gtactctggc ggccaaggct tccgccgtcg ccgaagtccc tagcttccag 600

-continued

```
tggctcgacc ggaacgtcac catcgacacc ctgatggtcc agactctgtc ccagatccgg    660

gctgccaata atgccggtgc caatcctccc tatgctggtg agttacatgg cggcgacttg    720

ccttctcgtc ccccaccttt cttgacggga tcggttacct gacctggagg caaaacaaaa    780

ccagcccaac ttgtcgtcta cgacctcccc gaccgtgact gcgccgccgc tgcgtccaac    840

ggcgagtttt cgattgcaaa cggcggcgcc gccaactaca ggagctacat cgacgctatc    900

cgcaagcaca tcattgagta ctcggacatc cggatcatcc tggttatcga gcccgactcg    960

atggccaaca tggtgaccaa catgaacgtg gccaagtgca gcaacgccgc gtcgacgtac   1020

cacgagttga ccgtgtacgc gctcaagcag ctgaacctgc ccaacgtcgc catgtatctc   1080

gacgccggcc acgccggctg gctcggctgg cccgccaaca tccagcccgc cgccgacctg   1140

tttgccggca tctacaatga cgccggcaag ccggctgccg tccgcggcct ggccactaac   1200

gtcgccaact acaacgcctg gagtatcgct tcggccccgt cgtacacgtc ccctaaccct   1260

aactacgacg agaagcacta catcgaggcc ttcagcccgc tcctgaacgc ggccggcttc   1320

cccgcacgct tcattgtcga cactggccgc aacggcaaac aacctaccgg tatggttttt   1380

ttcttttttt ttctctgttc ccctccccct tccccttcag ttggcgtcca caaggtctct   1440

tagtcttgct tcttctcgga ccaaccttcc cccaccccca aaacgcaccg cccacaaccg   1500

ttcgactcta tactcttggg aatgggcgcc gaaactgacc gttcgacagg ccaacaacag   1560

tggggtgact ggtgcaatgt caagggcact ggctttggcg tgcgcccgac ggccaacacg   1620

ggccacgacc tggtcgatgc ctttgtctgg gtcaagcccg gcggcgagtc cgacggcaca   1680

agcgacacca gcgccgcccg ctacgactac cactgcggcc tgtccgatgc cctgcagcct   1740

gctccggagg ctggacagtg gttccaggcc tacttcgagc agctgctcac caacgccaac   1800

ccgcccttct aa                                                      1812
```

<210> SEQ ID NO 12
<211> LENGTH: 482
<212> TYPE: PRT
<213> ORGANISM: Myceliophthora thermophila

<400> SEQUENCE: 12

```
Met Ala Lys Lys Leu Phe Ile Thr Ala Ala Leu Ala Ala Ala Val Leu
1               5                   10                  15

Ala Ala Pro Val Ile Glu Glu Arg Gln Asn Cys Gly Ala Val Trp Thr
            20                  25                  30

Gln Cys Gly Gly Asn Gly Trp Gln Gly Pro Thr Cys Cys Ala Ser Gly
        35                  40                  45

Ser Thr Cys Val Ala Gln Asn Glu Trp Tyr Ser Gln Cys Leu Pro Asn
    50                  55                  60

Asn Gln Val Thr Ser Ser Asn Thr Pro Ser Ser Thr Ser Thr Ser Gln
65                  70                  75                  80

Arg Ser Ser Ser Thr Ser Ser Ser Ser Thr Arg Ser Gly Ser Ser Ser
                85                  90                  95

Ser Ser Thr Thr Thr Pro Pro Pro Val Ser Ser Pro Val Thr Ser Ile
            100                 105                 110

Pro Gly Gly Ala Thr Thr Thr Ala Ser Tyr Ser Gly Asn Pro Phe Ser
        115                 120                 125

Gly Val Arg Leu Phe Ala Asn Asp Tyr Tyr Arg Ser Glu Val His Asn
    130                 135                 140

Leu Ala Ile Pro Ser Met Thr Gly Thr Leu Ala Ala Lys Ala Ser Ala
145                 150                 155                 160
```

-continued

```
Val Ala Glu Val Pro Ser Phe Gln Trp Leu Asp Arg Asn Val Thr Ile
                165                 170                 175

Asp Thr Leu Met Val Gln Thr Leu Ser Gln Ile Arg Ala Ala Asn Asn
            180                 185                 190

Ala Gly Ala Asn Pro Pro Tyr Ala Ala Gln Leu Val Val Tyr Asp Leu
        195                 200                 205

Pro Asp Arg Asp Cys Ala Ala Ala Ala Ser Asn Gly Glu Phe Ser Ile
    210                 215                 220

Ala Asn Gly Gly Ala Ala Asn Tyr Arg Ser Tyr Ile Asp Ala Ile Arg
225                 230                 235                 240

Lys His Ile Ile Glu Tyr Ser Asp Ile Arg Ile Ile Leu Val Ile Glu
                245                 250                 255

Pro Asp Ser Met Ala Asn Met Val Thr Asn Met Asn Val Ala Lys Cys
            260                 265                 270

Ser Asn Ala Ala Ser Thr Tyr His Glu Leu Thr Val Tyr Ala Leu Lys
        275                 280                 285

Gln Leu Asn Leu Pro Asn Val Ala Met Tyr Leu Asp Ala Gly His Ala
    290                 295                 300

Gly Trp Leu Gly Trp Pro Ala Asn Ile Gln Pro Ala Ala Asp Leu Phe
305                 310                 315                 320

Ala Gly Ile Tyr Asn Asp Ala Gly Lys Pro Ala Ala Val Arg Gly Leu
                325                 330                 335

Ala Thr Asn Val Ala Asn Tyr Asn Ala Trp Ser Ile Ala Ser Ala Pro
            340                 345                 350

Ser Tyr Thr Ser Pro Asn Pro Asn Tyr Asp Glu Lys His Tyr Ile Glu
        355                 360                 365

Ala Phe Ser Pro Leu Leu Asn Ala Ala Gly Phe Pro Ala Arg Phe Ile
    370                 375                 380

Val Asp Thr Gly Arg Asn Gly Lys Gln Pro Thr Gly Gln Gln Gln Trp
385                 390                 395                 400

Gly Asp Trp Cys Asn Val Lys Gly Thr Gly Phe Gly Val Arg Pro Thr
                405                 410                 415

Ala Asn Thr Gly His Asp Leu Val Asp Ala Phe Val Trp Val Lys Pro
            420                 425                 430

Gly Gly Glu Ser Asp Gly Thr Ser Asp Thr Ser Ala Ala Arg Tyr Asp
        435                 440                 445

Tyr His Cys Gly Leu Ser Asp Ala Leu Gln Pro Ala Pro Glu Ala Gly
    450                 455                 460

Gln Trp Phe Gln Ala Tyr Phe Glu Gln Leu Leu Thr Asn Ala Asn Pro
465                 470                 475                 480

Pro Phe


<210> SEQ ID NO 13
<211> LENGTH: 1446
<212> TYPE: DNA
<213> ORGANISM: Thielavia terrestris

<400> SEQUENCE: 13

atggctcaga agctccttct cgccgccgcc cttgcggcca gcgccctcgc tgctcccgtc      60

gtcgaggagc gccagaactg cggttccgtc tggagccaat gcggcggcat tggctggtcc     120

ggcgcgacct gctgcgcttc gggcaatacc tgcgttgagc tgaacccgta ctactcgcag     180

tgcctgccca acagccaggt gactacctcg accagcaaga ccacctccac caccaccagg     240
```

```
agcagcacca ccagccacag cagcggtccc accagcacga gcaccaccac caccagcagt    300

cccgtggtca ctaccccgcc gagtacctcc atccccggcg gtgcctcgtc aacggccagc    360

tggtccggca acccgttctc gggcgtgcag atgtgggcca acgactacta cgcctccgag    420

gtctcgtcgc tggccatccc cagcatgacg ggcgccatgg ccaccaaggc ggccgaggtg    480

gccaaggtgc ccagcttcca gtggcttgac cgcaacgtca ccatcgacac gctgttcgcc    540

cacacgctgt cgcagatccg cgcggccaac cagaaaggcg ccaacccgcc ctacgcgggc    600

atcttcgtgg tctacgacct tccggaccgc gactgcgccg ccgccgcgtc caacggcgag    660

ttctccatcg cgaacaacgg ggcggccaac tacaagacgt acatcgacgc gatccggagc    720

ctcgtcatcc agtactcaga catccgcatc atcttcgtca tcgagcccga ctcgctggcc    780

aacatggtga ccaacctgaa cgtggccaag tgcgccaacg ccgagtcgac ctacaaggag    840

ttgaccgtct acgcgctgca gcagctgaac ctgcccaacg tggccatgta cctggacgcc    900

ggccacgccg gctggctcgg ctggcccgcc aacatccagc cggccgccaa cctcttcgcc    960

gagatctaca cgagcgccgg caagccggcc gccgtgcgcg gcctcgccac caacgtggcc   1020

aactacaacg gctggagcct ggccacgccg ccctcgtaca cccagggcga ccccaactac   1080

gacgagagcc actacgtcca ggccctcgcc ccgctgctca ccgccaacgg cttccccgcc   1140

cacttcatca ccgacaccgg ccgcaacggc aagcagccga ccggacaacg gcaatgggga   1200

gactggtgca acgttatcgg aactggcttc ggcgtgcgcc cgacgacaaa caccggcctc   1260

gacatcgagg acgccttcgt ctgggtcaag cccggcggcg agtgcgacgg cacgagcaac   1320

acgacctctc cccgctacga ctaccactgc ggcctgtcgg acgcgctgca gcctgctccg   1380

gaggccggca cttggttcca ggcctacttc gagcagctcc tgaccaacgc caacccgccc   1440

ttttaa                                                                1446
```

<210> SEQ ID NO 14
<211> LENGTH: 481
<212> TYPE: PRT
<213> ORGANISM: Thielavia terrestris

<400> SEQUENCE: 14

```
Met Ala Gln Lys Leu Leu Leu Ala Ala Ala Leu Ala Ala Ser Ala Leu
1               5                   10                  15

Ala Ala Pro Val Val Glu Glu Arg Gln Asn Cys Gly Ser Val Trp Ser
            20                  25                  30

Gln Cys Gly Gly Ile Gly Trp Ser Gly Ala Thr Cys Cys Ala Ser Gly
        35                  40                  45

Asn Thr Cys Val Glu Leu Asn Pro Tyr Tyr Ser Gln Cys Leu Pro Asn
    50                  55                  60

Ser Gln Val Thr Thr Ser Thr Ser Lys Thr Thr Ser Thr Thr Thr Arg
65                  70                  75                  80

Ser Ser Thr Thr Ser His Ser Ser Gly Pro Thr Ser Thr Ser Thr Thr
                85                  90                  95

Thr Thr Ser Ser Pro Val Val Thr Thr Pro Pro Ser Thr Ser Ile Pro
            100                 105                 110

Gly Gly Ala Ser Ser Thr Ala Ser Trp Ser Gly Asn Pro Phe Ser Gly
        115                 120                 125

Val Gln Met Trp Ala Asn Asp Tyr Tyr Ala Ser Glu Val Ser Ser Leu
    130                 135                 140

Ala Ile Pro Ser Met Thr Gly Ala Met Ala Thr Lys Ala Ala Glu Val
145                 150                 155                 160
```

```
Ala Lys Val Pro Ser Phe Gln Trp Leu Asp Arg Asn Val Thr Ile Asp
                165                 170                 175

Thr Leu Phe Ala His Thr Leu Ser Gln Ile Arg Ala Ala Asn Gln Lys
            180                 185                 190

Gly Ala Asn Pro Pro Tyr Ala Gly Ile Phe Val Val Tyr Asp Leu Pro
        195                 200                 205

Asp Arg Asp Cys Ala Ala Ala Ala Ser Asn Gly Glu Phe Ser Ile Ala
    210                 215                 220

Asn Asn Gly Ala Ala Asn Tyr Lys Thr Tyr Ile Asp Ala Ile Arg Ser
225                 230                 235                 240

Leu Val Ile Gln Tyr Ser Asp Ile Arg Ile Ile Phe Val Ile Glu Pro
                245                 250                 255

Asp Ser Leu Ala Asn Met Val Thr Asn Leu Asn Val Ala Lys Cys Ala
            260                 265                 270

Asn Ala Glu Ser Thr Tyr Lys Glu Leu Thr Val Tyr Ala Leu Gln Gln
        275                 280                 285

Leu Asn Leu Pro Asn Val Ala Met Tyr Leu Asp Ala Gly His Ala Gly
    290                 295                 300

Trp Leu Gly Trp Pro Ala Asn Ile Gln Pro Ala Ala Asn Leu Phe Ala
305                 310                 315                 320

Glu Ile Tyr Thr Ser Ala Gly Lys Pro Ala Ala Val Arg Gly Leu Ala
                325                 330                 335

Thr Asn Val Ala Asn Tyr Asn Gly Trp Ser Leu Ala Thr Pro Pro Ser
            340                 345                 350

Tyr Thr Gln Gly Asp Pro Asn Tyr Asp Glu Ser His Tyr Val Gln Ala
        355                 360                 365

Leu Ala Pro Leu Leu Thr Ala Asn Gly Phe Pro Ala His Phe Ile Thr
    370                 375                 380

Asp Thr Gly Arg Asn Gly Lys Gln Pro Thr Gly Gln Arg Gln Trp Gly
385                 390                 395                 400

Asp Trp Cys Asn Val Ile Gly Thr Gly Phe Gly Val Arg Pro Thr Thr
                405                 410                 415

Asn Thr Gly Leu Asp Ile Glu Asp Ala Phe Val Trp Val Lys Pro Gly
            420                 425                 430

Gly Glu Cys Asp Gly Thr Ser Asn Thr Thr Ser Pro Arg Tyr Asp Tyr
        435                 440                 445

His Cys Gly Leu Ser Asp Ala Leu Gln Pro Ala Pro Glu Ala Gly Thr
    450                 455                 460

Trp Phe Gln Ala Tyr Phe Glu Gln Leu Leu Thr Asn Ala Asn Pro Pro
465                 470                 475                 480

Phe
```

<210> SEQ ID NO 15
<211> LENGTH: 1543
<212> TYPE: DNA
<213> ORGANISM: Trichophaea saccata

<400> SEQUENCE: 15

```
ggcacgaggg ctgccagcgt attcgcagca gatcgatcga ctcgaggacc acatcgcatc      60

atgaagaact tccttctggc gtccgcgctg atcgcggttg ccgcagctca gcagagtgct     120

tggggacagt gcggtggaat tggctggact ggcgcgacga cttgtatctc tggctacacg     180

tgctcaaaga tcaacgacta ctattcccag tgcattccgg gtacggcttc aaccaccact     240
```

```
caaggcggcg gcaatggcgg aggaaacggc ggtacaacga ctactcccac taccactcca    300

gcggccagta acaccaacaa cccgttctcc ggcaagaccc aatgggcgaa cccttactac    360

gcttccgagg tctcgagcat cgccatcccg tccctcgttg ccgccggaaa caccgcgctg    420

gcttccgccg cggccaaggt tgcccaggtc ccctccttca cctggttgga cacccgcgcc    480

aaagttccga gcgtgcgcac ctaccttcaa tccatcaagg acgccggcac caagaacgtg    540

atcgtcccga tcgtggtcta cgatctcccg gaacgagact gtgcagcggc cgcctccaac    600

ggagagctct cgctcgccaa caacggtacc gcaatttaca aggcagacta catcgaccag    660

atctacaaca tcctcgccga cttcccgaca attcccgtcg cgctgattat cgagccggat    720

tccctcgcta acttggttac gaacttgaat gtggccaagt gttcgaacgc tgagtccgcg    780

tataagacgc tcatcgctta tgcggtgcag aagtttggta ccctgtcgaa tgtggtgcag    840

tatctcgacg gcggccacgg tggatggctc ggatggcccg cgaatcttcc gcctgctgcg    900

cagctgttcg cccagatccg gcagagcgct ggaagtccgg cgaatctgag ggtttggct     960

actaacgttg ctaactacaa cgcttggtcc attgctacct gcccatctta cacttccccc   1020

aaccctaact gcgacgagaa acgatacata gccgctatgt cctccgcact cgccgcccag   1080

ggctggtcca acacccacta catcgtcgac caaggccgca gcggcaagca gccgaccggc   1140

cagctccagc agggcgattg gtgcaacgcc ctgggaaccg gctttggaat tcgtcctgat   1200

acaaccccgg atgatcccaa ccttgatgct ttcgtgtggg ttaagccggg tggtgaatcg   1260

gatggtacca gcaatacttc ctcgacccgc tatgattatc attgtggaca gagcgatgcg   1320

ctacaaccgg ccccggaggc gggaacgtgg ttccaggcgt attttgtgca gttgctgcag   1380

aatgctaatc ctagcttcac gtaagcttgg gagcgtgggg gttggaagat gtgtattgta   1440

tgtgtagata gagaaaaact gttggcctat tcaggactaa gtttgggcgt ctgggttctg   1500

tttcttcgcg taggtagacg tgaacttgat gaacttgagc gtg                     1543
```

```
<210> SEQ ID NO 16
<211> LENGTH: 447
<212> TYPE: PRT
<213> ORGANISM: Trichophaea saccata

<400> SEQUENCE: 16

Met Lys Asn Phe Leu Leu Ala Ser Ala Leu Ile Ala Val Ala Ala Ala
1               5                   10                  15

Gln Gln Ser Ala Trp Gly Gln Cys Gly Gly Ile Gly Trp Thr Gly Ala
            20                  25                  30

Thr Thr Cys Ile Ser Gly Tyr Thr Cys Ser Lys Ile Asn Asp Tyr Tyr
        35                  40                  45

Ser Gln Cys Ile Pro Gly Thr Ala Ser Thr Thr Thr Gln Gly Gly Gly
    50                  55                  60

Asn Gly Gly Gly Asn Gly Gly Thr Thr Thr Thr Pro Thr Thr Thr Pro
65                  70                  75                  80

Ala Ala Ser Asn Thr Asn Asn Pro Phe Ser Gly Lys Thr Gln Trp Ala
                85                  90                  95

Asn Pro Tyr Tyr Ala Ser Glu Val Ser Ser Ile Ala Ile Pro Ser Leu
            100                 105                 110

Val Ala Ala Gly Asn Thr Ala Leu Ala Ser Ala Ala Ala Lys Val Ala
        115                 120                 125

Gln Val Pro Ser Phe Thr Trp Leu Asp Thr Arg Ala Lys Val Pro Ser
    130                 135                 140
```

```
Val Arg Thr Tyr Leu Gln Ser Ile Lys Asp Ala Gly Thr Lys Asn Val
145                 150                 155                 160

Ile Val Pro Ile Val Val Tyr Asp Leu Pro Glu Arg Asp Cys Ala Ala
                165                 170                 175

Ala Ala Ser Asn Gly Glu Leu Ser Leu Ala Asn Asn Gly Thr Ala Ile
            180                 185                 190

Tyr Lys Ala Asp Tyr Ile Asp Gln Ile Tyr Asn Ile Leu Ala Asp Phe
        195                 200                 205

Pro Thr Ile Pro Val Ala Leu Ile Ile Glu Pro Asp Ser Leu Ala Asn
    210                 215                 220

Leu Val Thr Asn Leu Asn Val Ala Lys Cys Ser Asn Ala Glu Ser Ala
225                 230                 235                 240

Tyr Lys Thr Leu Ile Ala Tyr Ala Val Gln Lys Phe Gly Thr Leu Ser
                245                 250                 255

Asn Val Val Gln Tyr Leu Asp Gly Gly His Gly Gly Trp Leu Gly Trp
            260                 265                 270

Pro Ala Asn Leu Pro Pro Ala Ala Gln Leu Phe Ala Gln Ile Arg Gln
        275                 280                 285

Ser Ala Gly Ser Pro Ala Asn Leu Arg Gly Leu Ala Thr Asn Val Ala
    290                 295                 300

Asn Tyr Asn Ala Trp Ser Ile Ala Thr Cys Pro Ser Tyr Thr Ser Pro
305                 310                 315                 320

Asn Pro Asn Cys Asp Glu Lys Arg Tyr Ile Ala Ala Met Ser Ser Ala
                325                 330                 335

Leu Ala Ala Gln Gly Trp Ser Asn Thr His Tyr Ile Val Asp Gln Gly
            340                 345                 350

Arg Ser Gly Lys Gln Pro Thr Gly Gln Leu Gln Gln Gly Asp Trp Cys
        355                 360                 365

Asn Ala Leu Gly Thr Gly Phe Gly Ile Arg Pro Asp Thr Thr Pro Asp
    370                 375                 380

Asp Pro Asn Leu Asp Ala Phe Val Trp Val Lys Pro Gly Gly Glu Ser
385                 390                 395                 400

Asp Gly Thr Ser Asn Thr Ser Ser Thr Arg Tyr Asp Tyr His Cys Gly
                405                 410                 415

Gln Ser Asp Ala Leu Gln Pro Ala Pro Glu Ala Gly Thr Trp Phe Gln
            420                 425                 430

Ala Tyr Phe Val Gln Leu Leu Gln Asn Ala Asn Pro Ser Phe Thr
        435                 440                 445
```

<210> SEQ ID NO 17
<211> LENGTH: 1713
<212> TYPE: DNA
<213> ORGANISM: Aspergillus fumigatus

<400> SEQUENCE: 17

```
atgaagcacc ttgcatcttc catcgcattg actctactgt tgcctgccgt gcaggcccag      60

cagaccgtat ggggccaatg tatgttctgg ctgtcactgg aataagactg tatcaactgc     120

tgatatgctt ctaggtggcg gccaaggctg gtctggcccg acgagctgtg ttgccggcgc     180

agcctgtagc acactgaatc cctgtatgtt agatatcgtc ctgagtggag acttatactg     240

acttccttag actacgctca gtgtatcccg ggagccaccg cgacgtccac caccctcacg     300

acgacgacgg cggcgacgac gacatcccag accaccacca aacctaccac gactggtcca     360

actacatccg cacccaccgt gaccgcatcc ggtaaccctt tcagcggcta ccagctgtat     420
```

```
gccaacccct actactcctc cgaggtccat actctggcca tgccttctct gcccagctcg    480

ctgcagccca aggctagtgc tgttgctgaa gtgccctcat ttgtttggct gtaagtggcc    540

ttatcccaat actgagacca actctctgac agtcgtagcg acgttgccgc caaggtgccc    600

actatgggaa cctacctggc cgacattcag gccaagaaca aggccggcgc caaccctcct    660

atcgctggta tcttcgtggt ctacgacttg ccggaccgtg actgcgccgc tctggccagt    720

aatggcgagt actcaattgc caacaacggt gtggccaact acaaggcgta cattgacgcc    780

atccgtgctc agctggtgaa gtactctgac gttcacacca tcctcgtcat cggtaggccg    840

tacacctccg ttgcgcgccg cctttctctg acatcttgca gaacccgaca gcttggccaa    900

cctggtgacc aacctcaacg tcgccaaatg cgccaatgcg cagagcgcct acctggagtg    960

tgtcgactat gctctgaagc agctcaacct gcccaacgtc gccatgtacc tcgacgcagg   1020

tatgcctcac ttcccgcatt ctgtatccct tccagacact aactcatcag gccatgcggg   1080

ctggctcgga tggcccgcca acttgggccc cgccgcaaca ctcttcgcca aagtctacac   1140

cgacgcgggt tcccccgcgg ctgttcgtgg cctggccacc aacgtcgcca actacaacgc   1200

ctggtcgctc agtacctgcc cctcctacac ccagggagac cccaactgcg acgagaagaa   1260

gtacatcaac gccatggcgc ctcttctcaa ggaagccggc ttcgatgccc acttcatcat   1320

ggatacctgt aagtgcttat tccaatcgcc gatgtgtgcc gactaatcaa tgtttcagcc   1380

cggaatggcg tccagcccac gaagcaaaac gcctggggtg actggtgcaa cgtcatcggc   1440

accggcttcg gtgttcgccc ctcgactaac accggcgatc cgctccagga tgcctttgtg   1500

tggatcaagc ccggtggaga gagtgatggc acgtccaact cgacttcccc ccggtatgac   1560

gcgcactgcg gatatagtga tgctctgcag cctgctcctg aggctggtac ttggttccag   1620

gtatgtcatc cattagccag atgagggata agtgactgac ggacctaggc ctactttgag   1680

cagcttctga ccaacgctaa cccgtccttt taa                                1713
```

<210> SEQ ID NO 18
<211> LENGTH: 454
<212> TYPE: PRT
<213> ORGANISM: Aspergillus fumigatus

<400> SEQUENCE: 18

```
Met Lys His Leu Ala Ser Ser Ile Ala Leu Thr Leu Leu Leu Pro Ala
1               5                   10                  15

Val Gln Ala Gln Gln Thr Val Trp Gly Gln Cys Gly Gly Gln Gly Trp
            20                  25                  30

Ser Gly Pro Thr Ser Cys Val Ala Gly Ala Ala Cys Ser Thr Leu Asn
        35                  40                  45

Pro Tyr Tyr Ala Gln Cys Ile Pro Gly Ala Thr Ala Thr Ser Thr Thr
    50                  55                  60

Leu Thr Thr Thr Thr Ala Ala Thr Thr Thr Ser Gln Thr Thr Thr Lys
65                  70                  75                  80

Pro Thr Thr Thr Gly Pro Thr Thr Ser Ala Pro Thr Val Thr Ala Ser
                85                  90                  95

Gly Asn Pro Phe Ser Gly Tyr Gln Leu Tyr Ala Asn Pro Tyr Tyr Ser
            100                 105                 110

Ser Glu Val His Thr Leu Ala Met Pro Ser Leu Pro Ser Ser Leu Gln
        115                 120                 125

Pro Lys Ala Ser Ala Val Ala Glu Val Pro Ser Phe Val Trp Leu Asp
    130                 135                 140
```

```
Val Ala Ala Lys Val Pro Thr Met Gly Thr Tyr Leu Ala Asp Ile Gln
145                 150                 155                 160

Ala Lys Asn Lys Ala Gly Ala Asn Pro Pro Ile Ala Gly Ile Phe Val
                165                 170                 175

Val Tyr Asp Leu Pro Asp Arg Asp Cys Ala Ala Leu Ala Ser Asn Gly
            180                 185                 190

Glu Tyr Ser Ile Ala Asn Asn Gly Val Ala Asn Tyr Lys Ala Tyr Ile
        195                 200                 205

Asp Ala Ile Arg Ala Gln Leu Val Lys Tyr Ser Asp Val His Thr Ile
    210                 215                 220

Leu Val Ile Glu Pro Asp Ser Leu Ala Asn Leu Val Thr Asn Leu Asn
225                 230                 235                 240

Val Ala Lys Cys Ala Asn Ala Gln Ser Ala Tyr Leu Glu Cys Val Asp
                245                 250                 255

Tyr Ala Leu Lys Gln Leu Asn Leu Pro Asn Val Ala Met Tyr Leu Asp
            260                 265                 270

Ala Gly His Ala Gly Trp Leu Gly Trp Pro Ala Asn Leu Gly Pro Ala
        275                 280                 285

Ala Thr Leu Phe Ala Lys Val Tyr Thr Asp Ala Gly Ser Pro Ala Ala
    290                 295                 300

Val Arg Gly Leu Ala Thr Asn Val Ala Asn Tyr Asn Ala Trp Ser Leu
305                 310                 315                 320

Ser Thr Cys Pro Ser Tyr Thr Gln Gly Asp Pro Asn Cys Asp Glu Lys
                325                 330                 335

Lys Tyr Ile Asn Ala Met Ala Pro Leu Leu Lys Glu Ala Gly Phe Asp
            340                 345                 350

Ala His Phe Ile Met Asp Thr Ser Arg Asn Gly Val Gln Pro Thr Lys
        355                 360                 365

Gln Asn Ala Trp Gly Asp Trp Cys Asn Val Ile Gly Thr Gly Phe Gly
    370                 375                 380

Val Arg Pro Ser Thr Asn Thr Gly Asp Pro Leu Gln Asp Ala Phe Val
385                 390                 395                 400

Trp Ile Lys Pro Gly Gly Glu Ser Asp Gly Thr Ser Asn Ser Thr Ser
                405                 410                 415

Pro Arg Tyr Asp Ala His Cys Gly Tyr Ser Asp Ala Leu Gln Pro Ala
            420                 425                 430

Pro Glu Ala Gly Thr Trp Phe Gln Ala Tyr Phe Glu Gln Leu Leu Thr
        435                 440                 445

Asn Ala Asn Pro Ser Phe
    450
```

<210> SEQ ID NO 19
<211> LENGTH: 1502
<212> TYPE: DNA
<213> ORGANISM: Aspergillus terreus

<400> SEQUENCE: 19

```
ccatgaattc tcttacaaaa agcatcatcg ccgcagggct ggtcttccac ccacttgtcc      60

aggcccaaca accttcctcg tcttctccag gaaacccttc cttggcaacg tggaaatgca     120

cttctggcgg gggttgtgtg cagcaggata catcagtcgt cctagattgg ggtttccact     180

ggatccacac cagcagttct caatcctgca ccacctcctc cggtgtcaac tcggccctct     240

gccccgatga agcgacctgt gctaagaact gcgtgatcga tccggcaaac tacgtaacag     300

ctggcgtctc cacctcggga gacactttga cgatgcacca gtactaccaa aacaacgggg     360
```

```
tcaccaccaa tgcgtcaccg cgtctctatc tcctgggctc agacggcaac tatgtcatgc    420

tgaagctcct cggccaggaa cttagtttta atgtggattt gtcaacgctt ccgtgtggcg    480

agaacggtgc cttgtatctg tcagagatga gcgccaccgg tggaagaaac gaatacaaca    540

caggaggcgc ccaggtattg agattctgat cgtttcctta gacaacaccg tgtatgctga    600

caaatttcaa gtatggttct ggttactgtg acgcacaatc gccagtcatg gcatggagaa    660

acggcaccct caacaccagt ggccagggtt ttggctgcaa cgaaatggat atcctcgaag    720

ccaactcccg tgcaaactcc ttcacccctc acccctgcaa cggcaatgat tgcgataaag    780

gggggtgtgg attcaatccc tacgctctcg gccagcaaaa ctactggggc ccaggcggga    840

cggtcgacac gtccaagccg ttcactatca ccacgcagtt tatcaccgac gacggtacca    900

caactgggac tctgaaagag atccgccgtc aatacatcca aaacggtaag atcatcgcca    960

atgcgaagtc atcggctggg gtcgactcca tcaccgagcc atggtgcgaa tcagttgacg   1020

gcgctgctgc tacctacggt ggtctgaaga gaatgggtga ggccctcggc cggggaatgg   1080

ttctgatttt cagcatctgg aacgacgcag gcggcttcat gaactggctg gatagcggca   1140

gcgccggacc ctgcagtagc acggaaggaa atccgtcatt gattcaatct gcccatccgg   1200

atactcacgt ggtgttttcc aacatccgct ggggcgacat cggatcaacc tataccaatc   1260

cgggtggctc tggttctagt tccagctcta ctaggaccac aaccaagact acctccacca   1320

ctaccactac gaaaattacc actaccacct ccgcaggtgg tgctacccag acccactggg   1380

gccagtgtgg aggacaagga tggactgggc ctaccgcgtg tgcatcgccg tacacttgcc   1440

agaagcagaa tgagtggtac tctcagtgct tgtgaatagg tgcgtaacac atgcagactg   1500

cg                                                                  1502
```

<210> SEQ ID NO 20
<211> LENGTH: 471
<212> TYPE: PRT
<213> ORGANISM: Aspergillus terreus

<400> SEQUENCE: 20

```
Met Asn Ser Leu Thr Lys Ser Ile Ile Ala Ala Gly Leu Val Phe His
1               5                   10                  15

Pro Leu Val Gln Ala Gln Gln Pro Ser Ser Ser Ser Pro Gly Asn Pro
            20                  25                  30

Ser Leu Ala Thr Trp Lys Cys Thr Ser Gly Gly Gly Cys Val Gln Gln
        35                  40                  45

Asp Thr Ser Val Val Leu Asp Trp Gly Phe His Trp Ile His Thr Ser
    50                  55                  60

Ser Ser Gln Ser Cys Thr Thr Ser Ser Gly Val Asn Ser Ala Leu Cys
65                  70                  75                  80

Pro Asp Glu Ala Thr Cys Ala Lys Asn Cys Val Ile Asp Pro Ala Asn
                85                  90                  95

Tyr Val Thr Ala Gly Val Ser Thr Ser Gly Asp Thr Leu Thr Met His
            100                 105                 110

Gln Tyr Tyr Gln Asn Asn Gly Val Thr Thr Asn Ala Ser Pro Arg Leu
        115                 120                 125

Tyr Leu Leu Gly Ser Asp Gly Asn Tyr Val Met Leu Lys Leu Leu Gly
    130                 135                 140

Gln Glu Leu Ser Phe Asn Val Asp Leu Ser Thr Leu Pro Cys Gly Glu
145                 150                 155                 160
```

-continued

```
Asn Gly Ala Leu Tyr Leu Ser Glu Met Ser Ala Thr Gly Gly Arg Asn
                165                 170                 175

Glu Tyr Asn Thr Gly Gly Ala Gln Tyr Gly Ser Gly Tyr Cys Asp Ala
            180                 185                 190

Gln Ser Pro Val Met Ala Trp Arg Asn Gly Thr Leu Asn Thr Ser Gly
        195                 200                 205

Gln Gly Phe Gly Cys Asn Glu Met Asp Ile Leu Glu Ala Asn Ser Arg
    210                 215                 220

Ala Asn Ser Phe Thr Pro His Pro Cys Asn Gly Asn Asp Cys Asp Lys
225                 230                 235                 240

Gly Gly Cys Gly Phe Asn Pro Tyr Ala Leu Gly Gln Gln Asn Tyr Trp
                245                 250                 255

Gly Pro Gly Gly Thr Val Asp Thr Ser Lys Pro Phe Thr Ile Thr Thr
            260                 265                 270

Gln Phe Ile Thr Asp Asp Gly Thr Thr Thr Gly Thr Leu Lys Glu Ile
        275                 280                 285

Arg Arg Gln Tyr Ile Gln Asn Gly Lys Ile Ile Ala Asn Ala Lys Ser
    290                 295                 300

Ser Ala Gly Val Asp Ser Ile Thr Glu Pro Trp Cys Glu Ser Val Asp
305                 310                 315                 320

Gly Ala Ala Ala Thr Tyr Gly Gly Leu Lys Arg Met Gly Glu Ala Leu
                325                 330                 335

Gly Arg Gly Met Val Leu Ile Phe Ser Ile Trp Asn Asp Ala Gly Gly
            340                 345                 350

Phe Met Asn Trp Leu Asp Ser Gly Ser Ala Gly Pro Cys Ser Ser Thr
        355                 360                 365

Glu Gly Asn Pro Ser Leu Ile Gln Ser Ala His Pro Asp Thr His Val
    370                 375                 380

Val Phe Ser Asn Ile Arg Trp Gly Asp Ile Gly Ser Thr Tyr Thr Asn
385                 390                 395                 400

Pro Gly Gly Ser Gly Ser Ser Ser Ser Ser Thr Arg Thr Thr Thr Lys
                405                 410                 415

Thr Thr Ser Thr Thr Thr Thr Thr Lys Ile Thr Thr Thr Thr Ser Ala
            420                 425                 430

Gly Gly Ala Thr Gln Thr His Trp Gly Gln Cys Gly Gly Gln Gly Trp
        435                 440                 445

Thr Gly Pro Thr Ala Cys Ala Ser Pro Tyr Thr Cys Gln Lys Gln Asn
    450                 455                 460

Glu Trp Tyr Ser Gln Cys Leu
465                 470
```

<210> SEQ ID NO 21
<211> LENGTH: 1849
<212> TYPE: DNA
<213> ORGANISM: Trichoderma reesei

<400> SEQUENCE: 21

```
tgccatttct gacctggata ggttttccta tggtcattcc tataagagac acgctctttc      60

gtcggcccgt agatatcaga ttggtattca gtcgcacaga cgaaggtgag ttgatcctcc     120

aacatgagtt ctatgagccc cccccttgcc cccccccgtt caccttgacc tgcaatgaga     180

atcccacctt ttacaagagc atcaagaagt attaatggcg ctgaatagcc tctgctcgat     240

aatatctccc cgtcatcgac aatgaacaag tccgtggctc cattgctgct tgcagcgtcc     300

atactatatg gcggcgccgt cgcacagcag actgtctggg gccagtgtgg aggtattggt     360
```

```
tggagcggac ctacgaattg tgctcctggc tcagcttgtt cgaccctcaa tccttattat    420
gcgcaatgta ttccgggagc cactactatc accacttcga cccggccacc atccggtcca    480
accaccacca ccagggctac ctcaacaagc tcatcaactc cacccacgag ctctggggtc    540
cgatttgccg gcgttaacat cgcgggtttt gactttggct gtaccacaga gtgagtaccc    600
ttgtttcctg gtgttgctgg ctggttgggc gggtatacag cgaagcggac gcaagaacac    660
cgccggtccg ccaccatcaa gatgtgggtg gtaagcggcg gtgttttgta caactacctg    720
acagctcact caggaaatga gaattaatgg aagtcttgtt acagtggcac ttgcgttacc    780
tcgaaggttt atcctccgtt gaagaacttc accggctcaa acaactaccc cgatggcatc    840
ggccagatgc agcacttcgt caacgaggac gggatgacta ttttccgctt acctgtcgga    900
tggcagtacc tcgtcaacaa caatttgggc ggcaatcttg attccacgag catttccaag    960
tatgatcagc ttgttcaggg gtgcctgtct ctgggcgcat actgcatcgt cgacatccac   1020
aattatgctc gatggaacgg tgggatcatt ggtcagggcg gccctactaa tgctcaattc   1080
acgagccttt ggtcgcagtt ggcatcaaag tacgcatctc agtcgagggt gtggttcggc   1140
atcatgaatg agccccacga cgtgaacatc aacacctggg ctgccacggt ccaagaggtt   1200
gtaaccgcaa tccgcaacgc tggtgctacg tcgcaattca tctctttgcc tggaaatgat   1260
tggcaatctg ctggggcttt catatccgat ggcagtgcag ccgccctgtc tcaagtcacg   1320
aacccggatg ggtcaacaac gaatctgatt tttgacgtgc acaaatactt ggactcagac   1380
aactccggta ctcacgccga atgtactaca aataacattg acggcgcctt ttctccgctt   1440
gccacttggc tccgacagaa caatcgccag gctatcctga cagaaaccgg tggtggcaac   1500
gttcagtcct gcatacaaga catgtgccag caaatccaat atctcaacca gaactcagat   1560
gtctatcttg gctatgttgg ttggggtgcc ggatcatttg atagcacgta tgtcctgacg   1620
gaaacaccga ctggcagtgg taactcatgg acggacacat ccttggtcag ctcgtgtctc   1680
gcaagaaagt agcactctga gctgaatgca gaagcctcgc caacgtttgt atctcgctat   1740
caaacatagt agctactcta tgaggctgtc tgttctcgat ttcagcttta tatagtttca   1800
tcaaacagta catattccct ctgtggccac gcaaaaaaaa aaaaaaaaa              1849
```

<210> SEQ ID NO 22
<211> LENGTH: 418
<212> TYPE: PRT
<213> ORGANISM: Trichoderma reesei

<400> SEQUENCE: 22

```
Met Asn Lys Ser Val Ala Pro Leu Leu Leu Ala Ala Ser Ile Leu Tyr
1               5                   10                  15

Gly Gly Ala Val Ala Gln Gln Thr Val Trp Gly Gln Cys Gly Gly Ile
            20                  25                  30

Gly Trp Ser Gly Pro Thr Asn Cys Ala Pro Gly Ser Ala Cys Ser Thr
        35                  40                  45

Leu Asn Pro Tyr Tyr Ala Gln Cys Ile Pro Gly Ala Thr Thr Ile Thr
    50                  55                  60

Thr Ser Thr Arg Pro Pro Ser Gly Pro Thr Thr Thr Thr Arg Ala Thr
65                  70                  75                  80

Ser Thr Ser Ser Ser Thr Pro Pro Thr Ser Ser Gly Val Arg Phe Ala
                85                  90                  95

Gly Val Asn Ile Ala Gly Phe Asp Phe Gly Cys Thr Thr Asp Gly Thr
            100                 105                 110
```

```
Cys Val Thr Ser Lys Val Tyr Pro Pro Leu Lys Asn Phe Thr Gly Ser
        115                 120                 125

Asn Asn Tyr Pro Asp Gly Ile Gly Gln Met Gln His Phe Val Asn Glu
    130                 135                 140

Asp Gly Met Thr Ile Phe Arg Leu Pro Val Gly Trp Gln Tyr Leu Val
145                 150                 155                 160

Asn Asn Asn Leu Gly Gly Asn Leu Asp Ser Thr Ser Ile Ser Lys Tyr
                165                 170                 175

Asp Gln Leu Val Gln Gly Cys Leu Ser Leu Gly Ala Tyr Cys Ile Val
            180                 185                 190

Asp Ile His Asn Tyr Ala Arg Trp Asn Gly Gly Ile Ile Gly Gln Gly
        195                 200                 205

Gly Pro Thr Asn Ala Gln Phe Thr Ser Leu Trp Ser Gln Leu Ala Ser
    210                 215                 220

Lys Tyr Ala Ser Gln Ser Arg Val Trp Phe Gly Ile Met Asn Glu Pro
225                 230                 235                 240

His Asp Val Asn Ile Asn Thr Trp Ala Ala Thr Val Gln Glu Val Val
                245                 250                 255

Thr Ala Ile Arg Asn Ala Gly Ala Thr Ser Gln Phe Ile Ser Leu Pro
            260                 265                 270

Gly Asn Asp Trp Gln Ser Ala Gly Ala Phe Ile Ser Asp Gly Ser Ala
        275                 280                 285

Ala Ala Leu Ser Gln Val Thr Asn Pro Asp Gly Ser Thr Thr Asn Leu
    290                 295                 300

Ile Phe Asp Val His Lys Tyr Leu Asp Ser Asp Asn Ser Gly Thr His
305                 310                 315                 320

Ala Glu Cys Thr Thr Asn Asn Ile Asp Gly Ala Phe Ser Pro Leu Ala
                325                 330                 335

Thr Trp Leu Arg Gln Asn Asn Arg Gln Ala Ile Leu Thr Glu Thr Gly
            340                 345                 350

Gly Gly Asn Val Gln Ser Cys Ile Gln Asp Met Cys Gln Gln Ile Gln
        355                 360                 365

Tyr Leu Asn Gln Asn Ser Asp Val Tyr Leu Gly Tyr Val Gly Trp Gly
    370                 375                 380

Ala Gly Ser Phe Asp Ser Thr Tyr Val Leu Thr Glu Thr Pro Thr Gly
385                 390                 395                 400

Ser Gly Asn Ser Trp Thr Asp Thr Ser Leu Val Ser Ser Cys Leu Ala
                405                 410                 415

Arg Lys
```

<210> SEQ ID NO 23
<211> LENGTH: 1188
<212> TYPE: DNA
<213> ORGANISM: Myceliophthora thermophila

<400> SEQUENCE: 23

```
cgacttgaaa cgccccaaat gaagtcctcc atcctcgcca gcgtcttcgc cacgggcgcc      60

gtggctcaaa gtggtccgtg gcagcaatgt ggtggcatcg gatggcaagg atcgaccgac     120

tgtgtgtcgg gctaccactg cgtctaccag aacgattggt acagccagtg cgtgcctggc     180

gcggcgtcga caacgctgca gacatcgacc acgtccaggc ccaccgccac cagcaccgcc     240

cctccgtcgt ccaccacctc gcctagcaag ggcaagctga agtggctcgg cagcaacgag     300

tcgggcgccg agttcgggga gggcaattac cccggcctct ggggcaagca cttcatcttc     360
```

```
ccgtcgactt cggcgattca gacgctcatc aatgatggat acaacatctt ccggatcgac    420

ttctcgatgg agcgtctggt gcccaaccag ttgacgtcgt ccttcgacca gggttacctc    480

cgcaacctga ccgaggtggt caacttcgtg acgaacgcgg gcaagtacgc cgtcctggac    540

ccgcacaact acggccggta ctacggcaac atcatcacgg acacgaacgc gttccggacc    600

ttctggacca acctggccaa gcagttcgcc tccaactcgc tcgtcatctt cgacaccaac    660

aacgagtaca acacgatgga ccagaccctg gtgctcaacc tcaaccaggc cgccatcgac    720

ggcatccggg ccgccggcgc gacctcgcag tacatcttcg tcgagggcaa cgcgtggagc    780

ggggcctgga gctggaacac gaccaacacc aacatggccg ccctgacgga cccgcagaac    840

aagatcgtgt acgagatgca ccagtacctc gactcggaca gctcgggcac ccacgccgag    900

tgcgtcagca gcaccatcgg cgcccagcgc gtcgtcggag ccacccagtg gctccgcgcc    960

aacggcaagc tcggcgtcct cggcgagttc gccggcggcg ccaacgccgt ctgccagcag   1020

gccgtcaccg gcctcctcga ccacctccag gacaacagcg acgtctggct gggtgccctc   1080

tggtgggccg ccggtccctg gtggggcgac tacatgtact cgttcgagcc tccttcgggc   1140

accggctatg tcaactacaa ctcgatcttg aagaagtact tgccgtaa                1188
```

<210> SEQ ID NO 24
<211> LENGTH: 389
<212> TYPE: PRT
<213> ORGANISM: Myceliophthora thermophila

<400> SEQUENCE: 24

```
Met Lys Ser Ser Ile Leu Ala Ser Val Phe Ala Thr Gly Ala Val Ala
1               5                   10                  15

Gln Ser Gly Pro Trp Gln Gln Cys Gly Gly Ile Gly Trp Gln Gly Ser
            20                  25                  30

Thr Asp Cys Val Ser Gly Tyr His Cys Val Tyr Gln Asn Asp Trp Tyr
        35                  40                  45

Ser Gln Cys Val Pro Gly Ala Ala Ser Thr Thr Leu Gln Thr Ser Thr
    50                  55                  60

Thr Ser Arg Pro Thr Ala Thr Ser Thr Ala Pro Pro Ser Ser Thr Thr
65                  70                  75                  80

Ser Pro Ser Lys Gly Lys Leu Lys Trp Leu Gly Ser Asn Glu Ser Gly
                85                  90                  95

Ala Glu Phe Gly Glu Gly Asn Tyr Pro Gly Leu Trp Gly Lys His Phe
            100                 105                 110

Ile Phe Pro Ser Thr Ser Ala Ile Gln Thr Leu Ile Asn Asp Gly Tyr
        115                 120                 125

Asn Ile Phe Arg Ile Asp Phe Ser Met Glu Arg Leu Val Pro Asn Gln
    130                 135                 140

Leu Thr Ser Ser Phe Asp Gln Gly Tyr Leu Arg Asn Leu Thr Glu Val
145                 150                 155                 160

Val Asn Phe Val Thr Asn Ala Gly Lys Tyr Ala Val Leu Asp Pro His
                165                 170                 175

Asn Tyr Gly Arg Tyr Tyr Gly Asn Ile Ile Thr Asp Thr Asn Ala Phe
            180                 185                 190

Arg Thr Phe Trp Thr Asn Leu Ala Lys Gln Phe Ala Ser Asn Ser Leu
        195                 200                 205

Val Ile Phe Asp Thr Asn Asn Glu Tyr Asn Thr Met Asp Gln Thr Leu
    210                 215                 220
```

Val Leu Asn Leu Asn Gln Ala Ala Ile Asp Gly Ile Arg Ala Ala Gly
225 230 235 240

Ala Thr Ser Gln Tyr Ile Phe Val Glu Gly Asn Ala Trp Ser Gly Ala
245 250 255

Trp Ser Trp Asn Thr Thr Asn Thr Asn Met Ala Ala Leu Thr Asp Pro
260 265 270

Gln Asn Lys Ile Val Tyr Glu Met His Gln Tyr Leu Asp Ser Asp Ser
275 280 285

Ser Gly Thr His Ala Glu Cys Val Ser Ser Thr Ile Gly Ala Gln Arg
290 295 300

Val Val Gly Ala Thr Gln Trp Leu Arg Ala Asn Gly Lys Leu Gly Val
305 310 315 320

Leu Gly Glu Phe Ala Gly Gly Ala Asn Ala Val Cys Gln Gln Ala Val
325 330 335

Thr Gly Leu Leu Asp His Leu Gln Asp Asn Ser Asp Val Trp Leu Gly
340 345 350

Ala Leu Trp Trp Ala Ala Gly Pro Trp Trp Gly Asp Tyr Met Tyr Ser
355 360 365

Phe Glu Pro Pro Ser Gly Thr Gly Tyr Val Asn Tyr Asn Ser Ile Leu
370 375 380

Lys Lys Tyr Leu Pro
385

<210> SEQ ID NO 25
<211> LENGTH: 1008
<212> TYPE: DNA
<213> ORGANISM: Thermoascus aurantiacus

<400> SEQUENCE: 25
atgaagctcg gctctctcgt gctcgctctc agcgcagcta ggcttacact gtcggcccct 60
ctcgcagaca gaaagcagga gaccaagcgt gcgaaagtat tccaatggtt cggttcgaac 120
gagtccggtg ctgaattcgg aagccagaac cttccaggag tcgagggaaa ggattatata 180
tggcctgatc ccaacaccat tgacacattg atcagcaagg ggatgaacat ctttcgtgtc 240
ccctttatga tggagagatt ggttcccaac tcaatgaccg gctctccgga tccgaactac 300
ctggcagatc tcatagcgac tgtaaatgca atcacccaga aaggtgccta cgccgtcgtc 360
gatcctcata actacggcag atactacaat tctataatct cgagcccttc cgatttccag 420
accttctgga aaacggtcgc ctcacagttt gcttcgaatc cactggtcat cttcgacact 480
aataacgaat accacgatat ggaccagacc ttagtcctca atctcaacca ggccgctatc 540
gacggcatcc gttccgccgg agccacttcc cagtacatct ttgtcgaggg caattcgtgg 600
accggggcat ggacctggac gaacgtgaac gataacatga aaagcctgac cgacccatct 660
gacaagatca tatacgagat gcaccagtac ctggactctg acggatccgg gacatcagcg 720
acctgcgtat cttcgaccat cggtcaagag cgaatcacca gcgcaacgca gtggctcagg 780
gccaacggga agaagggcat catcggcgag tttgcgggcg gagccaacga cgtctgcgag 840
acggccatca cgggcatgct ggactacatg gcccagaaca cagacgtctg gactggcgcc 900
atctggtggg cggccgggcc gtggtgggga gactacatat tctccatgga gccggacaat 960
ggcatcgcgt atcagcagat acttcctatt ttgactccgt atctttga 1008

<210> SEQ ID NO 26
<211> LENGTH: 335
<212> TYPE: PRT

<213> ORGANISM: Thermoascus aurantiacus

<400> SEQUENCE: 26

```
Met Lys Leu Gly Ser Leu Val Leu Ala Leu Ser Ala Ala Arg Leu Thr
1               5                   10                  15

Leu Ser Ala Pro Leu Ala Asp Arg Lys Gln Glu Thr Lys Arg Ala Lys
            20                  25                  30

Val Phe Gln Trp Phe Gly Ser Asn Glu Ser Gly Ala Glu Phe Gly Ser
        35                  40                  45

Gln Asn Leu Pro Gly Val Glu Gly Lys Asp Tyr Ile Trp Pro Asp Pro
    50                  55                  60

Asn Thr Ile Asp Thr Leu Ile Ser Lys Gly Met Asn Ile Phe Arg Val
65                  70                  75                  80

Pro Phe Met Met Glu Arg Leu Val Pro Asn Ser Met Thr Gly Ser Pro
                85                  90                  95

Asp Pro Asn Tyr Leu Ala Asp Leu Ile Ala Thr Val Asn Ala Ile Thr
            100                 105                 110

Gln Lys Gly Ala Tyr Ala Val Val Asp Pro His Asn Tyr Gly Arg Tyr
        115                 120                 125

Tyr Asn Ser Ile Ile Ser Ser Pro Ser Asp Phe Gln Thr Phe Trp Lys
    130                 135                 140

Thr Val Ala Ser Gln Phe Ala Ser Asn Pro Leu Val Ile Phe Asp Thr
145                 150                 155                 160

Asn Asn Glu Tyr His Asp Met Asp Gln Thr Leu Val Leu Asn Leu Asn
                165                 170                 175

Gln Ala Ala Ile Asp Gly Ile Arg Ser Ala Gly Ala Thr Ser Gln Tyr
            180                 185                 190

Ile Phe Val Glu Gly Asn Ser Trp Thr Gly Ala Trp Thr Trp Thr Asn
        195                 200                 205

Val Asn Asp Asn Met Lys Ser Leu Thr Asp Pro Ser Asp Lys Ile Ile
    210                 215                 220

Tyr Glu Met His Gln Tyr Leu Asp Ser Asp Gly Ser Gly Thr Ser Ala
225                 230                 235                 240

Thr Cys Val Ser Ser Thr Ile Gly Gln Glu Arg Ile Thr Ser Ala Thr
                245                 250                 255

Gln Trp Leu Arg Ala Asn Gly Lys Lys Gly Ile Ile Gly Glu Phe Ala
            260                 265                 270

Gly Gly Ala Asn Asp Val Cys Glu Thr Ala Ile Thr Gly Met Leu Asp
        275                 280                 285

Tyr Met Ala Gln Asn Thr Asp Val Trp Thr Gly Ala Ile Trp Trp Ala
    290                 295                 300

Ala Gly Pro Trp Trp Gly Asp Tyr Ile Phe Ser Met Glu Pro Asp Asn
305                 310                 315                 320

Gly Ile Ala Tyr Gln Gln Ile Leu Pro Ile Leu Thr Pro Tyr Leu
                325                 330                 335
```

<210> SEQ ID NO 27
<211> LENGTH: 3060
<212> TYPE: DNA
<213> ORGANISM: Aspergillus fumigatus

<400> SEQUENCE: 27

```
atgagattcg gttggctcga ggtggccgct ctgacggccg cttctgtagc caatgcccag      60

gtttgtgatg ctttcccgtc attgtttcgg atatagttga caatagtcat ggaaataatc     120
```

-continued

```
aggaattggc tttctctcca ccattctacc cttcgccttg ggctgatggc cagggagagt    180
gggcagatgc ccatcgacgc gccgtcgaga tcgtttctca gatgacactg gcggagaagg    240
ttaaccttac aacgggtact gggtgggttg cgactttttt gttgacagtg agctttcttc    300
actgaccatc tacacagatg ggaaatggac cgatgcgtcg gtcaaaccgg cagcgttccc    360
aggtaagctt gcaattctgc aacaacgtgc aagtgtagtt gctaaaacgc ggtggtgcag    420
acttggtatc aactggggtc tttgtggcca ggattcccct ttgggtatcc gtttctgtga    480
gctataccccg cggagtcttt cagtccttgt attatgtgct gatgattgtc tctgtatagc    540
tgacctcaac tccgccttcc ctgctggtac taatgtcgcc gcgacatggg acaagacact    600
cgcctacctt cgtggcaagg ccatgggtga ggaattcaac gacaagggcg tggacatttt    660
gctggggcct gctgctggtc ctctcggcaa atacccggac ggcggcagaa tctgggaagg    720
cttctctcct gatccggttc tcactggtgt acttttcgcc gaaactatca agggtatcca    780
agacgcgggt gtgattgcta ctgccaagca ttacattctg aatgaacagg agcatttccg    840
acaggttggc gaggcccagg gatatggtta caacatcacg gagacgatca gctccaacgt    900
ggatgacaag accatgcacg agttgtacct ttggtgagta gttgacactg caaatgagga    960
ccttgattga tttgactgac ctggaatgca ggccctttgc agatgctgtg cgcggtaaga   1020
ttttccgtag acttgacctc gcgacgaaga aatcgctgac gaaccatcgt agctggcgtt   1080
ggcgctgtca tgtgttccta caatcaaatc aacaacagct acggttgtca aaacagtcaa   1140
actctcaaca agctcctcaa ggctgagctg ggcttccaag gcttcgtcat gagtgactgg   1200
agcgctcacc acagcggtgt cggcgctgcc ctcgctgggt tggatatgtc gatgcctgga   1260
gacatttcct tcgacgacgg actctccttc tggggcacga acctaactgt cagtgttctt   1320
aacggcaccg ttccagcctg gcgtgtcgat gacatggctg ttcgtatcat gaccgcgtac   1380
tacaaggttg gtcgtgaccg tcttcgtatt ccccctaact tcagctcctg gacccgggat   1440
gagtacggct gggagcattc tgctgtctcc gagggagcct ggaccaaggt gaacgacttc   1500
gtcaatgtgc agcgcagtca ctctcagatc atccgtgaga ttggtgccgc tagtacagtg   1560
ctcttgaaga acacgggtgc tcttcctttg accggcaagg aggttaaagt gggtgttctc   1620
ggtgaagacg ctggttccaa cccgtggggt gctaacggct gccccgaccg cggctgtgat   1680
aacggcactc ttgctatggc ctggggtagt ggtactgcca acttccctta ccttgtcacc   1740
cccgagcagg ctatccagcg agaggtcatc agcaacggcg gcaatgtctt tgctgtgact   1800
gataacgggg ctctcagcca gatggcagat gttgcatctc aatccaggtg agtgcgggct   1860
cttagaaaaa gaacgttctc tgaatgaagt tttttaacca ttgcgaacag cgtgtctttg   1920
gtgtttgtca acgccgactc tggagagggt ttcatcagtg tcgacggcaa cgagggtgac   1980
cgcaaaaatc tcactctgtg gaagaacggc gaggccgtca ttgacactgt tgtcagccac   2040
tgcaacaaca cgattgtggt tattcacagt gttgggcccg tcttgatcga ccggtggtat   2100
gataacccca acgtcactgc catcatctgg gccggcttgc ccggtcagga gagtggcaac   2160
tccctggtcg acgtgctcta tggccgcgtc aaccccagcg ccaagacccc gttcacctgg   2220
ggcaagactc gggagtctta cggggctccc ttgctcaccg agcctaacaa tggcaatggt   2280
gctccccagg atgatttcaa cgagggcgtc ttcattgact accgtcactt tgacaagcgc   2340
aatgagaccc ccatttatga gtttggccat ggcttgagct acaccacctt tggttactct   2400
caccttcggg ttcaggccct caatagttcg agttcggcat atgtcccgac tagcggagag   2460
accaagcctg cgccaaccta tggtgagatc ggtagtgccg ccgactacct gtatcccgag   2520
```

```
ggtctcaaaa gaattaccaa gtttatttac ccttggctca actcgaccga cctcgaggat   2580

tcttctgacg acccgaacta cggctgggag gactcggagt acattcccga aggcgctagg   2640

gatgggtctc ctcaacccct cctgaaggct ggcggcgctc ctggtggtaa ccctaccctt   2700

tatcaggatc ttgttagggt gtcggccacc ataaccaaca ctggtaacgt cgccggttat   2760

gaagtccctc aattggtgag tgacccgcat gttccttgcg ttgcaatttg gctaactcgc   2820

ttctagtatg tttcactggg cggaccgaac gagcctcggg tcgttctgcg caagttcgac   2880

cgaatcttcc tggctcctgg ggagcaaaag gtttggacca cgactcttaa ccgtcgtgat   2940

ctcgccaatt gggatgtgga ggctcaggac tgggtcatca caaagtaccc caagaaagtg   3000

cacgtcggca gctcctcgcg taagctgcct ctgagagcgc ctctgccccg tgtctactag   3060
```

<210> SEQ ID NO 28
<211> LENGTH: 863
<212> TYPE: PRT
<213> ORGANISM: Aspergillus fumigatus

<400> SEQUENCE: 28

```
Met Arg Phe Gly Trp Leu Glu Val Ala Ala Leu Thr Ala Ala Ser Val
1               5                   10                  15

Ala Asn Ala Gln Glu Leu Ala Phe Ser Pro Pro Phe Tyr Pro Ser Pro
            20                  25                  30

Trp Ala Asp Gly Gln Gly Glu Trp Ala Asp Ala His Arg Arg Ala Val
        35                  40                  45

Glu Ile Val Ser Gln Met Thr Leu Ala Glu Lys Val Asn Leu Thr Thr
    50                  55                  60

Gly Thr Gly Trp Glu Met Asp Arg Cys Val Gly Gln Thr Gly Ser Val
65                  70                  75                  80

Pro Arg Leu Gly Ile Asn Trp Gly Leu Cys Gly Gln Asp Ser Pro Leu
                85                  90                  95

Gly Ile Arg Phe Ser Asp Leu Asn Ser Ala Phe Pro Ala Gly Thr Asn
            100                 105                 110

Val Ala Ala Thr Trp Asp Lys Thr Leu Ala Tyr Leu Arg Gly Lys Ala
        115                 120                 125

Met Gly Glu Glu Phe Asn Asp Lys Gly Val Asp Ile Leu Leu Gly Pro
    130                 135                 140

Ala Ala Gly Pro Leu Gly Lys Tyr Pro Asp Gly Gly Arg Ile Trp Glu
145                 150                 155                 160

Gly Phe Ser Pro Asp Pro Val Leu Thr Gly Val Leu Phe Ala Glu Thr
                165                 170                 175

Ile Lys Gly Ile Gln Asp Ala Gly Val Ile Ala Thr Ala Lys His Tyr
            180                 185                 190

Ile Leu Asn Glu Gln Glu His Phe Arg Gln Val Gly Glu Ala Gln Gly
        195                 200                 205

Tyr Gly Tyr Asn Ile Thr Glu Thr Ile Ser Ser Asn Val Asp Asp Lys
    210                 215                 220

Thr Met His Glu Leu Tyr Leu Trp Pro Phe Ala Asp Ala Val Arg Ala
225                 230                 235                 240

Gly Val Gly Ala Val Met Cys Ser Tyr Asn Gln Ile Asn Asn Ser Tyr
                245                 250                 255

Gly Cys Gln Asn Ser Gln Thr Leu Asn Lys Leu Leu Lys Ala Glu Leu
            260                 265                 270

Gly Phe Gln Gly Phe Val Met Ser Asp Trp Ser Ala His His Ser Gly
```

-continued

```
        275                 280                 285

Val Gly Ala Ala Leu Ala Gly Leu Asp Met Ser Met Pro Gly Asp Ile
    290                 295                 300

Ser Phe Asp Asp Gly Leu Ser Phe Trp Gly Thr Asn Leu Thr Val Ser
305                 310                 315                 320

Val Leu Asn Gly Thr Val Pro Ala Trp Arg Val Asp Asp Met Ala Val
                325                 330                 335

Arg Ile Met Thr Ala Tyr Tyr Lys Val Gly Arg Asp Arg Leu Arg Ile
            340                 345                 350

Pro Pro Asn Phe Ser Ser Trp Thr Arg Asp Glu Tyr Gly Trp Glu His
        355                 360                 365

Ser Ala Val Ser Glu Gly Ala Trp Thr Lys Val Asn Asp Phe Val Asn
    370                 375                 380

Val Gln Arg Ser His Ser Gln Ile Ile Arg Glu Ile Gly Ala Ala Ser
385                 390                 395                 400

Thr Val Leu Leu Lys Asn Thr Gly Ala Leu Pro Leu Thr Gly Lys Glu
                405                 410                 415

Val Lys Val Gly Val Leu Gly Glu Asp Ala Gly Ser Asn Pro Trp Gly
            420                 425                 430

Ala Asn Gly Cys Pro Asp Arg Gly Cys Asp Asn Gly Thr Leu Ala Met
        435                 440                 445

Ala Trp Gly Ser Gly Thr Ala Asn Phe Pro Tyr Leu Val Thr Pro Glu
    450                 455                 460

Gln Ala Ile Gln Arg Glu Val Ile Ser Asn Gly Gly Asn Val Phe Ala
465                 470                 475                 480

Val Thr Asp Asn Gly Ala Leu Ser Gln Met Ala Asp Val Ala Ser Gln
                485                 490                 495

Ser Ser Val Ser Leu Val Phe Val Asn Ala Asp Ser Gly Glu Gly Phe
            500                 505                 510

Ile Ser Val Asp Gly Asn Glu Gly Asp Arg Lys Asn Leu Thr Leu Trp
        515                 520                 525

Lys Asn Gly Glu Ala Val Ile Asp Thr Val Val Ser His Cys Asn Asn
    530                 535                 540

Thr Ile Val Val Ile His Ser Val Gly Pro Val Leu Ile Asp Arg Trp
545                 550                 555                 560

Tyr Asp Asn Pro Asn Val Thr Ala Ile Ile Trp Ala Gly Leu Pro Gly
                565                 570                 575

Gln Glu Ser Gly Asn Ser Leu Val Asp Val Leu Tyr Gly Arg Val Asn
            580                 585                 590

Pro Ser Ala Lys Thr Pro Phe Thr Trp Gly Lys Thr Arg Glu Ser Tyr
        595                 600                 605

Gly Ala Pro Leu Leu Thr Glu Pro Asn Asn Gly Asn Gly Ala Pro Gln
    610                 615                 620

Asp Asp Phe Asn Glu Gly Val Phe Ile Asp Tyr Arg His Phe Asp Lys
625                 630                 635                 640

Arg Asn Glu Thr Pro Ile Tyr Glu Phe Gly His Gly Leu Ser Tyr Thr
                645                 650                 655

Thr Phe Gly Tyr Ser His Leu Arg Val Gln Ala Leu Asn Ser Ser Ser
            660                 665                 670

Ser Ala Tyr Val Pro Thr Ser Gly Glu Thr Lys Pro Ala Pro Thr Tyr
        675                 680                 685

Gly Glu Ile Gly Ser Ala Ala Asp Tyr Leu Tyr Pro Glu Gly Leu Lys
    690                 695                 700
```

Arg Ile Thr Lys Phe Ile Tyr Pro Trp Leu Asn Ser Thr Asp Leu Glu
705 710 715 720

Asp Ser Ser Asp Asp Pro Asn Tyr Gly Trp Glu Asp Ser Glu Tyr Ile
725 730 735

Pro Glu Gly Ala Arg Asp Gly Ser Pro Gln Pro Leu Leu Lys Ala Gly
740 745 750

Gly Ala Pro Gly Gly Asn Pro Thr Leu Tyr Gln Asp Leu Val Arg Val
755 760 765

Ser Ala Thr Ile Thr Asn Thr Gly Asn Val Ala Gly Tyr Glu Val Pro
770 775 780

Gln Leu Tyr Val Ser Leu Gly Gly Pro Asn Glu Pro Arg Val Val Leu
785 790 795 800

Arg Lys Phe Asp Arg Ile Phe Leu Ala Pro Gly Glu Gln Lys Val Trp
805 810 815

Thr Thr Thr Leu Asn Arg Arg Asp Leu Ala Asn Trp Asp Val Glu Ala
820 825 830

Gln Asp Trp Val Ile Thr Lys Tyr Pro Lys Lys Val His Val Gly Ser
835 840 845

Ser Ser Arg Lys Leu Pro Leu Arg Ala Pro Leu Pro Arg Val Tyr
850 855 860

<210> SEQ ID NO 29
<211> LENGTH: 2800
<212> TYPE: DNA
<213> ORGANISM: Penicillium brasilianum

<400> SEQUENCE: 29
tgaaaatgca gggttctaca atctttctgg ctttcgcctc atgggcgagc caggttgctg 60
ccattgcgca gcccatacag aagcacgagg tttgttttat cttgctcatg gacgtgcttt 120
gacttgacta attgttttac atacagcccg gatttctgca cgggccccaa gccatagaat 180
cgttctcaga accgttctac ccgtcgccct ggatgaatcc tcacgccgag ggctgggagg 240
ccgcatatca gaaagctcaa gattttgtct cgcaactcac tatcttggag aaaataaatc 300
tgaccaccgg tgttgggtaa gtctctccga ctgcttctgg gtcacggtgc gacgagccac 360
tgactttttg aagctgggaa aatgggccgt gtgtaggaaa cactggatca attcctcgtc 420
tcggattcaa aggattttgt acccaggatt caccacaggg tgttcggttc gcagattatt 480
cctccgcttt cacatctagc caaatggccg ccgcaacatt tgaccgctca attctttatc 540
aacgaggcca agccatggca caggaacaca aggctaaggg tatcacaatt caattgggcc 600
ctgttgccgg ccctctcggt cgcatccccg agggcggccg caactgggaa ggattctccc 660
ctgatcctgt cttgactggt atagccatgg ctgagacaat taagggcatg caggatactg 720
gagtgattgc ttgcgctaaa cattatattg gaaacgagca ggagcacttc cgtcaagtgg 780
gtgaagctgc gggtcacgga tacactattt ccgatactat ttcatctaat attgacgacc 840
gtgctatgca tgagctatac ttgtggccat ttgctgatgc cgttcgcgct ggtgtgggtt 900
ctttcatgtg ctcatactct cagatcaaca actcctacgg atgccaaaac agtcagaccc 960
tcaacaagct cctcaagagc gaattgggct tccaaggctt tgtcatgagc gattggggtg 1020
cccatcactc tggagtgtca tcggcgctag ctggacttga tatgagcatg ccgggtgata 1080
ccgaatttga ttctggcttg agcttctggg gctctaacct caccattgca attctgaacg 1140
gcacggttcc cgaatggcgc ctggatgaca tggcgatgcg aattatggct gcatacttca 1200

-continued

```
aagttggcct tactattgag gatcaaccag atgtcaactt caatgcctgg acccatgaca   1260

cctacggata taaatacgct tatagcaagg aagattacga gcaggtcaac tggcatgtcg   1320

atgttcgcag cgaccacaat aagctcattc gcgagactgc cgcgaagggt acagttctgc   1380

tgaagaacaa ctttcatgct ctccctctga agcagcccag gttcgtggcc gtcgttggtc   1440

aggatgccgg gccaaacccc aagggcccta acggctgcgc agaccgagga tgcgaccaag   1500

gcactctcgc aatgggatgg ggctcagggt ctaccgaatt cccttacctg gtcactcctg   1560

acactgctat tcagtcaaag gtcctcgaat acgggggtcg atacgagagt atttttgata   1620

actatgacga caatgctatc ttgtcgcttg tctcacagcc tgatgcaacc tgtatcgttt   1680

ttgcaaatgc cgattccggt gaaggctaca tcactgtcga caacaactgg ggtgaccgca   1740

acaatctgac cctctggcaa aatgccgatc aagtgattag cactgtcagc tcgcgatgca   1800

acaacacaat cgttgttctc cactctgtcg gaccagtgtt gctaaatggt atatatgagc   1860

acccgaacat cacagctatt gtctgggcag ggatgccagg cgaagaatct ggcaatgctc   1920

tcgtggatat tctttggggc aatgttaacc ctgccggtcg cactccgttc acctgggcca   1980

aaagtcgaga ggactatggc actgatataa tgtacgagcc caacaacggc cagcgtgcgc   2040

ctcagcagga tttcaccgag agcatctacc tcgactaccg ccatttcgac aaagctggta   2100

tcgagccaat ttacgagttt ggattcggcc tctcctatac caccttcgaa tactctgacc   2160

tccgtgttgt gaagaagtat gttcaaccat acagtcccac gaccggcacc ggtgctcaag   2220

caccttccat cggacagcca cctagccaga acctggatac ctacaagttc cctgctacat   2280

acaagtacat caaaaccttc atttatccct acctgaacag cactgtctcc ctccgcgctg   2340

cttccaagga tcccgaatac ggtcgtacag actttatccc accccacgcg cgtgatggct   2400

cccctcaacc tctcaacccc gctggagacc cagtggccag tggtggaaac aacatgctct   2460

acgacgaact ttacgaggtc actgcacaga tcaaaaacac tggcgacgtg gccggcgacg   2520

aagtcgtcca gctttacgta gatctcgggg gtgacaaccc gcctcgtcag ttgagaaact   2580

ttgacaggtt ttatctgctg cccggtcaga gctcaacatt ccgggctaca ttgacgcgcc   2640

gtgatttgag caactgggat attgaggcgc agaactggcg agttacggaa tcgcctaaga   2700

gagtgtatgt tggacggtcg agtcgggatt tgccgctgag ctcacaattg gagtaatgat   2760

catgtctacc aatagatgtt gaatgtctgg tgtggatatt                         2800
```

<210> SEQ ID NO 30
<211> LENGTH: 878
<212> TYPE: PRT
<213> ORGANISM: Penicillium brasilianum

<400> SEQUENCE: 30

```
Met Gln Gly Ser Thr Ile Phe Leu Ala Phe Ala Ser Trp Ala Ser Gln
1               5                   10                  15

Val Ala Ala Ile Ala Gln Pro Ile Gln Lys His Glu Pro Gly Phe Leu
            20                  25                  30

His Gly Pro Gln Ala Ile Glu Ser Phe Ser Glu Pro Phe Tyr Pro Ser
        35                  40                  45

Pro Trp Met Asn Pro His Ala Glu Gly Trp Glu Ala Ala Tyr Gln Lys
    50                  55                  60

Ala Gln Asp Phe Val Ser Gln Leu Thr Ile Leu Glu Lys Ile Asn Leu
65                  70                  75                  80

Thr Thr Gly Val Gly Trp Glu Asn Gly Pro Cys Val Gly Asn Thr Gly
                85                  90                  95
```

```
Ser Ile Pro Arg Leu Gly Phe Lys Gly Phe Cys Thr Gln Asp Ser Pro
            100                 105                 110

Gln Gly Val Arg Phe Ala Asp Tyr Ser Ser Ala Phe Thr Ser Ser Gln
        115                 120                 125

Met Ala Ala Ala Thr Phe Asp Arg Ser Ile Leu Tyr Gln Arg Gly Gln
    130                 135                 140

Ala Met Ala Gln Glu His Lys Ala Lys Gly Ile Thr Ile Gln Leu Gly
145                 150                 155                 160

Pro Val Ala Gly Pro Leu Gly Arg Ile Pro Glu Gly Gly Arg Asn Trp
                165                 170                 175

Glu Gly Phe Ser Pro Asp Pro Val Leu Thr Gly Ile Ala Met Ala Glu
            180                 185                 190

Thr Ile Lys Gly Met Gln Asp Thr Gly Val Ile Ala Cys Ala Lys His
        195                 200                 205

Tyr Ile Gly Asn Glu Gln Glu His Phe Arg Gln Val Gly Glu Ala Ala
    210                 215                 220

Gly His Gly Tyr Thr Ile Ser Asp Thr Ile Ser Ser Asn Ile Asp Asp
225                 230                 235                 240

Arg Ala Met His Glu Leu Tyr Leu Trp Pro Phe Ala Asp Ala Val Arg
                245                 250                 255

Ala Gly Val Gly Ser Phe Met Cys Ser Tyr Ser Gln Ile Asn Asn Ser
            260                 265                 270

Tyr Gly Cys Gln Asn Ser Gln Thr Leu Asn Lys Leu Leu Lys Ser Glu
        275                 280                 285

Leu Gly Phe Gln Gly Phe Val Met Ser Asp Trp Gly Ala His His Ser
    290                 295                 300

Gly Val Ser Ser Ala Leu Ala Gly Leu Asp Met Ser Met Pro Gly Asp
305                 310                 315                 320

Thr Glu Phe Asp Ser Gly Leu Ser Phe Trp Gly Ser Asn Leu Thr Ile
                325                 330                 335

Ala Ile Leu Asn Gly Thr Val Pro Glu Trp Arg Leu Asp Asp Met Ala
            340                 345                 350

Met Arg Ile Met Ala Ala Tyr Phe Lys Val Gly Leu Thr Ile Glu Asp
        355                 360                 365

Gln Pro Asp Val Asn Phe Asn Ala Trp Thr His Asp Thr Tyr Gly Tyr
    370                 375                 380

Lys Tyr Ala Tyr Ser Lys Glu Asp Tyr Glu Gln Val Asn Trp His Val
385                 390                 395                 400

Asp Val Arg Ser Asp His Asn Lys Leu Ile Arg Glu Thr Ala Ala Lys
                405                 410                 415

Gly Thr Val Leu Leu Lys Asn Asn Phe His Ala Leu Pro Leu Lys Gln
            420                 425                 430

Pro Arg Phe Val Ala Val Val Gly Gln Asp Ala Gly Pro Asn Pro Lys
        435                 440                 445

Gly Pro Asn Gly Cys Ala Asp Arg Gly Cys Asp Gln Gly Thr Leu Ala
    450                 455                 460

Met Gly Trp Gly Ser Gly Ser Thr Glu Phe Pro Tyr Leu Val Thr Pro
465                 470                 475                 480

Asp Thr Ala Ile Gln Ser Lys Val Leu Glu Tyr Gly Gly Arg Tyr Glu
                485                 490                 495

Ser Ile Phe Asp Asn Tyr Asp Asp Asn Ala Ile Leu Ser Leu Val Ser
            500                 505                 510
```

```
Gln Pro Asp Ala Thr Cys Ile Val Phe Ala Asn Ala Asp Ser Gly Glu
        515                 520                 525

Gly Tyr Ile Thr Val Asp Asn Asn Trp Gly Asp Arg Asn Asn Leu Thr
    530                 535                 540

Leu Trp Gln Asn Ala Asp Gln Val Ile Ser Thr Val Ser Ser Arg Cys
545                 550                 555                 560

Asn Asn Thr Ile Val Val Leu His Ser Val Gly Pro Val Leu Leu Asn
                565                 570                 575

Gly Ile Tyr Glu His Pro Asn Ile Thr Ala Ile Val Trp Ala Gly Met
            580                 585                 590

Pro Gly Glu Glu Ser Gly Asn Ala Leu Val Asp Ile Leu Trp Gly Asn
        595                 600                 605

Val Asn Pro Ala Gly Arg Thr Pro Phe Thr Trp Ala Lys Ser Arg Glu
    610                 615                 620

Asp Tyr Gly Thr Asp Ile Met Tyr Glu Pro Asn Asn Gly Gln Arg Ala
625                 630                 635                 640

Pro Gln Gln Asp Phe Thr Glu Ser Ile Tyr Leu Asp Tyr Arg His Phe
                645                 650                 655

Asp Lys Ala Gly Ile Glu Pro Ile Tyr Glu Phe Gly Phe Gly Leu Ser
            660                 665                 670

Tyr Thr Thr Phe Glu Tyr Ser Asp Leu Arg Val Val Lys Lys Tyr Val
        675                 680                 685

Gln Pro Tyr Ser Pro Thr Thr Gly Thr Gly Ala Gln Ala Pro Ser Ile
    690                 695                 700

Gly Gln Pro Pro Ser Gln Asn Leu Asp Thr Tyr Lys Phe Pro Ala Thr
705                 710                 715                 720

Tyr Lys Tyr Ile Lys Thr Phe Ile Tyr Pro Tyr Leu Asn Ser Thr Val
                725                 730                 735

Ser Leu Arg Ala Ala Ser Lys Asp Pro Glu Tyr Gly Arg Thr Asp Phe
            740                 745                 750

Ile Pro Pro His Ala Arg Asp Gly Ser Pro Gln Pro Leu Asn Pro Ala
        755                 760                 765

Gly Asp Pro Val Ala Ser Gly Gly Asn Asn Met Leu Tyr Asp Glu Leu
    770                 775                 780

Tyr Glu Val Thr Ala Gln Ile Lys Asn Thr Gly Asp Val Ala Gly Asp
785                 790                 795                 800

Glu Val Val Gln Leu Tyr Val Asp Leu Gly Gly Asp Asn Pro Pro Arg
                805                 810                 815

Gln Leu Arg Asn Phe Asp Arg Phe Tyr Leu Leu Pro Gly Gln Ser Ser
            820                 825                 830

Thr Phe Arg Ala Thr Leu Thr Arg Arg Asp Leu Ser Asn Trp Asp Ile
        835                 840                 845

Glu Ala Gln Asn Trp Arg Val Thr Glu Ser Pro Lys Arg Val Tyr Val
    850                 855                 860

Gly Arg Ser Ser Arg Asp Leu Pro Leu Ser Ser Gln Leu Glu
865                 870                 875
```

<210> SEQ ID NO 31
<211> LENGTH: 2934
<212> TYPE: DNA
<213> ORGANISM: Aspergillus niger

<400> SEQUENCE: 31

```
atgaggttca cttcgatcga ggcggtggct ctgactgccg tctcgctggc cagcgctgta      60
```

-continued

```
cgtgccgtta ctttgtcctg agaattgcaa ttgtgcttaa ctagattcat ttgtttgttt    120
catcatcgct gacaatggtc ttttcatagg atgaattggc ctactcccca ccgtattacc    180
catcccccttg ggccaatggc cagggcgact gggcgcaggc ataccagcgc gctgttgata    240
ttgtctcgca aatgacattg gatgagaagg tcaatctgac cacaggaact gggtagggct    300
tacatggcgc aatctgtatg ctccggctaa caacttctag atgggaattg gaactatgtg    360
ttggtcagac tggcggtgtt ccccggtagg tttgaaaata ttgtcgagac aggggacatt    420
tattgattaa cggtgacaga ttgggagttc cgggaatgtg tttacaggat agccctctgg    480
gcgttcgcga ctgtaagcca tctgctgttg ttaggcttcg atgctctcac tgacacggcg    540
cagccgacta caactctgct ttccctgccg gcatgaacgt ggctgcaacc tgggacaaga    600
atctggcata ccttcgcggc aaggctatgg gtcaggaatt tagtgacaag ggtgccgata    660
tccaattggg tccagctgcc ggccctctcg gtagaagtcc cgacggtggt cgtaactggg    720
agggcttctc cccagaccct gccctaagtg gtgtgctctt tgccgagacc atcaagggta    780
tccaagatgc tggtgtggtt gcgacggcta agcactacat tgcttacgag caagagcatt    840
tccgtcaggc gcctgaagcc caaggttatg gatttaatat ttccgagagt ggaagtgcga    900
acctcgacga taagactatg cacgagctgt acctctggcc cttcgcggat gccatccgtg    960
caggtgctgg cgctgtgatg tgctcctaca accagatcaa caacagttat ggctgccaga   1020
acagctacac tctgaacaag ctgctcaagg ccgagctggg cttccagggc tttgtcatga   1080
gtgattgggc tgctcaccat gctggtgtga gtggtgcttt ggcaggattg gatatgtcta   1140
tgccaggaga cgtcgactac gacagtggta cgtcttactg ggtacaaac ttgaccatta   1200
gcgtgctcaa cggaacggtg ccccaatggc gtgttgatga catggctgtc cgcatcatgg   1260
ccgcctacta caaggtcgga cgtgaccgtc tgtggactcc tcccaacttc agctcatgga   1320
ccagagatga atacggctac aagtactact acgtgtcgga gggaccgtac gagaaggtca   1380
accagtacgt gaacgtgcaa cgcaaccaca gcgaactgat tcgccgcatt ggagcggaca   1440
gcacggtgct cctcaagaac gacggcgctc tgcctttgac tggtaaggag cgcctggtcg   1500
cgcttatcgg agaagatgcg ggctccaacc cttatggtgc caacggctgc agtgaccgtg   1560
gatgcgacaa tggaacattg gcgatgggct ggggaagtgg tactgccaac ttcccctact   1620
tggtgacccc cgagcaggcc atctcaaacg aggtgcttaa gcacaagaat ggtgtattca   1680
ccgccaccga taactgggct atcgatcaaa ttgaggcgct tgctaagacc gccaggtaag   1740
aagatctcca attttttttt cttgtactat ggatgctgac agcatgctag tgtctctctt   1800
gtctttgtca acgccgactc tggcgagggt tacatcaatg tggacggaaa cctgggtgac   1860
cgcaggaacc tgaccctgtg gaggaacggc gataatgtga tcaaggctgc tgctagcaac   1920
tgcaacaaca ccattgttgt cattcactct gtcggcccag tcttggttaa cgaatggtac   1980
gacaacccca atgttaccgc tatcctctgg ggtggtctgc ccggtcagga gtctggcaac   2040
tctcttgccg acgtcctcta tggccgtgtc aaccccggtg ccaagtcgcc ctttacctgg   2100
ggcaagactc gtgaggccta ccaagactac ttggtcaccg agcccaacaa cggcaacgga   2160
gcccctcagg aagacttcgt cgagggcgtc ttcattgact accgtggatt tgacaagcgc   2220
aacgagaccc cgatctacga gttcggctat ggtttaagct acaccacttt caactactcg   2280
aaccttgagg tgcaggtgct gagcgcccct gcatacgagc ctgcttcggg tgagaccgag   2340
gcagcgccaa ccttcggaga ggttggaaat gcgtcggatt acctctaccc cagcggattg   2400
cagagaatta ccaagttcat ctacccctgg ctcaacggta ccgatctcga ggcatcttcc   2460
```

```
ggggatgcta gctacgggca ggactcctcg gactatcttc cagagggagc caccgatggc   2520

tctgcgcaac cgatcctgcc tgctggtggc ggtcctggcg gcaaccctcg cctgtacgac   2580

gagctcatcc gcgtgtcagt gaccatcaag aacaccggca aggttgctgg tgatgaagtt   2640

ccccaactgg taagtaaaca tgaggtccga acgaggttga acaaagctaa tcagtcgcag   2700

tatgtttcgc ttggcggtcc caacgagccc aaaatcgtgc tgcgtcaatt cgagcgcatc   2760

acgctgcagc cgtcggagga gacgaagtgg agcacgactc tgacgcgccg tgaccttgca   2820

aactggaatg ttgagaagca ggactgggag attacgtcgt atcccaagat ggtgtttgtc   2880

ggaagctcct cgcggaagct gccgctccgg gcgtctctgc ctactgttca ctaa         2934
```

<210> SEQ ID NO 32
<211> LENGTH: 860
<212> TYPE: PRT
<213> ORGANISM: Aspergillus niger

<400> SEQUENCE: 32

```
Met Arg Phe Thr Ser Ile Glu Ala Val Ala Leu Thr Ala Val Ser Leu
1               5                   10                  15

Ala Ser Ala Asp Glu Leu Ala Tyr Ser Pro Pro Tyr Tyr Pro Ser Pro
            20                  25                  30

Trp Ala Asn Gly Gln Gly Asp Trp Ala Gln Ala Tyr Gln Arg Ala Val
        35                  40                  45

Asp Ile Val Ser Gln Met Thr Leu Asp Glu Lys Val Asn Leu Thr Thr
    50                  55                  60

Gly Thr Gly Trp Glu Leu Glu Leu Cys Val Gly Gln Thr Gly Gly Val
65                  70                  75                  80

Pro Arg Leu Gly Val Pro Gly Met Cys Leu Gln Asp Ser Pro Leu Gly
                85                  90                  95

Val Arg Asp Ser Asp Tyr Asn Ser Ala Phe Pro Ala Gly Met Asn Val
            100                 105                 110

Ala Ala Thr Trp Asp Lys Asn Leu Ala Tyr Leu Arg Gly Lys Ala Met
        115                 120                 125

Gly Gln Glu Phe Ser Asp Lys Gly Ala Asp Ile Gln Leu Gly Pro Ala
    130                 135                 140

Ala Gly Pro Leu Gly Arg Ser Pro Asp Gly Gly Arg Asn Trp Glu Gly
145                 150                 155                 160

Phe Ser Pro Asp Pro Ala Leu Ser Gly Val Leu Phe Ala Glu Thr Ile
                165                 170                 175

Lys Gly Ile Gln Asp Ala Gly Val Val Ala Thr Ala Lys His Tyr Ile
            180                 185                 190

Ala Tyr Glu Gln Glu His Phe Arg Gln Ala Pro Glu Ala Gln Gly Tyr
        195                 200                 205

Gly Phe Asn Ile Ser Glu Ser Gly Ser Ala Asn Leu Asp Asp Lys Thr
    210                 215                 220

Met His Glu Leu Tyr Leu Trp Pro Phe Ala Asp Ala Ile Arg Ala Gly
225                 230                 235                 240

Ala Gly Ala Val Met Cys Ser Tyr Asn Gln Ile Asn Asn Ser Tyr Gly
                245                 250                 255

Cys Gln Asn Ser Tyr Thr Leu Asn Lys Leu Leu Lys Ala Glu Leu Gly
            260                 265                 270

Phe Gln Gly Phe Val Met Ser Asp Trp Ala Ala His His Ala Gly Val
        275                 280                 285
```

-continued

```
Ser Gly Ala Leu Ala Gly Leu Asp Met Ser Met Pro Gly Asp Val Asp
    290                 295                 300

Tyr Asp Ser Gly Thr Ser Tyr Trp Gly Thr Asn Leu Thr Ile Ser Val
305                 310                 315                 320

Leu Asn Gly Thr Val Pro Gln Trp Arg Val Asp Asp Met Ala Val Arg
                325                 330                 335

Ile Met Ala Ala Tyr Tyr Lys Val Gly Arg Asp Arg Leu Trp Thr Pro
            340                 345                 350

Pro Asn Phe Ser Ser Trp Thr Arg Asp Glu Tyr Gly Tyr Lys Tyr Tyr
        355                 360                 365

Tyr Val Ser Glu Gly Pro Tyr Glu Lys Val Asn Gln Tyr Val Asn Val
    370                 375                 380

Gln Arg Asn His Ser Glu Leu Ile Arg Arg Ile Gly Ala Asp Ser Thr
385                 390                 395                 400

Val Leu Leu Lys Asn Asp Gly Ala Leu Pro Leu Thr Gly Lys Glu Arg
                405                 410                 415

Leu Val Ala Leu Ile Gly Glu Asp Ala Gly Ser Asn Pro Tyr Gly Ala
            420                 425                 430

Asn Gly Cys Ser Asp Arg Gly Cys Asp Asn Gly Thr Leu Ala Met Gly
        435                 440                 445

Trp Gly Ser Gly Thr Ala Asn Phe Pro Tyr Leu Val Thr Pro Glu Gln
    450                 455                 460

Ala Ile Ser Asn Glu Val Leu Lys His Lys Asn Gly Val Phe Thr Ala
465                 470                 475                 480

Thr Asp Asn Trp Ala Ile Asp Gln Ile Glu Ala Leu Ala Lys Thr Ala
                485                 490                 495

Ser Val Ser Leu Val Phe Val Asn Ala Asp Ser Gly Glu Gly Tyr Ile
            500                 505                 510

Asn Val Asp Gly Asn Leu Gly Asp Arg Arg Asn Leu Thr Leu Trp Arg
        515                 520                 525

Asn Gly Asp Asn Val Ile Lys Ala Ala Ala Ser Asn Cys Asn Asn Thr
    530                 535                 540

Ile Val Val Ile His Ser Val Gly Pro Val Leu Val Asn Glu Trp Tyr
545                 550                 555                 560

Asp Asn Pro Asn Val Thr Ala Ile Leu Trp Gly Gly Leu Pro Gly Gln
                565                 570                 575

Glu Ser Gly Asn Ser Leu Ala Asp Val Leu Tyr Gly Arg Val Asn Pro
            580                 585                 590

Gly Ala Lys Ser Pro Phe Thr Trp Gly Lys Thr Arg Glu Ala Tyr Gln
        595                 600                 605

Asp Tyr Leu Val Thr Glu Pro Asn Asn Gly Asn Gly Ala Pro Gln Glu
    610                 615                 620

Asp Phe Val Glu Gly Val Phe Ile Asp Tyr Arg Gly Phe Asp Lys Arg
625                 630                 635                 640

Asn Glu Thr Pro Ile Tyr Glu Phe Gly Tyr Gly Leu Ser Tyr Thr Thr
                645                 650                 655

Phe Asn Tyr Ser Asn Leu Glu Val Gln Val Leu Ser Ala Pro Ala Tyr
            660                 665                 670

Glu Pro Ala Ser Gly Glu Thr Glu Ala Ala Pro Thr Phe Gly Glu Val
        675                 680                 685

Gly Asn Ala Ser Asp Tyr Leu Tyr Pro Ser Gly Leu Gln Arg Ile Thr
    690                 695                 700

Lys Phe Ile Tyr Pro Trp Leu Asn Gly Thr Asp Leu Glu Ala Ser Ser
```

-continued

```
705                 710                 715                 720

Gly Asp Ala Ser Tyr Gly Gln Asp Ser Ser Asp Tyr Leu Pro Glu Gly
                725                 730                 735

Ala Thr Asp Gly Ser Ala Gln Pro Ile Leu Pro Ala Gly Gly Gly Pro
            740                 745                 750

Gly Gly Asn Pro Arg Leu Tyr Asp Glu Leu Ile Arg Val Ser Val Thr
        755                 760                 765

Ile Lys Asn Thr Gly Lys Val Ala Gly Asp Glu Val Pro Gln Leu Tyr
    770                 775                 780

Val Ser Leu Gly Gly Pro Asn Glu Pro Lys Ile Val Leu Arg Gln Phe
785                 790                 795                 800

Glu Arg Ile Thr Leu Gln Pro Ser Glu Glu Thr Lys Trp Ser Thr Thr
                805                 810                 815

Leu Thr Arg Arg Asp Leu Ala Asn Trp Asn Val Glu Lys Gln Asp Trp
            820                 825                 830

Glu Ile Thr Ser Tyr Pro Lys Met Val Phe Val Gly Ser Ser Ser Arg
        835                 840                 845

Lys Leu Pro Leu Arg Ala Ser Leu Pro Thr Val His
    850                 855                 860
```

<210> SEQ ID NO 33
<211> LENGTH: 799
<212> TYPE: DNA
<213> ORGANISM: Thermoascus aurantiacus

<400> SEQUENCE: 33

```
atgtcctttt ccaagataat tgctactgcc ggcgttcttg cctctgcttc tctagtggct     60

ggccatggct tcgttcagaa catcgtgatt gatggtaaaa agtatgtcat tgcaagacgc    120

acataagcgg caacagctga caatcgacag ttatggcggg tatctagtga accagtatcc    180

atacatgtcc aatcctccag aggtcatcgc ctggtctact acggcaactg atcttggatt    240

tgtggacggt actggatacc aaaccccaga tatcatctgc catagggggcg ccaagcctgg    300

agccctgact gctccagtct ctccaggagg aactgttgag cttcaatgga ctccatggcc    360

tgattctcac catggcccag ttatcaacta ccttgctccg tgcaatggtg attgttccac    420

tgtggataag acccaattag aattcttcaa aattgccgag agcggtctca tcaatgatga    480

caatcctcct gggatctggg cttcagacaa tctgatagca gccaacaaca gctggactgt    540

caccattcca accacaattg cacctggaaa ctatgttctg aggcatgaga ttattgctct    600

tcactcagct cagaaccagg atggtgccca gaactatccc cagtgcatca atctgcaggt    660

cactggaggt ggttctgata accctgctgg aactcttgga acggcactct accacgatac    720

cgatcctgga attctgatca acatctatca gaaactttcc agctatatca tccctggtcc    780

tcctctgtat actggttaa                                                  799
```

<210> SEQ ID NO 34
<211> LENGTH: 250
<212> TYPE: PRT
<213> ORGANISM: Thermoascus aurantiacus

<400> SEQUENCE: 34

```
Met Ser Phe Ser Lys Ile Ile Ala Thr Ala Gly Val Leu Ala Ser Ala
1               5                   10                  15

Ser Leu Val Ala Gly His Gly Phe Val Gln Asn Ile Val Ile Asp Gly
            20                  25                  30
```

```
Lys Lys Tyr Tyr Gly Gly Tyr Leu Val Asn Gln Tyr Pro Tyr Met Ser
        35                  40                  45

Asn Pro Pro Glu Val Ile Ala Trp Ser Thr Thr Ala Thr Asp Leu Gly
    50                  55                  60

Phe Val Asp Gly Thr Gly Tyr Gln Thr Pro Asp Ile Ile Cys His Arg
65                  70                  75                  80

Gly Ala Lys Pro Gly Ala Leu Thr Ala Pro Val Ser Pro Gly Gly Thr
                85                  90                  95

Val Glu Leu Gln Trp Thr Pro Trp Pro Asp Ser His His Gly Pro Val
            100                 105                 110

Ile Asn Tyr Leu Ala Pro Cys Asn Gly Asp Cys Ser Thr Val Asp Lys
        115                 120                 125

Thr Gln Leu Glu Phe Phe Lys Ile Ala Glu Ser Gly Leu Ile Asn Asp
    130                 135                 140

Asp Asn Pro Pro Gly Ile Trp Ala Ser Asp Asn Leu Ile Ala Ala Asn
145                 150                 155                 160

Asn Ser Trp Thr Val Thr Ile Pro Thr Thr Ile Ala Pro Gly Asn Tyr
                165                 170                 175

Val Leu Arg His Glu Ile Ile Ala Leu His Ser Ala Gln Asn Gln Asp
            180                 185                 190

Gly Ala Gln Asn Tyr Pro Gln Cys Ile Asn Leu Gln Val Thr Gly Gly
        195                 200                 205

Gly Ser Asp Asn Pro Ala Gly Thr Leu Gly Thr Ala Leu Tyr His Asp
    210                 215                 220

Thr Asp Pro Gly Ile Leu Ile Asn Ile Tyr Gln Lys Leu Ser Ser Tyr
225                 230                 235                 240

Ile Ile Pro Gly Pro Pro Leu Tyr Thr Gly
                245                 250
```

<210> SEQ ID NO 35
<211> LENGTH: 681
<212> TYPE: DNA
<213> ORGANISM: Thielavia terrestris

<400> SEQUENCE: 35

```
atgctcgcaa acggtgccat cgtcttcctg gccgccgccc tcggcgtcag tggccactac      60

acctggccac gggttaacga cggcgccgac tggcaacagg tccgtaaggc ggacaactgg     120

caggacaacg gctacgtcgg ggatgtcacg tcgccacaga tccgctgttt ccaggcgacc     180

ccgtccccgg ccccatccgt cctcaacacc acggccggct cgaccgtgac ctactgggcc     240

aaccccgacg tctaccaccc cgggcctgtg cagttttaca tggcccgcgt gcccgatggc     300

gaggacatca actcgtggaa cggcgacggc gccgtgtggt tcaaggtgta cgaggaccat     360

cctacctttg gcgctcagct cacatggccc agcacgggca agagctcgtt cgcggttccc     420

atccccccgt gcatcaagtc cggctactac ctcctccggg cggagcaaat cggcctgcac     480

gtcgcccaga gcgtaggcgg agcgcagttc tacatctcat gcgcccagct cagcgtcacc     540

ggcggcggca gcaccgagcc gccgaacaag gtggccttcc ccggcgctta cagtgcgacg     600

gacccgggca ttctgatcaa catctactac cctgttccca cgtcctacca gaaccccggc     660

ccggccgtct tcagctgctg a                                               681
```

<210> SEQ ID NO 36
<211> LENGTH: 226
<212> TYPE: PRT
<213> ORGANISM: Thielavia terrestris

<400> SEQUENCE: 36

```
Met Leu Ala Asn Gly Ala Ile Val Phe Leu Ala Ala Ala Leu Gly Val
1               5                   10                  15

Ser Gly His Tyr Thr Trp Pro Arg Val Asn Asp Gly Ala Asp Trp Gln
            20                  25                  30

Gln Val Arg Lys Ala Asp Asn Trp Gln Asp Asn Gly Tyr Val Gly Asp
        35                  40                  45

Val Thr Ser Pro Gln Ile Arg Cys Phe Gln Ala Thr Pro Ser Pro Ala
    50                  55                  60

Pro Ser Val Leu Asn Thr Thr Ala Gly Ser Thr Val Thr Tyr Trp Ala
65                  70                  75                  80

Asn Pro Asp Val Tyr His Pro Gly Pro Val Gln Phe Tyr Met Ala Arg
                85                  90                  95

Val Pro Asp Gly Glu Asp Ile Asn Ser Trp Asn Gly Asp Gly Ala Val
            100                 105                 110

Trp Phe Lys Val Tyr Glu Asp His Pro Thr Phe Gly Ala Gln Leu Thr
        115                 120                 125

Trp Pro Ser Thr Gly Lys Ser Ser Phe Ala Val Pro Ile Pro Pro Cys
    130                 135                 140

Ile Lys Ser Gly Tyr Tyr Leu Leu Arg Ala Glu Gln Ile Gly Leu His
145                 150                 155                 160

Val Ala Gln Ser Val Gly Gly Ala Gln Phe Tyr Ile Ser Cys Ala Gln
                165                 170                 175

Leu Ser Val Thr Gly Gly Gly Ser Thr Glu Pro Pro Asn Lys Val Ala
            180                 185                 190

Phe Pro Gly Ala Tyr Ser Ala Thr Asp Pro Gly Ile Leu Ile Asn Ile
        195                 200                 205

Tyr Tyr Pro Val Pro Thr Ser Tyr Gln Asn Pro Gly Pro Ala Val Phe
    210                 215                 220

Ser Cys
225
```

<210> SEQ ID NO 37
<211> LENGTH: 862
<212> TYPE: DNA
<213> ORGANISM: Aspergillus fumigatus

<400> SEQUENCE: 37

```
atgactttgt ccaagatcac ttccattgct ggccttctgg cctcagcgtc tctcgtggct     60

ggccacggct ttgtttctgg cattgttgct gatgggaaat agtatgtgct tgaaccacac    120

aaatgacagc tgcaacagct aacttctatt ccagttacgg agggtacctt gttaaccaat    180

acccctacat gagcaaccct cccgacacca ttgcctggtc caccaccgcc accgacctcg    240

gctttgtgga cggcaccggc taccagtctc cggatattat ctgccacaga gacgcaaaga    300

atggcaagtt gaccgcaacc gttgcagccg gttcacagat cgaattccag tggacgacgt    360

ggccagagtc tcaccatgga ccggtacgac gccgaagaga agagaacata ttgtgaccag    420

ataggctaac atagcatagt tgattactta cctcgctcca tgcaacggcg actgtgccac    480

cgtggacaag accaccctga agtttgtcaa gatcgccgct caaggcttga tcgacggctc    540

caacccacct ggtgtttggg ctgatgatga aatgatcgcc aacaacaaca cggccacagt    600

gaccattcct gcctcctatg cccccggaaa ctacgtcctt cgccacgaga tcatcgccct    660

tcactctgcg ggtaacctga acggcgcgca gaactacccc cagtgtttca acatccaaat    720
```

caccggtggc ggcagtgctc agggatctgg caccgctggc acgtccctgt acaagaatac 780
tgatcctggc atcaagtttg acatctactc ggatctgagc ggtggatacc ctattcctgg 840
tcctgcactg ttcaacgctt aa 862

<210> SEQ ID NO 38
<211> LENGTH: 250
<212> TYPE: PRT
<213> ORGANISM: Aspergillus fumigatus

<400> SEQUENCE: 38

Met Thr Leu Ser Lys Ile Thr Ser Ile Ala Gly Leu Leu Ala Ser Ala
1 5 10 15

Ser Leu Val Ala Gly His Gly Phe Val Ser Gly Ile Val Ala Asp Gly
20 25 30

Lys Tyr Tyr Gly Gly Tyr Leu Val Asn Gln Tyr Pro Tyr Met Ser Asn
35 40 45

Pro Pro Asp Thr Ile Ala Trp Ser Thr Thr Ala Thr Asp Leu Gly Phe
50 55 60

Val Asp Gly Thr Gly Tyr Gln Ser Pro Asp Ile Ile Cys His Arg Asp
65 70 75 80

Ala Lys Asn Gly Lys Leu Thr Ala Thr Val Ala Ala Gly Ser Gln Ile
85 90 95

Glu Phe Gln Trp Thr Thr Trp Pro Glu Ser His His Gly Pro Leu Ile
100 105 110

Thr Tyr Leu Ala Pro Cys Asn Gly Asp Cys Ala Thr Val Asp Lys Thr
115 120 125

Thr Leu Lys Phe Val Lys Ile Ala Ala Gln Gly Leu Ile Asp Gly Ser
130 135 140

Asn Pro Pro Gly Val Trp Ala Asp Asp Glu Met Ile Ala Asn Asn Asn
145 150 155 160

Thr Ala Thr Val Thr Ile Pro Ala Ser Tyr Ala Pro Gly Asn Tyr Val
165 170 175

Leu Arg His Glu Ile Ile Ala Leu His Ser Ala Gly Asn Leu Asn Gly
180 185 190

Ala Gln Asn Tyr Pro Gln Cys Phe Asn Ile Gln Ile Thr Gly Gly Gly
195 200 205

Ser Ala Gln Gly Ser Gly Thr Ala Gly Thr Ser Leu Tyr Lys Asn Thr
210 215 220

Asp Pro Gly Ile Lys Phe Asp Ile Tyr Ser Asp Leu Ser Gly Gly Tyr
225 230 235 240

Pro Ile Pro Gly Pro Ala Leu Phe Asn Ala
245 250

<210> SEQ ID NO 39
<211> LENGTH: 969
<212> TYPE: DNA
<213> ORGANISM: Penicillium pinophilum

<400> SEQUENCE: 39
atgccttcta ctaaagtcgc tgccctttct gctgttctag ctttggcctc cacggttgct 60
ggccatggtt ttgtgcaaaa catcgttatc gacggtaaat cttactctgg ataccttgtg 120
aatcagttcc cctacgagtc caacccacca gctgttattg ggtgggcaac aactgcaacc 180
gacctgggat tcgtcgctcc cagtgagtac accaatgcag acattatctg ccacaagaac 240

-continued

```
gccacacctg gcgcgctttc tgctccagtt gctgcagggg gcactgtcga gctccagtgg    300

actacatggc ccgatagtca tcacggtcct gtcatcagct acctcgccaa ctgcaatggc    360

aattgttcta ccgtggataa gactaagcta gactttgtca agattgacca aggtggtttg    420

atcgacgata ctaccccccc gggtacatgg gcttccgaca aacttatcgc tgccaacaac    480

agctggactg taactatccc ctccaccatc gcgcctggaa actacgtttt gcgccacgaa    540

atcattgctc ttcactccgc tggaaacgca gacggtgccc aaaactaccc tcaatgcatc    600

aacttggaga tcaccggcag cggaaccgcc gctccctctg gtaccgctgg cgaaaagctc    660

tacacctcta ctgaccccgg tatcttggtc aatatctacc aatccttgtc gacctacgtt    720

attcccggac caactctgtg gagcggtgct gccaatggcg ctgttgccac tggttctgct    780

actgcggttg ctacgactgc cactgcttct gcgaccgcta ctcctaccac acttgttacc    840

tctgtcgctc cagcttcatc tacctttgcc actgctgttg tgaccactgt cgctcctgca    900

gtaactgatg tcgtgactgt caccgatgta gttaccgtga ccaccgtcat caccactact    960

gtcctttaa                                                            969
```

<210> SEQ ID NO 40
<211> LENGTH: 322
<212> TYPE: PRT
<213> ORGANISM: Penicillium pinophilum

<400> SEQUENCE: 40

```
Met Pro Ser Thr Lys Val Ala Ala Leu Ser Ala Val Leu Ala Leu Ala
1               5                   10                  15

Ser Thr Val Ala Gly His Gly Phe Val Gln Asn Ile Val Ile Asp Gly
            20                  25                  30

Lys Ser Tyr Ser Gly Tyr Leu Val Asn Gln Phe Pro Tyr Glu Ser Asn
        35                  40                  45

Pro Pro Ala Val Ile Gly Trp Ala Thr Thr Ala Thr Asp Leu Gly Phe
    50                  55                  60

Val Ala Pro Ser Glu Tyr Thr Asn Ala Asp Ile Ile Cys His Lys Asn
65                  70                  75                  80

Ala Thr Pro Gly Ala Leu Ser Ala Pro Val Ala Ala Gly Gly Thr Val
                85                  90                  95

Glu Leu Gln Trp Thr Thr Trp Pro Asp Ser His His Gly Pro Val Ile
            100                 105                 110

Ser Tyr Leu Ala Asn Cys Asn Gly Asn Cys Ser Thr Val Asp Lys Thr
        115                 120                 125

Lys Leu Asp Phe Val Lys Ile Asp Gln Gly Gly Leu Ile Asp Asp Thr
    130                 135                 140

Thr Pro Pro Gly Thr Trp Ala Ser Asp Lys Leu Ile Ala Ala Asn Asn
145                 150                 155                 160

Ser Trp Thr Val Thr Ile Pro Ser Thr Ile Ala Pro Gly Asn Tyr Val
                165                 170                 175

Leu Arg His Glu Ile Ile Ala Leu His Ser Ala Gly Asn Ala Asp Gly
            180                 185                 190

Ala Gln Asn Tyr Pro Gln Cys Ile Asn Leu Glu Ile Thr Gly Ser Gly
        195                 200                 205

Thr Ala Ala Pro Ser Gly Thr Ala Gly Glu Lys Leu Tyr Thr Ser Thr
    210                 215                 220

Asp Pro Gly Ile Leu Val Asn Ile Tyr Gln Ser Leu Ser Thr Tyr Val
225                 230                 235                 240
```

-continued

```
Ile Pro Gly Pro Thr Leu Trp Ser Gly Ala Ala Asn Gly Ala Val Ala
                245                 250                 255

Thr Gly Ser Ala Thr Ala Val Ala Thr Thr Ala Thr Ala Ser Ala Thr
            260                 265                 270

Ala Thr Pro Thr Thr Leu Val Thr Ser Val Ala Pro Ala Ser Ser Thr
        275                 280                 285

Phe Ala Thr Ala Val Val Thr Thr Val Ala Pro Ala Val Thr Asp Val
    290                 295                 300

Val Thr Val Thr Asp Val Val Thr Val Thr Thr Val Ile Thr Thr Thr
305                 310                 315                 320

Val Leu


<210> SEQ ID NO 41
<211> LENGTH: 835
<212> TYPE: DNA
<213> ORGANISM: Penicillium sp.

<400> SEQUENCE: 41

atgctgtctt cgacgactcg caccctcgcc tttacaggcc ttgcgggcct tctgtccgct      60

cccctggtca aggcccatgg ctttgtccag ggcattgtca tcggtgacca attgtaagtc     120

cctctcttgc agttctgtcg attaactgct ggactgcttg cttgactccc tgctgactcc     180

caacagctac agcgggtaca tcgtcaactc gttcccctac gaatccaacc caccccccgt     240

catcggctgg gccacgaccg ccaccgacct gggcttcgtc gacggcacag gataccaagg     300

cccggacatc atctgccacc ggaatgcgac gcccgcgccg ctgacagccc ccgtggccgc     360

cggcggcacc gtcgagctgc agtggacgcc gtggccggac agccaccacg gacccgtcat     420

cacctacctg gcgccgtgca acggcaactg ctcgaccgtc gacaagacga cgctggagtt     480

cttcaagatc gaccagcagg gcctgatcga cgacacgagc ccgccgggca cctgggcgtc     540

ggacaacctc atcgccaaca acaatagctg gaccgtcacc attcccaaca gcgtcgcccc     600

cggcaactac gtcctgcgcc acgagatcat cgccctgcac tcggccaaca acaaggacgg     660

cgcccagaac tacccccagt gcatcaacat cgaggtcacg ggcggcggct ccgacgcgcc     720

tgagggtact ctgggcgagg atctctacca tgacaccgac ccgggcattc tggtcgacat     780

ttacgagccc attgcgacgt ataccattcc ggggccgcct gagccgacgt tctag          835


<210> SEQ ID NO 42
<211> LENGTH: 253
<212> TYPE: PRT
<213> ORGANISM: Penicillium sp.

<400> SEQUENCE: 42

Met Leu Ser Ser Thr Thr Arg Thr Leu Ala Phe Thr Gly Leu Ala Gly
1               5                   10                  15

Leu Leu Ser Ala Pro Leu Val Lys Ala His Gly Phe Val Gln Gly Ile
            20                  25                  30

Val Ile Gly Asp Gln Phe Tyr Ser Gly Tyr Ile Val Asn Ser Phe Pro
        35                  40                  45

Tyr Glu Ser Asn Pro Pro Pro Val Ile Gly Trp Ala Thr Thr Ala Thr
    50                  55                  60

Asp Leu Gly Phe Val Asp Gly Thr Gly Tyr Gln Gly Pro Asp Ile Ile
65                  70                  75                  80

Cys His Arg Asn Ala Thr Pro Ala Pro Leu Thr Ala Pro Val Ala Ala
                85                  90                  95
```

-continued

```
Gly Gly Thr Val Glu Leu Gln Trp Thr Pro Trp Pro Asp Ser His His
            100                 105                 110

Gly Pro Val Ile Thr Tyr Leu Ala Pro Cys Asn Gly Asn Cys Ser Thr
        115                 120                 125

Val Asp Lys Thr Thr Leu Glu Phe Phe Lys Ile Asp Gln Gln Gly Leu
    130                 135                 140

Ile Asp Asp Thr Ser Pro Pro Gly Thr Trp Ala Ser Asp Asn Leu Ile
145                 150                 155                 160

Ala Asn Asn Asn Ser Trp Thr Val Thr Ile Pro Asn Ser Val Ala Pro
                165                 170                 175

Gly Asn Tyr Val Leu Arg His Glu Ile Ile Ala Leu His Ser Ala Asn
            180                 185                 190

Asn Lys Asp Gly Ala Gln Asn Tyr Pro Gln Cys Ile Asn Ile Glu Val
        195                 200                 205

Thr Gly Gly Gly Ser Asp Ala Pro Glu Gly Thr Leu Gly Glu Asp Leu
    210                 215                 220

Tyr His Asp Thr Asp Pro Gly Ile Leu Val Asp Ile Tyr Glu Pro Ile
225                 230                 235                 240

Ala Thr Tyr Thr Ile Pro Gly Pro Pro Glu Pro Thr Phe
                245                 250
```

<210> SEQ ID NO 43
<211> LENGTH: 1107
<212> TYPE: DNA
<213> ORGANISM: Thielavia terrestris

<400> SEQUENCE: 43

```
atgccttctt tcgcctccaa gactctcctt tccaccctgg cgggtgccgc atccgtggcc     60

gcccacgggc acgtgtcgaa catcgtcatc aacggggtct cgtaccaggg ttacgatccg    120

acctccttcc cttacatgca gaacccgccc atcgtggtcg gctggactgc cgccgacacg    180

gacaacggct ttgttgcccc ggatgccttc gccagtggcg atatcatctg ccacaagaac    240

gccaccaacg ccaagggcca cgccgtggtc gccgcgggag acaagatctt catccagtgg    300

aacacatggc ccgagtccca ccacggcccc gtcatcgact acctcgcgag ctgcggcagc    360

gcgtcctgcg agaccgtcga caagaccaag ctcgagttct tcaagatcga cgaggtcggc    420

ctggtcgacg gcagctcggc gcccggtgtg tggggctccg accagctcat cgccaacaac    480

aactcgtggc tcgtcgagat cccgcccacc atcgcgccgg gcaactacgt cctgcgccac    540

gagatcatcg cgctgcacag cgccgaaaac gccgacggcg cccagaacta cccgcagtgc    600

ttcaacctgc agatcaccgg caccggcacc gccacccccct ccggcgtccc cggcacctcg    660

ctctacaccc cgaccgaccc gggcatcctc gtcaacatct acagcgcccc gatcacctac    720

accgtcccgg ggccggccct catctccggc gccgtcagca tcgcccagtc ctcctccgcc    780

atcaccgcct ccggcaccgc cctgaccggc tctgccaccg cacccgccgc cgccgctgct    840

accacaactt ccaccaccaa cgccgcggct gctgctacct ctgctgctgc tgctgctggt    900

acttccacaa ccaccaccag cgccgcggcc gtggtccaga cctcctcctc ctcctcctcc    960

gccccgtcct ctgccgccgc cgccgccacc accaccgcgg ctgccagcgc ccgccccgacc   1020

ggctgctcct ctggccgctc caggaagcag ccgcgccgcc acgcgcggga tatggtggtt   1080

gcgcgagggg ctgaggaggc aaactga                                        1107
```

<210> SEQ ID NO 44
<211> LENGTH: 368

```
<212> TYPE: PRT
<213> ORGANISM: Thielavia terrestris

<400> SEQUENCE: 44

Met Pro Ser Phe Ala Ser Lys Thr Leu Leu Ser Thr Leu Ala Gly Ala
1               5                   10                  15

Ala Ser Val Ala Ala His Gly His Val Ser Asn Ile Val Ile Asn Gly
            20                  25                  30

Val Ser Tyr Gln Gly Tyr Asp Pro Thr Ser Phe Pro Tyr Met Gln Asn
        35                  40                  45

Pro Pro Ile Val Val Gly Trp Thr Ala Ala Asp Thr Asp Asn Gly Phe
    50                  55                  60

Val Ala Pro Asp Ala Phe Ala Ser Gly Asp Ile Ile Cys His Lys Asn
65                  70                  75                  80

Ala Thr Asn Ala Lys Gly His Ala Val Val Ala Ala Gly Asp Lys Ile
                85                  90                  95

Phe Ile Gln Trp Asn Thr Trp Pro Glu Ser His His Gly Pro Val Ile
            100                 105                 110

Asp Tyr Leu Ala Ser Cys Gly Ser Ala Ser Cys Glu Thr Val Asp Lys
        115                 120                 125

Thr Lys Leu Glu Phe Phe Lys Ile Asp Glu Val Gly Leu Val Asp Gly
    130                 135                 140

Ser Ser Ala Pro Gly Val Trp Gly Ser Asp Gln Leu Ile Ala Asn Asn
145                 150                 155                 160

Asn Ser Trp Leu Val Glu Ile Pro Pro Thr Ile Ala Pro Gly Asn Tyr
                165                 170                 175

Val Leu Arg His Glu Ile Ile Ala Leu His Ser Ala Glu Asn Ala Asp
            180                 185                 190

Gly Ala Gln Asn Tyr Pro Gln Cys Phe Asn Leu Gln Ile Thr Gly Thr
        195                 200                 205

Gly Thr Ala Thr Pro Ser Gly Val Pro Gly Thr Ser Leu Tyr Thr Pro
    210                 215                 220

Thr Asp Pro Gly Ile Leu Val Asn Ile Tyr Ser Ala Pro Ile Thr Tyr
225                 230                 235                 240

Thr Val Pro Gly Pro Ala Leu Ile Ser Gly Ala Val Ser Ile Ala Gln
                245                 250                 255

Ser Ser Ser Ala Ile Thr Ala Ser Gly Thr Ala Leu Thr Gly Ser Ala
            260                 265                 270

Thr Ala Pro Ala Ala Ala Ala Ala Thr Thr Thr Ser Thr Thr Asn Ala
        275                 280                 285

Ala Ala Ala Ala Thr Ser Ala Ala Ala Ala Ala Gly Thr Ser Thr Thr
    290                 295                 300

Thr Thr Ser Ala Ala Ala Val Val Gln Thr Ser Ser Ser Ser Ser Ser
305                 310                 315                 320

Ala Pro Ser Ser Ala Ala Ala Ala Ala Thr Thr Thr Ala Ala Ala Ser
                325                 330                 335

Ala Arg Pro Thr Gly Cys Ser Ser Gly Arg Ser Arg Lys Gln Pro Arg
            340                 345                 350

Arg His Ala Arg Asp Met Val Val Ala Arg Gly Ala Glu Glu Ala Asn
        355                 360                 365


<210> SEQ ID NO 45
<211> LENGTH: 1327
<212> TYPE: DNA
<213> ORGANISM: Aspergillus aculeatus
```

<400> SEQUENCE: 45

```
aaaatggtcg gactgctttc aatcaccgcg gcgcttgccg cgactgtgtt gccaaacatt      60
gtctctgccg ttggtctgga tcaggctgca gttgccaaag gacttcaata ctttggcaca     120
gctacggata atcccgagct cacggatatt ccatacgtta ctcagctgaa caacaccgcg     180
gactttggtc aaattacccc tggaaactcg atgaagtggg atgccacaga accatctcag     240
ggcaccttca cgttcacgaa aggcgatgtc attgcagatc tggctgaggg taatggccaa     300
tatctccgat gtcatactct ggtttggtat aatcagctac ctagctgggt gactagcgga     360
acttggacta atgctactct caccgccgca ttgaagaacc acatcacgaa tgtggtgtcg     420
cactacaaag ggaaatgtct tcattgggac gtggtcaatg aggcgttgaa tgacgacgga     480
acctaccgca ccaacatctt ctacaccacc atcggcgaag cctacatccc cattgccttt     540
gccgcagcgg ctgcagccga cccggacgcg aagctgttct acaatgacta caacctcgaa     600
tacggcggcg ccaaagccgc cagcgcccgc gccattgtcc agctggtcaa gaatgcaggt     660
gccaagatcg acggggtagg gttgcaggcc catttcagcg tcggcaccgt gccgagtacg     720
agctcgctcg tctcggtgct gcaatctttc actgcgctcg gggtcgaggt cgcctacacg     780
gaggccgacg tgcgcattct cctgcccacc accgccacta ccctggccca acagtcgagc     840
gatttccagg ccctggtgca atcctgtgtg cagacaacgg gctgcgtcgg cttcactatc     900
tgggattgga cagataagta cagctgggtt cccagcacgt tctcgggcta tggggcggcg     960
ctaccctggg atgagaacct ggttaagaag cccgcgtaca atggcttgtt ggccggcatg    1020
ggggttacag ttaccactac gactaccacc accactgcta ctgccactgg taagactacg    1080
actaccacaa cgggtgccac gagcacgggg actacggctg cgcattgggg gcagtgtgga    1140
gggctcaact ggagtggacc gacggcgtgt gccactgggt acacctgcac ttatgtcaat    1200
gactattact cgcagtgtct gtgaagtata gcccaaccta aacctgccgg cgtgcttgcc    1260
attcagtcag tgagatttat atatcacaat actcaaaatt cattgctcga cctctgaaaa    1320
aaaaaaa                                                              1327
```

<210> SEQ ID NO 46
<211> LENGTH: 407
<212> TYPE: PRT
<213> ORGANISM: Aspergillus aculeatus

<400> SEQUENCE: 46

```
Lys Met Val Gly Leu Leu Ser Ile Thr Ala Ala Leu Ala Ala Thr Val
1               5                   10                  15

Leu Pro Asn Ile Val Ser Ala Val Gly Leu Asp Gln Ala Ala Val Ala
            20                  25                  30

Lys Gly Leu Gln Tyr Phe Gly Thr Ala Thr Asp Asn Pro Glu Leu Thr
        35                  40                  45

Asp Ile Pro Tyr Val Thr Gln Leu Asn Asn Thr Ala Asp Phe Gly Gln
    50                  55                  60

Ile Thr Pro Gly Asn Ser Met Lys Trp Asp Ala Thr Glu Pro Ser Gln
65                  70                  75                  80

Gly Thr Phe Thr Phe Thr Lys Gly Asp Val Ile Ala Asp Leu Ala Glu
                85                  90                  95

Gly Asn Gly Gln Tyr Leu Arg Cys His Thr Leu Val Trp Tyr Asn Gln
            100                 105                 110

Leu Pro Ser Trp Val Thr Ser Gly Thr Trp Thr Asn Ala Thr Leu Thr
```

```
        115                 120                 125

Ala Ala Leu Lys Asn His Ile Thr Asn Val Val Ser His Tyr Lys Gly
    130                 135                 140

Lys Cys Leu His Trp Asp Val Val Asn Glu Ala Leu Asn Asp Asp Gly
145                 150                 155                 160

Thr Tyr Arg Thr Asn Ile Phe Tyr Thr Thr Ile Gly Glu Ala Tyr Ile
                165                 170                 175

Pro Ile Ala Phe Ala Ala Ala Ala Ala Ala Asp Pro Asp Ala Lys Leu
            180                 185                 190

Phe Tyr Asn Asp Tyr Asn Leu Glu Tyr Gly Gly Ala Lys Ala Ala Ser
        195                 200                 205

Ala Arg Ala Ile Val Gln Leu Val Lys Asn Ala Gly Ala Lys Ile Asp
    210                 215                 220

Gly Val Gly Leu Gln Ala His Phe Ser Val Gly Thr Val Pro Ser Thr
225                 230                 235                 240

Ser Ser Leu Val Ser Val Leu Gln Ser Phe Thr Ala Leu Gly Val Glu
                245                 250                 255

Val Ala Tyr Thr Glu Ala Asp Val Arg Ile Leu Leu Pro Thr Thr Ala
            260                 265                 270

Thr Thr Leu Ala Gln Gln Ser Ser Asp Phe Gln Ala Leu Val Gln Ser
        275                 280                 285

Cys Val Gln Thr Thr Gly Cys Val Gly Phe Thr Ile Trp Asp Trp Thr
    290                 295                 300

Asp Lys Tyr Ser Trp Val Pro Ser Thr Phe Ser Gly Tyr Gly Ala Ala
305                 310                 315                 320

Leu Pro Trp Asp Glu Asn Leu Val Lys Lys Pro Ala Tyr Asn Gly Leu
                325                 330                 335

Leu Ala Gly Met Gly Val Thr Val Thr Thr Thr Thr Thr Thr Thr Thr
            340                 345                 350

Ala Thr Ala Thr Gly Lys Thr Thr Thr Thr Thr Thr Gly Ala Thr Ser
        355                 360                 365

Thr Gly Thr Thr Ala Ala His Trp Gly Gln Cys Gly Gly Leu Asn Trp
    370                 375                 380

Ser Gly Pro Thr Ala Cys Ala Thr Gly Tyr Thr Cys Thr Tyr Val Asn
385                 390                 395                 400

Asp Tyr Tyr Ser Gln Cys Leu
                405
```

<210> SEQ ID NO 47
<211> LENGTH: 1415
<212> TYPE: DNA
<213> ORGANISM: Aspergillus fumigatus

<400> SEQUENCE: 47

```
atggtccatc tatcttcatt ggcagcagcc ctggctgctc tgcctctgta tgtttaccca      60

ctcacgagag gaggaacagc tttgacattg ctatagtgta tatggagctg gcctgaacac     120

agcagccaaa gccaaaggac taaagtactt tggttccgcc acggacaatc cagagctcac     180

ggactctgcg tatgtcgcgc aactgagcaa caccgatgat tttggtcaaa tcacacccgg     240

aaactccatg aaggtttgct tacgtctgcc tccctggagc attgcctcaa aagctaattg     300

gttgttttgt ttggatagtg ggatgccacc gagccttctc agaattcttt ttcgttcgca     360

aatggagacg ccgtggtcaa tctggcgaac aagaatggcc agctgatgcg atgccatact     420

ctggtctggc acagtcagct accgaactgg ggtatgtaaa cgtcttgtct attctcaaat     480
```

```
actctctaac agttgacagt ctctagcggg tcatggacca atgcgaccct tttggcggcc    540

atgaagaatc atatcaccaa tgtggttact cactacaagg ggaagtgcta cgcctgggat    600

gttgtcaatg aaggtttgtt gctccatcta tcctcaatag ttcttttgaa actgacaagc    660

ctgtcaatct agccctgaac gaggacggta ctttccgtaa ctctgtcttc taccagatca    720

tcggcccagc atacattcct attgcgttcg ccacggctgc tgccgcagat cccgacgtga    780

aactctacta caacgactac aacattgaat actcaggcgc caaagcgact gctgcgcaga    840

atatcgtcaa gatgatcaag gcctacggcg cgaagatcga cggcgtcggc ctccaggcac    900

actttatcgt cggcagcact ccgagtcaat cggatctgac gaccgtcttg aagggctaca    960

ctgctctcgg cgttgaggtg gcctataccg aacttgacat ccgcatgcag ctgccctcga   1020

ccgccgcaaa gctggcccag cagtccactg acttccaagg cgtggccgca gcatgcgtta   1080

gcaccactgg ctgcgtgggt gtcactatct gggactggac cgacaagtac tcctgggtcc   1140

ccagcgtgtt ccaaggctac ggcgccccat tgccttggga tgagaactat gtgaagaagc   1200

cagcgtacga tggcctgatg gcgggtcttg gagcaagcgg ctccggcacc acaacgacca   1260

ctactactac ttctactacg acaggaggta cggaccctac tggagtcgct cagaaatggg   1320

gacagtgtgg cggtattggc tggaccgggc caacaacttg tgtcagtggt accacttgcc   1380

aaaagctgaa tgactggtac tcacagtgcc tgtaa                              1415
```

<210> SEQ ID NO 48
<211> LENGTH: 397
<212> TYPE: PRT
<213> ORGANISM: Aspergillus fumigatus

<400> SEQUENCE: 48

```
Met Val His Leu Ser Ser Leu Ala Ala Ala Leu Ala Ala Leu Pro Leu
1               5                   10                  15

Val Tyr Gly Ala Gly Leu Asn Thr Ala Ala Lys Ala Lys Gly Leu Lys
            20                  25                  30

Tyr Phe Gly Ser Ala Thr Asp Asn Pro Glu Leu Thr Asp Ser Ala Tyr
        35                  40                  45

Val Ala Gln Leu Ser Asn Thr Asp Asp Phe Gly Gln Ile Thr Pro Gly
    50                  55                  60

Asn Ser Met Lys Trp Asp Ala Thr Glu Pro Ser Gln Asn Ser Phe Ser
65                  70                  75                  80

Phe Ala Asn Gly Asp Ala Val Val Asn Leu Ala Asn Lys Asn Gly Gln
                85                  90                  95

Leu Met Arg Cys His Thr Leu Val Trp His Ser Gln Leu Pro Asn Trp
            100                 105                 110

Val Ser Ser Gly Ser Trp Thr Asn Ala Thr Leu Leu Ala Ala Met Lys
        115                 120                 125

Asn His Ile Thr Asn Val Val Thr His Tyr Lys Gly Lys Cys Tyr Ala
    130                 135                 140

Trp Asp Val Val Asn Glu Ala Leu Asn Glu Asp Gly Thr Phe Arg Asn
145                 150                 155                 160

Ser Val Phe Tyr Gln Ile Ile Gly Pro Ala Tyr Ile Pro Ile Ala Phe
                165                 170                 175

Ala Thr Ala Ala Ala Ala Asp Pro Asp Val Lys Leu Tyr Tyr Asn Asp
            180                 185                 190

Tyr Asn Ile Glu Tyr Ser Gly Ala Lys Ala Thr Ala Ala Gln Asn Ile
        195                 200                 205
```

Val Lys Met Ile Lys Ala Tyr Gly Ala Lys Ile Asp Gly Val Gly Leu
    210                 215                 220

Gln Ala His Phe Ile Val Gly Ser Thr Pro Ser Gln Ser Asp Leu Thr
225                 230                 235                 240

Thr Val Leu Lys Gly Tyr Thr Ala Leu Gly Val Glu Val Ala Tyr Thr
                245                 250                 255

Glu Leu Asp Ile Arg Met Gln Leu Pro Ser Thr Ala Ala Lys Leu Ala
            260                 265                 270

Gln Gln Ser Thr Asp Phe Gln Gly Val Ala Ala Ala Cys Val Ser Thr
        275                 280                 285

Thr Gly Cys Val Gly Val Thr Ile Trp Asp Trp Thr Asp Lys Tyr Ser
    290                 295                 300

Trp Val Pro Ser Val Phe Gln Gly Tyr Gly Ala Pro Leu Pro Trp Asp
305                 310                 315                 320

Glu Asn Tyr Val Lys Lys Pro Ala Tyr Asp Gly Leu Met Ala Gly Leu
                325                 330                 335

Gly Ala Ser Gly Ser Gly Thr Thr Thr Thr Thr Thr Thr Thr Ser Thr
            340                 345                 350

Thr Thr Gly Gly Thr Asp Pro Thr Gly Val Ala Gln Lys Trp Gly Gln
        355                 360                 365

Cys Gly Gly Ile Gly Trp Thr Gly Pro Thr Thr Cys Val Ser Gly Thr
    370                 375                 380

Thr Cys Gln Lys Leu Asn Asp Trp Tyr Ser Gln Cys Leu
385                 390                 395

<210> SEQ ID NO 49
<211> LENGTH: 1197
<212> TYPE: DNA
<213> ORGANISM: Trichophaea saccata

<400> SEQUENCE: 49
atgcgtacct tctcgtctct tctcggtgtt gcccttctct tgggtgcagc taatgcccag 60
gtcgcggttt ggggacagtg tggtggcatt ggttactctg gctcgacaac ctgcgctgcg 120
ggaacgactt gtgttaagct gaacgactac tactcccaat gccaacccgg cggtaccact 180
ttgacaacca ccaccaaacc cgccaccact accactacca ccacggcaac ttctccctca 240
tcttctcccg gattaaatgc cctggcacaa aagagcggcc ggtacttcgg tagtgcaact 300
gacaacccag agctctccga tgcggcatac attgccatcc tgagcaacaa aaacgagttt 360
gggatcatca cgcctggaaa ctcgatgaaa tgggatgcta ctgaaccgtc ccgcgggagt 420
ttctcgttca ctggtggaca gcaaattgtt gattttgcgc agggcaatgg gcaggctatc 480
agaggccata ctcttgtctg gtactcccag ttgccgtcct gggttactag cggaaacttc 540
gataaagcta cattgacatc gatcatgcaa aatcacatta caactcttgt cagccactgg 600
aagggccagc tcgcctactg ggatgttgtc aacgaagcat tcaacgatga tggcactttc 660
cgtcaaaacg tgttctacac aaccattgga gaggactaca tccagctcgc cttcgaagcc 720
gcccgtgccg ccgacccgac cgcaaagctc tgcatcaacg actacaacat cgagggcact 780
ggagccaagt caacagccat gtacaatctc gtctcgaagc tgaaatccgc cggcgttccc 840
atcgactgta ttggtgttca gggacacctc atcgtcggtg aagttcccac caccatccaa 900
gcaaaccttg cccagtttgc gtctttgggt gtggatgtcg cgatcacgga gctagatatc 960
agaatgacgc tgccatctac gactgcattg ctccagcagc aggctaagga ttacgtctcg 1020
gttgttacag cctgcatgaa tgttcccagg tgtatcggta tcaccatctg ggactacact 1080
gataaatact cttgggtgcc acaaaccttc agcggccagg gcgatgcttg cccatgggat 1140
gccaacctgc agaagaagcc agcctactcc gctattgcgt ctgctcttgc ggcttga 1197

<210> SEQ ID NO 50
<211> LENGTH: 398
<212> TYPE: PRT
<213> ORGANISM: Trichophaea saccata

<400> SEQUENCE: 50

Met Arg Thr Phe Ser Ser Leu Leu Gly Val Ala Leu Leu Leu Gly Ala
1 5 10 15

Ala Asn Ala Gln Val Ala Val Trp Gly Gln Cys Gly Gly Ile Gly Tyr
20 25 30

Ser Gly Ser Thr Thr Cys Ala Ala Gly Thr Thr Cys Val Lys Leu Asn
35 40 45

Asp Tyr Tyr Ser Gln Cys Gln Pro Gly Gly Thr Thr Leu Thr Thr Thr
50 55 60

Thr Lys Pro Ala Thr Thr Thr Thr Thr Thr Thr Ala Thr Ser Pro Ser
65 70 75 80

Ser Ser Pro Gly Leu Asn Ala Leu Ala Gln Lys Ser Gly Arg Tyr Phe
85 90 95

Gly Ser Ala Thr Asp Asn Pro Glu Leu Ser Asp Ala Ala Tyr Ile Ala
100 105 110

Ile Leu Ser Asn Lys Asn Glu Phe Gly Ile Ile Thr Pro Gly Asn Ser
115 120 125

Met Lys Trp Asp Ala Thr Glu Pro Ser Arg Gly Ser Phe Ser Phe Thr
130 135 140

Gly Gly Gln Gln Ile Val Asp Phe Ala Gln Gly Asn Gly Gln Ala Ile
145 150 155 160

Arg Gly His Thr Leu Val Trp Tyr Ser Gln Leu Pro Ser Trp Val Thr
165 170 175

Ser Gly Asn Phe Asp Lys Ala Thr Leu Thr Ser Ile Met Gln Asn His
180 185 190

Ile Thr Thr Leu Val Ser His Trp Lys Gly Gln Leu Ala Tyr Trp Asp
195 200 205

Val Val Asn Glu Ala Phe Asn Asp Asp Gly Thr Phe Arg Gln Asn Val
210 215 220

Phe Tyr Thr Thr Ile Gly Glu Asp Tyr Ile Gln Leu Ala Phe Glu Ala
225 230 235 240

Ala Arg Ala Ala Asp Pro Thr Ala Lys Leu Cys Ile Asn Asp Tyr Asn
245 250 255

Ile Glu Gly Thr Gly Ala Lys Ser Thr Ala Met Tyr Asn Leu Val Ser
260 265 270

Lys Leu Lys Ser Ala Gly Val Pro Ile Asp Cys Ile Gly Val Gln Gly
275 280 285

His Leu Ile Val Gly Glu Val Pro Thr Thr Ile Gln Ala Asn Leu Ala
290 295 300

Gln Phe Ala Ser Leu Gly Val Asp Val Ala Ile Thr Glu Leu Asp Ile
305 310 315 320

Arg Met Thr Leu Pro Ser Thr Thr Ala Leu Leu Gln Gln Gln Ala Lys
325 330 335

Asp Tyr Val Ser Val Val Thr Ala Cys Met Asn Val Pro Arg Cys Ile
340 345 350

Gly Ile Thr Ile Trp Asp Tyr Thr Asp Lys Tyr Ser Trp Val Pro Gln
        355                 360                 365

Thr Phe Ser Gly Gln Gly Asp Ala Cys Pro Trp Asp Ala Asn Leu Gln
    370                 375                 380

Lys Lys Pro Ala Tyr Ser Ala Ile Ala Ser Ala Leu Ala Ala
385                 390                 395

<210> SEQ ID NO 51
<211> LENGTH: 1440
<212> TYPE: DNA
<213> ORGANISM: Penicillium pinophilum

<400> SEQUENCE: 51
atgactctag taaaggctat tcttttagcg cttgctgtgg gccacgttgc ccaggcccaa 60
ttgaacacgg ccgcaaaagc agctggtcta ttgtactttg gtactgcggt tgacaatcca 120
gacttgagcg actccaaata tattgcaaac cttgagactg cggatttcgg tcagatcacg 180
ccagcaaatg caatgaaagt cagtggccaa tcactactgt atacaaccag ctaagtgatg 240
acaatttagt ggcaacccac cgagccgtct caaggctctt atactttcac tcagggtgac 300
cagattgcga gcctggccaa gtctaataat gactacttga gatgccacaa tctggtctgg 360
tacaaccagt tgccatcata cggtaagcaa gcatacgacc tccatgaatt gtcatccaac 420
atccacgata gcaagctgat acggtatctg tctagttact tcgggttcat ggacaaacgc 480
aacccttatt gctgccttga aggagcatat caatggagtt gtcacgcatt acaagggaca 540
atgctacgcg tgggatgttg taaacgaagg tatgcgatat tatatacagg ccctttctct 600
gcatccttac atctttttta tctccattct acgtaatcgt gtcgagctaa gtgaagtatc 660
tagccttgaa cgaagacggc acctatcgtc aaaatgtttt ctaccaatat ataggcgagg 720
catacattcc aattgcgttt gctgccgctg cagccgcgga ccctaatgcc aagttgtact 780
acaacgacta caacatcgaa tacgctgggt caaaggcaac tggtgctcag cgcattgtaa 840
aattaattca agctgctggt ggtcgtatcg atggcgtggg tcttcagtct cacttcattg 900
tgggacaaac ccctagtctt gctactcaga aagcaaacat ggctgctttt actgctctcg 960
gtgttgatgt tgccattact gagcttgaca ttcgtatgac tctcccggat accagcgctc 1020
ttcaaactca gcagtccacc gactaccaga ccaccactac tgcctgcgtc cagactaaag 1080
gctgtgttgg tatcacgcta tgggattaca cagacaagta ctcatgggtt cccggtacct 1140
tctctggcca gggtgatgct tgtccatggg actcaaatta caacaagaag ccggcatact 1200
atggtatcct tgctggctta caatctggca ctggttcttc atcgtcaact tctagcacca 1260
ccctaacaac caccacaaca cccactaccg cttcaagtac tacgtcaacg actagcacaa 1320
gcgctacctc aggtgctgca cactggggac aatgcggagg cattggctgg tctggtccta 1380
ccatttgtgt ttcgccctac acttgtcaag tgttgaaccc atactactcc caatgtttgt 1440

<210> SEQ ID NO 52
<211> LENGTH: 407
<212> TYPE: PRT
<213> ORGANISM: Penicillium pinophilum

<400> SEQUENCE: 52

Met Thr Leu Val Lys Ala Ile Leu Leu Ala Leu Ala Val Gly His Val
1               5                   10                  15

Ala Gln Ala Gln Leu Asn Thr Ala Ala Lys Ala Ala Gly Leu Leu Tyr
            20                  25                  30

```
Phe Gly Thr Ala Val Asp Asn Pro Asp Leu Ser Asp Ser Lys Tyr Ile
        35                  40                  45

Ala Asn Leu Glu Thr Ala Asp Phe Gly Gln Ile Thr Pro Ala Asn Ala
    50                  55                  60

Met Lys Trp Gln Pro Thr Glu Pro Ser Gln Gly Ser Tyr Thr Phe Thr
65                  70                  75                  80

Gln Gly Asp Gln Ile Ala Ser Leu Ala Lys Ser Asn Asn Asp Tyr Leu
                85                  90                  95

Arg Cys His Asn Leu Val Trp Tyr Asn Gln Leu Pro Ser Tyr Val Thr
            100                 105                 110

Ser Gly Ser Trp Thr Asn Ala Thr Leu Ile Ala Ala Leu Lys Glu His
        115                 120                 125

Ile Asn Gly Val Val Thr His Tyr Lys Gly Gln Cys Tyr Ala Trp Asp
    130                 135                 140

Val Val Asn Glu Ala Leu Asn Glu Asp Gly Thr Tyr Arg Gln Asn Val
145                 150                 155                 160

Phe Tyr Gln Tyr Ile Gly Glu Ala Tyr Ile Pro Ile Ala Phe Ala Ala
                165                 170                 175

Ala Ala Ala Ala Asp Pro Asn Ala Lys Leu Tyr Tyr Asn Asp Tyr Asn
            180                 185                 190

Ile Glu Tyr Ala Gly Ser Lys Ala Thr Gly Ala Gln Arg Ile Val Lys
        195                 200                 205

Leu Ile Gln Ala Ala Gly Gly Arg Ile Asp Gly Val Gly Leu Gln Ser
    210                 215                 220

His Phe Ile Val Gly Gln Thr Pro Ser Leu Ala Thr Gln Lys Ala Asn
225                 230                 235                 240

Met Ala Ala Phe Thr Ala Leu Gly Val Asp Val Ala Ile Thr Glu Leu
                245                 250                 255

Asp Ile Arg Met Thr Leu Pro Asp Thr Ser Ala Leu Gln Thr Gln Gln
            260                 265                 270

Ser Thr Asp Tyr Gln Thr Thr Thr Thr Ala Cys Val Gln Thr Lys Gly
        275                 280                 285

Cys Val Gly Ile Thr Leu Trp Asp Tyr Thr Asp Lys Tyr Ser Trp Val
    290                 295                 300

Pro Gly Thr Phe Ser Gly Gln Gly Asp Ala Cys Pro Trp Asp Ser Asn
305                 310                 315                 320

Tyr Asn Lys Lys Pro Ala Tyr Tyr Gly Ile Leu Ala Gly Leu Gln Ser
                325                 330                 335

Gly Thr Gly Ser Ser Ser Ser Thr Ser Ser Thr Thr Leu Thr Thr Thr
            340                 345                 350

Thr Thr Pro Thr Thr Ala Ser Ser Thr Thr Ser Thr Thr Ser Thr Ser
        355                 360                 365

Ala Thr Ser Gly Ala Ala His Trp Gly Gln Cys Gly Gly Ile Gly Trp
    370                 375                 380

Ser Gly Pro Thr Ile Cys Val Ser Pro Tyr Thr Cys Gln Val Leu Asn
385                 390                 395                 400

Pro Tyr Tyr Ser Gln Cys Leu
                405
```

<210> SEQ ID NO 53
<211> LENGTH: 1188
<212> TYPE: DNA
<213> ORGANISM: Thielavia terrestris

<400> SEQUENCE: 53
atggccctca aatcgctcct gttgacctcg ctggcaacgg ccggccttgt ggtcgccgat 60
ggcctcaacg tccgggctaa ggccgctggg aagaagtatt ttggcactga gatcagcacg 120
accgtcatga acgacgcgaa cgccaacaac atcgccaaga actcgcagga cttcggccag 180
tacacatgcg agaacgagat gaagttcgac gcgctcgagc cgtcccgcgg caccttcaac 240
tacgccaatg cggaccggat agtggcccag gcgcaagcca acggcatgct catgcgctgc 300
cacaacctcg tctggcacaa ccaagtgccg tcgtgggtga ccaatggcca cttcgacaac 360
gcgacgctga tcagcatcat gaagaaccac atcgccaacg tggtgggcca ctacaagggc 420
aagtgctacg cctgggatgt ggtcaacgag gccctgaacg aggacggcac gtaccgcacg 480
tcgggctccg tctggggctc gaccatcggc ccggcctaca tcccgatcgc cttcgcggcg 540
gcggcggagg ccgacccaga cgcgaagctc tactacaacg actacaactg cgaccgcgct 600
ggcgccaagg ccacgggcgc gcagaacctg atcaagatgg tcaagcagta cggcgcgccg 660
atccacggct tcggcatgca gggccacctg acgacgggac aggtgggctc ggcgtcgcag 720
tacgtgagca acatgcaggc gttcgcggcg ctcggcgtcg aggtggcctt cacggagctg 780
gacatcgcga cgccgtccag caaccccaac ttccagcagc aggcgaccga ctacgcgacc 840
atcgtgtcgg cgtgcaagca ggtcgacgcc tgcgtcggaa tcaccacctg gggcttcacc 900
gacaaataca cctggatcag caactcggac ccgctgccct gggactccaa cctgcagaag 960
aagccggcgt acaccgcgat cctgaacgcc tggggctcgt cgccgccgcc ttcgacgacg 1020
acgaccacgg ccgcgacgac cacaacgccg ccgagcgggg gtggcggcaa cggatgcacc 1080
gcgccgcact gggcccagtg cggtggcatc ggctactcgg gctgcaccac ctgcgaggct 1140
ccctacacgt gcaagtactc caacgactgg tactctcagt gcttgtaa 1188

<210> SEQ ID NO 54
<211> LENGTH: 395
<212> TYPE: PRT
<213> ORGANISM: Thielavia terrestris

<400> SEQUENCE: 54

Met Ala Leu Lys Ser Leu Leu Leu Thr Ser Leu Ala Thr Ala Gly Leu
1 5 10 15

Val Val Ala Asp Gly Leu Asn Val Arg Ala Lys Ala Ala Gly Lys Lys
20 25 30

Tyr Phe Gly Thr Glu Ile Ser Thr Thr Val Met Asn Asp Ala Asn Ala
35 40 45

Asn Asn Ile Ala Lys Asn Ser Gln Asp Phe Gly Gln Tyr Thr Cys Glu
50 55 60

Asn Glu Met Lys Phe Asp Ala Leu Glu Pro Ser Arg Gly Thr Phe Asn
65 70 75 80

Tyr Ala Asn Ala Asp Arg Ile Val Ala Gln Ala Gln Ala Asn Gly Met
85 90 95

Leu Met Arg Cys His Asn Leu Val Trp His Asn Gln Val Pro Ser Trp
100 105 110

Val Thr Asn Gly His Phe Asp Asn Ala Thr Leu Ile Ser Ile Met Lys
115 120 125

Asn His Ile Ala Asn Val Val Gly His Tyr Lys Gly Lys Cys Tyr Ala
130 135 140

Trp Asp Val Val Asn Glu Ala Leu Asn Glu Asp Gly Thr Tyr Arg Thr
145 150 155 160

```
Ser Gly Ser Val Trp Gly Ser Thr Ile Gly Pro Ala Tyr Ile Pro Ile
                165                 170                 175

Ala Phe Ala Ala Ala Ala Glu Ala Asp Pro Asp Ala Lys Leu Tyr Tyr
            180                 185                 190

Asn Asp Tyr Asn Cys Asp Arg Ala Gly Ala Lys Ala Thr Gly Ala Gln
        195                 200                 205

Asn Leu Ile Lys Met Val Lys Gln Tyr Gly Ala Pro Ile His Gly Phe
    210                 215                 220

Gly Met Gln Gly His Leu Thr Thr Gly Gln Val Gly Ser Ala Ser Gln
225                 230                 235                 240

Tyr Val Ser Asn Met Gln Ala Phe Ala Ala Leu Gly Val Glu Val Ala
                245                 250                 255

Phe Thr Glu Leu Asp Ile Ala Thr Pro Ser Ser Asn Pro Asn Phe Gln
            260                 265                 270

Gln Gln Ala Thr Asp Tyr Ala Thr Ile Val Ser Ala Cys Lys Gln Val
        275                 280                 285

Asp Ala Cys Val Gly Ile Thr Thr Trp Gly Phe Thr Asp Lys Tyr Thr
    290                 295                 300

Trp Ile Ser Asn Ser Asp Pro Leu Pro Trp Asp Ser Asn Leu Gln Lys
305                 310                 315                 320

Lys Pro Ala Tyr Thr Ala Ile Leu Asn Ala Trp Gly Ser Ser Pro Pro
                325                 330                 335

Pro Ser Thr Thr Thr Thr Thr Ala Ala Thr Thr Thr Thr Pro Pro Ser
            340                 345                 350

Gly Gly Gly Gly Asn Gly Cys Thr Ala Pro His Trp Ala Gln Cys Gly
        355                 360                 365

Gly Ile Gly Tyr Ser Gly Cys Thr Thr Cys Glu Ala Pro Tyr Thr Cys
    370                 375                 380

Lys Tyr Ser Asn Asp Trp Tyr Ser Gln Cys Leu
385                 390                 395
```

<210> SEQ ID NO 55
<211> LENGTH: 1038
<212> TYPE: DNA
<213> ORGANISM: Thermobifida fusca

<400> SEQUENCE: 55

```
atgaaccatg cccccgccag tctgaagagc cggagacgct tccggcccag actgctcatc     60

ggcaaggcgt tcgccgcggc actcgtcgcg gtcgtcacga tgatccccag tactgccgcc    120

cacgcggccg tgacctccaa ccagaccggg taccacgacg ggtacttcta ctcgttctgg    180

accgacgcgc ccggaacggt ctccatggag ctgggccctg gcggaaacta cagcacctcc    240

tggcggaaca ccgggaactt cgtcgccggt aagggatggg ccaccggtgg ccgccggacc    300

gtgacctact ccgccagctt caacccgtcg ggtaacgcct acctgaccct ctacgggtgg    360

acgcggaacc cgctcgtgga gtactacatc gtcgaaagct ggggcaccta ccggcccacc    420

ggtacctaca tgggcacggt gaccaccgac ggtggtacct acgacatcta caagaccacg    480

cggtacaacg cgccctccat cgaaggcacc cggaccttcg accagtactg gagcgtccgc    540

cagtccaagc ggaccagcgg taccatcacc gcggggaacc acttcgacgc gtgggcccgc    600

cacggtatgc acctcggaac ccacgactac atgatcatgg cgactgaggg ctaccagagc    660

agcggatcct ccaacgtgac gttgggcacc agcggcggtg gcaaccccgg tgggggcaac    720

ccccccggtg gcggcaaccc ccctggtggc ggtggctgca cggcgacgct gtccgcgggc    780
```

```
cagcagtgga acgaccgcta caacctcaac gtcaacgtca gcggctccaa caactggacc    840

gtgaccgtga acgttccgtg gccggcgagg atcatcgcca cctggaacat ccacgccagc    900

tacccggact cccagacctt ggttgcccgg cctaacggca acggcaacaa ctggggcatg    960

acgatcatgc acaacggcaa ctggacgtgg cccacggtgt cctgcagcgc caaccatcag   1020

caccaacacc agcattag                                                 1038


<210> SEQ ID NO 56
<211> LENGTH: 345
<212> TYPE: PRT
<213> ORGANISM: Thermobifida fusca

<400> SEQUENCE: 56

Met Asn His Ala Pro Ala Ser Leu Lys Ser Arg Arg Arg Phe Arg Pro
1               5                   10                  15

Arg Leu Leu Ile Gly Lys Ala Phe Ala Ala Ala Leu Val Ala Val Val
            20                  25                  30

Thr Met Ile Pro Ser Thr Ala Ala His Ala Ala Val Thr Ser Asn Gln
        35                  40                  45

Thr Gly Tyr His Asp Gly Tyr Phe Tyr Ser Phe Trp Thr Asp Ala Pro
    50                  55                  60

Gly Thr Val Ser Met Glu Leu Gly Pro Gly Gly Asn Tyr Ser Thr Ser
65                  70                  75                  80

Trp Arg Asn Thr Gly Asn Phe Val Ala Gly Lys Gly Trp Ala Thr Gly
                85                  90                  95

Gly Arg Arg Thr Val Thr Tyr Ser Ala Ser Phe Asn Pro Ser Gly Asn
            100                 105                 110

Ala Tyr Leu Thr Leu Tyr Gly Trp Thr Arg Asn Pro Leu Val Glu Tyr
        115                 120                 125

Tyr Ile Val Glu Ser Trp Gly Thr Tyr Arg Pro Thr Gly Thr Tyr Met
    130                 135                 140

Gly Thr Val Thr Thr Asp Gly Gly Thr Tyr Asp Ile Tyr Lys Thr Thr
145                 150                 155                 160

Arg Tyr Asn Ala Pro Ser Ile Glu Gly Thr Arg Thr Phe Asp Gln Tyr
                165                 170                 175

Trp Ser Val Arg Gln Ser Lys Arg Thr Ser Gly Thr Ile Thr Ala Gly
            180                 185                 190

Asn His Phe Asp Ala Trp Ala Arg His Gly Met His Leu Gly Thr His
        195                 200                 205

Asp Tyr Met Ile Met Ala Thr Glu Gly Tyr Gln Ser Ser Gly Ser Ser
    210                 215                 220

Asn Val Thr Leu Gly Thr Ser Gly Gly Gly Asn Pro Gly Gly Gly Asn
225                 230                 235                 240

Pro Pro Gly Gly Gly Asn Pro Pro Gly Gly Gly Gly Cys Thr Ala Thr
                245                 250                 255

Leu Ser Ala Gly Gln Gln Trp Asn Asp Arg Tyr Asn Leu Asn Val Asn
            260                 265                 270

Val Ser Gly Ser Asn Asn Trp Thr Val Thr Val Asn Val Pro Trp Pro
        275                 280                 285

Ala Arg Ile Ile Ala Thr Trp Asn Ile His Ala Ser Tyr Pro Asp Ser
    290                 295                 300

Gln Thr Leu Val Ala Arg Pro Asn Gly Asn Gly Asn Asn Trp Gly Met
305                 310                 315                 320
```

```
Thr Ile Met His Asn Gly Asn Trp Thr Trp Pro Thr Val Ser Cys Ser
                325                 330                 335

Ala Asn His Gln His Gln His Gln His
            340                 345


<210> SEQ ID NO 57
<211> LENGTH: 2394
<212> TYPE: DNA
<213> ORGANISM: Trichoderma reesei

<400> SEQUENCE: 57

atggtgaata acgcagctct tctcgccgcc ctgtcggctc tcctgcccac ggccctggcg      60

cagaacaatc aaacatacgc caactactct gctcagggcc agcctgatct ctaccccgag     120

acacttgcca cgctcacact ctcgttcccc gactgcgaac atggccccct caagaacaat     180

ctcgtctgtg actcatcggc cggctatgta gagcgagccc aggccctcat ctcgctcttc     240

accctcgagg agctcattct caacacgcaa aactcgggcc ccggcgtgcc tcgcctgggt     300

cttccgaact accaagtctg gaatgaggct ctgcacggct tggaccgcgc caacttcgcc     360

accaagggcg gccagttcga atgggcgacc tcgttcccca tgcccatcct cactacggcg     420

gccctcaacc gcacattgat ccaccagatt gccgacatca tctcgaccca agctcgagca     480

ttcagcaaca gcggccgtta cggtctcgac gtctatgcgc caaacgtcaa tggcttccga     540

agccccctct ggggccgtgg ccaggagacg cccggcgaag acgccttttt cctcagctcc     600

gcctatactt acgagtacat cacgggcatc cagggtggcg tcgaccctga gcacctcaag     660

gttgccgcca cggtgaagca ctttgccgga tacgacctcg agaactggaa caaccagtcc     720

cgtctcggtt tcgacgccat cataactcag caggacctct ccgaatacta cactccccag     780

ttcctcgctg cggcccgtta tgcaaagtca cgcagcttga tgtgcgcata caactccgtc     840

aacggcgtgc ccagctgtgc caacagcttc ttcctgcaga cgcttttgcg cgagagctgg     900

ggcttccccg aatggggata cgtctcgtcc gattgcgatg ccgtctacaa cgttttcaac     960

cctcatgact acgccagcaa ccagtcgtca gccgccgcca gctcactgcg agccggcacc    1020

gatatcgact gcggtcagac ttacccgtgg cacctcaacg agtcctttgt ggccggcgaa    1080

gtctcccgcg gcgagatcga gcggtccgtc acccgtctgt acgccaacct cgtccgtctc    1140

ggatacttcg acaagaagaa ccagtaccgc tcgctcggtt ggaaggatgt cgtcaagact    1200

gatgcctgga acatctcgta cgaggctgct gttgagggca tcgtcctgct caagaacgat    1260

ggcactctcc ctctgtccaa gaaggtgcgc agcattgctc tgatcggacc atgggccaat    1320

gccacaaccc aaatgcaagg caactactat ggccctgccc catacctcat cagccctctg    1380

gaagctgcta agaaggccgg ctatcacgtc aactttgaac tcggcacaga gatcgccggc    1440

aacagcacca ctggctttgc caaggccatt gctgccgcca agaagtcgga tgccatcatc    1500

tacctcggtg gaattgacaa caccattgaa caggagggcg ctgaccgcac ggacattgct    1560

tggcccggta atcagctgga tctcatcaag cagctcagcg aggtcggcaa acccccttgtc   1620

gtcctgcaaa tgggcggtgg tcaggtagac tcatcctcgc tcaagagcaa caagaaggtc    1680

aactccctcg tctggggcgg atatcccggc cagtcgggag gcgttgccct cttcgacatt    1740

ctctctggca agcgtgctcc tgccggccga ctggtcacca ctcagtaccc ggctgagtat    1800

gttcaccaat tcccccagaa tgacatgaac ctccgacccg atggaaagtc aaaccctgga    1860

cagacttaca tctggtacac cggcaaaccc gtctacgagt ttggcagtgg tctcttctac    1920

accaccttca aggagactct cgccagccac cccaagagcc tcaagttcaa cacctcatcg    1980
```

```
atcctctctg ctcctcaccc cggatacact tacagcgagc agattcccgt cttcaccttc   2040

gaggccaaca tcaagaactc gggcaagacg gagtccccat atacggccat gctgtttgtt   2100

cgcacaagca acgctggccc agccccgtac ccgaacaagt ggctcgtcgg attcgaccga   2160

cttgccgaca tcaagcctgg tcactcttcc aagctcagca tccccatccc tgtcagtgct   2220

ctcgcccgtg ttgattctca cggaaaccgg attgtatacc ccggcaagta tgagctagcc   2280

ttgaacaccg acgagtctgt gaagcttgag tttgagttgg tgggagaaga ggtaacgatt   2340

gagaactggc cgttggagga gcaacagatc aaggatgcta cacctgacgc ataa         2394


<210> SEQ ID NO 58
<211> LENGTH: 797
<212> TYPE: PRT
<213> ORGANISM: Trichoderma reesei

<400> SEQUENCE: 58

Met Val Asn Asn Ala Ala Leu Leu Ala Ala Leu Ser Ala Leu Leu Pro
1               5                   10                  15

Thr Ala Leu Ala Gln Asn Asn Gln Thr Tyr Ala Asn Tyr Ser Ala Gln
            20                  25                  30

Gly Gln Pro Asp Leu Tyr Pro Glu Thr Leu Ala Thr Leu Thr Leu Ser
        35                  40                  45

Phe Pro Asp Cys Glu His Gly Pro Leu Lys Asn Asn Leu Val Cys Asp
    50                  55                  60

Ser Ser Ala Gly Tyr Val Glu Arg Ala Gln Ala Leu Ile Ser Leu Phe
65                  70                  75                  80

Thr Leu Glu Glu Leu Ile Leu Asn Thr Gln Asn Ser Gly Pro Gly Val
                85                  90                  95

Pro Arg Leu Gly Leu Pro Asn Tyr Gln Val Trp Asn Glu Ala Leu His
            100                 105                 110

Gly Leu Asp Arg Ala Asn Phe Ala Thr Lys Gly Gly Gln Phe Glu Trp
        115                 120                 125

Ala Thr Ser Phe Pro Met Pro Ile Leu Thr Thr Ala Ala Leu Asn Arg
    130                 135                 140

Thr Leu Ile His Gln Ile Ala Asp Ile Ile Ser Thr Gln Ala Arg Ala
145                 150                 155                 160

Phe Ser Asn Ser Gly Arg Tyr Gly Leu Asp Val Tyr Ala Pro Asn Val
                165                 170                 175

Asn Gly Phe Arg Ser Pro Leu Trp Gly Arg Gly Gln Glu Thr Pro Gly
            180                 185                 190

Glu Asp Ala Phe Phe Leu Ser Ser Ala Tyr Thr Tyr Glu Tyr Ile Thr
        195                 200                 205

Gly Ile Gln Gly Gly Val Asp Pro Glu His Leu Lys Val Ala Ala Thr
    210                 215                 220

Val Lys His Phe Ala Gly Tyr Asp Leu Glu Asn Trp Asn Asn Gln Ser
225                 230                 235                 240

Arg Leu Gly Phe Asp Ala Ile Ile Thr Gln Gln Asp Leu Ser Glu Tyr
                245                 250                 255

Tyr Thr Pro Gln Phe Leu Ala Ala Ala Arg Tyr Ala Lys Ser Arg Ser
            260                 265                 270

Leu Met Cys Ala Tyr Asn Ser Val Asn Gly Val Pro Ser Cys Ala Asn
        275                 280                 285

Ser Phe Phe Leu Gln Thr Leu Leu Arg Glu Ser Trp Gly Phe Pro Glu
    290                 295                 300
```

```
Trp Gly Tyr Val Ser Ser Asp Cys Asp Ala Val Tyr Asn Val Phe Asn
305                 310                 315                 320

Pro His Asp Tyr Ala Ser Asn Gln Ser Ser Ala Ala Ala Ser Ser Leu
                325                 330                 335

Arg Ala Gly Thr Asp Ile Asp Cys Gly Gln Thr Tyr Pro Trp His Leu
            340                 345                 350

Asn Glu Ser Phe Val Ala Gly Glu Val Ser Arg Gly Glu Ile Glu Arg
        355                 360                 365

Ser Val Thr Arg Leu Tyr Ala Asn Leu Val Arg Leu Gly Tyr Phe Asp
    370                 375                 380

Lys Lys Asn Gln Tyr Arg Ser Leu Gly Trp Lys Asp Val Val Lys Thr
385                 390                 395                 400

Asp Ala Trp Asn Ile Ser Tyr Glu Ala Ala Val Glu Gly Ile Val Leu
                405                 410                 415

Leu Lys Asn Asp Gly Thr Leu Pro Leu Ser Lys Lys Val Arg Ser Ile
            420                 425                 430

Ala Leu Ile Gly Pro Trp Ala Asn Ala Thr Thr Gln Met Gln Gly Asn
        435                 440                 445

Tyr Tyr Gly Pro Ala Pro Tyr Leu Ile Ser Pro Leu Glu Ala Ala Lys
    450                 455                 460

Lys Ala Gly Tyr His Val Asn Phe Glu Leu Gly Thr Glu Ile Ala Gly
465                 470                 475                 480

Asn Ser Thr Thr Gly Phe Ala Lys Ala Ile Ala Ala Ala Lys Lys Ser
                485                 490                 495

Asp Ala Ile Ile Tyr Leu Gly Gly Ile Asp Asn Thr Ile Glu Gln Glu
            500                 505                 510

Gly Ala Asp Arg Thr Asp Ile Ala Trp Pro Gly Asn Gln Leu Asp Leu
        515                 520                 525

Ile Lys Gln Leu Ser Glu Val Gly Lys Pro Leu Val Val Leu Gln Met
    530                 535                 540

Gly Gly Gly Gln Val Asp Ser Ser Ser Leu Lys Ser Asn Lys Lys Val
545                 550                 555                 560

Asn Ser Leu Val Trp Gly Gly Tyr Pro Gly Gln Ser Gly Gly Val Ala
                565                 570                 575

Leu Phe Asp Ile Leu Ser Gly Lys Arg Ala Pro Ala Gly Arg Leu Val
            580                 585                 590

Thr Thr Gln Tyr Pro Ala Glu Tyr Val His Gln Phe Pro Gln Asn Asp
        595                 600                 605

Met Asn Leu Arg Pro Asp Gly Lys Ser Asn Pro Gly Gln Thr Tyr Ile
    610                 615                 620

Trp Tyr Thr Gly Lys Pro Val Tyr Glu Phe Gly Ser Gly Leu Phe Tyr
625                 630                 635                 640

Thr Thr Phe Lys Glu Thr Leu Ala Ser His Pro Lys Ser Leu Lys Phe
                645                 650                 655

Asn Thr Ser Ser Ile Leu Ser Ala Pro His Pro Gly Tyr Thr Tyr Ser
            660                 665                 670

Glu Gln Ile Pro Val Phe Thr Phe Glu Ala Asn Ile Lys Asn Ser Gly
        675                 680                 685

Lys Thr Glu Ser Pro Tyr Thr Ala Met Leu Phe Val Arg Thr Ser Asn
    690                 695                 700

Ala Gly Pro Ala Pro Tyr Pro Asn Lys Trp Leu Val Gly Phe Asp Arg
705                 710                 715                 720
```

```
Leu Ala Asp Ile Lys Pro Gly His Ser Ser Lys Leu Ser Ile Pro Ile
                725                 730                 735

Pro Val Ser Ala Leu Ala Arg Val Asp Ser His Gly Asn Arg Ile Val
            740                 745                 750

Tyr Pro Gly Lys Tyr Glu Leu Ala Leu Asn Thr Asp Glu Ser Val Lys
        755                 760                 765

Leu Glu Phe Glu Leu Val Gly Glu Glu Val Thr Ile Glu Asn Trp Pro
    770                 775                 780

Leu Glu Glu Gln Gln Ile Lys Asp Ala Thr Pro Asp Ala
785                 790                 795


<210> SEQ ID NO 59
<211> LENGTH: 2388
<212> TYPE: DNA
<213> ORGANISM: Talaromyces emersonii

<400> SEQUENCE: 59

atgatgactc ccacggcgat tctcaccgca gtggcggcgc tcctgcccac cgcgacatgg     60

gcacaggata accaaaccta tgccaattac tcgtcgcagt ctcagccgga cctgtttccc    120

cggaccgtcg cgaccatcga cctgtccttc cccgactgtg agaatggccc gctcagcacg    180

aacctggtgt gcaacaaatc ggccgatccc tgggcccgag ctgaggccct catctcgctc    240

tttaccctcg aagagctgat taacaacacc cagaacaccg ctcctggcgt gccccgtttg    300

ggtctgcccc agtatcaggt gtggaatgaa gctctgcacg gactggaccg cgccaatttc    360

tcccattcgg gcgaatacag ctgggccacg tccttcccca tgcccatcct gtcgatggcg    420

tccttcaacc ggaccctcat caaccagatt gcctccatca ttgcaacgca agcccgtgcc    480

ttcaacaacg ccggccgtta cggccttgac agctatgcgc ccaacatcaa tggcttccgc    540

agtcccctct ggggccgtgg acaggagacg cctggtgagg atgcgttctt cttgagttcc    600

acctatgcgt acgagtacat cacaggcctg cagggcggtg tcgacccaga gcatgtcaag    660

atcgtcgcga cggcgaagca cttcgccggc tatgatctgg agaactgggg caacgtctct    720

cggctggggt tcaatgctat catcacgcag caggatctct ccgagtacta cacccctcag    780

ttcctggcgt ctgctcgata cgccaagacg cgcagcatca tgtgctccta caatgcagtg    840

aatggagtcc caagctgtgc caactccttc ttcctccaga cgcttctccg agaaaacttt    900

gacttcgttg acgacgggta cgtctcgtcg gattgcgacg ccgtctacaa cgtcttcaac    960

ccacacggtt acgcccttaa ccagtcggga gccgctgcgg actcgctcct agcaggtacc   1020

gatatcgact gtggtcagac cttgccgtgg cacctgaatg agtccttcgt agaaggatac   1080

gtctcccgcg gtgatatcga gaaatccctc acccgtctct actcaaacct ggtgcgtctc   1140

ggctactttg acggcaacaa cagcgagtac cgcaacctca actggaacga cgtcgtgact   1200

acggacgcct ggaacatctc gtacgaggcc gcggtggaag gtatcaccct gctcaagaac   1260

gacggaacgc tgccgctgtc caagaaggtc cgcagcattg cgctcatcgg tccttgggcc   1320

aatgccacgg tgcagatgca gggtaactac tatggaacgc caccgtatct gatcagtccg   1380

ctggaagccg ccaaggccag tgggttcacg gtcaactatg cattcggtac caacatctcg   1440

accgattcta cccagtggtt cgcggaagcc atcgcggcgg cgaagaagtc ggacgtgatc   1500

atctacgccg gtggtattga caacacgatc gaggcagagg gacaggaccg cacggatctc   1560

aagtggccgg ggaaccagct ggatctgatc gagcagctca gccaggtggg caagcccttg   1620

gtcgtcctgc agatgggcgg tggccaggtg gattcgtcgt cactcaaggc caacaagaat   1680
```

```
gtcaacgctc tggtgtgggg tggctatccc ggacagtcgg gtggtgcggc cctgtttgac   1740

atccttacgg gcaagcgtgc gccggccggt cgtctggtga gcacgcagta cccggccgag   1800

tatgcgacgc agttcccggc caacgacatg aacctgcgtc cgaacggcag caacccggga   1860

cagacataca tctggtacac gggcacgccc gtgtatgagt tcggccacgg tctgttctac   1920

acggagttcc aggagtcggc tgcggcgggc acgaacaaga cgtcgacttt cgacattctg   1980

gaccttttct ccacccctca tccgggatac gagtacatcg agcaggttcc gttcatcaac   2040

gtgactgtgg acgtgaagaa cgtcggccac acgccatcgc cgtacacggg tctgttgttc   2100

gcgaacacga cagccgggcc caagccgtac ccgaacaaat ggctcgtcgg gttcgactgg   2160

ctgccgacga tccagccggg cgagactgcc aagttgacga tcccggtgcc gttgggcgcg   2220

attgcgtggg cggacgagaa cggcaacaag gtggtcttcc cgggcaacta cgaattggca   2280

ctgaacaatg agcgatcggt agtggtgtcg ttcacgctga cgggcgatgc ggcgactcta   2340

gagaaatggc ctttgtggga gcaggcggtt ccgggggtgc tgcagcaa                 2388


<210> SEQ ID NO 60
<211> LENGTH: 796
<212> TYPE: PRT
<213> ORGANISM: Talaromyces emersonii

<400> SEQUENCE: 60

Met Met Thr Pro Thr Ala Ile Leu Thr Ala Val Ala Ala Leu Leu Pro
1               5                   10                  15

Thr Ala Thr Trp Ala Gln Asp Asn Gln Thr Tyr Ala Asn Tyr Ser Ser
            20                  25                  30

Gln Ser Gln Pro Asp Leu Phe Pro Arg Thr Val Ala Thr Ile Asp Leu
        35                  40                  45

Ser Phe Pro Asp Cys Glu Asn Gly Pro Leu Ser Thr Asn Leu Val Cys
    50                  55                  60

Asn Lys Ser Ala Asp Pro Trp Ala Arg Ala Glu Ala Leu Ile Ser Leu
65                  70                  75                  80

Phe Thr Leu Glu Glu Leu Ile Asn Asn Thr Gln Asn Thr Ala Pro Gly
                85                  90                  95

Val Pro Arg Leu Gly Leu Pro Gln Tyr Gln Val Trp Asn Glu Ala Leu
            100                 105                 110

His Gly Leu Asp Arg Ala Asn Phe Ser His Ser Gly Glu Tyr Ser Trp
        115                 120                 125

Ala Thr Ser Phe Pro Met Pro Ile Leu Ser Met Ala Ser Phe Asn Arg
    130                 135                 140

Thr Leu Ile Asn Gln Ile Ala Ser Ile Ile Ala Thr Gln Ala Arg Ala
145                 150                 155                 160

Phe Asn Asn Ala Gly Arg Tyr Gly Leu Asp Ser Tyr Ala Pro Asn Ile
                165                 170                 175

Asn Gly Phe Arg Ser Pro Leu Trp Gly Arg Gly Gln Glu Thr Pro Gly
            180                 185                 190

Glu Asp Ala Phe Phe Leu Ser Ser Thr Tyr Ala Tyr Glu Tyr Ile Thr
        195                 200                 205

Gly Leu Gln Gly Gly Val Asp Pro Glu His Val Lys Ile Val Ala Thr
    210                 215                 220

Ala Lys His Phe Ala Gly Tyr Asp Leu Glu Asn Trp Gly Asn Val Ser
225                 230                 235                 240

Arg Leu Gly Phe Asn Ala Ile Ile Thr Gln Gln Asp Leu Ser Glu Tyr
                245                 250                 255
```

-continued

```
Tyr Thr Pro Gln Phe Leu Ala Ser Ala Arg Tyr Ala Lys Thr Arg Ser
            260                 265                 270

Ile Met Cys Ser Tyr Asn Ala Val Asn Gly Val Pro Ser Cys Ala Asn
        275                 280                 285

Ser Phe Phe Leu Gln Thr Leu Leu Arg Glu Asn Phe Asp Phe Val Asp
    290                 295                 300

Asp Gly Tyr Val Ser Ser Asp Cys Asp Ala Val Tyr Asn Val Phe Asn
305                 310                 315                 320

Pro His Gly Tyr Ala Leu Asn Gln Ser Gly Ala Ala Ala Asp Ser Leu
                325                 330                 335

Leu Ala Gly Thr Asp Ile Asp Cys Gly Gln Thr Leu Pro Trp His Leu
            340                 345                 350

Asn Glu Ser Phe Val Glu Gly Tyr Val Ser Arg Gly Asp Ile Glu Lys
        355                 360                 365

Ser Leu Thr Arg Leu Tyr Ser Asn Leu Val Arg Leu Gly Tyr Phe Asp
    370                 375                 380

Gly Asn Asn Ser Glu Tyr Arg Asn Leu Asn Trp Asn Asp Val Val Thr
385                 390                 395                 400

Thr Asp Ala Trp Asn Ile Ser Tyr Glu Ala Ala Val Glu Gly Ile Thr
                405                 410                 415

Leu Leu Lys Asn Asp Gly Thr Leu Pro Leu Ser Lys Lys Val Arg Ser
            420                 425                 430

Ile Ala Leu Ile Gly Pro Trp Ala Asn Ala Thr Val Gln Met Gln Gly
        435                 440                 445

Asn Tyr Tyr Gly Thr Pro Pro Tyr Leu Ile Ser Pro Leu Glu Ala Ala
    450                 455                 460

Lys Ala Ser Gly Phe Thr Val Asn Tyr Ala Phe Gly Thr Asn Ile Ser
465                 470                 475                 480

Thr Asp Ser Thr Gln Trp Phe Ala Glu Ala Ile Ala Ala Ala Lys Lys
                485                 490                 495

Ser Asp Val Ile Ile Tyr Ala Gly Gly Ile Asp Asn Thr Ile Glu Ala
            500                 505                 510

Glu Gly Gln Asp Arg Thr Asp Leu Lys Trp Pro Gly Asn Gln Leu Asp
        515                 520                 525

Leu Ile Glu Gln Leu Ser Gln Val Gly Lys Pro Leu Val Val Leu Gln
    530                 535                 540

Met Gly Gly Gly Gln Val Asp Ser Ser Ser Leu Lys Ala Asn Lys Asn
545                 550                 555                 560

Val Asn Ala Leu Val Trp Gly Gly Tyr Pro Gly Gln Ser Gly Gly Ala
                565                 570                 575

Ala Leu Phe Asp Ile Leu Thr Gly Lys Arg Ala Pro Ala Gly Arg Leu
            580                 585                 590

Val Ser Thr Gln Tyr Pro Ala Glu Tyr Ala Thr Gln Phe Pro Ala Asn
        595                 600                 605

Asp Met Asn Leu Arg Pro Asn Gly Ser Asn Pro Gly Gln Thr Tyr Ile
    610                 615                 620

Trp Tyr Thr Gly Thr Pro Val Tyr Glu Phe Gly His Gly Leu Phe Tyr
625                 630                 635                 640

Thr Glu Phe Gln Glu Ser Ala Ala Ala Gly Thr Asn Lys Thr Ser Thr
                645                 650                 655

Phe Asp Ile Leu Asp Leu Phe Ser Thr Pro His Pro Gly Tyr Glu Tyr
            660                 665                 670
```

```
Ile Glu Gln Val Pro Phe Ile Asn Val Thr Val Asp Val Lys Asn Val
        675                 680                 685

Gly His Thr Pro Ser Pro Tyr Thr Gly Leu Leu Phe Ala Asn Thr Thr
    690                 695                 700

Ala Gly Pro Lys Pro Tyr Pro Asn Lys Trp Leu Val Gly Phe Asp Trp
705                 710                 715                 720

Leu Pro Thr Ile Gln Pro Gly Glu Thr Ala Lys Leu Thr Ile Pro Val
                725                 730                 735

Pro Leu Gly Ala Ile Ala Trp Ala Asp Glu Asn Gly Asn Lys Val Val
            740                 745                 750

Phe Pro Gly Asn Tyr Glu Leu Ala Leu Asn Asn Glu Arg Ser Val Val
        755                 760                 765

Val Ser Phe Thr Leu Thr Gly Asp Ala Ala Thr Leu Glu Lys Trp Pro
    770                 775                 780

Leu Trp Glu Gln Ala Val Pro Gly Val Leu Gln Gln
785                 790                 795


<210> SEQ ID NO 61
<211> LENGTH: 1380
<212> TYPE: DNA
<213> ORGANISM: Trichoderma reesei

<400> SEQUENCE: 61

atggcgccct cagttacact gccgttgacc acggccatcc tggccattgc ccggctcgtc      60

gccgcccagc aaccgggtac cagcaccccc gaggtccatc ccaagttgac aacctacaag     120

tgtacaaagt ccgggggggtg cgtggcccag gacacctcgg tggtccttga ctggaactac    180

cgctggatgc acgacgcaaa ctacaactcg tgcaccgtca acggcggcgt caacaccacg     240

ctctgccctg acgaggcgac ctgtggcaag aactgcttca tcgagggcgt cgactacgcc     300

gcctcgggcg tcacgacctc gggcagcagc ctcaccatga accagtacat gcccagcagc     360

tctggcggct acagcagcgt ctctcctcgg ctgtatctcc tggactctga cggtgagtac     420

gtgatgctga agctcaacgg ccaggagctg agcttcgacg tcgacctctc tgctctgccg     480

tgtggagaga acggctcgct ctacctgtct cagatggacg agaacggggg cgccaaccag     540

tataacacgg ccggtgccaa ctacgggagc ggctactgcg atgctcagtg ccccgtccag     600

acatggagga acggcaccct caacactagc caccagggct tctgctgcaa cgagatggat     660

atcctggagg gcaactcgag ggcgaatgcc ttgacccctc actcttgcac ggccacggcc     720

tgcgactctg ccggttgcgg cttcaacccc tatggcagcg gctacaaaag ctactacggc     780

cccggagata ccgttgacac ctccaagacc ttcaccatca tcacccagtt caacacggac     840

aacggctcgc cctcgggcaa ccttgtgagc atcacccgca agtaccagca aaacggcgtc     900

gacatcccca gcgcccagcc cggcggcgac accatctcgt cctgcccgtc cgcctcagcc     960

tacggcggcc tcgccaccat gggcaaggcc ctgagcagcg gcatggtgct cgtgttcagc    1020

atttggaacg acaacagcca gtacatgaac tggctcgaca gcggcaacgc cggcccctgc    1080

agcagcaccg agggcaaccc atccaacatc ctggccaaca accccaacac gcacgtcgtc    1140

ttctccaaca tccgctgggg agacattggg tctactacga actcgactgc gcccccgccc    1200

ccgcctgcgt ccagcacgac gttttcgact acacggagga gctcgacgac ttcgagcagc    1260

ccgagctgca cgcagactca ctgggggcag tgcggtggca ttgggtacag cgggtgcaag    1320

acgtgcacgt cgggcactac gtgccagtat agcaacgact actactcgca atgcctttag    1380
```

<210> SEQ ID NO 62
<211> LENGTH: 459
<212> TYPE: PRT
<213> ORGANISM: Trichoderma reesei

<400> SEQUENCE: 62

```
Met Ala Pro Ser Val Thr Leu Pro Leu Thr Thr Ala Ile Leu Ala Ile
1               5                   10                  15

Ala Arg Leu Val Ala Ala Gln Gln Pro Gly Thr Ser Thr Pro Glu Val
            20                  25                  30

His Pro Lys Leu Thr Thr Tyr Lys Cys Thr Lys Ser Gly Gly Cys Val
        35                  40                  45

Ala Gln Asp Thr Ser Val Val Leu Asp Trp Asn Tyr Arg Trp Met His
    50                  55                  60

Asp Ala Asn Tyr Asn Ser Cys Thr Val Asn Gly Gly Val Asn Thr Thr
65                  70                  75                  80

Leu Cys Pro Asp Glu Ala Thr Cys Gly Lys Asn Cys Phe Ile Glu Gly
                85                  90                  95

Val Asp Tyr Ala Ala Ser Gly Val Thr Thr Ser Gly Ser Ser Leu Thr
            100                 105                 110

Met Asn Gln Tyr Met Pro Ser Ser Ser Gly Gly Tyr Ser Ser Val Ser
        115                 120                 125

Pro Arg Leu Tyr Leu Leu Asp Ser Asp Gly Glu Tyr Val Met Leu Lys
    130                 135                 140

Leu Asn Gly Gln Glu Leu Ser Phe Asp Val Asp Leu Ser Ala Leu Pro
145                 150                 155                 160

Cys Gly Glu Asn Gly Ser Leu Tyr Leu Ser Gln Met Asp Glu Asn Gly
                165                 170                 175

Gly Ala Asn Gln Tyr Asn Thr Ala Gly Ala Asn Tyr Gly Ser Gly Tyr
            180                 185                 190

Cys Asp Ala Gln Cys Pro Val Gln Thr Trp Arg Asn Gly Thr Leu Asn
        195                 200                 205

Thr Ser His Gln Gly Phe Cys Cys Asn Glu Met Asp Ile Leu Glu Gly
    210                 215                 220

Asn Ser Arg Ala Asn Ala Leu Thr Pro His Ser Cys Thr Ala Thr Ala
225                 230                 235                 240

Cys Asp Ser Ala Gly Cys Gly Phe Asn Pro Tyr Gly Ser Gly Tyr Lys
                245                 250                 255

Ser Tyr Tyr Gly Pro Gly Asp Thr Val Asp Thr Ser Lys Thr Phe Thr
            260                 265                 270

Ile Ile Thr Gln Phe Asn Thr Asp Asn Gly Ser Pro Ser Gly Asn Leu
        275                 280                 285

Val Ser Ile Thr Arg Lys Tyr Gln Gln Asn Gly Val Asp Ile Pro Ser
    290                 295                 300

Ala Gln Pro Gly Gly Asp Thr Ile Ser Ser Cys Pro Ser Ala Ser Ala
305                 310                 315                 320

Tyr Gly Gly Leu Ala Thr Met Gly Lys Ala Leu Ser Ser Gly Met Val
                325                 330                 335

Leu Val Phe Ser Ile Trp Asn Asp Asn Ser Gln Tyr Met Asn Trp Leu
            340                 345                 350

Asp Ser Gly Asn Ala Gly Pro Cys Ser Ser Thr Glu Gly Asn Pro Ser
        355                 360                 365

Asn Ile Leu Ala Asn Asn Pro Asn Thr His Val Val Phe Ser Asn Ile
    370                 375                 380
```

```
Arg Trp Gly Asp Ile Gly Ser Thr Thr Asn Ser Thr Ala Pro Pro Pro
385                 390                 395                 400

Pro Pro Ala Ser Ser Thr Thr Phe Ser Thr Thr Arg Arg Ser Ser Thr
                405                 410                 415

Thr Ser Ser Ser Pro Ser Cys Thr Gln Thr His Trp Gly Gln Cys Gly
            420                 425                 430

Gly Ile Gly Tyr Ser Gly Cys Lys Thr Cys Thr Ser Gly Thr Thr Cys
        435                 440                 445

Gln Tyr Ser Asn Asp Tyr Tyr Ser Gln Cys Leu
    450                 455
```

```
<210> SEQ ID NO 63
<211> LENGTH: 1545
<212> TYPE: DNA
<213> ORGANISM: Trichoderma reesei

<400> SEQUENCE: 63

atgtatcgga agttggccgt catctcggcc ttcttggcca cagctcgtgc tcagtcggcc      60

tgcactctcc aatcggagac tcacccgcct ctgacatggc agaaatgctc gtctggtggc     120

acgtgcactc aacagacagg ctccgtggtc atcgacgcca actggcgctg gactcacgct     180

acgaacagca gcacgaactg ctacgatggc aacacttgga gctcgaccct atgtcctgac     240

aacgagacct gcgcgaagaa ctgctgtctg gacggtgccg cctacgcgtc cacgtacgga     300

gttaccacga gcggtaacag cctctccatt ggctttgtca cccagtctgc gcagaagaac     360

gttggcgctc gcctttacct tatggcgagc gacacgacct accaggaatt caccctgctt     420

ggcaacgagt tctctttcga tgttgatgtt tcgcagctgc cgtgcggctt gaacggagct     480

ctctacttcg tgtccatgga cgcggatggt ggcgtgagca agtatcccac caacaccgct     540

ggcgccaagt acggcacggg gtactgtgac agccagtgtc cccgcgatct gaagttcatc     600

aatggccagg ccaacgttga gggctgggag ccgtcatcca acaacgcgaa cacgggcatt     660

ggaggacacg gaagctgctg ctctgagatg gatatctggg aggccaactc catctccgag     720

gctcttaccc cccacccttg cacgactgtc ggccaggaga tctgcgaggg tgatgggtgc     780

ggcggaactt actccgataa cagatatggc ggcacttgcg atcccgatgg ctgcgactgg     840

aacccatacc gcctgggcaa caccagcttc tacggccctg gctcaagctt taccctcgat     900

accaccaaga aattgaccgt tgtcacccag ttcgagacgt cgggtgccat caaccgatac     960

tatgtccaga atggcgtcac tttccagcag cccaacgccg agcttggtag ttactctggc    1020

aacgagctca acgatgatta ctgcacagct gaggaggcag aattcggcgg atcctctttc    1080

tcagacaagg gcggcctgac tcagttcaag aaggctacct ctggcggcat ggttctggtc    1140

atgagtctgt gggatgatta ctacgccaac atgctgtggc tggactccac ctacccgaca    1200

aacgagacct cctccacacc cggtgccgtg cgcggaagct gctccaccag ctccggtgtc    1260

cctgctcagg tcgaatctca gtctcccaac gccaaggtca ccttctccaa catcaagttc    1320

ggacccattg gcagcaccgg caaccctagc ggcggcaacc ctcccggcgg aaacccgcct    1380

ggcaccacca ccacccgccg cccagccact accactggaa gctctcccgg acctacccag    1440

tctcactacg gccagtgcgg cggtattggc tacagcggcc ccacggtctg cgccagcggc    1500

acaacttgcc aggtcctgaa cccttactac tctcagtgcc tgtaa                    1545
```

```
<210> SEQ ID NO 64
<211> LENGTH: 514
<212> TYPE: PRT
```

<213> ORGANISM: Trichoderma reesei

<400> SEQUENCE: 64

```
Met Tyr Arg Lys Leu Ala Val Ile Ser Ala Phe Leu Ala Thr Ala Arg
1               5                   10                  15

Ala Gln Ser Ala Cys Thr Leu Gln Ser Glu Thr His Pro Pro Leu Thr
            20                  25                  30

Trp Gln Lys Cys Ser Ser Gly Gly Thr Cys Thr Gln Gln Thr Gly Ser
        35                  40                  45

Val Val Ile Asp Ala Asn Trp Arg Trp Thr His Ala Thr Asn Ser Ser
    50                  55                  60

Thr Asn Cys Tyr Asp Gly Asn Thr Trp Ser Ser Thr Leu Cys Pro Asp
65                  70                  75                  80

Asn Glu Thr Cys Ala Lys Asn Cys Cys Leu Asp Gly Ala Ala Tyr Ala
                85                  90                  95

Ser Thr Tyr Gly Val Thr Thr Ser Gly Asn Ser Leu Ser Ile Gly Phe
            100                 105                 110

Val Thr Gln Ser Ala Gln Lys Asn Val Gly Ala Arg Leu Tyr Leu Met
        115                 120                 125

Ala Ser Asp Thr Thr Tyr Gln Glu Phe Thr Leu Leu Gly Asn Glu Phe
    130                 135                 140

Ser Phe Asp Val Asp Val Ser Gln Leu Pro Cys Gly Leu Asn Gly Ala
145                 150                 155                 160

Leu Tyr Phe Val Ser Met Asp Ala Asp Gly Gly Val Ser Lys Tyr Pro
                165                 170                 175

Thr Asn Thr Ala Gly Ala Lys Tyr Gly Thr Gly Tyr Cys Asp Ser Gln
            180                 185                 190

Cys Pro Arg Asp Leu Lys Phe Ile Asn Gly Gln Ala Asn Val Glu Gly
        195                 200                 205

Trp Glu Pro Ser Ser Asn Asn Ala Asn Thr Gly Ile Gly Gly His Gly
    210                 215                 220

Ser Cys Cys Ser Glu Met Asp Ile Trp Glu Ala Asn Ser Ile Ser Glu
225                 230                 235                 240

Ala Leu Thr Pro His Pro Cys Thr Thr Val Gly Gln Glu Ile Cys Glu
                245                 250                 255

Gly Asp Gly Cys Gly Gly Thr Tyr Ser Asp Asn Arg Tyr Gly Gly Thr
            260                 265                 270

Cys Asp Pro Asp Gly Cys Asp Trp Asn Pro Tyr Arg Leu Gly Asn Thr
        275                 280                 285

Ser Phe Tyr Gly Pro Gly Ser Ser Phe Thr Leu Asp Thr Thr Lys Lys
    290                 295                 300

Leu Thr Val Val Thr Gln Phe Glu Thr Ser Gly Ala Ile Asn Arg Tyr
305                 310                 315                 320

Tyr Val Gln Asn Gly Val Thr Phe Gln Gln Pro Asn Ala Glu Leu Gly
                325                 330                 335

Ser Tyr Ser Gly Asn Glu Leu Asn Asp Asp Tyr Cys Thr Ala Glu Glu
            340                 345                 350

Ala Glu Phe Gly Gly Ser Ser Phe Ser Asp Lys Gly Gly Leu Thr Gln
        355                 360                 365

Phe Lys Lys Ala Thr Ser Gly Gly Met Val Leu Val Met Ser Leu Trp
    370                 375                 380

Asp Asp Tyr Tyr Ala Asn Met Leu Trp Leu Asp Ser Thr Tyr Pro Thr
385                 390                 395                 400
```

-continued

```
Asn Glu Thr Ser Ser Thr Pro Gly Ala Val Arg Gly Ser Cys Ser Thr
                405                 410                 415

Ser Ser Gly Val Pro Ala Gln Val Glu Ser Gln Ser Pro Asn Ala Lys
            420                 425                 430

Val Thr Phe Ser Asn Ile Lys Phe Gly Pro Ile Gly Ser Thr Gly Asn
        435                 440                 445

Pro Ser Gly Gly Asn Pro Pro Gly Gly Asn Pro Pro Gly Thr Thr Thr
    450                 455                 460

Thr Arg Arg Pro Ala Thr Thr Thr Gly Ser Ser Pro Gly Pro Thr Gln
465                 470                 475                 480

Ser His Tyr Gly Gln Cys Gly Gly Ile Gly Tyr Ser Gly Pro Thr Val
                485                 490                 495

Cys Ala Ser Gly Thr Thr Cys Gln Val Leu Asn Pro Tyr Tyr Ser Gln
            500                 505                 510

Cys Leu
```

<210> SEQ ID NO 65
<211> LENGTH: 1611
<212> TYPE: DNA
<213> ORGANISM: Trichoderma reesei

<400> SEQUENCE: 65

```
atgattgtcg gcattctcac cacgctggct acgctggcca cactcgcagc tagtgtgcct      60

ctagaggagc ggcaagcttg ctcaagcgtc tggtaattat gtgaaccctc tcaagagacc     120

caaatactga gatatgtcaa ggggccaatg tggtggccag aattggtcgg gtccgacttg     180

ctgtgcttcc ggaagcacat gcgtctactc caacgactat tactcccagt gtcttcccgg     240

cgctgcaagc tcaagctcgt ccacgcgcgc cgcgtcgacg acttctcgag tatcccccac     300

aacatcccgg tcgagctccg cgacgcctcc acctggttct actactacca gagtacctcc     360

agtcggatcg ggaaccgcta cgtattcagg caaccctttt gttggggtca ctccttgggc     420

caatgcatat tacgcctctg aagttagcag cctcgctatt cctagcttga ctggagccat     480

ggccactgct gcagcagctg tcgcaaaggt tccctctttt atgtggctgt aggtcctccc     540

ggaaccaagg caatctgtta ctgaaggctc atcattcact gcagagatac tcttgacaag     600

acccctctca tggagcaaac cttggccgac atccgcaccg ccaacaagaa tggcggtaac     660

tatgccggac agtttgtggt gtatgacttg ccggatcgcg attgcgctgc ccttgcctcg     720

aatggcgaat actctattgc cgatggtggc gtcgccaaat ataagaacta tatcgacacc     780

attcgtcaaa ttgtcgtgga atattccgat atccggaccc tcctggttat tggtatgagt     840

ttaaacacct gcctcccccc ccccttccct tcctttcccg ccggcatctt gtcgttgtgc     900

taactattgt tccctcttcc agagcctgac tctcttgcca acctggtgac caacctcggt     960

actccaaagt gtgccaatgc tcagtcagcc taccttgagt gcatcaacta cgccgtcaca    1020

cagctgaacc ttccaaatgt tgcgatgtat ttggacgctg gccatgcagg atggcttggc    1080

tggccggcaa accaagaccc ggccgctcag ctatttgcaa atgtttacaa gaatgcatcg    1140

tctccgagag ctcttcgcgg attggcaacc aatgtcgcca actacaacgg gtggaacatt    1200

accagccccc catcgtacac gcaaggcaac gctgtctaca acgagaagct gtacatccac    1260

gctattggac gtcttcttgc caatcacggc tggtccaacg ccttcttcat cactgatcaa    1320

ggtcgatcgg gaaagcagcc taccggacag caacagtggg gagactggtg caatgtgatc    1380

ggcaccggat ttggtattcg cccatccgca aacactgggg actcgttgct ggattcgttt    1440
```

-continued

```
gtctgggtca agccaggcgg cgagtgtgac ggcaccagcg acagcagtgc gccacgattt   1500

gactcccact gtgcgctccc agatgccttg caaccggcgc ctcaagctgg tgcttggttc   1560

caagcctact ttgtgcagct tctcacaaac gcaaacccat cgttcctgta a            1611


<210> SEQ ID NO 66
<211> LENGTH: 471
<212> TYPE: PRT
<213> ORGANISM: Trichoderma reesei

<400> SEQUENCE: 66

Met Ile Val Gly Ile Leu Thr Thr Leu Ala Thr Leu Ala Thr Leu Ala
1               5                   10                  15

Ala Ser Val Pro Leu Glu Glu Arg Gln Ala Cys Ser Ser Val Trp Gly
            20                  25                  30

Gln Cys Gly Gly Gln Asn Trp Ser Gly Pro Thr Cys Cys Ala Ser Gly
        35                  40                  45

Ser Thr Cys Val Tyr Ser Asn Asp Tyr Tyr Ser Gln Cys Leu Pro Gly
    50                  55                  60

Ala Ala Ser Ser Ser Ser Ser Thr Arg Ala Ala Ser Thr Thr Ser Arg
65                  70                  75                  80

Val Ser Pro Thr Thr Ser Arg Ser Ser Ser Ala Thr Pro Pro Pro Gly
                85                  90                  95

Ser Thr Thr Thr Arg Val Pro Pro Val Gly Ser Gly Thr Ala Thr Tyr
            100                 105                 110

Ser Gly Asn Pro Phe Val Gly Val Thr Pro Trp Ala Asn Ala Tyr Tyr
        115                 120                 125

Ala Ser Glu Val Ser Ser Leu Ala Ile Pro Ser Leu Thr Gly Ala Met
    130                 135                 140

Ala Thr Ala Ala Ala Ala Val Ala Lys Val Pro Ser Phe Met Trp Leu
145                 150                 155                 160

Asp Thr Leu Asp Lys Thr Pro Leu Met Glu Gln Thr Leu Ala Asp Ile
                165                 170                 175

Arg Thr Ala Asn Lys Asn Gly Gly Asn Tyr Ala Gly Gln Phe Val Val
            180                 185                 190

Tyr Asp Leu Pro Asp Arg Asp Cys Ala Ala Leu Ala Ser Asn Gly Glu
        195                 200                 205

Tyr Ser Ile Ala Asp Gly Gly Val Ala Lys Tyr Lys Asn Tyr Ile Asp
    210                 215                 220

Thr Ile Arg Gln Ile Val Val Glu Tyr Ser Asp Ile Arg Thr Leu Leu
225                 230                 235                 240

Val Ile Glu Pro Asp Ser Leu Ala Asn Leu Val Thr Asn Leu Gly Thr
                245                 250                 255

Pro Lys Cys Ala Asn Ala Gln Ser Ala Tyr Leu Glu Cys Ile Asn Tyr
            260                 265                 270

Ala Val Thr Gln Leu Asn Leu Pro Asn Val Ala Met Tyr Leu Asp Ala
        275                 280                 285

Gly His Ala Gly Trp Leu Gly Trp Pro Ala Asn Gln Asp Pro Ala Ala
    290                 295                 300

Gln Leu Phe Ala Asn Val Tyr Lys Asn Ala Ser Ser Pro Arg Ala Leu
305                 310                 315                 320

Arg Gly Leu Ala Thr Asn Val Ala Asn Tyr Asn Gly Trp Asn Ile Thr
                325                 330                 335

Ser Pro Pro Ser Tyr Thr Gln Gly Asn Ala Val Tyr Asn Glu Lys Leu
            340                 345                 350
```

```
Tyr Ile His Ala Ile Gly Arg Leu Leu Ala Asn His Gly Trp Ser Asn
        355                 360                 365

Ala Phe Phe Ile Thr Asp Gln Gly Arg Ser Gly Lys Gln Pro Thr Gly
    370                 375                 380

Gln Gln Gln Trp Gly Asp Trp Cys Asn Val Ile Gly Thr Gly Phe Gly
385                 390                 395                 400

Ile Arg Pro Ser Ala Asn Thr Gly Asp Ser Leu Leu Asp Ser Phe Val
                405                 410                 415

Trp Val Lys Pro Gly Gly Glu Cys Asp Gly Thr Ser Asp Ser Ser Ala
            420                 425                 430

Pro Arg Phe Asp Ser His Cys Ala Leu Pro Asp Ala Leu Gln Pro Ala
        435                 440                 445

Pro Gln Ala Gly Ala Trp Phe Gln Ala Tyr Phe Val Gln Leu Leu Thr
    450                 455                 460

Asn Ala Asn Pro Ser Phe Leu
465                 470


<210> SEQ ID NO 67
<211> LENGTH: 17
<212> TYPE: DNA
<213> ORGANISM: Chaetomium thermophilum
<220> FEATURE:
<221> NAME/KEY: misc_feature
<222> LOCATION: (3)..(3)
<223> OTHER INFORMATION: N=A,C,G, OR T
<220> FEATURE:
<221> NAME/KEY: misc_feature
<222> LOCATION: (6)..(6)
<223> OTHER INFORMATION: N=A,C,G, OR T
<220> FEATURE:
<221> NAME/KEY: misc_feature
<222> LOCATION: (9)..(9)
<223> OTHER INFORMATION: N=A,C,G, OR T

<400> SEQUENCE: 67

ggnacnggnt aytgyga                                                      17


<210> SEQ ID NO 68
<211> LENGTH: 20
<212> TYPE: DNA
<213> ORGANISM: Chaetomium thermophilum

<400> SEQUENCE: 68

ggccacgcgt cgactagtac                                                   20


<210> SEQ ID NO 69
<211> LENGTH: 19
<212> TYPE: DNA
<213> ORGANISM: Chaetomium thermophilum

<400> SEQUENCE: 69

agatatccat ctcagagca                                                    19


<210> SEQ ID NO 70
<211> LENGTH: 17
<212> TYPE: DNA
<213> ORGANISM: Chaetomium thermophilum

<400> SEQUENCE: 70

gttggcatca ttggtcg                                                      17


<210> SEQ ID NO 71
```

-continued

<211> LENGTH: 20
<212> TYPE: DNA
<213> ORGANISM: Chaetomium thermophilum

<400> SEQUENCE: 71
atcctctcct tccagttttc 20

<210> SEQ ID NO 72
<211> LENGTH: 20
<212> TYPE: DNA
<213> ORGANISM: Chaetomium thermophilum

<400> SEQUENCE: 72
tatccaagta gtccacaacc 20

<210> SEQ ID NO 73
<211> LENGTH: 24
<212> TYPE: DNA
<213> ORGANISM: Chaetomium thermophilum

<400> SEQUENCE: 73
tcatgatgta caagaagttc gccg 24

<210> SEQ ID NO 74
<211> LENGTH: 25
<212> TYPE: DNA
<213> ORGANISM: Chaetomium thermophilum

<400> SEQUENCE: 74
tcatgattac aggcactggc tgtac 25

<210> SEQ ID NO 75
<211> LENGTH: 18
<212> TYPE: DNA
<213> ORGANISM: Myceliophthora thermophila

<400> SEQUENCE: 75
ctcgcagtcg cagtcaag 18

<210> SEQ ID NO 76
<211> LENGTH: 19
<212> TYPE: DNA
<213> ORGANISM: Myceliophthora thermophila

<400> SEQUENCE: 76
cggtcaggtt gcagtttag 19

<210> SEQ ID NO 77
<211> LENGTH: 22
<212> TYPE: DNA
<213> ORGANISM: Myceliophthora thermophila

<400> SEQUENCE: 77
tcatgaagca gtacctccag ta 22

<210> SEQ ID NO 78
<211> LENGTH: 28
<212> TYPE: DNA
<213> ORGANISM: Myceliophthora thermophila

<400> SEQUENCE: 78
ttaattaatt agacgttgac agtcgagc 28

<210> SEQ ID NO 79
<211> LENGTH: 25
<212> TYPE: DNA
<213> ORGANISM: Aspergillus fumigatus

<400> SEQUENCE: 79
gggcatgctg gcctccacct tctcc 25

<210> SEQ ID NO 80
<211> LENGTH: 30
<212> TYPE: DNA
<213> ORGANISM: Aspergillus fumigatus

<400> SEQUENCE: 80
gggttaatta actacaggca ctgagagtaa 30

<210> SEQ ID NO 81
<211> LENGTH: 17
<212> TYPE: DNA
<213> ORGANISM: Thermoascus aurantiacus
<220> FEATURE:
<221> NAME/KEY: misc_feature
<222> LOCATION: (3)..(3)
<223> OTHER INFORMATION: N=A,C,G, OR T
<220> FEATURE:
<221> NAME/KEY: misc_feature
<222> LOCATION: (6)..(6)
<223> OTHER INFORMATION: N=A,C,G, OR T
<220> FEATURE:
<221> NAME/KEY: misc_feature
<222> LOCATION: (9)..(9)
<223> OTHER INFORMATION: N=A,C,G, OR T

<400> SEQUENCE: 81
ggnacnggnt aytgyga 17

<210> SEQ ID NO 82
<211> LENGTH: 17
<212> TYPE: DNA
<213> ORGANISM: Thermoascus aurantiacus
<220> FEATURE:
<221> NAME/KEY: misc_feature
<222> LOCATION: (3)..(3)
<223> OTHER INFORMATION: N=A,C,G, OR T
<220> FEATURE:
<221> NAME/KEY: misc_feature
<222> LOCATION: (9)..(9)
<223> OTHER INFORMATION: N=A,C,G, OR T

<400> SEQUENCE: 82
tcnarccana rcatrtt 17

<210> SEQ ID NO 83
<211> LENGTH: 18
<212> TYPE: DNA
<213> ORGANISM: Thermoascus aurantiacus

<400> SEQUENCE: 83
gtagagatgc tgttggct 18

<210> SEQ ID NO 84
<211> LENGTH: 21
<212> TYPE: DNA
<213> ORGANISM: Thermoascus aurantiacus

<400> SEQUENCE: 84
tctcagcgca gcaggaaccg t 21

<210> SEQ ID NO 85
<211> LENGTH: 18
<212> TYPE: DNA
<213> ORGANISM: Thermoascus aurantiacus

<400> SEQUENCE: 85
agcgacagca ataacaat 18

<210> SEQ ID NO 86
<211> LENGTH: 23
<212> TYPE: DNA
<213> ORGANISM: Thermoascus aurantiacus

<400> SEQUENCE: 86
acatgtatca gcgcgctctt ctc 23

<210> SEQ ID NO 87
<211> LENGTH: 28
<212> TYPE: DNA
<213> ORGANISM: Thermoascus aurantiacus

<400> SEQUENCE: 87
ttaattaatt agttggcggt gaaggtcg 28

<210> SEQ ID NO 88
<211> LENGTH: 30
<212> TYPE: DNA
<213> ORGANISM: Myceliophthora thermophila

<400> SEQUENCE: 88
attggcagcc cggatctggg acagagtctg 30

<210> SEQ ID NO 89
<211> LENGTH: 30
<212> TYPE: DNA
<213> ORGANISM: Myceliophthora thermophila

<400> SEQUENCE: 89
ccggtcatgc taggaatggc gagattgtgg 30

<210> SEQ ID NO 90
<211> LENGTH: 24
<212> TYPE: DNA
<213> ORGANISM: Myceliophthora thermophila

<400> SEQUENCE: 90
gctgtaaact gcgaatgggt tcag 24

<210> SEQ ID NO 91
<211> LENGTH: 20
<212> TYPE: DNA
<213> ORGANISM: Myceliophthora thermophila

<400> SEQUENCE: 91
gggtcccaca tgctgcgcct 20

<210> SEQ ID NO 92
<211> LENGTH: 20
<212> TYPE: DNA
<213> ORGANISM: Myceliophthora thermophila

<400> SEQUENCE: 92
aaaattcacg agacgccggg 20

<210> SEQ ID NO 93
<211> LENGTH: 36
<212> TYPE: DNA
<213> ORGANISM: Myceliophthora thermophila

<400> SEQUENCE: 93
actggattta ccatggccaa gaagcttttc atcacc 36

<210> SEQ ID NO 94
<211> LENGTH: 38
<212> TYPE: DNA
<213> ORGANISM: Myceliophthora thermophila

<400> SEQUENCE: 94
tcacctctag ttaattaatt agaagggcgg gttggcgt 38

<210> SEQ ID NO 95
<211> LENGTH: 34
<212> TYPE: DNA
<213> ORGANISM: Trichophaea saccata

<400> SEQUENCE: 95
tcgcgatccg ttttcgcatt tatcgtgaaa cgct 34

<210> SEQ ID NO 96
<211> LENGTH: 33
<212> TYPE: DNA
<213> ORGANISM: Trichophaea saccata

<400> SEQUENCE: 96
ccgcaaacgc tggtgaaagt aaaagatgct gaa 33

<210> SEQ ID NO 97
<211> LENGTH: 20
<212> TYPE: DNA
<213> ORGANISM: Trichophaea saccata

<400> SEQUENCE: 97
agcgtttgcg gccgcgatcc 20

<210> SEQ ID NO 98
<211> LENGTH: 21
<212> TYPE: DNA
<213> ORGANISM: Trichophaea saccata

<400> SEQUENCE: 98
ttattcggtc gaaaaggatc c 21

<210> SEQ ID NO 99
<211> LENGTH: 40
<212> TYPE: DNA
<213> ORGANISM: Trichophaea saccata

<400> SEQUENCE: 99
acacaactgg ggatcctcat catgaagaac ttccttctgg 40

<210> SEQ ID NO 100
<211> LENGTH: 40
<212> TYPE: DNA
<213> ORGANISM: Trichophaea saccata

<400> SEQUENCE: 100
ccctctagat ctcgagttac gtgaagctag gattagcatt 40

<210> SEQ ID NO 101
<211> LENGTH: 37
<212> TYPE: DNA
<213> ORGANISM: Aspergillus fumigatus

<400> SEQUENCE: 101
actggattta ccatgaagca ccttgcatct tccatcg 37

<210> SEQ ID NO 102
<211> LENGTH: 34
<212> TYPE: DNA
<213> ORGANISM: Aspergillus fumigatus

<400> SEQUENCE: 102
tcacctctag ttaattaaaa ggacgggtta gcgt 34

<210> SEQ ID NO 103
<211> LENGTH: 37
<212> TYPE: DNA
<213> ORGANISM: Aspergillus terreus

<400> SEQUENCE: 103
taacaattgt caccatgaat tctcttacaa aaagcat 37

<210> SEQ ID NO 104
<211> LENGTH: 33
<212> TYPE: DNA
<213> ORGANISM: Aspergillus terreus

<400> SEQUENCE: 104
tatgcggccg cagtctgcat gtgttacgca cct 33

<210> SEQ ID NO 105
<211> LENGTH: 38
<212> TYPE: DNA
<213> ORGANISM: Trichoderma reesei

<400> SEQUENCE: 105
actggattta ccatgaacaa gtccgtggct ccattgct 38

<210> SEQ ID NO 106
<211> LENGTH: 38
<212> TYPE: DNA
<213> ORGANISM: Trichoderma reesei

<400> SEQUENCE: 106
tcacctctag ttaattaact actttcttgc gagacacg 38

<210> SEQ ID NO 107
<211> LENGTH: 20
<212> TYPE: DNA
<213> ORGANISM: Thermoascus aurantiacus
<220> FEATURE:
<221> NAME/KEY: misc_feature
<222> LOCATION: (9)..(9)
<223> OTHER INFORMATION: N=A,C,G OR T
<220> FEATURE:
<221> NAME/KEY: misc_feature
<222> LOCATION: (12)..(12)
<223> OTHER INFORMATION: N=A,C,G OR T
<220> FEATURE:
<221> NAME/KEY: misc_feature
<222> LOCATION: (15)..(15)
<223> OTHER INFORMATION: N=A,C,G OR T

<400> SEQUENCE: 107
aaygartcng gngcngaatt 20

<210> SEQ ID NO 108
<211> LENGTH: 20
<212> TYPE: DNA
<213> ORGANISM: Thermoascus aurantiacus
<220> FEATURE:
<221> NAME/KEY: misc_feature
<222> LOCATION: (9)..(9)
<223> OTHER INFORMATION: N=A,C,G, OR T
<220> FEATURE:
<221> NAME/KEY: misc_feature
<222> LOCATION: (12)..(12)
<223> OTHER INFORMATION: N=A,C,G, OR T
<220> FEATURE:
<221> NAME/KEY: misc_feature
<222> LOCATION: (15)..(15)
<223> OTHER INFORMATION: N=A,C,G, OR T

<400> SEQUENCE: 108
aaygartcng gngcngagtt 20

<210> SEQ ID NO 109
<211> LENGTH: 20
<212> TYPE: DNA
<213> ORGANISM: Thermoascus aurantiacus
<220> FEATURE:
<221> NAME/KEY: misc_feature
<222> LOCATION: (12)..(12)
<223> OTHER INFORMATION: N=A,C,G, OR T
<220> FEATURE:
<221> NAME/KEY: misc_feature
<222> LOCATION: (15)..(15)
<223> OTHER INFORMATION: N=A,C,G, OR T

<400> SEQUENCE: 109
aaygaragyg gngcngaatt 20

<210> SEQ ID NO 110
<211> LENGTH: 20
<212> TYPE: DNA
<213> ORGANISM: Thermoascus aurantiacus
<220> FEATURE:
<221> NAME/KEY: misc_feature
<222> LOCATION: (12)..(12)
<223> OTHER INFORMATION: N=A,C,G, OR T
<220> FEATURE:
<221> NAME/KEY: misc_feature
<222> LOCATION: (15)..(15)
<223> OTHER INFORMATION: N=A,C,G, OR T

<400> SEQUENCE: 110
aaygaragyg gngcngagtt 20

<210> SEQ ID NO 111
<211> LENGTH: 26
<212> TYPE: DNA
<213> ORGANISM: Thermoascus aurantiacus

<400> SEQUENCE: 111
gatctcatga agctcggctc tctcgt 26

<210> SEQ ID NO 112
<211> LENGTH: 32
<212> TYPE: DNA
<213> ORGANISM: Thermoascus aurantiacus

<400> SEQUENCE: 112
ttaattaatc aaagatacgg agtcaaaata gg 32

<210> SEQ ID NO 113
<211> LENGTH: 41
<212> TYPE: DNA
<213> ORGANISM: Aspergillus niger

<400> SEQUENCE: 113
acacaactgg ggatccacca tgaggttcac ttcgatcgag g 41

<210> SEQ ID NO 114
<211> LENGTH: 41
<212> TYPE: DNA
<213> ORGANISM: Aspergillus niger

<400> SEQUENCE: 114
agatctcgag aagcttagtg aacagtaggc agagacgccc g 41

<210> SEQ ID NO 115
<211> LENGTH: 37
<212> TYPE: DNA
<213> ORGANISM: Aspergillus fumigatus

<400> SEQUENCE: 115
actggattta ccatgacttt gtccaagatc acttcca 37

<210> SEQ ID NO 116
<211> LENGTH: 40
<212> TYPE: DNA
<213> ORGANISM: Aspergillus fumigatus

<400> SEQUENCE: 116
tcacctctag ttaattaagc gttgaacagt gcaggaccag 40

<210> SEQ ID NO 117
<211> LENGTH: 17
<212> TYPE: DNA
<213> ORGANISM: Aspergillus fumigatus

<400> SEQUENCE: 117
tgtcccttgt cgatgcg 17

<210> SEQ ID NO 118
<211> LENGTH: 17
<212> TYPE: DNA
<213> ORGANISM: Aspergillus fumigatus

<400> SEQUENCE: 118
cacatgactt ggcttcc 17

<210> SEQ ID NO 119
<211> LENGTH: 34
<212> TYPE: DNA
<213> ORGANISM: Penicillium pinophilum

<400> SEQUENCE: 119
tcgcgatccg ttttcgcatt tatcgtgaaa cgct 34

<210> SEQ ID NO 120
<211> LENGTH: 33
<212> TYPE: DNA
<213> ORGANISM: Penicillium pinophilum

<400> SEQUENCE: 120
ccgcaaacgc tggtgaaagt aaaagatgct gaa 33

<210> SEQ ID NO 121
<211> LENGTH: 20
<212> TYPE: DNA
<213> ORGANISM: Penicillium pinophilum

<400> SEQUENCE: 121
agcgtttgcg gccgcgatcc 20

<210> SEQ ID NO 122
<211> LENGTH: 21
<212> TYPE: DNA
<213> ORGANISM: Penicillium pinophilum

<400> SEQUENCE: 122
ttattcggtc gaaaaggatc c 21

<210> SEQ ID NO 123
<211> LENGTH: 48
<212> TYPE: DNA
<213> ORGANISM: Penicillium pinophilum

<400> SEQUENCE: 123
acacaactgg ggatccacca tgactctagt aaaggctatt cttttagc 48

<210> SEQ ID NO 124
<211> LENGTH: 40
<212> TYPE: DNA
<213> ORGANISM: Penicillium pinophilum

<400> SEQUENCE: 124
gtcaccctct agatcttcac aaacattggg agtagtatgg 40

<210> SEQ ID NO 125
<211> LENGTH: 41
<212> TYPE: DNA
<213> ORGANISM: Penicillium sp.

<400> SEQUENCE: 125
acacaactgg ggatccacca tgctgtcttc gacgactcgc a 41

<210> SEQ ID NO 126
<211> LENGTH: 41
<212> TYPE: DNA
<213> ORGANISM: Penicillium sp.

<400> SEQUENCE: 126
gtcaccctct agatctcgac ttcttctaga acgtcggctc a 41

<210> SEQ ID NO 127
<211> LENGTH: 32
<212> TYPE: DNA
<213> ORGANISM: Thielavia terrestris

<400> SEQUENCE: 127
actggattta ccatgccttc tttcgcctcc aa 32

<210> SEQ ID NO 128
<211> LENGTH: 38
<212> TYPE: DNA

<213> ORGANISM: Thielavia terrestris

<400> SEQUENCE: 128
tcacctctag ttaattaatc agtttgcctc ctcagccc 38

<210> SEQ ID NO 129
<211> LENGTH: 19
<212> TYPE: DNA
<213> ORGANISM: Trichophaea saccata

<400> SEQUENCE: 129
tgaaatggga tgctactga 19

<210> SEQ ID NO 130
<211> LENGTH: 20
<212> TYPE: DNA
<213> ORGANISM: Trichophaea saccata

<400> SEQUENCE: 130
caacgactac aacatcgagg 20

<210> SEQ ID NO 131
<211> LENGTH: 20
<212> TYPE: DNA
<213> ORGANISM: Trichophaea saccata

<400> SEQUENCE: 131
atttgctgtc caccagtgaa 20

<210> SEQ ID NO 132
<211> LENGTH: 34
<212> TYPE: DNA
<213> ORGANISM: Penicillium pinophilum

<400> SEQUENCE: 132
tcgcgatccg ttttcgcatt tatcgtgaaa cgct 34

<210> SEQ ID NO 133
<211> LENGTH: 33
<212> TYPE: DNA
<213> ORGANISM: Penicillium pinophilum

<400> SEQUENCE: 133
ccgcaaacgc tggtgaaagt aaaagatgct gaa 33

<210> SEQ ID NO 134
<211> LENGTH: 20
<212> TYPE: DNA
<213> ORGANISM: Penicillium pinophilum

<400> SEQUENCE: 134
agcgtttgcg gccgcgatcc 20

<210> SEQ ID NO 135
<211> LENGTH: 21
<212> TYPE: DNA
<213> ORGANISM: Penicillium pinophilum

<400> SEQUENCE: 135
ttattcggtc gaaaaggatc c 21

<210> SEQ ID NO 136
<211> LENGTH: 48

<212> TYPE: DNA
<213> ORGANISM: Penicillium pinophilum

<400> SEQUENCE: 136
acacaactgg ggatccacca tgactctagt aaaggctatt cttttagc 48

<210> SEQ ID NO 137
<211> LENGTH: 40
<212> TYPE: DNA
<213> ORGANISM: Penicillium pinophilum

<400> SEQUENCE: 137
gtcaccctct agatcttcac aaacattggg agtagtatgg 40

<210> SEQ ID NO 138
<211> LENGTH: 36
<212> TYPE: DNA
<213> ORGANISM: Thielavia terrestris

<400> SEQUENCE: 138
actggattta ccatggccct caaatcgctc ctgttg 36

<210> SEQ ID NO 139
<211> LENGTH: 36
<212> TYPE: DNA
<213> ORGANISM: Thielavia terrestris

<400> SEQUENCE: 139
tcacctctag ttaattaatt acaagcactg agagta 36

<210> SEQ ID NO 140
<211> LENGTH: 17
<212> TYPE: DNA
<213> ORGANISM: Thielavia terrestris

<400> SEQUENCE: 140
tgtcccttgt cgatgcg 17

<210> SEQ ID NO 141
<211> LENGTH: 17
<212> TYPE: DNA
<213> ORGANISM: Thielavia terrestris

<400> SEQUENCE: 141
cacatgactt ggcttcc 17

<210> SEQ ID NO 142
<211> LENGTH: 43
<212> TYPE: DNA
<213> ORGANISM: Thermobifida fusca

<400> SEQUENCE: 142
ctgaaaaaaa ggagaggata aagaatgaac catgcccccg cca 43

<210> SEQ ID NO 143
<211> LENGTH: 45
<212> TYPE: DNA
<213> ORGANISM: Thermobifida fusca

<400> SEQUENCE: 143
ctaatgctgg tgttggtgct gatggttggc gctgcaggac accgt 45

<210> SEQ ID NO 144

```
<211> LENGTH: 42
<212> TYPE: DNA
<213> ORGANISM: Thermobifida fusca

<400> SEQUENCE: 144

ctaatgctgg tgttggtgct gatgggggtt gtcaccgccg ct                    42

<210> SEQ ID NO 145
<211> LENGTH: 21
<212> TYPE: DNA
<213> ORGANISM: Thermobifida fusca

<400> SEQUENCE: 145

gagtatcgcc agtaaggggc g                                            21

<210> SEQ ID NO 146
<211> LENGTH: 29
<212> TYPE: DNA
<213> ORGANISM: Thermobifida fusca

<400> SEQUENCE: 146

tctttatcct ctcctttttt tcagagctc                                    29

<210> SEQ ID NO 147
<211> LENGTH: 50
<212> TYPE: DNA
<213> ORGANISM: Thermobifida fusca

<400> SEQUENCE: 147

catcagcacc aacaccagca tccgtaatcg catgttcaat ccgctccata             50

<210> SEQ ID NO 148
<211> LENGTH: 23
<212> TYPE: DNA
<213> ORGANISM: Thermobifida fusca

<400> SEQUENCE: 148

gcagccctaa aatcgcataa agc                                          23

<210> SEQ ID NO 149
<211> LENGTH: 22
<212> TYPE: DNA
<213> ORGANISM: Trichoderma reesei

<400> SEQUENCE: 149

gtgaataacg cagctcttct cg                                           22

<210> SEQ ID NO 150
<211> LENGTH: 25
<212> TYPE: DNA
<213> ORGANISM: Trichoderma reesei

<400> SEQUENCE: 150

ccttaattaa ttatgcgtca ggtgt                                        25

<210> SEQ ID NO 151
<211> LENGTH: 33
<212> TYPE: DNA
<213> ORGANISM: Trichoderma reesei

<400> SEQUENCE: 151

cggactgcgc accatggtga ataacgcagc tct                               33
```

<210> SEQ ID NO 152
<211> LENGTH: 35
<212> TYPE: DNA
<213> ORGANISM: Trichoderma reesei

<400> SEQUENCE: 152
tcgccacgga gcttattatg cgtcaggtgt agcat 35

<210> SEQ ID NO 153
<211> LENGTH: 37
<212> TYPE: DNA
<213> ORGANISM: Trichoderma reesei

<400> SEQUENCE: 153
tcttggatcc accatggtcg gactgctttc aatcacc 37

<210> SEQ ID NO 154
<211> LENGTH: 34
<212> TYPE: DNA
<213> ORGANISM: Trichoderma reesei

<400> SEQUENCE: 154
ttaactcgag tcacagacac tgcgagtaat agtc 34

<210> SEQ ID NO 155
<211> LENGTH: 33
<212> TYPE: DNA
<213> ORGANISM: Trichoderma reesei

<400> SEQUENCE: 155
cggactgcgc accatggtcg gactgctttc aat 33

<210> SEQ ID NO 156
<211> LENGTH: 35
<212> TYPE: DNA
<213> ORGANISM: Trichoderma reesei

<400> SEQUENCE: 156
tcgccacgga gcttatcaca gacactgcga gtaat 35

<210> SEQ ID NO 157
<211> LENGTH: 1467
<212> TYPE: DNA
<213> ORGANISM: Penicillium emersonii

<400> SEQUENCE: 157
atgcttcgac gggctcttct tctatcctct tccgccatcc ttgctgtcaa ggcacagcag 60
gccggcacgg cgacggcaga gaaccacccg cccctgacat ggcaggaatg caccgcccct 120
gggagctgca ccacccagaa cggggcggtc gttcttgatg cgaactggcg ttgggtgcac 180
gatgtgaacg gatacaccaa ctgctacacg ggcaatacct ggaaccccac gtactgccct 240
gacgacgaaa cctgcgccca gaactgtgcg ctggacggcg cggattacga gggcacctac 300
ggcgtgactt cgtcgggcag ctccttgaag ctcaatttcg tcaccgggtc gaacgtcgga 360
tcccgtctct acctgctgca ggacgactcg acctatcaga tcttcaagct tctgaaccgc 420
gagtttacct ttgacgtcga tgtctccaat cttccgtgcg gattgaacgg cgctctgtac 480
tttgtcgcca tggacgccga cggcggcgtg tccaagtacc cgaacaacaa ggctggtgcc 540
aagtacggaa ccgggtattg cgactcccaa tgcccacggg acctcaagtt catcgacggc 600
gaggtatgtc cagtggtaaa atcgatcgtc tcgtgaactt ctgctgacag gttcgatcta 660

-continued

```
caggccaacg tcgagggctg gcagccgtct tcgaacaacg ccaacaccgg aattggcgac    720

catggctcct gctgtgcgga gatggatgtc tgggaagcca acagcatctc caatgcggtc    780

actccgcacc cgtgcgacac gccaggccag acgatgtgct ctggcgatga ctgcggtggc    840

acatactcta acgatcgcta cgcgggaacc tgcgatcctg acggctgtga cttcaaccct    900

taccgcatgg gcaacacttc tttctacggg cctggcaaga tcatcgatac caccaagcct    960

ttcactgtcg tgacgcagtt cctcactgat gatggtacgg atactggaac tctcagcgag   1020

atcaagcgct tctacgtcca gaacggcaac gtcattccgc agcccaactc ggacatcagt   1080

gtcgtgaccg gcaactcgat cacgacggag ttctgtactg ctcagaagca ggcctttggc   1140

gacacggacg acttctctca gcacggtggc ctggccaaga tgggagcggc catgcagcag   1200

ggtatggtcc tggtgatgag tttgtgggac gactacgccg cgcagatgct gtggctggat   1260

tccgactacc cgacggatgc ggaccccacg accccctggta ttgcccgtgg aacgtgtccg   1320

acggactcgg gcgtcccatc ggatgtcgag tcgcagagcc ccaactccta cgtgacctac   1380

tcgaacatca agtttggtcc gatcaactcg accttcaccg cttcgtgagt cttggttaca   1440

tgtgaagtag acggaagttg ctctgcg                                          1467
```

<210> SEQ ID NO 158
<211> LENGTH: 455
<212> TYPE: PRT
<213> ORGANISM: Penicillium emersonii

<400> SEQUENCE: 158

```
Met Leu Arg Arg Ala Leu Leu Leu Ser Ser Ser Ala Ile Leu Ala Val
1               5                   10                  15

Lys Ala Gln Gln Ala Gly Thr Ala Thr Ala Glu Asn His Pro Pro Leu
            20                  25                  30

Thr Trp Gln Glu Cys Thr Ala Pro Gly Ser Cys Thr Thr Gln Asn Gly
        35                  40                  45

Ala Val Val Leu Asp Ala Asn Trp Arg Trp Val His Asp Val Asn Gly
    50                  55                  60

Tyr Thr Asn Cys Tyr Thr Gly Asn Thr Trp Asn Pro Thr Tyr Cys Pro
65                  70                  75                  80

Asp Asp Glu Thr Cys Ala Gln Asn Cys Ala Leu Asp Gly Ala Asp Tyr
                85                  90                  95

Glu Gly Thr Tyr Gly Val Thr Ser Ser Gly Ser Ser Leu Lys Leu Asn
            100                 105                 110

Phe Val Thr Gly Ser Asn Val Gly Ser Arg Leu Tyr Leu Leu Gln Asp
        115                 120                 125

Asp Ser Thr Tyr Gln Ile Phe Lys Leu Leu Asn Arg Glu Phe Thr Phe
    130                 135                 140

Asp Val Asp Val Ser Asn Leu Pro Cys Gly Leu Asn Gly Ala Leu Tyr
145                 150                 155                 160

Phe Val Ala Met Asp Ala Asp Gly Gly Val Ser Lys Tyr Pro Asn Asn
                165                 170                 175

Lys Ala Gly Ala Lys Tyr Gly Thr Gly Tyr Cys Asp Ser Gln Cys Pro
            180                 185                 190

Arg Asp Leu Lys Phe Ile Asp Gly Glu Ala Asn Val Glu Gly Trp Gln
        195                 200                 205

Pro Ser Ser Asn Asn Ala Asn Thr Gly Ile Gly Asp His Gly Ser Cys
    210                 215                 220

Cys Ala Glu Met Asp Val Trp Glu Ala Asn Ser Ile Ser Asn Ala Val
```

```
225                 230                 235                 240

Thr Pro His Pro Cys Asp Thr Pro Gly Gln Thr Met Cys Ser Gly Asp
                245                 250                 255

Asp Cys Gly Gly Thr Tyr Ser Asn Asp Arg Tyr Ala Gly Thr Cys Asp
            260                 265                 270

Pro Asp Gly Cys Asp Phe Asn Pro Tyr Arg Met Gly Asn Thr Ser Phe
        275                 280                 285

Tyr Gly Pro Gly Lys Ile Ile Asp Thr Thr Lys Pro Phe Thr Val Val
    290                 295                 300

Thr Gln Phe Leu Thr Asp Asp Gly Thr Asp Thr Gly Thr Leu Ser Glu
305                 310                 315                 320

Ile Lys Arg Phe Tyr Val Gln Asn Gly Asn Val Ile Pro Gln Pro Asn
                325                 330                 335

Ser Asp Ile Ser Val Val Thr Gly Asn Ser Ile Thr Thr Glu Phe Cys
            340                 345                 350

Thr Ala Gln Lys Gln Ala Phe Gly Asp Thr Asp Asp Phe Ser Gln His
        355                 360                 365

Gly Gly Leu Ala Lys Met Gly Ala Ala Met Gln Gln Gly Met Val Leu
    370                 375                 380

Val Met Ser Leu Trp Asp Asp Tyr Ala Ala Gln Met Leu Trp Leu Asp
385                 390                 395                 400

Ser Asp Tyr Pro Thr Asp Ala Asp Pro Thr Thr Pro Gly Ile Ala Arg
                405                 410                 415

Gly Thr Cys Pro Thr Asp Ser Gly Val Pro Ser Asp Val Glu Ser Gln
            420                 425                 430

Ser Pro Asn Ser Tyr Val Thr Tyr Ser Asn Ile Lys Phe Gly Pro Ile
        435                 440                 445

Asn Ser Thr Phe Thr Ala Ser
    450                 455


<210> SEQ ID NO 159
<211> LENGTH: 1590
<212> TYPE: DNA
<213> ORGANISM: Penicillium pinophilum

<400> SEQUENCE: 159

atgtctgcct tgaactcttt caatatgtac aagagcgccc tcatcttggg ctccttgctg      60

gcaacagctg gtgctcagca aattggtaca tataccgctg aaacccatcc ctctttgagc     120

tggtctactt gcaaatcggg tggtagctgc accacaaact ccggtgccat tacgttagat     180

gccaactggc gttgggtcca tggtgtcaat accagcacca actgctacac tggcaacact     240

tggaatagcg ccatctgcga cactgatgca tcctgtgccc aggactgtgc tctcgatggt     300

gctgactact ctggcacgta cggtatcact acctccggca actcactgcg cctgaacttc     360

gttaccggtt ccaacgtcgg atctcgtaca tacctgatgg ccgataacac ccactaccaa     420

atcttcgact tgttgaacca ggagttcacc ttcaccgtcg atgtctccca cctcccttgc     480

ggtttgaacg gtgccctcta cttcgtgacc atggatgccg acggtggcgt ctccaagtac     540

cccaacaaca aggccggtgc tcagtacggt gttggatact gtgactctca atgccctcgt     600

gacttgaagt tcatcgctgg tcaggccaac gttgagggct ggacgccctc cgccaacaac     660

gccaacactg gaattggcaa tcacggagct tgctgcgcgg agcttgatat ctgggaggca     720

aacagcatct cagaggcctt gactcctcac ccttgcgaca cacctggtct atctgtttgc     780

actactgatg cctgcggtgg tacctacagc tctgatcgtt acgccggtac ctgcgaccct     840
```

```
gatggatgtg acttcaaccc ttaccgtctt ggtgtcactg acttctacgg ctccggcaag    900

accgttgaca ccaccaagcc ctttaccgtt gtgactcaat tcgtcactaa cgacggtacc    960

tccaccggtt ccctctccga gatcagacgt tactacgttc agaacggcgt tgtcatcccc   1020

cagccttcct ccaagatctc cggaatcagc ggaaatgtca tcaactccga ctactgcgct   1080

gctgaaatct ccacctttgg cgggactgcc tccttcagca aacacggtgg cttgacaaac   1140

atggccgctg gtatggaagc tggtatggtc ttggtcatga gtttgtggga cgactactcc   1200

gtcaacatgc tctggctcga cagcacctac cctacaaacg cgactggtac ccccggtgcc   1260

gctcgtggta cctgcgctac cacttctggg gaccccaaga ccgttgaatc acaatccggc   1320

agctcctatg tcaccttctc tgacattcgg gttggtcctt tcaattctac gttcagcggt   1380

ggttctagca ccggtggcag cactactact accgctagcc gcaccaccac cacctcggcc   1440

tcttccacct ctacttccag cacctctact ggcactggag tcgctggtca ctggggtcag   1500

tgtggtggcc agggctggac tggtcctacc acctgtgtta gtggaaccac atgcaccgtc   1560

gtgaaccctt actactctca atgtttgtaa                                    1590
```

<210> SEQ ID NO 160
<211> LENGTH: 529
<212> TYPE: PRT
<213> ORGANISM: Penicillium pinophilum

<400> SEQUENCE: 160

```
Met Ser Ala Leu Asn Ser Phe Asn Met Tyr Lys Ser Ala Leu Ile Leu
1               5                   10                  15

Gly Ser Leu Leu Ala Thr Ala Gly Ala Gln Gln Ile Gly Thr Tyr Thr
            20                  25                  30

Ala Glu Thr His Pro Ser Leu Ser Trp Ser Thr Cys Lys Ser Gly Gly
        35                  40                  45

Ser Cys Thr Thr Asn Ser Gly Ala Ile Thr Leu Asp Ala Asn Trp Arg
    50                  55                  60

Trp Val His Gly Val Asn Thr Ser Thr Asn Cys Tyr Thr Gly Asn Thr
65                  70                  75                  80

Trp Asn Ser Ala Ile Cys Asp Thr Asp Ala Ser Cys Ala Gln Asp Cys
                85                  90                  95

Ala Leu Asp Gly Ala Asp Tyr Ser Gly Thr Tyr Gly Ile Thr Thr Ser
            100                 105                 110

Gly Asn Ser Leu Arg Leu Asn Phe Val Thr Gly Ser Asn Val Gly Ser
        115                 120                 125

Arg Thr Tyr Leu Met Ala Asp Asn Thr His Tyr Gln Ile Phe Asp Leu
    130                 135                 140

Leu Asn Gln Glu Phe Thr Phe Thr Val Asp Val Ser His Leu Pro Cys
145                 150                 155                 160

Gly Leu Asn Gly Ala Leu Tyr Phe Val Thr Met Asp Ala Asp Gly Gly
                165                 170                 175

Val Ser Lys Tyr Pro Asn Asn Lys Ala Gly Ala Gln Tyr Gly Val Gly
            180                 185                 190

Tyr Cys Asp Ser Gln Cys Pro Arg Asp Leu Lys Phe Ile Ala Gly Gln
        195                 200                 205

Ala Asn Val Glu Gly Trp Thr Pro Ser Ala Asn Asn Ala Asn Thr Gly
    210                 215                 220

Ile Gly Asn His Gly Ala Cys Cys Ala Glu Leu Asp Ile Trp Glu Ala
225                 230                 235                 240
```

```
Asn Ser Ile Ser Glu Ala Leu Thr Pro His Pro Cys Asp Thr Pro Gly
                245                 250                 255

Leu Ser Val Cys Thr Thr Asp Ala Cys Gly Gly Thr Tyr Ser Ser Asp
            260                 265                 270

Arg Tyr Ala Gly Thr Cys Asp Pro Asp Gly Cys Asp Phe Asn Pro Tyr
        275                 280                 285

Arg Leu Gly Val Thr Asp Phe Tyr Gly Ser Gly Lys Thr Val Asp Thr
    290                 295                 300

Thr Lys Pro Phe Thr Val Val Thr Gln Phe Val Thr Asn Asp Gly Thr
305                 310                 315                 320

Ser Thr Gly Ser Leu Ser Glu Ile Arg Arg Tyr Tyr Val Gln Asn Gly
                325                 330                 335

Val Val Ile Pro Gln Pro Ser Ser Lys Ile Ser Gly Ile Ser Gly Asn
            340                 345                 350

Val Ile Asn Ser Asp Tyr Cys Ala Ala Glu Ile Ser Thr Phe Gly Gly
        355                 360                 365

Thr Ala Ser Phe Ser Lys His Gly Gly Leu Thr Asn Met Ala Ala Gly
    370                 375                 380

Met Glu Ala Gly Met Val Leu Val Met Ser Leu Trp Asp Asp Tyr Ser
385                 390                 395                 400

Val Asn Met Leu Trp Leu Asp Ser Thr Tyr Pro Thr Asn Ala Thr Gly
                405                 410                 415

Thr Pro Gly Ala Ala Arg Gly Thr Cys Ala Thr Thr Ser Gly Asp Pro
            420                 425                 430

Lys Thr Val Glu Ser Gln Ser Gly Ser Ser Tyr Val Thr Phe Ser Asp
        435                 440                 445

Ile Arg Val Gly Pro Phe Asn Ser Thr Phe Ser Gly Gly Ser Ser Thr
    450                 455                 460

Gly Gly Ser Thr Thr Thr Thr Ala Ser Arg Thr Thr Thr Thr Ser Ala
465                 470                 475                 480

Ser Ser Thr Ser Thr Ser Ser Thr Ser Thr Gly Thr Gly Val Ala Gly
                485                 490                 495

His Trp Gly Gln Cys Gly Gly Gln Gly Trp Thr Gly Pro Thr Thr Cys
            500                 505                 510

Val Ser Gly Thr Thr Cys Thr Val Val Asn Pro Tyr Tyr Ser Gln Cys
        515                 520                 525

Leu
```

<210> SEQ ID NO 161
<211> LENGTH: 1678
<212> TYPE: DNA
<213> ORGANISM: Aspergillus terreus

<400> SEQUENCE: 161

```
atgccttcca cctacgatat ctacaagaag ctcctcctgc tggccagctt cctgagtgcc      60

tctcaggccc agcaggtcgg cacctccaag gccgaagtcc atccttcctt gacttggcaa     120

acttgcacca gcggcggtag ctgcaccacc gtcaacggca aggtcgtcgt tgacgccaac     180

tggcgctggg tccacaacgt cgacggctac aacaactgct atactggcaa tacctgggat     240

accactctct gccctgatga tgagacctgt gcctccaact gcgccctgga aggtgcggac     300

tactctggca cgtatggtgt caccaccagc ggcaactccc tgcggttgaa ctttgtcacc     360

caggcttcgc aaaagaacat cggatcccgt ctgtacctca tggaggacga cagcacctac     420
```

```
aagatgttca agctgctgaa ccaggagttc acctttgacg tggatgtctc gaacctcccc    480

tgcggtctga acggcgccgt ttactttgtc tccatggacg ccgatggtgg catggccaag    540

tacccggcca acaaggcggg cgcaaaggtg agcattgtgc ctttccgtcg accataccgt    600

gtatgctgac agattttagt acggcaccgg ctactgtgac tcgcagtgcc cgcgcgactt    660

gaagttcatc aacggcatgg ccaacgtcga gggctgggag ccctctgcca atgacgccaa    720

cgccggcacc ggcaaccacg gctcctgctg cgctgagatg gacatctggg aggccaacag    780

catctccacc gcgtacaccc cgcatccctg cgacaccccc ggtcaagtca tgtgcacggg    840

cgactcctgc ggcggcactt acagcagcga ccggtatggc ggcacgtgcg atccggatgg    900

atgcgacttc aactcgtacc gccagggcaa caagaccttc tatggccccg gcatgacggt    960

cgacaccaaa agcaagatca cggtggtgac gcagttcctc accaacgacg gcaccgcgtc   1020

cggcacgctc tccgagatca agcgcttcta cgtgcagaac ggcaaggtca tccccaactc   1080

ggagtcgacg tggtccggcg tgtcgggcaa ctcgatcacc accgcctact gcaacgcgca   1140

gaagacgctc ttcggcgaca cggatgtctt caccaagcac ggtggcatgg agggtatggg   1200

cgcggcgctg gccgagggca tggtgctcgt gctgagtctg tgggacgacc acaactccaa   1260

catgctctgg ctggacagca actaccccac cgacaagccc tcgacgaccc ccggcgtggc   1320

ccgcggctcg tgcgacatct cctcgggcga cccgaaggac gtggaggcca acgacgccaa   1380

cgcgtatgtg gtgtactcga acatcaaggt gggtcccatt ggctcgacct ttagcgggtc   1440

gactggcggc ggctccagct cgtccaccac cgccacctcc aagaccacca cgaccagcgc   1500

gaccaagacg acgaccacca ccaccaagac caccaccacc acgtctgcgt cgtccaccag   1560

caccggcgga gcgcagcact gggcccagtg cggcggtatt ggctggaccg gcccaaccac   1620

ctgtgtcgcg ccgtacacct gccagaagca gaacgactac tactcgcagt gcctgtag     1678
```

```
<210> SEQ ID NO 162
<211> LENGTH: 541
<212> TYPE: PRT
<213> ORGANISM: Aspergillus terreus

<400> SEQUENCE: 162

Met Pro Ser Thr Tyr Asp Ile Tyr Lys Lys Leu Leu Leu Leu Ala Ser
1               5                   10                  15

Phe Leu Ser Ala Ser Gln Ala Gln Gln Val Gly Thr Ser Lys Ala Glu
            20                  25                  30

Val His Pro Ser Leu Thr Trp Gln Thr Cys Thr Ser Gly Gly Ser Cys
        35                  40                  45

Thr Thr Val Asn Gly Lys Val Val Val Asp Ala Asn Trp Arg Trp Val
    50                  55                  60

His Asn Val Asp Gly Tyr Asn Asn Cys Tyr Thr Gly Asn Thr Trp Asp
65                  70                  75                  80

Thr Thr Leu Cys Pro Asp Asp Glu Thr Cys Ala Ser Asn Cys Ala Leu
                85                  90                  95

Glu Gly Ala Asp Tyr Ser Gly Thr Tyr Gly Val Thr Thr Ser Gly Asn
            100                 105                 110

Ser Leu Arg Leu Asn Phe Val Thr Gln Ala Ser Gln Lys Asn Ile Gly
        115                 120                 125

Ser Arg Leu Tyr Leu Met Glu Asp Asp Ser Thr Tyr Lys Met Phe Lys
    130                 135                 140

Leu Leu Asn Gln Glu Phe Thr Phe Asp Val Asp Val Ser Asn Leu Pro
145                 150                 155                 160
```

```
Cys Gly Leu Asn Gly Ala Val Tyr Phe Val Ser Met Asp Ala Asp Gly
                165                 170                 175

Gly Met Ala Lys Tyr Pro Ala Asn Lys Ala Gly Ala Lys Tyr Gly Thr
            180                 185                 190

Gly Tyr Cys Asp Ser Gln Cys Pro Arg Asp Leu Lys Phe Ile Asn Gly
        195                 200                 205

Met Ala Asn Val Glu Gly Trp Glu Pro Ser Ala Asn Asp Ala Asn Ala
    210                 215                 220

Gly Thr Gly Asn His Gly Ser Cys Cys Ala Glu Met Asp Ile Trp Glu
225                 230                 235                 240

Ala Asn Ser Ile Ser Thr Ala Tyr Thr Pro His Pro Cys Asp Thr Pro
                245                 250                 255

Gly Gln Val Met Cys Thr Gly Asp Ser Cys Gly Gly Thr Tyr Ser Ser
            260                 265                 270

Asp Arg Tyr Gly Gly Thr Cys Asp Pro Asp Gly Cys Asp Phe Asn Ser
        275                 280                 285

Tyr Arg Gln Gly Asn Lys Thr Phe Tyr Gly Pro Gly Met Thr Val Asp
    290                 295                 300

Thr Lys Ser Lys Ile Thr Val Val Thr Gln Phe Leu Thr Asn Asp Gly
305                 310                 315                 320

Thr Ala Ser Gly Thr Leu Ser Glu Ile Lys Arg Phe Tyr Val Gln Asn
                325                 330                 335

Gly Lys Val Ile Pro Asn Ser Glu Ser Thr Trp Ser Gly Val Ser Gly
            340                 345                 350

Asn Ser Ile Thr Thr Ala Tyr Cys Asn Ala Gln Lys Thr Leu Phe Gly
        355                 360                 365

Asp Thr Asp Val Phe Thr Lys His Gly Gly Met Glu Gly Met Gly Ala
    370                 375                 380

Ala Leu Ala Glu Gly Met Val Leu Val Leu Ser Leu Trp Asp Asp His
385                 390                 395                 400

Asn Ser Asn Met Leu Trp Leu Asp Ser Asn Tyr Pro Thr Asp Lys Pro
                405                 410                 415

Ser Thr Thr Pro Gly Val Ala Arg Gly Ser Cys Asp Ile Ser Ser Gly
            420                 425                 430

Asp Pro Lys Asp Val Glu Ala Asn Asp Ala Asn Ala Tyr Val Val Tyr
        435                 440                 445

Ser Asn Ile Lys Val Gly Pro Ile Gly Ser Thr Phe Ser Gly Ser Thr
    450                 455                 460

Gly Gly Gly Ser Ser Ser Ser Thr Thr Ala Thr Ser Lys Thr Thr Thr
465                 470                 475                 480

Thr Ser Ala Thr Lys Thr Thr Thr Thr Thr Thr Lys Thr Thr Thr Thr
                485                 490                 495

Thr Ser Ala Ser Ser Thr Ser Thr Gly Gly Ala Gln His Trp Ala Gln
            500                 505                 510

Cys Gly Gly Ile Gly Trp Thr Gly Pro Thr Thr Cys Val Ala Pro Tyr
        515                 520                 525

Thr Cys Gln Lys Gln Asn Asp Tyr Tyr Ser Gln Cys Leu
    530                 535                 540
```

<210> SEQ ID NO 163
<211> LENGTH: 1608
<212> TYPE: DNA
<213> ORGANISM: Neosartorya fischeri

<400> SEQUENCE: 163

```
atggcatccg caatttcttt ccaagtctac aggagtgcat tgattctgtc tgccttcctg     60
ccgtctatta cgcaggcgca gcagatcggc acatacacca ctgagaccca tccatcgatg    120
acatgggaga cctgcactag cggtggaagt tgtgccacca accagggctc tgtcgttatg    180
gatgcgaact ggcgatgggt ccaccaggtt ggcagcacca ccaactgcta tactggcaat    240
acttgggata cctccatctg cgataccgac gagacctgtg ccactgaatg tgcggttgac    300
ggagcagact acgaatcaac ctacggagtc accaccagcg gcagccagat ccgcctcaac    360
tttgtgacgc agaactcaaa tggtgccaat gtcggctccc gtctttacat gatggcggat    420
aatacacact accagatgtt caagctactg aaccaggagt tcacctttga cgtggtcgtg    480
tccaacctcc cctgtggctt gaacggggcc ctctactttg tgaccatgga tgaagatggc    540
ggtgtctcca aataccccaa taataaggct ggagcccaat acggcgtggg atattgcgat    600
tctcaatgtc cgcgcgatct taaatttatc caaggccagg caaatgtgga aggctggact    660
ccgtcgtcca acaacgaaaa cacgggactg ggcaattatg gatcttgctg cgccgagctg    720
gacatctggg aatccaacag catctctcag gctctgacac ctcatccatg tgatactgcc    780
accaacacta tgtgcactgg tgatgcctgc ggcggcacat atagcagtga tcggtatgct    840
ggcacttgcg acccggatgg ctgcgacttc aacccctacc gcatgggcaa taccacattc    900
tacggccccg ggaagacaat cgataccaac tcgcccttca ccgtggtgac gcagttcatt    960
acagatgacg gcaccgatac cggcaccttg tctgaaatcc gccgctacta tgtccagaac   1020
ggcgttacct acgcccagcc tgactcagac atcagtggta ttaccggcaa cgccataaac   1080
gctgactact gcactgccga gaatactgtc tttgacgggc cgggtacatt tgccaagcac   1140
ggtgggtttt ccgccatgtc cgaggccatg tctaccggta tggtactggt catgtcgctc   1200
tgggacgatt actacgcgga tatgctctgg cttgacagca cctatcccac taatgcgtct   1260
tcgtcgaccc caggtgctgt ccgtggttcc tgctcgaccg actccggtgt ccccgccacc   1320
attgaatccg agagtcctga ttcgtatgtg acctattcga acatcaaagt tggtccgatc   1380
ggatcaacct tcagcagcgg ttctggctct ggaagctctg gctctggaag ttccggctcg   1440
gcttcgacct cgaccacctc caccaagacc acagctgcaa cgagcacctc gactgccgtg   1500
gcgcagcact atagccagtg tggtggccag gactggactg gcccgactac ttgtgtctct   1560
ccttatacct gccaagtgca gaacgcgtac tattctcagt gtctgtag                1608
```

<210> SEQ ID NO 164
<211> LENGTH: 535
<212> TYPE: PRT
<213> ORGANISM: Neosartorya fischeri

<400> SEQUENCE: 164

```
Met Ala Ser Ala Ile Ser Phe Gln Val Tyr Arg Ser Ala Leu Ile Leu
1               5                   10                  15

Ser Ala Phe Leu Pro Ser Ile Thr Gln Ala Gln Gln Ile Gly Thr Tyr
            20                  25                  30

Thr Thr Glu Thr His Pro Ser Met Thr Trp Glu Thr Cys Thr Ser Gly
        35                  40                  45

Gly Ser Cys Ala Thr Asn Gln Gly Ser Val Val Met Asp Ala Asn Trp
    50                  55                  60

Arg Trp Val His Gln Val Gly Ser Thr Thr Asn Cys Tyr Thr Gly Asn
65                  70                  75                  80
```

-continued

```
Thr Trp Asp Thr Ser Ile Cys Asp Thr Asp Glu Thr Cys Ala Thr Glu
                85                  90                  95

Cys Ala Val Asp Gly Ala Asp Tyr Glu Ser Thr Tyr Gly Val Thr Thr
            100                 105                 110

Ser Gly Ser Gln Ile Arg Leu Asn Phe Val Thr Gln Asn Ser Asn Gly
        115                 120                 125

Ala Asn Val Gly Ser Arg Leu Tyr Met Met Ala Asp Asn Thr His Tyr
    130                 135                 140

Gln Met Phe Lys Leu Leu Asn Gln Glu Phe Thr Phe Asp Val Asp Val
145                 150                 155                 160

Ser Asn Leu Pro Cys Gly Leu Asn Gly Ala Leu Tyr Phe Val Thr Met
                165                 170                 175

Asp Glu Asp Gly Gly Val Ser Lys Tyr Pro Asn Asn Lys Ala Gly Ala
            180                 185                 190

Gln Tyr Gly Val Gly Tyr Cys Asp Ser Gln Cys Pro Arg Asp Leu Lys
        195                 200                 205

Phe Ile Gln Gly Gln Ala Asn Val Glu Gly Trp Thr Pro Ser Ser Asn
    210                 215                 220

Asn Glu Asn Thr Gly Leu Gly Asn Tyr Gly Ser Cys Cys Ala Glu Leu
225                 230                 235                 240

Asp Ile Trp Glu Ser Asn Ser Ile Ser Gln Ala Leu Thr Pro His Pro
                245                 250                 255

Cys Asp Thr Ala Thr Asn Thr Met Cys Thr Gly Asp Ala Cys Gly Gly
            260                 265                 270

Thr Tyr Ser Ser Asp Arg Tyr Ala Gly Thr Cys Asp Pro Asp Gly Cys
        275                 280                 285

Asp Phe Asn Pro Tyr Arg Met Gly Asn Thr Thr Phe Tyr Gly Pro Gly
    290                 295                 300

Lys Thr Ile Asp Thr Asn Ser Pro Phe Thr Val Val Thr Gln Phe Ile
305                 310                 315                 320

Thr Asp Asp Gly Thr Asp Thr Gly Thr Leu Ser Glu Ile Arg Arg Tyr
                325                 330                 335

Tyr Val Gln Asn Gly Val Thr Tyr Ala Gln Pro Asp Ser Asp Ile Ser
            340                 345                 350

Gly Ile Thr Gly Asn Ala Ile Asn Ala Asp Tyr Cys Thr Ala Glu Asn
        355                 360                 365

Thr Val Phe Asp Gly Pro Gly Thr Phe Ala Lys His Gly Gly Phe Ser
    370                 375                 380

Ala Met Ser Glu Ala Met Ser Thr Gly Met Val Leu Val Met Ser Leu
385                 390                 395                 400

Trp Asp Asp Tyr Tyr Ala Asp Met Leu Trp Leu Asp Ser Thr Tyr Pro
                405                 410                 415

Thr Asn Ala Ser Ser Ser Thr Pro Gly Ala Val Arg Gly Ser Cys Ser
            420                 425                 430

Thr Asp Ser Gly Val Pro Ala Thr Ile Glu Ser Glu Ser Pro Asp Ser
        435                 440                 445

Tyr Val Thr Tyr Ser Asn Ile Lys Val Gly Pro Ile Gly Ser Thr Phe
    450                 455                 460

Ser Ser Gly Ser Gly Ser Gly Ser Ser Gly Ser Gly Ser Ser Gly Ser
465                 470                 475                 480

Ala Ser Thr Ser Thr Thr Ser Thr Lys Thr Thr Ala Ala Thr Ser Thr
                485                 490                 495

Ser Thr Ala Val Ala Gln His Tyr Ser Gln Cys Gly Gly Gln Asp Trp
```

```
            500                 505                 510

Thr Gly Pro Thr Thr Cys Val Ser Pro Tyr Thr Cys Gln Val Gln Asn
        515                 520                 525

Ala Tyr Tyr Ser Gln Cys Leu
    530                 535


<210> SEQ ID NO 165
<211> LENGTH: 1581
<212> TYPE: DNA
<213> ORGANISM: Aspergillus nidulans

<400> SEQUENCE: 165

atggcatctt cattccagtg gtacaaagct ctcctctttt tctcttctct gctttctgca      60

gtgcaagccc agaaggtcgg cactcagcaa gctgaagtgc accccggcct gacctggcag     120

acctgcacga gctccggcag ctgcaccacc gtcaacggcg aggtcactat tgacgcaaac     180

tggcgctggc tgcacaccgt caatgggtac accaactgct atactggcaa cgaatgggat     240

acctccatct gcaccagcaa cgaggtttgc gcggaacaat gcgctgtcga cggtgctaac     300

tatgcctcca catacggcat caccacatcc ggcagctcgc tgcgtctgaa cttcgtcacg     360

cagtcgcagc agaagaatat cggttccaga gtctatctca tggatgacga ggatacatac     420

accatgttct acctgctcaa caaggaattc acttttgacg tcgacgtctc cgagctcccc     480

tgcggtctca acggggcggt ctactttgtg tctatggacg ccgacggcgg caaatcccgc     540

tatgccacca acgaagccgg tgccaaatac ggcacgggat actgcgactc tcagtgcccg     600

cgggacctca agttcatcaa cggcgtcgcc aacgtcgagg gctgggaatc ctccgatacg     660

aaccccaacg gcggcgtcgg caatcacggc tcctgctgcg cagagatgga tatctgggag     720

gcaaacagca tttccactgc tttcactccc catccctgcg ataccccggg ccagaccctc     780

tgcaccggtg actcatgcgg tgggacctat agcaacgacc gctacggcgg cacctgcgac     840

cccgatggct gcgactttaa ctcctaccgt caggggaaca agaccttcta cgggccaggc     900

ctgacagtcg acacgaacag cccggtcaca gtggtgaccc agttcctgac agacgacaac     960

acggacacag gcaccctctc ggaaatcaaa cgcttctatg tccagaacgg cgtcgtcatc    1020

cccaactccg agtcgaccta ccccgctaat ccgggtaact cgatcacaac ggagttctgc    1080

gagtcgcaaa aggaactctt cggcgacgtc gatgttttct ccgcccacgg cggcatggcg    1140

ggcatgggcg ccgcgttgga acaaggcatg gtccttgtac tgtccctgtg ggacgacaac    1200

tactcaaaca tgctctggct cgactcgaat taccccacgg acgcggaccc gactcaacca    1260

ggtatcgcgc gcgggacgtg cccgacggac tcgggcgttc cgtctggagt cgaggcccaa    1320

tatccgaatg cgtatgtcgt gtactcgaac atcaagtttg gtcctattgg aagtaccttt    1380

ggcaacggtg gaggctcagg gccaacaaca acggtgacga cgagtaccgc tactagtaca    1440

actagctcgg cgacgtcgac ggctaccggt caggcgcagc actgggagca gtgtggtggg    1500

aatggctgga ctggtccgac ggtctgcgct agcccctggg cttgcacagt ggtgaactca    1560

tggtactcgc agtgtctgta a                                              1581


<210> SEQ ID NO 166
<211> LENGTH: 526
<212> TYPE: PRT
<213> ORGANISM: Aspergillus nidulans

<400> SEQUENCE: 166

Met Ala Ser Ser Phe Gln Trp Tyr Lys Ala Leu Leu Phe Phe Ser Ser
```

-continued

```
1               5                   10                  15

Leu Leu Ser Ala Val Gln Ala Gln Lys Val Gly Thr Gln Gln Ala Glu
            20                  25                  30

Val His Pro Gly Leu Thr Trp Gln Thr Cys Thr Ser Ser Gly Ser Cys
        35                  40                  45

Thr Thr Val Asn Gly Glu Val Thr Ile Asp Ala Asn Trp Arg Trp Leu
    50                  55                  60

His Thr Val Asn Gly Tyr Thr Asn Cys Tyr Thr Gly Asn Glu Trp Asp
65                  70                  75                  80

Thr Ser Ile Cys Thr Ser Asn Glu Val Cys Ala Glu Gln Cys Ala Val
                85                  90                  95

Asp Gly Ala Asn Tyr Ala Ser Thr Tyr Gly Ile Thr Thr Ser Gly Ser
            100                 105                 110

Ser Leu Arg Leu Asn Phe Val Thr Gln Ser Gln Gln Lys Asn Ile Gly
        115                 120                 125

Ser Arg Val Tyr Leu Met Asp Asp Glu Asp Thr Tyr Thr Met Phe Tyr
    130                 135                 140

Leu Leu Asn Lys Glu Phe Thr Phe Asp Val Asp Val Ser Glu Leu Pro
145                 150                 155                 160

Cys Gly Leu Asn Gly Ala Val Tyr Phe Val Ser Met Asp Ala Asp Gly
                165                 170                 175

Gly Lys Ser Arg Tyr Ala Thr Asn Glu Ala Gly Ala Lys Tyr Gly Thr
            180                 185                 190

Gly Tyr Cys Asp Ser Gln Cys Pro Arg Asp Leu Lys Phe Ile Asn Gly
        195                 200                 205

Val Ala Asn Val Glu Gly Trp Glu Ser Ser Asp Thr Asn Pro Asn Gly
    210                 215                 220

Gly Val Gly Asn His Gly Ser Cys Cys Ala Glu Met Asp Ile Trp Glu
225                 230                 235                 240

Ala Asn Ser Ile Ser Thr Ala Phe Thr Pro His Pro Cys Asp Thr Pro
                245                 250                 255

Gly Gln Thr Leu Cys Thr Gly Asp Ser Cys Gly Gly Thr Tyr Ser Asn
            260                 265                 270

Asp Arg Tyr Gly Gly Thr Cys Asp Pro Asp Gly Cys Asp Phe Asn Ser
        275                 280                 285

Tyr Arg Gln Gly Asn Lys Thr Phe Tyr Gly Pro Gly Leu Thr Val Asp
    290                 295                 300

Thr Asn Ser Pro Val Thr Val Val Thr Gln Phe Leu Thr Asp Asp Asn
305                 310                 315                 320

Thr Asp Thr Gly Thr Leu Ser Glu Ile Lys Arg Phe Tyr Val Gln Asn
                325                 330                 335

Gly Val Val Ile Pro Asn Ser Glu Ser Thr Tyr Pro Ala Asn Pro Gly
            340                 345                 350

Asn Ser Ile Thr Thr Glu Phe Cys Glu Ser Gln Lys Glu Leu Phe Gly
        355                 360                 365

Asp Val Asp Val Phe Ser Ala His Gly Gly Met Ala Gly Met Gly Ala
    370                 375                 380

Ala Leu Glu Gln Gly Met Val Leu Val Leu Ser Leu Trp Asp Asp Asn
385                 390                 395                 400

Tyr Ser Asn Met Leu Trp Leu Asp Ser Asn Tyr Pro Thr Asp Ala Asp
                405                 410                 415

Pro Thr Gln Pro Gly Ile Ala Arg Gly Thr Cys Pro Thr Asp Ser Gly
            420                 425                 430
```

```
Val Pro Ser Gly Val Glu Ala Gln Tyr Pro Asn Ala Tyr Val Val Tyr
        435                 440                 445

Ser Asn Ile Lys Phe Gly Pro Ile Gly Ser Thr Phe Gly Asn Gly Gly
    450                 455                 460

Gly Ser Gly Pro Thr Thr Thr Val Thr Thr Ser Thr Ala Thr Ser Thr
465                 470                 475                 480

Thr Ser Ser Ala Thr Ser Thr Ala Thr Gly Gln Ala Gln His Trp Glu
                485                 490                 495

Gln Cys Gly Gly Asn Gly Trp Thr Gly Pro Thr Val Cys Ala Ser Pro
            500                 505                 510

Trp Ala Cys Thr Val Val Asn Ser Trp Tyr Ser Gln Cys Leu
        515                 520                 525
```

<210> SEQ ID NO 167
<211> LENGTH: 1752
<212> TYPE: DNA
<213> ORGANISM: Fennellia nivea

<400> SEQUENCE: 167

```
atgggacggg tttcttctct tgcgcttgcc cttctgcttc ctgctgtgca ggcccagcag     60

accctctggg gtcaatgtac gattccttct tgttgcggat atacgccttt actgactggg    120

gacaggcggt ggcattggat ggacaggagc aaccaactgt gtcgctggtg ctgcttgtag    180

cacgcagaat ccttgtatgg ttcatgccgc tcttcagctc agacatctac tgaccgttta    240

gactatgcgc agtgcctccc tgcgacggcg accacctcca ccaccctgac caccacgacc    300

aggtctacca ctaccacgac ggcaacgtcc accacgtctc agggctcatc ttcaagctcc    360

tctacgacta cgacaaagtc gacgagcacc accaccggct cttctaccac catcacctct    420

gcgccgtccg gcaacccgtt cagtggatat caactctatg ccaaccctta ctattcttcc    480

gaggtccaca ccctcgccat gccctccctt gctagctccc ttctgccggc tgccagtgct    540

gccgccaagg ttccctcgtt cacctggctg tatgtattct tcgtgatttg tatcatttcc    600

atctgaccac cgcagggaca ccgctgccaa agtgccgacc atgggcacct acctggcgga    660

catcaaggcc aagaacgccg ctggtgccaa cccgcccatt gctgcccagt tcgtcgtcta    720

cgatcttccc gatcgtgact gtgctgccct ggctagcaat ggcgagtact cgattgcgaa    780

caacggtgtt gccaactaca aggcgtacat tgactccatc cgggcccagt tggtgaaata    840

cccggacgtc cacaccatcc ttgttatcgg tacgctcgtg cccatggttg ttctcaatct    900

atttacaata ctaactctca acagagcccg atagcttggc caacctggtc accaacctga    960

acgtggccaa atgcgccaac gcccagagcg cgtatctgga gtgcgtcaac tacgccctga   1020

tcaacctgaa cctgcccaac gttgccatgt acatcgacgc tggtacgcat accacgcact   1080

cccccgttat accctcgctc acatttcttt aggacacgcc ggctggctcg gatggcccgc   1140

caacatcggc cccgcggcca ccctcttcgc cggggtgtac aatgacgccg gctctcccgc   1200

tgcactgcgc ggcctcgcga ccaacgtcgc caactacaac gccttcagca tcagcacctg   1260

cccgtcctac acgtcgggcg acgccaactg cgacgaaaac cgctacatca acgccttggc   1320

ccctctcttg aaatcggctg gcttcgatgc gcattttatc gttgatactg gttcgtatta   1380

tcttcccagc gagttgacag gttctgacag acgcaggtcg caacggtgtc cagcctacta   1440

agcagcaggc ttggggcgat tggtgcaacg tcatcggcac tggattcggt gtccggccga   1500

ccactaacac tggcaattcg ctggttgatg cgtttgtctg ggttaagcct ggcggcgaga   1560
```

```
gcgatggcac ctccaactct agctctccgc ggtacgatgc gcactgtgga tacagtgatg   1620

cgctccagcc tgctcctgag gccggaacct ggttccaggt gagttctttt ctggtgtagt   1680

gggactcggg tagctgacaa tatgcaggcg tactttgagc agcttctgac caacgctaac   1740

cctgcgttct ga                                                       1752


<210> SEQ ID NO 168
<211> LENGTH: 469
<212> TYPE: PRT
<213> ORGANISM: Fennellia nivea

<400> SEQUENCE: 168

Met Gly Arg Val Ser Ser Leu Ala Leu Ala Leu Leu Leu Pro Ala Val
1               5                   10                  15

Gln Ala Gln Gln Thr Leu Trp Gly Gln Cys Gly Gly Ile Gly Trp Thr
            20                  25                  30

Gly Ala Thr Asn Cys Val Ala Gly Ala Ala Cys Ser Thr Gln Asn Pro
        35                  40                  45

Tyr Tyr Ala Gln Cys Leu Pro Ala Thr Ala Thr Thr Ser Thr Thr Leu
    50                  55                  60

Thr Thr Thr Thr Arg Ser Thr Thr Thr Thr Thr Ala Thr Ser Thr Thr
65                  70                  75                  80

Ser Gln Gly Ser Ser Ser Ser Ser Ser Thr Thr Thr Thr Lys Ser Thr
                85                  90                  95

Ser Thr Thr Thr Gly Ser Ser Thr Thr Ile Thr Ser Ala Pro Ser Gly
            100                 105                 110

Asn Pro Phe Ser Gly Tyr Gln Leu Tyr Ala Asn Pro Tyr Tyr Ser Ser
        115                 120                 125

Glu Val His Thr Leu Ala Met Pro Ser Leu Ala Ser Ser Leu Leu Pro
    130                 135                 140

Ala Ala Ser Ala Ala Ala Lys Val Pro Ser Phe Thr Trp Leu Asp Thr
145                 150                 155                 160

Ala Ala Lys Val Pro Thr Met Gly Thr Tyr Leu Ala Asp Ile Lys Ala
                165                 170                 175

Lys Asn Ala Ala Gly Ala Asn Pro Pro Ile Ala Ala Gln Phe Val Val
            180                 185                 190

Tyr Asp Leu Pro Asp Arg Asp Cys Ala Ala Leu Ala Ser Asn Gly Glu
        195                 200                 205

Tyr Ser Ile Ala Asn Asn Gly Val Ala Asn Tyr Lys Ala Tyr Ile Asp
    210                 215                 220

Ser Ile Arg Ala Gln Leu Val Lys Tyr Pro Asp Val His Thr Ile Leu
225                 230                 235                 240

Val Ile Glu Pro Asp Ser Leu Ala Asn Leu Val Thr Asn Leu Asn Val
                245                 250                 255

Ala Lys Cys Ala Asn Ala Gln Ser Ala Tyr Leu Glu Cys Val Asn Tyr
            260                 265                 270

Ala Leu Ile Asn Leu Asn Leu Pro Asn Val Ala Met Tyr Ile Asp Ala
        275                 280                 285

Gly His Ala Gly Trp Leu Gly Trp Pro Ala Asn Ile Gly Pro Ala Ala
    290                 295                 300

Thr Leu Phe Ala Gly Val Tyr Asn Asp Ala Gly Ser Pro Ala Ala Leu
305                 310                 315                 320

Arg Gly Leu Ala Thr Asn Val Ala Asn Tyr Asn Ala Phe Ser Ile Ser
                325                 330                 335
```

-continued

```
Thr Cys Pro Ser Tyr Thr Ser Gly Asp Ala Asn Cys Asp Glu Asn Arg
            340                 345                 350

Tyr Ile Asn Ala Leu Ala Pro Leu Leu Lys Ser Ala Gly Phe Asp Ala
        355                 360                 365

His Phe Ile Val Asp Thr Gly Arg Asn Gly Val Gln Pro Thr Lys Gln
    370                 375                 380

Gln Ala Trp Gly Asp Trp Cys Asn Val Ile Gly Thr Gly Phe Gly Val
385                 390                 395                 400

Arg Pro Thr Thr Asn Thr Gly Asn Ser Leu Val Asp Ala Phe Val Trp
                405                 410                 415

Val Lys Pro Gly Gly Glu Ser Asp Gly Thr Ser Asn Ser Ser Ser Pro
            420                 425                 430

Arg Tyr Asp Ala His Cys Gly Tyr Ser Asp Ala Leu Gln Pro Ala Pro
        435                 440                 445

Glu Ala Gly Thr Trp Phe Gln Ala Tyr Phe Glu Gln Leu Leu Thr Asn
    450                 455                 460

Ala Asn Pro Ala Phe
465


<210> SEQ ID NO 169
<211> LENGTH: 1744
<212> TYPE: DNA
<213> ORGANISM: Penicillium emersonii

<400> SEQUENCE: 169

atgcggaatc ttcttgctct tgcaccggcc gcgctgcttg tcggcgcagc ggaagcgcag      60

caatccctct ggggacaatg tgagtagctc ctaaacgtct ctttgaggga ttatgtctga     120

ctgctcaggc ggcgggagtt cgtggactgg cgcaacgagc tgtgctgctg gagcgacgtg     180

cagcacgatc aatccttgta cgtctgctaa acgataattc tgcattgttg acttgctaac     240

tgcgtagact acgcacaatg cgtccctgca acggccactc cgaccacgct gacgacaacg     300

acaaaaccaa cgtccaccgg cggcgctgct ccaacgactc ctcctccgac aacgactgga     360

acaacgacat cgcccgtcgt caccaggccc gcgtctgcct ccggcaaccc gttcgaaggc     420

taccagctct acgccaatcc gtactatgcg tcggaggtga ttagtttggc aattccctcg     480

ctgagcagcg agctggttcc caaggcgagc gaggtggcca aggtgccgtc tttcgtctgg     540

ctgtaagtaa attcccccag gctgtcattt ccccttactg atcttgtcca gcgaccaagc     600

cgccaaggtg cccagcatgg gtgactatct gaaagacatc cagtcgcaga acgcagccgg     660

cgcagacccc ccgattgcag gcatctttgt cgtctacgac ctgcctgacc gtgactgcgc     720

ggctgcagcc agcaatggcg agttctccat cgccaacaac ggcgtcgccc tgtacaagca     780

gtacatcgac tcgatccgcg agcagctgac gacctattca gatgtgcaca ccatcctggt     840

catcggtagt tccagtcctc ttctgtgatg ttgatgaaaa atactgactg actcccgcag     900

aacccgacag cctggccaac ctggtcacca acctgaacgt gccgaaatgc gcaaatgccc     960

aggacgccta tctcgaatgc atcaactacg ccatcaccca gctcgatctg cccaacgtgg    1020

ccatgtatct tgatgctggt gagtcctcac atacaagtga ataaaaataa aactgatgca    1080

gtgcaggaca cgccggatgg ctaggctggc aagccaacct cgcccccgcc gcccagctgt    1140

ttgcctcggt gtacaagaac gcctcctcgc cggcatccgt ccgcggtctc gccaccaacg    1200

tcgccaacta caacgcctgg tcgatcagcc cgtgcccgtc gtacacgcag ggcgactcca    1260

actgcgacga ggaggactac gtgaatgccc tggggccgct gctccaggaa cagggattcc    1320
```

cggcgtactt tatcactgat acatgtaagc cttaccccag aacccctcca tagaaggtca 1380
atctaacggt aatgtacagc ccgcaatggc gtccaaccca ccaagcaaag ccaatggggc 1440
gactggtgca acgtcatcgg cacgggcttc ggcgtccggc ccacgaccga caccggcaat 1500
cctctcgagg acgccttcgt ctgggtcaag cccggtggcg agagcgatgg cacgtccaac 1560
acgacctctc cgcggtacga ctaccactgc gggctgagcg atgcgctgca gccggcgccg 1620
gaggcgggga cttggttcca ggtatgatgc gccttcgtat tagcaattac gatacatgtg 1680
catgctgacc atgcgacagg cgtactttga gcagttgctc acgaatgcta acccgctgtt 1740
ctag 1744

<210> SEQ ID NO 170
<211> LENGTH: 459
<212> TYPE: PRT
<213> ORGANISM: Penicillium emersonii

<400> SEQUENCE: 170

Met Arg Asn Leu Leu Ala Leu Ala Pro Ala Ala Leu Leu Val Gly Ala
1               5                   10                  15

Ala Glu Ala Gln Gln Ser Leu Trp Gly Gln Cys Gly Gly Ser Ser Trp
            20                  25                  30

Thr Gly Ala Thr Ser Cys Ala Ala Gly Ala Thr Cys Ser Thr Ile Asn
        35                  40                  45

Pro Tyr Tyr Ala Gln Cys Val Pro Ala Thr Ala Thr Pro Thr Thr Leu
    50                  55                  60

Thr Thr Thr Thr Lys Pro Thr Ser Thr Gly Gly Ala Ala Pro Thr Thr
65                  70                  75                  80

Pro Pro Pro Thr Thr Thr Gly Thr Thr Thr Ser Pro Val Val Thr Arg
                85                  90                  95

Pro Ala Ser Ala Ser Gly Asn Pro Phe Glu Gly Tyr Gln Leu Tyr Ala
            100                 105                 110

Asn Pro Tyr Tyr Ala Ser Glu Val Ile Ser Leu Ala Ile Pro Ser Leu
        115                 120                 125

Ser Ser Glu Leu Val Pro Lys Ala Ser Glu Val Ala Lys Val Pro Ser
    130                 135                 140

Phe Val Trp Leu Asp Gln Ala Ala Lys Val Pro Ser Met Gly Asp Tyr
145                 150                 155                 160

Leu Lys Asp Ile Gln Ser Gln Asn Ala Ala Gly Ala Asp Pro Pro Ile
                165                 170                 175

Ala Gly Ile Phe Val Val Tyr Asp Leu Pro Asp Arg Asp Cys Ala Ala
            180                 185                 190

Ala Ala Ser Asn Gly Glu Phe Ser Ile Ala Asn Asn Gly Val Ala Leu
        195                 200                 205

Tyr Lys Gln Tyr Ile Asp Ser Ile Arg Glu Gln Leu Thr Thr Tyr Ser
    210                 215                 220

Asp Val His Thr Ile Leu Val Ile Glu Pro Asp Ser Leu Ala Asn Leu
225                 230                 235                 240

Val Thr Asn Leu Asn Val Pro Lys Cys Ala Asn Ala Gln Asp Ala Tyr
                245                 250                 255

Leu Glu Cys Ile Asn Tyr Ala Ile Thr Gln Leu Asp Leu Pro Asn Val
            260                 265                 270

Ala Met Tyr Leu Asp Ala Gly His Ala Gly Trp Leu Gly Trp Gln Ala
        275                 280                 285

Asn Leu Ala Pro Ala Ala Gln Leu Phe Ala Ser Val Tyr Lys Asn Ala

-continued

```
    290                 295                 300

Ser Ser Pro Ala Ser Val Arg Gly Leu Ala Thr Asn Val Ala Asn Tyr
305                 310                 315                 320

Asn Ala Trp Ser Ile Ser Pro Cys Pro Ser Tyr Thr Gln Gly Asp Ser
                325                 330                 335

Asn Cys Asp Glu Glu Asp Tyr Val Asn Ala Leu Gly Pro Leu Leu Gln
            340                 345                 350

Glu Gln Gly Phe Pro Ala Tyr Phe Ile Thr Asp Thr Ser Arg Asn Gly
        355                 360                 365

Val Gln Pro Thr Lys Gln Ser Gln Trp Gly Asp Trp Cys Asn Val Ile
    370                 375                 380

Gly Thr Gly Phe Gly Val Arg Pro Thr Thr Asp Thr Gly Asn Pro Leu
385                 390                 395                 400

Glu Asp Ala Phe Val Trp Val Lys Pro Gly Gly Glu Ser Asp Gly Thr
                405                 410                 415

Ser Asn Thr Thr Ser Pro Arg Tyr Asp Tyr His Cys Gly Leu Ser Asp
            420                 425                 430

Ala Leu Gln Pro Ala Pro Glu Ala Gly Thr Trp Phe Gln Ala Tyr Phe
        435                 440                 445

Glu Gln Leu Leu Thr Asn Ala Asn Pro Leu Phe
    450                 455
```

<210> SEQ ID NO 171
<211> LENGTH: 1701
<212> TYPE: DNA
<213> ORGANISM: Penicillium pinophilum

<400> SEQUENCE: 171

```
atgttgcgat atctttccac cgttgccgcc acggcaattc tgaccggagt tgaagctcag     60

caatcagtct ggggacaatg taagaagtct cttgagaagc ttcaagttaa gaataatcca    120

cggttgttga caatcttgga aacatatagg tggcggccaa ggctggtctg gcgcgacttc    180

atgcgccgcc ggttctacgt gcagcactct aaacccttgt aaggtgccag ctgattagta    240

tgttggctct aattcctgac gccaattgtt cattagacta cgcacaatgt atccctggta    300

ccgctacttc aactacattg gtgaaaacaa cgtcttctac cagcgtcgga acgacatcgc    360

cgccgacaac aaccacgacg aaagctagta ccactgctac taccactgcc gctgcatccg    420

gaaacccttt ctctggttac cagctttatg ccaatccgta ctattcttca gaagtacaca    480

ctcttgccat cccatctttg actggctcgc tcgctgctgc tgctaccaaa gctgccgaga    540

tcccctcatt tgtctggctg tgagtgttcc cgagaacatc cagttgagtg atataaatat    600

atgcatggag atttcctaaa cctctatagt gacacggcag ccaaagtgcc tacaatgggc    660

acctacttgg ccaacattga ggctgcaaac aaggctggcg ccagcccacc tattgccggt    720

atcttcgttg tctatgacct gcctgaccgt gactgtgcag ctgctgcaag taatggcgaa    780

tacactgtag caaacaacgg tgttgcaaac tacaaggctt acatcgacag cattgtggca    840

cagttgaaag cttatcccga tgtgcacaca atccttatca ttggtacgtt ctctactatt    900

gggtcttgaa gaggtactct tgagagaaat ttgtgtctaa caaatcgccg atctacagag    960

cctgatagtc tcgccaacat ggtcaccaat ctgtctacag ccaagtgtgc tgaggctcaa   1020

tctgcatact atgagtgcgt caactacgca ttgatcaacc tcaacttggc caacgtggcc   1080

atgtacattg atgctggtca tgctggttgg ctcggatggt ctgcgaatct ttcaccagcg   1140

gctcaactct tcgcaacagt ctataagaat gcaagtgccc ctgcatctct tcgtggattg   1200
```

```
gccaccaacg ttgccaacta caacgcttgg tcgatcagca gcccaccctc atacacatct   1260

ggcgactcca actacgacga aaagctctac atcaacgctt tgtctcctct cctgacatct   1320

aacggctggc ctaacgctca cttcatcatg gatacttgta agtgtgttgc ggatgaatca   1380

agtgctcggt ttactaactg aacttcttta gcccgaaacg gtgttcaacc gactaagcag   1440

caggcatggg gtgactggtg caatgtgatc ggaaccggct tcggtgttca accgacaaca   1500

aatactggtg acccacttga ggatgccttt gtctgggtca agccaggtgg tgaaagtgat   1560

ggtacatcaa acagttccgc tactcgttac gatttccatt gcggctacag tgatgcactt   1620

caacccgccc ccgaggctgg gacttggttc caagcatact ttgtccagct tttgacaaat   1680

gccaacccag ctttggtcta g                                              1701


<210> SEQ ID NO 172
<211> LENGTH: 457
<212> TYPE: PRT
<213> ORGANISM: Penicillium pinophilum

<400> SEQUENCE: 172

Met Leu Arg Tyr Leu Ser Thr Val Ala Ala Thr Ala Ile Leu Thr Gly
1               5                   10                  15

Val Glu Ala Gln Gln Ser Val Trp Gly Gln Cys Gly Gly Gln Gly Trp
            20                  25                  30

Ser Gly Ala Thr Ser Cys Ala Ala Gly Ser Thr Cys Ser Thr Leu Asn
        35                  40                  45

Pro Tyr Tyr Ala Gln Cys Ile Pro Gly Thr Ala Thr Ser Thr Thr Leu
    50                  55                  60

Val Lys Thr Thr Ser Ser Thr Ser Val Gly Thr Thr Ser Pro Pro Thr
65                  70                  75                  80

Thr Thr Thr Thr Lys Ala Ser Thr Thr Ala Thr Thr Thr Ala Ala Ala
                85                  90                  95

Ser Gly Asn Pro Phe Ser Gly Tyr Gln Leu Tyr Ala Asn Pro Tyr Tyr
            100                 105                 110

Ser Ser Glu Val His Thr Leu Ala Ile Pro Ser Leu Thr Gly Ser Leu
        115                 120                 125

Ala Ala Ala Ala Thr Lys Ala Ala Glu Ile Pro Ser Phe Val Trp Leu
    130                 135                 140

Asp Thr Ala Ala Lys Val Pro Thr Met Gly Thr Tyr Leu Ala Asn Ile
145                 150                 155                 160

Glu Ala Ala Asn Lys Ala Gly Ala Ser Pro Pro Ile Ala Gly Ile Phe
                165                 170                 175

Val Val Tyr Asp Leu Pro Asp Arg Asp Cys Ala Ala Ala Ala Ser Asn
            180                 185                 190

Gly Glu Tyr Thr Val Ala Asn Asn Gly Val Ala Asn Tyr Lys Ala Tyr
        195                 200                 205

Ile Asp Ser Ile Val Ala Gln Leu Lys Ala Tyr Pro Asp Val His Thr
    210                 215                 220

Ile Leu Ile Ile Glu Pro Asp Ser Leu Ala Asn Met Val Thr Asn Leu
225                 230                 235                 240

Ser Thr Ala Lys Cys Ala Glu Ala Gln Ser Ala Tyr Tyr Glu Cys Val
                245                 250                 255

Asn Tyr Ala Leu Ile Asn Leu Asn Leu Ala Asn Val Ala Met Tyr Ile
            260                 265                 270

Asp Ala Gly His Ala Gly Trp Leu Gly Trp Ser Ala Asn Leu Ser Pro
```

-continued

```
        275                 280                 285

Ala Ala Gln Leu Phe Ala Thr Val Tyr Lys Asn Ala Ser Ala Pro Ala
    290                 295                 300

Ser Leu Arg Gly Leu Ala Thr Asn Val Ala Asn Tyr Asn Ala Trp Ser
305                 310                 315                 320

Ile Ser Ser Pro Pro Ser Tyr Thr Ser Gly Asp Ser Asn Tyr Asp Glu
                325                 330                 335

Lys Leu Tyr Ile Asn Ala Leu Ser Pro Leu Leu Thr Ser Asn Gly Trp
            340                 345                 350

Pro Asn Ala His Phe Ile Met Asp Thr Ser Arg Asn Gly Val Gln Pro
        355                 360                 365

Thr Lys Gln Gln Ala Trp Gly Asp Trp Cys Asn Val Ile Gly Thr Gly
    370                 375                 380

Phe Gly Val Gln Pro Thr Thr Asn Thr Gly Asp Pro Leu Glu Asp Ala
385                 390                 395                 400

Phe Val Trp Val Lys Pro Gly Gly Glu Ser Asp Gly Thr Ser Asn Ser
                405                 410                 415

Ser Ala Thr Arg Tyr Asp Phe His Cys Gly Tyr Ser Asp Ala Leu Gln
            420                 425                 430

Pro Ala Pro Glu Ala Gly Thr Trp Phe Gln Ala Tyr Phe Val Gln Leu
        435                 440                 445

Leu Thr Asn Ala Asn Pro Ala Leu Val
    450                 455
```

<210> SEQ ID NO 173
<211> LENGTH: 1233
<212> TYPE: DNA
<213> ORGANISM: Aspergillus fumigatus

<400> SEQUENCE: 173

```
atgaaattcg gtagcattgt gctcattgct gctgcggcag gcttcgcggt ggctgctcct     60

gcaaagagag cttcggtatt tcaatgttgg ttccctgtgg taaagttgga ttaaaaggac    120

actaacatac tgcagggttc ggaagcaatg agtctggagc agagtttggc gaaaatacca    180

ttcctggctc ttatgtatgt tgtgcatctg agagaagtat actgctgctg acaacatcaa    240

ggggaaagaa ttcatcttcc cggacccttc tacaatcagc acattgatcg ggaagggcat    300

gaacatcttc cggattcaat tcctcatgga gagactggtg ccaagctcta tgacaggctc    360

ctataacgag gagtaccttg ccaatctgac atcggtgggt ttgagcagca gcatgttgga    420

ctgtatgagg ctgactcgac caggttgtgg acgctgtcac caaggcagga tcttatgcta    480

ttttggaccc acacaacttt ggcagatagt gagtaatgcc cggcatactg tggacttgtt    540

ctaacgccac tcagcaatgg tcagattatc tccagcaccg acgacttcaa gaccttctgg    600

cagaatctgg ctggaaagtt caagtccaac aatctcgtca tctttgatac tagtatggct    660

aactcatttg gttctgatga gcttcactga ccccggatgt tagacaatga gtatcacgac    720

atggaccaga cactggtact gaacctcaac caggccgcta tcaacggtat ccgcgctgca    780

ggagccacct cgcaatacat ctttgtggag ggcaactcct ggaccggcgc ctggacctgg    840

gccgacgtca atgacaacct gaaggctctg accgaccccc aggataagat cgtctacgag    900

atgcaccagt atctcgactc ggatggatcc ggcaccgcgg agagctgcgt gtctaccacg    960

attggtaagg agcgggtttc ggccgcaaca aagtggctca aggataacgg caaggttggc   1020

atcattggtg agttcgctgg tggcgtcaat gatcagtgcc ggaccgctat ttcaggaatg   1080
```

```
ctggagtact tggctcagaa cacagacgtg tggaagggag ctctctggtg ggcggctggc   1140

ccctggtggg gaaactatat gttcaacatg gagcctccga gcggtgcagc ttatgtgggc   1200

atgttggaca tcttggagcc ctacctgggt tga                                1233
```

<210> SEQ ID NO 174
<211> LENGTH: 329
<212> TYPE: PRT
<213> ORGANISM: Aspergillus fumigatus

<400> SEQUENCE: 174

```
Met Lys Phe Gly Ser Ile Val Leu Ile Ala Ala Ala Ala Gly Phe Ala
1               5                   10                  15

Val Ala Ala Pro Ala Lys Arg Ala Ser Val Phe Gln Trp Phe Gly Ser
            20                  25                  30

Asn Glu Ser Gly Ala Glu Phe Gly Glu Asn Thr Ile Pro Gly Ser Tyr
        35                  40                  45

Gly Lys Glu Phe Ile Phe Pro Asp Pro Ser Thr Ile Ser Thr Leu Ile
    50                  55                  60

Gly Lys Gly Met Asn Ile Phe Arg Ile Gln Phe Leu Met Glu Arg Leu
65                  70                  75                  80

Val Pro Ser Ser Met Thr Gly Ser Tyr Asn Glu Glu Tyr Leu Ala Asn
                85                  90                  95

Leu Thr Ser Val Val Asp Ala Val Thr Lys Ala Gly Ser Tyr Ala Ile
            100                 105                 110

Leu Asp Pro His Asn Phe Gly Arg Tyr Asn Gly Gln Ile Ile Ser Ser
        115                 120                 125

Thr Asp Asp Phe Lys Thr Phe Trp Gln Asn Leu Ala Gly Lys Phe Lys
    130                 135                 140

Ser Asn Asn Leu Val Ile Phe Asp Thr Asn Asn Glu Tyr His Asp Met
145                 150                 155                 160

Asp Gln Thr Leu Val Leu Asn Leu Asn Gln Ala Ala Ile Asn Gly Ile
                165                 170                 175

Arg Ala Ala Gly Ala Thr Ser Gln Tyr Ile Phe Val Glu Gly Asn Ser
            180                 185                 190

Trp Thr Gly Ala Trp Thr Trp Ala Asp Val Asn Asp Asn Leu Lys Ala
        195                 200                 205

Leu Thr Asp Pro Gln Asp Lys Ile Val Tyr Glu Met His Gln Tyr Leu
    210                 215                 220

Asp Ser Asp Gly Ser Gly Thr Ala Glu Ser Cys Val Ser Thr Thr Ile
225                 230                 235                 240

Gly Lys Glu Arg Val Ser Ala Ala Thr Lys Trp Leu Lys Asp Asn Gly
                245                 250                 255

Lys Val Gly Ile Ile Gly Glu Phe Ala Gly Gly Val Asn Asp Gln Cys
            260                 265                 270

Arg Thr Ala Ile Ser Gly Met Leu Glu Tyr Leu Ala Gln Asn Thr Asp
        275                 280                 285

Val Trp Lys Gly Ala Leu Trp Trp Ala Ala Gly Pro Trp Trp Gly Asn
    290                 295                 300

Tyr Met Phe Asn Met Glu Pro Pro Ser Gly Ala Ala Tyr Val Gly Met
305                 310                 315                 320

Leu Asp Ile Leu Glu Pro Tyr Leu Gly
                325
```

<210> SEQ ID NO 175

<211> LENGTH: 1381
<212> TYPE: DNA
<213> ORGANISM: Neosartorya fischeri

<400> SEQUENCE: 175
atgaaggctt cgactattat ctgtgcactt ctccccttg ctttggcggt gccgaatgcg 60
aggcgggctt ctgggtttgt ttgtatgttt ccctttcttc tcttcatcgc agaagctgac 120
ggtgagatag ggtttggaag taacgagtct ggcgccgagt ttggagagac caagctcccg 180
ggcgtgctgg ggacggatta tatctggccc gatgcgtcga ctatcaagac tctgcatgat 240
gccgggatga acatcttccg tgttgcgttc cggatggaga ggctcatccc ggataagatg 300
acggggactc cagatgcgac gtacatgaat gatctcaagg cggttggtct gctgatctgg 360
gtgttgaggc gtcgctgacg aggatagact gtcaatgcga ttacgagtct gggggcgtat 420
gcggtgattg atccccataa ctatggaaga tagtgagttt gttgctgcct tgcttctgat 480
gtgagacagt gctgacggca cagctacggg aacatcatct cgtcgactga cgactttgct 540
gcgttctgga agaccgtggc tgcccagttt gcgtccaatg accatgtcat ttttgacacc 600
agtatgtttc catcagtttt gaaatgaagg acaagctgac ggaacagaca atgagtacca 660
tgatatggac cagacgctcg ttctcaacct caaccaggct gccatcaacg ccatccgtgc 720
tgcaggcgcc acctcgcagt acatttttgt cgagggcaac tcgtggtccg gcgcgtggac 780
ctggaccaac gtcaacgaca acctcaaggc cctcaccgac cctcaggata agatcgtcta 840
cgagatgcac cagtatctcg actcagacgg gtccggcacg tcggccacct gcgtgagctc 900
caccatcggc caggagcgcg tgcagtccgc cacacagtgg ttgaagacca atggtaagaa 960
aggtatcata ggcgagttcg ctggaggccc caacagcgtg tgccagtccg ctgtcacagg 1020
catgcttgac tacttgtctg ccaactcgga tgtgtggatg ggcgcagcat ggtgggccgc 1080
tggtccctgg tgggcagatt atatgttcag catggagccg ccgtctggca ctggctatca 1140
gaactatctc tcgttgttga agccgtattt cgtcggtggt tcgggtggta accctccaac 1200
gaccaccacg acaactacca gcaagcctac tacgaccact accacggctg ggaaccctgg 1260
cggcaccggg gtcgcacagc actggggcca gtgtggtgga attggatgga agggtccgac 1320
tgcctgcgcc acgccatata cctgccagaa gctgaacgac tactactctc aatgcctgta 1380
g 1381

<210> SEQ ID NO 176
<211> LENGTH: 412
<212> TYPE: PRT
<213> ORGANISM: Neosartorya fischeri

<400> SEQUENCE: 176

Met Lys Ala Ser Thr Ile Ile Cys Ala Leu Leu Pro Leu Ala Leu Ala
1 5 10 15

Val Pro Asn Ala Arg Arg Ala Ser Gly Phe Val Cys Met Phe Pro Phe
20 25 30

Leu Leu Phe Ile Ala Glu Ala Asp Gly Glu Ile Gly Phe Gly Ser Asn
35 40 45

Glu Ser Gly Ala Glu Phe Gly Glu Thr Lys Leu Pro Gly Val Leu Gly
50 55 60

Thr Asp Tyr Ile Trp Pro Asp Ala Ser Thr Ile Lys Thr Leu His Asp
65 70 75 80

Ala Gly Met Asn Ile Phe Arg Val Ala Phe Arg Met Glu Arg Leu Ile
85 90 95

```
Pro Asp Lys Met Thr Gly Thr Pro Asp Ala Thr Tyr Met Asn Asp Leu
            100                 105                 110

Lys Ala Thr Val Asn Ala Ile Thr Ser Leu Gly Ala Tyr Ala Val Ile
        115                 120                 125

Asp Pro His Asn Tyr Gly Arg Tyr Tyr Gly Asn Ile Ile Ser Ser Thr
    130                 135                 140

Asp Asp Phe Ala Ala Phe Trp Lys Thr Val Ala Ala Gln Phe Ala Ser
145                 150                 155                 160

Asn Asp His Val Ile Phe Asp Thr Asn Asn Glu Tyr His Asp Met Asp
                165                 170                 175

Gln Thr Leu Val Leu Asn Leu Asn Gln Ala Ala Ile Asn Ala Ile Arg
            180                 185                 190

Ala Ala Gly Ala Thr Ser Gln Tyr Ile Phe Val Glu Gly Asn Ser Trp
        195                 200                 205

Ser Gly Ala Trp Thr Trp Thr Asn Val Asn Asp Asn Leu Lys Ala Leu
    210                 215                 220

Thr Asp Pro Gln Asp Lys Ile Val Tyr Glu Met His Gln Tyr Leu Asp
225                 230                 235                 240

Ser Asp Gly Ser Gly Thr Ser Ala Thr Cys Val Ser Ser Thr Ile Gly
                245                 250                 255

Gln Glu Arg Val Gln Ser Ala Thr Gln Trp Leu Lys Thr Asn Gly Lys
            260                 265                 270

Lys Gly Ile Ile Gly Glu Phe Ala Gly Gly Pro Asn Ser Val Cys Gln
        275                 280                 285

Ser Ala Val Thr Gly Met Leu Asp Tyr Leu Ser Ala Asn Ser Asp Val
    290                 295                 300

Trp Met Gly Ala Ala Trp Trp Ala Ala Gly Pro Trp Trp Ala Asp Tyr
305                 310                 315                 320

Met Phe Ser Met Glu Pro Pro Ser Gly Thr Gly Tyr Gln Asn Tyr Leu
                325                 330                 335

Ser Leu Leu Lys Pro Tyr Phe Val Gly Gly Ser Gly Gly Asn Pro Pro
            340                 345                 350

Thr Thr Thr Thr Thr Thr Thr Ser Lys Pro Thr Thr Thr Thr Thr Thr
        355                 360                 365

Ala Gly Asn Pro Gly Gly Thr Gly Val Ala Gln His Trp Gly Gln Cys
    370                 375                 380

Gly Gly Ile Gly Trp Lys Gly Pro Thr Ala Cys Ala Thr Pro Tyr Thr
385                 390                 395                 400

Cys Gln Lys Leu Asn Asp Tyr Tyr Ser Gln Cys Leu
                405                 410
```

<210> SEQ ID NO 177
<211> LENGTH: 2940
<212> TYPE: DNA
<213> ORGANISM: Aspergillus aculeatus

<400> SEQUENCE: 177

```
atgaagctca gttggcttga ggcggctgcc ttgacggctg cttcagtcgt cagcgctgta      60

tgttggcttt ttttgacctc ctcgctgctt ctagatattt ggtgtgaggc tgacaattcg     120

tgctctacag gatgaactgg cgttctctcc tcctttctac ccctctccgt gggccaatgg     180

ccagggagag tgggcggaag cctaccagcg tgcagtggcc attgtatccc agatgactct     240

ggatgagaag gtcaacctga ccaccggaac tgggtaatga cactacagct gctgcgagat     300
```

-continued

```
gaatcgcctg ctaacgagct tctagatggg agctggagaa gtgcgtcggt cagactggtg    360
gtgtcccaag gtaggacccc cggataaaaa catgtgttca gttggctaac cgacgatcgc    420
tgtctagact gaacatcggt ggcatgtgtc ttcaggacag tcccttggga attcgtgata    480
gtaagtcttg atacaactgg agctcggccg ttgacactct tgctcacaat gtgttctgca    540
ggtgactaca attcggcttt ccctgctggt gtcaacgttg ctgcgacatg ggacaagaac    600
cttgcttatc tacgtggtca ggctatgggt caagagttca gtgacaaagg aattgatgtt    660
caattgggac cggccgcggg tcccctcggc aggagccctg atggaggtcg caactgggaa    720
ggtttctctc cagacccggc tcttactggt gtgctctttg cggagacgat taagggtatt    780
caagacgctg gtgtcgtggc gacagccaag cattacattc tcaatgagca agagcatttc    840
cgccaggtcg cagaggctgc gggctacgga ttcaatatct ccgacacgat cagctctaac    900
gttgatgaca agaccattca tgaaatgtac ctctggccct tcgcggatgc cgttcgcgcc    960
ggcgttggcg ccatcatgtg ttcctacaac cagatcaaca acagctacgg ttgccagaac   1020
agttacactc tgaacaagct tctgaaggcc gagctcggct tccagggctt tgtgatgtct   1080
gactggggtg ctcaccacag tggtgttggt tctgctttgg ccggcttgga tatgtcaatg   1140
cctggcgata tcaccttcga ttctgccact agtttctggg gtaccaacct gaccattgct   1200
gtgctcaacg gtaccgtccc gcagtggcgc gttgacgaca tggctgtccg tatcatggct   1260
gcctactaca aggttggccg cgaccgcctg taccagccgc ctaacttcag ctcctggact   1320
cgcgatgaat acggcttcaa gtatttctac ccccaggaag ggccctatga gaaggtcaat   1380
cactttgtca atgtgcagcg caaccacagc gaggttattc gcaagttggg agcagacagt   1440
actgttctac tgaagaacaa caatgccctg ccgctgaccg gaaaggagcg caaagttgcg   1500
atcctgggtg aagatgctgg atccaactcg tacggtgcca atggctgctc tgaccgtggc   1560
tgtgacaacg gtactcttgc tatggcttgg ggtagcggca ctgccgaatt cccatatctc   1620
gtgacccctg agcaggctat tcaagccgag gtgctcaagc ataagggcag cgtctacgcc   1680
atcacggaca actgggcgct gagccaggtg gagaccctcg ctaaacaagc caggtaagtt   1740
ctgtcgtcca tacattggag gtatatgttt tcagtgaact gacaagtgtc tccgtagtgt   1800
ctctcttgta tttgtcaact cggacgcggg agagggctat atctccgtgg acggaaacga   1860
gggcgaccgc aacaacctca ccctctggaa gaacggcgac aacctcatca aggctgctgc   1920
aaacaactgc aacaacacca tcgttgtcat ccactccgtt ggacctgttt tggttgacga   1980
gtggtatgac caccccaacg ttactgccat cctctgggcg ggcttgccag gccaggagtc   2040
tggcaactcc ttggctgacg tgctctacgg ccgcgtcaac ccgggcgcca aatctccatt   2100
cacctggggc aagacgaggg aggcgtacgg ggattacctt gtccgtgagc tcaacaacgg   2160
caacggagct ccccaagatg atttctcgga aggtgttttc attgactacc gcggattcga   2220
caagcgcaat gagaccccga tctacgagtt cggacatggt ctgagctaca ccactttcaa   2280
ctactctggc cttcacatcc aggttctcaa cgcttcctcc aacgctcaag tagccactga   2340
gactggcgcc gctcccacct tcggacaagt cggcaatgcc tctgactacg tgtaccctga   2400
gggattgacc agaatcagca agttcatcta tccctggctt aattccacag acctgaaggc   2460
ctcatctggc gacccgtact atggagtcga caccgcggag cacgtgcccg agggtgctac   2520
tgatggctct ccgcagcccg ttctgcctgc cggtggtggc ttcggtggta acccgcgcct   2580
ctacgatgag ttgatccgtg tttcggtgac agtcaagaac actggtcgtg ttgccggtga   2640
tgctgtgcct caattggtaa ttagatcctc gtgcagtatt ggttccagat gctaaccgct   2700
```

```
tgctagtatg tttcccttgg tggacccaat gagcccaagg ttgtgttgcg caaattcgac   2760

cgcctcaccc tcaagccctc cgaggagacg gtgtggacga ctaccctgac ccgccgcgat   2820

ctgtctaact gggacgttgc ggctcaggac tgggtcatca cttcttaccc gaagaaggtc   2880

catgttggta gctcttcgcg tcagctgccc cttcacgcgg cgctcccgaa ggtgcaataa   2940


<210> SEQ ID NO 178
<211> LENGTH: 860
<212> TYPE: PRT
<213> ORGANISM: Aspergillus aculeatus

<400> SEQUENCE: 178

Met Lys Leu Ser Trp Leu Glu Ala Ala Ala Leu Thr Ala Ala Ser Val
1               5                   10                  15

Val Ser Ala Asp Glu Leu Ala Phe Ser Pro Pro Phe Tyr Pro Ser Pro
            20                  25                  30

Trp Ala Asn Gly Gln Gly Glu Trp Ala Glu Ala Tyr Gln Arg Ala Val
        35                  40                  45

Ala Ile Val Ser Gln Met Thr Leu Asp Glu Lys Val Asn Leu Thr Thr
    50                  55                  60

Gly Thr Gly Trp Glu Leu Glu Lys Cys Val Gly Gln Thr Gly Gly Val
65                  70                  75                  80

Pro Arg Leu Asn Ile Gly Gly Met Cys Leu Gln Asp Ser Pro Leu Gly
                85                  90                  95

Ile Arg Asp Ser Asp Tyr Asn Ser Ala Phe Pro Ala Gly Val Asn Val
            100                 105                 110

Ala Ala Thr Trp Asp Lys Asn Leu Ala Tyr Leu Arg Gly Gln Ala Met
        115                 120                 125

Gly Gln Glu Phe Ser Asp Lys Gly Ile Asp Val Gln Leu Gly Pro Ala
    130                 135                 140

Ala Gly Pro Leu Gly Arg Ser Pro Asp Gly Gly Arg Asn Trp Glu Gly
145                 150                 155                 160

Phe Ser Pro Asp Pro Ala Leu Thr Gly Val Leu Phe Ala Glu Thr Ile
                165                 170                 175

Lys Gly Ile Gln Asp Ala Gly Val Val Ala Thr Ala Lys His Tyr Ile
            180                 185                 190

Leu Asn Glu Gln Glu His Phe Arg Gln Val Ala Glu Ala Ala Gly Tyr
        195                 200                 205

Gly Phe Asn Ile Ser Asp Thr Ile Ser Ser Asn Val Asp Asp Lys Thr
    210                 215                 220

Ile His Glu Met Tyr Leu Trp Pro Phe Ala Asp Ala Val Arg Ala Gly
225                 230                 235                 240

Val Gly Ala Ile Met Cys Ser Tyr Asn Gln Ile Asn Asn Ser Tyr Gly
                245                 250                 255

Cys Gln Asn Ser Tyr Thr Leu Asn Lys Leu Leu Lys Ala Glu Leu Gly
            260                 265                 270

Phe Gln Gly Phe Val Met Ser Asp Trp Gly Ala His His Ser Gly Val
        275                 280                 285

Gly Ser Ala Leu Ala Gly Leu Asp Met Ser Met Pro Gly Asp Ile Thr
    290                 295                 300

Phe Asp Ser Ala Thr Ser Phe Trp Gly Thr Asn Leu Thr Ile Ala Val
305                 310                 315                 320

Leu Asn Gly Thr Val Pro Gln Trp Arg Val Asp Asp Met Ala Val Arg
                325                 330                 335
```

```
Ile Met Ala Ala Tyr Tyr Lys Val Gly Arg Asp Arg Leu Tyr Gln Pro
            340                 345                 350

Pro Asn Phe Ser Ser Trp Thr Arg Asp Glu Tyr Gly Phe Lys Tyr Phe
        355                 360                 365

Tyr Pro Gln Glu Gly Pro Tyr Glu Lys Val Asn His Phe Val Asn Val
    370                 375                 380

Gln Arg Asn His Ser Glu Val Ile Arg Lys Leu Gly Ala Asp Ser Thr
385                 390                 395                 400

Val Leu Leu Lys Asn Asn Asn Ala Leu Pro Leu Thr Gly Lys Glu Arg
                405                 410                 415

Lys Val Ala Ile Leu Gly Glu Asp Ala Gly Ser Asn Ser Tyr Gly Ala
            420                 425                 430

Asn Gly Cys Ser Asp Arg Gly Cys Asp Asn Gly Thr Leu Ala Met Ala
        435                 440                 445

Trp Gly Ser Gly Thr Ala Glu Phe Pro Tyr Leu Val Thr Pro Glu Gln
    450                 455                 460

Ala Ile Gln Ala Glu Val Leu Lys His Lys Gly Ser Val Tyr Ala Ile
465                 470                 475                 480

Thr Asp Asn Trp Ala Leu Ser Gln Val Glu Thr Leu Ala Lys Gln Ala
                485                 490                 495

Ser Val Ser Leu Val Phe Val Asn Ser Asp Ala Gly Glu Gly Tyr Ile
            500                 505                 510

Ser Val Asp Gly Asn Glu Gly Asp Arg Asn Asn Leu Thr Leu Trp Lys
        515                 520                 525

Asn Gly Asp Asn Leu Ile Lys Ala Ala Ala Asn Asn Cys Asn Asn Thr
    530                 535                 540

Ile Val Val Ile His Ser Val Gly Pro Val Leu Val Asp Glu Trp Tyr
545                 550                 555                 560

Asp His Pro Asn Val Thr Ala Ile Leu Trp Ala Gly Leu Pro Gly Gln
                565                 570                 575

Glu Ser Gly Asn Ser Leu Ala Asp Val Leu Tyr Gly Arg Val Asn Pro
            580                 585                 590

Gly Ala Lys Ser Pro Phe Thr Trp Gly Lys Thr Arg Glu Ala Tyr Gly
        595                 600                 605

Asp Tyr Leu Val Arg Glu Leu Asn Asn Gly Asn Gly Ala Pro Gln Asp
    610                 615                 620

Asp Phe Ser Glu Gly Val Phe Ile Asp Tyr Arg Gly Phe Asp Lys Arg
625                 630                 635                 640

Asn Glu Thr Pro Ile Tyr Glu Phe Gly His Gly Leu Ser Tyr Thr Thr
                645                 650                 655

Phe Asn Tyr Ser Gly Leu His Ile Gln Val Leu Asn Ala Ser Ser Asn
            660                 665                 670

Ala Gln Val Ala Thr Glu Thr Gly Ala Ala Pro Thr Phe Gly Gln Val
        675                 680                 685

Gly Asn Ala Ser Asp Tyr Val Tyr Pro Glu Gly Leu Thr Arg Ile Ser
    690                 695                 700

Lys Phe Ile Tyr Pro Trp Leu Asn Ser Thr Asp Leu Lys Ala Ser Ser
705                 710                 715                 720

Gly Asp Pro Tyr Tyr Gly Val Asp Thr Ala Glu His Val Pro Glu Gly
                725                 730                 735

Ala Thr Asp Gly Ser Pro Gln Pro Val Leu Pro Ala Gly Gly Gly Phe
            740                 745                 750
```

-continued

```
Gly Gly Asn Pro Arg Leu Tyr Asp Glu Leu Ile Arg Val Ser Val Thr
        755                 760                 765

Val Lys Asn Thr Gly Arg Val Ala Gly Asp Ala Val Pro Gln Leu Tyr
    770                 775                 780

Val Ser Leu Gly Gly Pro Asn Glu Pro Lys Val Val Leu Arg Lys Phe
785                 790                 795                 800

Asp Arg Leu Thr Leu Lys Pro Ser Glu Glu Thr Val Trp Thr Thr Thr
                805                 810                 815

Leu Thr Arg Arg Asp Leu Ser Asn Trp Asp Val Ala Ala Gln Asp Trp
            820                 825                 830

Val Ile Thr Ser Tyr Pro Lys Lys Val His Val Gly Ser Ser Ser Arg
        835                 840                 845

Gln Leu Pro Leu His Ala Ala Leu Pro Lys Val Gln
    850                 855                 860
```

```
<210> SEQ ID NO 179
<211> LENGTH: 2935
<212> TYPE: DNA
<213> ORGANISM: Aspergillus kawachii

<400> SEQUENCE: 179

atgaggttca ctttgattga ggcggtggct ctcactgctg tctcgctggc cagcgctgta      60

cgtgccgttc ctttgtcctg tgaattgcaa ttgtgctcaa ttagattcac ttgtttgtac     120

catcatcgct gacaatggtc tattcatagg atgaattggc ttactcccca ccgtattacc     180

catccccttg ggccaatggc cagggcgact gggcgcaggc ataccagcgc gctgttgata     240

ttgtctcgca gatgacattg gctgagaagg tcaatctgac cacaggaact gggtaggact     300

tacaaggcgc aatctgtatg ctccggctaa caacctctag atgggaattg gagctatgtg     360

ttggtcagac tggcggggtt ccccggtagg tttgaaaaga atgtcgagac agggggcatt     420

cattgattaa cggcgacaga ttgggagttc cgggaatgtg tttacaggat agccctctgg     480

gcgttcgcga ctgtaagcca tctgctgttg ttaggctttg atgctcttac tgacacgtcg     540

cagccgacta caactctgct ttcccttccg gtatgaacgt ggctgcaacc tgggacaaga     600

atctggcata cctccgcggc aaggctatgg gtcaggaatt tagtgacaag ggtgccgata     660

tccaattggg tccagctgcc ggccctctcg gtagaagtcc cgacggtggt cgtaactggg     720

agggcttctc ccccgacccg gccctaagtg gtgtgctctt tgcagagacc atcaagggta     780

tccaagatgc tggtgtggtc gcgacggcta agcactacat tgcctacgag caagagcatt     840

tccgtcaggc gcctgaagcc caaggttatg gatttaacat ttccgagagt ggaagcgcga     900

acctcgacga taagactatg cacgagctgt acctctggcc cttcgcggat gccatccgtg     960

cgggtgctgg cgctgtgatg tgctcctaca accagatcaa caacagctat ggctgccaga    1020

acagctacac tctgaacaag ctgctcaagg ccgagctggg tttccagggc tttgtcatga    1080

gtgattgggc ggctcaccat gctggtgtga gtggtgcttt ggcaggattg gatatgtcta    1140

tgccaggaga cgtcgactac gacagtggta cgtcttactg ggtacaaac ctgaccgtta    1200

gcgtgctcaa cggaacggtg ccccaatggc gtgttgatga catggctgtc cgcatcatgg    1260

ccgcctacta caaggtcggc cgtgaccgtc tgtggactcc tcccaacttc agctcatgga    1320

ccagagatga atacggctac aagtactact atgtgtcgga gggaccgtac gagaaggtca    1380

accactacgt gaacgtgcaa cgcaaccaca gcgaactgat ccgccgcatt ggagcggaca    1440

gcacggtgct cctcaagaac gacggcgctc tgcctttgac tggtaaggag cgcctggtcg    1500
```

-continued

```
cgcttatcgg agaagatgcg ggctccaacc cttatggtgc caacggctgc agtgaccgtg   1560

gatgcgacaa tggaacattg gcgatgggct ggggaagtgg tactgccaac ttcccatacc   1620

tggtgacccc cgagcaggcc atctcaaacg aggtgctcaa gaacaagaat ggtgtattca   1680

ccgccaccga taactgggct atcgatcaga ttgaggcgct tgctaagacc gccaggtaag   1740

aagatctcca attcttttgt ttcttgtgca atggatgctg acaacgtgct agtgtctctc   1800

ttgtctttgt caacgccgac tctggcgagg gttacatcaa tgtcgacgga aacctgggtg   1860

accgcaggaa cctgaccctg tggaggaacg gcgataatgt gatcaaggct gctgctagca   1920

actgcaacaa caccattgtt atcattcact ctgtcggccc agtcttggtt aacgaatggt   1980

acgacaaccc caatgttacc gctattctct ggggtggtct gcccggtcag gagtctggca   2040

actctcttgc cgacgtcctc tatggccgtg tcaaccccgg tgccaagtcg ccctttacct   2100

ggggcaagac tcgtgaggcc taccaagatt acttggtcac cgagcccaac aacggcaatg   2160

gagcccccca ggaagacttc gtcgagggcg tcttcattga ctaccgcgga ttcgacaagc   2220

gcaacgagac cccgatctac gagttcggct atggtctgag ctacaccact ttcaactact   2280

cgaaccttga ggtgcaggtt ctgagcgccc ccgcgtacga gcctgcttcg ggtgagactg   2340

aggcagcgcc aacttttgga gaggttggaa atgcgtcgaa ttacctctac cccgacggac   2400

tgcagaaaat caccaagttc atctacccct ggctcaacag taccgatctc gaggcatctt   2460

ctggggatgc tagctacgga caggactcct cggactatct tcccgaggga gccaccgatg   2520

gctctgcgca accgatcctg cctgctggtg gcggtcctgg cggcaaccct cgcctgtacg   2580

acgagctcat ccgcgtgtcg gtgaccatca agaacaccgg caaggttgct ggtgatgaag   2640

ttccccaact ggtaagtaac agaagaaccg aacgatgttg aacaaagcta atcagtcgca   2700

gtatgtttcc cttggcggcc ccaacgagcc caagatcgtg ctgcgtcaat tcgagcgcat   2760

cacgctgcag ccgtcagagg agacgaagtg gagcacgact ctgacgcgcc gtgaccttgc   2820

aaactggaat gttgagaagc aggactggga gattacgtcg tatcccaaga tggtgtttgt   2880

cggaagctcc tcgcggaagc tgccgctccg ggcgtctctg cctactgttc actaa        2935
```

<210> SEQ ID NO 180
<211> LENGTH: 860
<212> TYPE: PRT
<213> ORGANISM: Aspergillus kawachii

<400> SEQUENCE: 180

```
Met Arg Phe Thr Leu Ile Glu Ala Val Ala Leu Thr Ala Val Ser Leu
1               5                   10                  15

Ala Ser Ala Asp Glu Leu Ala Tyr Ser Pro Pro Tyr Tyr Pro Ser Pro
            20                  25                  30

Trp Ala Asn Gly Gln Gly Asp Trp Ala Gln Ala Tyr Gln Arg Ala Val
        35                  40                  45

Asp Ile Val Ser Gln Met Thr Leu Ala Glu Lys Val Asn Leu Thr Thr
    50                  55                  60

Gly Thr Gly Trp Glu Leu Glu Leu Cys Val Gly Gln Thr Gly Gly Val
65                  70                  75                  80

Pro Arg Leu Gly Val Pro Gly Met Cys Leu Gln Asp Ser Pro Leu Gly
                85                  90                  95

Val Arg Asp Ser Asp Tyr Asn Ser Ala Phe Pro Ser Gly Met Asn Val
            100                 105                 110

Ala Ala Thr Trp Asp Lys Asn Leu Ala Tyr Leu Arg Gly Lys Ala Met
        115                 120                 125
```

```
Gly Gln Glu Phe Ser Asp Lys Gly Ala Asp Ile Gln Leu Gly Pro Ala
    130                 135                 140

Ala Gly Pro Leu Gly Arg Ser Pro Asp Gly Gly Arg Asn Trp Glu Gly
145                 150                 155                 160

Phe Ser Pro Asp Pro Ala Leu Ser Gly Val Leu Phe Ala Glu Thr Ile
                165                 170                 175

Lys Gly Ile Gln Asp Ala Gly Val Val Ala Thr Ala Lys His Tyr Ile
            180                 185                 190

Ala Tyr Glu Gln Glu His Phe Arg Gln Ala Pro Glu Ala Gln Gly Tyr
        195                 200                 205

Gly Phe Asn Ile Ser Glu Ser Gly Ser Ala Asn Leu Asp Asp Lys Thr
    210                 215                 220

Met His Glu Leu Tyr Leu Trp Pro Phe Ala Asp Ala Ile Arg Ala Gly
225                 230                 235                 240

Ala Gly Ala Val Met Cys Ser Tyr Asn Gln Ile Asn Asn Ser Tyr Gly
                245                 250                 255

Cys Gln Asn Ser Tyr Thr Leu Asn Lys Leu Leu Lys Ala Glu Leu Gly
            260                 265                 270

Phe Gln Gly Phe Val Met Ser Asp Trp Ala Ala His His Ala Gly Val
        275                 280                 285

Ser Gly Ala Leu Ala Gly Leu Asp Met Ser Met Pro Gly Asp Val Asp
    290                 295                 300

Tyr Asp Ser Gly Thr Ser Tyr Trp Gly Thr Asn Leu Thr Val Ser Val
305                 310                 315                 320

Leu Asn Gly Thr Val Pro Gln Trp Arg Val Asp Asp Met Ala Val Arg
                325                 330                 335

Ile Met Ala Ala Tyr Tyr Lys Val Gly Arg Asp Arg Leu Trp Thr Pro
            340                 345                 350

Pro Asn Phe Ser Ser Trp Thr Arg Asp Glu Tyr Gly Tyr Lys Tyr Tyr
        355                 360                 365

Tyr Val Ser Glu Gly Pro Tyr Glu Lys Val Asn His Tyr Val Asn Val
    370                 375                 380

Gln Arg Asn His Ser Glu Leu Ile Arg Arg Ile Gly Ala Asp Ser Thr
385                 390                 395                 400

Val Leu Leu Lys Asn Asp Gly Ala Leu Pro Leu Thr Gly Lys Glu Arg
                405                 410                 415

Leu Val Ala Leu Ile Gly Glu Asp Ala Gly Ser Asn Pro Tyr Gly Ala
            420                 425                 430

Asn Gly Cys Ser Asp Arg Gly Cys Asp Asn Gly Thr Leu Ala Met Gly
        435                 440                 445

Trp Gly Ser Gly Thr Ala Asn Phe Pro Tyr Leu Val Thr Pro Glu Gln
    450                 455                 460

Ala Ile Ser Asn Glu Val Leu Lys Asn Lys Asn Gly Val Phe Thr Ala
465                 470                 475                 480

Thr Asp Asn Trp Ala Ile Asp Gln Ile Glu Ala Leu Ala Lys Thr Ala
                485                 490                 495

Ser Val Ser Leu Val Phe Val Asn Ala Asp Ser Gly Glu Gly Tyr Ile
            500                 505                 510

Asn Val Asp Gly Asn Leu Gly Asp Arg Arg Asn Leu Thr Leu Trp Arg
        515                 520                 525

Asn Gly Asp Asn Val Ile Lys Ala Ala Ala Ser Asn Cys Asn Asn Thr
    530                 535                 540
```

```
Ile Val Ile Ile His Ser Val Gly Pro Val Leu Val Asn Glu Trp Tyr
545                 550                 555                 560

Asp Asn Pro Asn Val Thr Ala Ile Leu Trp Gly Gly Leu Pro Gly Gln
                565                 570                 575

Glu Ser Gly Asn Ser Leu Ala Asp Val Leu Tyr Gly Arg Val Asn Pro
            580                 585                 590

Gly Ala Lys Ser Pro Phe Thr Trp Gly Lys Thr Arg Glu Ala Tyr Gln
        595                 600                 605

Asp Tyr Leu Val Thr Glu Pro Asn Asn Gly Asn Gly Ala Pro Gln Glu
    610                 615                 620

Asp Phe Val Glu Gly Val Phe Ile Asp Tyr Arg Gly Phe Asp Lys Arg
625                 630                 635                 640

Asn Glu Thr Pro Ile Tyr Glu Phe Gly Tyr Gly Leu Ser Tyr Thr Thr
                645                 650                 655

Phe Asn Tyr Ser Asn Leu Glu Val Gln Val Leu Ser Ala Pro Ala Tyr
            660                 665                 670

Glu Pro Ala Ser Gly Glu Thr Glu Ala Ala Pro Thr Phe Gly Glu Val
        675                 680                 685

Gly Asn Ala Ser Asn Tyr Leu Tyr Pro Asp Gly Leu Gln Lys Ile Thr
    690                 695                 700

Lys Phe Ile Tyr Pro Trp Leu Asn Ser Thr Asp Leu Glu Ala Ser Ser
705                 710                 715                 720

Gly Asp Ala Ser Tyr Gly Gln Asp Ser Ser Asp Tyr Leu Pro Glu Gly
                725                 730                 735

Ala Thr Asp Gly Ser Ala Gln Pro Ile Leu Pro Ala Gly Gly Gly Pro
            740                 745                 750

Gly Gly Asn Pro Arg Leu Tyr Asp Glu Leu Ile Arg Val Ser Val Thr
        755                 760                 765

Ile Lys Asn Thr Gly Lys Val Ala Gly Asp Glu Val Pro Gln Leu Tyr
    770                 775                 780

Val Ser Leu Gly Gly Pro Asn Glu Pro Lys Ile Val Leu Arg Gln Phe
785                 790                 795                 800

Glu Arg Ile Thr Leu Gln Pro Ser Glu Glu Thr Lys Trp Ser Thr Thr
                805                 810                 815

Leu Thr Arg Arg Asp Leu Ala Asn Trp Asn Val Glu Lys Gln Asp Trp
            820                 825                 830

Glu Ile Thr Ser Tyr Pro Lys Met Val Phe Val Gly Ser Ser Ser Arg
        835                 840                 845

Lys Leu Pro Leu Arg Ala Ser Leu Pro Thr Val His
    850                 855                 860
```

<210> SEQ ID NO 181
<211> LENGTH: 3062
<212> TYPE: DNA
<213> ORGANISM: Aspergillus clavatus

<400> SEQUENCE: 181

```
atgaggttca gctggcttga ggtcgccgtg acggctgcct cattggccaa tgccaatgtt      60

tgtattcctc tgttcccttg gtatggtttg tgatccttgt tgaccatcgt atctgcatga     120

tcaggaatta gtctcttccc ctccatttta cccgtcgcct tgggcaaatg gtcagggaga     180

atgggcggag gcgcatcaac gcgctgtcga gatcgtttct cagatgacac tcacagaaaa     240

agtcaacttg acaacgggca ctgggtacgt gatgcgaagg aatacttgga aaaagatggt     300

tcaatacact gacactgtcc tccagttgga tgatggaaga atgcgttggt cagacaggca     360
```

gtgttcctcg gtgagtttga tctacgtgcg atgtatcgta tctcttgacc gaacgctgag 420
acagtattgc agacttggta tcaactgggg tctttgcggt caagattccc ccctgggtat 480
ccgtttttgt aagctacgcc cccgatttct acccttcatt tgtgtccact ctgctaacgg 540
ttctgctatg cagccgacct caattcggct ttccctgctg gcatcaatgt tgcggcaaca 600
tgggataaga cgctcgcgta cctccgtggc aaggcaatgg gtgaagagtt caatgacaag 660
ggtatcgata tccaactggg cccggctgct ggtcccctgg ggaaatatcc cgatggtggt 720
cggatctggg aaggcttctc tcccgaccca gctcttactg gcgtgctttt cgcagagacc 780
atcaagggta ttcaggatgc tggcgtgatt gctactgcca agcattacat tctcaacgaa 840
caggagcagt tccgtcaggt tgcggaggcc cagggatacg gatataacat caccgagact 900
ctgagttcca atgtggatga taagactatg cacgaattgt atctctggtg agtagtgcag 960
cccatctttg gttgaaaacc aactgacttt ggagaaggcc attcgcagat gctgtgcgcg 1020
gtaagatctt ggaatatgcc ctggtccatc tcgtgttact aaccttcaca cagctggtgt 1080
gggcgctatc atgtgttcct acaaccagat caacaacagc tacggttgcc agaacagcca 1140
gactttgaac aagttgctga aggccgagct tggcttccag ggctttgtca tgagcgactg 1200
gagcgcccac cacagcggtg ttggcgctgc tctggctggc ttggacatgt cgatgcctgg 1260
cgacatttct tttgatgatg gtctctcttt ctggggtgcc aatatgacgg ttggtgtcct 1320
gaacgggacc atcccggcct ggcgcgtgga cgacatggct gtccgtatca tgacggctta 1380
ctacaaggtt ggacgcgatc gccttcgcgt tccccccaac ttcagctcgt ggactagaga 1440
cgaatacggc tacgagcatg ctgctgtttc cgagggagcc tggaaaaagg tcaatgattt 1500
tgtcaacgtg caacgcgacc atgcccagct gatccgcgag gttggctccg ctagcactgt 1560
gcttctcaag aacgttggtg cactcccgct aaccggcaaa gagcgtaaag tgggtatctt 1620
tggagaagat gctggctcga acccatgggg ccccaacggc tgcgaaaacc ggggctgcga 1680
caatggaacc cttgcgatgg cttggggtag cggtactgcc gagttccctt atctcgtgac 1740
accagagcag gcaatccaga gcgaggtcat caagaacggg ggcaatgtct tccccgtgac 1800
tcataacggc gcgctgaccc agatggcgaa tattgcctct caatcttcgt gagtgacctc 1860
tttcagatgc attccttctc agcttgaata ctaacggatc attggacagc gtctcgcttg 1920
tgtttgtcaa tgccgacgct ggagaaggat tcatcagtgt tgatggtaac attggtgacc 1980
gcaagaacct caccctttgg aagaatggcg aggaagtcat caagactgtg gctagccata 2040
gcaacaacac cgtcgttgtt atccacagtg tcggcccaat cctggtcgat gaatggcatg 2100
acaaccccaa catcacggct atcctctggg ccggcttgcc cggccaggag agcggcaact 2160
ccattgccga cgtgctttac ggccgtgtca accccagcgc caagacccct ttcacctggg 2220
gcaagacgcg cgaatcctac ggtgctcccc tggtcactaa gcctaacaat ggcaatggag 2280
ctccccagga tgatttcagc gaaggtgtct tcattgacta ccgttacttt gacaagcgta 2340
acgagacgcc ggtttatgaa ttcggcttcg gattgagcta cacctccttt ggctattctc 2400
accttcgcgt ccaacctctg aatggttcca cttatgtccc tgccaccggc acgactggac 2460
ctgcgccagc ttacggaagt atcggtagcg ctgcggatta cttgttcccc gaggggctca 2520
agaggattac caagttcatc tatccatggc tgaactcgac cgacctcaag gcttcctctg 2580
cagacccgaa ctacggctgg gaggactccg agtacattcc cgaggctgct accgatggct 2640
ctcctcagcc tattctcaag gcgggcggtg ctcctggtgg caatcccact ctttaccacg 2700
acttggtcaa ggtgtccgct accatcacca acacgggtaa tgttgcgggc tacgaggttc 2760
ctcaactggt gagtgaccta gactactatt ccttgaggag aggcgcattt ccgctgacct 2820
gtatctagta tgtgtctctt ggtggaccca atgagccccg agtcgttctg cgcaagttcg 2880
accgcatcca cctcgccccc ggagagcaga aggtctggac cacaacgctg acgcgccgtg 2940
atctcgccaa ctgggacgtg gaagcgcagg actgggtcat caccaagtat cccaagaggg 3000
tttacgtcgg aagctcctct cgaaagctcc cgctgagagc acctctgccc cgggtacagt 3060
aa 3062

<210> SEQ ID NO 182
<211> LENGTH: 860
<212> TYPE: PRT
<213> ORGANISM: Aspergillus clavatus

<400> SEQUENCE: 182

Met Arg Phe Ser Trp Leu Glu Val Ala Val Thr Ala Ala Ser Leu Ala
1 5 10 15

Asn Ala Asn Glu Leu Val Ser Ser Pro Pro Phe Tyr Pro Ser Pro Trp
20 25 30

Ala Asn Gly Gln Gly Glu Trp Ala Glu Ala His Gln Arg Ala Val Glu
35 40 45

Ile Val Ser Gln Met Thr Leu Thr Glu Lys Val Asn Leu Thr Thr Gly
50 55 60

Thr Gly Trp Met Met Glu Glu Cys Val Gly Gln Thr Gly Ser Val Pro
65 70 75 80

Arg Leu Gly Ile Asn Trp Gly Leu Cys Gly Gln Asp Ser Pro Leu Gly
85 90 95

Ile Arg Phe Ser Asp Leu Asn Ser Ala Phe Pro Ala Gly Ile Asn Val
100 105 110

Ala Ala Thr Trp Asp Lys Thr Leu Ala Tyr Leu Arg Gly Lys Ala Met
115 120 125

Gly Glu Glu Phe Asn Asp Lys Gly Ile Asp Ile Gln Leu Gly Pro Ala
130 135 140

Ala Gly Pro Leu Gly Lys Tyr Pro Asp Gly Gly Arg Ile Trp Glu Gly
145 150 155 160

Phe Ser Pro Asp Pro Ala Leu Thr Gly Val Leu Phe Ala Glu Thr Ile
165 170 175

Lys Gly Ile Gln Asp Ala Gly Val Ile Ala Thr Ala Lys His Tyr Ile
180 185 190

Leu Asn Glu Gln Glu Gln Phe Arg Gln Val Ala Glu Ala Gln Gly Tyr
195 200 205

Gly Tyr Asn Ile Thr Glu Thr Leu Ser Ser Asn Val Asp Asp Lys Thr
210 215 220

Met His Glu Leu Tyr Leu Trp Pro Phe Ala Asp Ala Val Arg Ala Gly
225 230 235 240

Val Gly Ala Ile Met Cys Ser Tyr Asn Gln Ile Asn Asn Ser Tyr Gly
245 250 255

Cys Gln Asn Ser Gln Thr Leu Asn Lys Leu Leu Lys Ala Glu Leu Gly
260 265 270

Phe Gln Gly Phe Val Met Ser Asp Trp Ser Ala His His Ser Gly Val
275 280 285

Gly Ala Ala Leu Ala Gly Leu Asp Met Ser Met Pro Gly Asp Ile Ser
290 295 300

-continued

```
Phe Asp Asp Gly Leu Ser Phe Trp Gly Ala Asn Met Thr Val Gly Val
305                 310                 315                 320

Leu Asn Gly Thr Ile Pro Ala Trp Arg Val Asp Asp Met Ala Val Arg
                325                 330                 335

Ile Met Thr Ala Tyr Tyr Lys Val Gly Arg Asp Arg Leu Arg Val Pro
            340                 345                 350

Pro Asn Phe Ser Ser Trp Thr Arg Asp Glu Tyr Gly Tyr Glu His Ala
        355                 360                 365

Ala Val Ser Glu Gly Ala Trp Lys Lys Val Asn Asp Phe Val Asn Val
    370                 375                 380

Gln Arg Asp His Ala Gln Leu Ile Arg Glu Val Gly Ser Ala Ser Thr
385                 390                 395                 400

Val Leu Leu Lys Asn Val Gly Ala Leu Pro Leu Thr Gly Lys Glu Arg
                405                 410                 415

Lys Val Gly Ile Phe Gly Glu Asp Ala Gly Ser Asn Pro Trp Gly Pro
            420                 425                 430

Asn Gly Cys Glu Asn Arg Gly Cys Asp Asn Gly Thr Leu Ala Met Ala
        435                 440                 445

Trp Gly Ser Gly Thr Ala Glu Phe Pro Tyr Leu Val Thr Pro Glu Gln
    450                 455                 460

Ala Ile Gln Ser Glu Val Ile Lys Asn Gly Gly Asn Val Phe Pro Val
465                 470                 475                 480

Thr His Asn Gly Ala Leu Thr Gln Met Ala Asn Ile Ala Ser Gln Ser
                485                 490                 495

Ser Val Ser Leu Val Phe Val Asn Ala Asp Ala Gly Glu Gly Phe Ile
            500                 505                 510

Ser Val Asp Gly Asn Ile Gly Asp Arg Lys Asn Leu Thr Leu Trp Lys
        515                 520                 525

Asn Gly Glu Glu Val Ile Lys Thr Val Ala Ser His Ser Asn Asn Thr
    530                 535                 540

Val Val Val Ile His Ser Val Gly Pro Ile Leu Val Asp Glu Trp His
545                 550                 555                 560

Asp Asn Pro Asn Ile Thr Ala Ile Leu Trp Ala Gly Leu Pro Gly Gln
                565                 570                 575

Glu Ser Gly Asn Ser Ile Ala Asp Val Leu Tyr Gly Arg Val Asn Pro
            580                 585                 590

Ser Ala Lys Thr Pro Phe Thr Trp Gly Lys Thr Arg Glu Ser Tyr Gly
        595                 600                 605

Ala Pro Leu Val Thr Lys Pro Asn Asn Gly Asn Gly Ala Pro Gln Asp
    610                 615                 620

Asp Phe Ser Glu Gly Val Phe Ile Asp Tyr Arg Tyr Phe Asp Lys Arg
625                 630                 635                 640

Asn Glu Thr Pro Val Tyr Glu Phe Gly Phe Gly Leu Ser Tyr Thr Ser
                645                 650                 655

Phe Gly Tyr Ser His Leu Arg Val Gln Pro Leu Asn Gly Ser Thr Tyr
            660                 665                 670

Val Pro Ala Thr Gly Thr Thr Gly Pro Ala Pro Ala Tyr Gly Ser Ile
        675                 680                 685

Gly Ser Ala Ala Asp Tyr Leu Phe Pro Glu Gly Leu Lys Arg Ile Thr
    690                 695                 700

Lys Phe Ile Tyr Pro Trp Leu Asn Ser Thr Asp Leu Lys Ala Ser Ser
705                 710                 715                 720

Ala Asp Pro Asn Tyr Gly Trp Glu Asp Ser Glu Tyr Ile Pro Glu Ala
```

```
                725                 730                 735

Ala Thr Asp Gly Ser Pro Gln Pro Ile Leu Lys Ala Gly Gly Ala Pro
            740                 745                 750

Gly Gly Asn Pro Thr Leu Tyr His Asp Leu Val Lys Val Ser Ala Thr
        755                 760                 765

Ile Thr Asn Thr Gly Asn Val Ala Gly Tyr Glu Val Pro Gln Leu Tyr
    770                 775                 780

Val Ser Leu Gly Gly Pro Asn Glu Pro Arg Val Val Leu Arg Lys Phe
785                 790                 795                 800

Asp Arg Ile His Leu Ala Pro Gly Glu Gln Lys Val Trp Thr Thr Thr
                805                 810                 815

Leu Thr Arg Arg Asp Leu Ala Asn Trp Asp Val Glu Ala Gln Asp Trp
            820                 825                 830

Val Ile Thr Lys Tyr Pro Lys Arg Val Tyr Val Gly Ser Ser Ser Arg
        835                 840                 845

Lys Leu Pro Leu Arg Ala Pro Leu Pro Arg Val Gln
    850                 855                 860


<210> SEQ ID NO 183
<211> LENGTH: 3032
<212> TYPE: DNA
<213> ORGANISM: Thielavia terrestris

<400> SEQUENCE: 183

atgaagcctg ccattgtgct ttccagcctg gcctgcagcg gtcttgctgc cgccagtgcg      60

gtcagctcgt cggacaaggt atggttaact tgcaggttcc gtcgcattcg tctcccctt     120

cattcccccct ttttcccttc tcccgccgtt gcagcgaagg ctgcgagagt ccattcattg     180

gaccctcttg ttttattttc cgttccaagc atcgcccggg aagttcaccc gctgccaaga     240

ttcgctttag ccagattggc gagcccgttg cgcgttgcaa cccgctcccg ccatgcggct     300

cagatctgcg gctcaatggc tcctcgtgct cccggcgaga agcagcggtc ttgctgacaa     360

aaactcccac cagccgcttg agaaaaggac actcgcaacg tcggaacctt tctacccgtc     420

gccatggatg aacccggacg ccgacggttg gaccgaggcc tatgcccgcg ctaaggagtt     480

cgtctcccgg atgacgctgc tggagaaggt caacctgacc acgggggttg ggtaagtgcg     540

aaccgggcct gggaccgtgg aatgcgagct gtgctgatcg tcctgcagct gggaggcgga     600

gcagtgcgtc ggccaggtgg gcgccattcc tcgcctgggc ctgcggagct tgtgcatgca     660

ggactctccg ctcggtgtcc gggggaccga cttcaactcc gggttccctt ccggccagac     720

ggcggccgcc accttcgatc gcggcctgat ctaccggcgc ggctatgcca tgggccagga     780

ggccaggggc aagggagtca atgtcctgct cggacctgtt gccggccccc ttggacgtgc     840

ccctaccggc ggtcggaact gggaagggtt ctcccctgac cctgttctca ccggcgtggg     900

catggccgag tccatcaagg gcatccaaga cgccggcacg attgcttgtg cgaagcactt     960

tattggcaac gagcaaggtg agccgcgatt gcagtcccgg ggctttccga gaggaagaac    1020

gtgctaacag acgtgcagag cacttcaggc aagtggggga ggcgcaaggt tacgggttca    1080

acatcagcga ggccctgtcg tccaacattg acgacaagac cctgcacgag ctctacctct    1140

ggccgtttgc ggacgccgtg agggccggcg tcggctccgt catgtgctcg taccagcagc    1200

tcaacaactc gtacagctgc cagaactcca agctcctgaa tggcctgctc aagggcgaac    1260

tcggtttcca gggcttcgtc atgagcgatt ggcaggccca gcacacgggc gccgcaagcg    1320

ctgttgccgg cctcgacatg accatgccgg gagacaccga gttcaacacg ggccggagct    1380
```

actggggcgc caacctgacg ctcgcggtgc tcaacggcac cgtccccgcc taccgcatcg 1440
acgacatggc catgcgcatc atggccgcct tcttcaaggt caacaaggac atcaagctgg 1500
accccatcaa cttctccttc tggaccctgg acacgtacgg cccgattcac tgggcggcgc 1560
agacgggcta ccagcagatc aactaccacg tggatgtgcg agccgaccac ggcagcctta 1620
tccgggagat cggcgccaag ggaaccgtgc tcctcaagaa caccggctct ctgcccttga 1680
agaagccgaa attcctggcc gtgattggcg aggacgccgg ccccaacacc agcgggccga 1740
actcttgctc cgacagggga tgtgacaatg gcactctcgc catgggctgg ggttccggca 1800
ccgccaactt cccgtacgtc gtcacgcccg atgccgcgct gcaggcgcag gccctccagg 1860
acggttcgcg ctacgagagc atcctgtcca actatgcgac atcgcaaata aaggctcttg 1920
tgtcacaagc caacgtgaca gcaatcgtct ttgtcaacgc cgactcgggc gagggctaca 1980
tcaatgtgga cggaaacatg ggcgaccgga agaacctgac gctgtggaag gatggcgacg 2040
cgctggtcaa gaacgtggcc agctggtgct ccaacaccat cgtcgtgatc cattccccgg 2100
gcccggttct gctgaccgag tggtacaaca gccccaacgt taccgctatc ctctgggccg 2160
gtctccccgg ccaagagtcc ggcaactcga tcgccgacgt tctgtacggc agggtcaacc 2220
ctgccgcgcg gtcgccgttc acgtggggcc caacccgcga gagttacggg accgatgttc 2280
tctacacgcc gaacaacggc aacggcgcgc cgcaggacga cttcaccgag ggcgtcttca 2340
tcgactaccg ctactttgac aagaccaact cgtccgtcat ttacgagttc ggccacggcc 2400
tcagctacac cacgtttgag tacagcaaca tccgggtaca gaagtcgaac gcgggcaagt 2460
acgagcccac gacgggcaag acctcgcccg cgcccacctt tggcaacttc tcgaccaacc 2520
tcaaagacta cgtgttcccg agccacgagt tcccttacgt ttacgagtac atctatcctt 2580
acctcaacac gaccgacccc aaggcggcct cgggcgacgc gaactacggc cagacggccg 2640
acaagttcct cccgccgcac gcgaccgact cgtcggccca gccgctgctg cgctcgtcgg 2700
gcaagaactc gccgggcggc aaccggcagt tgtacgacgt catgtacacg atcacggccg 2760
acatcaagaa cacgggctcg atcgtcggcg aggaggtgcc gcagctgtac gtcgcgctgg 2820
gcgggccgga cgaccccaag gtgcagctgc gcgactttga ccgcatccgc atcgacccgg 2880
gcaagacggc gcagttccgc ggcacgctga cccgcaggga cctgagcaac tgggatacga 2940
cgctgcagga ctgggtcatt agcaagtaca agaagacggc gtatgtgggg aggagcagcc 3000
ggaagctgga cttgagcatt gagttgccgt ga 3032

<210> SEQ ID NO 184
<211> LENGTH: 872
<212> TYPE: PRT
<213> ORGANISM: Thielavia terrestris

<400> SEQUENCE: 184

Met Lys Pro Ala Ile Val Leu Ser Ser Leu Ala Cys Ser Gly Leu Ala
1 5 10 15

Ala Ala Ser Ala Val Ser Ser Ser Asp Lys Pro Leu Glu Lys Arg Thr
20 25 30

Leu Ala Thr Ser Glu Pro Phe Tyr Pro Ser Pro Trp Met Asn Pro Asp
35 40 45

Ala Asp Gly Trp Thr Glu Ala Tyr Ala Arg Ala Lys Glu Phe Val Ser
50 55 60

Arg Met Thr Leu Leu Glu Lys Val Asn Leu Thr Thr Gly Val Gly Trp
65 70 75 80

-continued

```
Glu Ala Glu Gln Cys Val Gly Gln Val Gly Ala Ile Pro Arg Leu Gly
                85                  90                  95

Leu Arg Ser Leu Cys Met Gln Asp Ser Pro Leu Gly Val Arg Gly Thr
            100                 105                 110

Asp Phe Asn Ser Gly Phe Pro Ser Gly Gln Thr Ala Ala Ala Thr Phe
        115                 120                 125

Asp Arg Gly Leu Ile Tyr Arg Arg Gly Tyr Ala Met Gly Gln Glu Ala
    130                 135                 140

Arg Gly Lys Gly Val Asn Val Leu Leu Gly Pro Val Ala Gly Pro Leu
145                 150                 155                 160

Gly Arg Ala Pro Thr Gly Gly Arg Asn Trp Glu Gly Phe Ser Pro Asp
                165                 170                 175

Pro Val Leu Thr Gly Val Gly Met Ala Glu Ser Ile Lys Gly Ile Gln
            180                 185                 190

Asp Ala Gly Thr Ile Ala Cys Ala Lys His Phe Ile Gly Asn Glu Gln
        195                 200                 205

Glu His Phe Arg Gln Val Gly Glu Ala Gln Gly Tyr Gly Phe Asn Ile
    210                 215                 220

Ser Glu Ala Leu Ser Ser Asn Ile Asp Asp Lys Thr Leu His Glu Leu
225                 230                 235                 240

Tyr Leu Trp Pro Phe Ala Asp Ala Val Arg Ala Gly Val Gly Ser Val
                245                 250                 255

Met Cys Ser Tyr Gln Gln Leu Asn Asn Ser Tyr Ser Cys Gln Asn Ser
            260                 265                 270

Lys Leu Leu Asn Gly Leu Leu Lys Gly Glu Leu Gly Phe Gln Gly Phe
        275                 280                 285

Val Met Ser Asp Trp Gln Ala Gln His Thr Gly Ala Ala Ser Ala Val
    290                 295                 300

Ala Gly Leu Asp Met Thr Met Pro Gly Asp Thr Glu Phe Asn Thr Gly
305                 310                 315                 320

Arg Ser Tyr Trp Gly Ala Asn Leu Thr Leu Ala Val Leu Asn Gly Thr
                325                 330                 335

Val Pro Ala Tyr Arg Ile Asp Asp Met Ala Met Arg Ile Met Ala Ala
            340                 345                 350

Phe Phe Lys Val Asn Lys Asp Ile Lys Leu Asp Pro Ile Asn Phe Ser
        355                 360                 365

Phe Trp Thr Leu Asp Thr Tyr Gly Pro Ile His Trp Ala Ala Gln Thr
    370                 375                 380

Gly Tyr Gln Gln Ile Asn Tyr His Val Asp Val Arg Ala Asp His Gly
385                 390                 395                 400

Ser Leu Ile Arg Glu Ile Gly Ala Lys Gly Thr Val Leu Leu Lys Asn
                405                 410                 415

Thr Gly Ser Leu Pro Leu Lys Lys Pro Lys Phe Leu Ala Val Ile Gly
            420                 425                 430

Glu Asp Ala Gly Pro Asn Thr Ser Gly Pro Asn Ser Cys Ser Asp Arg
        435                 440                 445

Gly Cys Asp Asn Gly Thr Leu Ala Met Gly Trp Gly Ser Gly Thr Ala
    450                 455                 460

Asn Phe Pro Tyr Val Val Thr Pro Asp Ala Ala Leu Gln Ala Gln Ala
465                 470                 475                 480

Leu Gln Asp Gly Ser Arg Tyr Glu Ser Ile Leu Ser Asn Tyr Ala Thr
                485                 490                 495
```

```
Ser Gln Ile Lys Ala Leu Val Ser Gln Ala Asn Val Thr Ala Ile Val
            500                 505                 510

Phe Val Asn Ala Asp Ser Gly Glu Gly Tyr Ile Asn Val Asp Gly Asn
        515                 520                 525

Met Gly Asp Arg Lys Asn Leu Thr Leu Trp Lys Asp Gly Asp Ala Leu
    530                 535                 540

Val Lys Asn Val Ala Ser Trp Cys Ser Asn Thr Ile Val Val Ile His
545                 550                 555                 560

Ser Pro Gly Pro Val Leu Leu Thr Glu Trp Tyr Asn Ser Pro Asn Val
                565                 570                 575

Thr Ala Ile Leu Trp Ala Gly Leu Pro Gly Gln Glu Ser Gly Asn Ser
            580                 585                 590

Ile Ala Asp Val Leu Tyr Gly Arg Val Asn Pro Ala Ala Arg Ser Pro
        595                 600                 605

Phe Thr Trp Gly Pro Thr Arg Glu Ser Tyr Gly Thr Asp Val Leu Tyr
    610                 615                 620

Thr Pro Asn Asn Gly Asn Gly Ala Pro Gln Asp Asp Phe Thr Glu Gly
625                 630                 635                 640

Val Phe Ile Asp Tyr Arg Tyr Phe Asp Lys Thr Asn Ser Ser Val Ile
                645                 650                 655

Tyr Glu Phe Gly His Gly Leu Ser Tyr Thr Thr Phe Glu Tyr Ser Asn
            660                 665                 670

Ile Arg Val Gln Lys Ser Asn Ala Gly Lys Tyr Glu Pro Thr Thr Gly
        675                 680                 685

Lys Thr Ser Pro Ala Pro Thr Phe Gly Asn Phe Ser Thr Asn Leu Lys
    690                 695                 700

Asp Tyr Val Phe Pro Ser His Glu Phe Pro Tyr Val Tyr Glu Tyr Ile
705                 710                 715                 720

Tyr Pro Tyr Leu Asn Thr Thr Asp Pro Lys Ala Ala Ser Gly Asp Ala
                725                 730                 735

Asn Tyr Gly Gln Thr Ala Asp Lys Phe Leu Pro Pro His Ala Thr Asp
            740                 745                 750

Ser Ser Ala Gln Pro Leu Leu Arg Ser Ser Gly Lys Asn Ser Pro Gly
        755                 760                 765

Gly Asn Arg Gln Leu Tyr Asp Val Met Tyr Thr Ile Thr Ala Asp Ile
    770                 775                 780

Lys Asn Thr Gly Ser Ile Val Gly Glu Glu Val Pro Gln Leu Tyr Val
785                 790                 795                 800

Ala Leu Gly Gly Pro Asp Asp Pro Lys Val Gln Leu Arg Asp Phe Asp
                805                 810                 815

Arg Ile Arg Ile Asp Pro Gly Lys Thr Ala Gln Phe Arg Gly Thr Leu
            820                 825                 830

Thr Arg Arg Asp Leu Ser Asn Trp Asp Thr Thr Leu Gln Asp Trp Val
        835                 840                 845

Ile Ser Lys Tyr Lys Lys Thr Ala Tyr Val Gly Arg Ser Ser Arg Lys
    850                 855                 860

Leu Asp Leu Ser Ile Glu Leu Pro
865                 870
```

<210> SEQ ID NO 185
<211> LENGTH: 2793
<212> TYPE: DNA
<213> ORGANISM: Penicillium oxalicum

<400> SEQUENCE: 185

```
atgaggagct caacgacggt tctggccttt gtgtcatacg ggagttttgg gattgcggca     60
gcgaagccca tacaagagca caaggtatga acggttttct ttaagggaga acgcgagata    120
taacgattcg agagtaacgg gcactgacca ttttgttctc tcaaagcccg agcttctgaa    180
tagctttcac ggctttcaga ttgaagagcc gtattcgccg ccgttttatc cctcgccatg    240
gatgaatcct cgtgctgaag gctgggagga tgcgtatcag aaggcgcttg catttgtctc    300
tcaactgacg ttactcgaga aggtcaatct gacgacgggt gttgggtgag tgattgccct    360
tttcctctat gatctgtgcg acagtgggct gaacatgttc aaagttggga aaacggacca    420
tgtgtaggaa ataccggatc ggtccctcgc cttggcttca aggggctttg cttgcaagac    480
tctcctcaag gtgtgagatt tgccgactat gcatctgctt tcacgtccag tcagatggct    540
gctgccacat ttgacaagac ggttctttat gagcgtggtg ttgccatggc tcaagagcac    600
aagggcaagg gcatcacggt gcaactgggc cccgtcgctg gccctttggg ccgcgcccct    660
gaaggaggcc gaaactggga aggattctcg cccgatcccg tcctgaacgg cattgcgatg    720
gccgagacca tcaagggcat gcaagatacc ggagtcttgg cctgcgcgaa acattatgtt    780
ggaaacgaac aagagcactt ccgacaagca ggcgagtctg ccgggcatgg atacaacatt    840
gctgaatcga tctcgtcgaa cattgacgat cgtactatgc atgaaatgta cttgtggcct    900
tttgctgatg ccgtacgtgc tggagtggca tcttttatgt gctcctacaa ccagatcaac    960
aactcgtacg gatgccaaaa cagtcacact ctaaacaaac tcctcaagag cgagttgggc   1020
ttccaagggt tcgtgatgag tgactggcaa gcacaacact ctggagtatc gtcggcgctg   1080
gccgggctcg atatgacaat gccaggagat actgaattcg acaccggact cagcttttgg   1140
ggatccaatc tcactattgc ggttctgaac ggcaccgtgc ccgagtggag gattgacgat   1200
atggcgatgc ggatcatggc cgcttatttc aaagtcggtc tgacaattga agatcagcct   1260
gacgtgaatt tcaactcatg gacctacgat acctatggtt acaaatactt ttacagcaag   1320
gagggttacg agaaagtgaa ctggcatgtc gacgtgcgtg caaaccacgc ccaacagatt   1380
cgtgagacgg ccgcaaaggg aactgtgctt ctcaaaaaca ccaatggtgc tcttccgctg   1440
aaacgacctt ccttcgtcgc cgttgttggc gaagatgcgg gtccaaatcc caagggtccg   1500
aatgggtgtc ctgatcgtgg ctgcgatgag ggaaccctgg cgatgggatg ggatctggc    1560
tcgacccagt tcccgttcct tgttactcca gactctgcga ttcaagccaa ggtcttggag   1620
tatggtggcc gatatgagag tattttggac aactacgatg aaagtgccat ctccgcactg   1680
gtctcgcagc ctgatgctac ttgcatcgtc tttggcaact cggattctgg cgaagctttc   1740
atcaccgtcg acggcaactg gggggatcgg aataacctca ctctttggca aaatgccgac   1800
gcggtgatcc gcaatgtcag tgctctgtgc agcaacacca ttgtcgttct tcacactgtc   1860
ggccctgtgc tgttgaccga ttactatgag caccccaaca tcacagccat tgtctgggcc   1920
ggcctacctg gcgaagaatc agggaatgct cttgtcgata tcctctgggg cgatgtcaac   1980
ccagccggtc gcacgccatt cacatgggcc aagagccgtg aagactatgg cacagacgtg   2040
atgtatgtgc ccaacaacgg cgaacaggca ccccagcaat ccttctccga aggcatcttc   2100
cttgactacc ggcattttga ccaagctggc attgatccca tctacgagtt cggccacggt   2160
ctctcatata ccaatttctc atactctgac ctccgcatcg tcaccaaaca cgttcgtccc   2220
tatcgaccca cgacaggcat gaccacgcaa gcacctatca tcggacccct ccccagccca   2280
aacctcaccg agtatcaatt ccctgctact ttcaaataca tcccggcctt tatctatccc   2340
```

```
tacctcaaca gcacagagtc cctccgcgcc gcctcaaaag accctcacta cggcagcacc   2400

gcattcattc cccctcatgc cctcgacagc tccccacagc ctctcaaccc agcgggtgac   2460

cccatcgcct ccggcggtaa cagtatgctc tatcaggagc tctacgaaat caccgccaaa   2520

atcaccaaca ccggcaatct agccggtgac gaggttgtcc aactgtacgt caacctcggt   2580

ggcgacaatc ctcctcgaca gcttcgagga tttgaccgaa tccacctcct gcccggccag   2640

agtaaggtgt tccgagcgac gttgacacgt cgggacttga gtaattggga cgttgcggcg   2700

cagaattggc gcatcatcag gtccgccaag gaggtttatg tcggacgctc aagtcgagat   2760

ctgcccttga gcgcgcgatt ggagtcatgg taa                               2793


<210> SEQ ID NO 186
<211> LENGTH: 872
<212> TYPE: PRT
<213> ORGANISM: Penicillium oxalicum

<400> SEQUENCE: 186

Met Arg Ser Ser Thr Thr Val Leu Ala Phe Val Ser Tyr Gly Ser Phe
1               5                   10                  15

Gly Ile Ala Ala Ala Lys Pro Ile Gln Glu His Lys Ile Glu Glu Pro
            20                  25                  30

Tyr Ser Pro Pro Phe Tyr Pro Ser Pro Trp Met Asn Pro Arg Ala Glu
        35                  40                  45

Gly Trp Glu Asp Ala Tyr Gln Lys Ala Leu Ala Phe Val Ser Gln Leu
    50                  55                  60

Thr Leu Leu Glu Lys Val Asn Leu Thr Thr Gly Val Gly Trp Glu Asn
65                  70                  75                  80

Gly Pro Cys Val Gly Asn Thr Gly Ser Val Pro Arg Leu Gly Phe Lys
                85                  90                  95

Gly Leu Cys Leu Gln Asp Ser Pro Gln Gly Val Arg Phe Ala Asp Tyr
            100                 105                 110

Ala Ser Ala Phe Thr Ser Ser Gln Met Ala Ala Ala Thr Phe Asp Lys
        115                 120                 125

Thr Val Leu Tyr Glu Arg Gly Val Ala Met Ala Gln Glu His Lys Gly
    130                 135                 140

Lys Gly Ile Thr Val Gln Leu Gly Pro Val Ala Gly Pro Leu Gly Arg
145                 150                 155                 160

Ala Pro Glu Gly Gly Arg Asn Trp Glu Gly Phe Ser Pro Asp Pro Val
                165                 170                 175

Leu Asn Gly Ile Ala Met Ala Glu Thr Ile Lys Gly Met Gln Asp Thr
            180                 185                 190

Gly Val Leu Ala Cys Ala Lys His Tyr Val Gly Asn Glu Gln Glu His
        195                 200                 205

Phe Arg Gln Ala Gly Glu Ser Ala Gly His Gly Tyr Asn Ile Ala Glu
    210                 215                 220

Ser Ile Ser Ser Asn Ile Asp Asp Arg Thr Met His Glu Met Tyr Leu
225                 230                 235                 240

Trp Pro Phe Ala Asp Ala Val Arg Ala Gly Val Ala Ser Phe Met Cys
                245                 250                 255

Ser Tyr Asn Gln Ile Asn Asn Ser Tyr Gly Cys Gln Asn Ser His Thr
            260                 265                 270

Leu Asn Lys Leu Leu Lys Ser Glu Leu Gly Phe Gln Gly Phe Val Met
        275                 280                 285

Ser Asp Trp Gln Ala Gln His Ser Gly Val Ser Ser Ala Leu Ala Gly
```

-continued

```
    290                 295                 300

Leu Asp Met Thr Met Pro Gly Asp Thr Glu Phe Asp Thr Gly Leu Ser
305                 310                 315                 320

Phe Trp Gly Ser Asn Leu Thr Ile Ala Val Leu Asn Gly Thr Val Pro
                325                 330                 335

Glu Trp Arg Ile Asp Asp Met Ala Met Arg Ile Met Ala Ala Tyr Phe
            340                 345                 350

Lys Val Gly Leu Thr Ile Glu Asp Gln Pro Asp Val Asn Phe Asn Ser
        355                 360                 365

Trp Thr Tyr Asp Thr Tyr Gly Tyr Lys Tyr Phe Tyr Ser Lys Glu Gly
    370                 375                 380

Tyr Glu Lys Val Asn Trp His Val Asp Val Arg Ala Asn His Ala Gln
385                 390                 395                 400

Gln Ile Arg Glu Thr Ala Ala Lys Gly Thr Val Leu Leu Lys Asn Thr
                405                 410                 415

Asn Gly Ala Leu Pro Leu Lys Arg Pro Ser Phe Val Ala Val Val Gly
            420                 425                 430

Glu Asp Ala Gly Pro Asn Pro Lys Gly Pro Asn Gly Cys Pro Asp Arg
        435                 440                 445

Gly Cys Asp Glu Gly Thr Leu Ala Met Gly Trp Gly Ser Gly Ser Thr
    450                 455                 460

Gln Phe Pro Phe Leu Val Thr Pro Asp Ser Ala Ile Gln Ala Lys Val
465                 470                 475                 480

Leu Glu Tyr Gly Gly Arg Tyr Glu Ser Ile Leu Asp Asn Tyr Asp Glu
                485                 490                 495

Ser Ala Ile Ser Ala Leu Val Ser Gln Pro Asp Ala Thr Cys Ile Val
            500                 505                 510

Phe Gly Asn Ser Asp Ser Gly Glu Ala Phe Ile Thr Val Asp Gly Asn
        515                 520                 525

Trp Gly Asp Arg Asn Asn Leu Thr Leu Trp Gln Asn Ala Asp Ala Val
    530                 535                 540

Ile Arg Asn Val Ser Ala Leu Cys Ser Asn Thr Ile Val Val Leu His
545                 550                 555                 560

Thr Val Gly Pro Val Leu Leu Thr Asp Tyr Tyr Glu His Pro Asn Ile
                565                 570                 575

Thr Ala Ile Val Trp Ala Gly Leu Pro Gly Glu Glu Ser Gly Asn Ala
            580                 585                 590

Leu Val Asp Ile Leu Trp Gly Asp Val Asn Pro Ala Gly Arg Thr Pro
        595                 600                 605

Phe Thr Trp Ala Lys Ser Arg Glu Asp Tyr Gly Thr Asp Val Met Tyr
    610                 615                 620

Val Pro Asn Asn Gly Glu Gln Ala Pro Gln Gln Ser Phe Ser Glu Gly
625                 630                 635                 640

Ile Phe Leu Asp Tyr Arg His Phe Asp Gln Ala Gly Ile Asp Pro Ile
                645                 650                 655

Tyr Glu Phe Gly His Gly Leu Ser Tyr Thr Asn Phe Ser Tyr Ser Asp
            660                 665                 670

Leu Arg Ile Val Thr Lys His Val Arg Pro Tyr Arg Pro Thr Thr Gly
        675                 680                 685

Met Thr Thr Gln Ala Pro Ile Ile Gly Pro Leu Pro Ser Pro Asn Leu
    690                 695                 700

Thr Glu Tyr Gln Phe Pro Ala Thr Phe Lys Tyr Ile Pro Ala Phe Ile
705                 710                 715                 720
```

```
Tyr Pro Tyr Leu Asn Ser Thr Glu Ser Leu Arg Ala Ala Ser Lys Asp
                725                 730                 735

Pro His Tyr Gly Ser Thr Ala Phe Ile Pro Pro His Ala Leu Asp Ser
            740                 745                 750

Ser Pro Gln Pro Leu Asn Pro Ala Gly Asp Pro Ile Ala Ser Gly Gly
        755                 760                 765

Asn Ser Met Leu Tyr Gln Glu Leu Tyr Glu Ile Thr Ala Lys Ile Thr
    770                 775                 780

Asn Thr Gly Asn Leu Ala Gly Asp Glu Val Val Gln Leu Tyr Val Asn
785                 790                 795                 800

Leu Gly Gly Asp Asn Pro Pro Arg Gln Leu Arg Gly Phe Asp Arg Ile
                805                 810                 815

His Leu Leu Pro Gly Gln Ser Lys Val Phe Arg Ala Thr Leu Thr Arg
            820                 825                 830

Arg Asp Leu Ser Asn Trp Asp Val Ala Ala Gln Asn Trp Arg Ile Ile
        835                 840                 845

Arg Ser Ala Lys Glu Val Tyr Val Gly Arg Ser Ser Arg Asp Leu Pro
    850                 855                 860

Leu Ser Ala Arg Leu Glu Ser Trp
865                 870


<210> SEQ ID NO 187
<211> LENGTH: 2964
<212> TYPE: DNA
<213> ORGANISM: Penicillium oxalicum

<400> SEQUENCE: 187

atgaagctcg agtggctgga agccacggtg cttgcggccg ccacggttgc tagtgcaaag      60

gtatgttgcc gaatgtaccc ccagttgact tgcgatgact cccaagttgt ttttctttgt     120

gtttactagt ggatctgaca caaatacttt tggtgatata ggatcttgcc tactctcccc     180

ccttctatcc ttctccatgg gcaaccggtg aaggtgaatg ggccgaggcc tacaagaagg     240

ctgtggactt tgtttctggt ctgactcttg ccgagaaggt caacatcacg accggtgctg     300

ggtaggtcca tgcgctgaag atgattgctc tgtgtatgca cattgcggct gacaattgtg     360

tccagatggg aacaggagcg ttgtgtgggt gagaccggcg gtgtccctcg gtaagattgt     420

actctcatct aatatcctct tgggtccagc aaagggcaaa tcaaattgac atgcgaaccg     480

ttgaatcaga cttggaatgt ggggaatgtg catgcaagat tctcctctcg gcgttcgtaa     540

tggtgagaca aactctttct caaggatgat tcacttcacg cgaaagacta accaaccgaa     600

tgtagccgac tacagctctg ccttccccgc cggtgtgaat gtggctgcca cctgggaccg     660

acgactcgcg taccagcgtg gtacggccat gggcgaggag catcgcgaca agggtgtcga     720

cgtgcagctt ggccccgtcg ctggtccatt gggcaagaac cccgacggtg gtcgtggctg     780

ggaaggcttt tctcccgatc cggttctgac cggtgttatg gtggccgaga caatcaaggg     840

tatccaagat gctggtgtca ttgcttgcgc caagcacttc atcatgaatg agcaggagca     900

cttccgccag gcgggtgaag cccagggata cggattcaat atttctcaga gtttgagctc     960

caacgtcgat gacaagacca tgcacgagct gtacttgtgg ccgtttgtcg attcggttcg    1020

ggccggtgtg ggttccgtca tgtgctctta caaccagatc aacaacagct acgggtgctc    1080

caacagctac acgctcaaca aattgctcaa gggcgagctc ggctttcagg gcttcgtcat    1140

gagcgactgg ggtgcgcacc acagcggtgt cggtgacgcc cttgccggtc tcgacatgtc    1200
```

-continued

```
tatgcccggt gatgtgattc ttggtagccc ctactccttc tggggaacta acttgaccgt   1260

ctctgtgctg aacagcacca tccccgaatg gcgtctggat gacatggccg ttcgtatcat   1320

ggctgcctac tacaaggtcg gcagagatcg tcatcgcact cctcccaact tcagctcctg   1380

gacccgcgat gagtacggct acgagcactt tattgtccag gagaactatg tcaagctcaa   1440

cgagcgtgtc aatgttcaac gtgatcatgc caacgtcatc cgcaagattg gctccgacag   1500

tatcgtgatg ctcaagaaca acgggggtct gcctttgact catcaagagc gtctggtggc   1560

tatcttgggc gaggatgctg gttccaacgc ctacggcgcc aacggctgca gtgaccgagg   1620

ctgtgacaac ggtaccttgg ccatgggctg ggcagtgga acggccaact tcccctacct   1680

gatcactccc gagcaagcca ttcagaatga ggttctcaac tacggcaacg gtgacaccaa   1740

tgtctttgct gtcacagaca acggtgccct cagccaaatg gctgcccttg cttcaaccgc   1800

aagtgttgca ttggtgttcg tcaacgctga ttcgggcgag ggctacatca gtgtggacgg   1860

caacgagggc gatcgcaaga acatgaccct gtggaagaac ggcgaggagc tgatcaagac   1920

cgccactgcc aactgcaaca acaccatcgt catcatgcac acccccaacg ccgtcctggt   1980

cgattcatgg tacgacaatg agaacatcac tgccattctg tgggctggta tgcccggcca   2040

agagagtggt cgtagcttgg ttgatgttct ctacggccgc acgaaccctg gtggcaagac   2100

ccccttcacc tggggtaagg agcgcaagga ttggggatct cctcttctga ctaaacccaa   2160

caacggccac ggtgctcctc aggatgactt caccgatgtt ctgattgact atcgccgttt   2220

cgacaaggac aacgtggagc ccatcttcga gttcggcttc ggtctgagct acaccaaatt   2280

tgagttctct gacatccagg tcaaggcgct gaatcacggc gagtacaacg ccaccgtggg   2340

caagaccaag cctgcccctt cgttgggcaa gcctggtaat gcctccgatc atctgttccc   2400

cagcaacatc aaccgtgtgc gacagtacct ttacccttac ctgaactcga ccgatctgaa   2460

ggcgtctgcc aacgaccctg actatggcat gaatgcatcg gcgtacattc ctccccatgc   2520

caccgacagc gacccacagg accttctccc cgccagcgga ccttccggtg gcaaccctgg   2580

tttgtttgag gaccttattg aggtgactgc tactgtcacc aacaccggct cagttactgg   2640

tgacgaggtt ccccagctgg taagttctcc cgaattccga ctccaagcgc tttgcgcgag   2700

attgaggttt ctgacaggaa tgttatatag tacgtttcgc ttggcggtgc cgatgacccc   2760

gttaaggtcc tccgtgcctt cgaccgtgtc acgatcgccc ctggtcagaa gctccggtgg   2820

acagcaaccc tcaaccgtcg tgatctgtcc aactgggatg tcccatcaca gaactggatc   2880

atctcagacg cccccaagaa ggtgtgggtg ggcaactcgt cgcgcaagct gcctctttca   2940

gccgatctgc ccaaggtgca gtaa                                          2964
```

<210> SEQ ID NO 188
<211> LENGTH: 861
<212> TYPE: PRT
<213> ORGANISM: Penicillium oxalicum

<400> SEQUENCE: 188

```
Met Lys Leu Glu Trp Leu Glu Ala Thr Val Leu Ala Ala Ala Thr Val
1               5                   10                  15

Ala Ser Ala Lys Asp Leu Ala Tyr Ser Pro Pro Phe Tyr Pro Ser Pro
            20                  25                  30

Trp Ala Thr Gly Glu Gly Glu Trp Ala Glu Ala Tyr Lys Lys Ala Val
        35                  40                  45

Asp Phe Val Ser Gly Leu Thr Leu Ala Glu Lys Val Asn Ile Thr Thr
    50                  55                  60
```

```
Gly Ala Gly Trp Glu Gln Glu Arg Cys Val Gly Glu Thr Gly Gly Val
65                  70                  75                  80

Pro Arg Leu Gly Met Trp Gly Met Cys Met Gln Asp Ser Pro Leu Gly
                85                  90                  95

Val Arg Asn Ala Asp Tyr Ser Ser Ala Phe Pro Ala Gly Val Asn Val
            100                 105                 110

Ala Ala Thr Trp Asp Arg Arg Leu Ala Tyr Gln Arg Gly Thr Ala Met
        115                 120                 125

Gly Glu Glu His Arg Asp Lys Gly Val Asp Val Gln Leu Gly Pro Val
    130                 135                 140

Ala Gly Pro Leu Gly Lys Asn Pro Asp Gly Gly Arg Gly Trp Glu Gly
145                 150                 155                 160

Phe Ser Pro Asp Pro Val Leu Thr Gly Val Met Val Ala Glu Thr Ile
                165                 170                 175

Lys Gly Ile Gln Asp Ala Gly Val Ile Ala Cys Ala Lys His Phe Ile
            180                 185                 190

Met Asn Glu Gln Glu His Phe Arg Gln Ala Gly Glu Ala Gln Gly Tyr
        195                 200                 205

Gly Phe Asn Ile Ser Gln Ser Leu Ser Ser Asn Val Asp Asp Lys Thr
    210                 215                 220

Met His Glu Leu Tyr Leu Trp Pro Phe Val Asp Ser Val Arg Ala Gly
225                 230                 235                 240

Val Gly Ser Val Met Cys Ser Tyr Asn Gln Ile Asn Asn Ser Tyr Gly
                245                 250                 255

Cys Ser Asn Ser Tyr Thr Leu Asn Lys Leu Leu Lys Gly Glu Leu Gly
            260                 265                 270

Phe Gln Gly Phe Val Met Ser Asp Trp Gly Ala His His Ser Gly Val
        275                 280                 285

Gly Asp Ala Leu Ala Gly Leu Asp Met Ser Met Pro Gly Asp Val Ile
    290                 295                 300

Leu Gly Ser Pro Tyr Ser Phe Trp Gly Thr Asn Leu Thr Val Ser Val
305                 310                 315                 320

Leu Asn Ser Thr Ile Pro Glu Trp Arg Leu Asp Asp Met Ala Val Arg
                325                 330                 335

Ile Met Ala Ala Tyr Tyr Lys Val Gly Arg Asp Arg His Arg Thr Pro
            340                 345                 350

Pro Asn Phe Ser Ser Trp Thr Arg Asp Glu Tyr Gly Tyr Glu His Phe
        355                 360                 365

Ile Val Gln Glu Asn Tyr Val Lys Leu Asn Glu Arg Val Asn Val Gln
    370                 375                 380

Arg Asp His Ala Asn Val Ile Arg Lys Ile Gly Ser Asp Ser Ile Val
385                 390                 395                 400

Met Leu Lys Asn Asn Gly Gly Leu Pro Leu Thr His Gln Glu Arg Leu
                405                 410                 415

Val Ala Ile Leu Gly Glu Asp Ala Gly Ser Asn Ala Tyr Gly Ala Asn
            420                 425                 430

Gly Cys Ser Asp Arg Gly Cys Asp Asn Gly Thr Leu Ala Met Gly Trp
        435                 440                 445

Gly Ser Gly Thr Ala Asn Phe Pro Tyr Leu Ile Thr Pro Glu Gln Ala
    450                 455                 460

Ile Gln Asn Glu Val Leu Asn Tyr Gly Asn Gly Asp Thr Asn Val Phe
465                 470                 475                 480
```

```
Ala Val Thr Asp Asn Gly Ala Leu Ser Gln Met Ala Ala Leu Ala Ser
                485                 490                 495

Thr Ala Ser Val Ala Leu Val Phe Val Asn Ala Asp Ser Gly Glu Gly
            500                 505                 510

Tyr Ile Ser Val Asp Gly Asn Glu Gly Asp Arg Lys Asn Met Thr Leu
        515                 520                 525

Trp Lys Asn Gly Glu Glu Leu Ile Lys Thr Ala Thr Ala Asn Cys Asn
    530                 535                 540

Asn Thr Ile Val Ile Met His Thr Pro Asn Ala Val Leu Val Asp Ser
545                 550                 555                 560

Trp Tyr Asp Asn Glu Asn Ile Thr Ala Ile Leu Trp Ala Gly Met Pro
                565                 570                 575

Gly Gln Glu Ser Gly Arg Ser Leu Val Asp Val Leu Tyr Gly Arg Thr
            580                 585                 590

Asn Pro Gly Gly Lys Thr Pro Phe Thr Trp Gly Lys Glu Arg Lys Asp
        595                 600                 605

Trp Gly Ser Pro Leu Leu Thr Lys Pro Asn Asn Gly His Gly Ala Pro
    610                 615                 620

Gln Asp Asp Phe Thr Asp Val Leu Ile Asp Tyr Arg Arg Phe Asp Lys
625                 630                 635                 640

Asp Asn Val Glu Pro Ile Phe Glu Phe Gly Phe Gly Leu Ser Tyr Thr
                645                 650                 655

Lys Phe Glu Phe Ser Asp Ile Gln Val Lys Ala Leu Asn His Gly Glu
            660                 665                 670

Tyr Asn Ala Thr Val Gly Lys Thr Lys Pro Ala Pro Ser Leu Gly Lys
        675                 680                 685

Pro Gly Asn Ala Ser Asp His Leu Phe Pro Ser Asn Ile Asn Arg Val
    690                 695                 700

Arg Gln Tyr Leu Tyr Pro Tyr Leu Asn Ser Thr Asp Leu Lys Ala Ser
705                 710                 715                 720

Ala Asn Asp Pro Asp Tyr Gly Met Asn Ala Ser Ala Tyr Ile Pro Pro
                725                 730                 735

His Ala Thr Asp Ser Asp Pro Gln Asp Leu Leu Pro Ala Ser Gly Pro
            740                 745                 750

Ser Gly Gly Asn Pro Gly Leu Phe Glu Asp Leu Ile Glu Val Thr Ala
        755                 760                 765

Thr Val Thr Asn Thr Gly Ser Val Thr Gly Asp Glu Val Pro Gln Leu
    770                 775                 780

Tyr Val Ser Leu Gly Gly Ala Asp Asp Pro Val Lys Val Leu Arg Ala
785                 790                 795                 800

Phe Asp Arg Val Thr Ile Ala Pro Gly Gln Lys Leu Arg Trp Thr Ala
                805                 810                 815

Thr Leu Asn Arg Arg Asp Leu Ser Asn Trp Asp Val Pro Ser Gln Asn
            820                 825                 830

Trp Ile Ile Ser Asp Ala Pro Lys Lys Val Trp Val Gly Asn Ser Ser
        835                 840                 845

Arg Lys Leu Pro Leu Ser Ala Asp Leu Pro Lys Val Gln
    850                 855                 860
```

<210> SEQ ID NO 189
<211> LENGTH: 2925
<212> TYPE: DNA
<213> ORGANISM: Talaromyces emersonii

<400> SEQUENCE: 189

-continued

```
atgaggaacg ggttgctcaa ggtcgccgcc cttgcggccg cgtccgccgt caatggcgag     60
gtacgtgcac tctacgccca tgcatggaga attcgtcttt tctctaaccg tccacaatag    120
aacctggcgt attcacctcc cttctaccct tcgccgtggg ccaatggaca gggcgactgg    180
gcagaggcct accagaaggc cgtccagttt gtgtcccaac tcaccctggc cgagaaggtc    240
aacctgacca ccggaactgg gtacgttgac tgatgaaacc tttggatcca cgccatgttc    300
ggactgctga cattgtcaaa gttgggagca ggaccgatgt gtcggtcaag tgggtagcat    360
cccaaggtat gttgattcga gtccccgatc cggttcgctg tggatgctga ctggactgtc    420
aattaggctg ggtttccctg gactttgcat gcaggactct ccgctgggcg ttcgagacag    480
tatgcttgtt catccccgca gtatctcgag catgtgctaa tgcgtttccg caacagctga    540
ctacaactcg gccttccctg ccggtgtcaa tgtcgctgct acctgggacc ggaatctcgc    600
ctaccgtcgc ggcgtagcga tgggcgagga gcatcgcggc aaaggtgtcg acgtgcagct    660
gggccctgtg gccggcccgc tgggcaggtc tcccgatgcg ggcagaaact gggaaggttt    720
cgccccggat cccgtgctga ccggaaacat gatggcgtca accatccagg gtattcaaga    780
tgctggcgtc attgcttgcg ccaagcattt catcctctac gagcaggagc acttccgtca    840
aggcgctcag gacggctatg atatctccga cagtatcagt gccaacgctg acgacaagac    900
gatgcacgag ttgtacttgt ggcccttcgc cgatgctgtt cgcgcgggcg tcggttccgt    960
catgtgctcc tacaaccagg tgaacaacag ctatgcctgc tccaacagct acaccatgaa   1020
caagctgctc aagagcgaac tcggtttcca aggcttcgtc atgaccgact ggggtggcca   1080
ccacagtggt gtgggttccg ccctcgctgg tttggatatg tcgatgcccg gagacattgc   1140
cttcgacagt ggcacttcct tctggggcac gaacctgacc gtcgccgtgc tcaatggcag   1200
tattcccgag tggcgtgttg atgacatggc tgtccgtatc atgtcggctt actacaaagt   1260
cggccgcgac cgctacagcg tccccatcaa ctttgactcg tggaccctgg atacctatgg   1320
tcctgagcac tatgcggtgg gccagggcca gaccaagatt aacgagcacg ttgatgtccg   1380
cggcaaccac gccgaaatca tccacgaaat cggtgctgcc agcgccgtcc ttcttaagaa   1440
caagggtggc cttcctttga cgggcaccga gcggtttgtc ggtgttttcg gagaggatgc   1500
cggatccaac ccctggggtg tgaacggctg cagtgaccga ggctgcgaca atggtacatt   1560
ggccatgggc tggggcagtg gtactgctaa cttcccctat ctggtgacgc cggagcaggc   1620
gatccagaga gaagtcttgt cccgaaacgg aaccttcacc gccatcacgg acaatggcgc   1680
tcttgctgag atggcggcag ccgcctctca ggccgagtaa gtatttccgc tgtcctcgag   1740
ctctctaaag gacgtgactg acccgttcat agtacttgtc tggtcttcgc caacgccgac   1800
tccggtgaag gttacatcac cgtcgacggc aatgagggtg accggaagaa tctgaccctg   1860
tggcaagggg cggatcaggt catccacaac gtctctgcca actgcaacaa caccgtcgtg   1920
gtgttgcaca ctgtcggccc cgttttgatc gatgattggt atgaccaccc caacgtcacg   1980
gccattctct gggctggtct tccgggccag gagagcggta actcgctcgt cgatgtcctc   2040
tacggccggg tcaaccctgg tggaaagact ccgttcactt ggggacgcgc ccgggacgat   2100
tacggtgcgc ctttgatcgt caagccgaac aatggcaagg gcgccccgca gcaggacttt   2160
actgagggta tcttcatcga ctaccgtcgg tttgacaagt acaacatcac cccatctac   2220
gagttcggat tcggtctgag ctacactacc tttgagttct ctcagctcaa tgtgcagccg   2280
atcaatgcgc cgccgtacac tcctgcctcc ggcttcacca aggcagcgca gtcattcggc   2340
```

```
cagccttcca acgcttcgga caacctgtac cccagcgaca tcgagcgggt cccgttgtac   2400

atctacccat ggctcaactc caccgatttg aaggcgtccg ccaatgaccc tgactatggg   2460

ttgcctacgg agaagtacgt tcctcccaac gccacgaacg gcgacccgca gcccattgac   2520

ccggctggcg gtgctcctgg tggcaacccg agtctgtatg agcctgttgc tcgggtcacc   2580

accatcatca ccaacaccgg taaggttacg ggtgacgagg ttcctcaact ggtaagtgtc   2640

ccaacattgg ttgctggagg tcccttttac tgacttcaac tcaagtacgt ctctcttggc   2700

ggtcccgatg acgctcccaa ggttcttcgt ggcttcgacc gtatcaccct tgcgcctggt   2760

cagcagtact tgtggacgac caccctgacg aggcgcgaca tctcgaactg ggaccctgtc   2820

acccagaact gggtcgtgac caactatacc aagacgattt atgttggcaa ctcgtcccgc   2880

aacctgcctt tgcaggcgcc ccttaagcca taccctggaa tttaa                   2925


<210> SEQ ID NO 190
<211> LENGTH: 858
<212> TYPE: PRT
<213> ORGANISM: Talaromyces emersonii

<400> SEQUENCE: 190

Met Arg Asn Gly Leu Leu Lys Val Ala Ala Leu Ala Ala Ala Ser Ala
1               5                   10                  15

Val Asn Gly Glu Asn Leu Ala Tyr Ser Pro Pro Phe Tyr Pro Ser Pro
            20                  25                  30

Trp Ala Asn Gly Gln Gly Asp Trp Ala Glu Ala Tyr Gln Lys Ala Val
        35                  40                  45

Gln Phe Val Ser Gln Leu Thr Leu Ala Glu Lys Val Asn Leu Thr Thr
    50                  55                  60

Gly Thr Gly Trp Glu Gln Asp Arg Cys Val Gly Gln Val Gly Ser Ile
65                  70                  75                  80

Pro Arg Leu Gly Phe Pro Gly Leu Cys Met Gln Asp Ser Pro Leu Gly
                85                  90                  95

Val Arg Asp Thr Asp Tyr Asn Ser Ala Phe Pro Ala Gly Val Asn Val
            100                 105                 110

Ala Ala Thr Trp Asp Arg Asn Leu Ala Tyr Arg Arg Gly Val Ala Met
        115                 120                 125

Gly Glu Glu His Arg Gly Lys Gly Val Asp Val Gln Leu Gly Pro Val
    130                 135                 140

Ala Gly Pro Leu Gly Arg Ser Pro Asp Ala Gly Arg Asn Trp Glu Gly
145                 150                 155                 160

Phe Ala Pro Asp Pro Val Leu Thr Gly Asn Met Met Ala Ser Thr Ile
                165                 170                 175

Gln Gly Ile Gln Asp Ala Gly Val Ile Ala Cys Ala Lys His Phe Ile
            180                 185                 190

Leu Tyr Glu Gln Glu His Phe Arg Gln Gly Ala Gln Asp Gly Tyr Asp
        195                 200                 205

Ile Ser Asp Ser Ile Ser Ala Asn Ala Asp Asp Lys Thr Met His Glu
    210                 215                 220

Leu Tyr Leu Trp Pro Phe Ala Asp Ala Val Arg Ala Gly Val Gly Ser
225                 230                 235                 240

Val Met Cys Ser Tyr Asn Gln Val Asn Asn Ser Tyr Ala Cys Ser Asn
                245                 250                 255

Ser Tyr Thr Met Asn Lys Leu Leu Lys Ser Glu Leu Gly Phe Gln Gly
            260                 265                 270
```

-continued

```
Phe Val Met Thr Asp Trp Gly Gly His His Ser Gly Val Gly Ser Ala
        275                 280                 285

Leu Ala Gly Leu Asp Met Ser Met Pro Gly Asp Ile Ala Phe Asp Ser
    290                 295                 300

Gly Thr Ser Phe Trp Gly Thr Asn Leu Thr Val Ala Val Leu Asn Gly
305                 310                 315                 320

Ser Ile Pro Glu Trp Arg Val Asp Asp Met Ala Val Arg Ile Met Ser
                325                 330                 335

Ala Tyr Tyr Lys Val Gly Arg Asp Arg Tyr Ser Val Pro Ile Asn Phe
            340                 345                 350

Asp Ser Trp Thr Leu Asp Thr Tyr Gly Pro Glu His Tyr Ala Val Gly
        355                 360                 365

Gln Gly Gln Thr Lys Ile Asn Glu His Val Asp Val Arg Gly Asn His
    370                 375                 380

Ala Glu Ile Ile His Glu Ile Gly Ala Ala Ser Ala Val Leu Leu Lys
385                 390                 395                 400

Asn Lys Gly Gly Leu Pro Leu Thr Gly Thr Glu Arg Phe Val Gly Val
                405                 410                 415

Phe Gly Glu Asp Ala Gly Ser Asn Pro Trp Gly Val Asn Gly Cys Ser
            420                 425                 430

Asp Arg Gly Cys Asp Asn Gly Thr Leu Ala Met Gly Trp Gly Ser Gly
        435                 440                 445

Thr Ala Asn Phe Pro Tyr Leu Val Thr Pro Glu Gln Ala Ile Gln Arg
    450                 455                 460

Glu Val Leu Ser Arg Asn Gly Thr Phe Thr Ala Ile Thr Asp Asn Gly
465                 470                 475                 480

Ala Leu Ala Glu Met Ala Ala Ala Ala Ser Gln Ala Asp Thr Cys Leu
                485                 490                 495

Val Phe Ala Asn Ala Asp Ser Gly Glu Gly Tyr Ile Thr Val Asp Gly
            500                 505                 510

Asn Glu Gly Asp Arg Lys Asn Leu Thr Leu Trp Gln Gly Ala Asp Gln
        515                 520                 525

Val Ile His Asn Val Ser Ala Asn Cys Asn Asn Thr Val Val Val Leu
    530                 535                 540

His Thr Val Gly Pro Val Leu Ile Asp Asp Trp Tyr Asp His Pro Asn
545                 550                 555                 560

Val Thr Ala Ile Leu Trp Ala Gly Leu Pro Gly Gln Glu Ser Gly Asn
                565                 570                 575

Ser Leu Val Asp Val Leu Tyr Gly Arg Val Asn Pro Gly Gly Lys Thr
            580                 585                 590

Pro Phe Thr Trp Gly Arg Ala Arg Asp Asp Tyr Gly Ala Pro Leu Ile
        595                 600                 605

Val Lys Pro Asn Asn Gly Lys Gly Ala Pro Gln Gln Asp Phe Thr Glu
    610                 615                 620

Gly Ile Phe Ile Asp Tyr Arg Arg Phe Asp Lys Tyr Asn Ile Thr Pro
625                 630                 635                 640

Ile Tyr Glu Phe Gly Phe Gly Leu Ser Tyr Thr Thr Phe Glu Phe Ser
                645                 650                 655

Gln Leu Asn Val Gln Pro Ile Asn Ala Pro Pro Tyr Thr Pro Ala Ser
            660                 665                 670

Gly Phe Thr Lys Ala Ala Gln Ser Phe Gly Gln Pro Ser Asn Ala Ser
        675                 680                 685

Asp Asn Leu Tyr Pro Ser Asp Ile Glu Arg Val Pro Leu Tyr Ile Tyr
```

```
    690                 695                 700

Pro Trp Leu Asn Ser Thr Asp Leu Lys Ala Ser Ala Asn Asp Pro Asp
705                 710                 715                 720

Tyr Gly Leu Pro Thr Glu Lys Tyr Val Pro Pro Asn Ala Thr Asn Gly
                725                 730                 735

Asp Pro Gln Pro Ile Asp Pro Ala Gly Gly Ala Pro Gly Gly Asn Pro
            740                 745                 750

Ser Leu Tyr Glu Pro Val Ala Arg Val Thr Thr Ile Ile Thr Asn Thr
        755                 760                 765

Gly Lys Val Thr Gly Asp Glu Val Pro Gln Leu Tyr Val Ser Leu Gly
    770                 775                 780

Gly Pro Asp Asp Ala Pro Lys Val Leu Arg Gly Phe Asp Arg Ile Thr
785                 790                 795                 800

Leu Ala Pro Gly Gln Gln Tyr Leu Trp Thr Thr Thr Leu Thr Arg Arg
                805                 810                 815

Asp Ile Ser Asn Trp Asp Pro Val Thr Gln Asn Trp Val Val Thr Asn
            820                 825                 830

Tyr Thr Lys Thr Ile Tyr Val Gly Asn Ser Ser Arg Asn Leu Pro Leu
        835                 840                 845

Gln Ala Pro Leu Lys Pro Tyr Pro Gly Ile
    850                 855
```

<210> SEQ ID NO 191
<211> LENGTH: 871
<212> TYPE: DNA
<213> ORGANISM: Thermoascus crustaceus

<400> SEQUENCE: 191

```
atggcctttt cccagataat ggctattacc ggcgtttttc ttgcctctgc ttccctggtg     60

gctggccatg gctttgttca gaatatcgtg attgatggta aaaggtacct aactacctac    120

cttactatct gatgtcattt acaagaaagg gcacagacac aagcggcaaa aaaaagaaag    180

aaagaaagaa agaaagaaag ctgacaaaaa ttcaacaagt tatggcgggt acatcgtgaa    240

ccaatatcca tacatgtcag atcctccgga ggtcgtcggc tggtctacca ccgcaaccga    300

cctcggattc gtggacggta ccggatacca aggacctgat atcatctgcc acaggggcgc    360

caagcctgca gccctgactg cccaagtggc cgccggagga accgtcaagc tggaatggac    420

tccatggcct gattctcacc acggcccggt gatcaactac cttgctcctt gcaacggtga    480

ctgttccacc gtggacaaga cccaattgaa attcttcaag atcgcccagg ccggtctcat    540

cgatgacaac agtcctcctg gtatctgggc ctcagacaat ctgatagcgg ccaacaacag    600

ctggactgtc accatcccaa ccacaactgc acctggaaac tatgttctaa ggcatgagat    660

cattgctctc cactcagctg ggaacaagga tggtgcgcag aactatcccc agtgcatcaa    720

cctgaaggtc actggaaatg gttctggcaa tcctcctgct ggtgctcttg gaacggcact    780

ctacaaggat acagatccgg gaattctgat caatatctac cagaaacttt ccagctatgt    840

tattcctggt cctgctttgt acactggtta g                                   871
```

<210> SEQ ID NO 192
<211> LENGTH: 251
<212> TYPE: PRT
<213> ORGANISM: Thermoascus crustaceus

<400> SEQUENCE: 192

```
Met Ala Phe Ser Gln Ile Met Ala Ile Thr Gly Val Phe Leu Ala Ser
```

-continued

```
1               5                   10                  15

Ala Ser Leu Val Ala Gly His Gly Phe Val Gln Asn Ile Val Ile Asp
            20                  25                  30

Gly Lys Ser Tyr Gly Gly Tyr Ile Val Asn Gln Tyr Pro Tyr Met Ser
        35                  40                  45

Asp Pro Pro Glu Val Val Gly Trp Ser Thr Thr Ala Thr Asp Leu Gly
    50                  55                  60

Phe Val Asp Gly Thr Gly Tyr Gln Gly Pro Asp Ile Ile Cys His Arg
65                  70                  75                  80

Gly Ala Lys Pro Ala Ala Leu Thr Ala Gln Val Ala Ala Gly Gly Thr
                85                  90                  95

Val Lys Leu Glu Trp Thr Pro Trp Pro Asp Ser His His Gly Pro Val
            100                 105                 110

Ile Asn Tyr Leu Ala Pro Cys Asn Gly Asp Cys Ser Thr Val Asp Lys
        115                 120                 125

Thr Gln Leu Lys Phe Phe Lys Ile Ala Gln Ala Gly Leu Ile Asp Asp
    130                 135                 140

Asn Ser Pro Pro Gly Ile Trp Ala Ser Asp Asn Leu Ile Ala Ala Asn
145                 150                 155                 160

Asn Ser Trp Thr Val Thr Ile Pro Thr Thr Thr Ala Pro Gly Asn Tyr
                165                 170                 175

Val Leu Arg His Glu Ile Ile Ala Leu His Ser Ala Gly Asn Lys Asp
            180                 185                 190

Gly Ala Gln Asn Tyr Pro Gln Cys Ile Asn Leu Lys Val Thr Gly Asn
        195                 200                 205

Gly Ser Gly Asn Pro Pro Ala Gly Ala Leu Gly Thr Ala Leu Tyr Lys
    210                 215                 220

Asp Thr Asp Pro Gly Ile Leu Ile Asn Ile Tyr Gln Lys Leu Ser Ser
225                 230                 235                 240

Tyr Val Ile Pro Gly Pro Ala Leu Tyr Thr Gly
                245                 250
```

<210> SEQ ID NO 193
<211> LENGTH: 1386
<212> TYPE: DNA
<213> ORGANISM: Talaromyces emersonii

<400> SEQUENCE: 193

```
atggttcgcc tcagtccagt cctgctggca tcgatcgcag gctctggcct gcctctgtac      60

gcacaagcag ccggcctcaa caccgccgcc aaagccgtcg gcctgaaata cttcggcacg     120

gcgaccgaca accccgaact gagcgacacc gcgtacgaga cggagctgaa caacacgcag     180

gatttcgggc agttgacacc tgcgaattcg atgaaagtga gtctgacacc cccccccccc     240

cctgggcgag tgagtgagtt cgacgctgat ggtttttgca gtgggacgca accgagcccc     300

agcaaaacac tttcacgttc agcggcggcg atcagatcgc taacctggcc aaggcgaatg     360

gccagatgtt gaggtgccat aatcttgttt ggtataatca gttgccgtcg tggggtatgt     420

atagtacctg cgtgcttgtt tgtaatgatt gtcttggctg atttgtgaag tcaccggtgg     480

atcctggacc aacgagacgc tgcttgctgc catgaagaat cacatcacaa acgtcgttac     540

ccattacaag ggccagtgct atgcatggga tgtcgtgaat gagggtgcgt ccatataatt     600

gctgttacta tcgagaggaa tcagctaatg acgacagccc tcaacgacga cggcacctac     660

cgcagcaacg tcttctacca gtatatcggg gaggcgtaca tccccatcgc cttcgcgacg     720
```

```
gccgccgccg ccgaccccga cgccaagctg tactacaacg actacaacat cgagtacccc    780

ggcgtcaagg ccacggcggc gcagaacatc gtcaagctgg tgcagtcgta cggcgcgcgc    840

atcgacggcg tcggcctgca gtcgcacttc atcgtgggcc agacgcccag cacgagcgcc    900

cagcagcaga acatggctgc cttcaccgcg ctgggcgtcg aggtcgccat caccgagctc    960

gacatccgca tgcagctgcc cgagacgtcc gcgcagctga cacagcaggc gaccgactac   1020

cagagcacgg tccaggcctg cgtcaacacc gacagctgcg tcggcatcac cctctgggac   1080

tggaccgaca agtactcgtg ggtgcccagc accttctcag gctggggcga cgcctgtccc   1140

tgggacgaca actaccagaa gaagcccgcg tacaacggca tcctcactgc tctgggaggc   1200

acgccctcct ccagtaccag ctacaccctc acgccgacga cgacctcgag cggcggcagt   1260

ggcagcccga ctgacgtggc tcagcattgg gagcagtgcg gtggcctggg ctggactggg   1320

ccgacggttt gcgccagtgg cttcacttgc actgtcatca acgagtatta ctcgcagtgt   1380

ctgtaa                                                              1386


<210> SEQ ID NO 194
<211> LENGTH: 403
<212> TYPE: PRT
<213> ORGANISM: Talaromyces emersonii

<400> SEQUENCE: 194

Met Val Arg Leu Ser Pro Val Leu Leu Ala Ser Ile Ala Gly Ser Gly
1               5                   10                  15

Leu Pro Leu Tyr Ala Gln Ala Ala Gly Leu Asn Thr Ala Ala Lys Ala
            20                  25                  30

Val Gly Leu Lys Tyr Phe Gly Thr Ala Thr Asp Asn Pro Glu Leu Ser
        35                  40                  45

Asp Thr Ala Tyr Glu Thr Glu Leu Asn Asn Thr Gln Asp Phe Gly Gln
    50                  55                  60

Leu Thr Pro Ala Asn Ser Met Lys Trp Asp Ala Thr Glu Pro Gln Gln
65                  70                  75                  80

Asn Thr Phe Thr Phe Ser Gly Gly Asp Gln Ile Ala Asn Leu Ala Lys
                85                  90                  95

Ala Asn Gly Gln Met Leu Arg Cys His Asn Leu Val Trp Tyr Asn Gln
            100                 105                 110

Leu Pro Ser Trp Val Thr Gly Gly Ser Trp Thr Asn Glu Thr Leu Leu
        115                 120                 125

Ala Ala Met Lys Asn His Ile Thr Asn Val Val Thr His Tyr Lys Gly
    130                 135                 140

Gln Cys Tyr Ala Trp Asp Val Val Asn Glu Ala Leu Asn Asp Asp Gly
145                 150                 155                 160

Thr Tyr Arg Ser Asn Val Phe Tyr Gln Tyr Ile Gly Glu Ala Tyr Ile
                165                 170                 175

Pro Ile Ala Phe Ala Thr Ala Ala Ala Ala Asp Pro Asp Ala Lys Leu
            180                 185                 190

Tyr Tyr Asn Asp Tyr Asn Ile Glu Tyr Pro Gly Val Lys Ala Thr Ala
        195                 200                 205

Ala Gln Asn Ile Val Lys Leu Val Gln Ser Tyr Gly Ala Arg Ile Asp
    210                 215                 220

Gly Val Gly Leu Gln Ser His Phe Ile Val Gly Gln Thr Pro Ser Thr
225                 230                 235                 240

Ser Ala Gln Gln Gln Asn Met Ala Ala Phe Thr Ala Leu Gly Val Glu
                245                 250                 255
```

-continued

```
Val Ala Ile Thr Glu Leu Asp Ile Arg Met Gln Leu Pro Glu Thr Ser
            260                 265                 270

Ala Gln Leu Thr Gln Gln Ala Thr Asp Tyr Gln Ser Thr Val Gln Ala
        275                 280                 285

Cys Val Asn Thr Asp Ser Cys Val Gly Ile Thr Leu Trp Asp Trp Thr
    290                 295                 300

Asp Lys Tyr Ser Trp Val Pro Ser Thr Phe Ser Gly Trp Gly Asp Ala
305                 310                 315                 320

Cys Pro Trp Asp Asp Asn Tyr Gln Lys Lys Pro Ala Tyr Asn Gly Ile
                325                 330                 335

Leu Thr Ala Leu Gly Gly Thr Pro Ser Ser Ser Thr Ser Tyr Thr Leu
            340                 345                 350

Thr Pro Thr Thr Thr Ser Ser Gly Gly Ser Gly Ser Pro Thr Asp Val
        355                 360                 365

Ala Gln His Trp Glu Gln Cys Gly Gly Leu Gly Trp Thr Gly Pro Thr
    370                 375                 380

Val Cys Ala Ser Gly Phe Thr Cys Thr Val Ile Asn Glu Tyr Tyr Ser
385                 390                 395                 400

Gln Cys Leu


<210> SEQ ID NO 195
<211> LENGTH: 1387
<212> TYPE: DNA
<213> ORGANISM: Penicillium sp.

<400> SEQUENCE: 195

atggttcgcc tcagtccagt cctgctggca tcgatcgcag gctctggcct gcctctgtac      60

gcacaagcag ccggcctcaa caccgccgcc aaagccatcg gcctgaaata cttcggcacg     120

gcgaccgaca accccgaact gagcgacacc gcgtacgaga cggaactgaa caacacgcag     180

gatttcgggc agttgacacc tgcgaattcg atgaaggtga gtctgacagc tccccccct      240

cctggggtga gtgagtgagt tcgacgctaa tggtttttgc agtgggacgc aaccgagccc     300

cagcaaaaca ctttcacgtt cagcggcggc gatcagatcg ctaacctggc caaggcgaat     360

ggccagatgt tgaggtgcca taatcttgtt tggtataatc agttgccgtc gtggggtatg     420

tatagtacct gcgtacttgt ttgtaatgat tgtcttggct gatttgtgaa gtcaccggtg     480

gatcctggac caacgagacg ctgcttgctg ccatgaagaa tcacatcacc aacgtcgtta     540

cccattacaa gggccagtgc tatgcatggg atgtcgtgaa tgagggtacg tccatataat     600

tgctgttact atcgagagga atcagctaat gacgacagcc ctcaacgacg acggcaccta     660

ccgcagcaac gtcttctacc agtatatcgg ggaggcgtac atccccatcg ccttcgcgac     720

ggccgccgcc gccgaccccg acgccaagct gtactacaac gactacaaca tcgagtaccc     780

cggcgccaag gccacggcgg cgcagaacat cgtcaagctg gtgcagtcgt acggggcgcg     840

catcgacggc gtcggcctgc agtcgcactt catcgtgggc cagacgccca gcacgagcgc     900

ccagcagcag aacatggccg ccttcaccgc gctgggcgtc gaggtcgcca tcaccgagct     960

cgacatccgc atgcagctgc ccgagacgtc cgcgcagctg acgcagcagg cgaccgacta    1020

ccagagcacg gtccaggcct gcgtcaacac cgacagctgc gtcggcatta ccctctggga    1080

ctggaccgac aagtactcgt gggtgcccag caccttctca ggctggggcg acgcctgtcc    1140

ctgggacgac aactaccaga agaaacccgc gtacaacggc atcctcactg ctctgggagg    1200

cacgccctcc tccagtacca gctacaccct cacgccgacg acgacctcaa gcggcggcag    1260
```

tggcagcccg actgacgtgg cccagcattg ggagcagtgc ggtggcctgg gctggactgg 1320
gccgacggtt tgcgccagtg gcttcacttg cactgtcatc aacgagtatt actcgcagtg 1380
tctgtaa 1387

<210> SEQ ID NO 196
<211> LENGTH: 403
<212> TYPE: PRT
<213> ORGANISM: Penicillium sp.

<400> SEQUENCE: 196

Met Val Arg Leu Ser Pro Val Leu Leu Ala Ser Ile Ala Gly Ser Gly
1 5 10 15

Leu Pro Leu Tyr Ala Gln Ala Ala Gly Leu Asn Thr Ala Ala Lys Ala
20 25 30

Ile Gly Leu Lys Tyr Phe Gly Thr Ala Thr Asp Asn Pro Glu Leu Ser
35 40 45

Asp Thr Ala Tyr Glu Thr Glu Leu Asn Asn Thr Gln Asp Phe Gly Gln
50 55 60

Leu Thr Pro Ala Asn Ser Met Lys Trp Asp Ala Thr Glu Pro Gln Gln
65 70 75 80

Asn Thr Phe Thr Phe Ser Gly Gly Asp Gln Ile Ala Asn Leu Ala Lys
85 90 95

Ala Asn Gly Gln Met Leu Arg Cys His Asn Leu Val Trp Tyr Asn Gln
100 105 110

Leu Pro Ser Trp Val Thr Gly Gly Ser Trp Thr Asn Glu Thr Leu Leu
115 120 125

Ala Ala Met Lys Asn His Ile Thr Asn Val Val Thr His Tyr Lys Gly
130 135 140

Gln Cys Tyr Ala Trp Asp Val Val Asn Glu Ala Leu Asn Asp Asp Gly
145 150 155 160

Thr Tyr Arg Ser Asn Val Phe Tyr Gln Tyr Ile Gly Glu Ala Tyr Ile
165 170 175

Pro Ile Ala Phe Ala Thr Ala Ala Ala Ala Asp Pro Asp Ala Lys Leu
180 185 190

Tyr Tyr Asn Asp Tyr Asn Ile Glu Tyr Pro Gly Ala Lys Ala Thr Ala
195 200 205

Ala Gln Asn Ile Val Lys Leu Val Gln Ser Tyr Gly Ala Arg Ile Asp
210 215 220

Gly Val Gly Leu Gln Ser His Phe Ile Val Gly Gln Thr Pro Ser Thr
225 230 235 240

Ser Ala Gln Gln Gln Asn Met Ala Ala Phe Thr Ala Leu Gly Val Glu
245 250 255

Val Ala Ile Thr Glu Leu Asp Ile Arg Met Gln Leu Pro Glu Thr Ser
260 265 270

Ala Gln Leu Thr Gln Gln Ala Thr Asp Tyr Gln Ser Thr Val Gln Ala
275 280 285

Cys Val Asn Thr Asp Ser Cys Val Gly Ile Thr Leu Trp Asp Trp Thr
290 295 300

Asp Lys Tyr Ser Trp Val Pro Ser Thr Phe Ser Gly Trp Gly Asp Ala
305 310 315 320

Cys Pro Trp Asp Asp Asn Tyr Gln Lys Lys Pro Ala Tyr Asn Gly Ile
325 330 335

Leu Thr Ala Leu Gly Gly Thr Pro Ser Ser Ser Thr Ser Tyr Thr Leu

```
            340                 345                 350

Thr Pro Thr Thr Thr Ser Ser Gly Gly Ser Gly Ser Pro Thr Asp Val
        355                 360                 365

Ala Gln His Trp Glu Gln Cys Gly Gly Leu Gly Trp Thr Gly Pro Thr
    370                 375                 380

Val Cys Ala Ser Gly Phe Thr Cys Thr Val Ile Asn Glu Tyr Tyr Ser
385                 390                 395                 400

Gln Cys Leu


<210> SEQ ID NO 197
<211> LENGTH: 1191
<212> TYPE: DNA
<213> ORGANISM: Meripilus giganteus

<400> SEQUENCE: 197

atgaagttct ccgcgacctt ctcagcactc gccgcgctga tcccctacgc cctcgctcag      60

tccccagaat ggggccaatg cggcggcact ggctggacag gcgccacgac ctgcgtgtcg     120

ggcaccgtgt gcacggtgat caatccgtat tactcgcaat gtctccccgg aagtgcgaca     180

tccgcaacgt ctagcgctcc cagctctacc actacgacag gctcatccgc acccagcgcg     240

agtggtctgc acacgctggc gaaggcggcg ggcaagctct acttcggcac agcgacggac     300

aatccagagt tgaccgacac cgcctacgtc acgaagctca gcgataacaa ggagttcggc     360

cagatcaccc caggcaacag tatgaaatgg gacgctacgg agccgactcg cgggacgttc     420

acgttcacga acggagacgt agttgcgaac ctggcgaaga acaacgggca gctgctgcgc     480

gggcacaact gcgtgtggca caaccagctc ccgagctggg tatccaatgg gcagttcacc     540

gcggcggacc tcacggacgt catccagacg cactgtggca cggtcgtagg acattacaag     600

ggccagattt attcttggga tgttgtgaac gagcctttca acgacgacgg cacctggcgc     660

acggatgttt tctataacac gctcggcacg tcctacgtcg ccatcgcgct caaagccgcg     720

cgcgctgccg accccgccgc caaactctac atcaacgact acaacatcga gcagacgggc     780

gccaagtcgg ccgcgatgct cgcgctcgtc aaggagctcc tcgcggacgg cgtgcccctc     840

gacggcgtcg gctttcagag ccacttcatc gtcggcgcgg tgccgggcag cctccagcag     900

acgctcgagc agttcaccgc gctcgggctc gaggtcgcga tcacggagct cgacatccgc     960

atgacgctcc ccgcgacgga cgcgctcctc gcgcagcagc agaaggacta cgaggcggtt    1020

gtgcaggcgt gcatgaatgt gaacggctgt gtgggcgtca cgatctggga ctggacggac    1080

aagtactcgt gggtgccgtc gaccttctct ggccagggcg ccgctctccc ttgggatgag    1140

aacttcaaca agaagcccgc gtacagcggt attacagcag cacttgcata a             1191


<210> SEQ ID NO 198
<211> LENGTH: 396
<212> TYPE: PRT
<213> ORGANISM: Meripilus giganteus

<400> SEQUENCE: 198

Met Lys Phe Ser Ala Thr Phe Ser Ala Leu Ala Ala Leu Ile Pro Tyr
1               5                   10                  15

Ala Leu Ala Gln Ser Pro Glu Trp Gly Gln Cys Gly Gly Thr Gly Trp
            20                  25                  30

Thr Gly Ala Thr Thr Cys Val Ser Gly Thr Val Cys Thr Val Ile Asn
        35                  40                  45

Pro Tyr Tyr Ser Gln Cys Leu Pro Gly Ser Ala Thr Ser Ala Thr Ser
```

```
    50                  55                  60

Ser Ala Pro Ser Ser Thr Thr Thr Thr Gly Ser Ser Ala Pro Ser Ala
65                  70                  75                  80

Ser Gly Leu His Thr Leu Ala Lys Ala Ala Gly Lys Leu Tyr Phe Gly
                85                  90                  95

Thr Ala Thr Asp Asn Pro Glu Leu Thr Asp Thr Ala Tyr Val Thr Lys
            100                 105                 110

Leu Ser Asp Asn Lys Glu Phe Gly Gln Ile Thr Pro Gly Asn Ser Met
        115                 120                 125

Lys Trp Asp Ala Thr Glu Pro Thr Arg Gly Thr Phe Thr Phe Thr Asn
    130                 135                 140

Gly Asp Val Val Ala Asn Leu Ala Lys Asn Asn Gly Gln Leu Leu Arg
145                 150                 155                 160

Gly His Asn Cys Val Trp His Asn Gln Leu Pro Ser Trp Val Ser Asn
                165                 170                 175

Gly Gln Phe Thr Ala Ala Asp Leu Thr Asp Val Ile Gln Thr His Cys
            180                 185                 190

Gly Thr Val Val Gly His Tyr Lys Gly Gln Ile Tyr Ser Trp Asp Val
        195                 200                 205

Val Asn Glu Pro Phe Asn Asp Asp Gly Thr Trp Arg Thr Asp Val Phe
    210                 215                 220

Tyr Asn Thr Leu Gly Thr Ser Tyr Val Ala Ile Ala Leu Lys Ala Ala
225                 230                 235                 240

Arg Ala Ala Asp Pro Ala Ala Lys Leu Tyr Ile Asn Asp Tyr Asn Ile
                245                 250                 255

Glu Gln Thr Gly Ala Lys Ser Ala Ala Met Leu Ala Leu Val Lys Glu
            260                 265                 270

Leu Leu Ala Asp Gly Val Pro Leu Asp Gly Val Gly Phe Gln Ser His
        275                 280                 285

Phe Ile Val Gly Ala Val Pro Gly Ser Leu Gln Gln Thr Leu Glu Gln
    290                 295                 300

Phe Thr Ala Leu Gly Leu Glu Val Ala Ile Thr Glu Leu Asp Ile Arg
305                 310                 315                 320

Met Thr Leu Pro Ala Thr Asp Ala Leu Leu Ala Gln Gln Gln Lys Asp
                325                 330                 335

Tyr Glu Ala Val Val Gln Ala Cys Met Asn Val Asn Gly Cys Val Gly
            340                 345                 350

Val Thr Ile Trp Asp Trp Thr Asp Lys Tyr Ser Trp Val Pro Ser Thr
        355                 360                 365

Phe Ser Gly Gln Gly Ala Ala Leu Pro Trp Asp Glu Asn Phe Asn Lys
    370                 375                 380

Lys Pro Ala Tyr Ser Gly Ile Thr Ala Ala Leu Ala
385                 390                 395
```

<210> SEQ ID NO 199
<211> LENGTH: 1083
<212> TYPE: DNA
<213> ORGANISM: Dictyoglomus thermophilum

<400> SEQUENCE: 199

```
atgtttctta aaaaacttag taagttgctc ttagtcgtac tacttgtcgc agtgtatacg      60

caagttaatg ctcaaacgtc tataacacta acaagtaatg caagcggtac ttttgatggc     120

tactactatg aactatggaa agatacaggg aatacaacca tgactgtata cacacaagga     180
```

-continued

```
aggtttagct gtcagtggag caatataaac aatgcattat tcagaacagg taagaagtac    240

aaccaaaact ggcagtcatt aggcactatt agaatcacct actcagccac atataatcct    300

aatggtaact cctacttatg tatctatggt tggtctacta atcctttagt agagttttac    360

attgtagaaa gttggggtaa ttggcgtcca ccaggtgcaa cctctcttgg acaggttact    420

atcgacggtg gtacctatga catttacaga actacccgtg taaatcagcc atctattgtc    480

ggtacagcta cttttgatca atattggagt gtaaggacat ctaagagaac aagtggaaca    540

gtcactgtaa cagatcactt tagggcatgg gcaaatagag gtttaaacct tggtactatt    600

gatcaaatta ctctttgtgt tgaaggatat caaagcagtg gttcggctaa tataacacaa    660

aatacttttt ctcaaggtag cagtagtgga agtagtgggg gcagtagtgg tagtacaaca    720

actactagaa tagaatgtga aaacatgtca ttaagtgggc cctatgtatc aagaattaca    780

aatccattta atggtatagc tctttatgca aatggagata ctgcaagagc tacagtaaac    840

ttcccagcaa gtcgtaacta taatttcagg ttaagaggat gcggaaataa caataattta    900

gctcgggttg atttacgaat agatgggagg actgtaggta cgttctatta tcagggaaca    960

tatccttggg aggctcctat agacaatgta tacgtgagtg caggttctca tacagtggaa   1020

attacagtta cggctgataa tgggacatgg gatgtttatg cagattatct ggtgatacag   1080

taa                                                                 1083


<210> SEQ ID NO 200
<211> LENGTH: 360
<212> TYPE: PRT
<213> ORGANISM: Dictyoglomus thermophilum

<400> SEQUENCE: 200

Met Phe Leu Lys Lys Leu Ser Lys Leu Leu Leu Val Val Leu Leu Val
1               5                   10                  15

Ala Val Tyr Thr Gln Val Asn Ala Gln Thr Ser Ile Thr Leu Thr Ser
            20                  25                  30

Asn Ala Ser Gly Thr Phe Asp Gly Tyr Tyr Tyr Glu Leu Trp Lys Asp
        35                  40                  45

Thr Gly Asn Thr Thr Met Thr Val Tyr Thr Gln Gly Arg Phe Ser Cys
    50                  55                  60

Gln Trp Ser Asn Ile Asn Asn Ala Leu Phe Arg Thr Gly Lys Lys Tyr
65                  70                  75                  80

Asn Gln Asn Trp Gln Ser Leu Gly Thr Ile Arg Ile Thr Tyr Ser Ala
                85                  90                  95

Thr Tyr Asn Pro Asn Gly Asn Ser Tyr Leu Cys Ile Tyr Gly Trp Ser
            100                 105                 110

Thr Asn Pro Leu Val Glu Phe Tyr Ile Val Glu Ser Trp Gly Asn Trp
        115                 120                 125

Arg Pro Pro Gly Ala Thr Ser Leu Gly Gln Val Thr Ile Asp Gly Gly
    130                 135                 140

Thr Tyr Asp Ile Tyr Arg Thr Thr Arg Val Asn Gln Pro Ser Ile Val
145                 150                 155                 160

Gly Thr Ala Thr Phe Asp Gln Tyr Trp Ser Val Arg Thr Ser Lys Arg
                165                 170                 175

Thr Ser Gly Thr Val Thr Val Thr Asp His Phe Arg Ala Trp Ala Asn
            180                 185                 190

Arg Gly Leu Asn Leu Gly Thr Ile Asp Gln Ile Thr Leu Cys Val Glu
        195                 200                 205
```

-continued

```
Gly Tyr Gln Ser Ser Gly Ser Ala Asn Ile Thr Gln Asn Thr Phe Ser
    210                 215                 220

Gln Gly Ser Ser Ser Gly Ser Ser Gly Gly Ser Ser Gly Ser Thr Thr
225                 230                 235                 240

Thr Thr Arg Ile Glu Cys Glu Asn Met Ser Leu Ser Gly Pro Tyr Val
                245                 250                 255

Ser Arg Ile Thr Asn Pro Phe Asn Gly Ile Ala Leu Tyr Ala Asn Gly
            260                 265                 270

Asp Thr Ala Arg Ala Thr Val Asn Phe Pro Ala Ser Arg Asn Tyr Asn
        275                 280                 285

Phe Arg Leu Arg Gly Cys Gly Asn Asn Asn Asn Leu Ala Arg Val Asp
    290                 295                 300

Leu Arg Ile Asp Gly Arg Thr Val Gly Thr Phe Tyr Tyr Gln Gly Thr
305                 310                 315                 320

Tyr Pro Trp Glu Ala Pro Ile Asp Asn Val Tyr Val Ser Ala Gly Ser
                325                 330                 335

His Thr Val Glu Ile Thr Val Thr Ala Asp Asn Gly Thr Trp Asp Val
            340                 345                 350

Tyr Ala Asp Tyr Leu Val Ile Gln
        355                 360


<210> SEQ ID NO 201
<211> LENGTH: 2412
<212> TYPE: DNA
<213> ORGANISM: Aspergillus aculeatus

<400> SEQUENCE: 201

atggctgtgg cggctcttgc tctgctggcg cttttgcctc aagctctggc ccaacataac      60

agcagctacg tggattacaa cgtcgaggcc aacccggact tgtttccgca atgtctggac     120

acaatctcct tgtccttccc cgactgccag agcggtcctc tgagcaagaa cctcgtctgc     180

gactcgaccg cctcgcccta tgaccgcgcc gcggccctga tctccctctt caccctcgag     240

gagctcattg ccaacactgg taacaccagc cccggtgtcc ctcgtctggg tctacctcca     300

taccaggtct ggagtgaggc cttgcatggc ctggaccgcg gcaatttcac cgacgagggg     360

gcttacagct gggcgacatc cttcccctcg cccattctct ccgctgctgc cttcaatcgc     420

accctgatca accagatcgc atccattatc tcaactcagg ggcgcgcctt caataacgcc     480

ggccgctacg gtctcgatgt ctacgccccc aacatcaatg ccttccgtca tcccgtctgg     540

gggcgcggac aggaaactcc gggcgaggat gcgtatactc tcacagccgc ctacgcctac     600

gaatacatca cgggtatcca gggtggcgtg gacccagagc atctgaagct cgcagcgaca     660

gccaagcact ttgccggcta tgacatcgag aactgggaca accactcccg gctggggaac     720

gatgtcaaca tcacgcagca agacctggcc gagtactaca cgccgcagtt cctcgtggcc     780

acgcgcgatg cccgcgtcca cagcgtcatg tgctcgtaca acgccgtcaa cggcgtgccc     840

agctgctcca acaccttctt cctgcagacg ctcctgcgcg acaccttctc cttcgttgac     900

cacggctacg tctccggcga ttgcggtgcc gtctacggcg ttttcaaccc ccacggctac     960

gcggccaacg agtccagcgc cgccgccgac tccatcctcg ccggcaccga catcgactgc    1020

ggcacctcct accaatacca cttcaacgag tccatcacca ccagggcggt cgcccgcgac    1080

gacatcgagc gcggcctcac ccggctatac gccaacctcg tccggctagg ctacttcgag    1140

ggcaacagca gcagcagcag cccgtaccgc agcctgagct ggtccgacgt ccagaagaca    1200

gacgcatgga acatttccta cgaagcggcc gtcgagggca tcgtcctcct gaagaacgac    1260
```

```
ggcgccctcc cgcttccctc ctcctcctcc tcgggcaaga ataaatccat cgccctcatc   1320

ggcccctggg ccaacgccac cacccagctc cagggcaact actacggcgc ggcgccatac   1380

ctcatcagcc cggtcgacgc cttcacggcc gccggctaca cggtccacta cgcccccggc   1440

acggagatct ccacgaactc gacggcgaac ttcagcgccg cgctctccgc cgcgcgcgcc   1500

gccgacacca tcgtattctt cggagggatc gacaacacca tcgaggcgga agcccaagac   1560

cgcagctcga tcgcctggcc cggcaaccaa ctcgagctga tctcgcaact ggccgcgcag   1620

aaatccgagt cccagcccct ggtggtgtac cagatgggcg gcgggcaggt cgactcctcc   1680

gccctgaaag cgaatccgaa ggtcaacgcc ctcctctggg gcggctaccc gggccaatcc   1740

ggcggcctcg ccctccgcga catcctcacg ggcgcccgcg ccccggccgg ccgcctcacc   1800

acgacccagt accccgccgc ctacgccgag agcttctcgg cgctcgacat gaacctgcgg   1860

cccaacacca ccaccaacaa cccaggccaa acctacatgt ggtacaccgg cgaacccgtc   1920

tacgaattcg gccacggcct cttctacacc accttcaagg ctgcccccgc agcggcgaag   1980

aagtatacct tcaacatcac agacctcacc tcctccgcgc acccggacac caccaccgtc   2040

gcccaacgca ccctcttcaa cttcacggcg accatcacga actctggggc ccgggactcc   2100

gattacaccg ccctggtgtt cgccaacacc tcgagtgcgg gcccgtcccc gtacccgaac   2160

aaatggctcg tcgggttcga taggctcgct gctgtggcca aggagggggg cacgacggtg   2220

ttgaatgtgc ccgtggcggt ggatcggttg gccagggtgg atgacaatgg gaattccgtg   2280

ctgtttccgg ggcggtatga ggtggccttg aataatgagc gcgaggtcgt ggttgaggtg   2340

gagttggtgg gggaggcggt ggtgttggtg aagtggccgg aggaggtgca gggggtgcag   2400

ggggatgagt ag                                                        2412
```

<210> SEQ ID NO 202
<211> LENGTH: 803
<212> TYPE: PRT
<213> ORGANISM: Aspergillus aculeatus

<400> SEQUENCE: 202

```
Met Ala Val Ala Ala Leu Ala Leu Leu Ala Leu Leu Pro Gln Ala Leu
1               5                   10                  15

Ala Gln His Asn Ser Ser Tyr Val Asp Tyr Asn Val Glu Ala Asn Pro
            20                  25                  30

Asp Leu Phe Pro Gln Cys Leu Asp Thr Ile Ser Leu Ser Phe Pro Asp
        35                  40                  45

Cys Gln Ser Gly Pro Leu Ser Lys Asn Leu Val Cys Asp Ser Thr Ala
    50                  55                  60

Ser Pro Tyr Asp Arg Ala Ala Ala Leu Ile Ser Leu Phe Thr Leu Glu
65                  70                  75                  80

Glu Leu Ile Ala Asn Thr Gly Asn Thr Ser Pro Gly Val Pro Arg Leu
                85                  90                  95

Gly Leu Pro Pro Tyr Gln Val Trp Ser Glu Ala Leu His Gly Leu Asp
            100                 105                 110

Arg Gly Asn Phe Thr Asp Glu Gly Ala Tyr Ser Trp Ala Thr Ser Phe
        115                 120                 125

Pro Ser Pro Ile Leu Ser Ala Ala Ala Phe Asn Arg Thr Leu Ile Asn
    130                 135                 140

Gln Ile Ala Ser Ile Ile Ser Thr Gln Gly Arg Ala Phe Asn Asn Ala
145                 150                 155                 160
```

-continued

```
Gly Arg Tyr Gly Leu Asp Val Tyr Ala Pro Asn Ile Asn Ala Phe Arg
                165                 170                 175

His Pro Val Trp Gly Arg Gly Gln Glu Thr Pro Gly Glu Asp Ala Tyr
            180                 185                 190

Thr Leu Thr Ala Ala Tyr Ala Tyr Glu Tyr Ile Thr Gly Ile Gln Gly
        195                 200                 205

Gly Val Asp Pro Glu His Leu Lys Leu Ala Ala Thr Ala Lys His Phe
    210                 215                 220

Ala Gly Tyr Asp Ile Glu Asn Trp Asp Asn His Ser Arg Leu Gly Asn
225                 230                 235                 240

Asp Val Asn Ile Thr Gln Gln Asp Leu Ala Glu Tyr Tyr Thr Pro Gln
                245                 250                 255

Phe Leu Val Ala Thr Arg Asp Ala Arg Val His Ser Val Met Cys Ser
            260                 265                 270

Tyr Asn Ala Val Asn Gly Val Pro Ser Cys Ser Asn Thr Phe Phe Leu
        275                 280                 285

Gln Thr Leu Leu Arg Asp Thr Phe Ser Phe Val Asp His Gly Tyr Val
    290                 295                 300

Ser Gly Asp Cys Gly Ala Val Tyr Gly Val Phe Asn Pro His Gly Tyr
305                 310                 315                 320

Ala Ala Asn Glu Ser Ser Ala Ala Ala Asp Ser Ile Leu Ala Gly Thr
                325                 330                 335

Asp Ile Asp Cys Gly Thr Ser Tyr Gln Tyr His Phe Asn Glu Ser Ile
            340                 345                 350

Thr Thr Arg Ala Val Ala Arg Asp Asp Ile Glu Arg Gly Leu Thr Arg
        355                 360                 365

Leu Tyr Ala Asn Leu Val Arg Leu Gly Tyr Phe Glu Gly Asn Ser Ser
    370                 375                 380

Ser Ser Ser Pro Tyr Arg Ser Leu Ser Trp Ser Asp Val Gln Lys Thr
385                 390                 395                 400

Asp Ala Trp Asn Ile Ser Tyr Glu Ala Ala Val Glu Gly Ile Val Leu
                405                 410                 415

Leu Lys Asn Asp Gly Ala Leu Pro Leu Pro Ser Ser Ser Ser Ser Gly
            420                 425                 430

Lys Asn Lys Ser Ile Ala Leu Ile Gly Pro Trp Ala Asn Ala Thr Thr
        435                 440                 445

Gln Leu Gln Gly Asn Tyr Tyr Gly Ala Ala Pro Tyr Leu Ile Ser Pro
    450                 455                 460

Val Asp Ala Phe Thr Ala Ala Gly Tyr Thr Val His Tyr Ala Pro Gly
465                 470                 475                 480

Thr Glu Ile Ser Thr Asn Ser Thr Ala Asn Phe Ser Ala Ala Leu Ser
                485                 490                 495

Ala Ala Arg Ala Ala Asp Thr Ile Val Phe Phe Gly Gly Ile Asp Asn
            500                 505                 510

Thr Ile Glu Ala Glu Ala Gln Asp Arg Ser Ser Ile Ala Trp Pro Gly
        515                 520                 525

Asn Gln Leu Glu Leu Ile Ser Gln Leu Ala Ala Gln Lys Ser Glu Ser
    530                 535                 540

Gln Pro Leu Val Val Tyr Gln Met Gly Gly Gly Gln Val Asp Ser Ser
545                 550                 555                 560

Ala Leu Lys Ala Asn Pro Lys Val Asn Ala Leu Leu Trp Gly Gly Tyr
                565                 570                 575

Pro Gly Gln Ser Gly Gly Leu Ala Leu Arg Asp Ile Leu Thr Gly Ala
```

```
            580                 585                 590

Arg Ala Pro Ala Gly Arg Leu Thr Thr Thr Gln Tyr Pro Ala Ala Tyr
        595                 600                 605

Ala Glu Ser Phe Ser Ala Leu Asp Met Asn Leu Arg Pro Asn Thr Thr
    610                 615                 620

Thr Asn Asn Pro Gly Gln Thr Tyr Met Trp Tyr Thr Gly Glu Pro Val
625                 630                 635                 640

Tyr Glu Phe Gly His Gly Leu Phe Tyr Thr Thr Phe Lys Ala Ala Pro
                645                 650                 655

Ala Ala Ala Lys Lys Tyr Thr Phe Asn Ile Thr Asp Leu Thr Ser Ser
            660                 665                 670

Ala His Pro Asp Thr Thr Thr Val Ala Gln Arg Thr Leu Phe Asn Phe
        675                 680                 685

Thr Ala Thr Ile Thr Asn Ser Gly Ala Arg Asp Ser Asp Tyr Thr Ala
    690                 695                 700

Leu Val Phe Ala Asn Thr Ser Ser Ala Gly Pro Ser Pro Tyr Pro Asn
705                 710                 715                 720

Lys Trp Leu Val Gly Phe Asp Arg Leu Ala Ala Val Ala Lys Glu Gly
                725                 730                 735

Gly Thr Thr Val Leu Asn Val Pro Val Ala Val Asp Arg Leu Ala Arg
            740                 745                 750

Val Asp Asp Asn Gly Asn Ser Val Leu Phe Pro Gly Arg Tyr Glu Val
        755                 760                 765

Ala Leu Asn Asn Glu Arg Glu Val Val Val Glu Val Glu Leu Val Gly
    770                 775                 780

Glu Ala Val Val Leu Val Lys Trp Pro Glu Glu Val Gln Gly Val Gln
785                 790                 795                 800

Gly Asp Glu
```

<210> SEQ ID NO 203
<211> LENGTH: 2454
<212> TYPE: DNA
<213> ORGANISM: Aspergillus aculeatus

<400> SEQUENCE: 203

```
atggctgtgg cggctcttgc tctgctggcg ctgttgcccc aagctctggc ccaacataac      60

agcagctacg tggattacaa cgtcgaggcc aacccggact tgtttccgca atgtctggat     120

acaatctcct tgtccttccc cgactgccag agcggtcctc tgagcaagaa cgtcgtctgc     180

gactcgaccg cctcgcccta tgaccgcgcc gcggccctga tctccctctt caccctcgag     240

gagctcatcg ccaacactgg taataccagc ccgggtgtcc cgcgtctagg tctgcctcca     300

taccaagtct ggagtgaggc cttgcatggc ctggaccgcg gcaatttcac ggacgagggg     360

gcttacagct gggcgacatc cttcccctcg cccattctct ccgctgctgc ctttaatcgc     420

accctgatca accagatcgc ctccattatc tcaactcagg gtcgcgcctt caacaacgcc     480

ggccgctacg gtctcgatgt ctacgccccc aacatcaatg ccttccgtca ccccgtctgg     540

ggtcgcggac aggaaactcc gggcgaggat gcgtacactc tcacagccgc ctacgcctac     600

gaatacatca cgggtatcca gggtggcgtg gacccagagc atctgaagct cgcagcaaca     660

gccaagcact ttgccggcta tgacatcgag aactgggaca accactcccg gctggggaac     720

gatgtcaaca tcacgcagca agacctggcc gagtactaca cgccgcagtt cctcgtggcc     780

acgcgcgatg cccgcgttca cagtgttatg tgctcctaca acgccgtcaa cggcgtgccc     840
```

-continued

```
agctgctcca acaccttctt cctgcagacc ctcctgcgcg acaccttctc cttcgtcgac    900

cacggctacg tctccggcga ctgcggcgcc gtctacggcg tcttcaaccc ccacggctac    960

gcggccaacg agtccagtgc cgccgccgac tctatcctcg ctggcaccga catcgattgc   1020

ggcacctcct accagtacca cttcaatgag tccatcacca ccggggcggt cgcccgcgac   1080

gacatcgagc gcgggctcat ccggctgtac gccaacctcg tccggctggg ctacttcgac   1140

ggcaacagca gcagcagcag cccgtaccgc agcctgagct ggtccgacgt ccaaaagaca   1200

gacgcatgga acatctccta cgaagcggca gtcgagggca tcgtcctcct gaagaatgac   1260

ggcgccctcc cgcttccctc ctcctcctcg ggtaagaaca aatccatcgc cctcatcggc   1320

ccctgggcca acgccaccac ccagctccag ggcaactact acggcgcggc gccatacctc   1380

atcagcccag tcgacgcctt cacggccgcc ggctacacgg tccactacgc cgccggcacg   1440

gagatctcca cgaactcgac ggcgaacttc agcgccgcgc tctccgccgc gcgcgccgcc   1500

gacaccatcg tattcttcgg cgggatcgac aacaccatcg aggcggaagc ccaagaccgc   1560

agctcgatcg cctggcccgg caaccagctc gagctgatcg cgcaactggc cgcgcagaaa   1620

tccgagtccc agcccctggt ggtgtaccaa atgggcggcg ggcaggtcga ctcgtccgcc   1680

ctgaaagcaa acccgaaggt caacgccctc ctctggggcg gctacccggg ccaatccggc   1740

ggcctcgccc tccgcgacat cctcacgggc gcccgcgccc cggccggccg cctcaccacg   1800

acccagtacc ccgcctccta cgccgagagc ttctcggcgc tcgacatgaa cctgcggcct   1860

aacaccacca ccaacaaccc aggccaaacc tacatgtggt acaccggcga acccgtctac   1920

gaattcggcc acggcctctt ctacaccacc ttcaaggctt cctccctgcc ctcttccacc   1980

cagaacacga cctccgcagc agcagcggca gcagcagcga agaagtatac attcaacatc   2040

acagacctca cctcctccgc acacccggac accaccaccg tcgcccaaca caccctcttc   2100

aacttcacgg cgtccatcac gaattccggg gccagggact ccgattacac cgccctgctg   2160

tacgccaaca cctcgagtgc gggcccgtcc ccgtacccga ataaatggct cgtcgggttc   2220

gataggctcg gtgccgtggc caaggagggg ggcacggcgg tgttgaatgt gcctgtggcg   2280

gtggatcggt tggcgagggt cgatgacgac gggaattccg tgctgtttcc ggggcgctat   2340

gaggtggcct tgaataatga gcgcgaggtc gtggtcgagg tcgagttggt gggggaggcg   2400

gtggtgttgg tgaagtggcc ggaggaggtg caggggggtgg cgggggatga gtaa         2454
```

<210> SEQ ID NO 204
<211> LENGTH: 817
<212> TYPE: PRT
<213> ORGANISM: Aspergillus aculeatus

<400> SEQUENCE: 204

```
Met Ala Val Ala Ala Leu Ala Leu Leu Ala Leu Leu Pro Gln Ala Leu
1               5                   10                  15

Ala Gln His Asn Ser Ser Tyr Val Asp Tyr Asn Val Glu Ala Asn Pro
            20                  25                  30

Asp Leu Phe Pro Gln Cys Leu Asp Thr Ile Ser Leu Ser Phe Pro Asp
        35                  40                  45

Cys Gln Ser Gly Pro Leu Ser Lys Asn Val Val Cys Asp Ser Thr Ala
    50                  55                  60

Ser Pro Tyr Asp Arg Ala Ala Ala Leu Ile Ser Leu Phe Thr Leu Glu
65                  70                  75                  80

Glu Leu Ile Ala Asn Thr Gly Asn Thr Ser Pro Gly Val Pro Arg Leu
                85                  90                  95
```

-continued

```
Gly Leu Pro Pro Tyr Gln Val Trp Ser Glu Ala Leu His Gly Leu Asp
            100                 105                 110

Arg Gly Asn Phe Thr Asp Glu Gly Ala Tyr Ser Trp Ala Thr Ser Phe
        115                 120                 125

Pro Ser Pro Ile Leu Ser Ala Ala Ala Phe Asn Arg Thr Leu Ile Asn
    130                 135                 140

Gln Ile Ala Ser Ile Ile Ser Thr Gln Gly Arg Ala Phe Asn Asn Ala
145                 150                 155                 160

Gly Arg Tyr Gly Leu Asp Val Tyr Ala Pro Asn Ile Asn Ala Phe Arg
                165                 170                 175

His Pro Val Trp Gly Arg Gly Gln Glu Thr Pro Gly Glu Asp Ala Tyr
            180                 185                 190

Thr Leu Thr Ala Ala Tyr Ala Tyr Glu Tyr Ile Thr Gly Ile Gln Gly
        195                 200                 205

Gly Val Asp Pro Glu His Leu Lys Leu Ala Ala Thr Ala Lys His Phe
    210                 215                 220

Ala Gly Tyr Asp Ile Glu Asn Trp Asp Asn His Ser Arg Leu Gly Asn
225                 230                 235                 240

Asp Val Asn Ile Thr Gln Gln Asp Leu Ala Glu Tyr Tyr Thr Pro Gln
                245                 250                 255

Phe Leu Val Ala Thr Arg Asp Ala Arg Val His Ser Val Met Cys Ser
            260                 265                 270

Tyr Asn Ala Val Asn Gly Val Pro Ser Cys Ser Asn Thr Phe Phe Leu
        275                 280                 285

Gln Thr Leu Leu Arg Asp Thr Phe Ser Phe Val Asp His Gly Tyr Val
    290                 295                 300

Ser Gly Asp Cys Gly Ala Val Tyr Gly Val Phe Asn Pro His Gly Tyr
305                 310                 315                 320

Ala Ala Asn Glu Ser Ser Ala Ala Ala Asp Ser Ile Leu Ala Gly Thr
                325                 330                 335

Asp Ile Asp Cys Gly Thr Ser Tyr Gln Tyr His Phe Asn Glu Ser Ile
            340                 345                 350

Thr Thr Gly Ala Val Ala Arg Asp Asp Ile Glu Arg Gly Leu Ile Arg
        355                 360                 365

Leu Tyr Ala Asn Leu Val Arg Leu Gly Tyr Phe Asp Gly Asn Ser Ser
    370                 375                 380

Ser Ser Ser Pro Tyr Arg Ser Leu Ser Trp Ser Asp Val Gln Lys Thr
385                 390                 395                 400

Asp Ala Trp Asn Ile Ser Tyr Glu Ala Ala Val Glu Gly Ile Val Leu
                405                 410                 415

Leu Lys Asn Asp Gly Ala Leu Pro Leu Pro Ser Ser Ser Ser Gly Lys
            420                 425                 430

Asn Lys Ser Ile Ala Leu Ile Gly Pro Trp Ala Asn Ala Thr Thr Gln
        435                 440                 445

Leu Gln Gly Asn Tyr Tyr Gly Ala Ala Pro Tyr Leu Ile Ser Pro Val
    450                 455                 460

Asp Ala Phe Thr Ala Ala Gly Tyr Thr Val His Tyr Ala Ala Gly Thr
465                 470                 475                 480

Glu Ile Ser Thr Asn Ser Thr Ala Asn Phe Ser Ala Ala Leu Ser Ala
                485                 490                 495

Ala Arg Ala Ala Asp Thr Ile Val Phe Phe Gly Gly Ile Asp Asn Thr
            500                 505                 510
```

```
Ile Glu Ala Glu Ala Gln Asp Arg Ser Ser Ile Ala Trp Pro Gly Asn
        515                 520                 525

Gln Leu Glu Leu Ile Ala Gln Leu Ala Ala Gln Lys Ser Glu Ser Gln
    530                 535                 540

Pro Leu Val Val Tyr Gln Met Gly Gly Gly Gln Val Asp Ser Ser Ala
545                 550                 555                 560

Leu Lys Ala Asn Pro Lys Val Asn Ala Leu Leu Trp Gly Gly Tyr Pro
                565                 570                 575

Gly Gln Ser Gly Gly Leu Ala Leu Arg Asp Ile Leu Thr Gly Ala Arg
            580                 585                 590

Ala Pro Ala Gly Arg Leu Thr Thr Thr Gln Tyr Pro Ala Ser Tyr Ala
        595                 600                 605

Glu Ser Phe Ser Ala Leu Asp Met Asn Leu Arg Pro Asn Thr Thr Thr
    610                 615                 620

Asn Asn Pro Gly Gln Thr Tyr Met Trp Tyr Thr Gly Glu Pro Val Tyr
625                 630                 635                 640

Glu Phe Gly His Gly Leu Phe Tyr Thr Thr Phe Lys Ala Ser Ser Leu
                645                 650                 655

Pro Ser Ser Thr Gln Asn Thr Thr Ser Ala Ala Ala Ala Ala Ala Ala
            660                 665                 670

Ala Lys Lys Tyr Thr Phe Asn Ile Thr Asp Leu Thr Ser Ser Ala His
        675                 680                 685

Pro Asp Thr Thr Thr Val Ala Gln His Thr Leu Phe Asn Phe Thr Ala
    690                 695                 700

Ser Ile Thr Asn Ser Gly Ala Arg Asp Ser Asp Tyr Thr Ala Leu Leu
705                 710                 715                 720

Tyr Ala Asn Thr Ser Ser Ala Gly Pro Ser Pro Tyr Pro Asn Lys Trp
                725                 730                 735

Leu Val Gly Phe Asp Arg Leu Gly Ala Val Ala Lys Glu Gly Gly Thr
            740                 745                 750

Ala Val Leu Asn Val Pro Val Ala Val Asp Arg Leu Ala Arg Val Asp
        755                 760                 765

Asp Asp Gly Asn Ser Val Leu Phe Pro Gly Arg Tyr Glu Val Ala Leu
    770                 775                 780

Asn Asn Glu Arg Glu Val Val Val Glu Val Glu Leu Val Gly Glu Ala
785                 790                 795                 800

Val Val Leu Val Lys Trp Pro Glu Glu Val Gln Gly Val Ala Gly Asp
                805                 810                 815

Glu
```

<210> SEQ ID NO 205
<211> LENGTH: 2376
<212> TYPE: DNA
<213> ORGANISM: Aspergillus fumigatus

<400> SEQUENCE: 205

```
atggcggttg ccaaatctat tgctgccgtg ctggtagcac tgttgcctgg tgcgcttgct     60

caggcgaata caagctatgt tgattacaat gtggaggcga atccggatct cacccctcag    120

tcggtcgcta cgattgacct gtcctttccc gactgcgaga atggaccgct cagcaagact    180

ctcgtttgcg acacgtcggc tcggccgcat gaccgagctg ctgccctggt ttccatgttc    240

accttcgagg agctggtgaa caacacaggc aacactagcc ctggtgttcc aagacttggt    300

ctccctccgt accaagtatg gagcgaggct ctccatggac ttgaccgcgc caacttcaca    360
```

aacgagggag agtacagctg ggccacctcg ttccccatgc ctatcctgac aatgtcggcc 420
ttgaaccgaa ccctgatcaa ccagatcgcg accatcatcg caactcaagg acgagctttc 480
aataacgttg ggcggtatgg gctggacgtg tacgccccga atataaatgc attcagatcg 540
gctatgtggg gaagaggtca agagaccccc ggagaagacg cttactgcct ggcatcggcg 600
tatgcgtacg agtatatcac tggcatccag ggtggtgttg atccggaaca cctcaagttg 660
gtggccactg ccaaacacta tgcgggctac gatcttgaga actgggacgg tcactcccgt 720
ttgggcaacg atatgaacat tacacagcag gaactttccg aatactacac ccctcagttc 780
cttgttgcag ccagagacgc caaagtgcac agtgtcatgt gctcctacaa cgcggtaaat 840
ggggtgccca gctgcgcaaa ctcgttcttc ctccagaccc tcctccgtga cacattcggc 900
ttcgtcgagg atggttatgt atccagcgac tgcgactcgg cgtacaatgt ctggaacccg 960
cacgagtttg cggccaacat cacgggggcc gctgcagact ctatccgggc ggggacggac 1020
attgattgcg gcactactta tcaatactat ttcggcgaag cctttgacga gcaagaggtc 1080
acccgtgcag aaatcgaaag aggtgtgatc cgcctgtaca gcaacttggt gcgtctcggc 1140
tatttcgatg gcaatggaag cgtgtatcgg gacctgacgt ggaatgatgt cgtgaccacg 1200
gatgcctgga atatctcata cgaagccgct gtagaaggca ttgtcctact gaagaacgat 1260
ggaaccttgc ctctcgccaa gtcggtccgc agtgttgcat tgattgggcc ctggatgaat 1320
gtgacgactc agcttcaggg caactacttt ggaccggcgc cttatctgat tagtccgttg 1380
aatgccttcc agaattctga cttcgacgtg aactacgctt tcggcacgaa catttcatcc 1440
cactccacag atgggttttc cgaggcgttg tctgctgcga agaaatccga cgtcatcata 1500
ttcgcgggcg ggattgacaa cactttggaa gcagaagcca tggatcgcat gaatatcaca 1560
tggcccggca atcagctaca gctcatcgac cagttgagcc aactcggcaa accgctgatc 1620
gtcctccaga tgggcggcgg ccaagtcgac tcctcctcgc tcaagtccaa caagaatgtc 1680
aactccctga tctggggtgg ataccccgga caatccggcg ggcaggctct cctagacatc 1740
atcaccggca agcgcgcccc cgccggccga ctcgtggtca cgcagtaccc ggccgaatac 1800
gcaacccagt tccccgccac cgacatgagc ctgcggcctc acggcaataa tcccggccag 1860
acctacatgt ggtacaccgg caccccgtc tacgagtttg gccacgggct cttctacacg 1920
accttccacg cctccctccc tggcaccggc aaggacaaga cctccttcaa catccaagac 1980
ctcctcacgc agccgcatcc gggcttcgca aacgtcgagc aaatgccttt gctcaacttc 2040
accgtgacga tcaccaatac cggcaaggtc gcttccgact acactgctat gctcttcgcg 2100
aacaccaccg cgggacctgc tccatacccg aacaagtggc tcgtcggctt cgaccggctg 2160
gcgagcctgg aaccgcacag gtcgcagact atgaccatcc ccgtgactat cgacagcgtg 2220
gctcgtacgg atgaggccgg caatcgggtt ctctacccgg gaaagtacga gttggccctg 2280
aacaatgagc ggtcggttgt ccttcagttt gtgctgacag gccgagaggc tgtgattttc 2340
aagtggcctg tagagcagca gcagatttcg tctgcg 2376

<210> SEQ ID NO 206
<211> LENGTH: 792
<212> TYPE: PRT
<213> ORGANISM: Aspergillus fumigatus

<400> SEQUENCE: 206

Met Ala Val Ala Lys Ser Ile Ala Ala Val Leu Val Ala Leu Leu Pro
1 5 10 15

-continued

```
Gly Ala Leu Ala Gln Ala Asn Thr Ser Tyr Val Asp Tyr Asn Val Glu
            20                  25                  30

Ala Asn Pro Asp Leu Thr Pro Gln Ser Val Ala Thr Ile Asp Leu Ser
        35                  40                  45

Phe Pro Asp Cys Glu Asn Gly Pro Leu Ser Lys Thr Leu Val Cys Asp
    50                  55                  60

Thr Ser Ala Arg Pro His Asp Arg Ala Ala Ala Leu Val Ser Met Phe
65                  70                  75                  80

Thr Phe Glu Glu Leu Val Asn Asn Thr Gly Asn Thr Ser Pro Gly Val
                85                  90                  95

Pro Arg Leu Gly Leu Pro Pro Tyr Gln Val Trp Ser Glu Ala Leu His
            100                 105                 110

Gly Leu Asp Arg Ala Asn Phe Thr Asn Glu Gly Glu Tyr Ser Trp Ala
        115                 120                 125

Thr Ser Phe Pro Met Pro Ile Leu Thr Met Ser Ala Leu Asn Arg Thr
    130                 135                 140

Leu Ile Asn Gln Ile Ala Thr Ile Ile Ala Thr Gln Gly Arg Ala Phe
145                 150                 155                 160

Asn Asn Val Gly Arg Tyr Gly Leu Asp Val Tyr Ala Pro Asn Ile Asn
                165                 170                 175

Ala Phe Arg Ser Ala Met Trp Gly Arg Gly Gln Glu Thr Pro Gly Glu
            180                 185                 190

Asp Ala Tyr Cys Leu Ala Ser Ala Tyr Ala Tyr Glu Tyr Ile Thr Gly
        195                 200                 205

Ile Gln Gly Gly Val Asp Pro Glu His Leu Lys Leu Val Ala Thr Ala
    210                 215                 220

Lys His Tyr Ala Gly Tyr Asp Leu Glu Asn Trp Asp Gly His Ser Arg
225                 230                 235                 240

Leu Gly Asn Asp Met Asn Ile Thr Gln Gln Glu Leu Ser Glu Tyr Tyr
                245                 250                 255

Thr Pro Gln Phe Leu Val Ala Ala Arg Asp Ala Lys Val His Ser Val
            260                 265                 270

Met Cys Ser Tyr Asn Ala Val Asn Gly Val Pro Ser Cys Ala Asn Ser
        275                 280                 285

Phe Phe Leu Gln Thr Leu Leu Arg Asp Thr Phe Gly Phe Val Glu Asp
    290                 295                 300

Gly Tyr Val Ser Ser Asp Cys Asp Ser Ala Tyr Asn Val Trp Asn Pro
305                 310                 315                 320

His Glu Phe Ala Ala Asn Ile Thr Gly Ala Ala Ala Asp Ser Ile Arg
                325                 330                 335

Ala Gly Thr Asp Ile Asp Cys Gly Thr Thr Tyr Gln Tyr Tyr Phe Gly
            340                 345                 350

Glu Ala Phe Asp Glu Gln Glu Val Thr Arg Ala Glu Ile Glu Arg Gly
        355                 360                 365

Val Ile Arg Leu Tyr Ser Asn Leu Val Arg Leu Gly Tyr Phe Asp Gly
    370                 375                 380

Asn Gly Ser Val Tyr Arg Asp Leu Thr Trp Asn Asp Val Val Thr Thr
385                 390                 395                 400

Asp Ala Trp Asn Ile Ser Tyr Glu Ala Ala Val Glu Gly Ile Val Leu
                405                 410                 415

Leu Lys Asn Asp Gly Thr Leu Pro Leu Ala Lys Ser Val Arg Ser Val
            420                 425                 430

Ala Leu Ile Gly Pro Trp Met Asn Val Thr Thr Gln Leu Gln Gly Asn
```

```
        435                 440                 445

Tyr Phe Gly Pro Ala Pro Tyr Leu Ile Ser Pro Leu Asn Ala Phe Gln
    450                 455                 460

Asn Ser Asp Phe Asp Val Asn Tyr Ala Phe Gly Thr Asn Ile Ser Ser
465                 470                 475                 480

His Ser Thr Asp Gly Phe Ser Glu Ala Leu Ser Ala Ala Lys Lys Ser
                485                 490                 495

Asp Val Ile Ile Phe Ala Gly Gly Ile Asp Asn Thr Leu Glu Ala Glu
            500                 505                 510

Ala Met Asp Arg Met Asn Ile Thr Trp Pro Gly Asn Gln Leu Gln Leu
        515                 520                 525

Ile Asp Gln Leu Ser Gln Leu Gly Lys Pro Leu Ile Val Leu Gln Met
    530                 535                 540

Gly Gly Gly Gln Val Asp Ser Ser Ser Leu Lys Ser Asn Lys Asn Val
545                 550                 555                 560

Asn Ser Leu Ile Trp Gly Gly Tyr Pro Gly Gln Ser Gly Gly Gln Ala
                565                 570                 575

Leu Leu Asp Ile Ile Thr Gly Lys Arg Ala Pro Ala Gly Arg Leu Val
            580                 585                 590

Val Thr Gln Tyr Pro Ala Glu Tyr Ala Thr Gln Phe Pro Ala Thr Asp
        595                 600                 605

Met Ser Leu Arg Pro His Gly Asn Asn Pro Gly Gln Thr Tyr Met Trp
    610                 615                 620

Tyr Thr Gly Thr Pro Val Tyr Glu Phe Gly His Gly Leu Phe Tyr Thr
625                 630                 635                 640

Thr Phe His Ala Ser Leu Pro Gly Thr Gly Lys Asp Lys Thr Ser Phe
                645                 650                 655

Asn Ile Gln Asp Leu Leu Thr Gln Pro His Pro Gly Phe Ala Asn Val
            660                 665                 670

Glu Gln Met Pro Leu Leu Asn Phe Thr Val Thr Ile Thr Asn Thr Gly
        675                 680                 685

Lys Val Ala Ser Asp Tyr Thr Ala Met Leu Phe Ala Asn Thr Thr Ala
    690                 695                 700

Gly Pro Ala Pro Tyr Pro Asn Lys Trp Leu Val Gly Phe Asp Arg Leu
705                 710                 715                 720

Ala Ser Leu Glu Pro His Arg Ser Gln Thr Met Thr Ile Pro Val Thr
                725                 730                 735

Ile Asp Ser Val Ala Arg Thr Asp Glu Ala Gly Asn Arg Val Leu Tyr
            740                 745                 750

Pro Gly Lys Tyr Glu Leu Ala Leu Asn Asn Glu Arg Ser Val Val Leu
        755                 760                 765

Gln Phe Val Leu Thr Gly Arg Glu Ala Val Ile Phe Lys Trp Pro Val
    770                 775                 780

Glu Gln Gln Gln Ile Ser Ser Ala
785                 790
```

<210> SEQ ID NO 207
<211> LENGTH: 38
<212> TYPE: DNA
<213> ORGANISM: Penicillium emersonii

<400> SEQUENCE: 207
acacaactgg ggatccacca tgcttcgacg ggctcttc 38

<210> SEQ ID NO 208
<211> LENGTH: 40
<212> TYPE: DNA
<213> ORGANISM: Penicillium emersonii

<400> SEQUENCE: 208
gtcaccctct agatctcgca gagcaacttc cgtctacttc 40

<210> SEQ ID NO 209
<211> LENGTH: 40
<212> TYPE: DNA
<213> ORGANISM: Penicillium pinophilum

<400> SEQUENCE: 209
acacaactgg ggatccacca tgtctgcctt gaactctttc 40

<210> SEQ ID NO 210
<211> LENGTH: 43
<212> TYPE: DNA
<213> ORGANISM: Penicillium pinophilum

<400> SEQUENCE: 210
gtcaccctct agatcttcac aaacattgag agtagtaagg gtt 43

<210> SEQ ID NO 211
<211> LENGTH: 29
<212> TYPE: DNA
<213> ORGANISM: Aspergillus terreus

<400> SEQUENCE: 211
taagaattca ccatgccttc cacctacga 29

<210> SEQ ID NO 212
<211> LENGTH: 32
<212> TYPE: DNA
<213> ORGANISM: Aspergillus terreus

<400> SEQUENCE: 212
tatgcggccg cattctccta gacaccccgc at 32

<210> SEQ ID NO 213
<211> LENGTH: 29
<212> TYPE: DNA
<213> ORGANISM: Neosartorya fischeri

<400> SEQUENCE: 213
taagaattca ccatgccttc cacctacga 29

<210> SEQ ID NO 214
<211> LENGTH: 32
<212> TYPE: DNA
<213> ORGANISM: Neosartorya fischeri

<400> SEQUENCE: 214
tatgcggccg cattctccta gacaccccgc at 32

<210> SEQ ID NO 215
<211> LENGTH: 35
<212> TYPE: DNA
<213> ORGANISM: Aspergillus nidulans

<400> SEQUENCE: 215
taacaattga ccatggcatc ttcattccag ttgta 35

<210> SEQ ID NO 216
<211> LENGTH: 33
<212> TYPE: DNA
<213> ORGANISM: Aspergillus nidulans

<400> SEQUENCE: 216
tatgcggccg cgtctcccat ttacgaccca cca 33

<210> SEQ ID NO 217
<211> LENGTH: 41
<212> TYPE: DNA
<213> ORGANISM: Fennellia nivea

<400> SEQUENCE: 217
acacaactgg ggatccacca tgggacgggt ttcttctctt g 41

<210> SEQ ID NO 218
<211> LENGTH: 39
<212> TYPE: DNA
<213> ORGANISM: Fennellia nivea

<400> SEQUENCE: 218
gtcaccctct agatctaaga acaccccgca aagaaagtc 39

<210> SEQ ID NO 219
<211> LENGTH: 42
<212> TYPE: DNA
<213> ORGANISM: Penicillium emersonii

<400> SEQUENCE: 219
acacaactgg ggatccacca tgcggaatct tcttgctctt gc 42

<210> SEQ ID NO 220
<211> LENGTH: 41
<212> TYPE: DNA
<213> ORGANISM: Penicillium emersonii

<400> SEQUENCE: 220
gtcaccctct agatctctag aacagcgggt tagcattcgt g 41

<210> SEQ ID NO 221
<211> LENGTH: 40
<212> TYPE: DNA
<213> ORGANISM: Penicillium pinophilum

<400> SEQUENCE: 221
acacaactgg ggatccacca tgttgcgata tctttccacc 40

<210> SEQ ID NO 222
<211> LENGTH: 39
<212> TYPE: DNA
<213> ORGANISM: Penicillium pinophilum

<400> SEQUENCE: 222
gtcaccctct agatcttcat ctagaccaaa gctgggttg 39

<210> SEQ ID NO 223
<211> LENGTH: 36
<212> TYPE: DNA
<213> ORGANISM: Aspergillus fumigatus

<400> SEQUENCE: 223
actggattta ccatgaaatt cggtagcatt gtgctc 36

<210> SEQ ID NO 224
<211> LENGTH: 43
<212> TYPE: DNA
<213> ORGANISM: Aspergillus fumigatus

<400> SEQUENCE: 224
tcacctctag ttaattaatc aacccaggta gggctccaag atg 43

<210> SEQ ID NO 225
<211> LENGTH: 39
<212> TYPE: DNA
<213> ORGANISM: Neosartorya fischeri

<400> SEQUENCE: 225
taagaattca ccatgaaggc ttcgactatt atctgtgca 39

<210> SEQ ID NO 226
<211> LENGTH: 32
<212> TYPE: DNA
<213> ORGANISM: Neosartorya fischeri

<400> SEQUENCE: 226
tatgcggccg cacggcaatc caagtcattc aa 32

<210> SEQ ID NO 227
<211> LENGTH: 44
<212> TYPE: DNA
<213> ORGANISM: Aspergillus aculeatus

<400> SEQUENCE: 227
acacaactgg ggatccacca tgaagctcag ttggcttgag gcgg 44

<210> SEQ ID NO 228
<211> LENGTH: 44
<212> TYPE: DNA
<213> ORGANISM: Aspergillus aculeatus

<400> SEQUENCE: 228
agatctcgag aagcttattg caccttcggg agcgccgcgt gaag 44

<210> SEQ ID NO 229
<211> LENGTH: 44
<212> TYPE: DNA
<213> ORGANISM: Aspergillus kawachii

<400> SEQUENCE: 229
acacaactgg ggatccacca tgaggttcac tttgattgag gcgg 44

<210> SEQ ID NO 230
<211> LENGTH: 45
<212> TYPE: DNA
<213> ORGANISM: Aspergillus kawachii

<400> SEQUENCE: 230
agatctcgag aagcttagtg aacagtaggc agagacgccc ggagc 45

<210> SEQ ID NO 231
<211> LENGTH: 44
<212> TYPE: DNA
<213> ORGANISM: Aspergillus clavatus

<400> SEQUENCE: 231

-continued acacaactgg ggatccacca tgaggttcag ctggcttgag gtcg 44

<210> SEQ ID NO 232
<211> LENGTH: 42
<212> TYPE: DNA
<213> ORGANISM: Aspergillus clavatus

<400> SEQUENCE: 232
agatctcgag aagcttactg tacccggggc agaggtgctc tc 42

<210> SEQ ID NO 233
<211> LENGTH: 46
<212> TYPE: DNA
<213> ORGANISM: Thielavia terrestris
<220> FEATURE:
<221> NAME/KEY: misc_feature
<222> LOCATION: (45)..(45)
<223> OTHER INFORMATION: V=A, C, OR G
<220> FEATURE:
<221> NAME/KEY: misc_feature
<222> LOCATION: (46)..(46)
<223> OTHER INFORMATION: N=A, C, G, OR T

<400> SEQUENCE: 233
gactagttct agatcgcgag cggccgccct tttttttttt ttttvn 46

<210> SEQ ID NO 234
<211> LENGTH: 16
<212> TYPE: DNA
<213> ORGANISM: Thielavia terrestris

<400> SEQUENCE: 234
tcgacccacg cgtccg 16

<210> SEQ ID NO 235
<211> LENGTH: 12
<212> TYPE: DNA
<213> ORGANISM: Thielavia terrestris

<400> SEQUENCE: 235
cggacgcgtg gg 12

<210> SEQ ID NO 236
<211> LENGTH: 17
<212> TYPE: DNA
<213> ORGANISM: Thielavia terrestris

<400> SEQUENCE: 236
gtaaaacgac ggccagt 17

<210> SEQ ID NO 237
<211> LENGTH: 19
<212> TYPE: DNA
<213> ORGANISM: Thielavia terrestris

<400> SEQUENCE: 237
aggaaacagc tatgaccat 19

<210> SEQ ID NO 238
<211> LENGTH: 20
<212> TYPE: DNA
<213> ORGANISM: Thielavia terrestris

<400> SEQUENCE: 238
atttaggtga cactatagaa 20

<210> SEQ ID NO 239
<211> LENGTH: 20
<212> TYPE: DNA
<213> ORGANISM: Thielavia terrestris

<400> SEQUENCE: 239
taatacgact cactataggg 20

<210> SEQ ID NO 240
<211> LENGTH: 32
<212> TYPE: DNA
<213> ORGANISM: Thielavia terrestris

<400> SEQUENCE: 240
actggattta ccatgaagcc tgccattgtg ct 32

<210> SEQ ID NO 241
<211> LENGTH: 38
<212> TYPE: DNA
<213> ORGANISM: Thielavia terrestris

<400> SEQUENCE: 241
tcacctctag ttaattaatc acggcaactc aatgctca 38

<210> SEQ ID NO 242
<211> LENGTH: 35
<212> TYPE: DNA
<213> ORGANISM: Penicillium oxalicum
<220> FEATURE:
<221> NAME/KEY: misc_feature
<222> LOCATION: (25)..(25)
<223> OTHER INFORMATION: Y= C OR T
<220> FEATURE:
<221> NAME/KEY: misc_feature
<222> LOCATION: (27)..(27)
<223> OTHER INFORMATION: N= A, C, G, OR T
<220> FEATURE:
<221> NAME/KEY: misc_feature
<222> LOCATION: (30)..(30)
<223> OTHER INFORMATION: N= A, C, G, OR T
<220> FEATURE:
<221> NAME/KEY: misc_feature
<222> LOCATION: (33)..(33)
<223> OTHER INFORMATION: N= A, C, G, OR T

<400> SEQUENCE: 242
atgaccctgg ccgaaaaagt caacytnacn acngg 35

<210> SEQ ID NO 243
<211> LENGTH: 35
<212> TYPE: DNA
<213> ORGANISM: Penicillium oxalicum
<220> FEATURE:
<221> NAME/KEY: misc_feature
<222> LOCATION: (26)..(26)
<223> OTHER INFORMATION: S= C OR G
<220> FEATURE:
<221> NAME/KEY: misc_feature
<222> LOCATION: (27)..(27)
<223> OTHER INFORMATION: N= A, C, G, OR T
<220> FEATURE:
<221> NAME/KEY: misc_feature
<222> LOCATION: (30)..(30)
<223> OTHER INFORMATION: N= A, C, G, OR T
<220> FEATURE:
<221> NAME/KEY: misc_feature
<222> LOCATION: (33)..(33)
<223> OTHER INFORMATION: Y= C OR T

<400> SEQUENCE: 243
ggtggccgga actgggaagg cttctsnccn gaycc 35

<210> SEQ ID NO 244
<211> LENGTH: 36
<212> TYPE: DNA
<213> ORGANISM: Penicillium oxalicum
<220> FEATURE:
<221> NAME/KEY: misc_feature
<222> LOCATION: (24)..(24)
<223> OTHER INFORMATION: N= A,C, G, OR T
<220> FEATURE:
<221> NAME/KEY: misc_feature
<222> LOCATION: (28)..(28)
<223> OTHER INFORMATION: W= A OR T
<220> FEATURE:
<221> NAME/KEY: misc_feature
<222> LOCATION: (29)..(29)
<223> OTHER INFORMATION: S= C OR G
<220> FEATURE:
<221> NAME/KEY: misc_feature
<222> LOCATION: (30)..(30)
<223> OTHER INFORMATION: N= A, C, G, OR T
<220> FEATURE:
<221> NAME/KEY: misc_feature
<222> LOCATION: (33)..(33)
<223> OTHER INFORMATION: Y= C OR T

<400> SEQUENCE: 244
gagctgggct tccagggctt tgtnatgwsn gaytgg 36

<210> SEQ ID NO 245
<211> LENGTH: 32
<212> TYPE: DNA
<213> ORGANISM: Penicillium oxalicum
<220> FEATURE:
<221> NAME/KEY: misc_feature
<222> LOCATION: (21)..(21)
<223> OTHER INFORMATION: Y=C OR T
<220> FEATURE:
<221> NAME/KEY: misc_feature
<222> LOCATION: (25)..(25)
<223> OTHER INFORMATION: W= A OR T
<220> FEATURE:
<221> NAME/KEY: misc_feature
<222> LOCATION: (26)..(26)
<223> OTHER INFORMATION: S= C OR G
<220> FEATURE:
<221> NAME/KEY: misc_feature
<222> LOCATION: (27)..(27)
<223> OTHER INFORMATION: N= A, C, G, OR T

<400> SEQUENCE: 245
agcgctttgg ccggcctcga yatgwsnatg cc 32

<210> SEQ ID NO 246
<211> LENGTH: 27
<212> TYPE: DNA
<213> ORGANISM: Penicillium oxalicum
<220> FEATURE:
<221> NAME/KEY: misc_feature
<222> LOCATION: (21)..(21)
<223> OTHER INFORMATION: K= G OR T
<220> FEATURE:
<221> NAME/KEY: misc_feature
<222> LOCATION: (22)..(22)
<223> OTHER INFORMATION: N= A,C, G, OR T
<220> FEATURE:
<221> NAME/KEY: misc_feature
<222> LOCATION: (24)..(24)
<223> OTHER INFORMATION: K= G OR T
<220> FEATURE:
<221> NAME/KEY: misc_feature

<222> LOCATION: (25)..(25)
<223> OTHER INFORMATION: N= A, C, G, OR T

<400> SEQUENCE: 246
atcccagttg ctcaggtccc knckngt                                    27

<210> SEQ ID NO 247
<211> LENGTH: 33
<212> TYPE: DNA
<213> ORGANISM: Penicillium oxalicum
<220> FEATURE:
<221> NAME/KEY: misc_feature
<222> LOCATION: (19)..(19)
<223> OTHER INFORMATION: N= A,C ,G, OR T
<220> FEATURE:
<221> NAME/KEY: misc_feature
<222> LOCATION: (22)..(22)
<223> OTHER INFORMATION: R= A OR G
<220> FEATURE:
<221> NAME/KEY: misc_feature
<222> LOCATION: (25)..(25)
<223> OTHER INFORMATION: N= A,C ,G, OR T
<220> FEATURE:
<221> NAME/KEY: misc_feature
<222> LOCATION: (28)..(28)
<223> OTHER INFORMATION: R= A OR G
<220> FEATURE:
<221> NAME/KEY: misc_feature
<222> LOCATION: (31)..(31)
<223> OTHER INFORMATION: Y = C OR T

<400> SEQUENCE: 247
aaaggttgtg tagctcagnc crtgnccraa ytc                             33

<210> SEQ ID NO 248
<211> LENGTH: 33
<212> TYPE: DNA
<213> ORGANISM: Penicillium oxalicum
<220> FEATURE:
<221> NAME/KEY: misc_feature
<222> LOCATION: (22)..(22)
<223> OTHER INFORMATION: R= A OR G
<220> FEATURE:
<221> NAME/KEY: misc_feature
<222> LOCATION: (25)..(25)
<223> OTHER INFORMATION: N= A, C, G, OR T
<220> FEATURE:
<221> NAME/KEY: misc_feature
<222> LOCATION: (28)..(28)
<223> OTHER INFORMATION: N= A, C, G, OR T
<220> FEATURE:
<221> NAME/KEY: misc_feature
<222> LOCATION: (31)..(31)
<223> OTHER INFORMATION: Y= C OR T

<400> SEQUENCE: 248
gtcaaagtgg cggtagtcga traanacncc ytc                             33

<210> SEQ ID NO 249
<211> LENGTH: 39
<212> TYPE: DNA
<213> ORGANISM: Penicillium oxalicum
<220> FEATURE:
<221> NAME/KEY: misc_feature
<222> LOCATION: (34)..(34)
<223> OTHER INFORMATION: R= A OR G
<220> FEATURE:
<221> NAME/KEY: misc_feature
<222> LOCATION: (37)..(37)
<223> OTHER INFORMATION: N= A,C, G, OR T
<220> FEATURE:
<221> NAME/KEY: misc_feature
<222> LOCATION: (39)..(39)

<223> OTHER INFORMATION: R= A OR G

<400> SEQUENCE: 249
ggtgggcgag ttgccgacgg ggttgactct gccrtanar 39

<210> SEQ ID NO 250
<211> LENGTH: 39
<212> TYPE: DNA
<213> ORGANISM: Penicillium oxalicum
<220> FEATURE:
<221> NAME/KEY: misc_feature
<222> LOCATION: (28)..(28)
<223> OTHER INFORMATION: N= A,C, G, OR T
<220> FEATURE:
<221> NAME/KEY: misc_feature
<222> LOCATION: (31)..(31)
<223> OTHER INFORMATION: N= A,C, G, OR T
<220> FEATURE:
<221> NAME/KEY: misc_feature
<222> LOCATION: (34)..(34)
<223> OTHER INFORMATION: R= A OR G
<220> FEATURE:
<221> NAME/KEY: misc_feature
<222> LOCATION: (37)..(37)
<223> OTHER INFORMATION: N= A, C ,G, OR T

<400> SEQUENCE: 250
gccgggcaga ccggcccaga ggatggcngt nacrttngg 39

<210> SEQ ID NO 251
<211> LENGTH: 39
<212> TYPE: DNA
<213> ORGANISM: Penicillium oxalicum
<220> FEATURE:
<221> NAME/KEY: misc_feature
<222> LOCATION: (28)..(28)
<223> OTHER INFORMATION: N= A, C, G, OR T
<220> FEATURE:
<221> NAME/KEY: misc_feature
<222> LOCATION: (31)..(31)
<223> OTHER INFORMATION: D= A, G, OR T
<220> FEATURE:
<221> NAME/KEY: misc_feature
<222> LOCATION: (34)..(34)
<223> OTHER INFORMATION: N= A, C, G, OR T
<220> FEATURE:
<221> NAME/KEY: misc_feature
<222> LOCATION: (37)..(37)
<223> OTHER INFORMATION: R= A OR G

<400> SEQUENCE: 251
caggacgggg ccaaccgagt gaatgacnac datngtrtt 39

<210> SEQ ID NO 252
<211> LENGTH: 21
<212> TYPE: DNA
<213> ORGANISM: Penicillium oxalicum

<400> SEQUENCE: 252
caccaacacc ggcaatctag c 21

<210> SEQ ID NO 253
<211> LENGTH: 25
<212> TYPE: DNA
<213> ORGANISM: Penicillium oxalicum

<400> SEQUENCE: 253
ggtgacgagg ttgtccaact gtacg 25

<210> SEQ ID NO 254
<211> LENGTH: 18
<212> TYPE: DNA
<213> ORGANISM: Penicillium oxalicum

<400> SEQUENCE: 254
cttgaagcca aggcgagg 18

<210> SEQ ID NO 255
<211> LENGTH: 24
<212> TYPE: DNA
<213> ORGANISM: Penicillium oxalicum

<400> SEQUENCE: 255
tccggtattt cctacacatg gtcc 24

<210> SEQ ID NO 256
<211> LENGTH: 43
<212> TYPE: DNA
<213> ORGANISM: Penicillium oxalicum

<400> SEQUENCE: 256
agatctcgag aagcttacca tgactccaat cgcgcgctca agg 43

<210> SEQ ID NO 257
<211> LENGTH: 46
<212> TYPE: DNA
<213> ORGANISM: Penicillium oxalicum

<400> SEQUENCE: 257
acacaactgg ggatccacca tgaggagctc aacgacggtt ctggcc 46

<210> SEQ ID NO 258
<211> LENGTH: 35
<212> TYPE: DNA
<213> ORGANISM: Penicillium oxalicum
<220> FEATURE:
<221> NAME/KEY: misc_feature
<222> LOCATION: (25)..(25)
<223> OTHER INFORMATION: Y= C OR T
<220> FEATURE:
<221> NAME/KEY: misc_feature
<222> LOCATION: (27)..(27)
<223> OTHER INFORMATION: N= A, C, G, OR T
<220> FEATURE:
<221> NAME/KEY: misc_feature
<222> LOCATION: (30)..(30)
<223> OTHER INFORMATION: N= A, C, G, OR T
<220> FEATURE:
<221> NAME/KEY: misc_feature
<222> LOCATION: (33)..(33)
<223> OTHER INFORMATION: N= A, C, G, OR T

<400> SEQUENCE: 258
atgaccctgg ccgaaaaagt caacytnacn acngg 35

<210> SEQ ID NO 259
<211> LENGTH: 35
<212> TYPE: DNA
<213> ORGANISM: Penicillium oxalicum
<220> FEATURE:
<221> NAME/KEY: misc_feature
<222> LOCATION: (26)..(26)
<223> OTHER INFORMATION: S= C OR G
<220> FEATURE:
<221> NAME/KEY: misc_feature
<222> LOCATION: (27)..(27)
<223> OTHER INFORMATION: N= A, C, G, OR T
<220> FEATURE:

<221> NAME/KEY: misc_feature
<222> LOCATION: (30)..(30)
<223> OTHER INFORMATION: N= A, C, G, OR T
<220> FEATURE:
<221> NAME/KEY: misc_feature
<222> LOCATION: (33)..(33)
<223> OTHER INFORMATION: Y= C OR T

<400> SEQUENCE: 259
ggtggccgga actgggaagg cttctsnccn gaycc 35

<210> SEQ ID NO 260
<211> LENGTH: 36
<212> TYPE: DNA
<213> ORGANISM: Penicillium oxalicum
<220> FEATURE:
<221> NAME/KEY: misc_feature
<222> LOCATION: (24)..(24)
<223> OTHER INFORMATION: N= A, C, G, OR T
<220> FEATURE:
<221> NAME/KEY: misc_feature
<222> LOCATION: (28)..(28)
<223> OTHER INFORMATION: W= A OR T
<220> FEATURE:
<221> NAME/KEY: misc_feature
<222> LOCATION: (29)..(29)
<223> OTHER INFORMATION: S= C OR G
<220> FEATURE:
<221> NAME/KEY: misc_feature
<222> LOCATION: (30)..(30)
<223> OTHER INFORMATION: N= A, C, G, OR T
<220> FEATURE:
<221> NAME/KEY: misc_feature
<222> LOCATION: (33)..(33)
<223> OTHER INFORMATION: Y= C OR T

<400> SEQUENCE: 260
gagctgggct tccagggctt tgtnatgwsn gaytgg 36

<210> SEQ ID NO 261
<211> LENGTH: 32
<212> TYPE: DNA
<213> ORGANISM: Penicillium oxalicum
<220> FEATURE:
<221> NAME/KEY: misc_feature
<222> LOCATION: (21)..(21)
<223> OTHER INFORMATION: Y= C OR T
<220> FEATURE:
<221> NAME/KEY: misc_feature
<222> LOCATION: (25)..(25)
<223> OTHER INFORMATION: W= A OR T
<220> FEATURE:
<221> NAME/KEY: misc_feature
<222> LOCATION: (26)..(26)
<223> OTHER INFORMATION: S= C OR G
<220> FEATURE:
<221> NAME/KEY: misc_feature
<222> LOCATION: (27)..(27)
<223> OTHER INFORMATION: N= A, C, G, OR T

<400> SEQUENCE: 261
agcgctttgg ccggcctcga yatgwsnatg cc 32

<210> SEQ ID NO 262
<211> LENGTH: 27
<212> TYPE: DNA
<213> ORGANISM: Penicillium oxalicum
<220> FEATURE:
<221> NAME/KEY: misc_feature
<222> LOCATION: (21)..(21)
<223> OTHER INFORMATION: K= G OR T
<220> FEATURE:
<221> NAME/KEY: misc_feature
<222> LOCATION: (22)..(22)
<223> OTHER INFORMATION: N= A, C, G, OR T
<220> FEATURE:
<221> NAME/KEY: misc_feature
<222> LOCATION: (24)..(24)
<223> OTHER INFORMATION: K= G OR T
<220> FEATURE:
<221> NAME/KEY: misc_feature
<222> LOCATION: (25)..(25)
<223> OTHER INFORMATION: N= A, C, G, OR T

<400> SEQUENCE: 262
atcccagttg ctcaggtccc kncknqt 27

<210> SEQ ID NO 263
<211> LENGTH: 33
<212> TYPE: DNA
<213> ORGANISM: Penicillium oxalicum
<220> FEATURE:
<221> NAME/KEY: misc_feature
<222> LOCATION: (19)..(19)
<223> OTHER INFORMATION: N= A,C ,G, OR T
<220> FEATURE:
<221> NAME/KEY: misc_feature
<222> LOCATION: (22)..(22)
<223> OTHER INFORMATION: R= A OR G
<220> FEATURE:
<221> NAME/KEY: misc_feature
<222> LOCATION: (25)..(25)
<223> OTHER INFORMATION: N= A, C, G, OR T
<220> FEATURE:
<221> NAME/KEY: misc_feature
<222> LOCATION: (28)..(28)
<223> OTHER INFORMATION: R= A OR G
<220> FEATURE:
<221> NAME/KEY: misc_feature
<222> LOCATION: (31)..(31)
<223> OTHER INFORMATION: Y= C OR T

<400> SEQUENCE: 263
aaaggttgtg tagctcagnc crtgnccraa ytc 33

<210> SEQ ID NO 264
<211> LENGTH: 33
<212> TYPE: DNA
<213> ORGANISM: Penicillium oxalicum
<220> FEATURE:
<221> NAME/KEY: misc_feature
<222> LOCATION: (22)..(22)
<223> OTHER INFORMATION: R= A OR G
<220> FEATURE:
<221> NAME/KEY: misc_feature
<222> LOCATION: (25)..(25)
<223> OTHER INFORMATION: N= A, C, G, OR T
<220> FEATURE:
<221> NAME/KEY: misc_feature
<222> LOCATION: (28)..(28)
<223> OTHER INFORMATION: N= A, C, G, OR T
<220> FEATURE:
<221> NAME/KEY: misc_feature
<222> LOCATION: (31)..(31)
<223> OTHER INFORMATION: Y= C OR T

<400> SEQUENCE: 264
gtcaaagtgg cggtagtcga traanacncc ytc 33

<210> SEQ ID NO 265
<211> LENGTH: 39
<212> TYPE: DNA
<213> ORGANISM: Penicillium oxalicum
<220> FEATURE:
<221> NAME/KEY: misc_feature
<222> LOCATION: (34)..(34)

<223> OTHER INFORMATION: R= A OR G
<220> FEATURE:
<221> NAME/KEY: misc_feature
<222> LOCATION: (37)..(37)
<223> OTHER INFORMATION: N= A, C, G, OR T
<220> FEATURE:
<221> NAME/KEY: misc_feature
<222> LOCATION: (39)..(39)
<223> OTHER INFORMATION: R= A OR G

<400> SEQUENCE: 265
ggtgggcgag ttgccgacgg ggttgactct gccrtanar 39

<210> SEQ ID NO 266
<211> LENGTH: 39
<212> TYPE: DNA
<213> ORGANISM: Penicillium oxalicum
<220> FEATURE:
<221> NAME/KEY: misc_feature
<222> LOCATION: (28)..(28)
<223> OTHER INFORMATION: N= A, C, G, OR T
<220> FEATURE:
<221> NAME/KEY: misc_feature
<222> LOCATION: (31)..(31)
<223> OTHER INFORMATION: N= A, C, G, OR T
<220> FEATURE:
<221> NAME/KEY: misc_feature
<222> LOCATION: (34)..(34)
<223> OTHER INFORMATION: R= A OR G
<220> FEATURE:
<221> NAME/KEY: misc_feature
<222> LOCATION: (37)..(37)
<223> OTHER INFORMATION: N= A, C, G, OR T

<400> SEQUENCE: 266
gccgggcaga ccggcccaga ggatggcngt nacrttngg 39

<210> SEQ ID NO 267
<211> LENGTH: 39
<212> TYPE: DNA
<213> ORGANISM: Penicillium oxalicum
<220> FEATURE:
<221> NAME/KEY: misc_feature
<222> LOCATION: (28)..(28)
<223> OTHER INFORMATION: N= A, C, G, OR T
<220> FEATURE:
<221> NAME/KEY: misc_feature
<222> LOCATION: (31)..(31)
<223> OTHER INFORMATION: D= A, G, OR T
<220> FEATURE:
<221> NAME/KEY: misc_feature
<222> LOCATION: (34)..(34)
<223> OTHER INFORMATION: N= A, C, G, OR T
<220> FEATURE:
<221> NAME/KEY: misc_feature
<222> LOCATION: (37)..(37)
<223> OTHER INFORMATION: R= A OR G

<400> SEQUENCE: 267
caggacgggg ccaaccgagt gaatgacnac datngtrtt 39

<210> SEQ ID NO 268
<211> LENGTH: 42
<212> TYPE: DNA
<213> ORGANISM: Penicillium oxalicum

<400> SEQUENCE: 268
acacaactgg ggatccacca tgaagctcga gtggctggaa gc 42

<210> SEQ ID NO 269
<211> LENGTH: 40

<212> TYPE: DNA
<213> ORGANISM: Penicillium oxalicum

<400> SEQUENCE: 269
agatctcgag aagcttactg caccttgggc agatcggctg 40

<210> SEQ ID NO 270
<211> LENGTH: 44
<212> TYPE: DNA
<213> ORGANISM: Talaromyces emersonii

<400> SEQUENCE: 270
acacaactgg ggatccacca tgaggaacgg gttgctcaag gtcg 44

<210> SEQ ID NO 271
<211> LENGTH: 42
<212> TYPE: DNA
<213> ORGANISM: Talaromyces emersonii

<400> SEQUENCE: 271
agatctcgag aagcttaaat tccagggtat ggcttaaggg gc 42

<210> SEQ ID NO 272
<211> LENGTH: 19
<212> TYPE: DNA
<213> ORGANISM: Thermoascus crustaceus
<220> FEATURE:
<221> NAME/KEY: misc_feature
<222> LOCATION: (3)..(3)
<223> OTHER INFORMATION: N= A, C, G, OR T
<220> FEATURE:
<221> NAME/KEY: misc_feature
<222> LOCATION: (6)..(6)
<223> OTHER INFORMATION: N= A, C, G, OR T
<220> FEATURE:
<221> NAME/KEY: misc_feature
<222> LOCATION: (9)..(9)
<223> OTHER INFORMATION: Y= C OR T
<220> FEATURE:
<221> NAME/KEY: misc_feature
<222> LOCATION: (12)..(12)
<223> OTHER INFORMATION: N= A, C, G, OR T
<220> FEATURE:
<221> NAME/KEY: misc_feature
<222> LOCATION: (15)..(15)
<223> OTHER INFORMATION: N= A, C, G, OR T

<400> SEQUENCE: 272
gcnacngayc tnggntttg 19

<210> SEQ ID NO 273
<211> LENGTH: 19
<212> TYPE: DNA
<213> ORGANISM: Thermoascus crustaceus
<220> FEATURE:
<221> NAME/KEY: misc_feature
<222> LOCATION: (3)..(3)
<223> OTHER INFORMATION: N= A, C, G, OR T
<220> FEATURE:
<221> NAME/KEY: misc_feature
<222> LOCATION: (6)..(6)
<223> OTHER INFORMATION: N= A, C, G, OR T
<220> FEATURE:
<221> NAME/KEY: misc_feature
<222> LOCATION: (9)..(9)
<223> OTHER INFORMATION: Y= C OR T
<220> FEATURE:
<221> NAME/KEY: misc_feature
<222> LOCATION: (12)..(12)
<223> OTHER INFORMATION: N= A, C, G, OR T
<220> FEATURE:

<221> NAME/KEY: misc_feature
<222> LOCATION: (15)..(15)
<223> OTHER INFORMATION: N= A, C, G, OR T

<400> SEQUENCE: 273
gcnacngayc tnggnttcg 19

<210> SEQ ID NO 274
<211> LENGTH: 19
<212> TYPE: DNA
<213> ORGANISM: Thermoascus crustaceus
<220> FEATURE:
<221> NAME/KEY: misc_feature
<222> LOCATION: (3)..(3)
<223> OTHER INFORMATION: N= A, C, G, OR T
<220> FEATURE:
<221> NAME/KEY: misc_feature
<222> LOCATION: (6)..(6)
<223> OTHER INFORMATION: N= A, C, G, OR T
<220> FEATURE:
<221> NAME/KEY: misc_feature
<222> LOCATION: (9)..(9)
<223> OTHER INFORMATION: Y= C OR T
<220> FEATURE:
<221> NAME/KEY: misc_feature
<222> LOCATION: (12)..(12)
<223> OTHER INFORMATION: R= A OR G
<220> FEATURE:
<221> NAME/KEY: misc_feature
<222> LOCATION: (15)..(15)
<223> OTHER INFORMATION: N= A, C, G, OR T
<220> FEATURE:
<221> NAME/KEY: misc_feature
<222> LOCATION: (18)..(18)
<223> OTHER INFORMATION: Y= C OR T
<220> FEATURE:
<221> NAME/KEY: misc_feature
<222> LOCATION: (18)..(18)
<223> OTHER INFORMATION: Y= C OR T

<400> SEQUENCE: 274
gcnacngayt trggnttyg 19

<210> SEQ ID NO 275
<211> LENGTH: 20
<212> TYPE: DNA
<213> ORGANISM: Thermoascus crustaceus
<220> FEATURE:
<221> NAME/KEY: misc_feature
<222> LOCATION: (3)..(3)
<223> OTHER INFORMATION: Y= C OR T
<220> FEATURE:
<221> NAME/KEY: misc_feature
<222> LOCATION: (6)..(6)
<223> OTHER INFORMATION: N= A, C, G, OR T
<220> FEATURE:
<221> NAME/KEY: misc_feature
<222> LOCATION: (9)..(9)
<223> OTHER INFORMATION: R= A OR G
<220> FEATURE:
<221> NAME/KEY: misc_feature
<222> LOCATION: (12)..(12)
<223> OTHER INFORMATION: R= A OR G
<220> FEATURE:
<221> NAME/KEY: misc_feature
<222> LOCATION: (15)..(15)
<223> OTHER INFORMATION: Y= C OR T
<220> FEATURE:
<221> NAME/KEY: misc_feature
<222> LOCATION: (18)..(18)
<223> OTHER INFORMATION: N= A, C, G, OR T

<400> SEQUENCE: 275
caytgnggrt arttytgngc 20

<210> SEQ ID NO 276
<211> LENGTH: 21
<212> TYPE: DNA
<213> ORGANISM: Thermoascus crustaceus

<400> SEQUENCE: 276
tgcaaggagc aaggtagttg a 21

<210> SEQ ID NO 277
<211> LENGTH: 22
<212> TYPE: DNA
<213> ORGANISM: Thermoascus crustaceus

<400> SEQUENCE: 277
gagtccattc cagcttgacg gt 22

<210> SEQ ID NO 278
<211> LENGTH: 20
<212> TYPE: DNA
<213> ORGANISM: Thermoascus crustaceus

<400> SEQUENCE: 278
tcagacaatc tgatagcggc 20

<210> SEQ ID NO 279
<211> LENGTH: 21
<212> TYPE: DNA
<213> ORGANISM: Thermoascus crustaceus

<400> SEQUENCE: 279
atcccaacca caactgcacc t 21

<210> SEQ ID NO 280
<211> LENGTH: 44
<212> TYPE: DNA
<213> ORGANISM: Thermoascus crustaceus

<400> SEQUENCE: 280
acacaactgg ggatccacca tggccttttc ccagataatg gcta 44

<210> SEQ ID NO 281
<211> LENGTH: 36
<212> TYPE: DNA
<213> ORGANISM: Thermoascus crustaceus

<400> SEQUENCE: 281
gtcaccctct agatctggat cgcaggagcg ttcaga 36

<210> SEQ ID NO 282
<211> LENGTH: 38
<212> TYPE: DNA
<213> ORGANISM: Talaromyces emersonii

<400> SEQUENCE: 282
acacaactgg ggatccacca tggttcgcct cagtccag 38

<210> SEQ ID NO 283
<211> LENGTH: 44
<212> TYPE: DNA
<213> ORGANISM: Talaromyces emersonii

<400> SEQUENCE: 283
gtcaccctct agatctttac agacactgcg agtaatactc attg 44

<210> SEQ ID NO 284
<211> LENGTH: 25
<212> TYPE: DNA
<213> ORGANISM: Dictyoglomus thermophilum

<400> SEQUENCE: 284
ggatccatta tgtagggcgt aaagc 25

<210> SEQ ID NO 285
<211> LENGTH: 31
<212> TYPE: DNA
<213> ORGANISM: Dictyoglomus thermophilum

<400> SEQUENCE: 285
ttagcaagct taatcacttt aatgccctca g 31

<210> SEQ ID NO 286
<211> LENGTH: 31
<212> TYPE: DNA
<213> ORGANISM: Dictyoglomus thermophilum

<400> SEQUENCE: 286
tgattaagct tgctaatccg caggacactt c 31

<210> SEQ ID NO 287
<211> LENGTH: 26
<212> TYPE: DNA
<213> ORGANISM: Dictyoglomus thermophilum

<400> SEQUENCE: 287
ggtaccaaca ctgcctctct catctc 26

<210> SEQ ID NO 288
<211> LENGTH: 48
<212> TYPE: DNA
<213> ORGANISM: Dictyoglomus thermophilum

<400> SEQUENCE: 288
cttttagttc atcgatcgca tcggctgctc agacatcaat cacactta 48

<210> SEQ ID NO 289
<211> LENGTH: 49
<212> TYPE: DNA
<213> ORGANISM: Dictyoglomus thermophilum

<400> SEQUENCE: 289
ctagggttga tgctggtgtt ggtgctgatg gctgccctga gagaaagtg 49

<210> SEQ ID NO 290
<211> LENGTH: 21
<212> TYPE: DNA
<213> ORGANISM: Dictyoglomus thermophilum

<400> SEQUENCE: 290
gagtatcgcc agtaaggggc g 21

<210> SEQ ID NO 291
<211> LENGTH: 22
<212> TYPE: DNA
<213> ORGANISM: Dictyoglomus thermophilum

<400> SEQUENCE: 291
agccgatgcg atcgatgaac ta 22

<210> SEQ ID NO 292
<211> LENGTH: 53
<212> TYPE: DNA
<213> ORGANISM: Dictyoglomus thermophilum

<400> SEQUENCE: 292
catcagcacc aacaccagca ccagccataa tcgcatgttc aatccgctcc ata 53

<210> SEQ ID NO 293
<211> LENGTH: 23
<212> TYPE: DNA
<213> ORGANISM: Dictyoglomus thermophilum

<400> SEQUENCE: 293
gcagccctaa aatcgcataa agc 23

<210> SEQ ID NO 294
<211> LENGTH: 40
<212> TYPE: DNA
<213> ORGANISM: Dictyoglomus thermophilum

<400> SEQUENCE: 294
gagctctata aaaatgagga gggaaccgaa tgaagaaacc 40

<210> SEQ ID NO 295
<211> LENGTH: 28
<212> TYPE: DNA
<213> ORGANISM: Dictyoglomus thermophilum

<400> SEQUENCE: 295
acgcgtttag ctgccctgag agaaagtg 28

<210> SEQ ID NO 296
<211> LENGTH: 20
<212> TYPE: DNA
<213> ORGANISM: Dictyoglomus thermophilum

<400> SEQUENCE: 296
ccgttgggga aaattgtcgc 20

<210> SEQ ID NO 297
<211> LENGTH: 20
<212> TYPE: DNA
<213> ORGANISM: Dictyoglomus thermophilum

<400> SEQUENCE: 297
gcgacaattt tccccaacgg 20

<210> SEQ ID NO 298
<211> LENGTH: 37
<212> TYPE: DNA
<213> ORGANISM: Aspergillus aculeatus

<400> SEQUENCE: 298
acacaactgg ggatccacca tggctgtggc ggctctt 37

<210> SEQ ID NO 299
<211> LENGTH: 35
<212> TYPE: DNA
<213> ORGANISM: Aspergillus aculeatus

<400> SEQUENCE: 299
agatctcgag aagcttacta ctcatccccc tgcac 35

<210> SEQ ID NO 300
<211> LENGTH: 47
<212> TYPE: DNA
<213> ORGANISM: Aspergillus aculeatus

<400> SEQUENCE: 300
acacaactgg ggatccacca tggctgtggc ggctcttgct ctgctgg 47

<210> SEQ ID NO 301
<211> LENGTH: 45
<212> TYPE: DNA
<213> ORGANISM: Aspergillus aculeatus

<400> SEQUENCE: 301
agatctcgag aagcttactc atcccccgcc accccctgca cctcc 45

<210> SEQ ID NO 302
<211> LENGTH: 36
<212> TYPE: DNA
<213> ORGANISM: Aspergillus fumigatus

<400> SEQUENCE: 302
actggattta ccatggcggt tgccaaatct attgct 36

<210> SEQ ID NO 303
<211> LENGTH: 38
<212> TYPE: DNA
<213> ORGANISM: Aspergillus fumigatus

<400> SEQUENCE: 303
tcacctctag ttaattaatc acgcagacga aatctgct 38

<210> SEQ ID NO 304
<211> LENGTH: 696
<212> TYPE: DNA
<213> ORGANISM: Dictyoglomus thermophilum

<400> SEQUENCE: 304
atgaagaaac cgttggggaa aattgtcgca agcaccgcac tactcatttc tgttgctttt 60
agttcatcga tcgcatcggc tgctcagaca tcaatcacac ttacatctaa cgcatcaggc 120
acattcgacg gctattacta cgagctttgg aaggacacag gcaacacgac tatgactgta 180
tacactcaag gtcgcttctc atgccagtgg tctaacatca acaacgcgct tttccgcacg 240
ggcaagaagt acaaccagaa ctggcaatct cttggcacta tccgcatcac ttattctgcg 300
acatacaacc cgaacggcaa ctcttacctt tgtatctacg gctggtctac gaacccgctt 360
gttgagttct acatcgtaga gtcttggggc aactggcgtc ctcctggcgc aacatctctt 420
ggccaggtta caatcgatgg tggcacatat gacatctacc gcactactcg cgttaaccag 480
cctagcatcg ttggcacagc tactttcgac caatactgga gcgttcgcac tagcaagcgc 540
acatctggca cagttacggt tacggaccac tttcgcgcat gggcaaatcg tggccttaac 600
cttggcacaa tcgaccaaat cacactttgt gttgagggct accagtcttc tggcagcgca 660
aacatcactc aaaacacttt ctctcagggc agctaa 696

<210> SEQ ID NO 305
<211> LENGTH: 231

```
<212> TYPE: PRT
<213> ORGANISM: Dictyoglomus thermophilum

<400> SEQUENCE: 305

Met Lys Lys Pro Leu Gly Lys Ile Val Ala Ser Thr Ala Leu Leu Ile
1               5                   10                  15

Ser Val Ala Phe Ser Ser Ser Ile Ala Ser Ala Ala Gln Thr Ser Ile
            20                  25                  30

Thr Leu Thr Ser Asn Ala Ser Gly Thr Phe Asp Gly Tyr Tyr Tyr Glu
        35                  40                  45

Leu Trp Lys Asp Thr Gly Asn Thr Thr Met Thr Val Tyr Thr Gln Gly
    50                  55                  60

Arg Phe Ser Cys Gln Trp Ser Asn Ile Asn Asn Ala Leu Phe Arg Thr
65                  70                  75                  80

Gly Lys Lys Tyr Asn Gln Asn Trp Gln Ser Leu Gly Thr Ile Arg Ile
                85                  90                  95

Thr Tyr Ser Ala Thr Tyr Asn Pro Asn Gly Asn Ser Tyr Leu Cys Ile
            100                 105                 110

Tyr Gly Trp Ser Thr Asn Pro Leu Val Glu Phe Tyr Ile Val Glu Ser
        115                 120                 125

Trp Gly Asn Trp Arg Pro Pro Gly Ala Thr Ser Leu Gly Gln Val Thr
    130                 135                 140

Ile Asp Gly Gly Thr Tyr Asp Ile Tyr Arg Thr Thr Arg Val Asn Gln
145                 150                 155                 160

Pro Ser Ile Val Gly Thr Ala Thr Phe Asp Gln Tyr Trp Ser Val Arg
                165                 170                 175

Thr Ser Lys Arg Thr Ser Gly Thr Val Thr Val Thr Asp His Phe Arg
            180                 185                 190

Ala Trp Ala Asn Arg Gly Leu Asn Leu Gly Thr Ile Asp Gln Ile Thr
        195                 200                 205

Leu Cys Val Glu Gly Tyr Gln Ser Ser Gly Ser Ala Asn Ile Thr Gln
    210                 215                 220

Asn Thr Phe Ser Gln Gly Ser
225                 230
```

COMPOSITIONS FOR SACCHARIFICATION OF CELLULOSIC MATERIAL

CROSS-REFERENCE TO RELATED APPLICATION

This application is a divisional of U.S. patent application Ser. No. 16/115,930, filed Aug. 29, 2018, now U.S. Pat. No. 10,648,009, which is a divisional of U.S. patent application Ser. No. 15/422,245 filed Feb. 1, 2017, now U.S. Pat. No. 10,072,280, which is a divisional of U.S. patent application Ser. No. 14/885,555 filed Oct. 16, 2015, now U.S. Pat. No. 9,587,262, which is a divisional of U.S. patent application Ser. No. 14/052,360 filed Oct. 11, 2013, now U.S. Pat. No. 9,175,277, which is a divisional of U.S. patent application Ser. No. 12/940,952 filed Nov. 5, 2010, now U.S. Pat. No. 8,580,536, which claims the benefit of U.S. Provisional Application Ser. No. 61/259,014 filed Nov. 6, 2009, which are incorporated herein by reference.

STATEMENT AS TO RIGHTS TO INVENTIONS MADE UNDER FEDERALLY SPONSORED RESEARCH AND DEVELOPMENT

This invention was made in part with Government support under Cooperative Agreement DE-FC36-08GO18080 awarded by the Department of Energy. The government has certain rights in this invention.

REFERENCE TO A SEQUENCE LISTING

This application contains a Sequence Listing in computer readable form. The computer readable form is incorporated herein by reference.

REFERENCE TO DEPOSITS OF BIOLOGICAL MATERIAL

This application contains a reference to deposits of biological material, which deposits are incorporated herein by reference.

BACKGROUND OF THE INVENTION

Field of the Invention

The present invention relates to enzyme compositions for high temperature saccharification of cellulosic material and to uses thereof.

Description of the Related Art

Cellulose is a polymer of the simple sugar glucose linked by beta-1,4 bonds. Many microorganisms produce enzymes that hydrolyze beta-linked glucans. These enzymes include endoglucanases, cellobiohydrolases, and beta-glucosidases. Endoglucanases digest the cellulose polymer at random locations, opening it to attack by cellobiohydrolases. Cellobiohydrolases sequentially release molecules of cellobiose from the ends of the cellulose polymer. Cellobiose is a water-soluble beta-1,4-linked dimer of glucose. Beta-glucosidases hydrolyze cellobiose to glucose.

The conversion of lignocellulosic feedstocks into ethanol has the advantages of the ready availability of large amounts of feedstock, the desirability of avoiding burning or land filling the materials, and the cleanliness of the ethanol fuel. Wood, agricultural residues, herbaceous crops, and municipal solid wastes have been considered as feedstocks for ethanol production. These materials primarily consist of cellulose, hemicellulose, and lignin. Once the cellulose is converted to glucose, the glucose is easily fermented by yeast into ethanol.

There is a need in the art for new enzyme compositions to increase efficiency and to provide cost-effective enzyme solutions for high temperature saccharification of cellulosic material.

The present invention provides compositions for high temperature saccharification of cellulosic material and to uses thereof.

SUMMARY OF THE INVENTION

The present invention relates to enzyme compositions, comprising two or more (several) components selected from the group consisting of:

(I) a polypeptide having cellobiohydrolase I activity selected from the group consisting of:

(A) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 2; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 1, (ii) the genomic DNA sequence of the mature polypeptide coding sequence of SEQ ID NO: 1, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 1;

(B) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 4; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 3, (ii) the genomic DNA sequence of the mature polypeptide coding sequence of SEQ ID NO: 3, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 3;

(C) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 6; (b) a polypeptide encoded by a polynucleotide that hybridizes under preferably at least medium-high stringency conditions, more preferably at least high stringency conditions, and most preferably very high stringency conditions with (i)

the mature polypeptide coding sequence of SEQ ID NO: 5, (ii) the cDNA sequence of the mature polypeptide coding sequence of SEQ ID NO: 5, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 5;

(D) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 8; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 7, (ii) the genomic DNA sequence of the mature polypeptide coding sequence of SEQ ID NO: 7, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 7;

(E) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 158; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 157, (ii) the genomic DNA sequence of the mature polypeptide coding sequence of SEQ ID NO: 157, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 157;

(F) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 160; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 159, (ii) the genomic DNA sequence of the mature polypeptide coding sequence of SEQ ID NO: 159, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 159;

(G) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 162; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 161, (ii) the genomic DNA sequence of the mature polypeptide coding sequence of SEQ ID NO: 161, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 161;

(H) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 164; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 163, (ii) the genomic DNA sequence of the mature polypeptide coding sequence of SEQ ID NO: 163, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 163; and (I) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 166; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 165, (ii) the genomic DNA sequence of the mature polypeptide coding sequence of SEQ ID NO: 165, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 165;

(II) a polypeptide having cellobiohydrolase II activity selected from the group consisting of:

(A) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 10; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 9, (ii) the cDNA sequence of the mature polypeptide coding sequence of SEQ ID NO: 9, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 9;

(B) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 12; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 11, (ii) the cDNA sequence of the mature polypeptide coding sequence of SEQ ID NO: 11, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 11;

(C) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 14; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 13, (ii) the genomic DNA sequence of the mature polypeptide coding sequence of SEQ ID NO: 13, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 13;

(D) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 16; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 15, (ii) the genomic DNA sequence of the mature polypeptide coding sequence of SEQ ID NO: 15, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 15;

(E) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 18; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 17, (ii) the cDNA sequence of the mature polypeptide coding sequence of SEQ ID NO: 17, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 17;

(F) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 168; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 167, (ii) the cDNA sequence of the mature polypeptide coding sequence of SEQ ID NO: 167, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 167;

(G) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 170; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 169, (ii) the cDNA sequence of the mature polypeptide coding sequence of SEQ ID NO: 169, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 169; and (H) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 172; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 172, (ii) the cDNA sequence of the mature polypeptide coding sequence of SEQ ID NO: 172, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 172;

(III) a polypeptide having endoglucanase I activity selected from the group consisting of: (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 20; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 19, (ii) the cDNA sequence of the mature polypeptide coding sequence of SEQ ID NO: 19, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 19;

(IV) a polypeptide having endoglucanase II activity selected from the group consisting of:

(A) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 22; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 21, (ii) the genomic DNA sequence of the mature polypeptide coding sequence of SEQ ID NO: 21, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 21;

(B) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 24; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 23, (ii) the cDNA sequence of the mature polypeptide coding sequence of SEQ ID NO: 23, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 23;

(C) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 26; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 25, (ii) the genomic DNA sequence of the mature polypeptide coding sequence of SEQ ID NO: 25, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 25;

(D) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 174; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 173, (ii) the genomic DNA sequence of the mature polypeptide coding sequence of SEQ ID NO: 173, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 173; and (E) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 176; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 175, (ii) the genomic DNA sequence of the mature polypeptide coding sequence of SEQ ID NO: 175, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 175; and (V) a polypeptide having beta-glucosidase activity selected from the group consisting of:

(A) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 28; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 27, (ii) the cDNA sequence of the mature polypeptide coding sequence of SEQ ID NO: 27, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 27;

(B) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 30; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 29, (ii) the cDNA sequence of the mature polypeptide coding sequence of SEQ ID NO: 29, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 29;

(C) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 32; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 31, (ii) the cDNA sequence of the mature polypeptide coding sequence of SEQ ID NO: 31, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 31;

(D) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 178; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 177, (ii) the cDNA sequence of the mature polypeptide coding sequence of SEQ ID NO: 177, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 177;

(E) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 180; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 179, (ii) the cDNA sequence of the mature polypeptide coding sequence of SEQ ID NO: 179, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 179;

(F) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 182; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 181, (ii) the cDNA sequence of the mature polypeptide coding sequence of SEQ ID NO: 181, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 181;

(G) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 184; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 183, (ii) the cDNA sequence of the mature polypeptide coding sequence of SEQ ID NO: 183, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 183;

(H) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 186; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 185, (ii) the cDNA sequence of the mature polypeptide coding sequence of SEQ ID NO: 185, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 185;

(I) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 188; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 187, (ii) the cDNA sequence of the mature polypeptide coding sequence of SEQ ID NO: 187, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 187; and (J) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 190; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 189, (ii) the cDNA sequence of the mature polypeptide coding sequence of SEQ ID NO: 189, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 189.

The present invention also relates to host cells encoding such an enzyme composition and methods of producing such an enzyme composition.

The present invention also relates to methods for degrading or converting a cellulosic material, comprising: treating the cellulosic material with such an enzyme composition.

The present invention also relates to methods for producing a fermentation product, comprising:

(a) saccharifying a cellulosic material with such an enzyme composition;

(b) fermenting the saccharified cellulosic material with one or more (several) fermenting microorganisms to produce the fermentation product; and (c) recovering the fermentation product from the fermentation.

The present invention also relates to methods of fermenting a cellulosic material, comprising: fermenting the cellulosic material with one or more (several) fermenting microorganisms, wherein the cellulosic material is saccharified with such an enzyme composition.

DEFINITIONS

Figure 1:
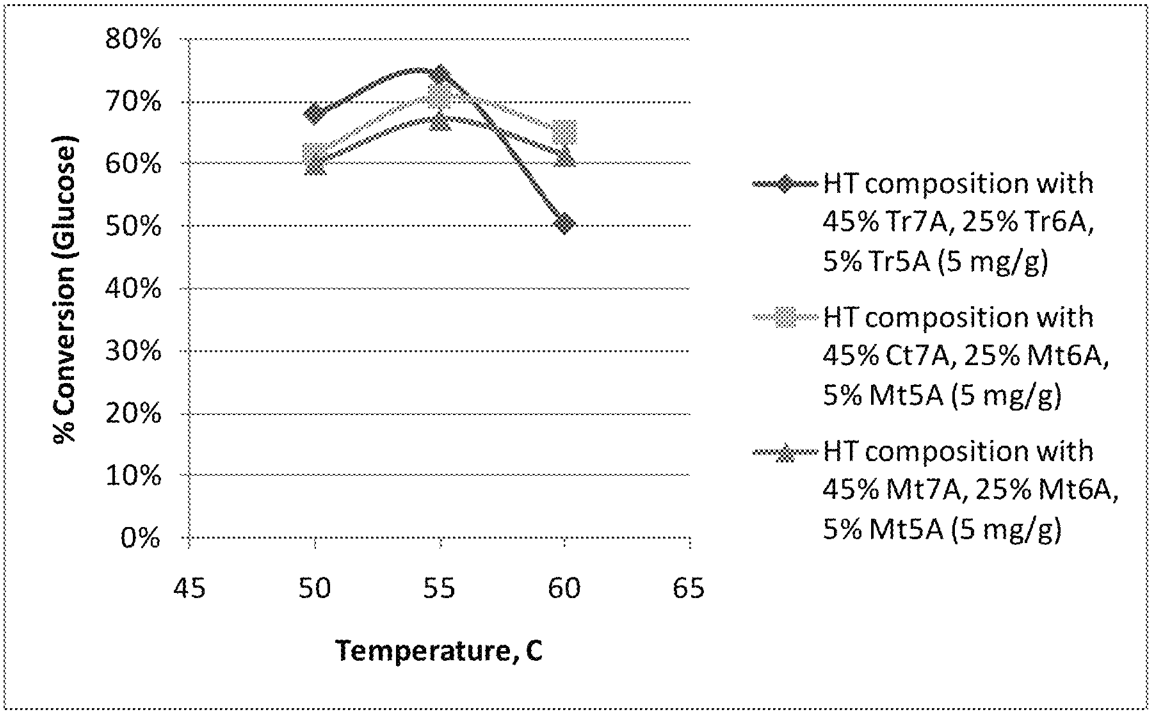
FIG. 1 shows a comparison of two enzyme compositions with a *Trichoderma reesei*-based composition in hydrolysis of milled washed PCS at 50° C., 55° C., and 60° C.

Cellulolytic enzyme or cellulase: The term "cellulolytic enzyme" or "cellulase" means one or more (several) enzymes that hydrolyze a cellulosic material. Such enzymes include endoglucanase(s), cellobiohydrolase(s), beta-glucosidase(s), or combinations thereof. The two basic approaches for measuring cellulolytic activity include: (1) measuring the total cellulolytic activity, and (2) measuring the individual cellulolytic activities (endoglucanases, cellobiohydrolases, and beta-glucosidases) as reviewed in Zhang et al., Outlook for cellulase improvement: Screening and selection strategies, 2006, *Biotechnology Advances* 24: 452-481. Total cellulolytic activity is usually measured using insoluble substrates, including Whatman N21 filter paper, microcrystalline cellulose, bacterial cellulose, algal cellulose, cotton, pretreated lignocellulose, etc. The most common total cellulolytic activity assay is the filter paper assay using Whatman No. 1 filter paper as the substrate. The assay was established by the International Union of Pure and Applied Chemistry (IUPAC) (Ghose, 1987, Measurement of cellulase activities, *Pure Appl. Chem.* 59: 257-68).

For purposes of the present invention, cellulolytic enzyme activity is determined by measuring the increase in hydrolysis of a cellulosic material by cellulolytic enzyme(s) under the following conditions: 1-20 mg of cellulolytic enzyme protein/g of cellulose in PCS for 3-7 days at 50° C. compared to a control hydrolysis without addition of cellulolytic enzyme protein. Typical conditions are 1 ml reactions, washed or unwashed PCS, 5% insoluble solids, 50 mM sodium acetate pH 5, 1 mM $MnSO_4$, 50° C., 72 hours, sugar analysis by AMINEX® HPX-87H column (Bio-Rad Laboratories, Inc., Hercules, Calif., USA).

Endoglucanase: The term "endoglucanase" means an endo-1,4-(1,3;1,4)-beta-D-glucan 4-glucanohydrolase (E.C. 3.2.1.4), which catalyses endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components. Endoglucanase activity can be determined by measuring reduction in substrate viscosity or increase in reducing ends determined by a reducing sugar assay (Zhang et al., 2006, *Biotechnology Advances* 24: 452-481). For purposes of the present invention, endoglucanase activity is determined using carboxymethyl cellulose (CMC) as substrate according to the procedure of Ghose, 1987, *Pure and Appl. Chem.* 59: 257-268, at pH 5, 40° C.

Cellobiohydrolase: The term "cellobiohydrolase" means a 1,4-beta-D-glucan cellobiohydrolase (E.C. 3.2.1.91), which catalyzes the hydrolysis of 1,4-beta-D-glucosidic linkages in cellulose, cellooligosaccharides, or any beta-1,4-linked glucose containing polymer, releasing cellobiose from the reducing or non-reducing ends of the chain (Teeri, 1997, Crystalline cellulose degradation: New insight into the function of cellobiohydrolases, *Trends in Biotechnology* 15: 160-167; Teeri et al., 1998, *Trichoderma reesei* cellobiohydrolases: why so efficient on crystalline cellulose?, *Biochem. Soc. Trans.* 26: 173-178). For purposes of the present invention, cellobiohydrolase activity is determined according to the procedures described by Lever et al., 1972, *Anal. Biochem.* 47: 273-279; van Tilbeurgh et al., 1982, *FEBS Letters,* 149: 152-156; van Tilbeurgh and Claeyssens, 1985, *FEBS Letters,* 187: 283-288; and Tomme et al., 1988, *Eur. J. Biochem.* 170: 575-581. In the present invention, the Lever et al. method can be employed to assess hydrolysis of cellulose in corn stover, while the methods of van Tilbeurgh et al. and Tomme et al. can be used to determine the cellobiohydrolase activity on a fluorescent disaccharide derivative, 4-methylumbelliferyl-β-D-lactoside.

Beta-glucosidase: The term "beta-glucosidase" means a beta-D-glucoside glucohydrolase (E.C. 3.2.1.21), which catalyzes the hydrolysis of terminal non-reducing beta-D-glucose residues with the release of beta-D-glucose. For purposes of the present invention, beta-glucosidase activity is determined according to the basic procedure described by Venturi et al., 2002, Extracellular beta-D-glucosidase from *Chaetomium thermophilum* var. *coprophilum*: production, purification and some biochemical properties, *J. Basic Microbiol.* 42: 55-66. One unit of beta-glucosidase is defined as 1.0 μmole of p-nitrophenolate anion produced per minute at 25° C., pH 4.8 from 1 mM p-nitrophenyl-beta-D-glucopyranoside as substrate in 50 mM sodium citrate containing 0.01% TWEEN® 20.

Polypeptide having cellulolytic enhancing activity: The term "polypeptide having cellulolytic enhancing activity" means a GH61 polypeptide that catalyzes the enhancement of the hydrolysis of a cellulosic material by enzyme having cellulolytic activity. For purposes of the present invention, cellulolytic enhancing activity is determined by measuring the increase in reducing sugars or the increase of the total of cellobiose and glucose from the hydrolysis of a cellulosic material by cellulolytic enzyme under the following conditions: 1-50 mg of total protein/g of cellulose in PCS, wherein total protein is comprised of 50-99.5% w/w cellulolytic enzyme protein and 0.5-50% w/w protein of a GH61 polypeptide having cellulolytic enhancing activity for 1-7 days at 50° C. compared to a control hydrolysis with equal total protein loading without cellulolytic enhancing activity (1-50 mg of cellulolytic protein/g of cellulose in PCS). In a preferred aspect, a mixture of CELLUCLAST® 1.5 L (Novozymes A/S, Bagsvrd, Denmark) in the presence of 2-3% of total protein weight *Aspergillus oryzae* beta-glucosidase (recombinantly produced in *Aspergillus oryzae* according to WO 02/095014) or 2-3% of total protein weight *Aspergillus fumigatus* beta-glucosidase (recombinantly produced in *Aspergillus oryzae* as described in WO 2002/095014) of cellulase protein loading is used as the source of the cellulolytic activity.

The GH61 polypeptides having cellulolytic enhancing activity enhance the hydrolysis of a cellulosic material catalyzed by enzyme having cellulolytic activity by reducing the amount of cellulolytic enzyme required to reach the same degree of hydrolysis preferably at least 1.01-fold, more preferably at least 1.05-fold, more preferably at least 1.10-fold, more preferably at least 1.25-fold, more preferably at least 1.5-fold, more preferably at least 2-fold, more preferably at least 3-fold, more preferably at least 4-fold, more preferably at least 5-fold, even more preferably at least 10-fold, and most preferably at least 20-fold.

Hemicellulolytic enzyme or hemicellulase: The term "hemicellulolytic enzyme" or "hemicellulase" means one or more (several) enzymes that hydrolyze a hemicellulosic material. See, for example, Shallom, D. and Shoham, Y. Microbial hemicellulases. *Current Opinion In Microbiology,* 2003, 6(3): 219-228). Hemicellulases are key components in the degradation of plant biomass. Examples of hemicellulases include, but are not limited to, an acetylmannan esterase, an acetyxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The substrates of these enzymes, the hemicelluloses, are a heterogeneous group of branched and linear polysaccharides that are bound via hydrogen bonds to the cellulose microfibrils in the plant cell wall, crosslinking them into a robust network. Hemicelluloses are also covalently attached to lignin, forming together with cellulose a highly complex structure. The variable structure and organization of hemicelluloses require the concerted action of many enzymes for its complete degradation. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families marked by numbers. Some families, with overall similar fold, can be further grouped into clans, marked alphabetically (e.g., GH-A). A most informative and updated classification of these and other carbohydrate active enzymes is available on the Carbohydrate-Active Enzymes (CAZy) database. Hemicellulolytic enzyme activities can be measured according to Ghose and Bisaria, 1987, *Pure &Appl. Chem.* 59: 1739-1752.

Xylan degrading activity or xylanolytic activity: The term "xylan degrading activity" or "xylanolytic activity" means a biological activity that hydrolyzes xylan-containing material. The two basic approaches for measuring xylanolytic activity include: (1) measuring the total xylanolytic activity, and (2) measuring the individual xylanolytic activities (e.g., endoxylanases, beta-xylosidases, arabinofuranosidases, alpha-glucuronidases, acetylxylan esterases, feruloyl esterases, and alpha-glucuronyl esterases). Recent progress in assays of xylanolytic enzymes was summarized in several publications including Biely and Puchard, Recent progress in the assays of xylanolytic enzymes, 2006, *Journal of the Science of Food and Agriculture* 86(11): 1636-1647; Spanikova and Biely, 2006, Glucuronoyl esterase—Novel carbohydrate esterase produced by *Schizophyllum commune, FEBS Letters* 580(19): 4597-4601; Herrmann, Vrsanska, Jurickova, Hirsch, Biely, and Kubicek, 1997, The beta-D-xylosidase of *Trichoderma reesei* is a multifunctional beta-D-xylan xylohydrolase, *Biochemical Journal* 321: 375-381.

Total xylan degrading activity can be measured by determining the reducing sugars formed from various types of xylan, including, for example, oat spelt, beechwood, and larchwood xylans, or by photometric determination of dyed xylan fragments released from various covalently dyed xylans. The most common total xylanolytic activity assay is based on production of reducing sugars from polymeric 4-O-methyl glucuronoxylan as described in Bailey, Biely, Poutanen, 1992, Interlaboratory testing of methods for assay of xylanase activity, *Journal of Biotechnology* 23(3): 257-270. Xylanase activity can also be determined with 0.2% AZCL-arabinoxylan as substrate in 0.01% Triton X-100 and 200 mM sodium phosphate buffer pH 6 at 37° C. One unit of xylanase activity is defined as 1.0 μmole of azurine produced per minute at 37° C., pH 6 from 0.2% AZCL-arabinoxylan as substrate in 200 mM sodium phosphate pH 6 buffer.

For purposes of the present invention, xylan degrading activity is determined by measuring the increase in hydrolysis of birchwood xylan (Sigma Chemical Co., Inc., St. Louis, Mo., USA) by xylan-degrading enzyme(s) under the following typical conditions: 1 ml reactions, 5 mg/ml substrate (total solids), 5 mg of xylanolytic protein/g of substrate, 50 mM sodium acetate pH 5, 50° C., 24 hours, sugar analysis using p-hydroxybenzoic acid hydrazide (PHBAH) assay as described by Lever, 1972, A new reaction for colorimetric determination of carbohydrates, *Anal. Biochem* 47: 273-279.

Xylanase: The term "xylanase" means a 1,4-beta-D-xylan-xylohydrolase (E.C. 3.2.1.8) that catalyzes the endohydrolysis of 1,4-beta-D-xylosidic linkages in xylans. For purposes of the present invention, xylanase activity is determined with 0.2% AZCL-arabinoxylan as substrate in 0.01% Triton X-100 and 200 mM sodium phosphate buffer pH 6 at 37° C. One unit of xylanase activity is defined as 1.0 μmole of azurine produced per minute at 37° C., pH 6 from 0.2% AZCL-arabinoxylan as substrate in 200 mM sodium phosphate pH 6 buffer.

Beta-xylosidase: The term "beta-xylosidase" means a beta-D-xyloside xylohydrolase (E.C. 3.2.1.37) that catalyzes the exo-hydrolysis of short beta (1→4)-xylooligosaccharides, to remove successive D-xylose residues from the non-reducing termini. For purposes of the present invention, one unit of beta-xylosidase is defined as 1.0 μmole of p-nitrophenolate anion produced per minute at 40° C., pH 5 from 1 mM p-nitrophenyl-beta-D-xyloside as substrate in 100 mM sodium citrate containing 0.01% TWEEN® 20.

Acetylxylan esterase: The term "acetylxylan esterase" means a carboxylesterase (EC 3.1.1.72) that catalyses the hydrolysis of acetyl groups from polymeric xylan, acetylated xylose, acetylated glucose, alpha-napthyl acetate, and p-nitrophenyl acetate. For purposes of the present invention, acetylxylan esterase activity is determined using 0.5 mM p-nitrophenylacetate as substrate in 50 mM sodium acetate pH 5.0 containing 0.01% TWEEN™ 20. One unit of acetylxylan esterase is defined as the amount of enzyme capable of releasing 1 μmole of p-nitrophenolate anion per minute at pH 5, 25° C.

Feruloyl esterase: The term "feruloyl esterase" means a 4-hydroxy-3-methoxycinnamoyl-sugar hydrolase (EC 3.1.1.73) that catalyzes the hydrolysis of the 4-hydroxy-3-methoxycinnamoyl (feruloyl) group from an esterified sugar, which is usually arabinose in "natural" substrates, to produce ferulate (4-hydroxy-3-methoxycinnamate). Feruloyl esterase is also known as ferulic acid esterase, hydroxycinnamoyl esterase, FAE-III, cinnamoyl ester hydrolase, FAEA, cinnAE, FAE-I, or FAE-II. For purposes of the present invention, feruloyl esterase activity is determined using 0.5 mM p-nitrophenylferulate as substrate in 50 mM sodium acetate pH 5.0. One unit of feruloyl esterase equals the amount of enzyme capable of releasing 1 μmole of p-nitrophenolate anion per minute at pH 5, 25° C.

Alpha-glucuronidase: The term "alpha-glucuronidase" means an alpha-D-glucosiduronate glucuronohydrolase (EC 3.2.1.139) that catalyzes the hydrolysis of an alpha-D-glucuronoside to D-glucuronate and an alcohol. For purposes of the present invention, alpha-glucuronidase activity is determined according to de Vries, 1998, *J. Bacteriol.* 180: 243-249. One unit of alpha-glucuronidase equals the amount of enzyme capable of releasing 1 μmole of glucuronic or 4-O-methylglucuronic acid per minute at pH 5, 40° C.

Alpha-L-arabinofuranosidase: The term "alpha-L-arabinofuranosidase" means an alpha-L-arabinofuranoside arabinofuranohydrolase (EC 3.2.1.55) that catalyzes the hydrolysis of terminal non-reducing alpha-L-arabinofuranoside residues in alpha-L-arabinosides. The enzyme acts on alpha-L-arabinofuranosides, alpha-L-arabinans containing (1,3)- and/or (1,5)-linkages, arabinoxylans, and arabinogalactans. Alpha-L-arabinofuranosidase is also known as arabinosidase, alpha-arabinosidase, alpha-L-arabinosidase, alpha-arabinofuranosidase, polysaccharide alpha-L-arabinofuranosidase, alpha-L-arabinofuranoside hydrolase, L-arabinosidase, or alpha-L-arabinanase. For purposes of the present invention, alpha-L-arabinofuranosidase activity is determined using 5 mg of medium viscosity wheat arabinoxylan (Megazyme International Ireland, Ltd., Bray, Co. Wicklow, Ireland) per ml of 100 mM sodium acetate pH 5 in a total volume of 200 μl for 30 minutes at 40° C. followed by arabinose analysis by AMINEX® HPX-87H column chromatography (Bio-Rad Laboratories, Inc., Hercules, Calif., USA).

Family 3, 5, 6, 7, 10, 11, or 61, or GH3, GH5, GH6, GH7, GH10, GH11, or GH61, or Cel3, Cel5, Cel6 or Cel7: The terms "Family 3", "Family 5", "Family 6", "Family 7", "Family 10", "Family 11", "Family 61", "GH3", "GH5", "GH6", "GH7", "GH10", "GH11", "GH61", "Cel3", "Cel5", "Cel6", or "Cel7" are defined herein as a polypeptide falling into the glycoside hydrolase Families 3, 5, 6, 7, 10, 11, and 61 according to Henrissat B., 1991, A classification of glycosyl hydrolases based on amino-acid sequence similarities, *Biochem. J.* 280: 309-316, and Henrissat and Bairoch, 1996, Updating the sequence-based classification of glycosyl hydrolases, *Biochem. J.* 316: 695-696.

Cellulosic material: The cellulosic material can be any material containing cellulose. The predominant polysaccharide in the primary cell wall of biomass is cellulose, the second most abundant is hemicellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Cellulose is generally found, for example, in the stems, leaves, hulls, husks, and cobs of plants or leaves, branches, and wood of trees. The cellulosic material can be, but is not limited to, herbaceous material, agricultural residue, forestry residue, municipal solid waste, waste paper, and pulp and paper mill residue (see, for example, Wiselogel et al., 1995, in Handbook on Bioethanol (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnology*, T. Scheper, managing editor, Volume 65, pp. 23-40, Springer-Verlag, New York). It is understood herein that the cellulose may be in the form of lignocellulose, a plant cell wall material containing lignin, cellulose, and hemicellulose in a mixed matrix. In a preferred aspect, the cellulosic material is lignocellulose.

In one aspect, the cellulosic material is herbaceous material. In another aspect, the cellulosic material is agricultural residue. In another aspect, the cellulosic material is forestry residue. In another aspect, the cellulosic material is municipal solid waste. In another aspect, the cellulosic material is waste paper. In another aspect, the cellulosic material is pulp and paper mill residue.

In another aspect, the cellulosic material is corn stover. In another aspect, the cellulosic material is corn fiber. In another aspect, the cellulosic material is corn cob. In another aspect, the cellulosic material is orange peel. In another aspect, the cellulosic material is rice straw. In another aspect, the cellulosic material is wheat straw. In another aspect, the cellulosic material is switch grass. In another aspect, the cellulosic material is miscanthus. In another aspect, the cellulosic material is bagasse. In another aspect, the cellulosic material is softwood. In another aspect, the cellulosic material is hardwood.

In another aspect, the cellulosic material is microcrystalline cellulose. In another aspect, the cellulosic material is bacterial cellulose. In another aspect, the cellulosic material is algal cellulose. In another aspect, the cellulosic material is cotton linter. In another aspect, the cellulosic material is amorphous phosphoric-acid treated cellulose. In another aspect, the cellulosic material is filter paper.

The cellulosic material may be used as is or may be subjected to pretreatment, using conventional methods known in the art, as described herein. In a preferred aspect, the cellulosic material is pretreated.

Pretreated corn stover: The term "PCS" or "Pretreated Corn Stover" means a cellulosic material derived from corn stover by treatment with heat and dilute sulfuric acid.

Isolated or purified: The term "isolated" or "purified" means a polypeptide or polynucleotide that is removed from at least one component with which it is naturally associated. For example, a polypeptide may be at least 1% pure, e.g., at least 5% pure, at least 10% pure, at least 20% pure, at least 40% pure, at least 60% pure, at least 80% pure, at least 90% pure, or at least 95% pure, as determined by SDS-PAGE, and a polynucleotide may be at least 1% pure, e.g., at least 5% pure, at least 10% pure, at least 20% pure, at least 40% pure, at least 60% pure, at least 80% pure, at least 90% pure, or at least 95% pure, as determined by agarose electrophoresis.

Mature polypeptide: The term "mature polypeptide" means a polypeptide in its final form following translation and any post-translational modifications, such as N-terminal processing, C-terminal truncation, glycosylation, phosphorylation, etc. It is known in the art that a host cell may produce a mixture of two of more different mature polypeptides (i.e., with a different C-terminal and/or N-terminal amino acid) expressed by the same polynucleotide. The mature polypeptide can be predicted using the SignalP program (Nielsen et al., 1997, *Protein Engineering* 10: 1-6).

Mature polypeptide coding sequence: The term "mature polypeptide coding sequence" is defined herein as a nucleotide sequence that encodes a mature polypeptide having biological activity. The mature polypeptide coding sequence can be predicted using the SignalP program (Nielsen et al., 1997, supra).

Sequence Identity: The relatedness between two amino acid sequences or between two nucleotide sequences is described by the parameter "sequence identity".

For purposes of the present invention, the degree of sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−Total Number of Gaps in Alignment)

For purposes of the present invention, the degree of sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of Alignment−Total Number of Gaps in Alignment)

Polypeptide fragment: The term "fragment" means a polypeptide having one or more (several) amino acids deleted from the amino and/or carboxyl terminus of a mature polypeptide; wherein the fragment has biological activity.

Subsequence: The term "subsequence" means a polynucleotide having one or more (several) nucleotides deleted from the 5' and/or 3' end of a mature polypeptide coding sequence; wherein the subsequence encodes a fragment having biological activity.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Coding sequence: The term "coding sequence" means a polynucleotide, which directly specifies the amino acid sequence of a polypeptide. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant polynucleotide.

cDNA: The term "cDNA" means a DNA molecule that can be prepared by reverse transcription from a mature, spliced, mRNA molecule obtained from a eukaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence of the present invention.

Control sequences: The term "control sequences" means all components necessary for the expression of a polynucleotide encoding a polypeptide. Each control sequence may be native or foreign to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Operably linked: The term "operably linked" means a configuration in which a control sequence is placed at an appropriate position relative to the coding sequence of a polynucleotide such that the control sequence directs the expression of the coding sequence.

Expression: The term "expression" includes any step involved in the production of the polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to additional nucleotides that provide for its expression.

Host cell: The term "host cell" means any cell type that is susceptible to transformation, transfection, transduction, and the like with a nucleic acid construct or expression vector comprising a polynucleotide of the present invention. The term "host cell" encompasses any progeny of a parent cell that is not identical to the parent cell due to mutations that occur during replication.

DETAILED DESCRIPTION OF THE INVENTION

Enzyme Compositions

The present invention relates to enzyme compositions, comprising two or more (several) components selected from the group consisting of:

(I) a polypeptide having cellobiohydrolase I activity selected from the group consisting of:

(A) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 2; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 1, (ii) the genomic DNA sequence of the mature polypeptide coding sequence of SEQ ID NO: 1, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 1;

(B) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 4; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 3, (ii) the genomic DNA sequence of the mature polypeptide coding sequence of SEQ ID NO: 3, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 3;

(C) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 6; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 5, (ii) the cDNA sequence of the mature polypeptide coding sequence of SEQ ID NO: 5, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 5;

(D) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 8; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 7, (ii) the genomic DNA sequence of the mature polypeptide coding sequence of SEQ ID NO: 7, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 7;

(E) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 158; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 157, (ii) the genomic DNA sequence of the mature polypeptide coding sequence of SEQ ID NO: 157, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 157;

(F) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 160; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 159, (ii) the genomic DNA sequence of the mature polypeptide coding sequence of SEQ ID NO: 159, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 159;

(G) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 162; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 161, (ii) the genomic DNA sequence of the mature polypeptide coding sequence of SEQ ID NO: 161, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 161;

(H) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 164; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 163, (ii) the genomic DNA sequence of the mature polypeptide coding sequence of SEQ ID NO: 163, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 163; and (I) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 166; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 165, (ii) the genomic DNA sequence of the mature polypeptide coding sequence of SEQ ID NO: 165, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 165;

(II) a polypeptide having cellobiohydrolase II activity selected from the group consisting of:

(A) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 10; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 9, (ii) the cDNA sequence of the mature polypeptide coding sequence of SEQ ID NO: 9, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 9;

(B) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 12; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 11, (ii) the cDNA sequence of the mature polypeptide coding sequence of SEQ ID NO: 11, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 11;

(C) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 14; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 13, (ii) the genomic DNA sequence of the mature polypeptide coding sequence of SEQ ID NO: 13, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 13;

(D) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 16; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 15, (ii) the genomic DNA sequence of the mature polypeptide coding sequence of SEQ ID NO: 15, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 15;

(E) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 18; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 17, (ii) the cDNA sequence of the mature polypeptide coding sequence of SEQ ID NO: 17, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 17;

(F) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 168; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 167, (ii) the cDNA sequence of the mature polypeptide coding sequence of SEQ ID NO: 167, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 167;

(G) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 170; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 169, (ii) the cDNA sequence of the mature polypeptide coding sequence of SEQ ID NO: 169, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 169; and (H) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 172; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 172, (ii) the cDNA sequence of the mature polypeptide coding sequence of SEQ ID NO: 172, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 172;

(III) a polypeptide having endoglucanase I activity selected from the group consisting of: (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 20; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 19, (ii) the cDNA sequence of the mature polypeptide coding sequence of SEQ ID NO: 19, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 19;

(IV) a polypeptide having endoglucanase II activity selected from the group consisting of:

(A) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 22; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 21, (ii) the genomic DNA sequence of the mature polypeptide coding sequence of SEQ ID NO: 21, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 21;

(B) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 24; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 23, (ii) the cDNA sequence of the mature polypeptide coding sequence of SEQ ID NO: 23, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 23;

(C) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 26; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 25, (ii) the genomic DNA sequence of the mature polypeptide coding sequence of SEQ ID NO: 25, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 25;

(D) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 174; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 173, (ii) the genomic DNA sequence of the mature polypeptide coding sequence of SEQ ID NO: 173, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 173; and (E) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 176; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 175, (ii) the genomic DNA sequence of the mature polypeptide coding sequence of SEQ ID NO: 175, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 175; and (V) a polypeptide having beta-glucosidase activity selected from the group consisting of:

(A) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 28; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 27, (ii) the cDNA sequence of the mature polypeptide coding sequence of SEQ ID NO: 27, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 27;

(B) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 30; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 29, (ii) the cDNA sequence of the mature polypeptide coding sequence of SEQ ID NO: 29, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 29;

(C) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 32; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 31, (ii) the cDNA sequence of the mature polypeptide coding sequence of SEQ ID NO: 31, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 31;

(D) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 178; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 177, (ii) the cDNA sequence of the mature polypeptide coding sequence of SEQ ID NO: 177, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 177;

(E) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 180; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 179, (ii) the cDNA sequence of the mature polypeptide coding sequence of SEQ ID NO: 179, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 179;

(F) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 182; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 181, (ii) the cDNA sequence of the mature polypeptide coding sequence of SEQ ID NO: 181, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 181;

(G) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 184; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 183, (ii) the cDNA sequence of the mature polypeptide coding sequence of SEQ ID NO: 183, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 183;

(H) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 186; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 185, (ii) the cDNA sequence of the mature polypeptide coding sequence of SEQ ID NO: 185, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 185;

(I) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 188; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 187, (ii) the cDNA sequence of the mature polypeptide coding sequence of SEQ ID NO: 187, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 187; and (J) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 190; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 189, (ii) the cDNA sequence of the mature polypeptide coding sequence of SEQ ID NO: 189, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 189.

In a preferred aspect, the polypeptide having cellobiohydrolase I activity is a *Chaetomium thermophilum* Cel7A cellobiohydrolase I of the mature polypeptide of SEQ ID NO: 2. In another aspect, the *Chaetomium thermophilum* Cel7A cellobiohydrolase I is encoded by the mature polypeptide coding sequence of SEQ ID NO: 1.

In another aspect, the polypeptide having cellobiohydrolase I activity is a *Myceliophthora thermophila* Cel7A cellobiohydrolase I of the mature polypeptide of SEQ ID NO: 4. In another aspect, the *Myceliophthora thermophila* Cel7A cellobiohydrolase I is encoded by the mature polypeptide coding sequence of SEQ ID NO: 3.

In another aspect, the polypeptide having cellobiohydrolase I activity is a *Aspergillus fumigatus* Cel7A cellobiohydrolase I of the mature polypeptide of SEQ ID NO: 6. In another aspect, the *Aspergillus fumigatus* Cel7A cellobiohydrolase I is encoded by the mature polypeptide coding sequence of SEQ ID NO: 5.

In another aspect, the polypeptide having cellobiohydrolase I activity is a *Thermoascus aurantiacus* Cel7A cellobiohydrolase I of the mature polypeptide of SEQ ID NO: 8. In another aspect, the *Thermoascus aurantiacus* Cel7A cellobiohydrolase I is encoded by the mature polypeptide coding sequence of SEQ ID NO: 7.

In another aspect, the polypeptide having cellobiohydrolase I activity is a *Penicillium emersonii* Cel7 cellobiohydrolase I of the mature polypeptide of SEQ ID NO: 158. In another aspect, the *Penicillium emersonii* Cel7 cellobiohydrolase I is encoded by the mature polypeptide coding sequence of SEQ ID NO: 157.

In another aspect, the polypeptide having cellobiohydrolase I activity is a *Penicillium pinophilum* Cel7 cellobiohydrolase I of the mature polypeptide of SEQ ID NO: 160. In another aspect, the *Penicillium pinophilum* Cel7A cellobiohydrolase I is encoded by the mature polypeptide coding sequence of SEQ ID NO: 159.

In another aspect, the polypeptide having cellobiohydrolase I activity is an *Aspergillus terreus* Cel7 cellobiohydrolase I of the mature polypeptide of SEQ ID NO: 162. In another aspect, the *Aspergillus terreus* Cel7 cellobiohydrolase I is encoded by the mature polypeptide coding sequence of SEQ ID NO: 161.

In another aspect, the polypeptide having cellobiohydrolase I activity is a *Neosartorya fischeri* Cel7 cellobiohydrolase I of the mature polypeptide of SEQ ID NO: 164. In another aspect, the *Neosartorya fischeri* Cel7 cellobiohydrolase I is encoded by the mature polypeptide coding sequence of SEQ ID NO: 163.

In another aspect, the polypeptide having cellobiohydrolase I activity is an *Aspergillus nidulans* Cel7 cellobiohydrolase I of the mature polypeptide of SEQ ID NO: 166. In another aspect, the *Aspergillus nidulans* Cel7 cellobiohydrolase I is encoded by the mature polypeptide coding sequence of SEQ ID NO: 165.

In another aspect, the polypeptide having cellobiohydrolase II activity is a *Myceliophthora thermophila* Cel6A cellobiohydrolase II of the mature polypeptide of SEQ ID NO: 10. In another aspect, the *Myceliophthora thermophila* Cel6A cellobiohydrolase II is encoded by the mature polypeptide coding sequence of SEQ ID NO: 9.

In another aspect, the polypeptide having cellobiohydrolase II activity is a *Myceliophthora thermophila* Cel6B cellobiohydrolase II of the mature polypeptide of SEQ ID NO: 12. In another aspect, the *Myceliophthora thermophila* Cel6B cellobiohydrolase II is encoded by the mature polypeptide coding sequence of SEQ ID NO: 11.

In another aspect, the polypeptide having cellobiohydrolase II activity is a *Thielavia terrestris* Cel6A cellobiohydrolase II of the mature polypeptide of SEQ ID NO: 14. In another aspect, the *Thielavia terrestris* Cel6A cellobiohydrolase II is encoded by the mature polypeptide coding sequence of SEQ ID NO: 13.

In another aspect, the polypeptide having cellobiohydrolase II activity is a *Trichophaea saccata* CBS 804.70 Cel6A cellobiohydrolase II of the mature polypeptide of SEQ ID NO: 16. In another aspect, the *Trichophaea saccata* Cel6A cellobiohydrolase II is encoded by the mature polypeptide coding sequence of SEQ ID NO: 15.

In another aspect, the polypeptide having cellobiohydrolase II activity is an *Aspergillus fumigatus* Cel6A cellobiohydrolase II of the mature polypeptide of SEQ ID NO: 18. In another aspect, the *Aspergillus fumigatus* Cel6A cellobiohydrolase II is encoded by the mature polypeptide coding sequence of SEQ ID NO: 17.

In another aspect, the polypeptide having cellobiohydrolase II activity is a *Fennellia nivea* Cel6 cellobiohydrolase II of the mature polypeptide of SEQ ID NO: 168. In another aspect, the *Fennellia nivea* Cel6 cellobiohydrolase II is encoded by the mature polypeptide coding sequence of SEQ ID NO: 167.

In another aspect, the polypeptide having cellobiohydrolase II activity is a *Penicillium emersonii* Cel6A cellobiohydrolase II of the mature polypeptide of SEQ ID NO: 170. In another aspect, the *Penicillium emersonii* Cel6A cellobiohydrolase II is encoded by the mature polypeptide coding sequence of SEQ ID NO: 169.

In another aspect, the polypeptide having cellobiohydrolase II activity is a *Penicillium pinophilum* Cel6A cellobiohydrolase II of the mature polypeptide of SEQ ID NO: 172. In another aspect, the *Penicillium pinophilum* Cel6A cellobiohydrolase II is encoded by the mature polypeptide coding sequence of SEQ ID NO: 171.

In another aspect, the polypeptide having endoglucanase I activity is a *Aspergillus terreus* Cel7A endoglucanase I of the mature polypeptide of SEQ ID NO: 20. In another aspect, the *Aspergillus terreus* Cel7A endoglucanase I is encoded by the mature polypeptide coding sequence of SEQ ID NO: 19.

In another aspect, the polypeptide having endoglucanase II activity is a *Trichoderma reesei* Cel5A endoglucanase II of the mature polypeptide of SEQ ID NO: 22. In another aspect, the *Trichoderma reesei* Cel5A endoglucanase II is encoded by the mature polypeptide coding sequence of SEQ ID NO: 21.

In another aspect, the polypeptide having endoglucanase II activity is a *Myceliophthora thermophila* Cel5A endoglucanase II of the mature polypeptide of SEQ ID NO: 24. In another aspect, the *Myceliophthora thermophila* Cel5A endoglucanase II is encoded by the mature polypeptide coding sequence of SEQ ID NO: 23.

In another aspect, the polypeptide having endoglucanase II activity is a *Thermoascus aurantiacus* Cel5A endoglucanase II of the mature polypeptide of SEQ ID NO: 26. In another aspect, the *Thermoascus aurantiacus* Cel5A endoglucanase II is encoded by the mature polypeptide coding sequence of SEQ ID NO: 25.

In another aspect, the polypeptide having endoglucanase II activity is an *Aspergillus fumigatus* Cel5 endoglucanase II of the mature polypeptide of SEQ ID NO: 174. In another aspect, the *Aspergillus fumigatus* Cel5 endoglucanase II is encoded by the mature polypeptide coding sequence of SEQ ID NO: 173.

In another aspect, the polypeptide having endoglucanase II activity is a *Neosartorya fischeri* Cel5 endoglucanase II of the mature polypeptide of SEQ ID NO: 176. In another aspect, the *Neosartorya fischeri* Cel5 endoglucanase II is encoded by the mature polypeptide coding sequence of SEQ ID NO: 175.

In another aspect, the polypeptide having beta-glucosidase activity is a *Aspergillus fumigatus* beta-glucosidase of the mature polypeptide of SEQ ID NO: 28. In another aspect, the *Aspergillus fumigatus* beta-glucosidase is encoded by the mature polypeptide coding sequence of SEQ ID NO: 27.

In another aspect, the polypeptide having beta-glucosidase activity is a *Penicillium brasilianum* beta-glucosidase of the mature polypeptide of SEQ ID NO: 30. In another aspect, the *Penicillium brasilianum* beta-glucosidase is encoded by the mature polypeptide coding sequence of SEQ ID NO: 29.

In another aspect, the polypeptide having beta-glucosidase activity is a *Aspergillus niger* beta-glucosidase of the mature polypeptide of SEQ ID NO: 32. In another aspect, the *Aspergillus niger* beta-glucosidase is encoded by the mature polypeptide coding sequence of SEQ ID NO: 31.

In another aspect, the polypeptide having beta-glucosidase activity is an *Aspergillus aculeatus* Cel3 beta-glucosidase of the mature polypeptide of SEQ ID NO: 178. In another aspect, the *Aspergillus aculeatus* Cel3 beta-glucosidase is encoded by the mature polypeptide coding sequence of SEQ ID NO: 177.

In another aspect, the polypeptide having beta-glucosidase activity is an *Aspergillus kawashii* Cel3 beta-glucosidase of the mature polypeptide of SEQ ID NO: 180. In another aspect, the *Aspergillus kawashii* Cel3 beta-glucosidase is encoded by the mature polypeptide coding sequence of SEQ ID NO: 179.

In another aspect, the polypeptide having beta-glucosidase activity is an *Aspergillus clavatus* Cel3 beta-glucosidase of the mature polypeptide of SEQ ID NO: 182. In another aspect, the *Aspergillus clavatus* Cel3 beta-glucosidase is encoded by the mature polypeptide coding sequence of SEQ ID NO: 181.

In another aspect, the polypeptide having beta-glucosidase activity is a *Thielavia terrestris* NRRL 8126 Cel3 beta-glucosidase of the mature polypeptide of SEQ ID NO: 184. In another aspect, the *Thielavia terrestris* NRRL 8126 Cel3 beta-glucosidase is encoded by the mature polypeptide coding sequence of SEQ ID NO: 183.

In another aspect, the polypeptide having beta-glucosidase activity is a *Penicillium oxalicum* Cel3 beta-glucosidase of the mature polypeptide of SEQ ID NO: 186. In another aspect, the *Penicillium oxalicum* Cel3 beta-glucosidase is encoded by the mature polypeptide coding sequence of SEQ ID NO: 185.

In another aspect, the polypeptide having beta-glucosidase activity is a *Penicillium oxalicum* Cel3 beta-glucosidase of the mature polypeptide of SEQ ID NO: 188. In another aspect, the *Penicillium oxalicum* Cel3 beta-glucosidase is encoded by the mature polypeptide coding sequence of SEQ ID NO: 187.

In another aspect, the polypeptide having beta-glucosidase activity is a *Talaromyces emersonii* Cel3 beta-glucosidase of the mature polypeptide of SEQ ID NO: 190. In another aspect, the *Talaromyces emersonii* Cel3 beta-glucosidase is encoded by the mature polypeptide coding sequence of SEQ ID NO: 189.

In one aspect, the enzyme composition further comprises or even further comprises a polypeptide having cellulolytic enhancing activity selected from the group consisting of:

(I) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 34; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 33, (ii) the cDNA sequence of the mature polypeptide coding sequence of SEQ ID NO: 33, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 33;

(II) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 36; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 35, (ii) the genomic DNA sequence of the mature polypeptide coding sequence of SEQ ID NO: 35, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 35;

(III) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 38; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 37, (ii) the cDNA sequence of the mature polypeptide coding sequence of SEQ ID NO: 37, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 37;

(IV) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 40; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 39, (ii) the cDNA sequence of the mature polypeptide coding sequence of SEQ ID NO: 39, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 39;

(V) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 42; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 41, (ii) the cDNA sequence of the mature polypeptide coding sequence of SEQ ID NO: 41, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 41;

(VI) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 44; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 43, (ii) the cDNA sequence of the mature polypeptide coding sequence of SEQ ID NO: 43, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 43;

(VII) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 192; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 191, (ii) the cDNA sequence of the mature polypeptide coding sequence of SEQ ID NO: 191, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 191; and (VIII) a combination of any of I, II, III, IV, V, VI, and VII.

In a preferred aspect, the polypeptide having cellulolytic enhancing activity is a *Thermoascus aurantiacus* GH61A polypeptide having cellulolytic enhancing activity of the mature polypeptide of SEQ ID NO: 34. In another aspect, the *Thermoascus aurantiacus* GH61A polypeptide having cellulolytic enhancing activity is encoded by the mature polypeptide coding sequence of SEQ ID NO: 33.

In another aspect, the polypeptide having cellulolytic enhancing activity is a *Thielavia terrestris* GH61E polypeptide having cellulolytic enhancing activity of the mature polypeptide of SEQ ID NO: 36. In another aspect, the *Thielavia terrestris* GH61E polypeptide having cellulolytic enhancing activity is encoded by the mature polypeptide coding sequence of SEQ ID NO: 35.

In another aspect, the polypeptide having cellulolytic enhancing activity is a *Aspergillus fumigatus* GH61B polypeptide having cellulolytic enhancing activity of the mature polypeptide of SEQ ID NO: 38. In another aspect, the *Aspergillus fumigatus* GH61B polypeptide having cellulolytic enhancing activity is encoded by the mature polypeptide coding sequence of SEQ ID NO: 37.

In another aspect, the polypeptide having cellulolytic enhancing activity is a *Penicillium pinophilum* GH61 polypeptide having cellulolytic enhancing activity of the mature polypeptide of SEQ ID NO: 40. In another aspect, the *Penicillium pinophilum* GH61A polypeptide having cellulolytic enhancing activity is encoded by the mature polypeptide coding sequence of SEQ ID NO: 39.

In another aspect, the polypeptide having cellulolytic enhancing activity is a *Penicillium* sp. GH61A polypeptide having cellulolytic enhancing activity of the mature polypeptide of SEQ ID NO: 42. In another aspect, the *Penicillium* sp. GH61 polypeptide having cellulolytic enhancing activity is encoded by the mature polypeptide coding sequence of SEQ ID NO: 41.

In another aspect, the polypeptide having cellulolytic enhancing activity is a *Thielavia terrestris* GH61N polypeptide having cellulolytic enhancing activity of the mature polypeptide of SEQ ID NO: 44. In another aspect, the *Thielavia terrestris* GH61N polypeptide having cellulolytic enhancing activity is encoded by the mature polypeptide coding sequence of SEQ ID NO: 43.

In another aspect, the polypeptide having cellulolytic enhancing activity is a *Thermoascus crustaceus* GH61A polypeptide having cellulolytic enhancing activity of the mature polypeptide of SEQ ID NO: 192. In another aspect, the *Thermoascus crustaceus* GH61A polypeptide having cellulolytic enhancing activity is encoded by the mature polypeptide coding sequence of SEQ ID NO: 191.

In another aspect, the enzyme composition further comprises or even further comprises a polypeptide having xylanase activity. In a preferred aspect, the polypeptide having xylanase activity is a Family 10 polypeptide having xylanase activity. In another aspect, the polypeptide having xylanase activity is a Family 11 polypeptide having xylanase activity.

In a more preferred aspect, the Family 10 polypeptide having xylanase activity is selected from the group consisting of:

(I) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 46; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 45, (ii) the genomic DNA sequence of the mature polypeptide coding sequence of SEQ ID NO: 45, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 45;

(II) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 48; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 47, (ii) the cDNA sequence of the mature polypeptide coding sequence of SEQ ID NO: 47, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 47;

(III) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 50; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 49, (ii) the genomic DNA sequence of the mature polypeptide coding sequence of SEQ ID NO: 49, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 49;

(IV) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 52; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 51, (ii) the cDNA sequence of the mature polypeptide coding sequence of SEQ ID NO: 51, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 51;

(V) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 54; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 53, (ii) the genomic DNA sequence of the mature polypeptide coding sequence of SEQ ID NO: 53, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 53;

(VI) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 194; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 193, (ii) the genomic DNA sequence of the mature polypeptide coding sequence of SEQ ID NO: 193, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 193;

(VII) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 196; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 195, (ii) the genomic DNA sequence of the mature polypeptide coding sequence of SEQ ID NO: 195, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 195; and (VIII) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 198; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 197, (ii) the genomic DNA sequence of the mature polypeptide coding sequence of SEQ ID NO: 197, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 197.

In one aspect, the enzyme compositions comprise *Aspergillus fumigatus* Cel 7A CBHI, *Aspergillus fumigatus* Cel 6A CBHII, *Thermoascus aurantiacus* Cel5A EGII, *Penicillium* sp GH61A polypeptide having cellulolytic enhancing activity, *Aspergillus fumigatus* GH3A beta-glucosidase, *Aspergillus fumigatus* GH10C xylanase, and *Talaromyces emersonii* GH3 beta-xylosidase.

In another aspect, the enzyme compositions comprise *Aspergillus fumigatus* Cel 7A CBHI, *Aspergillus fumigatus* Cel 6A CBHII, *Thermoascus aurantiacus* Cel5A EGII, *Penicillium* sp GH61A polypeptide having cellulolytic enhancing activity, *Aspergillus aculeatus* GH3 beta-glucosidase, *Aspergillus fumigatus* GH100 xylanase, and *Talaromyces emersonii* GH3 beta-xylosidase.

In another aspect, the enzyme compositions comprise *Aspergillus fumigatus* Cel 7A CBHI, *Aspergillus fumigatus* Cel 6A CBHII, *Thermoascus aurantiacus* Cel5A EGII, *Penicillium* sp GH61A polypeptide having cellulolytic enhancing activity, *Aspergillus fumigatus* GH3A beta-glucosidase, *Trichophaea saccata* GH10 xylanase, and *Talaromyces emersonii* GH3 beta-xylosidase.

In another aspect, the enzyme compositions comprise *Aspergillus fumigatus* Cel 7A CBHI, *Aspergillus fumigatus* Cel 6A CBHII, *Thermoascus aurantiacus* Cel5A EGII, *Penicillium* sp GH61A polypeptide having cellulolytic enhancing activity, *Aspergillus aculeatus* GH3 beta-glucosidase, *Trichophaea saccata* GH10 xylanase, and *Talaromyces emersonii* GH3 beta-xylosidase.

In another aspect, the enzyme compositions comprise *Penicillium emersonii* Cel 7 CBHI, *Aspergillus fumigatus* Cel 6A CBHII, *Thermoascus aurantiacus* Cel5A EGII, *Penicillium* sp GH61A polypeptide having cellulolytic enhancing activity, *Aspergillus fumigatus* GH3A beta-glucosidase, *Aspergillus fumigatus* GH10C xylanase, and *Talaromyces emersonii* GH3 beta-xylosidase.

In another aspect, the enzyme compositions comprise *Penicillium emersonii* Cel 7 CBHI, *Aspergillus fumigatus* Cel 6A CBHII, *Thermoascus aurantiacus* Cel5A EGII, *Penicillium* sp GH61A polypeptide having cellulolytic enhancing activity, *Aspergillus aculeatus* GH3 beta-glucosidase, *Aspergillus fumigatus* GH100 xylanase, and *Talaromyces emersonii* GH3 beta-xylosidase.

In another aspect, the enzyme compositions comprise *Penicillium emersonii* Cel 7 CBHI, *Aspergillus fumigatus* Cel 6A CBHII, *Thermoascus aurantiacus* Cel5A EGII, *Penicillium* sp GH61A polypeptide having cellulolytic enhancing activity, *Aspergillus fumigatus* GH3A beta-glucosidase, *Trichophaea saccata* GH10 xylanase, and *Talaromyces emersonii* GH3 beta-xylosidase.

In another aspect, the enzyme compositions comprise *Penicillium emersonii* Cel 7 CBHI, *Aspergillus fumigatus* Cel 6A CBHII, *Thermoascus aurantiacus* Cel5A EGII, *Penicillium* sp GH61A polypeptide having cellulolytic enhancing activity, *Aspergillus aculeatus* GH3 beta-glucosidase, *Trichophaea saccata* GH10 xylanase, and *Talaromyces emersonii* GH3 beta-xylosidase.

In another aspect, the enzyme compositions comprise *Thermoascus aurantiacus* Cel 7A CBHI, *Aspergillus fumigatus* Cel 6A CBHII, *Thermoascus aurantiacus* Cel5A EGII, *Penicillium* sp GH61A polypeptide having cellulolytic enhancing activity, *Aspergillus fumigatus* GH3A beta-glucosidase, *Aspergillus fumigatus* GH100 xylanase, and *Talaromyces emersonii* GH3 beta-xylosidase.

In another aspect, the enzyme compositions comprise *Thermoascus aurantiacus* Cel 7A CBHI, *Aspergillus fumigatus* Cel 6A CBHII, *Thermoascus aurantiacus* Cel5A EGII, *Penicillium* sp GH61A polypeptide having cellulolytic enhancing activity, *Aspergillus aculeatus* GH3 beta-glucosidase, *Aspergillus fumigatus* GH100 xylanase, and *Talaromyces emersonii* GH3 beta-xylosidase.

In another aspect, the enzyme compositions comprise *Thermoascus aurantiacus* Cel 7A CBHI, *Aspergillus fumigatus* Cel 6A CBHII, *Thermoascus aurantiacus* Cel5A EGII, *Penicillium* sp GH61A polypeptide having cellulolytic enhancing activity, *Aspergillus fumigatus* GH3A beta-glucosidase, *Trichophaea saccata* GH10 xylanase, and *Talaromyces emersonii* GH3 beta-xylosidase.

In another aspect, the enzyme compositions comprise *Thermoascus aurantiacus* Cel 7A CBHI, *Aspergillus fumigatus* Cel 6A CBHII, *Thermoascus aurantiacus* Cel5A EGII, *Penicillium* sp GH61A polypeptide having cellulolytic enhancing activity, *Aspergillus aculeatus* GH3 beta-glucosidase, *Trichophaea saccata* GH10 xylanase, and *Talaromyces emersonii* GH3 beta-xylosidase.

In another aspect, the enzyme compositions comprise *Aspergillus fumigatus* Cel 7A CBHI, *Aspergillus fumigatus* Cel 6A CBHII, *Aspergillus fumigatus* Cel5A EGII, *Penicillium* sp GH61A polypeptide having cellulolytic enhancing activity, *Aspergillus fumigatus* GH3A beta-glucosidase, *Aspergillus fumigatus* GH100 xylanase, and *Talaromyces emersonii* GH3 beta-xylosidase.

In another aspect, the enzyme compositions comprise *Aspergillus fumigatus* Cel 7A CBHI, *Aspergillus fumigatus* Cel 6A CBHII, *Aspergillus fumigatus* Cel5A EGII, *Penicillium* sp GH61A polypeptide having cellulolytic enhancing activity, *Aspergillus aculeatus* GH3 beta-glucosidase, *Aspergillus fumigatus* GH10C xylanase, and *Talaromyces emersonii* GH3 beta-xylosidase.

In another aspect, the enzyme compositions comprise *Aspergillus fumigatus* Cel 7A CBHI, *Aspergillus fumigatus* Cel 6A CBHII, *Aspergillus fumigatus* Cel5A EGII, *Penicillium* sp GH61A polypeptide having cellulolytic enhancing activity, *Aspergillus fumigatus* GH3A beta-glucosidase, *Trichophaea saccata* GH10 xylanase, and *Talaromyces emersonii* GH3 beta-xylosidase.

In another aspect, the enzyme compositions comprise *Aspergillus fumigatus* Cel 7A CBHI, *Aspergillus fumigatus* Cel 6A CBHII, *Aspergillus fumigatus* Cel5A EGII, *Penicillium* sp GH61A polypeptide having cellulolytic enhancing activity, *Aspergillus aculeatus* GH3 beta-glucosidase, *Trichophaea saccata* GH10 xylanase, and *Talaromyces emersonii* GH3 beta-xylosidase.

In another aspect, the enzyme compositions comprise *Penicillium emersonii* Cel 7 CBHI, *Aspergillus fumigatus* Cel 6A CBHII, *Aspergillus fumigatus* Cel5A EGII, *Penicillium* sp GH61A polypeptide having cellulolytic enhancing activity, *Aspergillus fumigatus* GH3A beta-glucosidase, *Aspergillus fumigatus* GH100 xylanase, and *Talaromyces emersonii* GH3 beta-xylosidase.

In another aspect, the enzyme compositions comprise *Penicillium emersonii* Cel 7 CBHI, *Aspergillus fumigatus* Cel 6A CBHII, *Aspergillus fumigatus* Cel5A EGII, *Penicillium* sp GH61A polypeptide having cellulolytic enhancing activity, *Aspergillus aculeatus* GH3 beta-glucosidase, *Aspergillus fumigatus* GH10C xylanase, and *Talaromyces emersonii* GH3 beta-xylosidase.

In another aspect, the enzyme compositions comprise *Penicillium emersonii* Cel 7 CBHI, *Aspergillus fumigatus* Cel 6A CBHII, *Aspergillus fumigatus* Cel5A EGII, *Penicillium* sp GH61A polypeptide having cellulolytic enhancing activity, *Aspergillus fumigatus* GH3A beta-glucosidase, *Trichophaea saccata* GH10 xylanase, and *Talaromyces emersonii* GH3 beta-xylosidase.

In another aspect, the enzyme compositions comprise *Penicillium emersonii* Cel 7 CBHI, *Aspergillus fumigatus* Cel 6A CBHII, *Aspergillus fumigatus* Cel5A EGII, *Penicillium* sp GH61A polypeptide having cellulolytic enhancing activity, *Aspergillus aculeatus* GH3 beta-glucosidase, *Trichophaea saccata* GH10 xylanase, and *Talaromyces emersonii* GH3 beta-xylosidase.

In another aspect, the enzyme compositions comprise *Thermoascus aurantiacus* Cel 7A CBHI, *Aspergillus fumigatus* Cel 6A CBHII, *Aspergillus fumigatus* Cel5A EGII, *Penicillium* sp GH61A polypeptide having cellulolytic enhancing activity, *Aspergillus fumigatus* GH3A beta-glucosidase, *Aspergillus fumigatus* GH100 xylanase, and *Talaromyces emersonii* GH3 beta-xylosidase.

In another aspect, the enzyme compositions comprise *Thermoascus aurantiacus* Cel 7A CBHI, *Aspergillus fumigatus* Cel 6A CBHII, *Aspergillus fumigatus* Cel5A EGII, *Penicillium* sp GH61A polypeptide having cellulolytic enhancing activity, *Aspergillus aculeatus* GH3 beta-glucosidase, *Aspergillus fumigatus* GH100 xylanase, and *Talaromyces emersonii* GH3 beta-xylosidase.

In another aspect, the enzyme compositions comprise *Thermoascus aurantiacus* Cel 7A CBHI, *Aspergillus fumigatus* Cel 6A CBHII, *Aspergillus fumigatus* Cel5A EGII, *Penicillium* sp GH61A polypeptide having cellulolytic enhancing activity, *Aspergillus fumigatus* GH3A beta-glucosidase, *Trichophaea saccata* GH10 xylanase, and *Talaromyces emersonii* GH3 beta-xylosidase.

In another aspect, the enzyme compositions comprise *Thermoascus aurantiacus* Cel 7A CBHI, *Aspergillus fumigatus* Cel 6A CBHII, *Aspergillus fumigatus* Cel5A EGII, *Penicillium* sp GH61A polypeptide having cellulolytic enhancing activity, *Aspergillus aculeatus* GH3 beta-glucosidase, *Trichophaea saccata* GH10 xylanase, and *Talaromyces emersonii* GH3 beta-xylosidase.

In another aspect, the enzyme compositions comprise *Aspergillus fumigatus* Cel 7A CBHI, *Aspergillus fumigatus* Cel 6A CBHII, *Thermoascus aurantiacus* Cel5A EGII, *Aspergillus fumigatus* GH61B polypeptide having cellulolytic enhancing activity, *Aspergillus fumigatus GH*3A beta-glucosidase, *Aspergillus fumigatus* GH10C xylanase, and *Talaromyces emersonii* GH3 beta-xylosidase.

In another aspect, the enzyme compositions comprise *Aspergillus fumigatus* Cel 7A CBHI, *Aspergillus fumigatus* Cel 6A CBHII, *Thermoascus aurantiacus* Cel5A EGII, *Aspergillus fumigatus* GH61B polypeptide having cellulolytic enhancing activity, *Aspergillus aculeatus* GH3 beta-glucosidase, *Aspergillus fumigatus* GH100 xylanase, and *Talaromyces emersonii* GH3 beta-xylosidase.

In another aspect, the enzyme compositions comprise *Aspergillus fumigatus* Cel 7A CBHI, *Aspergillus fumigatus* Cel 6A CBHII, *Thermoascus aurantiacus* Cel5A EGII, *Aspergillus fumigatus* GH61B polypeptide having cellulolytic enhancing activity, *Aspergillus fumigatus* GH3A beta-glucosidase, *Trichophaea saccata* GH10 xylanase, and *Talaromyces emersonii* GH3 beta-xylosidase.

In another aspect, the enzyme compositions comprise *Aspergillus fumigatus* Cel 7A CBHI, *Aspergillus fumigatus* Cel 6A CBHII, *Thermoascus aurantiacus* Cel5A EGII, *Aspergillus fumigatus* GH61B polypeptide having cellulolytic enhancing activity, *Aspergillus aculeatus* GH3 beta-glucosidase, *Trichophaea saccata* GH10 xylanase, and *Talaromyces emersonii* GH3 beta-xylosidase.

In another aspect, the enzyme compositions comprise *Penicillium emersonii* Cel 7 CBHI, *Aspergillus fumigatus* Cel 6A CBHII, *Thermoascus aurantiacus* Cel5A EGII, *Aspergillus fumigatus* GH61B polypeptide having cellulolytic enhancing activity, *Aspergillus fumigatus* GH3A beta-glucosidase, *Aspergillus fumigatus* GH10C xylanase, and *Talaromyces emersonii* GH3 beta-xylosidase.

In another aspect, the enzyme compositions comprise *Penicillium emersonii* Cel 7 CBHI, *Aspergillus fumigatus* Cel 6A CBHII, *Thermoascus aurantiacus* Cel5A EGII, *Aspergillus fumigatus* GH61B polypeptide having cellulolytic enhancing activity, *Aspergillus aculeatus* GH3 beta-glucosidase, *Aspergillus fumigatus* GH100 xylanase, and *Talaromyces emersonii* GH3 beta-xylosidase.

In another aspect, the enzyme compositions comprise *Penicillium emersonii* Cel 7 CBHI, *Aspergillus fumigatus* Cel 6A CBHII, *Thermoascus aurantiacus* Cel5A EGII, *Aspergillus fumigatus* GH61B polypeptide having cellulolytic enhancing activity, *Aspergillus fumigatus* GH3A beta-glucosidase, *Trichophaea saccata* GH10 xylanase, and *Talaromyces emersonii* GH3 beta-xylosidase.

In another aspect, the enzyme compositions comprise *Penicillium emersonii* Cel 7 CBHI, *Aspergillus fumigatus* Cel 6A CBHII, *Thermoascus aurantiacus* Cel5A EGII, *Aspergillus fumigatus* GH61B polypeptide having cellulolytic enhancing activity, *Aspergillus aculeatus* GH3 beta-glucosidase, *Trichophaea saccata* GH10 xylanase, and *Talaromyces emersonii* GH3 beta-xylosidase.

In another aspect, the enzyme compositions comprise *Thermoascus aurantiacus* Cel 7A CBHI, *Aspergillus fumigatus* Cel 6A CBHII, *Thermoascus aurantiacus* Cel5A EGII, *Aspergillus fumigatus* GH61B polypeptide having cellulolytic enhancing activity, *Aspergillus fumigatus* GH3A beta-glucosidase, *Aspergillus fumigatus* GH10C xylanase, and *Talaromyces emersonii* GH3 beta-xylosidase.

In another aspect, the enzyme compositions comprise *Thermoascus aurantiacus* Cel 7A CBHI, *Aspergillus fumigatus* Cel 6A CBHII, *Thermoascus aurantiacus* Cel5A EGII, *Aspergillus fumigatus* GH61B polypeptide having cellulolytic enhancing activity, *Aspergillus aculeatus* GH3 beta-glucosidase, *Aspergillus fumigatus* GH100 xylanase, and *Talaromyces emersonii* GH3 beta-xylosidase.

In another aspect, the enzyme compositions comprise *Thermoascus aurantiacus* Cel 7A CBHI, *Aspergillus fumigatus* Cel 6A CBHII, *Thermoascus aurantiacus* Cel5A EGII, *Aspergillus fumigatus* GH61B GH61 polypeptides having cellulolytic enhancing activity, *Aspergillus fumigatus* GH3A beta-glucosidase, *Trichophaea saccata* GH10 xylanase, and *Talaromyces emersonii* GH3 beta-xylosidase.

In another aspect, the enzyme compositions comprise *Thermoascus aurantiacus* Cel 7A CBHI, *Aspergillus fumigatus* Cel 6A CBHII, *Thermoascus aurantiacus* Cel5A EGII, *Aspergillus fumigatus* GH61B polypeptide having cellulolytic enhancing activity, *Aspergillus aculeatus* GH3 beta-glucosidase, *Trichophaea saccata* GH10 xylanase, and *Talaromyces emersonii* GH3 beta-xylosidase.

In another aspect, the enzyme compositions comprise the enzyme compositions comprise *Aspergillus fumigatus* Cel 7A CBHI, *Aspergillus fumigatus* Cel 6A CBHII, *Aspergillus fumigatus* Cel5A EGII, *Aspergillus fumigatus* GH61B polypeptide having cellulolytic enhancing activity, *Aspergillus fumigatus* GH3A beta-glucosidase, *Aspergillus fumigatus* GH10C xylanase, and *Talaromyces emersonii* GH3 beta-xylosidase.

In another aspect, the enzyme compositions comprise *Aspergillus fumigatus* Cel 7A CBHI, *Aspergillus fumigatus* Cel 6A CBHII, *Aspergillus fumigatus* Cel5A EGII, *Aspergillus fumigatus* GH61B polypeptide having cellulolytic enhancing activity, *Aspergillus aculeatus* GH3 beta-glucosidase, *Aspergillus fumigatus* GH10C xylanase, and *Talaromyces emersonii* GH3 beta-xylosidase.

In another aspect, the enzyme compositions comprise *Aspergillus fumigatus* Cel 7A CBHI, *Aspergillus fumigatus* Cel 6A CBHII, *Aspergillus fumigatus* Cel5A EGII, *Aspergillus fumigatus* GH61B polypeptide having cellulolytic enhancing activity, *Aspergillus fumigatus* GH3A beta-glucosidase, *Trichophaea saccata* GH10 xylanase, and *Talaromyces emersonii* GH3 beta-xylosidase.

In another aspect, the enzyme compositions comprise *Aspergillus fumigatus* Cel 7A CBHI, *Aspergillus fumigatus* Cel 6A CBHII, *Aspergillus fumigatus* Cel5A EGII, *Aspergillus fumigatus* GH61B polypeptide having cellulolytic enhancing activity, *Aspergillus aculeatus* GH3 beta-glucosidase, *Trichophaea saccata* GH10 xylanase, and *Talaromyces emersonii* GH3 beta-xylosidase.

In another aspect, the enzyme compositions comprise *Penicillium emersonii* Cel 7 CBHI, *Aspergillus fumigatus* Cel 6A CBHII, *Aspergillus fumigatus* Cel5A EGII, *Aspergillus fumigatus* GH61B polypeptide having cellulolytic enhancing activity, *Aspergillus fumigatus* GH3A beta-glucosidase, *Aspergillus fumigatus* GH100 xylanase, and *Talaromyces emersonii* GH3 beta-xylosidase.

In another aspect, the enzyme compositions comprise *Penicillium emersonii* Cel 7 CBHI, *Aspergillus fumigatus* Cel 6A CBHII, *Aspergillus fumigatus* Cel5A EGII, *Aspergillus fumigatus* GH61B polypeptide having cellulolytic enhancing activity, *Aspergillus aculeatus* GH3 beta-glucosidase, *Aspergillus fumigatus* GH100 xylanase, and *Talaromyces emersonii* GH3 beta-xylosidase.

In another aspect, the enzyme compositions comprise *Penicillium emersonii* Cel 7 CBHI, *Aspergillus fumigatus* Cel 6A CBHII, *Aspergillus fumigatus* Cel5A EGII, *Asper-*

*gillus fumigatus* GH61B polypeptide having cellulolytic enhancing activity, *Aspergillus fumigatus* GH3A beta-glucosidase, *Trichophaea saccata* GH10 xylanase, and *Talaromyces emersonii* GH3 beta-xylosidase.

In another aspect, the enzyme compositions comprise *Penicillium emersonii* Cel 7 CBHI, *Aspergillus fumigatus* Cel 6A CBHII, *Aspergillus fumigatus* Cel5A EGII, *Aspergillus fumigatus* GH61B polypeptide having cellulolytic enhancing activity, *Aspergillus aculeatus* GH3 beta-glucosidase, *Trichophaea saccata* GH10 xylanase, and *Talaromyces emersonii* GH3 beta-xylosidase.

In another aspect, the enzyme compositions comprise *Thermoascus aurantiacus* Cel 7A CBHI, *Aspergillus fumigatus* Cel 6A CBHII, *Aspergillus fumigatus* Cel5A EGII, *Aspergillus fumigatus* GH61B polypeptide having cellulolytic enhancing activity, *Aspergillus fumigatus GH*3A beta-glucosidase, *Aspergillus fumigatus* GH10C xylanase, and *Talaromyces emersonii* GH3 beta-xylosidase.

In another aspect, the enzyme compositions comprise *Thermoascus aurantiacus* Cel 7A CBHI, *Aspergillus fumigatus* Cel 6A CBHII, *Aspergillus fumigatus* Cel5A EGII, *Aspergillus fumigatus* GH61B polypeptide having cellulolytic enhancing activity, *Aspergillus aculeatus* GH3 beta-glucosidase, *Aspergillus fumigatus* GH100 xylanase, and *Talaromyces emersonii* GH3 beta-xylosidase.

In another aspect, the enzyme compositions comprise *Thermoascus aurantiacus* Cel 7A CBHI, *Aspergillus fumigatus* Cel 6A CBHII, *Aspergillus fumigatus* Cel5A EGII, *Aspergillus fumigatus* GH61B polypeptide having cellulolytic enhancing activity, *Aspergillus fumigatus* GH3A beta-glucosidase, *Trichophaea saccata* GH10 xylanase, and *Talaromyces emersonii* GH3 beta-xylosidase.

In another aspect, the enzyme compositions comprise *Thermoascus aurantiacus* Cel 7A CBHI, *Aspergillus fumigatus* Cel 6A CBHII, *Aspergillus fumigatus* Cel5A EGII, *Aspergillus fumigatus* GH61B polypeptide having cellulolytic enhancing activity, *Aspergillus aculeatus* GH3 beta-glucosidase, *Trichophaea saccata* GH10 xylanase, and *Talaromyces emersonii* GH3 beta-xylosidase.

In another aspect, the enzyme compositions comprise *Aspergillus fumigatus* Cel 7A CBHI, *Aspergillus fumigatus* Cel 6A CBHII, *Thermoascus aurantiacus* Cel5A EGII, *Thermoascus aurantiacus* GH61A polypeptide having cellulolytic enhancing activity, *Aspergillus fumigatus* GH3A beta-glucosidase, *Aspergillus fumigatus* GH100 xylanase, and *Talaromyces emersonii* GH3 beta-xylosidase.

In another aspect, the enzyme compositions comprise *Aspergillus fumigatus* Cel 7A CBHI, *Aspergillus fumigatus* Cel 6A CBHII, *Thermoascus aurantiacus* Cel5A EGII, *Thermoascus aurantiacus* GH61A polypeptide having cellulolytic enhancing activity, *Aspergillus aculeatus* GH3 beta-glucosidase, *Aspergillus fumigatus* GH10C xylanase, and *Talaromyces emersonii* GH3 beta-xylosidase.

In another aspect, the enzyme compositions comprise *Aspergillus fumigatus* Cel 7A CBHI, *Aspergillus fumigatus* Cel 6A CBHII, *Thermoascus aurantiacus* Cel5A EGII, *Thermoascus aurantiacus* GH61A polypeptide having cellulolytic enhancing activity, *Aspergillus fumigatus* GH3A beta-glucosidase, *Trichophaea saccata* GH10 xylanase, and *Talaromyces emersonii* GH3 beta-xylosidase.

In another aspect, the enzyme compositions comprise *Aspergillus fumigatus* Cel 7A CBHI, *Aspergillus fumigatus* Cel 6A CBHII, *Thermoascus aurantiacus* Cel5A EGII, *Thermoascus aurantiacus* GH61A polypeptide having cellulolytic enhancing activity, *Aspergillus aculeatus* GH3 beta-glucosidase, *Trichophaea saccata* GH10 xylanase, and *Talaromyces emersonii* GH3 beta-xylosidase.

In another aspect, the enzyme compositions comprise *Penicillium emersonii* Cel 7 CBHI, *Aspergillus fumigatus* Cel 6A CBHII, *Thermoascus aurantiacus* Cel5A EGII, *Thermoascus aurantiacus* GH61A polypeptide having cellulolytic enhancing activity, *Aspergillus fumigatus* GH3A beta-glucosidase, *Aspergillus fumigatus* GH10C xylanase, and *Talaromyces emersonii* GH3 beta-xylosidase.

In another aspect, the enzyme compositions comprise *Penicillium emersonii* Cel 7 CBHI, *Aspergillus fumigatus* Cel 6A CBHII, *Thermoascus aurantiacus* Cel5A EGII, *Thermoascus aurantiacus* GH61A polypeptide having cellulolytic enhancing activity, *Aspergillus aculeatus* GH3 beta-glucosidase, *Aspergillus fumigatus* GH100 xylanase, and *Talaromyces emersonii* GH3 beta-xylosidase.

In another aspect, the enzyme compositions comprise *Penicillium emersonii* Cel 7 CBHI, *Aspergillus fumigatus* Cel 6A CBHII, *Thermoascus aurantiacus* Cel5A EGII, *Thermoascus aurantiacus* GH61A polypeptide having cellulolytic enhancing activity, *Aspergillus fumigatus* GH3A beta-glucosidase, *Trichophaea saccata* GH10 xylanase, and *Talaromyces emersonii* GH3 beta-xylosidase.

In another aspect, the enzyme compositions comprise *Penicillium emersonii* Cel 7 CBHI, *Aspergillus fumigatus* Cel 6A CBHII, *Thermoascus aurantiacus* Cel5A EGII, *Thermoascus aurantiacus* GH61A polypeptide having cellulolytic enhancing activity, *Aspergillus aculeatus* GH3 beta-glucosidase, *Trichophaea saccata* GH10 xylanase, and *Talaromyces emersonii* GH3 beta-xylosidase.

In another aspect, the enzyme compositions comprise *Thermoascus aurantiacus* Cel 7A CBHI, *Aspergillus fumigatus* Cel 6A CBHII, *Thermoascus aurantiacus* Cel5A EGII, *Thermoascus aurantiacus* GH61A polypeptide having cellulolytic enhancing activity, *Aspergillus fumigatus* GH3A beta-glucosidase, *Aspergillus fumigatus* GH100 xylanase, and *Talaromyces emersonii* GH3 beta-xylosidase.

In another aspect, the enzyme compositions comprise *Thermoascus aurantiacus* Cel 7A CBHI, *Aspergillus fumigatus* Cel 6A CBHII, *Thermoascus aurantiacus* Cel5A EGII, *Thermoascus aurantiacus* GH61A polypeptide having cellulolytic enhancing activity, *Aspergillus aculeatus* GH3 beta-glucosidase, *Aspergillus fumigatus* GH10C xylanase, and *Talaromyces emersonii* GH3 beta-xylosidase.

In another aspect, the enzyme compositions comprise *Thermoascus aurantiacus* Cel 7A CBHI, *Aspergillus fumigatus* Cel 6A CBHII, *Thermoascus aurantiacus* Cel5A EGII, *Thermoascus aurantiacus* GH61A polypeptide having cellulolytic enhancing activity, *Aspergillus fumigatus* GH3A beta-glucosidase, *Trichophaea saccata* GH10 xylanase, and *Talaromyces emersonii* GH3 beta-xylosidase.

In another aspect, the enzyme compositions comprise *Thermoascus aurantiacus* Cel 7A CBHI, *Aspergillus fumigatus* Cel 6A CBHII, *Thermoascus aurantiacus* Cel5A EGII, *Thermoascus aurantiacus* GH61A polypeptide having cellulolytic enhancing activity, *Aspergillus aculeatus* GH3 beta-glucosidase, *Trichophaea saccata* GH10 xylanase, and *Talaromyces emersonii* GH3 beta-xylosidase.

In another aspect, the enzyme compositions comprise *Aspergillus fumigatus* Cel 7A CBHI, *Aspergillus fumigatus* Cel 6A CBHII, *Aspergillus fumigatus* Cel5A EGII, *Thermoascus aurantiacus* GH61A polypeptide having cellulolytic enhancing activity, *Aspergillus fumigatus GH*3A beta-glucosidase, *Aspergillus fumigatus* GH10C xylanase, and *Talaromyces emersonii* GH3 beta-xylosidase.

In another aspect, the enzyme compositions comprise *Aspergillus fumigatus* Cel 7A CBHI, *Aspergillus fumigatus* Cel 6A CBHII, *Aspergillus fumigatus* Cel5A EGII, *Thermoascus aurantiacus* GH61A polypeptide having cellulolytic enhancing activity, *Aspergillus aculeatus GH*3 beta-glucosidase, *Aspergillus fumigatus* GH100 xylanase, and *Talaromyces emersonii* GH3 beta-xylosidase.

In another aspect, the enzyme compositions comprise *Aspergillus fumigatus* Cel 7A CBHI, *Aspergillus fumigatus* Cel 6A CBHII, *Aspergillus fumigatus* Cel5A EGII, *Thermoascus aurantiacus* GH61A polypeptide having cellulolytic enhancing activity, *Aspergillus fumigatus GH*3A beta-glucosidase, *Trichophaea saccata* GH10 xylanase, and *Talaromyces emersonii* GH3 beta-xylosidase.

In another aspect, the enzyme compositions comprise *Aspergillus fumigatus* Cel 7A CBHI, *Aspergillus fumigatus* Cel 6A CBHII, *Aspergillus fumigatus* Cel5A EGII, *Thermoascus aurantiacus* GH61A polypeptide having cellulolytic enhancing activity, *Aspergillus aculeatus GH*3 beta-glucosidase, *Trichophaea saccata* GH10 xylanase, and *Talaromyces emersonii* GH3 beta-xylosidase.

In another aspect, the enzyme compositions comprise *Penicillium emersonii* Cel 7 CBHI, *Aspergillus fumigatus* Cel 6A CBHII, *Aspergillus fumigatus* Cel5A EGII, *Thermoascus aurantiacus* GH61A polypeptide having cellulolytic enhancing activity, *Aspergillus fumigatus GH*3A beta-glucosidase, *Aspergillus fumigatus* GH10C xylanase, and *Talaromyces emersonii* GH3 beta-xylosidase.

In another aspect, the enzyme compositions comprise *Penicillium emersonii* Cel 7 CBHI, *Aspergillus fumigatus* Cel 6A CBHII, *Aspergillus fumigatus* Cel5A EGII, *Thermoascus aurantiacus* GH61A polypeptide having cellulolytic enhancing activity, *Aspergillus aculeatus GH*3 beta-glucosidase, *Aspergillus fumigatus* GH100 xylanase, and *Talaromyces emersonii* GH3 beta-xylosidase.

In another aspect, the enzyme compositions comprise *Penicillium emersonii* Cel 7 CBHI, *Aspergillus fumigatus* Cel 6A CBHII, *Aspergillus fumigatus* Cel5A EGII, *Thermoascus aurantiacus* GH61A polypeptide having cellulolytic enhancing activity, *Aspergillus fumigatus* GH3A beta-glucosidase, *Trichophaea saccata* GH10 xylanase, and *Talaromyces emersonii* GH3 beta-xylosidase.

In another aspect, the enzyme compositions comprise *Penicillium emersonii* Cel 7 CBHI, *Aspergillus fumigatus* Cel 6A CBHII, *Aspergillus fumigatus* Cel5A EGII, *Thermoascus aurantiacus* GH61A polypeptide having cellulolytic enhancing activity, *Aspergillus aculeatus* GH3 beta-glucosidase, *Trichophaea saccata* GH10 xylanase, and *Talaromyces emersonii* GH3 beta-xylosidase.

In another aspect, the enzyme compositions comprise *Thermoascus aurantiacus* Cel 7A CBHI, *Aspergillus fumigatus* Cel 6A CBHII, *Aspergillus fumigatus* Cel5A EGII, *Thermoascus aurantiacus* GH61A polypeptide having cellulolytic enhancing activity, *Aspergillus fumigatus* GH3A beta-glucosidase, *Aspergillus fumigatus* GH10C xylanase, and *Talaromyces emersonii* GH3 beta-xylosidase.

In another aspect, the enzyme compositions comprise *Thermoascus aurantiacus* Cel 7A CBHI, *Aspergillus fumigatus* Cel 6A CBHII, *Aspergillus fumigatus* Cel5A EGII, *Thermoascus aurantiacus* GH61A polypeptide having cellulolytic enhancing activity, *Aspergillus aculeatus* GH3 beta-glucosidase, *Aspergillus fumigatus* GH100 xylanase, and *Talaromyces emersonii* GH3 beta-xylosidase.

In another aspect, the enzyme compositions comprise *Thermoascus aurantiacus* Cel 7A CBHI, *Aspergillus fumigatus* Cel 6A CBHII, *Aspergillus fumigatus* Cel5A EGII, *Thermoascus aurantiacus* GH61A polypeptide having cellulolytic enhancing activity, *Aspergillus fumigatus* GH3A beta-glucosidase, *Trichophaea saccata* GH10 xylanase, and *Talaromyces emersonii* GH3 beta-xylosidase.

In another aspect, the enzyme compositions comprise *Thermoascus aurantiacus* Cel 7A CBHI, *Aspergillus fumigatus* Cel 6A CBHII, *Aspergillus fumigatus* Cel5A EGII, *Thermoascus aurantiacus* GH61A polypeptide having cellulolytic enhancing activity, *Aspergillus aculeatus* GH3 beta-glucosidase, *Trichophaea saccata* GH10 xylanase, and *Talaromyces emersonii* GH3 beta-xylosidase.

Enzyme Composition Components and Polynucleotides Thereof

In first aspect, the isolated polypeptides having cellobiohydrolase I activity comprise amino acid sequences having a degree of identity to the mature polypeptide of SEQ ID NO: 2 of preferably at least 80%, more preferably at least 85%, even more preferably at least 90%, most preferably at least 95%, and even most preferably at least 96%, at least 97%, at least 98%, or at least 99%, which have cellobiohydrolase I activity (hereinafter “homologous polypeptides”). In a preferred aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 2.

In one aspect, a polypeptide having cellobiohydrolase I activity comprises or consists of the amino acid sequence of SEQ ID NO: 2 or an allelic variant thereof; or a fragment thereof having cellobiohydrolase I activity. In another aspect, the polypeptide comprises or consists of the amino acid sequence of SEQ ID NO: 2. In another aspect, the polypeptide comprises or consists of the mature polypeptide of SEQ ID NO: 2. In another aspect, the polypeptide comprises or consists of amino acids 19 to 530 of SEQ ID NO: 2, or an allelic variant thereof; or a fragment thereof having cellobiohydrolase I activity. In another aspect, the polypeptide comprises or consists of amino acids 19 to 530 of SEQ ID NO: 2.

In another first aspect, the isolated polypeptides having cellobiohydrolase I activity comprise amino acid sequences having a degree of identity to the mature polypeptide of SEQ ID NO: 4 of preferably at least 80%, more preferably at least 85%, even more preferably at least 90%, most preferably at least 95%, and even most preferably at least 96%, at least 97%, at least 98%, or at least 99%, which have cellobiohydrolase I activity (hereinafter “homologous polypeptides”). In one aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 4.

In one aspect, a polypeptide having cellobiohydrolase I activity comprises or consists of the amino acid sequence of SEQ ID NO: 4 or an allelic variant thereof; or a fragment thereof having cellobiohydrolase I activity. In another aspect, the polypeptide comprises or consists of the amino acid sequence of SEQ ID NO: 4. In another aspect, the polypeptide comprises or consists of the mature polypeptide of SEQ ID NO: 4. In another aspect, the polypeptide comprises or consists of amino acids 21 to 450 of SEQ ID NO: 4, or an allelic variant thereof; or a fragment thereof having cellobiohydrolase I activity. In another aspect, the polypeptide comprises or consists of amino acids 21 to 450 of SEQ ID NO: 4.

In another first aspect, the isolated polypeptides having cellobiohydrolase I activity comprise amino acid sequences having a degree of identity to the mature polypeptide of SEQ ID NO: 6 of preferably at least 80%, more preferably at least 85%, even more preferably at least 90%, most preferably at least 95%, and even most preferably at least 96%, at least 97%, at least 98%, or at least 99%, which have cellobiohydrolase I activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 6.

In one aspect, a polypeptide having cellobiohydrolase I activity comprises or consists of the amino acid sequence of SEQ ID NO: 6 or an allelic variant thereof; or a fragment thereof having cellobiohydrolase I activity. In another aspect, the polypeptide comprises or consists of the amino acid sequence of SEQ ID NO: 6. In another aspect, the polypeptide comprises or consists of the mature polypeptide of SEQ ID NO: 6. In another aspect, the polypeptide comprises or consists of amino acids 27 to 532 of SEQ ID NO: 6, or an allelic variant thereof; or a fragment thereof having cellobiohydrolase I activity. In another aspect, the polypeptide comprises or consists of amino acids 27 to 532 of SEQ ID NO: 6.

In another first aspect, the isolated polypeptides having cellobiohydrolase I activity comprise amino acid sequences having a degree of identity to the mature polypeptide of SEQ ID NO: 8 of preferably at least 80%, more preferably at least 85%, even more preferably at least 90%, most preferably at least 95%, and even most preferably at least 96%, at least 97%, at least 98%, or at least 99%, which have cellobiohydrolase I activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 8.

In one aspect, a polypeptide having cellobiohydrolase I activity comprises or consists of the amino acid sequence of SEQ ID NO: 8 or an allelic variant thereof; or a fragment thereof having cellobiohydrolase I activity. In another aspect, the polypeptide comprises or consists of the amino acid sequence of SEQ ID NO: 8. In another aspect, the polypeptide comprises or consists of the mature polypeptide of SEQ ID NO: 8. In another aspect, the polypeptide comprises or consists of amino acids 18 to 457 of SEQ ID NO: 8, or an allelic variant thereof; or a fragment thereof having cellobiohydrolase I activity. In another aspect, the polypeptide comprises or consists of amino acids 18 to 457 of SEQ ID NO: 8.

In another first aspect, the isolated polypeptides having cellobiohydrolase I activity comprise amino acid sequences having a degree of identity to the mature polypeptide of SEQ ID NO: 158 of preferably at least 80%, more preferably at least 85%, even more preferably at least 90%, most preferably at least 95%, and even most preferably at least 96%, at least 97%, at least 98%, or at least 99%, which have cellobiohydrolase I activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 158.

In one aspect, a polypeptide having cellobiohydrolase I activity comprises or consists of or consists of the amino acid sequence of SEQ ID NO: 158 or an allelic variant thereof; or a fragment thereof having cellobiohydrolase I activity. In another aspect, the polypeptide comprises or consists of or consists of the amino acid sequence of SEQ ID NO: 158. In another aspect, the polypeptide comprises or consists of or consists of the mature polypeptide of SEQ ID NO: 158. In another aspect, the polypeptide comprises or consists of or consists of amino acids 19 to 455 of SEQ ID NO: 158, or an allelic variant thereof; or a fragment thereof having cellobiohydrolase I activity. In another aspect, the polypeptide comprises or consists of or consists of amino acids 19 to 455 of SEQ ID NO: 158.

In another first aspect, the isolated polypeptides having cellobiohydrolase I activity comprise amino acid sequences having a degree of identity to the mature polypeptide of SEQ ID NO: 160 of preferably at least 80%, more preferably at least 85%, even more preferably at least 90%, most preferably at least 95%, and even most preferably at least 96%, at least 97%, at least 98%, or at least 99%, which have cellobiohydrolase I activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 160.

In one aspect, a polypeptide having cellobiohydrolase I activity comprises or consists of the amino acid sequence of SEQ ID NO: 160 or an allelic variant thereof; or a fragment thereof having cellobiohydrolase I activity. In another aspect, the polypeptide comprises or consists of the amino acid sequence of SEQ ID NO: 160. In another aspect, the polypeptide comprises or consists of the mature polypeptide of SEQ ID NO: 160. In another aspect, the polypeptide comprises or consists of amino acids 26 to 529 of SEQ ID NO: 160, or an allelic variant thereof; or a fragment thereof having cellobiohydrolase I activity. In another aspect, the polypeptide comprises or consists of amino acids 26 to 529 of SEQ ID NO: 160.

In another first aspect, the isolated polypeptides having cellobiohydrolase I activity comprise amino acid sequences having a degree of identity to the mature polypeptide of SEQ ID NO: 162 of preferably at least 80%, more preferably at least 85%, even more preferably at least 90%, most preferably at least 95%, and even most preferably at least 96%, at least 97%, at least 98%, or at least 99%, which have cellobiohydrolase I activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 162.

In one aspect, a polypeptide having cellobiohydrolase I activity comprises or consists of the amino acid sequence of SEQ ID NO: 162 or an allelic variant thereof; or a fragment thereof having cellobiohydrolase I activity. In another aspect, the polypeptide comprises or consists of the amino acid sequence of SEQ ID NO: 162. In another aspect, the polypeptide comprises or consists of the mature polypeptide of SEQ ID NO: 162. In another aspect, the polypeptide comprises or consists of amino acids 24 to 541 of SEQ ID NO: 162, or an allelic variant thereof; or a fragment thereof having cellobiohydrolase I activity. In another aspect, the polypeptide comprises or consists of amino acids 24 to 541 of SEQ ID NO: 162.

In another first aspect, the isolated polypeptides having cellobiohydrolase I activity comprise amino acid sequences having a degree of identity to the mature polypeptide of SEQ ID NO: 164 of preferably at least 80%, more preferably at least 85%, even more preferably at least 90%, most preferably at least 95%, and even most preferably at least 96%, at least 97%, at least 98%, or at least 99%, which have cellobiohydrolase I activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 164.

In one aspect, a polypeptide having cellobiohydrolase I activity comprises or consists of the amino acid sequence of SEQ ID NO: 164 or an allelic variant thereof; or a fragment thereof having cellobiohydrolase I activity. In another aspect, the polypeptide comprises or consists of the amino acid sequence of SEQ ID NO: 164. In another aspect, the polypeptide comprises or consists of the mature polypeptide of SEQ ID NO: 164. In another aspect, the polypeptide comprises or consists of amino acids 27 to 535 of SEQ ID NO: 164, or an allelic variant thereof; or a fragment thereof having cellobiohydrolase I activity. In another aspect, the polypeptide comprises or consists of amino acids 27 to 535 of SEQ ID NO: 164.

In another first aspect, the isolated polypeptides having cellobiohydrolase I activity comprise amino acid sequences having a degree of identity to the mature polypeptide of SEQ ID NO: 166 of preferably at least 80%, more preferably at least 85%, even more preferably at least 90%, most preferably at least 95%, and even most preferably at least 96%, at least 97%, at least 98%, or at least 99%, which have cellobiohydrolase I activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 166.

In one aspect, a polypeptide having cellobiohydrolase I activity comprises or consists of the amino acid sequence of SEQ ID NO: 166 or an allelic variant thereof; or a fragment thereof having cellobiohydrolase I activity. In another aspect, the polypeptide comprises or consists of the amino acid sequence of SEQ ID NO: 166. In another aspect, the polypeptide comprises or consists of the mature polypeptide of SEQ ID NO: 166. In another aspect, the polypeptide comprises or consists of amino acids 24 to 526 of SEQ ID NO: 166, or an allelic variant thereof; or a fragment thereof having cellobiohydrolase I activity. In another aspect, the polypeptide comprises or consists of amino acids 24 to 526 of SEQ ID NO: 166.

In another first aspect, the isolated polypeptides having cellobiohydrolase II activity comprise amino acid sequences having a degree of identity to the mature polypeptide of SEQ ID NO: 10 of preferably at least 80%, more preferably at least 85%, even more preferably at least 90%, most preferably at least 95%, and even most preferably at least 96%, at least 97%, at least 98%, or at least 99%, which have cellobiohydrolase II activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 10.

In one aspect, a polypeptide having cellobiohydrolase II activity comprises or consists of the amino acid sequence of SEQ ID NO: 10 or an allelic variant thereof; or a fragment thereof having cellobiohydrolase II activity. In another aspect, the polypeptide comprises or consists of the amino acid sequence of SEQ ID NO: 10. In another aspect, the polypeptide comprises or consists of the mature polypeptide of SEQ ID NO: 10. In another aspect, the polypeptide comprises or consists of amino acids 18 to 482 of SEQ ID NO: 10, or an allelic variant thereof; or a fragment thereof having cellobiohydrolase II activity. In another aspect, the polypeptide comprises or consists of amino acids 18 to 482 of SEQ ID NO: 10.

In another first aspect, the isolated polypeptides having cellobiohydrolase II activity comprise amino acid sequences having a degree of identity to the mature polypeptide of SEQ ID NO: 12 of preferably at least 80%, more preferably at least 85%, even more preferably at least 90%, most preferably at least 95%, and even most preferably at least 96%, at least 97%, at least 98%, or at least 99%, which have cellobiohydrolase II activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 12.

In one aspect, a polypeptide having cellobiohydrolase II activity comprises or consists of the amino acid sequence of SEQ ID NO: 12 or an allelic variant thereof; or a fragment thereof having cellobiohydrolase II activity. In another aspect, the polypeptide comprises or consists of the amino acid sequence of SEQ ID NO: 12. In another aspect, the polypeptide comprises or consists of the mature polypeptide of SEQ ID NO: 12. In another aspect, the polypeptide comprises or consists of amino acids 18 to 482 of SEQ ID NO: 12, or an allelic variant thereof; or a fragment thereof having cellobiohydrolase II activity. In another aspect, the polypeptide comprises or consists of amino acids 18 to 482 of SEQ ID NO: 12.

In another first aspect, the isolated polypeptides having cellobiohydrolase II activity comprise amino acid sequences having a degree of identity to the mature polypeptide of SEQ ID NO: 14 of preferably at least 80%, more preferably at least 85%, even more preferably at least 90%, most preferably at least 95%, and even most preferably at least 96%, at least 97%, at least 98%, or at least 99%, which have cellobiohydrolase II activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 14.

In one aspect, a polypeptide having cellobiohydrolase II activity comprises or consists of the amino acid sequence of SEQ ID NO: 14 or an allelic variant thereof; or a fragment thereof having cellobiohydrolase II activity. In another aspect, the polypeptide comprises or consists of the amino acid sequence of SEQ ID NO: 14. In another aspect, the polypeptide comprises or consists of the mature polypeptide of SEQ ID NO: 14. In another aspect, the polypeptide comprises or consists of amino acids 18 to 481 of SEQ ID NO: 14, or an allelic variant thereof; or a fragment thereof having cellobiohydrolase II activity. In another aspect, the polypeptide comprises or consists of amino acids 18 to 481 of SEQ ID NO: 14.

In another first aspect, the isolated polypeptides having cellobiohydrolase II activity comprise amino acid sequences having a degree of identity to the mature polypeptide of SEQ ID NO: 16 of preferably at least 80%, more preferably at least 85%, even more preferably at least 90%, most preferably at least 95%, and even most preferably at least 96%, at least 97%, at least 98%, or at least 99%, which have cellobiohydrolase II activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 16.

In one aspect, a polypeptide having cellobiohydrolase II activity comprises or consists of the amino acid sequence of SEQ ID NO: 16 or an allelic variant thereof; or a fragment thereof having cellobiohydrolase II activity. In another aspect, the polypeptide comprises or consists of the amino acid sequence of SEQ ID NO: 16. In another aspect, the polypeptide comprises or consists of the mature polypeptide of SEQ ID NO: 16. In another aspect, the polypeptide comprises or consists of amino acids 17 to 447 of SEQ ID NO: 16, or an allelic variant thereof; or a fragment thereof having cellobiohydrolase II activity. In another aspect, the polypeptide comprises or consists of amino acids 17 to 447 of SEQ ID NO: 16.

In another first aspect, the isolated polypeptides having cellobiohydrolase II activity comprise amino acid sequences having a degree of identity to the mature polypeptide of SEQ ID NO: 18 of preferably at least 80%, more preferably at least 85%, even more preferably at least 90%, most preferably at least 95%, and even most preferably at least 96%, at least 97%, at least 98%, or at least 99%, which have cellobiohydrolase II activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 18.

In one aspect, a polypeptide having cellobiohydrolase II activity comprises or consists of the amino acid sequence of SEQ ID NO: 18 or an allelic variant thereof; or a fragment thereof having cellobiohydrolase II activity. In another aspect, the polypeptide comprises or consists of the amino acid sequence of SEQ ID NO: 18. In another aspect, the polypeptide comprises or consists of the mature polypeptide of SEQ ID NO: 18. In another aspect, the polypeptide comprises or consists of amino acids 20 to 454 of SEQ ID NO: 18, or an allelic variant thereof; or a fragment thereof having cellobiohydrolase II activity. In another aspect, the polypeptide comprises or consists of amino acids 20 to 454 of SEQ ID NO: 18.

In another first aspect, the isolated polypeptides having cellobiohydrolase II activity comprise amino acid sequences having a degree of identity to the mature polypeptide of SEQ ID NO: 168 of preferably at least 80%, more preferably at least 85%, even more preferably at least 90%, most preferably at least 95%, and even most preferably at least 96%, at least 97%, at least 98%, or at least 99%, which have cellobiohydrolase II activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 168.

In one aspect, a polypeptide having cellobiohydrolase II activity comprises or consists of the amino acid sequence of SEQ ID NO: 168 or an allelic variant thereof; or a fragment thereof having cellobiohydrolase II activity. In another aspect, the polypeptide comprises or consists of the amino acid sequence of SEQ ID NO: 168. In another aspect, the polypeptide comprises or consists of the mature polypeptide of SEQ ID NO: 168. In another aspect, the polypeptide comprises or consists of amino acids 19 to 469 of SEQ ID NO: 168, or an allelic variant thereof; or a fragment thereof having cellobiohydrolase II activity. In another aspect, the polypeptide comprises or consists of amino acids 19 to 469 of SEQ ID NO: 168.

In another first aspect, the isolated polypeptides having cellobiohydrolase II activity comprise amino acid sequences having a degree of identity to the mature polypeptide of SEQ ID NO: 170 of preferably at least 80%, more preferably at least 85%, even more preferably at least 90%, most preferably at least 95%, and even most preferably at least 96%, at least 97%, at least 98%, or at least 99%, which have cellobiohydrolase II activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 170.

In one aspect, a polypeptide having cellobiohydrolase II activity comprises or consists of the amino acid sequence of SEQ ID NO: 170 or an allelic variant thereof; or a fragment thereof having cellobiohydrolase II activity. In another aspect, the polypeptide comprises or consists of the amino acid sequence of SEQ ID NO: 170. In another aspect, the polypeptide comprises or consists of the mature polypeptide of SEQ ID NO: 170. In another aspect, the polypeptide comprises or consists of amino acids 20 to 459 of SEQ ID NO: 170, or an allelic variant thereof; or a fragment thereof having cellobiohydrolase II activity. In another aspect, the polypeptide comprises or consists of amino acids 20 to 459 of SEQ ID NO: 170.

In another first aspect, the isolated polypeptides having cellobiohydrolase II activity comprise amino acid sequences having a degree of identity to the mature polypeptide of SEQ ID NO: 172 of preferably at least 80%, more preferably at least 85%, even more preferably at least 90%, most preferably at least 95%, and even most preferably at least 96%, at least 97%, at least 98%, or at least 99%, which have cellobiohydrolase II activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 172.

In one aspect, a polypeptide having cellobiohydrolase II activity comprises or consists of the amino acid sequence of SEQ ID NO: 172 or an allelic variant thereof; or a fragment thereof having cellobiohydrolase II activity. In another aspect, the polypeptide comprises or consists of the amino acid sequence of SEQ ID NO: 172. In another aspect, the polypeptide comprises or consists of the mature polypeptide of SEQ ID NO: 172. In another aspect, the polypeptide comprises or consists of amino acids 20 to 457 of SEQ ID NO: 172, or an allelic variant thereof; or a fragment thereof having cellobiohydrolase II activity. In another aspect, the polypeptide comprises or consists of amino acids 20 to 457 of SEQ ID NO: 172.

In another first aspect, the isolated polypeptides having endoglucanase I activity comprise amino acid sequences having a degree of identity to the mature polypeptide of SEQ ID NO: 20 of preferably at least 80%, more preferably at least 85%, even more preferably at least 90%, most preferably at least 95%, and even most preferably at least 96%, at least 97%, at least 98%, or at least 99%, which have endoglucanase I activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 20.

In one aspect, a polypeptide having endoglucanase I activity comprises or consists of the amino acid sequence of SEQ ID NO: 20 or an allelic variant thereof; or a fragment thereof having endoglucanase I activity. In another aspect, the polypeptide comprises or consists of the amino acid sequence of SEQ ID NO: 20. In another aspect, the polypeptide comprises or consists of the mature polypeptide of SEQ ID NO: 20. In another aspect, the polypeptide comprises or consists of amino acids 22 to 471 of SEQ ID NO: 20, or an allelic variant thereof; or a fragment thereof having endoglucanase I activity. In another aspect, the polypeptide comprises or consists of amino acids 22 to 471 of SEQ ID NO: 20.

In another first aspect, the isolated polypeptides having endoglucanase II activity comprise amino acid sequences having a degree of identity to the mature polypeptide of SEQ ID NO: 22 of preferably at least 80%, more preferably at least 85%, even more preferably at least 90%, most preferably at least 95%, and even most preferably at least 96%, at least 97%, at least 98%, or at least 99%, which have endoglucanase II activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 22.

In one aspect, a polypeptide having endoglucanase II activity comprises or consists of the amino acid sequence of SEQ ID NO: 22 or an allelic variant thereof; or a fragment thereof having endoglucanase II activity. In another aspect, the polypeptide comprises or consists of the amino acid sequence of SEQ ID NO: 22. In another aspect, the polypeptide comprises or consists of the mature polypeptide of SEQ ID NO: 22. In another aspect, the polypeptide comprises or consists of amino acids 22 to 418 of SEQ ID NO: 22, or an allelic variant thereof; or a fragment thereof having endoglucanase II activity. In another aspect, the polypeptide comprises or consists of amino acids 22 to 418 of SEQ ID NO: 22.

In another first aspect, the isolated polypeptides having endoglucanase II activity comprise amino acid sequences having a degree of identity to the mature polypeptide of SEQ ID NO: 24 of preferably at least 80%, more preferably at least 85%, even more preferably at least 90%, most preferably at least 95%, and even most preferably at least 96%, at least 97%, at least 98%, or at least 99%, which have endoglucanase II activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 24.

In one aspect, a polypeptide having endoglucanase II activity comprises or consists of the amino acid sequence of SEQ ID NO: 24 or an allelic variant thereof; or a fragment thereof having endoglucanase II activity. In another aspect, the polypeptide comprises or consists of the amino acid sequence of SEQ ID NO: 24. In another aspect, the polypeptide comprises or consists of the mature polypeptide of SEQ ID NO: 24. In another aspect, the polypeptide comprises or consists of amino acids 17 to 389 of SEQ ID NO: 24, or an allelic variant thereof; or a fragment thereof having endoglucanase II activity. In another aspect, the polypeptide comprises or consists of amino acids 17 to 389 of SEQ ID NO: 24.

In another first aspect, the isolated polypeptides having endoglucanase II activity comprise amino acid sequences having a degree of identity to the mature polypeptide of SEQ ID NO: 26 of preferably at least 80%, more preferably at least 85%, even more preferably at least 90%, most preferably at least 95%, and even most preferably at least 96%, at least 97%, at least 98%, or at least 99%, which have endoglucanase II activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 26.

In another first aspect, the isolated polypeptides having endoglucanase II activity comprise amino acid sequences having a degree of identity to the mature polypeptide of SEQ ID NO: 174 of preferably at least 80%, more preferably at least 85%, even more preferably at least 90%, most preferably at least 95%, and even most preferably at least 96%, at least 97%, at least 98%, or at least 99%, which have endoglucanase II activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 174.

In one aspect, a polypeptide having endoglucanase II activity comprises or consists of the amino acid sequence of SEQ ID NO: 174 or an allelic variant thereof; or a fragment thereof having endoglucanase II activity. In another aspect, the polypeptide comprises or consists of the amino acid sequence of SEQ ID NO: 174. In another aspect, the polypeptide comprises or consists of the mature polypeptide of SEQ ID NO: 174. In another aspect, the polypeptide comprises or consists of amino acids 19 to 329 of SEQ ID NO: 174, or an allelic variant thereof; or a fragment thereof having endoglucanase II activity. In another aspect, the polypeptide comprises or consists of amino acids 19 to 329 of SEQ ID NO: 174.

In another first aspect, the isolated polypeptides having endoglucanase II activity comprise amino acid sequences having a degree of identity to the mature polypeptide of SEQ ID NO: 176 of preferably at least 80%, more preferably at least 85%, even more preferably at least 90%, most preferably at least 95%, and even most preferably at least 96%, at least 97%, at least 98%, or at least 99%, which have endoglucanase II activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 176.

In one aspect, a polypeptide having endoglucanase II activity comprises or consists of the amino acid sequence of SEQ ID NO: 176 or an allelic variant thereof; or a fragment thereof having endoglucanase II activity. In another aspect, the polypeptide comprises or consists of the amino acid sequence of SEQ ID NO: 176. In another aspect, the polypeptide comprises or consists of the mature polypeptide of SEQ ID NO: 176. In another aspect, the polypeptide comprises or consists of amino acids 17 to 412 of SEQ ID NO: 176, or an allelic variant thereof; or a fragment thereof having endoglucanase II activity. In another aspect, the polypeptide comprises or consists of amino acids 17 to 412 of SEQ ID NO: 176.

In one aspect, a polypeptide having endoglucanase II activity comprises or consists of the amino acid sequence of SEQ ID NO: 26 or an allelic variant thereof; or a fragment thereof having endoglucanase II activity. In another aspect, the polypeptide comprises or consists of the amino acid sequence of SEQ ID NO: 26. In another aspect, the polypeptide comprises or consists of the mature polypeptide of SEQ ID NO: 26. In another aspect, the polypeptide comprises or consists of amino acids 31 to 335 of SEQ ID NO: 26, or an allelic variant thereof; or a fragment thereof having endoglucanase II activity. In another aspect, the polypeptide comprises or consists of amino acids 31 to 335 of SEQ ID NO: 26.

In another first aspect, the isolated polypeptides having beta-glucosidase activity comprise amino acid sequences having a degree of identity to the mature polypeptide of SEQ ID NO: 28 of preferably at least 80%, more preferably at least 85%, even more preferably at least 90%, most preferably at least 95%, and even most preferably at least 96%, at least 97%, at least 98%, or at least 99%, which have beta-glucosidase activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 28.

In one aspect, a polypeptide having beta-glucosidase activity comprises or consists of the amino acid sequence of SEQ ID NO: 28 or an allelic variant thereof; or a fragment thereof having beta-glucosidase activity. In another aspect, the polypeptide comprises or consists of the amino acid sequence of SEQ ID NO: 28. In another aspect, the polypeptide comprises or consists of the mature polypeptide of SEQ ID NO: 28. In another aspect, the polypeptide comprises or consists of amino acids 20 to 863 of SEQ ID NO: 28, or an allelic variant thereof; or a fragment thereof having beta-glucosidase activity. In another aspect, the polypeptide comprises or consists of amino acids 20 to 863 of SEQ ID NO: 28.

In another first aspect, the isolated polypeptides having beta-glucosidase activity comprise amino acid sequences having a degree of identity to the mature polypeptide of SEQ ID NO: 30 of preferably at least 80%, more preferably at least 85%, even more preferably at least 90%, most preferably at least 95%, and even most preferably at least 96%, at least 97%, at least 98%, or at least 99%, which have beta-glucosidase activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 30.

In one aspect, a polypeptide having beta-glucosidase activity comprises or consists of the amino acid sequence of SEQ ID NO: 30 or an allelic variant thereof; or a fragment thereof having beta-glucosidase activity. In another aspect, the polypeptide comprises or consists of the amino acid sequence of SEQ ID NO: 30. In another aspect, the polypeptide comprises or consists of the mature polypeptide of SEQ ID NO: 30. In another aspect, the polypeptide comprises or consists of amino acids 37 to 878 of SEQ ID NO: 30, or an allelic variant thereof; or a fragment thereof having beta-glucosidase activity. In another aspect, the polypeptide comprises or consists of amino acids 37 to 878 of SEQ ID NO: 30.

In another first aspect, the isolated polypeptides having beta-glucosidase activity comprise amino acid sequences having a degree of identity to the mature polypeptide of SEQ ID NO: 32 of preferably at least 80%, more preferably at least 85%, even more preferably at least 90%, most preferably at least 95%, and even most preferably at least 96%, at least 97%, at least 98%, or at least 99%, which have beta-glucosidase activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 32.

In one aspect, a polypeptide having beta-glucosidase activity comprises or consists of the amino acid sequence of SEQ ID NO: 32 or an allelic variant thereof; or a fragment thereof having beta-glucosidase activity. In another aspect, the polypeptide comprises or consists of the amino acid sequence of SEQ ID NO: 32. In another aspect, the polypeptide comprises or consists of the mature polypeptide of SEQ ID NO: 32. In another aspect, the polypeptide comprises or consists of amino acids 20 to 860 of SEQ ID NO: 32, or an allelic variant thereof; or a fragment thereof having beta-glucosidase activity. In another aspect, the polypeptide comprises or consists of amino acids 20 to 860 of SEQ ID NO: 32.

In another first aspect, the isolated polypeptides having beta-glucosidase activity comprise amino acid sequences having a degree of identity to the mature polypeptide of SEQ ID NO: 178 of preferably at least 80%, more preferably at least 85%, even more preferably at least 90%, most preferably at least 95%, and even most preferably at least 96%, at least 97%, at least 98%, or at least 99%, which have beta-glucosidase activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 178.

In one aspect, a polypeptide having beta-glucosidase activity comprises or consists of the amino acid sequence of SEQ ID NO: 178 or an allelic variant thereof; or a fragment thereof having beta-glucosidase activity. In another aspect, the polypeptide comprises or consists of the amino acid sequence of SEQ ID NO: 178. In another aspect, the polypeptide comprises or consists of the mature polypeptide of SEQ ID NO: 178. In another aspect, the polypeptide comprises or consists of amino acids 20 to 680 of SEQ ID NO: 178, or an allelic variant thereof; or a fragment thereof having beta-glucosidase activity. In another aspect, the polypeptide comprises or consists of amino acids 20 to 680 of SEQ ID NO: 178.

In another first aspect, the isolated polypeptides having beta-glucosidase activity comprise amino acid sequences having a degree of identity to the mature polypeptide of SEQ ID NO: 180 of preferably at least 80%, more preferably at least 85%, even more preferably at least 90%, most preferably at least 95%, and even most preferably at least 96%, at least 97%, at least 98%, or at least 99%, which have beta-glucosidase activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 180.

In one aspect, a polypeptide having beta-glucosidase activity comprises or consists of the amino acid sequence of SEQ ID NO: 180 or an allelic variant thereof; or a fragment thereof having beta-glucosidase activity. In another aspect, the polypeptide comprises or consists of the amino acid sequence of SEQ ID NO: 180. In another aspect, the polypeptide comprises or consists of the mature polypeptide of SEQ ID NO: 180. In another aspect, the polypeptide comprises or consists of amino acids 20 to 860 of SEQ ID NO: 180, or an allelic variant thereof; or a fragment thereof having beta-glucosidase activity. In another aspect, the polypeptide comprises or consists of amino acids 20 to 860 of SEQ ID NO: 180.

In another first aspect, the isolated polypeptides having beta-glucosidase activity comprise amino acid sequences having a degree of identity to the mature polypeptide of SEQ ID NO: 182 of preferably at least 80%, more preferably at least 85%, even more preferably at least 90%, most preferably at least 95%, and even most preferably at least 96%, at least 97%, at least 98%, or at least 99%, which have beta-glucosidase activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 182.

In one aspect, a polypeptide having beta-glucosidase activity comprises or consists of the amino acid sequence of SEQ ID NO: 182 or an allelic variant thereof; or a fragment thereof having beta-glucosidase activity. In another aspect, the polypeptide comprises or consists of the amino acid sequence of SEQ ID NO: 182. In another aspect, the polypeptide comprises or consists of the mature polypeptide of SEQ ID NO: 182. In another aspect, the polypeptide comprises or consists of amino acids 19 to 860 of SEQ ID NO: 182, or an allelic variant thereof; or a fragment thereof having beta-glucosidase activity. In another aspect, the polypeptide comprises or consists of amino acids 19 to 860 of SEQ ID NO: 182.

In another first aspect, the isolated polypeptides having beta-glucosidase activity comprise amino acid sequences having a degree of identity to the mature polypeptide of SEQ ID NO: 184 of preferably at least 80%, more preferably at least 85%, even more preferably at least 90%, most preferably at least 95%, and even most preferably at least 96%, at least 97%, at least 98%, or at least 99%, which have beta-glucosidase activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 184.

In one aspect, a polypeptide having beta-glucosidase activity comprises or consists of the amino acid sequence of SEQ ID NO: 184 or an allelic variant thereof; or a fragment thereof having beta-glucosidase activity. In another aspect, the polypeptide comprises or consists of the amino acid sequence of SEQ ID NO: 184. In another aspect, the polypeptide comprises or consists of the mature polypeptide of SEQ ID NO: 184. In another aspect, the polypeptide comprises or consists of amino acids 19 to 872 of SEQ ID NO: 184, or an allelic variant thereof; or a fragment thereof having beta-glucosidase activity. In another aspect, the polypeptide comprises or consists of amino acids 19 to 872 of SEQ ID NO: 184.

In another first aspect, the isolated polypeptides having beta-glucosidase activity comprise amino acid sequences having a degree of identity to the mature polypeptide of SEQ ID NO: 186 of preferably at least 80%, more preferably at least 85%, even more preferably at least 90%, most preferably at least 95%, and even most preferably at least 96%, at least 97%, at least 98%, or at least 99%, which have beta-glucosidase activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 186.

In one aspect, a polypeptide having beta-glucosidase activity comprises or consists of the amino acid sequence of SEQ ID NO: 186 or an allelic variant thereof; or a fragment thereof having beta-glucosidase activity. In another aspect, the polypeptide comprises or consists of the amino acid sequence of SEQ ID NO: 186. In another aspect, the polypeptide comprises or consists of the mature polypeptide of SEQ ID NO: 186. In another aspect, the polypeptide comprises or consists of amino acids 22 to 883 of SEQ ID NO: 186, or an allelic variant thereof; or a fragment thereof having beta-glucosidase activity. In another aspect, the polypeptide comprises or consists of amino acids 22 to 883 of SEQ ID NO: 186.

In another first aspect, the isolated polypeptides having beta-glucosidase activity comprise amino acid sequences having a degree of identity to the mature polypeptide of SEQ ID NO: 188 of preferably at least 80%, more preferably at least 85%, even more preferably at least 90%, most preferably at least 95%, and even most preferably at least 96%, at least 97%, at least 98%, or at least 99%, which have beta-glucosidase activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 188.

In one aspect, a polypeptide having beta-glucosidase activity comprises or consists of the amino acid sequence of SEQ ID NO: 188 or an allelic variant thereof; or a fragment thereof having beta-glucosidase activity. In another aspect, the polypeptide comprises or consists of the amino acid sequence of SEQ ID NO: 188. In another aspect, the polypeptide comprises or consists of the mature polypeptide of SEQ ID NO: 188. In another aspect, the polypeptide comprises or consists of amino acids 22 to 861 of SEQ ID NO: 188, or an allelic variant thereof; or a fragment thereof having beta-glucosidase activity. In another aspect, the polypeptide comprises or consists of amino acids 22 to 861 of SEQ ID NO: 188.

In another first aspect, the isolated polypeptides having beta-glucosidase activity comprise amino acid sequences having a degree of identity to the mature polypeptide of SEQ ID NO: 190 of preferably at least 80%, more preferably at least 85%, even more preferably at least 90%, most preferably at least 95%, and even most preferably at least 96%, at least 97%, at least 98%, or at least 99%, which have beta-glucosidase activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 190.

In one aspect, a polypeptide having beta-glucosidase activity comprises or consists of the amino acid sequence of SEQ ID NO: 190 or an allelic variant thereof; or a fragment thereof having beta-glucosidase activity. In another aspect, the polypeptide comprises or consists of the amino acid sequence of SEQ ID NO: 190. In another aspect, the polypeptide comprises or consists of the mature polypeptide of SEQ ID NO: 190. In another aspect, the polypeptide comprises or consists of amino acids 22 to 861 of SEQ ID NO: 190, or an allelic variant thereof; or a fragment thereof having beta-glucosidase activity. In another aspect, the polypeptide comprises or consists of amino acids 22 to 861 of SEQ ID NO: 190.

In another first aspect, the isolated GH61 polypeptides having cellulolytic enhancing activity comprise amino acid sequences having a degree of identity to the mature polypeptide of SEQ ID NO: 34 of preferably at least 80%, more preferably at least 85%, even more preferably at least 90%, most preferably at least 95%, and even most preferably at least 96%, at least 97%, at least 98%, or at least 99%, which have cellulolytic enhancing activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 34.

In one aspect, a polypeptide having cellulolytic enhancing activity comprises or consists of the amino acid sequence of SEQ ID NO: 34 or an allelic variant thereof; or a fragment thereof having cellulolytic enhancing activity. In another aspect, the polypeptide comprises or consists of the amino acid sequence of SEQ ID NO: 34. In another aspect, the polypeptide comprises or consists of the mature polypeptide of SEQ ID NO: 34. In another aspect, the polypeptide comprises or consists of amino acids 23 to 250 of SEQ ID NO: 34, or an allelic variant thereof; or a fragment thereof having cellulolytic enhancing activity. In another aspect, the polypeptide comprises or consists of amino acids 23 to 250 of SEQ ID NO: 34.

In another first aspect, the isolated GH61 polypeptides having cellulolytic enhancing activity comprise amino acid sequences having a degree of identity to the mature polypeptide of SEQ ID NO: 36 of preferably at least 80%, more preferably at least 85%, even more preferably at least 90%, most preferably at least 95%, and even most preferably at least 96%, at least 97%, at least 98%, or at least 99%, which have cellulolytic enhancing activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 36.

In one aspect, a polypeptide having cellulolytic enhancing activity comprises or consists of the amino acid sequence of SEQ ID NO: 36 or an allelic variant thereof; or a fragment thereof having cellulolytic enhancing activity. In another aspect, the polypeptide comprises or consists of the amino acid sequence of SEQ ID NO: 36. In another aspect, the polypeptide comprises or consists of the mature polypeptide of SEQ ID NO: 36. In another aspect, the polypeptide comprises or consists of amino acids 20 to 258 of SEQ ID NO: 36, or an allelic variant thereof; or a fragment thereof having cellulolytic enhancing activity. In another aspect, the polypeptide comprises or consists of amino acids 20 to 258 of SEQ ID NO: 36.

In another first aspect, the isolated GH61 polypeptides having cellulolytic enhancing activity comprise amino acid sequences having a degree of identity to the mature polypeptide of SEQ ID NO: 38 of preferably at least 80%, more preferably at least 85%, even more preferably at least 90%, most preferably at least 95%, and even most preferably at least 96%, at least 97%, at least 98%, or at least 99%, which have cellulolytic enhancing activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 38.

In one aspect, a polypeptide having cellulolytic enhancing activity comprises or consists of the amino acid sequence of SEQ ID NO: 38 or an allelic variant thereof; or a fragment thereof having cellulolytic enhancing activity. In another aspect, the polypeptide comprises or consists of the amino acid sequence of SEQ ID NO: 38. In another aspect, the polypeptide comprises or consists of the mature polypeptide of SEQ ID NO: 38. In another aspect, the polypeptide comprises or consists of amino acids 22 to 250 of SEQ ID NO: 38, or an allelic variant thereof; or a fragment thereof having cellulolytic enhancing activity. In another aspect, the polypeptide comprises or consists of amino acids 22 to 250 of SEQ ID NO: 38.

In another first aspect, the isolated GH61 polypeptides having cellulolytic enhancing activity comprise amino acid sequences having a degree of identity to the mature polypeptide of SEQ ID NO: 40 of preferably at least 80%, more preferably at least 85%, even more preferably at least 90%, most preferably at least 95%, and even most preferably at least 96%, at least 97%, at least 98%, or at least 99%, which have cellulolytic enhancing activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 40.

In one aspect, a polypeptide having cellulolytic enhancing activity comprises or consists of the amino acid sequence of SEQ ID NO: 40 or an allelic variant thereof; or a fragment thereof having cellulolytic enhancing activity. In another aspect, the polypeptide comprises or consists of the amino acid sequence of SEQ ID NO: 40. In another aspect, the polypeptide comprises or consists of the mature polypeptide of SEQ ID NO: 40. In another aspect, the polypeptide comprises or consists of amino acids 22 to 322 of SEQ ID NO: 40, or an allelic variant thereof; or a fragment thereof having cellulolytic enhancing activity. In another aspect, the polypeptide comprises or consists of amino acids 22 to 322 of SEQ ID NO: 40.

In another first aspect, the isolated GH61 polypeptides having cellulolytic enhancing activity comprise amino acid sequences having a degree of identity to the mature polypeptide of SEQ ID NO: 42 of preferably at least 80%, more preferably at least 85%, even more preferably at least 90%, most preferably at least 95%, and even most preferably at least 96%, at least 97%, at least 98%, or at least 99%, which have cellulolytic enhancing activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 42.

In one aspect, a polypeptide having cellulolytic enhancing activity comprises or consists of the amino acid sequence of SEQ ID NO: 42 or an allelic variant thereof; or a fragment thereof having cellulolytic enhancing activity. In another aspect, the polypeptide comprises or consists of the amino acid sequence of SEQ ID NO: 42. In another aspect, the polypeptide comprises or consists of the mature polypeptide of SEQ ID NO: 42. In another aspect, the polypeptide comprises or consists of amino acids 26 to 253 of SEQ ID NO: 42, or an allelic variant thereof; or a fragment thereof having cellulolytic enhancing activity. In another aspect, the polypeptide comprises or consists of amino acids 26 to 253 of SEQ ID NO: 42.

In another first aspect, the isolated GH61 polypeptides having cellulolytic enhancing activity comprise amino acid sequences having a degree of identity to the mature polypeptide of SEQ ID NO: 44 of preferably at least 80%, more preferably at least 85%, even more preferably at least 90%, most preferably at least 95%, and even most preferably at least 96%, at least 97%, at least 98%, or at least 99%, which have cellulolytic enhancing activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 44.

In one aspect, a polypeptide having cellulolytic enhancing activity comprises or consists of the amino acid sequence of SEQ ID NO: 44 or an allelic variant thereof; or a fragment thereof having cellulolytic enhancing activity. In another aspect, the polypeptide comprises or consists of the amino acid sequence of SEQ ID NO: 44. In another aspect, the polypeptide comprises or consists of the mature polypeptide of SEQ ID NO: 44. In another aspect, the polypeptide comprises or consists of amino acids 22 to 368 of SEQ ID NO: 44, or an allelic variant thereof; or a fragment thereof having cellulolytic enhancing activity. In another aspect, the polypeptide comprises or consists of amino acids 22 to 368 of SEQ ID NO: 44.

In another first aspect, the isolated GH61 polypeptides having cellulolytic enhancing activity comprise amino acid sequences having a degree of identity to the mature polypeptide of SEQ ID NO: 192 of preferably at least 80%, more preferably at least 85%, even more preferably at least 90%, most preferably at least 95%, and even most preferably at least 96%, at least 97%, at least 98%, or at least 99%, which have cellulolytic enhancing activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 192.

In one aspect, a polypeptide having cellulolytic enhancing activity comprises or consists of the amino acid sequence of SEQ ID NO: 192 or an allelic variant thereof; or a fragment thereof having cellulolytic enhancing activity. In another aspect, the polypeptide comprises or consists of the amino acid sequence of SEQ ID NO: 192. In another aspect, the polypeptide comprises or consists of the mature polypeptide of SEQ ID NO: 192. In another aspect, the polypeptide comprises or consists of amino acids 23 to 251 of SEQ ID NO: 186, or an allelic variant thereof; or a fragment thereof having cellulolytic enhancing activity. In another aspect, the polypeptide comprises or consists of amino acids 23 to 251 of SEQ ID NO: 186.

In another first aspect, the isolated GH10 polypeptides having xylanase activity comprise amino acid sequences having a degree of identity to the mature polypeptide of SEQ ID NO: 46, of at preferably at least 80%, more preferably at least 85%, even more preferably at least 90%, most preferably at least 95%, and even most preferably at least 96%, at least 97%, at least 98%, or at least 99%, which have xylanase activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 46.

In one aspect, a GH10 polypeptide having xylanase activity comprises or consists of the amino acid sequence of SEQ ID NO: 46 or an allelic variant thereof; or a fragment thereof that has xylanase activity. In another aspect, the polypeptide comprises or consists of the amino acid sequence of SEQ ID NO: 46. In another aspect, the polypeptide comprises or consists of the mature polypeptide of SEQ ID NO: 46. In another aspect, the polypeptide comprises or consists of amino acids 23 to 406 of SEQ ID NO: 46, or an allelic variant thereof; or a fragment thereof that has xylanase activity. In another aspect, the polypeptide comprises or consists of amino acids 23 to 406 of SEQ ID NO: 46.

In another first aspect, the isolated GH10 polypeptides having xylanase activity comprise amino acid sequences having a degree of identity to the mature polypeptide of SEQ ID NO: 48, of preferably at least 80%, more preferably at least 85%, even more preferably at least 90%, most preferably at least 95%, and even most preferably at least 96%, at least 97%, at least 98%, or at least 99%, which have xylanase activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 48.

In one aspect, a GH10 polypeptide having xylanase activity comprises or consists of the amino acid sequence of SEQ ID NO: 48 or an allelic variant thereof; or a fragment thereof that has xylanase activity. In another aspect, the polypeptide comprises or consists of the amino acid sequence of SEQ ID NO: 48. In another aspect, the polypeptide comprises or consists of the mature polypeptide of SEQ ID NO: 48. In another aspect, the polypeptide comprises or consists of amino acids 20 to 397 of SEQ ID NO: 48, or an allelic variant thereof; or a fragment thereof that has xylanase activity. In another aspect, the polypeptide comprises or consists of amino acids 20 to 397 of SEQ ID NO: 48.

In another first aspect, the isolated GH10 polypeptides having xylanase activity comprise amino acid sequences having a degree of identity to the mature polypeptide of SEQ ID NO: 50, of preferably at least 80%, more preferably at least 85%, even more preferably at least 90%, most preferably at least 95%, and even most preferably at least 96%, at least 97%, at least 98%, or at least 99%, which have xylanase activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 50.

In one aspect, a GH10 polypeptide having xylanase activity comprises or consists of the amino acid sequence of SEQ ID NO: 50 or an allelic variant thereof; or a fragment thereof that has xylanase activity. In another aspect, the polypeptide comprises or consists of the amino acid sequence of SEQ ID NO: 50. In another aspect, the polypeptide comprises or consists of the mature polypeptide of SEQ ID NO: 50. In another aspect, the polypeptide comprises or consists of amino acids 20 to 398 of SEQ ID NO: 50, or an allelic variant thereof; or a fragment thereof that has xylanase activity. In another aspect, the polypeptide comprises or consists of amino acids 20 to 398 of SEQ ID NO: 50.

In another first aspect, the isolated GH10 polypeptides having xylanase activity comprise amino acid sequences having a degree of identity to the mature polypeptide of SEQ ID NO: 52, of preferably at least 80%, more preferably at least 85%, even more preferably at least 90%, most preferably at least 95%, and even most preferably at least 96%, at least 97%, at least 98%, or at least 99%, which have xylanase activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 52.

In one aspect, a GH10 polypeptide having xylanase activity comprises or consists of the amino acid sequence of SEQ ID NO: 50 or an allelic variant thereof; or a fragment thereof that has xylanase activity. In another aspect, the polypeptide comprises or consists of the amino acid sequence of SEQ ID NO: 52. In another aspect, the polypeptide comprises or consists of the mature polypeptide of SEQ ID NO: 52. In another aspect, the polypeptide comprises or consists of amino acids 20 to 407 of SEQ ID NO: 52, or an allelic variant thereof; or a fragment thereof that has xylanase activity. In another aspect, the polypeptide comprises or consists of amino acids 20 to 407 of SEQ ID NO: 52.

In another first aspect, the isolated GH10 polypeptides having xylanase activity comprise amino acid sequences having a degree of identity to the mature polypeptide of SEQ ID NO: 54, of preferably at least 80%, more preferably at least 85%, even more preferably at least 90%, most preferably at least 95%, and even most preferably at least 96%, at least 97%, at least 98%, or at least 99%, which have xylanase activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 54.

In one aspect, a GH10 polypeptide having xylanase activity comprises or consists of the amino acid sequence of SEQ ID NO: 50 or an allelic variant thereof; or a fragment thereof that has xylanase activity. In another aspect, the polypeptide comprises or consists of the amino acid sequence of SEQ ID NO: 54. In another aspect, the polypeptide comprises or consists of the mature polypeptide of SEQ ID NO: 54. In another aspect, the polypeptide comprises or consists of amino acids 20 to 395 of SEQ ID NO: 54, or an allelic variant thereof; or a fragment thereof that has xylanase activity. In another aspect, the polypeptide comprises or consists of amino acids 20 to 395 of SEQ ID NO: 54.

In another first aspect, the isolated GH10 polypeptides having xylanase activity comprise amino acid sequences having a degree of identity to the mature polypeptide of SEQ ID NO: 194, of preferably at least 80%, more preferably at least 85%, even more preferably at least 90%, most preferably at least 95%, and even most preferably at least 96%, at least 97%, at least 98%, or at least 99%, which have xylanase activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 194.

A GH10 polypeptide having xylanase activity comprises or consists of the amino acid sequence of SEQ ID NO: 194 or an allelic variant thereof; or a fragment thereof that has xylanase activity. In another aspect, the polypeptide comprises or consists of the amino acid sequence of SEQ ID NO: 194. In another aspect, the polypeptide comprises or consists of the mature polypeptide of SEQ ID NO: 194. In another aspect, the polypeptide comprises or consists of amino acids 24 to 403 of SEQ ID NO: 194, or an allelic variant thereof; or a fragment thereof that has xylanase activity. In another aspect, the polypeptide comprises or consists of amino acids 24 to 403 of SEQ ID NO: 194.

In another first aspect, the isolated GH10 polypeptides having xylanase activity comprise amino acid sequences having a degree of identity to the mature polypeptide of SEQ ID NO: 196, of preferably at least 80%, more preferably at least 85%, even more preferably at least 90%, most preferably at least 95%, and even most preferably at least 96%, at least 97%, at least 98%, or at least 99%, which have xylanase activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 196.

A GH10 polypeptide having xylanase activity comprises or consists of the amino acid sequence of SEQ ID NO: 194 or an allelic variant thereof; or a fragment thereof that has xylanase activity. In another aspect, the polypeptide comprises or consists of the amino acid sequence of SEQ ID NO: 196. In another aspect, the polypeptide comprises or consists of the mature polypeptide of SEQ ID NO: 196. In another aspect, the polypeptide comprises or consists of amino acids 24 to 403 of SEQ ID NO: 196, or an allelic variant thereof; or a fragment thereof that has xylanase activity. In another aspect, the polypeptide comprises or consists of amino acids 24 to 403 of SEQ ID NO: 196.

In another first aspect, the isolated GH10 polypeptides having xylanase activity comprise amino acid sequences having a degree of identity to the mature polypeptide of SEQ ID NO: 198, of preferably at least 80%, more preferably at least 85%, even more preferably at least 90%, most preferably at least 95%, and even most preferably at least 96%, at least 97%, at least 98%, or at least 99%, which have xylanase activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 198.

A GH10 polypeptide having xylanase activity comprises or consists of the amino acid sequence of SEQ ID NO: 194 or an allelic variant thereof; or a fragment thereof that has xylanase activity. In another aspect, the polypeptide comprises or consists of the amino acid sequence of SEQ ID NO: 198. In another aspect, the polypeptide comprises or consists of the mature polypeptide of SEQ ID NO: 198. In another aspect, the polypeptide comprises or consists of amino acids 20 to 396 of SEQ ID NO: 198, or an allelic variant thereof; or a fragment thereof that has xylanase activity. In another aspect, the polypeptide comprises or consists of amino acids 20 to 396 of SEQ ID NO: 198.

In another first aspect, the isolated GH11 polypeptides having xylanase activity comprise amino acid sequences having a degree of identity to the mature polypeptide of SEQ ID NO: 56, of preferably at least 80%, more preferably at least 85%, even more preferably at least 90%, most preferably at least 95%, and even most preferably at least 96%, at least 97%, at least 98%, or at least 99%, which have xylanase activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 56.

In one aspect, a GH11 polypeptide having xylanase activity comprises or consists of the amino acid sequence of SEQ ID NO: 56 or an allelic variant thereof; or a fragment thereof that has xylanase activity. In another aspect, the polypeptide comprises or consists of the amino acid sequence of SEQ ID NO: 56. In another aspect, the polypeptide comprises or consists of the mature polypeptide of SEQ ID NO: 56. In another aspect, the polypeptide comprises or consists of amino acids 43 to 338 of SEQ ID NO: 56, or an allelic variant thereof; or a fragment thereof that has xylanase activity. In another aspect, the polypeptide comprises or consists of amino acids 43 to 338 of SEQ ID NO: 56. In another aspect, the polypeptide comprises or consists of amino acids 43 to 338 of SEQ ID NO: 56. In another aspect, the polypeptide consists of the amino acid sequence of SEQ ID NO: 56 or an allelic variant thereof; or a fragment thereof that has xylanase activity.

In another first aspect, the isolated GH11 polypeptides having xylanase activity comprise amino acid sequences having a degree of identity to the mature polypeptide of SEQ ID NO: 200 or SEQ ID NO: 305, of preferably at least 80%, more preferably at least 85%, even more preferably at least 90%, most preferably at least 95%, and even most preferably at least 96%, at least 97%, at least 98%, or at least 99%, which have xylanase activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 200 or SEQ ID NO: 305.

A GH11 polypeptide having xylanase activity comprises or consists of the amino acid sequence of SEQ ID NO: 200, or an allelic variant thereof; or a fragment thereof that has xylanase activity, or SEQ ID NO: 305 or a fragment thereof that has xylanase activity. In another aspect, the polypeptide comprises or consists of the amino acid sequence of SEQ ID NO: 200 or SEQ ID NO: 305. In another aspect, the polypeptide comprises or consists of the mature polypeptide of SEQ ID NO: 200 or SEQ ID NO: 305. In another aspect, the polypeptide comprises or consists of amino acids 25 to 360 of SEQ ID NO: 200, or an allelic variant thereof; or a fragment thereof that has xylanase activity, or amino acids 29 to 231 of SEQ ID NO: 305 or a fragment thereof that has xylanase activity. In another aspect, the polypeptide comprises or consists of amino acids 25 to 360 of SEQ ID NO: 200 or amino acids 29 to 231 of SEQ ID NO: 305. In another aspect, the polypeptide comprises or consists of amino acids 25 to 360 of SEQ ID NO: 200 or amino acids 29 to 231 of SEQ ID NO: 305.

In another first aspect, the isolated polypeptides having beta-xylosidase activity comprise amino acid sequences having a degree of identity to the mature polypeptide of SEQ ID NO: 58, of preferably at least 80%, more preferably at least 85%, even more preferably at least 90%, most preferably at least 95%, and even most preferably at least 96%, at least 97%, at least 98%, or at least 99%, which have beta-xylosidase activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 58.

In one aspect, a polypeptide having beta-xylosidase activity comprises or consists of the amino acid sequence of SEQ ID NO: 58 or an allelic variant thereof; or a fragment thereof that has beta-xylosidase activity. In another aspect, the polypeptide comprises or consists of the amino acid sequence of SEQ ID NO: 58. In another aspect, the polypeptide comprises or consists of the mature polypeptide of SEQ ID NO: 58. In another aspect, the polypeptide comprises or consists of amino acids 21 to 797 of SEQ ID NO: 58, or an allelic variant thereof; or a fragment thereof that has beta-xylosidase activity. In another aspect, the polypeptide comprises or consists of amino acids 21 to 797 of SEQ ID NO: 58.

In another first aspect, the isolated polypeptides having beta-xylosidase activity comprise amino acid sequences having a degree of identity to the mature polypeptide of SEQ ID NO: 60, of preferably at least 80%, more preferably at least 85%, even more preferably at least 90%, most preferably at least 95%, and even most preferably at least 96%, at least 97%, at least 98%, or at least 99%, which have beta-xylosidase activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 60.

In one aspect, a polypeptide having beta-xylosidase activity comprises or consists of the amino acid sequence of SEQ ID NO: 60 or an allelic variant thereof; or a fragment thereof that has beta-xylosidase activity. In another aspect, the polypeptide comprises or consists of the amino acid sequence of SEQ ID NO: 60. In another aspect, the polypeptide comprises or consists of the mature polypeptide of SEQ ID NO: 60. In another aspect, the polypeptide comprises or consists of amino acids 22 to 795 of SEQ ID NO: 60, or an allelic variant thereof; or a fragment thereof that has beta-xylosidase activity. In another aspect, the polypeptide comprises or consists of amino acids 22 to 795 of SEQ ID NO: 60.

In another first aspect, the isolated polypeptides having beta-xylosidase activity comprise amino acid sequences having a degree of identity to the mature polypeptide of SEQ ID NO: 202, of preferably at least 80%, more preferably at least 85%, even more preferably at least 90%, most preferably at least 95%, and even most preferably at least 96%, at least 97%, at least 98%, or at least 99%, which have beta-xylosidase activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 202.

In one aspect, a polypeptide having beta-xylosidase activity comprises or consists of the amino acid sequence of SEQ ID NO: 202 or an allelic variant thereof; or a fragment thereof that has beta-xylosidase activity. In another aspect, the polypeptide comprises or consists of the amino acid sequence of SEQ ID NO: 202. In another aspect, the polypeptide comprises or consists of the mature polypeptide of SEQ ID NO: 202. In another aspect, the polypeptide comprises or consists of amino acids 18 to 803 of SEQ ID NO: 202, or an allelic variant thereof; or a fragment thereof that has beta-xylosidase activity. In another aspect, the polypeptide comprises or consists of amino acids 18 to 803 of SEQ ID NO: 202.

In one aspect, a polypeptide having beta-xylosidase activity comprises or consists of the amino acid sequence of SEQ ID NO: 204 or an allelic variant thereof; or a fragment thereof that has beta-xylosidase activity. In another aspect, the polypeptide comprises or consists of the amino acid sequence of SEQ ID NO: 204. In another aspect, the polypeptide comprises or consists of the mature polypeptide of SEQ ID NO: 204. In another aspect, the polypeptide comprises or consists of amino acids 18 to 817 of SEQ ID NO: 204, or an allelic variant thereof; or a fragment thereof that has beta-xylosidase activity. In another aspect, the polypeptide comprises or consists of amino acids 18 to 817 of SEQ ID NO: 204.

In another first aspect, the isolated polypeptides having beta-xylosidase activity comprise amino acid sequences having a degree of identity to the mature polypeptide of SEQ ID NO: 206, of preferably at least 80%, more preferably at least 85%, even more preferably at least 90%, most preferably at least 95%, and even most preferably at least 96%, at least 97%, at least 98%, or at least 99%, which have beta-xylosidase activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 206.

In one aspect, a polypeptide having beta-xylosidase activity comprises or consists of the amino acid sequence of SEQ ID NO: 206 or an allelic variant thereof; or a fragment thereof that has beta-xylosidase activity. In another aspect, the polypeptide comprises or consists of the amino acid sequence of SEQ ID NO: 206. In another aspect, the polypeptide comprises or consists of the mature polypeptide of SEQ ID NO: 206. In another aspect, the polypeptide comprises or consists of amino acids 21 to 792 of SEQ ID NO: 206, or an allelic variant thereof; or a fragment thereof that has beta-xylosidase activity. In another aspect, the polypeptide comprises or consists of amino acids 21 to 792 of SEQ ID NO: 206.

In a second aspect, the isolated polypeptides having cellobiohydrolase I activity are encoded by polynucleotides that hybridize under preferably medium-high stringency conditions, more preferably high stringency conditions, and most preferably very high stringency conditions with (i) the mature polypeptide coding sequence of SEQ ID NO: 1, (ii) the genomic DNA sequence of the mature polypeptide coding sequence of SEQ ID NO: 1, or (iii) a full-length complementary strand of (i) or (ii) (J. Sambrook, E. F. Fritsch, and T. Maniatis, 1989, supra).

In another second aspect, the isolated polypeptides having cellobiohydrolase I activity are encoded by polynucleotides that hybridize under preferably medium-high stringency conditions, more preferably high stringency conditions, and most preferably very high stringency conditions with (i) the mature polypeptide coding sequence of SEQ ID NO: 3, (ii) the genomic DNA sequence of the mature polypeptide coding sequence of SEQ ID NO: 3, or (iii) a full-length complementary strand of (i) or (ii).

In another second aspect, the isolated polypeptides having cellobiohydrolase I activity are encoded by polynucleotides that hybridize under preferably medium-high stringency conditions, more preferably high stringency conditions, and most preferably very high stringency conditions with (i) the mature polypeptide coding sequence of SEQ ID NO: 5, (ii) the cDNA sequence of the mature polypeptide coding sequence of SEQ ID NO: 5, or (iii) a full-length complementary strand of (i) or (ii).

In another second aspect, the isolated polypeptides having cellobiohydrolase I activity are encoded by polynucleotides that hybridize under preferably medium-high stringency conditions, more preferably high stringency conditions, and most preferably very high stringency conditions with (i) the mature polypeptide coding sequence of SEQ ID NO: 7, (ii) the genomic DNA sequence of the mature polypeptide coding sequence of SEQ ID NO: 7, or (iii) a full-length complementary strand of (i) or (ii).

In another second aspect, the isolated polypeptides having cellobiohydrolase I activity are encoded by polynucleotides that hybridize under preferably medium-high stringency conditions, more preferably high stringency conditions, and most preferably very high stringency conditions with (i) the mature polypeptide coding sequence of SEQ ID NO: 157, (ii) the cDNA sequence of the mature polypeptide coding sequence of SEQ ID NO: 157, or (iii) a full-length complementary strand of (i) or (ii).

In another second aspect, the isolated polypeptides having cellobiohydrolase I activity are encoded by polynucleotides that hybridize under preferably medium-high stringency conditions, more preferably high stringency conditions, and most preferably very high stringency conditions with (i) the mature polypeptide coding sequence of SEQ ID NO: 159, (ii) the cDNA sequence of the mature polypeptide coding sequence of SEQ ID NO: 159, or (iii) a full-length complementary strand of (i) or (ii).

In another second aspect, the isolated polypeptides having cellobiohydrolase I activity are encoded by polynucleotides that hybridize under preferably medium-high stringency conditions, more preferably high stringency conditions, and most preferably very high stringency conditions with (i) the mature polypeptide coding sequence of SEQ ID NO: 161, (ii) the cDNA sequence of the mature polypeptide coding sequence of SEQ ID NO: 161, or (iii) a full-length complementary strand of (i) or (ii).

In another second aspect, the isolated polypeptides having cellobiohydrolase I activity are encoded by polynucleotides that hybridize under preferably medium-high stringency conditions, more preferably high stringency conditions, and most preferably very high stringency conditions with (i) the mature polypeptide coding sequence of SEQ ID NO: 163, (ii) the cDNA sequence of the mature polypeptide coding sequence of SEQ ID NO: 163, or (iii) a full-length complementary strand of (i) or (ii).

In another second aspect, the isolated polypeptides having cellobiohydrolase I activity are encoded by polynucleotides that hybridize under preferably medium-high stringency conditions, more preferably high stringency conditions, and most preferably very high stringency conditions with (i) the mature polypeptide coding sequence of SEQ ID NO: 165, (ii) the cDNA sequence of the mature polypeptide coding sequence of SEQ ID NO: 165, or (iii) a full-length complementary strand of (i) or (ii).

In another second aspect, the isolated polypeptides having cellobiohydrolase II activity are encoded by polynucleotides that hybridize under preferably medium-high stringency conditions, more preferably high stringency conditions, and most preferably very high stringency conditions with (i) the mature polypeptide coding sequence of SEQ ID NO: 9, (ii) the cDNA sequence of the mature polypeptide coding sequence of SEQ ID NO: 9, or (iii) a full-length complementary strand of (i) or (ii).

In another second aspect, the isolated polypeptides having cellobiohydrolase II activity are encoded by polynucleotides that hybridize under preferably medium-high stringency conditions, more preferably high stringency conditions, and most preferably very high stringency conditions with (i) the mature polypeptide coding sequence of SEQ ID NO: 11, (ii) the cDNA sequence of the mature polypeptide coding sequence of SEQ ID NO: 11, or (iii) a full-length complementary strand of (i) or (ii).

In another second aspect, the isolated polypeptides having cellobiohydrolase II activity are encoded by polynucleotides that hybridize under preferably medium-high stringency conditions, more preferably high stringency conditions, and most preferably very high stringency conditions with (i) the mature polypeptide coding sequence of SEQ ID NO: 13, (ii) the genomic DNA sequence of the mature polypeptide coding sequence of SEQ ID NO: 13, or (iii) a full-length complementary strand of (i) or (ii).

In another second aspect, the isolated polypeptides having cellobiohydrolase II activity are encoded by polynucleotides that hybridize under preferably medium-high stringency conditions, more preferably high stringency conditions, and most preferably very high stringency conditions with (i) the mature polypeptide coding sequence of SEQ ID NO: 15, (ii) the genomic DNA sequence of the mature polypeptide coding sequence of SEQ ID NO: 15, or (iii) a full-length complementary strand of (i) or (ii).

In another second aspect, the isolated polypeptides having cellobiohydrolase II activity are encoded by polynucleotides that hybridize under preferably medium-high stringency conditions, more preferably high stringency conditions, and most preferably very high stringency conditions with (i) the mature polypeptide coding sequence of SEQ ID NO: 17, (ii) the cDNA sequence of the mature polypeptide coding sequence of SEQ ID NO: 17, or (iii) a full-length complementary strand of (i) or (ii).

In another second aspect, the isolated polypeptides having cellobiohydrolase II activity are encoded by polynucleotides that hybridize under preferably medium-high stringency conditions, more preferably high stringency conditions, and most preferably very high stringency conditions with (i) the mature polypeptide coding sequence of SEQ ID NO: 167, (ii) the cDNA sequence of the mature polypeptide coding sequence of SEQ ID NO: 167, or (iii) a full-length complementary strand of (i) or (ii).

In another second aspect, the isolated polypeptides having cellobiohydrolase II activity are encoded by polynucleotides that hybridize under preferably medium-high stringency conditions, more preferably high stringency conditions, and most preferably very high stringency conditions with (i) the mature polypeptide coding sequence of SEQ ID NO: 169, (ii) the cDNA sequence of the mature polypeptide coding sequence of SEQ ID NO: 169, or (iii) a full-length complementary strand of (i) or (ii).

In another second aspect, the isolated polypeptides having cellobiohydrolase II activity are encoded by polynucleotides that hybridize under preferably medium-high stringency conditions, more preferably high stringency conditions, and most preferably very high stringency conditions with (i) the mature polypeptide coding sequence of SEQ ID NO: 171, (ii) the cDNA sequence of the mature polypeptide coding sequence of SEQ ID NO: 171, or (iii) a full-length complementary strand of (i) or (ii).

In another second aspect, the isolated polypeptides having endoglucanase I activity are encoded by polynucleotides that hybridize under preferably medium-high stringency conditions, more preferably high stringency conditions, and most preferably very high stringency conditions with (i) the mature polypeptide coding sequence of SEQ ID NO: 19, (ii) the cDNA sequence of the mature polypeptide coding sequence of SEQ ID NO: 19, or (iii) a full-length complementary strand of (i) or (ii).

In another second aspect, the isolated polypeptides having endoglucanase II activity are encoded by polynucleotides that hybridize under preferably medium-high stringency conditions, more preferably high stringency conditions, and most preferably very high stringency conditions with (i) the mature polypeptide coding sequence of SEQ ID NO: 21, (ii) the genomic DNA sequence of the mature polypeptide coding sequence of SEQ ID NO: 21, or (iii) a full-length complementary strand of (i) or (ii).

In another second aspect, the isolated polypeptides having endoglucanase II activity are encoded by polynucleotides that hybridize under preferably medium-high stringency conditions, more preferably high stringency conditions, and most preferably very high stringency conditions with (i) the mature polypeptide coding sequence of SEQ ID NO: 23, (ii) the cDNA sequence of the mature polypeptide coding sequence of SEQ ID NO: 23, or (iii) a full-length complementary strand of (i) or (ii).

In another second aspect, the isolated polypeptides having endoglucanase II activity are encoded by polynucleotides that hybridize under preferably medium-high stringency conditions, more preferably high stringency conditions, and most preferably very high stringency conditions with (i) the mature polypeptide coding sequence of SEQ ID NO: 25, (ii) the genomic DNA sequence of the mature polypeptide coding sequence of SEQ ID NO: 25, or (iii) a full-length complementary strand of (i) or (ii).

In another second aspect, the isolated polypeptides having endoglucanase II activity are encoded by polynucleotides that hybridize under preferably medium-high stringency conditions, more preferably high stringency conditions, and most preferably very high stringency conditions with (i) the mature polypeptide coding sequence of SEQ ID NO: 173, (ii) the cDNA sequence of the mature polypeptide coding sequence of SEQ ID NO: 173, or (iii) a full-length complementary strand of (i) or (ii).

In another second aspect, the isolated polypeptides having endoglucanase II activity are encoded by polynucleotides that hybridize under preferably medium-high stringency conditions, more preferably high stringency conditions, and most preferably very high stringency conditions with (i) the mature polypeptide coding sequence of SEQ ID NO: 175, (ii) the cDNA sequence of the mature polypeptide coding sequence of SEQ ID NO: 175, or (iii) a full-length complementary strand of (i) or (ii).

In another second aspect, the isolated polypeptides having beta-glucosidase activity are encoded by polynucleotides that hybridize under preferably medium-high stringency conditions, more preferably high stringency conditions, and most preferably very high stringency conditions with (i) the mature polypeptide coding sequence of SEQ ID NO: 27, (ii) the cDNA sequence of the mature polypeptide coding sequence of SEQ ID NO: 27, or (iii) a full-length complementary strand of (i) or (ii).

In another second aspect, the isolated polypeptides having beta-glucosidase activity are encoded by polynucleotides that hybridize under preferably medium-high stringency conditions, more preferably high stringency conditions, and most preferably very high stringency conditions with (i) the mature polypeptide coding sequence of SEQ ID NO: 29, (ii) the cDNA sequence of the mature polypeptide coding sequence of SEQ ID NO: 29, or (iii) a full-length complementary strand of (i) or (ii).

In another second aspect, the isolated polypeptides having beta-glucosidase activity are encoded by polynucleotides that hybridize under preferably medium-high stringency conditions, more preferably high stringency conditions, and most preferably very high stringency conditions with (i) the mature polypeptide coding sequence of SEQ ID NO: 31, (ii) the cDNA sequence of the mature polypeptide coding sequence of SEQ ID NO: 31, or (iii) a full-length complementary strand of (i) or (ii).

In another second aspect, the isolated polypeptides having beta-glucosidase activity are encoded by polynucleotides that hybridize under preferably medium-high stringency conditions, more preferably high stringency conditions, and most preferably very high stringency conditions with (i) the mature polypeptide coding sequence of SEQ ID NO: 177, (ii) the cDNA sequence of the mature polypeptide coding sequence of SEQ ID NO: 177, or (iii) a full-length complementary strand of (i) or (ii).

In another second aspect, the isolated polypeptides having beta-glucosidase activity are encoded by polynucleotides that hybridize under preferably medium-high stringency conditions, more preferably high stringency conditions, and most preferably very high stringency conditions with (i) the mature polypeptide coding sequence of SEQ ID NO: 179, (ii) the cDNA sequence of the mature polypeptide coding sequence of SEQ ID NO: 179, or (iii) a full-length complementary strand of (i) or (ii).

In another second aspect, the isolated polypeptides having beta-glucosidase activity are encoded by polynucleotides that hybridize under preferably medium-high stringency conditions, more preferably high stringency conditions, and most preferably very high stringency conditions with (i) the mature polypeptide coding sequence of SEQ ID NO: 181, (ii) the cDNA sequence of the mature polypeptide coding sequence of SEQ ID NO: 181, or (iii) a full-length complementary strand of (i) or (ii).

In another second aspect, the isolated polypeptides having beta-glucosidase activity are encoded by polynucleotides that hybridize under preferably medium-high stringency conditions, more preferably high stringency conditions, and most preferably very high stringency conditions with (i) the mature polypeptide coding sequence of SEQ ID NO: 183, (ii) the cDNA sequence of the mature polypeptide coding sequence of SEQ ID NO: 183, or (iii) a full-length complementary strand of (i) or (ii).

In another second aspect, the isolated polypeptides having beta-glucosidase activity are encoded by polynucleotides that hybridize under preferably medium-high stringency conditions, more preferably high stringency conditions, and most preferably very high stringency conditions with (i) the mature polypeptide coding sequence of SEQ ID NO: 185, (ii) the cDNA sequence of the mature polypeptide coding sequence of SEQ ID NO: 185, or (iii) a full-length complementary strand of (i) or (ii).

In another second aspect, the isolated polypeptides having beta-glucosidase activity are encoded by polynucleotides that hybridize under preferably medium-high stringency conditions, more preferably high stringency conditions, and most preferably very high stringency conditions with (i) the mature polypeptide coding sequence of SEQ ID NO: 187, (ii) the cDNA sequence of the mature polypeptide coding sequence of SEQ ID NO: 187, or (iii) a full-length complementary strand of (i) or (ii).

In another second aspect, the isolated polypeptides having beta-glucosidase activity are encoded by polynucleotides that hybridize under preferably medium-high stringency conditions, more preferably high stringency conditions, and most preferably very high stringency conditions with (i) the mature polypeptide coding sequence of SEQ ID NO: 189, (ii) the cDNA sequence of the mature polypeptide coding sequence of SEQ ID NO: 189, or (iii) a full-length complementary strand of (i) or (ii).

In another second aspect, the isolated GH61 polypeptides having cellulolytic enhancing activity are encoded by polynucleotides that hybridize under preferably medium-high stringency conditions, more preferably high stringency conditions, and most preferably very high stringency conditions with (i) the mature polypeptide coding sequence of SEQ ID NO: 33, (ii) the cDNA sequence of the mature polypeptide coding sequence of SEQ ID NO: 33, or (iii) a full-length complementary strand of (i) or (ii).

In another second aspect, the isolated GH61 polypeptides having cellulolytic enhancing activity are encoded by polynucleotides that hybridize under preferably medium-high stringency conditions, more preferably high stringency conditions, and most preferably very high stringency conditions with (i) the mature polypeptide coding sequence of SEQ ID NO: 35, (ii) the genomic DNA sequence of the mature polypeptide coding sequence of SEQ ID NO: 35, or (iii) a full-length complementary strand of (i) or (ii).

In another second aspect, the isolated GH61 polypeptides having cellulolytic enhancing activity are encoded by polynucleotides that hybridize under preferably medium-high stringency conditions, more preferably high stringency conditions, and most preferably very high stringency conditions with (i) the mature polypeptide coding sequence of SEQ ID NO: 37, (ii) the cDNA sequence of the mature polypeptide coding sequence of SEQ ID NO: 37, or (iii) a full-length complementary strand of (i) or (ii).

In another second aspect, the isolated GH61 polypeptides having cellulolytic enhancing activity are encoded by polynucleotides that hybridize under preferably medium-high stringency conditions, more preferably high stringency conditions, and most preferably very high stringency conditions with (i) the mature polypeptide coding sequence of SEQ ID NO: 39, (ii) the cDNA sequence of the mature polypeptide coding sequence of SEQ ID NO: 39, or (iii) a full-length complementary strand of (i) or (ii).

In another second aspect, the isolated GH61 polypeptides having cellulolytic enhancing activity are encoded by polynucleotides that hybridize under preferably medium-high stringency conditions, more preferably high stringency conditions, and most preferably very high stringency conditions with (i) the mature polypeptide coding sequence of SEQ ID NO: 41, (ii) the cDNA sequence of the mature polypeptide coding sequence of SEQ ID NO: 41, or (iii) a full-length complementary strand of (i) or (ii).

In another second aspect, the isolated GH61 polypeptides having cellulolytic enhancing activity are encoded by polynucleotides that hybridize under preferably medium-high stringency conditions, more preferably high stringency conditions, and most preferably very high stringency conditions with (i) the mature polypeptide coding sequence of SEQ ID NO: 43, (ii) the cDNA sequence of the mature polypeptide coding sequence of SEQ ID NO: 43, or (iii) a full-length complementary strand of (i) or (ii).

In another second aspect, the isolated GH10 polypeptides having xylanase activity is encoded by polynucleotides that hybridize under preferably medium stringency conditions, more preferably medium-high stringency conditions, even more preferably high stringency conditions, and most preferably very high stringency conditions with (i) the mature polypeptide coding sequence of SEQ ID NO: 191, (ii) the cDNA sequence of the mature polypeptide coding sequence of SEQ ID NO: 191, or (iii) a full-length complementary strand of (i) or (ii).

In another second aspect, the isolated GH10 polypeptides having xylanase activity are encoded by polynucleotides that hybridize under preferably medium-high stringency conditions, more preferably high stringency conditions, and most preferably very high stringency conditions with (i) the mature polypeptide coding sequence of SEQ ID NO: 45, (ii) the genomic DNA sequence of the mature polypeptide coding sequence of SEQ ID NO: 45, or (iii) a full-length complementary strand of (i) or (ii).

In another second aspect, the isolated GH10 polypeptides having xylanase activity are encoded by polynucleotides that hybridize under preferably medium-high stringency conditions, more preferably high stringency conditions, and most preferably very high stringency conditions with (i) the mature polypeptide coding sequence of SEQ ID NO: 47, (ii) the cDNA sequence of the mature polypeptide coding sequence of SEQ ID NO: 47, or (iii) a full-length complementary strand of (i) or (ii).

In another second aspect, the isolated GH10 polypeptides having xylanase activity is encoded by polynucleotides that hybridize under preferably medium stringency conditions, more preferably medium-high stringency conditions, even more preferably high stringency conditions, and most preferably very high stringency conditions with (i) the mature polypeptide coding sequence of SEQ ID NO: 49, (ii) the genomic DNA sequence of the mature polypeptide coding sequence of SEQ ID NO: 49, or (iii) a full-length complementary strand of (i) or (ii).

In another second aspect, the isolated GH10 polypeptides having xylanase activity is encoded by polynucleotides that hybridize under preferably medium stringency conditions, more preferably medium-high stringency conditions, even more preferably high stringency conditions, and most preferably very high stringency conditions with (i) the mature polypeptide coding sequence of SEQ ID NO: 51, (ii) the cDNA sequence of the mature polypeptide coding sequence of SEQ ID NO: 51, or (iii) a full-length complementary strand of (i) or (ii).

In another second aspect, the isolated GH10 polypeptides having xylanase activity is encoded by polynucleotides that hybridize under preferably medium stringency conditions, more preferably medium-high stringency conditions, even more preferably high stringency conditions, and most preferably very high stringency conditions with (i) the mature polypeptide coding sequence of SEQ ID NO: 53, (ii) the genomic DNA sequence of the mature polypeptide coding sequence of SEQ ID NO: 53, or (iii) a full-length complementary strand of (i) or (ii).

In another second aspect, the isolated GH10 polypeptides having xylanase activity is encoded by polynucleotides that hybridize under preferably medium stringency conditions, more preferably medium-high stringency conditions, even more preferably high stringency conditions, and most preferably very high stringency conditions with (i) the mature polypeptide coding sequence of SEQ ID NO: 193, (ii) the cDNA sequence of the mature polypeptide coding sequence of SEQ ID NO: 193, or (iii) a full-length complementary strand of (i) or (ii).

In another second aspect, the isolated GH10 polypeptides having xylanase activity is encoded by polynucleotides that hybridize under preferably medium stringency conditions, more preferably medium-high stringency conditions, even more preferably high stringency conditions, and most preferably very high stringency conditions with (i) the mature polypeptide coding sequence of SEQ ID NO: 195, (ii) the cDNA sequence of the mature polypeptide coding sequence of SEQ ID NO: 195, or (iii) a full-length complementary strand of (i) or (ii).

In another second aspect, the isolated GH10 polypeptides having xylanase activity is encoded by polynucleotides that hybridize under preferably medium stringency conditions, more preferably medium-high stringency conditions, even more preferably high stringency conditions, and most preferably very high stringency conditions with (i) the mature polypeptide coding sequence of SEQ ID NO: 197, (ii) the genomic DNA sequence of the mature polypeptide coding sequence of SEQ ID NO: 197, or (iii) a full-length complementary strand of (i) or (ii).

In another second aspect, the isolated GH11 polypeptides having xylanase activity is encoded by polynucleotides that hybridize under preferably medium stringency conditions, more preferably medium-high stringency conditions, even more preferably high stringency conditions, and most preferably very high stringency conditions with the mature polypeptide coding sequence of SEQ ID NO: 55 or its full-length complementary strand.

In another second aspect, the isolated GH11 polypeptides having xylanase activity is encoded by polynucleotides that hybridize under preferably medium stringency conditions, more preferably medium-high stringency conditions, even more preferably high stringency conditions, and most preferably very high stringency conditions with the mature polypeptide coding sequence of SEQ ID NO: 199 or SEQ ID NO: 304; or its full-length complementary strand.

In another second aspect, the isolated polypeptides having beta-xylosidase activity is encoded by polynucleotides that hybridize under preferably medium stringency conditions, more preferably medium-high stringency conditions, even more preferably high stringency conditions, and most preferably very high stringency conditions with (i) the mature polypeptide coding sequence of SEQ ID NO: 57, (ii) the genomic DNA sequence of the mature polypeptide coding sequence of SEQ ID NO: 57, or (iii) a full-length complementary strand of (i) or (ii).

In another second aspect, the isolated polypeptides having beta-xylosidase activity is encoded by polynucleotides that hybridize under preferably medium stringency conditions, more preferably medium-high stringency conditions, even more preferably high stringency conditions, and most preferably very high stringency conditions with (i) the mature polypeptide coding sequence of SEQ ID NO: 59, (ii) the cDNA sequence of the mature polypeptide coding sequence of SEQ ID NO: 59, or (iii) a full-length complementary strand of (i) or (ii).

In another second aspect, the isolated polypeptides having beta-xylosidase activity is encoded by polynucleotides that hybridize under preferably medium stringency conditions, more preferably medium-high stringency conditions, even more preferably high stringency conditions, and most preferably very high stringency conditions with (i) the mature polypeptide coding sequence of SEQ ID NO: 201, (ii) the cDNA sequence of the mature polypeptide coding sequence of SEQ ID NO: 201, or (iii) a full-length complementary strand of (i) or (ii).

In another second aspect, the isolated polypeptides having beta-xylosidase activity is encoded by polynucleotides that hybridize under preferably medium stringency conditions, more preferably medium-high stringency conditions, even more preferably high stringency conditions, and most preferably very high stringency conditions with (i) the mature polypeptide coding sequence of SEQ ID NO: 203, (ii) the cDNA sequence of the mature polypeptide coding sequence of SEQ ID NO: 203, or (iii) a full-length complementary strand of (i) or (ii).

In another second aspect, the isolated polypeptides having beta-xylosidase activity is encoded by polynucleotides that hybridize under preferably medium stringency conditions, more preferably medium-high stringency conditions, even more preferably high stringency conditions, and most preferably very high stringency conditions with (i) the mature polypeptide coding sequence of SEQ ID NO: 205, (ii) the cDNA sequence of the mature polypeptide coding sequence of SEQ ID NO: 205, or (iii) a full-length complementary strand of (i) or (ii).

The nucleotide sequence of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 157, 159, 161, 163, 165, 167, 169, 171, 173, 175, 177, 179, 181, 183, 185, 187, 189, 919, 193, 195, 197, 199, 201, 203, or 205; or a subsequence thereof; as well as the amino acid sequence of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 158, 160, 162, 164, 166, 168, 170, 172, 174, 176, 178, 180, 182, 184, 186, 188, 190, 192, 194, 196, 198, 200, 202, 204, or 206; or a fragment thereof; may be used to design nucleic acid probes to identify and clone DNA encoding polypeptides having enzyme activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, preferably at least 25, more preferably at least 35, and most preferably at least 70 nucleotides in length. It is, however, preferred that the nucleic acid probe is at least 100 nucleotides in length. For example, the nucleic acid probe may be at least 200 nucleotides, preferably at least 300 nucleotides, more preferably at least 400 nucleotides, or most preferably at least 500 nucleotides in length. Even longer probes may be used, e.g., nucleic acid probes that are preferably at least 600 nucleotides, more preferably at least 700 nucleotides, even more preferably at least 800 nucleotides, or most preferably at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may, therefore, be screened for DNA that hybridizes with the probes described above and encodes a polypeptide having enzyme or biological activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that is homologous with SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 157, 159, 161, 163, 165, 167, 169, 171, 173, 175, 177, 179, 181, 183, 185, 187, 189, 919, 193, 195, 197, 199, 201, 203, or 205 or a subsequence thereof, the carrier material is preferably used in a Southern blot.

For purposes of the present invention, hybridization indicates that the nucleotide sequence hybridizes to a labeled nucleic acid probe corresponding to the mature polypeptide coding sequence of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 157, 159, 161, 163, 165, 167, 169, 171, 173, 175, 177, 179, 181, 183, 185, 187, 189, 919, 193, 195, 197, 199, 201, 203, or 205; the cDNA sequence of or the genomic DNA sequence of the mature polypeptide coding sequence of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 157, 159, 161, 163, 165, 167, 169, 171, 173, 175, 177, 179, 181, 183, 185, 187, 189, 919, 193, 195, 197, 199, 201, 203, or 205; its full-length complementary strand; or a subsequence thereof; under very low to very high stringency conditions. Molecules to which the nucleic acid probe hybridizes under these conditions can be detected using, for example, X-ray film.

In one aspect, the nucleic acid probe is the mature polypeptide coding sequence of SEQ ID NO: 1. In another aspect, the nucleic acid probe is nucleotides 55 to 1590 of SEQ ID NO: 1. In another aspect, the nucleic acid probe is a polynucleotide sequence that encodes the polypeptide of SEQ ID NO: 2, or a subsequence thereof. In another aspect, the nucleic acid probe is SEQ ID NO: 1. In another aspect, the nucleic acid probe is the polynucleotide sequence contained in *Chaetomium thermophilum* CGMCC 0581, wherein the polynucleotide sequence thereof encodes a polypeptide having cellobiohydrolase I activity. In another aspect, the nucleic acid probe is the mature polypeptide coding region contained in *Chaetomium thermophilum* CGMCC 0581.

In another aspect, the nucleic acid probe is the mature polypeptide coding sequence of SEQ ID NO: 3. In another aspect, the nucleic acid probe is nucleotides 61 to 1350 of SEQ ID NO: 3. In another aspect, the nucleic acid probe is a polynucleotide sequence that encodes the polypeptide of SEQ ID NO: 4, or a subsequence thereof. In another aspect, the nucleic acid probe is SEQ ID NO: 3. In another aspect, the nucleic acid probe is the polynucleotide sequence contained in *Myceliophthora thermophila* CBS 117.65, wherein the polynucleotide sequence thereof encodes a polypeptide having cellobiohydrolase I activity. In another aspect, the nucleic acid probe is the mature polypeptide coding region contained in *Myceliophthora thermophila* CBS 117.65.

In another aspect, the nucleic acid probe is the mature polypeptide coding sequence of SEQ ID NO: 5. In another aspect, the nucleic acid probe is nucleotides 79 to 1596 of SEQ ID NO: 5. In another aspect, the nucleic acid probe is a polynucleotide sequence that encodes the polypeptide of SEQ ID NO: 6, or a subsequence thereof. In another aspect, the nucleic acid probe is SEQ ID NO: 5. In another aspect, the nucleic acid probe is the polynucleotide sequence contained in *Aspergillus fumigatus* NN055679, wherein the polynucleotide sequence thereof encodes a polypeptide having cellobiohydrolase I activity. In another aspect, the nucleic acid probe is the mature polypeptide coding region contained in *Aspergillus fumigatus* NN055679.

In another aspect, the nucleic acid probe is the mature polypeptide coding sequence of SEQ ID NO: 7. In another aspect, the nucleic acid probe is nucleotides 52 to 1374 of SEQ ID NO: 7. In another aspect, the nucleic acid probe is a polynucleotide sequence that encodes the polypeptide of SEQ ID NO: 8, or a subsequence thereof. In another aspect, the nucleic acid probe is SEQ ID NO: 7. In another aspect, the nucleic acid probe is the polynucleotide sequence contained in *Thermoascus aurantiacus* CGMCC 0583, wherein the polynucleotide sequence thereof encodes a polypeptide having cellobiohydrolase I activity. In another aspect, the nucleic acid probe is the mature polypeptide coding region contained in *Thermoascus aurantiacus* CGMCC 0583.

In another aspect, the nucleic acid probe is the mature polypeptide coding sequence of SEQ ID NO: 157. In another aspect, the nucleic acid probe is nucleotides 55 to 1428 of SEQ ID NO: 157. In another aspect, the nucleic acid probe is a polynucleotide sequence that encodes the polypeptide of SEQ ID NO: 158, or a subsequence thereof. In another aspect, the nucleic acid probe is SEQ ID NO: 157. In another aspect, the nucleic acid probe is the polynucleotide sequence contained in *Penicillium emersonii* NN051602, wherein the polynucleotide sequence thereof encodes a polypeptide having cellobiohydrolase I activity. In another aspect, the nucleic acid probe is the mature polypeptide coding region contained in *Penicillium emersonii* NN051602.

In another aspect, the nucleic acid probe is the mature polypeptide coding sequence of SEQ ID NO: 159. In another aspect, the nucleic acid probe is nucleotides 76 to 1590 of SEQ ID NO: 159. In another aspect, the nucleic acid probe is a polynucleotide sequence that encodes the polypeptide of SEQ ID NO: 160, or a subsequence thereof. In another aspect, the nucleic acid probe is SEQ ID NO: 159. In another aspect, the nucleic acid probe is the polynucleotide sequence contained in *Penicillium pinophilum* NN046877, wherein the polynucleotide sequence thereof encodes a polypeptide having cellobiohydrolase I activity. In another aspect, the nucleic acid probe is the mature polypeptide coding region contained in *Penicillium pinophilum* NN046877.

In another aspect, the nucleic acid probe is the mature polypeptide coding sequence of SEQ ID NO: 161. In another aspect, the nucleic acid probe is nucleotides 52 to 1374 of SEQ ID NO: 161. In another aspect, the nucleic acid probe is a polynucleotide sequence that encodes the polypeptide of SEQ ID NO: 162, or a subsequence thereof. In another aspect, the nucleic acid probe is SEQ ID NO: 161. In another aspect, the nucleic acid probe is the polynucleotide sequence contained in *Aspergillus terreus* ATCC 28865, wherein the polynucleotide sequence thereof encodes a polypeptide having cellobiohydrolase I activity. In another aspect, the nucleic acid probe is the mature polypeptide coding region contained in *Aspergillus terreus* ATCC 28865.

In another aspect, the nucleic acid probe is the mature polypeptide coding sequence of SEQ ID NO: 163. In another aspect, the nucleic acid probe is nucleotides 79 to 1605 of SEQ ID NO: 163. In another aspect, the nucleic acid probe is a polynucleotide sequence that encodes the polypeptide of SEQ ID NO: 164, or a subsequence thereof. In another aspect, the nucleic acid probe is SEQ ID NO: 162. In another aspect, the nucleic acid probe is the polynucleotide sequence contained in *Neosartorya fischeri* NRRL 181, wherein the polynucleotide sequence thereof encodes a polypeptide having cellobiohydrolase I activity. In another aspect, the nucleic acid probe is the mature polypeptide coding region contained in *Neosartorya fischeri* NRRL 181.

In another aspect, the nucleic acid probe is the mature polypeptide coding sequence of SEQ ID NO: 165. In another aspect, the nucleic acid probe is nucleotides 52 to 1374 of SEQ ID NO: 165. In another aspect, the nucleic acid probe is a polynucleotide sequence that encodes the polypeptide of SEQ ID NO: 166, or a subsequence thereof. In another aspect, the nucleic acid probe is SEQ ID NO: 165. In another aspect, the nucleic acid probe is the polynucleotide sequence contained in *Aspergillus nidulans* FGSCA4, wherein the polynucleotide sequence thereof encodes a polypeptide having cellobiohydrolase I activity. In another aspect, the nucleic acid probe is the mature polypeptide coding region contained in *Aspergillus nidulans* FGSCA4.

In another aspect, the nucleic acid probe is the mature polypeptide coding sequence of SEQ ID NO: 9. In another aspect, the nucleic acid probe is nucleotides 52 to 1799 of SEQ ID NO: 9. In another aspect, the nucleic acid probe is a polynucleotide sequence that encodes the polypeptide of SEQ ID NO: 10, or a subsequence thereof. In another aspect, the nucleic acid probe is SEQ ID NO: 9. In another aspect, the nucleic acid probe is the polynucleotide sequence contained in *Myceliophthora thermophila* CBS 117.65, wherein the polynucleotide sequence thereof encodes a polypeptide having cellobiohydrolase II activity. In another aspect, the nucleic acid probe is the mature polypeptide coding region contained in *Myceliophthora thermophila* CBS 117.65.

In another aspect, the nucleic acid probe is the mature polypeptide coding sequence of SEQ ID NO: 11. In another aspect, the nucleic acid probe is nucleotides 52 to 1809 of SEQ ID NO: 11. In another aspect, the nucleic acid probe is a polynucleotide sequence that encodes the polypeptide of SEQ ID NO: 12, or a subsequence thereof. In another aspect, the nucleic acid probe is SEQ ID NO: 11. In another aspect, the nucleic acid probe is the polynucleotide sequence contained in plasmid pSMai182 which is contained in *E. coli* NRRL B-50059 or contained in *Myceliophthora thermophila* CBS 202.73, wherein the polynucleotide sequence thereof encodes a polypeptide having cellobiohydrolase II activity. In another aspect, the nucleic acid probe is the mature polypeptide coding region contained in plasmid pSMai182 which is contained in *E. coli* NRRL B-50059 or contained in *Myceliophthora thermophila* CBS 202.73.

In another aspect, the nucleic acid probe is the mature polypeptide coding sequence of SEQ ID NO: 13. In another aspect, the nucleic acid probe is nucleotides 52 to 1443 of SEQ ID NO: 13. In another aspect, the nucleic acid probe is a polynucleotide sequence that encodes the polypeptide of SEQ ID NO: 14, or a subsequence thereof. In another aspect, the nucleic acid probe is SEQ ID NO: 13. In another aspect, the nucleic acid probe is the polynucleotide sequence contained in plasmid pTter6A which is contained in *E. coli* NRRL B-30802, wherein the polynucleotide sequence thereof encodes a polypeptide having cellobiohydrolase II activity. In another aspect, the nucleic acid probe is the mature polypeptide coding region contained in plasmid pTter6A which is contained in *E. coli* NRRL B-30802.

In another aspect, the nucleic acid probe is the mature polypeptide coding sequence of SEQ ID NO: 15. In another aspect, the nucleic acid probe is nucleotides 109 to 1401 of SEQ ID NO: 15. In another aspect, the nucleic acid probe is a polynucleotide sequence that encodes the polypeptide of SEQ ID NO: 16, or a subsequence thereof. In another aspect, the nucleic acid probe is SEQ ID NO: 15. In another aspect, the nucleic acid probe is the polynucleotide sequence contained in plasmid pMStr199 which is contained in *E. coli* DSM 23379, wherein the polynucleotide sequence thereof encodes a polypeptide having cellobiohydrolase II activity. In another aspect, the nucleic acid probe is the mature polypeptide coding region contained in plasmid pMStr199 which is contained in *E. coli* DSM 23379.

In another aspect, the nucleic acid probe is the mature polypeptide coding sequence of SEQ ID NO: 17. In another aspect, the nucleic acid probe is nucleotides 58 to 1700 of SEQ ID NO: 17. In another aspect, the nucleic acid probe is a polynucleotide sequence that encodes the polypeptide of SEQ ID NO: 18, or a subsequence thereof. In another aspect, the nucleic acid probe is SEQ ID NO: 17. In another aspect, the nucleic acid probe is the polynucleotide sequence contained in *Aspergillus fumigatus* NN055679, wherein the polynucleotide sequence thereof encodes a polypeptide having cellobiohydrolase II activity. In another aspect, the nucleic acid probe is the mature polypeptide coding region contained in *Aspergillus fumigatus NN*055679.

In another aspect, the nucleic acid probe is the mature polypeptide coding sequence of SEQ ID NO: 167. In another aspect, the nucleic acid probe is nucleotides 55 to 1749 of SEQ ID NO: 167. In another aspect, the nucleic acid probe is a polynucleotide sequence that encodes the polypeptide of SEQ ID NO: 168, or a subsequence thereof. In another aspect, the nucleic acid probe is SEQ ID NO: 167. In another aspect, the nucleic acid probe is the polynucleotide sequence contained in *Fennellia nivea* NN046949 or in pGEM-T-CBHII46949-2 which is contained in *E. coli* DSM 24143, wherein the polynucleotide sequence thereof encodes a polypeptide having cellobiohydrolase II activity. In another aspect, the nucleic acid probe is the mature polypeptide coding region contained in *Fennellia nivea* NN046949 or in pGEM-T-CBHII46949-2 which is contained in *E. coli* DSM 24143.

In another aspect, the nucleic acid probe is the mature polypeptide coding sequence of SEQ ID NO: 169. In another aspect, the nucleic acid probe is nucleotides 58 to 1744 of SEQ ID NO: 169. In another aspect, the nucleic acid probe is a polynucleotide sequence that encodes the polypeptide of SEQ ID NO: 170, or a subsequence thereof. In another aspect, the nucleic acid probe is SEQ ID NO: 169. In another aspect, the nucleic acid probe is the polynucleotide sequence contained in *Penicillium emersonii* NN051602, wherein the polynucleotide sequence thereof encodes a polypeptide having cellobiohydrolase II activity. In another aspect, the nucleic acid probe is the mature polypeptide coding region contained in *Penicillium emersonii* NN051602.

In another aspect, the nucleic acid probe is the mature polypeptide coding sequence of SEQ ID NO: 171. In another aspect, the nucleic acid probe is nucleotides 58 to 1701 of SEQ ID NO: 171. In another aspect, the nucleic acid probe is a polynucleotide sequence that encodes the polypeptide of SEQ ID NO: 172, or a subsequence thereof. In another aspect, the nucleic acid probe is SEQ ID NO: 171. In another aspect, the nucleic acid probe is the polynucleotide sequence contained in *Penicillium pinophilum* NN046877, wherein the polynucleotide sequence thereof encodes a polypeptide having cellobiohydrolase II activity. In another aspect, the nucleic acid probe is the mature polypeptide coding region contained in *Penicillium pinophilum* NN046877.

In another aspect, the nucleic acid probe is the mature polypeptide coding sequence of SEQ ID NO: 19. In another aspect, the nucleic acid probe is nucleotides 64 to 1502 of SEQ ID NO: 19. In another aspect, the nucleic acid probe is a polynucleotide sequence that encodes the polypeptide of SEQ ID NO: 20, or a subsequence thereof. In another aspect, the nucleic acid probe is SEQ ID NO: 19. In another aspect, the nucleic acid probe is the polynucleotide sequence contained in *Aspergillus terreus* ATCC 28865, wherein the polynucleotide sequence thereof encodes a polypeptide having endoglucanase I activity. In another aspect, the nucleic acid probe is the mature polypeptide coding region contained in *Aspergillus terreus* ATCC 28865.

In another aspect, the nucleic acid probe is the mature polypeptide coding sequence of SEQ ID NO: 21. In another aspect, the nucleic acid probe is nucleotides 64 to 1254 of SEQ ID NO: 21. In another aspect, the nucleic acid probe is a polynucleotide sequence that encodes the polypeptide of SEQ ID NO: 22, or a subsequence thereof. In another aspect, the nucleic acid probe is SEQ ID NO: 21. In another aspect, the nucleic acid probe is the polynucleotide sequence contained in *Trichoderma reesei* RutC30, wherein the polynucleotide sequence thereof encodes a polypeptide having endoglucanase II activity. In another aspect, the nucleic acid probe is the mature polypeptide coding region contained in *Trichoderma reesei* RutC30.

In another aspect, the nucleic acid probe is the mature polypeptide coding sequence of SEQ ID NO: 23. In another aspect, the nucleic acid probe is nucleotides 67 to 1185 of SEQ ID NO: 23. In another aspect, the nucleic acid probe is a polynucleotide sequence that encodes the polypeptide of SEQ ID NO: 24, or a subsequence thereof. In another aspect, the nucleic acid probe is SEQ ID NO: 23. In another aspect, the nucleic acid probe is the polynucleotide sequence contained in plasmid pCIC161 which is contained in *E. coli* NRRL B-30902, wherein the polynucleotide sequence thereof encodes a polypeptide having endoglucanase II activity. In another aspect, the nucleic acid probe is the mature polypeptide coding region contained in plasmid pCIC161 which is contained in *E. coli* NRRL B-30902.

In another aspect, the nucleic acid probe is the mature polypeptide coding sequence of SEQ ID NO: 25. In another aspect, the nucleic acid probe is nucleotides 91 to 1005 of SEQ ID NO: 25. In another aspect, the nucleic acid probe is a polynucleotide sequence that encodes the polypeptide of SEQ ID NO: 26, or a subsequence thereof. In another aspect, the nucleic acid probe is SEQ ID NO: 25. In another aspect, the nucleic acid probe is the polynucleotide sequence contained in *Thermoascus aurantiacus* CGMCC 0670, wherein the polynucleotide sequence thereof encodes a polypeptide having endoglucanase II activity. In another aspect, the nucleic acid probe is the mature polypeptide coding region contained in *Thermoascus aurantiacus* CGMCC 0670.

In another aspect, the nucleic acid probe is the mature polypeptide coding sequence of SEQ ID NO: 173. In another aspect, the nucleic acid probe is nucleotides 55 to 1260 of SEQ ID NO: 173. In another aspect, the nucleic acid probe is a polynucleotide sequence that encodes the polypeptide of SEQ ID NO: 174, or a subsequence thereof. In another aspect, the nucleic acid probe is SEQ ID NO: 173. In another aspect, the nucleic acid probe is the polynucleotide sequence contained in *Aspergillus fumigatus* NN051616, wherein the polynucleotide sequence thereof encodes a polypeptide having endoglucanase II activity. In another aspect, the nucleic acid probe is the mature polypeptide coding region contained in *Aspergillus fumigatus* NN051616.

In another aspect, the nucleic acid probe is the mature polypeptide coding sequence of SEQ ID NO: 175. In another aspect, the nucleic acid probe is nucleotides 49 to 1378 of SEQ ID NO: 175. In another aspect, the nucleic acid probe is a polynucleotide sequence that encodes the polypeptide of SEQ ID NO: 176, or a subsequence thereof. In another aspect, the nucleic acid probe is SEQ ID NO: 175. In another aspect, the nucleic acid probe is the polynucleotide sequence contained in *Neosartorya fischeri* NRRL 181, wherein the polynucleotide sequence thereof encodes a polypeptide having endoglucanase II activity. In another aspect, the nucleic acid probe is the mature polypeptide coding region contained in *Neosartorya fischeri* NRRL 181.

In another aspect, the nucleic acid probe is the mature polypeptide coding sequence of SEQ ID NO: 27. In another aspect, the nucleic acid probe is nucleotides 58 to 2580 of SEQ ID NO: 27. In another aspect, the nucleic acid probe is a polynucleotide sequence that encodes the polypeptide of SEQ ID NO: 28, or a subsequence thereof. In another aspect, the nucleic acid probe is SEQ ID NO: 27. In another aspect, the nucleic acid probe is the polynucleotide sequence contained in plasmid pEJG113 which is contained in *E. coli* NRRL B-30695, wherein the polynucleotide sequence thereof encodes a polypeptide having beta-glucosidase activity. In another aspect, the nucleic acid probe is the mature polypeptide coding region contained in plasmid pEJG113 which is contained in *E. coli* NRRL B-30695.

In another aspect, the nucleic acid probe is the mature polypeptide coding sequence of SEQ ID NO: 29. In another aspect, the nucleic acid probe is nucleotides 171 to 2753 of SEQ ID NO: 29. In another aspect, the nucleic acid probe is a polynucleotide sequence that encodes the polypeptide of SEQ ID NO: 30, or a subsequence thereof. In another aspect, the nucleic acid probe is SEQ ID NO: 29. In another aspect, the nucleic acid probe is the polynucleotide sequence contained in plasmid pKKAB which is contained in *E. coli* NRRL B-30860, wherein the polynucleotide sequence thereof encodes a polypeptide having beta-glucosidase activity. In another aspect, the nucleic acid probe is the mature polypeptide coding region contained in plasmid pKKAB which is contained in *E. coli* NRRL B-30860.

In another aspect, the nucleic acid probe is the mature polypeptide coding sequence of SEQ ID NO: 31. In another aspect, the nucleic acid probe is nucleotides 58 to 2934 of SEQ ID NO: 31. In another aspect, the nucleic acid probe is a polynucleotide sequence that encodes the polypeptide of SEQ ID NO: 32, or a subsequence thereof. In another aspect, the nucleic acid probe is SEQ ID NO: 31. In another aspect, the nucleic acid probe is the polynucleotide sequence contained in *Aspergillus niger* IBT 10140, wherein the polynucleotide sequence thereof encodes a polypeptide having beta-glucosidase activity. In another aspect, the nucleic acid probe is the mature polypeptide coding region contained in *Aspergillus niger* IBT 10140.

In another aspect, the nucleic acid probe is the mature polypeptide coding sequence of SEQ ID NO: 177. In another aspect, the nucleic acid probe is nucleotides 58 to 2937 of SEQ ID NO: 177. In another aspect, the nucleic acid probe is a polynucleotide sequence that encodes the polypeptide of SEQ ID NO: 178, or a subsequence thereof. In another aspect, the nucleic acid probe is SEQ ID NO: 177. In another aspect, the nucleic acid probe is the polynucleotide sequence contained in *Aspergillus aculeatus* WDCM190, which encodes a polypeptide having beta-glucosidase activity. In another aspect, the nucleic acid probe is the mature polypeptide coding region contained in *Aspergillus aculeatus* WDCM190.

In another aspect, the nucleic acid probe is the mature polypeptide coding sequence of SEQ ID NO: 179. In another aspect, the nucleic acid probe is nucleotides 58 to 2932 of SEQ ID NO: 179. In another aspect, the nucleic acid probe is a polynucleotide sequence that encodes the polypeptide of SEQ ID NO: 180, or a subsequence thereof. In another aspect, the nucleic acid probe is SEQ ID NO: 179. In another aspect, the nucleic acid probe is the polynucleotide sequence contained in *Aspergillus kawashii* IFO4308, which encodes a polypeptide having beta-glucosidase activity. In another aspect, the nucleic acid probe is the mature polypeptide coding region contained in *Aspergillus kawashii* IFO4308.

In another aspect, the nucleic acid probe is the mature polypeptide coding sequence of SEQ ID NO: 181. In another aspect, the nucleic acid probe is nucleotides 55 to 3059 of SEQ ID NO: 181. In another aspect, the nucleic acid probe is a polynucleotide sequence that encodes the polypeptide of SEQ ID NO: 182, or a subsequence thereof. In another aspect, the nucleic acid probe is SEQ ID NO: 181. In another aspect, the nucleic acid probe is the polynucleotide sequence contained in *Aspergillus clavatus* NRRL 1, which encodes a polypeptide having beta-glucosidase activity. In another aspect, the nucleic acid probe is the mature polypeptide coding region contained in *Aspergillus clavatus* NRRL 1.

In another aspect, the nucleic acid probe is the mature polypeptide coding sequence of SEQ ID NO: 183. In another aspect, the nucleic acid probe is nucleotides 55 to 3029 of SEQ ID NO: 183. In another aspect, the nucleic acid probe is a polynucleotide sequence that encodes the polypeptide of SEQ ID NO: 184, or a subsequence thereof. In another aspect, the nucleic acid probe is SEQ ID NO: 183. In another aspect, the nucleic acid probe is the polynucleotide sequence contained in *Thielavia terrestris* NRRL 8126, which encodes a polypeptide having beta-glucosidase activity. In another aspect, the nucleic acid probe is the mature polypeptide coding region contained in *Thielavia terrestris* NRRL 8126.

In another aspect, the nucleic acid probe is the mature polypeptide coding sequence of SEQ ID NO: 185. In another aspect, the nucleic acid probe is nucleotides 64 to 2790 of SEQ ID NO: 185. In another aspect, the nucleic acid probe is a polynucleotide sequence that encodes the polypeptide of SEQ ID NO: 186, or a subsequence thereof. In another aspect, the nucleic acid probe is SEQ ID NO: 185. In another aspect, the nucleic acid probe is the polynucleotide sequence contained in pUC19 D55EX which is contained in *E. coli* NRRL B-50395, wherein the polynucleotide sequence thereof encodes a polypeptide having beta-glucosidase activity. In another aspect, the nucleic acid probe is the mature polypeptide coding region contained in in pUC19 D55EX which is contained in *E. coli* NRRL B-50395.

In another aspect, the nucleic acid probe is the mature polypeptide coding sequence of SEQ ID NO: 187. In another aspect, the nucleic acid probe is nucleotides 64 to 2790 of SEQ ID NO: 187. In another aspect, the nucleic acid probe is a polynucleotide sequence that encodes the polypeptide of SEQ ID NO: 188, or a subsequence thereof. In another aspect, the nucleic acid probe is SEQ ID NO: 187. In another aspect, the nucleic acid probe is the polynucleotide sequence contained in *Penicillium oxalicum* IBT5387, wherein the polynucleotide sequence thereof encodes a polypeptide having beta-glucosidase activity. In another aspect, the nucleic acid probe is the mature polypeptide coding region contained in *Penicillium oxalicum* IBT5387.

In another aspect, the nucleic acid probe is the mature polypeptide coding sequence of SEQ ID NO: 189. In another aspect, the nucleic acid probe is nucleotides 58 to 2961 of SEQ ID NO: 189. In another aspect, the nucleic acid probe is a polynucleotide sequence that encodes the polypeptide of SEQ ID NO: 190, or a subsequence thereof. In another aspect, the nucleic acid probe is SEQ ID NO: 189. In another aspect, the nucleic acid probe is the polynucleotide sequence contained in *Talaromyces emersonii* CBS 549.92, wherein the polynucleotide sequence thereof encodes a polypeptide having beta-glucosidase activity. In another aspect, the nucleic acid probe is the mature polypeptide coding region contained in *Talaromyces emersonii* CBS 549.92.

In another aspect, the nucleic acid probe is the mature polypeptide coding sequence of SEQ ID NO: 33. In another aspect, the nucleic acid probe is nucleotides 67 to 796 of SEQ ID NO: 33. In another aspect, the nucleic acid probe is a polynucleotide sequence that encodes the polypeptide of SEQ ID NO: 34, or a subsequence thereof. In another aspect, the nucleic acid probe is SEQ ID NO: 33. In another aspect, the nucleic acid probe is the polynucleotide sequence contained in plasmid pDZA2-7 which is contained in *E. coli* NRRL B-30704, wherein the polynucleotide sequence thereof encodes a polypeptide having cellulolytic enhancing activity. In another aspect, the nucleic acid probe is the mature polypeptide coding region contained in plasmid pDZA2-7 which is contained in *E. coli* NRRL B-30704.

In another aspect, the nucleic acid probe is the mature polypeptide coding sequence of SEQ ID NO: 35. In another aspect, the nucleic acid probe is nucleotides 58 to 900 of SEQ ID NO: 35. In another aspect, the nucleic acid probe is a polynucleotide sequence that encodes the polypeptide of SEQ ID NO: 36, or a subsequence thereof. In another aspect, the nucleic acid probe is SEQ ID NO: 35. In another aspect, the nucleic acid probe is the polynucleotide sequence contained in plasmid pTter61E which is contained in *E. coli* NRRL B-30814, wherein the polynucleotide sequence thereof encodes a polypeptide having cellulolytic enhancing activity. In another aspect, the nucleic acid probe is the mature polypeptide coding region contained in plasmid pTter61E which is contained in *E. coli* NRRL B-30814.

In another aspect, the nucleic acid probe is the mature polypeptide coding sequence of SEQ ID NO: 37. In another aspect, the nucleic acid probe is nucleotides 64 to 859 of SEQ ID NO: 37. In another aspect, the nucleic acid probe is a polynucleotide sequence that encodes the polypeptide of SEQ ID NO: 38, or a subsequence thereof. In another aspect, the nucleic acid probe is SEQ ID NO: 37. In another aspect, the nucleic acid probe is the polynucleotide sequence contained in *Aspergillus fumigatus* NN051616, wherein the polynucleotide sequence thereof encodes a polypeptide having cellulolytic enhancing activity. In another aspect, the nucleic acid probe is the mature polypeptide coding region contained in *Aspergillus fumigatus* NN051616.

In another aspect, the nucleic acid probe is the mature polypeptide coding sequence of SEQ ID NO: 39. In another aspect, the nucleic acid probe is nucleotides 64 to 1018 of SEQ ID NO: 39. In another aspect, the nucleic acid probe is a polynucleotide sequence that encodes the polypeptide of SEQ ID NO: 40, or a subsequence thereof. In another aspect, the nucleic acid probe is SEQ ID NO: 39. In another aspect, the nucleic acid probe is the polynucleotide sequence contained in *Penicillim pinophilum* NN046877, wherein the polynucleotide sequence thereof encodes a polypeptide having cellulolytic enhancing activity. In another aspect, the nucleic acid probe is the mature polypeptide coding region contained in plasmid pGEM-T-Ppin7 which is contained in *E. coli* DSM 22711.

In another aspect, the nucleic acid probe is the mature polypeptide coding sequence of SEQ ID NO: 41. In another aspect, the nucleic acid probe is nucleotides 76 to 832 of SEQ ID NO: 41. In another aspect, the nucleic acid probe is a polynucleotide sequence that encodes the polypeptide of SEQ ID NO: 42, or a subsequence thereof. In another aspect, the nucleic acid probe is SEQ ID NO: 41. In another aspect, the nucleic acid probe is the polynucleotide sequence contained in plasmid pGEM-T-GH61D23Y4 which is contained in *E. coli* DSM 22882, wherein the polynucleotide sequence thereof encodes a polypeptide having cellulolytic enhancing activity. In another aspect, the nucleic acid probe is the mature polypeptide coding region contained in plasmid pGEM-T-GH61D23Y4 which is contained in *E. coli* DSM 22882.

In another aspect, the nucleic acid probe is the mature polypeptide coding sequence of SEQ ID NO: 43. In another aspect, the nucleic acid probe is nucleotides 64 to 1104 of SEQ ID NO: 43. In another aspect, the nucleic acid probe is a polynucleotide sequence that encodes the polypeptide of SEQ ID NO: 44, or a subsequence thereof. In another aspect, the nucleic acid probe is SEQ ID NO: 43. In another aspect, the nucleic acid probe is the polynucleotide sequence contained in plasmid pAG68 which is contained in *E. coli* NRRL B-50320, wherein the polynucleotide sequence thereof encodes a polypeptide having cellulolytic enhancing activity. In another aspect, the nucleic acid probe is the mature polypeptide coding region contained in plasmid pAG68 which is contained in *E. coli* NRRL B-50320.

In another aspect, the nucleic acid probe is the mature polypeptide coding sequence of SEQ ID NO: 191. In another aspect, the nucleic acid probe is nucleotides 64 to 1104 of SEQ ID NO: 191. In another aspect, the nucleic acid probe is a polynucleotide sequence that encodes the polypeptide of SEQ ID NO: 192, or a subsequence thereof. In another aspect, the nucleic acid probe is SEQ ID NO: 191. In another aspect, the nucleic acid probe is the polynucleotide sequence contained in plasmid pGEM-T-GH61a51486 which is contained in *E. coli* DSM 22656, wherein the polynucleotide sequence thereof encodes a polypeptide having cellulolytic enhancing activity. In another aspect, the nucleic acid probe is the mature polypeptide coding region contained in plasmid pGEM-T-GH61a51486 which is contained in *E. coli* DSM 22656.

In another aspect, the nucleic acid probe is the mature polypeptide coding sequence of SEQ ID NO: 45. In another aspect, the nucleic acid probe is nucleotides 69 to 1314 of SEQ ID NO: 45. In another aspect, the nucleic acid probe is a polynucleotide sequence that encodes the polypeptide of SEQ ID NO: 46, or a subsequence thereof. In another aspect, the nucleic acid probe is SEQ ID NO: 45. In another aspect, the nucleic acid probe is the polynucleotide sequence contained in *Aspergillus aculeatus* CBS 101.43, wherein the polynucleotide sequence thereof encodes a polypeptide having xylanase activity. In another aspect, the nucleic acid probe is the mature polypeptide coding region contained in *Aspergillus aculeatus* CBS 101,43.

In another aspect, the nucleic acid probe is the mature polypeptide coding sequence of SEQ ID NO: 47. In another aspect, the nucleic acid probe is nucleotides 107 to 1415 of SEQ ID NO: 47. In another aspect, the nucleic acid probe is a polynucleotide sequence that encodes the polypeptide of SEQ ID NO: 48, or a subsequence thereof. In another aspect, the nucleic acid probe is SEQ ID NO: 47. In another aspect, the nucleic acid probe is the polynucleotide sequence contained in plasmid pHyGe001 which is contained in *E. coli* NRRL B-30703, wherein the polynucleotide sequence thereof encodes a polypeptide having xylanase activity. In another aspect, the nucleic acid probe is the mature polypeptide coding region contained in plasmid pHyGe001 which is contained in *E. coli* NRRL B-30703.

In another aspect, the nucleic acid probe is the mature polypeptide coding sequence of SEQ ID NO: 49. In another aspect, the nucleic acid probe is nucleotides 58 to 1194 of SEQ ID NO: 49. In another aspect, the nucleic acid probe is a polynucleotide sequence that encodes the polypeptide of SEQ ID NO: 50, or a subsequence thereof. In another aspect, the nucleic acid probe is SEQ ID NO: 49. In another aspect, the nucleic acid probe is the polynucleotide sequence contained in plasmid pTF12Xy1170 which is contained in *E. coli* NRRL B-50309, wherein the polynucleotide sequence thereof encodes a polypeptide having xylanase activity. In another aspect, the nucleic acid probe is the mature polypeptide coding region contained in plasmid pTF12Xy1170 which is contained in *E. coli* NRRL B-50309.

In another aspect, the nucleic acid probe is the mature polypeptide coding sequence of SEQ ID NO: 51. In another aspect, the nucleic acid probe is nucleotides 58 to 1439 of SEQ ID NO: 51. In another aspect, the nucleic acid probe is a polynucleotide sequence that encodes the polypeptide of SEQ ID NO: 52, or a subsequence thereof. In another aspect, the nucleic acid probe is SEQ ID NO: 51. In another aspect, the nucleic acid probe is the polynucleotide sequence contained in plasmid pGEM-T-Ppin3 which is contained in *E. coli* DSM 22922, wherein the polynucleotide sequence thereof encodes a polypeptide having xylanase activity. In another aspect, the nucleic acid probe is the mature polypeptide coding region contained in plasmid pGEM-T-Ppin3 which is contained in *E. coli* DSM 22922.

In another aspect, the nucleic acid probe is the mature polypeptide coding sequence of SEQ ID NO: 53. In another aspect, the nucleic acid probe is nucleotides 58 to 1185 of SEQ ID NO: 53. In another aspect, the nucleic acid probe is a polynucleotide sequence that encodes the polypeptide of SEQ ID NO: 54, or a subsequence thereof. In another aspect, the nucleic acid probe is SEQ ID NO: 53. In another aspect, the nucleic acid probe is the polynucleotide sequence contained in *Thielavia terrestris* NRRL 8126, wherein the polynucleotide sequence thereof encodes a polypeptide having xylanase activity. In another aspect, the nucleic acid probe is the mature polypeptide coding region contained in *Thielavia terrestris* NRRL 8126.

In another aspect, the nucleic acid probe is the mature polypeptide coding sequence of SEQ ID NO: 193. In another aspect, the nucleic acid probe is nucleotides 70 to 1383 of SEQ ID NO: 193. In another aspect, the nucleic acid probe is a polynucleotide sequence that encodes the polypeptide of SEQ ID NO: 194, or a subsequence thereof. In another aspect, the nucleic acid probe is SEQ ID NO: 193. In another aspect, the nucleic acid probe is the polynucleotide sequence contained in *Talaromyces emersonii* NN050022, wherein the polynucleotide sequence thereof encodes a polypeptide having xylanase activity. In another aspect, the nucleic acid probe is the mature polypeptide coding region contained in *Talaromyces emersonii* NN050022.

In another aspect, the nucleic acid probe is the mature polypeptide coding sequence of SEQ ID NO: 195. In another aspect, the nucleic acid probe is nucleotides 70 to 1384 of SEQ ID NO: 195. In another aspect, the nucleic acid probe is a polynucleotide sequence that encodes the polypeptide of SEQ ID NO: 196, or a subsequence thereof. In another aspect, the nucleic acid probe is SEQ ID NO: 195. In another aspect, the nucleic acid probe is the polynucleotide sequence contained in pMMar26 which is contained in *E. coli* NRRL B-50266, wherein the polynucleotide sequence thereof encodes a polypeptide having xylanase activity. In another aspect, the nucleic acid probe is the mature polypeptide coding region contained in pMMar26 which is contained in *E. coli* NRRL B-50266.

In another aspect, the nucleic acid probe is the mature polypeptide coding sequence of SEQ ID NO: 197. In another aspect, the nucleic acid probe is nucleotides 58 to 1188 of SEQ ID NO: 197. In another aspect, the nucleic acid probe is a polynucleotide sequence that encodes the polypeptide of SEQ ID NO: 198, or a subsequence thereof. In another aspect, the nucleic acid probe is SEQ ID NO: 197. In another aspect, the nucleic acid probe is the polynucleotide sequence contained in *E. coli* DSM 10361, wherein the polynucleotide sequence thereof encodes a polypeptide having xylanase activity. In another aspect, the nucleic acid probe is the mature polypeptide coding region contained in *E. coli* DSM 10361.

In another aspect, the nucleic acid probe is the mature polypeptide coding sequence of SEQ ID NO: 55. In another aspect, the nucleic acid probe is nucleotides 127 to 1014 of SEQ ID NO: 55. In another aspect, the nucleic acid probe is a polynucleotide sequence that encodes the polypeptide of SEQ ID NO: 56, or a subsequence thereof. In another aspect, the nucleic acid probe is SEQ ID NO: 55. In another aspect, the nucleic acid probe is the polynucleotide sequence contained in *Thermobifida fusca* DSM 22883, wherein the polynucleotide sequence thereof encodes a polypeptide having xylanase activity. In another aspect, the nucleic acid probe is the mature polypeptide coding region contained in *Thermobifida fusca* DSM 22883.

In another aspect, the nucleic acid probe is the mature polypeptide coding sequence of SEQ ID NO: 55. In another aspect, the nucleic acid probe is nucleotides 85 to 693 of SEQ ID NO: 55. In another aspect, the nucleic acid probe is a polynucleotide sequence that encodes the polypeptide of SEQ ID NO: 56, or a subsequence thereof. In another aspect, the nucleic acid probe is SEQ ID NO: 55. In another aspect, the nucleic acid probe is the polynucleotide sequence contained in *Dictyoglomus thermophilum* ATCC 35947, wherein the polynucleotide sequence thereof encodes a polypeptide having xylanase activity. In another aspect, the nucleic acid probe is the mature polypeptide coding region contained in *Dictyoglomus thermophilum* ATCC 35947.

In another aspect, the nucleic acid probe is the mature polypeptide coding sequence of SEQ ID NO: 57. In another aspect, the nucleic acid probe is nucleotides 61 to 2391 of SEQ ID NO: 57. In another aspect, the nucleic acid probe is a polynucleotide sequence that encodes the polypeptide of SEQ ID NO: 58, or a subsequence thereof. In another aspect, the nucleic acid probe is SEQ ID NO: 57. In another aspect, the nucleic acid probe is the polynucleotide sequence contained in *Trichoderma reesei* RutC30, wherein the polynucleotide sequence thereof encodes a polypeptide having beta-xylosidase activity. In another aspect, the nucleic acid probe is the mature polypeptide coding region contained in *Trichoderma reesei* RutC30.

In another aspect, the nucleic acid probe is the mature polypeptide coding sequence of SEQ ID NO: 59. In another aspect, the nucleic acid probe is nucleotides 64 to 2388 of SEQ ID NO: 59. In another aspect, the nucleic acid probe is a polynucleotide sequence that encodes the polypeptide of SEQ ID NO: 60, or a subsequence thereof. In another aspect, the nucleic acid probe is SEQ ID NO: 59. In another aspect, the nucleic acid probe is the polynucleotide sequence contained in *Talaromyces emersonii* CBS 393.64, wherein the polynucleotide sequence thereof encodes a polypeptide having beta-xylosidase activity. In another aspect, the nucleic acid probe is the mature polypeptide coding region contained in *Talaromyces emersonii CBS* 393.64.

In another aspect, the nucleic acid probe is the mature polypeptide coding sequence of SEQ ID NO: 201. In another aspect, the nucleic acid probe is nucleotides 52 to 2409 of SEQ ID NO: 201. In another aspect, the nucleic acid probe is a polynucleotide sequence that encodes the polypeptide of SEQ ID NO: 202, or a subsequence thereof. In another aspect, the nucleic acid probe is SEQ ID NO: 201. In another aspect, the nucleic acid probe is the polynucleotide sequence contained in *Aspergillus aculeatus* CBS 172.66, wherein the polynucleotide sequence thereof encodes a polypeptide having beta-xylosidase activity. In another aspect, the nucleic acid probe is the mature polypeptide coding region contained in *Aspergillus aculeatus* CBS 172.66.

In another aspect, the nucleic acid probe is the mature polypeptide coding sequence of SEQ ID NO: 203. In another aspect, the nucleic acid probe is nucleotides 52 to 2451 of SEQ ID NO: 203. In another aspect, the nucleic acid probe is a polynucleotide sequence that encodes the polypeptide of SEQ ID NO: 204, or a subsequence thereof. In another aspect, the nucleic acid probe is SEQ ID NO: 203. In another aspect, the nucleic acid probe is the polynucleotide sequence contained in *Aspergillus aculeatus* CBS 186.67, wherein the polynucleotide sequence thereof encodes a polypeptide having beta-xylosidase activity. In another aspect, the nucleic acid probe is the mature polypeptide coding region contained in *Aspergillus aculeatus* CBS 186.67.

In another aspect, the nucleic acid probe is the mature polypeptide coding sequence of SEQ ID NO: 205. In another aspect, the nucleic acid probe is nucleotides 61 to 2376 of SEQ ID NO: 205. In another aspect, the nucleic acid probe is a polynucleotide sequence that encodes the polypeptide of SEQ ID NO: 206, or a subsequence thereof. In another aspect, the nucleic acid probe is SEQ ID NO: 205. In another aspect, the nucleic acid probe is the polynucleotide sequence contained in *Aspergillus fumigatus* NN051616, wherein the polynucleotide sequence thereof encodes a polypeptide having beta-xylosidase activity. In another aspect, the nucleic acid probe is the mature polypeptide coding region contained in *Aspergillus fumigatus* NN051616.

For long probes of at least 100 nucleotides in length, very low to very high stringency conditions are defined as prehybridization and hybridization at 42° C. in 5×SSPE, 0.3% SDS, 200 micrograms/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally. The carrier material is finally washed three times each for 15 minutes using 2×SSC, 0.2% SDS at 45° C. (very low stringency), at 50° C. (low stringency), at 55° C. (medium stringency), at 60° C. (medium-high stringency), at 65° C. (high stringency), and at 70° C. (very high stringency).

For short probes of about 15 nucleotides to about 70 nucleotides in length, stringency conditions are defined as prehybridization and hybridization at about 5° C. to about 10° C. below the calculated $T_m$ using the calculation according to Bolton and McCarthy (1962, *Proc. Natl. Acad. Sci. USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally. The carrier material is finally washed once in 6×SCC plus 0.1% SDS for 15 minutes and twice each for 15 minutes using 6×SSC at 5° C. to 10° C. below the calculated $T_m$.

In a third aspect, the isolated polypeptides having cellobiohydrolase I activity are encoded by polynucleotides comprising or consisting of nucleotide sequences that have a degree of identity to the mature polypeptide coding sequence of SEQ ID NO: 1 of preferably at least 80%, more preferably at least 85%, even more preferably at least 90%, most preferably at least 95%, and even most preferably at least 96%, at least 97%, at least 98%, or at least 99%, which encode a polypeptide having cellobiohydrolase I activity.

In another third aspect, the isolated polypeptides having cellobiohydrolase I activity are encoded by polynucleotides comprising or consisting of nucleotide sequences that have a degree of identity to the mature polypeptide coding sequence of SEQ ID NO: 3 of preferably at least 80%, more preferably at least 85%, even more preferably at least 90%, most preferably at least 95%, and even most preferably at least 96%, at least 97%, at least 98%, or at least 99%, which encode a polypeptide having cellobiohydrolase I activity.

In another third aspect, the isolated polypeptides having cellobiohydrolase I activity are encoded by polynucleotides comprising or consisting of nucleotide sequences that have a degree of identity to the mature polypeptide coding sequence of SEQ ID NO: 5 of preferably at least 80%, more preferably at least 85%, even more preferably at least 90%, most preferably at least 95%, and even most preferably at least 96%, at least 97%, at least 98%, or at least 99%, which encode a polypeptide having cellobiohydrolase I activity.

In another third aspect, the isolated polypeptides having cellobiohydrolase I activity are encoded by polynucleotides comprising or consisting of nucleotide sequences that have a degree of identity to the mature polypeptide coding sequence of SEQ ID NO: 7 of preferably at least 80%, more preferably at least 85%, even more preferably at least 90%, most preferably at least 95%, and even most preferably at least 96%, at least 97%, at least 98%, or at least 99%, which encode a polypeptide having cellobiohydrolase I activity.

In another third aspect, the isolated polypeptides having cellobiohydrolase I activity are encoded by polynucleotides comprising or consisting of nucleotide sequences that have a degree of identity to the mature polypeptide coding sequence of SEQ ID NO: 157 of preferably at least 80%, more preferably at least 85%, even more preferably at least 90%, most preferably at least 95%, and even most preferably at least 96%, at least 97%, at least 98%, or at least 99%, which encode a polypeptide having cellobiohydrolase I activity.

In another third aspect, the isolated polypeptides having cellobiohydrolase I activity are encoded by polynucleotides comprising or consisting of nucleotide sequences that have a degree of identity to the mature polypeptide coding sequence of SEQ ID NO: 159 of preferably at least 80%, more preferably at least 85%, even more preferably at least 90%, most preferably at least 95%, and even most preferably at least 96%, at least 97%, at least 98%, or at least 99%, which encode a polypeptide having cellobiohydrolase I activity.

In another third aspect, the isolated polypeptides having cellobiohydrolase I activity are encoded by polynucleotides comprising or consisting of nucleotide sequences that have a degree of identity to the mature polypeptide coding sequence of SEQ ID NO: 161 of preferably at least 80%, more preferably at least 85%, even more preferably at least 90%, most preferably at least 95%, and even most preferably at least 96%, at least 97%, at least 98%, or at least 99%, which encode a polypeptide having cellobiohydrolase I activity.

In another third aspect, the isolated polypeptides having cellobiohydrolase I activity are encoded by polynucleotides comprising or consisting of nucleotide sequences that have a degree of identity to the mature polypeptide coding sequence of SEQ ID NO: 163 of preferably at least 80%, more preferably at least 85%, even more preferably at least 90%, most preferably at least 95%, and even most preferably at least 96%, at least 97%, at least 98%, or at least 99%, which encode a polypeptide having cellobiohydrolase I activity.

In another third aspect, the isolated polypeptides having cellobiohydrolase I activity are encoded by polynucleotides comprising or consisting of nucleotide sequences that have a degree of identity to the mature polypeptide coding sequence of SEQ ID NO: 165 of preferably at least 80%, more preferably at least 85%, even more preferably at least 90%, most preferably at least 95%, and even most preferably at least 96%, at least 97%, at least 98%, or at least 99%, which encode a polypeptide having cellobiohydrolase I activity.

In another third aspect, the isolated polypeptides having cellobiohydrolase II activity are encoded by polynucleotides comprising or consisting of nucleotide sequences that have a degree of identity to the mature polypeptide coding sequence of SEQ ID NO: 9 of preferably at least 80%, more preferably at least 85%, even more preferably at least 90%, most preferably at least 95%, and even most preferably at least 96%, at least 97%, at least 98%, or at least 99%, which encode a polypeptide having cellobiohydrolase II activity.

In another third aspect, the isolated polypeptides having cellobiohydrolase II activity are encoded by polynucleotides comprising or consisting of nucleotide sequences that have a degree of identity to the mature polypeptide coding sequence of SEQ ID NO: 11 of preferably at least 80%, more preferably at least 85%, even more preferably at least 90%, most preferably at least 95%, and even most preferably at least 96%, at least 97%, at least 98%, or at least 99%, which encode a polypeptide having cellobiohydrolase II activity.

In another third aspect, the isolated polypeptides having cellobiohydrolase II activity are encoded by polynucleotides comprising or consisting of nucleotide sequences that have a degree of identity to the mature polypeptide coding sequence of SEQ ID NO: 13 of preferably at least 80%, more preferably at least 85%, even more preferably at least 90%, most preferably at least 95%, and even most preferably at least 96%, at least 97%, at least 98%, or at least 99%, which encode a polypeptide having cellobiohydrolase II activity.

In another third aspect, the isolated polypeptides having cellobiohydrolase II activity are encoded by polynucleotides comprising or consisting of nucleotide sequences that have a degree of identity to the mature polypeptide coding sequence of SEQ ID NO: 15 of preferably at least 80%, more preferably at least 85%, even more preferably at least 90%, most preferably at least 95%, and even most preferably at least 96%, at least 97%, at least 98%, or at least 99%, which encode a polypeptide having cellobiohydrolase II activity.

In another third aspect, the isolated polypeptides having cellobiohydrolase II activity are encoded by polynucleotides comprising or consisting of nucleotide sequences that have a degree of identity to the mature polypeptide coding sequence of SEQ ID NO: 17 of preferably at least 80%, more preferably at least 85%, even more preferably at least 90%, most preferably at least 95%, and even most preferably at least 96%, at least 97%, at least 98%, or at least 99%, which encode a polypeptide having cellobiohydrolase II activity.

In another third aspect, the isolated polypeptides having cellobiohydrolase II activity are encoded by polynucleotides comprising or consisting of nucleotide sequences that have a degree of identity to the mature polypeptide coding sequence of SEQ ID NO: 167 of preferably at least 80%, more preferably at least 85%, even more preferably at least 90%, most preferably at least 95%, and even most preferably at least 96%, at least 97%, at least 98%, or at least 99%, which encode a polypeptide having cellobiohydrolase II activity.

In another third aspect, the isolated polypeptides having cellobiohydrolase II activity are encoded by polynucleotides comprising or consisting of nucleotide sequences that have a degree of identity to the mature polypeptide coding sequence of SEQ ID NO: 169 of preferably at least 80%, more preferably at least 85%, even more preferably at least 90%, most preferably at least 95%, and even most preferably at least 96%, at least 97%, at least 98%, or at least 99%, which encode a polypeptide having cellobiohydrolase II activity.

In another third aspect, the isolated polypeptides having cellobiohydrolase II activity are encoded by polynucleotides comprising or consisting of nucleotide sequences that have a degree of identity to the mature polypeptide coding sequence of SEQ ID NO: 171 of preferably at least 80%, more preferably at least 85%, even more preferably at least 90%, most preferably at least 95%, and even most preferably at least 96%, at least 97%, at least 98%, or at least 99%, which encode a polypeptide having cellobiohydrolase II activity.

In another third aspect, the isolated polypeptides having endoglucanase I activity are encoded by polynucleotides comprising or consisting of nucleotide sequences that have a degree of identity to the mature polypeptide coding sequence of SEQ ID NO: 19 of preferably at least 80%, more preferably at least 85%, even more preferably at least 90%, most preferably at least 95%, and even most preferably at least 96%, at least 97%, at least 98%, or at least 99%, which encode a polypeptide having endoglucanase I activity.

In another third aspect, the isolated polypeptides having endoglucanase II activity are encoded by polynucleotides comprising or consisting of nucleotide sequences that have a degree of identity to the mature polypeptide coding sequence of SEQ ID NO: 21 of preferably at least 80%, more preferably at least 85%, even more preferably at least 90%, most preferably at least 95%, and even most preferably at least 96%, at least 97%, at least 98%, or at least 99%, which encode a polypeptide having endoglucanase II activity.

In another third aspect, the isolated polypeptides having endoglucanase II activity are encoded by polynucleotides comprising or consisting of nucleotide sequences that have a degree of identity to the mature polypeptide coding sequence of SEQ ID NO: 23 of preferably at least 80%, more preferably at least 85%, even more preferably at least 90%, most preferably at least 95%, and even most preferably at least 96%, at least 97%, at least 98%, or at least 99%, which encode a polypeptide having endoglucanase II activity.

In another third aspect, the isolated polypeptides having endoglucanase II activity are encoded by polynucleotides comprising or consisting of nucleotide sequences that have a degree of identity to the mature polypeptide coding sequence of SEQ ID NO: 25 of preferably at least 80%, more preferably at least 85%, even more preferably at least 90%, most preferably at least 95%, and even most preferably at least 96%, at least 97%, at least 98%, or at least 99%, which encode a polypeptide having endoglucanase II activity.

In another third aspect, the isolated polypeptides having endoglucanase II activity are encoded by polynucleotides comprising or consisting of nucleotide sequences that have a degree of identity to the mature polypeptide coding sequence of SEQ ID NO: 173 of preferably at least 80%, more preferably at least 85%, even more preferably at least 90%, most preferably at least 95%, and even most preferably at least 96%, at least 97%, at least 98%, or at least 99%, which encode a polypeptide having endoglucanase II activity.

In another third aspect, the isolated polypeptides having endoglucanase II activity are encoded by polynucleotides comprising or consisting of nucleotide sequences that have a degree of identity to the mature polypeptide coding sequence of SEQ ID NO: 175 of preferably at least 80%, more preferably at least 85%, even more preferably at least 90%, most preferably at least 95%, and even most preferably at least 96%, at least 97%, at least 98%, or at least 99%, which encode a polypeptide having endoglucanase II activity.

In another third aspect, the isolated polypeptides having beta-glucosidase activity are encoded by polynucleotides comprising or consisting of nucleotide sequences that have a degree of identity to the mature polypeptide coding sequence of SEQ ID NO: 27 of preferably at least 80%, more preferably at least 85%, even more preferably at least 90%, most preferably at least 95%, and even most preferably at least 96%, at least 97%, at least 98%, or at least 99%, which encode a polypeptide having beta-glucosidase activity.

In another third aspect, the isolated polypeptides having beta-glucosidase activity are encoded by polynucleotides comprising or consisting of nucleotide sequences that have a degree of identity to the mature polypeptide coding sequence of SEQ ID NO: 29 of preferably at least 80%, more preferably at least 85%, even more preferably at least 90%, most preferably at least 95%, and even most preferably at least 96%, at least 97%, at least 98%, or at least 99%, which encode a polypeptide having beta-glucosidase activity.

In another third aspect, the isolated polypeptides having beta-glucosidase activity are encoded by polynucleotides comprising or consisting of nucleotide sequences that have a degree of identity to the mature polypeptide coding sequence of SEQ ID NO: 31 of preferably at least 80%, more preferably at least 85%, even more preferably at least 90%, most preferably at least 95%, and even most preferably at least 96%, at least 97%, at least 98%, or at least 99%, which encode a polypeptide having beta-glucosidase activity.

In another third aspect, the isolated polypeptides having beta-glucosidase activity are encoded by polynucleotides comprising or consisting of nucleotide sequences that have a degree of identity to the mature polypeptide coding sequence of SEQ ID NO: 177 of preferably at least 80%, more preferably at least 85%, even more preferably at least 90%, most preferably at least 95%, and even most preferably at least 96%, at least 97%, at least 98%, or at least 99%, which encode a polypeptide having beta-glucosidase activity.

In another third aspect, the isolated polypeptides having beta-glucosidase activity are encoded by polynucleotides comprising or consisting of nucleotide sequences that have a degree of identity to the mature polypeptide coding sequence of SEQ ID NO: 179 of preferably at least 80%, more preferably at least 85%, even more preferably at least 90%, most preferably at least 95%, and even most preferably at least 96%, at least 97%, at least 98%, or at least 99%, which encode a polypeptide having beta-glucosidase activity.

In another third aspect, the isolated polypeptides having beta-glucosidase activity are encoded by polynucleotides comprising or consisting of nucleotide sequences that have a degree of identity to the mature polypeptide coding sequence of SEQ ID NO: 181 of preferably at least 80%, more preferably at least 85%, even more preferably at least 90%, most preferably at least 95%, and even most preferably at least 96%, at least 97%, at least 98%, or at least 99%, which encode a polypeptide having beta-glucosidase activity.

In another third aspect, the isolated polypeptides having beta-glucosidase activity are encoded by polynucleotides comprising or consisting of nucleotide sequences that have a degree of identity to the mature polypeptide coding sequence of SEQ ID NO: 183 of preferably at least 80%, more preferably at least 85%, even more preferably at least 90%, most preferably at least 95%, and even most preferably at least 96%, at least 97%, at least 98%, or at least 99%, which encode a polypeptide having beta-glucosidase activity.

In another third aspect, the isolated polypeptides having beta-glucosidase activity are encoded by polynucleotides comprising or consisting of nucleotide sequences that have a degree of identity to the mature polypeptide coding sequence of SEQ ID NO: 185 of preferably at least 80%, more preferably at least 85%, even more preferably at least 90%, most preferably at least 95%, and even most preferably at least 96%, at least 97%, at least 98%, or at least 99%, which encode a polypeptide having beta-glucosidase activity.

In another third aspect, the isolated polypeptides having beta-glucosidase activity are encoded by polynucleotides comprising or consisting of nucleotide sequences that have a degree of identity to the mature polypeptide coding sequence of SEQ ID NO: 187 of preferably at least 80%, more preferably at least 85%, even more preferably at least 90%, most preferably at least 95%, and even most preferably at least 96%, at least 97%, at least 98%, or at least 99%, which encode a polypeptide having beta-glucosidase activity.

In another third aspect, the isolated polypeptides having beta-glucosidase activity are encoded by polynucleotides comprising or consisting of nucleotide sequences that have a degree of identity to the mature polypeptide coding sequence of SEQ ID NO: 189 of preferably at least 80%, more preferably at least 85%, even more preferably at least 90%, most preferably at least 95%, and even most preferably at least 96%, at least 97%, at least 98%, or at least 99%, which encode a polypeptide having beta-glucosidase activity.

In another third aspect, the isolated GH61 polypeptides having cellulolytic enhancing activity are encoded by polynucleotides comprising or consisting of nucleotide sequences that have a degree of identity to the mature polypeptide coding sequence of SEQ ID NO: 33 of preferably at least 80%, more preferably at least 85%, even more preferably at least 90%, most preferably at least 95%, and even most preferably at least 96%, at least 97%, at least 98%, or at least 99%, which encode a polypeptide having cellulolytic enhancing activity.

In another third aspect, the isolated GH61 polypeptides having cellulolytic enhancing activity are encoded by polynucleotides comprising or consisting of nucleotide sequences that have a degree of identity to the mature polypeptide coding sequence of SEQ ID NO: 35 of preferably at least 80%, more preferably at least 85%, even more preferably at least 90%, most preferably at least 95%, and even most preferably at least 96%, at least 97%, at least 98%, or at least 99%, which encode a polypeptide having cellulolytic enhancing activity.

In another third aspect, the isolated GH61 polypeptides having cellulolytic enhancing activity are encoded by polynucleotides comprising or consisting of nucleotide sequences that have a degree of identity to the mature polypeptide coding sequence of SEQ ID NO: 37 of preferably at least 80%, more preferably at least 85%, even more preferably at least 90%, most preferably at least 95%, and even most preferably at least 96%, at least 97%, at least 98%, or at least 99%, which encode a polypeptide having cellulolytic enhancing activity.

In another third aspect, the isolated GH61 polypeptides having cellulolytic enhancing activity are encoded by polynucleotides comprising or consisting of nucleotide sequences that have a degree of identity to the mature polypeptide coding sequence of SEQ ID NO: 39 of preferably at least 80%, more preferably at least 85%, even more preferably at least 90%, most preferably at least 95%, and even most preferably at least 96%, at least 97%, at least 98%, or at least 99%, which encode a polypeptide having cellulolytic enhancing activity.

In another third aspect, the isolated GH61 polypeptides having cellulolytic enhancing activity are encoded by polynucleotides comprising or consisting of nucleotide sequences that have a degree of identity to the mature polypeptide coding sequence of SEQ ID NO: 41 of preferably at least 80%, more preferably at least 85%, even more preferably at least 90%, most preferably at least 95%, and even most preferably at least 96%, at least 97%, at least 98%, or at least 99%, which encode a polypeptide having cellulolytic enhancing activity.

In another third aspect, the isolated GH61 polypeptides having cellulolytic enhancing activity are encoded by polynucleotides comprising or consisting of nucleotide sequences that have a degree of identity to the mature polypeptide coding sequence of SEQ ID NO: 43 of preferably at least 80%, more preferably at least 85%, even more preferably at least 90%, most preferably at least 95%, and even most preferably at least 96%, at least 97%, at least 98%, or at least 99%, which encode a polypeptide having cellulolytic enhancing activity.

In another third aspect, the isolated GH61 polypeptides having cellulolytic enhancing activity are encoded by polynucleotides comprising or consisting of nucleotide sequences that have a degree of identity to the mature polypeptide coding sequence of SEQ ID NO: 191 of preferably at least 80%, more preferably at least 85%, even more preferably at least 90%, most preferably at least 95%, and even most preferably at least 96%, at least 97%, at least 98%, or at least 99%, which encode a polypeptide having cellulolytic enhancing activity.

In another third aspect, the isolated polypeptides having xylanase activity are encoded by polynucleotides comprising or consisting of nucleotide sequences that have a degree of identity to the mature polypeptide coding sequence of SEQ ID NO: 45 of preferably at least 80%, more preferably at least 85%, even more preferably at least 90%, most preferably at least 95%, and even most preferably at least 96%, at least 97%, at least 98%, or at least 99%, which encode a polypeptide having xylanase activity.

In another third aspect, the isolated polypeptides having xylanase activity are encoded by polynucleotides comprising or consisting of nucleotide sequences that have a degree of identity to the mature polypeptide coding sequence of SEQ ID NO: 47 of preferably at least 80%, more preferably at least 85%, even more preferably at least 90%, most preferably at least 95%, and even most preferably at least 96%, at least 97%, at least 98%, or at least 99%, which encode a polypeptide having xylanase activity.

In another third aspect, the isolated polypeptides having xylanase activity are encoded by polynucleotides comprising or consisting of nucleotide sequences that have a degree of identity to the mature polypeptide coding sequence of SEQ ID NO: 49 of preferably at least 80%, more preferably at least 85%, even more preferably at least 90%, most preferably at least 95%, and even most preferably at least 96%, at least 97%, at least 98%, or at least 99%, which encode a polypeptide having xylanase activity.

In another third aspect, the isolated polypeptides having xylanase activity are encoded by polynucleotides comprising or consisting of nucleotide sequences that have a degree of identity to the mature polypeptide coding sequence of SEQ ID NO: 51 of preferably at least 80%, more preferably at least 85%, even more preferably at least 90%, most preferably at least 95%, and even most preferably at least 96%, at least 97%, at least 98%, or at least 99%, which encode a polypeptide having xylanase activity.

In another third aspect, the isolated polypeptides having xylanase activity are encoded by polynucleotides comprising or consisting of nucleotide sequences that have a degree of identity to the mature polypeptide coding sequence of SEQ ID NO: 53 of preferably at least 80%, more preferably at least 85%, even more preferably at least 90%, most preferably at least 95%, and even most preferably at least 96%, at least 97%, at least 98%, or at least 99%, which encode a polypeptide having xylanase activity.

In another third aspect, the isolated polypeptides having xylanase activity are encoded by polynucleotides comprising or consisting of nucleotide sequences that have a degree of identity to the mature polypeptide coding sequence of SEQ ID NO: 193 of preferably at least 80%, more preferably at least 85%, even more preferably at least 90%, most preferably at least 95%, and even most preferably at least 96%, at least 97%, at least 98%, or at least 99%, which encode a polypeptide having xylanase activity.

In another third aspect, the isolated polypeptides having xylanase activity are encoded by polynucleotides comprising or consisting of nucleotide sequences that have a degree of identity to the mature polypeptide coding sequence of SEQ ID NO: 195 of preferably at least 80%, more preferably at least 85%, even more preferably at least 90%, most preferably at least 95%, and even most preferably at least 96%, at least 97%, at least 98%, or at least 99%, which encode a polypeptide having xylanase activity.

In another third aspect, the isolated polypeptides having xylanase activity are encoded by polynucleotides comprising or consisting of nucleotide sequences that have a degree of identity to the mature polypeptide coding sequence of SEQ ID NO: 197 of preferably at least 80%, more preferably at least 85%, even more preferably at least 90%, most preferably at least 95%, and even most preferably at least 96%, at least 97%, at least 98%, or at least 99%, which encode a polypeptide having xylanase activity.

In another third aspect, the isolated polypeptides having xylanase activity are encoded by polynucleotides comprising or consisting of nucleotide sequences that have a degree of identity to the mature polypeptide coding sequence of SEQ ID NO: 55 of preferably at least 80%, more preferably at least 85%, even more preferably at least 90%, most preferably at least 95%, and even most preferably at least 96%, at least 97%, at least 98%, or at least 99%, which encode a polypeptide having xylanase activity.

In another third aspect, the isolated polypeptides having xylanase activity are encoded by polynucleotides comprising or consisting of nucleotide sequences that have a degree of identity to the mature polypeptide coding sequence of SEQ ID NO: 199 or SEQ ID NO: 304 of preferably at least 80%, more preferably at least 85%, even more preferably at least 90%, most preferably at least 95%, and even most preferably at least 96%, at least 97%, at least 98%, or at least 99%, which encode a polypeptide having xylanase activity.

In another third aspect, the isolated polypeptides having beta-xylosidase activity are encoded by polynucleotides comprising or consisting of nucleotide sequences that have a degree of identity to the mature polypeptide coding sequence of SEQ ID NO: 57 of preferably at least 80%, more preferably at least 85%, even more preferably at least 90%, most preferably at least 95%, and even most preferably at least 96%, at least 97%, at least 98%, or at least 99%, which encode a polypeptide having beta-xylosidase activity.

In another third aspect, the isolated polypeptides having beta-xylosidase activity are encoded by polynucleotides comprising or consisting of nucleotide sequences that have a degree of identity to the mature polypeptide coding sequence of SEQ ID NO: 59 of preferably at least 80%, more preferably at least 85%, even more preferably at least 90%, most preferably at least 95%, and even most preferably at least 96%, at least 97%, at least 98%, or at least 99%, which encode a polypeptide having beta-xylosidase activity.

In another third aspect, the isolated polypeptides having beta-xylosidase activity are encoded by polynucleotides comprising or consisting of nucleotide sequences that have a degree of identity to the mature polypeptide coding sequence of SEQ ID NO: 201 of preferably at least 80%, more preferably at least 85%, even more preferably at least 90%, most preferably at least 95%, and even most preferably at least 96%, at least 97%, at least 98%, or at least 99%, which encode a polypeptide having beta-xylosidase activity.

In another third aspect, the isolated polypeptides having beta-xylosidase activity are encoded by polynucleotides comprising or consisting of nucleotide sequences that have a degree of identity to the mature polypeptide coding sequence of SEQ ID NO: 203 of preferably at least 80%, more preferably at least 85%, even more preferably at least 90%, most preferably at least 95%, and even most preferably at least 96%, at least 97%, at least 98%, or at least 99%, which encode a polypeptide having beta-xylosidase activity.

In another third aspect, the isolated polypeptides having beta-xylosidase activity are encoded by polynucleotides comprising or consisting of nucleotide sequences that have a degree of identity to the mature polypeptide coding sequence of SEQ ID NO: 205 of preferably at least 80%, more preferably at least 85%, even more preferably at least 90%, most preferably at least 95%, and even most preferably at least 96%, at least 97%, at least 98%, or at least 99%, which encode a polypeptide having beta-xylosidase activity.

Techniques used to isolate or clone a polynucleotide encoding a polypeptide are known in the art and include isolation from genomic DNA, preparation from cDNA, or a combination thereof. The cloning of a polynucleotide from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligated activated transcription (LAT) and nucleotide sequence-based amplification (NASBA) may be used. The polynucleotides may be cloned from any strain and thus, for example, may be an allelic or species variant of the polypeptide encoding region of the nucleotide sequence.

In a fourth aspect, the isolated polynucleotides encoding polypeptides having cellobiohydrolase I activity comprise or consist of nucleotide sequences that have a degree of identity to the mature polypeptide coding sequence of SEQ ID NO: 1 of preferably at least 80%, more preferably at least 85%, even more preferably at least 90%, most preferably at least 95%, and even most preferably at least 96%, at least 97%, at least 98%, or at least 99%, which encode a polypeptide having cellobiohydrolase I activity.

In one aspect, the isolated polynucleotide encoding a polypeptide having cellobiohydrolase I activity comprises or consists of the nucleotide sequence of SEQ ID NO: 1. In another aspect, the nucleotide sequence comprises or consists of the sequence contained in *Chaetomium thermophilum* CGMCC 0581. In another aspect, the nucleotide sequence comprises or consists of the mature polypeptide coding sequence of SEQ ID NO: 1. In another aspect, the nucleotide sequence comprises or consists of nucleotides 55 to 1590 of SEQ ID NO: 1. In another aspect, the nucleotide sequence comprises or consists of the mature polypeptide coding sequence contained in *Chaetomium thermophilum* CGMCC 0581.

In another fourth aspect, the isolated polynucleotides encoding polypeptides having cellobiohydrolase I activity comprise or consist of nucleotide sequences that have a degree of identity to the mature polypeptide coding sequence of SEQ ID NO: 3 of preferably at least 80%, more preferably at least 85%, even more preferably at least 90%, most preferably at least 95%, and even most preferably at least 96%, at least 97%, at least 98%, or at least 99%, which encode a polypeptide having cellobiohydrolase I activity.

In one aspect, the isolated polynucleotide encoding a polypeptide having cellobiohydrolase I activity comprises or consists of the nucleotide sequence of SEQ ID NO: 3. In another aspect, the nucleotide sequence comprises or consists of the sequence contained in *Myceliophthora thermophila* CBS 117.65. In another aspect, the nucleotide sequence comprises or consists of the mature polypeptide coding sequence of SEQ ID NO: 3. In another aspect, the nucleotide sequence comprises or consists of nucleotides 61 to 1350 of SEQ ID NO: 3. In another aspect, the nucleotide sequence comprises or consists of the mature polypeptide coding sequence contained in *Myceliophthora thermophila* CBS 117.65.

In another fourth aspect, the isolated polynucleotides encoding polypeptides having cellobiohydrolase I activity comprise or consist of nucleotide sequences that have a degree of identity to the mature polypeptide coding sequence of SEQ ID NO: 5 of preferably at least 80%, more preferably at least 85%, even more preferably at least 90%, most preferably at least 95%, and even most preferably at least 96%, at least 97%, at least 98%, or at least 99%, which encode a polypeptide having cellobiohydrolase I activity.

In one aspect, the isolated polynucleotide encoding a polypeptide having cellobiohydrolase I activity comprises or consists of the nucleotide sequence of SEQ ID NO: 5. In another aspect, the nucleotide sequence comprises or consists of the sequence contained in *Aspergillus fumigatus* NN055679. In another aspect, the nucleotide sequence comprises or consists of the mature polypeptide coding sequence of SEQ ID NO: 5. In another aspect, the nucleotide sequence comprises or consists of nucleotides 79 to 1596 of SEQ ID NO: 5. In another aspect, the nucleotide sequence comprises or consists of the mature polypeptide coding sequence contained in *Aspergillus fumigatus* NN055679.

In another fourth aspect, the isolated polynucleotides encoding polypeptides having cellobiohydrolase I activity comprise or consist of nucleotide sequences that have a degree of identity to the mature polypeptide coding sequence of SEQ ID NO: 7 of preferably at least 80%, more preferably at least 85%, even more preferably at least 90%, most preferably at least 95%, and even most preferably at least 96%, at least 97%, at least 98%, or at least 99%, which encode a polypeptide having cellobiohydrolase I activity.

In one aspect, the isolated polynucleotide encoding a polypeptide having cellobiohydrolase I activity comprises or consists of the nucleotide sequence of SEQ ID NO: 7. In another aspect, the nucleotide sequence comprises or consists of the sequence contained in *Thermoascus aurantiacus* CGMCC 0583. In another aspect, the nucleotide sequence comprises or consists of the mature polypeptide coding sequence of SEQ ID NO: 7. In another aspect, the nucleotide sequence comprises or consists of nucleotides 52 to 1374 of SEQ ID NO: 7. In another aspect, the nucleotide sequence comprises or consists of the mature polypeptide coding sequence contained in *Thermoascus aurantiacus* CGMCC 0583.

In another fourth aspect, the isolated polynucleotides encoding polypeptides having cellobiohydrolase I activity comprise or consist of nucleotide sequences that have a degree of identity to the mature polypeptide coding sequence of SEQ ID NO: 157 of preferably at least 80%, more preferably at least 85%, even more preferably at least 90%, most preferably at least 95%, and even most preferably at least 96%, at least 97%, at least 98%, or at least 99%, which encode a polypeptide having cellobiohydrolase I activity.

In one aspect, the isolated polynucleotide encoding a polypeptide having cellobiohydrolase I activity comprises or consists of the nucleotide sequence of SEQ ID NO: 157. In another aspect, the nucleotide sequence comprises or consists of the sequence contained in *Penicillium emersonii* NN051602. In another aspect, the nucleotide sequence comprises or consists of the mature polypeptide coding sequence of SEQ ID NO: 157. In another aspect, the nucleotide sequence comprises or consists of nucleotides 55 to 1428 of SEQ ID NO: 157. In another aspect, the nucleotide sequence comprises or consists of the mature polypeptide coding sequence contained in *Penicillium emersonii* NN051602

In another fourth aspect, the isolated polynucleotides encoding polypeptides having cellobiohydrolase I activity comprise or consist of nucleotide sequences that have a degree of identity to the mature polypeptide coding sequence of SEQ ID NO: 159 of preferably at least 80%, more preferably at least 85%, even more preferably at least 90%, most preferably at least 95%, and even most preferably at least 96%, at least 97%, at least 98%, or at least 99%, which encode a polypeptide having cellobiohydrolase I activity.

In one aspect, the isolated polynucleotide encoding a polypeptide having cellobiohydrolase I activity comprises or consists of the nucleotide sequence of SEQ ID NO: 159. In another aspect, the nucleotide sequence comprises or consists of the sequence contained in *Penicillium pinophilum* NN046877. In another aspect, the nucleotide sequence comprises or consists of the mature polypeptide coding sequence of SEQ ID NO: 159. In another aspect, the nucleotide sequence comprises or consists of nucleotides 76 to 1590 of SEQ ID NO: 159. In another aspect, the nucleotide sequence comprises or consists of the mature polypeptide coding sequence contained in *Penicillium pinophilum* NN046877.

In another fourth aspect, the isolated polynucleotides encoding polypeptides having cellobiohydrolase I activity comprise or consist of nucleotide sequences that have a degree of identity to the mature polypeptide coding sequence of SEQ ID NO: 161 of preferably at least 80%, more preferably at least 85%, even more preferably at least 90%, most preferably at least 95%, and even most preferably at least 96%, at least 97%, at least 98%, or at least 99%, which encode a polypeptide having cellobiohydrolase I activity.

In one aspect, the isolated polynucleotide encoding a polypeptide having cellobiohydrolase I activity comprises or consists of the nucleotide sequence of SEQ ID NO: 161. In another aspect, the nucleotide sequence comprises or consists of the sequence contained in *Aspergillus terreus* ATCC 28865. In another aspect, the nucleotide sequence comprises or consists of the mature polypeptide coding sequence of SEQ ID NO: 161. In another aspect, the nucleotide sequence comprises or consists of nucleotides 70 to 1675 of SEQ ID NO: 161. In another aspect, the nucleotide sequence comprises or consists of the mature polypeptide coding sequence contained in *Aspergillus terreus* ATCC 28865.

In another fourth aspect, the isolated polynucleotides encoding polypeptides having cellobiohydrolase I activity comprise or consist of nucleotide sequences that have a degree of identity to the mature polypeptide coding sequence of SEQ ID NO: 163 of preferably at least 80%, more preferably at least 85%, even more preferably at least 90%, most preferably at least 95%, and even most preferably at least 96%, at least 97%, at least 98%, or at least 99%, which encode a polypeptide having cellobiohydrolase I activity.

In one aspect, the isolated polynucleotide encoding a polypeptide having cellobiohydrolase I activity comprises or consists of the nucleotide sequence of SEQ ID NO: 163. In another aspect, the nucleotide sequence comprises or consists of the sequence contained in *Neosartorya fischeri* NRRL 181. In another aspect, the nucleotide sequence comprises or consists of the mature polypeptide coding sequence of SEQ ID NO: 163. In another aspect, the nucleotide sequence comprises or consists of nucleotides 79 to 1605 of SEQ ID NO: 163. In another aspect, the nucleotide sequence comprises or consists of the mature polypeptide coding sequence contained in *Neosartorya fischeri* NRRL 181.

In another fourth aspect, the isolated polynucleotides encoding polypeptides having cellobiohydrolase I activity comprise or consist of nucleotide sequences that have a degree of identity to the mature polypeptide coding sequence of SEQ ID NO: 165 of preferably at least 80%, more preferably at least 85%, even more preferably at least 90%, most preferably at least 95%, and even most preferably at least 96%, at least 97%, at least 98%, or at least 99%, which encode a polypeptide having cellobiohydrolase I activity.

In one aspect, the isolated polynucleotide encoding a polypeptide having cellobiohydrolase I activity comprises or consists of the nucleotide sequence of SEQ ID NO: 165. In another aspect, the nucleotide sequence comprises or consists of the sequence contained in *Aspergillus nidulans* strain FGSCA4. In another aspect, the nucleotide sequence comprises or consists of the mature polypeptide coding sequence of SEQ ID NO: 165. In another aspect, the nucleotide sequence comprises or consists of nucleotides 70 to 1578 of SEQ ID NO: 165. In another aspect, the nucleotide sequence comprises or consists of the mature polypeptide coding sequence contained in *Aspergillus nidulans* strain FGSCA4.

In another fourth aspect, the isolated polynucleotides encoding polypeptides having cellobiohydrolase II activity comprise or consist of nucleotide sequences that have a degree of identity to the mature polypeptide coding sequence of SEQ ID NO: 9 of preferably at least 80%, more preferably at least 85%, even more preferably at least 90%, most preferably at least 95%, and even most preferably at least 96%, at least 97%, at least 98%, or at least 99%, which encode a polypeptide having cellobiohydrolase II activity.

In one aspect, the isolated polynucleotide encoding a polypeptide having cellobiohydrolase II activity comprises or consists of the nucleotide sequence of SEQ ID NO: 9. In another aspect, the nucleotide sequence comprises or consists of the sequence contained in *Myceliophthora thermophila* CBS 117.65. In another aspect, the nucleotide sequence comprises or consists of the mature polypeptide coding sequence of SEQ ID NO: 9. In another aspect, the nucleotide sequence comprises or consists of nucleotides 52 to 1799 of SEQ ID NO: 9. In another aspect, the nucleotide sequence comprises or consists of the mature polypeptide coding sequence contained in *Myceliophthora thermophila* CBS 117.65.

In another fourth aspect, the isolated polynucleotides encoding polypeptides having cellobiohydrolase II activity comprise or consist of nucleotide sequences that have a degree of identity to the mature polypeptide coding sequence of SEQ ID NO: 11 of preferably at least 80%, more preferably at least 85%, even more preferably at least 90%, most preferably at least 95%, and even most preferably at least 96%, at least 97%, at least 98%, or at least 99%, which encode a polypeptide having cellobiohydrolase II activity.

In one aspect, the isolated polynucleotide encoding a polypeptide having cellobiohydrolase II activity comprises or consists of the nucleotide sequence of SEQ ID NO: 11. In another aspect, the nucleotide sequence comprises or consists of the sequence contained in plasmid pSMai182 which is contained in *E. coli* NRRL B-50059 or contained in *Myceliophthora thermophila* CBS 202.73. In another aspect, the nucleotide sequence comprises or consists of the mature polypeptide coding sequence of SEQ ID NO: 11. In another aspect, the nucleotide sequence comprises or consists of nucleotides 52 to 1809 of SEQ ID NO: 11. In another aspect, the nucleotide sequence comprises or consists of the mature polypeptide coding sequence contained in *Myceliophthora thermophila* CBS 202.73 or contained in plasmid pSMai182 which is contained in *E. coli* NRRL B-50059.

In another fourth aspect, the isolated polynucleotides encoding polypeptides having cellobiohydrolase II activity comprise or consist of nucleotide sequences that have a degree of identity to the mature polypeptide coding sequence of SEQ ID NO: 13 of preferably at least 80%, more preferably at least 85%, even more preferably at least 90%, most preferably at least 95%, and even most preferably at least 96%, at least 97%, at least 98%, or at least 99%, which encode a polypeptide having cellobiohydrolase II activity.

In one aspect, the isolated polynucleotide encoding a polypeptide having cellobiohydrolase II activity comprises or consists of the nucleotide sequence of SEQ ID NO: 13. In another aspect, the nucleotide sequence comprises or consists of the sequence contained in plasmid pTter6A which is contained in *E. coli* NRRL B-30802. In another aspect, the nucleotide sequence comprises or consists of the mature polypeptide coding sequence of SEQ ID NO: 13. In another aspect, the nucleotide sequence comprises or consists of nucleotides 52 to 1443 of SEQ ID NO: 13. In another aspect, the nucleotide sequence comprises or consists of the mature polypeptide coding sequence contained in plasmid pTter6A which is contained in *E. coli* NRRL B-30802.

In another fourth aspect, the isolated polynucleotides encoding polypeptides having cellobiohydrolase II activity comprise or consist of nucleotide sequences that have a degree of identity to the mature polypeptide coding sequence of SEQ ID NO: 15 of preferably at least 80%, more preferably at least 85%, even more preferably at least 90%, most preferably at least 95%, and even most preferably at least 96%, at least 97%, at least 98%, or at least 99%, which encode a polypeptide having cellobiohydrolase II activity.

In one aspect, the isolated polynucleotide encoding a polypeptide having cellobiohydrolase II activity comprises or consists of the nucleotide sequence of SEQ ID NO: 15. In another aspect, the nucleotide sequence comprises or consists of the sequence contained in plasmid pMStr199 which is contained in *E. coli* DSM 23379. In another aspect, the nucleotide sequence comprises or consists of the mature polypeptide coding sequence of SEQ ID NO: 15. In another aspect, the nucleotide sequence comprises or consists of nucleotides 109 to 1401 of SEQ ID NO: 15. In another aspect, the nucleotide sequence comprises or consists of the mature polypeptide coding sequence contained in plasmid pMStr199 which is contained in *E. coli* DSM 23379.

In another fourth aspect, the isolated polynucleotides encoding polypeptides having cellobiohydrolase II activity comprise or consist of nucleotide sequences that have a degree of identity to the mature polypeptide coding sequence of SEQ ID NO: 17 of preferably at least 80%, more preferably at least 85%, even more preferably at least 90%, most preferably at least 95%, and even most preferably at least 96%, at least 97%, at least 98%, or at least 99%, which encode a polypeptide having cellobiohydrolase II activity.

In one aspect, the isolated polynucleotide encoding a polypeptide having cellobiohydrolase II activity comprises or consists of the nucleotide sequence of SEQ ID NO: 17. In another aspect, the nucleotide sequence comprises or consists of the sequence contained in *Aspergillus fumigatus* NN055679. In another aspect, the nucleotide sequence comprises or consists of the mature polypeptide coding sequence of SEQ ID NO: 17. In another aspect, the nucleotide sequence comprises or consists of nucleotides 58 to 1700 of SEQ ID NO: 17. In another aspect, the nucleotide sequence comprises or consists of the mature polypeptide coding sequence contained in *Aspergillus fumigatus* NN055679.

In another fourth aspect, the isolated polynucleotides encoding polypeptides having cellobiohydrolase II activity comprise or consist of nucleotide sequences that have a degree of identity to the mature polypeptide coding sequence of SEQ ID NO: 167 of preferably at least 80%, more preferably at least 85%, even more preferably at least 90%, most preferably at least 95%, and even most preferably at least 96%, at least 97%, at least 98%, or at least 99%, which encode a polypeptide having cellobiohydrolase II activity.

In one aspect, the isolated polynucleotide encoding a polypeptide having cellobiohydrolase II activity comprises or consists of the nucleotide sequence of SEQ ID NO: 167. In another aspect, the nucleotide sequence comprises or consists of the sequence contained in pGEM-T-CBHII46949-2 which is contained in *E. coli* DSM 24143. In another aspect, the nucleotide sequence comprises or consists of the mature polypeptide coding sequence of SEQ ID NO: 167. In another aspect, the nucleotide sequence comprises or consists of nucleotides 55 to 1749 of SEQ ID NO: 167. In another aspect, the nucleotide sequence comprises or consists of the mature polypeptide coding sequence contained in pGEM-T-CBHII46949-2 which is contained in *E. coli* DSM 24143.

In another fourth aspect, the isolated polynucleotides encoding polypeptides having cellobiohydrolase II activity comprise or consist of nucleotide sequences that have a degree of identity to the mature polypeptide coding sequence of SEQ ID NO: 169 of preferably at least 80%, more preferably at least 85%, even more preferably at least 90%, most preferably at least 95%, and even most preferably at least 96%, at least 97%, at least 98%, or at least 99%, which encode a polypeptide having cellobiohydrolase II activity.

In one aspect, the isolated polynucleotide encoding a polypeptide having cellobiohydrolase II activity comprises or consists of the nucleotide sequence of SEQ ID NO: 169. In another aspect, the nucleotide sequence comprises or consists of the sequence contained in *Penicillium emersonii* NN051602. In another aspect, the nucleotide sequence comprises or consists of the mature polypeptide coding sequence of SEQ ID NO: 169. In another aspect, the nucleotide sequence comprises or consists of nucleotides 58 to 1744 of SEQ ID NO: 169. In another aspect, the nucleotide sequence comprises or consists of the mature polypeptide coding sequence contained in *Penicillium emersonii* NN051602.

In another fourth aspect, the isolated polynucleotides encoding polypeptides having cellobiohydrolase II activity comprise or consist of nucleotide sequences that have a degree of identity to the mature polypeptide coding sequence of SEQ ID NO: 171 of preferably at least 80%, more preferably at least 85%, even more preferably at least 90%, most preferably at least 95%, and even most preferably at least 96%, at least 97%, at least 98%, or at least 99%, which encode a polypeptide having cellobiohydrolase I activity.

In one aspect, the isolated polynucleotide encoding a polypeptide having cellobiohydrolase II activity comprises or consists of the nucleotide sequence of SEQ ID NO: 171. In another aspect, the nucleotide sequence comprises or consists of the sequence contained in *Penicillium pinophilum* NN046877. In another aspect, the nucleotide sequence comprises or consists of the mature polypeptide coding sequence of SEQ ID NO: 171. In another aspect, the nucleotide sequence comprises or consists of nucleotides 58 to 1701 of SEQ ID NO: 171. In another aspect, the nucleotide sequence comprises or consists of the mature polypeptide coding sequence contained in *Penicillium pinophilum* NN046877.

In another fourth aspect, the isolated polynucleotides encoding polypeptides having endoglucanase I activity comprise or consist of nucleotide sequences that have a degree of identity to the mature polypeptide coding sequence of SEQ ID NO: 19 of preferably at least 80%, more preferably at least 85%, even more preferably at least 90%, most preferably at least 95%, and even most preferably at least 96%, at least 97%, at least 98%, or at least 99%, which encode a polypeptide having endoglucanase I activity.

In one aspect, the isolated polynucleotide encoding a polypeptide having endoglucanase I activity comprises or consists of the nucleotide sequence of SEQ ID NO: 19. In another aspect, the nucleotide sequence comprises or consists of the sequence contained in *Aspergillus terreus ATCC* 28865. In another aspect, the nucleotide sequence comprises or consists of the mature polypeptide coding sequence of SEQ ID NO: 19. In another aspect, the nucleotide sequence comprises or consists of nucleotides 64 to 1502 of SEQ ID NO: 19. In another aspect, the nucleotide sequence comprises or consists of the mature polypeptide coding sequence contained in *Aspergillus terreus* ATCC 28865.

In another fourth aspect, the isolated polynucleotides encoding polypeptides having endoglucanase II activity comprise or consist of nucleotide sequences that have a degree of identity to the mature polypeptide coding sequence of SEQ ID NO: 21 of preferably at least 80%, more preferably at least 85%, even more preferably at least 90%, most preferably at least 95%, and even most preferably at least 96%, at least 97%, at least 98%, or at least 99%, which encode a polypeptide having endoglucanase II activity.

In one aspect, the isolated polynucleotide encoding a polypeptide having endoglucanase II activity comprises or consists of the nucleotide sequence of SEQ ID NO: 21. In another aspect, the nucleotide sequence comprises or consists of the sequence contained in *Trichoderma reesei* RutC30. In another aspect, the nucleotide sequence comprises or consists of the mature polypeptide coding sequence of SEQ ID NO: 21. In another aspect, the nucleotide sequence comprises or consists of nucleotides 64 to 1254 of SEQ ID NO: 21. In another aspect, the nucleotide sequence comprises or consists of the mature polypeptide coding sequence contained in *Trichoderma reesei* RutC30.

In another fourth aspect, the isolated polynucleotides encoding polypeptides having endoglucanase II activity comprise or consist of nucleotide sequences that have a degree of identity to the mature polypeptide coding sequence of SEQ ID NO: 23 of preferably at least 80%, more preferably at least 85%, even more preferably at least 90%, most preferably at least 95%, and even most preferably at least 96%, at least 97%, at least 98%, or at least 99%, which encode a polypeptide having endoglucanase II activity.

In one aspect, the isolated polynucleotide encoding a polypeptide having endoglucanase II activity comprises or consists of the nucleotide sequence of SEQ ID NO: 23. In another aspect, the nucleotide sequence comprises or consists of the sequence contained in plasmid pCIC161 which is contained in *E. coli* NRRL B-30902. In another aspect, the nucleotide sequence comprises or consists of the mature polypeptide coding sequence of SEQ ID NO: 23. In another aspect, the nucleotide sequence comprises or consists of nucleotides 67 to 1185 of SEQ ID NO: 23. In another aspect, the nucleotide sequence comprises or consists of the mature polypeptide coding sequence contained in plasmid pCIC161 which is contained in *E. coli* NRRL B-30902.

In another fourth aspect, the isolated polynucleotides encoding polypeptides having endoglucanase II activity comprise or consist of nucleotide sequences that have a degree of identity to the mature polypeptide coding sequence of SEQ ID NO: 25 of preferably at least 80%, more preferably at least 85%, even more preferably at least 90%, most preferably at least 95%, and even most preferably at least 96%, at least 97%, at least 98%, or at least 99%, which encode a polypeptide having endoglucanase II activity.

In one aspect, the isolated polynucleotide encoding a polypeptide having endoglucanase II activity comprises or consists of the nucleotide sequence of SEQ ID NO: 25. In another aspect, the nucleotide sequence comprises or consists of the sequence contained in *Thermoascus aurantiacus* CGMCC 0670. In another aspect, the nucleotide sequence comprises or consists of the mature polypeptide coding sequence of SEQ ID NO: 25. In another aspect, the nucleotide sequence comprises or consists of nucleotides 91 to 1005 of SEQ ID NO: 25. In another aspect, the nucleotide sequence comprises or consists of the mature polypeptide coding sequence contained in *Thermoascus aurantiacus* CGMCC 0670.

In another fourth aspect, the isolated polynucleotides encoding polypeptides having endoglucanase II activity comprise or consist of nucleotide sequences that have a degree of identity to the mature polypeptide coding sequence of SEQ ID NO: 173 of preferably at least 80%, more preferably at least 85%, even more preferably at least 90%, most preferably at least 95%, and even most preferably at least 96%, at least 97%, at least 98%, or at least 99%, which encode a polypeptide having endoglucanase II activity.

In one aspect, the isolated polynucleotide encoding a polypeptide having endoglucanase II activity comprises or consists of the nucleotide sequence of SEQ ID NO: 173. In another aspect, the nucleotide sequence comprises or consists of the sequence contained in p *Aspergillus fumigatus* NN051616. In another aspect, the nucleotide sequence comprises or consists of the mature polypeptide coding sequence of SEQ ID NO: 173. In another aspect, the nucleotide sequence comprises or consists of nucleotides 55 to 1230 of SEQ ID NO: 173. In another aspect, the nucleotide sequence comprises or consists of the mature polypeptide coding sequence contained in *Aspergillus fumigatus* NN051616.

In another fourth aspect, the isolated polynucleotides encoding polypeptides having endoglucanase II activity comprise or consist of nucleotide sequences that have a degree of identity to the mature polypeptide coding sequence of SEQ ID NO: 175 of preferably at least 80%, more preferably at least 85%, even more preferably at least 90%, most preferably at least 95%, and even most preferably at least 96%, at least 97%, at least 98%, or at least 99%, which encode a polypeptide having endoglucanase II activity.

In one aspect, the isolated polynucleotide encoding a polypeptide having endoglucanase II activity comprises or consists of the nucleotide sequence of SEQ ID NO: 175. In another aspect, the nucleotide sequence comprises or consists of the sequence contained in *Neosartorya fischeri* NRRL 181. In another aspect, the nucleotide sequence comprises or consists of the mature polypeptide coding sequence of SEQ ID NO: 175. In another aspect, the nucleotide sequence comprises or consists of nucleotides 49 to 1378 of SEQ ID NO: 175. In another aspect, the nucleotide sequence comprises or consists of the mature polypeptide coding sequence contained in *Neosartorya fischeri* NRRL 181.

In another fourth aspect, the isolated polynucleotides encoding polypeptides having beta-glucosidase activity comprise or consist of nucleotide sequences that have a degree of identity to the mature polypeptide coding sequence of SEQ ID NO: 27 of preferably at least 80%, more preferably at least 85%, even more preferably at least 90%, most preferably at least 95%, and even most preferably at least 96%, at least 97%, at least 98%, or at least 99%, which encode a polypeptide having beta-glucosidase activity.

In one aspect, the isolated polynucleotide encoding a polypeptide having beta-glucosidase activity comprises or consists of the nucleotide sequence of SEQ ID NO: 27. In another aspect, the nucleotide sequence comprises or consists of the sequence contained in plasmid pEJG113 which is contained in *E. coli* NRRL B-30695. In another aspect, the nucleotide sequence comprises or consists of the mature polypeptide coding sequence of SEQ ID NO: 27. In another aspect, the nucleotide sequence comprises or consists of nucleotides 58 to 2580 of SEQ ID NO: 27. In another aspect, the nucleotide sequence comprises or consists of the mature polypeptide coding sequence contained in plasmid pEJG113 which is contained in *E. coli* NRRL B-30695.

In another fourth aspect, the isolated polynucleotides encoding polypeptides having beta-glucosidase activity comprise or consist of nucleotide sequences that have a degree of identity to the mature polypeptide coding sequence of SEQ ID NO: 29 of preferably at least 80%, more preferably at least 85%, even more preferably at least 90%, most preferably at least 95%, and even most preferably at least 96%, at least 97%, at least 98%, or at least 99%, which encode a polypeptide having beta-glucosidase activity.

In one aspect, the isolated polynucleotide encoding a polypeptide having beta-glucosidase activity comprises or consists of the nucleotide sequence of SEQ ID NO: 29. In another aspect, the nucleotide sequence comprises or consists of the sequence contained in plasmid pKKAB which is contained in *E. coli* NRRL B-30860. In another aspect, the nucleotide sequence comprises or consists of the mature polypeptide coding sequence of SEQ ID NO: 29. In another aspect, the nucleotide sequence comprises or consists of nucleotides 171 to 2753 of SEQ ID NO: 29. In another aspect, the nucleotide sequence comprises or consists of the mature polypeptide coding sequence contained in plasmid pKKAB which is contained in *E. coli* NRRL B-30860.

In another fourth aspect, the isolated polynucleotides encoding polypeptides having beta-glucosidase activity comprise or consist of nucleotide sequences that have a degree of identity to the mature polypeptide coding sequence of SEQ ID NO: 31 of preferably at least 80%, more preferably at least 85%, even more preferably at least 90%, most preferably at least 95%, and even most preferably at least 96%, at least 97%, at least 98%, or at least 99%, which encode a polypeptide having beta-glucosidase activity.

In one aspect, the isolated polynucleotide encoding a polypeptide having beta-glucosidase activity comprises or consists of the nucleotide sequence of SEQ ID NO: 31. In another aspect, the nucleotide sequence comprises or consists of the sequence contained in *Aspergillus niger* IBT 10140. In another aspect, the nucleotide sequence comprises or consists of the mature polypeptide coding sequence of SEQ ID NO: 31. In another aspect, the nucleotide sequence comprises or consists of nucleotides 58 to 2934 of SEQ ID NO: 31. In another aspect, the nucleotide sequence comprises or consists of the mature polypeptide coding sequence contained in *Aspergillus niger* IBT 10140.

In another fourth aspect, the isolated polynucleotides encoding polypeptides having beta-glucosidase activity comprise or consist of nucleotide sequences that have a degree of identity to the mature polypeptide coding sequence of SEQ ID NO: 177 of preferably at least 80%, more preferably at least 85%, even more preferably at least 90%, most preferably at least 95%, and even most preferably at least 96%, at least 97%, at least 98%, or at least 99%, which encode a polypeptide having beta-glucosidase activity.

In one aspect, the isolated polynucleotide encoding a polypeptide having beta-glucosidase activity comprises or consists of the nucleotide sequence of SEQ ID NO: 177. In another aspect, the nucleotide sequence comprises or consists of the sequence contained in *Aspergillus aculeatus* WDCM190. In another aspect, the nucleotide sequence comprises or consists of the mature polypeptide coding sequence of SEQ ID NO: 177. In another aspect, the nucleotide sequence comprises or consists of nucleotides 58 to 2937 of SEQ ID NO: 177. In another aspect, the nucleotide sequence comprises or consists of the mature polypeptide coding sequence contained in *Aspergillus aculeatus* WDCM190.

In another fourth aspect, the isolated polynucleotides encoding polypeptides having beta-glucosidase activity comprise or consist of nucleotide sequences that have a degree of identity to the mature polypeptide coding sequence of SEQ ID NO: 179 of preferably at least 80%, more preferably at least 85%, even more preferably at least 90%, most preferably at least 95%, and even most preferably at least 96%, at least 97%, at least 98%, or at least 99%, which encode a polypeptide having beta-glucosidase activity.

In one aspect, the isolated polynucleotide encoding a polypeptide having beta-glucosidase activity comprises or consists of the nucleotide sequence of SEQ ID NO: 179. In another aspect, the nucleotide sequence comprises or consists of the sequence contained in *Aspergillus kawashii* IFO4308. In another aspect, the nucleotide sequence comprises or consists of the mature polypeptide coding sequence of SEQ ID NO: 179. In another aspect, the nucleotide sequence comprises or consists of nucleotides 58 to 2932 of SEQ ID NO: 179. In another aspect, the nucleotide sequence comprises or consists of the mature polypeptide coding sequence contained in *Aspergillus kawashii* IFO4308.

In another fourth aspect, the isolated polynucleotides encoding polypeptides having beta-glucosidase activity comprise or consist of nucleotide sequences that have a degree of identity to the mature polypeptide coding sequence of SEQ ID NO: 181 of preferably at least 80%, more preferably at least 85%, even more preferably at least 90%, most preferably at least 95%, and even most preferably at least 96%, at least 97%, at least 98%, or at least 99%, which encode a polypeptide having beta-glucosidase activity.

In one aspect, the isolated polynucleotide encoding a polypeptide having beta-glucosidase activity comprises or consists of the nucleotide sequence of SEQ ID NO: 181. In another aspect, the nucleotide sequence comprises or consists of the sequence contained in p *Aspergillus clavatus* NRRL 1. In another aspect, the nucleotide sequence comprises or consists of the mature polypeptide coding sequence of SEQ ID NO: 181. In another aspect, the nucleotide sequence comprises or consists of nucleotides 55 to 3059 of SEQ ID NO: 181. In another aspect, the nucleotide sequence comprises or consists of the mature polypeptide coding sequence contained in *Aspergillus clavatus* NRRL 1.

In another fourth aspect, the isolated polynucleotides encoding polypeptides having beta-glucosidase activity comprise or consist of nucleotide sequences that have a degree of identity to the mature polypeptide coding sequence of SEQ ID NO: 183 of preferably at least 80%, more preferably at least 85%, even more preferably at least 90%, most preferably at least 95%, and even most preferably at least 96%, at least 97%, at least 98%, or at least 99%, which encode a polypeptide having beta-glucosidase activity.

In one aspect, the isolated polynucleotide encoding a polypeptide having beta-glucosidase activity comprises or consists of the nucleotide sequence of SEQ ID NO: 183. In another aspect, the nucleotide sequence comprises or consists of the sequence contained in *Thielavia terrestris* NRRL 8126. In another aspect, the nucleotide sequence comprises or consists of the mature polypeptide coding sequence of SEQ ID NO: 183. In another aspect, the nucleotide sequence comprises or consists of nucleotides 55 to 3029 of SEQ ID NO: 183. In another aspect, the nucleotide sequence comprises or consists of the mature polypeptide coding sequence contained in *Thielavia terrestris* NRRL 8126.

In another fourth aspect, the isolated polynucleotides encoding polypeptides having beta-glucosidase activity comprise or consist of nucleotide sequences that have a degree of identity to the mature polypeptide coding sequence of SEQ ID NO: 185 of preferably at least 80%, more preferably at least 85%, even more preferably at least 90%, most preferably at least 95%, and even most preferably at least 96%, at least 97%, at least 98%, or at least 99%, which encode a polypeptide having beta-glucosidase activity.

In one aspect, the isolated polynucleotide encoding a polypeptide having beta-glucosidase activity comprises or consists of the nucleotide sequence of SEQ ID NO: 185. In another aspect, the nucleotide sequence comprises or consists of the sequence contained in pUC19 D55EX which is contained in *E. coli* NRRL B-50395. In another aspect, the nucleotide sequence comprises or consists of the mature polypeptide coding sequence of SEQ ID NO: 185. In another aspect, the nucleotide sequence comprises or consists of nucleotides 64 to 2790 of SEQ ID NO: 185. In another aspect, the nucleotide sequence comprises or consists of the mature polypeptide coding sequence contained in pUC19 D55EX which is contained in *E. coli* NRRL B-50395.

In another fourth aspect, the isolated polynucleotides encoding polypeptides having beta-glucosidase activity comprise or consist of nucleotide sequences that have a degree of identity to the mature polypeptide coding sequence of SEQ ID NO: 187 of preferably at least 80%, more preferably at least 85%, even more preferably at least 90%, most preferably at least 95%, and even most preferably at least 96%, at least 97%, at least 98%, or at least 99%, which encode a polypeptide having beta-glucosidase activity.

In one aspect, the isolated polynucleotide encoding a polypeptide having beta-glucosidase activity comprises or consists of the nucleotide sequence of SEQ ID NO: 187. In another aspect, the nucleotide sequence comprises or consists of the sequence contained in *Penicillium oxalicum*. In another aspect, the nucleotide sequence comprises or consists of the mature polypeptide coding sequence of SEQ ID NO: 187. In another aspect, the nucleotide sequence comprises or consists of nucleotides 64 to 2790 of SEQ ID NO: 187. In another aspect, the nucleotide sequence comprises or consists of the mature polypeptide coding sequence contained in *Penicillium oxalicum.*

In another fourth aspect, the isolated polynucleotides encoding polypeptides having beta-glucosidase activity comprise or consist of nucleotide sequences that have a degree of identity to the mature polypeptide coding sequence of SEQ ID NO: 189 of preferably at least 80%, more preferably at least 85%, even more preferably at least 90%, most preferably at least 95%, and even most preferably at least 96%, at least 97%, at least 98%, or at least 99%, which encode a polypeptide having beta-glucosidase activity.

In one aspect, the isolated polynucleotide encoding a polypeptide having beta-glucosidase activity comprises or consists of the nucleotide sequence of SEQ ID NO: 189. In another aspect, the nucleotide sequence comprises or consists of the sequence contained in *Talaromyces emersonii* CBS 549.92. In another aspect, the nucleotide sequence comprises or consists of the mature polypeptide coding sequence of SEQ ID NO: 189. In another aspect, the nucleotide sequence comprises or consists of nucleotides 58 to 2961 of SEQ ID NO: 189. In another aspect, the nucleotide sequence comprises or consists of the mature polypeptide coding sequence contained in *Talaromyces emersonii* CBS 549.92.

In another fourth aspect, the isolated polynucleotides encoding GH61 polypeptides having cellulolytic enhancing activity comprise or consist of nucleotide sequences that have a degree of identity to the mature polypeptide coding sequence of SEQ ID NO: 33 of preferably at least 80%, more preferably at least 85%, even more preferably at least 90%, most preferably at least 95%, and even most preferably at least 96%, at least 97%, at least 98%, or at least 99%, which encode a polypeptide having cellulolytic enhancing activity.

In one aspect, the isolated polynucleotide encoding a polypeptide having cellulolytic enhancing activity comprises or consists of the nucleotide sequence of SEQ ID NO: 33. In another aspect, the nucleotide sequence comprises or consists of the sequence contained in plasmid pDZA2-7 which is contained in *E. coli* NRRL B-30704. In another aspect, the nucleotide sequence comprises or consists of the mature polypeptide coding sequence of SEQ ID NO: 33. In another aspect, the nucleotide sequence comprises or consists of nucleotides 67 to 796 of SEQ ID NO: 33. In another aspect, the nucleotide sequence comprises or consists of the mature polypeptide coding sequence contained in plasmid pDZA2-7 which is contained in *E. coli* NRRL B-30704.

In another fourth aspect, the isolated polynucleotides encoding GH61 polypeptides having cellulolytic enhancing activity comprise or consist of nucleotide sequences that have a degree of identity to the mature polypeptide coding sequence of SEQ ID NO: 35 of preferably at least 80%, more preferably at least 85%, even more preferably at least 90%, most preferably at least 95%, and even most preferably at least 96%, at least 97%, at least 98%, or at least 99%, which encode a polypeptide having cellulolytic enhancing activity.

In one aspect, the isolated polynucleotide encoding a polypeptide having cellulolytic enhancing activity comprises or consists of the nucleotide sequence of SEQ ID NO: 35. In another aspect, the nucleotide sequence comprises or consists of the sequence contained in plasmid pTter61E which is contained in *E. coli* NRRL B-30814. In another aspect, the nucleotide sequence comprises or consists of the mature polypeptide coding sequence of SEQ ID NO: 35. In another aspect, the nucleotide sequence comprises or consists of nucleotides 58 to 900 of SEQ ID NO: 35. In another aspect, the nucleotide sequence comprises or consists of the mature polypeptide coding sequence contained in plasmid pTter61E which is contained in *E. coli* NRRL B-30814.

In another fourth aspect, the isolated polynucleotides encoding GH61 polypeptides having cellulolytic enhancing activity comprise or consist of nucleotide sequences that have a degree of identity to the mature polypeptide coding sequence of SEQ ID NO: 37 of preferably at least 80%, more preferably at least 85%, even more preferably at least 90%, most preferably at least 95%, and even most preferably at least 96%, at least 97%, at least 98%, or at least 99%, which encode a polypeptide having cellulolytic enhancing activity.

In one aspect, the isolated polynucleotide encoding a polypeptide having cellulolytic enhancing activity comprises or consists of the nucleotide sequence of SEQ ID NO: 37. In another aspect, the nucleotide sequence comprises or consists of the sequence contained in *Aspergillus fumigatus* NN051616. In another aspect, the nucleotide sequence comprises or consists of the mature polypeptide coding sequence of SEQ ID NO: 37. In another aspect, the nucleotide sequence comprises or consists of nucleotides 64 to 859 of SEQ ID NO: 37. In another aspect, the nucleotide sequence comprises or consists of the mature polypeptide coding sequence contained in *Aspergillus fumigatus* NN051616.

In another fourth aspect, the isolated polynucleotides encoding GH61 polypeptides having cellulolytic enhancing activity comprise or consist of nucleotide sequences that have a degree of identity to the mature polypeptide coding sequence of SEQ ID NO: 39 of preferably at least 80%, more preferably at least 85%, even more preferably at least 90%, most preferably at least 95%, and even most preferably at least 96%, at least 97%, at least 98%, or at least 99%, which encode a polypeptide having cellulolytic enhancing activity.

In one aspect, the isolated polynucleotide encoding a polypeptide having cellulolytic enhancing activity comprises or consists of the nucleotide sequence of SEQ ID NO: 39. In another aspect, the nucleotide sequence comprises or consists of the sequence contained in plasmid pGEM-T-Ppin7 which is contained in *E. coli* DSM 22711. In another aspect, the nucleotide sequence comprises or consists of the mature polypeptide coding sequence of SEQ ID NO: 39. In another aspect, the nucleotide sequence comprises or consists of nucleotides 64 to 1018 of SEQ ID NO: 39. In another aspect, the nucleotide sequence comprises or consists of the mature polypeptide coding sequence contained in plasmid pGEM-T-Ppin7 which is contained in *E. coli* DSM 22711.

In another fourth aspect, the isolated polynucleotides encoding GH61 polypeptides having cellulolytic enhancing activity comprise or consist of nucleotide sequences that have a degree of identity to the mature polypeptide coding sequence of SEQ ID NO: 41 of preferably at least 80%, more preferably at least 85%, even more preferably at least 90%, most preferably at least 95%, and even most preferably at least 96%, at least 97%, at least 98%, or at least 99%, which encode a polypeptide having cellulolytic enhancing activity.

In one aspect, the isolated polynucleotide encoding a polypeptide having cellulolytic enhancing activity comprises or consists of the nucleotide sequence of SEQ ID NO: 41. In another aspect, the nucleotide sequence comprises or consists of the sequence contained in plasmid pGEM-T-GH61D23Y4 which is contained in *E. coli* DSM 22882. In another aspect, the nucleotide sequence comprises or consists of the mature polypeptide coding sequence of SEQ ID NO: 41. In another aspect, the nucleotide sequence comprises or consists of nucleotides 76 to 832 of SEQ ID NO: 41. In another aspect, the nucleotide sequence comprises or consists of the mature polypeptide coding sequence contained in plasmid pGEM-T-GH61D23Y4 which is contained in *E. coli* DSM 22882.

In another fourth aspect, the isolated polynucleotides encoding GH61 polypeptides having cellulolytic enhancing activity comprise or consist of nucleotide sequences that have a degree of identity to the mature polypeptide coding sequence of SEQ ID NO: 43 of preferably at least 80%, more preferably at least 85%, even more preferably at least 90%, most preferably at least 95%, and even most preferably at least 96%, at least 97%, at least 98%, or at least 99%, which encode a polypeptide having cellulolytic enhancing activity.

In one aspect, the isolated polynucleotide encoding a polypeptide having cellulolytic enhancing activity comprises or consists of the nucleotide sequence of SEQ ID NO: 43. In another aspect, the nucleotide sequence comprises or consists of the sequence contained in plasmid pAG68 which is contained in *E. coli* NRRL B-50320. In another aspect, the nucleotide sequence comprises or consists of the mature polypeptide coding sequence of SEQ ID NO: 43. In another aspect, the nucleotide sequence comprises or consists of nucleotides 64 to 1104 of SEQ ID NO: 43. In another aspect, the nucleotide sequence comprises or consists of the mature polypeptide coding sequence contained in plasmid pAG68 which is contained in *E. coli* NRRL B-50320.

In another fourth aspect, the isolated polynucleotides encoding GH61 polypeptides having cellulolytic enhancing activity comprise or consist of nucleotide sequences that have a degree of identity to the mature polypeptide coding sequence of SEQ ID NO: 191 of preferably at least 80%, more preferably at least 85%, even more preferably at least 90%, most preferably at least 95%, and even most preferably at least 96%, at least 97%, at least 98%, or at least 99%, which encode a GH61 polypeptide having cellulolytic enhancing activity.

In one aspect, the isolated polynucleotide encoding a GH61 polypeptide having cellulolytic enhancing activity comprises or consists of the nucleotide sequence of SEQ ID NO: 191. In another aspect, the nucleotide sequence comprises or consists of the sequence contained in pGEM-T-GH61a51486 which is contained in *E. coli* DSM 22656. In another aspect, the nucleotide sequence comprises or consists of the mature polypeptide coding sequence of SEQ ID NO: 191. In another aspect, the nucleotide sequence comprises or consists of nucleotides 67 to 868 of SEQ ID NO: 191. In another aspect, the nucleotide sequence comprises or consists of the mature polypeptide coding sequence contained in pGEM-T-GH61a51486 which is contained in *E. coli* NRRL DSM 22656.

In another fourth aspect, the isolated polynucleotides encoding polypeptides having xylanase activity comprise or consist of nucleotide sequences that have a degree of identity to the mature polypeptide coding sequence of SEQ ID NO: 45 of preferably at least 80%, more preferably at least 85%, even more preferably at least 90%, most preferably at least 95%, and even most preferably at least 96%, at least 97%, at least 98%, or at least 99%, which encode an active polypeptide.

In one aspect, the isolated polynucleotide encoding a polypeptide having xylanase activity comprises or consists of the nucleotide sequence of SEQ ID NO: 45. In another aspect, the nucleotide sequence comprises or consists of the sequence contained in *Aspergillus aculeatus* CBS 101.43. In another aspect, the nucleotide sequence comprises or consists of the mature polypeptide coding sequence of SEQ ID NO: 45. In another aspect, the nucleotide sequence comprises or consists of nucleotides 69 to 1314 of SEQ ID NO: 45. In another aspect, the nucleotide sequence comprises or consists of the mature polypeptide coding sequence contained in *Aspergillus aculeatus* CBS 101.43.

In another fourth aspect, the isolated polynucleotides encoding polypeptides having xylanase activity comprise or consist of nucleotide sequences that have a degree of identity to the mature polypeptide coding sequence of SEQ ID NO: 47 of preferably at least 80%, more preferably at least 85%, even more preferably at least 90%, most preferably at least 95%, and even most preferably at least 96%, at least 97%, at least 98%, or at least 99%, which encode an active polypeptide.

In one aspect, the isolated polynucleotide encoding a polypeptide having xylanase activity comprises or consists of the nucleotide sequence of SEQ ID NO: 47. In another aspect, the nucleotide sequence comprises or consists of the sequence contained in plasmid pHyGe009 which is contained in *E. coli* NRRL B-30703. In another aspect, the nucleotide sequence comprises or consists of the mature polypeptide coding sequence of SEQ ID NO: 47. In another aspect, the nucleotide sequence comprises or consists of nucleotides 107 to 1415 of SEQ ID NO: 47. In another aspect, the nucleotide sequence comprises or consists of the mature polypeptide coding sequence contained in plasmid pHyGe009 which is contained in *E. coli* NRRL B-30703.

In another fourth aspect, the isolated polynucleotides encoding polypeptides having xylanase activity comprise or consist of nucleotide sequences that have a degree of identity to the mature polypeptide coding sequence of SEQ ID NO: 49 of preferably at least 80%, more preferably at least 85%, even more preferably at least 90%, most preferably at least 95%, and even most preferably at least 96%, at least 97%, at least 98%, or at least 99%, which encode an active polypeptide.

In one aspect, the isolated polynucleotide encoding a polypeptide having xylanase activity comprises or consists of the nucleotide sequence of SEQ ID NO: 49. In another aspect, the nucleotide sequence comprises or consists of the sequence contained in plasmid pTF12Xy1170 which is contained in *E. coli* NRRL B-50309. In another aspect, the nucleotide sequence comprises or consists of the mature polypeptide coding sequence of SEQ ID NO: 49. In another aspect, the nucleotide sequence comprises or consists of nucleotides 58 to 1194 of SEQ ID NO: 49. In another aspect, the nucleotide sequence comprises or consists of the mature polypeptide coding sequence contained in plasmid pTF12Xy1170 which is contained in *E. coli* NRRL B-50309.

In another fourth aspect, the isolated polynucleotides encoding polypeptides having xylanase activity comprise or consist of nucleotide sequences that have a degree of identity to the mature polypeptide coding sequence of SEQ ID NO: 51 of preferably at least 80%, more preferably at least 85%, even more preferably at least 90%, most preferably at least 95%, and even most preferably at least 96%, at least 97%, at least 98%, or at least 99%, which encode an active polypeptide.

In one aspect, the isolated polynucleotide encoding a polypeptide having xylanase activity comprises or consists of the nucleotide sequence of SEQ ID NO: 51. In another aspect, the nucleotide sequence comprises or consists of the sequence contained in plasmid pGEM-T-Ppin3 which is contained in *E. coli* DSM 22922. In another aspect, the nucleotide sequence comprises or consists of the mature polypeptide coding sequence of SEQ ID NO: 51. In another aspect, the nucleotide sequence comprises or consists of nucleotides 58 to 1439 of SEQ ID NO: 51. In another aspect, the nucleotide sequence comprises or consists of the mature polypeptide coding sequence contained in plasmid pGEM-T-Ppin3 which is contained in *E. coli* DSM 22922.

In another fourth aspect, the isolated polynucleotides encoding polypeptides having xylanase activity comprise or consist of nucleotide sequences that have a degree of identity to the mature polypeptide coding sequence of SEQ ID NO: 53 of preferably at least 80%, more preferably at least 85%, even more preferably at least 90%, most preferably at least 95%, and even most preferably at least 96%, at least 97%, at least 98%, or at least 99%, which encode an active polypeptide.

In one aspect, the isolated polynucleotide encoding a polypeptide having xylanase activity comprises or consists of the nucleotide sequence of SEQ ID NO: 53. In another aspect, the nucleotide sequence comprises or consists of the sequence contained in *Thielavia terrestris* NRRL 8126. In another aspect, the nucleotide sequence comprises or consists of the mature polypeptide coding sequence of SEQ ID NO: 53. In another aspect, the nucleotide sequence comprises or consists of nucleotides 58 to 1185 of SEQ ID NO: 53. In another aspect, the nucleotide sequence comprises or consists of the mature polypeptide coding sequence contained in *Thielavia terrestris* NRRL 8126.

In another fourth aspect, the isolated polynucleotides encoding polypeptides having xylanase activity comprise or consist of nucleotide sequences that have a degree of identity to the mature polypeptide coding sequence of SEQ ID NO: 193 of preferably at least 80%, more preferably at least 85%, even more preferably at least 90%, most preferably at least 95%, and even most preferably at least 96%, at least 97%, at least 98%, or at least 99%, which encode a polypeptide having xylanase activity.

In one aspect, the isolated polynucleotide encoding a polypeptide having xylanase activity comprises or consists of the nucleotide sequence of SEQ ID NO: 193. In another aspect, the nucleotide sequence comprises or consists of the sequence contained in *Talaromyces emersonii* NN05002. In another aspect, the nucleotide sequence comprises or consists of the mature polypeptide coding sequence of SEQ ID NO: 193. In another aspect, the nucleotide sequence comprises or consists of nucleotides 70 to 1383 of SEQ ID NO: 193. In another aspect, the nucleotide sequence comprises or consists of the mature polypeptide coding sequence contained in *Talaromyces emersonii* NN05002.

In another fourth aspect, the isolated polynucleotides encoding polypeptides having xylanase activity comprise or consist of nucleotide sequences that have a degree of identity to the mature polypeptide coding sequence of SEQ ID NO: 195 of preferably at least 80%, more preferably at least 85%, even more preferably at least 90%, most preferably at least 95%, and even most preferably at least 96%, at least 97%, at least 98%, or at least 99%, which encode a polypeptide having xylanase activity.

In one aspect, the isolated polynucleotide encoding a polypeptide having xylanase activity comprises or consists of the nucleotide sequence of SEQ ID NO: 195. In another aspect, the nucleotide sequence comprises or consists of the sequence contained in pMMar26 which is contained in *E. coli* NRRL B-50266. In another aspect, the nucleotide sequence comprises or consists of the mature polypeptide coding sequence of SEQ ID NO: 195. In another aspect, the nucleotide sequence comprises or consists of nucleotides 70 to 1384 of SEQ ID NO: 195. In another aspect, the nucleotide sequence comprises or consists of the mature polypeptide coding sequence contained in pMMar26 which is contained in *E. coli* NRRL B-50266.

In another fourth aspect, the isolated polynucleotides encoding polypeptides having xylanase activity comprise or consist of nucleotide sequences that have a degree of identity to the mature polypeptide coding sequence of SEQ ID NO: 197 of preferably at least 80%, more preferably at least 85%, even more preferably at least 90%, most preferably at least 95%, and even most preferably at least 96%, at least 97%, at least 98%, or at least 99%, which encode a polypeptide having xylanase activity.

In one aspect, the isolated polynucleotide encoding a polypeptide having xylanase activity comprises or consists of the nucleotide sequence of SEQ ID NO: 197. In another aspect, the nucleotide sequence comprises or consists of the sequence contained in *E. coli* DSM 10361. In another aspect, the nucleotide sequence comprises or consists of the mature polypeptide coding sequence of SEQ ID NO: 197. In another aspect, the nucleotide sequence comprises or consists of nucleotides 58 to 1188 of SEQ ID NO: 197. In another aspect, the nucleotide sequence comprises or consists of the mature polypeptide coding sequence contained in *E. coli* DSM 10361.

In another fourth aspect, the isolated polynucleotides encoding polypeptides having xylanase activity comprise or consist of nucleotide sequences that have a degree of identity to the mature polypeptide coding sequence of SEQ ID NO: 55 of preferably at least 80%, more preferably at least 85%, even more preferably at least 90%, most preferably at least 95%, and even most preferably at least 96%, at least 97%, at least 98%, or at least 99%, which encode an active polypeptide.

In one aspect, the isolated polynucleotide encoding a polypeptide having xylanase activity comprises or consists of the nucleotide sequence of SEQ ID NO: 55. In another aspect, the nucleotide sequence comprises or consists of the sequence contained in *Thermobifida fusca* DSM 22883. In another aspect, the nucleotide sequence comprises or consists of the mature polypeptide coding sequence of SEQ ID NO: 55. In another aspect, the nucleotide sequence comprises or consists of nucleotides 127 to 1014 of SEQ ID NO: 55. In another aspect, the nucleotide sequence comprises or consists of the mature polypeptide coding sequence contained in *Thermobifida fusca* DSM 22883.

In another fourth aspect, the isolated polynucleotides encoding polypeptides having xylanase activity comprise or consist of nucleotide sequences that have a degree of identity to the mature polypeptide coding sequence of SEQ ID NO: 199 or SEQ ID NO: 304 of preferably at least 80%, more preferably at least 85%, even more preferably at least 90%, most preferably at least 95%, and even most preferably at least 96%, at least 97%, at least 98%, or at least 99%, which encode a polypeptide having xylanase activity.

In one aspect, the isolated polynucleotide encoding a polypeptide having xylanase activity comprises or consists of the nucleotide sequence of SEQ ID NO: 199 or SEQ ID NO: 304. In another aspect, the nucleotide sequence comprises or consists of the sequence contained in *Dictyoglomus thermophilum* ATCC 35947. In another aspect, the nucleotide sequence comprises or consists of the mature polypeptide coding sequence of SEQ ID NO: 199 or SEQ ID NO: 304. In another aspect, the nucleotide sequence comprises or consists of nucleotides 76 to 1137 of SEQ ID NO: 199 or nucleotides 85 to 693 of SEQ ID NO: 304. In another aspect, the nucleotide sequence comprises or consists of the mature polypeptide coding sequence contained in *Dictyoglomus thermophilum* ATCC 35947.

In another fourth aspect, the isolated polynucleotides encoding polypeptides having beta-xylosidase activity comprise or consist of nucleotide sequences that have a degree of identity to the mature polypeptide coding sequence of SEQ ID NO: 57 of preferably at least 80%, more preferably at least 85%, even more preferably at least 90%, most preferably at least 95%, and even most preferably at least 96%, at least 97%, at least 98%, or at least 99%, which encode an active polypeptide.

In one aspect, the isolated polynucleotide encoding a polypeptide having beta-xylosidase activity comprises or consists of the nucleotide sequence of SEQ ID NO: 57. In another aspect, the nucleotide sequence comprises or consists of the sequence contained in *Trichoderma reesei* RutC30. In another aspect, the nucleotide sequence comprises or consists of the mature polypeptide coding sequence of SEQ ID NO: 57. In another aspect, the nucleotide sequence comprises or consists of nucleotides 61 to 2391 of SEQ ID NO: 57. In another aspect, the nucleotide sequence comprises or consists of the mature polypeptide coding sequence contained in *Trichoderma reesei* RutC30.

In another fourth aspect, the isolated polynucleotides encoding polypeptides having beta-xylosidase activity comprise or consist of nucleotide sequences that have a degree of identity to the mature polypeptide coding sequence of SEQ ID NO: 59 of preferably at least 80%, more preferably at least 85%, even more preferably at least 90%, most preferably at least 95%, and even most preferably at least 96%, at least 97%, at least 98%, or at least 99%, which encode an active polypeptide.

In one aspect, the isolated polynucleotide encoding a polypeptide having beta-xylosidase activity comprises or consists of the nucleotide sequence of SEQ ID NO: 59. In another aspect, the nucleotide sequence comprises or consists of the sequence contained in *Talaromyces emersonii* CBS 393.64. In another aspect, the nucleotide sequence comprises or consists of the mature polypeptide coding sequence of SEQ ID NO: 59. In another aspect, the nucleotide sequence comprises or consists of nucleotides 64 to 2388 of SEQ ID NO: 59. In another aspect, the nucleotide sequence comprises or consists of the mature polypeptide coding sequence contained in *Talaromyces emersonii* CBS 393.64.

In another fourth aspect, the isolated polynucleotides encoding polypeptides having beta-xylosidase activity comprise or consist of nucleotide sequences that have a degree of identity to the mature polypeptide coding sequence of SEQ ID NO: 201 of preferably at least 80%, more preferably at least 85%, even more preferably at least 90%, most preferably at least 95%, and even most preferably at least 96%, at least 97%, at least 98%, or at least 99%, which encode a polypeptide having beta-xylosidase activity.

In one aspect, the isolated polynucleotide encoding a polypeptide having beta-xylosidase activity comprises or consists of the nucleotide sequence of SEQ ID NO: 201. In another aspect, the nucleotide sequence comprises or consists of the sequence contained in *Aspergillus aculeatus* CBS 172.66. In another aspect, the nucleotide sequence comprises or consists of the mature polypeptide coding sequence of SEQ ID NO: 201. In another aspect, the nucleotide sequence comprises or consists of nucleotides 52 to 2409 of SEQ ID NO: 201. In another aspect, the nucleotide sequence comprises or consists of the mature polypeptide coding sequence contained in *Aspergillus aculeatus* CBS 172.66.

In another fourth aspect, the isolated polynucleotides encoding polypeptides having beta-xylosidase activity comprise or consist of nucleotide sequences that have a degree of identity to the mature polypeptide coding sequence of SEQ ID NO: 203 of preferably at least 80%, more preferably at least 85%, even more preferably at least 90%, most preferably at least 95%, and even most preferably at least 96%, at least 97%, at least 98%, or at least 99%, which encode a polypeptide having beta-xylosidase activity.

In one aspect, the isolated polynucleotide encoding a polypeptide having beta-xylosidase activity comprises or consists of the nucleotide sequence of SEQ ID NO: 203. In another aspect, the nucleotide sequence comprises or consists of the sequence contained in *Aspergillus aculeatus* CBS 186.67. In another aspect, the nucleotide sequence comprises or consists of the mature polypeptide coding sequence of SEQ ID NO: 203. In another aspect, the nucleotide sequence comprises or consists of nucleotides 52 to 2451 of SEQ ID NO: 203. In another aspect, the nucleotide sequence comprises or consists of the mature polypeptide coding sequence contained in *Aspergillus aculeatus* CBS 186.67.

In another fourth aspect, the isolated polynucleotides encoding polypeptides having beta-xylosidase activity comprise or consist of nucleotide sequences that have a degree of identity to the mature polypeptide coding sequence of SEQ ID NO: 205 of preferably at least 80%, more preferably at least 85%, even more preferably at least 90%, most preferably at least 95%, and even most preferably at least 96%, at least 97%, at least 98%, or at least 99%, which encode a polypeptide having beta-xylosidase activity.

In one aspect, the isolated polynucleotide encoding a polypeptide having beta-xylosidase activity comprises or consists of the nucleotide sequence of SEQ ID NO: 205. In another aspect, the nucleotide sequence comprises or consists of the sequence contained in *Aspergillus fumigatus* NN051616. In another aspect, the nucleotide sequence comprises or consists of the mature polypeptide coding sequence of SEQ ID NO: 205. In another aspect, the nucleotide sequence comprises or consists of nucleotides 61 to 2376 of SEQ ID NO: 205. In another aspect, the nucleotide sequence comprises or consists of the mature polypeptide coding sequence contained in *Aspergillus fumigatus* NN051616.

In a fifth aspect, the isolated polynucleotides encoding polypeptides having cellobiohydrolase I activity hybridize under preferably medium-high stringency conditions, more preferably high stringency conditions, and most preferably very high stringency conditions with (i) the mature polypeptide coding sequence of SEQ ID NO: 1, (ii) the genomic DNA sequence of the mature polypeptide coding sequence of SEQ ID NO: 1, or (iii) a full-length complementary strand of (i) or (ii).

In another fifth aspect, the isolated polynucleotides encoding polypeptides having cellobiohydrolase I activity hybridize under preferably medium-high stringency conditions, more preferably high stringency conditions, and most preferably very high stringency conditions with (i) the mature polypeptide coding sequence of SEQ ID NO: 3, (ii) the genomic DNA sequence of the mature polypeptide coding sequence of SEQ ID NO: 3, or (iii) a full-length complementary strand of (i) or (ii).

In another fifth aspect, the isolated polynucleotides encoding polypeptides having cellobiohydrolase I activity hybridize under preferably medium-high stringency conditions, more preferably high stringency conditions, and most preferably very high stringency conditions with (i) the mature polypeptide coding sequence of SEQ ID NO: 5, (ii) the cDNA sequence of the mature polypeptide coding sequence of SEQ ID NO: 5, or (iii) a full-length complementary strand of (i) or (ii).

In another fifth aspect, the isolated polynucleotides encoding polypeptides having cellobiohydrolase I activity hybridize under preferably medium-high stringency conditions, more preferably high stringency conditions, and most preferably very high stringency conditions with (i) the mature polypeptide coding sequence of SEQ ID NO: 7, (ii) the genomic DNA sequence of the mature polypeptide coding sequence of SEQ ID NO: 7, or (iii) a full-length complementary strand of (i) or (ii).

In another fifth aspect, the isolated polynucleotides encoding polypeptides having cellobiohydrolase I activity hybridize under preferably medium-high stringency conditions, more preferably high stringency conditions, and most preferably very high stringency conditions with (i) the mature polypeptide coding sequence of SEQ ID NO: 157, (ii) the cDNA sequence of the mature polypeptide coding sequence of SEQ ID NO: 157, or (iii) a full-length complementary strand of (i) or (ii).

In another fifth aspect, the isolated polynucleotides encoding polypeptides having cellobiohydrolase I activity hybridize under preferably medium-high stringency conditions, more preferably high stringency conditions, and most preferably very high stringency conditions with (i) the mature polypeptide coding sequence of SEQ ID NO: 159, (ii) the cDNA sequence of the mature polypeptide coding sequence of SEQ ID NO: 159, or (iii) a full-length complementary strand of (i) or (ii).

In another fifth aspect, the isolated polynucleotides encoding polypeptides having cellobiohydrolase I activity hybridize under preferably medium-high stringency conditions, more preferably high stringency conditions, and most preferably very high stringency conditions with (i) the mature polypeptide coding sequence of SEQ ID NO: 161, (ii) the cDNA sequence of the mature polypeptide coding sequence of SEQ ID NO: 161, or (iii) a full-length complementary strand of (i) or (ii).

In another fifth aspect, the isolated polynucleotides encoding polypeptides having cellobiohydrolase I activity hybridize under preferably medium-high stringency conditions, more preferably high stringency conditions, and most preferably very high stringency conditions with (i) the mature polypeptide coding sequence of SEQ ID NO: 163, (ii) the cDNA sequence of the mature polypeptide coding sequence of SEQ ID NO: 163, or (iii) a full-length complementary strand of (i) or (ii).

In another fifth aspect, the isolated polynucleotides encoding polypeptides having cellobiohydrolase I activity hybridize under preferably medium-high stringency conditions, more preferably high stringency conditions, and most preferably very high stringency conditions with (i) the mature polypeptide coding sequence of SEQ ID NO: 165, (ii) the cDNA sequence of the mature polypeptide coding sequence of SEQ ID NO: 165, or (iii) a full-length complementary strand of (i) or (ii).

In another fifth aspect, the isolated polynucleotides encoding polypeptides having cellobiohydrolase II activity hybridize under preferably medium-high stringency conditions, more preferably high stringency conditions, and most preferably very high stringency conditions with (i) the mature polypeptide coding sequence of SEQ ID NO: 9, (ii) the cDNA sequence of the mature polypeptide coding sequence of SEQ ID NO: 9, or (iii) a full-length complementary strand of (i) or (ii).

In another fifth aspect, the isolated polynucleotides encoding polypeptides having cellobiohydrolase II activity hybridize under preferably medium-high stringency conditions, more preferably high stringency conditions, and most preferably very high stringency conditions with (i) the mature polypeptide coding sequence of SEQ ID NO: 11, (ii) the cDNA sequence of the mature polypeptide coding sequence of SEQ ID NO: 11, or (iii) a full-length complementary strand of (i) or (ii).

In another fifth aspect, the isolated polynucleotides encoding polypeptides having cellobiohydrolase II activity hybridize under preferably medium-high stringency conditions, more preferably high stringency conditions, and most preferably very high stringency conditions with (i) the mature polypeptide coding sequence of SEQ ID NO: 13, (ii) the genomic DNA sequence of the mature polypeptide coding sequence of SEQ ID NO: 13, or (iii) a full-length complementary strand of (i) or (ii).

In another fifth aspect, the isolated polynucleotides encoding polypeptides having cellobiohydrolase II activity hybridize under preferably medium-high stringency conditions, more preferably high stringency conditions, and most preferably very high stringency conditions with (i) the mature polypeptide coding sequence of SEQ ID NO: 15, (ii) the genomic DNA sequence of the mature polypeptide coding sequence of SEQ ID NO: 15, or (iii) a full-length complementary strand of (i) or (ii).

In another fifth aspect, the isolated polynucleotides encoding polypeptides having cellobiohydrolase II activity hybridize under preferably medium-high stringency conditions, more preferably high stringency conditions, and most preferably very high stringency conditions with (i) the mature polypeptide coding sequence of SEQ ID NO: 17, (ii) the cDNA sequence of the mature polypeptide coding sequence of SEQ ID NO: 17, or (iii) a full-length complementary strand of (i) or (ii).

In another fifth aspect, the isolated polynucleotides encoding polypeptides having cellobiohydrolase II activity hybridize under preferably medium-high stringency conditions, more preferably high stringency conditions, and most preferably very high stringency conditions with (i) the mature polypeptide coding sequence of SEQ ID NO: 167, (ii) the cDNA sequence of the mature polypeptide coding sequence of SEQ ID NO: 167, or (iii) a full-length complementary strand of (i) or (ii).

In another fifth aspect, the isolated polynucleotides encoding polypeptides having cellobiohydrolase II activity hybridize under preferably medium-high stringency conditions, more preferably high stringency conditions, and most preferably very high stringency conditions with (i) the mature polypeptide coding sequence of SEQ ID NO: 169, (ii) the cDNA sequence of the mature polypeptide coding sequence of SEQ ID NO: 169, or (iii) a full-length complementary strand of (i) or (ii).

In another fifth aspect, the isolated polynucleotides encoding polypeptides having cellobiohydrolase II activity hybridize under preferably medium-high stringency conditions, more preferably high stringency conditions, and most preferably very high stringency conditions with (i) the mature polypeptide coding sequence of SEQ ID NO: 171, (ii) the cDNA sequence of the mature polypeptide coding sequence of SEQ ID NO: 171, or (iii) a full-length complementary strand of (i) or (ii).

In another fifth aspect, the isolated polynucleotides encoding polypeptides having endoglucanase I activity hybridize under preferably medium-high stringency conditions, more preferably high stringency conditions, and most preferably very high stringency conditions with (i) the mature polypeptide coding sequence of SEQ ID NO: 19, (ii) the cDNA sequence of the mature polypeptide coding sequence of SEQ ID NO: 19, or (iii) a full-length complementary strand of (i) or (ii).

In another fifth aspect, the isolated polynucleotides encoding polypeptides having endoglucanase II activity hybridize under preferably medium-high stringency conditions, more preferably high stringency conditions, and most preferably very high stringency conditions with (i) the mature polypeptide coding sequence of SEQ ID NO: 21, (ii) the genomic DNA sequence of the mature polypeptide coding sequence of SEQ ID NO: 21, or (iii) a full-length complementary strand of (i) or (ii).

In another fifth aspect, the isolated polynucleotides encoding polypeptides having endoglucanase II activity hybridize under preferably medium-high stringency conditions, more preferably high stringency conditions, and most preferably very high stringency conditions with (i) the mature polypeptide coding sequence of SEQ ID NO: 23, (ii) the cDNA sequence of the mature polypeptide coding sequence of SEQ ID NO: 23, or (iii) a full-length complementary strand of (i) or (ii).

In another fifth aspect, the isolated polynucleotides encoding polypeptides having endoglucanase II activity hybridize under preferably medium-high stringency conditions, more preferably high stringency conditions, and most preferably very high stringency conditions with (i) the mature polypeptide coding sequence of SEQ ID NO: 25, (ii) the genomic DNA sequence of the mature polypeptide coding sequence of SEQ ID NO: 25, or (iii) a full-length complementary strand of (i) or (ii).

In another fifth aspect, the isolated polynucleotides encoding polypeptides having endoglucanase II activity hybridize under preferably medium-high stringency conditions, more preferably high stringency conditions, and most preferably very high stringency conditions with (i) the mature polypeptide coding sequence of SEQ ID NO: 173, (ii) the cDNA sequence of the mature polypeptide coding sequence of SEQ ID NO: 173, or (iii) a full-length complementary strand of (i) or (ii).

In another fifth aspect, the isolated polynucleotides encoding polypeptides having endoglucanase II activity hybridize under preferably medium-high stringency conditions, more preferably high stringency conditions, and most preferably very high stringency conditions with (i) the mature polypeptide coding sequence of SEQ ID NO: 175, (ii) the cDNA sequence of the mature polypeptide coding sequence of SEQ ID NO: 175, or (iii) a full-length complementary strand of (i) or (ii).

In another fifth aspect, the isolated polynucleotides encoding polypeptides having beta-glucosidase activity hybridize under preferably medium-high stringency conditions, more preferably high stringency conditions, and most preferably very high stringency conditions with (i) the mature polypeptide coding sequence of SEQ ID NO: 27, (ii) the cDNA sequence of the mature polypeptide coding sequence of SEQ ID NO: 27, or (iii) a full-length complementary strand of (i) or (ii).

In another fifth aspect, the isolated polynucleotides encoding polypeptides having beta-glucosidase activity hybridize under preferably medium-high stringency conditions, more preferably high stringency conditions, and most preferably very high stringency conditions with (i) the mature polypeptide coding sequence of SEQ ID NO: 29, (ii) the cDNA sequence of the mature polypeptide coding sequence of SEQ ID NO: 29, or (iii) a full-length complementary strand of (i) or (ii).

In another fifth aspect, the isolated polynucleotides encoding polypeptides having beta-glucosidase activity hybridize under preferably medium-high stringency conditions, more preferably high stringency conditions, and most preferably very high stringency conditions with (i) the mature polypeptide coding sequence of SEQ ID NO: 31, (ii) the cDNA sequence of the mature polypeptide coding sequence of SEQ ID NO: 31, or (iii) a full-length complementary strand of (i) or (ii).

In another fifth aspect, the isolated polynucleotides encoding polypeptides having beta-glucosidase activity hybridize under preferably medium-high stringency conditions, more preferably high stringency conditions, and most preferably very high stringency conditions with (i) the mature polypeptide coding sequence of SEQ ID NO: 177, (ii) the cDNA sequence of the mature polypeptide coding sequence of SEQ ID NO: 177, or (iii) a full-length complementary strand of (i) or (ii).

In another fifth aspect, the isolated polynucleotides encoding polypeptides having beta-glucosidase activity hybridize under preferably medium-high stringency conditions, more preferably high stringency conditions, and most preferably very high stringency conditions with (i) the mature polypeptide coding sequence of SEQ ID NO: 179, (ii) the cDNA sequence of the mature polypeptide coding sequence of SEQ ID NO: 179, or (iii) a full-length complementary strand of (i) or (ii).

In another fifth aspect, the isolated polynucleotides encoding polypeptides having beta-glucosidase activity hybridize under preferably medium-high stringency conditions, more preferably high stringency conditions, and most preferably very high stringency conditions with (i) the mature polypeptide coding sequence of SEQ ID NO: 181, (ii) the cDNA sequence of the mature polypeptide coding sequence of SEQ ID NO: 181, or (iii) a full-length complementary strand of (i) or (ii).

In another fifth aspect, the isolated polynucleotides encoding polypeptides having beta-glucosidase activity hybridize under preferably medium-high stringency conditions, more preferably high stringency conditions, and most preferably very high stringency conditions with (i) the mature polypeptide coding sequence of SEQ ID NO: 183, (ii) the cDNA sequence of the mature polypeptide coding sequence of SEQ ID NO: 183, or (iii) a full-length complementary strand of (i) or (ii).

In another fifth aspect, the isolated polynucleotides encoding polypeptides having beta-glucosidase activity hybridize under preferably medium-high stringency conditions, more preferably high stringency conditions, and most preferably very high stringency conditions with (i) the mature polypeptide coding sequence of SEQ ID NO: 185, (ii) the cDNA sequence of the mature polypeptide coding sequence of SEQ ID NO: 185, or (iii) a full-length complementary strand of (i) or (ii).

In another fifth aspect, the isolated polynucleotides encoding polypeptides having beta-glucosidase activity hybridize under preferably medium-high stringency conditions, more preferably high stringency conditions, and most preferably very high stringency conditions with (i) the mature polypeptide coding sequence of SEQ ID NO: 187, (ii) the cDNA sequence of the mature polypeptide coding sequence of SEQ ID NO: 187, or (iii) a full-length complementary strand of (i) or (ii).

In another fifth aspect, the isolated polynucleotides encoding polypeptides having beta-glucosidase activity hybridize under preferably medium-high stringency conditions, more preferably high stringency conditions, and most preferably very high stringency conditions with (i) the mature polypeptide coding sequence of SEQ ID NO: 189, (ii) the cDNA sequence of the mature polypeptide coding sequence of SEQ ID NO: 189, or (iii) a full-length complementary strand of (i) or (ii).

In another fifth aspect, the isolated polynucleotides encoding GH61 polypeptides having cellulolytic enhancing activity hybridize under preferably medium-high stringency conditions, more preferably high stringency conditions, and most preferably very high stringency conditions with (i) the mature polypeptide coding sequence of SEQ ID NO: 33, (ii) the cDNA sequence of the mature polypeptide coding sequence of SEQ ID NO: 33, or (iii) a full-length complementary strand of (i) or (ii).

In another fifth aspect, the isolated polynucleotides encoding GH61 polypeptides having cellulolytic enhancing activity hybridize under preferably medium-high stringency conditions, more preferably high stringency conditions, and most preferably very high stringency conditions with (i) the mature polypeptide coding sequence of SEQ ID NO: 35, (ii) the genomic DNA sequence of the mature polypeptide coding sequence of SEQ ID NO: 35, or (iii) a full-length complementary strand of (i) or (ii).

In another fifth aspect, the isolated polynucleotides encoding GH61 polypeptides having cellulolytic enhancing activity hybridize under preferably medium-high stringency conditions, more preferably high stringency conditions, and most preferably very high stringency conditions with (i) the mature polypeptide coding sequence of SEQ ID NO: 37, (ii) the cDNA sequence of the mature polypeptide coding sequence of SEQ ID NO: 37, or (iii) a full-length complementary strand of (i) or (ii).

In another fifth aspect, the isolated polynucleotides encoding GH61 polypeptides having cellulolytic enhancing activity hybridize under preferably medium-high stringency conditions, more preferably high stringency conditions, and most preferably very high stringency conditions with (i) the mature polypeptide coding sequence of SEQ ID NO: 39, (ii) the cDNA sequence of the mature polypeptide coding sequence of SEQ ID NO: 39, or (iii) a full-length complementary strand of (i) or (ii).

In another fifth aspect, the isolated polynucleotides encoding GH61 polypeptides having cellulolytic enhancing activity hybridize under preferably medium-high stringency conditions, more preferably high stringency conditions, and most preferably very high stringency conditions with (i) the mature polypeptide coding sequence of SEQ ID NO: 41, (ii) the cDNA sequence of the mature polypeptide coding sequence of SEQ ID NO: 41, or (iii) a full-length complementary strand of (i) or (ii).

In another fifth aspect, the isolated polynucleotides encoding GH61 polypeptides having cellulolytic enhancing activity hybridize under preferably medium-high stringency conditions, more preferably high stringency conditions, and most preferably very high stringency conditions with (i) the mature polypeptide coding sequence of SEQ ID NO: 43, (ii) the cDNA sequence of the mature polypeptide coding sequence of SEQ ID NO: 43, or (iii) a full-length complementary strand of (i) or (ii).

In another fifth aspect, the isolated polynucleotides encoding GH61 polypeptides having cellulolytic enhancing activity hybridize under preferably medium-high stringency conditions, more preferably high stringency conditions, and most preferably very high stringency conditions with (i) the mature polypeptide coding sequence of SEQ ID NO: 191, (ii) the cDNA sequence of the mature polypeptide coding sequence of SEQ ID NO: 191, or (iii) a full-length complementary strand of (i) or (ii).

In another fifth aspect, the isolated polynucleotides encoding polypeptides having xylanase activity hybridize under preferably medium-high stringency conditions, more preferably high stringency conditions, and most preferably very high stringency conditions with (i) the mature polypeptide coding sequence of SEQ ID NO: 45, (ii) the genomic DNA sequence of the mature polypeptide coding sequence of SEQ ID NO: 45, or (iii) a full-length complementary strand of (i) or (ii).

In another fifth aspect, the isolated polynucleotides encoding polypeptides having xylanase activity hybridize under preferably medium-high stringency conditions, more preferably high stringency conditions, and most preferably very high stringency conditions with (i) the mature polypeptide coding sequence of SEQ ID NO: 47, (ii) the cDNA sequence of the mature polypeptide coding sequence of SEQ ID NO: 47, or (iii) a full-length complementary strand of (i) or (ii).

In another fifth aspect, the isolated polynucleotides encoding polypeptides having xylanase activity hybridize under preferably medium-high stringency conditions, more preferably high stringency conditions, and most preferably very high stringency conditions with (i) the mature polypeptide coding sequence of SEQ ID NO: 49, (ii) the genomic DNA sequence of the mature polypeptide coding sequence of SEQ ID NO: 49, or (iii) a full-length complementary strand of (i) or (ii).

In another fifth aspect, the isolated polynucleotides encoding polypeptides having xylanase activity hybridize under preferably medium-high stringency conditions, more preferably high stringency conditions, and most preferably very high stringency conditions with (i) the mature polypeptide coding sequence of SEQ ID NO: 51, (ii) the cDNA sequence of the mature polypeptide coding sequence of SEQ ID NO: 51, or (iii) a full-length complementary strand of (i) or (ii).

In another fifth aspect, the isolated polynucleotides encoding polypeptides having xylanase activity hybridize under preferably medium-high stringency conditions, more preferably high stringency conditions, and most preferably very high stringency conditions with (i) the mature polypeptide coding sequence of SEQ ID NO: 53, (ii) the genomic DNA sequence of the mature polypeptide coding sequence of SEQ ID NO: 53, or (iii) a full-length complementary strand of (i) or (ii).

In another fifth aspect, the isolated polynucleotides encoding polypeptides having xylanase activity hybridize under preferably medium-high stringency conditions, more preferably high stringency conditions, and most preferably very high stringency conditions with (i) the mature polypeptide coding sequence of SEQ ID NO: 193, (ii) the cDNA sequence of the mature polypeptide coding sequence of SEQ ID NO: 193, or (iii) a full-length complementary strand of (i) or (ii).

In another fifth aspect, the isolated polynucleotides encoding polypeptides having xylanase activity hybridize under preferably medium-high stringency conditions, more preferably high stringency conditions, and most preferably very high stringency conditions with (i) the mature polypeptide coding sequence of SEQ ID NO: 195, (ii) the cDNA sequence of the mature polypeptide coding sequence of SEQ ID NO: 195, or (iii) a full-length complementary strand of (i) or (ii).

In another fifth aspect, the isolated polynucleotides encoding polypeptides having xylanase activity hybridize under preferably medium-high stringency conditions, more preferably high stringency conditions, and most preferably very high stringency conditions with (i) the mature polypeptide coding sequence of SEQ ID NO: 197, (ii) the genomic DNA sequence of the mature polypeptide coding sequence of SEQ ID NO: 197, or (iii) a full-length complementary strand of (i) or (ii).

In another fifth aspect, the isolated polynucleotides encoding polypeptides having xylanase activity hybridize under preferably medium-high stringency conditions, more preferably high stringency conditions, and most preferably very high stringency conditions with the mature polypeptide coding sequence of SEQ ID NO: 55 or its full-length complementary strand.

In another fifth aspect, the isolated polynucleotides encoding polypeptides having xylanase activity hybridize under preferably medium-high stringency conditions, more preferably high stringency conditions, and most preferably very high stringency conditions with (i) the mature polypeptide coding sequence of SEQ ID NO: 199 or SEQ ID NO: 304, (ii) the cDNA sequence of the mature polypeptide coding sequence of SEQ ID NO: 199 or SEQ ID NO: 304, or (iii) a full-length complementary strand of (i) or (ii).

In another fifth aspect, the isolated polynucleotides encoding polypeptides having beta-xylosidase activity hybridize under preferably medium-high stringency conditions, more preferably high stringency conditions, and most preferably very high stringency conditions with (i) the mature polypeptide coding sequence of SEQ ID NO: 57, (ii) the genomic DNA sequence of the mature polypeptide coding sequence of SEQ ID NO: 57, or (iii) a full-length complementary strand of (i) or (ii).

In another fifth aspect, the isolated polynucleotides encoding polypeptides having beta-xylosidase activity hybridize under preferably medium-high stringency conditions, more preferably high stringency conditions, and most preferably very high stringency conditions with (i) the mature polypeptide coding sequence of SEQ ID NO: 59, (ii) the cDNA sequence of the mature polypeptide coding sequence of SEQ ID NO: 59, or (iii) a full-length complementary strand of (i) or (ii).

In another fifth aspect, the isolated polynucleotides encoding polypeptides having beta-xylosidase activity hybridize under preferably medium-high stringency conditions, more preferably high stringency conditions, and most preferably very high stringency conditions with (i) the mature polypeptide coding sequence of SEQ ID NO: 201, (ii) the cDNA sequence of the mature polypeptide coding sequence of SEQ ID NO: 201, or (iii) a full-length complementary strand of (i) or (ii).

In another fifth aspect, the isolated polynucleotides encoding polypeptides having beta-xylosidase activity hybridize under preferably medium-high stringency conditions, more preferably high stringency conditions, and most preferably very high stringency conditions with (i) the mature polypeptide coding sequence of SEQ ID NO: 203, (ii) the cDNA sequence of the mature polypeptide coding sequence of SEQ ID NO: 203, or (iii) a full-length complementary strand of (i) or (ii).

In another fifth aspect, the isolated polynucleotides encoding polypeptides having beta-xylosidase activity hybridize under preferably medium-high stringency conditions, more preferably high stringency conditions, and most preferably very high stringency conditions with (i) the mature polypeptide coding sequence of SEQ ID NO: 205, (ii) the cDNA sequence of the mature polypeptide coding sequence of SEQ ID NO: 205, or (iii) a full-length complementary strand of (i) or (ii).

Sources of Polypeptides Having Cellobiohydrolase I, Cellobiohydrolase II, Endoglucanase I, Endoglucanase II, Beta-Glucosidase, Cellulolytic Enhancing, Xylanase, or Beta-Xylosidase Activity A polypeptide having cellobiohydrolase I, cellobiohydrolase II, endoglucanase I, endoglucanase II, beta-glucosidase, cellulolytic enhancing, xylanase, or beta-xylosidase activity may be obtained from microorganisms of any genus. For purposes of the present invention, the term "obtained from" as used herein in connection with a given source shall mean that the polypeptide encoded by a nucleotide sequence is produced by the source or by a strain in which the nucleotide sequence from the source has been inserted. In a preferred aspect, the polypeptide obtained from a given source is secreted extracellularly.

A polypeptide having cellobiohydrolase I, cellobiohydrolase II, endoglucanase I, endoglucanase II, beta-glucosidase, cellulolytic enhancing, xylanase, or beta-xylosidase activity may be a bacterial polypeptide. For example, the polypeptide may be a gram positive bacterial polypeptide such as a *Bacillus, Streptococcus, Streptomyces, Staphylococcus, Enterococcus, Lactobacillus, Lactococcus, Clostridium, Geobacillus*, or *Oceanobacillus* polypeptide, or a Gram negative bacterial polypeptide such as an *E. coli, Pseudomonas, Salmonella, Campylobacter, Helicobacter, Flavobacterium, Fusobacterium, Ilyobacter, Neisseria*, or *Ureaplasma* polypeptide.

In a preferred aspect, the polypeptide is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, or *Bacillus thuringiensis* polypeptide.

In another preferred aspect, the polypeptide is a *Streptococcus equisimilis, Streptococcus pyogenes, Streptococcus uberis*, or *Streptococcus equi* subsp. *Zooepidemicus* polypeptide.

In another preferred aspect, the polypeptide is a *Streptomyces achromogenes, Streptomyces avermitilis, Streptomyces coelicolor, Streptomyces griseus*, or *Streptomyces lividans* polypeptide.

A polypeptide having cellobiohydrolase I, cellobiohydrolase II, endoglucanase I, endoglucanase II, beta-glucosidase, cellulolytic enhancing activity, xylanase, or beta-xylosidase may also be a fungal polypeptide, and more preferably a yeast polypeptide such as a *Candida, Kluyveromyces, Pichia, Saccharomyces, Schizosaccharomyces*, or *Yarrowia* polypeptide; or more preferably a filamentous fungal polypeptide such as an *Acremonium, Agaricus, Alternaria, Aspergillus, Aureobasidium, Botryosphaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella*, or *Xylaria* polypeptide.

In a preferred aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* polypeptide.

In another preferred aspect, the polypeptide is an *Acremonium cellulolyticus, Aspergillus aculeatus, Aspergillus awamori, Aspergillus fumigatus, Aspergillus foetidus, Aspergillus japonicus, Aspergillus nidulans, Aspergillus niger, Aspergillus oryzae, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia spededonium, Thielavia setosa, Thielavia subthermophila, Thielavia terrestris, Trichoderma harzianum, Trichoderma koningii, Trichoderma longibrachiatum, Trichoderma reesei*, or *Trichoderma viride* polypeptide.

In another aspect, the polypeptide having cellobiohydrolase I activity is a *Chaetomium thermophilum* CGMCC 0581 Cel7A polypeptide having cellobiohydrolase I activity, i.e., the polypeptide comprising the mature polypeptide of SEQ ID NO: 2.

In another aspect, the polypeptide having cellobiohydrolase I activity is a *Myceliophthora thermophila* CBS 117.65 Cel7A polypeptide having cellobiohydrolase I activity, i.e., the polypeptide comprising the mature polypeptide of SEQ ID NO: 4.

In another aspect, the polypeptide having cellobiohydrolase I activity is an *Aspergillus fumigatus* NN055679 Cel7A polypeptide having cellobiohydrolase I activity, i.e., the polypeptide comprising the mature polypeptide of SEQ ID NO: 6.

In another aspect, the polypeptide having cellobiohydrolase I activity is a *Thermoascus aurantiacus* CGMCC 0583 Cel7A polypeptide having cellobiohydrolase I activity, i.e., the polypeptide comprising the mature polypeptide of SEQ ID NO: 8.

In another aspect, the polypeptide having cellobiohydrolase I activity is a *Penicillium emersonii* NN051602 Cel7 polypeptide having cellobiohydrolase I activity, i.e., the polypeptide comprising the mature polypeptide of SEQ ID NO: 158.

In another aspect, the polypeptide having cellobiohydrolase I activity is a *Penicillium pinophilum* NN046877 Cel7 polypeptide having cellobiohydrolase I activity, i.e., the polypeptide comprising the mature polypeptide of SEQ ID NO: 160.

In another aspect, the polypeptide having cellobiohydrolase I activity is an *Aspergillus terreus* ATCC 28865 Cel7 polypeptide having cellobiohydrolase I activity, i.e., the polypeptide comprising the mature polypeptide of SEQ ID NO: 162.

In another aspect, the polypeptide having cellobiohydrolase I activity is a *Neosartorya fischeri* NRRL 181 Cel7 polypeptide having cellobiohydrolase I activity, i.e., the polypeptide comprising the mature polypeptide of SEQ ID NO: 164.

In another aspect, the polypeptide having cellobiohydrolase I activity is an *Aspergillus nidulans* FGSCA4 Cel7 polypeptide having cellobiohydrolase I activity, i.e., the polypeptide comprising the mature polypeptide of SEQ ID NO: 166.

In another aspect, the polypeptide having cellobiohydrolase II activity is a *Myceliophthora thermophila* CBS 117.65 Cel6A polypeptide having cellobiohydrolase II activity, i.e., the polypeptide comprising the mature polypeptide of SEQ ID NO: 10.

In another aspect, the polypeptide having cellobiohydrolase II activity is a *Myceliophthora thermophila* CBS 202.75

Cel6B polypeptide having cellobiohydrolase II activity, i.e., the polypeptide comprising the mature polypeptide of SEQ ID NO: 12.

In another aspect, the polypeptide having cellobiohydrolase II activity is a *Thielavia terrestris* NRRL 8126 Cel6A polypeptide having cellobiohydrolase II activity, i.e., the polypeptide comprising the mature polypeptide of SEQ ID NO: 14.

In another aspect, the polypeptide having cellobiohydrolase II activity is a *Trichophaea saccata* CBS 804.70 Cel6 polypeptide having cellobiohydrolase II activity, i.e., the polypeptide comprising the mature polypeptide of SEQ ID NO: 16.

In another aspect, the polypeptide having cellobiohydrolase II activity is a *Aspergillus fumigatus* NN055679 Cel6A polypeptide having cellobiohydrolase II activity, i.e., the polypeptide comprising the mature polypeptide of SEQ ID NO: 18.

In another aspect, the polypeptide having cellobiohydrolase II activity is a *Fennellia nivea* NN046949 Cel6 polypeptide having cellobiohydrolase II activity, i.e., the polypeptide comprising the mature polypeptide of SEQ ID NO: 168.

In another aspect, the polypeptide having cellobiohydrolase II activity is a *Penicillium emersonii* NN051602 Cel6A polypeptide having cellobiohydrolase II activity, i.e., the polypeptide comprising the mature polypeptide of SEQ ID NO: 170.

In another aspect, the polypeptide having cellobiohydrolase II activity is a *Penicillium pinophilum* NN046877 Cel6A polypeptide having cellobiohydrolase II activity, i.e., the polypeptide comprising the mature polypeptide of SEQ ID NO: 172.

In another aspect, the polypeptide having endoglucanase I activity is an *Aspergillus terreus* ATCC 28865 Cel6A polypeptide having endoglucanase I activity, i.e., the polypeptide comprising the mature polypeptide of SEQ ID NO: 20.

In another aspect, the polypeptide having endoglucanase II activity is a *Trichoderma reesei* RutC30 Cel5A polypeptide having endoglucanase II activity, i.e., the polypeptide comprising the mature polypeptide of SEQ ID NO: 22.

In another aspect, the polypeptide having endoglucanase II activity is a *Myceliophthora thermophila* CBS 202.75 Cel5A polypeptide having endoglucanase II activity, i.e., the polypeptide comprising the mature polypeptide of SEQ ID NO: 24.

In another aspect, the polypeptide having endoglucanase II activity is a *Thermoascus aurantiacus* CGMCC 0670 Cel5A polypeptide having endoglucanase II activity, i.e., the polypeptide comprising the mature polypeptide of SEQ ID NO: 26.

In another aspect, the polypeptide having endoglucanase II activity is an *Aspergillus fumigatus* NN051616 Cel5 polypeptide having endoglucanase II activity, i.e., the polypeptide comprising the mature polypeptide of SEQ ID NO: 174.

In another aspect, the polypeptide having endoglucanase II activity is a *Neosartorya fischeri* NRRL 181 polypeptide having endoglucanase II activity, i.e., the polypeptide comprising the mature polypeptide of SEQ ID NO: 176.

In another aspect, the polypeptide having beta-glucosidase activity is an *Aspergillus fumigatus* NN055679 Cel5A polypeptide having beta-glucosidase activity, i.e., the polypeptide comprising the mature polypeptide of SEQ ID NO: 28.

In another aspect, the polypeptide having beta-glucosidase activity is a *Penicillium brasilianum* IBT 20888 Cel5A polypeptide having beta-glucosidase activity, i.e., the polypeptide comprising the mature polypeptide of SEQ ID NO: 30.

In another aspect, the polypeptide having beta-glucosidase activity is an *Aspergillus niger* IBT 10140 GH3 polypeptide having beta-glucosidase activity, i.e., the polypeptide comprising the mature polypeptide of SEQ ID NO: 32.

In another aspect, the polypeptide having beta-glucosidase activity is an *Aspergillus aculeatus* WDCM190 Cel3 polypeptide having beta-glucosidase activity, i.e., the polypeptide comprising the mature polypeptide of SEQ ID NO: 178.

In another aspect, the polypeptide having beta-glucosidase activity is an *Aspergillus kawashii* IFO4308 Cel3 polypeptide having beta-glucosidase activity, i.e., the polypeptide comprising the mature polypeptide of SEQ ID NO: 180.

In another aspect, the polypeptide having beta-glucosidase activity is an *Aspergillus clavatus* NRRL 1 Cel3 polypeptide having beta-glucosidase activity, i.e., the polypeptide comprising the mature polypeptide of SEQ ID NO: 182.

In another aspect, the polypeptide having beta-glucosidase activity is a *Thielavia terrestris* NRRL 8126 Cel3 polypeptide having beta-glucosidase activity, i.e., the polypeptide comprising the mature polypeptide of SEQ ID NO: 184.

In another aspect, the polypeptide having beta-glucosidase activity is a *Penicillium oxalicum* IBT5387 Cel3 polypeptide having beta-glucosidase activity, i.e., the polypeptide comprising the mature polypeptide of SEQ ID NO: 186.

In another aspect, the polypeptide having beta-glucosidase activity is a *Penicillium oxalicum* IBT5387 Cel3 polypeptide having beta-glucosidase activity, i.e., the polypeptide comprising the mature polypeptide of SEQ ID NO: 188.

In another aspect, the polypeptide having beta-glucosidase activity is a *Talaromyces emersonii* CBS 549.92 Cel3 polypeptide having beta-glucosidase activity, i.e., the polypeptide comprising the mature polypeptide of SEQ ID NO: 190.

In another aspect, the polypeptide having cellulolytic enhancing activity is a *Thermoascus aurantiacus* CGMCC 0583 GH61A polypeptide having cellulolytic enhancing activity, i.e., the polypeptide comprising the mature polypeptide of SEQ ID NO: 34.

In another aspect, the polypeptide having cellulolytic enhancing activity is a *Thielavia terrestris* NRRL 8126 GH61E polypeptide having cellulolytic enhancing activity, i.e., the polypeptide comprising the mature polypeptide of SEQ ID NO: 36.

In another aspect, the polypeptide having cellulolytic enhancing activity is an *Aspergillus fumigatus* NN051616 GH61B polypeptide having cellulolytic enhancing activity, i.e., the polypeptide comprising the mature polypeptide of SEQ ID NO: 38.

In another aspect, the polypeptide having cellulolytic enhancing activity is a *Penicillium pinophilum* NN046877 GH61A polypeptide having cellulolytic enhancing activity, i.e., the polypeptide comprising the mature polypeptide of SEQ ID NO: 40.

In another aspect, the polypeptide having cellulolytic enhancing activity is a *Penicillium* sp. NN051602 GH61A polypeptide having cellulolytic enhancing activity, i.e., the polypeptide comprising the mature polypeptide of SEQ ID NO: 42.

In another aspect, the polypeptide having cellulolytic enhancing activity is a *Thielavia terrestris* NRRL 8126 GH61N polypeptide having cellulolytic enhancing activity, i.e., the polypeptide comprising the mature polypeptide of SEQ ID NO: 44.

In another aspect, the polypeptide having cellulolytic enhancing activity is a *Thermoascus crustaceus* CBS 181.67 GH61A polypeptide having cellulolytic enhancing activity, i.e., the polypeptide comprising the mature polypeptide of SEQ ID NO: 192.

In another aspect, the polypeptide having xylanase activity is an *Aspergillus aculeatus* CBS 101.43 polypeptide having xylanase activity, i.e., the polypeptide comprising the mature polypeptide of SEQ ID NO: 46.

In another aspect, the polypeptide having xylanase activity is an *Aspergillus fumigatus* NN055679 polypeptide having xylanase activity, i.e., the polypeptide comprising the mature polypeptide of SEQ ID NO: 48.

In another aspect, the polypeptide having xylanase activity is a *Trichophaea saccata CBS* 804.70 polypeptide having xylanase activity, i.e., the polypeptide comprising the mature polypeptide of SEQ ID NO: 50.

In another aspect, the polypeptide having xylanase activity is a *Penicillium pinophilum* NN046877 polypeptide having xylanase activity, i.e., the polypeptide comprising the mature polypeptide of SEQ ID NO: 52.

In another aspect, the polypeptide having xylanase activity is a *Thielavia terrestris* NRRL 8126 polypeptide having xylanase activity, i.e., the polypeptide comprising the mature polypeptide of SEQ ID NO: 54.

In another aspect, the polypeptide having xylanase activity is a *Talaromyces emersonii NN*050022 polypeptide having xylanase activity, i.e., the polypeptide comprising of the mature polypeptide of SEQ ID NO: 194.

In another aspect, the polypeptide having xylanase activity is a *Penicillium* sp. NN51602 polypeptide having xylanase activity, i.e., the polypeptide comprising of the mature polypeptide of SEQ ID NO: 196.

In another aspect, the polypeptide having xylanase activity is a *Meripilus giganteus* CBS 521.95 polypeptide having xylanase activity, i.e., the polypeptide comprising of the mature polypeptide of SEQ ID NO: 198.

In another aspect, the polypeptide having xylanase activity is a *Thermobifida fusca* DSM 22883 polypeptide having xylanase activity, i.e., the polypeptide comprising the mature polypeptide of SEQ ID NO: 56.

In another aspect, the polypeptide having xylanase activity is a *Dictyoglomus thermophilum* ATCC 35947 polypeptide having xylanase activity, i.e., the polypeptide comprising the mature polypeptide of SEQ ID NO: 200 or SEQ ID NO: 305.

In another aspect, the polypeptide having beta-xylosidase activity is a *Trichoderma reesei* RutC30 polypeptide having beta-xylosidase activity, i.e., the polypeptide comprising the mature polypeptide of SEQ ID NO: 58.

In another aspect, the polypeptide having beta-xylosidase activity is a *Talaromyces emersonii* CBS 393.64 polypeptide having beta-xylosidase activity, i.e., the polypeptide comprising the mature polypeptide of SEQ ID NO: 60.

In another aspect, the Family 3 polypeptide having beta-xylosidase activity is an *Aspergillus aculeatus* CBS 172.66 polypeptide having beta-xylosidase activity, i.e., the polypeptide comprising the mature polypeptide of SEQ ID NO: 202.

In another aspect, the Family 3 polypeptide having beta-xylosidase activity is an *Aspergillus aculeatus* CBS 186.67 polypeptide having beta-xylosidase activity, i.e., the polypeptide comprising the mature polypeptide of SEQ ID NO: 204.

In another aspect, the Family 3 polypeptide having beta-xylosidase activity is an *Aspergillus fumigatus* NN051616 polypeptide having beta-xylosidase activity, i.e., the polypeptide comprising the mature polypeptide of SEQ ID NO: 206.

It will be understood that for the aforementioned species the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The polynucleotide may then be obtained by similarly screening a genomic or cDNA library of such a microorganism. Once a polynucleotide encoding a polypeptide has been detected with the probe(s), the polynucleotide can be isolated or cloned by utilizing techniques that are well known to those of ordinary skill in the art (see, e.g., Sambrook et al., 1989, supra).

Such polypeptides also include fused polypeptides or cleavable fusion polypeptides in which another polypeptide is fused at the N-terminus or the C-terminus of the polypeptide or fragment thereof. A fused polypeptide is produced by fusing a nucleotide sequence (or a portion thereof) encoding another polypeptide to a nucleotide sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and *Stevens,* 2003, *Drug Discovery World* 4: 35-48.

Nucleic Acid Constructs

A nucleic acid construct comprising an isolated polynucleotide encoding a polypeptide component of an enzyme composition of the present invention may be constructed by operably linking the polynucleotide to one or more (several) control sequences that direct the expression of the coding sequence in a suitable host cell under conditions compatible with the control sequences. Manipulation of the polynucleotide's sequence prior to its insertion into a vector may be desirable or necessary depending on the expression vector. The techniques for modifying polynucleotide sequences utilizing recombinant DNA methods are well known in the art.

The control sequence may be an appropriate promoter sequence, a nucleotide sequence that is recognized by a host cell for expression of a polynucleotide encoding a polypeptide. The promoter sequence contains transcriptional control sequences that mediate the expression of the polypeptide. The promoter may be any nucleotide sequence that shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, *Proceedings of the National Academy of Sciences USA* 75: 3727-3731), as well as the tac promoter (DeBoer et al., 1983, *Proceedings of the National Academy of Sciences USA* 80: 21-25). Further promoters are described in "Useful proteins from recombinant bacteria" in *Scientific American,* 1980, 242: 74-94; and in Sambrook et al., 1989, supra.

Examples of suitable promoters for directing the transcription of the nucleic acid constructs in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Dania (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from a gene encoding a neutral alpha-amylase in *Aspergilli* in which the untranslated leader has been replaced by an untranslated leader from a gene encoding triose phosphate isomerase in *Aspergilli*; non-limiting examples include modified promoters from the gene encoding neutral alpha-amylase in *Aspergillus niger* in which the untranslated leader has been replaced by an untranslated leader from the gene encoding triose phosphate isomerase in *Aspergillus nidulans* or *Aspergillus oryzae*); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a suitable transcription terminator sequence, a sequence recognized by a host cell to terminate transcription. The terminator sequence is operably linked to the 3' terminus of the nucleotide sequence encoding the polypeptide. Any terminator that is functional in the host cell of choice may be used in the present invention.

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA that is important for translation by the host cell. The leader sequence is operably linked to the 5' terminus of the nucleotide sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleotide sequence and, when transcribed, is recognized by the host cell as a signal to add polyadenosine residues to transcribed mRNA. Any polyadenylation sequence that is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. The foreign signal peptide coding sequence may be required where the coding sequence does not naturally contain a signal peptide coding sequence. Alternatively, the foreign signal peptide coding sequence may simply replace the natural signal peptide coding sequence in order to enhance secretion of the polypeptide. However, any signal peptide coding sequence that directs the expressed polypeptide into the secretory pathway of a host cell of choice may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present at the N-terminus of a polypeptide, the propeptide sequence is positioned next to the N-terminus of a polypeptide and the signal peptide sequence is positioned next to the N-terminus of the propeptide sequence.

It may also be desirable to add regulatory sequences that allow the regulation of the expression of the polypeptide relative to the growth of the host cell. Examples of regulatory systems are those that cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked with the regulatory sequence.

Expression Vectors

The various nucleic acids and control sequences described herein may be joined together to construct a recombinant expression vector that may include one or more (several) convenient restriction sites to allow for insertion or substitution of an isolated polynucleotide encoding a polypeptide component of the enzyme composition at such sites. Alternatively, a polynucleotide sequence may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vectors preferably contain one or more (several) selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are the dal genes from *Bacillus subtilis* or *Bacillus licheniformis*, or markers that confer antibiotic resistance such as ampicillin, kanamycin, chloramphenicol, or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus.*

The vectors preferably contain an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or nonhomologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of identity to the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" is defined herein as a nucleotide sequence that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMß1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Research* 15: 9163-9175; WO 00/24883). Isolation of the AMA1 gene and construction of plasmids or vectors comprising the gene can be accomplished according to the methods disclosed in WO 00/24883.

More than one copy of a polynucleotide may be inserted into a host cell to increase production of the gene product. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors are well known to one skilled in the art (see, e.g., Sambrook et al., 1989, supra).

Host Cells

The present invention also relates to recombinant host cells, comprising one or more isolated polynucleotides encoding polypeptide components of the enzyme composition, which are advantageously used in the recombinant production of the polypeptides. A vector is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram positive bacterium or a Gram negative bacterium. Gram positive bacteria include, but not limited to, *Bacillus, Streptococcus, Streptomyces, Staphylococcus, Enterococcus, Lactobacillus, Lactococcus, Clostridium, Geobacillus*, and *Oceanobacillus*. Gram negative bacteria include, but not limited to, *E. coli, Pseudomonas, Salmonella, Campylobacter, Helicobacter, Flavobacterium, Fusobacterium, Ilyobacter, Neisseria*, and *Ureaplasma*.

The bacterial host cell may be any *Bacillus* cell. *Bacillus* cells useful in the practice of the present invention include, but are not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

In a preferred aspect, the bacterial host cell is a *Bacillus amyloliquefaciens, Bacillus lentus, Bacillus licheniformis, Bacillus stearothermophilus* or *Bacillus subtilis* cell. In a more preferred aspect, the bacterial host cell is a *Bacillus amyloliquefaciens* cell. In another more preferred aspect, the bacterial host cell is a *Bacillus clausii* cell. In another more preferred aspect, the bacterial host cell is a *Bacillus licheniformis* cell. In another more preferred aspect, the bacterial host cell is a *Bacillus subtilis* cell.

The bacterial host cell may also be any *Streptococcus* cell. *Streptococcus* cells useful in the practice of the present invention include, but are not limited to, *Streptococcus equisimilis, Streptococcus pyogenes, Streptococcus uberis*, and *Streptococcus equi* subsp. *Zooepidemicus* cells.

In a preferred aspect, the bacterial host cell is a *Streptococcus equisimilis* cell. In another preferred aspect, the bacterial host cell is a *Streptococcus pyogenes* cell. In another preferred aspect, the bacterial host cell is a *Streptococcus uberis* cell. In another preferred aspect, the bacterial host cell is a *Streptococcus equi* subsp. *Zooepidemicus* cell.

The bacterial host cell may also be any *Streptomyces* cell. *Streptomyces* cells useful in the practice of the present invention include, but are not limited to, *Streptomyces achromogenes, Streptomyces avermitilis, Streptomyces coelicolor, Streptomyces griseus*, and *Streptomyces lividans* cells.

In a preferred aspect, the bacterial host cell is a *Streptomyces achromogenes* cell. In another preferred aspect, the bacterial host cell is a *Streptomyces avermitilis* cell. In another preferred aspect, the bacterial host cell is a *Streptomyces coelicolor* cell. In another preferred aspect, the bacterial host cell is a *Streptomyces griseus* cell. In another preferred aspect, the bacterial host cell is a *Streptomyces lividans* cell.

The introduction of DNA into a *Bacillus* cell may, for instance, be effected by protoplast transformation (see, e.g., Chang and Cohen, 1979, *Molecular General Genetics* 168: 111-115), by using competent cells (see, e.g., Young and Spizizen, 1961, *Journal of Bacteriology* 81: 823-829, or Dubnau and Davidoff-Abelson, 1971, *Journal of Molecular Biology* 56: 209-221), by electroporation (see, e.g., Shigekawa and Dower, 1988, *Biotechniques* 6: 742-751), or by conjugation (see, e.g., Koehler and Thorne, 1987, *Journal of Bacteriology* 169: 5271-5278). The introduction of DNA into an *E coli* cell may, for instance, be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may, for instance, be effected by protoplast transformation and electroporation (see, e.g., Gong et al., 2004, *Folia Microbiol.* (*Praha*) 49: 399-405), by conjugation (see, e.g., Mazodier et al., 1989, *J. Bacteriol.* 171: 3583-3585), or by transduction (see, e.g., Burke et al., 2001, *Proc. Natl. Acad. Sci. USA* 98: 6289-6294). The introduction of DNA into a *Pseudomonas* cell may, for instance, be effected by electroporation (see, e.g., Choi et al., 2006, *J. Microbiol. Methods* 64: 391-397) or by conjugation (see, e.g., Pinedo and Smets, 2005, *Appl. Environ. Microbiol.* 71: 51-57). The introduction of DNA into a *Streptococcus* cell may, for instance, be effected by natural competence (see, e.g., Perry and Kuramitsu, 1981, *Infect. Immun.* 32: 1295-1297), by protoplast transformation (see, e.g., Catt and Jollick, 1991, *Microbios.* 68: 189-207, by electroporation (see, e.g., Buckley et al., 1999, *Appl. Environ. Microbiol.* 65: 3800-3804) or by conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

In a preferred aspect, the host cell is a fungal cell. "Fungi" as used herein includes the phyla Ascomycota, Basidiomycota, Chytridiomycota, and Zygomycota (as defined by Hawksworth et al., *In, Ainsworth and Bisby's Dictionary of The Fungi,* 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred aspect, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series* No. 9, 1980).

In an even more preferred aspect, the yeast host cell is a *Candida, Hansenula, Kluyveromyces, Pichia, Saccharomyces, Schizosaccharomyces*, or *Yarrowia* cell.

In a most preferred aspect, the yeast host cell is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* cell. In another most preferred aspect, the yeast host cell is a *Kluyveromyces lactis* cell. In another most preferred aspect, the yeast host cell is a *Yarrowia lipolytica* cell.

In another more preferred aspect, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred aspect, the filamentous fungal host cell is an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phiebia, Piromyces, Pleurotus, Schizophyllum, Talaromyces, Thermoascus, Thielavia, Tolypocladium, Trametes*, or *Trichoderma* cell.

In a most preferred aspect, the filamentous fungal host cell is an *Aspergillus awamori, Aspergillus fumigatus, Aspergillus foetidus, Aspergillus japonicus, Aspergillus nidulans, Aspergillus niger* or *Aspergillus oryzae* cell. In another most preferred aspect, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium suiphureum, Fusarium torulosum, Fusarium trichothecioides*, or *Fusarium venenatum* cell. In another most preferred aspect, the filamentous fungal host cell is a *Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Coprinus cinereus, Coriolus hirsutus, Humicola insolens, Humicola lanuginosa, Mucor miehei, Myceliophthora thermophila, Neurospora crassa, Penicillium purpurogenum, Phanerochaete chrysosporium, Phiebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

The present invention also relates to methods of producing an enzyme composition of the present invention, comprising: (a) cultivating a recombinant host cell, as described herein, under conditions conducive for production of the enzyme composition; and (b) recovering the enzyme composition.

In the production methods of the present invention, the cells are cultivated in a nutrient medium suitable for production of the enzyme composition using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the enzyme composition to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the components of the enzyme composition are secreted into the nutrient medium, the enzyme composition can be recovered directly from the medium. If the components of the enzyme composition are not secreted into the medium, the enzyme composition can be recovered from cell lysates.

The polypeptide components may be detected using methods known in the art that are specific for the polypeptides. These detection methods may include use of specific antibodies, formation of an enzyme product, or disappearance of an enzyme substrate.

The resulting enzyme composition may be recovered using methods known in the art. For example, the enzyme composition may be recovered from the nutrient medium by conventional procedures including, but not limited to, centrifugation, filtration, extraction, spray-drying, evaporation, or precipitation.

An enzyme composition of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989) to obtain substantially pure polypeptides.

Methods of Processing Cellulosic Material

The present invention also relates to methods for degrading or converting a cellulosic material, comprising: treating the cellulosic material with an enzyme composition of the present invention. In a preferred aspect, the method further comprises recovering the degraded or converted cellulosic material.

The present invention also relates to methods of producing a fermentation product, comprising: (a) saccharifying a cellulosic material with an enzyme composition of the present invention; (b) fermenting the saccharified cellulosic material with one or more fermenting microorganisms to produce the fermentation product; and (c) recovering the fermentation product from the fermentation.

The present invention also relates to methods of fermenting a cellulosic material, comprising: fermenting the cellulosic material with one or more fermenting microorganisms, wherein the cellulosic material is saccharified with an enzyme composition of the present invention. In a preferred aspect, the fermenting of the cellulosic material produces a fermentation product. In another preferred aspect, the method further comprises recovering the fermentation product from the fermentation.

The methods of the present invention can be used to saccharify a cellulosic material to fermentable sugars and convert the fermentable sugars to many useful substances, e.g., chemicals and fuels. The production of a desired fermentation product from cellulosic material typically involves pretreatment, enzymatic hydrolysis (saccharification), and fermentation.

The processing of cellulosic material according to the present invention can be accomplished using processes conventional in the art. Moreover, the methods of the present invention can be implemented using any conventional biomass processing apparatus configured to operate in accordance with the invention.

Hydrolysis (saccharification) and fermentation, separate or simultaneous, include, but are not limited to, separate hydrolysis and fermentation (SHF); simultaneous saccharification and fermentation (SSF); simultaneous saccharification and cofermentation (SSCF); hybrid hydrolysis and fermentation (HHF); separate hydrolysis and co-fermentation (SHCF), (hybrid hydrolysis and fermentation (HHCF), and direct microbial conversion (DMC). SHF uses separate process steps to first enzymatically hydrolyze lignocellulose to fermentable sugars, e.g., glucose, cellobiose, cellotriose, and pentose sugars, and then ferment the fermentable sugars to ethanol. In SSF, the enzymatic hydrolysis of lignocellulose and the fermentation of sugars to ethanol are combined in one step (Philippidis, G. P., 1996, Cellulose bioconversion technology, in *Handbook on Bioethanol: Production and Utilization*, Wyman, C. E., ed., Taylor & Francis, Washington, D.C., 179-212). SSCF involves the cofermentation of multiple sugars (Sheehan, J., and Himmel, M., 1999, Enzymes, energy and the environment: A strategic perspective on the U.S. Department of Energy's research and development activities for bioethanol, *Biotechnol. Prog.* 15: 817-827). HHF involves a separate hydrolysis step, and in addition a simultaneous saccharification and hydrolysis step, which can be carried out in the same reactor. The steps in an HHF process can be carried out at different temperatures, i.e., high temperature enzymatic saccharification followed by SSF at a lower temperature that the fermentation strain can tolerate. DMC combines all three processes (enzyme production, lignocellulose hydrolysis, and fermentation) in one or more steps where the same organism is used to produce the enzymes for conversion of the lignocellulose to fermentable sugars and to convert the fermentable sugars into a final product (Lynd, L. R., Weimer, P. J., van Zyl, W. H., and Pretorius, I. S., 2002, Microbial cellulose utilization: Fundamentals and biotechnology, *Microbiol. Mol. Biol. Reviews* 66: 506-577). It is understood herein that any method known in the art comprising pretreatment, enzymatic hydrolysis (saccharification), fermentation, or a combination thereof can be used in the practicing the methods of the present invention.

A conventional apparatus can include a fed-batch stirred reactor, a batch stirred reactor, a continuous flow stirred reactor with ultrafiltration, and/or a continuous plug-flow column reactor (Fernanda de Castilhos Corazza, Flávio Faria de Moraes, Gisella Maria Zanin and Ivo Neitzel, 2003, Optimal control in fed-batch reactor for the cellobiose hydrolysis, *Acta Scientiarum. Technology* 25: 33-38; Gusakov, A. V., and Sinitsyn, A. P., 1985, Kinetics of the enzymatic hydrolysis of cellulose: 1. A mathematical model for a batch reactor process, *Enz. Microb. Technol.* 7: 346-352), an attrition reactor (Ryu, S. K., and Lee, J. M., 1983, Bioconversion of waste cellulose by using an attrition bioreactor, *Biotechnol. Bioeng.* 25: 53-65), or a reactor with intensive stirring induced by an electromagnetic field (Gusakov, A. V., Sinitsyn, A. P., Davydkin, I. Y., Davydkin, V. Y., Protas, O. V., 1996, Enhancement of enzymatic cellulose hydrolysis using a novel type of bioreactor with intensive stirring induced by electromagnetic field, *Appl. Biochem. Biotechnol.* 56: 141-153). Additional reactor types include fluidized bed, upflow blanket, immobilized, and extruder type reactors for hydrolysis and/or fermentation.

Pretreatment. In practicing the methods of the present invention, any pretreatment process known in the art can be used to disrupt the plant cell wall components (Chandra et al., 2007, Substrate pretreatment: The key to effective enzymatic hydrolysis of lignocellulosics? *Adv. Biochem. Engin./Biotechnol.* 108: 67-93; Galbe and Zacchi, 2007, Pretreatment of lignocellulosic materials for efficient bioethanol production, *Adv. Biochem. Engin./Biotechnol.* 108: 41-65; Hendriks and Zeeman, 2009, Pretreatments to enhance the digestibility of lignocellulosic biomass, *Bioresource Technol.* 100: 10-18; Mosier et al., 2005, Features of promising technologies for pretreatment of lignocellulosic biomass, *Bioresource Technol.* 96: 673-686; Taherzadeh and Karimi, 2008, Pretreatment of lignocellulosic wastes to improve ethanol and biogas production: A review, *Int. J. of Mol. Sci.* 9: 1621-1651; Yang and Wyman, 2008, Pretreatment: the key to unlocking low-cost cellulosic ethanol, *Biofuels Bioproducts and Biorefining-Biofpr* 2: 26-40).

Mechanical Pretreatment. The term "mechanical pretreatment" refers to various types of grinding or milling (e.g., dry milling, wet milling, or vibratory ball milling) to disrupt and/or reduce particle sizeplant cell wall components of the cellulosic material.

Chemical Pretreatment. In practicing the methods of the present invention, any chemical pretreatment process known in the art can be used to disrupt plant cell wall components of the cellulosic material (Chandra et al., 2007, supra; Galbe and Zacchi, 2007, Pretreatment of lignocellulosic materials for efficient bioethanol production, *Adv. Biochem. Engin./Biotechnol.* 108: 41-65; Hendriks and Zeeman, 2009, Pretreatments to enhance the digestibility of lignocellulosic biomass, *Bioresource Technol.* 100: 10-18; Mosier et al., 2005, Features of promising technologies for pretreatment of lignocellulosic biomass, *Bioresource Technol.* 96: 673-686; Taherzadeh and Karimi, 2008, Pretreatment of lignocellulosic wastes to improve ethanol and biogas production: A review, *Int. J. of Mol. Sci.* 9: 1621-1651; Yang and Wyman, 2008, Pretreatment: the key to unlocking low-cost cellulosic ethanol, *Biofuels Bioproducts and Biorefining-Biofpr.* 2: 26-40).

Conventional chemical pretreatments include, but are not limited to, steam pretreatment (with or without explosion), dilute acid pretreatment, hot water pretreatment, alkaline pretreatment, lime pretreatment, wet oxidation, wet explosion, ammonia fiber explosion, organosolv pretreatment, and biological pretreatment. Additional pretreatments include ammonia percolation, ultrasound, electroporation, microwave, supercritical $CO_2$, supercritical $H_2O$, ozone, and gamma irradiation pretreatments.

The cellulosic material can be chemically pretreated before hydrolysis and/or fermentation. Pretreatment is preferably performed prior to the hydrolysis. Alternatively, the pretreatment can be carried out simultaneously with enzyme hydrolysis to release fermentable sugars, such as glucose, cellobiose, and/or xylose. In most cases the pretreatment step itself can result in some conversion of the cellulosic material to fermentable sugars (even in absence of enzymes).

Steam Pretreatment: In steam pretreatment, the cellulosic material is heated to disrupt the plant cell wall components, including lignin, hemicellulose, and cellulose to make the cellulose and other fractions, e.g., hemicellulose, accessible to enzymes. The cellulosic material is passed to or through a reaction vessel where steam is injected to increase the temperature to the required temperature and pressure and is retained therein for the desired reaction time. Steam pretreatment is preferably done at 140-230° C., more preferably 160-200° C., and most preferably 170-190° C., where the optimal temperature range depends on any addition of a chemical catalyst. Residence time for the steam pretreatment is preferably 1-15 minutes, more preferably 3-12 minutes, and most preferably 4-10 minutes, where the optimal residence time depends on temperature range and any addition of a chemical catalyst. Steam pretreatment allows for relatively high solids loadings, so that cellulosic material is generally only moist during the pretreatment. The steam pretreatment is often combined with an explosive discharge of the material after the pretreatment, which is known as steam explosion, that is, rapid flashing to atmospheric pressure and turbulent flow of the material to increase the accessible surface area by fragmentation (Duff and Murray, 1996, *Bioresource Technology* 855: 1-33; Galbe and Zacchi, 2002, *Appl. Microbiol. Biotechnol.* 59: 618-628; U.S. Patent Application No. 20020164730). During steam pretreatment, hemicellulose acetyl groups are cleaved and the resulting acid autocatalyzes partial hydrolysis of the hemicellulose to monosaccharides and oligosaccharides. Lignin is removed to only a limited extent.

A catalyst such as $H_2SO_4$ or $SO_2$ (typically 0.3 to 3% w/w) is often added prior to steam pretreatment, which decreases the time and temperature, increases the recovery, and improves enzymatic hydrolysis (Ballesteros et al., 2006, *Appl. Biochem. Biotechnol.* 129-132: 496-508; Varga et al., 2004, *Appl. Biochem. Biotechnol.* 113-116: 509-523; Sassner et al., 2006, *Enzyme Microb. Technol.* 39: 756-762).

Chemical Pretreatment: The term "chemical treatment" refers to any chemical pretreatment that promotes the separation and/or release of cellulose, hemicellulose, and/or lignin. Examples of suitable chemical pretreatment processes include, for example, dilute acid pretreatment, lime pretreatment, wet oxidation, ammonia fiber/freeze explosion (AFEX), ammonia percolation (APR), and organosolv pretreatments.

In dilute acid pretreatment, the cellulosic material is mixed with dilute acid, typically $H_2SO_4$, and water to form a slurry, heated by steam to the desired temperature, and after a residence time flashed to atmospheric pressure. The dilute acid pretreatment can be performed with a number of reactor designs, e.g., plug-flow reactors, counter-current reactors, or continuous counter-current shrinking bed reactors (Duff and Murray, 1996, supra; Schell et al., 2004, *Bioresource Technol.* 91: 179-188; Lee et al., 1999, *Adv. Biochem. Eng. Biotechnol.* 65: 93-115).

Several methods of pretreatment under alkaline conditions can also be used. These alkaline pretreatments include, but are not limited to, lime pretreatment, wet oxidation, ammonia percolation (APR), and ammonia fiber/freeze explosion (AFEX).

Lime pretreatment is performed with calcium carbonate, sodium hydroxide, or ammonia at low temperatures of 85-150° C. and residence times from 1 hour to several days (Wyman et al., 2005, *Bioresource Technol.* 96: 1959-1966; Mosier et al., 2005, *Bioresource Technol.* 96: 673-686). WO 2006/110891, WO 2006/11899, WO 2006/11900, and WO 2006/110901 disclose pretreatment methods using ammonia.

Wet oxidation is a thermal pretreatment performed typically at 180-200° C. for 5-15 minutes with addition of an oxidative agent such as hydrogen peroxide or over-pressure of oxygen (Schmidt and Thomsen, 1998, *Bioresource Technol.* 64: 139-151; Palonen et al., 2004, *Appl. Biochem. Biotechnol.* 117: 1-17; Varga et al., 2004, *Biotechnol. Bioeng.* 88: 567-574; Martin et al., 2006, *J. Chem. Technol. Biotechnol.* 81: 1669-1677). The pretreatment is performed at preferably 1-40% dry matter, more preferably 2-30% dry matter, and most preferably 5-20% dry matter, and often the initial pH is increased by the addition of alkali such as sodium carbonate.

A modification of the wet oxidation pretreatment method, known as wet explosion (combination of wet oxidation and steam explosion), can handle dry matter up to 30%. In wet explosion, the oxidizing agent is introduced during pretreatment after a certain residence time. The pretreatment is then ended by flashing to atmospheric pressure (WO 2006/032282).

Ammonia fiber explosion (AFEX) involves treating the cellulosic material with liquid or gaseous ammonia at moderate temperatures such as 90-100° C. and high pressure such as 17-20 bar for 5-10 minutes, where the dry matter content can be as high as 60% (Gollapalli et al., 2002, *Appl. Biochem. Biotechnol.* 98: 23-35; Chundawat et al., 2007, *Biotechnol. Bioeng.* 96: 219-231; Alizadeh et al., 2005, *Appl. Biochem. Biotechnol.* 121: 1133-1141; Teymouri et al., 2005, *Bioresource Technol.* 96: 2014-2018). AFEX pretreatment results in the depolymerization of cellulose and partial hydrolysis of hemicellulose. Lignin-carbohydrate complexes are cleaved.

Organosolv pretreatment delignifies the cellulosic material by extraction using aqueous ethanol (40-60% ethanol) at 160-200° C. for 30-60 minutes (Pan et al., 2005, *Biotechnol. Bioeng.* 90: 473-481; Pan et al., 2006, *Biotechnol. Bioeng.* 94: 851-861; Kurabi et al., 2005, *Appl. Biochem. Biotechnol.* 121: 219-230). Sulphuric acid is usually added as a catalyst. In organosolv pretreatment, the majority of hemicellulose is removed.

Other examples of suitable pretreatment methods are described by Schell et al., 2003, *Appl. Biochem. and Biotechnol.* Vol. 105-108, p. 69-85, and Mosier et al., 2005, *Bioresource Technology* 96: 673-686, and U.S. Published Application 2002/0164730.

In one aspect, the chemical pretreatment is preferably carried out as an acid treatment, and more preferably as a continuous dilute and/or mild acid treatment. The acid is typically sulfuric acid, but other acids can also be used, such as acetic acid, citric acid, nitric acid, phosphoric acid, tartaric acid, succinic acid, hydrogen chloride, or mixtures thereof. Mild acid treatment is conducted in the pH range of preferably 1-5, more preferably 1-4, and most preferably 1-3. In one aspect, the acid concentration is in the range from preferably 0.01 to 20 wt % acid, more preferably 0.05 to 10 wt % acid, even more preferably 0.1 to 5 wt % acid, and most preferably 0.2 to 2.0 wt % acid. The acid is contacted with the cellulosic material and held at a temperature in the range of preferably 160-220° C., and more preferably 165-195° C., for periods ranging from seconds to minutes to, e.g., 1 second to 60 minutes.

In another aspect, pretreatment is carried out as an ammonia fiber explosion step (AFEX pretreatment step).

In another aspect, pretreatment takes place in an aqueous slurry. In preferred aspects, the cellulosic material is present during pretreatment in amounts preferably between 10-80 wt %, more preferably between 20-70 wt %, and most preferably between 30-60 wt %, such as around 50 wt %. The pretreated cellulosic material can be unwashed or washed using any method known in the art, e.g., washed with water.

Biological Pretreatment: The term "biological pretreatment" refers to any biological pretreatment that promotes the separation and/or release of cellulose, hemicellulose, and/or lignin from the cellulosic material. Biological pretreatment techniques can involve applying lignin-solubilizing microorganisms (see, for example, Hsu, T.-A., 1996, Pretreatment of biomass, in *Handbook on Bioethanol: Production and Utilization*, Wyman, C. E., ed., Taylor & Francis, Washington, D.C., 179-212; Ghosh and Singh, 1993, Physicochemical and biological treatments for enzymatic/microbial conversion of cellulosic biomass, *Adv. Appl. Microbiol.* 39: 295-333; McMillan, J. D., 1994, Pretreating lignocellulosic biomass: a review, in *Enzymatic Conversion of Biomass for Fuels Production*, Himmel, M. E., Baker, J. O., and Overend, R. P., eds., *ACS Symposium Series* 566, American Chemical Society, Washington, D.C., chapter 15; Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Olsson and Hahn-Hagerdal, 1996, Fermentation of lignocellulosic hydrolysates for ethanol production, *Enz. Microb. Tech.* 18: 312-331; and Vallander and Eriksson, 1990, Production of ethanol from lignocellulosic materials: State of the art, *Adv. Biochem. Eng./Biotechnol.* 42: 63-95).

Physical Pretreatment. The term "physical pretreatment" refers to any pretreatment that promotes the separation and/or release of cellulose, hemicellulose, and/or lignin from the cellulosic material. For example, physical pretreatment can involve irradiation (e.g., microwave irradiation), steaming/steam explosion, hydrothermolysis, and combinations thereof.

Physical pretreatment can involve high pressure and/or high temperature (steam explosion). In one aspect, high pressure means pressure in the range of preferably about 300 to about 600 psi, more preferably about 350 to about 550 psi, and most preferably about 400 to about 500 psi, such as around 450 psi. In another aspect, high temperature means temperatures in the range of about 100 to about 300° C., preferably about 140 to about 235° C. In a preferred aspect, physical pretreatment is performed in a batch-process, steam gun hydrolyzer system that uses high pressure and high temperature as defined above, e.g., a Sunds Hydrolyzer available from Sunds Defibrator AB, Sweden.

The cellulosic material can be subjected to pre-soaking, wetting, washing, or conditioning prior to pretreatment using methods known in the art.

Combined Physical and Chemical Pretreatment: The cellulosic material can be pretreated both physically and chemically. For instance, the pretreatment step can involve dilute or mild acid treatment and high temperature and/or pressure treatment. The physical and chemical pretreatments can be carried out sequentially or simultaneously, as desired. A mechanical pretreatment can also be included.

Accordingly, in a preferred aspect, the cellulosic material is subjected to mechanical, chemical, or physical pretreatment, or any combination thereof, to promote the separation and/or release of cellulose, hemicellulose, and/or lignin.

Saccharification. In the hydrolysis step, also known as saccharification, the cellulosic material, e.g., pretreated, is hydrolyzed to break down cellulose and alternatively also hemicellulose to fermentable sugars, such as glucose, cellobiose, xylose, xylulose, arabinose, mannose, galactose, and/or soluble oligosaccharides. The hydrolysis is performed enzymatically by an enzyme composition of the present invention.

Enzymatic hydrolysis is preferably carried out in a suitable aqueous environment under conditions that can be readily determined by one skilled in the art. In a preferred aspect, hydrolysis is performed under conditions suitable for the activity of the enzyme(s), i.e., optimal for the enzyme(s). The hydrolysis can be carried out as a fed batch or continuous process where the pretreated cellulosic material (substrate) is fed gradually to, for example, an enzyme containing hydrolysis solution.

The saccharification is generally performed in stirred-tank reactors or fermentors under controlled pH, temperature, and mixing conditions. Suitable process time, temperature and pH conditions can readily be determined by one skilled in the art. For example, the saccharification can last up to 200 hours, but is typically performed for preferably about 12 to about 96 hours, more preferably about 16 to about 72 hours, and most preferably about 24 to about 48 hours. The temperature is in the range of preferably about 25° C. to about 70° C., more preferably about 30° C. to about 65° C., and more preferably about 40° C. to 60° C., in particular about 50° C. The pH is in the range of preferably about 3 to about 8, more preferably about 3.5 to about 7, and most preferably about 4 to about 6, in particular about pH 5. The dry solids content is in the range of preferably about 5 to about 50 wt %, more preferably about 10 to about 40 wt %, and most preferably about 20 to about 30 wt %.

In a preferred aspect, an effective amount of an enzyme composition of the present invention is about 0.5 to about 50 mg, preferably at about 0.5 to about 40 mg, more preferably at about 0.5 to about 30 mg, more preferably at about 0.75 to about 20 mg, more preferably at about 0.75 to about 15 mg, even more preferably at about 1.0 to about 10 mg, and most preferably at about 2.0 to about 5 mg per g of cellulose in a cellulosic material.

Fermentation. The fermentable sugars obtained from the hydrolyzed cellulosic material can be fermented by one or more (several) fermenting microorganisms capable of fermenting the sugars directly or indirectly into a desired fermentation product. "Fermentation" or "fermentation process" refers to any fermentation process or any process comprising a fermentation step. Fermentation processes also include fermentation processes used in the consumable alcohol industry (e.g., beer and wine), dairy industry (e.g., fermented dairy products), leather industry, and tobacco industry. The fermentation conditions depend on the desired fermentation product and fermenting organism and can easily be determined by one skilled in the art.

In the fermentation step, sugars, released from cellulosic material as a result of the pretreatment and enzymatic hydrolysis steps, are fermented to a product, e.g., ethanol, by a fermenting organism, such as yeast. Hydrolysis (saccharification) and fermentation can be separate or simultaneous, as described herein.

Any suitable hydrolyzed cellulosic material can be used in the fermentation step in practicing the present invention. The material is generally selected based on the desired fermentation product, i.e., the substance to be obtained from the fermentation, and the process employed, as is well known in the art.

The term "fermentation medium" is understood herein to refer to a medium before the fermenting microorganism(s) is(are) added, such as, a medium resulting from a saccharification process, as well as a medium used in a simultaneous saccharification and fermentation process (SSF).

"Fermenting microorganism" refers to any microorganism, including bacterial and fungal organisms, suitable for use in a desired fermentation process to produce a fermentation product. The fermenting organism can be $C_6$ and/or $C_5$ fermenting organisms, or a combination thereof. Both $C_6$ and $C_5$ fermenting organisms are well known in the art. Suitable fermenting microorganisms are able to ferment, i.e., convert, sugars, such as glucose, xylose, xylulose, arabinose, maltose, mannose, galactose, or oligosaccharides, directly or indirectly into the desired fermentation product.

Examples of bacterial and fungal fermenting organisms producing ethanol are described by Lin et al., 2006, *Appl. Microbiol. Biotechnol.* 69: 627-642.

Examples of fermenting microorganisms that can ferment $C_6$ sugars include bacterial and fungal organisms, such as yeast. Preferred yeast includes strains of the *Saccharomyces* spp., preferably *Saccharomyces cerevisiae.*

Examples of fermenting organisms that can ferment $C_5$ sugars include bacterial and fungal organisms, such as some yeast. Preferred $C_5$ fermenting yeast include strains of *Pichia*, preferably *Pichia stipitis*, such as *Pichia stipitis* CBS 5773; strains of *Candida*, preferably *Candida boidinii, Candida brassicae, Candida sheatae, Candida diddensii, Candida pseudotropicalis*, or *Candida utilis.*

Other fermenting organisms include strains of *Zymomonas*, such as *Zymomonas mobilis; Hansenula*, such as *Hansenula anomala; Kluyveromyces*, such as *K. fragilis; Schizosaccharomyces*, such as *S. pombe; E. coli*, especially *E. coli* strains that have been genetically modified to improve the yield of ethanol; *Clostridium*, such as *Clostridium acetobutylicum, Chlostridium thermocellum*, and *Chlostridium phytofermentans; Geobacillus* sp.; *Thermoanaerobacter*, such as *Thermoanaerobacter saccharolyticum*; and *Bacillus*, such as *Bacillus coagulans.*

In a preferred aspect, the yeast is a *Saccharomyces* spp. In a more preferred aspect, the yeast is *Saccharomyces cerevisiae.* In another more preferred aspect, the yeast is *Saccharomyces distaticus.* In another more preferred aspect, the yeast is *Saccharomyces uvarum.* In another preferred aspect, the yeast is a *Kluyveromyces.* In another more preferred aspect, the yeast is *Kluyveromyces marxianus.* In another more preferred aspect, the yeast is *Kluyveromyces fragilis.* In another preferred aspect, the yeast is a *Candida.* In another more preferred aspect, the yeast is *Candida boidinii.* In another more preferred aspect, the yeast is *Candida brassicae.* In another more preferred aspect, the yeast is *Candida diddensii.* In another more preferred aspect, the yeast is *Candida pseudotropicalis.* In another more preferred aspect, the yeast is *Candida utilis.* In another preferred aspect, the yeast is a *Clavispora.* In another more preferred aspect, the yeast is *Clavispora lusitaniae.* In another more preferred aspect, the yeast is *Clavispora opuntiae.* In another preferred aspect, the yeast is a *Pachysolen.* In another more preferred aspect, the yeast is *Pachysolen tannophilus.* In another preferred aspect, the yeast is a *Pichia.* In another more preferred aspect, the yeast is a *Pichia stipitis.* In another preferred aspect, the yeast is a *Bretannomyces.* In another more preferred aspect, the yeast is *Bretannomyces clausenii* (Philippidis, G. P., 1996, Cellulose bioconversion technology, in *Handbook on Bioethanol: Production and Utilization*, Wyman, C. E., ed., Taylor & Francis, Washington, D.C., 179-212).

Bacteria that can efficiently ferment hexose and pentose to ethanol include, for example, *Zymomonas mobilis, Clostridium acetobutylicum, Clostridium thermocellum, Chlostridium phytofermentans, Geobacillus* sp., *Thermoanaerobacter saccharolyticum*, and *Bacillus coagulans* (Philippidis, 1996, supra).

In a preferred aspect, the bacterium is a *Zymomonas.* In a more preferred aspect, the bacterium is *Zymomonas mobilis.* In another preferred aspect, the bacterium is a *Clostridium.* In another more preferred aspect, the bacterium is *Clostridium thermocellum.*

Commercially available yeast suitable for ethanol production includes, e.g., ETHANOL RED™ yeast (available from Fermentis/Lesaffre, USA), FALI™ (available from Fleischmann's Yeast, USA), SUPERSTART™ and THERMOSACC™ fresh yeast (available from Ethanol Technology, WI, USA), BIOFERM™ AFT and XR (available from NABC—North American Bioproducts Corporation, GA, USA), GERT STRAND™ (available from Gert Strand AB, Sweden), and FERMIOL™ (available from DSM Specialties).

In a preferred aspect, the fermenting microorganism has been genetically modified to provide the ability to ferment pentose sugars, such as xylose utilizing, arabinose utilizing, and xylose and arabinose co-utilizing microorganisms.

The cloning of heterologous genes into various fermenting microorganisms has led to the construction of organisms capable of converting hexoses and pentoses to ethanol (cofermentation) (Chen and Ho, 1993, Cloning and improving the expression of *Pichia stipitis* xylose reductase gene in *Saccharomyces cerevisiae, Appl. Biochem. Biotechnol.* 39-40: 135-147; Ho et al., 1998, Genetically engineered *Saccharomyces* yeast capable of effectively cofermenting glucose and xylose, *Appl. Environ. Microbiol.* 64: 1852-1859; Kotter and Ciriacy, 1993, Xylose fermentation by *Saccharomyces cerevisiae, Appl. Microbiol. Biotechnol.* 38: 776-783; Walfridsson et al., 1995, Xylose-metabolizing *Saccharomyces cerevisiae* strains overexpressing the TKL1 and TAL1 genes encoding the pentose phosphate pathway enzymes transketolase and transaldolase, *Appl. Environ. Microbiol.* 61: 4184-4190; Kuyper et al., 2004, Minimal metabolic engineering of *Saccharomyces cerevisiae* for efficient anaerobic xylose fermentation: a proof of principle, *FEMS Yeast Research* 4: 655-664; Beall et al., 1991, Parametric studies of ethanol production from xylose and other sugars by recombinant *Escherichia coli, Biotech. Bioeng.* 38: 296-303; Ingram et al., 1998, Metabolic engineering of bacteria for ethanol production, *Biotechnol. Bioeng.* 58: 204-214; Zhang et al., 1995, Metabolic engineering of a pentose metabolism pathway in ethanologenic *Zymomonas mobilis, Science* 267: 240-243; Deanda et al., 1996, Development of an arabinose-fermenting *Zymomonas mobilis* strain by metabolic pathway engineering, *Appl. Environ. Microbiol.* 62: 4465-4470; WO 2003/062430, xylose isomerase).

In a preferred aspect, the genetically modified fermenting microorganism is *Saccharomyces cerevisiae*. In another preferred aspect, the genetically modified fermenting microorganism is *Zymomonas mobilis*. In another preferred aspect, the genetically modified fermenting microorganism is *Escherichia coli*. In another preferred aspect, the genetically modified fermenting microorganism is *Klebsiella oxytoca*. In another preferred aspect, the genetically modified fermenting microorganism is *Kluyveromyces* sp.

It is well known in the art that the organisms described above can also be used to produce other substances, as described herein.

The fermenting microorganism is typically added to the degraded lignocellulose or hydrolysate and the fermentation is performed for about 8 to about 96 hours, such as about 24 to about 60 hours. The temperature is typically between about 26° C. to about 60° C., in particular about 32° C. or 50° C., and at about pH 3 to about pH 8, such as around pH 4-5, 6, or 7.

In a preferred aspect, the yeast and/or another microorganism is applied to the degraded cellulosic material and the fermentation is performed for about 12 to about 96 hours, such as typically 24-60 hours. In a preferred aspect, the temperature is preferably between about 20° C. to about 60° C., more preferably about 25° C. to about 50° C., and most preferably about 32° C. to about 50° C., in particular about 32° C. or 50° C., and the pH is generally from about pH 3 to about pH 7, preferably around pH 4-7. However, some fermenting organisms, e.g., bacteria, have higher fermentation temperature optima. Yeast or another microorganism is preferably applied in amounts of approximately $10^5$ to $10^{12}$, preferably from approximately $10^7$ to $10^{10}$, especially approximately $2\times10^8$ viable cell count per ml of fermentation broth. Further guidance in respect of using yeast for fermentation can be found in, e.g., "The Alcohol Textbook" (Editors K. Jacques, T. P. Lyons and D. R. Kelsall, Nottingham University Press, United Kingdom 1999), which is hereby incorporated by reference.

For ethanol production, following the fermentation the fermented slurry is distilled to extract the ethanol. The ethanol obtained according to the methods of the invention can be used as, e.g., fuel ethanol, drinking ethanol, i.e., potable neutral spirits, or industrial ethanol.

A fermentation stimulator can be used in combination with any of the processes described herein to further improve the fermentation process, and in particular, the performance of the fermenting microorganism, such as, rate enhancement and ethanol yield. A "fermentation stimulator" refers to stimulators for growth of the fermenting microorganisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, for example, Alfenore et al., Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Fermentation products: A fermentation product can be any substance derived from the fermentation. The fermentation product can be, without limitation, an alcohol (e.g., arabinitol, butanol, ethanol, glycerol, methanol, 1,3-propanediol, sorbitol, and xylitol); an organic acid (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); a ketone (e.g., acetone); an amino acid (e.g., aspartic acid, glutamic acid, glycine, lysine, serine, and threonine); and a gas (e.g., methane, hydrogen ($H_2$), carbon dioxide ($CO_2$), and carbon monoxide (CO)). The fermentation product can also be protein as a high value product.

In a preferred aspect, the fermentation product is an alcohol. It will be understood that the term "alcohol" encompasses a substance that contains one or more hydroxyl moieties. In a more preferred aspect, the alcohol is arabinitol. In another more preferred aspect, the alcohol is butanol. In another more preferred aspect, the alcohol is ethanol. In another more preferred aspect, the alcohol is glycerol. In another more preferred aspect, the alcohol is methanol. In another more preferred aspect, the alcohol is 1,3-propanediol. In another more preferred aspect, the alcohol is sorbitol. In another more preferred aspect, the alcohol is xylitol. See, for example, Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Silveira, M. M., and Jonas, R., 2002, The biotechnological production of sorbitol, *Appl. Microbiol. Biotechnol.* 59: 400-408; Nigam, P., and Singh, D., 1995, Processes for fermentative production of xylitol—a sugar substitute, *Process Biochemistry* 30 (2): 117-124;

Ezeji, T. C., Qureshi, N. and Blaschek, H. P., 2003, Production of acetone, butanol and ethanol by *Clostridium beijerinckii* BA101 and in situ recovery by gas stripping, *World Journal of Microbiology and Biotechnology* 19 (6): 595-603.

In another preferred aspect, the fermentation product is an organic acid. In another more preferred aspect, the organic acid is acetic acid. In another more preferred aspect, the organic acid is acetonic acid. In another more preferred aspect, the organic acid is adipic acid. In another more preferred aspect, the organic acid is ascorbic acid. In another more preferred aspect, the organic acid is citric acid. In another more preferred aspect, the organic acid is 2,5-diketo-D-gluconic acid. In another more preferred aspect, the organic acid is formic acid. In another more preferred aspect, the organic acid is fumaric acid. In another more preferred aspect, the organic acid is glucaric acid. In another more preferred aspect, the organic acid is gluconic acid. In another more preferred aspect, the organic acid is glucuronic acid. In another more preferred aspect, the organic acid is glutaric acid. In another preferred aspect, the organic acid is 3-hydroxypropionic acid. In another more preferred aspect, the organic acid is itaconic acid. In another more preferred aspect, the organic acid is lactic acid. In another more preferred aspect, the organic acid is malic acid. In another more preferred aspect, the organic acid is malonic acid. In another more preferred aspect, the organic acid is oxalic acid. In another more preferred aspect, the organic acid is propionic acid. In another more preferred aspect, the organic acid is succinic acid. In another more preferred aspect, the organic acid is xylonic acid. See, for example, Chen, R., and Lee, Y. Y., 1997, Membrane-mediated extractive fermentation for lactic acid production from cellulosic biomass, *Appl. Biochem. Biotechnol.* 63-65: 435-448.

In another preferred aspect, the fermentation product is a ketone. It will be understood that the term "ketone" encompasses a substance that contains one or more ketone moieties. In another more preferred aspect, the ketone is acetone. See, for example, Qureshi and Blaschek, 2003, supra.

In another preferred aspect, the fermentation product is an amino acid. In another more preferred aspect, the organic acid is aspartic acid. In another more preferred aspect, the amino acid is glutamic acid. In another more preferred aspect, the amino acid is glycine. In another more preferred aspect, the amino acid is lysine. In another more preferred aspect, the amino acid is serine. In another more preferred aspect, the amino acid is threonine. See, for example, Richard, A., and Margaritis, A., 2004, Empirical modeling of batch fermentation kinetics for poly(glutamic acid) production and other microbial biopolymers, *Biotechnology and Bioengineering* 87 (4): 501-515.

In another preferred aspect, the fermentation product is a gas. In another more preferred aspect, the gas is methane. In another more preferred aspect, the gas is $H_2$. In another more preferred aspect, the gas is $CO_2$. In another more preferred aspect, the gas is CO. See, for example, Kataoka, N., A. Miya, and K. Kiriyama, 1997, Studies on hydrogen production by continuous culture system of hydrogen-producing anaerobic bacteria, *Water Science and Technology* 36 (6-7): 41-47; and Gunaseelan V. N. in *Biomass and Bioenergy*, Vol. 13 (1-2), pp. 83-114, 1997, Anaerobic digestion of biomass for methane production: A review.

Recovery. The fermentation product(s) can be optionally recovered from the fermentation medium using any method known in the art including, but not limited to, chromatography, electrophoretic procedures, differential solubility, distillation, or extraction. For example, alcohol is separated from the fermented cellulosic material and purified by conventional methods of distillation. Ethanol with a purity of up to about 96 vol. % can be obtained, which can be used as, for example, fuel ethanol, drinking ethanol, i.e., potable neutral spirits, or industrial ethanol.

The present invention is further described by the following examples that should not be construed as limiting the scope of the invention.

EXAMPLES

Materials

Chemicals used as buffers and substrates were commercial products of at least reagent grade.

Media

PDA plates were composed of 39 grams of potato dextrose agar and deionized water to 1 liter.

Minimal medium plates were composed of 6 g of $NaNO_3$, 0.52 g of KCl, 1.52 g of $KH_2PO_4$, 1 ml of COVE trace elements solution, 20 g of Noble agar, 20 ml of 50% glucose, 2.5 ml of $MgSO_4.7H_2O$, 20 ml of a 0.02% biotin solution, and deionized water to 1 liter.

COVE trace elements solution was composed of 0.04 g of $Na_2B_4O_7.10H_2O$, 0.4 g of $CuSO_4.5H_2O$, 1.2 g of $FeSO_4.7H_2O$, 0.7 g of $MnSO_4.H_2O$, 0.8 g of $Na_2MoO_2.2H_2O$, 10 g of $ZnSO_4.7H_2O$, and deionized water to 1 liter.

MDU2BP medium was composed per liter of 45 g of maltose, 1 g of $MgSO_4.7H_2O$, 1 g of NaCl, 2 g of $K_2SO_4$, 12 g of $KH_2PO_4$, 7 g of yeast extract, 2 g of urea, and 0.5 ml of AMG trace metals solution; pH 5.0.

AMG trace metals solution was composed per liter of 14.3 g of $ZnSO_4.7H_2O$, 2.5 g of $CuSO_4.5H_2O$, 0.5 g of $NiCl_2.6H_2O$, 13.8 g of $FeSO_4.7H_2O$, 8.5 g of $MnSO_4.7H_2O$, and 3 g of citric acid.

NNCYP-PCS medium was composed of 5.0 g of $NaNO_3$, 3.0 g of $NH_4Cl$, 2.0 g of MES, 2.5 g of citric acid, 0.2 g of $CaCl_2$ $2H_2O$, 1.0 g of Bacto Peptone, 5.0 g of yeast extract, 0.2 g of $MgSO_4$ $7H_2O$, 4.0 g of $K_2HPO_4$, 1.0 ml of COVE trace elements solution, 2.5 g of glucose, 25.0 g of pretreated corn stover (PCS), and deionized water to 1 liter.

2×YT medium was composed per liter of 16 g of tryptone, 10 g of yeast extract, and 5 g of NaCl.

2×YT plates were composed per liter of 16 g of tryptone, 10 g of yeast extract, 5 g of NaCl and 15 g of Noble agar.

YG agar plates were composed per liter of 5.0 g of yeast extract, 10.0 g of glucose, and 20.0 g of agar.

YEG medium was composed per liter of 20 g of dextrose and 5 g of yeast extract.

LB medium was composed per liter of 10 g of tryptone, 5 g of yeast extract, and 5 g of sodium chloride.

LB agar plates were composed of 10 g of tryptone, 5 g of yeast extract, 10 g of sodium chloride, 15 g of agar, and 1 liter of distilled water.

YP medium was composed per liter of 10 g of yeast extract and 20 g of Bacto peptone.

MEX-1 medium was composed per liter of 20 g of soya bean meal, 15 g of wheat bran, 10 g of microcrystalline cellulose (AVICEL®; FMC, Philadelphia, Pa., USA), 5 g of maltodextrin, 3 g of Bactopeptone, 0.2 g of pluronic, and 1 g of olive oil.

LB ampicillin medium was composed per liter of 10 g of tryptone, 5 g of yeast extract, 5 g of sodium chloride, and 50 mg of ampicillin (filter sterilized, added after autoclaving).

LB ampicillin plates were composed of 15 g of bacto agar per liter of LB ampicillin medium.

MY25 medium was composed per liter of 25 g of maltodextrin, 2 g of $MgSO_4.7H_2O$, 10 g of $KH_2PO_4$, 2 g of citric acid, 2 g of $K_2SO_4$, 2 g of urea, 10 g of yeast extract, and 1.5 ml of AMG trace metals solution, adjusted to pH 6.

YPD medium was composed of 1% yeast extract, 2% peptone, and filter-sterilized 2% glucose added after autoclaving.

YPM medium was composed of 1% yeast extract, 2% peptone, and filter-sterilized 2% maltodextrin added after autoclaving.

SC-URA medium with glucose or galactose was composed of 100 ml of 10× Basal salts, 25 ml of 20% casamino acids without vitamins, 10 ml of 1% tryptophan, 4 ml of 5% threonine (filter sterilized, added after autoclaving), and 100 ml of 20% glucose or 100 ml of 20% galactose (filter sterilized, added after autoclaving), and deionized water to 1 liter.

10× Basal salts solution was composed of 75 g of yeast nitrogen base, 113 g of succinic acid, 68 g of NaOH, and deionized water to 1 liter.

SC-agar plates were composed of 20 g of agar per liter of SC-URA medium (with glucose or galactose as indicated).

0.1% AZCL xylan SC-URA agar plates with galactose were composed of 20 g of agar per liter of SC-URA medium with galactose and 0.1% AZCL oat xylan (Megazyme, Wicklow, Ireland).

SC-URA medium with galactose was composed of 900 ml of SC-Grund Agar (autoclaved), 4 ml of 5% threonine (filter sterilized), and 100 ml of 20% galactose (filter sterilized).

SC-Grund Agar was composed of 7.5 g Yeast Nitrogen Base (without amino acids), 11.3 g of succinic acid, 6.8 g of sodium hydroxide, 5.6 g of casamino acids, 0.1 g of L-tryptophan, 20 g of agar, and deionized water to 1 liter.

COVE plates were composed per liter of 342.3 g of sucrose, 25 g of Noble agar, 20 ml of COVE salts solution, 10 mM acetamide, and 15 or 20 mM CsCl. The solution was adjusted to pH 7.0 before autoclaving.

COVE2 plates were composed per liter of 30 g of sucrose, 20 ml of COVE salts solution, 20 ml of 1 M acetamide, and 25 g of Agar Noble.

COVE salts solution was composed per liter of 26 g of KCl, 26 g of $MgSO_4.7H_2O$, 76 g of $KH_2PO_4$, and 50 ml of COVE trace metals.

YPG medium was composed per liter of 10 g of yeast extract, 10 g of Bacto peptone, and 20 g of glucose.

M410 medium was composed per liter of 50 g of maltose, 50 g of glucose, 2 g of $MgSO_4$-$7H_2O$, 2 g of $KH_2PO_4$, 4 g of citric acid anhydrous powder, 8 g of yeast extract, 2 g of urea, 0.5 g of AMG trace metals solution, and 0.5 g of $CaCl_2$ at pH 6.0.

SOC medium was composed of 2% tryptone, 0.5% yeast extract, 10 mM NaCl, 2.5 mM KCl, 10 mM $MgCl_2$, and 10 mM $MgSO_4$; sterilized by autoclaving and then filter-sterilized glucose was added to 20 mM.

SY50 medium was composed per liter of 50 g of sucrose, 2 g of $MgSO_4.7H_2O$, 10 g of $KH_2PO_4$, anhydrous, 2 g of $K_2SO_4$, 2 g of citric acid, 10 g of yeast extract, 2 g of urea, 0.5 g of $CaCl_2.2H_2O$, and 0.5 g of 200×AMG trace metals solution, pH 6.0.

200×AMG trace metals solution was composed per liter of 3 g of citric acid, 14.3 g of $ZnSO_4.7H_2O$, 2.5 g of $CuSO_4.5H_2O$, 13.8 g of $FeSO_4.7H_2O$, and 8.5 g of $MnSO_4.H_2O$.

Cal-18 medium was composed per liter of 40 g of yeast extract, 1.3 g of magnesium sulfate, 50 g of maltodextrin, 20 g of $NaH_2PO_4$, and 0.1 g of antifoam.

Cellulase-inducing medium was composed of 20 g of cellulose, 10 g of corn steep solids, 1.45 g of $(NH_4)_2SO_4$, 2.08 g of $KH_2PO_4$, 0.28 g of $CaCl_2$, 0.42 g of $MgSO_4.7H_2O$, 0.42 ml of *Trichoderma* trace metals solution, and 1-2 drops of antifoam.

*Trichoderma* trace metals solution was composed per liter of 216 g of $FeCl_3.6H_2O$, 58 g of $ZnSO_4.7H_2O$, 27 g of $MnSO_4.H_2O$, 10 g of $CuSO_4.5H_2O$, 2.4 g of $H_3BO_3$, and 336 g of citric acid.

TE was composed of 10 mM Tris pH 7.4 and 0.1 mM EDTA.

YPM medium contained 1% yeast extract, 2% of peptone, and 2% of maltose in deionized water.

MY50 medium was composed of 50 g of Maltodextrin, 2 g of MgSO47H2O, 10 g of $KH_2PO_4$, 2 g of K2SO4, 2 g of citric acid, 10 g of yeast extract, 2 g of urea, 0.5 ml of AMG trace metals solution, and distilled water to 1 liter.

AMG trace metals solution was composed per liter of 14.3 g of $ZnSO_4.7H_2O$, 2.5 g of $CuSO_4.5H_2O$, 0.5 g of $NiCl_2.6H_2O$, 13.8 g of $FeSO_4.7H_2O$, 8.5 g of $MnSO_4.7H_2O$, 3 g of citric acid, and distilled water to 1 liter.

50× Vogels medium was composed per liter of 150 g of sodium citrate, 250 g of $KH_2PO_4$, 10 g of $MgSO_4.7H_2O$, 10 g of $CaCl_2.2H_2O$, 2.5 ml of biotin stock solution, 5.0 ml of AMG trace metals solution, and distilled water to 1 liter.

COVE agar selective plates were composed of 218 g sorbitol, 20 g agar, 20 ml COVE salts solution, 10 mM acetamide, 15 mM CsCl, and deionized water to 1 liter. The solution was adjusted to pH 7.0 before autoclaving.

COVE salts solution was composed of 26 g KCl, 26 g $MgSO_4.7H_2O$, 76 g $KH_2PO_4$, 50 ml COVE trace metals solution, and deionized water to 1 liter.

COVE trace metals solution was composed of 0.04 g $Na_2B_4O_7.10H_2O$, 0.4 g $CuSO_4.5H_2O$, 1.2 g $FeSO_4.7H_2O$, 0.7 g $MnSO_4.H_2O$, 0.8 g $Na_2MoO_2.2H_2O$, 10 g $ZnSO_4.7H_2O$, and deionized water to 1 liter.

YP+2% glucose medium was composed of 1% yeast extract, 2% peptone and 2% glucose in deionized water.

YP+2% maltodextrin medium is composed of 2% peptone, 2% maltodextrin, and 1% yeast extract in deionized water.

DAP-2C-1 medium is composed of 3% maltodextrin, 1.1% magnesium sulfate, 0.52% tri-potassium phosphate, 0.2% citric acid, 0.1% potassium dihydrogen phosphate, 0.1% Dowfax 63N10, 0.05% yeast extract, and 0.05% of a trace element solution (1.39% ferrous sulfate, 0.845% maganese sulfate, 0.68% zinc chloride, 0.3% citric acid, 0.25% copper sulfate, and 0.013% nickel chloride) in deionized water.

DAP-2C-1 medium is composed of 2% glucose, 1.1% magnesium sulfate, 1.0% maltose, 0.52% tri-potassium phosphate, 0.2% citric acid, 0.1% potassium dihydrogen phosphate, 0.1% Dowfax 63N10, 0.05% yeast extract, and 0.05% of a trace element solution (1.39% ferrous sulfate, 0.845% maganese sulfate, 0.68% zinc chloride, 0.3% citric acid, 0.25% copper sulfate, and 0.013% nickel chloride) in deionized water.

Example 1: Preparation of *Chaetomium thermophilum* CGMCC 0581 Cel7A Cellobiohydrolase I The *Chaetomium thermophilum* CGMCC 0581 Cel7A cellobiohydrolase I (CBHI) gene (SEQ ID NO: 1 [DNA sequence] and SEQ ID NO: 2 [deduced amino acid sequence]) was isolated according to WO 2003/000941 and expressed in *Aspergillus oryzae* JaL250 (WO 99/61651).

The fungal strain *Chaetomium thermophilum* CGMCC 0581 was grown on agar plate composed of 0.5% yeast extract, 1% glucose and 2% agar for 3 days at 45° C. The fully grown culture was used to inoculate shake flasks containing liquid medium composed of 3% soymeal, 1.5% maltose, and 0.5% peptone. The flasks were incubated at 45° C. for 48 hours with shaking. The mycelia were harvested by centrifugation of the culture broth at 8000 rpm, 4° C. for 30 minutes, transferred into a clean plastic bag followed by immediate freezing in liquid nitrogen, and stored at −80° C. before total RNA was isolated.

The frozen mycelia were grounded into a very fine powder with a sterilized mortar and pestle baked at 200° C. for 24 hours. An RNEASY® Plant Mini Kit (QIAGEN Inc., Valencia, Calif., USA) was used to isolate total RNA according to the manufacturer's instructions.

First strand cDNA synthesis from the total RNA was performed using a 3' RACE System for Rapid Amplification of cDNA Ends (Invitrogen Corporation, Carlsbad, Calif., USA) according to the manufacturer's instructions. The first strand cDNA of 3' RACE was used as PCR template for PCR screening.

Two oligonucleotides shown below were used for PCR screening of cDNA of *Chaetomium thermophilum* CGMCC 0581. The forward primer was derived from an alignment of conserved regions of cellobiohydrolase I genes and the reverse primer was provided by the 3' RACE System.

```
Forward primer:
                                        (SEQ ID NO: 67)
5'-GGnACnGGnTA(t/c)TG(t/c)GA-3'

Reverse primer:
                                        (SEQ ID NO: 68)
5'-GGCCACGCGTCGACTAGTAC-3'
```

One hundred picomoles of the forward primer and 10 picomoles of the reverse primer were used in a PCR reaction composed of 2 μl of the first strand cDNA of 3' RACE, 5 μl of 10× Taq DNA polymerase buffer (Promega Corporation, Madison, Wis., USA), 3 μl of 25 mM $MgCl_2$, 1 μl of 10 mM dNTP, and 2.5 units of Taq DNA polymerase (Promega Corporation, Madison, Wis., USA) in a final volume of 50 μl. The amplification was performed in a thermocycler programmed for 1 cycle at 95° C. for 3 minutes; 30 cycles each at 95° C. for 30 seconds, 50° C. for 30 seconds, and 72° C. for 50 seconds; and 1 cycle at 72 C for 10 minutes. The heat block then went to a 4° C. soak cycle.

The reaction products were isolated by 1.0% agarose gel electrophoresis using TBE buffer where an approximately 1.3 kb product band was excised from the gel, and purified using a WIZARD® PCR Preps DNA Purification System (Promega Corporation, Madison, Wis., USA) according to the manufacturer's instructions. The PCR product was sequenced using a 377 DNA Analyzer (Applied Biosystems Inc, Foster City, Calif., USA). Sequencing showed that the 1.3 kb fragment was homologous to cellobiohydrolase I.

Two oligos shown below were designed for the 5' end cloning of the *Chaetomium thermophilum* CGMCC 0581 Cel7A cellobiohydrolase I by using a 5' RACE System for Rapid Amplification of cDNA Ends (Invitrogen Corporation, Carlsbad, Calif., USA).

```
Primer 4310AS1:
                                        (SEQ ID NO: 69)
5'-AGATATCCATCTCAGAGCA-3'
```

-continued

```
Primer 4310AS2:
                                        (SEQ ID NO: 70)
5'-GTTGGCATCATTGGTCG-3'
```

The gene specific primer 4310AS1 was used for the first strand cDNA synthesis using a 5' RACE System according to the manufacturer's instructions. The first strand cDNA of 5' RACE (5 μl) was used as template for PCR amplification composed of 5 μl of 10×Taq DNA polymerase buffer, 3 μl of 25 mM $MgCl_2$, 1 μl of 10 mM dNTP, 1 μl of 10 μM 4310AS2 primer, 1 μl of 10 μM primer AAP (Abridged Anchor Primer, provided by the kit), and 2.5 units of Taq DNA polymerase in a final volume of 50 μl. The amplification was performed in a thermocycler programmed for 1 cycle at 94° C. for 3 minutes; 30 cycles each at 95° C. for 30 seconds, 50° C. for 30 seconds, and 72° C. for 50 seconds; and 1 cycle at 72° C. for 10 minutes. The heat block then went to a 4° C. soak cycle.

The PCR products were isolated by 1.0% agarose gel electrophoresis using TBE buffer and purified using a WIZARD® PCR Preps DNA Purification System. A dominant DNA fragment of 0.8 kb was confirmed to be the 5' end of *Chaetomium thermophilum* CGMCC 0581 Cel7A cellobiohydrolase I gene by sequencing using a 377 DNA Analyzer.

Two primers shown below were designed based on the sequence information from both 5' and 3' end cloning. They were used for full-length cloning of the *Chaetomium thermophilum CGMCC* 0581 Cel7A cellobiohydrolase I gene.

```
Primer 4310S:
                                        (SEQ ID NO: 71)
5'-ATCCTCTCCTTCCAGTTTTC-3'

Primer 4310AS:
                                        (SEQ ID NO: 72)
5'-TATCCAAGTAGTCCACAACC-3'
```

Ten picomoles of the above two primers were used in a PCR reaction composed of 5 μl of first strand cDNA of 3' RACE, 5 μl of 10×Taq DNA polymerase buffer, 3 μl of 25 mM $MgCl_2$, 1 μl of 10 mM dNTP, and 2.5 units of Taq DNA polymerase in a final volume of 50 μl. The amplification was performed in a thermocycler programmed for 1 cycle at 95° C. for 3 minutes; 30 cycles each at 95° C. for 50 seconds, 55° C. for 50 seconds, and 72° C. for 90 seconds; and 1 cycle at 72° C. for 10 minutes. The heat block then went to a 4° C. soak cycle.

The reaction products were isolated by 1.0% agarose gel electrophoresis using TBE buffer where an approximately 1.5 kb product band was excised from the gel, and purified using a WIZARD® PCR Preps DNA Purification System. The PCR fragment was then ligated to pGEM-T using a pGEM-T Vector System (Promega Corporation, Madison, Wis., USA). The plasmid DNA was confirmed by sequencing using a 377 DNA Analyzer. The correct clone was designated pT43-10.

Two synthetic oligonucleotide primers containing Bsp HI sites at their ends, shown below, were designed to PCR amplify the full-length open reading frame of the *Chaetomium thermophilum* CGMCC 0581 Family GH7A cellobiohydrolase I gene. A Rapid Ligation Kit (Roche Applied Science, Indianapolis, Ind., USA) was used to clone the fragment into pAILo2 (WO 2004/099228).

```
PCR Forward primer:
                                    (SEQ ID NO: 73)
5'-TCATGATGTACAAGAAGTTCGCCG-3'

PCR Reverse primer:
                                    (SEQ ID NO: 74)
5'-TCATGATTACAGGCACTGGCTGTAC-3'
```

Bold letters represent coding sequence. The underlined sequence contains sequence identity to the BspHI restriction site.

Fifty picomoles of each of the primers above were used in a PCR reaction containing 50 ng of plasmid pT43-10 containing the *Chaetomium thermophilum* CGMCC 0581 cellobiohydrolase I gene, 1× Pwo Amplification Buffer with $MgSO_4$ (Boehringer Mannheim, Indianapolis, Ind., USA), 4 μl of 10 mM blend of dATP, dTTP, dGTP, and dCTP, and 2.5 units of Pwo DNA Polymerase (Boehringer Mannheim, Indianapolis, Ind., USA), in a final volume of 50 μl. A DNA ENGINE™ Thermal Cycler (MJ Research, Waltham, Mass., USA) was used to amplify the fragment programmed for one cycle at 94° C. for 2 minutes; 35 cycles each at 94° C. for 30 seconds, 62° C. for 30 seconds, and 72° C. for 1.5 minutes. After the 35 cycles, the reaction was incubated at 72° C. for 10 minutes and then cooled at 10° C. until further processed.

A 1.6 kb PCR reaction product was isolated on a 0.8% GTG® agarose gel (Cambrex Bioproducts, East Rutherford, N.J., USA) using 40 mM Tris base-20 mM sodium acetate-1 mM disodium EDTA (TAE) buffer and 0.1 μg of ethidium bromide per ml. The DNA band was visualized with the aid of a DARKREADER™ Transilluminator (Clare Chemical Research, Dolores, Colo., USA) to avoid UV-induced mutations. The 1.6 kb DNA band was excised with a disposable razor blade and purified with an ULTRAFREE® DA spin cup (Millipore, Billerica, Mass., USA) according to the manufacturer's instructions.

The purified PCR fragment was cloned into pCR®4Blunt-TOPO® (Invitrogen, Carlsbad, Calif., USA) using a TOPO® Blunt Cloning Kit (Invitrogen, Carlsbad, Calif., USA) according to the manufacturer's instructions. PCR clones containing the coding regions of interest were sequenced to Phred Q values of at least 40 to insure that there were no PCR induced errors. All sequence aligments were performed with Consed (University of Washington). One of the clones was determined to have the expected sequence and was selected and re-named CtPCR. The CtPCR clone containing the *C. thermophilum* cellobiohydrolase I coding region was digested with Bsp HI and gel purified as described above. This DNA fragment was then ligated into the Nco I restriction site of pAILo2 with a Rapid Ligation Kit. Expression clones were confirmed by restriction digestion and sequenced to confirm that the junction vector-insert was correct. Plasmid DNA for transformation was prepared with a Midi-Prep Kit (QIAGEN Inc., Valencia, Calif., USA). The final clone was re-named pAILo4.

*Aspergillus oryzae* JaL250 protoplasts were prepared according to the method of Christensen et al., 1988, *Bio/Technology* 6: 1419-1422. Eight micrograms of pAILo4 (as well as pAILo2 as a vector control) were used to transform *Aspergillus oryzae* JaL250 protoplasts. Twelve transformants were isolated to individual PDA plates and incubated for 5 days at 34° C. Confluent spore plates were washed with 5 ml of 0.01% TWEEN® 80 and the spore suspension was used to inoculate 25 ml of MDU2BP medium in 125 ml glass shake flasks. Transformant cultures were incubated at 34° C. with constant shaking at 200 rpm. At day five post-inoculation, cultures were centrifuged at 6000×g and their supernatants collected. Five microliters of each supernatant were mixed with an equal volume of 2× loading buffer (10% beta-mercaptoethanol) and loaded onto a 1.5 mm 8%-16% Tris-glycine SDS-PAGE gel and stained with SIMPLY BLUE™ SafeStain (Invitrogen, Carlsbad, Calif., USA). SDS-PAGE profiles of the culture broths showed that twelve out of twelve transformants had a new protein band of approximately 66 kDa. Transformant number 12 was selected and designated *A. oryzae* JaI250AILo4.

Shake flask medium was composed per liter of 50 g of glucose, 2 g of $MgSO_4.7H_2O$, 10 g of $KH_2PO_4$, 2 g of $K_2SO_4$, 0.5 g of $CaCl_2.2H_2O$, 2 g of citric acid, 10 g of yeast extract, 0.5 g of AMG trace metals solution, and 2 g of urea. AMG trace metals solution was composed per liter of 13.8 g of $FeSO_4.7H_2O$, 14.3 g of $ZnSO_4.7H_2O$, 8.5 g of $MnSO_4.H_2O$, 2.5 g of $CuSO_4.5H_2O$, 0.5 g of $NiCl_2.6H_2O$ and 3.0 g of citric acid monohydrate.

One hundred ml of shake flask medium was added to a 500 ml shake flask. The shake flask was inoculated with a glycerol spore stock of *A. oryzae* JaI250AILo4 and incubated at 34° C. on an orbital shaker at 200 rpm for 24 hours. Fifty ml of the shake flask broth was used to inoculate a fermentation vessel.

Fermentation batch medium was composed per liter of 25 g of sucrose, 2 g of $MgSO_4.7H_2O$, 2 g of $KH_2PO_4$, 3 g of $K_2SO_4$, 5 g of $(NH_4)_2HPO_4$, 1 g of citric acid, 10 g of yeast extract, 0.5 g of AMG trace metals solution, and 0.55 g of pluronic antifoam. Fermentation feed medium was composed per liter of 320 g of maltose, 5 g of pluronic antifoam, and 1 g of citric acid monohydrate.

A total of 2 liters of the fermentation batch medium was added to a glass jacketed fermentor. The fermentation vessel was maintained at a temperature of 34° C. and the pH was controlled at 7 for 180 hours using 10% $NH_4OH$ and 10% $H_3PO_4$. Air was added to the vessel at a rate of 1 vvm and the broth was agitated by Rushton impeller rotating at 1100 rpm. Feed was started at a rate of 4 g per hour when the batch sucrose was consumed as indicated by a rise in the dissolved oxygen reading (at approximately 18-24 hours). At the end of the fermentation, whole broth was harvested from the vessel and centrifuged at 3000×g to remove the biomass. The supernatant was sterile filtered and stored at 5 to 10° C.

A 350 ml (3.15 g total protein) aliquot of the filtered *A. oryzae* JaI250AILo4 fermentation broth (AOC18-7) containing recombinant *Chaetomium thermophilum* Cel7A cellobiohydrolase I was concentrated and desalted, and then purified over a Q SEPHAROSE® Big Bead column (GE Healthcare, Piscataway, N.J., USA) in 20 mM Tris-HCl pH 8, over a linear 0 to 1 M NaCl gradient. Fractions were pooled based on SDS-PAGE, concentrated and buffer-exchanged to 25 mM Tris-HCl, pH 8. The purified cellobiohydrolase I (approximately 800 mg total) was approximately 90% pure by SDS-PAGE. Protein concentration was determined using a Microplate BOA™ Protein Assay Kit (Thermo Fischer Scientific, Waltham, Mass., USA) in which bovine serum albumin was used as a protein standard.

Example 2: Preparation of *Myceliophthora thermophila* CBS 117.65 Cel7A Cellobiohydrolase I The *Myceliophthora thermophila* CBS 117.65 Cel7A cellobiohydrolase I (CBHI) gene (SEQ ID NO: 3 [DNA sequence] and SEQ ID NO: 4 [deduced amino acid sequence]) was isolated according to WO 2003/000941 and expressed in *Aspergillus oryzae* JaL250.

Two synthetic oligonucleotide primers, shown below, were designed to PCR amplify the full-length open reading frame from *Myceliophthora thermophila* CBS 117.65 encoding the Family Cel7A cellobiohydrolase I.

```
PCR Forward primer:
                                (SEQ ID NO: 75)
5'-ctcgcagtcgcagtcaag-3'

PCR Reverse primer:
                                (SEQ ID NO: 76)
5'-cggtcaggttgcagtttag-3'
```

Thirty picomoles of each of the primers above were used in an amplification reaction containing 50 ng of DNA consisting of a pool of *Myceliophtora thermophila* CBS 117.65 cDNA prepared according to U.S. Pat. No. 6,242,237, 1× EXPAND™ PCR Buffer (Roche Diagnostics, Mannheim, Germany), 4 μl of 2.5 mM blend of dATP, dTTP, dGTP, and dCTP, 0.75 μl of EXPAND™ DNA Polymerase (Roche Diagnostics, Mannheim, Germany), in a final volume of 50 μl. The amplification of the fragment was performed in a thermocycler programmed for one cycle at 94° C. for 5 minutes; and 35 cycles each at 94° C. for 1 minute, 54° C. for 1 minute, and 72° C. for 2 minutes. After the 30 cycles, the reaction was incubated at 72° C. for 10 minutes and then cooled at room temperature until further processed.

A 1.3 kb PCR product was isolated by 1% agarose gel electrophoresis using TBE buffer and 0.1 μg of ethidium bromide per ml. The 1.3 kb DNA band was excised with a disposable razor blade and purified using a JETSORB Gel Extraction Kit (Genomed GmbH, Löhne, Germany) according to the manufacturer's instructions.

The purified PCR fragment was cloned into pCR®4Blunt-TOPO® according to the manufacturer's instructions. PCR clones containing the coding regions of interest were sequenced. One of the clones having the expected sequence was selected and named pDAu27#15.

Two synthetic oligonucleotide primers containing a Bsp HI restriction site on the forward primer and a Pac I restriction site on the reverse primer, shown below, were designed to PCR amplify the full-length open reading frame of the *Myceliophthora thermophila* CBS 117.65 Cel7A cellobiohydrolase I from pDAu27#15. A Rapid Ligation Kit was used to clone the fragment into pAILo2 (WO 2004/099228).

PCR Forward primer:
(SEQ ID NO: 77)
5'-TCATGAAGCAGTACCTCCAGTA-3'

PCR Reverse primer:
(SEQ ID NO: 78)
5'-TTAATTAATTAGACGTTGACAGTCGAGC-3'

Bold letters represent coding sequence. The underlined sequence contains sequence identity to the Bsp HI and Pac I restriction sites.

Fifty picomoles of each of the primers above were used in a PCR reaction containing 50 ng of plasmid pDAu27#15 containing the *Myceliophthora thermophila* CBS 117.65 cellobiohydrolase II gene, 1× Pfx Amplification Buffer (Invitrogen, Carlsbad, Calif., USA), 6 μl of 10 mM blend of dATP, dTTP, dGTP, and dCTP, 2.5 units of PLATINUM® Pfx DNA Polymerase (Invitrogen, Carlsbad, Calif., USA), 1 μl of 50 mM MgSO4, and 2.5 μl of 10×pCRx Enhancer solution (Invitrogen, Carlsbad, Calif., USA) in a final volume of 50 μl. A DNA ENGINE™ Thermal Cycler was used to amplify the fragment programmed for one cycle at 98° C. for 2 minutes; and 35 cycles each at 94° C. for 30 seconds, 58° C. for 30 seconds, and 68° C. for 1.5 minutes. After the 35 cycles, the reaction was incubated at 68° C. for 10 minutes and then cooled at 10° C. until further processed.

A 1.3 kb PCR reaction product was isolated on a 0.8% GTG® agarose gel using TAE buffer and 0.1 μg of ethidium bromide per ml. The DNA band was visualized with the aid of a DARKREADER™ Transilluminator to avoid UV-induced mutations. The 1.3 kb DNA band was excised with a disposable razor blade and purified with an ULTRAFREE® DA spin cup according to the manufacturer's instructions.

The purified PCR fragment was cloned into pCR®4Blunt-TOPO® according to the manufacturer's instructions. PCR clones containing the coding region of interest were sequenced to Phred Q values of at least 40 to insure that there were no PCR induced errors. All sequence aligments were performed with Consed (University of Washington). One of the clones that was shown to have the expected sequence was selected and re-named MtPCR. The MtPCR clone containing the *M. thermophila* cellobiohydrolase I coding region was double digested with Bsp HI and Bss SI and a 352 bp fragment was gel purified as described above. Another aliquot of MtPCR was also double digested with Bss SI and Pac I and a 1009 bp fragment was gel purified as described above. These DNA fragments were then ligated into pAILo2 previously digested with Nco I and Pac I in a three-way ligation using a Rapid Ligation Kit. Expression clones were confirmed by restriction digestion and sequenced to confirm that the junction vector-insert was correct. Plasmid DNA for transformation was prepared with a Midi-Prep Kit. The final clone was re-named pAILo10.

*Aspergillus oryzae* JaL250 protoplasts were prepared according to the method of Christensen et al., 1988, supra. Six micrograms of pAILo10 (as well as pAILo2 as a vector control) were used to transform *Aspergillus oryzae* JaL250 protoplasts. Eight transformants were isolated to individual PDA plates and incubated for five days at 34° C. Confluent spore plates were washed with 5 ml of 0.01% TWEEN® 80 and the spore suspension was used to inoculate 25 ml of MDU2BP medium in 125 ml glass shake flasks. Transformant cultures were incubated at 34° C. with constant shaking at 200 rpm. At day five post-inoculation, cultures were centrifuged at 6000×g and their supernatants collected. Five microliters of each supernatant were mixed with an equal volume of 2× loading buffer (10% beta-mercaptoethanol) and loaded onto a 1.5 mm 8%-16% Tris-glycine SDS-PAGE gel and stained with SIMPLY BLUE™ SafeStain. SDS-PAGE profiles of the culture broths showed that eight out of eight transformants had a new protein band of approximately 50 kDa. Transformant number 8 was selected for further studies and designated *A. oryzae* JaL250AILo10.

A new fully confluent spore plate was prepared as described above. Spores were collected with 5 ml of an aqueous solution of 0.01% TWEEN® 80 and two more washes with MDU2BP medium to maximize the number of spores collected. The spore suspension was then used to inoculate 500 ml of MDU2BP medium in a two-liter Fernbach flask. The *A. oryzae* JaL250AILo10 liquid culture was then incubated at 34° C. with shaking at 200 rpm. At day five post-inoculation the culture broth was collected by filtration on a 500 milliliter, 75 mm Nylon filter unit with a pore size of 0.45 μm.

The culture filtrate was desalted and buffer exchanged in 20 mM Tris, 150 mM NaCl pH 8.5, using a HIPREP® 26/10 desalting column (GE Healthcare, Piscataway, N.J., USA) according to the manufacturer's instructions Protein concentration was determined using a Microplate BCA™ Protein Assay Kit in which bovine serum albumin was used as a protein standard.

Example 3: Preparation of *Aspergillus fumigatus* NN055679 Cel7A Cellobiohydrolase I A tfasty search (Pearson et al., 1997, Genomics 46:24-36) of the *Aspergillus fumigatus* partial genome sequence (The Institute for Genomic Research, Rockville, Md.) was performed using as query a Cel7 cellobiohydrolase protein sequence from *Trichoderma reesei* (Accession No. P00725). Several genes were identified as putative Family GH7 homologs based upon a high degree of similarity to the query sequence at the amino acid level. One genomic region with significant identity to the query sequence was chosen for further study, and the corresponding gene was named cel7A.

Two synthetic oligonucleotide primers shown below were designed to PCR amplify an *Aspergillus fumigatus* NN055679 cel7A cellobiohydrolase I gene (SEQ ID NO: 5 [DNA sequence] and SEQ ID NO: 6 [deduced amino acid sequence]) from genomic DNA of *Aspergillus fumigatus* prepared as described in WO 2005/047499.

```
Forward primer:
                                    (SEQ ID NO: 79)
5'-gggcATGCTGGCCTCCACCTTCTCC-3'

Reverse primer:
                                    (SEQ ID NO: 80)
5'-gggttaattaaCTACAGGCACTGAGAGTAA-3'
```

Upper case letters represent the coding sequence. The remainder of the sequence provides restriction endonuclease sites for Sph I and Pac I in the forward and reverse sequences, respectively. Using these primers, the *Aspergillus fumigatus* cel7A gene was amplified using standard PCR methods and the reaction product isolated by 1% agarose gel electrophoresis using TAE buffer and purified using a QIAQUICK® Gel Extraction Kit (QIAGEN Inc., Valencia, Calif., USA) according to the manufacturer's instructions.

The fragment was digested with Sph I and Pac I and ligated into the expression vector pAILo2 also digested with Sph I and Pac I according to standard procedures. The ligation products were transformed into *E. coli* XL10 SOLOPACK® cells (Stratagene, La Jolla, Calif., USA) according to the manufacturer's instructions. An *E. coli* transformant containing a plasmid of the correct size was detected by restriction digestion and plasmid DNA was prepared using a BIOROBOT® 9600 (QIAGEN Inc., Valencia, Calif., USA). DNA sequencing of the insert gene from this plasmid was performed with a Perkin-Elmer Applied Biosystems Model 377 XL Automated DNA Sequencer (Perkin-Elmer/Applied Biosystems, Inc., Foster City, Calif., USA) using dye-terminator chemistry (Giesecke et al., 1992, *Journal of Virology Methods* 38: 47-60) and primer walking strategy. Nucleotide sequence data were scrutinized for quality and all sequences were compared to each other with assistance of PHRED/PHRAP software (University of Washington, Seattle, Wash., USA). The nucleotide sequence was shown to match the genomic sequence determined by TIGR (SEQ ID NO: 5 [DNA sequence] and SEQ ID NO: 6 [deduced amino acid sequence]). The resulting plasmid was named pEJG93.

*Aspergillus oryzae* JaL250 protoplasts were prepared according to the method of Christensen et al., 1988, supra. Five μg of pEJG93 (as well as pAILo2 as a vector control) was used to transform *Aspergillus oryzae* JaL250.

The transformation of *Aspergillus oryzae* JaL250 with pEJG93 yielded about 100 transformants. Ten transformants were isolated to individual PDA plates.

Confluent PDA plates of five of the ten transformants were washed with 5 ml of 0.01% TWEEN® 20 and inoculated separately into 25 ml of MDU2BP medium in 125 ml glass shake flasks and incubated at 34° C., 250 rpm. Five days after incubation, 0.5 μl of supernatant from each culture was analyzed using 8-16% Tris-Glycine SDS-PAGE gels (Invitrogen, Carlsbad, Calif., USA) according to the manufacturer's instructions. SDS-PAGE profiles of the cultures showed that one of the transformants had a major band of approximately 70 kDa. This transformant was named *Aspergillus oryzae* JaL250EJG93.

Five hundred ml of shake flask medium were added to a 2800 ml shake flask. The shake flask medium was composed of 45 g of maltose, 2 g of K2HPO$_4$, 12 g of $KH_2PO_4$, 1 g of NaCl, 1 g of $MgSO_4.7H_2O$, 7 g of yeast extract, 2 g of urea, and 0.5 ml of trace elements solution. The trace elements solution was composed per liter of 13.8 g of $FeSO_4.7H_2O$, 14.3 g of $ZnSO_4.7H_2O$, 8.5 g of $MnSO_4$. $H_2O$, 2.5 g of $CuSO_4.5H_2O$, 0.5 g of $NiCl_2.6H_2O$, 3 g of citric acid, and deionized water to 1 liter. Two shake flasks were inoculated with a suspension of a PDA plate of *Aspergillus oryzae* JaL250EJG93 with 0.01% TWEEN® 80 and incubated at 34° C. on an orbital shaker at 200 rpm for 120 hours. The broth was filtered using a 0.7 μm Whatman glass filter GF/F (Whatman, Piscataway, N.J., USA) followed by a 0.22 μm EXPRESS™ Plus Membrane (Millipore, Bedford, Mass., USA).

Filtered broth was concentrated and buffer exchanged using a tangential flow concentrator (Pall Filtron, Northborough, Mass., USA) equipped with a 10 kDa polyethersulfone membrane (Pall Filtron, Northborough, Mass., USA) with 20 mM Tris-HCl pH 8.5. Protein concentration was determined using a Microplate BCA™ Protein Assay Kit in which bovine serum albumin was used as a protein standard.

Example 4: Preparation of *Thermoascus aurantiacus* CGMCC 0583 Cel7A Cellobiohydrolase I The *Thermoascus aurantiacus* CGMCC 0583 Cel7A cellobiohydrolase I (CBHI) gene (SEQ ID NO: 7 [DNA sequence] and SEQ ID NO: 8 [deduced amino acid sequence]) was isolated according to WO 2003/000941 and expressed in *Aspergillus oryzae* JaL250.

The fungal strain *Thermoascus aurantiacus* CGMCC 0583 was grown on an agar plate composed of 0.5% yeast extract, 1% glucose, and 2% agar for 3 days at 45° C. The fully grown culture was used to inoculate shake flasks containing liquid medium composed of 3% soymeal, 1.5% maltose, and 0.5% peptone. The flasks were incubated at 45° C. for 48 hours with shaking. The mycelia were harvested by centrifugation of the culture broth at 8000 rpm, 4° C. for 30 minutes, transferred into a clean plastic bag followed by immediate freezing in liquid nitrogen, and stored at −80° C. before total RNA was isolated.

The frozen mycelia were grounded into a very fine powder with a sterilized mortar and pestle baked at 200° C.

for 24 hours. An RNEASY® Plant Mini Kit was used to isolate total RNA according to the manufacturer's instructions.

First strand cDNA synthesis from the total RNA was performed using a 3' RACE System for Rapid Amplification of cDNA Ends according to the manufacturer's instructions. The first strand cDNA of 3' RACE was used as PCR template for PCR screening.

Two oligonucleotides shown below were used for PCR screening of cDNA of *Thermoascus aurantiacus* CGMCC 0583. The forward primer was derived from an alignment of conserved regions of cellobiohydrolase I genes and the reverse primer was provided by the 3' RACE System.

```
Forward primer:
                                    (SEQ ID NO: 81)
5'-GGnACnGGnTA(t/c)TG(t/c)GA-3'

Reverse primer:
                                    (SEQ ID NO: 82)
5'-TCnA(a/g)CCAnA(a/g)CAT(a/g)TT-3'
```

One hundred picomoles of the above primers were used in a PCR reaction composed of 2 μl of the first strand cDNA of 3' RACE, 5 μl of 10×Taq DNA polymerase buffer, 3 μl of 25 mM $MgCl_2$, 1 μl of 10 mM dNTP, and 2.5 units of Taq DNA polymerase in a final volume of 50 μl. The amplification was performed in a thermocycler programmed for 1 cycle at 95° C. for 3 minutes; 30 cycles each at 95° C. for 30 seconds, 50° C. for 30 seconds, and 72° C. for 50 seconds; and 1 cycle at 72° C. for 10 minutes. The heat block then went to a 4° C. soak cycle.

The reaction products were isolated by 1.0% agarose gel electrophoresis using TBE buffer where an approximately 0.65 kb product band was excised from the gel, and purified using a WIZARD® PCR Preps DNA Purification System according to the manufacturer's instructions. The PCR product was sequenced using a 377 DNA Analyzer. Sequencing showed that the 0.65 kb fragment was homologous to cellobiohydrolase I.

Two oligos were designed for 5' end cloning of *Thermoascus aurantiacus* CGMCC 0583 Cel7A cellobiohydrolase I by using a 5' RACE System for Rapid Amplification of cDNA Ends.

```
Primer 025AS1:
                                    (SEQ ID NO: 83)
5'-GTAGAGATGCTGTTGGCT-3'

Primer 025AS1.5:
                                    (SEQ ID NO: 84)
5'-TCTCAGCGCAGCAGGAACCGT-3'
```

The gene specific primer 025AS1 was used for first strand cDNA synthesis using the 5' RACE System according to the manufacturer's instructions. The first strand cDNA of 5' RACE was used as template for a PCR amplification composed of 5 μl of 10×Taq DNA polymerase buffer, 3 μl of 25 mM $MgCl_2$, 1 μl of 10 mM dNTP, 2 μl of 10 μM primer 025AS1.5, 2 μl of 10 μM primer AAP (Abridged Anchor Primer, provided by the kit), and 2.5 units of Taq DNA polymerase in a final volume of 50 μl. The amplification was performed in a thermocycler programmed for 1 cycle at 94° C. for 2 minutes; 30 cycles each at 94° C. for 40 seconds, 55° C. for 40 seconds, and 72° C. for 60 seconds; and 1 cycle at 72° C. for 10 minutes. The heat block then went to a 4° C. soak cycle.

The PCR products were isolated by 1.0% agarose gel electrophoresis using TBE buffer and purified using a WIZARD® PCR Preps DNA Purification System. A dominant DNA fragment at 0.8 kb was confirmed to be the 5' end of *Thermoascus aurantiacus* CGMCC 0583 Cel7A cellobiohydrolase I gene by sequencing using a 377 DNA Analyzer.

One forward primer, 1F shown below, was designed based on the sequence information of the 5' end cloning. Primer 1F was used for the full-length cloning of the *Thermoascus aurantiacus* CGMCC 0583 Cel7A cellobiohydrolase I gene together with primer AUAP (provided by the kit) as the reverse primer.

```
Primer 1F:
                                    (SEQ ID NO: 85)
5'-AGCGACAGCAATAACAAT-3'
```

Ten picomoles of the above 2 primers were used in a PCR reaction composed of the 4 μl of first strand cDNA of 3' RACE, 5 μl of 10×Taq DNA polymerase buffer, 3 μl of 25 mM $MgCl_2$ 1 μl of 10 mM dNTP, and 2.5 units of Taq DNA polymerase in a final volume of 50 μl. The amplification was performed in a thermocycler programmed for 1 cycle at 95° C. for 2 minutes; 30 cycles each at 95° C. for 40 seconds, 58° C. for 40 seconds, and 72° C. for 90 seconds; and 1 cycle at 72° C. for 10 minutes. The heat block then went to a 4° C. soak cycle.

The reaction products were isolated by 1.0% agarose gel electrophoresis using TBE buffer where an approximately 1.7 kb product band was excised from the gel, and purified using a WIZARD® PCR Preps DNA Purification System. The PCR fragment was then ligated to pGEM-T using a pGEM-T Vector System. The plasmid DNA was confirmed by sequencing using a 377 DNA Analyzer. The correct clone was designated pT002-5.

Two synthetic oligonucleotide primers shown below containing Bsp LU11I sites on the forward primer and Pac I at the reverse primer were designed to PCR amplify the full-length open reading frame of the *Thermoascus aurantiacus* CGMCC 0583 Cel7A cellobiohydrolase I gene. A Rapid Ligation Kit was used to clone the fragment into pAILo2.

PCR Forward primer:
(SEQ ID NO: 86)
5'-ACATGTATCAGCGCGCTCTTCTC-3'

PCR Reverse primer:
(SEQ ID NO: 87)
5'-TTAATTAATTAGTTGGCGGTGAAGGTCG-3'

Bold letters represent coding sequence. The underlined sequence contains sequence identity to the Bsp LU11I and Pac I restriction sites.

Fifty picomoles of each of the primers above were used in a PCR reaction containing 50 ng of plasmid pT002-5, 1×Pwo Amplification Buffer with $MgSO_4$, 4 μl of 10 mM blend of dATP, dTTP, dGTP, and dCTP, and 2.5 units of Pwo DNA Polymerase, in a final volume of 50 μl. A DNA ENGINE™ Thermal Cycler was used to amplify the fragment programmed for one cycle at 94° C. for 2 minutes; and 25 cycles each at 94° C. for 30 seconds, 59° C. for 30 seconds, and 72° C. for 1.5 minutes. After the 25 cycles, the reaction was incubated at 72° C. for 10 minutes and then cooled at 10° C. until further processed.

A 1.3 kb PCR reaction product was isolated on a 0.8% GTG® agarose gel using TAE buffer and 0.1 μg of ethidium bromide per ml. The DNA band was visualized with the aid of a DARKREADER™ Transilluminator to avoid UV-induced mutations. The 1.3 kb DNA band was excised with a disposable razor blade and purified with an ULTRAFREE® DA spin cup according to the manufacturer's instructions.

The purified PCR fragment was cloned into pCR®4Blunt-TOPO® according to the manufacturer's instructions. PCR clones containing the coding region of interest were sequenced to Phred Q values of at least 40 to insure that there were no PCR induced errors. All sequence aligments were performed with Consed (University of Washington). One of the clones that was shown to have the expected sequence was selected and re-named TaPCR. The TaPCR clone containing the *T. aurantiacus* cellobiohydrolase I coding region was double digested with the restriction enzymes Bsp LU11I and Pac I and gel purified as described above. This DNA fragment was then ligated into pAILo2 previously digested with Nco I and Pac I using a Rapid Ligation Kit. Expression clones were confirmed by restriction digestion and sequenced to confirm that the junction vector-insert was correct. Plasmid DNA for transformation was prepared with a Midi-Prep Kit. The final clone was re-named pAILo6.

*Aspergillus oryzae* JaL250 protoplasts were prepared according to the method of Christensen et al., 1988, supra. Ten micrograms of pAILo6 were used to transform the *Aspergillus oryzae* JaL250 protoplasts. Twelve transformants were isolated to individual PDA plates and incubated for 5 days at 34° C. Confluent spore plates were washed with 5 ml of 0.01% TWEEN® 80 and the spore suspension was used to inoculate 25 ml of MDU2BP medium in 125 ml glass shake flasks. Transformant cultures were incubated at 34° C. with constant shaking at 200 rpm. At day five post-inoculation, cultures were centrifuged at 6000×g and their supernatants collected. Five microliters of each supernatant were mixed with an equal volume of 2× loading buffer (10% beta-mercaptoethanol) and analyzed by SDS-PAGE using a 1.5 mm 8%-16% Tris-glycine SDS-PAGE gel and stained with SIMPLY BLUE™ SafeStain. SDS-PAGE profiles of the culture broths showed that eleven out of twelve transformants had a new protein band of approximately 60 kDa. Transformant number 12 was selected for further studies and designated *A. oryzae* JaL250AILo6.

A spore stock suspension was prepared from a 5 day plate culture of *A. oryzae* JaL250AILo6 by adding 10 ml of 0.1% TWEEN® 20 to the culture plate to release the spores. A shake flask culture was started by inoculating 100 μl of the spore stock to a 250 ml baffled flask containing 50 ml of M410 medium pH 6.0. The shake flask was grown at 34° C. for 5 days with shaking a 250 rpm. The culture was filtered through a 0.2 μm pore filter device and the filtrate was recovered for protein purification.

A 50 ml volume of the filtrate was desalted and buffer exchanged in 20 mM sodium acetate pH 5.0 using an ECONO-PAC® 10-DG desalting column according to the manufacturer's instructions. Protein concentration was determined using a Microplate BCA™ Protein Assay Kit in which bovine serum albumin was used as a protein standard.

Example 5: Preparation of *Myceliophthora thermophila* CBS 117.65 Cel6A Cellobiohydrolase II The *Myceliophthora thermophila* CBS 117.65 Cel6A cellobiohydrolase II (SEQ ID NO: 9 [DNA sequence] and SEQ ID NO: 10 [deduced amino acid sequence]) was obtained according to the procedure described below.

One hundred ml of shake flask medium was added to a 500 ml shake flask. The shake flask medium was composed per liter of 15 g of glucose, 4 g of $K_2HPO_4$, 1 g of NaCl, 0.2 g of $MgSO_4.7H_2O$, 2 g of MES free acid, 1 g of Bacto Peptone, 5 g of yeast extract, 2.5 g of citric acid, 0.2 g of $CaCl_2.2H_2O$, 5 g of $NH_4NO_3$, and 1 ml of trace elements solution. The trace elements solution was composed per liter of 1.2 g of $FeSO_4.7H_2O$, 10 g of $ZnSO_4.7H_2O$, 0.7 g of $MnSO_4.H_2O$, 0.4 g of $CuSO_4.5H_2O$, 0.4 g of $Na_2B_4O_7.10H_2O$, and 0.8 g of $Na_2MoO_2.2H_2O$. The shake flask was inoculated with two plugs from a solid plate culture of *Myceliophthora thermophila* strain CBS 117.65 and incubated at 45° C. with shaking at 200 rpm for 48 hours. Fifty ml of the shake flask broth was used to inoculate a 2 liter fermentation vessel.

Fermentation batch medium was composed per liter of 5 g of yeast extract, 176 g of powdered cellulose, 2 g of glucose, 1 g of NaCl, 1 g of Bacto Peptone, 4 g of K2HPO$_4$, 0.2 g of $CaCl_2.2H_2O$, 0.2 g of $MgSO_4.7H_2O$, 2.5 g of citric acid, 5 g of $NH_4NO_3$, 1.8 ml of anti-foam, and 1 ml of trace elements solution (above). Fermentation feed medium was composed of water and antifoam.

A total of 1.8 liters of the fermentation batch medium was added to a two liter glass jacketed fermentor (Applikon Biotechnology, Schiedam, Netherlands). Fermentation feed medium was dosed at a rate of 4 g/l/hr for a period of 72 hours. The fermentation vessel was maintained at a temperature of 45° C. and pH was controlled using an Applikon 1030 control system (Applikon Biotechnology, Schiedam, Netherlands) to a set-point of 5.6+/−0.1. Air was added to the vessel at a rate of 1 vvm and the broth was agitated by Rushton impeller rotating at 1100 to 1300 rpm. At the end of the fermentation, whole broth was harvested from the vessel and centrifuged at 3000×g to remove the biomass.

The harvested broth obtained above was centrifuged in 500 ml bottles at 13,000×g for 20 minutes at 4° C. and then sterile filtered using a 0.22 μm polyethersulfone membrane (Millipore, Bedford, Mass., USA). The filtered broth was concentrated and buffer exchanged with 20 mM Tris-HCl pH 8.5 using a tangential flow concentrator equipped with a 10 kDa polyethersulfone membrane at approximately 20 psi. To decrease the amount of pigment, the concentrate was applied to a 60 ml Q SEPHAROSE™ Big Bead column equilibrated with 20 mM Tris-HCl pH 8.5, and step eluted with equilibration buffer containing 600 mM NaCl. Flow-through and eluate fractions were examined on 8-16% CRITERION® SDS-PAGE gels (Bio-Rad Laboratories, Inc., Hercules, Calif., USA) stained with GELCODE® Blue Stain Reagent (Bio-Rad Laboratories, Inc., Hercules, Calif., USA). The flow-through fraction contained the *Myceliophthora thermophila* Cel6A cellobiohydrolase as judged by the presence of a band corresponding to the apparent molecular weight of the protein by SDS-PAGE (approximately 75 kDa).

The flow-through fraction was concentrated using an ultrafiltration device (Millipore, Bedford, Mass., USA) equipped with a 10 kDa polyethersulfone membrane at 40 psi, 4° C. and mixed with an equal volume of 20 mM Tris-HCl pH 7.5 containing 3.4 M ammonium sulfate for a final concentration of 1.7 M ammonium sulfate. The sample was filtered (0.2 μM syringe filter, polyethersulfone membrane, Whatman, Maidstone, United Kingdom) to remove particulate matter prior to loading onto a PHENYL SUPEROSE™ column (HR 16/10, GE Healthcare, Piscataway, N.J., USA) equilibrated with 1.7 M ammonium sulfate in 20 mM Tris-HCl pH 7.5. Bound proteins were eluted with a 12 column volume decreasing salt gradient of 1.7 M ammonium sulfate to 0 M ammonium sulfate in 20 mM Tris-HCl pH 7.5. Fractions were analyzed by 8-16% SDS-PAGE gel electrophoresis as described above, which revealed that the *Myceliophthora thermophila* Cel6A cellobiohydrolase eluted at the very end of the gradient (approximately 20 mM ammonium sulfate).

Fractions containing the Cel6A cellobiohydrolase II were pooled and diluted 10-fold in 20 mM Tris-HCl pH 9.0 (to lower the salt and raise the pH) and then applied to a 1 ml RESOURCE™ Q column (GE Healthcare, Piscataway, N.J., USA) equilibrated with 20 mM Tris-HCl pH 9.0. Bound proteins were eluted with a 20 column volume salt gradient from 0 mM to 550 mM NaCl in 20 mM Tris-HCl pH 9.0. *M. thermophila* Cel6A cellobiohydrolase II eluted as a single peak early in the gradient (~25 mM NaCl). The cellobiohydrolase II was >90% pure as judged by SDS-PAGE. Protein concentrations were determined using a BCA Protein Assay Kit (Pierce, Rockford, Ill., USA) in which bovine serum albumin was used as a protein standard.

Example 6: Preparation of Recombinant *Myceliophthora thermophila* CBS 202.75 Cel6A Cellobiohydrolase II

*Myceliophthora thermophila* CBS 202.75 was grown in 100 ml of YEG medium in a baffled shake flask at 45° C. for 2 days with shaking at 200 rpm. Mycelia were harvested by filtration using MIRACLOTH® (Calbiochem, La Jolla, Calif., USA), washed twice in deionized water, and frozen under liquid nitrogen. Frozen mycelia were ground, by mortar and pestle, to a fine powder, and total DNA was isolated using a DNEASY® Plant Maxi Kit (QIAGEN Inc., Valencia, Calif., USA).

A full-length Family 6 cellobiohydrolase gene (Cel6A) was isolated from *Myceliophthora thermophila* CBS 202.75 using a GENOMEWALKER™ Universal Kit (Clontech Laboratories, Inc., Mountain View, Calif., USA) according to the manufacturer's instructions. Briefly, total genomic DNA from *Myceliophthora thermophila* CBS 202.75 was digested separately with four different restriction enzymes (Dra I, Eco RV, Pvu II, and Stu I) that leave blunt ends. Each batch of digested genomic DNA was then ligated separately to the GENOMEWALKER™ Adaptor (Clontech Laboratories, Inc., Mountain View, Calif., USA) to create four libraries. These libraries were then employed as templates in PCR reactions using two gene-specific primers shown below, one for primary PCR and one for secondary PCR. The primers were designed based on a partial Family 6 cellobiohydrolase gene (Cel6A) sequence from *Myceliophthora thermophila* (WO 2004/056981).

```
Primer MtCel6A-R4:
                                    (SEQ ID NO: 88)
5'-ATTGGCAGCCCGGATCTGGGACAGAGTCTG-3'

Primer MtCel6A-R5:
                                    (SEQ ID NO: 89)
5'-CCGGTCATGCTAGGAATGGCGAGATTGTGG-3'
```

The primary amplifications were composed of 1 μl (approximately 6 ng) of each library as template, 0.4 mM each of dATP, dTTP, dGTP, and dCTP, 10 μmol of Adaptor Primer 1 (Clontech Laboratories, Inc., Mountain View, Calif., USA), 10 μmol of primer MtCel6A-R4, 1× ADVANTAGE® GC-Melt LA Buffer (Clontech Laboratories, Inc., Mountain View, Calif., USA), and 1.25 units of ADVANTAGE® GC Genomic Polymerase Mix (Clontech Laboratories, Inc., Mountain View, Calif., USA) in a final volume of 25 μl. The amplification reactions were incubated in an EPPENDORF® MASTERCYCLER® 5333 (Eppendorf Scientific, Inc., Westbury, N.Y., USA) programmed for pre-denaturing at 94° C. for 1 minute; 7 cycles each at a denaturing temperature of 94° C. for 30 seconds; annealing and elongation at 72° C. for 5 minutes; and 32 cycles each at 67° C. for 5 minutes.

The secondary amplifications were composed of 1 μl of each primary PCR product as template, 0.4 mM each of dATP, dTTP, dGTP, and dCTP, 10 μmol of Adaptor Primer 2 (Clontech Laboratories, Inc., Mountain View, Calif., USA), 10 μmol of primer MtCel6A-R5, 1× ADVANTAGE® GC-Melt LA Buffer, and 1.25 units of ADVANTAGE® GC Genomic Polymerase Mix in a final volume of 25 μl. The amplifications were incubated in an EPPENDORF® MASTERCYCLER® 5333 programmed for pre-denaturing at 94° C. for 1 minute; 5 cycles each at a denaturing temperature of 94° C. for 30 seconds; annealing and elongation at 72° C. for 5 minutes; and 20 cycles at 67° C. for 5 minutes.

The reaction products were isolated by 1.0% agarose gel electrophoresis using TAE buffer where a 3.5 kb product band from the Eco RV library was excised from the gel, purified using a QIAQUICK® Gel Extraction Kit according to the manufacturer's instructions, and sequenced.

DNA sequencing of the 3.5 kb PCR fragment was performed with a Perkin-Elmer Applied Biosystems Model 377 XL Automated DNA Sequencer (Perkin-Elmer/Applied Biosystems, Inc., Foster City, Calif., USA) using dye-terminator chemistry (Giesecke et al., 1992, *Journal of Virology Methods* 38: 47-60) and primer walking strategy. The following gene specific primers were used for sequencing:

```
MtCel6A-F2:
                                    (SEQ ID NO: 90)
5'-GCTGTAAACTGCGAATGGGTTCAG-3'

MtCel6A-F3:
                                    (SEQ ID NO: 91)
5'-GGGTCCCACATGCTGCGCCT-3'

MtCel6A-R8:
                                    (SEQ ID NO: 92)
5'-AAAATTCACGAGACGCCGGG-3'
```

Nucleotide sequence data were scrutinized for quality and all sequences were compared to each other with assistance of PHRED/PHRAP software (University of Washington, Seattle, Wash., USA). The 3.5 kb sequence was compared and aligned with a partial Family 6 cellobiohydrolase gene (Cel6A) sequence from *Myceliophthora thermophila* (WO 2004/056981).

A gene model for the *Myceliophthora thermophila* sequence was constructed based on similarity of the encoded protein to homologous glycoside hydrolase Family 6 proteins from *Thielavia terrestris, Chaetomium thermophilum, Humicola insolens*, and *Trichoderma reesei*. The nucleotide sequence and deduced amino acid sequence of the *Myceliophthora thermophila* CBS 202.75 Cel6A cellobiohydrolase II gene are shown in SEQ ID NO: 11 and SEQ ID NO: 12, respectively. The genomic fragment encodes a polypeptide of 482 amino acids, interrupted by 3 introns of 96, 87, and 180 bp. The % G+C content of the gene and the mature coding sequence are 61.6% and 64%, respectively. Using the SignalP software program (Nielsen et al., 1997, *Protein Engineering* 10: 1-6), a signal peptide of 17 residues was predicted. The predicted mature protein contains 465 amino acids with a molecular mass of 49.3 kDa.

Two synthetic oligonucleotide primers shown below were designed to PCR amplify the *Myceliophthora thermophila* cellobiohydrolase gene from the genomic DNA prepared above for construction of an *Aspergillus oryzae* expression vector. An IN-FUSION™ Cloning Kit (BD Biosciences, Palo Alto, Calif., USA) was used to clone the fragment directly into the expression vector pAILo2, without the need for restriction digestion and ligation.

```
MtCel6A-F4:
                                      (SEQ ID NO: 93)
5'-ACTGGATTTACCATGGCCAAGAAGCTTTTCATCACC-3'

MtCel6A-R9:
                                      (SEQ ID NO: 94)
5'-TCACCTCTAGTTAATTAATTAGAAGGGCGGGTTGGCGT-3'
```

Bold letters represent coding sequence. The remaining sequence is homologous to the insertion sites of pAILo2.

Fifty picomoles of each of the primers above were used in a PCR reaction composed of 100 ng of *Myceliophthora thermophila* genomic DNA, 1× ADVANTAGE® GC-Melt LA Buffer, 0.4 mM each of dATP, dTTP, dGTP, and dCTP, and 1.25 units of ADVANTAGE® GC Genomic Polymerase Mix in a final volume of 25 μl. The amplification reaction was incubated in an EPPENDORF® MASTERCYCLER® 5333 programmed for 1 cycle at 94° C. for 1 minutes; and 30 cycles each at 94° C. for 30 seconds, 62° C. for 30 seconds, and 72° C. for 2 minutes. The heat block then went to a 4° C. soak cycle.

The reaction products were isolated by 1.0% agarose gel electrophoresis using TAE buffer where a 1842 bp product band was excised from the gel, and purified using a QIAQUICK® Gel Extraction Kit according to the manufacturer's instructions.

Plasmid pAILo2 was digested with Nco I and Pac I, isolated by 1.0% agarose gel electrophoresis using TAE buffer, and purified using a QIAQUICK® Gel Extraction Kit according to the manufacturer's instructions.

The gene fragment and the digested vector were ligated together using an IN-FUSION™ Cloning Kit resulting in pSMai180 in which transcription of the cellobiohydrolase gene was under the control of a NA2-tpi promoter (a modified promoter from the gene encoding neutral alpha-amylase in *Aspergillus niger* in which the untranslated leader has been replaced by an untranslated leader from the gene encoding triose phosphate isomerase in *Aspergillus nidulans*). The ligation reaction (50 μl) was composed of 1× IN-FUSION™ Buffer (BD Biosciences, Palo Alto, Calif., USA), 1×BSA (BD Biosciences, Palo Alto, Calif., USA), 1 μl of IN-FUSION™ enzyme (diluted 1:10) (BD Biosciences, Palo Alto, Calif., USA), 100 ng of pAILo2 digested with Nco I and Pac I, and 50 ng of the *Myceliophthora thermophila* Cel6A purified PCR product. The reaction was incubated at room temperature for 30 minutes. One μl of the reaction was used to transform *E. coli* XL10 SOLOPACK® Gold cells. An *E. coli* transformant containing pSMai180 was detected by restriction digestion and plasmid DNA was prepared using a BIOROBOT® 9600. The *Myceliophthora thermophila* Cel6A insert in pSMai180 was confirmed by DNA sequencing.

The same 1842 bp PCR fragment was cloned into pCR®2.1-TOPO® (Invitrogen, Carlsbad, Calif., USA) using a TOPO® TA CLONING® Kit to generate pSMai182. The *Myceliophthora thermophila* cel6A gene insert in pSMai182 was confirmed by DNA sequencing. *E. coli* pSMai182 was deposited with the *Agricultural Research* Service Patent Culture Collection, Northern Regional Research Center, 1815 University Street, Peoria, Ill., 61604, on Sep. 6, 2007.

The *Myceliophthora thermophila* Family 6 cellobiohydrolase Cel6A gene was expressed in *Aspergillus oryzae* JaL355. *A. oryzae* JaL355 (WO 2002/40694) protoplasts were prepared according to the method of Christensen et al., 1988, supra. Three μg of pSMai180 were used to transform *Aspergillus oryzae* JaL355.

The transformation of *Aspergillus oryzae* JaL355 with pSMai180 yielded about 50 transformants. Twenty transformants were isolated to individual Minimal medium plates.

Confluent Minimal Medium plates of the 20 transformants were washed with 5 ml of 0.01% TWEEN® 20 and inoculated separately into 25 ml of MDU2BP medium in 125 ml glass shake flasks and incubated at 34° C., 250 rpm. After 5 days incubation, 5 μl of supernatant from each culture were analyzed using 8-16% CRITERION® SDS-PAGE gels and a CRITERION® Cell (Bio-Rad Laboratories, Inc., Hercules, Calif., USA), according to the manufacturer's instructions. The resulting gel was stained with BIO-SAFE™ Coomassie Stain (Bio-Rad Laboratories, Inc., Hercules, Calif., USA). SDS-PAGE profiles of the cultures showed that the majority of the transformants had a major band of approximately 70 kDa.

A confluent plate of one transformant, designated transformant 14, was washed with 10 ml of 0.01% TWEEN® 20 and inoculated into a 2 liter Fernbach flask containing 500 ml of MDU2BP medium to generate broth for characterization of the enzyme. The culture was harvested on day 5 and filtered using a 0.22 μm EXPRESS™ Plus Membrane.

The filtered broth was concentrated and buffer exchanged using a tangential flow concentrator equipped with a 10 kDa polyethersulfone membrane with 20 mM Tris-HCl pH 8.0. The concentrated and buffer exchanged broth was adjusted to 20 mM Tris-HCl pH 8.0-1.2 M $(NH_4)_2SO_4$ and applied to a Phenyl SUPEROSE™ column (HR 16/10) equilibrated with 20 mM Tris-HCl pH 8.0-1.2 M $(NH_4)_2SO_4$. Bound proteins were eluted with a linear gradient over 10 column volumes from 300 to 0 mM $(NH_4)_2SO_4$ in 20 mM Tris-HCl pH 8.0. SDS-PAGE of eluate fractions showed a major band at approximately 70 kDa. These fractions were then concentrated and buffer exchanged by centrifugal concentration using a VIVASPIN™ centrifugal concentrator (10 kDa polyethersulfone membrane, Sartorius, Göttingen, Germany) into 20 mM Tris-HCl pH 8.0. Protein concentration was determined using a Microplate BCA™ Protein Assay Kit in which bovine serum albumin was used as a protein standard.

Example 7: Preparation of *Thielavia terrestris* NRRL 8126 Cel6A Cellobiohydrolase II (CBHII)

*Thielavia terrestris* NRRL 8126 Cel6A cellobiohydrolase II (SEQ ID NO: 13 [DNA sequence] and SEQ ID NO: 14 [deduced amino acid sequence]) was recombinantly prepared according to WO 2006/074435 using *Trichoderma reesei* as a host.

Culture filtrate was desalted and buffer exchanged in 20 mM Tris-150 mM sodium chloride pH 8.5 using an ECONO-PAC® 10-DG desalting column according to the manufacturer's instructions. Protein concentration was determined using a Microplate BCA™ Protein Assay Kit in which bovine serum albumin was used as a protein standard.

Example 8: Preparation of *Trichophaea saccata* CBS 804.70 Cellobiohydrolase II (CBHII)

The *Trichophaea saccata* CBS 804.70 cellobiohydrolase II (CBHII) (SEQ ID NO: 15 [DNA sequence] and SEQ ID NO: 16 [deduced amino acid sequence]) was prepared as described below.

*Trichophaea saccata* CBS 804.70 was inoculated onto a PDA plate and incubated for 7 days at 28° C. Several mycelia-PDA agar plugs were inoculated into 750 ml shake flasks containing 100 ml of MEX-1 medium. The flasks were incubated at 37° C. for 9 days with shaking at 150 rpm. The fungal mycelia were harvested by filtration through MIRACLOTH® (Calbiochem, San Diego, Calif., USA) before being frozen in liquid nitrogen. The mycelia were then pulverized into a powder by milling the frozen mycelia together with an equal volume of dry ice in a coffee grinder precooled with liquid nitrogen. The powder was transferred into a liquid nitrogen prechilled mortar and pestle and ground to a fine powder with a small amount of baked quartz sand. The powdered mycelial material was kept at −80° C. until use.

Total RNA was prepared from the frozen, powdered mycelia of *Trichophaea saccata* CBS 804.70 by extraction with guanidium thiocyanate followed by ultracentrifugation through a 5.7 M CsCl cushion according to Chirgwin et al., 1979, *Biochemistry* 18: 5294-5299. The polyA enriched RNA was isolated by oligo (dT)-cellulose affinity chromatography according to Aviv et al., 1972, *Proc. Natl. Acad. Sci. USA* 69: 1408-1412.

Double stranded cDNA was synthesized according to the general methods of Gubler and Hoffman, 1983, *Gene* 25: 263-269; Sambrook, J., Fritsch, E. F., and Maniantis, T. Molecular cloning: *A Laboratory Manual*, 2$^{nd}$ ed., 1989, Cold Spring Harbor Laboratory, Cold Spring Harbor, N.Y.; and Kofod et al., 1994, *J. Biol. Chem.* 269: 29182-29189, using a polyA-Not I primer (Promega Corp., Madison, Wis., USA). After synthesis, the cDNA was treated with mung bean nuclease, blunt ended with T4 DNA polymerase, and ligated to a 50-fold molar excess of Eco RI adaptors (Invitrogen Corp., Carlsbad, Calif., USA). The cDNA was cleaved with Not I and the cDNA was size fractionated by 0.8% agarose gel electrophoresis using in 44 mM Tris base, 44 mM boric acid, 0.5 mM EDTA (TBE) buffer. The fraction of cDNA of 700 bp and larger was excised from the gel and purified using a GFX® PCR DNA and Gel Band Purification Kit (GE Healthcare Life Sciences, Piscataway, N.J., USA) according to the manufacturer's instructions.

The prepared cDNA was then directionally cloned by ligation into Eco RI-Not I cleaved pMHas5 (WO 03/044049) using a Rapid Ligation Kit (Roche Diagnostics GmbH, Penzberg, Germany) according to the manufacturer's instructions. The ligation mixture was electroporated into *E. coli* DH10B cells (Invitrogen Corp., Carlsbad, Calif., USA) using a GENE PULSER® and Pulse Controller (Bio-Rad Laboratories, Inc., Hercules, Calif., USA) at 50 µF, 25 mAmp, 1.8 kV with a 2 mm gap cuvette according to the manufacturer's procedure.

The electroporated cells were spread onto LB plates supplemented with 50 µg of kanamycin per ml. A cDNA plasmid pool was prepared from approximately 30,000 total transformants of the original cDNA-pMHas5 vector ligation. Plasmid DNA was prepared directly from the pool of colonies using a QIAPREP® Spin Midi/Maxiprep Kit (QIAGEN GmbH Corporation, Hilden, Germany). The cDNA library was designated SBL521-2.

A transposon containing plasmid designated pSigA4 was constructed from the pSigA2 transposon containing plasmid described in WO 01/77315 in order to create an improved version of the signal trapping transposon of pSigA2 with decreased selection background. The pSigA2 transposon contains a signal less beta-lactamase construct encoded on the transposon itself. PCR was used to create a deletion of the intact beta-lactamase gene found on the plasmid backbone using a proofreading PROOFSTART® DNA polymerase (QIAGEN GmbH Corporation, Hilden, Germany) and the following 5' phosphorylated primers (TAG Copenhagen, Denmark):

```
SigA2NotU-P:
                                        (SEQ ID NO: 95)
5'-TCGCGATCCGTTTTCGCATTTATCGTGAAACGCT-3'

SigA2NotD-P:
                                        (SEQ ID NO: 96)
5'-CCGCAAACGCTGGTGAAAGTAAAAGATGCTGAA-3'
```

The amplification reaction was composed of 1 µl of pSigA2 (10 ng/µl), 5 µl of 10× ProofStart Buffer (QIAGEN GmbH Corporation, Hilden, Germany), 2.5 µl of dNTP mix (20 mM), 0.5 µl of SigA2NotU-P (10 mM), 0.5 µl of SigA2NotD-P (10 mM), 10 µl of Q solution (QIAGEN GmbH Corporation, Hilden, Germany), and 31.25 µl of deionized water. A DNA ENGINE™ Thermal Cycler (MJ Research Inc., Waltham, Mass., USA) was used for the amplification programmed for 1 cycle at 95° C. for 5 minutes; and 20 cycles each at 94° C. for 30 seconds, 62° C. for 30 seconds, and 72° C. for 4 minutes.

A 3.9 kb PCR reaction product was isolated by 0.8% agarose gel electrophoresis using TAE buffer and 0.1 µg of ethidium bromide per ml. The DNA band was visualized with the aid of an Eagle Eye Imaging System (Stratagene, La Jolla, Calif., USA) at 360 nm. The 3.9 kb DNA band was excised from the gel and purified by using a GFX® PCR DNA and Gel Band Purification Kit according to the manufacturer's instructions.

The 3.9 kb fragment was self-ligated at 16° C. overnight with 10 units of T4 DNA ligase (New England Biolabs, Inc., Beverly, Mass., USA), 9 µl of the 3.9 kb PCR fragment, and 1 µl of 10× ligation buffer (New England Biolabs, Inc., Beverly, Mass., USA). The ligation was heat inactivated for 10 minutes at 65° C. and then digested with Dpn I at 37° C. for 2 hours. After incubation, the digestion was purified using a GFX® PCR DNA and Gel Band Purification Kit.

The purified material was then transformed into *E. coli* TOP10 competent cells (Invitrogen Corp., Carlsbad, Calif., USA) according to the manufacturer's instructions. The transformation mixture was plated onto LB plates supplemented with 25 µg of chloramphenicol per ml. Plasmid minipreps were prepared from several transformants and digested with Bgl II. One plasmid with the correct construction was chosen. The plasmid was designated pSigA4. Plasmid pSigA4 contains the Bgl II flanked transposon SigA2 identical to that disclosed in WO 01/77315.

A 60 µl sample of plasmid pSigA4 DNA (0.3 µg/µl) was digested with Bgl II and separated by 0.8% agarose gel electrophoresis using TAE buffer. A SigA2 transposon DNA band of 2 kb was eluted with 200 µl of EB buffer (QIAGEN GmbH Corporation, Hilden, Germany) and purified using a GFX® PCR DNA and Gel Band Purification Kit according to the manufacturer's instructions and eluted in 200 µl of EB buffer. SigA2 was used for transposon assisted signal trapping.

A complete description of transposon assisted signal trapping can be found in WO 01/77315. A cDNA plasmid pool was prepared from 30,000 total transformants of the original cDNA-pMHas5 vector ligation. Plasmid DNA was prepared directly from a pool of colonies recovered from solid LB selective medium using a QIAPREP® Spin Midi/Maxiprep Kit. The plasmid pool was treated with transposon SigA2 and MuA transposase (Finnzymes OY, Espoo, Finland) according to the manufacturer's instructions.

For in vitro transposon tagging of the *Trichophaea saccata* CBS 804.70 cDNA library, 4 or 8 µl of SigA2 transposon containing approximately 2.6 µg of DNA were mixed with 1 µl of the plasmid DNA pool of the *Trichophaea saccata* CBS 804.70 cDNA library containing 2 µg of DNA, 2 µl of MuA transposase (0.22 µg/µl), and 5 µl of 5× buffer (Finnzymes OY, Espoo, Finland) in a total volume of 50 µl and incubated at 30° C. for 3.5 hours followed by heat inactivation at 75° C. for 10 minutes. The DNA was precipitated by addition of 5 µl of 3 M sodium acetate pH 5 and 110 µl of 96% ethanol and centrifuged for 30 minutes at 10,000×g. The pellet was washed in 70% ethanol, air dried at room temperature, and resuspended in 10 µl of 10 mM Tris, pH 8, 1 mM EDTA (TE) buffer.

A 1.5 µl volume of the transposon tagged plasmid pool was electroporated into 20 µl of *E. coli* DH10B ultracompetent cells (Gibco-BRL, Gaithersburg Md., USA) according to the manufacturer's instructions using a GENE PULSER® and Pulse Controller (Bio-Rad Laboratories, Inc., Hercules, Calif., USA) at 50 uF, 25 mAmp, 1.8 kV with a 2 mm gap cuvette according to the manufacturer's procedure.

The electroporated cells were incubated in SOC medium with shaking at 250 rpm for 2 hours at 28° C. before being plated on the following selective media: LB medium supplemented with 50 µg of kanamycin per ml; LB medium supplemented with 50 µg of kanamycin per ml and 15 µg of chloramphenicol per ml; and/or LB medium supplemented with 50 µg of kanamycin per ml, 15 µg of chloramphencol per ml, and 12.5 µg of ampicillin per ml.

From dilution plating of the electroporation onto LB medium supplemented with kanamycin and chloramphencol medium, it was determined that approximately 72,000 colonies were present containing a cDNA library plasmid with a SigA2 transposition per electroporation and that approximately 69 colonies were recovered under triple selection (LB, kanamycin, chorlamphenicol, ampicillin). Further electroporation and plating experiments were performed until 445 total colonies were recovered under triple selection. The colonies were miniprepped using a QIAPREP® 96 Turbo Miniprep Kit (QIAGEN GmbH Corporation, Hilden, Germany). Plasmids were sequenced with the transposon forward and reverse primers (primers A and B), shown below, according to the procedure disclosed in WO 2001/77315 (page 28)

```
Primer A:
                                    (SEQ ID NO: 97)
5'-AGCGTTTGCGGCCGCGATCC-3'

Primer B:
                                    (SEQ ID NO: 98)
5'-TTATTCGGTCGAAAAGGATCC-3'
```

The *Trichophaea saccata* Family GH6 cDNA encoding cellobiohydrolase was subcloned into the *Aspergillus* expression vector pMStr57 (WO 2004/032648) by PCR amplifying the protein coding sequence from the cDNA library SBL0521, described above, with the two synthetic oligonucleotide primers shown below.

```
Primer 848:
                                    (SEQ ID NO: 99)
5'-ACACAACTGGGGATCCTCATCATGAAGAACTTCCTTCTGG-3'

Primer 849:
                                    (SEQ ID NO: 100)
5'-CCCTCTAGATCTCGAGTTACGTGAAGCTAGGATTAGCATT-3'
```

The amplification was performed using IPROOF™ High Fidelity 2× Master Mix (Bio-Rad Laboratories, Inc., Hercules, Calif., USA) following the manufacturer's instructions. The amplification reaction was composed of SBL0521 pool DNA as template, 25 µmol each of primers 848 and 849, and 25 µl of IPROOF™ High Fidelity 2× Master Mix in a final volume of 50 µl. The amplification was performed by pre-denaturing at 98° C. for 2 minutes; 5 cycles each with denaturing at 98° C. for 10 seconds, annealing at 65° C. for 10 seconds, and elongation at 72° C. for 1 minute; and 25 cycles each with denaturing at 98° C. for 10 seconds, and combined annealing extension at 72° C. for 1 minute. A final elongation was made at 72° C. for 10 minutes.

A PCR product of 1.4 kb was separated from residual reaction components using a GFX® PCR DNA and Gel Band Purification Kit according to the manufacturer's instructions.

The PCR fragment was cloned into Barn HI and Xho I digested pMStr57 using an IN-FUSION™ Dry-Down PCR Cloning Kit (Clontech Laboratories, Inc., Mountain View, Calif., USA). Approximately 50 ng of PCR product and 200 ng of vector in a total volume of 10 µl were added to the IN-FUSION™ Dry-Down pellet. The reaction was performed according to the manufacturer's instructions. The *Trichophaea saccata* Family GH6 cellobiohydrolase encoding DNA of the resulting *Aspergillus* expression construct, pMStr179, was sequenced and the sequence agreed completely with the cellobiohydrolase coding sequence of SEQ ID NO: 16.

The same PCR fragment was cloned into the pCR®-BluntII-TOPO vector (Invitrogen, Life Technologies, Carlsbad, Calif., USA) using a Zero Blunt TOPO PCR Cloning Kit, to generate pMStr199. The *Trichophaea saccata* Family GH6 cellobiohydrolase encoding DNA of pMStr199 was sequenced and the sequence agreed completely with the cellobiohydrolase coding sequence of SEQ ID NO: 1. *E. coli* strain NN059165, containing pMStr199, was deposited with the Deutsche Sammlung von Mikroorganismen and Zellkulturen GmbH (DSM), Braunschweig, Germany, on Feb. 24, 2010 and assigned the accession number DSM 23379.

The nucleotide sequence and deduced amino acid sequence of the *Trichophaea saccata* cellobiohydrolase cDNA are shown in SEQ ID NO: 1 and SEQ ID NO: 2, respectively. The coding sequence is 1344 bp including the stop codon. The encoded predicted protein is 447 amino acids. Using the SignalP program (Nielsen et al., 1997, *Protein Engineering* 10: 1-6), a signal peptide of 16 residues was predicted. The predicted mature protein contains 431 amino acids with a predicted molecular mass of 45.3 kDa and an isoelectric pH of 5.06.

A comparative pairwise global alignment of amino acid sequences was determined using the Needleman-Wunsch algorithm (Needleman and Wunsch, 1970, *J. Mol. Biol.* 48: 443-453) as implemented in the Needle program of EMBOSS with gap open penalty of 10, gap extension penalty of 0.5, and the EBLOSUM62 matrix. The alignment showed that the deduced amino acid sequence of the *Trichophaea saccata* cDNA encoding a Family GH6 polypeptide having cellobiohydrolase activity shares 64% identity (excluding gaps) to the deduced amino acid sequence of a cellobiohydrolase from *Aspergillus fumigatus* (GENESEQP:ABB80166).

The *Aspergillus oryzae* strain BECh2 (WO 2000/39322) was transformed with pMStr179 according to Christensen et al., 1988, *Biotechnology* 6, 1419-1422 and WO 2004/032648. Ten transformants were cultured for 4 days at 30° C. in 750 μl of DAP2C-1 medium (WO 2004/032648), in which 2% glucose was substituted for maltodextrin. Samples were monitored by SDS-PAGE using a CRITERION™ XT Precast 12% Bis-Tris gel (Bio-Rad Laboratories, Inc., Hercules, Calif., USA) according to the manufacturer's instructions. LMW standards from an Amersham Low Molecular Weight Calibration Kit for SDS Electrophoresis (GE Healthcare UK Limited, Buckinghamshire, UK) were used as molecular weight markers. The gel was stained with INSTANTBLUE™ (Expedeon Protein Solutions, Cambridge, UK). Eight transformants produced a novel protein doublet in the range of 55-60 kDa.

Two of these transformants, designated *Aspergillus oryzae* MStr335 and MStr336, were isolated twice by dilution streaking conidia on selective medium (amdS) containing 0.01% TRITON® X-100 to limit colony size.

Spores from four confluent COVE N slants of *Aspergillus oryzae* MStr335 spores were collected with a solution of 0.01% TWEEN® 20 and used to inoculate 21 shake flasks each containing 150 ml of DAP2C-1 medium (WO 2004/032648) in which 2% glucose was substituted for maltodextrin. The flasks were incubated at 30° C. with constant shaking at 200 rpm for 3 days. Fungal mycelia and spores were removed at harvesting by first filtering the fermentation broth through a sandwich of 3 glass microfiber filters with increasing particle retention sizes of 1.6 μm, 1.2 μm and 0.7 μm, and then filtering through a 0.45 μm filter. Protein concentration was determined using a Microplate BCA™ Protein Assay Kit in which bovine serum albumin was used as a protein standard.

Example 9: Preparation of *Aspergillus fumigatus* Cellobiohydrolase II

*Aspergillus fumigatus* NN055679 cellobiohydrolase II (CBHII) (SEQ ID NO: 17 [DNA sequence] and SEQ ID NO: 18 [deduced amino acid sequence]) was prepared according to the following procedure.

Two synthetic oligonucleotide primers, shown below, were designed to PCR amplify the full-length open reading frame of the *Aspergillus fumigatus* Family 6A glycosyl hydrolase from genomic DNA. A TOPO Cloning kit was used to clone the PCR product. An IN-FUSION™ Cloning Kit was used to clone the fragment into pAILo2.

Forward primer:
(SEQ ID NO: 101)
5'-ACTGGATTTACCATGAAGCACCTTGCATCTTCCATCG-3'

Reverse primer:
(SEQ ID NO: 102)
5'-TCACCTCTAGTTAATTAAAAGGACGGGTTAGCGT-3'

Bold letters represent coding sequence. The remaining sequence contains sequence identity compared with the insertion sites of pAILo2.

Fifty picomoles of each of the primers above were used in a PCR reaction containing 500 ng of *Aspergillus fumigatus* genomic DNA, 1× ThermoPol Taq reaction buffer (New England Biolabs, Ipswich, Mass., USA), 6 μl of 10 mM blend of dATP, dTTP, dGTP, and dCTP, 0.1 unit of Taq DNA Polymerase (New England Biolabs, Ipswich, Mass., USA), in a final volume of 50 μl. An EPPENDORF® MASTERCYCLER® 5333 was used to amplify the fragment programmed for one cycle at 98° C. for 2 minutes; and 35 cycles each at 96° C. for 30 seconds, 61° C. for 30 seconds, and 72° C. for 2 minutes. After the 35 cycles, the reaction was incubated at 72° C. for 10 minutes and then cooled at 10° C. until further processed. To remove the A-tails produced by Taq the reaction was incubated for 10 minutes at 68° C. in the presence of 1 unit of Pfx DNA polymerase (Invitrogen, Carlsbad, Calif., USA).

A 1.3 kb PCR reaction product was isolated on a 0.8% GTG-agarose gel (Cambrex Bioproducts, East Rutherford, N.J., USA) using TAE buffer and 0.1 μg of ethidium bromide per ml. The DNA band was visualized with the aid of a DARK READER™ (Clare Chemical Research, Dolores, Colo.) to avoid UV-induced mutations. The 1.3 kb DNA band was excised with a disposable razor blade and purified with an Ultrafree-DA spin cup (Millipore, Billerica, Mass.) according to the manufacturer's instructions.

The purified 1.3 kb PCR product was cloned into the PCR4Blunt-TOPO vector (Invitrogen). Two microliters of the purified PCR product were mixed with one microliter of a 2M Sodium chloride solution and one microliter of the Topo vector. The reaction was incubated at room temperature for 15 minutes and then two microliters of the Topo reaction were used to transform *E. coli* TOP10 competent cells according to the manufacturer's instructions. Two aliquots of 100 microliters each of the transformation reaction were spread onto two 150 mm 2xYT-Amp plates and incubated overnight at 37° C.

Eight recombinant colonies were used to inoculate liquid cultures containing three milliliters of LB supplemented with 100 μg of ampicillin per milliliter of media. Plasmid DNA was prepared from these cultures using a BIOROBOT® 9600. Clones were analyzed by restriction digest. Plasmid DNA from each clone was digested with the enzyme Eco RI according to the manufacturer instructions (NEB, Ipswich, Mass., USA) and analyzed by agarose gel electrophoresis as above. Six out of eight clones had the expected restriction digest pattern from these, clones 2, 4, 5, 6, 7 and 8 were selected to be sequenced to confirm that there were no mutations in the cloned insert. Sequence analysis of their 5-prime and 3-prime ends indicated that clones 2, 6 and 7 had the correct sequence. These three clones were selected for re-cloning into pAILo2. One microliter aliquot of each clone was mixed with 17 μl of diluted TE (1:10 dilution) and 1 μl of this mix was used to re-amplify the *Aspergillus fumigatus* glycosyl hydrolase 6A coding region.

Fifty picomoles of each of the primers above were used in a PCR reaction containing 1 μl of the diluted mix of clones 2, 6 and 7, 1× Pfx Amplification Buffer (Invitrogen, Carlsbad, Calif., USA), 6 μl of 10 mM blend of dATP, dTTP, dGTP, and dCTP, 2.5 units of PLATINUM® Pfx DNA Polymerase, 1 μl of 50 mM $MgSO_4$, in a final volume of 50 μl. An EPPENDORF® MASTERCYCLER® 5333 was used to amplify the fragment programmed for one cycle at 98° C. for 2 minutes; and 35 cycles each at 94° C. for 30 seconds, 61° C. for 30 seconds, and 68° C. for 1.5 minutes. After the 35 cycles, the reaction was incubated at 68° C. for 10 minutes and then cooled at 10° C. until further processed. A 1.3 kb PCR reaction product was isolated on a 0.8% GTG-agarose gel using TAE buffer and 0.1 μg of ethidium bromide per ml. The DNA band was visualized with the aid of a DARKREADER™ Transilluminator to avoid UV-induced mutations. The 1.0 kb DNA band was excised with a disposable razor blade and purified with an Ultrafree-DA spin cup (Millipore, Billerica, Mass.) according to the manufacturer's instructions.

The vector pAILo2 was linearized by digestion with Nco I and Pac I (using conditions specified by the manufacturer). The fragment was purified by gel electrophoresis and ultrafiltration as described above. Cloning of the purified PCR fragment into the linearized and purified pAILo2 vector was performed with an IN-FUSION™ Cloning Kit. The reaction (20 μl) contained 1× IN-FUSION™ Buffer, 1×BSA, 1 μl of IN-FUSION™ enzyme (diluted 1:10), 100 ng of pAILo2 digested with Nco I and Pac I, and 50 ng of the *Aspergillus fumigatus* GH6A purified PCR product. The reaction was incubated at room temperature for 30 minutes. A 2 μl sample of the reaction was used to transform *E. coli* TOP10 competent cells according to the manufacturer's instructions. After the recovery period, two 100 μl aliquots from the transformation reaction were plated onto 150 mm 2×YT plates supplemented with 100 μg of ampicillin per ml. The plates were incubated overnight at 37° C. A set of eight putative recombinant clones was selected at random from the selection plates and plasmid DNA was prepared from each one using a BIOROBOT® 9600. Clones were analyzed by Pst I restriction digest. Seven out of eight clones had the expected restriction digest pattern. Clones 1. 2 and 3 were then sequenced to confirm that there were no mutations in the cloned insert. Clone #2 was selected and designated pAILo33.

*Aspergillus fumigatus* cel6A (JaL355 ALLO33 Exp03191) was grown to obtain culture broth for the purification of a cellobiosehydrolase II.

Seven hundred and fifty ml of shake flask medium were added to a 2800 ml shake flask. The shake flask medium was composed per liter of 45 g of maltose, 2 g of $K2HPO_4$, 12 g of $KH_2PO_4$, 1 g of NaCl, 1 g of $MgSO_4.7H_2O$, 7 g of yeast extract, 2 g of urea, and 0.5 ml of trace elements solution. The trace elements solution was composed per liter of 13.8 g of $FeSO_4.7H_2O$, 14.3 g of $ZnSO_4.7H_2O$, 8.5 g of $MnSO_4.H_2O$, 2.5 g of $CuSO_4.5H_2O$, 0.5 g of $NiCl_2.6H_2O$, and 3 g of citric acid. Two shake flasks were inoculated by suspension of a PDA plate of *Aspergillus fumigatus* cel6A with 0.01% TWEEN® 20 and incubated at 34° C. on an orbital shaker at 200 rpm for 120 hours.

The broth was filtered using 0.7 μm glass filter GF/F (Whatman, Piscataway, N.J., USA) and then using a 0.22 μm EXPRESS™ Plus Membrane (Millipore, Bedford, Mass., USA).

The filtered broth was concentrated and buffer exchanged using a tangential flow concentrator (Pall Filtron, Northborough, Mass., USA) equipped with a 10 kDa polyethersulfone membrane (Pall Filtron, Northborough, Mass., USA) with 20 mM Tris-HCl pH 8.0. Protein concentration was determined using a Microplate BCA™ Protein Assay Kit in which bovine serum albumin was used as a protein standard.

Example 10: Preparation of *Aspergillus terreus* ATCC 28865 Cel7 Endoglucanase I The *Aspergillus terreus* ATCC 28865 Cel7 endoglucanase I gene (SEQ ID NO: 19 [DNA sequence] and SEQ ID NO: 20 [deduced amino acid sequence]) was cloned and expressed in *Aspergillus oryzae* as described below.

Two synthetic oligonucleotide primers, shown below, were designed to PCR amplify the endoglucanase I gene from *Aspergillus terreus* ATCC 28865 genomic DNA. Genomic DNA was isolated using a FASTDNA® Spin Kit for Soil (MP Biomedicals, Solon, Ohio, USA).

```
Primer #226:
                                    (SEQ ID NO: 103)
5'-TAACAATTGTCACCATGAATTCTCTTACAAAAAGCAT-3'

Primer #227:
                                    (SEQ ID NO: 104)
5'-TATGCGGCCGCAGTCTGCATGTGTTACGCACCT-3'
```

The amplification reaction was composed of 1 μl of *Aspergillus terreus* ATCC 28865 genomic DNA, 12.5 μl of 2× REDDYMIX™ PCR Buffer (Thermo Fisher Scientific Inc., Waltham, Mass., USA), 1 μl of primer #226 (5 μM), 1 μl of #227 (5 μM), and 9.5 μl of $H_2O$. The amplification reaction was incubated in a PTC-200 DNA ENGINE™ Thermal Cycler (MJ Research Inc., Waltham, Mass., USA) programmed for 1 cycle at 94° C. for 2 minutes; and 35 cycles each at 94° C. for 15 seconds and 60° C. for 1.5 minutes.

A 1.44 kb PCR reaction product was isolated by 1% agarose gel electrophoresis using TAE buffer and staining with SYBR® Safe DNA gel stain (Invitrogen Corp., Carlsbad, Calif., USA). The DNA band was visualized with the aid of an EAGLE EYE® Imaging System (Stratagene, La Jolla, Calif., USA) and a DARKREADER® Transilluminator. The 1.44 kb DNA band was excised from the gel and purified using a GFX® PCR DNA and Gel Band Purification Kit according to the manufacturer's instructions.

The 1.44 kb fragment was cleaved with Mfe I and Not I and purified using a GFX® PCR DNA and Gel Band Purification Kit according to the manufacturer's instructions.

The cleaved 1.44 kb fragment was then directionally cloned by ligation into Eco RI-Not I cleaved pXYG1051 (WO 2005/080559) using T4 ligase (Promega, Madison, Wis., USA) according to the manufacturer's instructions. The ligation mixture was transformed into *E. coli*-TOP10F competent cells (Invitrogen Corp., Carlsbad, Calif., USA) according to the manufacturer's instructions. The transformation mixture was plated onto LB plates supplemented with 100 μg of ampicillin per ml. Plasmid minipreps were prepared from several transformants and sequenced. One plasmid with the correct *Aspergillus terreus* GH7 coding sequence (SEQ ID NO: 13) was chosen. The plasmid was designated pXYG1051-NP003857. The expression vector pXYG1051 contains the same neutral amylase II (NA2) promoter derived from *Aspergillus niger*, and terminator elements as pCaHj483 (disclosed in Example 4 of WO 98/00529). Furthermore pXYG1051 has pUC18 derived sequences for selection and propagation in *E. coli*, and pDSY82 (disclosed in Example 4 of U.S. Pat. No. 5,958,727) derived sequences for selection and expression in *Aspergillus* facilitated by the pyrG gene of *Aspergillus oryzae*, which encodes orotidine decarboxylase and is used to complement a pyrG mutant *Aspergillus* strain.

The expression plasmid pXYG1051-NP003857 was transformed into *Aspergillus oryzae JaL*355 as described in WO 98/00529. Transformants were purified on selection plates through single conidia prior to sporulating them on PDA plates. Production of the *Aspergillus terreus* GH7 polypeptide by the transformants was analyzed from culture supernatants of 1 ml 96 deep well stationary cultivations at 26° C. in YP medium with 2% maltodextrin. Expression was verified by SDS-PAGE using a NUPAGE® NOVEX® 4-12% Bis-Tris Gel with 50 mM 2-(N-morpholino)ethanesulfonic acid (MES) buffer (Invitrogen Corporation, Carlsbad, Calif., USA) by Coomassie blue staining. One transformant was selected for further work and designated *Aspergillus oryzae* 28.4.

For larger scale production, *Aspergillus oryzae* 28.4 spores were spread onto a PDA plate and incubated for five days at 37° C. The confluent spore plate was washed twice with 5 ml of 0.01% TWEEN® 20 to maximize the number of spores collected. The spore suspension was then used to inoculate twenty-five 500 ml flasks containing 100 ml of YPM medium. The culture was incubated at 30° C. with constant shaking at 85 rpm. At day four post-inoculation, the culture broth was collected by filtration through a triple layer of glass microfiber filters of 1.6 μm, 1.2 μm, and 0.7 μm (Whatman, Piscataway, N.J., USA). Fresh culture broth from this transformant produced a band of GH7 protein of approximately 64 kDa. The identity of this band as the *Aspergillus terreus* GH7 polypeptide was verified by peptide sequencing using standard techniques.

Two liters of the filtered broth was concentrated to 400 ml and washed with 50 mM HEPES pH 7.0 using a SARTOFLOW® Alpha Plus Crossflow System with a 10 kDa cut-off (Sartorius Stedim Biotech S.A., Aubagne Cedex, France). Ammonium sulphate was added to a final concentration of 1 M and dissolved in the ultrafiltrate. The solution was loaded onto a Source 15 Phenyl XK 26/20 50 ml column (GE Healthcare, HiHerod, Denmark). After loading the column was washed with 150 ml of 1 M ammonium sulphate and eluted with 1 column volume of 50% ethanol in a 0% to 100% gradient followed by 5 column volumes of 50% ethanol at a flow rate of 10 ml per minute. Fractions of 10 ml were collected and analyzed by SDS-PAGE. Fractions 3 to 8 were pooled and diluted to 1000 ml with 50 mM HEPES pH 7.0 before loading onto a Q SEPHAROSE® Fast Flow XK26/20 60 ml column (GE Healthcare, HiHerod, Denmark). After loading the column was washed 3 times with 60 ml of 50 mM HEPES pH 7.0 and eluded with 100 ml of 50 mM HEPES pH 7.0, 1 M NaCl at a flow rate of 10 ml per minute. Fractions of 10 ml were collected and analyzed by SDS-PAGE. The flow through and first wash were pooled and concentrated to 400 ml and washed with 50 mM HEPES pH 7.0 using a SARTOFLOW® Alpha plus Crossflow System with a 10 kDa cut-off. Further concentration was conducted using a VIVASPIN™ centrifugal concentrator according to the manufacturer's instructions to a final volume of 80 ml. The protein concentration was determined by $A_{280}/A_{260}$ absorbance.

Example 11: Preparation of *Trichoderma reesei* RutC30 Cel5A Endoglucanase II The *Trichoderma reesei* RutC30 Cel5A endoglucanase II gene (SEQ ID NO: 21 [DNA sequence] and SEQ ID NO: 22 [deduced amino acid sequence]) was cloned and expressed in *Aspergillus oryzae* as described below.

Two synthetic oligonucleotide primers, shown below, were designed to PCR amplify the endoglucanase II gene from *Trichoderma reesei* RutC30 genomic DNA. Genomic DNA was isolated using a DNEASY® Plant Maxi Kit. An IN-FUSION™ PCR Cloning Kit was used to clone the fragment directly into pAILo2 (WO 2004/099228).

Forward primer:

(SEQ ID NO: 105)

5'-ACTGGATTTACCATGAACAAGTCCGTGGCTCCATTGCT-3'

Reverse primer:

(SEQ ID NO: 106)

5'-TCACCTCTAGTTAATTAACTACTTTCTTGCGAGACACG-3'

Bold letters represent coding sequence. The remaining sequence contains sequence identity to insertion sites of pAILo2.

Fifty picomoles of each of the primers above were used in a PCR reaction containing 200 ng of *Trichoderma reesei* genomic DNA, 1× Pfx Amplification Buffer (Invitrogen, Carlsbad, Calif., USA), 6 μl of 10 mM blend of dATP, dTTP, dGTP, and dCTP, 2.5 units of PLATINUM® Pfx DNA polymerase, and 1 μl of 50 mM $MgSO_4$ in a final volume of 50 μl. The amplification reaction was incubated in an EPPENDORF® MASTERCYCLER® 5333 programmed for one cycle at 98° C. for 2 minutes; and 35 cycles each at 94° C. for 30 seconds, 61° C. for 30 seconds, and 68° C. for 1.5 minutes. After the 35 cycles, the reaction was incubated at 68° C. for 10 minutes and then cooled at 10° C. A 1.5 kb PCR reaction product was isolated on a 0.8% GTG® agarose gel using TAE buffer and 0.1 μg of ethidium bromide per ml. The DNA band was visualized with the aid of a DARKREADER™ Transilluminator. The 1.5 kb DNA band was excised with a disposable razor blade and purified using an ULTRAFREE® DA spin cup according to the manufacturer's instructions.

Plasmid pAILo2 was linearized by digestion with Nco I and Pac I. The plasmid fragment was purified by gel electrophoresis and ultrafiltration as described above. Cloning of the purified PCR fragment into the linearized and purified pAILo2 vector was performed using an IN-FUSION™ PCR Cloning Kit. The reaction (20 μl) contained 1× IN-FUSION™ Buffer, 1×BSA, 1 μl of IN-FUSION™ enzyme (diluted 1:10), 100 ng of pAILo2 digested with Nco I and Pac I, and 100 ng of the *Trichoderma reesei* Cel5A endoglucanase II PCR product. The reaction was incubated at room temperature for 30 minutes. A 2 μl sample of the reaction was used to transform *E. coli* XL10 SOLOPACK® Gold cells according to the manufacturer's instructions. After a recovery period, two 100 μl aliquots from the transformation reaction were plated onto 150 mm 2×YT plates supplemented with 100 μg of ampicillin per ml. The plates were incubated overnight at 37° C. A set of 3 putative recombinant clones was recovered the selection plates and plasmid DNA was prepared from each one using a BIOROBOT® 9600. Clones were analyzed by Pci I/Bsp LU11 I restriction digestion. One clone with the expected restriction digestion pattern was then sequenced to confirm that there were no mutations in the cloned insert. Clone #3 was selected and designated pAILo27.

*Aspergillus oryzae* JaL250 protoplasts were prepared according to the method of Christensen et al., 1988, supra. Five micrograms of pAILo27 (as well as pAILo2 as a control) were used to transform *Aspergillus oryzae* JaL250 protoplasts.

The transformation of *Aspergillus oryzae* JaL250 with pAILo27 yielded about 50 transformants. Eleven transformants were isolated to individual PDA plates and incubated for five days at 34° C.

Confluent spore plates were washed with 3 ml of 0.01% TWEEN® 80 and the spore suspension was used to inoculate 25 ml of MDU2BP medium in 125 ml glass shake flasks. Transformant cultures were incubated at 34° C. with constant shaking at 200 rpm. At day five post-inoculation, cultures were centrifuged at 6000×g and their supernatants collected. Five microliters of each supernatant were mixed with an equal volume of 2× loading buffer (10% beta-mercaptoethanol) and loaded onto a 1.5 mm 8%-16% Tris-glycine SDS-PAGE gel and stained with SIMPLYBLUE™ SafeStain (Invitrogen Corp., Carlsbad, Calif., USA). SDS-PAGE profiles of the culture broths showed that ten out of eleven transformants produced a new protein band of approximately 45 kDa. Transformant number 1, designated *Aspergillus oryzae JaL*250AILo27, was cultivated in a fermentor.

One hundred ml of shake flask medium were added to a 500 ml shake flask. The shake flask medium was composed per liter of 50 g of sucrose, 10 g of $KH_2PO_4$, 0.5 g of $CaCl_2$, 2 g of $MgSO_4.7H_2O$, 2 g of $K_2SO_4$, 2 g of urea, 10 g of yeast extract, 2 g of citric acid, and 0.5 ml of trace metals solution. The trace metals solution was composed per liter of 13.8 g of $FeSO_4.7H_2O$, 14.3 g of $ZnSO_4.7H_2O$, 8.5 g of $MnSO_4.H_2O$, 2.5 g of $CuSO_4.5H_2O$, and 3 g of citric acid. The shake flask was inoculated with two plugs of *Aspergillus oryzae* JaL250AILo27 from a PDA plate and incubated at 34° C. on an orbital shaker at 200 rpm for 24 hours. Fifty ml of the shake flask broth was used to inoculate a 3 liter fermentation vessel.

A total of 1.8 liters of the fermentation batch medium was added to a three liter glass jacketed fermentor (Applikon Biotechnology, Schiedam, Netherlands). The fermentation batch medium was composed per liter of 10 g of yeast extract, 24 g of sucrose, 5 g of $(NH_4)_2SO_4$, 2 g of $KH_2PO_4$, 0.5 g of $CaCl_2.2H_2O$, 2 g of $MgSO_4.7H_2O$, 1 g of citric acid, 2 g of $K_2SO_4$, 0.5 ml of anti-foam, and 0.5 ml of trace metals solution. Trace metals solution was composed per liter of 13.8 g of $FeSO_4.7H_2O$, 14.3 g of $ZnSO_4.7H_2O$, 8.5 g of $MnSO_4.H_2O$, 2.5 g of $CuSO_4.5H_2O$, and 3 g of citric acid. Fermentation feed medium was composed of maltose. Fermentation feed medium was dosed at a rate of 0 to 4.4 g/l/hr for a period of 185 hours. The fermentation vessel was maintained at a temperature of 34° C. and pH was controlled using an Applikon 1030 control system (Applikon Biotechnology, Schiedam, Netherlands) to a set-point of 6.1+/−0.1. Air was added to the vessel at a rate of 1 vvm and the broth was agitated by a Rushton impeller rotating at 1100 to 1300 rpm. At the end of the fermentation, whole broth was harvested from the vessel and centrifuged at 3000×g to remove the biomass. The supernatant was sterile filtered and stored at 5 to 10° C.

The supernatant was desalted and buffer-exchanged in 20 mM Bis-Tris pH 6.0 using a HIPREP® 26/10 desalting column according to the manufacturer's instructions. The buffer exchanged sample was loaded onto a MonoQ® column (GE Healthcare, Piscataway, N.J., USA) equilibrated with 20 mM Bis-Tris pH 6.0, and the bound protein was eluted with a linear gradient from 0 to 1000 mM sodium chloride. Protein fractions were pooled and buffer exchanged into 1.2 M $(NH_4)_2SO_4$-20 mM Tris-HCl pH 8.5. The sample was loaded onto a Phenyl SUPEROSE™ column (HR 16/10) equilibrated with 1.2 M $(NH_4)_2SO_4$–20 mM Tris-HCl pH 8.0. Bound proteins were eluted with a linear gradient over 20 column volumes from 1.2 to 0 M $(NH_4)_2SO_4$ in 20 mM Tris-HCl pH 8.5. The fractions were pooled, concentrated, and loaded onto a SUPERDEX® 75 HR 26/60 column (GE Healthcare, Piscataway, N.J., USA) equilibrated with 20 mM Tris-150 mM sodium chloride pH 8.5. Fractions were pooled and concentrated in 20 mM Tris-150 mM sodium chloride pH 8.5. Protein concentration was determined using a Microplate BCA™ Protein Assay Kit in which bovine serum albumin was used as a protein standard.

Example 12: Preparation of *Myceliophthora thermophila* CBS 202.75 Cel5A Endoglucanase II

*Myceliophthora thermophila* CBS 202.75 Cel5A endoglucanase II (EGII) (SEQ ID NO: 23 [DNA sequence] and SEQ ID NO: 24 [deduced amino acid sequence]) was prepared recombinantly according to WO 2007/109441 using *Aspergillus oryzae* HowB104 as a host.

The culture filtrate was desalted and buffer-exchanged in 20 mM Tris pH 8.0 using a HIPREP® 26/10 desalting column according to the manufacturer's instructions. The buffer exchanged sample was applied to a MonoQ® column equilibrated with 20 mM Tris pH 8.0, and the bound protein was eluted with a gradient from 0 to 500 mM sodium chloride. Fractions were pooled and concentrated in 20 mM Tris pH 8.0. Protein concentration was determined using a Microplate BCA™ Protein Assay Kit in which bovine serum albumin was used as a protein standard.

Example 13: Preparation of *Thermoascus aurantiacus* CGMCC 0670 Cel5A Endoglucanase II

*Thermoascus aurantiacus* CGMCC 0670 cDNA encoding a Cel5A endoglucanase II (SEQ ID NO: 25 [DNA sequence] and SEQ ID NO: 26 [deduced amino acid sequence]) was cloned according to the following procedure. The *T. aurantiacus* strain was grown in 80 ml of CBH1 medium (2.5% AVICEL®, 0.5% glucose, 0.14% $(NH_4)_2SO_4$) in 500 ml Erlenmeyer baffled flasks at 45° C. for 3 days with shaking at 165 rpm. Mycelia were harvested by centrifugation at 7000 rpm for 30 minutes and stored at −80C before use for RNA extraction. RNA was isolated from 100 mg of mycelia using a RNEASY® Plant Mini Kit.

The cDNA for the *Thermoascus aurantiacus* endoglucanase was isolated by RT PCR using a 3' RACE system and a 5' RACE system and primers BG025-1, BG025-2, BG025-3, and BG025-4 shown below to the N-terminal amino acids.

```
Primer BG025-1:
                                        (SEQ ID NO: 107)
5'-AA(T/C)GA(A/G)TC(T/C/A/G)GG(T/C/A/G)GC(T/C/A/G)

GAATT-3'

Primer BG025-2:
                                        (SEQ ID NO: 108)
5'-AA(T/C)GA(A/G)TC(T/C/A/G)GG(T/C/A/G)GC(T/C/A/G)

GAGTT-3'

Primer BG025-3:
                                        (SEQ ID NO: 109)
5'-AA(T/C)GA(A/G)AG(T/C)GG(T/C/A/G)GC(T/C/A/G)

GAATT-3'

Primer BG025-4:
                                        (SEQ ID NO: 110)
5'-AA(T/C)GA(A/G)AG(T/C)GG(T/C/A/G)GC(T/C/A/G)

GAGTT-3'
```

The RT PCR products were ligated into plasmid pGEM-T using a pGEM-T Vector System and transformed into *E. coli* strain JM109. A single clone harboring a plasmid named pBGC1009 containing the endoglucanase cDNA was isolated.

PCR primers were designed to amplify the cDNA encoding the *T aurantiacus* endoglucanase from plasmid pBGC1009. Restriction enzyme sites Bsp HI and Pac I were incorporated for in-frame cloning into *Aspergillus oryzae* expression plasmid pBM120a (WO 2006/039541).

```
Primer 996261:
                                        (SEQ ID NO: 111)
5'-GATCTCATGAAGCTCGGCTCTCTCGT-3'
BspHI

Primer 996167:
                                        (SEQ ID NO: 112)
5'-TTAATTAATCAAAGATACGGAGTCAAAATAGG-3'
PacI
```

The fragment of interest was amplified by PCR using an EXPAND™ High Fidelity PCR System. The PCR amplification reaction mixture contained 1 μl of 0.09 μg/μl pBGC1009, 1 μl of primer 996261 (50 μmol/μl), 1 μl of primer 996167 (50 μmol/μl), 5 μl of 10×PCR buffer with 15 mM $MgCl_2$, 1 μl of dNTP mix (10 mM each), 37.25 μl of water, and 0.75 μl (3.5 U/μl) of DNA polymerase mix. An EPPENDORF® MASTERCYCLER® thermocycler was used to amplify the fragment programmed for 1 cycle at 94° C. for 2 minutes; 10 cycles each at 94° C. for 15 seconds, 55° C. for 30 seconds, 72° C. for 1.5 minutes; 15 cycles each at 94° C. for 15 seconds, 55° C. for 30 seconds, and 72° C. for 1.5 minutes plus 5 second elongation at each successive cycle; 1 cycle at 72° C. for 7 minutes; and a 4° C. hold.

The 1008 bp PCR product was purified by 1% agarose gel electrophoresis using TAE buffer, excised from the gel, and purified using a QIAQUICK® Gel Purification Kit (QIAGEN Inc., Valencia, Calif., USA). The purified product was ligated directly into pCR®2.1-TOPO® according to the manufacturer's instructions. The resulting plasmid was named pBM124a.

Plasmid pBM124a was digested with Bsp HI and Pac 1, purified by 1% agarose gel electrophoresis using TAE buffer, excised from the gel, and purified using a QIAQUICK® Gel Purification Kit. The plasmid fragment was ligated to the vector pBM120a, which was digested with Nco I and Pac I. The resulting expression plasmid was designated pBM123a. Plasmid pBM123a contains a duplicate NA2-TPI promoter driving expression of the *Thermoascus aurantiacus* endoglucanase cDNA clone, the AMG terminator, and amdS as a selectable marker.

*Aspergillus oryzae* BECh2 (WO 2000/139322) protoplasts were prepared according to the method of Christensen et al., 1988, supra. Six μg of pBM123a were used to transform *Aspergillus oryzae* BECh2. Primary transformants were selected on COVE plates for 5 days. Transformants were spore purified twice prior to shake flask analysis.

Spores of the transformants were inoculated into 25 ml of MY25 medium in 125 ml shake flasks. The cultures were incubated at 34° C., 200 rpm on a platform shaker for five days. On day 3 and day 5, culture supernatants were harvested and clarified by centrifugation to remove mycelia. Twenty microliters of supernatant from three transformants were analyzed using a CRITERION® stain-free, 10-20% gradient SDS-PAGE gel (Bio-Rad Laboratories, Inc., Hercules, Calif., USA) according to the manufacturer's instructions. SDS-PAGE profiles of the cultures showed that all transformants had a new major band of approximately 32 kDa. One transformant was chosen and named EXP00858.

Plastic, non-baffled 500 ml shake flasks containing 100 ml of SY50 medium were inoculated with 0.1 ml of a spore stock of EXP00858, and incubated at 34° C., 200 rpm for 24 hours to produce a seed culture. Fifty ml of the seed culture was inoculated into a 2 liter fermentation tank containing 2 liters of medium composed per liter of 0.5 g of pluronic acid, 30 g of sucrose, 2 g of $MgSO_4.7H_2O$, 2 g of anhydrous $KH_2PO_4$, 1 g of citric acid, 2 g of $(NH_4)_2SO_4$, 1 g of $K_2SO_4$, 20 g of yeast extract, and 0.5 g of 200×AMG trace metals solution, pH 5.0. The fermentation was fed with a maltose feed. The pH was controlled using 5N $H_3PO_4$ and 15% $NH_4OH$ and maintained at 5.0 and then raised to 5.25. Temperature was maintained 34.0° C.+/−1.0° C. Agitation was 1000 rpm. Airflow was 1.0 vvm.

A 200 ml volume of cell-free supernatant was diluted to 1 liter with deionized water. The pH was adjusted to 8 and the sample filter sterilized using a 0.22 μm polyethersulphone (PES) filter. The filter sterilized sample was loaded onto a 250 ml Q SEPHAROSE™ Fast Flow column (GE Healthcare, Piscataway, N.J., USA) pre-equilibrated with 25 mM Tris pH 8. The enzyme was eluted from the column with a 0 to 1 M NaOH gradient in the same buffer. The fractions containing beta-glucosidase activity were pooled (400 ml) and the enzyme concentration calculated from the theoretic extinction coefficient and the absorbance of the sample at 280 nm.

Example 14: Preparation of *Aspergillus fumigatus* NN055679 Cel3A Beta-Glucosidase

*Aspergillus fumigatus* NN055679 Cel3A beta-glucosidase (SEQ ID NO: 27 [DNA sequence] and SEQ ID NO: 28 [deduced amino acid sequence]) was recombinantly prepared according to WO 2005/047499 using *Trichoderma reesei* RutC30 as a host.

Filtered broth was concentrated and buffer exchanged using a tangential flow concentrator equipped with a 10 kDa polyethersulfone membrane with 20 mM Tris-HCl pH 8.5. The sample was loaded onto a Q SEPHAROSE® High Performance column (GE Healthcare, Piscataway, N.J., USA) equilibrated in 20 mM Tris pH 8.5, and bound proteins were eluted with a linear gradient from 0-600 mM sodium chloride. The fractions were concentrated and loaded onto a SUPERDEX® 75 HR 26/60 column equilibrated with 20 mM Tris-150 mM sodium chloride pH 8.5. Protein concentration was determined using a Microplate BCA™ Protein Assay Kit in which bovine serum albumin was used as a protein standard.

Example 15: Preparation of *Penicillium brasilianum* IBT 20888 Cel3A Beta-Glucosidase

*Penicillium brasilianum* IBT 20888 Cel3A beta-glucosidase (SEQ ID NO: 29 [DNA sequence] and SEQ ID NO: 30 [deduced amino acid sequence]) was recombinantly prepared according to WO 2007/019442 using *Aspergillus oryzae* as a host.

Filtered broth was concentrated and buffer exchanged using a tangential flow concentrator equipped with a 10 kDa polyethersulfone membrane with 20 mM Tris-HCl pH 8.0. The sample was loaded onto a Q SEPHAROSE® High Performance column (GE Healthcare, Piscataway, N.J., USA) equilibrated in 20 mM Tris pH 8.0, and bound proteins were eluted with a linear gradient from 0-600 mM sodium chloride. The fractions were concentrated into 20 mM Tris pH 8.0. Protein concentration was determined using a Microplate BCA™ Protein Assay Kit in which bovine serum albumin was used as a protein standard.

Example 16: Preparation of *Aspergillus niger* IBT 10140 Cel3 Beta-Glucosidase

The *Aspergillus niger* IBT 10140 Cel3 beta-glucosidase gene (SEQ ID NO: 31 [DNA sequence] and SEQ ID NO: 32 [deduced amino acid sequence]) was isolated by PCR using two cloning primers GH3-9.1f and GH3-9.1r shown below, which were designed based on the publicly available *Aspergillus niger*Cel3 sequence (CAK48740.1) for direct cloning using an IN-FUSION™ Cloning Kit.

```
Primer GH3-9.1f:
                                   (SEQ ID NO: 113)
acacaactggggatccaccatgaggttcacttcgatcgagg

Primer GH3-9.1r:
                                   (SEQ ID NO: 114)
agatctcgagaagcttaGTGAACAGTAGGCAGAGACGCCCG
```

A PCR reaction was performed with genomic DNA prepared from *Aspergillus niger* strain NN005810 in order to amplify the full-length gene. The genomic DNA was isolated using a FASTDNA® Spin Kit (MP Biomedicals, Santa Ana, Calif., USA). The PCR reaction was composed of 1 μl of genomic DNA, 0.75 μl of primer GH3-9.1f (10 μM), 0.75 μl of primer GH3-9.1r (10 μM), 3 μl of 5×HF buffer (Finnzymes Oy, Finland), 0.25 μl of 50 mM $MgCl_2$, 0.3 μl of 10 mM dNTP, 0.15 μl of PHUSION® DNA polymerase (Finnzymes Oy, Finland), and PCR-grade water up to 15 μl. The PCR reaction was performed using a DYAD® PCR machine (Bio-Rad Laboratories, Inc., Hercules, Calif., USA) programmed for 2 minutes at 98° C. followed by 10 touchdown cycles at 98° C. for 15 seconds, 70° C. (−1° C./cycle) for 30 seconds, and 72° C. for 2 minutes 30 seconds; and 25 cycles each at 98° C. for 15 seconds, 60° C. for 30 seconds, 72° C. for 2 minutes 30 seconds; and 5 minutes at 72° C.

The reaction products were isolated by 1.0% agarose gel electrophoresis using TAE buffer where an approximately 2.6 kb PCR product band was excised from the gel and purified using a GFX® PCR DNA and Gel Band Purification Kit according to manufacturer's instructions. DNA corresponding to the *A. niger* Cel3 beta-glucosidase gene was cloned into the expression vector pDAu109 (WO 2005/042735) linearized with Barn HI and Hind III, using an IN-FUSION™ Dry-Down PCR Cloning Kit according to the manufacturer's instructions.

A 2.5 μl volume of the diluted ligation mixture was used to transform *E. coli* TOP10 chemically competent cells. Three colonies were selected on LB agar plates containing 100 μg of ampicillin per ml and cultivated overnight in 3 ml of LB medium supplemented with 100 μg of ampicillin per ml. Plasmid DNA was purified using an E.Z.N.A.® Plasmid Mini Kit (Omega Bio-Tek, Inc., Norcross, Ga., USA) according to the manufacturer's instructions. The *A. niger* Cel3 beta-glucosidase gene sequence was verified by Sanger sequencing before heterologous expression.

Protoplasts of *Aspergillus oryzae* BECh2 (WO 2000/39322) were prepared as described in WO 95/02043. One hundred microliters of protoplast suspension were mixed with 2.5-15 μg of the *Aspergillus* expression vector and 250 μl of 10 mM $CaCl_2$-10 mM Tris-HCl pH 7.5-60% PEG 4000 (PEG 4000; Applichem, Omaha, Nebr., USA) (polyethylene glycol, molecular weight 4,000) were added and gently mixed. The mixture was incubated at 37° C. for 30 minutes and the protoplasts were spread on COVE plates for transformant selection. After incubation for 4-7 days at 37° C., spores of sixteen transformants were picked up and inoculated into YPM medium. After 4 days cultivation at 30° C. culture broth was analyzed in order to identified the best transformants based on their ability to produce *A. niger* Cel3 beta-glucosidase. The screening was based on intensity of the band corresponding to the heterologous expressed protein determined by SDS-PAGE and activity of the enzyme on 4-nitrophenyl-beta-D-glucopyranoside (pNPG) using an assay was modified from Hagerdal et al., 1979, *Biotechnology and Bioengineering* 21: 345-355: 10 μl of culture broth was mixed with 90 μl of assay reagent containing 10 μl of 0.1% TWEEN®, 10 μl of 1 M sodium citrate pH 5, 4 μl of 100 mM pNPG substrate (Sigma Aldrich) solubilized in DMSO (0.4% final volume in stock solution), and filtered water. The assay was incubated for 30 minutes at 37° C. and the absorbance was analyzed at 405 nm before and after addition of 100 μl of 1 M sodium carbonate pH 10. The highest absorbance values at 405 nm were correlated to the SDS-PAGE data for selection of the best transformant.

Spores of the best transformant were spread on COVE plates containing 0.01% TRITON® X-100 in order to isolate single colonies. The spreading was repeated twice in total on COVE sucrose medium (Cove, 1996, *Biochim. Biophys. Acta* 133: 51-56) containing 1 M sucrose and 10 mM sodium nitrate, supplemented with 10 mM acetamide and 15 mM CsCl. Fermentation was then performed in 250 ml shake flasks using YP medium containing 2% maltodextrin for 4 days at 30° C. with shaking at 100 rpm.

A 2 liter volume of culture supernatant (EXP02895) was filtered with a 0.7 μm glass fiber filter and then sterile filtered using a 0.22 μm PES membrane (Nalgene Thermo Fisher Scientific, Rochester, N.Y., USA). The filtered supernatant was concentrated and diafiltered using cross-flow Sartocon Slice Cassettes (non Cellulose) with 10 kDa cut-off (Sartorius Stedim Biotech S.A., Aubagne Cedex, France). The final volume was adjusted to 500 ml and pH adjusted to 4.5 by slowly adding dilute 10% acetic acid. The final ionic strength was under 4 MSi.

A 50 ml XK26 column (GE Healthcare, HiHerod, Denmark) was packed with Xpressline ProA (UpFront Chromatography A/S, Copenhagen, Denmark) equilibrated with 50 mM sodium acetate pH 4.5 buffer. The filtered supernatant was loaded onto the column using a P500 Pump (GE Health Care, HiHerod, Denmark) at a flow of 45 ml per minute and washed with 50 mM sodium acetate pH 4.5 buffer until all unbound material was eluted. The bound protein was eluted with 50 mM Tris pH 8 buffer using an ÄKTAexplorer System (GE Healthcare, HiHerod, Denmark). Fractions were collected and monitored by UV absorbance at 280 nm. The eluted protein were pooled and adjusted to pH 7 by slowly adding 0.5 M Tris base with a final ionic strength under 4 MSi.

A 50 ml Q SEPHAROSE® Fast Flow column was equilibrated with 50 mM HEPES pH 7 buffer (buffer A). The column was then washed to remove unbound material by washing with 50 mM HEPES pH 7 buffer until the UV absorbance of the wash was below 0.05 at 280 nm. The bound protein was eluted using a linear salt gradient of 0 to 1 M NaCl in 50 mM HEPES pH 7 buffer as buffer B (10 column volume) using an ÄKTAexplorer System. Purity of protein fractions was determined by SDS-PAGE analysis using a 4-20% Tris-Glycine Gel (Invitrogen Carlsbad, Calif., USA) according to the manufacturer's instructions. Staining after electrophoresis was performed using INSTANT BLUE™ (Expedeon Ltd., Cambridgeshire, UK) according to the manufacturer's instructions. Fractions showing expected protein bands were pooled. Identification of the protein was determined by MS-Edman degradation using standard methods.

Example 17: Preparation of *Thermoascus aurantiacus* CGMCC 0583 GH61A Polypeptide Having Cellulolytic Enhancing Activity

*Thermoascus aurantiacus* CGMCC 0583 GH61A polypeptide having cellulolytic enhancing activity (SEQ ID NO: 33 [DNA sequence] and SEQ ID NO: 34 [deduced amino acid sequence]) was recombinantly prepared according to WO 2005/074656 using *Aspergillus oryzae* JaL250 as a host. The recombinantly produced *Thermoascus aurantiacus* GH61A polypeptide was first concentrated by ultrafiltration using a 10 kDa membrane, buffer exchanged into 20 mM Tris-HCl pH 8.0, and then purified using a 100 ml Q SEPHAROSE® Big Beads column (GE Healthcare, Piscataway, N.J., USA) with 600 ml of a 0-600 mM NaCl linear gradient in the same buffer. Fractions of 10 ml were collected and pooled based on SDS-PAGE.

The pooled fractions (90 ml) were then further purified using a 20 ml MONO Q® column (GE Healthcare, Piscataway, N.J., USA) with 500 ml of a 0-500 mM NaCl linear gradient in the same buffer. Fractions of 6 ml were collected and pooled based on SDS-PAGE. The pooled fractions (24 ml) were concentrated by ultrafiltration using a 10 kDa membrane, and chromatographed using a 320 ml SUPERDEX® 75 SEC column (GE Healthcare, Piscataway, N.J., USA) with isocratic elution of approximately 1.3 liters of 150 mM NaCl-20 mM Tris-HCl pH 8.0. Fractions of 20 ml were collected and pooled based on SDS-PAGE. Protein concentration was determined using a Microplate BCA™ Protein Assay Kit in which bovine serum albumin was used as a protein standard.

Example 18: Preparation of *Thielavia terrestris* NRRL 8126 GH61E Polypeptide Having Cellulolytic Enhancing Activity

*Thielavia terrestris* NRRL 8126 GH61E polypeptide having cellulolytic enhancing activity (SEQ ID NO: 35 [DNA sequence] and SEQ ID NO: 36 [deduced amino acid sequence]) was recombinantly prepared according to U.S. Pat. No. 7,361,495 using *Aspergillus oryzae* JaL250 as a host.

Filtered culture broth was desalted and buffer-exchanged into 20 mM sodium acetate-150 mM NaCl pH 5.0 using a HIPREP® 26/10 Desalting Column according to the manufacturer's instructions. Protein concentration was determined using a Microplate BCA™ Protein Assay Kit in which bovine serum albumin was used as a protein standard.

Example 19: Preparation of *Aspergillus fumigatus* NN051616 GH61B Polypeptide Having Cellulolytic Enhancing Activity A tblastn search (Altschul et al., 1997, *Nucleic Acids Res.* 25: 3389-3402) of the *Aspergillus fumigatus* partial genome sequence (The Institute for Genomic Research, Rockville, Md.) was performed using as query several known GH61 proteins including GH61A from *Thermoascus aurantiacus* (GeneSeqP Accession Number AEC05922). Several genes were identified as putative Family GH61 homologs based upon a high degree of similarity to the query sequences at the amino acid level. One genomic region of approximately 850 bp with greater than 70% identity to the *Thermoascus aurantiacus* GH61A sequence at the amino acid level was chosen for further study.

*Aspergillus fumigatus* NN051616 was grown and harvested as described in U.S. Pat. No. 7,244,605. Frozen mycelia were ground, by mortar and pestle, to a fine powder and genomic DNA was isolated using a DNEASY® Plant Kit according to manufacturer's instructions.

Two synthetic oligonucleotide primers shown below were designed to PCR amplify the *Aspergillus fumigatus* Family GH61B protein gene from the genomic DNA. An IN-FUSION® Cloning Kit was used to clone the fragment directly into the expression vector pAILo2, without the need for restriction digestion and ligation.

Forward primer:
(SEQ ID NO: 115)
5'-ACTGGATTTACCATGACTTTGTCCAAGATCACTTCCA-3'

Reverse primer:
(SEQ ID NO: 116)
5'-TCACCTCTAGTTAATTAAGCGTTGAACAGTGCAGGACCAG-3'

Bold letters represent coding sequence. The remaining sequence is homologous to the insertion sites of pAILo2.

Fifty picomoles of each of the primers above were used in a PCR reaction containing 204 ng of *Aspergillus fumigatus* genomic DNA, 1× Pfx Amplification Buffer (Invitrogen, Carlsbad, Calif., USA), 1.5 μl of 10 mM blend of dATP, dTTP, dGTP, and dCTP, 2.5 units of PLATINUM® Pfx DNA Polymerase, and 1 μl of 50 mM $MgSO_4$ in a final volume of 50 μl. The amplification was performed using an EPPENDORF® MASTERCYCLER® 5333 epgradient S (Eppendorf Scientific, Inc., Westbury, N.Y., USA) programmed for one cycle at 94° C. for 3 minutes; and 30 cycles each at 94° C. for 30 seconds, 56° C. for 30 seconds, and 72° C. for 1 minutes. The heat block was then held at 72° C. for 15 minutes followed by a 4° C. soak cycle.

The reaction products were isolated by 1.0% agarose gel electrophoresis using TAE buffer where an approximately 850 bp product band was excised from the gel and purified using a MINELUTE® Gel Extraction Kit (QIAGEN Inc., Valencia, Calif., USA) according to the manufacturer's instructions.

The fragment was then cloned into pAILo2 using an IN-FUSION® Cloning Kit. The vector was digested with Nco I and Pac I. The fragment was purified by gel electrophoresis as above and a QIAQUICK® Gel Purification Kit. The gene fragment and the digested vector were combined together in a reaction resulting in the expression plasmid pAG43 in which transcription of the Family GH61B protein gene was under the control of the NA2-tpi promoter. The recombination reaction (20 μl) was composed of 1× IN-FUSION® Buffer, 1×BSA, 1 μl of IN-FUSION® enzyme (diluted 1:10), 166 ng of pAILo2 digested with Nco I and Pac I, and 110 ng of the *Aspergillus fumigatus* GH61B protein purified PCR product. The reaction was incubated at 37° C. for 15 minutes followed by 15 minutes at 50° C. The reaction was diluted with 40 μl of 10 mM Tris-0.1 M EDTA buffer and 2.5 μl of the diluted reaction was used to transform *E. coli* SOLOPACK® Gold cells. An *E. coli* transformant containing pAG43 (GH61B protein gene) was identified by restriction enzyme digestion and plasmid DNA was prepared using a BIOROBOT® 9600.

DNA sequencing of the 862 bp PCR fragment was performed with a Perkin-Elmer Applied Biosystems Model 377 XL Automated DNA Sequencer using dye-terminator chemistry (Giesecke et al., 1992, supra) and primer walking strategy. The following vector specific primers were used for sequencing:

```
pAllo2 5 Seq:
                                 (SEQ ID NO: 117)
5' TGTCCCTTGTCGATGCG 3'

pAllo2 3 Seq:
                                 (SEQ ID NO: 118)
5' CACATGACTTGGCTTCC 3'
```

Nucleotide sequence data were scrutinized for quality and all sequences were compared to each other with assistance of PHRED/PHRAP software (University of Washington, Seattle, Wash., USA).

A gene model for the *Aspergillus fumigatus* sequence was constructed based on similarity of the encoded protein to the *Thermoascus aurantiacus* GH61A protein (GeneSeqP Accession Number AEC05922). The nucleotide sequence and deduced amino acid sequence, are shown in SEQ ID NO: 37 and SEQ ID NO: 38, respectively. The genomic fragment encodes a polypeptide of 250 amino acids, interrupted by 2 introns of 53 and 56 bp. The % G+C content of the gene and the mature coding sequence are 53.9% and 57%, respectively. Using the SignalP software program (Nielsen et al., 1997, *Protein Engineering* 10: 1-6), a signal peptide of 21 residues was predicted. The predicted mature protein contains 221 amino acids with a predicted molecular mass of 23.39 kDa.

*Aspergillus oryzae* JaL355 protoplasts were prepared according to the method of Christensen et al., 1988, supra. Six μg of pAG43 were used to transform *Aspergillus oryzae JaL*355. Twenty-six transformants were isolated to individual PDA plates.

Confluent PDA plates of 24 transformants were each washed with 5 ml of 0.01% TWEEN® 20 and the spores were each collected. Eight μl of each spore stock was added to 1 ml of YPG, YPM, and M410 media separately in 24 well plates and incubated at 34° C. After 3 days of incubation, 7.5 μl of supernatant from four transformants were analyzed using a CRITERION® stain-free, 8-16% gradient SDS-PAGE gel according to the manufacturer's instructions. Based on this gel, M410 was chosen as the best medium. Five days after incubation, 7.5 μl of supernatant from each M410 culture was analyzed using a CRITERION® stain-free, 8-16% gradient SDS-PAGE gel. SDS-PAGE profiles of the cultures showed that several transformants had a new major band of approximately 25 kDa.

A confluent plate of one transformant (grown on PDA) was washed with 5 ml of 0.01% TWEEN® 20 and inoculated into four 500 ml Erlenmeyer flasks containing 100 ml of M410 medium to generate broth for characterization of the enzyme. The flasks were harvested on day 5 (300 ml), filtered using a 0.22 μm EXPRESS™ Plus Membrane, and stored at 4° C.

The filtered shake flask broth containing *Aspergillus fumigatus* GH61B polypeptide having cellulolytic enhancing activity was concentrated using a 10 kDa MWCO Amicon Ultra centrifuge concentrator (Millipore, Bedford, Mass., USA) to approximately 10-fold smaller volume. The concentrated filtrate was buffer-exchanged and desalted using a BIO-GEL® P6 desalting column (Bio-Rad Laboratories, Inc., Hercules, Calif., USA) pre-equilibrated in 20 mM Tris-(hydroxymethyl)aminomethane (Sigma, St. Louis, Mo., USA), pH 8.0, according to the manufacturer's instructions with the following exception: 3 ml of sample was loaded and eluted with 3 ml of buffer. Concentrated, desalted GH61B protein was quantified using a BCA protein assay using bovine serum albumin as a protein concentration standard. Quantification was performed in triplicate. Enzyme purity was confirmed using 8-16% gradient SDS-PAGE at 200 volts for 1 hour and staining with BIO-SAFE™ Coomassie Stain.

Example 20: Preparation of *Penicillium pinophilum* GH61 Polypeptide Having Cellulolytic Enhancing Activity

*Penicillium pinophilum* GH61 polypeptide having cellulolytic enhancing activity SEQ ID NO: 39 [DNA sequence] and SEQ ID NO: 40 [deduced amino acid sequence]) was prepared according to the procedure described below.

Compost samples were collected from Yunnan, China on Dec. 12, 2000. *Penicillium pinophilum* NN046877 was isolated using single spore isolation techniques on PDA plates at 45° C. *Penicillium pinophilum* strain NN046877 was inoculated onto a PDA plate and incubated for 4 days at 37° C. in the darkness. Several mycelia-PDA plugs were inoculated into 500 ml shake flasks containing 100 ml of NNCYP-PCS medium. The flasks were incubated for 5 days at 37° C. with shaking at 160 rpm. The mycelia were collected at day 4 and day 5. The mycelia from each day were frozen in liquid nitrogen and stored in a −80° C. freezer until use.

The frozen mycelia were transferred into a liquid nitrogen prechilled mortar and pestle and ground to a fine powder. Total RNA was prepared from the powdered mycelia of each day by extraction with TRIZOL™ reagent (Invitrogen Corporation, Carlsbad, Calif., USA). The polyA enriched RNA was isolated using a mTRAP™ Total Kit (Active Motif, Carlsbad, Calif., USA).

Double stranded cDNA from each day was synthesized with a SMART™ cDNA library Construction Kit (Clontech Laboratories, Inc., Mountain View, Calif., USA). The cDNA was cleaved with Sfi I and the cDNA was size fractionated by 0.8% agarose gel electrophoresis using TBE buffer. The fraction of cDNA of 500 bp and larger was excised from the gel and purified using a GFX® PCR DNA and Gel Band Purification Kit according to the manufacturer's instructions. Then equal amounts of cDNA from day 4 and day 5 were pooled for library construction.

The pooled cDNA was then directionally cloned by ligation into Sfi I cleaved pMHas7 (WO 2009/037253) using T4 ligase (New England Biolabs, Inc., Beverly, Mass., USA) according to the manufacturer's instructions. The ligation mixture was electroporated into *E. coli* ELECTROMAX™ DH10B™ cells (Invitrogen Corp., Carlsbad, Calif., USA) using a GENE PULSER® and Pulse Controller (Bio-Rad Laboratories, Inc., Hercules, Calif., USA) at 25 uF, 25 mAmp, 1.8 kV with a 1 mm gap cuvette according to the manufacturer's procedure.

The electroporated cells were plated onto LB plates supplemented with 50 mg of kanamycin per liter. A cDNA plasmid pool was prepared from 60,000 total transformants of the original pMHas7 vector ligation. Plasmid DNA was prepared directly from the pool of colonies using a QIAGEN® Plasmid Kit (QIAGEN Inc., Valencia, Calif., USA).

A transposon containing plasmid designated pSigA4 was constructed from the pSigA2 transposon containing plasmid described WO 2001/77315 in order to create an improved version of the signal trapping transposon of pSigA2 with decreased selection background. The pSigA2 transposon contains a signal less beta-lactamase construct encoded on the transposon itself. PCR was used to create a deletion of the intact beta lactamase gene found on the plasmid backbone using a proofreading Pfu Turbo polymerase PROOFSTART™ (QIAGEN GmbH Corporation, Hilden, Germany) and the following 5' phosphorylated primers (TAG Copenhagen, Denmark):

```
SigA2NotU-P:
                                   (SEQ ID NO: 119)
5'-TCGCGATCCGTTTTCGCATTTATCGTGAAACGCT-3'

SigA2NotD-P:
                                   (SEQ ID NO: 120)
5'-CCGCAAACGCTGGTGAAAGTAAAAGATGCTGAA-3'
```

The amplification reaction was composed of 1 μl of pSigA2 (10 ng/μl), 5 μl of 10× PROOFSTART™ Buffer (QIAGEN GmbH Corporation, Hilden, Germany), 2.5 μl of dNTP mix (20 mM), 0.5 μl of SigA2NotU-P (10 mM), 0.5 μl of SigA2NotD-P (10 mM), 10 μl of Q solution (QIAGEN GmbH Corporation, Hilden, Germany), and 31.25 μl of deionized water. A DNA ENGINE™ Thermal Cycler (MJ Research Inc., Waltham, Mass., USA) was used for amplification programmed for one cycle at 95° C. for 5 minutes; and 20 cycles each at 94° C. for 30 seconds, 62° C. for 30 seconds, and 72° C. for 4 minutes.

A 3.9 kb PCR reaction product was isolated by 0.8% agarose gel electrophoresis using TAE buffer and 0.1 μg of ethidium bromide per ml. The DNA band was visualized with the aid of an EAGLE EYE® Imaging System (Stratagene, La Jolla, Calif., USA) at 360 nm. The 3.9 kb DNA band was excised from the gel and purified using a GFX® PCR DNA and Gel Band Purification Kit according to the manufacturer's instructions.

The 3.9 kb fragment was self-ligated at 16° C. overnight with 10 units of T4 DNA ligase (New England Biolabs, Inc., Beverly, Mass., USA), 9 μl of the 3.9 kb PCR fragment, and 1 μl of 10× ligation buffer (New England Biolabs, Inc., Beverly, Mass., USA). The ligation was heat inactivated for 10 minutes at 65° C. and then digested with Dpn I at 37° C. for 2 hours. After incubation, the digestion was purified using a GFX® PCR DNA and Gel Band Purification Kit.

The purified material was then transformed into *E. coli* TOP10 competent cells according to the manufacturer's instructions. The transformation mixture was plated onto LB plates supplemented with 25 μg of chloramphenicol per ml. Plasmid minipreps were prepared from several transformants and digested with Bgl II. One plasmid with the correct construction was chosen. The plasmid was designated pSigA4. Plasmid pSigA4 contains the Bgl II flanked transposon SigA2 identical to that disclosed in WO 2001/77315.

A 60 μl sample of plasmid pSigA4 DNA (0.3 μg/μl) was digested with Bgl II and separated by 0.8% agarose gel electrophoresis using TBE buffer. A SigA2 transposon DNA band of 2 kb was eluted with 200 μl of EB buffer (QIAGEN GmbH Corporation, Hilden, Germany) and purified using a GFX® PCR DNA and Gel Band Purification Kit according to the manufacturer's instructions and eluted in 200 μl of EB buffer. SigA2 was used for transposon assisted signal trapping.

A complete description of transposon assisted signal trapping is described in WO 2001/77315. The plasmid pool was treated with transposon SigA2 and HYPERMU™ transposase (EPICENTRE Biotechnologies, Madison, Wis., USA) according to the manufacturer's instructions.

For in vitro transposon tagging of the *Penicillium pinophilum* cDNA library, 2 μl of SigA2 transposon containing approximately 100 ng of DNA were mixed with 1 μl of the plasmid DNA pool of the *Penicillium pinophilum* cDNA library containing 1 μg of DNA, 1 μl of HYPERMU™ transposase, and 2 μl of 10× buffer (EPICENTRE Biotechnologies, Madison, Wis., USA) in a total volume of 20 μl and incubated at 30° C. for 3 hours followed by adding 2 μl of stop buffer (EPICENTRE Biotechnologies, Madison, Wis., USA) and heat inactivation at 75° C. for 10 minutes. The DNA was precipitated by addition of 2 μl of 3 M sodium acetate pH 5 and 55 μl of 96% ethanol and centrifuged for 30 minutes at 10,000×g, 4° C. The pellet was washed in 70% ethanol, air dried at room temperature, and resuspended in 10 μl of deionized water.

A 2 μl volume of the transposon tagged plasmid pool was electroporated into 50 μl of *E. coli* ELECTROMAX™ DH10B™ cells (Invitrogen Corp., Carlsbad, Calif., USA) according to the manufacturer's instructions using a GENE PULSER® and Pulse Controller at 25 uF, 25 mAmp, 1.8 kV with a 1 mm gap cuvette according to the manufacturer's procedure.

The electroporated cells were incubated in SOC medium with shaking at 225 rpm for 1 hour at 37° C. before being plated onto the following selective media: LB medium supplemented with 50 μg of kanamycin per ml; LB medium supplemented with 50 μg of kanamycin per ml and 15 μg of chloramphencol per ml; and LB medium supplemented with 50 μg of kanamycin per ml, 15 μg of chloramphencol per ml, and 30 μg of ampicillin per ml.

From plating of the electroporation onto LB medium supplemented with kanamycin, chloramphencol and ampicillin, approximately 200 colonies per 50 μl were observed after 3 days at 30° C. All colonies were replica plated onto LB kanamycin, chloramphenicol, and ampicillin medium described above. Five hundred colonies were recovered under this selection condition. The DNA from each colony was sequenced with the transposon forward and reverse primers (primers A and B), shown below, according to the procedure disclosed in WO 2001/77315 (page 28).

```
Primer A:
                                   (SEQ ID NO: 121)
5'-agcgtttgcggccgcgatcc-3'

Primer B:
                                   (SEQ ID NO: 122)
5'-ttattcggtcgaaaaggatcc-3'
```

DNA sequences were obtained from SinoGenoMax Co., Ltd (Beijing, China). Primer A and primer B sequence reads for each plasmid were trimmed to remove vector and transposon sequence. The assembled sequences were grouped into contigs by using the program PhredPhrap (Ewing et al., 1998, *Genome Research* 8: 175-185; Ewing and Green, 1998, *Genome Research* 8: 186-194). All contigs were subsequently compared to sequences available in standard public DNA and protein sequences databases (TrEMBL, SWALL, PDB, EnsemblPep, GeneSeqP) using the program BLASTX 2.0a19MP-WashU [14 Jul. 1998] [Build linux-x86 18:51:44 30 Jul. 1998] (Gish et al., 1993, *Nat. Genet.* 3: 266-72). The family GH10 xylanase candidate was identified directly by analysis of the BlastX results.

*Penicillium pinophilum* NN046877 was grown on a PDA agar plate at 37° C. for 4-5 days. Mycelia were collected directly from the agar plate into a sterilized mortar and frozen under liquid nitrogen. Frozen mycelia were ground, by mortar and pestle, to a fine powder, and genomic DNA was isolated using a DNEASY® Plant Mini Kit (QIAGEN Inc., Valencia, Calif., USA).

Based on the *Penicillium pinophilum* GH10 xylanase gene information obtained as described above, oligonucleotide primers, shown below, were designed to amplify the GH61 gene from genomic DNA of *Penicillium pinophilum* GH10 NN046877. An IN-FUSION® CF Dry-down Cloning Kit was used to clone the fragment directly into the expression vector pPFJO355, without the need for restriction digestion and ligation.

```
Sense primer:
                                          SEQ ID NO: 123)
5'-ACACAACTGGGGATCCACCATGACTCTAGTAAAGGCTATTCT

TTTAGC-3'

Antisense primer:
                                          (SEQ ID NO: 124)
5'-GTCACCCTCTAGATCTTCACAAACATTGGGAGTAGTATGG-3'
```

Bold letters represented the coding sequence and the remaining sequence was homologous to insertion sites of pPFJO355.

The expression vector pPFJO355 contains the *Aspergillus oryzae* TAKA-amylase promoter, *Aspergillus niger* glucoamylase terminator elements, pUC19 derived sequences for selection and propagation in *E. coli*, and an *Aspergillus nidulans* pyrG gene, which encodes an orotidine decarboxylase for selection of a transformant of a pyrG mutant *Aspergillus* strain.

Twenty picomoles of each of the primers above were used in a PCR reaction composed of *Penicillium* sp. NN051602 genomic DNA, 10 µl of 5×GC Buffer (Finnzymes Oy, Espoo, Finland), 1.5 µl of DMSO, 2.5 mM each of dATP, dTTP, dGTP, and dCTP, and 0.6 unit of PHUSION™ High-Fidelity DNA Polymerase (Finnzymes Oy, Espoo, Finland), in a final volume of 50 µl. The amplification was performed using a Peltier Thermal Cycler (MJ Research Inc., South San Francisco, Calif., USA) programmed for denaturing at 98° C. for 1 minutes; 5 cycles of denaturing at 98° C. for 15 seconds, annealing at 56° C. for 30 seconds, with a 1° C. increase per cycle and elongation at 72° C. for 75 seconds; and 25 cycles each at 98° C. for 15 seconds, 65C for 30 seconds and 72° C. for 75 seconds; and a final extension at 72° C. for 10 minutes. The heat block then went to a 4° C. soak cycle.

The reaction products were isolated by 1.0% agarose gel electrophoresis using TBE buffer where an approximately 1.4 kb product band was excised from the gel, and purified using an ILLUSTRA® GFX® PCR DNA and Gel Band Purification Kit according to the manufacturer's instructions.

Plasmid pPFJO355 was digested with Barn I and Bgl II, isolated by 1.0% agarose gel electrophoresis using TBE buffer, and purified using an ILLUSTRA® GFX® PCR DNA and Gel Band Purification Kit according to the manufacturer's instructions.

The gene fragment and the digested vector were ligated together using an IN-FUSION® CF Dry-down PCR Cloning Kit resulting in pPpin3 in which transcription of the *Penicillium pinophilum* GH10 xylanase gene was under the control of a promoter from the gene for *Aspergillus oryzae* alpha-amylase. In brief, 30 ng of pPFJO355 digested with Barn I and Bgl II, and 60 ng of the *Penicillium pinophilum* GH10 xylanase gene purified PCR product were added to a reaction vial and resuspended in a final volume of 10 µl with addition of deionized water. The reaction was incubated at 37° C. for 15 minutes and then 50° C. for 15 minutes. Three µl of the reaction were used to transform *E. coli* TOP10 competent cells. An *E. coli* transformant containing pPpin3 was detected by colony PCR and plasmid DNA was prepared using a QIAprep Spin Miniprep Kit (QIAGEN Inc., Valencia, Calif., USA). The *Penicillium pinophilum GH*10 xylanase gene insert in pPpin3 was confirmed by DNA sequencing using a 3730XL DNA Analyzer (Applied Biosystems Inc, Foster City, Calif., USA).

The same PCR fragment was cloned into vector pGEM-T using a pGEM-T Vector System to generate pGEM-T-Ppin3. The *Penicillium pinophilum* GH10 xylanase gene contained in pGEM-T-Ppin3 was confirmed by DNA sequencing using a 3730XL DNA Analyzer. *E. coli* strain T-Ppin3, containing pGEM-T-Ppin3, was deposited with the Deutsche Sammlung von Mikroorganismen und Zellkulturen GmbH (DSM), D-38124 Braunschweig, Germany on Sep. 7, 2009, and assigned accession number DSM 22922.

DNA sequencing of the *Penicillium pinophilum* genomic clone encoding a GH10 polypeptide having xylanase activity was performed with an Applied Biosystems Model 3700 Automated DNA Sequencer using version 3.1 BIG-DYE™ terminator chemistry (Applied Biosystems, Inc., Foster City, Calif., USA) and dGTP chemistry (Applied Biosystems, Inc., Foster City, Calif., USA) and primer walking strategy. Nucleotide sequence data were scrutinized for quality and all sequences were compared to each other with assistance of PHRED/PHRAP software (University of Washington, Seattle, Wash., USA).

The nucleotide sequence and deduced amino acid sequence of the *Penicillium pinophilum* gh10 gene are shown in SEQ ID NO: 39 and SEQ ID NO: 40, respectively. The coding sequence is 1442 bp including the stop codon and is interrupted by three introns of 51 bp (199-249), 73 bp (383-455), and 94 bp (570-663). The encoded predicted protein is 407 amino acids. The % G+C of the coding sequence of the gene (including introns) is 47.99% G+C and the mature polypeptide coding sequence is 49.22%. Using the SignalP program (Nielsen et al., 1997*, Protein Engineering* 10: 1-6), a signal peptide of 19 residues was predicted. The predicted mature protein contains 388 amino acids with a predicted molecular mass of 41.5 kDa and an isoelectric pH of 5.03.

A comparative pairwise global alignment of amino acid sequences was determined using the Needleman-Wunsch algorithm (Needleman and Wunsch, 1970*, J. Mol. Biol.* 48: 443-453) as implemented in the Needle program of EMBOSS with gap open penalty of 10, gap extension penalty of 0.5, and the EBLOSUM62 matrix. The alignment showed that the deduced amino acid sequence of the *Penicillium pinophilum* gene encoding the GH10 polypeptide having xylanase activity shares 76% and 87% identity (excluding gaps) to the deduced amino acid sequence of a predicted GH10 family protein from *Talaromyces emersonii* (AAU99346) and *Penicillium marneffei* (B6QN64), respectively.

*Aspergillus oryzae* HowB101 (WO 95/35385 Example 1) protoplasts were prepared according to the method of Christensen et al., 1988, *Bio/Technology* 6: 1419-1422. Three µg of pPpin3 were transformed into *Aspergillus oryzae* HowB101.

The transformation of *Aspergillus oryzae* HowB101 with pPpin3 yielded about 50 transformants. Twelve transformants were isolated to individual Minimal medium plates.

Four transformants were inoculated separately into 3 ml of YPM medium in a 24-well plate and incubated at 30° C.

with shaking at 150 rpm. After 3 days incubation, 20 μl of supernatant from each culture were analyzed by SDS-PAGE using a NUPAGE® NOVEX® 4-12% Bis-Tris Gel with MES buffer according to the manufacturer's instructions. The resulting gel was stained with INSTANT® Blue (Expedeon Ltd., Babraham Cambridge, UK). SDS-PAGE profiles of the cultures showed that the majority of the transformants had a major band of approximately 55 kDa. The expression strain was designated *Aspergillus oryzae* EXP02765.

A slant of one transformant, designated transformant 2, was washed with 10 ml of YPM and inoculated into a 2 liter flask containing 400 ml of YPM medium to generate broth for characterization of the enzyme. The culture was harvested on day 3 and filtered using a 0.45 μm DURAPORE® Membrane (Millipore, Bedford, Mass., USA).

A 1 liter volume of supernatant of the recombinant *Aspergillus oryzae* strain EXP02765 was precipitated with ammonium sulfate (80% saturation) and redissolved in 50 ml of 25 mM sodium acetate pH 4.3, and then dialyzed against the same buffer and filtered through a 0.45 μm filter. The solution was applied to a 40 ml Q SEPHAROSE™ Fast Flow column column equilibrated in 25 mM sodium acetate pH 4.3. The recombinant GH10 protein did not bind to the column. The fractions with xylanase activity were collected and evaluated by SDS-PAGE as described above. Fractions containing a band of approximately 55 kDa were pooled. The pooled solution was concentrated by ultrafiltration.

Example 21: Preparation of *Penicillium* sp. GH61 Polypeptide Having Cellulolytic Enhancing Activity

*Penicillium* sp. GH61 polypeptide having cellulolytic enhancing activity SEQ ID NO: 41 [DNA sequence] and SEQ ID NO: 42 [deduced amino acid sequence]) according to the following procedure.

A compost sample was collected from Yunnan, China. *Penicillium* sp. NN051602 was isolated using single spore isolation techniques on PDA plates at 45° C. The *Penicillium* sp. strain was inoculated onto a PDA plate and incubated for 4 days at 45° C. in the darkness. Several mycelia-PDA plugs were inoculated into 500 ml shake flasks containing 100 ml of NNCYP-PCS medium. The flasks were incubated for 6 days at 45° C. with shaking at 160 rpm. The mycelia were collected at day 4, day 5, and day 6. Then the mycelia from each day were combined and frozen in liquid nitrogen, and then stored in a −80° C. freezer until use.

The frozen mycelia were transferred into a liquid nitrogen prechilled mortar and pestle and ground to a fine powder. Total RNA was prepared from the powdered mycelia by extraction with TRIZOL® reagent and purified using a RNEASY® Mini Kit according to the manufacturer's protocol. Fifty micrograms of total RNA was submitted to sequencing as described above.

Total RNA enriched for polyA sequences with the mRNASeq protocol was sequenced using an ILLUMINA® GA2 system (Illumina, Inc., San Diego, Calif., USA). The raw 36 base pair reads were assembled with an in-house developed assembler. The assembled sequences were analyzed using standard bioinformatics methods for gene finding and functional prediction. ESTscan 2.0 was used for gene prediction. NCBI blastall version 2.2.10 and HMMER version 2.1.1 were used to predict function based on structural homology. The Family GH61 candidate was identified directly by analysis of the Blast results.

*Penicillium* sp. NN051602 was grown on a PDA agar plate at 45° C. for 3 days. Mycelia were collected directly from the agar plate into a sterilized mortar and frozen under liquid nitrogen. Frozen mycelia were ground, by mortar and pestle, to a fine powder, and genomic DNA was isolated using a DNEASY® Plant Mini Kit (QIAGEN Inc., Valencia, Calif., USA).

Based on the ILLUMINA® sequencing information of the *Penicillium* sp. GH61 gene obtained as described above, oligonucleotide primers, shown below, were designed to amplify the GH61 gene from genomic DNA of *Penicillium* sp. NN051602. An IN-FUSION® CF Dry-down Cloning Kit (Clontech Laboratories, Inc., Mountain View, Calif., USA) was used to clone the fragment directly into the expression vector pPFJO355, without the need for restriction digestion and ligation.

Sense primer:
(SEQ ID NO: 125)
5'-ACACAACTGGGGATCCACCATGCTGTCTTCGACGACTCGCA-3'

Antisense primer:
(SEQ ID NO: 126)
5'-GTCACCCTCTAGATCTCGACTTCTTCTAGAACGTCGGCTCA-3'

Bold letters represented the coding sequence and the remaining sequence was homologous to insertion sites of pPFJO355.

Twenty picomoles of each of the primers above were used in a PCR reaction composed of *Penicillium* sp. NN051602 genomic DNA, 10 μl of 5×GC Buffer, 1.5 μl of DMSO, 2.5 mM each of dATP, dTTP, dGTP, and dCTP, and 0.6 unit of PHUSION™ High-Fidelity DNA Polymerase (Finnzymes Oy, Espoo, Finland) in a final volume of 50 μl. The amplification was performed using a Peltier Thermal Cycler programmed for denaturing at 98° C. for 1 minutes; 5 cycles of denaturing at 98° C. for 15 seconds, annealing at 63° C. for 30 seconds, with a 1° C. increase per cycle and elongation at 72° C. for 60 seconds; and 25 cycles each at 98° C. for 15 seconds and 72° C. for 60 seconds; and a final extension at 72° C. for 5 minutes. The heat block then went to a 4° C. soak cycle.

The reaction products were isolated by 1.0% agarose gel electrophoresis using TBE buffer where an approximately 0.9 kb product band was excised from the gel, and purified using an ILLUSTRA® GFX® PCR DNA and Gel Band Purification Kit according to the manufacturer's instructions.

Plasmid pPFJO355 was digested with Barn I and Bgl II, isolated by 1.0% agarose gel electrophoresis using TBE buffer, and purified using an ILLUSTRA® GFX® PCR DNA and Gel Band Purification Kit according to the manufacturer's instructions.

The gene fragment and the digested vector were ligated together using an IN-FUSION® CF Dry-down PCR Cloning Kit resulting in pGH61D23Y4 in which transcription of the *Penicillium* sp. GH61 gene was under the control of a promoter from the gene for *Aspergillus oryzae* alpha-amylase. In brief, 30 ng of pPFJO355 digested with Barn I and Bgl II, and 60 ng of the *Penicillium* sp. GH61 gene purified PCR product were added to a reaction vial and resuspended in a final volume of 10 μl with addition of deionized water. The reaction was incubated at 37° C. for 15 minutes and then 50° C. for 15 minutes. Three μl of the reaction were used to transform *E. coli* TOP10 competent cells. An *E. coli* transformant containing pGH61D23Y4 was detected by colony PCR and plasmid DNA was prepared using a QIAprep Spin Miniprep Kit (QIAGEN Inc., Valencia, Calif., USA). The *Penicillium* sp. GH61 gene insert in pGH61D23Y4 was confirmed by DNA sequencing using a 3730XL DNA Analyzer.

The same PCR fragment was cloned into vector pGEM-T using a pGEM-T Vector System to generate pGEM-T-GH61D23Y4. The *Penicillium* sp. GH61 gene insert in pGEM-T-GH61D23Y4 was confirmed by DNA sequencing using a 3730XL DNA Analyzer. *E. coli* strain T-51602, containing pGEM-T-GH61D23Y4, was deposited with the Deutsche Sammlung von Mikroorganismen and Zellkulturen GmbH (DSM), Mascheroder Weg 1 B, D-38124 Braunschweig, Germany on Aug. 26, 2009 and assigned accession number DSM 22882.

DNA sequencing of the *Penicillium* sp. genomic clone encoding a GH61A polypeptide having cellulolytic-enhancing activity was performed with an Applied Biosystems Model 3700 Automated DNA Sequencer using version 3.1 BIG-DYE™ terminator chemistry (Applied Biosystems, Inc., Foster City, Calif., USA) and dGTP chemistry (Applied Biosystems, Inc., Foster City, Calif., USA) and primer walking strategy. Nucleotide sequence data were scrutinized for quality and all sequences were compared to each other with assistance of PHRED/PHRAP software (University of Washington, Seattle, Wash., USA).

The nucleotide sequence and deduced amino acid sequence of the *Penicillium* sp. gh61a gene are shown in SEQ ID NO: 45 and SEQ ID NO: 46, respectively. The coding sequence is 835 bp including the stop codon and is interrupted by one intron of 73 bp (114-186). The encoded predicted protein is 253 amino acids. The % G+C of the coding sequence of the gene (including introns) is 63.35% G+C and the mature polypeptide coding sequence is 64.62%. Using the SignalP program (Nielsen et al., 1997, *Protein Engineering* 10: 1-6), a signal peptide of 25 residues was predicted. The predicted mature protein contains 228 amino acids with a predicted molecular mass of 24.33 kDa and an isoelectric pH of 4.17.

A comparative pairwise global alignment of amino acid sequences was determined using the Needleman-Wunsch algorithm (Needleman and Wunsch, 1970, *J. Mol. Biol.* 48: 443-453) as implemented in the Needle program of EMBOSS with gap open penalty of 10, gap extension penalty of 0.5, and the EBLOSUM62 matrix. The alignment showed that the deduced amino acid sequence of the *Penicillium* gene encoding the GH61A polypeptide having cellulolytic-enhancing activity shares 74% identity (excluding gaps) to the deduced amino acid sequence of a predicted GH61 family protein from *Thermoascus aurantiacus* (GENESEQP:AUM 17198).

*Aspergillus oryzae* HowB101 (WO 95/35385 Example 1) protoplasts were prepared according to the method of Christensen et al., 1988, *Bio/Technology* 6: 1419-1422. Three µg of pGH61D23Y4 were used to transform *Aspergillus oryzae* HowB101.

The transformation of *Aspergillus oryzae* HowB101 with pGH61D23Y4 yielded about 50 transformants. Twelve transformants were isolated to individual Minimal medium plates.

Six transformants were inoculated separately into 3 ml of YPM medium in a 24-well plate and incubated at 30° C., 150 rpm. After 3 days incubation, 20 µl of supernatant from each culture were analyzed on a NUPAGE® NOVEX® 4-12% Bis-Tris Gel with MES buffer according to the manufacturer's instructions. The resulting gel was stained with INSTANT® Blue (Expedeon Ltd., Babraham Cambridge, UK). SDS-PAGE profiles of the cultures showed that the majority of the transformants had a major band of approximately 45 kDa. The expression strain was designated as *Aspergillus oryzae* EXP03089.

A slant of one transformant, designated transformant 1, was washed with 10 ml of YPM medium and inoculated into a 2 liter flask containing 400 ml of YPM medium to generate broth for characterization of the enzyme. The culture was harvested on day 3 and filtered using a 0.45 µm DURAPORE Membrane (Millipore, Bedford, Mass., USA).

A 400 ml volume of the filtered broth of the recombinant strain *Aspergillus oryzae* EXP03089 was precipitated with ammonium sulfate (80% saturation) and redissolved in 20 ml of 25 mM sodium acetate pH 5.0 buffer, and then dialyzed against the same buffer and filtered through a 0.45 µm filter. The solution was applied to a 30 ml Q SEPHAROSE® Fast Flow column (GE Healthcare, Buckinghamshire, UK) equilibrated in 25 mM sodium acetate pH 5.0. The recombinant GH61 protein was eluted with a linear NaCl gradient (0-0.4 M). Fractions eluted with 0.1-0.2 M NaCl were collected and dialyzed against the same equilibration buffer. The sample was further purified on a MONO Q® column (GE Healthcare, Buckinghamshire, UK) with a linear NaCl gradient (0-0.3 M). Fractions were evaluated by SDS-PAGE. Fractions containing a band of approximately 45 kDa were pooled. The pooled solution was concentrated by ultrafiltration.

Example 22: Preparation of *Thielavia terrestris* GH61N Polypeptide Having Cellulolytic Enhancing Activity

*Thielavia terrestris* NRRL 8126 (SEQ ID NO: 43 [DNA sequence] and SEQ ID NO: 44 [deduced amino acid sequence]) was prepared according to the following procedure.

Genomic sequence information was generated by the U.S. Department of Energy Joint Genome Institute (JGI). A preliminary assembly of the genome was downloaded from JGI and analyzed using the Pedant-Pro™ Sequence Analysis Suite (Biomax Informatics AG, Martinsried, Germany). Gene models constructed by the software were used as a starting point for detecting GH61 homologues in the genome. More precise gene models were constructed manually using multiple known GH61 protein sequences as a guide.

To generate genomic DNA for PCR amplification, *Thielavia terrestris* NRRL 8126 was grown in 50 ml of NNCYP medium supplemented with 1% glucose in a baffled shake flask at 42° C. and 200 rpm for 24 hours. Mycelia were harvested by filtration, washed twice in TE (10 mM Tris-1 mM EDTA), and frozen under liquid nitrogen. A pea-size piece of frozen mycelia was suspended in 0.7 ml of 1% lithium dodecyl sulfate in TE and disrupted by agitation with an equal volume of 0.1 mm zirconia/silica beads (Biospec Products, Inc., Bartlesville, Okla., USA) for 45 seconds in a FastPrep FP120 (ThermoSavant, Holbrook, N.Y., USA). Debris was removed by centrifugation at 13,000×g for 10 minutes and the cleared supernatant was brought to 2.5 M ammonium acetate and incubated on ice for 20 minutes. After the incubation period, the nucleic acids were precipitated by addition of 2 volumes of ethanol. After centrifugation for 15 minutes in a microfuge at 4° C., the pellet was washed in 70% ethanol and air dried. The DNA was resuspended in 120 µl of 0.1×TE and incubated with 1 µl of DNase-free RNase A at 37° C. for 20 minutes. Ammonium acetate was added to 2.5 M and the DNA was precipitated with 2 volumes of ethanol. The pellet was washed in 70% ethanol, air dried, and resuspended in TE buffer.

Two synthetic oligonucleotide primers shown below were designed to PCR amplify the *Thielavia terrestris* Family GH61N gene from the genomic DNA. An IN-FUSION™ Cloning Kit was used to clone the fragment directly into the expression vector, pAILo2 (WO 2005/074647), without the need for restriction digests and ligation.

```
Forward primer:
                                    (SEQ ID NO: 127)
5'-ACTGGATTTACCATGCCTTCTTTCGCCTCCAA-3'

Reverse primer:
                                    (SEQ ID NO: 128)
5'-TCACCTCTAGTTAATTAATCAGTTTGCCTCCTCAGCCC-3'
```

Bold letters represent coding sequence. The remaining sequence is homologous to the insertion sites of pAILo2.

Fifty picomoles of each of the primers above were used in a PCR reaction containing 1 μg of *Thielavia terrestris* genomic DNA, 1× ADVANTAGE® GC-Melt LA Buffer (BD Biosciences, Palo Alto, Calif., USA), 1 μl of 10 mM blend of dATP, dTTP, dGTP, and dCTP, 1.25 units of ADVANTAGE® GC Genomic LA Polymerase Mix (BD Biosciences, Palo Alto, Calif., USA), in a final volume of 25 μl. The amplification conditions were one cycle at 94° C. for 1 minute; and 30 cycles each at 94° C. for 30 seconds, 60.5° C. for 30 seconds, and 72° C. for 1 minute. The heat block was then held at 72° C. for 5 minutes followed by a 4° C. soak cycle.

The reaction products were isolated by 1.0% agarose gel electrophoresis using TAE buffer where an approximately 1.1 kb product band was excised from the gel and purified using a MINELUTE® Gel Extraction Kit (QIAGEN Inc., Valencia, Calif., USA) according to the manufacturer's instructions.

The fragment was then cloned into pAILo2 using an IN-FUSION™ Cloning Kit. The vector was digested with Nco I and Pac I. The fragment was purified by 1.0% agarose gel electrophoresis using TAE buffer, excised from the gel, and purified using a QIAQUICK® Gel Extraction Kit (QIAGEN Inc., Valencia, Calif., USA). The gene fragment and the digested vector were combined together in a reaction resulting in the expression plasmid pAG66, in which transcription of the Family GH61N gene was under the control of the NA2-tpi promoter (a modified promoter from the gene encoding neutral alpha-amylase in *Aspergillus niger* in which the untranslated leader has been replaced by an untranslated leader from the gene encoding triose phosphate isomerase in *Aspergillus nidulans*). The recombination reaction (20 μl) was composed of 1× IN-FUSION™ Buffer (BD Biosciences, Palo Alto, Calif., USA), 1×BSA (BD Biosciences, Palo Alto, Calif., USA), 1 μl of IN-FUSION™ enzyme (diluted 1:10) (BD Biosciences, Palo Alto, Calif., USA), 186 ng of pAILo2 digested with Nco I and Pac I, and 96.6 ng of the *Thielavia terrestris* GH61N purified PCR product. The reaction was incubated at 37° C. for 15 minutes followed by 15 minutes at 50° C. The reaction was diluted with 40 μl of TE buffer and 2.5 μl of the diluted reaction was used to transform *E. coli* TOP10 Competent cells. An *E. coli* transformant containing pAG66 (GH61N gene) was identified by restriction enzyme digestion and plasmid DNA was prepared using a BIOROBOT® 9600.

*Aspergillus oryzae* JaL355 protoplasts were prepared according to the method of Christensen et al., 1988, *Bio/Technology* 6: 1419-1422. Five μg of pAG43 was used to transform *Aspergillus oryzae* JaL355. Three transformants were isolated to individual PDA plates.

Plugs were taken from the original transformation plate of each of the three transformants and added separately to 1 ml of M410 medium in 24 well plates, which were incubated at 34° C. Five days after incubation, 7.5 μl of supernatant from each culture was analyzed using CRITERION® stain-free, 8-16% gradient SDS-PAGE, (Bio-Rad Laboratories, Inc., Hercules, Calif., USA) according to the manufacturer's instructions. SDS-PAGE profiles of the cultures showed that several transformants had new major bands of approximately 70 kDa and 35 kDa.

Confluent PDA plates of two of the transformants were washed with 5 ml of 0.01% TWEEN® 20 and inoculated into five 500 ml Erlenmeyer flask containing 100 ml of M410 medium and incubated to generate broth for characterization of the enzyme. The flasks were harvested on days 3 and 5 and filtered using a 0.22 μm stericup suction filter (Millipore, Bedford, Mass.).

Example 23: Preparation of *Aspergillus aculeatus* CBS 101.43 GH10 Xylanase 11

*Aspergillus aculeatus* CBS 101.43 GH10 xylanase II (SEQ ID NO: 45 [DNA sequence] and SEQ ID NO: 46 [deduced amino acid sequence]) was purified from SHEARZYME® 2X-CDN01013. The sample was desalted and buffer-exchanged in 20 mM Bis-Tris pH 6.0 using a HIPREP® 26/10 desalting column according to the manufacturer's instructions. The buffer exchanged sample was applied to a Q SEPHAROSE® Big Beads column (64 ml) equilibrated with 20 mM Bis-Tris pH 6.0, and the bound protein was eluted with a gradient from 0 to 500 mM sodium chloride over 10 column volumes. Fractions were pooled and concentrated into 200 mM sodium chloride-20 mM Bis-Tris pH 6.0. Protein concentration was determined using a Microplate BCA™ Protein Assay Kit with bovine serum albumin as a protein standard.

Example 24: Preparation of *Aspergillus fumigatus* NN055679 GH10 Xylanase

*Aspergillus fumigatus* NN055679 GH10 xylanase (xyn3) (SEQ ID NO: 47 [DNA sequence] and SEQ ID NO: 48 [deduced amino acid sequence]) was prepared recombinantly according to WO 2006/078256 using *Aspergillus oryzae* BECh2 (WO 2000/39322) as a host.

The filtered broth was desalted and buffer-exchanged into 20 mM Tris –150 mM NaCl pH 8.5 using a HIPREP® 26/10 Desalting Column according to the manufacturer's instructions. Protein concentration was determined using a Microplate BCA™ Protein Assay Kit with bovine serum albumin as a protein standard.

Example 25: Preparation of *Trichophaea saccata* CBS 804.70 GH10 Xylanase

*Trichophaea saccata* CBS 804.70 was inoculated onto a PDA plate and incubated for 7 days at 28° C. Several mycelia-PDA agar plugs were inoculated into 750 ml shake flasks containing 100 ml of MEX-1 medium. The flasks were agitated at 150 rpm for 9 days at 37° C. The fungal mycelia were harvested by filtration through MIRACLOTH® (Calbiochem, San Diego, Calif., USA) before being frozen in liquid nitrogen. The mycelia were then pulverized into a powder by milling the frozen mycelia together with an equal volume of dry ice in a coffee grinder precooled with liquid nitrogen. The powder was transferred into a liquid nitrogen prechilled mortor and pestle and ground to a fine powder with a small amount of baked quartz sand. The powdered mycelial material was kept at −80° C. until use.

Total RNA was prepared from the frozen, powdered mycelium of *Trichophaea saccata* CBS 804.70 by extraction with guanidium thiocyanate followed by ultracentrifugation through a 5.7 M CsCl cushion according to Chirgwin et al., 1979, *Biochemistry* 18: 5294-5299. The polyA enriched RNA was isolated by oligo (dT)-cellulose affinity chromatography according to Aviv et al., 1972, *Proc. Natl. Acad. Sci. USA* 69: 1408-1412.

Double stranded cDNA was synthesized according to the general methods of Gubler and Hoffman, 1983, *Gene* 25: 263-269; Sambrook, J., Fritsch, E. F., and Maniantis, T. Molecular cloning: A Laboratory Manual, 2nd ed., 1989, Cold Spring Harbor Laboratory, Cold Spring Harbor, N.Y.; and Kofod et al., 1994, *J. Biol. Chem.* 269: 29182-29189, using a polyA-Not I primer (Promega Corp., Madison, Wis., USA). After synthesis, the cDNA was treated with mung bean nuclease, blunt ended with T4 DNA polymerase, and ligated to a 50-fold molar excess of Eco RI adaptors (Invitrogen Corp., Carlsbad, Calif., USA). The cDNA was cleaved with Not I and the cDNA was size fractionated by 0.8% agarose gel electrophoresis using TBE buffer. The fraction of cDNA of 700 bp and larger was excised from the gel and purified using a GFX® PCR DNA and Gel Band Purification Kit according to the manufacturer's instructions.

The directional, size-fractioned cDNA was ligated into Eco RI-Not I cleaved pYES 2.0 (Invitrogen, Carlsbad, Calif., USA). The ligation reactions were performed by incubation at 16° C. for 12 hours, then heating at 70° C. for 20 minutes, and finally addition of 10 μl of water to each tube. One μl of each ligation mixture was electroporated into 40 μl of electrocompetent *E. coli* DH10B cells (Invitrogen Corp., Carlsbad, Calif., USA) as described by Sambrook et al., 1989, supra.

The *Trichophaea saccata* CBS 804.70 library was established in *E. coli* consisting of pools. Each pool was made by spreading transformed *E. coli* on LB ampicillin plates, yielding 15,000-30,000 colonies/plate after incubation at 37° C. for 24 hours. Twenty ml of LB medium was added to the plate and the cells were suspended therein. The cell suspension was shaken in a 50 ml tube for 1 hour at 37° C.

Plasmid DNA from several of the library pools of *T. saccata* CBS 804.70 was isolated using a Midi Plasmid Kit (QIAGEN Inc., Valencia, Calif., USA), according to the manufacturer's instructions, and stored at −20° C.

One μl aliquots of purified plasmid DNA from several of the library pools were transformed into *S. cerevisiae* W3124 by electroporation (Becker and Guarante, 1991, *Methods Enzymol.* 194: 182-187) and the transformants were plated onto SC-agar plates containing 2% glucose and incubated at 30° C. In total, 50-100 plates containing 250-400 yeast colonies were obtained from each pool. After 3-5 days of incubation, the SC agar plates were replica plated onto a set of 0.1% AZCL xylan (oat) SC-URA agar plates with galactose. The plates were incubated for 2-4 days at 30° C. and xylanase positive colonies were identified as colonies surrounded by a blue halo. The positive clones were streak-purified and obtained strain CBS 521.95 as single colonies.

Xylanase-expressing yeast colonies were inoculated into 5 ml of YPD medium in 25 ml tubes. The tubes were shaken overnight at 30° C. One ml of the culture was centrifugated to pellet the yeast cells.

DNA was isolated according to WO 94/14953 and dissolved in 50 μl of water. The DNA was transformed into *E. coli* DH10B using standard procedures (Sambrook et al., 1989, supra).

Plasmid DNA was isolated from the *E. coli* transformants using standard procedures (Sambrook et al., 1989, supra). Plasmids were sequenced using both pYES primers as sequencing primers. One specific plasmid clone of 1283 bp designated TF12Xy1170 was found to encode a Family 10 glycoside hydrolase protein and was further characterized. More reliable sequence was obtained by further sequencing of the fragment using the specific primers shown below designed based on the initial sequence:

```
TF12Xyl170F1:
                               (SEQ ID NO: 129)
  5'-TGAAATGGGATGCTACTGA-3'

TF12Xyl170F2:
                               (SEQ ID NO: 130)
  5'-CAACGACTACAACATCGAGG-3'

TF12Xyl170R1:
                               (SEQ ID NO: 131)
  5'-ATTTGCTGTCCACCAGTGAA-3'
```

One plasmid matching the original cDNA sequence was designated pTF12Xy1170 and the *E. coli* strain containing this clone was designated *E. coli* pTF12Xy1170 and deposited on Jul. 28, 2009, with the *Agricultural Research* Service Patent Culture Collection, Northern Regional Research Center, Peoria, Ill., USA, and given the accession number NRRL B-50309.

The nucleotide sequence and deduced amino acid sequence of the *Trichophaea saccata* gh10a gene are shown in SEQ ID NO: 49 and SEQ ID NO: 50, respectively. The coding sequence is 1197 bp including the stop codon. The encoded predicted protein contains 398 amino acids. The % G+C of the coding region of the gene is 53.6% and the mature polypeptide coding region is also 53.6%. Using the SignalP program, version 3 (Nielsen et al., 1997, *Protein Engineering* 10: 1-6), a signal peptide of 19 residues was predicted. The predicted mature protein contains 379 amino acids with a molecular mass of 40.4 kDa.

Analysis of the deduced amino acid sequence of the gh10a gene with the Interproscan program (Zdobnov and Apweiler, 2001, *Bioinformatics* 17: 847-848) showed that the GH10A protein contained the core sequence typical of a Family 10 glycoside hydrolase, extending from approximately amino acid residue 65 to residue 377 of the predicted mature polypeptide. The GH10A protein also contained the sequence signature of a type 1 fungal cellulose binding domain (CBMI). This sequence signature known as Prosite Entry PS00562 (Sigrist et al., 2002, *Brief Bioinform.* 3: 265-274) was present from amino acid residue 8 to residue 35 of the predicted mature polypeptide.

A comparative pairwise global alignment of amino acid sequences was determined using the Needleman-Wunsch algorithm (Needleman and Wunsch, 1970, *J. Mol. Biol.* 48: 443-453) as implemented in the Needle program of EMBOSS with gap open penalty of 10, gap extension penalty of 0.5, and the EBLOSUM62 matrix. The alignment showed that the deduced amino acid sequence of the *Trichophaea saccata* gene encoding the GH10A mature polypeptide shared 62.6% and 62.0% identity (excluding gaps) to the deduced amino acid sequences of Family 10 glycoside hydrolase proteins from *Phanerochaete chrys-*

*osporium* and *Meripilus giganteus*, respectively (accession numbers UNIPROT:B7SIW2 and GENESEQP:AAW23327, respectively).

The *Trichophaea saccata* CBS 804.70 gh10a gene was excised from the pTF12xyl170 using Bam HI and Xho 1, and ligated into the *Aspergillus* expression vector pDAu109 (WO 2005/042735), also digested with Bam HI and Xho 1, using standard methods (Sambrook et al., 1989, supra). The ligation reaction was transformed into *E. coli* TOP10 chemically competent cells according to the manufacturer's instructions. Eight colonies were grown overnight in LB ampicillin medium and plasmid DNA was isolated using a QIAprep Spin Miniprep Kit (QIAGEN Inc., Valencia, Calif., USA) according to the manufacturer's directions. Plasmids containing the correct size inserts were sequenced to determine integrity and orientation of the insert. Plasmid pDAu81#5 was found to be error free and was therefore chosen for scale-up.

Protoplasts of *Aspergillus oryzae* BECH2 (WO 2000/39322) were prepared as described in WO 95/02043. *A. oryzae* BECh2 was constructed as described in WO 00139322. One hundred microliters of protoplast suspension were mixed with 5-25 μg of the *Aspergillus* expression vector pDAu81#5 in 10 μl of STC composed of 1.2 M sorbitol, 10 mM Tris-HCl, pH 7.5, 10 mM $CaCl_2$ (Christensen et al., 1988, *Bio/Technology* 6: 1419-1422). The mixture was left at room temperature for 25 minutes. Two hundred microliters of 60% PEG 4000 (BDH, Poole, England) (polyethylene glycol, molecular weight 4,000), 10 mM $CaCl_2$, and 10 mM Tris-HCl pH 7.5 were added and gently mixed and finally 0.85 ml of the same solution was added and gently mixed. The mixture was left at room temperature for 25 minutes, centrifuged at 2,500×g for 15 minutes, and the pellet was resuspended in 2 ml of 1.2 M sorbitol. This sedimentation process was repeated, and the protoplasts were spread on COVE plates. After incubation for 4-7 days at 37° C. spores were picked and spread on COVE plates containing 0.01% TRITON® X-100 in order to isolate single colonies. The spreading was repeated twice more on COVE sucrose medium (Cove, 1996, *Biochim. Biophys. Acta* 133: 51-56) containing 1 M sucrose and 10 mM sodium nitrate.

Ten of the transformants were inoculated in 10 ml of YPG medium. After 3-4 days of incubation at 30° C., 200 rpm, the supernatant was removed and analyzed by SDS-PAGE 10% Bis-Tris gels (Invitrogen, Carlsbad, Calif., USA) as recommended by the manufacturer. Gels were stained with Coomassie blue and all isolates displayed a diffuse band between 35 and 45 kDa. These transformants were analyzed further for xylanase activity at pH 6.0 using a modified AZCL-arabinoxylan as substrate isolated from wheat (Megazyme, Wicklow, Ireland) in 0.2 M sodium phosphate pH 6.0 buffer containing 0.01% TRITON® X-100 according to the manufacturer's instructions. The transformant producing the highest level of activity was chosen for production of the xylanase.

The transformant producing the highest level of activity was grown using standard methods. The broth was filtered using Whatmann glass filters GF/D, GF/A, GF/C, GF/F (2.7 μm, 1.6 μm, 1.2 μm and 0.7 μm, respectively) (Whatman, Piscataway, N.J., USA) followed by filtration using a NALGENE® bottle top 0.45 μm filter (Thermo Fisher Scientific, Rochester, N.Y., USA).

Ammonia sulfate was added to the filtered broth to a final concentration of 3 M and the precipitate was collected after centrifugation at 10,000×g for 30 minutes. The precipitate was dissolved in 10 mM Tris/HCl pH 8.0 and dialyzed against 10 mM Tris/HCl pH 8.0 overnight. The dialyzed preparation was applied to a 150 ml Q SEPHAROSE® Fast Flow column equilibrated with 10 mM Tris/HCl pH 8.0 and the enzyme was eluted with a 1050 ml (7 column volumes) linear salt gradient from 0 to 1 M NaCl in 10 mM Tris/HCl pH 8.0. Elution was followed at 280 nm and fractions were collected and assayed for xylanase activity using 0.2% AZCL-Arabinoxylan from wheat in 0.2 M sodium phosphate buffer pH 6.0 containing 0.01% TRITON® X-100. Fractions containing xylanase activity were pooled and stored at −20° C.

Example 26: Preparation of *Penicillium pinophilum* GH10 Xylanase

*Penicillium pinophilum* GH10 xylanase (SEQ ID NO: 51 [DNA sequence] and SEQ ID NO: 52 [deduced amino acid sequence]) was prepared according to the following procedure. Compost samples were collected from Yunnan, China on Dec. 12, 2000.

*Penicillium pinophilum* NN046877 was isolated using single spore isolation techniques on PDA plates at 45° C. *Penicillium pinophilum* strain NN046877 was inoculated onto a PDA plate and incubated for 4 days at 37° C. in the darkness. Several mycelia-PDA plugs were inoculated into 500 ml shake flasks containing 100 ml of NNCYP-PCS medium. The flasks were incubated for 5 days at 37° C. with shaking at 160 rpm. The mycelia were collected at day 4 and day 5. The mycelia from each day were frozen in liquid nitrogen and stored in a −80° C. freezer until use.

The frozen mycelia were transferred into a liquid nitrogen prechilled mortar and pestle and ground to a fine powder. Total RNA was prepared from the powdered mycelia of each day by extraction with TRIZOL™ reagent. The polyA enriched RNA was isolated using a mTRAP™ Total Kit.

Double stranded cDNA from each day was synthesized with a SMART™ cDNA library Construction Kit (Clontech Laboratories, Inc., Mountain View, Calif., USA). The cDNA was cleaved with Sfi I and the cDNA was size fractionated by 0.8% agarose gel electrophoresis using TBE buffer. The fraction of cDNA of 500 bp and larger was excised from the gel and purified using a GFX® PCR DNA and Gel Band Purification Kit according to the manufacturer's instructions. Then equal amounts of cDNA from day 4 and day 5 were pooled for library construction.

The pooled cDNA was then directionally cloned by ligation into Sfi I cleaved pMHas7 (WO 2009/037253) using T4 ligase (New England Biolabs, Inc., Beverly, Mass., USA) according to the manufacturer's instructions. The ligation mixture was electroporated into *E. coli* ELECTROMAX™ DH10B™ cells (Invitrogen Corp., Carlsbad, Calif., USA) using a GENE PULSER® and Pulse Controller (Bio-Rad Laboratories, Inc., Hercules, Calif., USA) at 25 uF, 25 mAmp, 1.8 kV with a 1 mm gap cuvette according to the manufacturer's procedure.

The electroporated cells were plated onto LB plates supplemented with 50 mg of kanamycin per liter. A cDNA plasmid pool was prepared from 60,000 total transformants of the original pMHas7 vector ligation. Plasmid DNA was prepared directly from the pool of colonies using a QIAGEN® Plasmid Kit (QIAGEN Inc., Valencia, Calif., USA).

A transposon containing plasmid designated pSigA4 was constructed from the pSigA2 transposon containing plasmid described WO 2001/77315 in order to create an improved version of the signal trapping transposon of pSigA2 with decreased selection background. The pSigA2 transposon contains a signal less beta-lactamase construct encoded on the transposon itself. PCR was used to create a deletion of the intact beta lactamase gene found on the plasmid backbone using a proofreading Pfu Turbo polymerase PROOFSTART™ (QIAGEN GmbH Corporation, Hilden, Germany) and the following 5' phosphorylated primers (TAG Copenhagen, Denmark):

```
SigA2NotU-P:
                                    (SEQ ID NO: 132)
5'-TCGCGATCCGTTTTCGCATTTATCGTGAAACGCT-3'

SigA2NotD-P:
                                    (SEQ ID NO: 133)
5'-CCGCAAACGCTGGTGAAAGTAAAAGATGCTGAA-3'
```

The amplification reaction was composed of 1 μl of pSigA2 (10 ng/μl), 5 μl of 10× PROOFSTART™ Buffer (QIAGEN GmbH Corporation, Hilden, Germany), 2.5 μl of dNTP mix (20 mM), 0.5 μl of SigA2NotU-P (10 mM), 0.5 μl of SigA2NotD-P (10 mM), 10 μl of Q solution (QIAGEN GmbH Corporation, Hilden, Germany), and 31.25 μl of deionized water. A DNA ENGINE™ Thermal Cycler (MJ Research Inc., Waltham, Mass., USA) was used for amplification programmed for one cycle at 95° C. for 5 minutes; and 20 cycles each at 94° C. for 30 seconds, 62° C. for 30 seconds, and 72° C. for 4 minutes.

A 3.9 kb PCR reaction product was isolated by 0.8% agarose gel electrophoresis using TAE buffer and 0.1 μg of ethidium bromide per ml. The DNA band was visualized with the aid of an EAGLE EYE® Imaging System (Stratagene, La Jolla, Calif., USA) at 360 nm. The 3.9 kb DNA band was excised from the gel and purified using a GFX® PCR DNA and Gel Band Purification Kit according to the manufacturer's instructions.

The 3.9 kb fragment was self-ligated at 16° C. overnight with 10 units of T4 DNA ligase (New England Biolabs, Inc., Beverly, Mass., USA), 9 μl of the 3.9 kb PCR fragment, and 1 μl of 10× ligation buffer (New England Biolabs, Inc., Beverly, Mass., USA). The ligation was heat inactivated for 10 minutes at 65° C. and then digested with Dpn I at 37° C. for 2 hours. After incubation, the digestion was purified using a GFX® PCR DNA and Gel Band Purification Kit.

The purified material was then transformed into *E. coli* TOP10 competent cells according to the manufacturer's instructions. The transformation mixture was plated onto LB plates supplemented with 25 μg of chloramphenicol per ml. Plasmid minipreps were prepared from several transformants and digested with Bgl II. One plasmid with the correct construction was chosen. The plasmid was designated pSigA4. Plasmid pSigA4 contains the Bgl II flanked transposon SigA2 identical to that disclosed in WO 2001/77315.

A 60 μl sample of plasmid pSigA4 DNA (0.3 μg/μl) was digested with Bgl II and separated by 0.8% agarose gel electrophoresis using TBE buffer. A SigA2 transposon DNA band of 2 kb was eluted with 200 μl of EB buffer (QIAGEN GmbH Corporation, Hilden, Germany) and purified using a GFX® PCR DNA and Gel Band Purification Kit according to the manufacturer's instructions and eluted in 200 μl of EB buffer. SigA2 was used for transposon assisted signal trapping.

A complete description of transposon assisted signal trapping is described in WO 2001/77315. The plasmid pool was treated with transposon SigA2 and HYPERMU™ transposase (EPICENTRE Biotechnologies, Madison, Wis., USA) according to the manufacturer's instructions.

For in vitro transposon tagging of the *Penicillium pinophilum* cDNA library, 2 μl of SigA2 transposon containing approximately 100 ng of DNA were mixed with 1 μl of the plasmid DNA pool of the *Penicillium pinophilum* cDNA library containing 1 μg of DNA, 1 μl of HYPERMU™ transposase, and 2 μl of 10× buffer (EPICENTRE Biotechnologies, Madison, Wis., USA) in a total volume of 20 μl and incubated at 30° C. for 3 hours followed by adding 2 μl of stop buffer (EPICENTRE Biotechnologies, Madison, Wis., USA) and heat inactivation at 75° C. for 10 minutes. The DNA was precipitated by addition of 2 μl of 3 M sodium acetate pH 5 and 55 μl of 96% ethanol and centrifuged for 30 minutes at 10,000×g, 4° C. The pellet was washed in 70% ethanol, air dried at room temperature, and resuspended in 10 μl of deionized water.

A 2 μl volume of the transposon tagged plasmid pool was electroporated into 50 μl of *E. coli* ELECTROMAX™ DH10B™ cells (Invitrogen Corp., Carlsbad, Calif., USA) according to the manufacturer's instructions using a GENE PULSER® and Pulse Controller at 25 uF, 25 mAmp, 1.8 kV with a 1 mm gap cuvette according to the manufacturer's procedure.

The electroporated cells were incubated in SOC medium with shaking at 225 rpm for 1 hour at 37° C. before being plated onto the following selective media: LB medium supplemented with 50 μg of kanamycin per ml; LB medium supplemented with 50 μg of kanamycin per ml and 15 μg of chloramphencol per ml; and LB medium supplemented with 50 μg of kanamycin per ml, 15 μg of chloramphencol per ml, and 30 μg of ampicillin per ml.

From plating of the electroporation onto LB medium supplemented with kanamycin, chloramphencol and ampicillin, approximately 200 colonies per 50 μl were observed after 3 days at 30° C. All colonies were replica plated onto LB kanamycin, chloramphenicol, and ampicillin medium described above. Five hundred colonies were recovered under this selection condition. The DNA from each colony was sequenced with the transposon forward and reverse primers (primers A and B), shown below, according to the procedure disclosed in WO 2001/77315 (page 28).

```
Primer A:
                                    (SEQ ID NO: 134)
5'-agcgtttgcggccgcgatcc-3'

Primer B:
                                    (SEQ ID NO: 135)
5'-ttattcggtcgaaaaggatcc-3'
```

DNA sequences were obtained from SinoGenoMax Co., Ltd (Beijing, China). Primer A and primer B sequence reads for each plasmid were trimmed to remove vector and transposon sequence. The assembled sequences were grouped into contigs by using the program PhredPhrap (Ewing et al., 1998, *Genome Research* 8: 175-185; Ewing and Green, 1998, *Genome Research* 8: 186-194). All contigs were subsequently compared to sequences available in standard public DNA and protein sequences databases (TrEMBL, SWALL, PDB, EnsemblPep, GeneSeqP) using the program BLASTX 2.0a19MP-WashU [14 Jul. 1998] [Build linux-x86 18:51:44 30 Jul. 1998] (Gish et al., 1993, *Nat. Genet.* 3: 266-72). The family GH10 xylanase candidate was identified directly by analysis of the BlastX results.

*Penicillium pinophilum* NN046877 was grown on a PDA agar plate at 37° C. for 4-5 days. Mycelia were collected directly from the agar plate into a sterilized mortar and frozen under liquid nitrogen. Frozen mycelia were ground, by mortar and pestle, to a fine powder, and genomic DNA was isolated using a DNEASY® Plant Mini Kit (QIAGEN Inc., Valencia, Calif., USA).

Based on the *Penicillium pinophilum* GH10 xylanase gene information obtained as described above, oligonucleotide primers, shown below, were designed to amplify the GH61 gene from genomic DNA of *Penicillium pinophilum* GH10 NN046877. An IN-FUSION® CF Dry-down Cloning Kit (Clontech Laboratories, Inc., Mountain View, Calif., USA) was used to clone the fragment directly into the expression vector pPFJO355, without the need for restriction digestion and ligation.

```
Sense primer:
                                        (SEQ ID NO: 136)
5'-
ACACAACTGGGGATCCACCATGACTCTAGTAAAGGCTATTCTTTTAGC-
3'

Antisense primer:
                                        (SEQ ID NO: 137)
5'-GTCACCCTCTAGATCTTCACAAACATTGGGAGTAGTATGG-3'
```

Bold letters represented the coding sequence and the remaining sequence was homologous to insertion sites of pPFJO355.

Twenty picomoles of each of the primers above were used in a PCR reaction composed of *Penicillium* sp. NN051602 genomic DNA, 10 μl of 5×GC Buffer, 1.5 μl of DMSO, 2.5 mM each of dATP, dTTP, dGTP, and dCTP, and 0.6 unit of PHUSION™ High-Fidelity DNA Polymerase, in a final volume of 50 μl. The amplification was performed using a Peltier Thermal Cycler programmed for denaturing at 98° C. for 1 minutes; 5 cycles of denaturing at 98° C. for 15 seconds, annealing at 56° C. for 30 seconds, with a 1° C. increase per cycle and elongation at 72° C. for 75 seconds; and 25 cycles each at 98° C. for 15 seconds, 65C for 30 seconds and 72° C. for 75 seconds; and a final extension at 72° C. for 10 minutes. The heat block then went to a 4° C. soak cycle.

The reaction products were isolated by 1.0% agarose gel electrophoresis using TBE buffer where an approximately 1.4 kb product band was excised from the gel, and purified using an ILLUSTRA® GFX® PCR DNA and Gel Band Purification Kit according to the manufacturer's instructions.

Plasmid pPFJO355 was digested with Barn I and Bgl II, isolated by 1.0% agarose gel electrophoresis using TBE buffer, and purified using an ILLUSTRA® GFX® PCR DNA and Gel Band Purification Kit according to the manufacturer's instructions.

The gene fragment and the digested vector were ligated together using an IN-FUSION® CF Dry-down PCR Cloning Kit resulting in pPpin3 in which transcription of the *Penicillium pinophilum* GH10 xylanase gene was under the control of a promoter from the gene for *Aspergillus oryzae* alpha-amylase. In brief, 30 ng of pPFJO355 digested with Barn I and Bgl II, and 60 ng of the *Penicillium pinophilum* GH10 xylanase gene purified PCR product were added to a reaction vial and resuspended in a final volume of 10 μl with addition of deionized water. The reaction was incubated at 37° C. for 15 minutes and then 50° C. for 15 minutes. Three μl of the reaction were used to transform *E. coli* TOP10 competent cells. An *E. coli* transformant containing pPpin3 was detected by colony PCR and plasmid DNA was prepared using a QIAprep Spin Miniprep Kit (QIAGEN Inc., Valencia, Calif., USA). The *Penicillium pinophilum* GH10 xylanase gene insert in pPpin3 was confirmed by DNA sequencing using a 3730XL DNA Analyzer.

The same PCR fragment was cloned into vector pGEM-T using a pGEM-T Vector System to generate pGEM-T-Ppin3. The *Penicillium pinophilum* GH10 xylanase gene contained in pGEM-T-Ppin3 was confirmed by DNA sequencing using a 3730XL DNA Analyzer. *E. coli* strain T-Ppin3, containing pGEM-T-Ppin3, was deposited with the Deutsche Sammlung von Mikroorganismen und Zellkulturen GmbH (DSM), D-38124 Braunschweig, Germany on Sep. 7, 2009, and assigned accession number DSM 22922.

DNA sequencing of the *Penicillium pinophilum* genomic clone encoding a GH10 polypeptide having xylanase activity was performed with an Applied Biosystems Model 3700 Automated DNA Sequencer using version 3.1 BIG-DYE™ terminator chemistry (Applied Biosystems, Inc., Foster City, Calif., USA) and dGTP chemistry (Applied Biosystems, Inc., Foster City, Calif., USA) and primer walking strategy. Nucleotide sequence data were scrutinized for quality and all sequences were compared to each other with assistance of PHRED/PHRAP software (University of Washington, Seattle, Wash., USA).

The nucleotide sequence and deduced amino acid sequence of the *Penicillium pinophilum* gh10 gene are shown in SEQ ID NO: 51 and SEQ ID NO: 52, respectively. The coding sequence is 1442 bp including the stop codon and is interrupted by three introns of 51 bp (199-249), 73 bp (383-455), and 94 bp (570-663). The encoded predicted protein is 407 amino acids. The % G+C of the coding sequence of the gene (including introns) is 47.99% G+C and the mature polypeptide coding sequence is 49.22%. Using the SignalP program (Nielsen et al., 1997, *Protein Engineering* 10: 1-6), a signal peptide of 19 residues was predicted. The predicted mature protein contains 388 amino acids with a predicted molecular mass of 41.5 kDa and an isoelectric pH of 5.03.

A comparative pairwise global alignment of amino acid sequences was determined using the Needleman-Wunsch algorithm (Needleman and Wunsch, 1970, *J. Mol. Biol.* 48: 443-453) as implemented in the Needle program of EMBOSS with gap open penalty of 10, gap extension penalty of 0.5, and the EBLOSUM62 matrix. The alignment showed that the deduced amino acid sequence of the *Penicillium pinophilum* gene encoding the GH10 polypeptide having xylanase activity shares 76% and 87% identity (excluding gaps) to the deduced amino acid sequence of a predicted GH10 family protein from *Talaromyces emersonii* (AAU99346) and *Penicillium marneffei* (B6QN64), respectively.

*Aspergillus oryzae* HowB101 (WO 95/35385 Example 1) protoplasts were prepared according to the method of Christensen et al., 1988, *Bio/Technology* 6: 1419-1422. Three μg of pPpin3 were transformed into *Aspergillus oryzae* HowB101.

The transformation of *Aspergillus oryzae* HowB101 with pPpin3 yielded about 50 transformants. Twelve transformants were isolated to individual Minimal medium plates.

Four transformants were inoculated separately into 3 ml of YPM medium in a 24-well plate and incubated at 30° C. with shaking at 150 rpm. After 3 days incubation, 20 μl of supernatant from each culture were analyzed by SDS-PAGE using a NUPAGE® NOVEX® 4-12% Bis-Tris Gel with MES buffer according to the manufacturer's instructions. The resulting gel was stained with INSTANT® Blue (Expedeon Ltd., Babraham Cambridge, UK). SDS-PAGE profiles of the cultures showed that the majority of the transformants had a major band of approximately 55 kDa. The expression strain was designated *Aspergillus oryzae* EXP02765.

A slant of one transformant, designated transformant 2, was washed with 10 ml of YPM and inoculated into a 2 liter flask containing 400 ml of YPM medium to generate broth for characterization of the enzyme. The culture was harvested on day 3 and filtered using a 0.45 μm DURAPORE® Membrane (Millipore, Bedford, Mass., USA).

A 1 liter volume of supernatant of the recombinant *Aspergillus oryzae* strain EXP02765 was precipitated with ammonium sulfate (80% saturation) and redissolved in 50 ml of 25 mM sodium acetate pH 4.3, and then dialyzed against the same buffer and filtered through a 0.45 μm filter. The solution was applied to a 40 ml Q SEPHAROSE™ Fast Flow column column equilibrated in 25 mM sodium acetate pH 4.3. The recombinant GH10 protein did not bind to the column. The fractions with xylanase activity were collected and evaluated by SDS-PAGE as described above. Fractions containing a band of approximately 55 kDa were pooled. The pooled solution was concentrated by ultrafiltration.

Example 27: Preparation of *Thielavia terrestris* GH10E Xylanase

*Thielavia terrestris* NRRL 8126 GH10E xylanase (SEQ ID NO: 53 [DNA sequence] and SEQ ID NO: 54 [deduced amino acid sequence]) was prepared according to the following procedure.

Two synthetic oligonucleotide primers shown below were designed to PCR amplify the *Thielavia terrestris* gh10e gene from genomic DNA. An InFusion Cloning Kit (Clontech, Mountain View, Calif.) was used to clone the fragment directly into the expression vector, pAILo2 (WO 2005/074647).

```
Forward primer:
                                        (SEQ ID NO: 138)
5'-ACTGGATTTACCATGGCCCTCAAATCGCTCCTGTTG-3'

Reverse primer:
                                        (SEQ ID NO: 139)
5'-TCACCTCTAGTTAATTAATTACAAGCACTGAGAGTA-3'
```

Bold letters represent coding sequence. The remaining sequence is homologous to the insertion sites of pAILo2.

Fifty picomoles of each of the primers above were used in a PCR reaction containing 2 μg of *Thielavia terrestris* genomic DNA, 1× Pfx Amplification Buffer (Invitrogen, Carlsbad, Calif., USA), 2×PCR, Enhancer solution (Invitrogen, Carlsbad, Calif., USA), 1.5 μl of 10 mM blend of dATP, dTTP, dGTP, and dCTP, 2.5 units of PLATINUM® Pfx DNA Polymerase, and 1 μl of 50 mM $MgSO_4$ in a final volume of 50 μl. The amplification conditions were one cycle at 94° C. for 2 minutes; and 30 cycles each at 94° C. for 15 seconds, 59.5° C. for 30 seconds, and 68° C. for 150 seconds. The heat block was then held at 68° C. for 7 minutes followed by a 4° C. soak cycle.

The reaction products were isolated on a 1.0% agarose gel using TAE buffer and an approximately 1.2 kb product band was excised from the gel and purified using a MINELUTE® Gel Extraction Kit (QIAGEN Inc., Valencia, Calif., USA) according to the manufacturer's instructions.

The fragment was then cloned into pAILo2 using an IN-FUSION™ Cloning Kit. The vector was digested with Nco I and Pac I (using conditions specified by the manufacturer). The fragment was purified by gel electrophoresis as above and a QIAQUICK® Gel Extraction Kit. The gene fragment and the digested vector were combined together in a reaction resulting in the expression plasmid pAG29, in which transcription of the gh10e gene was under the control of the NA2-tpi promoter (a hybrid of the promoters from the genes for *Aspergillus niger* neutral alpha-amylase and *Aspergillus nidulans* triose phosphate isomerase). The recombination reaction (10 μl) was composed of 1× InFusion Buffer (Clontech, Mountain View, Calif., USA), 1×BSA (Clontech, Mountain View, Calif., USA), 0.5 μl of InFusion enzyme (diluted 1:10) (Clontech, Mountain View, Calif., USA), 93 ng of pAILo2 digested with Nco I and Pac I, and 1 μl of the *Thielavia terrestris* gh10e purified PCR product. The reaction was incubated at 37° C. for 15 minutes followed by 15 minutes at 50° C. The reaction was diluted with 40 μl of TE buffer and 2.5 μl of the diluted reaction was used to transform *E. coli* SOLOPACK® Gold cells.

Plasmid DNA was prepared using a BIOROBOT® 9600 and a restriction enzyme digest performed. Putative pAG29 clones were digested with Pst I. The plasmid DNA from these clones was then sequenced to identify clones without PCR induced errors. Sequencing reactions contained 1.5 μl of plasmid DNA, 4.5 μl of water, and 4 μl of sequencing master-mix containing 1 μl of 5× sequencing buffer (Millipore, Billerica, Mass., USA), 1 μl of BIGDYE™ terminator (Applied Biosystems, Inc., Foster City, Calif., USA), 1 μl of water and one of the following primers at 3.2 μmoles per reaction.

```
pAlLo2 5'
                              (SEQ ID NO: 140)
5'-TGTCCCTTGTCGATGCG-3'

pAlLo2 3'
                              (SEQ ID NO: 141)
5'-CACATGACTTGGCTTCC-3'
```

*Aspergillus oryzae* JaL355 protoplasts were prepared according to the method of Christensen et al., 1988, *Bio/Technology* 6: 1419-1422. Five μg of pAG29 was used to transform *Aspergillus oryzae* JaL355. Twenty-four transformants were isolated to individual PDA plates.

Confluent PDA plates of 24 transformants were washed with 5 ml of 0.01% TWEEN® 20 and spores collected. Eight μl of each spore stock was added to 1 ml of YPG, YPM, and M410 separately in 24 well plates and incubated at 34° C. Three days after incubation, 7.5 μl of supernatant from selected culture was analyzed using Criterion stain-free, 8-16% gradient SDS-PAGE, (BioRad, Hercules, Calif.) according to the manufacturer's instructions. SDS-PAGE profiles of the cultures showed that several transformants had a new major band of approximately 50 kDa and the best expression in M410. After a total of six days of incubation, all M410 cultures were sampled as described above and analyzed using Criterion stain-free, 8-16% gradient SDS-PAGE gel, (BioRad, Hercules, Calif.) at which point the transformant exhibiting the best expression was selected.
A confluent PDA plate of the top transformant was washed with 5 ml of 0.01% TWEEN® 20 and inoculated into five 500 ml Erlenmeyer flask containing 100 ml of M410 medium to generate broth for characterization of the enzyme. The flasks were harvested on day 5. Broths were filtered using a 0.22 μm stericup suction filter (Millipore, Bedford, Mass.).

Example 28: Preparation of *Thermobifida fusca* GH11 Xylanase

A linear integration vector-system was used for the expression cloning of a *Thermobifida fusca* DSM 22883 GH11 xylanase gene (SEQ ID NO: 55 [DNA sequence] and SEQ ID NO: 56 [deduced amino acid sequence]). The linear integration construct was a PCR fusion product made by fusion of each gene between two *Bacillus subtils* homologous chromosomal regions along with a strong promoter and a chloramphenicol resistance marker. The fusion was made by SOE PCR (Horton et al., 1989, *Gene* 77: 61-68). The SOE PCR method is also described in WO 2003/095658. Each gene was expressed under the control of a triple promoter system (as described in WO 99/43835), consisting of the promoters from *Bacillus licheniformis* alpha-amylase gene (amyL), *Bacillus amyloliquefaciens* alpha-amylase gene (amyQ), and the *Bacillus thuringiensis* cryIIIA promoter including stabilizing sequence. The gene coding for chloramphenicol acetyl-transferase was used as marker (Diderichsen et al., 1993, *Plasmid* 30: 312). The final gene construct was integrated into the *Bacillus* chromosome by homologous recombination into the pectate lyase locus.

The GH11 xylanase gene (SEQ ID NO: 55 [DNA sequence] and SEQ ID NO: 56 [deduced amino acid sequence]) was isolated from *Thermobifida fusca* DSM 22883 (NN018438) by a polymerase chain reaction (PCR1) using the primers shown in the table below. The primers are based on the protein sequence UNIPROT:Q5RZ98. *Thermobifida fusca* DSM 22883 was isolated from a soil sample obtained from Oahu, Hi. in 2001. The xylanase gene was cloned as a full-length gene and as a truncated gene. The genes were designed to contain a C-terminal HQHQHQH tag to ease purification but the His-tag was not used for the purification. The forward primer Ocs3 was designed so the gene was amplified from the start codon (ATG) and has 24 bases overhang (shown in italic in the table below). This overhang is complementary to part of one of the two linear vector fragments and is used when the PCR fragment and the vector fragments are assembled (described below). The reverse primer Ocs1 was designed to amplify the truncated version of the gene while the reverse primer Ocs2 was designed to amplify the full-length gene. Both Ocs1 and Ocs2 carry an overhang consisting of 24 bp encoding a HQHQHQH-tag and a stop codon (the overhang is shown in italic in the table below). This overhang is complementary to part of one of the two linear vector fragments and is used when the PCR fragment and the vector fragments are assembled (described below).

A PCR fragment was isolated containing the full-length xylanase gene and the short 24 bp flanking DNA sequences included in the primers as overhang. Another PCR fragment was isolated containing the truncated xylanase gene and the same short 24 bp flanking DNA sequences.

For each gene construct 3 fragments were PCR amplified: the gene fragment from genomic DNA from the *Thermobifida fusca* (NN018438), the upstream flanking fragment was amplified with primers 260558 and iMB1361Uni1, and the downstream flanking fragment was amplified with primers 260559 and oth432 from genomic DNA of the strain iMB1361 (described in patent application WO 2003095658). All primers used are listed in Table below.

| Amplification of | SPECIFIC PRIMER FORWARD | SPECIFIC PRIMER REVERSE |
|---|---|---|
| Full-length gene | OCS3: 5'-***CTGAAAAAAAGGAGAGGAT AAAGA***ATGAACCATGCCCCCG CCA-3' (SEQ ID NO: 142) | OCS2: 5'-***CTAATGCTGGTGTTGGTGC TGATG***GTTGGCGCTGCAGGA CACCGT-3' (SEQ ID NO: 143) |
| Truncated gene | OCS3: 5'-***CTGAAAAAAAGGAGAGGAT AAAGA***ATGAACCATGCCCCCG CCA 3' (SEQ ID NO: 142) | OCS1: 5'-***CTAATGCTGGTGTTGGTGC TGATG***GGGGTTGTCACCGCC GCT-3' (SEQ ID NO: 144) |
| Upstream flanking fragment | 260558: 5'-GAGTATCGCCAGTAAGGGG CG 3' (SEQ ID NO: 145) | iMB1361Uni1: 5'-TCTTTATCCTCTCCTTTTTTT CAGAGCTC 3' (SEQ ID NO: 146) |
| Downstream flanking fragment | oth432: 5'-CATCAGCACCAACACCAGCA TCCGTAATCGCATGTTCAATCC GCTCCATA 3' (SEQ ID NO: 147) | 260559: 5'-GCAGCCCTAAAATCGCATAA AGC-3' (SEQ ID NO: 148) |

The gene fragment was amplified using a proofreading polymerase PHUSION™ DNA Polymerase according to the manufacturer's instructions with the addition of 2% DMSO. The two flanking DNA fragments were amplified with an EXPAND™ High Fidelity PCR System according to the manufacturer's recommendations. The PCR conditions were as follows: one cycle at 94° C. for 2 minutes; 10 cycles each at 94° C. for 15 seconds, 50° C. for 45 seconds, 68° C. for 4 minutes; 20 cycles each at 94° C. for 15 seconds, 50° C. for 45 seconds, and 68° C. for 4 minutes (+20 seconds extension pr cycle); and one cycle at 68° C. for 10 minutes The 3 PCR fragments were subjected to a subsequent splicing by overlap extension (SOE) PCR reaction to assemble the 3 fragments into one linear vector construct. This was performed by mixing the 3 fragments in equal molar ratios and a new PCR reaction was run under the following conditions: one cycle at 94° C. for 2 minutes; 10 cycles each at 94° C. for 15 seconds, 50° C. for 45 seconds, and 68° C. for 5 minutes; 10 cycles each at 94° C. for 15 seconds, 50° C. for 45 seconds, and 68° C. for 8 minutes; 15 cycles each at 94° C. for 15 seconds, 50° C. for 45 seconds, and 68° C. for 8 minutes (in addition 20 seconds extra per cycle). After the first cycle the two end primers 260558 and 260559 were added (20 µMol of each). Two µl of the PCR product was transformed into *Bacillus subtilis*. Transformants were selected on LB plates supplemented with 6 µg of chloramphenicol per ml. The full-length xylanase coding sequence was integrated by homologous recombination into the genome of the *Bacillus subtilis* host TH1 (amy-, spo-, apr-, npr-; WO 2005/038024). The truncated xylanase coding sequence was integrated by homologous recombination into the genome of the *Bacillus subtilis* host PL2317 (amy-, spo-, apr-, npr-, xyl-).

Transformants were then screened for their ability to produce large amounts of active xylanase. The screening was based on intensity of the band corresponding to the heterologous expressed protein by SDS-PAGE analysis and activity of the enzyme on LB agar plates containing AZCL-xylan (Megazyme International Ireland, Ltd., Wicklow, Ireland).

One transformant, *Bacillus subtilis* EXP01687, was isolated which contained the full-length xylanase gene expressed in the host strain *Bacillus subtilis* TH1. The full-length xylanase gene sequence of *Bacillus subtilis* EXP01687 was confirmed by Sanger sequencing. The protein sequence differs by 2 amino acids from UNIPROT: Q5RZ98.

Another transformant, *Bacillus subtilis* EXP01672, was isolated which contains the truncated xylanase gene expressed in the host strain *Bacillus subtilis* PL2317. The truncated xylanase gene sequence of *Bacillus subtilis* EXP01672 was confirmed by Sanger sequencing to encode the secretion signal and mature amino acid sequence to proline at position 236 of SEQ ID NO: 56. The protein sequence differs by 2 amino acids from UNIPROT:Q5RZ98.

*Bacillus subtilis* EXP01687 was grown in 500 ml baffled Erlenmeyer flasks containing Cal-18 medium supplemented with 34 mg of chloramphenicol per liter for 2 days at 37° C. with shaking at 200 rpm. The enzyme was purified from the culture supernatant according to the protocol described below.

In step 1, the whole culture (800 ml) was centrifuged at 17,600×g for 30 minutes and then filtered through a SEITZ-EKS filter (Pall Seitzschenk Filtersystems GmbH, Bad Kreuznach, Germany). Sodium chloride was added to the filtered sample to 50 mM NaCl and the pH was adjusted to pH 7.5. The sample (750 ml) was applied to a 20 ml Ni SEPHAROSE® 6 Fast Flow column (GE Healthcare, Piscataway, N.J., USA) equilibrated with 50 mM $Na_2HPO_4$, 50 mM NaCl pH 7.5, and the bound protein was eluted with a 5 column volume gradient to 100% 50 mM $Na_2HPO_4$, 500 mM imidazol pH 7.5. The enzyme was found in the effluent by SDS-PAGE analysis revealing a protein of the correct size in the effluent and nothing of the correct size in the eluent. This result was confirmed by activity measurement using AZCL-arabinoxylan (wheat) as substrate as described above.

In step 2, ammonium sulfate was added to the effluent (of step 1) to 1 M and the pH adjusted to 7.5. The sample (800 ml) was applied to a 60 ml TOYOPEARL® Phenyl-650M column (TOSOH Corporation, Tokyo, Japan) equilibrated with 1 M ammonium sulfate pH 7.5. The bound protein was eluted with Milli-Q® ultrapure water (Millipore, Billerica, Mass., USA). Fractions with A280 were pooled (55 ml). The pooled fractions were desalted and buffer-exchanged with 25 mM acetic acid pH 4.5 using a HIPREP® 26/10 desalting column according to the manufacturer's instructions.

In step 3, the buffer exchanged sample of step 2 (110 ml) was diluted 2.5-fold with Milli-Q® ultrapure water and applied to a 10 ml SP SEPHAROSE® Fast Flow column (GE Healthcare, Piscataway, N.J., USA) equilibrated with 25 mM acetic acid pH 4.5. The bound protein was eluted with a five column volume gradient from 0 to 500 mM sodium chloride in 25 mM acetic acid pH 4.5. Based on SDS-PAGE analysis and A280 and $A_{260}$ fractions were pooled (10 ml).

In step 4, the pooled fractions of step 3 were diluted 25-fold with Milli-Q® ultrapure water and the pH was adjusted to pH 6.0 and applied to 10 ml SP SEPHAROSE® Fast Flow column equilibrated with 5 mM succinic acid pH 6.0. The bound protein was eluted with a ten column volume gradient from 0 to 500 mM sodium chloride in 5 mM succinic acid pH 6.0. Based on SDS-PAGE analysis and $A_{280}$ and $A_{260}$ fractions were pooled (12 ml). Separate portions of the pooled fractions were then subjected to three different steps (steps 5(a), 5(b), and 5(c)) described below.

In step 5(a), 6 ml of the pooled fractions of step 4 were diluted to 25 ml with Milli-Q® ultrapure water and the pH was adjusted to pH 9.0 and applied to a 1 ml RESOURCE™ Q column (GE Healthcare, Piscataway, N.J., USA) equilibrated with 25 mM boric acid pH 9.0. The bound protein was eluted with a ten column volume gradient from 0 to 500 mM sodium chloride in 25 mM boric acid pH 9.0. Based on A280 and $A_{260}$, the protein was in the effluent (35 ml). This sample was concentrated using an AMICON® ultrafiltration cell equipped with a 5 kDa cut-off membrane (Millipore, Billerica, Mass., USA).

In step 5(b), 3 ml of the pool of step 4 were diluted to 30 ml with Milli-Q® ultrapure water and pH was adjusted to pH 9.6 and applied to a 1 ml RESOURCE™ Q column equilibrated with 12.5 mM boric acid pH 9.7. The bound protein was eluted with a ten column volume gradient from 0 to 500 mM sodium chloride in 12.5 mM boric acid pH 9.7. Based on A280 and $A_{260}$ and SDS-PAGE analysis, the protein was in the effluent (36 ml).

In step 5(c), one quarter of the pool of step 4 was diluted with Milli-Q® ultrapure water and the pH was adjusted to pH 8.0 and applied to a 1 ml RESOURCE™ Q column equilibrated with 25 mM borate pH 8.0. The bound protein was eluted with a ten column volume gradient from 0 to 500 mM sodium chloride in 25 mM borate pH 8.0. Based on $A_{280}$ and $A_{260}$ and SDS-PAGE analysis, the protein was in the effluent (25 ml).

In step 6, the sample from step 5(a), the effluent from step 5(b), and the effluent from step 5(c) were pooled and diluted with 25 mM acetic acid pH 4.5, and the pH was adjusted to pH 4.58. The pooled sample (100 ml) was applied to a 1 ml HITRAP® SP Fast Flow column (GE Healthcare, Piscataway, N.J., USA) equilibrated with 25 mM acetic acid pH 4.5. The bound protein was eluted with one column volume gradient from 0 to 500 mM sodium chloride in 25 mM acetic acid pH 4.5. Based on SDS-PAGE analysis and A280 and $A_{260}$ fractions were pooled (3.5 ml). The MW of the purified xylanase was 20-25 kDa based on SDS-PAGE analysis.

Example 29: Preparation of *Trichoderma reesei* RutC30 GH3 Beta-Xylosidase

A *Trichoderma reesei* RutC30 beta-xylosidase gene (SEQ ID NO: 57 [DNA sequence] and SEQ ID NO: 58 [deduced amino acid sequence]) was isolated by screening a Lambda ZAP®-CMR XR Library prepared from *T. reesei* RutC30 genomic DNA using a Lambda ZAP®-CMR XR Library Construction Kit (Stratagene, La Jolla, Calif., USA) according to the manufacturer's instructions. *T. reesei* RutC30 genomic DNA was prepared using standard methods. A DNA segment encoding 2300 bp of the *T. reesei* beta-xylosidase was amplified using the PCR primers shown below.

```
Forward Primer:
                                (SEQ ID NO: 149)
5'-gtgaataacgcagctcttctcg-3'

Reverse Primer:
                                (SEQ ID NO: 150)
5'-ccttaattaattatgcgtcaggtgt-3'
```

Primer 994768 was designed to amplify from the first base after the beta-xylosidase start site and primer 994769 was designed with a Pac I site at the 5' end.

Fifty picomoles of each of the primers above were used in a PCR reaction consisting of 50 ng of plasmid DNA from the lamda zap library, 1 μl of 10 mM blend of dATP, dTTP, dGTP, and dCTP, 5 μl of 10× PLATINUM® Pfx DNA Polymerase Buffer, and 1 unit of PLATINUM® Pfx DNA Polymerase, in a final volume of 50 μl. An EPPENDORF® MASTERCYCLER® 5333 was used to amplify the DNA fragment programmed for one cycle at 95° C. for 3 minutes; and 30 cycles each at 94° C. for 45 seconds, 55° C. for 60 seconds, and 72° C. for 1 minute 30 seconds. After the 30 cycles, the reaction was incubated at 72° C. for 10 minutes and then cooled to 4° C. until further processing.

A 2.3 kb PCR product was purified by 1% agarose gel electrophoresis using TAE buffer, excised from the gel, and purified using a QIAQUICK® Gel Extraction Kit. The 2.3 kb PCR product was then digested with Pac I to facilitate insertion into pAILo1 (WO 2004/099228).

The pAILo1 vector was digested with Nco I and then filled in using T4 polymerase (Roche, Nutley, N.J., USA) according to manufacturer's instructions. A second enzyme, Pac I, was then used to digest the 5' end of pAILo1 and the reaction was purified by agarose gel electrophoresis as described above to isolate a 6.9 kb vector fragment.

The 2.3 kb beta-xylosidase fragment was then ligated into the 6.9 kb vector fragment and transformed into *E. coli* XL1-Blue Subcloning Competent Cells (Invitrogen, Carlsbad, Calif., USA) according to manufacturer's instructions. Transformants were screened using restriction digest analysis in order to identify those with the correct insert. A new expression vector, pSaMe04, was confirmed by sequencing using an AB13700 (Applied Biosystems, Foster City, Calif.) and dye terminator chemistry (Giesecke et al., 1992, *Journal of Virology Methods* 38: 47-60).

Two synthetic oligonucleotide primers shown below were designed to PCR amplify the *Trichoderma reesei* beta-xylosidase gene from pSaMe04 to construct a *Trichoderma* expression vector. An IN-FUSION™ Cloning Kit was used to clone the fragment directly into the expression vector pMJ09 (WO 2005/056772), without the need for restriction digestion and ligation.

```
TrBXYL-F (ID 064491):
                                      (SEQ ID NO: 151)
5'-CGGACTGCGCACCATGGTGAATAACGCAGCTCT-3'

TrBXYL-R (ID 064492):
                                      (SEQ ID NO: 152)
5'-TCGCCACGGAGCTTATTATGCGTCAGGTGTAGCAT-3'
```

Bold letters represent coding sequence. The remaining sequence is homologous to the insertion sites of pMJ09.

Fifty picomoles of each of the primers above were used in a PCR reaction composed of 50 ng of pSaMe04, 1 μl of 10 mM blend of dATP, dTTP, dGTP, and dCTP, 5 μl of 10× ACCUTAQ™ DNA Polymerase Buffer (Sigma-Aldrich, St. Louis, Mo., USA), and 5 units of ACCUTAQ™ DNA Polymerase (Sigma-Aldrich, St. Louis, Mo., USA), in a final volume of 50 μl. An EPPENDORF® MASTERCYCLER® 5333 was used to amplify the DNA fragment programmed for one cycle at 95° C. for 3 minutes; and 30 cycles each at 94° C. for 45 seconds, 55° C. for 60 seconds, and 72° C. for 1 minute 30 seconds. After the 30 cycles, the reaction was incubated at 72° C. for 10 minutes and then cooled to 4° C. until further processing.

The reaction products were isolated by 1.0% agarose gel electrophoresis using TAE buffer where a 1.2 kb product band was excised from the gel and purified using a QIAQUICK® Gel Extraction Kit according to the manufacturer's instructions.

The 1.2 kb fragment was then cloned into pMJ09 using an IN-FUSION™ Cloning Kit. The vector was digested with Nco I and Pac I and purified by agarose gel electrophoresis as described above. The gene fragment and the digested vector were ligated together in a reaction resulting in the expression plasmid pSaMe-TrBXYL in which transcription of the beta-xylosidase gene was under the control of the *T. reesei* cbh1 gene promoter. The ligation reaction (50 μl) was composed of 1× IN-FUSION™ Buffer, 1×BSA, 1 μl of IN-FUSION™ enzyme (diluted 1:10), 100 ng of pMJ09 digested with Nco I and Pac I, and 100 ng of the *Trichoderma reesei* beta-xylosidase purified PCR product. The reaction was incubated at room temperature for 30 minutes. One μl of the reaction was used to transform *E. coli* XL10 SOLOPACK® Gold cells. An *E. coli* transformant containing pSaMe-TrBXYL was detected by restriction enzyme digestion and plasmid DNA was prepared using a BIOROBOT® 9600. DNA sequencing of the *Trichoderma reesei* beta-xylosidase gene from pSaMe-TrBXYL was performed using dye-terminator chemistry (Giesecke et al., 1992, supra) and primer walking strategy.

Plasmid pSaMe-AaXYL was constructed to comprise the *Trichoderma reesei* cellobiohydrolase I gene promoter and terminator and the *Aspergillus aculeatus* GH10 xylanase coding sequence.

Cloning of the *Aspergillus aculeatus* xylanase followed the overall expression cloning protocol as outlined in H. Dalboge et al., 1994, *Mol. Gen. Genet.* 243: 253-260.

RNA was isolated from *Aspergillus aculeatus* CBS 101.43 mycelium. Poly(A)$^+$ RNA was isolated from total RNA by chromatography on oligo(dT)-cellulose. Double-stranded cDNA was synthesized as described by Maniatis et al. (Molecular cloning: a laboratory manual. Cold Spring Harbor Laboratory Press, 1982). After synthesis the cDNA was treated with mung bean nuclease, blunt-ended with T4 DNA polymerase, and ligated to non-palindromic Bst XI adaptors (Invitrogen, Carlsbad, Calif., USA). The cDNA was size fractionated by 1% agarose gel electrophoresis using TAE buffer where fragments ranging from 600 bp to 4000 bp were used in the library construction. The DNA was ligated into Bst XI-digested pYES 2.0 between the GAL1 promoter and the iso-1-cytochrome c terminator and transformed into *Escherichia coli* MC1061 cells (Stratagene, La Jolla, Calif., USA. The library was plated onto LB plates and incubated overnight at 37° C. The colonies were scraped from the plates and resuspended in LB medium supplemented with 100 μg of ampicillin per ml. Plasmid DNA was isolated using a Plasmid Midi Kit (QIAGEN Inc., Valenicia, Calif., USA). The purified plasmid DNA was pooled.

The purified plasmid DNA mixture was transformed into *Saccharomyces cerevisiae* W3124 cells (MATa; ura 3-52; leu 2-3, 112; his 3-D200; pep 4-1137; prcl::HIS3; prbl::LEU2; cir+; van den Hazel et al., 1992, *Eur. J. Biochem.* 207: 277-283). Cultivation, transformation and media were as described by Guthrie et al., 1991, *Meth. Enzymol.* Vol 194, Academic Press. The transformed cells were plated onto synthetic complete agar containing 2% glucose for 3 days at 30° C. After 3 days the colonies were replica plated to SC medium with 2% galactose and incubated for 4 days at 30° C. Xylanase expressing colonies were identified by 1% agarose overlay with 0.1% AZCL-Birch-Xylan at pH 4.5 (Dalboge, 2006, *FEMS Microbiology Reviews* 21: 29-42).

Colonies expressing xylanase activity were surrounded by a blue zone. Plasmid DNA, rescued from the positive colonies, contained a DNA insert of approximately 1.3 kb. Sequencing of the isolated gene fragment revealed a 1218 bp open reading frame encoding a polypeptide with a theoretical molecular weight of 43.0 kDa. The cDNA fragment was subcloned into the *Aspergillus* expression vector pHD464 (Dalbøge and Heldt-Hansen, 1994, *Mol. Gen. Genet.* 243, 253-260) digested with Barn HI and Xho i by cutting the done with Barn HI and Xho I and isolating the 1.2 kb cDNA insert (Christgau et al., 1996, *Biochem. J.* 319: 705-712) to generate plasmid pA2X2.

The *Aspergillus aculeatus* GH10 xylanase coding sequence was PCR amplified using plasmid pA2x2 as template and primers 153505 and 153506 shown below using standard methods to yield an approximately 1.2 kb fragment. The 1.2 kb fragment was digested with Barn HI and Xho I (introduced in the PCR primers) and cloned into vector pCaHj527 (WO 2004/099228). The resulting plasmid was designated pMT2155 in which the cDNA was under transcriptional control of the neutral amylase II (NA2) promoter from *A. niger* and the AMG terminator from *A. niger*.

```
Primer 153505:
                                        (SEQ ID NO: 153)
5'-TCTTGGATCCACCATGGTCGGACTGCTTTCAATCACC-3'

Primer 153506:
                                        (SEQ ID NO: 154)
5'-TTAACTCGAGTCACAGACACTGCGAGTAATAGTC-3'
```

Two synthetic oligonucleotide primers shown below were designed to PCR amplify the *Aspergillus aculeatus* GH10 gene from plasmid pMT2155 and introduce flanking regions for insertion into expression vector pMJ09 (WO 2005/056772). Bold letters represent coding sequence and the remaining sequence is homologous to the insertion sites of pMJ09.

Forward Primer:
(SEQ ID NO: 155)
5'-cggactgcgcaccatggtcggactgctttcaat-3'

Reverse Primer:
(SEQ ID NO: 156)
5'-tcgccacggagcttatcacagacactgcgagtaat-3'

Fifty picomoles of each of the primers above were used in a PCR reaction consisting of 50 ng of pMT2155, 1 μl of 10 mM blend of dATP, dTTP, dGTP, and dCTP, 5 μl of 10× ACCUTAQ™ DNA Polymerase Buffer, and 5 units of ACCUTAQ™ DNA Polymerase, in a final volume of 50 μl. An EPPENDORF® MASTERCYCLER® 5333 was used to amplify the DNA fragment programmed for one cycle at 95° C. for 3 minutes; and 30 cycles each at 94° C. for 45 seconds, 55° C. for 60 seconds, and 72° C. for 1 minute 30 seconds. After the 30 cycles, the reaction was incubated at 72° C. for 10 minutes and then cooled to 4° C. until further processing.

The reaction products were isolated on a 1.0% agarose gel using TAE buffer where a 1.2 kb product band was excised from the gel and purified using a QIAquick Gel Extraction Kit according to the manufacturer's instructions.

The fragment was then cloned into pMJ09 using an IN-FUSION™ Cloning Kit. The vector was digested with Nco I and Pac I and purified by agarose gel electrophoresis as described above. The 1.2 kb gene fragment and the digested vector were ligated together in a reaction resulting in the expression plasmid pSaMe-AaXYL in which transcription of the Family GH10 gene was under the control of the *T. reesei* cbh1 promoter. The ligation reaction (50 ul) was composed of 1× IN-FUSION™ Buffer, 1×BSA, 1 μl of IN-FUSION™ enzyme (diluted 1:10), 100 ng of pAILo2 digested with Nco I and Pac I, and 100 ng of the *Aspergillus aculeatus* GH10 xylanase purified PCR product. The reaction was incubated at room temperature for 30 minutes. One μl of the reaction was used to transform *E. coli* XL10 SOLOPACK® Gold cells according to the manufacturer. An *E. coli* transformant containing pSaMe-AaGH10 was detected by restriction enzyme digestion and plasmid DNA was prepared using a BIOROBOT® 9600. DNA sequencing of the *Aspergillus aculeatus* GH10 gene from pSaMe-AaXYL was performed using dye-terminator chemistry (Giesecke et al., 1992, supra) and primer walking strategy.

Plasmids pSaMe-AaXYL encoding the *Aspergillus aculeatus* GH10 endoglucanase and pSaMe-TrBXYL encoding the *Trichoderma reesei* beta-xylosidase were co-transformed into *Trichoderma reesei* RutC30 by PEG-mediated transformation (Penttila et al., 1987, *Gene* 61 155-164) to generate *T. reesei* strain SaMe-BXX13. Each plasmid contained the *Aspergillus nidulans* amdS gene to enable transformants to grow on acetamide as the sole nitrogen source.

*Trichoderma reesei* RutC30 was cultivated at 27° C. and 90 rpm in 25 ml of YP medium supplemented with 2% (w/v) glucose and 10 mM uridine for 17 hours. Mycelia were collected by filtration using a Vacuum Driven Disposable Filtration System (Millipore, Bedford, Mass., USA) and washed twice with deionized water and twice with 1.2 M sorbitol. Protoplasts were generated by suspending the washed mycelia in 20 ml of 1.2 M sorbitol containing 15 mg of GLUCANEX™ (Novozymes A/S, Bagsvaerd, Denmark) per ml and 0.36 units of chitinase (Sigma Chemical Co., St. Louis, Mo., USA) per ml and incubating for 15-25 minutes at 34° C. with gentle shaking at 90 rpm. Protoplasts were collected by centrifuging for 7 minutes at 400×g and washed twice with cold 1.2 M sorbitol. The protoplasts were counted using a haemacytometer and resuspended in STC to a final concentration of $1\times10^8$ protoplasts per ml. Excess protoplasts were stored in a Cryo 1° C. Freezing Container (Nalgene, Rochester, N.Y., USA) at −80° C.

Approximately 4 μg of plasmids pSaMe-AaXYL and pSaMe-TRBXYL were digested with Pme I and added to 100 μl of protoplast solution and mixed gently, followed by 250 μl of 10 mM $CaCl_2$-10 mM Tris-HCl pH 7.5-60% PEG 4000, mixed, and incubated at room temperature for 30 minutes. STC (3 ml) was then added and mixed and the transformation solution was plated onto COVE plates using *Aspergillus nidulans* amdS selection. The plates were incubated at 28° C. for 5-7 days. Transformants were subcultured onto COVE2 plates and grown at 28° C.

Over 40 transformants were subcultured onto fresh plates containing acetamide and allowed to sporulate for 7 days at 28° C.

The *Trichoderma reesei* transformants were cultivated in 125 ml baffled shake flasks containing 25 ml of cellulase-inducing medium at pH 6.0 by inoculating spores of the transformants and incubating at 28° C. and 200 rpm for 7 days. *Trichoderma reesei* RutC30 was run as a control. Culture broth samples were removed at day 5. One ml of each culture broth was centrifuged at 15,700×g for 5 minutes in a micro-centrifuge and the supernatants transferred to new tubes.

SDS-PAGE was performed using CRITERION® Tris-HCl (5% resolving) gels (Bio-Rad Laboratories, Inc.) with a CRITERION® System. Five μl of day 7 supernatants (see above) were suspended in 2× concentration of Laemmli Sample Buffer (Bio-Rad Laboratories, Inc., Hercules, Calif., USA) and boiled in the presence of 5% beta-mercaptoethanol for 3 minutes. The supernatant samples were loaded onto a polyacrylamide gel and subjected to electrophoresis with 1×Tris/Glycine/SDS as running buffer (Bio-Rad Laboratories, Inc., Hercules, Calif., USA). The resulting gel was stained with BIO-SAFE™ Coomassie Stain. The transformant showing the highest expression of both the *A. aculeatus* GH10 xylanase and the *T. reesei* beta-xylosidase based on the protein gel was designated *T. reesei* SaMe-BXX13.

*Trichoderma reesei* SaMe-BXX13 was cultivated in 500 ml baffled shake flasks containing 250 ml of cellulase-inducing medium at pH 6.0 inoculated with spores of *T. reesei* SaMe-BXX13. Shake flasks were incubated at 28° C. at 200 rpm for five days. The culture broth was then filtered using an 0.22 μm EXPRESS™ Plus Membrane.

The filtered broth was concentrated and buffer exchanged using a tangential flow concentrator equipped with a 10 kDa polyethersulfone membrane to pH 4.0 with acetic acid. Sample was loaded onto a SP SEPHAROSE® column equilibrated in 50 mM sodium acetate pH 4.0, eluting bound proteins with a gradient of 0-1000 mM sodium chloride. Fractions were buffer exchanged into 20 mM sodium phosphate pH 7.0 using a tangential flow concentrator and applied to a Phenyl SUPEROSE™ column (HR 16/10) equilibrated with 1.5 M $(NH_4)_2SO_4$-20 mM sodium phosphate pH 7.0. Bound proteins were eluted with a linear gradient over 20 column volumes from 1.5 to 0 M $(NH_4)_2SO_4$ in 20 mM Tris-HCl pH 7.0. The protein fractions were buffer exchanged into 20 mM TEA HCl pH 7.5 using a tangential flow concentrator. Sample was applied to a MonoQ® column, equilibrated in 20 mM TEA HCl pH 7.5, eluting bound proteins with a gradient from 0-300 mM sodium chloride. Buffer of final protein fractions was 20 mM TEA-100 mM sodium chloride pH 7.5. Protein concentration was determined using a Microplate BCA™ Protein Assay Kit in which bovine serum albumin was used as a protein standard.

Example 30: Preparation of *Talaromyces emersonii* CBS 393.64 GH3 Beta-Xylosidase

*Talaromyces emersonii* CBS 393.64 (NN005049) beta-xylosidase (SEQ ID NO: 59 [DNA sequence] and SEQ ID NO: 60 [deduced amino acid sequence]) was prepared recombinantly according to Rasmussen et al., 2006, *Biotechnology and Bioengineering* 94: 869-876 using *Aspergillus oryzae* JaL355 as a host (WO 2003/070956).

The *Talaromyces emersonii* beta-xylosidase was purified according to Rasmussen et al., 2006, supra.

Example 31: Preparation of *Trichoderma reesei* RutC30 Cel7B Endoglucanase I

*Trichoderma reesei* RutC30 Cel7B endoglucanase I (EGI) (SEQ ID NO: 61 [DNA sequence] and SEQ ID NO: 62 [deduced amino acid sequence]) was prepared recombinantly according to WO 2005/067531 using *Aspergillus oryzae* JaL250 as a host.

The harvested broth was centrifuged in 500 ml bottles at 13,000×g for 20 minutes at 4° C. and then sterile filtered using a 0.22 μm polyethersulfone membrane (Millipore, Bedford, Mass., USA). The filtered broth was concentrated and buffer exchanged with 20 mM Tris-HCl pH 8.5 using a tangential flow concentrator equipped with a 10 kDa polyethersulfone membrane. The sample was loaded onto a Q SEPHAROSE® High Performance column equilibrated with 20 mM Tris-HCl pH 8.5, and step eluted with equilibration buffer containing 600 mM NaCl. Flow-through and eluate fractions were analyzed by SGS-PAGE gel analysis using a CRITERION™ stain-free imaging system (Bio-Rad Laboratories, Inc., Hercules, Calif., USA). The eluate fractions containing *Trichoderma reesei* Cel7B EGI were pooled, concentrated and buffer exchanged into 20 mM Tris-HCl pH 8.5. Protein concentration was determined using a Microplate BCA™ Protein Assay Kit in which bovine serum albumin was used as a protein standard.

Example 32: Preparation of *Trichoderma reesei* RutC30 Cel7A Cellobiohydrolase I

*Trichoderma reesei* RutC30 Cel7A cellobiohydrolase I (CBHI) (SEQ ID NO: 63 [DNA sequence] and SEQ ID NO: 64 [deduced amino acid sequence]) was prepared as described by Ding and Xu, 2004, "Productive cellulase adsorption on cellulose" in Lignocellulose Biodegradation (Saha, B. C. ed.), Symposium Series 889, pp. 154-169, American Chemical Society, Washington, D.C. Protein concentration was determined using a Microplate BCA™ Protein Assay Kit in which bovine serum albumin was used as a protein standard.

Example 33: Preparation of *Trichoderma reesei* RutC30 Cel6A Cellobiohydrolase II The *Trichoderma reesei* RutC30 Cel6A cellobiohydrolase II gene (SEQ ID NO: 65 [DNA sequence] and SEQ ID NO: 66 [deduced amino acid sequence]) was isolated from *Trichoderma reesei* RutC30 as described in WO 2005/056772.

The *Trichoderma reesei* Cel6A cellobiohydrolase II gene was expressed in *Fusarium venenatum* using pEJG61 as an expression vector according to the procedures described in U.S. Published Application No. 20060156437. Fermentation was performed as described in U.S. Published Application No. 20060156437.

Filtered broth was desalted and buffer-exchanged into 20 mM sodium acetate-150 mM NaCl pH 5.0 using a HIPREP® 26/10 Desalting Column according to the manufacturer's instructions. Protein concentration was determined using a Microplate BCA™ Protein Assay Kit in which bovine serum albumin was used as a protein standard.

Example 34: Pretreated Corn Stover Hydrolysis Assay

Corn stover was pretreated at the U.S. Department of Energy National Renewable Energy Laboratory (NREL) using 1.4 wt % sulfuric acid at 165° C. and 107 psi for 8 minutes. The water-insoluble solids in the pretreated corn stover (PCS) contained 56.5% cellulose, 4.6% hemicellulose and 28.4% lignin. Cellulose and hemicellulose were determined by a two-stage sulfuric acid hydrolysis with subsequent analysis of sugars by high performance liquid chromatography using NREL Standard Analytical Procedure #002. Lignin was determined gravimetrically after hydrolyzing the cellulose and hemicellulose fractions with sulfuric acid using NREL Standard Analytical Procedure #003.

Unmilled, unwashed PCS (whole slurry PCS) was prepared by adjusting the pH of PCS to 5.0 by addition of 10 M NaOH with extensive mixing, and then autoclaving for 20 minutes at 120° C. The dry weight of the whole slurry PCS was 29%. The PCS was used unwashed or washed with water. Milled unwashed PCS (dry weight 32.35%) was prepared by milling whole slurry PCS in a Cosmos ICMG 40 wet multi-utility grinder (EssEmm Corporation, Tamil Nadu, India). Milled washed PCS (dry weight 32.35%) was prepared in the same manner, with subsequent washing with deionized water and decanting off the supernatant fraction repeatedly.

The hydrolysis of PCS was conducted using 2.2 ml deep-well plates (Axygen, Union City, Calif., USA) in a total reaction volume of 1.0 ml. The hydrolysis was performed with 50 mg of PCS (insoluble solids in case of unwashed PCS and total solids in case of washed PCS) per ml of 50 mM sodium acetate pH 5.0 buffer containing 1 mM manganese sulfate and various protein loadings of various enzyme compositions (expressed as mg protein per gram of cellulose). Enzyme compositions were prepared and then added simultaneously to all wells in a volume ranging from 50 μl to 200 μl, for a final volume of 1 ml in each reaction. The plate was then sealed using an ALPS-300™ plate heat sealer (Abgene, Epsom, United Kingdom), mixed thoroughly, and incubated at a specific temperature for 72 hours. All experiments reported were performed in triplicate.

Following hydrolysis, samples were filtered using a 0.45 μm MULTISCREEN® 96-well filter plate (Millipore, Bedford, Mass., USA) and filtrates analyzed for sugar content as described below. When not used immediately, filtered aliquots were frozen at −20° C. The sugar concentrations of samples diluted in 0.005 M $H_2SO_4$ were measured using a 4.6×250 mm AMINEX® HPX-87H column (Bio-Rad Laboratories, Inc., Hercules, Calif., USA) by elution with 0.05% w/w benzoic acid-0.005 M $H_2SO_4$ at 65° C. at a flow rate of 0.6 ml per minute, and quantitation by integration of the glucose, cellobiose, and xylose signals from refractive index detection (CHEMSTATION®, AGILENT® 1100 HPLC, Agilent Technologies, Santa Clara, Calif., USA) calibrated by pure sugar samples. The resultant glucose and cellobiose equivalents were used to calculate the percentage of cellulose conversion for each reaction.

Glucose, cellobiose, and xylose were measured individually. Measured sugar concentrations were adjusted for the appropriate dilution factor. In case of unwashed PCS, the net concentrations of enzymatically-produced sugars were determined by adjusting the measured sugar concentrations for corresponding background sugar concentrations in unwashed PCS at zero time point. All HPLC data processing was performed using MICROSOFT EXCEL™ software (Microsoft, Richland, Wash., USA).

The degree of cellulose conversion to glucose was calculated using the following equation:% conversion=glucose concentration/glucose concentration in a limit digest. To calculate total conversion the glucose and cellobiose values were combined. Cellobiose concentration was multiplied by 1.053 in order to convert to glucose equivalents and added to the glucose concentration. The degree of total cellulose conversion was calculated using the following equation:

% conversion=[glucose concentration+1.053×(cellobiose concentration)]/[(glucose concentration+1.053×(cellobiose concentration) in a limit digest].

The 1.053 factor for cellobiose takes into account the increase in mass when cellobiose is converted to glucose. In order to calculate % conversion, a 100% conversion point was set based on a cellulase control (50-100 mg of *Trichoderma reesei* cellulase per gram cellulose), and all values were divided by this number and then multiplied by 100. Triplicate data points were averaged and standard deviation was calculated.

Example 35: Evaluation of Several Cellulolytic Proteins Replacing CBHI, CBHII, and EGII Components in a Reconstituted *Trichoderma reesei*-Based Enzyme Composition for Improved Performance at 50° C., 55° C., and 60° C.

Several cellulolytic proteins were tested in various combinations at 50° C., 55° C., and 60° C. against a reconstituted *Trichoderma reesei*-based enzyme composition that included four major *Trichoderma reesei* cellulases (45% *Trichoderma reesei* Cel7A CBHI, 25% *Trichoderma reesei* Cel6A CBHII, 5% *Trichoderma reesei* Cel7B EGI, 5% *Trichoderma reesei* Cel5A EGII), a beta-glucosidase (10% *Aspergillus fumigatus* Cel3A beta-glucosidase), and a Family 61 polypeptide having cellulolytic enhancing activity (10% *Thermoascus aurantiacus* GH61A polypeptide).

The evaluated enzymes included *Chaetomium thermophilum* Cel7A CBHI, *Myceliophthora thermophila* Cel7A CBHI, *Myceliophthora thermophila* Cel6A CBHII, and *Myceliophthora thermophila* Cel5A EGII. All enzyme compositions contained 45% CBHI, 25% CBHII, 5% *Trichoderma reesei* Cel7B EGI, 5% EGII, 10% *Aspergillus fumigatus* beta-glucosidase, and 10% *Thermoascus aurantiacus* GH61A polypeptide having cellulolytic enhancing activity. All enzyme compositions, including the *Trichoderma reesei*-based composition, were applied at the same dosage of 5 mg protein per g cellulose.

The assay was performed as described in Example 34. The 1 ml reactions with 5% milled washed PCS were conducted for 72 hours in 50 mM sodium acetate pH 5.0 buffer containing 1 mM manganese sulfate. All reactions were performed in triplicate and involved single mixing at the beginning of hydrolysis.

The results as shown in FIG. 1 demonstrated that the best enzyme composition for cellulose hydrolysis included *Chaetomium thermophilum* Cel7A CBHI, *Myceliophthora thermophila* Cel6A CBHII, *Trichoderma reesei* Cel7B EGI, *Myceliophthora thermophila* Cel5A EGII, *Aspergillus fumigatus* beta-glucosidase, and *Thermoascus aurantiacus* GH61A polypeptide having cellulolytic enhancing activity. Replacement of the *Trichoderma reesei* Cel7A CBHI, Cel6A CBHII, and Cel5A EGII with *Chaetomium thermophilum* Cel7A CBHI, *Myceliophthora thermophila* Cel6A CBHII, and *Myceliophthora thermophila* Cel5A EGII significantly improved the degree of cellulose conversion to glucose at 60° C. (from 50% to 65%). The improved composition hydrolyzed milled washed PCS almost as efficiently at 60° C. (65% cellulose conversion to glucose) as the *Trichoderma reesei*—based composition at 50° C. (68%).

Example 36: Evaluation of GH61 Polypeptides Having Cellulolytic Enhancing Activity for the Ability to Enhance PCS-Hydrolyzing Activity of a High-Temperature Enzyme Composition at 50° C., 55° C., and 60° C.

*Thermoascus aurantiacus* GH61A polypeptide having cellulolytic enhancing activity and *Thielavia terrestris* GH61E polypeptide having cellulolytic enhancing activity, prepared as described herein, were tested at 10% total protein addition for the ability to stimulate a high-temperature cellulase composition at 50° C., 55° C., and 60° C. using milled washed PCS. The compositions consisting of 45% *Chaetomium thermophilum* Cel7A CBHI, 25% *Myceliophthora thermophila* Cel6A CBHII, 5% *Trichoderma reesei* Cel7B EGI, 5% *Myceliophthora thermophila* Cel5A EGII, 10% *Aspergillus fumigatus* beta-glucosidase, and 10%

GH61 polypeptide having cellulolytic enhancing activity were used for hydrolysis of milled washed PCS at 5 mg protein per g cellulose, and the results were compared with the results for a high-temperature enzyme composition without a GH61 polypeptide, which was used at 4.5 mg protein per g cellulose. The assay was performed as described in Example 34. The 1 ml reactions with 5% milled washed PCS were conducted for 72 hours in 50 mM sodium acetate pH 5.0 buffer containing 1 mM manganese sulfate. All reactions were performed in triplicate and involved single mixing at the beginning of hydrolysis.

Figure 2:
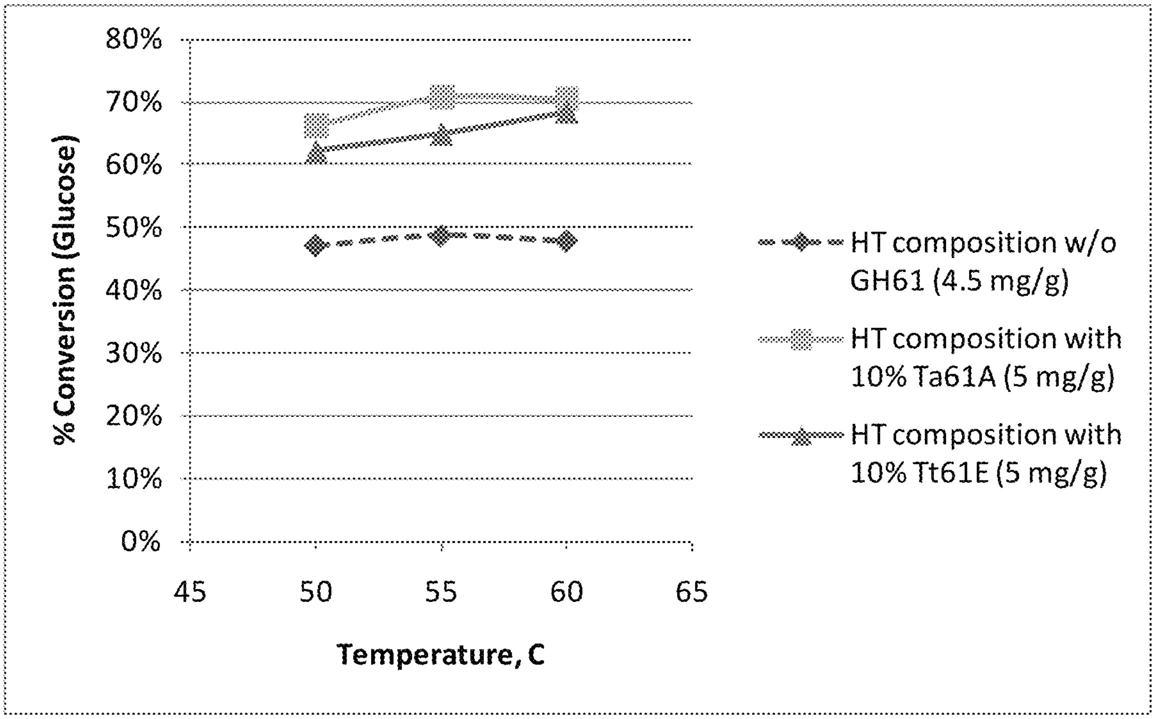
FIG. 2 shows the effect of *Thermoascus aurantiacus* GH61A or *Thielavia terrestris* GH61E GH61 polypeptides having cellulolytic enhancing activity on PCS-hydrolysing activity of a high-temperature enzyme composition at 50° C., 55° C., and 60° C.

The results shown in FIG. 2 demonstrated that the *Thermoascus aurantiacus* GH61A and *Thielavia terrestris* GH61E polypeptides were able to significantly enhance PCS-hydrolyzing activity of the high-temperature enzyme composition at all temperatures from 50° C. to 60° C., and that the stimulating effect was more pronounced at higher temperatures. At 60° C., a composition without a GH61 polypeptide showed 48% conversion of cellulose to glucose. For comparison, compositions that included *Thermoascus aurantiacus* GH61A or *Thielavia terrestris* GH61E polypeptides showed 70% and 68% conversion of cellulose to glucose, respectively.

Example 37: Evaluation of a Binary Composition of *Thermoascus aurantiacus* GH61A and *Thielavia terrestris* GH61E GH61 Polypeptides Having Cellulolytic Enhancing Activity for the Ability to Enhance PCS-Hydrolyzing Activity of a High-Temperature Enzyme Composition at 50° C., 55° C., and 60° C.

The boosting performance of a binary composition comprising equal amounts (on a protein basis) of *Thermoascus aurantiacus* GH61A and *Thielavia terrestris* GH61E GH61 polypeptides having cellulolytic enhancing activity was compared with the boosting performance of the individual GH61 proteins alone at equivalent total protein loading at 50° C., 55° C., and 60° C. The high-temperature enzyme compositions included 45% *Chaetomium thermophilum Cel*7A CBHI, 25% *Myceliophthora thermophila* Cel6A CBHII, 5% *Trichoderma reesei* Cel7B EGI, 5% *Myceliophthora thermophila* Cel5A EGII, 10% *Aspergillus fumigatus* beta-glucosidase, and 10% GH61 component (either an individual polypeptide or a binary composition). The total protein loading in hydrolysis reactions was 5 mg protein per g cellulose.

The assay was performed as described in Example 34. The 1 ml reactions with 5% milled washed PCS were conducted for 72 hours in 50 mM sodium acetate pH 5.0 buffer containing 1 mM manganese sulfate. All reactions were performed in triplicate and involved single mixing at the beginning of hydrolysis.

Figure 3:
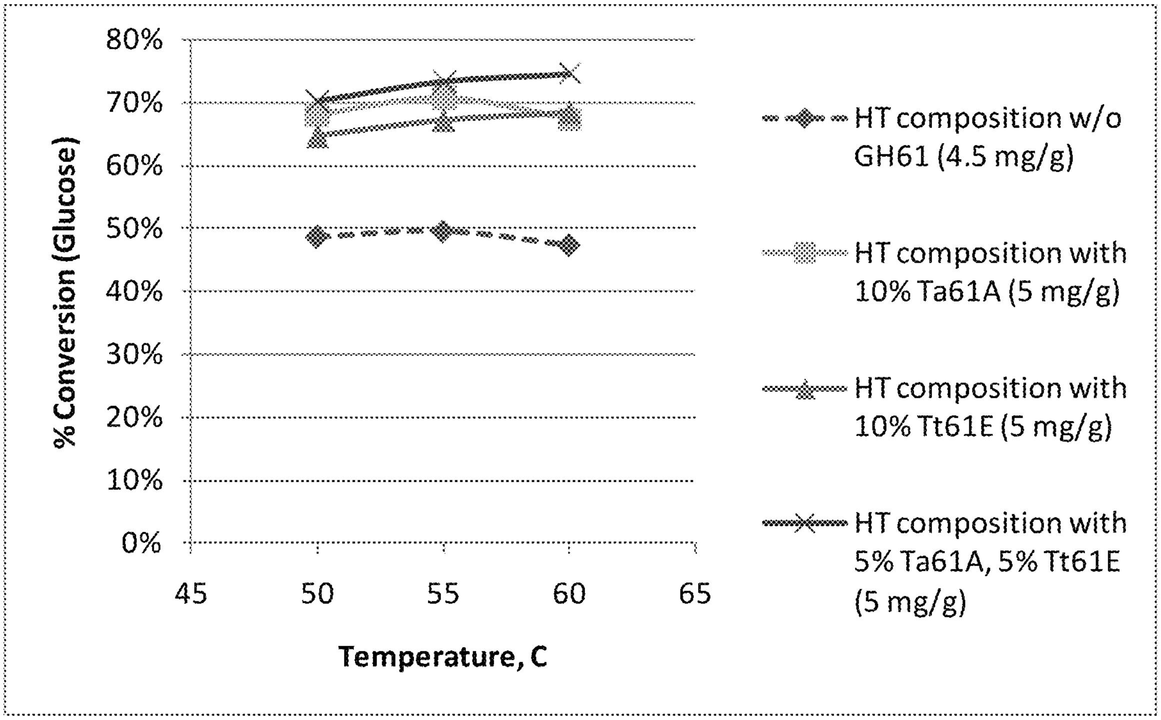
FIG. 3 shows the boosting performance of a binary composition comprising equal amounts of *Thermoascus aurantiacus* GH61A and *Thielavia terrestris* GH61E GH61 polypeptides having cellulolytic enhancing activity in comparison with the boosting performance of the individual GH61 polypeptides in hydrolysis of milled washed PCS at 50° C., 55° C., and 60° C.

The results shown in FIG. 3 demonstrated that the binary combination of the two GH61 polypeptides having cellulolytic enhancing activity, *Thermoascus aurantiacus* GH61A and *Thielavia terrestris* GH61E, provided greater enhancement than either of the GH61 proteins alone. The effect was especially pronounced at 60° C.

Example 38: Evaluation of Binary Compositions Containing Different Ratios of *Thermoascus aurantiacus* GH61A and *Thielavia terrestris* GH61E GH61 Polypeptides Having Cellulolytic Enhancing Activity for the Ability to Enhance PCS-Hydrolyzing Activity of a High-Temperature Enzyme Composition at 60° C.

After determining that a 1:1 composition of *Thermoascus aurantiacus* GH61A and *Thielavia terrestris* GH61E GH61 polypeptides having cellulolytic enhancing activity performed better in enhancing the PCS-hydrolyzing activity of a high-temperature enzyme composition than either protein alone, the effect was analyzed in more detail by examining different ratios of the *Thermoascus aurantiacus* GH61A and *Thielavia terrestris* GH61E polypeptides. The various binary compositions of the GH61 polypeptides were added at 0.5 mg protein per g cellulose to a high-temperature enzyme composition (4.5 mg protein per g cellulose) so that the final mixture consisted of 45% *Chaetomium thermophilum* Cel7A CBHI, 25% *Myceliophthora thermophila Cel*6A CBHII, 5% *Trichoderma reesei* Cel7B EGI, 5% *Myceliophthora thermophila* Cel5A EGII, 10% *Penicillium brasilianum* beta-glucosidase, and 10% GH61 component (either an individual GH61 polypeptide or a binary composition).

The assay was performed as described in Example 34. The 1 ml reactions with 5% milled washed PCS were conducted for 72 hours in 50 mM sodium acetate pH 5.0 buffer containing 1 mM manganese sulfate. All reactions were performed in triplicate and involved single mixing at the beginning of hydrolysis.

Figure 4:
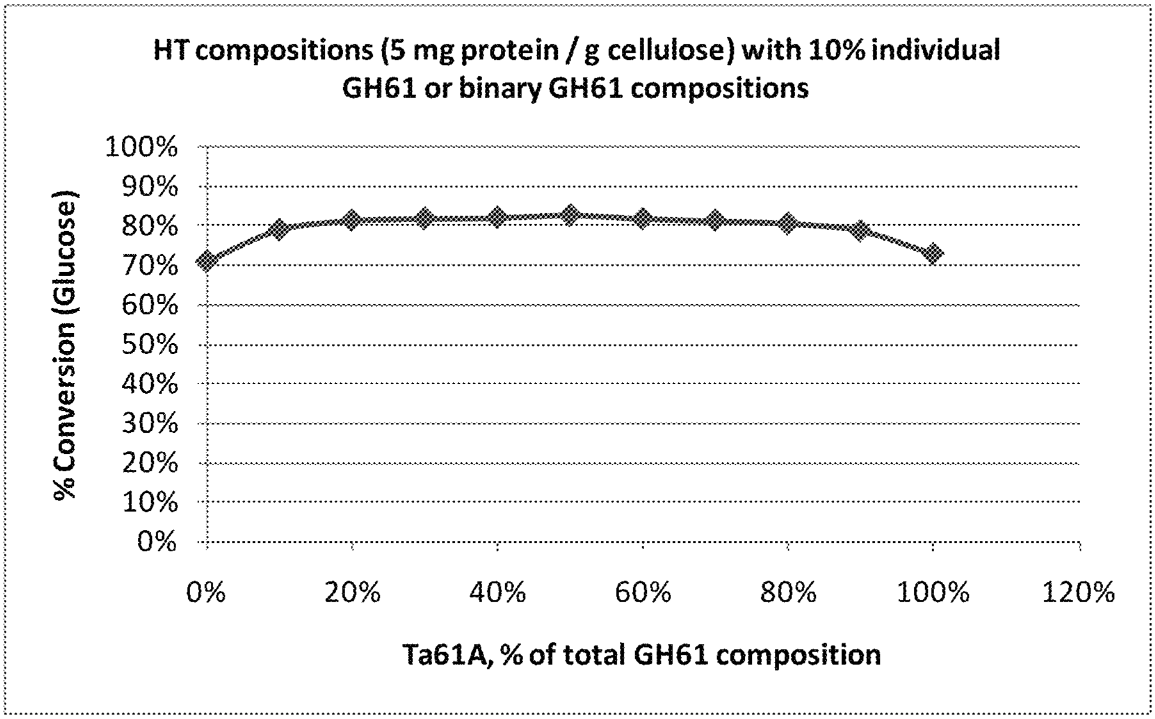
FIG. 4 shows the effect of compositions containing different ratios of *Thermoascus aurantiacus* GH61A and *Thielavia terrestris* GH61E polypeptides on PCS-hydrolysing activity of a high-temperature enzyme composition at 60° C.

The results are shown in Table 1 and FIG. 4. All binary compositions of *Thermoascus aurantiacus* GH61A and *Thielavia terrestris* GH61E GH61 polypeptides having cellulolytic enhancing activity provided significantly better enhancement of PCS hydrolysis by the high-temperature enzyme composition than either protein alone. The best performance was obtained for binary GH61 compositions that included at least 20% of either *Thermoascus aurantiacus* GH61A or *Thielavia terrestris* GH61E polypeptide having cellulolytic enhancing activity.

TABLE 1

Addition of binary GH61 polypeptide compositions (0.5 mg protein per g cellulose) to a high-temperature enzyme composition (4.5 mg protein per g cellulose) at 60° C.

| mg protein per g cellulose | | % of total GH61 addition | | |
|---|---|---|---|---|
| *Thermoascus aurantiacus* GH61A | *Thielavia terrestris* GH61E | *Thermoascus aurantiacus* GH61A | *Thielavia terrestris* GH61E | % Conversion |
| 0.00 | 0.00 | 0 | 0 | 47.9 |
| 0.00 | 0.50 | 0 | 100 | 71.0 |
| 0.05 | 0.45 | 10 | 90 | 79.0 |
| 0.10 | 0.40 | 20 | 80 | 81.3 |
| 0.15 | 0.35 | 30 | 70 | 81.8 |
| 0.20 | 0.30 | 40 | 60 | 82.0 |
| 0.25 | 0.25 | 50 | 50 | 82.7 |
| 0.30 | 0.20 | 60 | 40 | 81.8 |
| 0.35 | 0.15 | 70 | 30 | 81.2 |
| 0.40 | 0.10 | 80 | 20 | 80.6 |
| 0.45 | 0.05 | 90 | 10 | 78.8 |
| 0.50 | 0.00 | 100 | 0 | 72.8 |

Example 39: Evaluation of Different Levels of a Binary 1:1 Composition Comprising *Thermoascus aurantiacus* GH61A and *Thielavia terrestris* GH61E GH61 Polypeptides Having Cellulolytic Enhancing Activity for the Ability to Enhance PCS-Hydrolyzing Activity of a High-Temperature Enzyme Composition at 60° C.

The ability of *Thermoascus aurantiacus* GH61A polypeptide having cellulolytic enhancing activity, *Thielavia terrestris* GH61E polypeptide having cellulolytic enhancing activity, or their binary 1:1 composition (on a protein basis) to stimulate a high-temperature enzyme composition was examined by adding different GH61 protein loadings (0.125, 0.25, 0.5, 1.0, 1.5 mg protein per g cellulose) to a constant loading of the high-temperature enzyme composition (4.5 mg per g cellulose) at 60° C. The high-temperature enzyme composition contained 45% *Chaetomium thermophilum* Cel7A CBHI, 25% *Myceliophthora thermophila* Cel6A CBHII, 5% *Trichoderma reesei* Cel7B EGI, 5% *Myceliophthora thermophila* Cel5A EGII, and 10% *Penicillium brasilianum* Cel3A beta-glucosidase.

The assay was performed as described in Example 34. The 1 ml reactions with 5% milled washed PCS were conducted for 72 hours in 50 mM sodium acetate pH 5.0 buffer containing 1 mM manganese sulfate. All reactions were performed in triplicate and involved single mixing at the beginning of hydrolysis.

Figure 5:
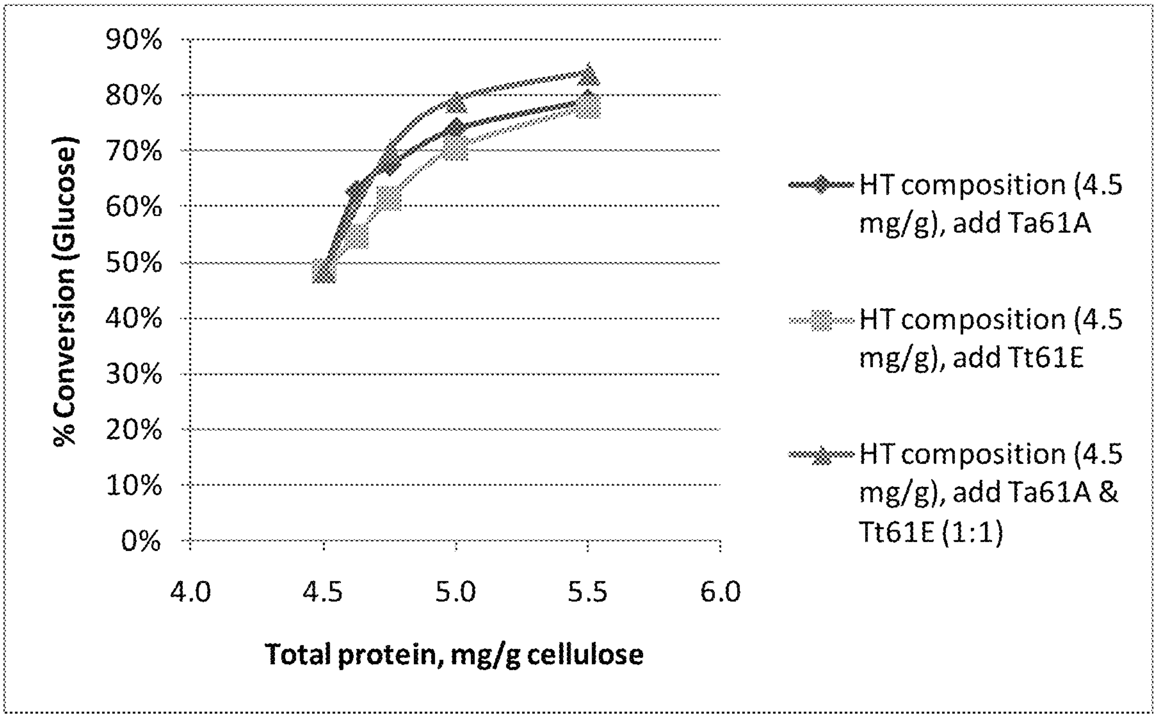
FIG. 5 shows the effect of different levels of individual *Thermoascus aurantiacus* GH61A and *Thielavia terrestris* GH61E GH61 polypeptides having cellulolytic enhancing activity and their binary 1:1 composition on PCS-hydrolyzing activity of a high-temperature enzyme composition at 60° C.

The results shown in FIG. 5 demonstrated that at equivalent protein loadings, the 1:1 compositions of *Thermoascus aurantiacus* GH61A and *Thielavia terrestris* GH61E GH61 polypeptides having cellulolytic enhancing activity provided greater PCS hydrolysis enhancement than either of the GH61 proteins alone. The effect was especially pronounced at relatively high additions of the GH61 proteins. The effect saturated when the level of the GH61 binary composition reached approximately 20% of the total protein loading.

Example 40: Effect of *Thermobifida fusca* GH11 Xylanase on Saccharification of Milled Washed PCS by a High-Temperature Enzyme Composition at 50-65° C.

The ability of *Thermobifida fusca* GH11 xylanase (0.5 mg protein per g cellulose) to stimulate saccharification of milled washed PCS by a high-temperature enzyme composition (5 mg protein per g cellulose) was examined at 50° C., 55° C., 60° C., and 65° C. For comparison, the high-temperature enzyme composition without a supplemental xylanase was tested at 5.0, 5.5, and 6.0 mg protein per g cellulose. The high-temperature enzyme composition included 45% *Chaetomium thermophilum* Cel7A CBHI, 25% *Myceliophthora thermophila* Cel6A CBHII, 5% *Trichoderma reesei* Cel7B EGI, 5% *Myceliophthora thermophila* Cel5A EGII, 10% *Penicillium brasilianum* Cel3A beta-glucosidase, and 10% *Thermoascus aurantiacus* GH61A polypeptide having cellulolytic enhancing activity.

The assay was performed as described in Example 34. The 1 ml reactions with 5% milled washed PCS were conducted for 72 hours in 50 mM sodium acetate pH 5.0 buffer containing 1 mM manganese sulfate. All reactions were performed in triplicate and involved single mixing at the beginning of hydrolysis.

Figure 6:
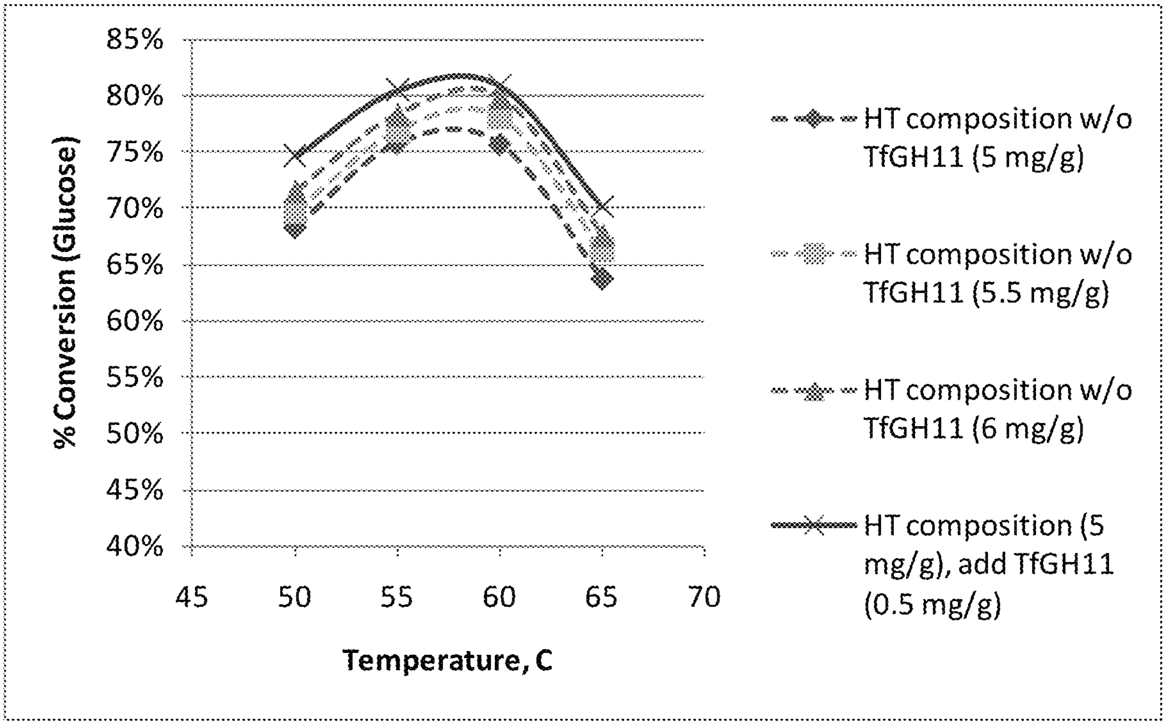
FIG. 6 shows the effect of a *Thermobifida fusca* GH11 xylanase on hydrolysis of milled washed PCS by a high-temperature enzyme composition at 50-65° C.

The results shown in FIG. 6 demonstrated that addition of *Thermobifida fusca* GH11 xylanase significantly improved performance of the high-temperature enzyme composition at all temperatures from 50° C. to 65° C., increasing the cellulose conversion to glucose by 4-7% after 72 hours of hydrolysis.

Example 41: Replacement of *Chaetomium thermophilum* Cel7A Cellobiohydrolase I in a High-Temperature Enzyme Composition with Various Thermostable CBHI Proteins at 50-65° C.

The ability of several thermostable CBHI proteins to replace *Chaetomium thermophilum* Cel7A CBHI in a high-temperature enzyme composition (4 mg total protein per g cellulose) was tested at 50° C., 55° C., 60° C., and 65° C. The high-temperature enzyme composition included 45% *Chaetomium thermophilum* Cel7A CBHI, 25% *Myceliophthora thermophila* Cel6A CBHII, 10% *Myceliophthora thermophila* Cel5A EGII, 5% *Thermoascus aurantiacus* GH61A polypeptide having cellulolytic enhancing activity, 5% *Thielavia terrestris* GH61E polypeptide having cellulolytic enhancing activity, and 10% *Penicillium brasilianum* Cel3A beta-glucosidase.

The following recombinant CBHI cellulases from an *Aspergillus oryzae* expression host were tested as a replacement for *Chaetomium thermophilum* Cel7A CBHI: *Myceliophthora thermophila* Cel7A, *Aspergillus fumigatus* Cel7A, and *Thermoascus aurantiacus* Cel7A.

The assay was performed as described in Example 34. The 1 ml reactions with 5% milled washed PCS were conducted for 72 hours in 50 mM sodium acetate pH 5.0 buffer containing 1 mM manganese sulfate. All reactions were performed in triplicate and involved single mixing at the beginning of hydrolysis.

Figure 7:
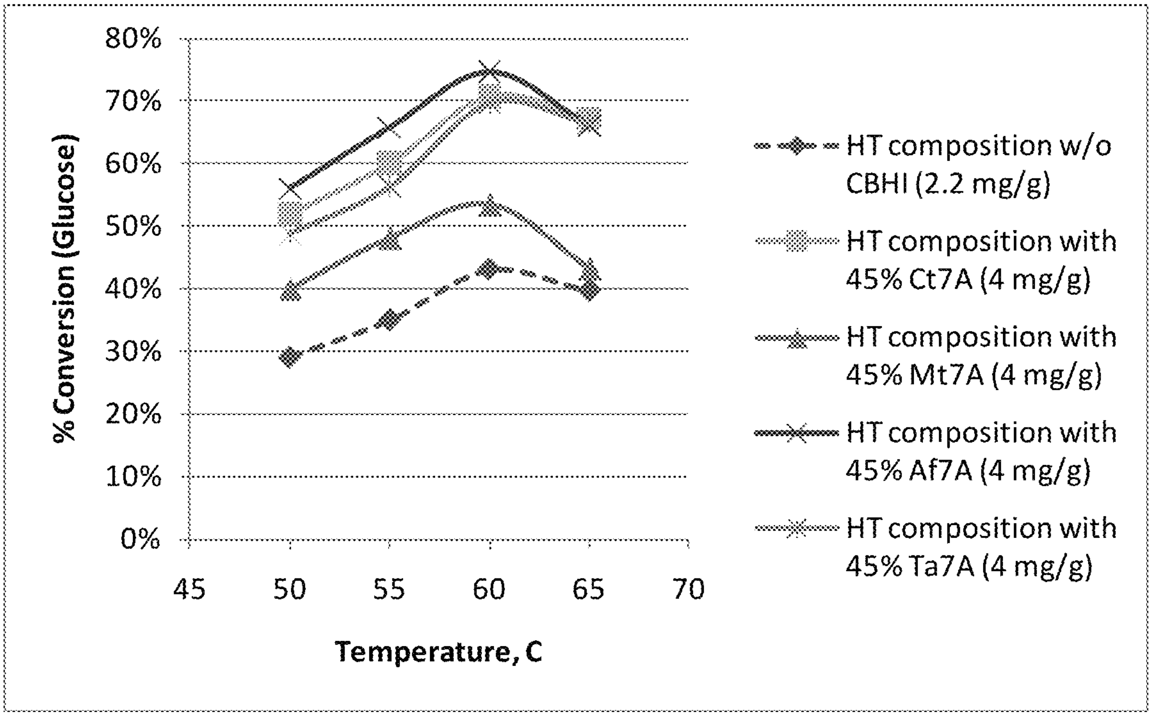
FIG. 7 shows the effect of replacing *Chaetomium thermophilum* Cel7A cellobiohydrolase I in a high-temperature enzyme composition with various thermostable cellobiohydrolase I proteins on hydrolysis of milled washed PCS at 50-65° C.

As shown in FIG. 7, the replacement of *Chaetomium thermophilum* Cel7A CBHI with *Aspergillus fumigatus* Cel7A CBHI gave the best hydrolysis results, providing an almost 6% improvement of the final hydrolysis yield at 60° C. Surprisingly, a native *Thermoascus aurantiacus* Cel7A CBHI, which contained no CBM, also showed a remarkably good performance at elevated temperatures.

Example 42: Comparison of High-Temperature Enzyme Compositions Containing *Aspergillus fumigatus* Cel7A CBHI or *Chaetomium thermophilum* Cel7A CBHI with *Trichoderma reesei*-Based Cellulase SaMe-MF268 (XCL-533) at 50° C. and 60° C.

Two high-temperature enzyme compositions that included either *Aspergillus fumigatus* Cel7A CBHI or *Chaetomium thermophilum* Cel7A CBHI were tested in comparison with *Trichoderma reesei*-based cellulase composition SaMe-MF268 (XCL-533) at four protein loadings (3.5, 4.0, 4.5, and 5.0 mg protein per g cellulose) and two temperatures (50° C. and 60° C.) using milled washed PCS as a substrate The high-temperature enzyme compositions included 45% Cel7A CBHI, 25% *Myceliophthora thermophila* Cel6A CBHII, 5% *Trichoderma reesei* Cel7B EGI, 5% *Myceliophthora thermophila* Cel5A EGII, 5% *Thermoascus aurantiacus* GH61A polypeptide having cellulolytic enhancing activity, 5% *Thielavia terrestris* GH61E polypeptide having cellulolytic enhancing activity, 7.5% *Penicillium brasilianum* GH3A beta-glucosidase, and 2.5% *Thermobifida fusca* GH11 xylanase. The *Trichoderma reesei*-based enzyme composition SaMe-MF268 (XCL-533) was obtained as described in WO 2008/151079. The composition comprises a *Thermoascus aurantiacus* GH61A polypeptide having cellulolytic enhancing activity, a beta-glucosidase fusion protein comprising the *Humicola insolens* endoglucanase V core polypeptide fused to the wild-type *Aspergillus oryzae* beta-glucosidase, a *Trichoderma reesei* Cel7A cellobiohydrolase I, a *Trichoderma reesei* Cel6A cellobiohydrolase II, a *Trichoderma reesei* Cel7B endoglucanase I, a *Trichoderma reesei* Cel5A endoglucanase II, a *Trichoderma reesei* Cel45A endoglucanase V, and a *Trichoderma reesei* Cel12A endoglucanase III.

The assay was performed as described in Example 34. The 1 ml reactions with 5% milled washed PCS were conducted for 72 hours in 50 mM sodium acetate pH 5.0 buffer containing 1 mM manganese sulfate. All reactions were performed in triplicate and involved single mixing at the beginning of hydrolysis.

Figure 8:
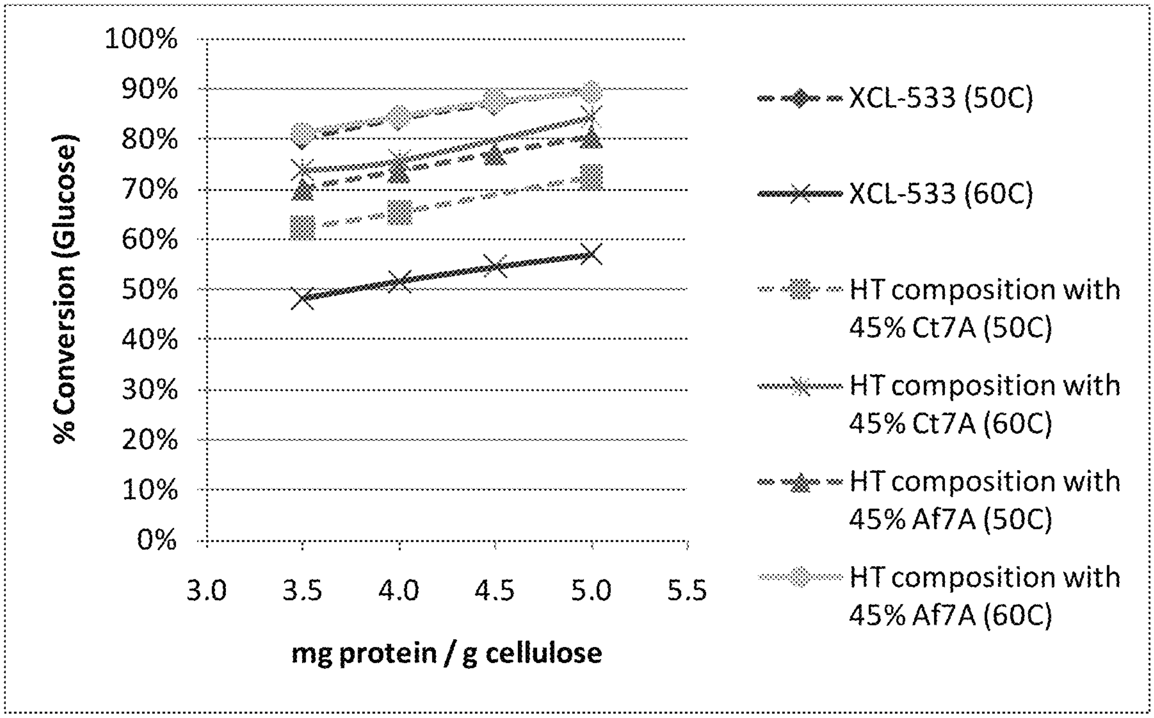
FIG. 8 shows a comparison of *Aspergillus fumigatus* Cel7A- and *Chaetomium thermophilum* Cel7A-based high-temperature enzyme compositions with *Trichoderma reesei*-based cellulase XCL-533 at 50° C. and 60° C. in hydrolysis of milled washed PCS.

Protein dose profiles for the *Aspergillus fumigatus* Cel7A CBHI-based composition in comparison with the *Chaetomium thermophilum* Cel7A CBHI-based composition and the *Trichoderma reesei*-based cellulase composition XCL-533 are shown in FIG. 8. The *Trichoderma reesei*-based cellulase composition XCL-533 showed poor performance at 60° C., while both high-temperature enzyme compositions were significantly activated by the temperature increase from 50° C. to 60° C. The high-temperature enzyme composition that included *Aspergillus fumigatus* Cel7A CBHI performed at 60° C. as well as the *Trichoderma reesei*-based cellulase composition XCL-533 performed at its optimum temperature of 50° C., requiring approximately 3.5 mg protein per g cellulose to achieve 80% conversion of cellulose to glucose in 72 hours. For the *Chaetomium thermophilum* Cel7A CBHI-based composition, the protein loading required to achieve the same degree of cellulose conversion at 60° C. was 4.5 mg protein per g cellulose.

Example 43: Hydrolysis Time-Course for *Aspergillus fumigatus* Cel7A CBHI-Based High-Temperature Enzyme Composition in Comparison with *Trichoderma reesei*-Based Cellulase Composition SaMe-MF268 at 50° C. and 60° C.

Hydrolysis performance of the *Aspergillus fumigatus* Cel7A CBHI-based high-temperature enzyme composition and the *Trichoderma reesei*-based cellulase composition SaMe-MF268 (XCL-533) was compared over a longer incubation time (five days) at 50° C. and 60° C. using milled washed PCS as a substrate. The *Aspergillus fumigatus* Cel7A CBHI-based enzyme composition included 45% *Aspergillus fumigatus* Cel7A CBHI, 25% *Myceliophthora thermophila* Cel6A CBHII, 5% *Trichoderma reesei* Cel7B EGI, 5% *Myceliophthora thermophila* Cel5A EGII, 5% *Thermoascus aurantiacus* GH61A polypeptide having cellulolytic enhancing activity, 5% *Thielavia terrestris* GH61E polypeptide having cellulolytic enhancing activity, 7.5% *Penicillium brasilianum* GH3A beta-glucosidase, and 2.5% *Thermobifida fusca* GH11 xylanase. The *Aspergillus fumigatus* Cel7A CBHI-based enzyme composition and the *Trichoderma reesei*-based cellulase composition XCL-533 were tested at four different protein loadings, 2.0, 3.0, 3.5, and 4.0 mg protein per g cellulose.

The assay was performed as described in Example 34. The 1 ml reactions with 5% milled washed PCS were conducted for 72 hours in 50 mM sodium acetate pH 5.0 buffer containing 1 mM manganese sulfate. All reactions were performed in triplicate and involved single mixing at the beginning of hydrolysis.

Figure 9:
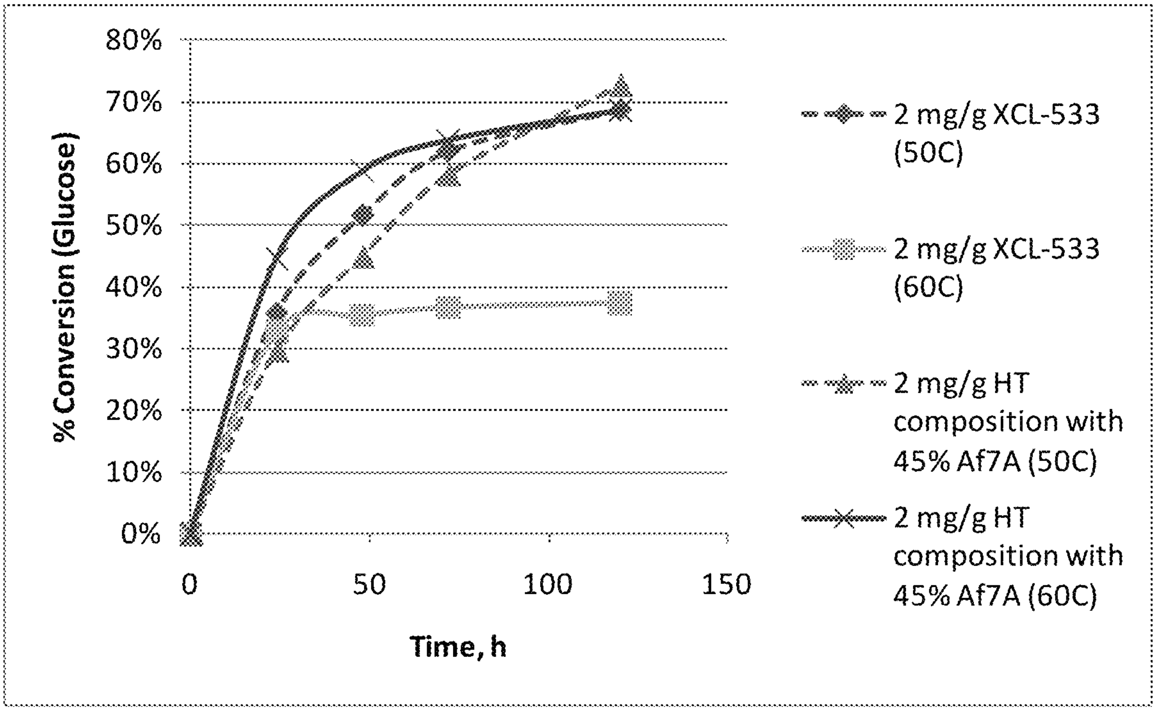
FIG. 9 shows the hydrolysis time-course for *Aspergillus fumigatus* Cel7A-based high-temperature enzyme composition in comparison with *Trichoderma reesei*-based cellulase XCL-533 at 50° C. and 60° C. (2 mg protein/g cellulose).

The time-course hydrolysis results for one of the four tested protein loadings (2 mg protein per g cellulose) are shown in FIG. 9. Similar trends were obtained for the three other protein loadings (data not shown). The *Trichoderma reesei*-based cellulase composition XCL-533 showed significantly reduced performance at 60° C., while the *Aspergillus fumigatus* Cel7A CBHI-based enzyme composition was significantly activated by the temperature increase from 50° C. to 60° C.

Comparison of the *Aspergillus fumigatus* Cel7A CBHI-based enzyme composition at 60° C. and the *Trichoderma reesei*-based cellulase composition XCL-533 at 50° C. showed that the high-temperature composition performed better than the *Trichoderma reesei*-based cellulase composition XCL-533 during the initial three days, and similarly to the *Trichoderma reesei*-based cellulase composition XCL-533 during the last two days of hydrolysis. Comparison of the *Aspergillus fumigatus* Cel7A CBHI-based enzyme composition and the *Trichoderma reesei*-based cellulase composition XCL-533 at the same temperature of 50° C. showed slower but steadier rates of glucose accumulation for the high-temperature composition in comparison with the *Trichoderma reesei*-based cellulase composition XCL-533, resulting in a better performance of the high-temperature composition in a long-term hydrolysis at 50° C. (5 days).

Example 44: Evaluation of Four Xylanases for Synergy with the *Aspergillus fumigatus Cel*7A CBH I-Based High-Temperature Enzyme Composition at 50° C., 55° C., and 60° C.

*Aspergillus aculeatus* GH10 xylanase II, *Aspergillus fumigatus* GH10 xyn3 xylanase, *Trichophaea saccata* GH10 xylanase, and *Thermobifida fusca* GH11 xylanase were assayed for synergy with a high-temperature enzyme composition containing Cel7A CBHI from *Aspergillus fumigatus* at 50° C., 55° C., and 60° C. using milled washed PCS as a substrate. The xylanases were added at 10% (0.35 mg protein per g cellulose) to a constant loading of the high-temperature enzyme composition (3.5 mg protein per g cellulose). The high-temperature enzyme composition included 45% *Aspergillus fumigatus* Cel7A CBHI, 25% *Myceliophthora thermophila* Cel6A CBHII, 5% *Trichoderma reesei* Cel7B EGI, 5% *Myceliophthora thermophila Cel*5A EGII, 5% *Thermoascus aurantiacus* GH61A polypeptide having cellulolytic enhancing activity, 5% *Thielavia terrestris* GH61E polypeptide having cellulolytic enhancing activity, and 10% *Penicillium brasilianum* Cel3A beta-glucosidase.

The assay was performed as described in Example 34. The 1 ml reactions with 5% milled washed PCS were conducted for 72 hours in 50 mM sodium acetate pH 5.0 buffer containing 1 mM manganese sulfate. All reactions were performed in triplicate and involved single mixing at the beginning of hydrolysis.

Figure 10:
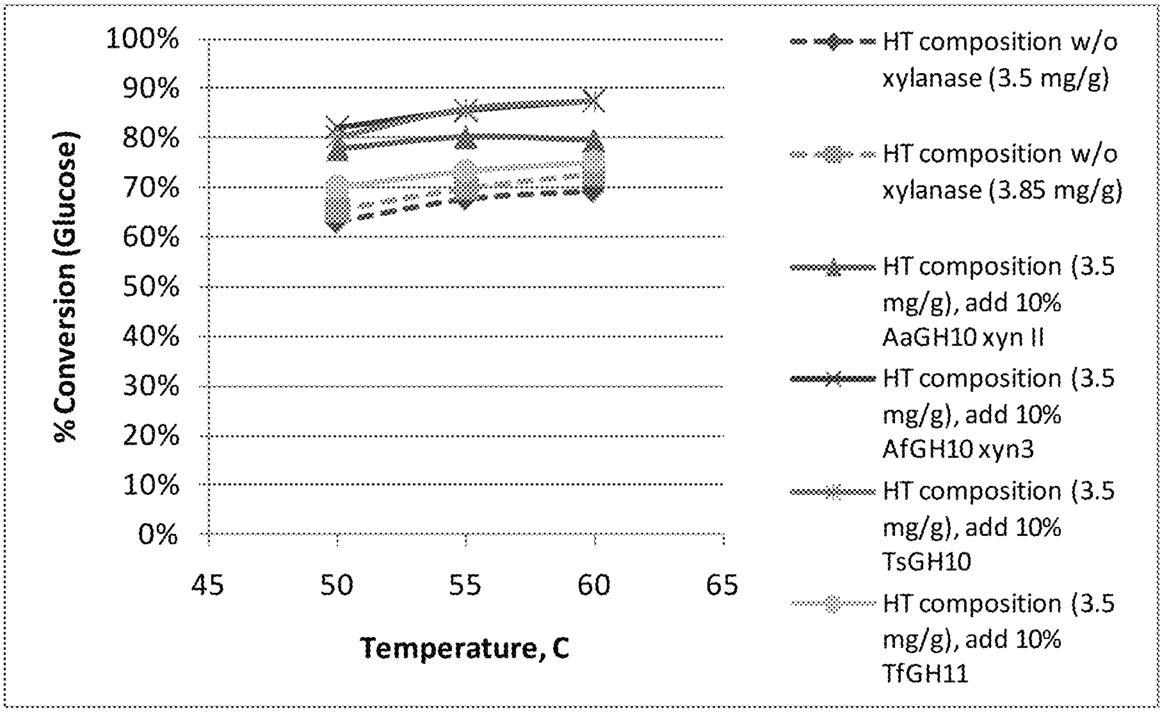
FIG. 10 shows an evaluation of *Aspergillus aculeatus* GH10 xylanase II, *Aspergillus fumigatus* GH10 xyn3 xylanase, *Trichophaea saccata* GH10 xylanase, and *Thermobifida fusca GH*11 xylanase at 10% addition (0.35 mg protein/g cellulose) to a high-temperature enzyme composition (3.5 mg protein/g cellulose) in hydrolysis of milled washed PCS at 50° C., 55° C., and 60° C.

The results shown in FIG. 10 demonstrated a considerable synergy between the xylanases and the high-temperature enzyme composition. At an equivalent protein loading (3.85 mg protein per g cellulose), all enzyme compositions that included xylanases achieved a significantly higher degree of cellulose conversion compared to the non-supplemented high-temperature enzyme composition. GH10 xylanases from *Aspergillus fumigatus* (xyn3) and *Trichophaea saccata* showed better performance than *Aspergillus aculeatus* GH10 xylanase II and *Thermobifida fusca* GH11 xylanase. The addition of the top two xylanases to the high-temperature enzyme composition resulted in an additional 11-16% conversion of cellulose to glucose in 72 hours compared to the non-supplemented enzyme composition (3.85 mg protein per g cellulose).

Example 45: Evaluation of *Aspergillus fumigatus* GH10 Xylanase Xyn3, *Trichophaea Saccata* GH10 Xylanase, and *Thermobifida fusca* GH11 Xylanase for Synergy with a High-Temperature Enzyme Composition at 60° C.

The ability of *Aspergillus fumigatus* GH10 xyn3 xylanase, *Trichophaea saccata* GH10 xylanase, and *Thermobifida fusca* GH11 xylanase to synergize with a high-temperature enzyme composition containing *Aspergillus fumigatus* Cel7A CBHI was further examined by adding different levels of each xylanase (1.25%, 2.5%, 5%, 10%, and 20%)

to a constant loading of the high-temperature enzyme composition (3 mg protein per g cellulose) at 60° C. using washed milled PCS as a substrate. The high-temperature enzyme composition included 45% *Aspergillus fumigatus* Cel7A CBHI, 25% *Myceliophthora thermophila* Cel6A CBHII, 5% *Trichoderma reesei* Cel7B EGI, 5% *Myceliophthora thermophila* Cel5A EGII, 5% *Thermoascus aurantiacus* GH61A polypeptide having cellulolytic enhancing activity, 5% *Thielavia terrestris* GH61E polypeptide having cellulolytic enhancing activity, and 10% *Penicillium brasilianum* Cel3A beta-glucosidase.

Figure 11:
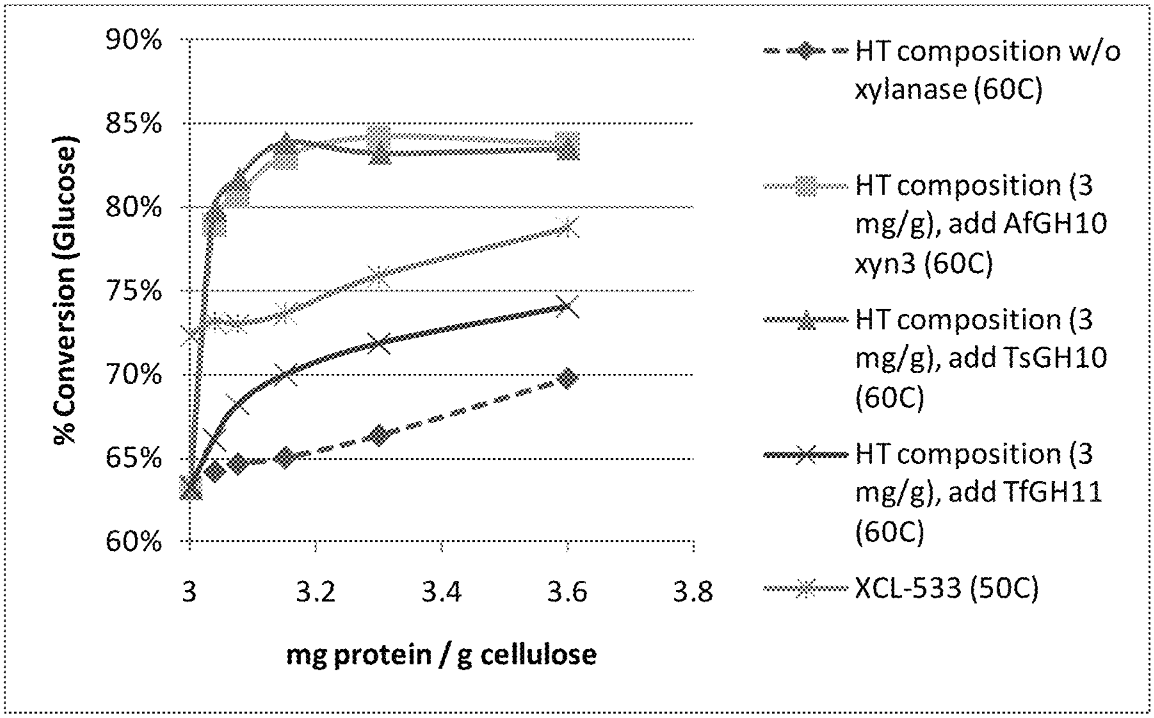
FIG. 11 shows an evaluation of *Aspergillus fumigatus* GH10 xyn3 xylanase, *Trichophaea saccata* GH10 xylanase, and *Thermobifida fusca* GH11 xylanase for synergy with a high-temperature enzyme composition in hydrolysis of milled washed PCS at 50° C., 55° C., and 60° C. Each xylanase was added at different levels (1.25%, 2.5%, 5%, 10%, and 20%) to a constant loading of the high-temperature enzyme composition (3 mg protein per g cellulose).

The assay was performed as described in Example 34. The 1 ml reactions with 5% milled washed PCS were conducted for 72 hours in 50 mM sodium acetate pH 5.0 buffer containing 1 mM manganese sulfate. All reactions were performed in triplicate and involved single mixing at the beginning of hydrolysis. The results are shown in FIG. 11.

*Aspergillus fumigatus* GH10 xyn3 and *Trichophaea saccata* GH10 xylanases performed similarly and showed better enhancement of PCS hydrolysis than *Thermobifida fusca* GH11 xylanase. The high-temperature enzyme composition supplemented with the GH10 xylanase from *Aspergillus fumigatus* or *Trichophaea saccata* significantly outperformed the *Trichoderma reesei*-based cellulase composition SaMe-MF268 (XCL-533) after 72 hours of incubation with milled washed PCS. The optimal addition level was about 5% for the *Aspergillus fumigatus* GH10 xyn3 and *Trichophaea saccata* GH10 xylanases and about 10% for the *Thermobifida fusca* GH11 xylanase. As shown in FIG. 11, the addition of either *Aspergillus fumigatus* GH10 xyn3 or *Trichophaea saccata* GH10 xylanase to the high-temperature composition at a level of only 5% at 60° C. enhanced the cellulose conversion to glucose from 65% to 83%. An equivalent loading of the *Trichoderma reesei*-based cellulase composition XCL-533 (3.15 mg protein per g cellulose) yielded 73% conversion of cellulose to glucose at 50° C.

Example 46: Comparison of *Aspergillus fumigatus* Cel7A-Based High-Temperature Enzyme Composition Containing *Aspergillus fumigatus* GH10 Xyn3 Xylanase with *Trichoderma reesei*-Based Cellulase SaMe-MF268

A high-temperature enzyme composition containing *Aspergillus fumigatus* GH10 xyn3 xylanase and the *Trichoderma reesei*-based cellulase composition SaMe-MF268 (XCL-533) were tested at three different protein loadings, 2.0, 3.0, and 4.0 mg protein per g cellulose, and the protein loading profile of the high-temperature enzyme composition at 60° C. was compared with the protein loading profile of the *Trichoderma reesei*-based cellulase composition XCL-533 at 50° C. The high-temperature enzyme composition contained 45% *Aspergillus fumigatus* Cel7A CBHI, 25% *Myceliophthora thermophila* Cel6A CBHII, 5% *Trichoderma reesei* Cel7B EGI, 5% *Myceliophthora thermophila* Cel5A EGII, 5% *Thermoascus aurantiacus* GH61A polypeptide having cellulolytic enhancing activity, 5% *Thielavia terrestris* GH61E polypeptide having cellulolytic enhancing activity, 5% *Penicillium brasilianum* Cel3A beta-glucosidase, and 5% *Aspergillus fumigatus* GH10 xyn3.

Figure 12:
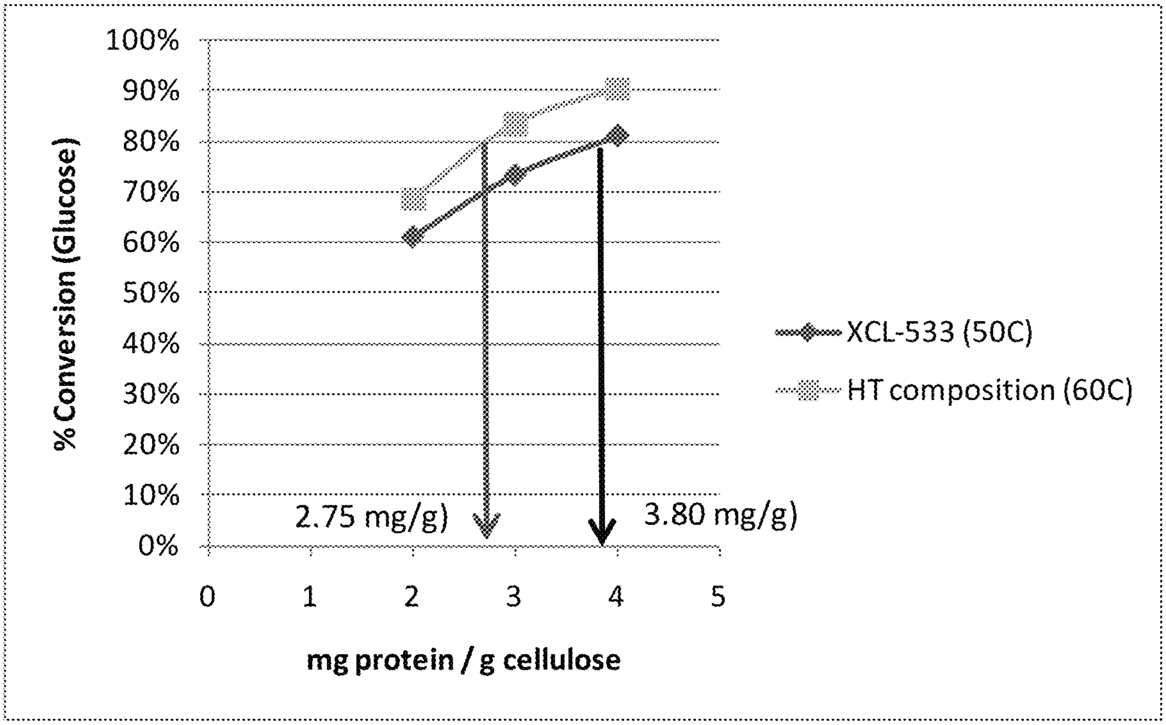
FIG. 12 shows a comparison of an improved high-temperature enzyme composition containing *Aspergillus fumigatus* GH10 xyn3 xylanase at 60° C. with *Trichoderma reesei*-based cellulase XCL-533 at 50° C. in hydrolysis of milled washed PCS.

The assay was performed as described in Example 34. The 1 ml reactions with 5% milled washed PCS were conducted for 72 hours in 50 mM sodium acetate pH 5.0 buffer containing 1 mM manganese sulfate. All reactions were performed in triplicate and involved single mixing at the beginning of hydrolysis. The results are shown in FIG. 12.

The experiment confirmed that the improved high-temperature enzyme composition containing *Aspergillus fumigatus* GH10 xyn3 xylanase significantly surpassed the performance of the *Trichoderma reesei*-based cellulase composition XCL-533. At 60° C., the high-temperature enzyme composition required a significantly lower protein loading (2.75 mg protein per g cellulose) than the *Trichoderma reesei*-based cellulase composition XCL-533 at 50° C. (3.80 mg protein per g cellulose) to hydrolyze 80% of cellulose to glucose in 72 hours.

Example 47: Comparison of High-Temperature Enzyme Compositions Containing *Aspergillus fumigatus* GH10 Xyn3 or *Trichophaea saccata* GH10 Xylanase with *Trichoderma reesei*-Based Cellulase SaMe-MF268 in Hydrolysis of Washed and Unwashed PCS Protein loading profiles of the improved high-temperature enzyme compositions containing either GH10 xylanase from *Aspergillus fumigatus* (xyn 3) or GH10 xylanase from *Trichophaea saccata* were compared with protein loading profiles of the *Trichoderma reesei*-based cellulase composition SaMe-MF268 (XCL-533) using milled washed and milled unwashed PCS. The high-temperature enzyme compositions included 45% *Aspergillus fumigatus* Cel7A CBHI, 25% *Myceliophthora thermophila* Cel6A CBHII, 5% *Trichoderma reesei Cel*7B EGI, 5% *Myceliophthora thermophila* Cel5A EGII, 5% *Thermoascus aurantiacus* GH61A polypeptide having cellulolytic enhancing activity, 5% *Thielavia terrestris* GH61E polypeptide having cellulolytic enhancing activity, 5% *Penicillium brasilianum* Cel3A beta-glucosidase, and 5% GH10 xylanase. The high-temperature enzyme compositions and the *Trichoderma reesei*-based cellulase composition XCL-533 were tested at five different protein loadings, 2.0, 3.0, 4.0, 5.0, and 6.0 mg protein per g cellulose. All reactions with the high-temperature enzyme compositions were performed at 60° C., while all reactions with the *Trichoderma reesei*-based cellulase composition XCL-533 were performed at 50° C.

The assay was performed as described in Example 34. The 1 ml reactions with milled washed or milled unwashed PCS were conducted for 72 hours in 50 mM sodium acetate pH 5.0 buffer containing 1 mM manganese sulfate. Washed PCS was used at 5% total solids, whereas unwashed PCS was used at 5% insoluble solids. All reactions were performed in triplicate and involved single mixing at the beginning of hydrolysis.

Figures 13A, 13B:
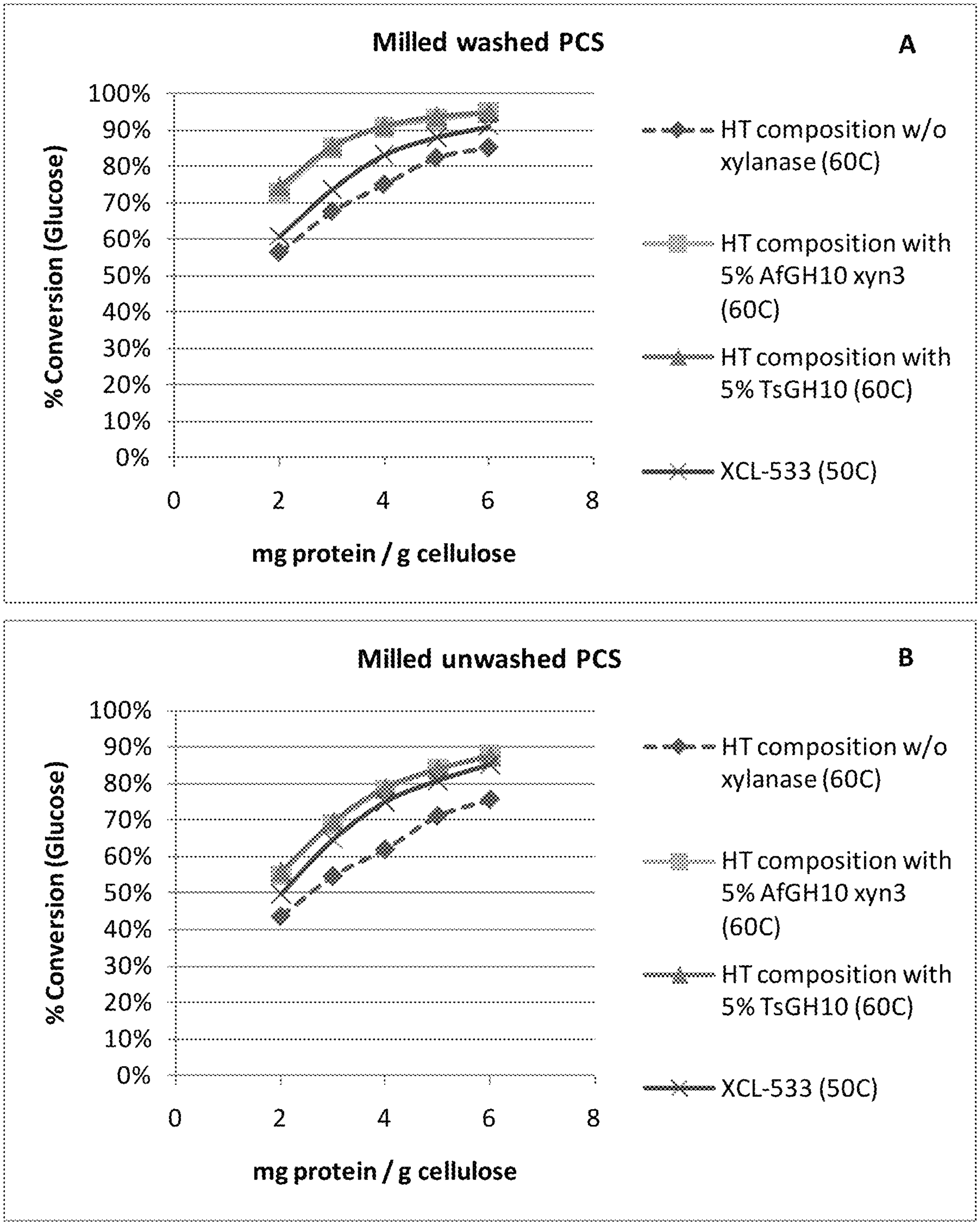
FIGS. 13A and 13B show a comparison of improved high-temperature enzyme compositions containing *Aspergillus fumigatus* GH10 xyn3 xylanase or *Trichophaea saccata* GH10 xylanase (60° C.) with *Trichoderma reesei*-based cellulase XCL-533 (50° C.) in hydrolysis of washed (A) and unwashed (B) PCS.

The results are shown in Table 2 and FIGS. 13A and 13B. The high-temperature enzyme compositions containing *Aspergillus fumigatus* GH10 xyn 3 xylanase or *Trichophaea saccata* GH10 xylanase showed similar performance, requiring similar protein loadings to achieve the same levels of cellulose conversion to glucose. The improved high-temperature enzyme compositions containing *Aspergillus fumigatus* GH10 xyn 3 xylanase or *Trichophaea saccata* GH10 xylanase outperformed the *Trichoderma reesei*-based cellulase composition XCL-533 on both washed (A) and unwashed (B) PCS.

TABLE 2

Protein loadings required for reaching 80% cellulose conversion of washed and unwashed PCS (mg protein per g cellulose). Temperature: 60° C. for high-temperature enzyme compositions, 50° C. for XCL-533.

| Composition | Washed PCS | Unwashed PCS |
|---|---|---|
| XCL-533 | 3.6 | 4.9 |
| High-temperature composition with *Aspergillus fumigatus* GH10 xyn3 xylanase | 2.6 | 4.2 |
| High-temperature composition with *Trichophaea saccata* GH10 xylanase | 2.5 | 4.2 |

Example 48: Effect of *Trichoderma reesei* GH3 and *Talaromyces emersonii* GH3 Beta-Xylosidases on Saccharification of Milled Unwashed PCS by a High-Temperature Enzyme Composition at 60° C.

The ability of two beta-xylosidases, *Trichoderma reesei* GH3 beta-xylosidase and *Talaromyces emersonii* GH3 beta-xylosidase, to enhance hydrolysis of milled unwashed PCS by a high-temperature enzyme composition was evaluated at 60° C. as described in Example 34. The 1 ml reactions with milled unwashed PCS (5% insoluble solids) were conducted for 72 hours in 50 mM sodium acetate pH 5.0 buffer containing 1 mM manganese sulfate. All reactions were performed in triplicate and involved single mixing at the beginning of hydrolysis. The results are shown in FIGS. 14A and 14B.

The high-temperature enzyme composition included 45% *Aspergillus fumigatus* Cel7A CBHI, 25% *Myceliophthora thermophila* Cel6A CBHII, 5% *Trichoderma reesei* Cel7B EGI, 5% *Myceliophthora thermophila* Cel5A EGII, 5% *Thermoascus aurantiacus* GH61A polypeptide having cellulolytic enhancing activity, 5% *Thielavia terrestris* GH61E polypeptide having cellulolytic enhancing activity, 5% *Aspergillus fumigatus* GH10 xyn3 xylanase, and 5% *Penicillium brasilianum* Cel3A beta glucosidase. The high-temperature enzyme composition (3 mg total protein per g cellulose) was supplemented with *Trichoderma reesei* GH3 beta-xylosidase and *Talaromyces emersonii* GH3 beta-xylosidase at 1%, 2%, 3.5%, 5%, and 10% replacement levels, and the hydrolysis results were compared with the results for the high-temperature enzyme composition containing no beta-xylosidase (0% replacement level).

Figures 14A, 14B:
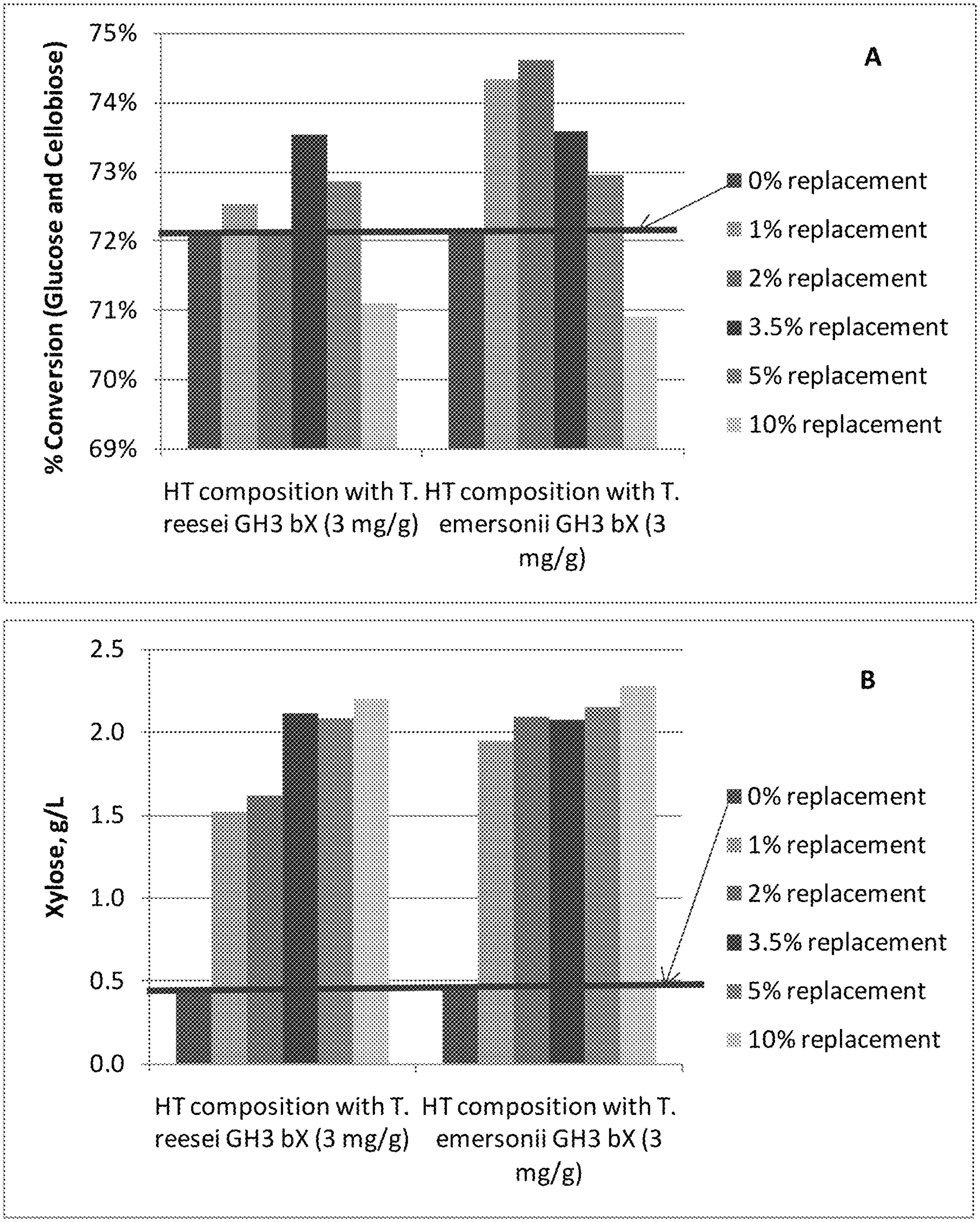
FIGS. 14A and 14B show the effect of replacement of protein in a high-temperature enzyme composition (3 mg protein per g cellulose) with GH3 beta-xylosidases from *Trichoderma reesei* and *Talaromyces emersonii* at 60° C.

As shown in FIG. 14A, the inclusion of *Trichoderma reesei* GH3 beta-xylosidase and *Talaromyces emersonii* GH3 beta-xylosidase in the high-temperature enzyme composition increased the level of enzymatically-produced monomeric xylose from approximately 0.5 g/L (0% beta-xylosidase replacement) to approximately 2 g/L. The optimal replacement levels were 3.5% for *Trichoderma reesei* GH3 beta-xylosidase and 1-2% for *Talaromyces emersonii* GH3 beta-xylosidase. As shown in FIG. 14B, the combined yield of glucose and cellobiose was increased by an additional 1.5% for a mixture containing 3.5% *Trichoderma reesei* GH3 beta-xylosidase and by an additional 2.5% for a mixture containing 2% *Talaromyces emersonii* GH3 beta-xylosidase.

These results demonstrated that both beta-xylosidases provided a small but significant benefit by increasing the degree of cellulose and hemicellulose conversion of milled unwashed PCS to soluble sugars (glucose, cellobiose and xylose). *Talaromyces emersonii* GH3 beta-xylosidase appeared to be slightly more active than *Trichoderma reesei* GH3 beta-xylosidase at 60° C., increasing the monomeric xylose level by approximately 1.5 g/L (FIG. 14A) and the cellulose conversion by an additional 2.5% (FIG. 14B) at a very low replacement level (1-2%) of the high-temperature enzyme composition.

Example 49: Evaluation of Four Cellobiohydrolases I Replacing a CBHI Component in a High-Temperature Enzyme Composition in Saccharification of Milled Unwashed PCS at 50-65° C.

The ability of four cellobiohydrolase I proteins to replace a CBHI component in a high-temperature enzyme composition (3 mg total protein per g cellulose) was tested at 50° C., 55° C., 60° C., and 65° C. using milled unwashed PCS as a substrate. The high-temperature enzyme composition included 35% CBHI, 25% *Myceliophthora thermophila* Cel6A CBHII, 15% *Thermoascus aurantiacus* Cel5A EGII, 15% *Thermoascus aurantiacus* GH61A polypeptide having cellulolytic enhancing activity, 5% *Aspergillus fumigatus* Cel3A beta-glucosidase, and 5% *Aspergillus fumigatus* GH10 xyn3 xylanase.

The following CBHI cellulases were tested in the high-temperature enzyme composition: *Trichoderma reesei* Cel7A CBHI, *Chaetomium thermophilum* Cel7A CBHI, *Aspergillus fumigatus* Cel7A CBHI, and *Thermoascus aurantiacus* Cel7A CBHI.

The assay was performed as described in Example 34. The 1 ml reactions with milled unwashed PCS (5% insoluble solids) were conducted for 72 hours in 50 mM sodium acetate pH 5.0 buffer containing 1 mM manganese sulfate. All reactions were performed in triplicate and involved single mixing at the beginning of hydrolysis.

Figure 15:
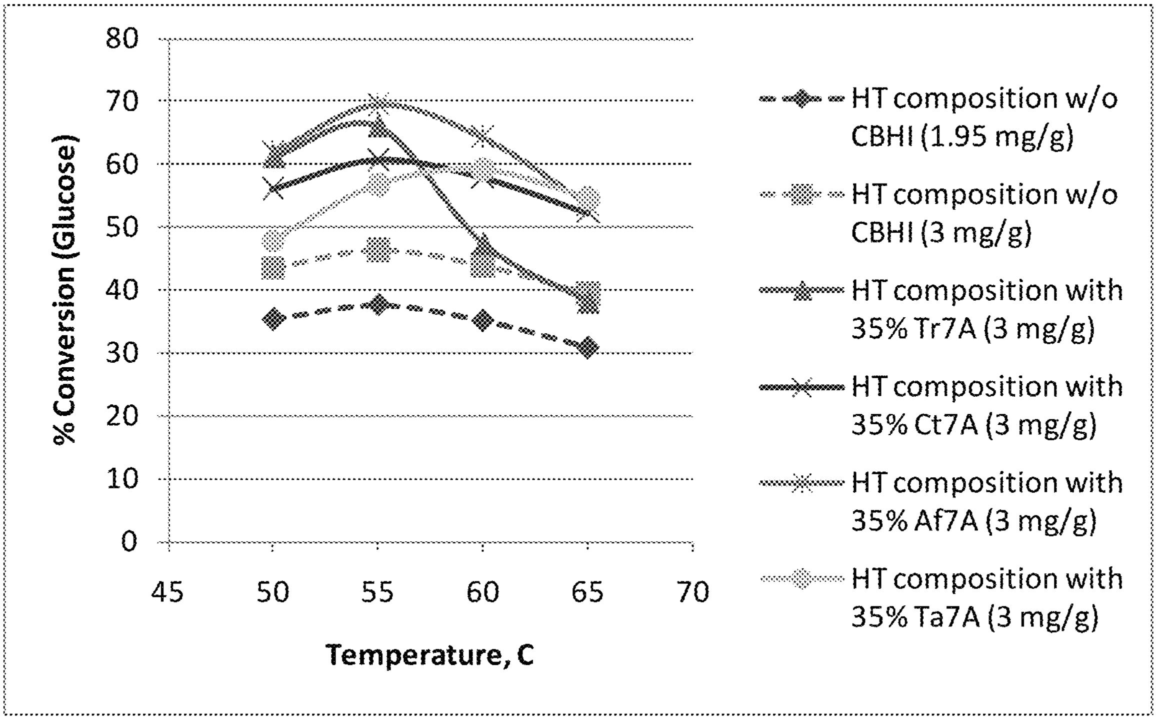
FIG. 15 shows a comparison of *Trichoderma reesei* Cel7A CBHI, *Chaetomium thermophilum* Cel7A CBHI, *Aspergillus fumigatus* Cel7A CBHI, and *Thermoascus aurantiacus* Cel7A CBHI replacing a CBHI component in a high-temperature enzyme composition in hydrolysis of milled unwashed PCS at 50-65° C.

As shown in FIG. 15, *Aspergillus fumigatus* Cel7A performed better than other cellobiohydrolases I at all temperatures from 50° C. to 65° C. *Chaetomium thermophilum* Cel7A also performed well in the entire range of temperatures, but the degree of cellulose conversion to glucose was lower compared to *Aspergillus fumigatus* Cel7A. *Trichoderma reesei* Cel7A did not perform well at temperatures above 55° C. *Thermoascus aurantiacus* Cel7A, which contained no CBM, showed a remarkably good performance at 60° C. and 65° C., but was less efficient in hydrolyzing the cellulose in unwashed PCS at lower temperatures (50° C. and 55° C.).

Example 50: Evaluation of Four Cellobiohydrolases II Replacing a CBHII Component in a High-Temperature Enzyme Composition in Saccharification of Milled Unwashed PCS at 50-65° C.

The ability of several cellobiohydrolase II proteins to replace a CBHII component in a high-temperature enzyme composition (3 mg total protein per g cellulose) was tested at 50° C., 55° C., 60° C., and 65° C. using milled unwashed PCS as a substrate. The high-temperature enzyme composition included 35% *Aspergillus fumigatus* Cel7A CBHI, 25% CBHII, 15% *Thermoascus aurantiacus* Cel5A EGII, 15% *Thermoascus aurantiacus* GH61A polypeptide having cellulolytic enhancing activity, 5% *Aspergillus fumigatus* Cel3A beta-glucosidase, and 5% *Aspergillus fumigatus* GH10 xyn3 xylanase.

The following CBHII cellulases were tested in the high-temperature enzyme composition: *Myceliophthora thermo-*

*phila* Cel6A CBHII, *Thielavia terrestris* Cel6A CBHII, *Aspergillus fumigatus* Cel6A CBHII, and *Trichophaea saccata* Cel6A CBHII.

The assay was performed as described in Example 34. The 1 ml reactions with milled unwashed PCS (5% insoluble solids) were conducted for 72 hours in 50 mM sodium acetate pH 5.0 buffer containing 1 mM manganese sulfate. All reactions were performed in triplicate and involved single mixing at the beginning of hydrolysis.

Figure 16:
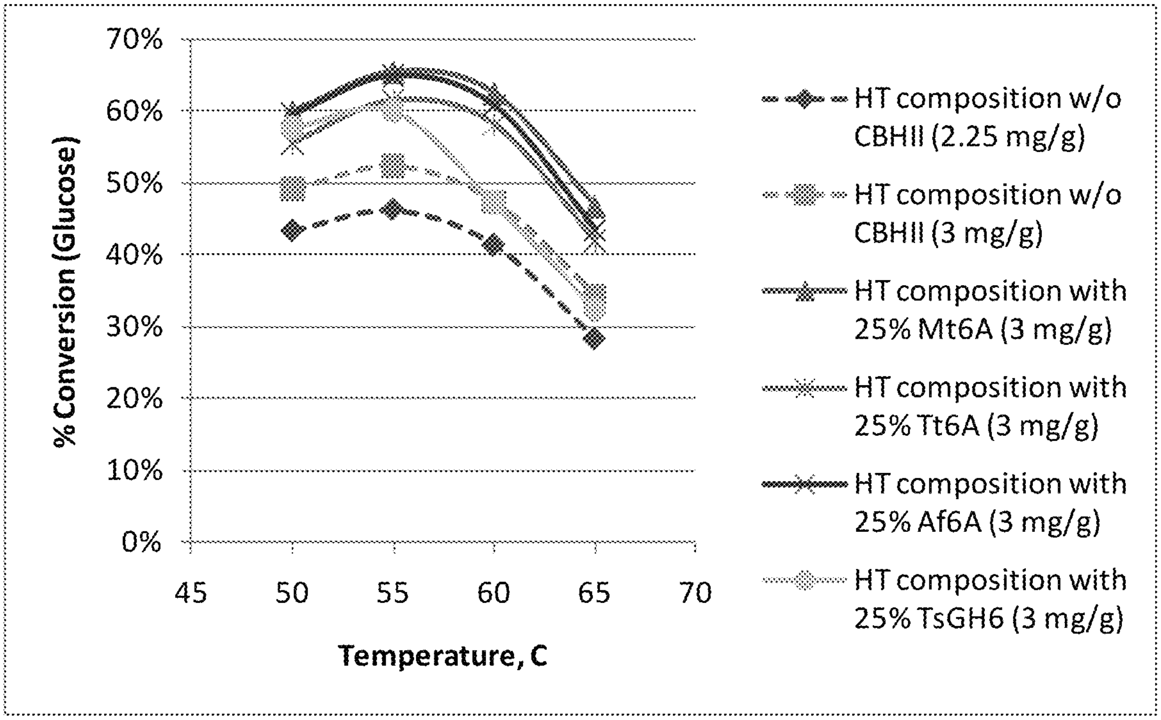
FIG. 16 shows a comparison of *Myceliophthora thermophila* Cel6A CBHII, *Thielavia terrestris* Cel6A CBHII, *Aspergillus fumigatus* Cel6A CBHII, and *Trichophaea saccata* Cel6A CBHII replacing a CBHII component in a high-temperature enzyme composition in hydrolysis of milled unwashed PCS at 50-65° C.

As shown in FIG. 16, CBHII from *Aspergillus fumigatus* performed about the same as CBHII from *Myceliophthora thermophila* at all temperatures, showing only a slightly lower hydrolysis at 60-65° C. *Thielavia terrestris* Cel6A CBHII had high thermostability and performed well in the entire range of temperatures, but the degree of cellulose conversion to glucose was lower compared to *Myceliophthora thermophila* Cel6A CBHII. *Trichophaea saccata* Cel6A CBHII had high activity at 50-55° C., but did not perform well at higher temperatures.

Example 51: Evaluation of Two Endoglucanases I Replacing an Endoglucanase Component in a High-Temperature Enzyme Composition in Saccharification of Milled Unwashed PCS at 50-65° C.

The ability of two endoglucanase I proteins to replace an endoglucanase component in a high-temperature enzyme composition (3 mg total protein per g cellulose) was tested at 50° C., 55° C., 60° C., and 65° C. using milled unwashed PCS as a substrate. The high-temperature enzyme composition included 35% *Aspergillus fumigatus* Cel7A CBHI, 25% *Myceliophthora thermophila* Cel6A CBHII, 15% EG cellulase, 15% *Thermoascus aurantiacus* GH61A polypeptide having cellulolytic enhancing activity, 5% *Aspergillus fumigatus* Cel3A beta-glucosidase, and 5% *Aspergillus fumigatus* GH10 xyn3 xylanase.

The following EGIs were tested in the high-temperature enzyme composition: *Trichoderma reesei* Cel7B EGI and *Aspergillus terreus* Cel7 EGI.

The assay was performed as described in Example 34. The 1 ml reactions with milled unwashed PCS (5% insoluble solids) were conducted for 72 hours in 50 mM sodium acetate pH 5.0 buffer containing 1 mM manganese sulfate. All reactions were performed in triplicate and involved single mixing at the beginning of hydrolysis.

Figure 17:
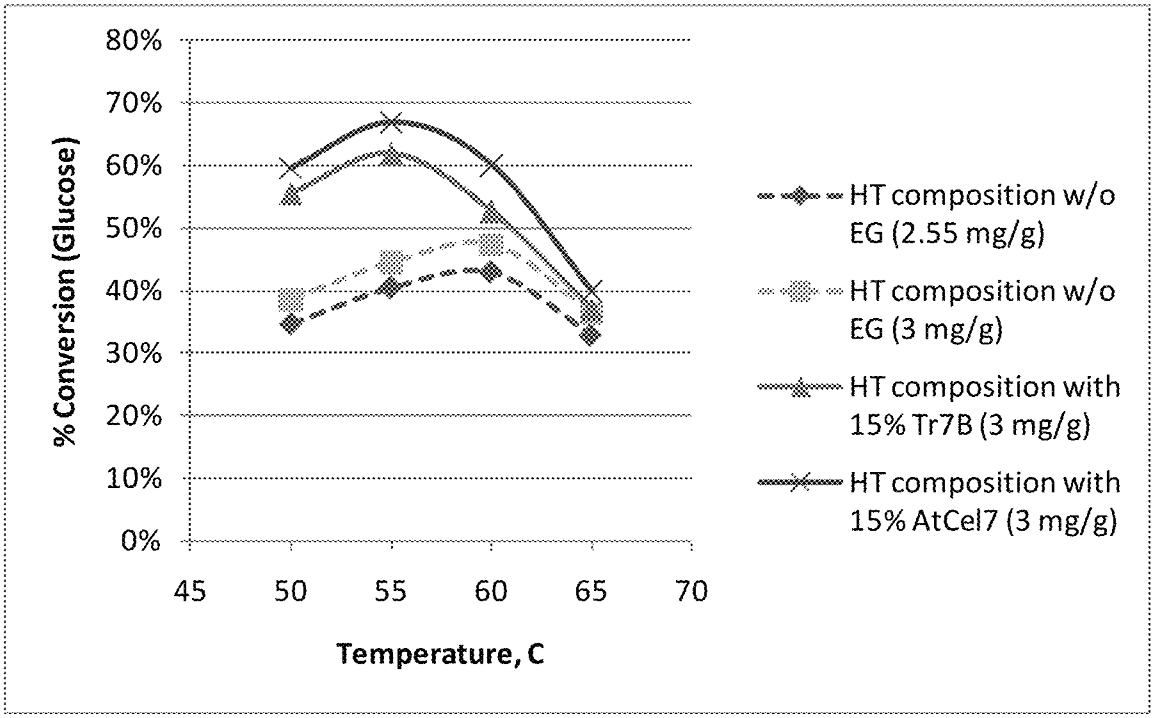
FIG. 17 shows a comparison of *Trichoderma reesei* Cel7B EGI and *Aspergillus terreus* Cel7 EGI replacing an endoglucanase component in a high-temperature enzyme composition in hydrolysis of milled unwashed PCS at 50-65° C.

As shown in FIG. 17, the high-temperature enzyme composition containing *Aspergillus terreus* Cel7 EGI performed significantly better than the high-temperature enzyme composition containing *Trichoderma reesei* Cel7B EGI within this temperature range.

Example 52: Evaluation of Three Endoglucanases II Replacing an Endoglucanase Component in a High-Temperature Enzyme Composition in Saccharification of Milled Unwashed PCS at 50-65° C.

The ability of three endoglucanase II proteins to replace an endoglucanase component in a high-temperature enzyme composition (3 mg total protein per g cellulose) was tested at 50° C., 55° C., 60° C., and 65° C. using milled unwashed PCS as a substrate. The high-temperature enzyme composition included 35% *Aspergillus fumigatus* Cel7A CBHI, 25% *Myceliophthora thermophila* Cel6A CBHII, 15% EG cellulase, 15% *Thermoascus aurantiacus* GH61A polypeptide having cellulolytic enhancing activity, 5% *Aspergillus fumigatus* Cel3A beta-glucosidase, and 5% *Aspergillus fumigatus* GH10 xyn3 xylanase.

The following EGIIs were tested in the high-temperature enzyme composition: *Trichoderma reesei* Cel5A EGII, *Myceliophthora thermophila* Cel5A EGII, and *Thermoascus aurantiacus* Cel5A EGII.

The assay was performed as described in Example 34. The 1 ml reactions with milled unwashed PCS (5% insoluble solids) were conducted for 72 hours in 50 mM sodium acetate pH 5.0 buffer containing 1 mM manganese sulfate. All reactions were performed in triplicate and involved single mixing at the beginning of hydrolysis.

Figure 18:
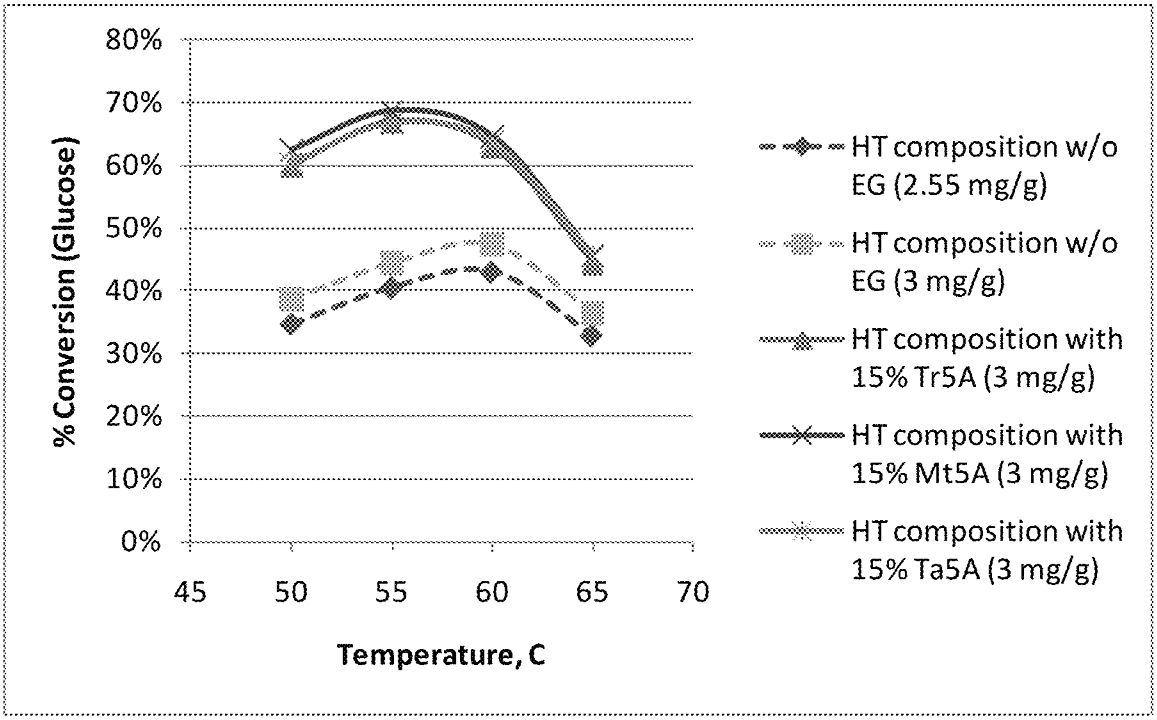
FIG. 18 shows a comparison of *Trichoderma reesei* Cel5A EGII, *Myceliophthora thermophila* Cel5A EGII, and *Thermoascus aurantiacus* Cel5A EGII replacing an endoglucanase component in a high-temperature enzyme composition in hydrolysis of milled unwashed PCS at 50-65° C.

As shown in FIG. 18, all endoglucanase II proteins performed similarly within this temperature range, with *Myceliophthora thermophila* Cel5A EGII slightly outperforming *Trichoderma reesei* Cel5A EGII and *Thermoascus aurantiacus* Cel5A EGII.

Example 53: Evaluation of Three Beta-Glucosidases Replacing a Beta-Glucosidase Component in a High-Temperature Enzyme Composition in Saccharification of Milled Unwashed PCS at 50-65° C.

In a first experiment, three beta-glucosidases, including *Aspergillus fumigatus* Cel3A beta-glucosidase, *Penicillium brasilianum* Cel3A beta-glucosidase, and *Aspergillus niger* Cel3 beta-glucosidase, were evaluated in a high-temperature enzyme composition at 50° C., 55° C., and 60° C. using milled unwashed PCS as a substrate. The high-temperature enzyme composition included 45% *Aspergillus fumigatus* Cel7A CBHI, 25% *Thielavia terrestris* Cel6A CBHII, 5% *Trichoderma reesei* Cel7B EGI, 5% *Thermoascus aurantiacus* Cel5A EGII, 5% *Thermoascus aurantiacus* GH61A polypeptide having cellulolytic enhancing activity, 5% *Thielavia terrestris* GH61E polypeptide having cellulolytic enhancing activity, 5% *Aspergillus fumigatus* GH10 xyn3 xylanase, and 5% beta-glucosidase. The high-temperature enzyme composition was used at 3.0 mg total protein per g cellulose.

The assay was performed as described in Example 34. The 1 ml reactions with milled unwashed PCS (5% insoluble solids) were conducted for 72 hours in 50 mM sodium acetate pH 5.0 buffer containing 1 mM manganese sulfate. All reactions were performed in triplicate and involved single mixing at the beginning of hydrolysis.

Figure 19:
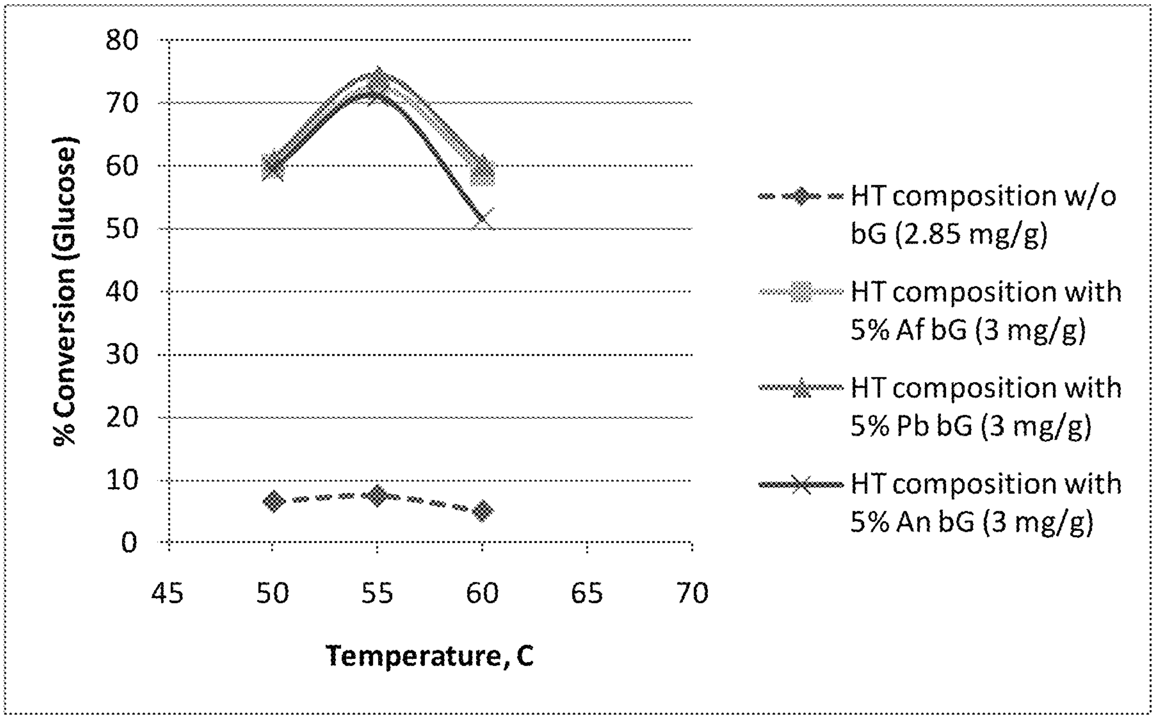
FIG. 19 shows a comparison of *Aspergillus fumigatus* Cel3A beta-glucosidase, *Penicillium brasilianum* Cel3A beta-glucosidase, and *Aspergillus niger* Cel3 beta-glucosidase in a high-temperature enzyme composition at 50-60° C. using milled unwashed PCS.

The results shown in FIG. 19 demonstrated that all three beta-glucosidases performed about the same at 50° C. and 55° C., whereas *Aspergillus niger* Cel3 beta-glucosidase showed slightly lower hydrolysis at 60° C. than the other two beta-glucosidases.

In a second experiment, *Aspergillus fumigatus* Cel3A beta-glucosidase and *Penicillium brasilianum* Cel3A beta-glucosidase were compared in a high-temperature enzyme composition at four temperatures, 50° C., 55° C., 60° C., and 65° C., using milled unwashed PCS as a substrate. The high-temperature enzyme composition included 35% *Aspergillus fumigatus* Cel7A CBHI, 25% *Myceliophthora thermophila* Cel6A CBHII, 15% *Thermoascus aurantiacus* Cel5A EGII, 15% *Thermoascus aurantiacus* GH61A polypeptide having cellulolytic enhancing activity, 5% beta-glucosidase, and 5% *Aspergillus fumigatus* GH10 xyn3 xylanase. The high-temperature enzyme composition was used at 3.0 mg total protein per g cellulose.

The assay was performed as described in Example 34. The 1 ml reactions with milled unwashed PCS (5% insoluble solids) were conducted for 72 hours in 50 mM sodium acetate pH 5.0 buffer containing 1 mM manganese sulfate. All reactions were performed in triplicate and involved single mixing at the beginning of hydrolysis.

Figure 20:
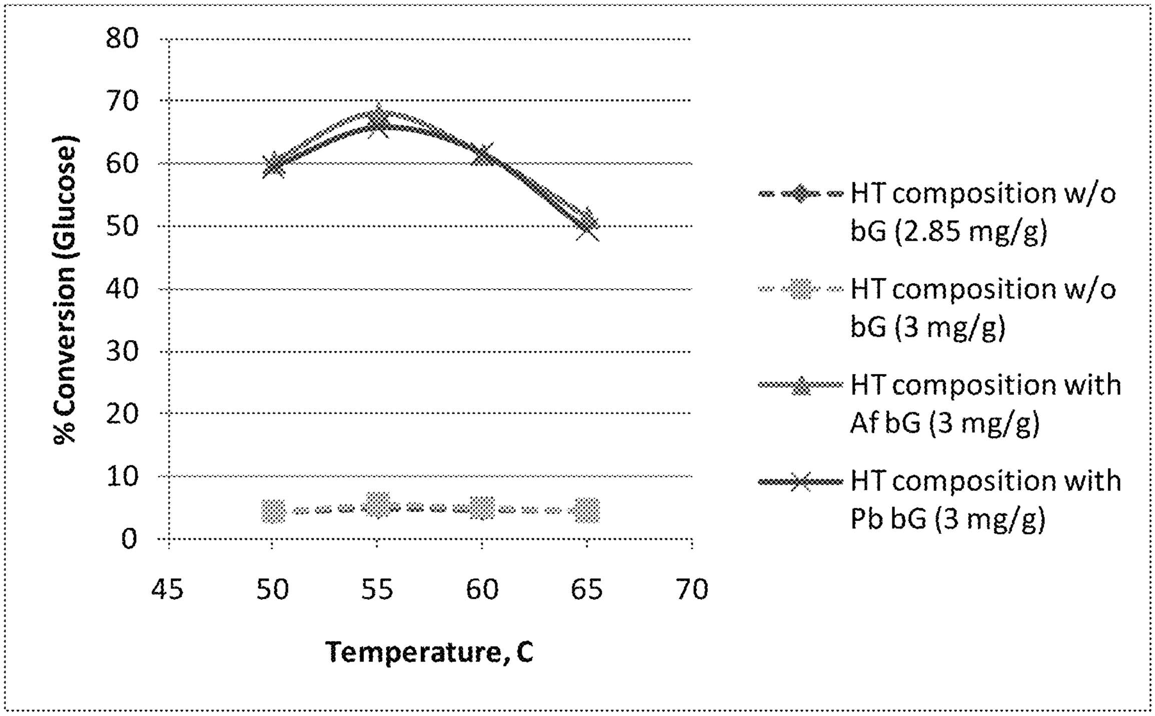
FIG. 20 shows a comparison of *Aspergillus fumigatus* Cel3A beta-glucosidase, *Penicillium brasilianum* Cel3A beta-glucosidase, and *Aspergillus niger* Cel3 beta-glucosidase in a high-temperature enzyme composition at 50-65° C. using milled unwashed PCS.

The results shown in FIG. 20 demonstrated that Cel3A beta-glucosidases from *Aspergillus fumigatus* and *Penicillium brasilianum* performed about the same within this temperature range.

Example 54: Evaluation of Six Xylanases Replacing a Xylanase Component in a High-Temperature Enzyme Composition in Saccharification of Milled Unwashed PCS at 50-65° C.

The ability of six xylanases to replace a xylanase component in a high-temperature enzyme composition (3 mg total protein per g cellulose) was tested at 50° C., 55° C., 60° C., and 65° C. using milled unwashed PCS as a substrate. The high-temperature enzyme composition included 35% *Aspergillus fumigatus* Cel7A CBHI, 25% *Myceliophthora thermophila* Cel6A CBHII, 15% *Thermoascus aurantiacus* Cel5A EGII, 15% *Thermoascus aurantiacus* GH61A polypeptide having cellulolytic enhancing activity, 5% *Aspergillus fumigatus* Cel3A beta-glucosidase, and 5% xylanase.

The following xylanases were tested in the high-temperature enzyme composition: *Aspergillus aculeatus* GH10 xyn II xylanase, *Aspergillus fumigatus* GH10 xyn3, *Trichophaea saccata* GH10 xylanase, *Thermobifida fusca* GH11 xylanase, *Penicillium pinophilum* GH10 xylanase, and *Thielavia terrestris* GH10E xylanase.

The assay was performed as described in Example 34. The 1 ml reactions with milled unwashed PCS (5% insoluble solids) were conducted for 72 hours in 50 mM sodium acetate pH 5.0 buffer containing 1 mM manganese sulfate. All reactions were performed in triplicate and involved single mixing at the beginning of hydrolysis.

Figure 21:
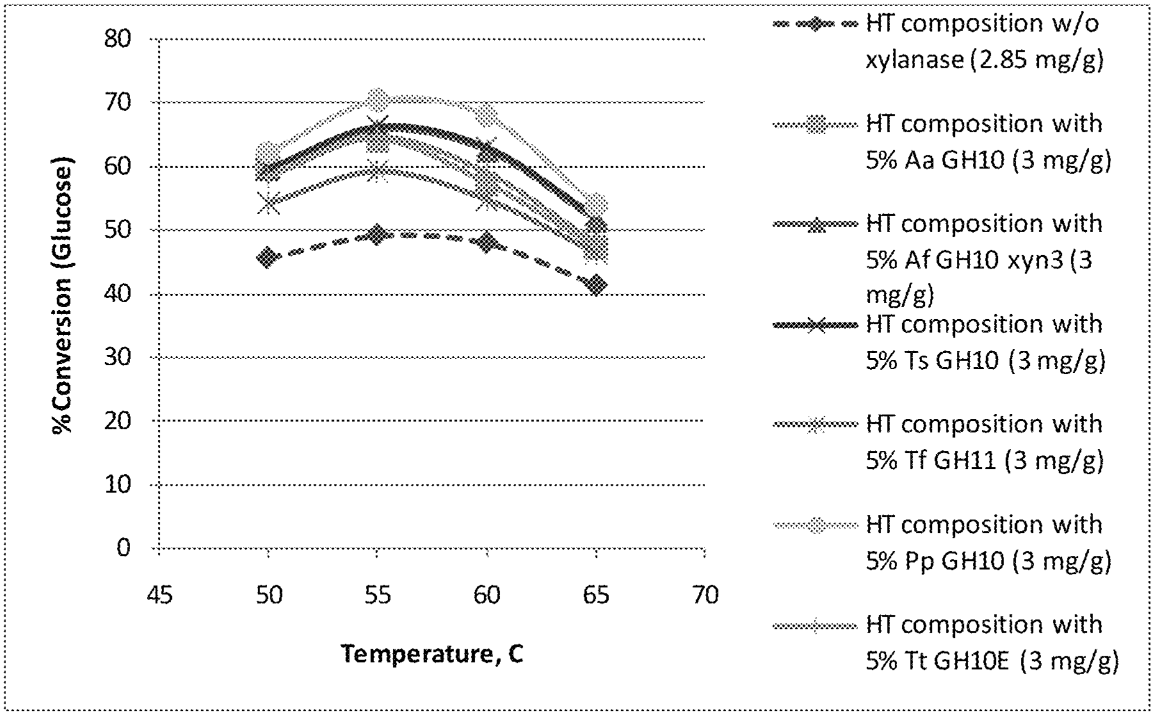
FIG. 21 shows a comparison of *Aspergillus aculeatus* GH10 xyn II xylanase, *Aspergillus fumigatus* GH10 xyn3, *Trichophaea saccata* GH10 xylanase, *Thermobifida fusca* GH11 xylanase, *Penicillium pinophilum* GH10 xylanase, and *Thielavia terrestris* GH10E xylanase replacing a xylanase component in a high-temperature enzyme composition in hydrolysis of milled unwashed PCS at 50-65° C.

As shown in FIG. 21, GH10 xylanase from *Penicillium pinophilum* was superior to GH10 xylanases from *Aspergillus fumigatus* and *Trichophaea saccata* at all temperatures from 50° C. to 65° C. The *Aspergillus aculeatus* GH10 and *Thielavia terrestris* GH10E xylanases performed about the same as the *Aspergillus fumigatus* GH10 and *Trichophaea saccata* GH10 xylanases at 50° C. and 55° C., but did not perform well at higher temperatures (60° C. and 65° C.). The *Thermobifida fusca* GH11 performed relatively well at 60° C. and 65° C., but overall the degree of cellulose conversion to glucose was lower compared to other xylanases.

Example 55: Evaluation of the Ability of Four GH61 Polypeptides Having Cellulolytic Enhancing Activity to Enhance PCS-Hydrolyzing Activity of a High-Temperature Enzyme Composition at 50-65° C. Using Milled Unwashed PCS The ability of four GH61 polypeptides having cellulolytic enhancing activity, *Thermoascus aurantiacus* GH61A, *Thielavia terrestris* GH61E, *Penicillium pinophilum* GH61, and *Aspergillus fumigatus* GH61B, to enhance the PCS-hydrolyzing activity of a high-temperature enzyme composition was evaluated using milled unwashed PCS at 50° C., 55° C., 60° C., and 65° C. The high-temperature enzyme composition included 35% *Aspergillus fumigatus* Cel7A CBHI, 25% *Myceliophthora thermophila* Cel6A CBHII, 15% *Thermoascus aurantiacus* Cel5A EGII, 15% GH61 polypeptide having cellulolytic enhancing activity, 5% *Aspergillus fumigatus* Cel3A beta-glucosidase, and 5% *Aspergillus fumigatus* GH10 xyn3 xylanase. The high-temperature enzyme composition was used at 3 mg total protein per g cellulose.

The assay was performed as described in Example 34. The 1 ml reactions with milled unwashed PCS (5% insoluble solids) were conducted for 72 hours in 50 mM sodium acetate pH 5.0 buffer containing 1 mM manganese sulfate. All reactions were performed in triplicate and involved single mixing at the beginning of hydrolysis.

Figure 22:
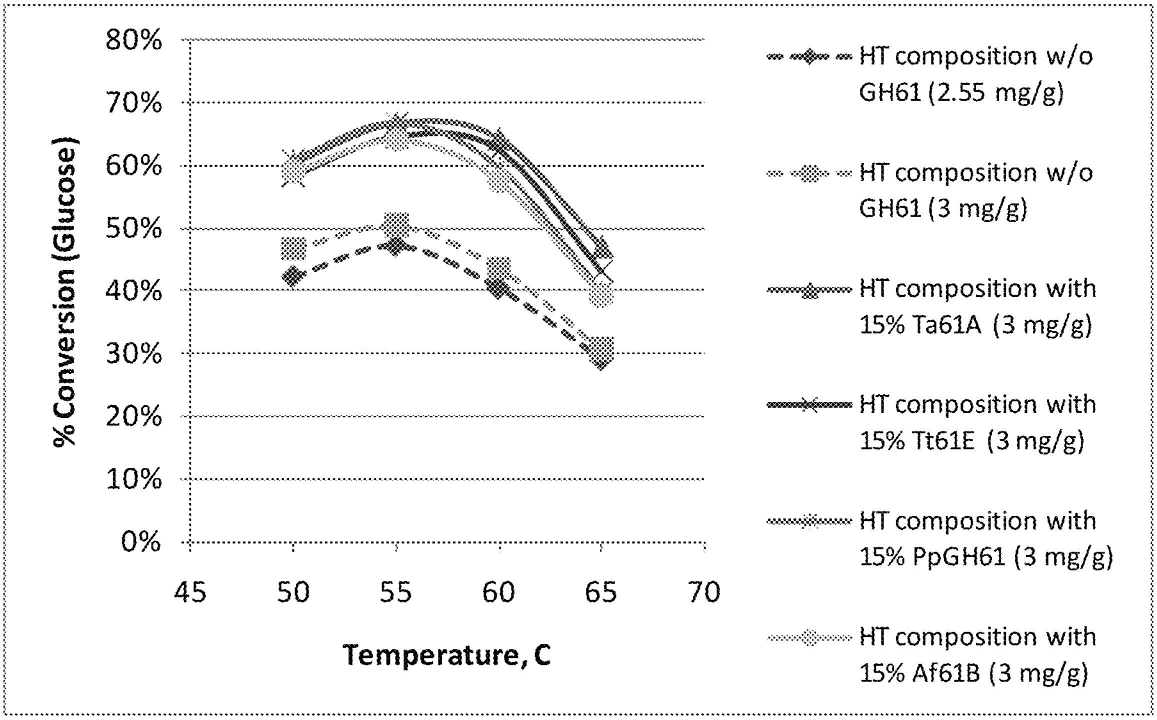
FIG. 22 shows a comparison of the cellulase-enhancing activity of *Thermoascus aurantiacus* GH61A, *Thielavia terrestris* GH61E, *Penicillium pinophilum* GH61, and *Aspergillus fumigatus* GH61B polypeptides replacing a GH61 component in a high-temperature enzyme composition in hydrolysis of milled unwashed PCS at 50-65° C.

As shown in FIG. 22, all four GH61 polypeptides showed a significant cellulase-enhancing activity, with *Thermoascus aurantiacus* GH61A polypeptide being the most efficient enhancer among the four within this temperature range. High-temperature enzyme compositions containing *Thermoascus aurantiacus* GH61A and *Thielavia terrestris* GH61E polypeptides performed better at higher temperatures (60° C. and 65° C.) than high-temperature enzyme compositions containing *Penicillium pinophilum* GH61 and *Aspergillus fumigatus* GH61B polypeptides.

Example 56: Evaluation of the Ability of Three GH61 Polypeptides Having Cellulolytic Enhancing Activity to Enhance PCS-Hydrolyzing Activity of a High-Temperature Enzyme Composition at 50-65° C. Using Milled Unwashed PCS The ability of three GH61 polypeptides having cellulolytic enhancing activity, *Thermoascus aurantiacus* GH61A, *Thielavia terrestris* GH61N, and *Penicillium* sp GH61A, to enhance the PCS-hydrolyzing activity of a high-temperature enzyme composition was evaluated using milled unwashed PCS at 50° C., 55° C., 60° C., and 65° C. The high-temperature enzyme composition included 45% *Aspergillus fumigatus* Cel7A CBHI, 25% *Myceliophthora thermophila Cel*6A CBHII, 10% *Myceliophthora thermophila* Cel5A EGII, 10% GH61 polypeptide, 5% *Aspergillus fumigatus* Cel3A beta-glucosidase, and 5% *Aspergillus fumigatus* GH10 xyn3 xylanase. The results for the enzyme compositions containing GH61 polypeptides (3 mg total protein per g cellulose) were compared with the results for a similar enzyme composition to which no GH61 polypeptide was added (2.7 mg total protein per g cellulose).

The assay was performed as described in Example 34. The 1 ml reactions with milled unwashed PCS (5% insoluble solids) were conducted for 72 hours in 50 mM sodium acetate pH 5.0 buffer containing 1 mM manganese sulfate. All reactions were performed in triplicate and involved single mixing at the beginning of hydrolysis.

Figure 23:
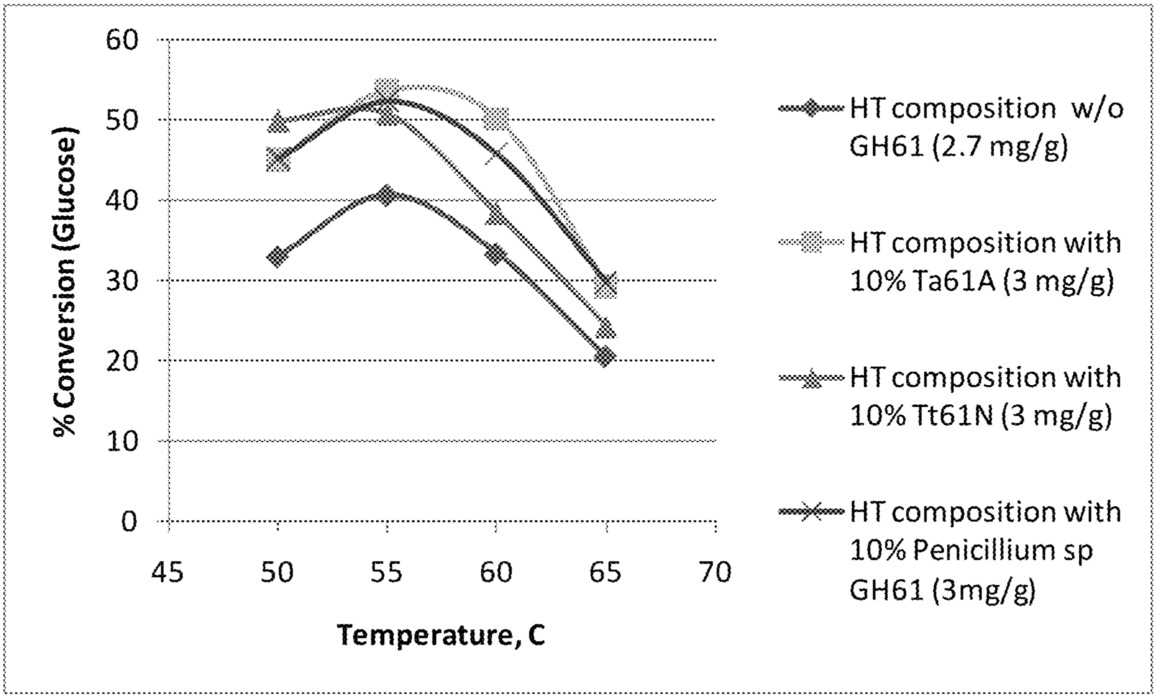
FIG. 23 shows a comparison of the cellulase-enhancing activity of *Thermoascus aurantiacus* GH61A, *Thielavia terrestris* GH61N, and *Penicillium* sp GH61A polypeptides replacing a GH61 component in a high-temperature enzyme composition in hydrolysis of milled unwashed PCS at 50-65° C.

As shown in FIG. 23, all three GH61 polypeptides showed a significant cellulase-enhancing activity, with *Thermoascus aurantiacus* GH61A polypeptide being the most efficient enhancer at 55-65° C., and *Thielavia terrestris* GH61N polypeptide slightly outperforming *Thermoascus aurantiacus* GH61A polypeptide at 50° C. The high-temperature enzyme composition containing *Penicillium* sp. GH61A polypeptide performed almost as well as the high-temperature enzyme composition containing *Thermoascus aurantiacus* GH61A polypeptide at all four temperatures (50-65° C.). *Thielavia terrestris* GH61N polypeptide performed well at 50° C. and 55° C., but showed a significant decline in performance at higher temperatures (60° C. and 65° C.).

Example 57: Hydrolysis of Milled Unwashed PCS by *Trichoderma reesei*-Based XCL-602 Cellulase at Different Replacement Levels by *Aspergillus fumigatus* Cel7A Cellobiohydrolase I, *Myceliophthora thermophila* Cel6A Cellobiohydrolase II, or their Binary Compositions at 50-60° C.

A *Trichoderma reesei* strain 981-08-D4-based cellulase containing *Aspergillus fumigatus* beta-glucosidase and *Thermoascus aurantiacus* GH61A polypeptide, designated *Trichoderma reesei*-based XCL-602 cellulase, was tested in 1-ml hydrolysis reactions at 50° C., 55° C., and 60° C. using milled unwashed PCS as a substrate. The *Trichoderma reesei*-based XCL-602 cellulase was used alone or in mixtures with *Aspergillus fumigatus* Cel7A CBHI (10%, 20%, 30% or 40% of total protein), *Myceliophthora thermophila* Cel6A CBHII (10% or 20% of total protein), or both *Aspergillus fumigatus* Cel7A CBHI and *Myceliophthora thermophila* Cel6A CBHII (10%/10%, 10%/20%, 20%/10%, 20%/20%, 30%/10%, 30%/20%, 40%/20% of total protein). The level of *Thermoascus aurantiacus* GH61A polypeptide in all *Trichoderma reesei* XCL-602 compositions was maintained constant at 8% of total protein. *Trichoderma reesei*-based enzyme composition SaMe-MF268 (XCL-533) was also included in the experiment. The non-replaced *Trichoderma reesei*-based XCL-602 cellulase and *Trichoderma reesei*-based XCL-533 cellulase and various *Trichoderma reesei* XCL-602 compositions containing *Aspergillus fumigatus* Cel7A CBHI and/or *Myceliophthora thermophila* Cel6A CBHII were used at 3 mg total protein per g cellulose.

The assay was performed as described in Example 34. The 1 ml reactions with 50 mg of insoluble PCS solids per ml were conducted for 72 hours in 50 mM sodium acetate pH 5.0 buffer containing 1 mM manganese sulfate. All reactions were performed in triplicate and involved single mixing at the beginning of hydrolysis.

Figure 24:
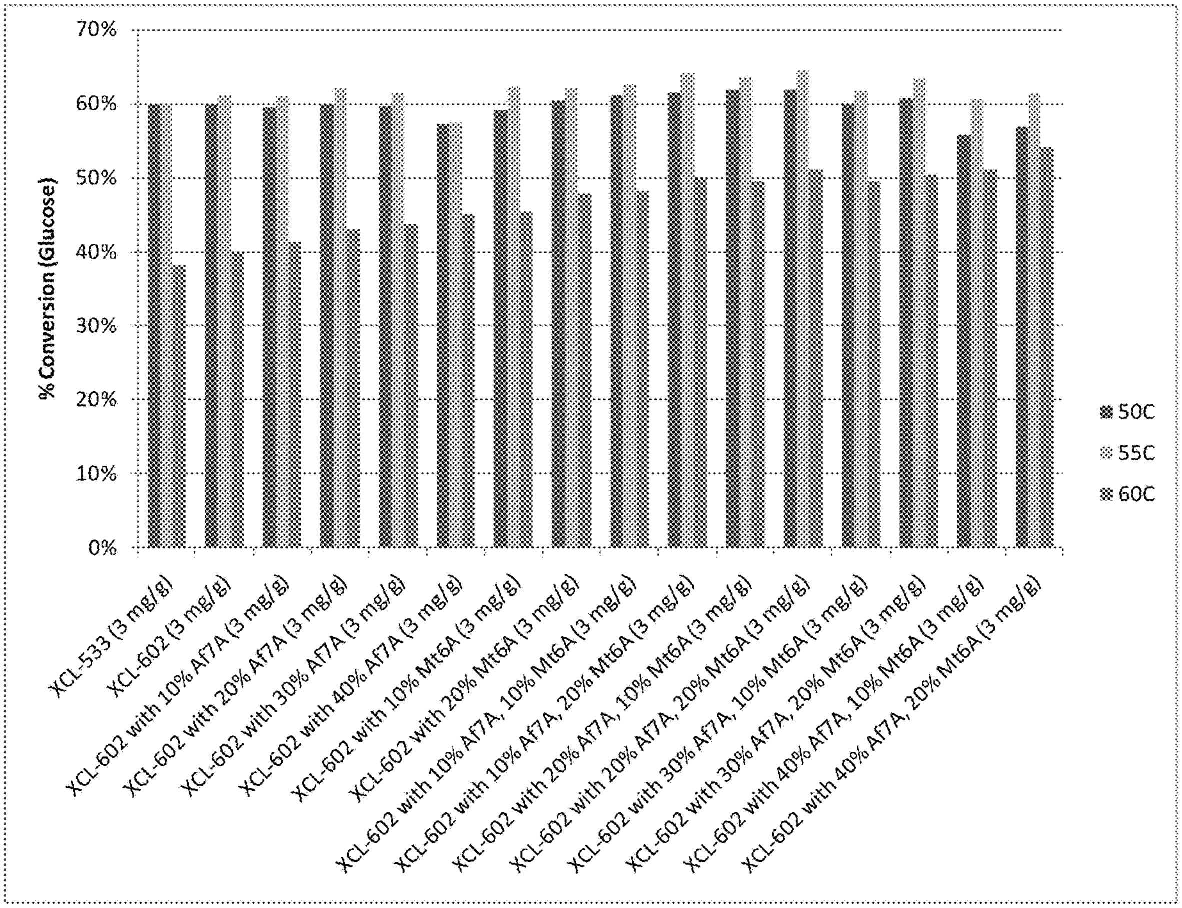
FIG. 24 shows the effect of *Trichoderma reesei*-based XCL-602 cellulase replacement by *Aspergillus fumigatus* Cel7A cellobiohydrolase I and/or *Myceliophthora thermophila* Cel6A cellobiohydrolase II on saccharification of milled unwashed PCS at 50-60° C.

The results shown in FIG. 24 demonstrated that non-replaced *Trichoderma reesei*-based XCL-602 cellulase performed about the same as non-replaced *Trichoderma reesei*-based XCL-533 cellulase at all three temperatures. At 50° C. and 55° C., the replacement of 10%, 20%, or 30% protein in XCL-602 cellulase by *Aspergillus fumigatus* Cel7A CBHI or the replacement of 10% or 20% protein in XCL-602 cellulase by *Myceliophthora thermophila* Cel6A CBHII did not have a significant effect on the degree of cellulose conversion to glucose after 72 hours of hydrolysis. The replacement of 40% protein in the *Trichoderma reesei*-based XCL-602 cellulase by *Aspergillus fumigatus* Cel7A CBHI had a negative effect on the degree of cellulose conversion to glucose at 50° C. and 55° C. At 60° C., the replacement of protein in the *Trichoderma reesei*-based XCL-602 cellulase by *Aspergillus fumigatus* Cel7A CBHI (10-40% of total protein) or *Myceliophthora thermophila* Cel6A CBHII (10-20% of total protein) significantly improved the hydrolysis over non-replaced *Trichoderma reesei*-based XCL-602 cellulase at an equivalent protein loading (3 mg protein per g cellulose). Higher replacement levels by *Aspergillus fumigatus* Cel7A CBHI or *Myceliophthora thermophila* Cel6A CBHII provided a greater hydrolysis enhancement over non-replaced XCL-602 cellulase at 60° C.

For the *Trichoderma reesei*-based XCL-602 cellulase compositions that included both *Aspergillus fumigatus* Cel7A CBHI and *Myceliophthora thermophila* Cel6A CBHII, the optimal replacement levels were 10-20% *Aspergillus fumigatus* Cel7A CBHI/10-20% *Myceliophthora thermophila* Cel6A CBHII at 50° C. and 55° C., and 40% *Aspergillus fumigatus* Cel7A CBHI/20% *Myceliophthora thermophila* Cel6A CBHII at 60° C.

Example 58: Hydrolysis of Milled Unwashed PCS by *Trichoderma reesei*-Based XCL-602 Cellulase Containing *Aspergillus fumigatus* Cel7A Cellobiohydrolase I and *Myceliophthora Thermophila* Cel6A Cellobiohydrolase II, and Additionally Supplemented by *Aspergillus Fumigatus* GH10 Xyn 3 and/or *Thielavia terrestris* GH61E at 50-60° C.

The *Trichoderma reesei*-based XCL-602 cellulase containing *Aspergillus fumigatus Cel*7A cellobiohydrolase I and *Myceliophthora thermophila* Cel6A cellobiohydrolase II was tested in 1-ml hydrolysis reactions at 50° C., 55° C. and 60° C. using milled unwashed PCS as a substrate. The *Trichoderma reesei*-based XCL-602 cellulase was used alone (3.0 mg protein per g cellulose) or with replacement by different binary compositions consisting of *Aspergillus fumigatus* Cel7A CBHI and *Myceliophthora thermophila* Cel6A CBHII (10%/10% or 40%/20% of total protein) to a total protein loading of 3 mg protein per g cellulose. The level of *Thermoascus aurantiacus* GH61A polypeptide in all *Trichoderma reesei* XCL-602-based compositions containing *Aspergillus fumigatus* Cel7A CBHI and *Myceliophthora thermophila* Cel6A CBHII was maintained constant at 8% of total protein. The *Trichoderma reesei* XCL-602-based compositions containing *Aspergillus fumigatus* Cel7A CBHI and *Myceliophthora thermophila Cel*6A CBHII (3 mg protein per g cellulose) were additionally supplemented with 5% *Aspergillus fumigatus* GH10 xyn 3 xylanase (0.15 mg protein per g cellulose), 5% *Thielavia terrestris* GH61E polypeptide (0.15 mg protein per g cellulose), or with a binary composition consisting of 5% *Aspergillus fumigatus* GH10 xyn 3 xylanase and 5% *Thielavia terrestris* GH61E polypeptide (0.30 mg protein per g cellulose). For comparison, the non-replaced *Trichoderma reesei*-based XCL-602 cellulase was used alone at 3.15 mg protein per g cellulose and 3.3 mg protein per g cellulose.

The assay was performed as described in Example 34. The 1 ml reactions with 50 mg of insoluble PCS solids per ml were conducted for 72 hours in 50 mM sodium acetate pH 5.0 buffer containing 1 mM manganese sulfate. All reactions were performed in triplicate and involved single mixing at the beginning of hydrolysis.

Figures 25A, 25B:
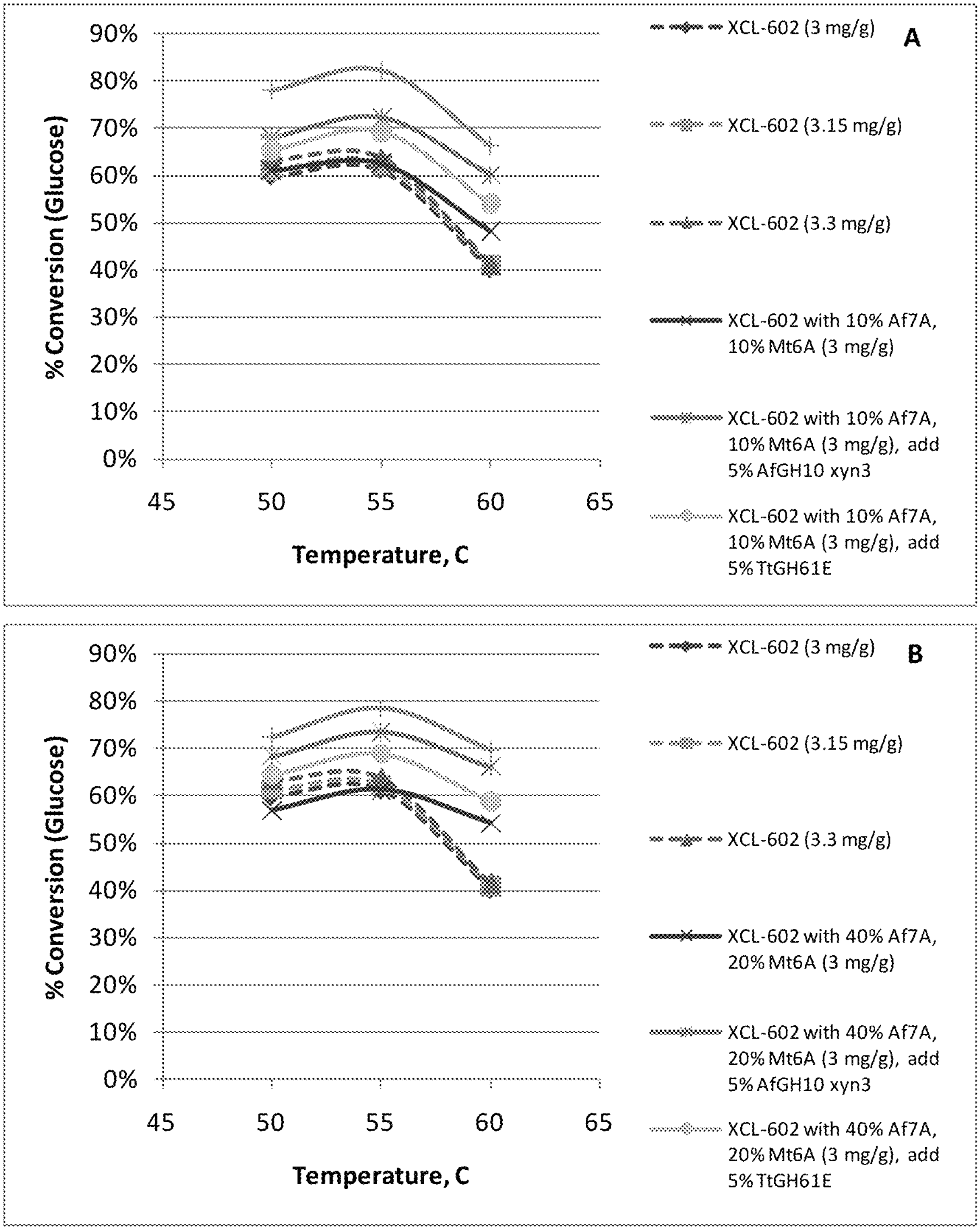
FIGS. 25A and 25B show the hydrolysis of milled unwashed PCS by *Trichoderma reesei*-based XCL-602 cellulase compositions containing *Aspergillus fumigatus* Cel7A cellobiohydrolase I and *Myceliophthora thermophila* Cel6A cellobiohydrolase II (3 mg total protein per g cellulose) and additionally supplemented by 5% *Aspergillus fumigatus* GH10 xyn 3 and/or 5% *Thielavia terrestris* GH61E at 50-60° C.

The results shown in FIGS. 25A and 25B demonstrated that the addition of 5% *Aspergillus fumigatus* GH10 xyn3 xylanase and/or 5% *Thielavia terrestris* GH61E polypeptide to the *Trichoderma reesei* XCL-602-based compositions containing *Aspergillus fumigatus* Cel7A CBHI and *Myceliophthora thermophila* Cel6A CBHII significantly improved the hydrolysis performance at all three temperatures, with a very large improvement obtained when both the *Aspergillus fumigatus* GH10 xyn3 xylanase and the *Thielavia terrestris* GH61E polypeptide were added together. The best XCL-602-based composition in this experiment (XCL-602 with 10% replacement by *Aspergillus fumigatus* Cel7A CBHI and 10% replacement by *Myceliophthora thermophila* Cel6A CBHII, and with additional supplementation by 5% *Aspergillus fumigatus GH*10 xyn3 xylanase and 5% *Thielavia terrestris* GH61E polypeptide) required 3.3 mg protein per g cellulose to achieve 82% conversion of cellulose to glucose in milled unwashed PCS after 72 hours of hydrolysis at 55° C. This represents a 1.5× reduction in protein loading compared to *Trichoderma reesei* XCL-533

(SaMe-MF268), which required 4.9 mg protein per g cellulose to achieve 80% conversion of cellulose to glucose in milled unwashed PCS after 72 hours of hydrolysis at 50° C. (Table 2).

Example 59: Hydrolysis of Milled Unwashed PCS by *Trichoderma reesei*-Based XCL-602 Cellulase Compositions Containing Different Replacement Levels of *Trichoderma reesei*-Based XCL-592 Cellulase at 50-60° C.

The *Trichoderma reesei*-based XCL-602 cellulase was tested alone (3.0 mg protein per g cellulose) or in mixtures with *Trichoderma reesei* RutC30-based cellulase containing *Aspergillus aculeatus* GH10 xylanase, designated as *Trichoderma reesei*-based XCL-592 cellulase. The *Trichoderma reesei*-based XCL-592 cellulase replaced 5%, 10%, 15%, 20%, or 25% of protein in the *Trichoderma reesei*-based XCL-602 cellulase to a total protein loading of 3 mg protein per g cellulose. The non-replaced *Trichoderma reesei*-based XCL-602 cellulase and XCL-602-based enzyme compositions were tested in 1-ml hydrolysis reactions at 50° C., 55° C. and 60° C. using milled unwashed PCS as a substrate. For comparison, *Trichoderma reesei*-based XCL-533 cellulase was tested at 4.5 mg protein per g cellulose.

The assay was performed as described in Example 34. The 1 ml reactions with 50 mg of insoluble PCS solids per ml were conducted for 72 hours in 50 mM sodium acetate pH 5.0 buffer containing 1 mM manganese sulfate. All reactions were performed in triplicate and involved single mixing at the beginning of hydrolysis.

Figure 26:
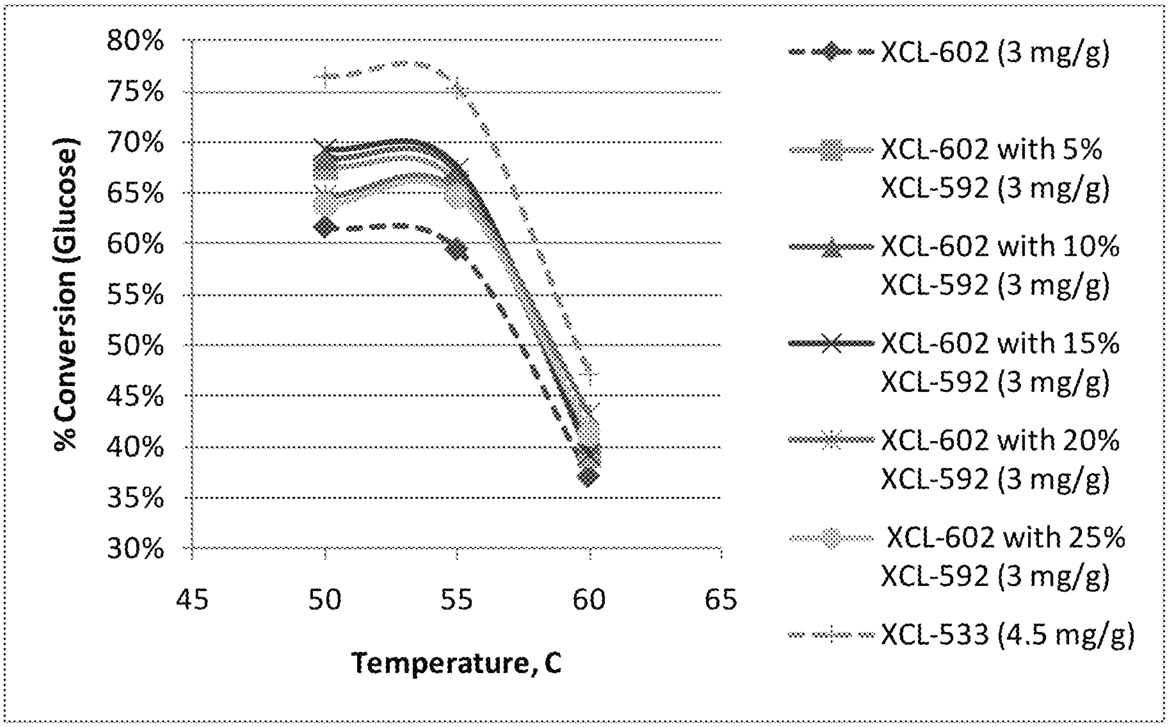
FIG. 26 shows the hydrolysis of milled unwashed PCS by *Trichoderma reesei*-based XCL-602 compositions containing different replacement levels of *Trichoderma reesei*-based XCL-592 cellulase at 50-60° C.

The results shown in FIG. 26 demonstrated that the optimal replacement level of *Trichoderma reesei*-based XCL-602 cellulase by *Trichoderma reesei*-based XCL-592 cellulase at 50° C. and 55° C. was between 10% and 15% of total protein. At 50° C. and 55° C., the best *Trichoderma reesei*-based XCL-602 cellulase compositions performed significantly better than *Trichoderma reesei*-based XCL-602 cellulase alone at an equivalent protein loading (3 mg protein per g cellulose), but were not able to reach the performance level obtained with *Trichoderma reesei*-based XCL-533 cellulase at 4.5 mg protein per g cellulose.

Example 60: Comparison of *Thermoascus aurantiacus* GH61A and *Thielavia terrestris* *GH*61E GH61 Polypeptides Having Cellulolytic Enhancing Activity Replacing 5% of Protein in *Trichoderma reesei*-Based XCL-602 Cellulase or XCL-602-Based Enzyme Composition in Hydrolysis of Milled Unwashed PCS at 50-60° C.

The *Trichoderma reesei*-based XCL-602 cellulase was tested alone and with 5% replacement by *Thermoascus aurantiacus* GH61A polypeptide having cellulolytic enhancing activity or *Thielavia terrestris* GH61E polypeptide having cellulolytic enhancing activity at 50-60° C. using milled unwashed PCS as a substrate. In addition, the *Trichoderma reesei*-based XCL-602 cellulase composition containing 30% *Aspergillus fumigatus* Cel7A CBHI, 20% *Myceliophthora thermophila* Cel6A CBHI,I and 5% *Thermoascus aurantiacus* GH61A polypeptide was tested in comparison with a similar composition containing *Thielavia terrestris* GH61E polypeptide instead of *Thermoascus aurantiacus* GH61A polypeptide. All compositions were tested at 3 mg protein per g cellulose.

The assay was performed as described in Example 34. The 1 ml reactions with 50 mg of insoluble PCS solids per ml were conducted for 72 hours in 50 mM sodium acetate pH 5.0 buffer containing 1 mM manganese sulfate. All reactions were performed in triplicate and involved single mixing at the beginning of hydrolysis.

Figures 27A, 27B:
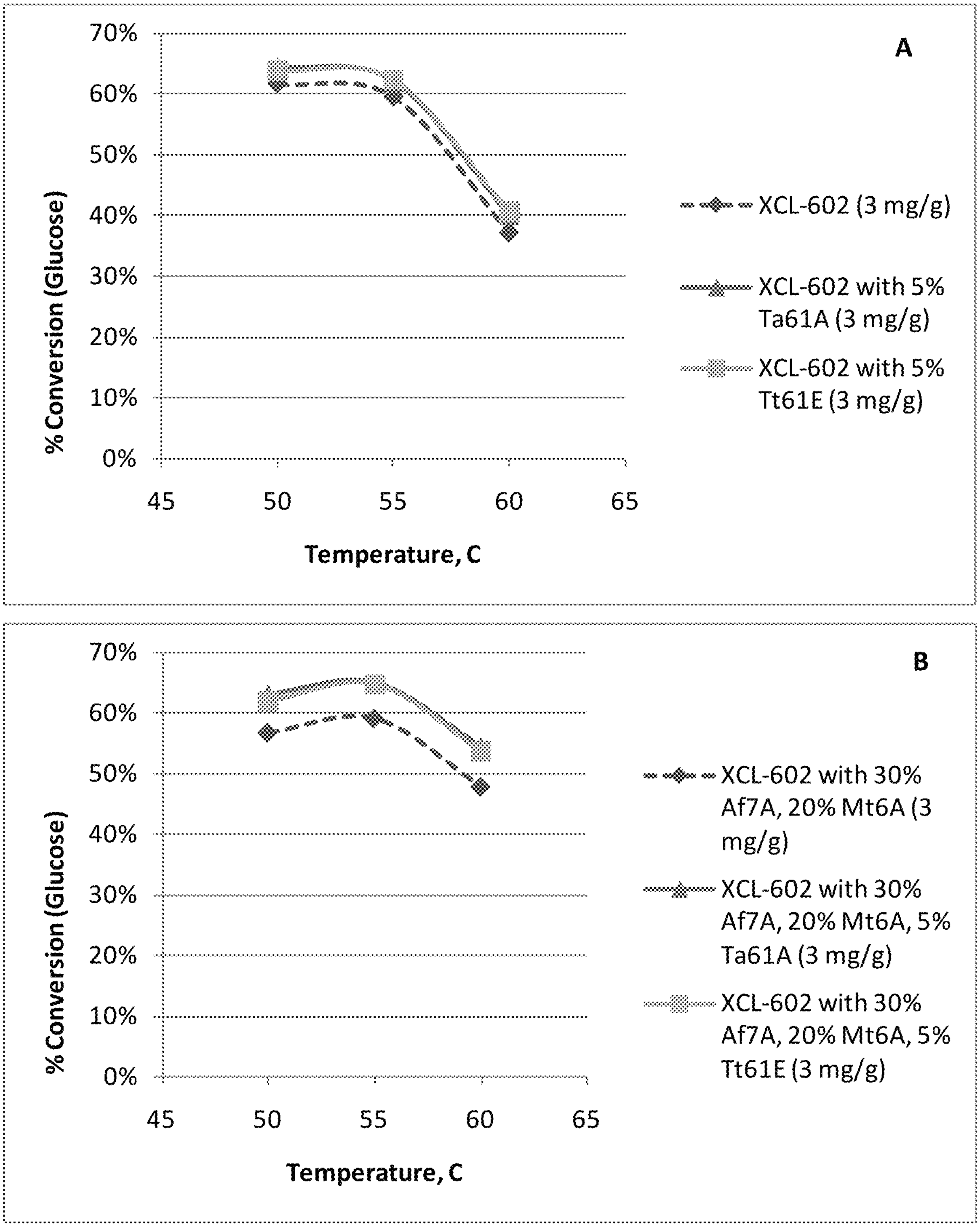
FIGS. 27A and 27B show a comparison of *Thermoascus aurantiacus* GH61A and *Thielavia terrestris* GH61E polypeptides replacing 5% of protein in *Trichoderma reesei*-based XCL-602 cellulase or XCL-602-based enzyme composition in hydrolysis of milled unwashed PCS at 50-60° C.

As shown in FIG. 27A, replacement of 5% protein in *Trichoderma reesei*-based XCL-602 cellulase by *Thielavia terrestris* GH61E polypeptide did not provide an advantage over the equivalent replacement by *Thermoascus aurantiacus* GH61A polypeptide. Similarly, as shown in FIG. 27B, the replacement of 5% protein in *Trichoderma reesei*-based XCL-602 cellulase by *Thielavia terrestris* GH61E polypeptide along with the 30% replacement by *Aspergillus fumigatus* Cel7A CBHI and 20% replacement by *Myceliophthora thermophila* Cel6A CBHII, did not provide an advantage over the equivalent replacement by *Thermoascus aurantiacus* GH61A polypeptide. Each GH61 polypeptide was tested at six different replacement levels ranging from 5% to 20%, and the conclusion was consistent for all replacement levels (data not shown). The results indicated that the *Thielavia terrestris* GH61E polypeptide did not synergize with the *Thermoascus aurantiacus* GH61A polypeptide under these conditions.

Example 61: Comparison of XCL-602-Based Enzyme Compositions Containing Different Replacement Levels of *Thermoascus aurantiacus* GH61A or *Thielavia terrestris* GH61E GH61 Polypeptides Having Cellulolytic Enhancing Activity in Hydrolysis of Milled Unwashed PCS at 50-60° C.

*Thermoascus aurantiacus* GH61A and *Thielavia terrestris* GH61E GH61 polypeptides having cellulolytic enhancing activity were tested separately at six different replacement levels (5%, 7.5%, 10%, 12.5%, 15%, and 20%) in different *Trichoderma reesei*-based XCL-602 cellulase compositions at 50-60° C. using milled unwashed PCS as a substrate. In one case, the *Trichoderma reesei*-based XCL-602 cellulase compositions comprised different replacement levels of a GH61 polypeptide along with a 5% replacement by *Aspergillus fumigatus* GH10 xyn3 xylanase. In another case, *Trichoderma reesei*-based XCL-602 cellulase compositions comprised different replacement levels of a GH61 polypeptide along with a 30% replacement by *Aspergillus fumigatus* Cel7A CBHI, a 20% replacement by *Myceliophthora thermophila* Cel6A CBHII, and a 5% replacement by *Aspergillus fumigatus* GH10 xyn3 xylanase. All enzyme compositions were tested at 3 mg total protein per g cellulose. For comparison, *Trichoderma reesei*-based XCL-533 cellulase was tested at 4.5 mg protein per g cellulose.

The assay was performed as described in Example 34. The 1 ml reactions with 50 mg of insoluble PCS solids per ml were conducted for 72 hours in 50 mM sodium acetate pH 5.0 buffer containing 1 mM manganese sulfate. All reactions were performed in triplicate and involved single mixing at the beginning of hydrolysis.

The results shown in Table 3 demonstrated that the optimal replacement level for both GH61 polypeptides at 50° C. and 55° C. was 10-12.5% of the total protein in the *Trichoderma reesei*-based XCL-602 cellulase compositions. At 60° C., the optimal replacement level for both GH61 polypeptides was 20% of the total protein in the *Trichoderma reesei*-based XCL-602 cellulase compositions. The equivalent replacement levels of the *Thermoascus aurantiacus* GH61A and *Thielavia terrestris* GH61E polypeptides in similar *Trichoderma reesei*-based XCL-602 cellulase compositions provided a similar enhancement of the cellulose hydrolysis in milled unwashed PCS at 50-60° C.

TABLE 3

Comparison of *Trichoderma reesei*-based XCL-602 cellulase compositions containing different replacement levels of *Thermoascus aurantiacus* GH61A or *Thielavia terrestris* GH61E polypeptidesin hydrolysis of milled unwashed PCS at 50-60° C.

| GH61 replacement level | 50° C. | 55° C. | 60° C. |
|---|---|---|---|
| XCL-602 with 5% replacement by *Aspergillus fumigatus* GH10 xyn3 xylanase and 0-20% replacement by a GH61 polypeptide (3 mg total protein per g cellulose) | | | |
| 0% *T. aurantiacus* GH61A | 67% | 66% | 42% |
| 5% *T. aurantiacus* GH61A | 69% | 69% | 46% |
| 7.5% *T. aurantiacus* GH61A | 69% | 69% | 47% |
| 10% *T. aurantiacus* GH61A | 69% | 69% | 49% |
| 12.5% *T. aurantiacus* GH61A | 69% | 69% | 49% |
| 15% *T. aurantiacus* GH61A | 69% | 69% | 49% |
| 20% *T. aurantiacus* GH61A | 66% | 69% | 51% |
| 0% *T. terrestris* GH61E | 67% | 66% | 42% |
| 5% *T. terrestris* GH61E | 68% | 69% | 45% |
| 7.5% *T. terrestris* GH61E | 68% | 68% | 46% |
| 10% *T. terrestris* GH61E | 68% | 68% | 47% |
| 12.5% *T. terrestris* GH61E | 65% | 68% | 48% |
| 15% *T. terrestris* GH61E | 64% | 67% | 48% |
| 20% *T. terrestris* GH61E | 62% | 65% | 49% |
| XCL-602 with 30% replacement by *Aspergillus fumigatus* Cel7A CBHI, 20% replacement by *Myceliophthora thermophila* Cel6A CBHII, 5% replacement by *Aspergillus fumigatus* GH10 xyn3 xylanase and 0-20% replacement by a GH61 polypeptide (3 mg total protein per g cellulose) | | | |
| 0% *T. aurantiacus* GH61A | 64% | 68% | 58% |
| 5% *T. aurantiacus* GH61A | 70% | 75% | 66% |
| 7.5% *T. aurantiacus* GH61A | 72% | 75% | 67% |
| 10% *T. aurantiacus* GH61A | 72% | 76% | 68% |
| 12.5% *T. aurantiacus* GH61A | 71% | 76% | 70% |
| 15% *T. aurantiacus* GH61A | 71% | 76% | 69% |
| 20% *T. aurantiacus* GH61A | 68% | 72% | 71% |
| 0% *T. terrestris* GH61E | 64% | 68% | 58% |
| 5% *T. terrestris* GH61E | 68% | 72% | 65% |
| 7.5% *T. terrestris* GH61E | 69% | 73% | 65% |
| 10% *T. terrestris* GH61E | 69% | 74% | 69% |
| 12.5% *T. terrestris* GH61E | 67% | 73% | 68% |
| 15% *T. terrestris* GH61E | 66% | 74% | 69% |
| 20% *T. terrestris* GH61E | 65% | 72% | 69% |

Example 62: Hydrolysis of Milled Unwashed PCS by Non-Replaced XCL-602 and Various XCL-602-Based Enzyme Compositions (3 mg Protein Per g Cellulose) in Comparison with *Trichoderma reesei*-Based XCL-533 Cellulase (4.5 mg Protein Per g Cellulose) at 50-60° C.

Example 61 was repeated using the same *Trichoderma reesei*-based XCL-602 cellulase compositions except that only one GH61 polypeptide (*Thermoascus aurantiacus* GH61A) was tested at a single replacement level (10% of total protein). The *Trichoderma reesei*-based XCL-602 cellulase and all *Trichoderma reesei*-based XCL-602 cellulase compositions were used at 3 mg total protein per g cellulose.

The assay was performed as described in Example 34. The 1 ml reactions with 50 mg of insoluble PCS solids per ml were conducted for 72 hours in 50 mM sodium acetate pH 5.0 buffer containing 1 mM manganese sulfate. All reactions were performed in triplicate and involved single mixing at the beginning of hydrolysis.

Figure 28A:
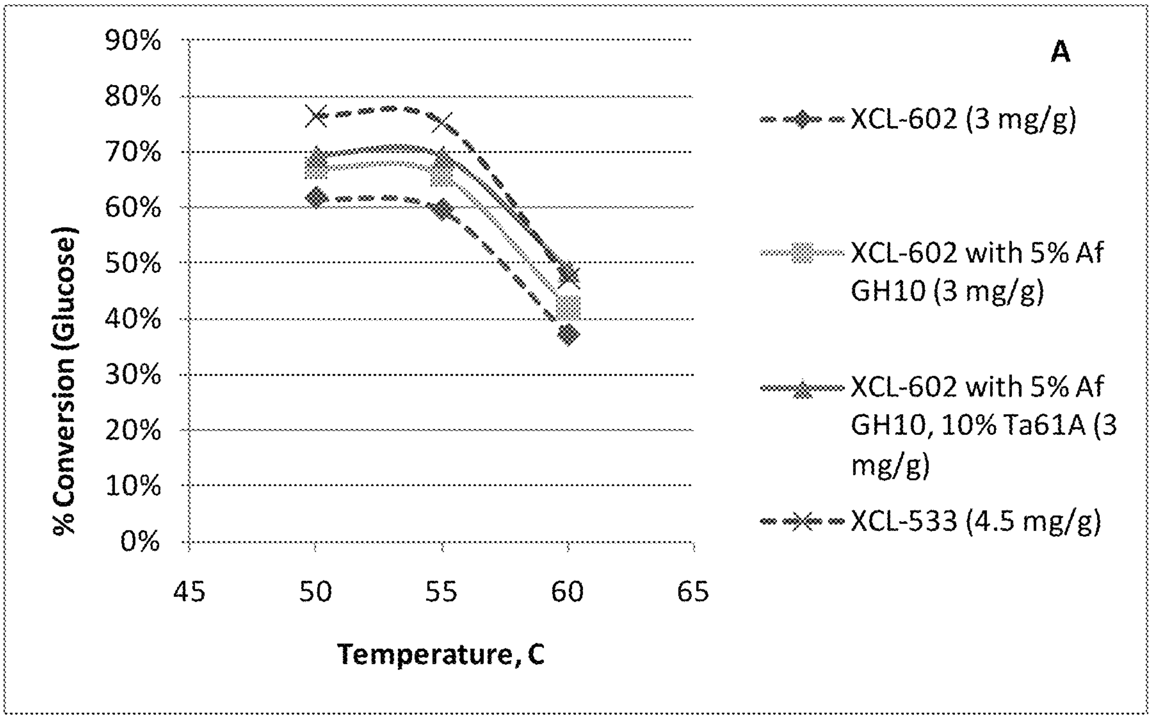
FIGS. 28A and 28B show the hydrolysis of milled unwashed PCS by non-replaced *Trichoderma reesei*-based XCL-602 cellulase and various XCL-602-based enzyme compositions (3 mg protein per g cellulose) in comparison with *Trichoderma reesei*-based XCL-533 cellulase (4.5 mg protein per g cellulose) at 50-60° C.
Figure 28B:
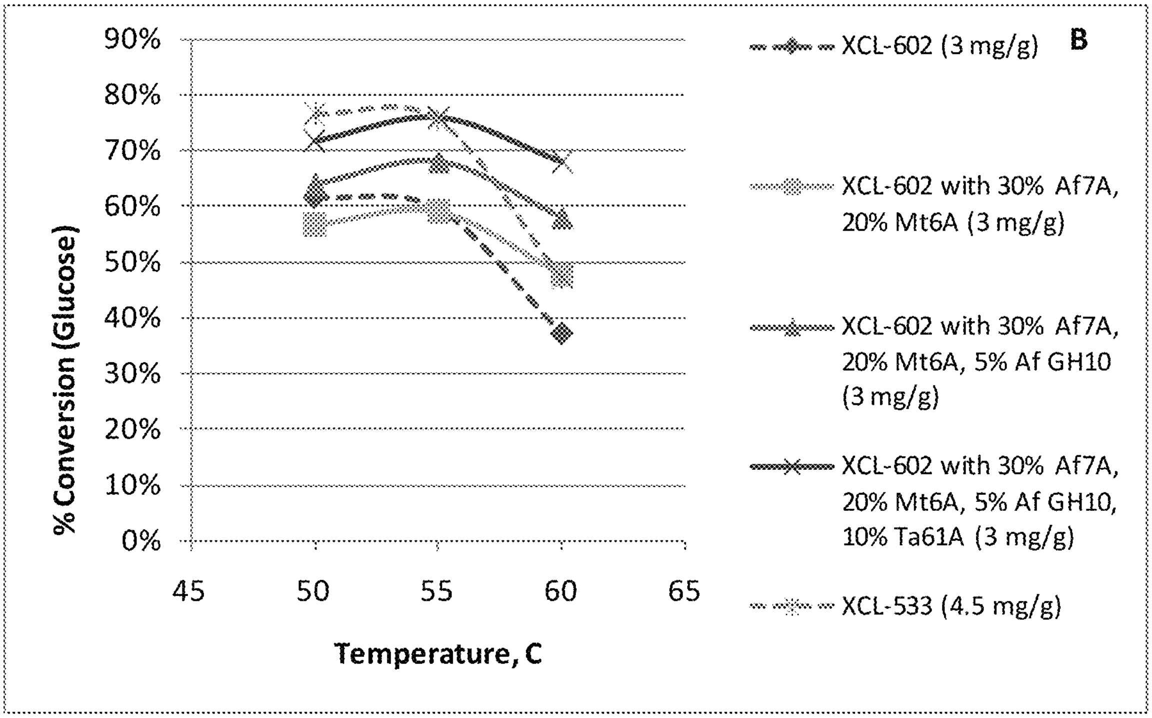

The results shown in FIG. 28A demonstrated that the replacement of *Trichoderma reesei*-based XCL-602 cellulase with a composition comprising 5% *Aspergillus fumigatus* GH10 xyn3 xylanase and 10% *Thermoascus aurantiacus* GH61A polypeptide to a total protein loading of 3 mg protein per g cellulose has significantly improved the hydrolysis yield over the non-replaced *Trichoderma reesei*-based XCL-602 cellulase at all three temperatures. As shown in FIG. 27B, the enhancement was even more pronounced when the *Trichoderma reesei*-based XCL-602 cellulase was additionally replaced with 30% *Aspergillus fumigatus* Cel7A CBHI and 20% *Myceliophthora thermophila* Cel6A CBHII. The results shown in FIG. 28B demonstrated that the replacement of *Trichoderma reesei*-based XCL-602 cellulase with 30% *Aspergillus fumigatus* Cel7A CBHI and 20% *Myceliophthora thermophila* Cel6A CBHII increased the degree of cellulose conversion to glucose after 72 hours of hydrolysis at 60° C. from 37% to 48%. Additional 5% replacement by *Aspergillus fumigatus* GH10 xyn3 xylanase increased the degree of cellulose conversion to glucose to 58%, and additional 10% replacement by *Thermoascus aurantiacus* GH61A polypeptide increased the degree of cellulose conversion to glucose to 68% compared to 37% obtained with non-replaced *Trichoderma reesei*-based XCL-602 cellulase. At 3 mg protein per g cellulose, the best XCL-602-based enzyme composition comprising the XCL-602 cellulase with 30% replacement by *Aspergillus fumigatus* Cel7A CBHI, 20% replacement by *Myceliophthora thermophila* Cel6A CBHII, 5% replacement by *Aspergillus fumigatus* GH10 xyn3 xylanase and 10% replacement by *Thermoascus aurantiacus* GH61A polypeptide, was capable of achieving the same cellulose conversion of milled unwashed PCS at 55° C. (76%) as non-replaced *Trichoderma reesei*-based XCL-602 cellulase at 4.5 mg protein per g cellulose and 50° C.—a 1.5-fold reduction in protein loading.

Example 63: Preparation of *Penicillium emersonii* Strain NN051602 GH7 Cellobiohydrolase I The *Penicillium emersonii* strain NN051602 Cel7 cellobiohydrolase I (SEQ ID NO: 157 [DNA sequence] and SEQ ID NO: 158 [deduced amino acid sequence]) was obtained according to the procedure described below.

*Penicillium emersonii* was grown on a PDA agar plate at 45° C. for 3 days. Mycelia were collected directly from the agar plate into a sterilized mortar and frozen under liquid nitrogen. Frozen mycelia were ground, by mortar and pestle, to a fine powder, and genomic DNA was isolated using a DNeasy® Plant Mini Kit (QIAGEN Inc., Valencia, Calif., USA).

Oligonucleotide primers, shown below, were designed to amplify the GH7 cellobiohydrolase I gene from genomic DNA of *Penicillium emersonii*. An IN-FUSION™ CF Dry-down Cloning Kit (Clontech Laboratories, Inc., Mountain View, Calif., USA) was used to clone the fragment directly into the expression vector pPFJO355, without the need for restriction digestion and ligation.

```
Sense primer:
                                    (SEQ ID NO: 207)
5'-ACACAACTGGGGATCCACC atgcttcgacgggctcttc-3'

Antisense primer:
                                    (SEQ ID NO: 208)
5'-GTCACCCTCTAGATCT CGCAGAGCAACTTCCGTCTACTTC-3'
```

Bold letters represented the coding sequence (for the sense primer) or the downstream sequence of the coding region (for the antisense primer). The remaining sequence was homologous to the insertion sites of pPFJO355.

Twenty picomoles of each of the primers above were used in a PCR reaction composed of *Penicillium emersonii* genomic DNA, 10 μl of 5×GC Buffer, 1.5 μl of DMSO, 2.5 mM each of dATP, dTTP, dGTP, and dCTP, and 0.6 unit of Phusion™ High-Fidelity DNA Polymerase in a final volume of 50 μl. The amplification was performed using a Peltier Thermal Cycler programmed for denaturing at 98° C. for 1 minute; 8 cycles of denaturing at 98° C. for 15 seconds, annealing at 65° C. for 30 seconds, with 1° C. decrease per cycle and elongation at 72° C. for 80 seconds; and another 23 cycles each at 98° C. for 15 seconds, 66° C. for 30 seconds and 72 C for 75 seconds; final extension at 72° C. for 7 minutes. The heat block then went to a 4° C. soak cycle.

The reaction products were isolated by 1.0% agarose gel electrophoresis using 90 mM Tris-borate and 1 mM EDTA (TBE) buffer where an approximately 1.4 kb product band was excised from the gel, and purified using an ILLUSTRA® GFX® PCR DNA and Gel Band Purification Kit according to the manufacturer's instructions.

Plasmid pPFJO355 was digested with Barn I and Bgl II, isolated by 1.0% agarose gel electrophoresis using TBE buffer, and purified using an ILLUSTRA® GFX® PCR DNA and Gel Band Purification Kit according to the manufacturer's instructions.

The gene fragment and the digested vector were ligated together using an IN-FUSION™ CF Dry-down PCR Cloning resulting in pGH7_ZY209383 in which transcription of the *Penicillium emersonii* GH7 cellobiohydrolase I gene was under the control of the *Aspergillus oryzae* TAKA amylase promoter from the gene for *Aspergillus oryzae* alpha-amylase. The cloning operation was according to the manufacturer's instruction. In brief, 30 ng of pPFJO355 digested with Barn I and Bgl II, and 60 ng of the *Penicillium emersonii* GH7 cellobiohydrolase I gene purified PCR product were added to the reaction vial and resuspended the powder in a final volume of 10 ul with addition of deionized water. The reaction was incubated at 37° C. for 15 minutes and then 50° C. for 15 minutes. Five μl of the reaction were used to transform *E. coli* TOP10 competent cells. An *E. coli* transformant containing pGH7_ZY209383 was detected by colony PCR and plasmid DNA was prepared using a QIAprep Spin Miniprep Kit (QIAGEN Inc., Valencia, Calif., USA). The *Penicillium emersonii* GH7 cellobiohydrolase I gene insert in pGH7_ZY209383 was confirmed by DNA sequencing using a 3730XL DNA Analyzer.

*Aspergillus oryzae* HowB101 (WO 95/35385) protoplasts were prepared according to the method of Christensen et al., 1988, *Bio/Technology* 6: 1419-1422 and transformed with 3 μg of pGH7_ZY209383. The transformation yielded about 50 transformants. Twelve transformants were isolated to individual Minimal medium plates.

Four transformants were inoculated separately into 3 ml of YPM medium in a 24-well plate and incubated at 30° C., 150 rpm. After 3 days incubation, 20 μl of supernatant from each culture were analyzed by SDS-PAGE using a NUPAGE® NOVEX® 4-12% Bis-Tris Gel with MES buffer according to the manufacturer's instructions. The resulting gel was stained with INSTANT® Blue. SDS-PAGE profiles of the cultures showed that the majority of the transformants had a major smeary band of approximately 50 kDa. The expression strain was designated as *A. oryzae* EXP03477.

A slant of *A. oryzae* EXP03477 was washed with 10 ml of YPM medium and inoculated into a 2 liter flask containing 400 ml of YPM medium to generate broth for characterization of the enzyme. The culture was harvested on day 3 and filtered using a 0.45 μm DURAPORE Membrane (Millipore, Bedford, Mass., USA).

A 1600 ml volume of filtered broth of *A. oryzae* EXP03477 was precipitated with ammonium sulfate (80% saturation), re-dissolved in 100 ml of 25 mM Bis-Tris pH 6.5 buffer, dialyzed against the same buffer, and filtered through a 0.45 μm filter; the final volume was 200 ml. The solution was applied to a 40 ml Q Sepharose® Fast Flow column equilibrated with 25 mM Bis-Tris pH 6.5, and the proteins were eluted with a linear NaCl gradient (0-0.4 M). Fractions with activity against PASC were collected and applied to a 40 ml Phenyl Sepharose™ HIC column (GE Healthcare, Piscataway, N.J., USA) equilibrated in 20 mM PBS with 1.8 M $(NH_4)_2SO_4$ pH 7 buffer, and the proteins were eluted with 20 mM PBS pH 7. Fractions from the column with activity toward phosphoric acid swollen cellulose (PASC) as substrate were analyzed by SDS-PAGE using a NUPAGE® NOVEX® 4-12% Bis-Tris Gel with MES buffer. Fractions with the correct molecular weight were pooled. Then the pooled solution was concentrated by ultrafiltration. Protein concentration was determined using a Microplate BCA™ Protein Assay Kit in which bovine serum albumin was used as a protein standard.

Example 64: Preparation of *Penicillium Pinophilium* Strain NN046877 GH7 Cellobiohydrolase I The *Penicillium pinophilium* strain NN046877 Cel7 cellobiohydrolase II (SEQ ID NO: 159 [DNA sequence] and SEQ ID NO: 160 [deduced amino acid sequence]) was obtained according to the procedure described below.

*Penicillium pinophilum* was grown on a PDA agar plate at 37° C. for 4-5 days. Mycelia were collected directly from the agar plate into a sterilized mortar and frozen under liquid nitrogen. Frozen mycelia were ground, by mortar and pestle, to a fine powder, and genomic DNA was isolated using a DNeasy® Plant Mini Kit.

Oligonucleotide primers, shown below, were designed to amplify the GH7 cellobiohydrolase I gene from the genomic DNA of *Penicillium pinophilum*. An IN-FUSION™ CF Dry-down Cloning Kit (Clontech Laboratories, Inc., Mountain View, Calif., USA) was used to clone the fragment directly into the expression vector pPFJO355, without the need for restriction digestion and ligation.

```
Sense primer:
                                    (SEQ ID NO: 209)
5'-ACACAACTGGGGATCCACCATGTCTGCCTTGAACTCTTTC-3'

Antisense primer:
                                    (SEQ ID NO: 210)
5'-GTCACCCTCTAGATCTTCACAAACATTGAGAGTAGTAAGGGTT-3'
```

Bold letters represented the coding sequence and the remaining sequence was homologous to the insertion sites of pPFJO355.

Twenty picomoles of each of the primers above were used in a PCR reaction composed of *Penicillium pinophilum* genomic DNA, 10 μl of 5×GC Buffer, 1.5 μl of DMSO, 2.5 mM each of dATP, dTTP, dGTP, and dCTP, and 0.6 unit of Phusion™ High-Fidelity DNA Polymerase in a final volume of 50 μl. The amplification was performed using a Peltier Thermal Cycler programmed for denaturing at 98° C. for 1 minute; 5 cycles of denaturing at 98° C. for 15 seconds, annealing at 56° C. for 30 seconds, with 1° C. increasing per cycle and elongation at 72° C. for 75 seconds; and another 25 cycles each at 98° C. for 15 seconds, 65C for 30 seconds and 72° C. for 75 seconds; final extension at 72° C. for 10 minutes. The heat block then went to a 4° C. soak cycle.

The reaction products were isolated by 1.0% agarose gel electrophoresis using 90 mM Tris-borate and 1 mM EDTA (TBE) buffer where an approximately 1.6 kb product band was excised from the gel, and purified using an ILLUSTRA® GFX® PCR DNA and Gel Band Purification Kit according to the manufacturer's instructions.

Plasmid pPFJO355 was digested with Barn I and Bgl II, isolated by 1.0% agarose gel electrophoresis using TBE buffer, and purified using an ILLUSTRA® GFX® PCR DNA and Gel Band Purification Kit according to the manufacturer's instructions.

The gene fragment and the digested vector were ligated together using an IN-FUSION™ CF Dry-down PCR Cloning resulting in pPpin6 in which transcription of the *Penicillium pinophilum* GH7 cellobiohydrolase I gene was under the control of the *Aspergillus oryzae* TAKA amylase promoter. In brief, 30 ng of pPFJO355 digested with Barn I and Bgl II, and 100 ng of the *Penicillium pinophilum* GH7 cellobiohydrolase I gene purified PCR product were added to a reaction vial and resuspended in a final volume of 10 µl with addition of deionized water. The reaction was incubated at 37° C. for 15 minutes and then 50° C. for 15 minutes. Three µl of the reaction were used to transform *E. coli* TOP10 competent cells. An *E. coli* transformant containing pPpin6 was detected by colony PCR and plasmid DNA was prepared using a QIAprep Spin Miniprep Kit (QIAGEN Inc., Valencia, Calif., USA). The *Penicillium pinophilum* GH7 cellobiohydrolase I gene insert in pPpin6 was confirmed by DNA sequencing using a 3730XL DNA Analyzer.

*Aspergillus oryzae* HowB101 (WO 95/35385) protoplasts were prepared according to the method of Christensen et al., 1988*, Bio/Technology* 6: 1419-1422 and transformed with 3 µg of pPpin6. The transformation yielded about 50 transformants. Four transformants were isolated to individual Minimal medium plates.

Four transformants were inoculated separately into 3 ml of YPM medium in a 24-well plate and incubated at 30° C., 150 rpm. After 3 days incubation, 20 µl of supernatant from each culture were analyzed by SDS-PAGE using a NUPAGE® NOVEX® 4-12% Bis-Tris Gel with MES buffer according to the manufacturer's instructions. The resulting gel was stained with INSTANT® Blue. SDS-PAGE profiles of the cultures showed that the majority of the transformants had a major smear band of approximately 60-90 kDa. The expression strain was designated as *A. oryzae* EXP02768.

A slant of *A. oryzae* EXP02768 was washed with 10 ml of YPM medium and inoculated into a 2 liter flask containing 400 ml of YPM medium to generate broth for characterization of the enzyme. The culture was harvested on day 3 and filtered using a 0.45 µm DURAPORE Membrane (Millipore, Bedford, Mass., USA).

A 1600 ml volume of the filtered broth of *A. oryzae* EXP02768 was precipitated with ammonium sulfate (80% saturation), re-dissolved in 100 ml of 25 mM Bis-Tris pH 6.0, dialyzed against the same buffer, and filtered through a 0.45 µm filter; the final volume was 200 ml. The solution was applied to a 40 ml Q Sepharose® Fast Flow column equilibrated in 25 mM Bis-Tris pH 6.0, and the proteins were eluted with a linear NaCl gradient (0-0.4 M). Fractions from the column with activity against pNP-β-D-lactopyranoside were analyzed by SDS-PAGE using a NUPAGE® NOVEX® 4-12% Bis-Tris Gel with MES buffer. Fractions with the correct molecular weight were pooled and concentrated by ultrafiltration. Protein concentration was determined using a Microplate BCA™ Protein Assay Kit in which bovine serum albumin was used as a protein standard.

Example 65: Preparation of *Aspergillus terreus* ATCC 28865 GH7 Cellobiohydrolase I The *Aspergillus terreus* ATCC 28865 GH7 cellobiohydrolase I (SEQ ID NO: 161 [DNA sequence] and SEQ ID NO: 162 [deduced amino acid sequence]) was obtained according to the procedure described below.

Two synthetic oligonucleotide primers, shown below, were designed to PCR amplify the cellobiohydrolase I gene from *Aspergillus terreus* ATCC 28865 genomic DNA. Genomic DNA was isolated using a FastDNA spin for Soil Kit (MP Biomedicals, OH, USA).

```
Primer #222:
                                    (SEQ ID NO: 211)
5'-TAAGAATTCACCATGCCTTCCACCTACGA-3'

Primer #302:
                                    (SEQ ID NO: 212)
5'-TATGCGGCCGCATTCTCCTAGACACCCCGCAT-3'
```

The amplification reaction was composed of 1 µl of *Aspergillus terreus* genomic DNA, 12.5 µl of 2× REDDY-MIX™ PCR Buffer (Thermo Fisher Scientific Inc., Waltham, Mass., USA), 1 µl of 5 µM primer #222, 1 µl of 5 µM primer #302, and 9.5 µl of $H_2O$. The amplification reaction was incubated in a PTC-200 DNA ENGINE™ Thermal Cycler programmed for 1 cycle at 94° C. for 2 minutes; and 35 cycles each at 94° C. for 15 seconds and 60° C. for 1.5 minutes.

A 1.7 kb PCR reaction product was isolated by 1% agarose gel electrophoresis using TAE buffer and staining with SYBR Safe DNA gel stain (Invitrogen Corp., Carlsbad, Calif., USA). The DNA band was visualized with the aid of an Eagle Eye Imaging System and a DarkReader Transilluminator (Clare Chemical Research, Dolores, Colo., USA). The 1.7 kb DNA band was excised from the gel and purified using a GFX® PCR DNA and Gel Band Purification Kit according to the manufacturer's instructions.

The 1.7 kb fragment was cleaved with EcoR I and Not I and purified using a GFX® PCR DNA and Gel Band Purification Kit according to the manufacturer's instructions.

The cleaved 1.7 kb fragment was then directionally cloned by ligation into Eco RI-Not I cleaved pXYG1051 (WO 2005/080559) using T4 ligase (Promega, Madison, Wis., USA) according to the manufacturer's instructions. The ligation mixture was transformed into *E. coli* TOP10F competent cells according to the manufacturer's instructions. The transformation mixture was plated onto LB plates supplemented with 100 µg of ampicillin per ml. Plasmid minipreps were prepared from several transformants and sequenced. One plasmid with the correct *Aspergillus terreus* GH7 coding sequence was chosen. The plasmid was designated pXYG1051-N P003568.

The expression plasmid pXYG1051-NP003568 was transformed into *Aspergillus oryzae* JaL355 as described in WO 98/00529. Transformants were purified on selection plates through single conidia prior to sporulating them on PDA plates. Production of the *Aspergillus terreus GH7* polypeptide by the transformants was analyzed from culture supernatants of 1 ml 96 deep well stationary cultivations at 26° C. in YP medium with 2% maltodextrin. Expression was verified by SDS-PAGE using a NUPAGE® NOVEX®

4-12% Bis-Tris Gel with MES buffer and Coomassie blue staining. One transformant was selected for further work and designated *Aspergillus oryzae* 64.1.

For larger scale production, *Aspergillus oryzae* 64.1 spores were spread onto a PDA plate and incubated for five days at 37° C. The confluent spore plate was washed twice with 5 ml of 0.01% TWEEN® 20 to maximize the number of spores collected. The spore suspension was then used to inoculate twenty-five 500 ml flasks containing 100 ml of YPG medium. The culture was incubated at 30° C. with constant shaking at 120 rpm. At day four post-inoculation, the culture broth was collected by filtration through a triple layer of Whatman glass microfiber filters of 1.6 μm, 1.2 μm, and 0.7 μm. Fresh culture broth from this transformant produced a band of GH7 protein of approximately 55 kDa. The identity of this band as the *Aspergillus terreus* GH7 polypeptide was verified by peptide sequencing.

Two liters of the filtered broth were concentrated to 400 ml and washed with 50 mM HEPES pH 7.0 using a SARTOFLOW® Alpha ultrafiltration system with a 10 kDa MW-CO (Sartorius Stedim Biotech S.A., Aubagne Cedex, France). Ammonium sulphate was added to a final concentration of 1 M and dissolved in the ultrafiltrate. The solution was applied on a Source 15 Phenyl XK 26/20 50 ml column (GE Healthcare, HiHerod, Denmark). After application the column was washed with 150 ml of 1 M ammonium sulphate and eluded with 1 column volume of 50% ethanol in a 0% to 100% gradient followed by 5 column volumes of 50% ethanol at a flow rate of 10 ml/minute. Fractions of 10 ml were collected and analyzed by SDS-PAGE. Fraction 3 to 8 were pooled and diluted to 1000 ml with 50 mM HEPES pH 7.0 before application on a Q Sepharose® Fast Flow column XK26/20 60 ml column (GE Healthcare, HiHerod, Denmark). After application the column was washed 3 times with 60 ml of 50 mM HEPES pH 7.0 and eluded with 100 ml of 50 mM HEPES pH 7.0, 1 M NaCl at a flow rate of 10 ml/minute. Fractions of 10 ml were collected and analyzed by SDS-PAGE. The flow-through and first wash were pooled and concentrated to 400 ml and washed with 50 mM HEPES pH 7.0 using the ultrafiltration system described above. Further concentration was conducted using a VIVASPIN™ centrifugal concentrator according to the manufacturer's instructions to a final volume of 80 ml. The protein concentration was determined by A280/A260 absorbance. Protein concentration was also determined using a Microplate BCA™ Protein Assay Kit in which bovine serum albumin was used as a protein standard.

Example 66: Preparation of *Neosartorya fischeri* Strain NRRL 181 GH7 Cellobiohydrolase I The *Neosartorya fischeri* NRRL 181 GH7 cellobiohydrolase I (SEQ ID NO: 163 [DNA sequence] and SEQ ID NO: 164 [deduced amino acid sequence]) was obtained according to the procedure described below.

Two synthetic oligonucleotide primers, shown below, were designed to PCR amplify the cellobiohydrolase I gene from *Neosartorya fischeri* genomic DNA. Genomic DNA was isolated using a FastDNA Spin for Soil Kit.

```
Primer #374:
                                    (SEQ ID NO: 213)
5'-TAAGAATTCACCATGCCTTCCACCTACGA-3'

Primer #375:
                                    (SEQ ID NO: 214)
5'-TATGCGGCCGCATTCTCCTAGACACCCCGCAT-3'
```

The amplification reaction was composed of 1 μl of *Neosartorya fischeri* genomic DNA, 12.5 μl of 2× REDDY-MIX™ PCR Buffer, 1 μl of 5 μM primer #374, 1 μl of 5 μM primer #375, and 9.5 μl of $H_2O$. The amplification reaction was incubated in a PTC-200 DNA ENGINE™ Thermal Cycler programmed for 1 cycle at 94° C. for 2 minutes; and 35 cycles each at 94° C. for 15 seconds and 60° C. for 1.5 minutes.

A 1.6 kb PCR reaction product was isolated by 1% agarose gel electrophoresis using TAE buffer and staining with SYBR Safe DNA gel stain. The DNA band was visualized with the aid of an Eagle Eye Imaging System and a DarkReader Transilluminator. The 1.6 kb DNA band was excised from the gel and purified using a GFX® PCR DNA and Gel Band Purification Kit according to the manufacturer's instructions.

The 1.6 kb fragment was cleaved with EcoR I and Not I and purified using a GFX® PCR DNA and Gel Band Purification Kit according to the manufacturer's instructions.

The cleaved 1.6 kb fragment was then directionally cloned by ligation into Eco RI-Not I cleaved pXYG1051 (WO 2005/080559) using T4 ligase according to the manufacturer's instructions. The ligation mixture was transformed into *E. coli* TOP10F competent cells according to the manufacturer's instructions. The transformation mixture was plated onto LB plates supplemented with 100 μg of ampicillin per ml. Plasmid minipreps were prepared from several transformants and sequenced. One plasmid with the correct *Neosartorya fischeri* GH7 cellobiohydrolase coding sequence was chosen. The plasmid was designated pXYG1051-NP003786.

The expression plasmid pXYG1051-NP003786 was transformed into *Aspergillus oryzae* JaL355 as described in WO 98/00529. Transformants were purified on selection plates to single conidia prior to sporulating them on PDA plates. Production of the *Neosartorya fischeri* GH7 cellobiohydrolase by the transformants was analyzed from culture supernatants of 1 ml 96 deep well stationary cultivations at 26° C. in YP medium with 2% maltodextrin. Expression was verified by SDS-PAGE using a NUPAGE® NOVEX® 4-12% Bis-Tris Gel with MES buffer and Coomassie blue staining. One transformant was selected for further work and designated *Aspergillus oryzae* 92.7.

For larger scale production, *Aspergillus oryzae* 92.7 spores were spread onto a PDA plate and incubated for five days at 37° C. The confluent spore plate was washed twice with 5 ml of 0.01% TWEEN® 20 to maximize the number of spores collected. The spore suspension was then used to inoculate twenty-five 500 ml flasks containing 100 ml of YPM medium. The culture was incubated at 26° C. with constant shaking at 120 rpm. At day five post-inoculation, the culture broth was collected by filtration through a triple layer of Whatman glass microfiber filters of 1.6 μm, 1.2 μm, and 0.7 μm. Fresh culture broth from this transformant produced a band of GH7 protein of approximately 70 kDa. The identity of this band as the *Neosartorya fischeri* GH7 cellobiohydrolase was verified by peptide sequencing.

Two liters of the filtered broth were concentrated to 400 ml and washed with 50 mM HEPES pH 7.0 using a SARTOFLOW® Alpha ultrafiltration system with a 10 kDa MW-CO. Ammonium sulphate was added to a final concentration of 1 M and dissolved in the ultrafiltrate. The solution was applied to a Source 15 Phenyl XK 26/20 50 ml column.

After application the column was washed with 150 ml of 1 M ammonium sulphate and eluded with 1 column volume of 50% ethanol in a 0% to 100% gradient followed by 5 column volumes of 50% ethanol at a flow rate of 10 ml/minute. Fractions of 10 ml were collected and analyzed by SDS-PAGE. Fraction 3 to 8 were pooled and diluted to 1000 ml with 50 mM HEPES pH 7.0 before application to a Q Sepharose® Fast Flow XK26/20 60 ml column. After application the column was washed 3 times with 60 ml of 50 mM HEPES pH 7.0 and eluded with 100 ml of 50 mM HEPES pH 7.0, 1 M NaCl at a flow rate of 10 ml/minute. Fractions of 10 ml were collected and analyzed by SDS-PAGE. The flow-through and first wash were pooled and concentrated to 400 ml and washed with 50 mM HEPES pH 7.0 using a SARTOFLOW® Alpha ultrafiltration system with a 10 kDa MW-CO. Further concentration was conducted using a VIVASPIN™ centrifugal concentrator according to the manufacturer's instructions to a final volume of 80 ml. The protein concentration determined by A280/A260 absorbance. Protein concentration was also determined using a Microplate BCA™ Protein Assay Kit in which bovine serum albumin was used as a protein standard.

Example 67: Preparation of *Aspergillus nidulans* Strain FGSCA4 GH7 Cellobiohydrolase I The *Aspergillus nidulans* strain FGSCA4 GH7 cellobiohydrolase I (SEQ ID NO: 165 [DNA sequence] and SEQ ID NO: 166 [deduced amino acid sequence]) was obtained according to the procedure described below.

Two synthetic oligonucleotide primers, shown below, were designed to PCR amplify the cellobiohydrolase I gene from *Aspergillus nidulans* genomic DNA. Genomic DNA was isolated using a FastDNA Spin for Soil Kit.

```
Primer #376:
                                    (SEQ ID NO: 215)
5'-TAACAATTGACCATGGCATCTTCATTCCAGTTGTA-3'

Primer #377:
                                    (SEQ ID NO: 216)
5'-TATGCGGCCGCGTCTCCCATTTACGACCCACCA-3'
```

The amplification reaction was composed of 1 μl of *Aspergillus nidulans* genomic DNA, 12.5 μl of 2× REDDY-MIX™ PCR Buffer, 1 μl of 5 μM primer #374, 1 μl of 5 μM primer #375, and 9.5 μl of $H_2O$. The amplification reaction was incubated in a PTC-200 DNA ENGINE™ Thermal Cycler programmed for 1 cycle at 94° C. for 2 minutes; and 35 cycles each at 94° C. for 15 seconds and 60° C. for 1.5 minutes.

A 1.6 kb PCR reaction product was isolated by 1% agarose gel electrophoresis using TAE buffer and staining with SYBR Safe DNA gel stain. The DNA band was visualized with the aid of an Eagle Eye Imaging System and a DarkReader Transilluminator. The 1.6 kb DNA band was excised from the gel and purified using a GFX® PCR DNA and Gel Band Purification Kit according to the manufacturer's instructions.

The 1.6 kb fragment was cleaved with Mfe I and Not I and purified using a GFX® PCR DNA and Gel Band Purification Kit according to the manufacturer's instructions.

The cleaved 1.6 kb fragment was then directionally cloned by ligation into Eco RI-Not I cleaved pXYG1051 (WO 2005/080559) using T4 ligase according to the manufacturer's instructions. The ligation mixture was transformed into *E. coli* TOP10F competent cells according to the manufacturer's instructions. The transformation mixture was plated onto LB plates supplemented with 100 μg of ampicillin per ml. Plasmid minipreps were prepared from several transformants and sequenced. One plasmid with the *Aspergillus nidulans* GH7 coding sequence was chosen. Two mutations introduced during PCR were identified which result in a change of Leu 7 to Trp and of Glu 436 to Gly relative to the public sequence Q8NK02. The plasmid was designated pXYG1051-NP003787.

The expression plasmid pXYG1051-NP003787 was transformed into *Aspergillus oryzae* JaL355 as described in WO 98/00529. Transformants were purified on selection plates to single conidia prior to sporulating them on PDA plates. Production of the *Aspergillus nidulans* GH7 cellobiohydrolase by the transformants was analyzed from culture supernatants of 1 ml 96 deep well stationary cultivations at 26° C. in YP medium with 2% maltodextrin. Expression was verified by SDS-PAGE using a NUPAGE® NOVEX® 4-12% Bis-Tris Gel with MES buffer and Coomassie blue staining. One transformant was selected for further work and designated *Aspergillus oryzae* 70.5.

For larger scale production, *Aspergillus oryzae* 70.5 spores were spread onto a PDA plate and incubated for five days at 37° C. The confluent spore plate was washed twice with 5 ml of 0.01% TWEEN® 20 to maximize the number of spores collected. The spore suspension was then used to inoculate twenty-five 500 ml flasks containing 100 ml of YPM medium. The culture was incubated at 26° C. with constant shaking at 120 rpm. At day six post-inoculation, the culture broth was collected by filtration through a triple layer of Whatman glass microfiber filters of 1.6 μm, 1.2 μm, and 0.7 μm. Fresh culture broth from this transformant produced a band of GH7 protein of approximately 54 kDa. The identity of this band as the *Aspergillus* nidulans GH7 cellobiohydrolase was verified by peptide sequencing.

Two liters of the filtered broth were concentrated to 400 ml and washed with 50 mM HEPES pH 7.0 using a SARTOFLOW® Alpha ultrafiltration system with a 10 kDa MW-CO. Ammonium sulphate was added to a final concentration of 1 M and dissolved in the ultrafiltrate. The solution was applied on a Source 15 Phenyl XK 26/20 50 ml column. After application the column was washed with 150 ml of 1 M ammonium sulphate and eluded with 1 column volume of 50% ethanol in a 0% to 100% gradient followed by 5 column volumes of 50% ethanol at a flow rate of 10 ml/minute. Fractions of 10 ml were collected and analyzed by SDS-PAGE. Fraction 3 to 8 were pooled and diluted to 1000 ml with 50 mM HEPES pH 7.0 before application on a Q Sepharose® Fast Flow XK26/20 60 ml column. After application the column was washed 3 times with 60 ml of 50 mM HEPES pH 7.0 and eluded with 100 ml of 50 mM HEPES pH 7.0, 1 M NaCl at a flow rate of 10 ml/minute. Fractions of 10 ml were collected and analyzed by SDS-PAGE. The flow-through and first wash were pooled and concentrated to 400 ml and washed with 50 mM HEPES pH 7.0 using a SARTOFLOW® Alpha ultrafiltration system with a 10 kDa MW-CO. Further concentration was conducted using a VIVASPIN™ centrifugal concentrator according to the manufacturer's instructions to a final volume of 80 ml. The protein concentration determined by A280/A260 absorbance. Protein concentration was also determined using a Microplate BCA™ Protein Assay Kit in which bovine serum albumin was used as a protein standard.

Example 68: Preparation of a *Fennellia nivea* Strain NN046949 GH6 Cellobiohydrolase II The *Fennellia nivea* strain NN046949 GH6 cellobiohydrolase II (SEQ ID NO: 167 [DNA sequence] and SEQ ID NO: 168 [deduced amino acid sequence]) was obtained according to the procedure described below.

*Fennellia nivea* strain NN046949 was isolated from a soil from Yunnan, China by directly plating the soil sample onto a PDA plate followed by incubation at 37° C. for 5 days. The strain was then purified by transferring the mycelia onto a YG agar plate. The *Fennellia nivea* strain NN046949 was identified as *Fennellia nivea* based on both morphological and molecular (ITS sequencing) characterization.

*Fennellia nivea* strain NN046949 was inoculated onto a PDA plate and incubated for 4 days at 37° C. in the darkness. Several mycelia-PDA plugs were inoculated into 500 ml shake flasks containing 100 ml of NNCYP-PCS medium. The flasks were incubated for 6 days at 37° C. with shaking at 160 rpm. The mycelia were collected at 4, 5, and 6 days, and each frozen in liquid nitrogen and stored in a −80° C. freezer until use.

The frozen *F. nivea* mycelia were mixed and transferred into a liquid nitrogen prechilled mortar and pestle and ground to a fine powder. Total RNA was prepared from the powdered mycelia of each day by extraction with TRIZOL® reagent and purified using a RNEASY® Plant Mini Kit according to the manufacturer's protocol. The polyA enriched RNA was isolated using a mTRAP™ Total Kit. Eighty-seven μs of total RNA was submitted for sequencing as described in Example 3.

Total RNA enriched for polyA sequences with the mRNASeq protocol were sequenced using an ILLUMINA® GA2 System (Illumina, Inc., San Diego, Calif., USA). The raw 75 base pair reads were assembled and the assembled sequences were analyzed using standard bioinformatics methods for gene finding and functional prediction. Briefly, ESTscan 2.0 was used for gene prediction. NCBI blastall version 2.2.10 and HMMER version 2.1.1 were used to predict function based on structural homology. The Family GH6 cellobiohydrolase was identified directly by analysis of the Blast results.

*Fennellia nivea* strain NN046949 was grown on PDA agar plate at 37° C. for 3 days. Mycelia were collected directly from the agar plate into a sterilized motar and frozen under liquid nitrogen. Frozen mycelia were ground, by mortar and pestle, to a fine powder, and genomic DNA was isolated using a DNEASY® Plant Mini Kit (QIAGEN Inc., Valencia, Calif., USA).

Based on the *F. nivea* GH6 cellobiohydrolase gene sequence obtained in Example 3, oligonucleotide primers, shown below, were designed to amplify the gene from genomic DNA of *Fennellia nivea*. An IN-FUSION™ CF Dry-down PCR Cloning Kit was used to clone the fragment directly into the expression vector pPFJO355, without the need for restriction digestion and ligation.

```
Sense primer:
                                      (SEQ ID NO: 217)
5'-ACACAACTGGGGATCCACCATGGGACGGGTTTCTTCTCTTG-3'

Antisense primer:
                                      (SEQ ID NO: 218)
5'-GTCACCCTCTAGATCTAAGAACACCCCGCAAAGAAAGTC-3'
```

Bold letters represent the coding sequence for the sense primer or the reverse compliment sequence downstream of the stop codon for the antisense primer. The remaining sequence is homologous to the insertion sites of pPFJO355.

Twenty picomoles of each of the primers above were used in a PCR reaction composed of *Fennellia nivea* genomic DNA, 10 μl of 5×GC Buffer, 1.5 μl of DMSO, 2 μl of 2.5 mM each of dATP, dTTP, dGTP, and dCTP, and 1 unit of Phusion™ High-Fidelity DNA Polymerase in a final volume of 50 μl. The amplification was performed using an Peltier Thermal Cycler programmed for denaturing at 98° C. for 1 minutes; 5 cycles of denaturing at 98° C. for 15 seconds, annealing at 70° C. for 30 seconds, with 1° C. decreasing per cycle and elongation at 72° C. for 30 seconds; 25 cycles each at 98° C. for 15 seconds and 72° C. for 90 seconds; and a final extension at 72° C. for 10 minutes. The heat block then went to a 4° C. soak cycle.

The reaction products were isolated by 1.0% agarose gel electrophoresis using TBE buffer where an approximately 1.8 kb product band was excised from the gel, and purified using an ILLUSTRA™ GFX™ PCR DNA and Gel Band Purification Kit (GE Healthcare, Buckinghamshire, UK) according to the manufacturer's instructions.

Plasmid pPFJO355 was digested with Barn I and Bgl II, isolated by 1.0% agarose gel electrophoresis using TBE buffer, and purified using an ILLUSTRA™ GFX™ PCR DNA and Gel Band Purification Kit according to the manufacturer's instructions. The gene fragment and the digested vector were ligated together using an IN-FUSION™ Dry Down PCR Cloning Kit resulting in pCBHII46949-2 in which transcription of the *Fennellia nivea* GH6 cellobiohydrolase gene was under the control of the *Aspergillus oryzae* TAKA alpha-amylase promoter. In brief, 30 ng of pPFJO355 digested with Barn I and Bgl II, and 50 ng of the *F. nivea* GH6 cellobiohydrolase gene purified PCR product were added to a reaction vial and resuspended in a final volume of 10 μl with addition of deionized water. The reaction was incubated at 37° C. for 15 minutes and then 50° C. for 15 minutes. Three μl of the reaction were used to transform *E. coli* TOP10 competent cells. An *E. coli* transformant containing pCBHII46949-2 was detected by colony PCR and plasmid DNA was prepared using a QIAprep Spin Miniprep Kit (QIAGEN Inc., Valencia, Calif., USA). The *F. nivea* GH6 cellobiohydrolase gene insert in pCBHII46949-2 was confirmed by DNA sequencing using a 3730XL DNA Analyzer.

The same gene fragment was then incubated in 10×Taq DNA polymerase mix (TIANGEN Biotech (Beijing) Co. Ltd., Beijing, China) at 72° C. for 20 minutes to add adenine to the 3' end of each nucleotide strand. Then the gene fragment was ligated to pGEM-T vector using a pGEM-T Vector System to generate pGEM-T-CBHII46949-2. The *Fennellia nivea* cellobiohydrolase gene insert in pGEM-T-CBHII46949-2 was confirmed by DNA sequencing using a 3730XL DNA Analyzer. *E. coli* strain T-CBHII46949-2, containing pGEM-T-CBHII46949-2, was deposited on Oct. 28, 2010 with the Deutsche Sammlung von Mikroorganismen und Zellkulturen GmbH (DSMZ), Mascheroder Weg 1 B, D-38124 Braunschweig, Germany assigned the accession number DSM 24143.

Nucleotide sequence data were scrutinized for quality and all sequences were compared to each other with assistance of PHRED/PHRAP software (University of Washington, Seattle, Wash., USA).

The nucleotide sequence and deduced amino acid sequence of the *F. nivea* cellobiohydrolase gene are shown in SEQ ID NO: 167 and SEQ ID NO: 168, respectively. The genomic fragment encodes a polypeptide of 469 amino acids, interrupted by 7 predicted introns of 49 bp (nucleotides 77-125), 247 bp (nucleotides 195-241), 46 bp (nucleotides 570-615), 55 bp (nucleotides 870-924), 50 bp (nucleotides 1063-1112), 46 bp (nucleotides 1371-1416), and 49 bp (nucleotides 1659-1707). The % G+C content of the full-length coding sequence and the mature coding sequence are 57.65% and 60.24%, respectively. Using the SignalP software program (Nielsen et al., 1997, *Protein Engineering* 10: 1-6), a signal peptide of 18 residues was predicted. The predicted mature protein contains 451 amino acids with a predicted molecular mass of 48.77 kDa and an isoelectric point of 5.17. Amino acids 112 to 469 are indicative of a Family 6 glycosyl hydrolase. Based on the deduced amino acid sequence, the cellobiohydrolase appears to fall into the cellobiohydrolase Family GH6 according to Coutinho and Henrissat, 1999, supra. Amino acids 22 to 50 are indicative of a CBM domain and amino acids 58 to 111 a linker region.

*Aspergillus oryzae* HowB101 (WO 95/35385) protoplasts were prepared according to the method of Christensen et al., 1988, *Bio/Technology* 6: 1419-1422 and transformed with 3 μg of pCBHII46949-2. The transformation yielded about 50 transformants. Four transformants were isolated to individual Minimal medium plates.

Four transformants were inoculated separately into 3 ml of YPM medium in 24-well plate and incubated at 30° C., 150 rpm. After 3 days incubation, 20 μl of supernatant from each culture were analyzed by SDS-PAGE using a NUPAGE® NOVEX® 4-12% Bis-Tris Gel with MES buffer according to the manufacturer's instructions. The resulting gel was stained with INSTANTBLUE™ (Expedeon Ltd., Babraham Cambridge, UK). SDS-PAGE profiles of the cultures showed that the majority of the transformants had a band of approximately 60 kDa. One transformant was chosen as the expression strain and designated *Aspergillus oryzae* EXP03324.

A slant of *Aspergillus oryzae* EXP03324 was washed with 10 ml of YPM medium and inoculated into 4 2-liter flasks, containing 400 ml of YPM medium for each, to generate broth for characterization of the enzyme. The culture was harvested on day 3 by filtering the culture against MIRACLOTH® (CALBIOCHEM, Inc. La Jolla, Calif., USA). The filtered culture broth was then again filtered using a 0.45 μm DURAPORE Membrane (Millipore, Bedford, Mass., USA).

A 1600 ml volume of the *Aspergillus oryzae* EXP03324 filtered broth was precipitated with ammonium sulfate (80% saturation), re-dissolved in 100 ml 25 mM Bis-Tris pH 6.5 buffer, dialyzed against the same buffer, and filtered through a 0.45 μm filter; the final volume was 200 ml. The solution was applied to a 40 ml Q Sepharose® Fast Flow column equilibrated in 25 mM Bis-Tris pH 6.5 buffer and the proteins were eluted with a linear 0-0.4 M NaCl gradient. Fractions from the column were analyzed by SDS-PAGE using a NUPAGE® NOVEX® 4-12% Bis-Tris Gel with MES buffer. Fractions with a molecular weight of 60 kDa were pooled. Then the pooled solution was concentrated by ultrafiltration and assayed for cellobiohydrolase activity using phosphoric acid swollen cellulose (PASC) as substrate. Protein concentration was determined using a Microplate BCA™ Protein Assay Kit in which bovine serum albumin was used as a protein standard.

A PASC stock slurry solution was prepared by moistening 5 g of AVICEL® (JRS Pharma GmbH & Co., Rosenberg, Germany) with water, followed by the addition of 150 ml of ice cold 85% o-phosphoric acid. The suspension was slowly stirred in an ice-bath for 1 hour. Then 500 ml of ice cold acetone were added while stirring. The slurry was filtered using MIRACLOTH® and then washed three times with 100 ml of ice-cold acetone (drained as dry as possible after each wash). Finally, the filtered slurry was washed twice with 500 ml of water, and again drained as dry as possible after each wash. The PASO was mixed with deionized water to a total volume of 500 ml to a concentration of 10 g/liter, blended to homogeneity using an ULTRA-TURRAX® Homogenizer (Cole-Parmer, Vernon Hills, Ill., USA), and stored in a refrigerator for up to one month.

The PASO stock solution was diluted with 50 mM sodium acetate pH 5.0 buffer to a concentration of 2 g/liter, and used as the substrate. To 150 μl of PASO stock solution, 20 μl of enzyme sample were added and the reaction mixture was incubated for 60 minutes with shaking at 850 rpm. At the end of the incubation, 50 μl of 2% NaOH were added to stop the reaction. The reaction mixture was centrifuged at 1,000×g. The released sugars were measured by first mixing 10 μl of the reaction mixture with 90 μl of 0.4% NaOH, followed by 50 μl of 1.5% p-hydroxybenzoic acid hydrazide in 2% NaOH (PHBAH, Sigma Chemical Co., St. Louis, Mo., USA). The mixture was boiled at 100° C. for 5 minutes, and then 100 μl were transferred to a microtiter plate for an absorbance reading at 410 nm using a Spectra Max M2 (Molecular Devices, Sunnyvale, Calif., USA). Blanks were made by omitting PASO in the hydrolysis step, and by replacing the hydrolysate with buffer in the sugar determination step.

The assay results demonstrated that the purified enzyme possessed cellobiohydrolase activity.

Example 69: Preparation of *Penicillium emersonii* Strain NN051602 GH6A Cellobiohydrolase II

*Penicillium emersonii* strain NN051602 GH6A cellobiohydrolase II (SEQ ID NO: 169 [DNA sequence] and SEQ ID NO: 170 [deduced amino acid sequence]) was obtained according to the procedure described below.

*Penicillium emersonii* was grown on a PDA agar plate at 45° C. for 3 days. Mycelia were collected directly from the agar plate into a sterilized mortar and frozen under liquid nitrogen. Frozen mycelia were ground, by mortar and pestle, to a fine powder, and genomic DNA was isolated using a DNeasy® Plant Mini Kit (QIAGEN Inc., Valencia, Calif., USA).

Oligonucleotide primers, shown below, were designed to amplify the GH6 cellobiohydrolase II gene from genomic DNA of *Penicillium emersonii*. An IN-FUSION™ CF Dry-down Cloning Kit was used to clone the fragment directly into the expression vector pPFJO355, without the need for restriction digestion and ligation.

Sense primer:
(SEQ ID NO: 219)
5'-ACACAACTGGGGATCCACCATGCGGAATCTTCTTGCTCTTGC-3'

Antisense primer:
(SEQ ID NO: 220)
5'-GTCACCCTCTAGATCTCTAGAACAGCGGGTTAGCATTCGTG-3'

Bold letters represented the coding sequence. The remaining sequence was homologous to the insertion sites of pPFJO355.

Twenty picomoles of each of the primers above were used in a PCR reaction composed of *Penicillium emersonii* genomic DNA, 10 μl of 5×HF Buffer, 1.5 μl of DMSO, 5 mM each of dATP, dTTP, dGTP, and dCTP, and 0.6 unit of Phusion™ High-Fidelity DNA Polymerase in a final volume of 50 μl. The amplification was performed using a Peltier Thermal Cycler programmed for denaturing at 98° C. for 1 minutes; 8 cycles of denaturing at 98° C. for 15 seconds, annealing at 66° C. for 30 seconds, with a 1° C. decrease per cycle and elongation at 72° C. for 70 seconds; and another 25 cycles each at 98° C. for 15 seconds, 62° C. for 30 seconds and 72° C. for 80 seconds; final extension at 72° C. for 5 minutes. The heat block then went to a 4° C. soak cycle.

The reaction products were isolated by 1.0% agarose gel electrophoresis using TBE buffer where an approximately 1.8 kb product band was excised from the gel, and purified using an ILLUSTRA® GFX® PCR DNA and Gel Band Purification Kit according to the manufacturer's instructions.

Plasmid pPFJO355 was digested with Barn I and Bgl II, isolated by 1.0% agarose gel electrophoresis using TBE buffer, and purified using an ILLUSTRA® GFX® PCR DNA and Gel Band Purification Kit according to the manufacturer's instructions.

The gene fragment and the digested vector were ligated together using an IN-FUSION™ CF Dry-down PCR Cloning resulting in pCBHII51602 in which transcription of the *Penicillium emersonii* GH6 cellobiohydrolase II gene was under the control of the *Aspergillus oryzae* TAKA amylase promoter. In brief, 30 ng of pPFJO355, digested with Barn I and Bgl II, and 60 ng of the *Penicillium emersonii* GH6 cellobiohydrolase II gene purified PCR product were added to a reaction vial and resuspended in a final volume of 10 µl with addition of deionized water. The reaction was incubated at 37° C. for 15 minutes and then 50° C. for 15 minutes. Three µl of the reaction were used to transform *E. coli* TOP10 competent cells. An *E. coli* transformant containing pCBHII51602 was detected by colony PCR and plasmid DNA was prepared using a QIAprep Spin Miniprep Kit (QIAGEN Inc., Valencia, Calif., USA). The *Penicillium emersonii* GH6 cellobiohydrolase II gene insert in pCBHII51602 was confirmed by DNA sequencing using a 3730XL DNA Analyzer.

*Aspergillus oryzae* HowB101 (WO 95/35385) protoplasts were prepared according to the method of Christensen et al., 1988, *Bio/Technology* 6: 1419-1422 and transformed with 3 µg of pCBHII51602. The transformation yielded about 50 transformants. Twelve transformants were isolated to individual Minimal medium plates.

Six transformants were inoculated separately into 3 ml of YPM medium in 24-well plate and incubated at 30° C., 150 rpm. After 3 days incubation, 20 µl of supernatant from each culture were analyzed by SDS-PAGE using a NUPAGE® NOVEX® 4-12% Bis-Tris Gel with MES buffer according to the manufacturer's instructions. The resulting gel was stained with INSTANT® Blue. SDS-PAGE profiles of the cultures showed that the majority of the transformants had a major smeary band of approximately 62 kDa. The expression strain was designated as *A. oryzae* EXP03259.

A slant of *A. oryzae* EXP03259 was washed with 10 ml of YPM medium and inoculated into a 2 liter flask containing 400 ml of YPM medium to generate broth for characterization of the enzyme. The culture was harvested on day 3 and filtered using a 0.45 µm DURAPORE Membrane.

A 1600 ml volume of filtered broth of *A. oryzae* EXP03259 was precipitated with ammonium sulfate (80% saturation), re-dissolved in 100 ml 2 of 5 mM Bis-Tris pH 6.0, dialyzed against the same buffer, and filtered through a 0.45 µm filter; the final volume was 200 ml. The solution was applied to a 40 ml Q Sepharose® Fast Flow column equilibrated with 25 mM Bis-Tris pH 6.0, and the proteins were eluted with a linear NaCl gradient (0-0.4 M). Fractions from the column with activity against PASC were analyzed by SDS-PAGE using a NUPAGE® NOVEX® 4-12% Bis-Tris Gel with MES buffer. Fractions with the correct molecular weight were pooled and concentrated by ultrafiltration. Protein concentration was determined using a Microplate BCA™ Protein Assay Kit in which bovine serum albumin was used as a protein standard.

Example 70: Preparation of *Penicillium pinophilum* Strain NN046877 GH6A Cellobiohydrolase II The *Penicillium pinophilum* strain NN046877 GH6A cellobiohydrolase II (SEQ ID NO: 171 [DNA sequence] and SEQ ID NO: 172 [deduced amino acid sequence]) was obtained according to the procedure described below.

*Penicillium pinophilum* was grown on a PDA agar plate at 37° C. for 4-5 days. Mycelia were collected directly from the agar plate into a sterilized mortar and frozen under liquid nitrogen. Frozen mycelia were ground, by mortar and pestle, to a fine powder, and genomic DNA was isolated using a DNeasy® Plant Mini Kit (QIAGEN Inc., Valencia, Calif., USA).

Oligonucleotide primers, shown below, were designed to amplify the GH6 cellobiohydrolase II gene from genomic DNA of *Penicillium pinophilum*. An IN-FUSION™ CF Dry-down Cloning Kit was used to clone the fragment directly into the expression vector pPFJO355, without the need for restriction digestion and ligation.

```
Sense primer:
                                   (SEQ ID NO: 221)
5'-ACACAACTGGGGATCCACCATGTTGCGATATCTTTCCACC-3'

Antisense primer:
                                   (SEQ ID NO: 222)
5'-GTCACCCTCTAGATCTTCATCTAGACCAAAGCTGGGTTG-3'
```

Bold letters represented the coding sequence and the remaining sequence was homologous to the insertion sites of pPFJO355.

Twenty picomoles of each of the primers above were used in a PCR reaction composed of *Penicillium pinophilum* genomic DNA, 10 µl of 5×GC Buffer, 1.5 µl of DMSO, 2.5 mM each of dATP, dTTP, dGTP, and dCTP, and 0.6 unit of Phusion™ High-Fidelity DNA Polymerase in a final volume of 50 µl. The amplification was performed using a Peltier Thermal Cycler programmed for denaturing at 98° C. for 1 minutes; 5 cycles of denaturing at 98° C. for 15 seconds, annealing at 56° C. for 30 seconds, with a 1° C. increase per cycle and elongation at 72° C. for 75 seconds; and another 25 cycles each at 98° C. for 15 seconds, 65C for 30 seconds and 72° C. for 75 seconds; final extension at 72° C. for 10 minutes. The heat block then went to a 4° C. soak cycle.

The reaction products were isolated by 1.0% agarose gel electrophoresis using TBE buffer where an approximately 1.7 kb product band was excised from the gel, and purified using an ILLUSTRA® GFX® PCR DNA and Gel Band Purification Kit according to the manufacturer's instructions.

Plasmid pPFJO355 was digested with Barn I and Bgl II, isolated by 1.0% agarose gel electrophoresis using TBE buffer, and purified using an ILLUSTRA® GFX® PCR DNA and Gel Band Purification Kit according to the manufacturer's instructions.

The gene fragment and the digested vector were ligated together using an IN-FUSION™ CF Dry-down PCR Cloning resulting in pPpin12 in which transcription of the *Penicillium pinophilum* GH6 cellobiohydrolase II gene was under the control of the *Aspergillus oryzae* TAKA amylase promoter. In brief, 30 ng of pPFJO355, digested with Barn I and Bgl II, and 60 ng of the *Penicillium pinophilum* GH6 cellobiohydrolase II gene purified PCR product were added to a reaction vial and resuspended in a final volume of 10 ul with addition of deionized water. The reaction was incubated at 37° C. for 15 minutes and then 50° C. for 15 minutes. Three μl of the reaction were used to transform *E. coli* TOP10 competent cells. An *E. coli* transformant containing pPpin12 was detected by colony PCR and plasmid DNA was prepared using a QIAprep Spin Miniprep Kit. The *Penicillium pinophilum* GH6 cellobiohydrolase II gene insert in pPpin12 was confirmed by DNA sequencing using a 3730XL DNA Analyzer.

*Aspergillus oryzae* HowB101 (WO9535385) protoplasts were prepared according to the method of Christensen et al., 1988, *Bio/Technology* 6: 1419-1422 and transformed with 3 μg of pPpin12. The transformation yielded about 50 transformants. Four transformants were isolated to individual Minimal medium plates.

Four transformants were inoculated separately into 3 ml of YPM medium in 24-well plate and incubated at 30° C., 150 rpm. After 3 days incubation, 20 μl of supernatant from each culture were analyzed by SDS-PAGE using a NUPAGE® NOVEX® 4-12% Bis-Tris Gel with MES buffer according to the manufacturer's instructions. The resulting gel was stained with INSTANT® Blue. SDS-PAGE profiles of the cultures showed that the majority of the transformants had a major band of approximately 65 kDa. The expression strain was designated *A. oryzae* EXP02774.

A slant of *A. oryzae* EXP02774 was washed with 10 ml of YPM medium and inoculated into a 2 liter flask containing 400 ml of YPM medium to generate broth for characterization of the enzyme. The culture was harvested on day 3 and filtered using a 0.45 μm DURAPORE Membrane.

A 1600 ml volume of the filtered broth of *A. oryzae* EXP02774 was precipitated with ammonium sulfate (80% saturation), re-dissolved in 100 ml 25 mM Bis-Tris pH 6.0, dialyzed against the same buffer, and filtered through a 0.45 μm filter; the final volume was 200 ml. The solution was applied to a 40 ml Q Sepharose® Fast Flow column equilibrated in 25 mM Bis-Tris pH 6.0, and the proteins were eluted with a linear NaCl gradient (0-0.4 M). Fractions from the column with activity against PASO were collected and applied to a 40 ml HITRAP® SP Fast Flow column equilibrated in 25 mM Bis-Tris pH 6.0, and the proteins were eluted with a linear NaCl gradient (0-0.4 M). Fractions from the column with activity against PASO were analyzed by SDS-PAGE using a NUPAGE® NOVEX® 4-12% Bis-Tris Gel with MES buffer. Fractions with the correct molecular weight were pooled and concentrated by ultrafiltration. Protein concentration was determined using a Microplate BCA™ Protein Assay Kit in which bovine serum albumin was used as a protein standard.

Example 71: Preparation of *Aspergillus fumigatus* Strain NN051616 GH5 Endoglucanase II The *Aspergillus fumigatus* strain NN051616 GH5 endoglucanase II (SEQ ID NO: 173 [DNA sequence] and SEQ ID NO: 174 [deduced amino acid sequence]) was obtained according to the procedure described below.

Two synthetic oligonucleotide primers shown below were designed to PCR amplify the *Aspergillus fumigatus* Family GH5 gene from the genomic DNA. An IN-FUSION™ Cloning Kit was used to clone the fragment directly into the expression vector, pAILo2 (WO 2005/074647), without the need for restriction digests and ligation.

```
Forward primer:
                                        (SEQ ID NO: 223)
5'-ACTGGATTTACCATGAAATTCGGTAGCATTGTGCTC-3'

Reverse primer:
                                        (SEQ ID NO: 224)
5'-TCACCTCTAGTTAATTAATCAACCCAGGTAGGGCTCCAAGATG-3'
```

Bold letters represent coding sequence. The remaining sequence is homologous to the insertion sites of pAILo2.

Fifteen picomoles of each of the primers above were used in a PCR reaction containing 200 ng of *Aspergillus fumigatus* genomic DNA, 1× Pfx Amplification Buffer (Invitrogen, Carlsbad, Calif., USA), 1 mM $MgSO_4$, 1.5 μl of 10 mM blend of dATP, dTTP, dGTP, and dCTP, 2.5 units of Pfx DNA polymerase (Invitrogen, Carlsbad, Calif., USA), in a final volume of 50 μl. The amplification conditions were one cycle at 98° C. for 3 minutes; and 30 cycles each at 98° C. for 30 seconds, 57° C. for 30 seconds, and 72° C. for 75 seconds. The heat block was then held at 72° C. for 15 minutes followed by a 4° C. soak cycle.

The reaction products were isolated on a 1.0% agarose gel using TAE buffer and a 2.4 kb product band was excised from the gel and purified using a MinElute® Gel Extraction Kit (QIAGEN Inc., Valencia, Calif.) according to the manufacturer's instructions.

The fragment was then cloned into pAILo2 using an IN-FUSION™ Cloning Kit. The vector was digested with Nco I and Pac I. The fragment was purified by gel electrophoresis and a QIAquick Kit (QIAGEN Inc., Valencia, Calif., USA). The gene fragment and the digested vector were combined together in a reaction resulting in the expression plasmid pAG10, in which transcription of the *Aspergillus fumigatus* Family GH5 gene was under the control of the NA2-tpi promoter (a hybrid of the promoters from the genes for *Aspergillus niger* neutral alpha-amylase and *Aspergillus oryzae* triose phosphate isomerase). The recombination reaction (20 μl) was composed of 1×I IN-FUSION™ Buffer (Clontech, Mountain View, Calif.), 1×BSA (Clontech, Mountain View, Calif.), 1 μl of IN-FUSION™ enzyme (diluted 1:10) (Clontech, Mountain View, Calif.), 180 ng of pAILo2 digested with Nco I and Pac I, and 80 ng of the *Aspergillus fumigatus* beta-xylosidase purified PCR product. The reaction was incubated at ambient temperature for 30 minutes. The reaction was diluted with 40 μl of TE buffer and 2.5 μl of the diluted reaction was used to transform *E. coli* SOLOPACK® Gold cells. An *E. coli* transformant containing pAG10 (*Aspergillus fumigatus* Family GH5 gene) was identified by restriction enzyme digestion and plasmid DNA was prepared using a QIAGEN BioRobot 9600. The pAG10 plasmid construct was sequenced using an Applied Biosystems 3130x1 Genetic Analyzer (Applied Biosystems, Foster City, Calif., USA) to verify the sequence.

*Aspergillus oryzae* JaL355 protoplasts were prepared according to the method of Christensen et al., 1988, *Bio/Technology* 6: 1419-1422 and transformed with 5 μg of pAG10. Three transformants were isolated to individual PDA plates.

Plugs taken from the original transformation plate of each of the three transformants were added to 1 ml of M410 medium separately in 24 well plates, which were incubated at 34° C. After five days of incubation, 7.5 μl of supernatant from each culture was analyzed using CRITERION® stain-free, 8-16% gradient SDS-PAGE, (Bio-Rad Laboratories, Inc., Hercules, Calif., USA) according to the manufacturer's instructions. SDS-PAGE profiles of the cultures showed that the transformants had a new major band of approximately 35 kDa.

Confluent PDA plate of the highest expressing transformant was washed with 5 ml of 0.01% TWEEN® 20 and inoculated into three 500 ml Erlenmeyer flasks, each containing 100 ml of M410 medium. Inoculated flasks were incubated with shaking for 3 days at 34° C. The broths were pooled and filtered through a 0.22 μm stericup suction filter (Millipore, Bedford, Mass., USA).

A 35 ml volume of filtered broth was buffer exchanged into 50 mM sodium acetate pH 5.0 using a 400 ml Sephadex G-25 column (GE Healthcare, United Kingdom) according to the manufacturer's instructions. Protein concentration was determined using a Microplate BCA™ Protein Assay Kit in which bovine serum albumin was used as a protein standard.

Example 72: Preparation of *Neosartorya fischeri* Strain NRRL 181 GH5 Endoglucanase II The *Neosartorya fischeri* NRRL 181 GH5 endoglucanase II (SEQ ID NO: 175 [DNA sequence] and SEQ ID NO: 176 [deduced amino acid sequence]) was obtained according to the procedure described below.

Two synthetic oligonucleotide primers, shown below, were designed to PCR amplify the endoglucanase gene from *Neosartorya fischeri* NRRL 181 genomic DNA. Genomic DNA was isolated using a FastDNA spin for Soil Kit.

```
Primer #350:
                                       (SEQ ID NO: 225)
5'-TAAGAATTCACCATGAAGGCTTCGACTATTATCTGTGCA-3'

Primer #358:
                                       (SEQ ID NO: 226)
5'-TATGCGGCCGCACGGCAATCCAAGTCATTCAA-3'
```

The amplification reaction was composed of 1 μl of *Neosartorya fischeri* genomic DNA, 12.5 μl of 2× REDDY-MIX™ PCR Buffer, 1 μl of 5 μM primer #374, 1 μl of 5 μM primer #375, and 9.5 μl of $H_2O$. The amplification reaction was incubated in a PTC-200 DNA ENGINE™ Thermal Cycler programmed for 1 cycle at 94° C. for 2 minutes; and 35 cycles each at 94° C. for 15 seconds and 60° C. for 1.5 minutes.

A 1.4 kb PCR reaction product was isolated by 1% agarose gel electrophoresis using TAE buffer and staining with SYBR Safe DNA gel stain. The DNA band was visualized with the aid of an Eagle Eye Imaging System and a DarkReader Transilluminator. The 1.4 kb DNA band was excised from the gel and purified using a GFX® PCR DNA and Gel Band Purification Kit according to the manufacturer's instructions.

The 1.4 kb fragment was cleaved with EcoR I and Not I and purified using a GFX® PCR DNA and Gel Band Purification Kit according to the manufacturer's instructions.

The cleaved 1.4 kb fragment was then directionally cloned by ligation into Eco RI-Not I cleaved pXYG1051 (WO 2005/080559) using T4 ligase according to the manufacturer's instructions. The ligation mixture was transformed into *E. coli* TOP10F competent cells according to the manufacturer's instructions. The transformation mixture was plated onto LB plates supplemented with 100 μg of ampicillin per ml. Plasmid minipreps were prepared from several transformants and sequenced. One plasmid with the correct *Neosartorya fischeri* GH5 coding sequence was chosen.

The expression plasmid pXYG1051-NP003772 was transformed into *Aspergillus oryzae JaL*355 as described in WO 98/00529. Transformants were purified on selection plates to single conidia prior to sporulating them on PDA plates. Production of the *Neosartorya fischeri* GH5 polypeptide by the transformants was analyzed from culture supernatants of 1 ml 96 deep well stationary cultivations at 26° C. in YP medium with 2% maltodextrin. Expression was verified SDS-PAGE using a NUPAGE® NOVEX® 4-12% Bis-Tris Gel with MES buffer and Coomassie blue staining. One transformant was selected for further work and designated *Aspergillus oryzae* 83.3.

For larger scale production, *Aspergillus oryzae* 83.3 spores were spread onto a PDA plate and incubated for five days at 37° C. The confluent spore plate was washed twice with 5 ml of 0.01% TWEEN® 20 to maximize the number of spores collected. The spore suspension was then used to inoculate twenty-five 500 ml flasks containing 100 ml of YPG medium. The culture was incubated at 26° C. with constant shaking at 120 rpm. At day five post-inoculation, the culture broth was collected by filtration through a triple layer of Whatman glass microfiber filters of 1.6 μm, 1.2 μm, and 0.7 μm. Fresh culture broth from this transformant produced a band of GH7 protein of approximately 46 kDa. The identity of this band as the *Neosartorya fischeri* GH5 polypeptide was verified by peptide sequencing.

Two liters of the filtered broth were concentrated to 400 ml and washed with 50 mM HEPES pH 7.0 using a SARTOFLOW® Alpha ultrafiltration system with a 10 kDa MW-CO. Ammonium sulphate was added to a final concentration of 1 M and dissolved in the ultrafiltrate. The solution was applied on a Source 15 Phenyl XK 26/20 50 ml column. After application the column was washed with 150 ml of 1 M ammonium sulphate and eluded with 1 column volume of 50% ethanol in a 0% to 100% gradient followed by 5 column volumes of 50% ethanol at a flow rate of 10 ml/minute. Fractions of 10 ml were collected and analyzed by SDS-PAGE. Fraction 3 to 8 were pooled and diluted to 1000 ml with 50 mM HEPES pH 7.0 before application on a Q Sepharose® Fast Flow column XK26/20 60 ml column. After application the column was washed 3 times with 60 ml of 50 mM HEPES pH 7.0 and eluded with 100 ml of 50 mM HEPES pH 7.0, 1 M NaCl at a flow rate of 10 ml/minute. Fractions of 10 ml were collected and analyzed by SDS-PAGE. The flow-through and first wash were pooled and concentrated to 400 ml and washed with 50 mM HEPES pH 7.0 using the ultrafiltration system described above. Further concentration was conducted using a VIVASPIN™ centrifugal concentrator according to the manufacturer's instructions to a final volume of 80 ml. The protein concentration was determined by A280/A260 absorbance. Protein concentration was also determined using a Microplate BCA™ Protein Assay Kit in which bovine serum albumin was used as a protein standard.

Example 73: Preparation of *Aspergillus aculeatus* Strain WDCM190 GH3 Beta-Glucosidase The *Aspergillus aculeatus* strain WDCM190 GH3 beta-glucosidase (SEQ ID NO: 177 [DNA sequence] and SEQ ID NO: 178 [deduced amino acid sequence]) was obtained according to the procedure described below.

To generate genomic DNA for PCR amplification, *Aspergillus aculeatus* WDCM 190 was propagated on PDA agar plates by growing at 26° C. for 7 days. Spores harvested from the PDA plates were inoculated into 25 ml of YP+2% glucose medium in a baffled shake flask and incubated at 26° C. for 48 hours with agitation at 200 rpm.

Genomic DNA was isolated according to a modified FastDNA® SPIN protocol (Qbiogene, Inc., Carlsbad, Calif., USA). Briefly, a FastDNA® SPIN Kit for Soil (Qbiogene, Inc., Carlsbad, Calif., USA) was used in a FastPrep® 24 Homogenization System (MP Biosciences, Santa Ana, Calif., USA). Two ml of fungal material were harvested by centrifugation at 14,000×g for 2 minutes. The supernatant was removed and the pellet resuspended in 500 μl of deionized water. The suspension was transferred to a Lysing Matrix E FastPrep® tube (Qbiogene, Inc., Carlsbad, Calif., USA) and 790 μl of sodium phosphate buffer and 100 μl of MT buffer from the FastDNA® SPIN Kit were added to the tube. The sample was then secured in a FastPrep® Instrument (Qbiogene, Inc., Carlsbad, Calif., USA) and processed for 60 seconds at a speed of 5.5 m/sec. The sample was then centrifuged at 14000×g for two minutes and the supernatant transferred to a clean EPPENDORF® tube. A 250 μl volume of PPS reagent from the FastDNA® SPIN Kit was added and then the sample was mixed gently by inversion. The sample was again centrifuged at 14000×g for 5 minutes. The supernatant was transferred to a 15 ml tube followed by 1 ml of Binding Matrix suspension from the FastDNA® SPIN Kit and then mixed by inversion for two minutes. The sample was placed in a stationary tube rack and the silica matrix was allowed to settle for 3 minutes. A 500 μl volume of the supernatant was removed and discarded and then the remaining sample was resuspended in the matrix. The sample was then transferred to a SPIN filter tube from the FastDNA® SPIN Kit and centrifuged at 14000×g for 1 minute. The catch tube was emptied and the remaining matrix suspension added to the SPIN filter tube. The sample was again centrifuged (14000×g, 1 minute). A 500 μl volume of SEWS-M solution from the FastDNA® SPIN Kit was added to the SPIN filter tube and the sample was centrifuged at the same speed for 1 minute. The catch tube was emptied and the SPIN filter replaced in the catch tube. The unit was centrifuged at 14000×g for 2 minutes to "dry" the matrix of residual SEWS-M wash solution. The SPIN filter was placed in a fresh catch tube and allowed to air dry for 5 minutes at room temperature. The matrix was gently resuspended in 100 μl of DES (DNase/Pyrogen free water) with a pipette tip. The unit was centrifuged (14000×g, 1 minute) to elute the genomic DNA followed by elution with 100 μl of 10 mM Tris, 0.1 mM EDTA, pH 8.0 by renewed centrifugation at 14000×g for 1 minute and the eluates were combined. The concentration of the DNA harvested from the catch tube was measured by a UV spectrophotometer at 260 nm.

The *Aspergillus aculeatus* Cel3 beta-glucosidase gene was isolated by PCR using two cloning primers GH3-8f and GH3-8r shown below, which were designed based on the publicly available *Aspergillus aculeatus* Cel3 mRNA sequence (Genbank D64088.1) for direct cloning by IN-FUSION™ strategy.

```
Primer GH3-8f:
                                        (SEQ ID NO: 227)
5'-acacaactggggatccaccatgaagctcagttggcttgaggc

gg-3'
```

-continued

```
Primer GH3-8r:
                                        (SEQ ID NO: 228)
5'-agatctcgagaagcttattgcaccttcgggagcgccgcgtga

ag-3'
```

A PCR reaction was performed with genomic DNA prepared from *Aspergillus aculeatus* strain (IAM2445; WDCM190) in order to amplify the full-length gene. The PCR reaction was composed of 1 μl of genomic DNA, 0.75 μl of primer GH3-8f (10 μM), 0.75 μl of primer GH3-8r (10 μM), 3 μl of 5×HF buffer, 0.25 μl of 50 mM $MgCl_2$, 0.3 μl of 10 mM dNTP, 0.15 μl of PHUSION® DNA polymerase, and PCR-grade water up to 15 μl. The PCR reaction was performed using a DYAD® PCR machine programmed for 2 minutes at 98° C. followed by 10 touchdown cycles at 98° C. for 15 seconds, 70° C. (−1° C./cycle) for 30 seconds, and 72° C. for 2 minutes 30 seconds; and 25 cycles each at 98° C. for 15 seconds, 60° C. for 30 seconds, 72° C. for 2 minutes 30 seconds, and 5 minutes at 72° C.

The reaction products were isolated by 1.0% agarose gel electrophoresis using TAE buffer where an approximately 2.9 kb PCR product band was excised from the gel and purified using a GFX® PCR DNA and Gel Band Purification Kit according to manufacturer's instructions. DNA corresponding to the *Aspergillus aculeatus* Cel3 beta-glucosidase gene was cloned into the expression vector pDAu109 (WO 2005042735) linearized with Barn HI and Hind III, using an IN-FUSION™ Dry-Down PCR Cloning Kit according to the manufacturer's instructions.

A 2.5 μl volume of the diluted ligation mixture was used to transform *E. coli* TOP10 chemically competent cells. Three colonies were selected on LB agar plates containing 100 μg of ampicillin per ml and cultivated overnight in 3 ml of LB medium supplemented with 100 μg of ampicillin per ml. Plasmid DNA was purified using an E.Z.N.A.® Plasmid Mini Kit according to the manufacturer's instructions. The *Aspergillus aculeatus* Cel3 beta-glucosidase gene sequence was verified by Sanger sequencing before heterologous expression.

The coding sequence is 2940 bp including the stop codon and is interrupted by 6 introns of 73 bp (nucleotides 58 to 130), 52 bp (nucleotides 274 to 325), 57 bp (nucleotides 371 to 427), 61 bp (nucleotides 481 to 541), 64 bp (nucleotides 1734 to 1797), and 50 bp (nucleotides 2657 to 2706). The encoded predicted protein is 860 amino acids. Using the SignalP program (Nielsen et al., 1997, *Protein Engineering* 10: 1-6), a signal peptide of 19 residues was predicted. The predicted mature protein contains 841 amino acids.

Protoplasts of *Aspergillus oryzae* BECh2 (WO 2000/39322) were prepared as described in WO 95/02043. One hundred microliters of protoplast suspension were mixed with 2.5-15 μg of the *Aspergillus* expression vector and 250 μl of 60% PEG 4000 (Applichem Inc. Omaha, Nebr., USA) (polyethylene glycol, molecular weight 4,000), 10 mM $CaCl_2$, and 10 mM Tris-HCl pH 7.5 were added and gently mixed. The mixture was incubated at 37° C. for 30 minutes and the protoplasts were spread on COVE sucrose (1 M) plates supplemented with 10 mM acetamide and 15 mM CsCl for transformant selection. After incubation for 4-7 days at 37° C. spores of several transformants were seeded on YP-2% maltodextrin medium. After 4 days cultivation at 30° C. culture broth was analyzed in order to identify the best transformants based on their ability to produce a large amount of active *Aspergillus aculeatus* Cel3 beta-glucosidase. The screening was based on intensity of the band corresponding to the heterologous expressed protein determined by SDS-PAGE and activity of the enzyme on 4-nitrophenyl-beta-D-glucopyranoside (pNPG) as described in Example 16 herein.

Spores of the best transformant designated were spread on COVE plates containing 0.01% TRITON® X-100 in order to isolate single colonies. The spreading was repeated twice in total on COVE sucrose medium (Cove, 1996, *Biochim. Biophys. Acta* 133: 51-56) containing 1 M sucrose and 10 mM sodium nitrate, supplemented with 10 mM acetamide and 15 mM CsCl. Fermentation was then carried out in 250 ml shake flasks using YP-2% maltodextrin medium for 4 days at 30° C. with shaking at 100 rpm. The broth was filtered using standard methods. Protein concentration was determined using a Microplate BCA™ Protein Assay Kit in which bovine serum albumin was used as a protein standard.

Example 74: Preparation of *Aspergillus kawashii* Strain IFO 4308 GH3 Beta-Glucosidase The *Aspergillus kawashii* strain IFO 4308 GH3 beta-glucosidase (SEQ ID NO: 179 [DNA sequence] and SEQ ID NO: 180 [deduced amino acid sequence]) was obtained according to the procedure described below.

To generate genomic DNA for PCR amplification, the fungi were propagated on PDA agar plates by growing at 26° C. for 7 days. Spores harvested from the PDA plates were used to inoculate 25 ml of YP+2% glucose medium in a baffled shake flask and incubated at 26° C. for 48 hours with agitation at 200 rpm.

Genomic DNA was isolated according to the procedure described in Example 73.

The *Aspergillus kawachii* beta-glucosidase gene was isolated by PCR using two cloning primers GH3-33f and GI-13-33r shown below, which were designed based on the publicly available *Aspergillus kawachii* full-length sequence (GenBank AB003470.1) for direct cloning by INFUSION™ strategy.

```
Primer GH3-33f:
                                        (SEQ ID NO: 229)
acacaactggggatccaccatgaggttcactttgattgaggcgg

Primer GH3-33r:
                                        (SEQ ID NO: 230)
agatctcgagaagcttaGTGAACAGTAGGCAGAGACGCCCGGAGC
```

A PCR reaction was performed with the genomic DNA prepared from *Aspergillus kawachii* IFO 4308 in order to amplify the full-length gene. The PCR reaction was composed of 1 μl of genomic DNA, 0.75 μl of primer GH3-33f (10 μM), 0.75 μl of primer GH3-33r (10 μM), 3 μl of 5×HF buffer, 0.25 μl of 50 mM $MgCl_2$, 0.3 μl of 10 mM dNTP, 0.15 μl of PHUSION® DNA polymerase, and PCR-grade water up to 15 μl. The PCR reaction was performed using a DYAD® PCR machine programmed for 2 minutes at 98° C. followed by 10 touchdown cycles at 98° C. for 15 seconds, 70° C. (−1° C./cycle) for 30 seconds, and 72° C. for 2 minutes 30 seconds; and 25 cycles each at 98° C. for 15 seconds, 60° C. for 30 seconds, 72° C. for 2 minutes 30 seconds, and 5 minutes at 72° C.

The reaction products were isolated by 1.0% agarose gel electrophoresis using TAE buffer where an approximately 2.9 kb PCR product band was excised from the gel and purified using a GFX® PCR DNA and Gel Band Purification Kit according to manufacturer's instructions. DNA corresponding to the *Aspergillus kawachii* beta-glucosidase gene was cloned into the expression vector pDAu109 (WO 2005042735) linearized with Barn HI and Hind III, using an IN-FUSION™' Dry-Down PCR Cloning Kit according to the manufacturer's instructions.

A 2.5 μl volume of the diluted ligation mixture was used to transform *E. coli* TOP10 chemically competent cells. Three colonies were selected on LB agar plates containing 100 μg of ampicillin per ml and cultivated overnight in 3 ml of LB medium supplemented with 100 μg of ampicillin per ml. Plasmid DNA was purified using an E.Z.N.A.® Plasmid Mini Kit according to the manufacturer's instructions. The *Aspergillus kawachii* beta-glucosidase gene sequence was verified by Sanger sequencing before heterologous expression.

The coding sequence is 2935 bp including the stop codon and is interrupted by 6 introns of 92 bp (nucleotides 58 to 149), 48 bp (nucleotides 293 to 340), 54 bp (nucleotides 386 to 439), 51 bp (nucleotides 493 to 543), 57 bp (nucleotides 1736 to 1792), and 50 bp (nucleotides 2652 to 2701). The encoded predicted protein is 860 amino acids. Using the SignalP program (Nielsen et al., 1997, *Protein Engineering* 10: 1-6), a signal peptide of 19 residues was predicted. The predicted mature protein contains 841 amino acids.

Protoplasts of *Aspergillus oryzae* BECh2 (WO 2000/39322) were prepared as described in WO 95/02043. One hundred microliters of protoplast suspension were mixed with 2.5-15 μg of the *Aspergillus* expression vector and 250 μl of 60% PEG 4000, 10 mM $CaCl_2$, and 10 mM Tris-HCl pH 7.5 were added and gently mixed. The mixture was incubated at 37° C. for 30 minutes and the protoplasts were spread on COVE sucrose (1 M) plates supplemented with 10 mM acetamide and 15 mM CsCl for transformant selection. After incubation for 4-7 days at 37° C. spores of several transformants were seeded on YP-2% maltodextrin medium. After 4 days cultivation at 30° C. culture broth was analyzed in order to identify the best transformants based on their ability to produce a large amount of active *Aspergillus kawachii* beta-glucosidase. The screening was based on intensity of the band corresponding to the heterologous expressed protein determined by SDS-PAGE and activity of the enzyme on 4-nitrophenyl-beta-D-glucopyranoside (pNPG) as described in Example 16 herein.

Spores of the best transformant were spread on COVE plates containing 0.01% TRITON® X-100 in order to isolate single colonies. The spreading was repeated twice in total on COVE sucrose medium (Cove, 1996, *Biochim. Biophys. Acta* 133: 51-56) containing 1 M sucrose and 10 mM sodium nitrate, supplemented with 10 mM acetamide and 15 mM CsCl. Fermentation was then carried out in 250 ml shake flasks using YP-2% maltodextrin medium for 4 days at 30° C. with shaking at 100 rpm. The broth was filtered using standard methods. Protein concentration was determined using a Microplate BCA™ Protein Assay Kit in which bovine serum albumin was used as a protein standard.

Example 75: Preparation of *Aspergillus clavatus* Strain NRRL 1 GH3 Beta-Glucosidase The *Aspergillus clavatus* strain NRRL 1 GH3 beta-glucosidase (SEQ ID NO: 181 [DNA sequence] and SEQ ID NO: 182 [deduced amino acid sequence]) was obtained according to the procedure described below.

Genomic DNA was isolated according to the procedure described in Example 73.

The *Aspergillus clavatus* beta-glucosidase gene was isolated by PCR using two cloning primers, GH3-10f and GH3-10r, shown below, which were designed based on the publicly available *Aspergillus clavatus* partial mRNA sequence (XM_001269581) for direct cloning by IN-FUSION™ strategy.

```
Primer GH3-10f:
                                        (SEQ ID NO: 231)
acacaactggggatccaccATGAGGTTCAGCTGGCTTGAGGTCG

Primer GH3-10r:
                                        (SEQ ID NO: 232)
agatctcgagaagcttaCTGTACCCGGGGCAGAGGTGCTCTC
```

A PCR reaction was performed with the genomic DNA prepared from *Aspergillus clavatus* NRRL1 in order to amplify the full-length gene. The PCR reaction was composed of 1 µl of genomic DNA, 0.75 µl of primer GH3-10f (10 µM), 0.75 µl of primer GH3-10r (10 µM), 3 µl of 5×HF buffer, 0.25 µl of 50 mM $MgCl_2$, 0.3 µl of 10 mM dNTP, 0.15 µl of PHUSION® DNA polymerase, and PCR-grade water up to 15 µl. The PCR reaction was performed using a DYAD® PCR machine programmed for 2 minutes at 98° C. followed by 10 touchdown cycles at 98° C. for 15 seconds, 70° C. (−1° C./cycle) for 30 seconds, and 72° C. for 2 minutes 30 seconds; and 25 cycles each at 98° C. for 15 seconds, 60° C. for 30 seconds, 72° C. for 2 minutes 30 seconds, and 5 minutes at 72° C.

The reaction products were isolated by 1.0% agarose gel electrophoresis using TAE buffer where an approximately 3.0 kb PCR product band was excised from the gel and purified using a GFX® PCR DNA and Gel Band Purification Kit according to manufacturer's instructions. DNA corresponding to the *Aspergillus clavatus* beta-glucosidase gene was cloned into the expression vector pDAu109 (WO 2005042735) linearized with Barn HI and Hind III, using an I N-FUSION™ Dry-Down PCR Cloning Kit according to the manufacturer's instructions.

A 2.5 µl volume of the diluted ligation mixture was used to transform *E. coli* TOP10 chemically competent cells. Three colonies were selected on LB agar plates containing 100 µg of ampicillin per ml and cultivated overnight in 3 ml of LB medium supplemented with 100 µg of ampicillin per ml. Plasmid DNA was purified using an E.Z.N.A.® Plasmid Mini Kit according to the manufacturer's instructions. The *Aspergillus clavatus* beta-glucosidase gene sequence was verified by Sanger sequencing before heterologous expression.

The coding sequence is 3062 bp including the stop codon and is interrupted by 8 introns of 67 bp (nucleotides 58 to 124), 61 bp (nucleotides 265 to 325), 62 bp (nucleotides 371 to 432), 65 bp (nucleotides 489 to 553), 50 bp (nucleotides 948 to 997), 53 bp (nucleotides 1021 to 1073), 61 bp (nucleotides 1849 to 1909), and 60 bp (nucleotides 2769 to 2828). The encoded predicted protein is 860 amino acids. Using the SignalP program (Nielsen et al., 1997, *Protein Engineering* 10: 1-6), a signal peptide of 18 residues was predicted. The predicted mature protein contains 842 amino acids.

Protoplasts of *Aspergillus oryzae* BECh2 (WO 2000/39322) were prepared as described in WO 95/02043. One hundred microliters of protoplast suspension were mixed with 2.5-15 µg of the *Aspergillus* expression vector and 250 µl of 60% PEG 4000, 10 mM $CaCl_2$, and 10 mM Tris-HCl pH 7.5 were added and gently mixed. The mixture was incubated at 37° C. for 30 minutes and the protoplasts were spread on COVE sucrose (1 M) plates supplemented with 10 mM acetamide and 15 mM CsCl for transformant selection. After incubation for 4-7 days at 37° C. spores of several transformants were seeded on YP-2% maltodextrin medium. After 4 days cultivation at 30° C. culture broth was analyzed in order to identify the best transformants based on their ability to produce a large amount of active *Aspergillus clavatus* beta-glycosidase. The screening was based on intensity of the band corresponding to the heterologous expressed protein determined by SDS-PAGE and activity of the enzyme on 4-nitrophenyl-beta-D-glucopyranoside (pNPG) as described in Example 16.

Spores of the best transformant were spread on COVE plates containing 0.01% TRITON® X-100 in order to isolate single colonies. The spreading was repeated twice in total on COVE sucrose medium (Cove, 1996, *Biochim. Biophys. Acta* 133: 51-56) containing 1 M sucrose and 10 mM sodium nitrate, supplemented with 10 mM acetamide and 15 mM CsCl. Fermentation was then carried out in 250 ml shake flasks using YP-2% maltodextrin medium for 4 days at 30° C. with shaking at 100 rpm. The broth was filtered using standard methods. Protein concentration was determined using a Microplate BCA™ Protein Assay Kit in which bovine serum albumin was used as a protein standard.

Example 76: Preparation of *Thielavia terrestris* NRRL 8126 GH3 Beta-Glucosidase The *Thielavia terrestris* GH3 beta-glucosidase (SEQ ID NO: 183 [DNA sequence] and SEQ ID NO: 184 [deduced amino acid sequence]) was obtained according to the procedure described below.

Three agarose plugs from culture of *Thielavia terrestris* NRRL 8126 grown on a PDA plate were inoculated into 100 ml of NNCYP medium supplemented with 1.5% glucose and incubated for 25 hours at 42° C. and 200 rpm on an orbital shaker. Fifty ml of this culture was used to inoculate 1.8 liter of NNCYP medium supplemented with 0.4% glucose and 52 g of powdered cellulose per liter and was incubated at 42° C. The pH was controlled at 5.0 by the addition of 15% ammonium hydroxide or 5 N phosphoric acid, as needed.

The fermentations were run at 42° C. with minimum dissolved oxygen at 25% at a 1.0 VVM air flow and an agitation at 1100 rpm. Feed medium was delivered into a 2 liter fermentation vessel at 0 hours with a feed rate of 6.0-8.0 g/hour for 120 hours. Pooled cultures were centrifuged at 3000×g for 10 minutes and the supernatant was filtered through a disposable filtering unit with a glass fiber prefilter (Nalgene, Rochester N.Y., USA). The filtrate was cooled to 4° C. for storage.

A 0.3 ml aliquot of the filtrate was precipitated with 10% trichloroacetic acid (TCA)-80% acetone for 20 minutes on ice. The suspension was centrifuged for 10 minutes at 13,000×g. The supernatant was removed and the protein pellet remaining was rinsed with cold acetone. The protein pellet was dissolved in 30 µl of 1× lithium dodecyl sulfate (LDS) SDS-PAGE loading buffer with 50 mM dithiothreitol (DTT) and heated at 80° C. for 10 minutes. A 15 µl sample was separated by SDS-PAGE using a 7 cm 4-12% NuPAGE Bis-Tris SDS-PAGE gradient gel and 2-(N-morpholino) ethanesulfonic acid (MES) running buffer. The SDS-PAGE was run under reducing conditions according to the manufacturer's recommended protocol (Invitrogen, Carlsbad, Calif., USA). The gel was removed from the cassette and rinsed 3 times with deionized water for at least 5 minutes each and stained with Bio-Safe Coomassie Stain (Bio-Rad Laboratories, Inc., Hercules, Calif., USA) for 1 hour followed by destaining with doubly-distilled water for more than 30 minutes. Protein bands observed at approximately 95 kD was excised and reduced with 50 μl of 10 mM DTT in 100 mM ammonium bicarbonate for 30 minutes. Following reduction, the gel pieces were alkylated with 50 μl of 55 mM iodoacetamide in 100 mM ammonium bicarbonate for 20 minutes. The dried gel pieces were allowed to re-hydrate in a trypsin digestion solution (6 ng/μl sequencing grade trypsin in 50 mM ammonium bicarbonate) for 30 minutes at room temperature, followed by an 8 hour digestion at 40° C. Each of the reaction steps described was followed by numerous washes and pre-washes with the desired solutions. Fifty μl of acetonitrile was used to de-hydrate the gel pieces between reactions and they were air-dried between steps. Peptides were extracted twice with 1% formic acid/2% acetonitrile in HPLC grade water for 30 minutes. Peptide extraction solutions were transferred to a 96 well PCR type microtiter plate that had been cooled to 10-15° C. Microtiter plates containing the recovered peptide solutions were sealed to prevent evaporation and stored at 4° C. until mass spectrometry analysis could be performed.

For de-novo peptide sequencing by tandem mass spectrometry, a Q-Tof micron", a hybrid orthogonal quadrupole time-of-flight mass spectrometer (Waters Micromass® MS Technologies, Milford, Mass., USA) was used for LC/MS/MS analysis. The Q-Tof micron" was fitted with an Ultimate™ capillary and nano-flow HPLC system which had been coupled with a FAMOS micro autosampler and a Switchos II column switching device (LCPackings, San Francisco, Calif., USA) for concentrating and desalting samples. Samples were loaded onto a guard column (300 μm ID×5 cm, C18 pepmap) fitted in the injection loop and washed with 0.1% formic acid in water at 40 μl/minute for 2 minutes using the Switchos II pump. Peptides were separated on a 75 μm ID×15 cm, C18, 3 μm, 100 Å PepMap™ (LC Packings, San Francisco, Calif., USA) nano-flow fused capillary column at a flow rate of 175 nl/minute from a split flow of 175 μl/minute using a NAN-75 calibrator (Dionex, Sunnyvale, Calif., USA). A step elution gradient of 5% to 80% acetonitrile in 0.1% formic acid was applied over a 45 minute interval. The column eluent was monitored at 215 nm and introduced into the Q-Tof Micron™ through an electrospray ion source fitted with the nanospray interface. The Q-Tof Micron™ is fully microprocessor controlled using Masslynx™ software version 3.5 (Waters Micromass® MS Technologies, Milford, Mass., USA). Data was acquired in survey scan mode and from a mass range of m/z 400 to 1990 with the switching criteria for MS to MS/MS to include an ion intensity of greater than 10.0 counts per second and charge states of +2, +3, and +4. Analysis spectra of up to 4 co-eluting species with a scan time of 1.9 seconds and inter-scan time of 0.1 seconds could be obtained. A cone voltage of 65 volts was typically used and the collision energy was programmed to be varied according to the mass and charge state of the eluting peptide and in the range of 10-60 volts. The acquired spectra were combined, smoothed and centered in an automated fashion and a peak list generated. This peak list was searched against selected public and private databases using ProteinLynx™ Global Server 1.1 software (Waters Micromass® MS Technologies, Milford, Mass.). Results from the ProteinLynx™ searches were evaluated and un-identified proteins were analyzed further by evaluating the MS/MS spectrums of each ion of interest and de-novo sequence was determined by identifying the y and b ion series and matching mass differences to the appropriate amino acid.

Peptide sequences obtained from de novo sequencing by mass spectrometry were obtained from several multiply charged ions for the approximately 95 kDa polypeptide gel band.

A doubly charged tryptic peptide ion of 524.76 m/z sequence was determined to be Ser-Pro-Phe-Thr-Trp-Gly-Pro-Thr-Arg (amino acids 607 to 615 of SEQ ID NO: 184). A second doubly charged tryptic peptide ion of 709.91 partial sequence was determined to be Gly-Val-Asn-Val-[Ile/Leu]-[Ile-Leu]-Gly-[Ile/Leu]-Gly-Pro (amino acids 148 to 155 of SEQ ID NO: 184). A second doubly charged tryptic peptide ion of 745.38 partial sequence was determined to be Pro-Pro-His-Ala-Thr-Asp (amino acids 747 to 752 of SEQ ID NO: 184). A third doubly charged tryptic peptide ion of 808.92 m/z sequence was determined to be Tyr-Glu-Ser-[Ile/Leu]-[Ile/Leu]-Ser-Asn-Tyr-Ala-Thr-Ser-Qln-[Ile/Leu]-Lys (amino acids 487 to 499 of SEQ ID NO: 184). A fourth doubly charged tryptic peptide ion of 1023.96 a partial sequence was determined to be Phe-Asn-Ser-Gly-Phe-Pro-Ser-Gly-Gln-Thr-Ala-Ala-Ala-Thr-Phe-Asp-Arg (amino acids 114 to 130 of SEQ ID NO: 184).

To generate genomic DNA for PCR amplification, *Thielavia terrestris* NRRL 8126 was grown in 50 ml of NNCYP medium supplemented with 1% glucose in a baffled shake flask at 42° C. and 200 rpm for 24 hours. Mycelia were harvested by filtration, washed twice in TE (10 mM Tris-1 mM EDTA), and frozen under liquid nitrogen. A pea-size piece of frozen mycelia was suspended in 0.7 ml of 1% lithium dodecyl sulfate in TE and disrupted by agitation with an equal volume of 0.1 mm zirconia/silica beads (Biospec Products, Inc., Bartlesville, Okla., USA) for 45 seconds in a FastPrep FP120 (ThermoSavant, Holbrook, N.Y., USA). Debris was removed by centrifugation at 13,000×g for 10 minutes and the cleared supernatant was brought to 2.5 M ammonium acetate and incubated on ice for 20 minutes. After the incubation period, the nucleic acids were precipitated by addition of 2 volumes of ethanol. After centrifugation for 15 minutes in a microfuge at 4° C., the pellet was washed in 70% ethanol and air dried. The DNA was resuspended in 120 μl of 0.1×TE and incubated with 1 μl of DNase-free RNase A at 37° C. for 20 minutes. Ammonium acetate was added to 2.5 M and the DNA was precipitated with 2 volumes of ethanol. The pellet was washed in 70% ethanol, air dried, and resuspended in TE buffer.

A low redundancy draft sequence of the *Thielavia terrestris* NRRL 8126 genome was generated by the Joint Genome Center (JGI), Walnut Creek, Calif., USA, using the whole genome shotgun method according to Martinez et al., 2008, *Nature Biotechnol.* 26: 553-560. Shotgun sequencing reads (approximately 18307) were assembled into contigs using the Phrap assembler (Ewing and Green, 1998, *Genome Res.* 8: 186-194).

A tblastn search (Altschul et al., 1997, *Nucleic Acids Res.* 25: 3389-3402) of the assembled contigs was carried out using as query a beta-glucosidase protein sequence from *Neurospora crassa* (UniProt accession number q7rwp2). A translated amino acid sequence with greater than 73.8% identity to the query sequence was identified.

The sequence was searched against public databases using blastp (Altschul et al., 1997, supra) and was found to be 80.1% identical to a beta-glucosidase from *Podospora anserina* (UniProt accession number B2AVE8).

The nucleotide sequence and deduced amino acid sequence of the *Thielavia terrestris* beta-glucosidase gene are shown in SEQ ID NO: 183 and SEQ ID NO: 184, respectively. The coding sequence is 3032 bp including the stop codon and is interrupted by three introns of 295 bp, 57 bp, and 61 bp. The encoded predicted protein is 872 amino acids. Using the SignalP program (Nielsen et al., 1997, *Protein Engineering* 10: 1-6), a signal peptide of 18 residues was predicted. The predicted mature protein contains 854 amino acids with a predicted molecular mass of 93 kDa and an isoelectric point of 5.57.

*Thielavia terrestris* NRRL 8126 was grown for 3 days on PDA plates at 45° C. Mycelia were scraped from the plates and approximately 100 mg of mycelia (wet weight) were used to inoculate 500 ml shake flasks containing 100 ml of either MY50 medium or 1× Vogel's medium supplemented with 2% microcrystalline cellulose (AVICEL®). Cultures were grown for 2, 3, 4 and 5 days at 45° C. with vigorous shaking. The mycelia were harvested by filtration through MIRACLOTH® (EMD Chemicals Inc., Gibbstown, N.J., USA), and quick frozen in liquid nitrogen.

To isolate total RNA frozen mycelia of *Thielavia terrestris* NRRL 8126 were ground in an electric coffee grinder. The ground material was mixed 1:1 v/v with 20 ml of FENAZOL™ (Ambion, Inc., Austin, Tex., USA) in a 50 ml tube. Once the mycelia were suspended, they were extracted with chloroform and three times with a mixture of phenol-chloroform-isoamyl alcohol 25:24:1 v/v/v. From the resulting aqueous phase, the RNA was precipitated by adding 1/10 volume of 3 M sodium acetate pH 5.2 and 1.25 volumes of isopropanol. The precipitated RNA was recovered by centrifugation at 12,000×g for 30 minutes at 4° C. The final pellet was washed with cold 70% ethanol, air dried, and resuspended in 500 ml of diethylpyrocarbonate treated water (DEPC-water).

RNA samples were pooled and the quality and quantity of the purified RNA was assessed with an AGILENT® 2100 Bioanalyzer (Agilent Technologies, Inc., Palo Alto, Calif., USA). A total of 630 μg of RNA was isolated.

Poly A+ RNA was isolated from total RNA using an Absolutely mRNA™ Purification Kit (Stratagene, La Jolla, Calif., USA) according to the manufacturer's instructions. cDNA synthesis and cloning was performed according to a procedure based on the SuperScript™ Plasmid System with Gateway® Technology for cDNA Synthesis and Cloning (Invitrogen, Carsbad, Calif., USA). 1-2 μg of poly A+ RNA, reverse transcriptase SuperScript II (Invitrogen, Carsbad, Calif., USA), and oligo dT-Not I primer 5'-GACTAGTTCTA-GATCGCGAGCGGCCGCCCTTTTTTTTTTTTTTTVN-3' (SEQ ID NO: 233) were used to synthesize first strand cDNA. Second strand synthesis was performed with *E. coli* DNA ligase, polymerase I, and RNase H followed by end repair using T4 DNA polymerase. The Sal I adaptor (5'-TCGACCCACGCGTCCG-3' [SEQ ID NO: 234] and 5'-CGGACGCGTGGG-3' [SEQ ID NO: 235]) was ligated to the cDNA, digested with Not I, and subsequently size selected (>2 kb) by 1.1% agarose gel electrophoresis using TAE buffer. The cDNA inserts were directionally ligated into Sal I and Not I digested vector pCMVsport6 (Invitrogen, Carsbad, Calif., USA). The ligation was transformed into ElectroMAX™ DH10B™ T1 cells (Invitrogen, Carsbad, Calif., USA).

Library quality was first assessed by randomly selecting 24 clones and PCR amplifying the cDNA inserts with the primers M13-F and M13-R shown below to determine the fraction of insertless clones.

```
Primer M13-F:
                                  (SEQ iD NO: 236)
5'-GTAAAACGACGGCCAGT-3'

Primer M13-R:
                                  (SEQ iD NO: 237)
5'-AGGAAACAGCTATGACCAT-3'
```

Colonies from each library were plated onto LB plates at a density of approximately 1000 colonies per plate. Plates were grown at 37° C. for 18 hours and then individual colonies were picked and each used to inoculate a well containing LB medium supplemented with 100 μg of ampicillin per ml in a 384 well plate (Nunc, Rochester, N.Y., USA). Clones were grown at 37° C. for 18 hours. Plasmid DNA for sequencing was produced by rolling circle amplification using a Templiphi™ Kit (GE Healthcare, Piscataway, N.J., USA). Subclone inserts were sequenced from both ends using primers complimentary to the flanking vector sequence as shown below and BigDye® terminator chemistry using a 3730 DNA Analyzer (Applied Biosystems, Foster City, Calif., USA).

```
Forward primer:
                                  (SEQ iD NO: 238)
5'-ATTTAGGTGACACTATAGAA-3'

Reverse primer:
                                  (SEQ ID NO: 239)
5'-TAATACGACTCACTATAGGG-3'
```

A clone showing 67.4% identity at the nucleotide level to a beta-glucosidase from *Aspergillus oryzae* (U.S. Published Application No. 2005233423) was identified.

Two synthetic oligonucleotide primers shown below were designed to PCR amplify the *Thielavia terrestris* Family GH3B beta-glucosidase gene from the cDNA clone. An IN-FUSION® Cloning Kit (BD Biosciences, Palo Alto, Calif., USA) was used to clone the fragment directly into the expression vector pAILo2 (WO 2005/074647), without the need for restriction digestion and ligation.

Forward primer:
(SEQ ID NO: 240)
5'-ACTGGATTTACCATGAAGCCTGCCATTGTGCT-3'

Reverse primer:
(SEQ ID NO: 241)
5'-TCACCTCTAGTTAATTAATCACGGCAACTCAATGCTCA-3'

Bold letters represent coding sequence. The remaining sequence is homologous to the insertion sites of pAILo2.

Fifty picomoles of each of the primers above were used in a PCR reaction containing 200 ng of plasmid cDNA, 1× 2× Advantage GC-Melt LA Buffer (Clonetech Laboratories, Inc., Mountain View, Calif., USA), 1 μl of 10 mM blend of dATP, dTTP, dGTP, and dCTP, and 1.25 units of Advantage GC Genomic LA Polymerase Mix (Clonetech Laboratories, Inc., Mountain View, Calif., USA) in a final volume of 50 μl. The amplification was performed using an EPPENDORF® MASTERCYCLER® 5333 epgradient S (Eppendorf Scientific, Inc., Westbury, N.Y., USA) programmed for one cycle at 94° C. for 1 minute; and 30 cycles each at 94° C. for 30 seconds, 60.5° C. for 30 seconds, and 72° C. for 3 minutes. The heat block was then held at 72° C. for 15 minutes followed by a 4° C. soak cycle.

The reaction products were isolated by 1.0% agarose gel electrophoresis using TAE buffer where an approximately 2.6 kb product band was excised from the gel and purified using a MINELUTE® Gel Extraction Kit (QIAGEN Inc., Valencia, Calif., USA) according to the manufacturer's instructions.

The fragment was then cloned into pAILo2 using an IN-FUSION® Cloning Kit. The vector was digested with Nco I and Pac I. The fragment was purified by gel electrophoresis as above and a QIAQUICK® Gel Purification Kit (QIAGEN Inc., Valencia, Calif., USA). The gene fragment and the digested vector were combined together in a reaction resulting in the expression plasmid pAG81, in which transcription of the Family GH3B protein gene was under the control of the NA2-tpi promoter (a hybrid of the promoters from the genes for *Aspergillus niger* neutral alpha-amylase and *Aspergillus nidulans* triose phosphate isomerase). The recombination reaction (10 μl) was composed of 1× IN-FUSION® Buffer (BD Biosciences, Palo Alto, Calif., USA), 1×BSA (BD Biosciences, Palo Alto, Calif., USA), 1 μl of IN-FUSION® enzyme (diluted 1:10) (BD Biosciences, Palo Alto, Calif., USA), 108 ng of pAILo2 digested with Nco I and Pac 1, and 94 ng of the *Thielavia terrestris* GH3B protein purified PCR product. The reaction was incubated at 37° C. for 15 minutes followed by 15 minutes at 50° C. The reaction was diluted with 40 μl of 10 mM Tris-0.1 M EDTA buffer and 2.5 μl of the diluted reaction was used to transform *E. coli* TOP10 Competent cells. An *E. coli* transformant containing pAG81 (GH3B protein gene) was identified by restriction enzyme digestion and plasmid DNA was prepared using a BIOROBOT® 9600. The plasmid construct was sequenced using an Applied Biosystems 3130xl Genetic Analyzer (Applied Biosystems, Foster City, Calif., USA) to verify the gene sequence.

*Aspergillus oryzae* JaL355 protoplasts were prepared according to the method of Christensen et al., 1988, *Bio/Technology* 6: 1419-1422, which were transformed with 5 μg of pAG81. Twenty-six transformants were isolated to individual PDA plates. A small plug from each transformant was used to inoculate 1 ml of M410 media in a 24 well plate and incubated at 34° C. After 5 days of incubation, 7.5 μl of supernatant from four transformants was analyzed using a CRITERION® stain-free, 8-16% gradient SDS-PAGE gel (Bio-Rad Laboratories, Inc., Hercules, Calif., USA) according to the manufacturer's instructions. SDS-PAGE profiles of the cultures showed that several transformants had a new major band of approximately 150 kDa.

A confluent PDA plate of the top transformant (was washed with 5 ml of 0.01% TWEEN® 20 and inoculated into 500 ml flasks each containing 100 ml of M410 medium to generate broth for characterization of the enzyme. The flasks were harvested on day 5, filtered using a 0.22 μm stericup suction filter (Millipore, Bedford, Mass., USA), and stored at 4° C.

A 45 ml aliquot of shake flask broth prepared was concentrated ten-fold using a VIVASPIN™ centrifugal concentrator with a molecular weight cut-off of 10 kDa and buffer-exchanged into 50 mM sodium acetate of pH 5. A 4 ml aliquot of the buffer-exchanged, concentrated broth was then diluted to a 10 ml volume with 1 M Tris-HCl pH 8 and water to a concentration of 20 mM Tris-HCl, and the pH adjusted to a final value of 8 using 2 N sodium hydroxide. The resulting material was then purified using a MONO Q™ 5/5 column (GE Healthcare, Piscataway, N.J., USA) equilibrated with 20 mM Tris-HCl buffer pH 7.8. Unbound material was washed from the column with 2 ml equilibration buffer, and then the column was eluted with a linear gradient from 0-500 mM sodium chloride in the equilibration buffer. Fractions of 0.3 ml were collected. Unbound material collected during column loading and unbound material washed from the column were pooled for a total volume of 12 ml. Five μl of the fractions, including the pooled unbound material, showing UV absorbance at 280 nm were analyzed using a CRITERION STAIN FREE™ 8-16% Tris-HCl SDS-PAGE gel (Bio-Rad Laboratories, Inc., Hercules, Calif., USA) according to the manufacturer's instructions. Precision Plus Protein™ unstained standards (Bio-Rad Laboratories, Inc., Hercules, Calif., USA) were used as molecular weight markers. The gel was removed from the cassette and imaged using a CRITERION STAIN FREE™ IMAGER (Bio-Rad Laboratories, Inc., Hercules, Calif., USA). The beta-glucosidase was identified in the pooled unbound material as a band at 150 kDa by SDS-PAGE. The 12 ml of pooled unbound material was concentrated as described above to a final volume of 2 ml. The concentrated material was purified using a HI LOAD™ 16/60 SUPERDEX™ 75 PREP GRADE column (GE Healthcare, Piscataway, N.J., USA) equilibrated with 20 mM Tris.HCl buffer of pH 7.8 containing 150 mM sodium chloride, and eluted with the equilibration buffer. Fractions of 3 ml were collected. Column fractions were analyzed by SDS-PAGE as described above. Fractions containing the purified beta-glucosidase, identified by a band at 150 kDa by SDS-PAGE, were pooled for a total volume of 6 ml. The pooled material was concentrated using a VIVASPIN™ centrifugal concentrator with a molecular weight cut-off of 5 kDa (GE Healthcare, Piscataway, N.J., USA) to a final volume of 0.4 ml. Protein concentration was determined using the Bio-Rad Protein Assay (Bio-Rad Laboratories, Inc., Hercules, Calif., USA).

The enzyme activity of the purified beta-glucosidase was measured using p-nitrophenyl-beta-D-glucopyranoside as substrate. A p-nitrophenyl-beta-D-glucopyranoside stock solution was made by dissolving p-nitrophenyl-beta-D-glucopyranoside in dimethylsulfoxide (DMSO) to constitute a 0.1 M solution. Before assay, a sample of the stock solution was diluted 100-fold in 100 mM sodium acetate pH 5 containing 0.01% TWEEN® 20 to a 1 mM solution. A 100 μl volume of 1 mM p-nitrophenyl-beta-D-glucopyranoside was mixed with each dilution of the enzyme for a 120 μl total volume, and then incubated at 40° C. for 20 minutes. Substrate alone, enzyme alone, and buffer alone were run as controls. p-Nitrophenol standard solutions of 0.40, 0.25, 0.20, 0.10, 0.05, and 0.02 mM were prepared by diluting a 10 mM stock solution in 100 mM sodium acetate pH 5 containing 0.01% TWEEN® 20. At 20 minutes, 50 μl of 1.0 M sodium carbonate buffer pH 10 was added to each well (including samples, substrate control, enzyme control, reagent control, and standards), mixed, and the absorbance at 405 nm immediately measured on a SPECTRAMAX™ 340 PC plate reader (Molecular Devices, Sunnyvale, Calif., USA). The activity measured was 84 units per mg of protein. One unit of activity was defined as the amount of enzyme capable of releasing 1 μmole of p-nitrophenolate anion per minute at pH 5, 40° C.

The enzyme activity of the purified beta-glucosidase was also measured with cellobiose. A 2 mg/ml stock solution of cellobiose was prepared in 50 mM sodium acetate pH 5 containing 0.01% TWEEN® 20, and 100 μl were combined with each enzyme dilution for a total volume of 150 μl and incubated at 50° C. for 30 minutes. Substrate alone, enzyme alone, and buffer alone were run as controls. Glucose standard solutions of 1.0, 0.50, 0.25, 0.125, 0.063, and 0.031 mg/ml were prepared in 50 mM sodium acetate pH 5. containing 0.01% TWEEN® 20. At 30 minutes, 50 μl of 0.5 M sodium hydroxide solution was added to each well (including samples, substrate control, enzyme control, reagent control, and standards), mixed, and then 20 μl of the mixture was transferred to a Costar® EIA/RIA 96-well plate (Corning Incorporated, Corning, N.Y., USA) and combined with 200 μl of GLUCOSE OXIDASE REAGENT (Pointe Scientific, Inc., Canton, Mich., USA), and allowed to stand at 25° C. for 20 minutes and then the absorbance at 500 nm was measured on a SPECTRAMAX™ 340 PC plate reader (Molecular Devices, Sunnyvale, Calif., USA). The activity measured was 264 units per mg of protein. One unit of activity was defined as the amount of enzyme capable of releasing 1 μmole of glucose per minute at pH 5, 50° C.

Example 77: Preparation of *Penicillium oxalicum* Strain IBT5387 GH3 Beta-Glucosidase The *Penicillium oxalicum* strain IBT5387 (Technical University of Denmark; NN005786) GH3 beta-glucosidase (SEQ ID NO: 185 [DNA sequence] and SEQ ID NO: 186 [deduced amino acid sequence]) was obtained according to the procedure described below.

*Aspergillus oryzae* BECh2 (WO 2000/39322) was used as a host cell for expressing the *P. oxalicum* strain IBT5387 Family GH3 beta-glucosidase gene.

A set of degenerate primers shown below were designed according to the strategy described by Rose et al., 1998, *Nucleic Acids Research* 26: 1628-1635, for cloning a gene encoding a beta-glucosidase (EC 3.2.1.21) belonging to Family GH3.

```
GH3scree.f1:
                                        (SEQ ID NO: 242)
atgaccctggccgaaaaagtcaacytnacnacngg

GH3scree.f2:
                                        (SEQ ID NO: 243)
ggtggccggaactgggaaggcttctsnccngaycc

GH3scree.f5:
                                        (SEQ ID NO: 244)
gagctgggcttccagggctttgtnatgwsngaytgg

GH3scree.f6:
                                        (SEQ ID NO: 245)
agcgctttggccggcctcgayatgwsnatgcc

GH3scree.r1:
                                        (SEQ ID NO: 246)
atcccagttgctcaggtcccknckngt

GH3scree.r2:
                                        (SEQ ID NO: 247)
aaaggttgtgtagctcagnccrtgnccraaytc

GH3scree.r3:
                                        (SEQ ID NO: 248)
gtcaaagtggcggtagtcgatraanacnccytc

GH3scree.r4:
                                        (SEQ ID NO: 249)
ggtgggcgagttgccgacggggttgactctgccrtanar

GH3scree.r5:
                                        (SEQ ID NO: 250)
gccgggcagaccggcccagaggatggcngtnacrttngg

GH3scree.r6:
                                        (SEQ ID NO: 251)
caggacggggccaaccgagtgaatgacnacdatngtrtt
```

PCR screening of *Penicillium oxalicum* strain IBT5387 was performed using two successive PCRs. The forward primers (GH3scree.f1, GH3scree.f2, GH3scree.f5, or GH3scree.f6) (0.33 μl of a 10 mM stock) were combined with the reverse primers (GH3scree.r1, GH3scree.r2, GH3scree.r3, GH3scree.r4, GH3scree.r5, or GH3scree.r6) (0.33 μl of a 10 mM stock) in a 10 μl mixture containing 0.33 μl of *P. oxalicum* genomic DNA and 5 μl of REDDYMIX™ Extensor PCR Master Mix 1 (ABgene Ltd., Surrey, United Kingdom). *P. oxalicum* genomic DNA was obtained according to the procedure described in the FastDNA® SPIN Kit (Q-BIOgene, Carlsbad, Calif., USA). The PCR reaction was performed using a DYAD® Thermal Cycler (Bio-Rad Laboratories, Inc., Hercules, Calif., USA) programmed for one cycle at 94° C. for 2 minutes; 9 cycles each at 94° C. for 15 seconds, 63° C. for 30 seconds with a decrease of 1° C. for each cycle, and 68° C. for 1 minutes 45 seconds; 24 cycles each at 94° C. for 15 seconds, 55° C. for 30 seconds, and 68° C. for 1 minutes 45 seconds; and extension at 68° C. for 7 minutes.

PCR products obtained during the first PCR were reamplified with their corresponding primers by transferring 0.5 μl of the first PCR reaction to a second 20 μl mixture containing the same concentration of primers, dNTPs, DNA polymerase, and buffer as the first PCR reaction. The second PCR was performed using a DYAD® Thermal Cycler programmed for one cycle at 94° C. for 2 minutes; 24 cycles each at 94° C. for 15 seconds, 58° C. for 30 seconds, and 68° C. for 1 minutes 45 seconds; and an extension at 68° C. for 7 minutes.

PCR products obtained during the second amplification were analyzed by 1% agarose gel electrophoresis using TAE buffer. Single bands ranging from 2000 to 800 nucleotides in size were excised from the gel and purified using a GFX® PCR DNA and Gel Band Purification Kit according to the manufacturer's instructions. Purified DNA samples were directly sequenced with primers used for amplification. Sequences were assembled in SeqMan v7.2.1 (DNA star, Madison, Wis., USA) into a contig that was used for designing primers shown below, based on recommendations of length and temperature described in a GENE WALKING SPEEDUP™ Kit (Seegene, Inc., Seoul, Korea).

```
5786GH3-51TSP1f:
                                        (SEQ ID NO: 252)
CACCAACACCGGCAATCTAGC

5786GH3-51TSP2f:
                                        (SEQ ID NO: 253)
GGTGACGAGGTTGTCCAACTGTACG

5786GH3-51TSP1r:
                                        (SEQ ID NO: 254)
CTTGAAGCCAAGGCGAGG

5786GH3-51TSP2r:
                                        (SEQ ID NO: 255)
TCCGGTATTTCCTACACATGGTCC
```

GeneWalking was based on the protocol from the GENE WALKING SPEEDUP™ Kit with some minor differences. Only two PCR amplifications were carried out and in both cases, the REDDYMIX™ Extensor PCR Master Mix 1 was used in place of the enzyme mix present in the Kit. GeneWalking PCR 1 was performed in a total volume of 15 μl by mixing 1.2 μl of primer 1 to 4 (2.5 mM) from the GENE WALKING SPEEDUP™ Kit with 0.3 μl of primer 5786GH3-51TSP1f or primer 5786GH3-51TSP1r (10 mM) in the presence of 7.5 μl of REDDYMIX™ Extensor PCR Master Mix 1, and 0.5 μl of *P. oxalicum* genomic DNA. The PCR was performed using a DYAD® Thermal Cycler programmed for one cycle at 94° C. for 3 minutes followed by 1 minute at 42° C. and 2 minutes at 68° C.; 30 cycles each at 94° C. for 30 seconds, 58° C. for 30 seconds, and 68° C.

for 1 minute and 40 seconds; and elongation at 68° C. for 7 minutes. A 0.5 μl aliquot of the amplification reaction was transferred to a second PCR tube containing a 20 μl mixture composed of 10 μl of REDDYMIX™ Extensor PCR Master Mix 1, 1 μl of primer 5 (10 mM) from the Kit, 1 μl of primers T5786GH3-51SP2f or 5786GH3-51TSP2r (10 mM). The amplification was performed in a DYAD® Thermal Cycler programmed for denaturation at 94° C. for 3 minutes; 35 cycles each at 94° C. for 30 seconds, 58° C. for 30 seconds, and 68° C. for 1 minute and 40 seconds; and elongation at 68° C. for 7 minutes.

The PCR products were analyzed by 1% agarose gel electrophoresis in TAE buffer. Single bands ranging from 700 to 1200 nucleotides in size were excised from the gel and purified using a GFX® PCR DNA and Gel Band Purification Kit according to manufacturer's instructions. Purified DNA samples were directly sequenced with the primers used for amplification.

Based on blastx analyses, the start and the stop codons of the gene were identified and the primers shown below were designed for cloning the gene into the expression vector pDAu109 (WO 2005042735) using an IN-FUSION™ Dry-Down PCR Cloning Kit.

```
5786GH3-51r1:
                                    (SEQ ID NO: 256)
agatctcgagaagcttaCCATGACTCCAATCGCGCGCTCAAGG

5786GH3-51f1:
                                    (SEQ ID NO: 257)
acacaactggggatccaccATGAGGAGCTCAACGACGGTTCTGGCC
```

The *P. oxalicum* beta-glucosidase gene was amplified by PCR using the two cloning primers described above with *P. oxalicum* strain IBT5387 genomic DNA. The PCR was composed of 1 μl of *P. oxalicum* genomic DNA, 0.75 μl of primer 5786GH3-51f1 (10 μM), 0.75 μl of primer 5786GH3-51r1 (10 μM), 3 μl of 5×HF buffer, 0.25 μl of 50 mM $MgCl_2$, 0.3 μl of 10 mM dNTP, 0.15 μl of PHUSION® DNA polymerase, and PCR-grade water to 15 μl. The amplification reaction was performed using a DYAD® Thermal Cycler programmed for 2 minutes at 98° C. followed by 10 touchdown cycles each at 98° C. for 15 seconds, 70° C. (−1° C./cycle) for 30 seconds, and 72° C. for 2 minutes and 30 seconds; and 25 cycles each at 98° C. for 15 seconds, 60° C. for 30 seconds, 72° C. for 2 minutes and 30 seconds, and 5 minutes at 72° C.

The reaction product was isolated by 1.0% agarose gel electrophoresis using TAE buffer where an approximately 2.8 kb PCR product band was excised from the gel and purified using a GFX® PCR DNA and Gel Band Purification Kit according to manufacturer's instructions. DNA corresponding to the *Penicillium oxalicum* beta-glucosidase gene was cloned into the expression vector pDAu109 (WO 2005042735) linearized with Barn HI and Hind III, using an IN-FUSION™ Dry-Down PCR Cloning Kit according to the manufacturer's instructions.

A 2.5 μl volume of the diluted ligation mixture was used to transform *E. coli* TOP10 chemically competent cells. Three colonies were selected on LB agar plates containing 100 μg of ampicillin per ml and cultivated overnight in 3 ml of LB medium supplemented with 100 μg of ampicillin per ml. Plasmid DNA was purified using an E.Z.N.A.® Plasmid Mini Kit according to the manufacturer's instructions. The *Penicillium oxalicum* beta-glucosidase gene sequence was verified by Sanger sequencing before heterologous expression. One plasmid designated pIF113#1 was selected for expressing the *P. oxalicum* beta-glucosidase in an *Aspergillus oryzae* host cell.

The coding sequence is 2793 bp including the stop codon with 2 predicted introns of 82 bp (nucleotides 85 to 116) and 59 bp (nucleotides 346 to 404). The encoded predicted protein is 883 amino acids. Using the SignalP program (Nielsen et al., 1997, *Protein Engineering* 10: 1-6), a signal peptide of 21 residues was predicted. The predicted mature protein contains 862 amino acids with a predicted molecular mass of 94.7 kDa and an isoelectric point of 5.04.

Protoplasts of *Aspergillus oryzae* BECh2 (WO 2000/39322) were prepared according to WO 95/002043. One hundred μl of protoplasts were mixed with 2.5-15 μg of the *Aspergillus* expression vector and 250 μl of 60% PEG 4000 (Applichem, Darmstadt, Germany) (polyethylene glycol, molecular weight 4,000), 10 mM $CaCl_2$, and 10 mM Tris-HCl pH 7.5 and gently mixed. The mixture was incubated at 37° C. for 30 minutes and the protoplasts were spread onto COVE plates for selection. After incubation for 4-7 days at 37° C. spores of sixteen transformants were inoculated into 0.5 ml of YP medium supplemented with 2% maltodextrin in 96 deep-well plates. After 4 days cultivation at 30° C., the culture broths were analyzed to identify the best transformants producing large amounts of active *P. oxalicum* beta-glucosidase. The analysis was based on SDS-PAGE and activity of the enzyme on 4-nitrophenyl-beta-D-glucopyranoside (pNPG) as described in Example 16.

Spores of the best transformant were spread on COVE plates containing 0.01% TRITON® X-100 in order to isolate single colonies. The spreading was repeated twice in total on COVE plates containing 10 mM sodium nitrate. Spores were then inoculated into 100 ml of YP medium supplemented with 2% maltodextrin in 250 ml shake flasks and incubated for 4 days at 30° C. with shaking at 100 rpm.

Combined supernatants of the shake flask cultures were first filtered using a glass micro fiber filter with a 0.7 μm pore size, and then sterile filtered using a filtration unit equipped with a PES (Polyether sulfone) with a 0.22 μm pore size (Nalge Nunc International, New York, N.Y. USA). The sterile filtered supernatant was then adjusted to a concentration of 2 M ammonium sulfate by slowly adding solid ammonium sulfate, dissolving by gentle stirring, and then filtering using a glass micro fiber filter with a 0.7 μm pore size. If there was any precipitate, it was discarded.

The filtered supernatant was applied to a 50 ml Toyopearl Phenyl-650M column (TOSOH Bioscience GmbH, Germany) equilibrated with 2 M ammonium sulfate in water and unbound material was eluted with 2 M ammonium sulfate until the UV absorbance at 280 nm was below 0.05. Bound protein was eluted with 50% ethanol as solution B using a step gradient. Ten ml fractions were collected and monitored by UV absorbance at 280 nm. The fractions were analyzed by SDS-PAGE and pooled the fractions containing protein with the expected molecular weight. The pooled fractions were dialyzed using 50 mM HEPES pH 7.5 buffer, so the ionic strength was below 4 MSi and the pH was 7.5.

The pooled protein was applied to a 50 ml Q Sepharose® Fast Flow column equilibrated with 50 mM HEPES pH 7.5 buffer and unbound material was eluted with 50 mM HEPES buffer pH 7.5. The bound protein was then eluted with a linear 20 column volume salt gradient in 50 mM HEPES buffer pH 7.5 containing 1 M NaCl as buffer B. Ten ml fractions of the eluate were collected and each were analyzed for purity of the protein by SDS-PAGE. The fractions with highest purity were pooled. Identity of the beta-glucosidase was confirmed by mass spectroscopy and protein identification was carried out by in gel digestion. Protein concentration was determined using a Microplate BCA™ Protein Assay Kit in which bovine serum albumin was used as a protein standard.

Example 78: Preparation of *Penicillium oxalicum* Strain IBT5387 GH3 Beta-Glucosidase The *Penicillium oxalicum* strain IBT5387 (Technical University of Denmark; NN005786) GH3 beta-glucosidase (SEQ ID NO: 187 [DNA sequence] and SEQ ID NO: 188 [deduced amino acid sequence]) was obtained according to the procedure described below.

Genomic DNA was isolated according to the procedure described in Example 73.

A set of degenerate primers (shown below) was hand-designed according to the strategy described by Rose et al., 1998*, Nucleic Acids Res.* 26: 1628-1635, for targetting beta-glucosidases (EC 3.2.1.21) belonging to Family GH3.

```
GH3scree.f1
                                    (SEQ ID NO: 258)
atgaccctggccgaaaaagtcaacytnacnacngg

GH3scree.f2
                                    (SEQ ID NO: 259)
ggtggccggaactgggaaggcttctsnccngaycc

GH3scree.f5
                                    (SEQ ID NO: 260)
gagctgggcttccagggctttgtnatgwsngaytgg

GH3scree.f6
                                    (SEQ ID NO: 261)
agcgctttggccggcctcgayatgwsnatgcc

GH3scree.r1
                                    (SEQ ID NO: 262)
atcccagttgctcaggtcccknckngt

GH3scree.r2
                                    (SEQ ID NO: 263)
aaaggttgtgtagctcagnccrtgnccraaytc

GH3scree.r3
                                    (SEQ ID NO: 264)
gtcaaagtggcggtagtcgatraanacnccytc

GH3scree.r4
                                    (SEQ ID NO: 265)
ggtgggcgagttgccgacggggttgactctgccrtanar

GH3scree.r5
                                    (SEQ ID NO: 266)
gccgggcagaccggcccagaggatggcngtnacrttngg

GH3scree.r6
                                    (SEQ ID NO: 267)
caggacggggccaaccgagtgaatgacnacdatngtrtt
```

PCR screening of *Penicillium oxalicum* strain IBT5387 genomic DNA was performed with two successive PCRs. Each forward primers (f1, f2, f5, and f6) (0.33 μl of a 10 mM stock) was combined with each reverse primers (r1, r2, r3, r4, r5, and r6) (0.33 μl of a 10 mM stock) in a 10 μl mix containing 0.33 μl genomic DNA, 5 μl of Reddy Mix Extensor PCR Master Mix 1 (Cat #AB-0794/A, ABgene UK, commercialized by Thermo Fisher Scientific). A hot-start PCR reaction was carried out in a DYAD® PCR machine for 2 minutes at 94° C. followed by 9 cycles each at 94° C. for 15 seconds, 63° C. for 30 seconds with a 1° C. decrease for each cycle, 68° C. for 1 minute 45 seconds, and followed by 24 cycles each at 94° C. for 15 seconds, 55° C. for 30 seconds, 68° C. for 1 minute 45 seconds, supplemented by a 7 minutes extension at 68° C. PCR-products produced during this first PCR were re-amplified with their corresponding primers by transferring 0.5 μl of the first PCR reaction to a second 20 μl mix containing the same concentration of primers, dNTPs, polymerase, and buffer than in the first PCR reaction. The second PCR was carried out on the same PCR block at 94° C. for 2 minutes followed by 24 cycles each at 94° C. for 15 seconds, 58° C. for 30 seconds, 68° C. for 1 minute 45 seconds and completed by a 7 minutes extension at 68° C. PCR products produced during the second amplification were analyzed on 1% agarose gel electrophoresis in TAE buffer. Single bands ranging from 2000 to 800 nts in size were collected and eluted using the GFX® PCR DNA and Gel Band Purification Kit according to manufacturer's instructions. Purified DNA samples were directly sequenced with primers used for amplification.

Sequences were assembled in SeqMan v7.2.1 (DNA star, Madison, Wis., USA) into a contig that was used for nblast searches (Altschul et al., 1997*, Nucleic Acids Res.* 25: 3389-3402) on publicly available sequences. Results of the search indicated that the sequence GenBank EU700488.1 was nearly identical to the contig identified. Therefore, the cloning primers 5786GH3-50f and 5786GH3-50r were designed based on the sequence information of the cds from GenBank EU700488.1 for IN-FUSION™ cloning according to the manufacturer instructions for cloning in the expression vector pDAu109 (WO 2005/042735).

```
5786GH3-50f1:
                                    (SEQ ID NO: 268)
5'-acacaactggggatccaccATGAAGCTCGAGTGGCTGGAAGC-3'

5786GH3-50r1
                                    (SEQ ID NO: 269)
5'-agatctcgagaagcttaCTGCACCTTGGGCAGATCGGCTG-3'
```

The *Penicillium oxalicum* beta-glucosidase gene was amplified by PCR using the two cloning primers described previously in a PCR reaction that was performed with genomic DNA prepared from the strain IBT5387 (from DTU received in 1992). The PCR reaction was composed of 1 μl of genomic DNA, 0.75 μl of primer 5786GH3-51f1 (10 μM); 0.75 μl of primer 5786GH3-51r1 (10 μM); 3 μl of 5×HF buffer, 0.25 μl of 50 mM $MgCl_2$, 0.3 μl of 10 mM dNTP; 0.15 μl of PHUSION® DNA polymerase, and PCR-grade water up to 15 μl. The PCR reaction was performed using a DYAD® PCR machine programmed for 2 minutes at 98° C. followed by 10 touchdown cycles at 98° C. for 15 seconds, 70° C. (−1° C./cycle) for 30 seconds, and 72° C. for 2 minutes 30 seconds; and 25 cycles each at 98° C. for 15 seconds, 60° C. for 30 seconds, 72° C. for 2 minutes 30 seconds, and 5 minutes at 72° C.

The reaction product was isolated by 1.0% agarose gel electrophoresis using TAE buffer where an approximately 2.8 kb PCR product band was excised from the gel and purified using a GFX® PCR DNA and Gel Band Purification Kit according to manufacturer's instructions. DNA corresponding to the *Penicillium oxalicum* beta-glucosidase gene was cloned into the expression vector pDAu109 (WO 2005042735) linearized with Barn HI and Hind III, using an I N-FUSION™ Dry-Down PCR Cloning Kit according to the manufacturer's instructions.

A 2.5 μl volume of the diluted ligation mixture was used to transform *E. coli* TOP10 chemically competent cells. Three colonies were selected on LB agar plates containing 100 μg of ampicillin per ml and cultivated overnight in 3 ml of LB medium supplemented with 100 μg of ampicillin per ml. Plasmid DNA was purified using an E.Z.N.A.® Plasmid Mini Kit according to the manufacturer's instructions. The *Penicillium oxalicum* beta-glucosidase gene sequence was verified by Sanger sequencing before heterologous expression.

The coding sequence is 2964 bp including the stop codon and is interrupted by 5 introns of 101 bp (nucleotides 61 to 161), 64 bp (nucleotides 302 to 365), 79 bp (nucleotides 411 to 489), 63 bp (nucleotides 543 to 605), and 71 bp (nucleotides 2660 to 2730). The encoded predicted protein is 861 amino acids. Using the SignalP program (Nielsen et al., 1997, *Protein Engineering* 10: 1-6), a signal peptide of 19 residues was predicted. The predicted mature protein contains 842 amino acids.

Protoplasts of *Aspergillus oryzae* BECh2 (WO 2000/39322) were prepared as described in WO 95/02043. One hundred microliters of protoplast suspension were mixed with 2.5-15 μg of the *Aspergillus* expression vector and 250 μl of 60% PEG 4000, 10 mM $CaCl_2$, and 10 mM Tris-HCl pH 7.5 were added and gently mixed. The mixture was incubated at 37° C. for 30 minutes and the protoplasts were spread on COVE sucrose (1 M) plates supplemented with 10 mM acetamide and 15 mM CsCl for transformant selection. After incubation for 4-7 days at 37° C. spores of several transformants were seeded on YP-2% maltodextrin medium. After 4 days cultivation at 30° C. culture broth was analyzed in order to identify the best transformants based on their ability to produce a large amount of active *Penicillium oxalicum* beta-glucosidase. The screening was based on intensity of the band corresponding to the heterologous expressed protein determined by SDS-PAGE and activity of the enzyme on 4-nitrophenyl-beta-D-glucopyranoside (pNPG) as described in Example 16.

Spores of the best transformant were spread on COVE plates containing 0.01% TRITON® X-100 in order to isolate single colonies. The spreading was repeated twice in total on COVE sucrose medium (Cove, 1996, *Biochim. Biophys. Acta* 133: 51-56) containing 1 M sucrose and 10 mM sodium nitrate, supplemented with 10 mM acetamide and 15 mM CsCl. Fermentation was then carried out in 250 ml shake flasks using DAP-2C-1 medium for 4 days at 30° C. with shaking at 100 rpm.

Filtered broth was concentrated and washed with deionized water using a tangential flow concentrator equipped with a Sartocon® Slice cassette with a 10 kDa MW-CO polyethersulfone membrane (Sartorius Stedim Biotech GmbH, Goettingen, Germany). The concentrate was added to M ammonium sulphate and loaded onto a Phenyl Toyopearl (650M) column (Tosoh Corporation, 3-8-2 Shiba, Minato-ku, Tokyo, Japan) equilibrated in 2 M ammonium sulphate, and bound proteins were eluted with 1 M ammonium sulphate. The eluted protein was buffer exchanged with 25 mM HEPES pH 7.5 with sodium chloride by ultrafiltration with a 10 kDa polyethersulfone membrane using Vivaspin 20 (Sartorius Stedim Biotech GmbH, Goettingen, Germany). Protein concentration was determined using a Microplate BCA™ Protein Assay Kit in which bovine serum albumin was used as a protein standard.

Example 79: Preparation of *Talaromyces emersonii* Strain CBS 549.92 GH3 Beta-Glucosidase The *Talaromyces emersonii* strain CBS 549.92 GH3 beta-glucosidase (SEQ ID NO: 189 [DNA sequence] and SEQ ID NO: 190 [deduced amino acid sequence]) was obtained according to the procedure described below.

Genomic DNA was isolated according to the procedure described in Example 73.

The *Talaromyces emersonii* beta-glucosidase gene was isolated by PCR using two cloning primers GH3-11f and GH3-11r shown below, which were designed based on the publicly available *Talaromyces emersonii* full-length sequence (Genbank AY072918.4) for direct cloning using the IN-FUSION™ strategy.

```
Primer GH3-11f:
                                       (SEQ ID NO: 270)
acacaactggggatccaccatgaggaacgggttgctcaaggtcg

Primer GH3-11r:
                                       (SEQ ID NO: 271)
agatctcgagaagcttaaattccagggtatggcttaaggggc
```

A PCR reaction was performed with genomic DNA prepared from *Talaromyces emersonii* strain CBS 549.92 in order to amplify the full-length gene. The PCR reaction was composed of 1 μl of genomic DNA, 0.75 μl of primer GH3-11f (10 μM); 0.75 μl of primer GH3-11r (10 μM); 3 μl of 5×HF buffer, 0.25 μl of 50 mM $MgCl_2$, 0.3 μl of 10 mM dNTP; 0.15 μl of PHUSION® DNA polymerase, and PCR-grade water up to 15 μl. The PCR reaction was performed using a DYAD® PCR machine programmed for 2 minutes at 98° C. followed by 10 touchdown cycles at 98° C. for 15 seconds, 70° C. (−1° C./cycle) for 30 seconds, and 72° C. for 2 minutes 30 seconds; and 25 cycles each at 98° C. for 15 seconds, 60° C. for 30 seconds, 72° C. for 2 minutes 30 seconds, and 5 minutes at 72° C.

The reaction product was isolated by 1.0% agarose gel electrophoresis using TAE buffer where an approximately 2.9 kb PCR product band was excised from the gel and purified using a GFX® PCR DNA and Gel Band Purification Kit according to manufacturer's instructions. DNA corresponding to the *Talaromyces emersonii* beta-glucosidase gene was cloned into the expression vector pDAu109 (WO 2005042735) linearized with Barn HI and Hind III, using an I N-FUSION™ Dry-Down PCR Cloning Kit according to the manufacturer's instructions.

A 2.5 μl volume of the diluted ligation mixture was used to transform *E. coli* TOP10 chemically competent cells. Three colonies were selected on LB agar plates containing 100 μg of ampicillin per ml and cultivated overnight in 3 ml of LB medium supplemented with 100 μg of ampicillin per ml. Plasmid DNA was purified using an E.Z.N.A.® Plasmid Mini Kit according to the manufacturer's instructions. The *Talaromyces emersonii* beta-glucosidase gene sequence was verified by Sanger sequencing before heterologous expression.

The coding sequence is 2925 bp including the stop codon and is interrupted by 6 introns of 60 bp (nucleotides 61 to 120), 61 bp (nucleotides 261 to 321), 60 bp (nucleotides 367 to 426), 57 bp (nucleotides 480 to 536), 56 bp (nucleotides 1717 to 1772), and 54 bp (nucleotides 2632 to 2685). The encoded predicted protein is 858 amino acids. Using the SignalP program (Nielsen et al., 1997, *Protein Engineering* 10: 1-6), a signal peptide of 19 residues was predicted. The predicted mature protein contains 839 amino acids.

Protoplasts of *Aspergillus oryzae* BECh2 (WO 2000/39322) were prepared as described in WO 95/02043. One hundred microliters of protoplast suspension were mixed with 2.5-15 μg of the *Aspergillus* expression vector and 250 μl of 60% PEG 4000, 10 mM $CaCl_2$, and 10 mM Tris-HCl pH 7.5 were added and gently mixed. The mixture was incubated at 37° C. for 30 minutes and the protoplasts were spread on COVE sucrose (1 M) plates supplemented with 10 mM acetamide and 15 mM CsCl for transformant selection. After incubation for 4-7 days at 37° C. spores of several transformants were seeded on YP-2% maltodextrin medium. After 4 days cultivation at 30° C. culture broth was analyzed in order to identify the best transformants based on their ability to produce a large amount of active *Talaromyces emersonii* beta-glucosidase. The screening was based on intensity of the band corresponding to the heterologous expressed protein determined by SDS-PAGE and activity of the enzyme on 4-nitrophenyl-beta-D-glucopyranoside (pNPG) as described in Example 16.

Spores of the best transformant were spread on COVE plates containing 0.01% TRITON® X-100 in order to isolate single colonies. The spreading was repeated twice in total on COVE sucrose medium (Cove, 1996, *Biochim. Biophys. Acta* 133: 51-56) containing 1 M sucrose and 10 mM sodium nitrate, supplemented with 10 mM acetamide and 15 mM CsCl. Fermentation was then carried out in 250 ml shake flasks using YP-2% maltodextrin medium for 4 days at 30° C. with shaking at 100 rpm. The broth was filtered using standard methods. Protein concentration was determined using a Microplate BCA™ Protein Assay Kit in which bovine serum albumin was used as a protein standard.

Example 80: Preparation of *Thermoascus crustaceus* Strain CBS 181.67 GH61A Polypeptide The *Thermoascus crustaceus* strain CBS 181.67 GH61A polypeptide having cellulolytic enhancing activity (SEQ ID NO: 191 [DNA sequence] and SEQ ID NO: 192 [deduced amino acid sequence]) was obtained according to the procedure described below.

*Aspergillus oryzae* strain HowB101 (WO 95/35385) was used as a host for recombinantly expressing the *Thermoascus crustaceus* GH61 polypeptides having cellulolytic enhancing activity.

*Thermoascus crustaceus* strain CBS 181.67 was inoculated onto a PDA plate and incubated for 3-4 days at 45° C. in the darkness. Several mycelia-PDA plugs were inoculated into 500 ml shake flasks containing 100 ml of NNCYP-PCS medium. The flasks were incubated for 6 days at 45° C. with shaking at 160 rpm. The mycelia were collected at day 3, day 4, day 5, and day 6. Then the mycelia from each day were combined and frozen in liquid nitrogen, and then stored in a −80° C. freezer until use.

Genomic DNA was extracted using a DNEASY® Plant Mini Kit (QIAGEN Inc., Valencia, Calif., USA). Total RNA was isolated by using a RNEASY® Plant Mini Kit. cDNA was synthesized by following the instructions of the 3' Rapid Amplification of cDNA End System (3' RACE) (Invitrogen Corporation, Carlsbad, Calif., USA).

Four degenerate primers shown below were designed based on conserved regions of known GH61 sequences.

```
GH61A scF1:
                                (SEQ ID NO: 272)
5'-GCNACNGAYCTNGGNTTTG-3'

GH61A scF2:
                                (SEQ ID NO: 273)
5'-GCNACNGAYCTNGGNTTCG-3'

GH61A scF3:
                                (SEQ ID NO: 274)
5'-GCNACNGAYTTRGGNTTYG-3'
```

-continued

```
GH61A scR1:
                                (SEQ ID NO: 275)
5'-CAYTGNGGRTARTTYTGNGC-3'
```

PCR was performed by using a combination of forward primers GH61A scF1, GH61 scF2, and GH61A scF3, and reverse primer GH61A scR1 and cDNA as template. The amplification reaction was composed of 5 μl of 10×PCR buffer (Invitrogen Corporation, Carlsbad, Calif., USA), 2 μl of 25 mM $MgCl_2$, 1 μl of 10 mM dNTP, 1 μl of 100 μM forward primer, 1 μl of 100 μM reverse primer, 2 μl of cDNA, 0.5 μl of Taq DNA polymerase High Fidelity (Invitrogen Corporation, Carlsbad, Calif., USA), and 37.5 μl of $H_2O$. The amplification was performed using an Peltier Thermal Cycler programmed for denaturing at 94° C. for 2 minutes; 30 cycles each at 94° C. for 40 seconds, 50° C. for 40 seconds, and 72° C. for 1 minute; and a final extension at 72° C. for 10 minutes.

A PCR product of approximately 500 base pairs was detected by 1% agarose gel electrophoresis using TBE buffer. The PCR fragment was excised from the gel and purified using an ILLUSTRA® GFX® PCR DNA and Gel Band Purification Kit according to the manufacturer's instructions, directly sequenced, and confirmed to be a GH61A partial gene by blast. Based on this partial sequence, new primers shown below were designed for 5' and 3' end cloning using a Genome Walking Kit (Takara Bio Inc., Otsu, Shiga, Japan):

```
61ASPR1:
                                (SEQ ID NO: 276)
5'-TGCAAGGAGCAAGGTAGTTGA-3'

61ASPR2:
                                (SEQ ID NO: 277)
5'-GAGTCCATTCCAGCTTGACGGT-3'

61ASPF1:
                                (SEQ ID NO: 278)
5'-TCAGACAATCTGATAGCGGC-3'

61ASPF2:
                                (SEQ ID NO: 279)
5'-ATCCCAACCACAACTGCACCT-3'
```

For 5' end and 3' end cloning, the primary amplifications were composed of 2 μl of genomic DNA as template, 2.5 mM each of dATP, dTTP, dGTP, and dCTP, 100 μmol of AP2 (provided by the Genome Walking Kit) and 10 μmol of primer 61ASPR1 for 5' end cloning or 100 μmol of AP3 (provided by the Genome Walking Kit), and 10 μmol of primer 61ASPF1 for 3' end cloning, 5 μl of 10×LA PCR Buffer II (provided by the Genome Walking Kit), and 2.5 units of TakaRa LA Taq DNA polymerase (provided by the Genome Walking Kit) in a final volume of 50 μl. The amplifications were performed using an Peltier Thermal Cycler programmed for pre-denaturing at 94° C. for 1 minute and 98° C. for 1 minute; five cycles each at a denaturing temperature of 94° C. for 30 seconds; annealing at 60° C. for 1 minute and elongation at 72° C. for 2 minutes; 1 cycle of denaturing at 94° C. for 30 seconds; annealing at 25° C. for 3 minutes and elongation at 72° C. for 2 minutes; fifteen repeats of 2 cycles at 94° C. for 30 seconds, 62° C. for 1 minutes, and 72° C. for 2 minutes; followed by 1 cycle at 94° C. for 30 seconds, 44° C. for 1 minutes, and 72° C. for 2 minutes; and a final extension at 72° C. for 10 minutes. The heat block then went to a 4° C. soak cycle.

The secondary amplifications were composed of 2 μl of 20× diluted primary PCR product as templates, 2.5 mM each of dATP, dTTP, dGTP, and dCTP, 100 μmol of AP2, and 10 pmol of primer 61ASPR2 for 5' end cloning or 100 μmol of AP3 and 10 μmol of primer 61ASPF2 for 3' end cloning, 5 μl of 10×LA PCR Buffer II, and 2.5 units of TakaRa LA Taq DNA polymerase in a final volume of 50 μl. The amplifications were performed using an Peltier Thermal Cycler programmed for fifteen repeats of 2 cycles of 94° C. for 30 seconds; 62° C. for 1 minutes; 72° C. for 2 minutes; followed by 1 cycle at 94° C. for 30 seconds, 44° C. for 1 minutes, and 72° C. for 2 minutes; and a final extension at 72° C. for 10 minutes. The heat block then went to a 4° C. soak cycle.

The PCR products from the 5' and 3' end PCR were recovered and sequenced. They were identified as the 5' end and 3' end of the GH61A polypeptide gene. Then the three sequences including the partial gene, 5' end, and 3' end were assembled to generate the full-length GH61A.

The obtained full-length gene showed that the sequence contains a coding region of 871 nucleotides including 1 intron and stop codon, and encodes 251 amino acids with a predicted signal peptide of 22 amino acids.

Based on the full-length *Thermoascus crustaceus* GH61A gene sequence, oligonucleotide primers, shown below, were designed to amplify the GH61A gene from genomic DNA of *Thermoascus crustaceus* CBS 181.67. An IN-FUSION® CF Dry-Down Cloning Kit (Clontech Laboratories, Inc., Mountain View, Calif., USA) was used to clone the fragment directly into the expression vector pPFJO355, without the need for restriction digestion and ligation.

```
Sense primer:
                                    (SEQ ID NO: 280)
5'-ACACAACTGGGGATCCACCATGGCCTTTTCCCAGATAATGGCTA-3'

Antisense primer:
                                    (SEQ ID NO: 281)
5'-GTCACCCTCTAGATCTGGATCGCAGGAGCGTTCAGA-3'
```

Bold letters represent the coding sequence for the sense primer and the downstream sequence of the stop codon for the antisense primer. The remaining sequence is homologous to the insertion sites of pPFJO355.

Twenty picomoles of each of the primers above were used in a PCR reaction composed of *Thermoascus crustaceus* genomic DNA, 10 μl of 5×GC Buffer, 1.5 μl of DMSO, 2 μl of 2.5 mM each of dATP, dTTP, dGTP, and dCTP, and 1 unit of PHUSION™ High-Fidelity DNA Polymerase in a final volume of 50 μl. The amplification was performed using a Peltier Thermal Cycler programmed for denaturing at 98° C. for 1 minute; 5 cycles of denaturing at 98° C. for 15 seconds, annealing at 70° C. for 30 seconds, with a 1° C. decrease per cycle, and elongation at 72° C. for 30 seconds; 25 cycles each at 98° C. for 15 seconds and 72° C. for 90 seconds; and a final extension at 72° C. for 10 minutes. The heat block then went to a 4° C. soak cycle.

The reaction products were isolated by 1.0% agarose gel electrophoresis using TBE buffer where an approximately 1.0 kb product band was excised from the gel, and purified using an ILLUSTRA® GFX® PCR DNA and Gel Band Purification Kit according to the manufacturer's instructions.

Plasmid pPFJO355 was digested with Barn HI and Bgl II, isolated by 1.0% agarose gel electrophoresis using TBE buffer, and purified using an ILLUSTRA® GFX® PCR DNA and Gel Band Purification Kit according to the manufacturer's instructions.

The gene fragment and the digested vector were ligated together using an IN-FUSION® CF Dry-Down PCR Cloning Kit resulting in pGH61a51486 in which transcription of the *Thermoascus crustaceus* GH61A gene was under the control of the *Aspergillus oryzae* TAKA-alpha-amylase promoter. In brief, 30 ng of pPFJO355 digested with Barn HI and Bgl II and 50 ng of the *Thermoascus crustaceus* GH61A gene purified PCR product were added to a reaction vial and resuspended in a final volume of 10 μl with deionized water. The reaction was incubated at 37° C. for 15 minutes and then 50° C. for 15 minutes. Three μl of the reaction were used to transform *E. coli* TOP10 competent cells according to the manufacturer's instructions. The transformation was spread on LB plates supplemented with 100 μg of ampicillin per ml and incubated at 37° C. for 1 day. An *E. coli* transformant containing a plasmid designated pGH61a51486 was detected by colony PCR and plasmid DNA was prepared using a QIAprep Spin Miniprep Kit (QIAGEN Inc., Valencia, Calif., USA). The *Thermoascus crustaceus* GH61A gene insert in pGH61a51486 was confirmed by DNA sequencing using a 3730XL DNA Analyzer.

The same PCR fragment was cloned into pGEM-T vector using a pGEM-T Vector System to generate pGEM-T-GH61a51486. The *Thermoascus crustaceus* GH61A gene insert in pGEM-T-GH61a51486 was confirmed by DNA sequencing using a 3730XL DNA Analyzer. *E. coli* strain T-51486A, designated NN059126, containing pGEM-T-GH61a51486, was deposited at the Deutsche Sammlung von Mikroorganismen and Zellkulturen GmbH (DSM), Mascheroder Braunschweig, Germany, on Jun. 10, 2009, and assigned accession number DSM 22656.

Nucleotide sequence data were scrutinized for quality and all sequences were compared to each other with assistance of PHRED/PHRAP software (University of Washington, Seattle, Wash., USA).

The nucleotide sequence and deduced amino acid sequence of the *Thermoascus crustaceus* gh61a gene are shown in SEQ ID NO: 191 and SEQ ID NO: 192, respectively. The coding sequence is 871 bp including the stop codon and is interrupted by one intron of 115 base pairs (nucleotides 105-219). The encoded predicted protein is 251 amino acids. The % G+C content of the full-length coding sequence and the mature coding sequence are 50.23% and 52.55%, respectively. Using the SignalP software program (Nielsen et al., 1997, *Protein Engineering* 10: 1-6), a signal peptide of 22 residues was predicted. The predicted mature protein contains 229 amino acids with a predicted molecular mass of 26.35 kDa.

*Aspergillus oryzae* HowB101 protoplasts were prepared according to the method of Christensen et al., 1988, *Bio/Technology* 6: 1419-1422 and transformed with 3 μg of pGH61a51486. The transformation yielded about 50 transformants. Twelve transformants were isolated to individual Minimal medium plates.

Four transformants were inoculated separately into 3 ml of YPM medium in a 24-well plate and incubated at 30° C. with shaking at 150 rpm. After 3 days incubation, 20 μl of supernatant from each culture were analyzed by SDS-PAGE using a NUPAGE® NOVEX® 4-12% Bis-Tris Gel with MES buffer according to the manufacturer's instructions. The resulting gel was stained with INSTANT BLUE™ (Expedeon Ltd., Babraham Cambridge, UK). SDS-PAGE profiles of the cultures showed that the majority of the transformants had a major band of approximately 30 kDa. The expression strain was designated *Aspergillus oryzae* EXP03151.

A slant of *Aspergillus oryzae* EXP03151 was washed with 10 ml of YPM medium and inoculated into a 2 liter flask containing 400 ml of YPM medium to generate broth for characterization of the enzyme. The culture was harvested on day 3 and filtered using a 0.45 μm DURAPORE® Membrane (Millipore, Bedford, Mass., USA).

The filtered broth was concentrated and buffer exchanged using a tangential flow concentrator equipped with a Sartocon® Slice cassette with a 10 kDa cut-off polyethersulfone membrane (Sartorius Stedim Biotech GmbH, Goettingen, Germany) with 25 mM HEPES, pH 7.0. The protein was applied to a Q Sepharose™ Fast Flow column (GE Healthcare, Piscataway, N.J., USA) equilibrated in 25 mM HEPES pH 7.0. The protein was recovered in the eluate. Protein concentration was determined using a Microplate BCA™ Protein Assay Kit in which bovine serum albumin was used as a protein standard.

Example 81: Preparation of *Talaromyces emersonii* Strain NN05002 GH10 Xylanase The *Talaromyces emersonii* strain NN05002 GH10 xylanase (SEQ ID NO: 193 [DNA sequence] and SEQ ID NO: 194 [deduced amino acid sequence]) was obtained according to the procedure described below.

*Talaromyces emersonii* was grown on a PDA agar plate at 45° C. for 3 days. Mycelia were collected directly from the agar plate into a sterilized mortar and frozen under liquid nitrogen. Frozen mycelia were ground, by mortar and pestle, to a fine powder, and genomic DNA was isolated using a DNeasy® Plant Mini Kit.

Oligonucleotide primers, shown below, were designed to amplify the GH10 xylanase gene from genomic DNA of *Talaromyces emersonii*. An IN-FUSION™ CF Dry-down Cloning Kit was used to clone the fragment directly into the expression vector pPFJO355, without the need for restriction digestion and ligation.

Sense primer:
(SEQ ID NO: 282)
5'-ACACAACTGGGGATCCACCATGGTTCGCCTCAGTCCAG-3'

Antisense primer:
(SEQ ID NO: 283)
5'-GTCACCCTCTAGATCTTTACAGACACTGCGAGTAATACTCATTG-3'

Bold letters represented the coding sequence. The remaining sequence was homologous to the insertion sites of pPFJO355.

Twenty picomoles of each of the primers above were used in a PCR reaction composed of *Talaromyces emersonii* genomic DNA, 10 μl of 5×GC Buffer, 1.5 μl of DMSO, 5 mM each of dATP, dTTP, dGTP, and dCTP, and 0.6 unit of Phusion™ High-Fidelity DNA Polymerase in a final volume of 50 μl. The amplification was performed using a Peltier Thermal Cycler programmed for denaturing at 98° C. for 40 seconds; 8 cycles of denaturing at 98° C. for 15 seconds, annealing at 65° C. for 30 seconds, with a 1° C. decrease per cycle and elongation at 72° C. for 80 seconds; and another 23 cycles each at 98° C. for 15 seconds, 58° C. for 30 seconds and 72° C. for 80 seconds; final extension at 72° C. for 7 minutes. The heat block then went to a 10° C. soak cycle.

The reaction products were isolated by 1.0% agarose gel electrophoresis using TBE buffer where an approximately 1.4 kb product band was excised from the gel, and purified using an ILLUSTRA® GFX® PCR DNA and Gel Band Purification Kit according to the manufacturer's instructions.

Plasmid pPFJO355 was digested with Barn I and Bgl II, isolated by 1.0% agarose gel electrophoresis using TBE buffer, and purified using an ILLUSTRA® GFX® PCR DNA and Gel Band Purification Kit according to the manufacturer's instructions.

The gene fragment and the digested vector were ligated together using an IN-FUSION™ CF Dry-down PCR Cloning resulting in pxynTe50022 in which transcription of the *Talaromyces emersonii* GH10 xylanase gene was under the control of the *Aspergillus oryzae* TAKA amylase promoter. In brief, 20 ng of pPFJO355 digested with Barn I and Bgl II, and 60 ng of the *Talaromyces emersonii* GH10 xylanase gene purified PCR product were added to a reaction vial and resuspended in a final volume of 10 μl with addition of deionized water. The reaction was incubated at 37° C. for 15 minutes and then 50° C. for 15 minutes. Three μl of the reaction were used to transform *E. coli* TOP10 competent cells. An *E. coli* transformant containing pxynTe50022 was detected by colony PCR and plasmid DNA was prepared using a QIAprep Spin Miniprep Kit. The *Talaromyces emersonii* GH10 xylanase gene insert in pxynTe50022 was confirmed by DNA sequencing using a 3730XL DNA Analyzer.

*Aspergillus oryzae* HowB101 (WO 95/35385) protoplasts were prepared according to the method of Christensen et al., 1988, *Bio/Technology* 6: 1419-1422 and transformed with 3 μg of pxynTe50022. The transformation yielded about 50 transformants. Twelve transformants were isolated to individual Minimal medium plates.

Four transformants were inoculated separately into 3 ml of YPM medium in a 24-well plate and incubated at 30° C., 150 rpm. After 3 days incubation, 20 μl of supernatant from each culture were analyzed by SDS-PAGE using a NUPAGE® NOVEX® 4-12% Bis-Tris Gel with MES buffer according to the manufacturer's instructions. The resulting gel was stained with INSTANT® Blue. SDS-PAGE profiles of the cultures showed that the majority of the transformants had a major smeary band of approximately 55 kDa. The expression strain was designated as *A. oryzae* EXP03373.

A slant of *A. oryzae* EXP03373 was washed with 10 ml of YPM medium and inoculated into six 2 liter flasks, each containing 400 ml of YPM medium, to generate broth for characterization of the enzyme. The culture was harvested on day 3 by filtering the culture through MIRACLOTH® (CALBIOCHEM, Inc. La Jolla, Calif., USA). The filtered culture broth was then again filtered using a 0.45 μm DURAPORE Membrane. Protein concentration was determined using a Microplate BCA™ Protein Assay Kit in which bovine serum albumin was used as a protein standard.

A 1600 ml volume of filtered broth supernatant of *A. oryzae* EXP03373 was precipitated with ammonium sulfate (80% saturation), re-dissolved in 100 ml of 25 mM Bis-Tris pH 6.0, dialyzed against the same buffer, and filtered through a 0.45 μm filter; the final volume was 200 ml. The solution was applied to a 40 ml Q Sepharose® Fast Flow column equilibrated with 25 mM Bis-Tris pH 6.0, and the proteins were eluted with a linear NaCl gradient (0-0.4 M). Fractions with activity against AZCL-xylan were analyzed by SDS-PAGE using a NUPAGE® NOVEX® 4-12% Bis-Tris Gel with MES buffer. Fractions with the correct molecular weight were pooled and concentrated by ultra filtration.

The supernatants were tested for endocellulase activity by microtiter plate assay as described below. A solution of 0.2% of the blue substrate AZCL-Xylan (Megazyme) was suspended in a 0.1 M sodium acetate buffer (pH 5.5) under stirring. The solution was distributed under stirring to a microtiter plate (200 μl to each well). Twenty μl of enzyme sample was added and incubated in an EPPENDORF® Thermomixer for 20 minutes at 50° C. and 650 rpm. A denatured enzyme sample (100° C. boiling for 20 minutes) was used as blank. After incubation the colored solution was separated from the solid by centrifugation at 3000 rpm for 5 minutes at 4° C. Then 150 μl of supernatant was transferred to a microtiter plate and the absorbance was measured using a Spectra Max M2 at 595 nm.

Example 82: Preparation of *Penicillium* sp. Strain NN51602 GH10 Xylanase

The *Penicillium* sp. strain NN51602 GH10 xylanase (SEQ ID NO: 195 [DNA sequence] and SEQ ID NO: 196 [deduced amino acid sequence]) was obtained according to PCT/US10/032034. Protein concentration was determined using a Microplate BCA™ Protein Assay Kit in which bovine serum albumin was used as a protein standard.

Example 83: Preparation of *Meripilus giganteus* Strain CBS 521.95 GH10 Xylanase The *Meripilus giganteus* strain CBS 521.95 GH10 xylanase (SEQ ID NO: 197 [DNA sequence] and SEQ ID NO: 198 [deduced amino acid sequence]) was recombinantly prepared according to WO 97/27290 except *Aspergillus oryzae* Bech2 (WO 2000/39322) was used as a host and pDAu75 as the expression vector. Vector pDAu75 is a derivative of pJa1721 (WO 03/008575). Plasmid pDAu75 mainly differs from pJa1721 in that the selection marker URA3 of *E. coli* has been disrupted by the insertion of the ampicillin resistance gene *E. coli* beta lactamase, which allows for rapid selection of positive recombinant *E. coli* clones using commercially available and highly competent strains on commonly used LB ampicillin plates. The ampicillin resistance gene is entirely removable using the two flanking Not I sites restoring a functional selection marker URA3. The techniques used for making pDAu75 from pJa1721 are common molecular biology techniques for DNA cloning. Cloning of the cDNA sequence of the *Meripilus giganteus* GH10 xylanase gene into pDAu75 was performed by a restriction/ligation cloning procedure from the xylanase producing yeast colony as described in WO 97/27290.

The broth was filtered using Whatmann glass filter GF/D, GF/A, GF/C, GF/F (2.7 μm, 1.6 μm, 1.2 μm and 0.7 μm, respectively) followed by filtration through a 0.45 μm filter.

Ammonia sulfate was added to the filtered broth to a final concentration of 3 M and the precipitate was collected after centrifugation at 10,000×g for 30 minutes. The precipitate was dissolved in 10 mM Tris/HCl pH 8.0 and dialyzed against 10 mM Tris/HCl pH 8.0 overnight. The dialyzed preparation was applied to a 150 ml Q SEPHAROSE® Fast Flow column equilibrated with 10 mM Tris/HCl pH 8.0 and the enzyme was eluted with a 1050 ml (7 column volumes) linear salt gradient from 0 to 1 M NaCl in 10 mM Tris/HCl pH 8.0. Elution was followed with A280 nm detection and fractions were collected and assayed for xylanase activity using 0.2% AZCL-Arabinoxylan from wheat (Megazyme) in 0.2 M sodium phosphate pH 6.0 plus 0.01% TRITON® X100. Fractions containing xylanase activity were pooled and stored at −20° C. Protein concentration was determined using a Microplate BCA™ Protein Assay Kit in which bovine serum albumin was used as a protein standard.

Example 84: Preparation of *Dictyoglomus thermophilum* Strain ATCC 35947 GH11 Xylanase The *Dictyoglomus thermophilum* GH11 xylanase (SEQ ID NO: 199 [DNA sequence] and SEQ ID NO: 200 [deduced amino acid sequence]) was recombinantly prepared according to the following procedure.

*Bacillus subtilis* strains were made competent using the method described by Anagnostopoulos and Spizizen, 1961, *Journal of Bacteriology* 81: 741-746. DNA sequencing was conducted with an ABI 3700 Sequencing (Applied Biosystems, Inc., Foster City, Calif., USA).

*Bacillus subtilis* strain SM025 was constructed as described below to delete an intracellular serine protease (ispA) gene in *Bacillus subtilis* strain A164410 (Bindel-Connelly et al., 2004, *J. Bacteriol.* 186: 4159-4167).

A deletion plasmid, pNNB194-ispAΔ, was constructed by splicing by overlap extension (SOE) (Horton et al., 1989, *Gene* 77: 61-8). Flanking DNA sequences 5' and 3' of the ispA gene were obtained by PCR amplification from chromosomal DNA derived from *Bacillus subtilis* strain 164Δ5 (U.S. Pat. No. 5,891,701) using primer pairs 994525/994526 and 994527/994528, respectively, shown below. Chromosomal DNA was obtained according to the procedure of Pitcher et al., 1989, *Lett. Appl. Microbiol.* 8: 151-156.

```
Primer 994525:
                                    (SEQ ID NO: 284)
5'-GGATCCATTATGTAGGGCGTAAAGC-3'

Primer 994526:
                                    (SEQ ID NO: 285)
5'-TTAGCAAGCTTAATCACTTTAATGCCCTCAG-3'

Primer 994527:
                                    (SEQ ID NO: 286)
5'-TGATTAAGCTTGCTAATCCGCAGGACACTTC-3'

Primer 994528:
                                    (SEQ ID NO: 287)
5'-GGTACCAACACTGCCTCTCTCATCTC-3'
```

PCR amplifications were conducted in 50 μl reactions composed of 10 ng of *Bacillus subtilis* strain 164Δ5 chromosomal DNA, 0.4 μM of each primer, 200 μM each of dATP, dCTP, dGTP, and dTTP, 1×PCR Buffer II (Applied Biosystems, Inc., Foster City, Calif., USA) with 2.5 mM $MgCl_2$, and 2.5 units of AmpliTaq GOLD® DNA Polymerase (Applied Biosystems, Inc., Foster City, Calif., USA). The reactions were performed in a ROBOCYCLER® 40 Temperature Cycler (Stratagene, Corp., La Jolla, Calif., USA) programmed for 1 cycle at 95° C. for 10 minutes; 25 cycles each at 95° C. for 1 minute, 50° C. for 1 minute, and 72° C. for 1 minute; and 1 cycle at 72° C. for 7 minutes.

The PCR products were resolved by 0.8% agarose gel electrophoresis using 0.5×TBE buffer (50 mM Tris base-50 mM boric acid-1 mM disodium EDTA). A band of approximately 400 bp obtained using the primer pair 994525/994526 for the 5' flanking DNA sequence of the ispA gene was excised from the gel and extracted using a QIAQUICK® Gel Extraction Kit (QIAGEN Inc., Valencia, Calif., USA). A band of approximately 400 bp obtained using the primer pair 994527/994528 for the 3' flanking DNA sequence of the ispA gene was excised from the gel and extracted using a QIAQUICK® Gel Extraction Kit.

The final SOE fragment was amplified using the same procedure above with the 400 bp fragments as templates and primers 994525 and 994528, shown above, to produce an ispA deletion fragment. The PCR product of approximately 800 kb was resolved by 0.8% agarose gel electrophoresis using 0.5×TBE buffer.

The final 800 kb SOE fragment was cloned into pCR®2.1 (Invitrogen, Carlsbad, Calif., USA) using a TA-TOPO® Cloning Kit (Invitrogen, Carlsbad, Calif., USA) and transformed into ONE SHOT® TOP10 Chemically Competent *E. coli* cells (Invitrogen, Carlsbad, Calif., USA) according to the manufacturer's instructions. Transformants were selected on 2×YT agar plates supplemented with 100 μg of ampicillin per ml and incubated at 37° C. for 16 hours. The DNA sequence of the cloned fragment was verified by DNA sequencing with M13 forward and reverse primers (Invitrogen, Inc, Carlsbad, Calif., USA). The plasmid was designated pCR®2.1-ispAΔ.

Plasmid pCR2.1-ispAΔ was digested with Barn HI and Asp718 and subjected to 0.8% agarose gel electrophoresis using 0.5×TBE buffer to isolate the ispA deletion fragment. A 800 bp fragment corresponding to the ispA deletion fragment was excised from the gel and extracted using a QIAQUICK® Gel Extraction Kit.

The temperature sensitive plasmid pNNB194 (pSK$^+$/pE194; U.S. Pat. No. 5,958,728) was digested with Barn HI and Asp718 and resolved by 0.8% agarose gel electrophoresis using 0.5×TBE buffer to isolate the vector fragment. A 6600 bp vector fragment of pNNB194 was excised from the gel and extracted using a QIAQUICK® Gel Extraction Kit.

The ispA deletion fragment and the pNNB194 fragment were ligated together using a Rapid DNA Ligation Kit (Roche Applied Science, Indianapolis, Ind., USA) and the ligation mix was transformed into *E. coli* SURE® cells (Stratagene Corp., La Jolla, Calif., USA) selecting for ampicillin resistance according to the manufacturer's instructions. Plasmid DNA was isolated from eight transformants using a BIOROBOT® 9600, digested with Barn HI and Asp718, and analyzed by agarose electrophoresis as described above to identify plasmids which harbored the ispAΔ fragment. One transformant was identified and designated pNNB194-ispAΔ.

Plasmid pNNB194-ispAΔ was introduced into *Bacillus subtilis* A164410 (Bindel-Connelly et al., 2004, *J. Bacteriol.* 186: 4159-4167) and integrated at the ispA locus by selective growth at 45° C. on Tryptose blood agar base (TBAB) plates supplemented with 1 μg of erythromycin and 25 μg of lincomycin per ml. The integrated plasmid was then excised by non-selective growth on LB medium at 34° C. Chromosomal DNA was isolated from several erythromycin sensitive clones according to the method of Pitcher et al., 1989, supra, and analyzed by PCR using primers 994525 and 994528 using the same method above to confirm the presence of the ispA deletion. One such clone was designated *Bacillus subtilis* SMO25.

A linear integration vector-system was used for the expression cloning of a synthetic *Dictyoglomus thermophilum* Family 11 xylanase gene without a binding domain and without a signal peptide. The synthetic gene sequence was based on the public gene sequence UNIPROT: P77853. The synthetic gene was codon optimized for expression in *Bacillus subtilis* following recommendations by Gustafsson et al., 2004, *Trends in Biotechnology* 22: 346-353. The synthetic gene was generated by DNA2.0 (Menlo Park, Calif., USA) and delivered as a cloned fragment in their standard cloning vector (kanamycin resistant). The xylanase gene was cloned as a truncated gene without binding domain and with the signal peptide from *Bacillus clausii* serine protease gene (aprH, SAVINASE™, Novo Nordisk A/S, Bagsvrd, Denmark) (included in the flanking region). The gene was designed to contain a C-terminal HQHQHQHQP tag to ease purification. The forward primer was designed so the gene was amplified from the signal peptide cleavage site and it had 26 bases overhang (shown in italic in the table below). This overhang was complementary to part of one of the two linear vector fragments and was used when the PCR fragment and the vector fragments were assembled (described below). The reverse primer was designed to amplify the truncated version of the gene and contained an overhang consisting of 30 bp encoding a HQHQHQHQP-tag and a stop codon (the overhang is shown in italic in the table below). This overhang was complementary to part of one of the two linear vector fragments and was used when the PCR fragment and the vector fragments were assembled (described below).

The linear integration construct was a PCR fusion product made by fusion of each gene between two *Bacillus* subtils homologous chromosomal regions along with a strong promoter and a chloramphenicol resistance marker. The fusion was made by splicing by overlap extension (SOE) (Horton et al., 1989, supra). The SOE PCR method is also described in WO 2003/095658. Each gene was expressed under the control of a triple promoter system (described in WO 99/43835), consisting of the promoters from *Bacillus licheniformis* alpha-amylase gene (amyL), *Bacillus amyloliquefaciens* alpha-amylase gene (amyQ), and the *Bacillus thuringiensis* cryIIIA promoter including the mRNA stabilizing sequence. The gene coding for chloramphenicol acetyl-transferase was used as marker (described, for example, by Diderichsen et al., 1993, *Plasmid* 30: 312). The final gene construct was integrated by homologous recombination into the pectate lyase locus of the *Bacillus* chromosome.

The GH11 xylanase gene was amplified from plasmid 7587 by PCR using the primers shown in the Table below 1 below. The plasmid 7587 contains the synthetic *Dictyoglomus thermophilum* GH11 xylanase gene (SEQ ID NO: 304 for the DNA sequence and SEQ ID NO: 305 for the deduced amino acid sequence) without a binding domain and without a signal peptide.

Three fragments were PCR amplified to make the construct: the gene fragment containing the truncated xylanase gene and the 26 bp and 30 bp flanking DNA sequences included in the primers as overhang, the upstream flanking fragment (including a signal peptide from Savinase and amplified with the primers 260558 and iMB1361Uni2) and the downstream flanking fragment (amplified with the primers 260559 and HQHQHQHQP-f). The flanking fragments were amplified from genomic DNA of the strain iMB1361 (described in patent application WO 2003/095658). All primers used are listed in the Table 1 below.

The gene fragment was amplified using a proofreading polymerase PHUSION™ DNA Polymerase according to the manufacturer's instructions. The two flanking DNA fragments were amplified with "Expand High Fidelity PCR System" (Roche-Applied-Science) according to standard procedures (following the manufacturer's recommendations). The PCR conditions were as follows: 94° C. for 2 minutes followed by 10 cycles of (94° C. for 15 seconds, 50° C. for 45 seconds, 68° C. for 4 minutes) followed by 20 cycles of (94° C. for 15 seconds, 50° C. for 45 seconds, 68° C. for 4 minutes (+20 seconds extension per cycle)) and ending with one cycle at 68° C. for 10 min. The 3 PCR fragments were subjected to a subsequent Splicing by Overlap Extension (SOE) PCR reaction to assemble the 3 fragments into one linear vector construct. This was performed by mixing the 3 fragments in equal molar ratios and a new PCR reaction were run under the following conditions: initial 2 minutes. at 94° C., followed by 10 cycles of (94° C. for 15 seconds, 50° C. for 45 seconds, 68° C. for 5 minutes), 10 cycles of (94° C. for 15 seconds, 50° C. for 45 seconds, 68° C. for 8 minutes), 15 cycles of (94° C. for 15 seconds, 50° C. for 45 seconds, 68° C. for 8 minutes in addition 20 seconds extra per cycle). After the 1st cycle the two end primers 260558 and 260559 were added (20 μMol of each). Two μl of the PCR product were transformed into *Bacillus subtilis*. Transformants were selected on LB plates supplemented with 6 μg of chloramphenicol per ml. The truncated xylanase construct was integrated by homologous recombination into the genome of the *Bacillus subtilis* host PL4250 (AprE−, NprE−, SrfC−, SpoIIAC−, AmyE−, comS+). One transformant, EXP01955, was selected for further work. The xylanase coding region was sequenced in this transformant. It contained one mutation leading to a change of the HQHQHQHQP-tag to a HQHQHQHQQ-tag) but no other mutations were observed.

minute, and 72° C. for 1 minute; and 1 cycle at 72° C. for 7 minutes. A PCR product of approximately 740 kb of the truncated xylanase gene was resolved by 0.8% agarose gel electrophoresis using 0.5×TBE buffer, excised from the gel, and extracted using a QIAQUICK® Gel Extraction Kit.

The 740 kb fragment was cloned into pCR®2.1 using a TA-TOPO® Cloning Kit according to the manufacturer's instructions and transformed into ONE SHOT® TOP10 Chemically Competent *E. coli* cells according to the manufacturer's instructions. Transformants were selected on 2×YT agar plates supplemented with 100 μg of ampicillin per ml and incubated at 37° C. for 16 hours. The DNA sequence of the cloned fragment was verified by DNA sequencing with M13 forward and reverse primers. The plasmid was designated pCR2.1-Dt xyl.

DNA sequencing revealed that there was an extra G at position 19 of the sequence encoding the aprH signal sequence. A QUIKCHANGE® XL Site-Directed Mutagenesis Kit (Stratagene Corp., La Jolla, Calif., USA) was utilized to correct the mistake in plasmid pCR2.1-Dt xyl using the following primers to delete the extra G residue:

TABLE 1

Primers used

| Amplification of | SPECIFIC PRIMER FORWARD | SPECIFIC PRIMER REVERSE |
|---|---|---|
| Truncated gene | FORWARD (SEQ ID NO: 288)<br>5'-*CTTTTAGTTCATCGATCGCATCGG CT*GCTCAGACATCAATCACACTTA-3' | REVERSE (SEQ ID NO: 289)<br>5'-*CTAGGGTTGATGCTGGTGTTGGTGC TGATG*GCTGCCCTGAGAGAAAGTG-3' |
| Upstream flanking fragment | 260558: (SEQ ID NO: 290)<br>5'-GAGTATCGCCAGTAAGGGGCG-3' | iMB1361Uni2 (SEQ ID NO: 291)<br>5' AGCCGATGCGATCGATGAACTA 3' |
| Downstream flanking fragment | HQHQHQHQP-f (SEQ ID NO: 292)<br>5'-CATCAGCACCAACACCAGCACCAG CCATAATCGCATGTTCAATCCGCTCCA TA-3' | 260559: (SEQ ID NO: 293)<br>5'-GCAGCCCTAAAATCGCATAAAG C-3' |

Chromosomal DNA from *Bacillus subtilis* strain EXP01955 was used as a template to PCR clone the *Bacillus clausii* serine protease gene (aprH, SAVINASE™, Novo Nordisk A/S, Bagsvrd, Denmark) signal sequence/mature *D. thermophilum* xylanase gene (CBM-deleted) into pCR2.1-TOPO using the following primers which introduce a Sac I site at the 5' end (just upstream of the aprH ribosome binding site) and a Mlu I site at the 3' end (just after the translation stop codon which was introduced after the Ser codon at position 691-693, thereby avoiding the incorporation of the HQHQHQHQQ-tag). Chromosomal DNA was obtained according to the procedure of Pitcher et al., 1989, supra.

```
Primer 062405:
                                    (SEQ ID NO: 294)
5'-GAGCTCTATAAAAATGAGGAGGGAACCGAATGAAGAAACC-3'

Primer 062406:
                                    (SEQ ID NO: 295)
5'-ACGCGTTTAGCTGCCCTGAGAGAAAGTG-3'
```

The PCR amplifications were conducted in 50 μl reactions composed of 10 ng of *B. subtilis* EXP01955 chromosomal DNA, 0.4 μM of each primer, 200 μM each of dATP, dCTP, dGTP, and dTTP, 1×PCR Buffer II with 2.5 mM $MgCl_2$, and 2.5 units of AmpliTaq GOLD® DNA Polymerase. The reactions were performed in a ROBOCYCLER® 40 Temperature Cycler programmed for 1 cycle at 95° C. for 10 minutes; 25 cycles each at 95° C. for 1 minute, 50° C. for 1

```
Primer 062535:
                                    (SEQ ID NO: 296)
5'-CCGTTGGGGAAAATTGTCGC-3'

Primer 062536:
                                    (SEQ ID NO: 297)
5'-GCGACAATTTTCCCCAACGG-3'
```

The kit was used according to the manufacturer's instructions and the change was successfully made resulting in plasmid pCR2.1-Dt xyl2.

Plasmid pCR2.1-Dt xyl2 and pMDT100 WO 2008/140615 were digested with Sac I and Mlu I. The digestions were each resolved by 0.8% agarose gel electrophoresis using 0.5×TBE buffer. A vector fragment of approximately 8.0 kb from pMDT100 and a xylanase gene fragment of approximately 700 bp from pCR2.1-Dt xyl2 were excised from the gels and extracted using a QIAQUICK® Gel Extraction Kit. The two purified fragments were ligated together using a Rapid DNA Ligation Kit.

Competent cells of *Bacillus subtilis* 16844 were transformed with the ligation products according to the method of Young and Spizizen, 1961, *Journal of Bacteriology* 81: 823-829, or Dubnau and Davidoff-Abelson, 1971, *Journal of Molecular Biology* 56: 209-221. *Bacillus subtilis* 16844 is derived from the *Bacillus subtilis* type strain 168 (BGSC 1A1, *Bacillus* Genetic Stock Center, Columbus, Ohio, USA) and has deletions in the spoIIAC, aprE, nprE, and amyE genes. The deletion of the four genes was performed essentially as described for *Bacillus subtilis* A164Δ5 (U.S. Pat. No. 5,891,701).

*Bacillus subtilis* transformants were selected at 37° C. after 16 hours of growth on TBAB plates supplemented with 5 μg of chloramphenicol per ml. To screen for integration of the plasmid by double cross-over at the amyE locus, *Bacillus subtilis* primary transformants were patched onto TBAB plates supplemented with 6 μg of neomycin per ml and onto TBAB plates supplemented with 5 μg of chloramphenicol per ml. Integration of the plasmid by double cross-over at the amyE locus does not incorporate the neomycin resistance gene and therefore renders the strain neomycin sensitive. A chloramphenicol resistant, neomycin sensitive transformant was identified, which harbored the *Dictyoglomus thermophilum* xylanase expression cassette in the amyE locus, and designated *Bacillus subtilis* 168 with pSMO271.

Genomic DNA was isolated from *Bacillus subtilis* 168 with pSMO271 (Pitcher et al., 1989, supra) and 0.1 μg was transformed into competent *Bacillus subtilis* SM025. Transformants were selected on TBAB plates supplemented with 5 μg of chloramphenicol per ml at 37° C. A chloramphenicol resistant transformant was single colony purified and designated *Bacillus subtilis* SM 047.

The *Bacillus subtilis* strain designated SM047 was streaked on agar slants and incubated for about 24 hours at 37° C. The agar medium was composed per liter of 10 g of soy peptone, 10 g of sucrose, 2 g of trisodium citrate dihydrate, 4 g of $KH_2PO_4$, 5 g of $Na_2HPO_4$, 15 g of Bacto agar, 0.15 mg of biotin, 2 ml of trace metals, and deionized water to 1 liter. The trace metals solution was composed of 1.59 g of $ZnSO_4.7\ H_2O$, 0.76 g of $CuSO_4.5\ H_2O$, 7.52 g of $FeSO_4.7\ H_2O$, 1.88 g of $MnSO_4.H_2O$, 20 g of citric acid, and deionized water to 1 liter. Approximately 15 ml of sterile buffer (7.0 g of $Na_2HPO_4$, 3.0 g of $KH_2PO_4$, 4.0 g of NaCl, 0.2 g of $MgSO_4.7\ H_2O$, and deionized water to 1 liter) was used to gently wash off some of the cells from the agar surface. The bacterial suspension was then used for inoculation of baffled shake flasks containing 100 ml of growth medium composed of 11 g of soy bean meal, 0.4 g of $Na_2HPO_4$, 5 drops of antifoam, and deionized water to 100 ml. The inoculated shake flasks were incubated at 37° C. for about 20 hours with shaking at 300 rpm, after which 100 ml (obtained by combining the media from two independent shake flasks with the same strain) were used for inoculation of a 3 liter fermentor with 900 ml of medium composed of 40 g of hydrolyzed potato protein, 6 g of $K_2SO_4$, 4 g of $Na_2HPO_4$, 12 g of $K_2HPO_4$, 4 g of $(NH_4)_2SO_4$, 0.5 g of $CaCO_3$, 2 g of citric acid; 4 g of $MgSO_4$, 40 ml of trace metals solution (described above), 1 mg of biotin (biotin was added as 1 ml of a 1 g per liter biotin solution in the buffer described above), 1.3 ml of antifoam, and deionized water to 1 liter. The medium was adjusted to pH 5.25 with phosphoric acid prior to being autoclaved.

The fermentation was carried out as a fed-batch fermentation with sucrose solution being the feed. The fermentation temperature was held constant at 37° C. The tanks were aerated with 3 liter air per minute, and the agitation rate was held in the range of 1,500-1,800 rpm. The fermentation time was around 60-70 hours. The pH was maintained in the range of pH 6.5-7.3.

The fermentation was assayed for xylanase activity according to the following procedure. Culture supernatants were diluted appropriately in 0.1 M sodium acetate pH 5.0. A purified *Dictyoglomus thermophilum* xylanase was diluted using 2-fold steps starting with a 1.71 μg/ml concentration and ending with a 0.03 μg/ml concentration in the sample buffer. A total of 40 μl of each dilution including standard was transferred to a 96-well flat bottom plate. Using a Biomek NX (Beckman Coulter, Fullerton Calif., USA), a 96-well pipetting workstation, 40 μl an Azo-Wheat arabinoxylan (Megazyme International, Ireland) substrate solution (1% w/v) was added to each well then incubated at 50° C. for 30 minutes. Upon completion of the incubation the reaction was stopped with 200 μl of ethanol (95% v/v). The samples were then incubated at ambient temperatures for 5 minutes followed by centrifugation at 3,000 rpm for 10 minutes. One hundred-fifty microliters of the supernatant was removed and dispensed into a new 96-well flat bottom plate. An optical density of 590 nm was obtained for the 96-well plate using a SPECTRAMAX® 250 μlate reader (Molecular Devices, Sunnvale Calif., USA). Sample concentrations were determined by extrapolation from the generated standard curve.

Filtrated broth was added to 2% v/v GC-850 (Gulbrandsen, S.C., USA) followed by centrifugation at 20,000×g for 20 minutes. The supernatant was again added 2% v/v GC-850 followed by centrifugation at 20,000×g for 20 minutes. The supernatant was concentrated using a tangential flow concentrator equipped with a Sartocon® Slice cassette with a 10 kDa MW-CO polyethersulfone membrane. The concentrate was 80° C. treated for 30 minutes and filtrated through a 1.2 μm glass microfibre filter (Whatman, International Ltd, Maidstone, England). The pH was adjusted to pH 8.0 and loaded onto a MEP HyperCel™ (Pall Corporation, East Hills, N.Y. USA) column. The bound proteins were eluted with 50 mM acetic acid pH 4.5. The eluted proteins were stirred with activated carbon 1% w/v (Picatif FGV 120, Pica, France) for 15 minutes and filtrated on 0.2 μm PES filter (Nalge Nunc International, New York, N.Y. USA). The pH was adjusted to pH 5.0 using 3 M Tris. Protein concentration was determined using a Microplate BCA™ Protein Assay Kit in which bovine serum albumin was used as a protein standard.

Example 85: Preparation of *Aspergillus aculeatus* Strain CBS 172.66 GH3 Beta-Xylosidase The *Aspergillus aculeatus* strain CBS 172.66 GH beta-xylosidase (SEQ ID NO: 201 [DNA sequence] and SEQ ID NO: 202 [deduced amino acid sequence]) was recombinantly prepared according to the following procedure.

*Aspergillus aculeatus* CBS 172.66 was used as the source of the polypeptide having beta-xylosidase activity.

Genomic sequence information was generated by the U.S. Department of Energy Joint Genome Institute (JGI). A preliminary assembly of the genome was downloaded from JGI and analyzed using the PedantPro™ Sequence Analysis Suite (Biomax Informatics AG, Martinsried, Germany). Gene models constructed by the software were used as a starting point for detecting GH3 homologues in the genome. More precise gene models were constructed manually using multiple known GH3 protein sequences as a guide.

To generate genomic DNA for PCR amplification, *Aspergillus aculeatus* CBS 172.66 was propagated on PDA agar plates by growing at 26° C. for 7 days. Spores harvested from the PDA plates were used to inoculate 25 ml of YP+2% glucose medium in a baffled shake flask and incubated at 26° C. for 48 hours with agitation at 200 rpm.

Genomic DNA was isolated according to a modified FastDNA® SPIN protocol (Qbiogene, Inc., Carlsbad, Calif., USA). Briefly a FastDNA® SPIN Kit for Soil (Qbiogene, Inc., Carlsbad, Calif., USA) was used in a FastPrep® 24 Homogenization System (MP Biosciences, Santa Ana, Calif., USA). Two ml of fungal material from the above cultures were harvested by centrifugation at 14,000×g for 2 minutes. The supernatant was removed and the pellet resuspended in 500 μl of deionized water. The suspension was transferred to a Lysing Matrix E FastPrep® tube (Qbiogene, Inc., Carlsbad, Calif., USA) and 790 μl of sodium phosphate buffer and 100 μl of MT buffer from the FastDNA® SPIN Kit were added to the tube. The sample was then secured in the FastPrep® Instrument (Qbiogene, Inc., Carlsbad, Calif., USA) and processed for 60 seconds at a speed of 5.5 m/sec. The sample was then centrifuged at 14,000×g for two minutes and the supernatant transferred to a clean EPPENDORF® tube. A 250 μl volume of PPS reagent from the FastDNA® SPIN Kit was added and then the sample was mixed gently by inversion. The sample was again centrifuged at 14,000×g for 5 minutes. The supernatant was transferred to a 15 ml tube followed by 1 ml of Binding Matrix suspension from the FastDNA® SPIN Kit and then mixed by inversion for two minutes. The sample was placed in a stationary tube rack and the silica matrix was allowed to settle for 3 minutes. A 500 μl volume of the supernatant was removed and discarded and then the remaining sample was resuspended in the matrix. The sample was then transferred to a SPIN filter tube from the FastDNA® SPIN Kit and centrifuged at 14,000×g for 1 minute. The catch tube was emptied and the remaining matrix suspension added to the SPIN filter tube. The sample was again centrifuged (14,000×g, 1 minute). A 500 μl volume of SEWS-M solution from the FastDNA® SPIN Kit was added to the SPIN filter tube and the sample was centrifuged at the same speed for 1 minute. The catch tube was emptied and the SPIN filter replaced in the catch tube. The unit was centrifuged at 14,000×g for 2 minutes to "dry" the matrix of residual SEWS-M wash solution. The SPIN filter was placed in a fresh catch tube and allowed to air dry for 5 minutes at room temperature. The matrix was gently resuspended in 100 μl of DES (DNase/Pyrogen free water) with a pipette tip. The unit was centrifuged (14,000×g, 1 minute) to elute the genomic DNA followed by elution with 100 μl of 10 mM Tris, 0.1 mM EDTA, pH 8.0 by renewed centrifugation at 14,000×g for 1 minute and the eluates were combined. The concentration of the DNA harvested from the catch tube was measured by a UV spectrophotometer at 260 nm.

Synthetic oligonucleotide primers shown below are designed to PCR amplify *Aspergillus aculeatus* CBS 172.66 GH3 genes from the genomic DNA prepared in Example 2. An IN-FUSION™ Cloning Kit (Clontech, Mountain View, Calif., USA) is used to clone the fragments directly into the expression vector pDau109 (WO 2005/042735).

```
Primer GH3-114f:
                                        (SEQ ID NO: 298)
5'-ACACAACTGGGGATCCACCATGGCTGTGGCGGCTCTT-3'

Primer GH3-114r:
                                        (SEQ ID NO: 299)
5'-AGATCTCGAGAAGCTTACTACTCATCCCCCTGCAC-3'
```

PCR reactions are carried out with genomic DNA prepared from Example 2 for amplification of the genes identified in Example 1. The PCR reaction is composed of 1 μl of genomic DNA, 1 μl of primer forward (f) (50 μM); 1 μl of primer reverse (r) (50 μM); 10 μl of 5×HF buffer, 2 μl of 10 mM dNTP; 1 μl of PHUSION® DNA polymerase, and PCR-grade water up to 50 μl. Primers GH3-114f and GH3-114r are used simultaneously.

The PCR reactions are performed using a DYAD® PCR machine programmed for 2 minutes at 98° C. followed by 20 touchdown cycles at 98° C. for 15 seconds, 70° C. (−1° C./cycle) for 30 seconds, and 72° C. for 2 minutes 30 seconds; and 25 cycles each at 98° C. for 15 seconds, 60° C. for 30 seconds, 72° C. for 2 minutes 30 seconds; and 5 minutes at 72° C.

The reaction products are isolated by 1.0% agarose gel electrophoresis using 40 mM Tris base, 20 mM sodium acetate, 1 mM disodium EDTA (TAE) buffer where approximately 2.5 to 3.0 kb PCR product bands are excised from the gels and purified using a GFX® PCR DNA and Gel Band Purification Kit according to manufacturer's instructions. DNA corresponding to the *A. aculeatus* GH3 genes are cloned into the expression vector pDAu109 (WO 2005042735) linearized with Barn HI and Hind III, using an IN-FUSION™ Dry-Down PCR Cloning Kit according to the manufacturer's instructions.

A 2.5 μl volume of the five times diluted ligation mixture is used to transform *E. coli* TOP10 chemically competent cells. Five colonies are selected on LB agar plates containing 100 μg of ampicillin per ml and cultivated overnight in 3 ml of LB medium supplemented with 100 μg of ampicillin per ml. Plasmid DNA is purified using an E.Z.N.A.® Plasmid Mini Kit according to the manufacturer's instructions. The *Aspergillus aculeatus* GH3 gene sequences were verified by Sanger sequencing with an Applied Biosystems Model 3700 Automated DNA Sequencer using version 3.1 BIG-DYE™ terminator chemistry (Applied Biosystems, Inc., Foster City, Calif., USA) (Applied Biosystems, Inc., Foster City, Calif., USA). Nucleotide sequence data are scrutinized for quality and all sequences are compared to each other with assistance of PHRED/PHRAP software (University of Washington, Seattle, Wash., USA).

The coding sequence is 2412 bp including the stop codon and contains no introns. The encoded predicted protein is 803 amino acids. Using the SignalP program (Nielsen et al., 1997, supra), a signal peptide of 17 residues was predicted. The predicted mature protein contains 786 amino acids.

Spores of the best transformant were spread on COVE plates containing 0.01% TRITON® X-100 in order to isolate single colonies. The spreading was repeated twice in total on COVE sucrose medium (Cove, 1996*, Biochim. Biophys. Acta* 133: 51-56) containing 1 M sucrose and 10 mM sodium nitrate, supplemented with 10 mM acetamide and 15 mM CsCl. Fermentation was then carried out in 250 ml shake flasks using DAP-2C-1 medium for 4 days at 30° C. with shaking at 100 rpm. The fermentation broth was filtered using standard methods.

Ammonium sulphate was added to the filtrated broth to a concentration of 2 M. After filtration using a 0.2 μm PES filter (Thermo Fisher Scientific, Roskilde, Denmark), the filtrate was loaded onto a Phenyl Sepharose™ 6 Fast Flow column (high sub) (GE Healthcare, Piscataway, N.J., USA) equilibrated in 25 mM HEPES pH 7.0 with 2 M ammonium sulphate, and bound proteins were eluted with 25 mM HEPES pH 7.0 with no ammonium sulphate. The fractions were pooled and applied to a Sephadex™ G-25 (medium) (GE Healthcare, Piscataway, N.J., USA) column equilibrated in 25 mM HEPES pH 7.0. The fractions were pooled and then applied to a SOURCE™ 15Q (GE Healthcare, Piscataway, N.J., USA) column equilibrated in 25 mM HEPES pH 7.0, and bound proteins were eluted with a linear gradient from 0-1000 mM sodium chloride. Protein concentration was determined using a Microplate BCA™ Protein Assay Kit in which bovine serum albumin was used as a protein standard.

Example 86: Preparation of *Aspergillus aculeatus* Strain CBS 186.67 GH3 Beta-Xylosidase The *Aspergillus aculeatus* strain CBS 186.67 GH3 beta-xylosidase (SEQ ID NO: 203 [DNA sequence] and SEQ ID NO: 204 [deduced amino acid sequence]) was recombinantly prepared according to the following procedure.

Genomic DNA was isolated according to the procedure described in Example 73.

The *Aspergillus aculeatus* beta-xylosidase gene was isolated by PCR using two cloning primers GH3-101f and GH3-101r, shown below, which were designed based on the publicly available *Aspergillus aculeatus* xyl2 full-length sequence (GenBank AB462375.1) for direct cloning using the IN-FUSION™ strategy.

```
Primer GH3-101f:
                                        (SEQ ID NO: 300)
5'-acacaactggggatccaccatggctgtggcggctcttgctctgc

tgg-3'

Primer GH3-101r:
                                        (SEQ ID NO: 301)
5'-agatctcgagaagcttaCTCATCCCCCGCCACCCCCTGCACCTC

C-3'
```

A PCR reaction was performed with genomic DNA prepared from *Aspergillus aculeatus* CBS 186.67 in order to amplify the full-length gene. The PCR reaction was composed of 1 μl of genomic DNA, 0.75 μl of primer GH3-101.1f (10 μM), 0.75 μl of primer GH3-101.1r (10 μM), 3 μl of 5×HF buffer, 0.25 μl of 50 mM $MgCl_2$, 0.3 μl of 10 mM dNTP, 0.15 μl of PHUSION® DNA polymerase, and PCR-grade water up to 15 μl. The PCR reaction was performed using a DYAD® PCR machine programmed for 2 minutes at 98° C. followed by 10 touchdown cycles at 98° C. for 15 seconds, 70° C. (−1° C./cycle) for 30 seconds, and 72° C. for 2 minutes 30 seconds; and 25 cycles each at 98° C. for 15 seconds, 60° C. for 30 seconds, 72° C. for 2 minutes 30 seconds, and 5 minutes at 72° C.

The reaction products were isolated by 1.0% agarose gel electrophoresis using TAE buffer where an approximately 2.4 kb PCR product band was excised from the gel and purified using a GFX® PCR DNA and Gel Band Purification Kit according to manufacturer's instructions. DNA corresponding to the *Aspergillus aculeatus* beta-xylosidase gene was cloned into the expression vector pDAu109 (WO 2005042735) linearized with Barn HI and Hind III, using an IN-FUSION™ Dry-Down PCR Cloning Kit according to the manufacturer's instructions.

A 2.5 μl volume of the diluted ligation mixture was used to transform *E. coli* TOP10 chemically competent cells. Three colonies were selected on LB agar plates containing 100 μg of ampicillin per ml and cultivated overnight in 3 ml of LB medium supplemented with 100 μg of ampicillin per ml. Plasmid DNA was purified using an E.Z.N.A.® Plasmid Mini Kit according to the manufacturer's instructions. The *Aspergillus aculeatus* beta-xylosidase gene sequence was verified by Sanger sequencing before heterologous expression.

The coding sequence is 2454 bp including the stop codon. The gene does not contain introns. The encoded predicted protein is 817 amino acids. Using the SignalP program (Nielsen et al., 1997, *Protein Engineering* 10: 1-6), a signal peptide of 17 residues was predicted. The predicted mature protein contains 800 amino acids.

Protoplasts of *Aspergillus oryzae* MT3568 were prepared as described in WO 95/02043. *A. oryzae* MT3568 is an amdS (acetamidase) disrupted gene derivative of *Aspergillus oryzae* JaL355 (WO 2002/40694) in which pyrG auxotrophy was restored by disrupting the *A. oryzae* acetamidase (amdS) gene with the pyrG gene. One hundred microliters of protoplast suspension were mixed with 2.5-15 μg of the *Aspergillus* expression vector and 250 μl of 60% PEG 4000, 10 mM $CaCl_2$, and 10 mM Tris-HCl pH 7.5 were added and gently mixed. The mixture was incubated at 37° C. for 30 minutes and the protoplasts were spread on COVE sucrose (1 M) plates supplemented with 10 mM acetamide and 15 mM CsCl for transformant selection. After incubation for 4-7 days at 37° C. spores of several transformants were seeded on YP-2% maltodextrin medium. After 4 days cultivation at 30° C. culture broth was analyzed in order to identify the best transformants based on their ability to produce a large amount of active *Aculeatus aculeatus* beta-xylosidase. The screening was based on intensity of the band corresponding to the heterologous expressed protein determined by SDS-PAGE and activity of the enzyme on 4-nitrophenyl-beta-D-xylopyranoside (pNPX) as follows. Ten μl of culture broth was mixed with 90 μl of assay reagent containing 10 μl of 0.1% TWEEN® 20, 10 μl of 1 M sodium citrate pH 5, 4 μl of 100 mM of pNPX substrate (Sigma Aldrich) solubilized in DMSO (0.4% final volume in stock solution), and filtered water. The assay was performed for 30 minutes at 37° C. and absorbance determined at 405 nm before and after addition of 100 μl of 1 M sodium carbonate pH 10. The highest absorbance values at 405 nm were correlated to the SDS-PAGE data for selection of the best transformant.

Spores of the best transformant designated *A. oryzae* EXP3611 were spread on COVE plates containing 0.01% TRITON® X-100 in order to isolate single colonies. The spreading was repeated twice in total on COVE sucrose medium (Cove, 1996, *Biochim. Biophys. Acta* 133: 51-56) containing 1 M sucrose and 10 mM sodium nitrate, supplemented with 10 mM acetamide and 15 mM CsCl. Fermentation was then carried out in 250 ml shake flasks using DAP-4C-1 medium for 4 days at 30° C. with shaking at 100 rpm. The fermentation broth was filtered using standard methods. Protein concentration was determined using a Microplate BCA™ Protein Assay Kit in which bovine serum albumin was used as a protein standard.

Example 87: Preparation of *Aspergillus fumigatus* Strain NN051616 GH3 Beta-Xylosidase Q0H905

The *Aspergillus fumigatus* strain NN051616 GH3 beta-xylosidase (SEQ ID NO: 205 [DNA sequence] and SEQ ID NO: 206 [deduced amino acid sequence]) was recombinantly prepared according to the following procedure.

Two synthetic oligonucleotide primers shown below were designed to PCR amplify the *Aspergillus fumigatus* beta xylosidase gene from the genomic DNA. An InFusion Cloning Kit (Clontech, Mountain View, Calif.) was used to clone the fragment directly into the expression vector, pAILo2 (WO 2005/074647), without the need for restriction digests and ligation.

Forward primer:
(SEQ ID NO: 302)
5'-ACTGGATTTACCATGGCGGTTGCCAAATCTATTGCT-3'

Reverse primer:
(SEQ ID NO: 303)
5'-TCACCTCTAGTTAATTAATCACGCAGACGAAATCTGCT-3'

Bold letters represent coding sequence. The remaining sequence is homologous to the insertion sites of pAILo2.

Fifteen picomoles of each of the primers above were used in a PCR reaction containing 250 ng of *Aspergillus fumigatus* genomic DNA, 1× Expand High Fidelity Buffer with $MgCl_2$ (Roche Applied Science, Indianapolis, Ind.), 1 μl of 10 mM blend of dATP, dTTP, dGTP, and dCTP, 0.75 units of Expand High fidelity Enzyme Mix (Roche Applied Science, Indianapolis, Ind.), in a final volume of 50 μl. The amplification conditions were one cycle at 94° C. for 2 minutes; 10 cycles each at 94° C. for 15 seconds, 56.5° C. for 30 seconds, and 72° C. for 2 minutes; and 20 cycles each at 94° C. for 15 seconds, 56.5° C. for 30 seconds, and 72° C. for 2 minutes plus 5 seconds per successive cycle. The heat block was then held at 72° C. for 7 minutes followed by a 4° C. soak cycle.

The reaction products were isolated on a 1.0% agarose gel using TAE buffer and a 2.4 kb product band was excised from the gel and purified using a MinElute® Gel Extraction Kit (QIAGEN Inc., Valencia, Calif.) according to the manufacturer's instructions.

The fragment was then cloned into pAILo2 using an InFusion Cloning Kit. The vector was digested with Nco I and Pac I (using conditions specified by the manufacturer). The fragment was purified by gel electrophoresis and QIAquick kit (QIAGEN Inc., Valencia, Calif.) gel purification. The gene fragment and the digested vector were combined together in a reaction resulting in the expression plasmid pAG57, in which transcription of the *Aspergillus fumigatus* beta-xylosidase gene was under the control of the NA2-tpi promoter (a hybrid of the promoters from the genes for *Aspergillus niger* neutral alpha-amylase and *Aspergillus oryzae* triose phosphate isomerase). The recombination reaction (20 μl) was composed of 1× InFusion Buffer (Clontech, Mountain View, Calif.), 1×BSA (Clontech, Mountain View, Calif.), 1 μl of InFusion enzyme (diluted 1:10) (Clontech, Mountain View, Calif.), 182 ng of pAILo2 digested with Nco I and Pac I, and 97.7 ng of the *Aspergillus fumigatus* beta-xylosidase purified PCR product. The reaction was incubated at 37° C. for 15 minutes followed by 15 minutes at 50° C. The reaction was diluted with 40 μl of TE buffer and 2.5 μl of the diluted reaction was used to transform *E. coli* Top10 Competent cells. An *E. coli* transformant containing pAG57 (*Aspergillus fumigatus* beta-xylosidase gene) was identified by restriction enzyme digestion and plasmid DNA was prepared using a BIOROBOT® 9600. The pAG57 plasmid construct was sequenced using an Applied Biosystems 3130xl Genetic Analyzer (Applied Biosystems, Foster City, Calif., USA) to verify the sequence.

*Aspergillus oryzae* JaL355 protoplasts were prepared according to the method of Christensen et al., 1988, *Bio/Technology* 6: 1419-1422 and transformed with 5 μg of pAG57. Twenty-four transformants were isolated to individual PDA plates.

Plugs taken from the original transformation plate of each of the twenty-four transformants were added to 1 ml of M410 separately in 24 well plates, which were incubated at 34° C. After three days of incubation, 7.5 μl of supernatant from each culture was analyzed using Criterion stain-free, 8-16% gradient SDS-PAGE, (BioRad, Hercules, Calif.) according to the manufacturer's instructions. SDS-PAGE profiles of the cultures showed that several transformants had a new major band of approximately 130 kDa.

Confluent PDA plate of the highest expressing transformant was washed with 5 ml of 0.01% TWEEN® 20 and inoculated into a 500 ml Erlenmeyer flask containing 100 ml of M410 medium. Inoculated flask was incubated with shaking for 3 days at 34° C. The broth was filtered through a 0.22 μm stericup suction filter (Millipore, Bedford, Mass.).

Filtered broth was concentrated and buffer exchanged using a tangential flow concentrator (Pall Filtron, Northborough, Mass., USA) equipped with a 10 kDa polyethersulfone membrane (Pall Filtron, Northborough, Mass., USA) with 50 mM sodium acetate pH 5.0. Protein concentration was determined using a Microplate BCA™ Protein Assay Kit in which bovine serum albumin was used as a protein standard.

Example 88: Evaluation of Two Cellobiohydrolases I Replacing a CBHI Component in a High-Temperature Enzyme Composition in Saccharification of Milled Unwashed PCS at 50-65° C.

The ability of two cellobiohydrolase I proteins to replace a CBHI component in a high-temperature enzyme composition (3 mg total protein per g cellulose) was tested at 50° C., 55° C., 60° C., and 65° C. using milled unwashed PCS as a substrate. The high-temperature enzyme composition included 37% CBHI, 25% *Aspergillus fumigatus* Cel6A CBHII, 10% *Myceliophthora thermophila* Cel5A EGII, 15% *Penicillium* sp. GH61A polypeptide having cellulolytic enhancing activity, 5% *Aspergillus fumigatus* Cel3A beta-glucosidase, 5% *Aspergillus fumigatus* GH10 xyn3 xylanase, and 3% *Trichoderma reesei* GH3 beta-xylosidase.

The following CBHIs were each tested in the high-temperature enzyme composition: *Aspergillus fumigatus* Cel7A CBHI and *Penicillium emersonii* Cel7A CBHI.

The assay was performed as described in Example 34. The 1 ml reactions with milled unwashed PCS (5% insoluble solids) were conducted for 72 hours in 50 mM sodium acetate pH 5.0 buffer containing 1 mM manganese sulfate. All reactions were performed in triplicate and involved single mixing at the beginning of hydrolysis.

Figure 29:
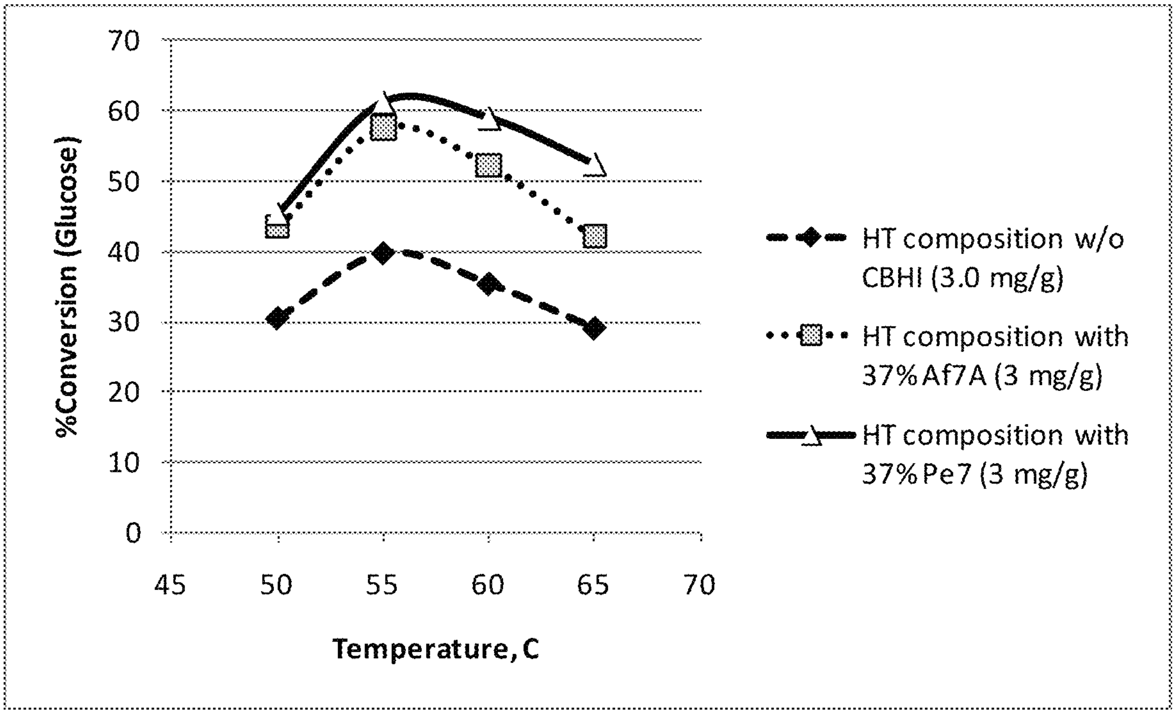
FIG. 29 shows a comparison of *Aspergillus fumigatus* Cel7A CBHI and *Penicillium emersonii* Cel7 CBHI in a high-temperature enzyme composition in hydrolysis of milled unwashed PCS at 50-65° C.

As shown in FIG. 29, *Penicillium emersonii* Cel7A CBHI performed the same as *Aspergillus fumigatus* Cel7A CBHI at 50° C. and performed better than *Aspergillus fumigatus* Cel7A CBHI at 55-65° C. (as the degree of cellulose conversion to glucose was higher for *Penicillium emersonii* Cel7A CBHI than *Aspergillus fumigatus* Cel7A CBHI at 55-65° C.).

Example 89: Evaluation of Two Cellobiohydrolases I Replacing a CBHI Component in a High-Temperature Enzyme Composition in Saccharification of Milled Unwashed PCS at 50-65° C.

The ability of two cellobiohydrolase I proteins to replace a CBHI component in a high-temperature enzyme composition (3 mg total protein per g cellulose) was tested at 50° C., 55° C., 60° C., and 65° C. using milled unwashed PCS as a substrate. The high-temperature enzyme composition included 40% CBHI, 25% *Aspergillus fumigatus* Cel6A CBHII, 10% *Myceliophthora thermophila* Cel5A EGII, 15% *Thermoascus aurantiacus* GH61A polypeptide having cellulolytic enhancing activity, 5% *Aspergillus fumigatus* GH10 xylanase, and 5% *Aspergillus fumigatus* Cel3A beta-glucosidase.

The following CBHIs were each tested in the high-temperature enzyme composition: *Aspergillus fumigatus* Cel7A CBHI and *Penicillium pinophilum* Cel7A CBHI. The high-temperature composition including *Aspergillus fumigatus* Cel7A CBHI was loaded at 3.3 mg total protein per gram cellulose instead of 3 mg total protein per gram cellulose, in which *Penicillium pinophilum* Cel7A CBHI was loaded.

The assay was performed as described in Example 34. The 1 ml reactions with 5% milled unwashed PCS were conducted for 72 hours in 50 mM sodium acetate pH 5.0 buffer containing 1 mM manganese sulfate. All reactions were performed in triplicate and involved single mixing at the beginning of hydrolysis.

Figure 30:
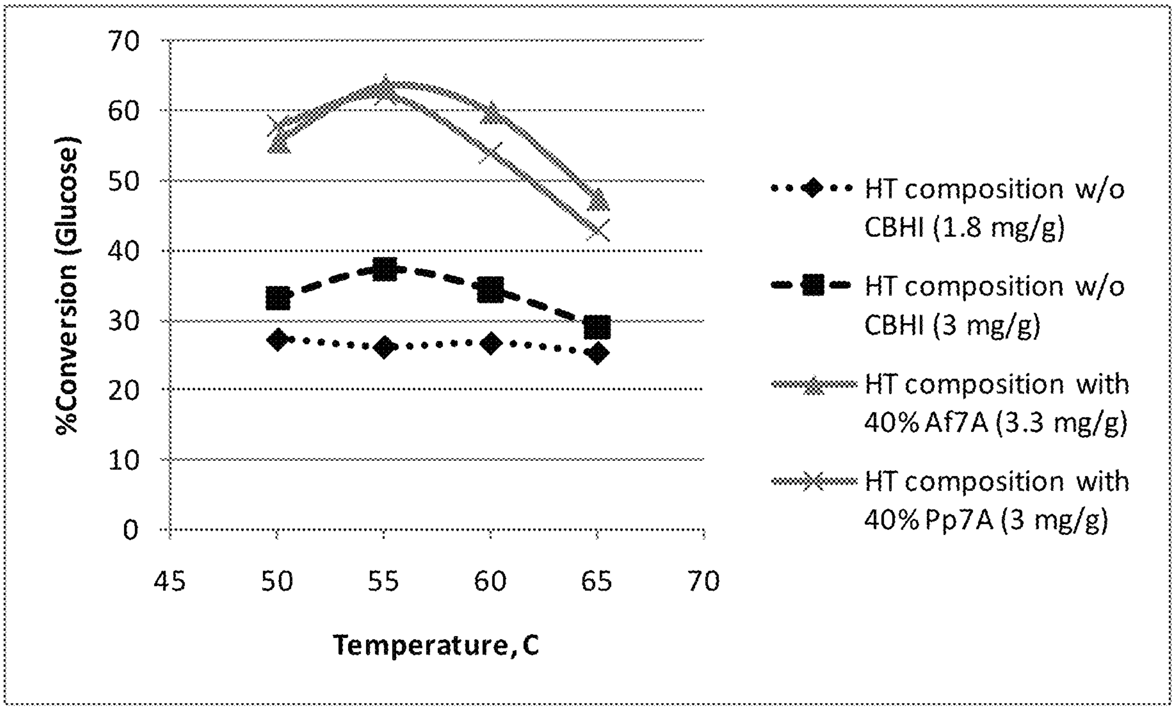
FIG. 30 shows an evaluation of *Aspergillus fumigatus* Cel7A CBHI and *Penicillium pinophilum* Cel7A CBHI in a high-temperature enzyme composition in hydrolysis of milled unwashed PCS at 50-65° C.

As shown in FIG. 30, *Penicillium pinophilum* Cel7A CBHI performed well in the entire range of temperatures. *Penicillium pinophilum* Cel7A CBHI performed about the same as *Aspergillus fumigatus* Cel7A CBHI at 50° C. and 55° C., but the performance was slightly lower compared to *Aspergillus fumigatus* Cel7A CBHI at 60° C. and 65° C.

Example 90: Evaluation of Two Cellobiohydrolases I Replacing a CBHI Component in a High-Temperature Enzyme Composition in Saccharification of Milled Unwashed PCS at 50-65° C.

The ability of two cellobiohydrolase I proteins to replace a CBHI component in a high-temperature enzyme composition (3 mg total protein per g cellulose) was tested at 50° C., 55° C., 60° C., and 65° C. using milled unwashed PCS as a substrate. The high-temperature enzyme composition included 37% CBHI, 25% *Aspergillus fumigatus* Cel6A CBHII, 10% *Myceliophthora thermophila* Cel5A EGII, 15% *Thermoascus aurantiacus* GH61A polypeptide having cellulolytic enhancing activity, 5% *Aspergillus fumigatus* Cel3A beta-glucosidase, 5% *Aspergillus fumigatus* GH10 xyn3 xylanase, and 3% *Trichoderma reesei* GH3 beta-xylosidase.

The following CBHIs were each tested in the high-temperature enzyme composition: *Aspergillus fumigatus* Cel7A CBHI and *Aspergillus terreus* Cel7A CBHI.

The assay was performed as described in Example 34. The 1 ml reactions with milled unwashed PCS (5% insoluble solids) were conducted for 72 hours in 50 mM sodium acetate pH 5.0 buffer containing 1 mM manganese sulfate. All reactions were performed in triplicate and involved single mixing at the beginning of hydrolysis.

Figure 31:
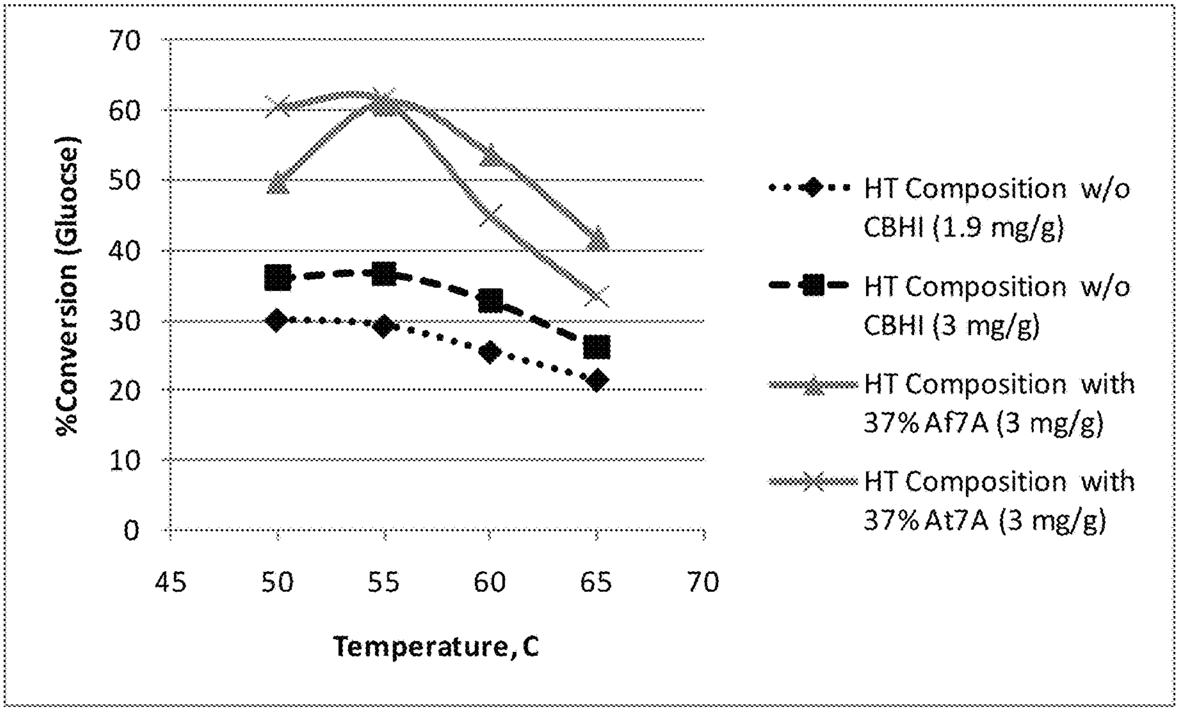
FIG. 31 shows an evaluation of *Aspergillus fumigatus* Cel7A CBHI and *Aspergillus terreus* Cel7A CBHI in a high-temperature enzyme composition in hydrolysis of milled unwashed PCS at 50-65° C.

As shown in FIG. 31, the performance of *Aspergillus terreus* Cel7A CBHI was the same as the performance of *Aspergillus fumigatus* Cel7A CBHI at 55° C. and lower at 60-65° C.; however, at 50° C., the degree of cellulose conversion to glucose was much higher for *Aspergillus terreus* Cel7A CBHI than *Aspergillus fumigatus* Cel7A CBHI at 50° C.

Example 91: Evaluation of Three Cellobiohydrolases I Replacing a CBHI Component in a High-Temperature Enzyme Composition in Saccharification of Milled Unwashed PCS at 50-60° C.

The ability of three cellobiohydrolase I proteins to replace a CBHI component in a high-temperature enzyme composition (3 mg total protein per g cellulose) was tested at 50° C., 55° C., and 60° C. using milled unwashed PCS as a substrate. The high-temperature enzyme composition included 45% CBHI, 25% *Thielavia terrestris* Cel6A CBHII, 5% *Trichoderma reesei* Cel7B EGI, 5% *Thermoascus aurantiacus* Cel5A EGII, 5% *Thermoascus aurantiacus* GH61A polypeptide having cellulolytic enhancing activity, 5% *Thielavia terrestris* GH61E polypeptide having cellulolytic enhancing activity, 5% *Aspergillus fumigatus* Cel3A beta-glucosidase, and 5% *Aspergillus fumigatus* GH10 xyn3 xylanase.

The following CBHIs were each tested in the high-temperature enzyme composition: *Aspergillus fumigatus* Cel7A CBHI, *Neosartorya fischeri* Cel7A CBHI, and *Aspergillus nidulans* Cel7A CBHI.

The assay was performed as described in Example 34. The 1 ml reactions with milled unwashed PCS (5% insoluble solids) were conducted for 72 hours in 50 mM sodium acetate pH 5.0 buffer containing 1 mM manganese sulfate. All reactions were performed in triplicate and involved single mixing at the beginning of hydrolysis.

Figure 32:
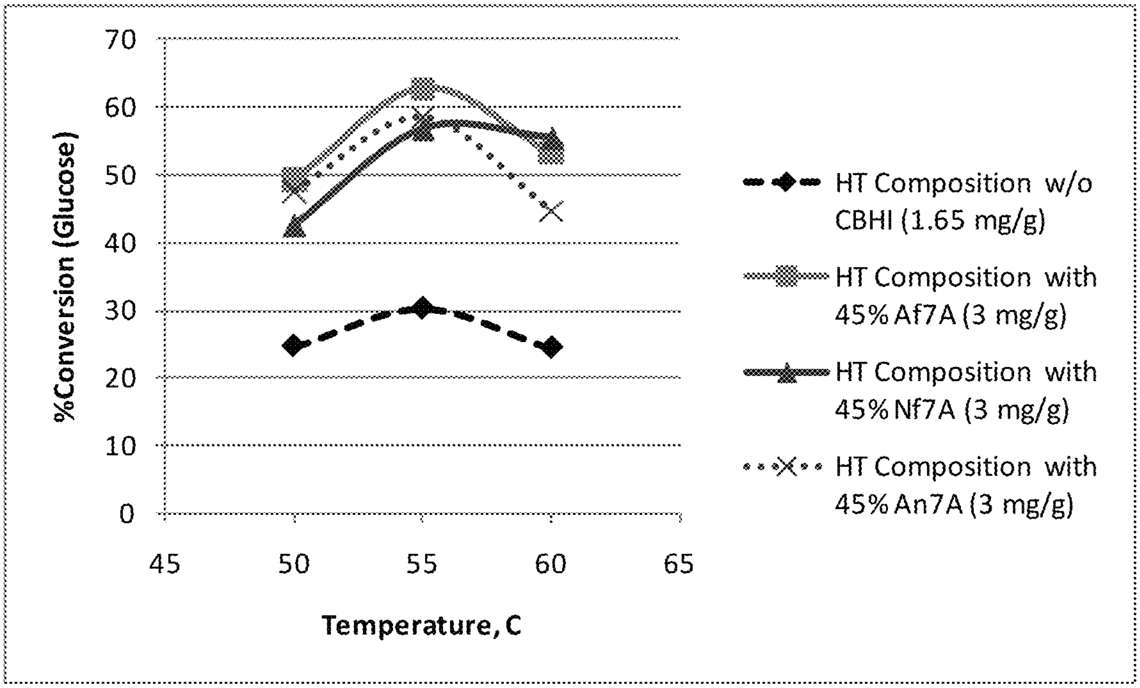
FIG. 32 shows an evaluation of *Aspergillus fumigatus* Cel7A CBHI, *Neosartorya fischeri* Cel7A CBHI, and *Aspergillus nidulans* Cel7A CBHI in a high-temperature enzyme composition in hydrolysis of milled unwashed PCS at 50-60° C.

As shown in FIG. 32, the performance of *Neosartorya fischeri* Cel7A CBHI was lower than the performance of *Aspergillus fumigatus* Cel7A CBHI at 50° C. and 55° C., but performance was the same at 60° C. *Aspergillus nidulans* Cel7A CBHI performed almost the same as *Aspergillus fumigatus* Cel7A CBHI at 50° C., but showed lower hydrolysis at 55° C. and 60° C.

Example 92: Evaluation of Two Cellobiohydrolases II Replacing a CBHII Component in a High-Temperature Enzyme Composition in Saccharification of Milled Unwashed PCS at 50-65° C.

The ability of two cellobiohydrolase II proteins to replace a CBHII component in a high-temperature enzyme composition (3 mg total protein per g cellulose) was tested at 50° C., 55° C., 60° C., and 65° C. using milled unwashed PCS as a substrate. The high-temperature enzyme composition included 37% *Aspergillus fumigatus* Cel7A CBHI, 25% CBHII, 10% *Myceliophthora thermophila* Cel5A EGII, 15% *Thermoascus aurantiacus* GH61A polypeptide having cellulolytic enhancing activity, 5% *Aspergillus fumigatus* Cel3A beta-glucosidase, 5% *Aspergillus fumigatus* GH10 xyn3 xylanase, and 3% *Trichoderma reesei* GH3 beta-xylosidase.

The following CBHIIs were each tested in the high-temperature enzyme composition: *Aspergillus fumigatus* Cel6A CBHII and *Finnellia nivea* Cel6A CBHII.

The assay was performed as described in Example 34. The 1 ml reactions with milled unwashed PCS (5% insoluble solids) were conducted for 72 hours in 50 mM sodium acetate pH 5.0 buffer containing 1 mM manganese sulfate. All reactions were performed in triplicate and involved single mixing at the beginning of hydrolysis.

Figure 33:
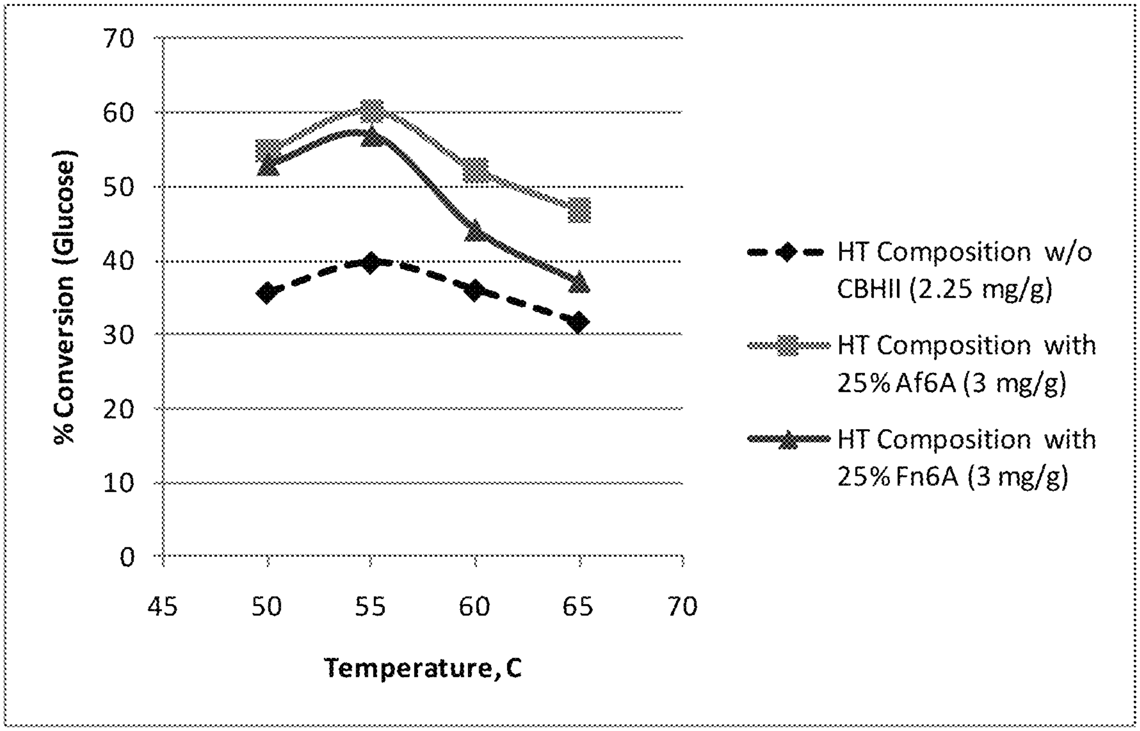
FIG. 33 shows an evaluation of *Aspergillus fumigatus* Cel6A CBHII and *Finnellia nivea* Cel6A CBHII in a high-temperature enzyme composition in hydrolysis of milled unwashed PCS at 50-65° C.

As shown in FIG. 33, *Finnellia nivea* Cel6A CBHII performed well at 50-55° C. as it showed hydrolysis levels similar to *Aspergillus fumigatus* Cel6A CBHII at 50-55° C., but the performance declined at 60-65° C.

Example 93: Evaluation of Three Cellobiohydrolases II Replacing a CBHII Component in a High-Temperature Enzyme Composition in Saccharification of Milled Unwashed PCS at 50-65° C.

The ability of three cellobiohydrolase II proteins to replace a CBHII component in a high-temperature enzyme composition (3 mg total protein per g cellulose) was tested at 50° C., 55° C., 60° C., and 65° C. using milled unwashed PCS as a substrate. The high-temperature enzyme composition included 37% *Aspergillus fumigatus* Cel7A CBHI, 25% CBHII, 10% *Trichoderma reesei* Cel5A EGII, 15% *Penicillium* sp. GH61A polypeptide having cellulolytic enhancing activity, 5% *Aspergillus fumigatus* Cel3A beta-glucosidase, 5% *Aspergillus fumigatus* GH10 xyn3 xylanase, and 3% *Trichoderma reesei* GH3 beta-xylosidase.

The following CBHIIs were each tested in the high-temperature enzyme composition: *Aspergillus fumigatus* Cel6A CBHII, *Penicillium emersonii* Cel6A CBHII, and *Penicillium pinophilum* Cel6A CBHII.

The assay was performed as described in Example 34. The 1 ml reactions with milled unwashed PCS (5% insoluble solids) were conducted for 72 hours in 50 mM sodium acetate pH 5.0 buffer containing 1 mM manganese sulfate. All reactions were performed in triplicate and involved single mixing at the beginning of hydrolysis.

Figure 34:
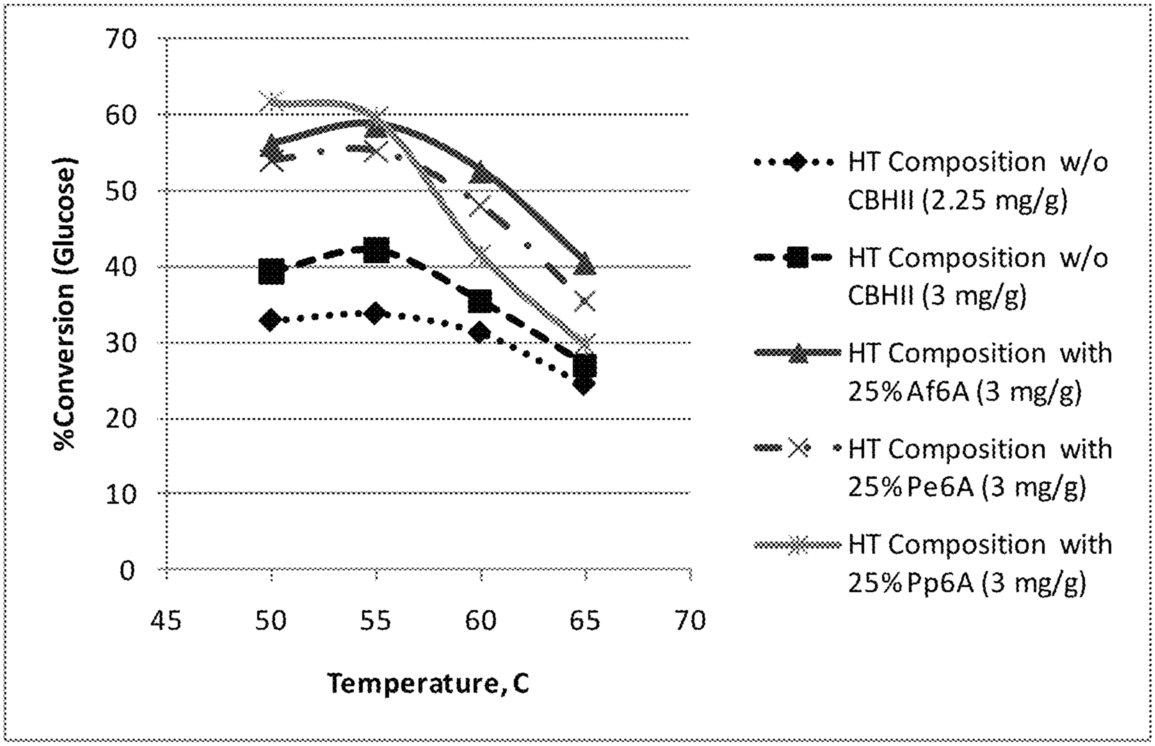
FIG. 34 shows an evaluation of *Aspergillus fumigatus* Cel6A CBHII, *Penicillium emersonii* Cel6A CBHII, and *Penicillium pinophilum* Cel6A CBHII proteins replacing a CBHII component in a high-temperature enzyme composition in hydrolysis of milled unwashed PCS at 50-65° C.

As shown in FIG. 34, *Penicillium emersonii* Cel6A CBHII performed well in the entire range of temperatures. *Penicillium emersonii* Cel6A CBHII performed almost as well as *Aspergillus fumigatus* Cel6A CBHII at 50° C., but performed slightly lower than *Aspergillus fumigatus* Cel6A CBHII at 55-65° C. The performance of *Penicillium pinophilum* Cel6A CBHII was comparable to that of *Aspergillus fumigatus* Cel6A CBHII at 50° C. and 55° C.; however, performance declined at 60° C. and 65° C.

Example 94: Evaluation of Three Endoglucanases II Replacing an Endoglucanase Component in a High-Temperature Enzyme Composition in Saccharification of Milled Unwashed PCS at 50-65° C.

The ability of three endoglucanase II proteins to replace an endoglucanase component in a high-temperature enzyme composition (3 mg total protein per g cellulose) was tested at 50° C., 55° C., 60° C., and 65° C. using milled unwashed PCS as a substrate. The high-temperature enzyme composition included 40% *Aspergillus fumigatus* Cel7A CBHI, 25% *Aspergillus fumigatus* Cel6A CBHII, 10% EG cellulase, 15% *Thermoascus aurantiacus* GH61A polypeptide having cellulolytic enhancing activity, 5% *Aspergillus fumigatus* Cel3A beta-glucosidase, and 5% *Aspergillus fumigatus* GH10 xyn3 xylanase.

The following EGIIs were each tested in the high-temperature enzyme composition: *Aspergillus fumigatus* Cel5A EGII, *Neosartorya fischeri* Cel5A EGII, and *Myceliophthora thermophila* Cel5A EGII.

The assay was performed as described in Example 34. The 1 ml reactions with milled unwashed PCS (5% insoluble solids) were conducted for 72 hours in 50 mM sodium acetate pH 5.0 buffer containing 1 mM manganese sulfate. All reactions were performed in triplicate and involved single mixing at the beginning of hydrolysis.

Figure 35:
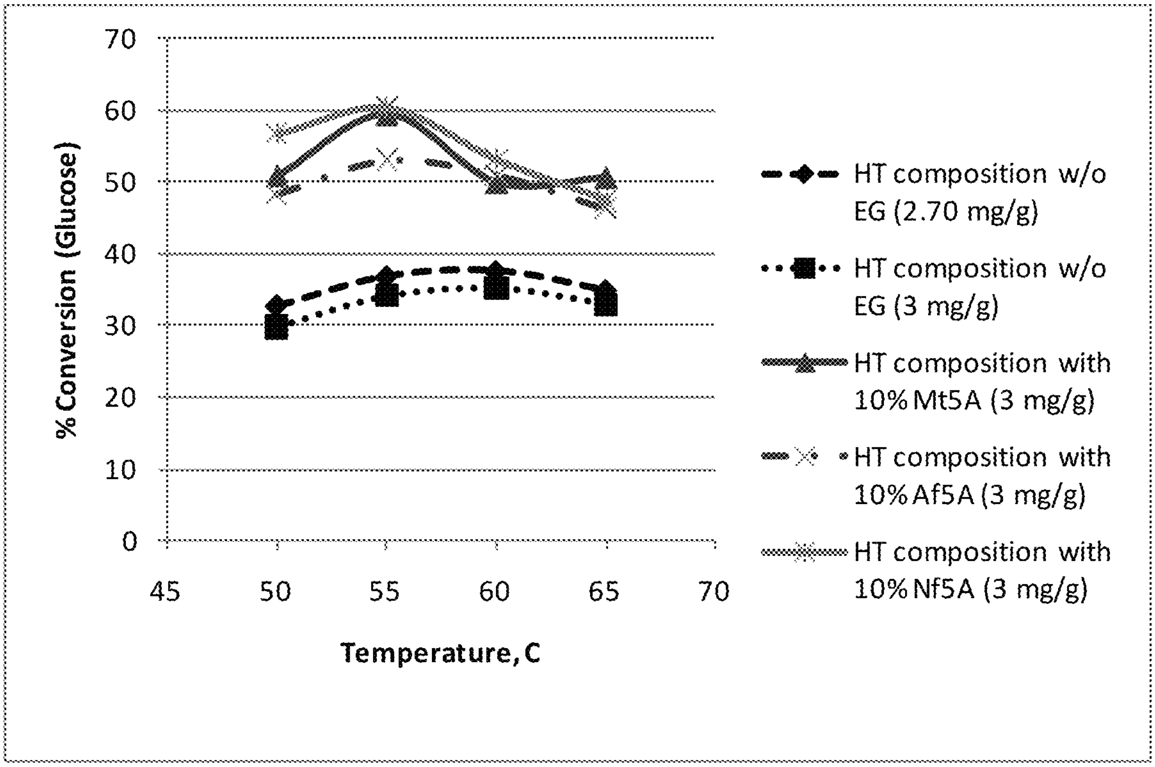
FIG. 35 shows an evaluation of *Aspergillus fumigatus* Cel5A EGII, *Neosartorya fischeri* Cel5A EGII, and *Myceliophthora thermophila* Cel5A EGII proteins replacing a EG component in a high-temperature enzyme composition in hydrolysis of milled unwashed PCS at 50-65° C.

As shown in FIG. 35, all endoglucanase II proteins performed similarly within this temperature range, with *Neosartorya fischeri* Cel5A EGII and *Myceliophthora thermophila* Cel5A EGII having similar activity at 50° C. and 55° C. and *Aspergillus fumigatus* Cel5A EGII having comparable activity to *Neosartorya fischeri* Cel5A EGII and *Myceliophthora thermophila* Cel5A EGII at 60° C. and 65° C.

Example 95: Evaluation of Two Beta-Glucosidases Replacing a Beta-Glucosidase Component in a High-Temperature Enzyme Composition in Saccharification of Milled Unwashed PCS at 50-65° C.

The ability of three beta-glucosidase proteins to replace a beta-glucosidase component in a high-temperature enzyme composition (3 mg total protein per g cellulose) was tested at 50° C., 55° C., 60° C., and 65° C. using milled unwashed PCS as a substrate. The high-temperature enzyme composition included 37% *Aspergillus fumigatus* Cel7A CBHI, 25% *Aspergillus fumigatus* Cel6A CBHII, 10% *Myceliophthora thermophila* Cel5A EGII, 15% *Thermoascus aurantiacus* GH61A polypeptide having cellulolytic enhancing activity, 5% beta-glucosidase, 5% *Aspergillus fumigatus* GH10 xyn3 xylanase, and 3% *Trichoderma reesei* GH3 beta-xylosidase.

The following beta-glucosidases were each tested in the high-temperature enzyme composition: *Aspergillus fumigatus* Cel3A beta-glucosidase and *Aspergillus aculeatus* beta-glucosidases.

The assay was performed as described in Example 34, with the exception of glucose background, in which 40 g per liter of glucose was included in the reactions. The 1 ml reactions with milled unwashed PCS (5% insoluble solids) were conducted for 72 hours in 50 mM sodium acetate pH 5.0 buffer containing 1 mM manganese sulfate. All reactions were performed in triplicate and involved single mixing at the beginning of hydrolysis.

Figure 36:
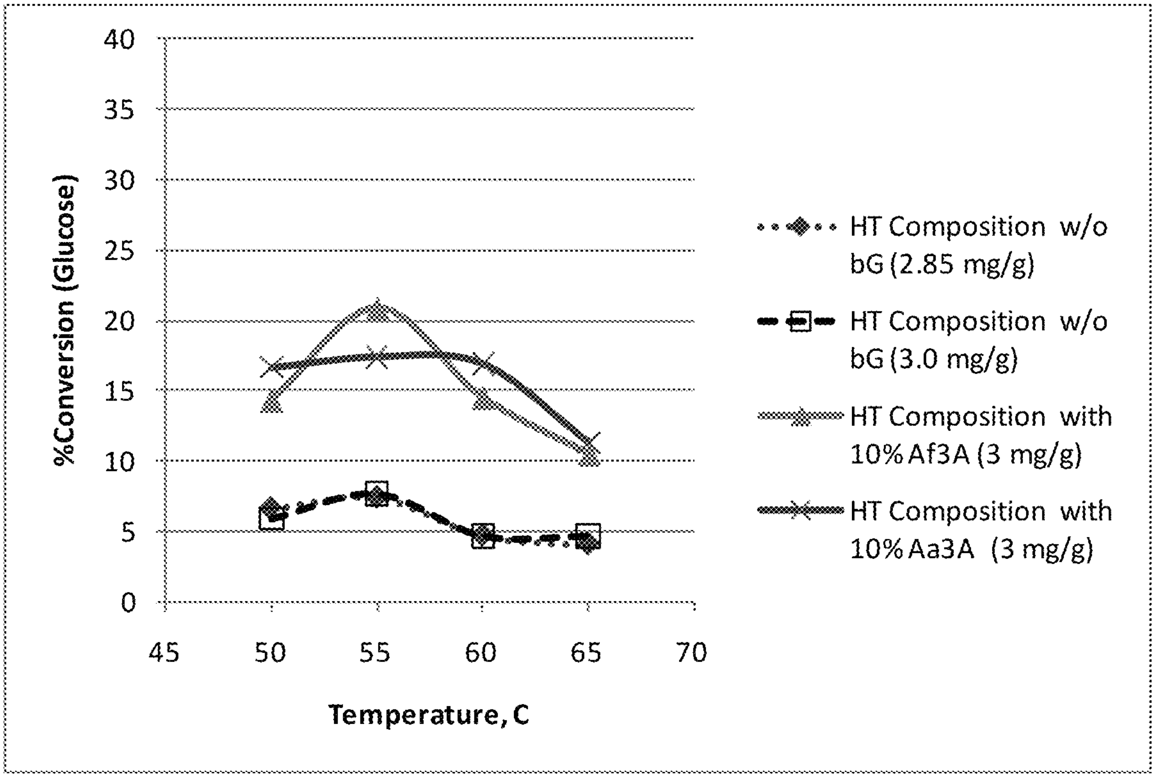
FIG. 36 shows an evaluation of *Aspergillus fumigatus* Cel3A beta-glucosidase and *Aspergillus aculeatus* beta-glucosidase in a high-temperature enzyme composition in hydrolysis of milled unwashed PCS at 50-65° C.

As shown in FIG. 36, *Aspergillus aculeatus* Cel3A beta-glucosidase had slightly higher or similar performance as *Aspergillus fumigatus* Cel3A beta-glucosidase at all temperatures

Example 96: Evaluation of Four Beta-Glucosidases Replacing a Beta-Glucosidase Component in a High-Temperature Enzyme Composition in Saccharification of Milled Unwashed PCS at 50-60° C.

Four beta-glucosidases, including *Aspergillus fumigatus* Cel3A beta-glucosidase, *Aspergillus kawashii* Cel3A beta-glucosidase, *Aspergillus clavatus* Cel3 beta-glucosidase, and *Talaromyces emersonii* Cel3A beta-glucosidase were each evaluated in a high-temperature enzyme composition at 50° C., 55° C., and 60° C. using milled unwashed PCS as a substrate. The high-temperature enzyme composition included 45% *Aspergillus fumigatus* Cel7A CBHI, 25% *Thielavia terrestris* Cel6A CBHII, 5% *Trichoderma reesei* Cel7B EGI, 5% *Thermoascus aurantiacus* Cel5A EGII, 5% *Thermoascus aurantiacus* GH61A polypeptide having cellulolytic enhancing activity, 5% *Thielavia terrestris* GH61E polypeptide having cellulolytic enhancing activity, 5% *Aspergillus fumigatus* GH10 xyn3 xylanase, and 5% beta-glucosidase. The high-temperature enzyme composition was used at 3.0 mg total protein per g cellulose.

The assay was performed as described in Example 34. The 1 ml reactions with milled unwashed PCS (5% insoluble solids) were conducted for 72 hours in 50 mM sodium acetate pH 5.0 buffer containing 1 mM manganese sulfate. All reactions were performed in triplicate and involved single mixing at the beginning of hydrolysis.

Figure 37:
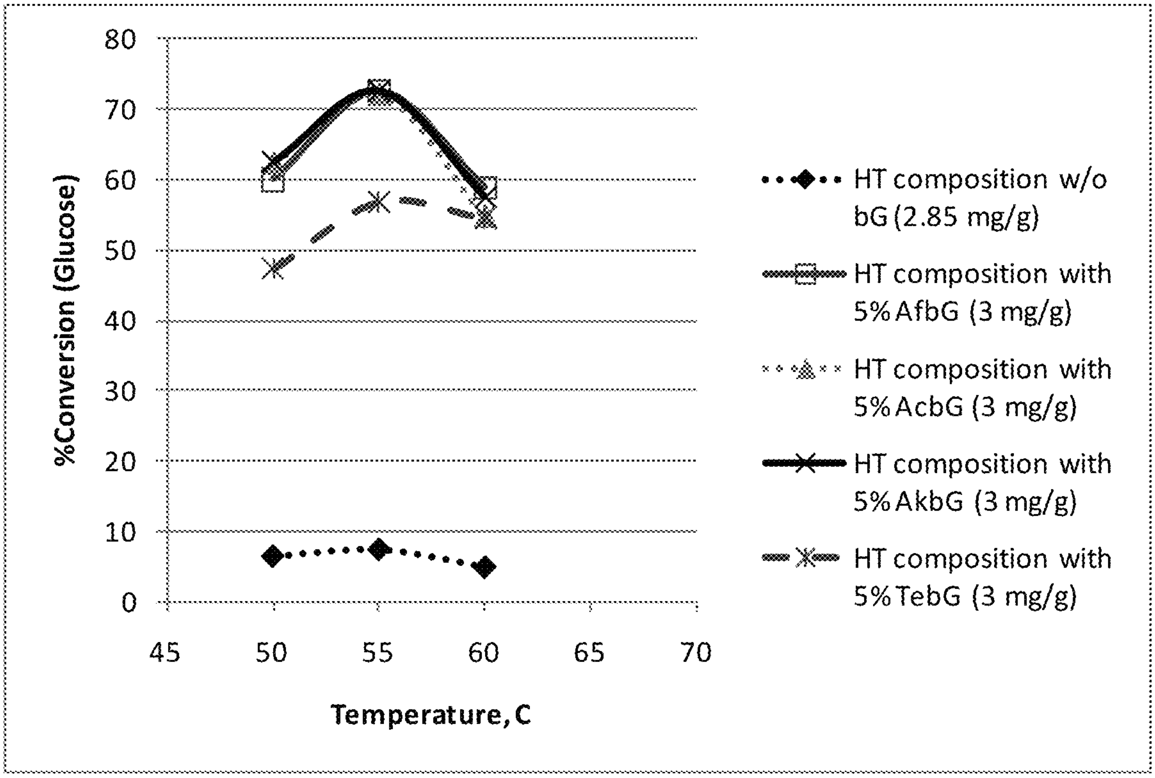
FIG. 37 shows an evaluation of *Aspergillus fumigatus* Cel3A beta-glucosidase, *Aspergillus kawashii* Cel3A beta-glucosidase, *Aspergillus clavatus* Cel3 beta-glucosidase, and *Talaromyces emersonii* Cel3A beta-glucosidase in a high-temperature enzyme composition in hydrolysis of milled unwashed PCS at 50-60° C.

The results shown in FIG. 37 demonstrated that all beta-glucosidases except *Talaromyces emersonii* Cel3A beta-glucosidase had similar performance all three temperatures. *Talaromyces emersonii* Cel3A beta-glucosidase had lower activity at 50° C. and 55° C. but had equivalent activity at 60° C.

Example 97: Evaluation of Three Beta-Glucosidases Replacing a Beta-Glucosidase Component in a High-Temperature Enzyme Composition in Saccharification of Milled Unwashed PCS at 50-65° C.

Three beta-glucosidases, including *Aspergillus fumigatus* Cel3A beta-glucosidase, *Penicillium oxalicum* Cel3A beta-glucosidase (Example 77), and *Penicillium oxalicum* Cel3A beta-glucosidase (Example 78) were each evaluated in a high-temperature enzyme composition at 50° C., 55° C., 60° C., and 65° C. using milled unwashed PCS as a substrate. The high-temperature enzyme composition included 40% *Aspergillus fumigatus* Cel7A CBHI, 25% *Aspergillus fumigatus* Cel6A CBHII, 10% *Myceliophthora thermophila* Cel5A EGII, 15% *Thermoascus aurantiacus* GH61A polypeptide having cellulolytic enhancing activity, 5% *Aspergillus fumigatus* GH10 xyn3 xylanase, and 5% beta-glucosidase. The high-temperature enzyme composition was used at 3.0 mg total protein per g cellulose.

The assay was performed as described in Example 34. The 1 ml reactions with milled unwashed PCS (5% insoluble solids) were conducted for 72 hours in 50 mM sodium acetate pH 5.0 buffer containing 1 mM manganese sulfate. All reactions were performed in triplicate and involved single mixing at the beginning of hydrolysis.

Figure 38:
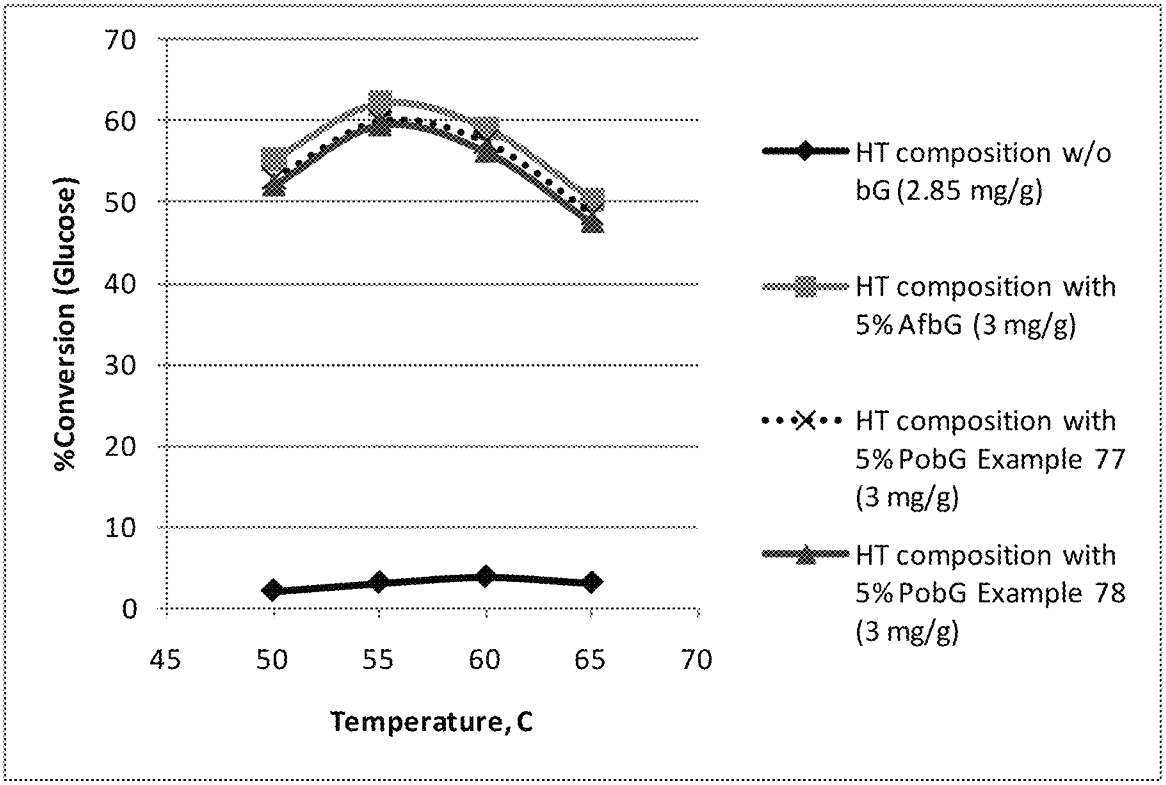
FIG. 38 shows an evaluation of *Aspergillus fumigatus* Cel3A beta-glucosidase, *Penicillium oxalicum* Cel3A beta-glucosidase (Example 77) and *Penicillium oxalicum* Cel3A beta-glucosidase (Example 78) in a high-temperature enzyme composition in hydrolysis of milled unwashed PCS at 50-65° C.

The results shown in FIG. 38 demonstrated that the beta-glucosidases had similar activity at all temperatures.

Example 98: Evaluation of the Ability of Three GH61 Polypeptides Having Cellulolytic Enhancing Activity to Enhance PCS-Hydrolyzing Activity of a High-Temperature Enzyme Composition at 50-65° C. Using Milled Washed PCS The ability of three GH61 polypeptides having cellulolytic enhancing activity, *Thermoascus aurantiacus* GH61A, *Penicllium* sp GH61A, and *Thermoascus crustaceus GH*61A, were each evaluated for their ability to enhance the PCS-hydrolyzing activity of a high-temperature enzyme composition using milled washed PCS at 50° C., 55° C., 60° C., and 65° C. Each GH61 polypeptide was separately added at 11.6% enzyme to a high temperature enzyme mixture. The high-temperature enzyme composition included 43.5% *Aspergillus fumigatus Cel*7A CBHI, 29% *Aspergillus fumigatus* Cel6A CBHII, 12% *Myceliophthora thermophila* Cel5A EGII, 6% *Aspergillus fumigatus* Cel3A beta-glucosidase, 6% *Aspergillus fumigatus* GH10 xyn3 xylanase, and 4% *Trichoderma reesei* GH3 beta-xylosidase. The results for the enzyme compositions containing GH61 polypeptides (2.3725 mg total protein per g cellulose) were compared with the results for a similar enzyme composition to which no GH61 polypeptide was added (2.125 mg total protein per g cellulose).

The assay was performed as described in Example 34. The 1 ml reactions with milled washed PCS (5% insoluble solids) were conducted for 72 hours in 50 mM sodium acetate pH 5.0 buffer containing 1 mM manganese sulfate. All reactions were performed in triplicate and involved single mixing at the beginning of hydrolysis.

Figure 39:
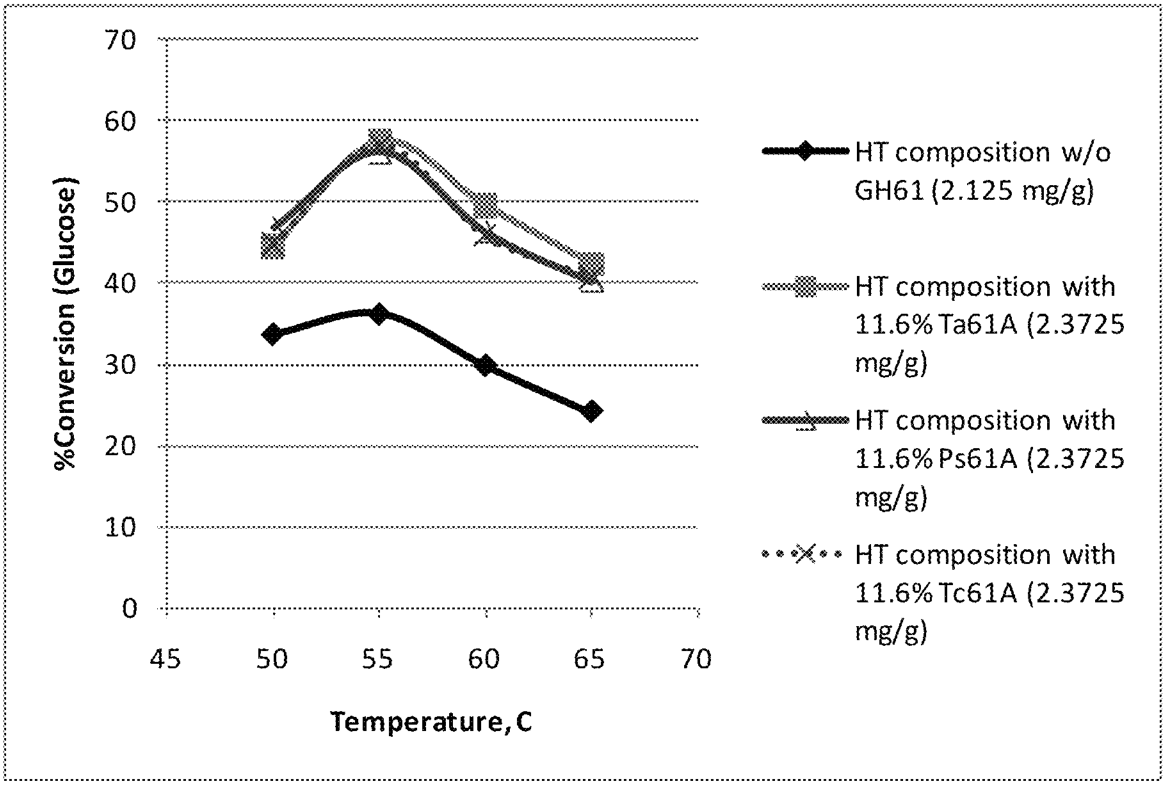
FIG. 39 shows an evaluation of three GH61 polypeptides having cellulolytic enhancing activity in a high-temperature enzyme composition in hydrolysis of milled washed PCS at 50-65° C.

As shown in FIG. 39, all three GH61 polypeptides showed significant cellulase-enhancing activity, with *Thermoascus aurantiacus* GH61A polypeptide, Penicllium sp GH61A polypeptide, and *Thermoascus crustaceus* GH61A polypeptide having similar enhancement at 50° C. and 55° C. while *Thermoascus aurantiacus* GH61A polypeptide had higher activity than Penicllium sp GH61A polypeptide and *Thermoascus crustaceus* GH61A polypeptide at 60° C. and 65° C.

Example 99: Evaluation of Three Xylanases Replacing a Xylanase Component in a High-Temperature Enzyme Composition in Saccharification of Milled Unwashed PCS at 50-65° C.

The ability of three xylanases to replace an xylanase component in a high-temperature enzyme composition (3 mg total protein per g cellulose) was tested at 50° C., 55° C., 60° C., and 65° C. using milled unwashed PCS as a substrate. The high-temperature enzyme composition included 37% *Aspergillus fumigatus* Cel7A CBHI, 25% *Aspergillus fumigatus* Cel6A CBHII, 10% *Myceliophthora thermophila* Cel5A EGII, 15% *Thermoascus aurantiacus* GH61A polypeptide having cellulolytic enhancing activity, 5% *Aspergillus fumigatus* Cel3A beta-glucosidase, 3% *Trichoderma reesei* GH3 beta-xylosidase and 5% xylanase.

The following xylanases were each tested in the high-temperature enzyme composition: *Aspergillus fumigatus* GH10 xylanase 3, *Talaromyces emersonii* GH10 xylanase, and *Penicillium emersonii* GH10 xylanase.

The assay was performed as described in Example 34. The 1 ml reactions with milled unwashed PCS (5% insoluble solids) were conducted for 72 hours in 50 mM sodium acetate pH 5.0 buffer containing 1 mM manganese sulfate. All reactions were performed in triplicate and involved single mixing at the beginning of hydrolysis.

Figure 40:
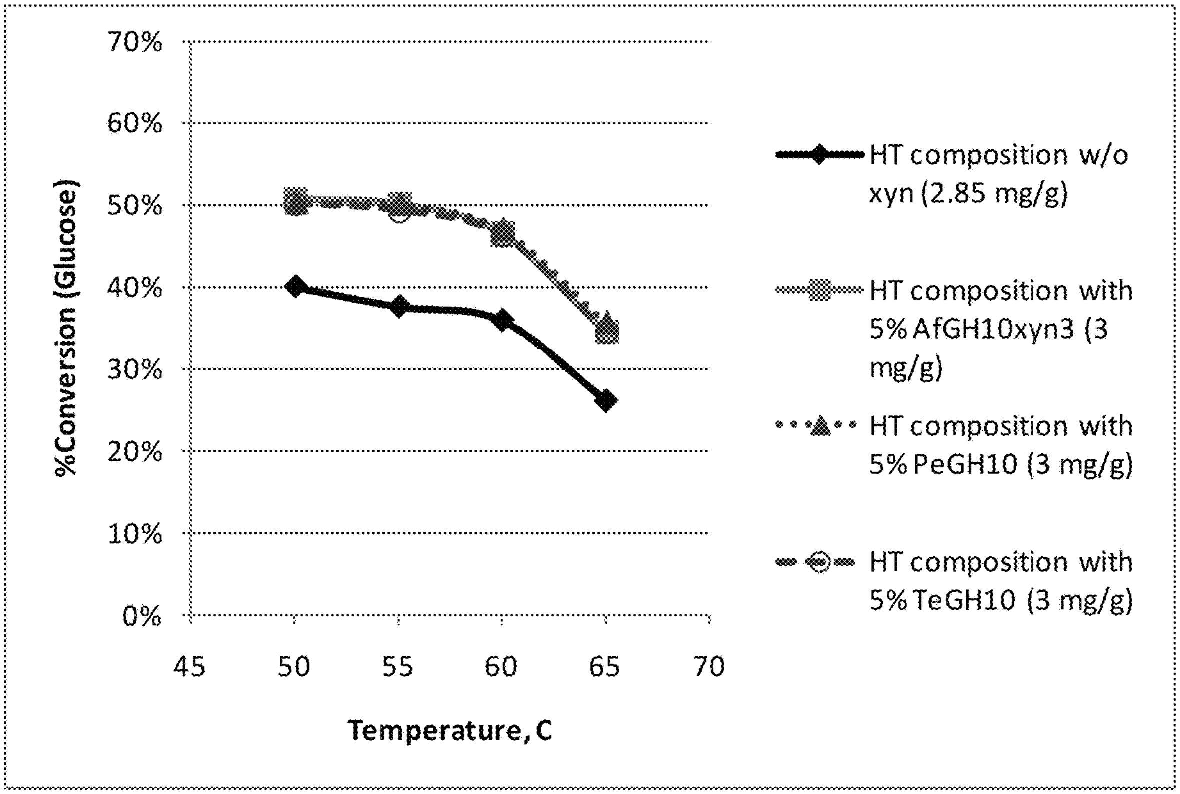
FIG. 40 shows an evaluation of three xylanases in a high-temperature enzyme composition in hydrolysis of milled unwashed PCS at 50-65° C.

As shown in FIG. 40, *Talaromyces emersonii* GH10 xylanase and *Penicillium emersonii* GH10 xylanase had similar activity as *Aspergillus fumigatus* GH10 xylanase 3 at all three temperatures.

Example 100: Evaluation of Three Xylanases by Adding a Xylanase Component to a High-Temperature Enzyme Composition in Saccharification of Milled Unwashed PCS at 50-60° C.

Three xylanases were each evaluated as a 10% addition to a high-temperature enzyme composition (3.5 mg total protein per g cellulose) at 50° C., 55° C., and 60° C. using milled unwashed PCS as a substrate. The high-temperature enzyme composition included 45% *Aspergillus fumigatus* Cel7A CBHI, 25% *Myceliophthora thermophila* Cel6A CBHII, 10% *Myceliophthora thermophila* Cel5A EGII, 5% *Thermoascus aurantiacus* GH61A polypeptide having cellulolytic enhancing activity, 5% *Thielavia terrestris* GH61E polypeptide having cellulolytic enhancing activity, and 5% *Penicillium brasilianum* Cel3A beta-glucosidase.

The following xylanases were each tested in the high-temperature enzyme composition: *Aspergillus fumigatus* GH10 xylanase (xyl3), *Meripilus giganteus* GH10 xylanase, and *Dictyoglomus thermophilum* GH11 xylanase.

The assay was performed as described in Example 34. The 1 ml reactions with milled unwashed PCS (5% insoluble solids) were conducted for 72 hours in 50 mM sodium acetate pH 5.0 buffer containing 1 mM manganese sulfate. All reactions were performed in triplicate and involved single mixing at the beginning of hydrolysis.

Figure 41:
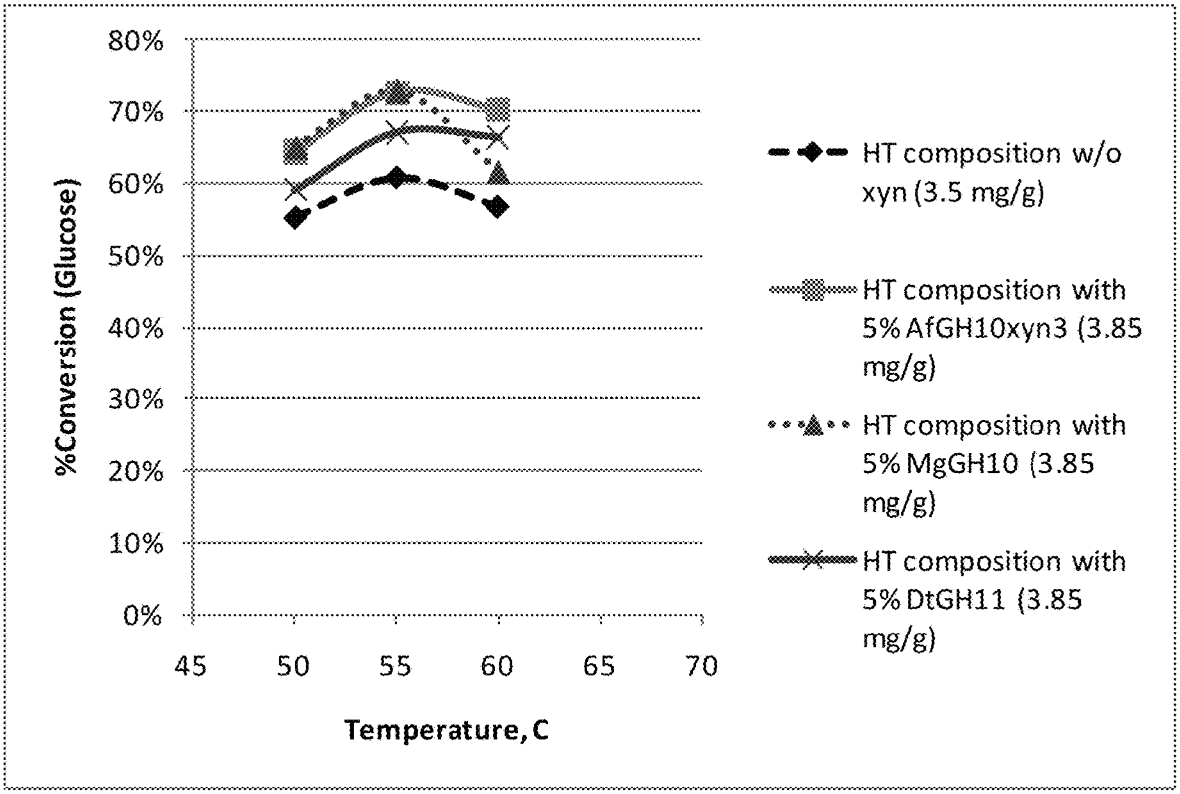
FIG. 41 shows an evaluation of three xylanases in a high-temperature enzyme composition in hydrolysis of milled unwashed PCS at 50-65° C.

As shown in FIG. 41, all three xylanase increased hydrolysis of the high-temperature enzyme composition. *Aspergillus fumigatus* GH10 xylanase and *Meripilus giganteus* GH10 xylanase had the same activity at 50° C. and 55° C. but *Aspergillus fumigatus* GH10 xylanase 3 had significantly higher activity at 60° C. than *Meripilus giganteus* GH10 xylanase. *Dictyoglomus thermophilum* GH11 xylanase had lower activity than *Aspergillus fumigatus* GH10 xylanase 3 at all three temperatures but *Dictyoglomus thermophilum* GH11 xylanase had increasing activity as temperature increases to 60° C.

Example 101: Comparison of XCL-602-Based Enzyme Compositions Containing Different Cellobiohydrolases and Xylanases in Hydrolysis of Milled Unwashed PCS at 50-60° C.

Four XCL-602 based enzyme compositions containing a different cellobiohydrolase and xylanase were tested at 50°

C., 55° C., and 60° C. using milled unwashed PCS as a substrate. The cellobiohydrolases tested in the XCL-602 based enzyme compositions were *Aspergillus fumigatus* Cel7A CBHI and *Penicillium emersonii* Cel7 CBHI. The xylanases tested were *Aspergillus fumigatus* GH10 xylanase 3 and *Trichophaea saccata* GH10 xylanase. The XCL-602 based enzyme compositions included 40% XCL-602, 20% CBHI, 20% *Aspergillus fumigatus* Cel6A CBHII, 12.5% *Penicillium* species GH61A, 5% xylanase, and 2.5% *Talaromyces emersonii* GH3 beta-xylosidase. XCL-602 based enzyme compositions containing *Aspergillus fumigatus* Cel7A CBHI were tested at 3.0, 5.0, and 7.0 mg protein per g cellulose while XCL-602 based enzyme compositions containing *Penicillium emersonii* Cel7 CBHI were tested at 3.0 mg protein per g cellulose. For comparison, *Trichoderma reesei*-based XCL-602 cellulase was tested at 3.0, 5.0, and 7.0 mg protein per g cellulose.

The assay was performed as described in Example 34. The 1 ml reactions with milled unwashed PCS (5% insoluble solids) were conducted for 72 hours in 50 mM sodium acetate pH 5.0 buffer containing 1 mM manganese sulfate. All reactions were performed in triplicate and involved single mixing at the beginning of hydrolysis.

Figure 42:
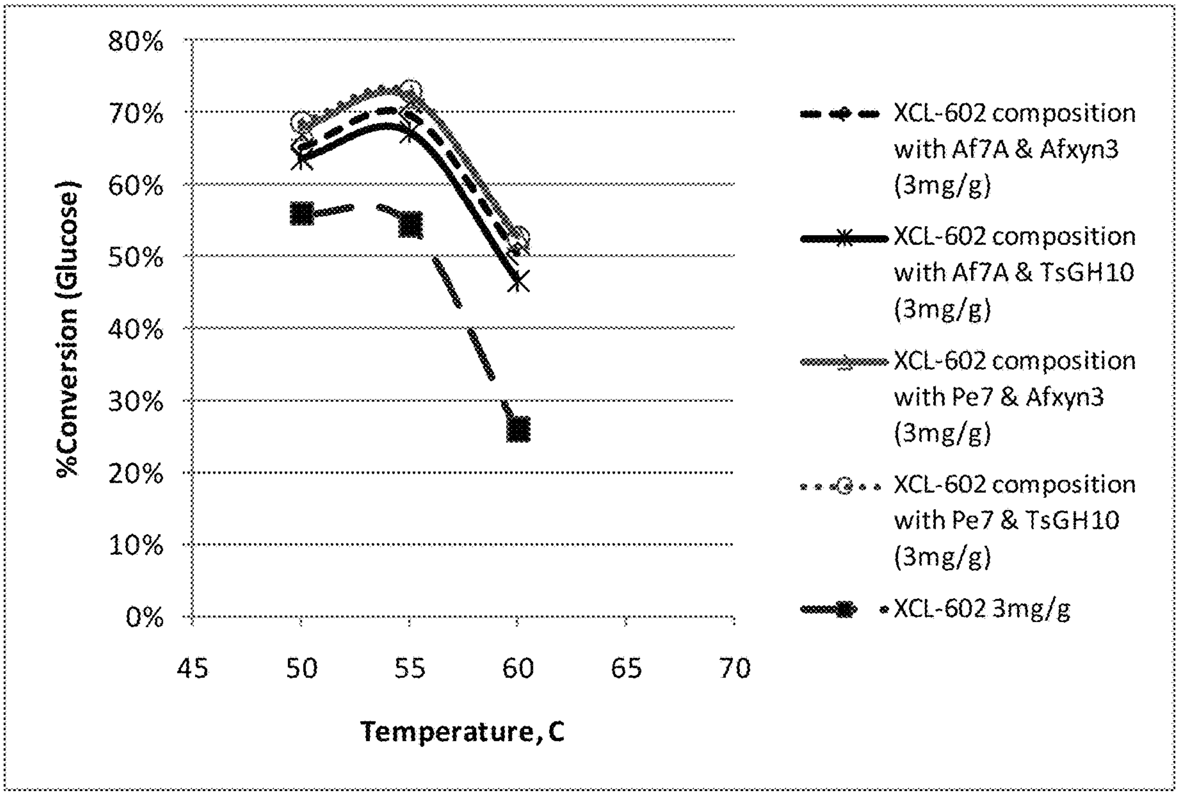
FIG. 42 shows the hydrolysis of milled unwashed PCS by non-replaced *Trichoderma reesei*-based XCL-602 cellulase and various XCL-602-based enzyme compositions containing different cellobiohydrolases and xylanases (3 mg protein per g cellulose) at 50-60° C.

The results for 3 mg protein per g cellulose are shown in FIG. 42. The two xylanases, *Aspergillus fumigatus* GH10 xylanase 3 and *Trichophaea saccata* GH10 xylanase showed similar performance in the XCL-602 based enzyme compositions with either *Aspergillus fumigatus* Cel7A CBHI or *Penicillium emersonii* Cel7 CBHI. For the CBHIs in the XCL-602 based enzyme compositions with either xylanase, *Penicillium emersonii* Cel7 CBHI had slightly higher performance than *Aspergillus fumigatus* Cel7A CBHI at all three temperatures. Finally, all XCL-602 based enzyme compositions replaced with CBHI, CBHII, GH61, xylanase, and beta-xylosidase had significantly higher hydrolysis over the non-replaced *Trichoderma reesei*-based XCL-602 cellulase at all three temperatures. At 80% glucose conversion, the XCL-602 based enzyme compositions containing *Aspergillus fumigatus* Cel7A CBHI and either xylanase at 55° C. required 4.3 mg protein per g cellulose while XCL-602 at 50° C. required 6.5 mg protein per g cellulose, a 1.5-fold reduction in protein loading.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. An isolated recombinant host cell encoding an enzyme composition comprising:

(I) a polypeptide having cellobiohydrolase I activity selected from the group consisting of: (a) a polypeptide comprising an amino acid sequence having at least 95% sequence identity to the mature polypeptide of SEQ ID NO: 6; (b) a polypeptide encoded by a polynucleotide that hybridizes under at least high stringency conditions with (i) the mature polypeptide coding sequence of SEQ ID NO: 5, (ii) the genomic DNA sequence of the mature polypeptide coding sequence of SEQ ID NO: 5, or (iii) the full-length complement of (i) or (ii), wherein high stringency conditions are defined as prehybridization and hybridization at 42° C. in 5×SSPE, 0.3% SDS, 200 micrograms/ml sheared and denatured salmon sperm DNA, and 50% formamide and washing three times each for 15 minutes using 2×SSC, 0.2% SDS at 65° C.; (c) a polypeptide encoded by a polynucleotide comprising a nucleotide sequence having at least 95% sequence identity to the mature polypeptide coding sequence of SEQ ID NO: 5; and (d) a polypeptide comprising the mature polypeptide of SEQ ID NO: 6;

(II) a polypeptide having cellobiohydrolase II activity selected from the group consisting of: (a) a polypeptide comprising an amino acid sequence having at least 95% sequence identity to the mature polypeptide of SEQ ID NO: 18; (b) a polypeptide encoded by a polynucleotide that hybridizes under at least high stringency conditions with (i) the mature polypeptide coding sequence of SEQ ID NO: 17, (ii) the cDNA sequence of the mature polypeptide coding sequence of SEQ ID NO: 17, or (iii) the full-length complement of (i) or (ii), wherein high stringency conditions are defined as prehybridization and hybridization at 42° C. in 5×SSPE, 0.3% SDS, 200 micrograms/ml sheared and denatured salmon sperm DNA, and 50% formamide and washing three times each for 15 minutes using 2×SSC, 0.2% SDS at 65° C.; (c) a polypeptide encoded by a polynucleotide comprising a nucleotide sequence having at least 95% sequence identity to the mature polypeptide coding sequence of SEQ ID NO: 17; and (d) a polypeptide comprising the mature polypeptide of SEQ ID NO: 18;

(III) a polypeptide having beta-glucosidase activity selected from the group consisting of: (a) a polypeptide comprising an amino acid sequence having at least 95% sequence identity to the mature polypeptide of SEQ ID NO: 28; (b) a polypeptide encoded by a polynucleotide that hybridizes under at least high stringency conditions with (i) the mature polypeptide coding sequence of SEQ ID NO: 27, (ii) the cDNA sequence of the mature polypeptide coding sequence of SEQ ID NO: 27, or (iii) the full-length complement of (i) or (ii), wherein high stringency conditions are defined as prehybridization and hybridization at 42° C. in 5×SSPE, 0.3% SDS, 200 micrograms/ml sheared and denatured salmon sperm DNA, and 50% formamide and washing three times each for 15 minutes using 2×SSC, 0.2% SDS at 65° C.; (c) a polypeptide encoded by a polynucleotide comprising a nucleotide sequence having at least 95% sequence identity to the mature polypeptide coding sequence of SEQ ID NO: 27; and (d) a polypeptide comprising the mature polypeptide of SEQ ID NO: 28; and (IV) a Family 10 polypeptide having xylanase activity is selected from the group consisting of: (a) a polypeptide comprising an amino acid sequence having at least 95% sequence identity to the mature polypeptide of SEQ ID NO: 48; (b) a polypeptide encoded by a polynucleotide that hybridizes under at least high stringency conditions with (i) the mature polypeptide coding sequence of SEQ ID NO: 47, (ii) the genomic DNA sequence of the mature polypeptide coding sequence of SEQ ID NO: 47, or (iii) the full-length complement of (i) or (ii), wherein high stringency conditions are defined as prehybridization and hybridization at 42° C. in 5×SSPE, 0.3% SDS, 200 micrograms/ml sheared and denatured salmon sperm DNA, and 50% formamide and washing three times each for 15 minutes using 2×SSC, 0.2% SDS at 65° C.; (c) a polypeptide encoded by a polynucleotide comprising a nucleotide sequence having at least 95% sequence identity to the mature polypeptide coding sequence of SEQ ID NO: 47; and (d) a polypeptide comprising the mature polypeptide of SEQ ID NO: 48;

(V) a polypeptide having beta-xylosidase activity selected from the group consisting of: (a) a polypeptide comprising an amino acid sequence having at least 95% sequence identity to the mature polypeptide of SEQ ID NO: 60; (b) a polypeptide encoded by a polynucleotide that hybridizes under at least high stringency conditions with (i) the mature polypeptide coding sequence of SEQ ID NO: 59, (ii) the genomic DNA sequence of the mature polypeptide coding sequence of SEQ ID NO: 59, or (iii) the full-length complement of (i) or (ii), wherein high stringency conditions are defined as prehybridization and hybridization at 42° C. in 5×SSPE, 0.3% SDS, 200 micrograms/ml sheared and denatured salmon sperm DNA, and 50% formamide and washing three times each for 15 minutes using 2×SSC, 0.2% SDS at 65° C.; (c) a polypeptide encoded by a polynucleotide comprising a nucleotide sequence having at least 95% sequence identity to the mature polypeptide coding sequence of SEQ ID NO: 59; and (d) a polypeptide comprising the mature polypeptide of SEQ ID NO: 60;

wherein saccharification of a cellulosic material is performed with the enzyme composition at a temperature in the range of about 40° C. to about 70° C.

2. The isolated recombinant host cell of claim 1, wherein the enzyme composition further comprises a GH61 polypeptide having cellulolytic enhancing activity.

3. The isolated recombinant host cell of claim 2, wherein the GH61 polypeptide having cellulolytic enhancing activity is one or more polypeptides selected from the group consisting of: (a) a polypeptide comprising an amino acid sequence having at least 95% sequence identity to the mature polypeptide of SEQ ID NO: 34 or 42; (b) a polypeptide encoded by a polynucleotide that hybridizes under at least high stringency conditions with (i) the mature polypeptide coding sequence of SEQ ID NO: 33 or 41, (ii) the cDNA sequence of the mature polypeptide coding sequence of SEQ ID NO: 33 or 41, or (iii) the full-length complement of (i) or (ii), wherein high stringency conditions are defined as prehybridization and hybridization at 42° C. in 5×SSPE, 0.3% SDS, 200 micrograms/ml sheared and denatured salmon sperm DNA, and 50% formamide and washing three times each for 15 minutes using 2×SSC, 0.2% SDS at 65° C.; (c) a polypeptide encoded by a polynucleotide comprising a nucleotide sequence having at least 95% sequence identity to the mature polypeptide coding sequence of SEQ ID NO: 33 or 41; and (d) a polypeptide comprising the mature polypeptide of SEQ ID NO: 34 or 42.

4. The isolated recombinant host cell of claim 1, wherein the enzyme composition further comprises a Family 11 polypeptide having xylanase activity.

5. The isolated recombinant host cell of claim 4, wherein the xylanase is selected from the group consisting of: (a) a polypeptide comprising an amino acid sequence having at least 95% sequence identity to the mature polypeptide of SEQ ID NO: 200; (b) a polypeptide encoded by a polynucleotide that hybridizes under at least high stringency conditions with the mature polypeptide coding sequence of SEQ ID NO: 199 or its full-length complement, wherein high stringency conditions are defined as prehybridization and hybridization at 42° C. in 5×SSPE, 0.3% SDS, 200 micrograms/ml sheared and denatured salmon sperm DNA, and 50% formamide and washing three times each for 15 minutes using 2×SSC, 0.2% SDS at 65° C.; (c) a polypeptide encoded by a polynucleotide comprising a nucleotide sequence having at least 95% sequence identity to the mature polypeptide coding sequence of SEQ ID NO: 199; and (d) a polypeptide comprising the mature polypeptide of SEQ ID NO: 200.

6. The isolated recombinant host cell of claim 1, wherein the enzyme composition further comprises one or more polypeptides having endoglucanase activity.

7. The isolated recombinant host cell of claim 6, wherein the polypeptide has endoglucanase I activity and is selected from the group consisting of: (a) a polypeptide comprising an amino acid sequence having at least 95% sequence identity to the mature polypeptide of SEQ ID NO: 20; (b) a polypeptide encoded by a polynucleotide that hybridizes under at least high stringency conditions with (i) the mature polypeptide coding sequence of SEQ ID NO: 19, (ii) the genomic DNA sequence of the mature polypeptide coding sequence of SEQ ID NO: 19, or (iii) the full-length complement of (i) or (ii), wherein high stringency conditions are defined as prehybridization and hybridization at 42° C. in 5×SSPE, 0.3% SDS, 200 micrograms/ml sheared and denatured salmon sperm DNA, and 50% formamide and washing three times each for 15 minutes using 2×SSC, 0.2% SDS at 65° C.; (c) a polypeptide encoded by a polynucleotide comprising a nucleotide sequence having at least 95% sequence identity to the mature polypeptide coding sequence of SEQ ID NO: 19; and (d) a polypeptide comprising the mature polypeptide of SEQ ID NO: 20.

8. The isolated recombinant host cell of claim 6, wherein the polypeptide has endoglucanase II activity and is selected from the group consisting of: (a) a polypeptide comprising an amino acid sequence having at least 95% sequence identity to the mature polypeptide of SEQ ID NO: 26; (b) a polypeptide encoded by a polynucleotide that hybridizes under at least high stringency conditions with (i) the mature polypeptide coding sequence of SEQ ID NO: 25, (ii) the genomic DNA sequence of the mature polypeptide coding sequence of SEQ ID NO: 25, or (iii) the full-length complement of (i) or (ii), wherein high stringency conditions are defined as prehybridization and hybridization at 42° C. in 5×SSPE, 0.3% SDS, 200 micrograms/ml sheared and denatured salmon sperm DNA, and 50% formamide and washing three times each for 15 minutes using 2×SSC, 0.2% SDS at 65° C.; (c) a polypeptide encoded by a polynucleotide comprising a nucleotide sequence having at least 95% sequence identity to the mature polypeptide coding sequence of SEQ ID NO: 25; and (d) a polypeptide comprising the mature polypeptide of SEQ ID NO: 26.

9. A method of producing an enzyme composition, comprising: (a) cultivating the recombinant host cell of claim 1 under conditions conducive for production of the enzyme composition; and (b) recovering the enzyme composition.

10. A method for degrading or converting a cellulosic material, comprising: treating the cellulosic material with an enzyme composition comprising:

(I) a polypeptide having cellobiohydrolase I activity selected from the group consisting of: (a) a polypeptide comprising an amino acid sequence having at least 95% sequence identity to the mature polypeptide of SEQ ID NO: 6; (b) a polypeptide encoded by a polynucleotide that hybridizes under at least high stringency conditions with (i) the mature polypeptide coding sequence of SEQ ID NO: 5, (ii) the genomic DNA sequence of the mature polypeptide coding sequence of SEQ ID NO: 5, or (iii) the full-length complement of (i) or (ii), wherein high stringency conditions are defined as prehybridization and hybridization at 42° C. in 5×SSPE, 0.3% SDS, 200 micrograms/ml sheared and denatured salmon sperm DNA, and 50% formamide and washing three times each for 15 minutes using 2×SSC, 0.2% SDS at 65° C.; (c) a polypeptide encoded by a polynucleotide comprising a nucleotide sequence having at least 95% sequence identity to the mature polypeptide coding sequence of SEQ ID NO: 5; and (d) a polypeptide comprising the mature polypeptide of SEQ ID NO: 6;

(II) a polypeptide having cellobiohydrolase II activity selected from the group consisting of: (a) a polypeptide comprising an amino acid sequence having at least 95% sequence identity to the mature polypeptide of SEQ ID NO: 18; (b) a polypeptide encoded by a polynucleotide that hybridizes under at least high stringency conditions with (i) the mature polypeptide coding sequence of SEQ ID NO: 17, (ii) the cDNA sequence of the mature polypeptide coding sequence of SEQ ID NO: 17, or (iii) the full-length complement of (i) or (ii), wherein high stringency conditions are defined as prehybridization and hybridization at 42° C. in 5×SSPE, 0.3% SDS, 200 micrograms/ml sheared and denatured salmon sperm DNA, and 50% formamide and washing three times each for 15 minutes using 2×SSC, 0.2% SDS at 65° C.; (c) a polypeptide encoded by a polynucleotide comprising a nucleotide sequence having at least 95% sequence identity to the mature polypeptide coding sequence of SEQ ID NO: 17; and (d) a polypeptide comprising the mature polypeptide of SEQ ID NO: 18;

(III) a polypeptide having beta-glucosidase activity selected from the group consisting of: (a) a polypeptide comprising an amino acid sequence having at least 95% sequence identity to the mature polypeptide of SEQ ID NO: 28; (b) a polypeptide encoded by a polynucleotide that hybridizes under at least high stringency conditions with (i) the mature polypeptide coding sequence of SEQ ID NO: 27, (ii) the cDNA sequence of the mature polypeptide coding sequence of SEQ ID NO: 27, or (iii) the full-length complement of (i) or (ii), wherein high stringency conditions are defined as prehybridization and hybridization at 42° C. in 5×SSPE, 0.3% SDS, 200 micrograms/ml sheared and denatured salmon sperm DNA, and 50% formamide and washing three times each for 15 minutes using 2×SSC, 0.2% SDS at 65° C.; (c) a polypeptide encoded by a polynucleotide comprising a nucleotide sequence having at least 95% sequence identity to the mature polypeptide coding sequence of SEQ ID NO: 27; and (d) a polypeptide comprising the mature polypeptide of SEQ ID NO: 28; and (IV) a Family 10 polypeptide having xylanase activity is selected from the group consisting of: (a) a polypeptide comprising an amino acid sequence having at least 95% sequence identity to the mature polypeptide of SEQ ID NO: 48; (b) a polypeptide encoded by a polynucleotide that hybridizes under at least high stringency conditions with (i) the mature polypeptide coding sequence of SEQ ID NO: 47, (ii) the genomic DNA sequence of the mature polypeptide coding sequence of SEQ ID NO: 47, or (iii) the full-length complement of (i) or (ii), wherein high stringency conditions are defined as prehybridization and hybridization at 42° C. in 5×SSPE, 0.3% SDS, 200 micrograms/ml sheared and denatured salmon sperm DNA, and 50% formamide and washing three times each for 15 minutes using 2×SSC, 0.2% SDS at 65° C.; (c) a polypeptide encoded by a polynucleotide comprising a nucleotide sequence having at least 95% sequence identity to the mature polypeptide coding sequence of SEQ ID NO: 47; and (d) a polypeptide comprising the mature polypeptide of SEQ ID NO: 48;

(V) a polypeptide having beta-xylosidase activity selected from the group consisting of: (a) a polypeptide comprising an amino acid sequence having at least 95% sequence identity to the mature polypeptide of SEQ ID NO: 60; (b) a polypeptide encoded by a polynucleotide that hybridizes under at least high stringency conditions with (i) the mature polypeptide coding sequence of SEQ ID NO: 59, (ii) the genomic DNA sequence of the mature polypeptide coding sequence of SEQ ID NO: 59, or (iii) the full-length complement of (i) or (ii), wherein high stringency conditions are defined as prehybridization and hybridization at 42° C. in 5×SSPE, 0.3% SDS, 200 micrograms/ml sheared and denatured salmon sperm DNA, and 50% formamide and washing three times each for 15 minutes using 2×SSC, 0.2% SDS at 65° C.; (c) a polypeptide encoded by a polynucleotide comprising a nucleotide sequence having at least 95% sequence identity to the mature polypeptide coding sequence of SEQ ID NO: 59; and (d) a polypeptide comprising the mature polypeptide of SEQ ID NO: 60;

wherein the degrading or converting of the cellulosic material is performed with the enzyme composition at a temperature in the range of about 40° C. to about 70° C.

11. The method of claim 10, wherein the enzyme composition further comprises a GH61 polypeptide having cellulolytic enhancing activity.

12. The method of claim 11, wherein the GH61 polypeptide having cellulolytic enhancing activity is one or more polypeptides selected from the group consisting of: (a) a polypeptide comprising an amino acid sequence having at least 95% sequence identity to the mature polypeptide of SEQ ID NO: 34 or 42; (b) a polypeptide encoded by a polynucleotide that hybridizes under at least high stringency conditions with (i) the mature polypeptide coding sequence of SEQ ID NO: 33 or 41, (ii) the cDNA sequence of the mature polypeptide coding sequence of SEQ ID NO: 33 or 41, or (iii) the full-length complement of (i) or (ii), wherein high stringency conditions are defined as prehybridization and hybridization at 42° C. in 5×SSPE, 0.3% SDS, 200 micrograms/ml sheared and denatured salmon sperm DNA, and 50% formamide and washing three times each for 15 minutes using 2×SSC, 0.2% SDS at 65° C.; (c) a polypeptide encoded by a polynucleotide comprising a nucleotide sequence having at least 95% sequence identity to the mature polypeptide coding sequence of SEQ ID NO: 33 or 41; and (d) a polypeptide comprising the mature polypeptide of SEQ ID NO: 34 or 42.

13. The method of claim 10, wherein the enzyme composition further comprises a Family 11 polypeptide having xylanase activity.

14. The method of claim 13, wherein the xylanase is selected from the group consisting of: (a) a polypeptide comprising an amino acid sequence having at least 95% sequence identity to the mature polypeptide of SEQ ID NO: 200; (b) a polypeptide encoded by a polynucleotide that hybridizes under at least high stringency conditions with the mature polypeptide coding sequence of SEQ ID NO: 199 or its full-length complement, wherein high stringency conditions are defined as prehybridization and hybridization at 42° C. in 5×SSPE, 0.3% SDS, 200 micrograms/ml sheared and denatured salmon sperm DNA, and 50% formamide and washing three times each for 15 minutes using 2×SSC, 0.2% SDS at 65° C.; (c) a polypeptide encoded by a polynucleotide comprising a nucleotide sequence having at least 95% sequence identity to the mature polypeptide coding sequence of SEQ ID NO: 199; and (d) a polypeptide comprising the mature polypeptide of SEQ ID NO: 200.

15. The method of claim 10, wherein the enzyme composition further comprises one or more polypeptides having endoglucanase activity.

16. The method of claim 15, wherein the polypeptide has endoglucanase I activity and is selected from the group consisting of: (a) a polypeptide comprising an amino acid sequence having at least 95% sequence identity to the mature polypeptide of SEQ ID NO: 20; (b) a polypeptide encoded by a polynucleotide that hybridizes under at least high stringency conditions with (i) the mature polypeptide coding sequence of SEQ ID NO: 19, (ii) the genomic DNA sequence of the mature polypeptide coding sequence of SEQ ID NO: 19, or (iii) the full-length complement of (i) or (ii), wherein high stringency conditions are defined as prehybridization and hybridization at 42° C. in 5×SSPE, 0.3% SDS, 200 micrograms/ml sheared and denatured salmon sperm DNA, and 50% formamide and washing three times each for 15 minutes using 2×SSC, 0.2% SDS at 65° C.; (c) a polypeptide encoded by a polynucleotide comprising a nucleotide sequence having at least 95% sequence identity to the mature polypeptide coding sequence of SEQ ID NO: 19; and (d) a polypeptide comprising the mature polypeptide of SEQ ID NO: 20.

17. The method of claim 15, wherein the polypeptide has endoglucanase II activity and is selected from the group consisting of: (a) a polypeptide comprising an amino acid sequence having at least 95% sequence identity to the mature polypeptide of SEQ ID NO: 26; (b) a polypeptide encoded by a polynucleotide that hybridizes under at least high stringency conditions with (i) the mature polypeptide coding sequence of SEQ ID NO: 25, (ii) the genomic DNA sequence of the mature polypeptide coding sequence of SEQ ID NO: 25, or (iii) the full-length complement of (i) or (ii), wherein high stringency conditions are defined as prehybridization and hybridization at 42° C. in 5×SSPE, 0.3% SDS, 200 micrograms/ml sheared and denatured salmon sperm DNA, and 50% formamide and washing three times each for 15 minutes using 2×SSC, 0.2% SDS at 65° C.; (c) a polypeptide encoded by a polynucleotide comprising a nucleotide sequence having at least 95% sequence identity to the mature polypeptide coding sequence of SEQ ID NO: 25; and (d) a polypeptide comprising the mature polypeptide of SEQ ID NO: 26.

18. The method of claim 10, wherein saccharification of the cellulosic material is performed with the enzyme composition at a temperature in the range of about 50° C. to about 65° C.

19. A method for producing a fermentation product, comprising:

(a) saccharifying a cellulosic material with an enzyme composition comprising:

(I) a polypeptide having cellobiohydrolase I activity selected from the group consisting of: (a) a polypeptide comprising an amino acid sequence having at least 95% sequence identity to the mature polypeptide of SEQ ID NO: 6; (b) a polypeptide encoded by a polynucleotide that hybridizes under at least high stringency conditions with (i) the mature polypeptide coding sequence of SEQ ID NO: 5, (ii) the genomic DNA sequence of the mature polypeptide coding sequence of SEQ ID NO: 5, or (iii) the full-length complement of (i) or (ii), wherein high stringency conditions are defined as prehybridization and hybridization at 42° C. in 5×SSPE, 0.3% SDS, 200 micrograms/ml sheared and denatured salmon sperm DNA, and 50% formamide and washing three times each for 15 minutes using 2×SSC, 0.2% SDS at 65° C.; (c) a polypeptide encoded by a polynucleotide comprising a nucleotide sequence having at least 95% sequence identity to the mature polypeptide coding sequence of SEQ ID NO: 5; and (d) a polypeptide comprising the mature polypeptide of SEQ ID NO: 6;

(II) a polypeptide having cellobiohydrolase II activity selected from the group consisting of: (a) a polypeptide comprising an amino acid sequence having at least 95% sequence identity to the mature polypeptide of SEQ ID NO: 18; (b) a polypeptide encoded by a polynucleotide that hybridizes under at least high stringency conditions with (i) the mature polypeptide coding sequence of SEQ ID NO: 17, (ii) the cDNA sequence of the mature polypeptide coding sequence of SEQ ID NO: 17, or (iii) the full-length complement of (i) or (ii), wherein high stringency conditions are defined as prehybridization and hybridization at 42° C. in 5×SSPE, 0.3% SDS, 200 micrograms/ml sheared and denatured salmon sperm DNA, and 50% formamide and washing three times each for 15 minutes using 2×SSC, 0.2% SDS at 65° C.; (c) a polypeptide encoded by a polynucleotide comprising a nucleotide sequence having at least 95% sequence identity to the mature polypeptide coding sequence of SEQ ID NO: 17; and (d) a polypeptide comprising the mature polypeptide of SEQ ID NO: 18;

(III) a polypeptide having beta-glucosidase activity selected from the group consisting of: (a) a polypeptide comprising an amino acid sequence having at least 95% sequence identity to the mature polypeptide of SEQ ID NO: 28; (b) a polypeptide encoded by a polynucleotide that hybridizes under at least high stringency conditions with (i) the mature polypeptide coding sequence of SEQ ID NO: 27, (ii) the cDNA sequence of the mature polypeptide coding sequence of SEQ ID NO: 27, or (iii) the full-length complement of (i) or (ii), wherein high stringency conditions are defined as prehybridization and hybridization at 42° C. in 5×SSPE, 0.3% SDS, 200 micrograms/ml sheared and denatured salmon sperm DNA, and 50% formamide and washing three times each for 15 minutes using 2×SSC, 0.2% SDS at 65° C.; (c) a polypeptide encoded by a polynucleotide comprising a nucleotide sequence having at least 95% sequence identity to the mature polypeptide coding sequence of SEQ ID NO: 27; and (d) a polypeptide comprising the mature polypeptide of SEQ ID NO: 28; and (IV) a Family 10 polypeptide having xylanase activity is selected from the group consisting of: (a) a polypeptide comprising an amino acid sequence having at least 95% sequence identity to the mature polypeptide of SEQ ID NO: 48; (b) a polypeptide encoded by a polynucleotide that hybridizes under at least high stringency conditions with (i) the mature polypeptide coding sequence of SEQ ID NO: 47, (ii) the genomic DNA sequence of the mature polypeptide coding sequence of SEQ ID NO: 47, or (iii) the full-length complement of (i) or (ii), wherein high stringency conditions are defined as prehybridization and hybridization at 42° C. in 5×SSPE, 0.3% SDS, 200 micrograms/ml sheared and denatured salmon sperm DNA, and 50% formamide and washing three times each for 15 minutes using 2×SSC, 0.2% SDS at 65° C.; (c) a polypeptide encoded by a polynucleotide comprising a nucleotide sequence having at least 95% sequence identity to the mature polypeptide coding sequence of SEQ ID NO: 47; and (d) a polypeptide comprising the mature polypeptide of SEQ ID NO: 48;

(V) a polypeptide having beta-xylosidase activity selected from the group consisting of: (a) a polypeptide comprising an amino acid sequence having at least 95% sequence identity to the mature polypeptide of SEQ ID NO: 60; (b) a polypeptide encoded by a polynucleotide that hybridizes under at least high stringency conditions with (i) the mature polypeptide coding sequence of SEQ ID NO: 59, (ii) the genomic DNA sequence of the mature polypeptide coding sequence of SEQ ID NO: 59, or (iii) the full-length complement of (i) or (ii), wherein high stringency conditions are defined as prehybridization and hybridization at 42° C. in 5×SSPE, 0.3% SDS, 200 micrograms/ml sheared and denatured salmon sperm DNA, and 50% formamide and washing three times each for 15 minutes using 2×SSC, 0.2% SDS at 65° C.; (c) a polypeptide encoded by a polynucleotide comprising a nucleotide sequence having at least 95% sequence identity to the mature polypeptide coding sequence of SEQ ID NO: 59; and (d) a polypeptide comprising the mature polypeptide of SEQ ID NO: 60;

wherein the saccharification of the cellulosic material is performed with the enzyme composition at a temperature in the range of about 40° C. to about 70° C.;

(b) fermenting the saccharified cellulosic material with one or more fermenting microorganisms to produce the fermentation product; and (c) recovering the fermentation product from the fermentation.

20. The method of claim 19, wherein the enzyme composition further comprises a GH61 polypeptide having cellulolytic enhancing activity.

21. The method of claim 20, wherein the GH61 polypeptide having cellulolytic enhancing activity is one or more polypeptides selected from the group consisting of: (a) a polypeptide comprising an amino acid sequence having at least 95% sequence identity to the mature polypeptide of SEQ ID NO: 34 or 42; (b) a polypeptide encoded by a polynucleotide that hybridizes under at least high stringency conditions with (i) the mature polypeptide coding sequence of SEQ ID NO: 33 or 41, (ii) the cDNA sequence of the mature polypeptide coding sequence of SEQ ID NO: 33 or 41, or (iii) the full-length complement of (i) or (ii), wherein high stringency conditions are defined as prehybridization and hybridization at 42° C. in 5×SSPE, 0.3% SDS, 200 micrograms/ml sheared and denatured salmon sperm DNA, and 50% formamide and washing three times each for 15 minutes using 2×SSC, 0.2% SDS at 65° C.; (c) a polypeptide encoded by a polynucleotide comprising a nucleotide sequence having at least 95% sequence identity to the mature polypeptide coding sequence of SEQ ID NO: 33 or 41; and (d) a polypeptide comprising the mature polypeptide of SEQ ID NO: 34 or 42.

22. The method of claim 19, wherein the enzyme composition further comprises a Family 11 polypeptide having xylanase activity.

23. The method of claim 22, wherein the xylanase is selected from the group consisting of: (a) a polypeptide comprising an amino acid sequence having at least 95% sequence identity to the mature polypeptide of SEQ ID NO: 200; (b) a polypeptide encoded by a polynucleotide that hybridizes under at least high stringency conditions with the mature polypeptide coding sequence of SEQ ID NO: 199 or its full-length complement, wherein high stringency conditions are defined as prehybridization and hybridization at 42° C. in 5×SSPE, 0.3% SDS, 200 micrograms/ml sheared and denatured salmon sperm DNA, and 50% formamide and washing three times each for 15 minutes using 2×SSC, 0.2% SDS at 65° C.; (c) a polypeptide encoded by a polynucleotide comprising a nucleotide sequence having at least 95% sequence identity to the mature polypeptide coding sequence of SEQ ID NO: 199; and (d) a polypeptide comprising the mature polypeptide of SEQ ID NO: 200.

24. The method of claim 19, wherein the enzyme composition further comprises one or more polypeptides having endoglucanase activity.

25. The method of claim 24, wherein the polypeptide has endoglucanase I activity and is selected from the group consisting of: (a) a polypeptide comprising an amino acid sequence having at least 95% sequence identity to the mature polypeptide of SEQ ID NO: 20; (b) a polypeptide encoded by a polynucleotide that hybridizes under at least high stringency conditions with (i) the mature polypeptide coding sequence of SEQ ID NO: 19, (ii) the genomic DNA sequence of the mature polypeptide coding sequence of SEQ ID NO: 19, or (iii) the full-length complement of (i) or (ii), wherein high stringency conditions are defined as prehybridization and hybridization at 42° C. in 5×SSPE, 0.3%

SDS, 200 micrograms/ml sheared and denatured salmon sperm DNA, and 50% formamide and washing three times each for 15 minutes using 2×SSC, 0.2% SDS at 65° C.; (c) a polypeptide encoded by a polynucleotide comprising a nucleotide sequence having at least 95% sequence identity to the mature polypeptide coding sequence of SEQ ID NO: 19; and (d) a polypeptide comprising the mature polypeptide of SEQ ID NO: 20.

26. The method of claim 24, wherein the polypeptide has endoglucanase II activity and is selected from the group consisting of: (a) a polypeptide comprising an amino acid sequence having at least 95% sequence identity to the mature polypeptide of SEQ ID NO: 26; (b) a polypeptide encoded by a polynucleotide that hybridizes under at least high stringency conditions with (i) the mature polypeptide coding sequence of SEQ ID NO: 25, (ii) the genomic DNA sequence of the mature polypeptide coding sequence of SEQ ID NO: 25, or (iii) the full-length complement of (i) or (ii), wherein high stringency conditions are defined as prehybridization and hybridization at 42° C. in 5×SSPE, 0.3% SDS, 200 micrograms/ml sheared and denatured salmon sperm DNA, and 50% formamide and washing three times each for 15 minutes using 2×SSC, 0.2% SDS at 65° C.; (c) a polypeptide encoded by a polynucleotide comprising a nucleotide sequence having at least 95% sequence identity to the mature polypeptide coding sequence of SEQ ID NO: 25; and (d) a polypeptide comprising the mature polypeptide of SEQ ID NO: 26.

27. The method of claim 19, wherein saccharification of the cellulosic material is performed with the enzyme composition at a temperature in the range of about 50° C. to about 65° C.

28. A method of fermenting a cellulosic material, comprising: fermenting the cellulosic material with one or more fermenting microorganisms, wherein the cellulosic material is saccharified with an enzyme composition comprising:

(I) a polypeptide having cellobiohydrolase I activity selected from the group consisting of: (a) a polypeptide comprising an amino acid sequence having at least 95% sequence identity to the mature polypeptide of SEQ ID NO: 6; (b) a polypeptide encoded by a polynucleotide that hybridizes under at least high stringency conditions with (i) the mature polypeptide coding sequence of SEQ ID NO: 5, (ii) the genomic DNA sequence of the mature polypeptide coding sequence of SEQ ID NO: 5, or (iii) the full-length complement of (i) or (ii), wherein high stringency conditions are defined as prehybridization and hybridization at 42° C. in 5×SSPE, 0.3% SDS, 200 micrograms/ml sheared and denatured salmon sperm DNA, and 50% formamide and washing three times each for 15 minutes using 2×SSC, 0.2% SDS at 65° C.; (c) a polypeptide encoded by a polynucleotide comprising a nucleotide sequence having at least 95% sequence identity to the mature polypeptide coding sequence of SEQ ID NO: 5; and (d) a polypeptide comprising the mature polypeptide of SEQ ID NO: 6;

(II) a polypeptide having cellobiohydrolase II activity selected from the group consisting of: (a) a polypeptide comprising an amino acid sequence having at least 95% sequence identity to the mature polypeptide of SEQ ID NO: 18; (b) a polypeptide encoded by a polynucleotide that hybridizes under at least high stringency conditions with (i) the mature polypeptide coding sequence of SEQ ID NO: 17, (ii) the cDNA sequence of the mature polypeptide coding sequence of SEQ ID NO: 17, or (iii) the full-length complement of (i) or (ii), wherein high stringency conditions are defined as prehybridization and hybridization at 42° C. in 5×SSPE, 0.3% SDS, 200 micrograms/mi sheared and denatured salmon sperm DNA, and 50% formamide and washing three times each for 15 minutes using 2×SSC, 0.2% SDS at 65° C.; (c) a polypeptide encoded by a polynucleotide comprising a nucleotide sequence having at least 95% sequence identity to the mature polypeptide coding sequence of SEQ ID NO: 17; and (d) a polypeptide comprising the mature polypeptide of SEQ ID NO: 18;

(III) a polypeptide having beta-glucosidase activity selected from the group consisting of: (a) a polypeptide comprising an amino acid sequence having at least 95% sequence identity to the mature polypeptide of SEQ ID NO: 28; (b) a polypeptide encoded by a polynucleotide that hybridizes under at least high stringency conditions with (i) the mature polypeptide coding sequence of SEQ ID NO: 27, (ii) the cDNA sequence of the mature polypeptide coding sequence of SEQ ID NO: 27, or (iii) the full-length complement of (i) or (ii), wherein high stringency conditions are defined as prehybridization and hybridization at 42° C. in 5×SSPE, 0.3% SDS, 200 micrograms/mi sheared and denatured salmon sperm DNA, and 50% formamide and washing three times each for 15 minutes using 2×SSC, 0.2% SDS at 65° C.; (c) a polypeptide encoded by a polynucleotide comprising a nucleotide sequence having at least 95% sequence identity to the mature polypeptide coding sequence of SEQ ID NO: 27; and (d) a polypeptide comprising the mature polypeptide of SEQ ID NO: 28; and (IV) a Family 10 polypeptide having xylanase activity is selected from the group consisting of: (a) a polypeptide comprising an amino acid sequence having at least 95% sequence identity to the mature polypeptide of SEQ ID NO: 48; (b) a polypeptide encoded by a polynucleotide that hybridizes under at least high stringency conditions with (i) the mature polypeptide coding sequence of SEQ ID NO: 47, (ii) the genomic DNA sequence of the mature polypeptide coding sequence of SEQ ID NO: 47, or (iii) the full-length complement of (i) or (ii), wherein high stringency conditions are defined as prehybridization and hybridization at 42° C. in 5×SSPE, 0.3% SDS, 200 micrograms/ml sheared and denatured salmon sperm DNA, and 50% formamide and washing three times each for 15 minutes using 2×SSC, 0.2% SDS at 65° C.; (c) a polypeptide encoded by a polynucleotide comprising a nucleotide sequence having at least 95% sequence identity to the mature polypeptide coding sequence of SEQ ID NO: 47; and (d) a polypeptide comprising the mature polypeptide of SEQ ID NO: 48;

(V) a polypeptide having beta-xylosidase activity selected from the group consisting of: (a) a polypeptide comprising an amino acid sequence having at least 95% sequence identity to the mature polypeptide of SEQ ID NO: 60; (b) a polypeptide encoded by a polynucleotide that hybridizes under at least high stringency conditions with (i) the mature polypeptide coding sequence of SEQ ID NO: 59, (ii) the genomic DNA sequence of the mature polypeptide coding sequence of SEQ ID NO: 59, or (iii) the full-length complement of (i) or (ii), wherein high stringency conditions are defined as prehybridization and hybridization at 42° C. in 5×SSPE, 0.3% SDS, 200 micrograms/ml sheared and denatured salmon sperm DNA, and 50% formamide and washing three times each for 15 minutes using 2×SSC, 0.2% SDS at 65° C.; (c) a polypeptide encoded by a polynucleotide comprising a nucleotide sequence having at least 95% sequence identity to the mature polypeptide coding sequence of SEQ ID NO: 59; and (d) a polypeptide comprising the mature polypeptide of SEQ ID NO: 60;

wherein the saccharification of the cellulosic material is performed with the enzyme composition at a temperature in the range of about 40° C. to about 70° C.

29. The method of claim 28, wherein the enzyme composition further comprises a GH61 polypeptide having cellulolytic enhancing activity.

30. The method of claim 29, wherein the GH61 polypeptide having cellulolytic enhancing activity is one or more polypeptides selected from the group consisting of: (a) a polypeptide comprising an amino acid sequence having at least 95% sequence identity to the mature polypeptide of SEQ ID NO: 34 or 42; (b) a polypeptide encoded by a polynucleotide that hybridizes under at least high stringency conditions with (i) the mature polypeptide coding sequence of SEQ ID NO: 33 or 41, (ii) the cDNA sequence of the mature polypeptide coding sequence of SEQ ID NO: 33 or 41, or (iii) the full-length complement of (i) or (ii), wherein high stringency conditions are defined as prehybridization and hybridization at 42° C. in 5×SSPE, 0.3% SDS, 200 micrograms/ml sheared and denatured salmon sperm DNA, and 50% formamide and washing three times each for 15 minutes using 2×SSC, 0.2% SDS at 65° C.; (c) a polypeptide encoded by a polynucleotide comprising a nucleotide sequence having at least 95% sequence identity to the mature polypeptide coding sequence of SEQ ID NO: 33 or 41; and (d) a polypeptide comprising the mature polypeptide of SEQ ID NO: 34 or 42.

31. The method of claim 28, wherein the enzyme composition further comprises a Family 11 polypeptide having xylanase activity.

32. The method of claim 31, wherein the xylanase is selected from the group consisting of: (a) a polypeptide comprising an amino acid sequence having at least 95% sequence identity to the mature polypeptide of SEQ ID NO: 200; (b) a polypeptide encoded by a polynucleotide that hybridizes under at least high stringency conditions with the mature polypeptide coding sequence of SEQ ID NO: 199 or its full-length complement, wherein high stringency conditions are defined as prehybridization and hybridization at 42° C. in 5×SSPE, 0.3% SDS, 200 micrograms/ml sheared and denatured salmon sperm DNA, and 50% formamide and washing three times each for 15 minutes using 2×SSC, 0.2% SDS at 65° C.; (c) a polypeptide encoded by a polynucleotide comprising a nucleotide sequence having at least 95% sequence identity to the mature polypeptide coding sequence of SEQ ID NO: 199; and (d) a polypeptide comprising the mature polypeptide of SEQ ID NO: 200.

33. The method of claim 28, wherein the enzyme composition further comprises one or more polypeptides having endoglucanase activity.

34. The method of claim 33, wherein the polypeptide has endoglucanase I activity and is selected from the group consisting of: (a) a polypeptide comprising an amino acid sequence having at least 95% sequence identity to the mature polypeptide of SEQ ID NO: 20; (b) a polypeptide encoded by a polynucleotide that hybridizes under at least high stringency conditions with (i) the mature polypeptide coding sequence of SEQ ID NO: 19, (ii) the genomic DNA sequence of the mature polypeptide coding sequence of SEQ ID NO: 19, or (iii) the full-length complement of (i) or (ii), wherein high stringency conditions are defined as prehybridization and hybridization at 42° C. in 5×SSPE, 0.3% SDS, 200 micrograms/ml sheared and denatured salmon sperm DNA, and 50% formamide and washing three times each for 15 minutes using 2×SSC, 0.2% SDS at 65° C.; (c) a polypeptide encoded by a polynucleotide comprising a nucleotide sequence having at least 95% sequence identity to the mature polypeptide coding sequence of SEQ ID NO: 19; and (d) a polypeptide comprising the mature polypeptide of SEQ ID NO: 20.

35. The method of claim 33, wherein the polypeptide has endoglucanase II activity and is selected from the group consisting of: (a) a polypeptide comprising an amino acid sequence having at least 95% sequence identity to the mature polypeptide of SEQ ID NO: 26; (b) a polypeptide encoded by a polynucleotide that hybridizes under at least high stringency conditions with (i) the mature polypeptide coding sequence of SEQ ID NO: 25, (ii) the genomic DNA sequence of the mature polypeptide coding sequence of SEQ ID NO: 25, or (iii) the full-length complement of (i) or (ii), wherein high stringency conditions are defined as prehybridization and hybridization at 42° C. in 5×SSPE, 0.3% SDS, 200 micrograms/ml sheared and denatured salmon sperm DNA, and 50% formamide and washing three times each for 15 minutes using 2×SSC, 0.2% SDS at 65° C.; (c) a polypeptide encoded by a polynucleotide comprising a nucleotide sequence having at least 95% sequence identity to the mature polypeptide coding sequence of SEQ ID NO: 25; and (d) a polypeptide comprising the mature polypeptide of SEQ ID NO: 26.

36. The method of claim 28, wherein saccharification of the cellulosic material is performed with the enzyme composition at a temperature in the range of about 50° C. to about 65° C.

* * * * *